US012514118B2

(12) United States Patent
Lee et al.

(10) Patent No.: US 12,514,118 B2
(45) Date of Patent: Dec. 30, 2025

(54) HETEROCYCLIC COMPOUND, ORGANIC LIGHT EMITTING DEVICE COMPRISING THE SAME, METHOD FOR MANUFACTURING THE SAME AND COMPOSITION FOR ORGANIC MATERIAL LAYER OF ORGANIC LIGHT EMITTING DEVICE

(71) Applicant: LT MATERIALS CO., LTD., Yongin (KR)

(72) Inventors: Yong-Hui Lee, Yongin (KR); Jun-Tae Mo, Yongin (KR); Ji-Un Kim, Yongin (KR); Dong-Jun Kim, Yongin (KR)

(73) Assignee: LT MATERIALS CO., LTD., Yongin (KR)

( * ) Notice: Subject to any disclaimer, the term of this patent is extended or adjusted under 35 U.S.C. 154(b) by 986 days.

(21) Appl. No.: 17/552,734

(22) Filed: Dec. 16, 2021

(65) Prior Publication Data

US 2023/0083073 A1 Mar. 16, 2023

(30) Foreign Application Priority Data

Dec. 24, 2020 (KR) ........................ 10-2020-0183664

(51) Int. Cl.

| | |
|---|---|
| ***C07D 307/91*** | (2006.01) |
| ***C07D 307/77*** | (2006.01) |
| ***C07D 405/04*** | (2006.01) |
| ***C07D 405/10*** | (2006.01) |
| ***C07D 405/14*** | (2006.01) |
| ***C09K 11/06*** | (2006.01) |
| ***H10K 85/60*** | (2023.01) |
| *H10K 50/11* | (2023.01) |
| *H10K 71/16* | (2023.01) |
| *H10K 101/10* | (2023.01) |

(52) U.S. Cl.

CPC ....... *H10K 85/6574* (2023.02); *C07D 307/77* (2013.01); *C07D 307/91* (2013.01); *C07D 405/04* (2013.01); *C07D 405/10* (2013.01); *C07D 405/14* (2013.01); *C09K 11/06* (2013.01); *H10K 85/615* (2023.02); *H10K 85/626* (2023.02); *H10K 85/633* (2023.02); *H10K 85/636* (2023.02); *H10K 85/654* (2023.02); *C07B 2200/05* (2013.01); *C09K 2211/1018* (2013.01); *H10K 50/11* (2023.02); *H10K 71/164* (2023.02); *H10K 2101/10* (2023.02)

(58) Field of Classification Search

None

See application file for complete search history.

(56) References Cited

U.S. PATENT DOCUMENTS

| | | | | |
|---|---|---|---|---|
| 4,356,429 | A | 10/1982 | Tang | |
| 9,938,287 | B1 | 4/2018 | Kim et al. | |
| 2017/0125689 | A1 | 5/2017 | Lee et al. | |
| 2017/0279053 | A1 | 9/2017 | Shin et al. | |
| 2018/0083197 | A1 | 3/2018 | Park et al. | |
| 2018/0358563 | A1 | 12/2018 | Park et al. | |
| 2019/0047992 | A1 | 2/2019 | Park et al. | |
| 2019/0241548 | A1 | 8/2019 | Park et al. | |
| 2020/0136052 | A1 | 4/2020 | So et al. | |
| 2020/0287140 | A1 | 9/2020 | Chae et al. | |
| 2020/0321530 | A1 | 10/2020 | Lee et al. | |
| 2020/0403157 | A1 | 12/2020 | Kim et al. | |
| 2021/0091314 | A1 | 3/2021 | Shin et al. | |
| 2021/0300888 | A1 | 9/2021 | Park et al. | |
| 2021/0340103 | A1 | 11/2021 | Mun et al. | |
| 2022/0089610 | A1 | 3/2022 | Mo et al. | |
| 2022/0416174 | A1* | 12/2022 | Uno | C07F 7/0814 |

FOREIGN PATENT DOCUMENTS

| | | | | |
|---|---|---|---|---|
| EP | 3 730 490 | A1 | 10/2020 | |
| EP | 3 909 946 | A2 | 11/2021 | |
| JP | 2019-505475 | A | 2/2019 | |
| KR | 10-2016-0139159 | A | 12/2016 | |
| KR | 10-2017-0096770 | A | 8/2017 | |
| KR | 10-2019-0013363 | A | 2/2019 | |
| KR | 10-2076958 | B1 | 2/2020 | |
| KR | 10-2020-0136122 | A | 12/2020 | |
| TW | 202033740 | A | 9/2020 | |
| WO | WO 2015/194791 | A2 | 12/2015 | |
| WO | WO 2018/056649 | A1 | 3/2016 | |
| WO | WO 2017/090918 | A1 | 6/2017 | |
| WO | WO 2018/169261 | A1 | 9/2018 | |
| WO | WO 2019/231226 | A1 | 12/2019 | |
| WO | WO-2020091506 | A1 * | 5/2020 | C07F 7/0812 |

OTHER PUBLICATIONS

Machine translation of WO-2020091506-A1, translation generated Nov. 2024, 35 pages. (Year: 2024).*

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenylamino)triphenylamine (m-MTDATA), as Hole-Transport Materials", Advanced Materials, 1994, vol. 6. No. 9, pp. 677-679.

Extended European Search Report for European Application No. 21213610.5, dated May 16, 2022.

European Office Action for European Application No. 21 213 610.5, dated Oct. 18, 2024.

* cited by examiner

*Primary Examiner* — Robert S Loewe

(74) *Attorney, Agent, or Firm* — Birch, Stewart, Kolasch & Birch, LLP

(57) ABSTRACT

The present specification relates to a heterocyclic compound represented by Chemical Formula 1, an organic light emitting device including the same, a method for manufacturing the same, and a composition for an organic material layer.

17 Claims, 2 Drawing Sheets

【FIG. 1】
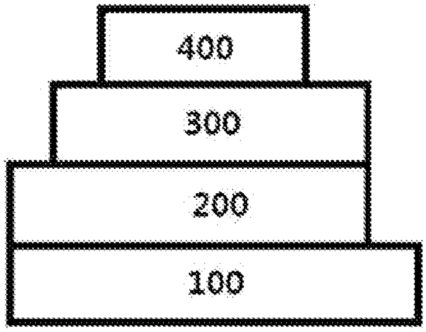
【FIG. 2】
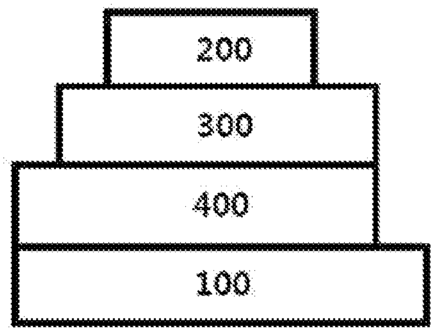

【FIG. 3】
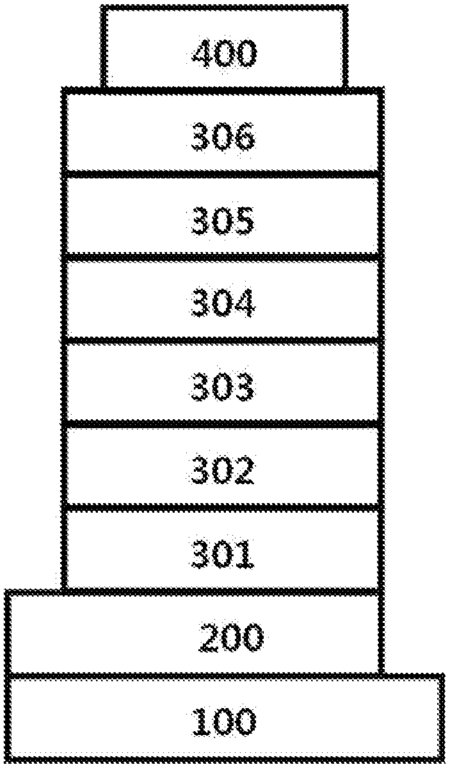

HETEROCYCLIC COMPOUND, ORGANIC LIGHT EMITTING DEVICE COMPRISING THE SAME, METHOD FOR MANUFACTURING THE SAME AND COMPOSITION FOR ORGANIC MATERIAL LAYER OF ORGANIC LIGHT EMITTING DEVICE

TECHNICAL FIELD

This application claims priority to and the benefits of Korean Patent Application No. 10-2020-0183664, filed with the Korean Intellectual Property Office on Dec. 24, 2020, the entire contents of which are incorporated herein by reference.

The present specification relates to a heterocyclic compound, an organic light emitting device including the same, a method for manufacturing the same, and a composition for an organic material layer.

BACKGROUND ART

An organic electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

Studies on an organic light emitting device including a compound capable of satisfying conditions required for materials usable in an organic light emitting device, for example, satisfying proper energy level, electrochemical stability, thermal stability and the like, and having a chemical structure capable of performing various roles required in an organic light emitting device depending on substituents have been required.

PRIOR ART DOCUMENTS

Patent Documents (Patent Document 1) U.S. Pat. No. 4,356,429

DISCLOSURE

Technical Problem

The present disclosure is directed to providing a heterocyclic compound, an organic light emitting device including the same, a method for manufacturing the same, and a composition for an organic material layer.

Technical Solution

One embodiment of the present application provides a heterocyclic compound represented by the following Chemical Formula 1.

[Chemical Formula 1]

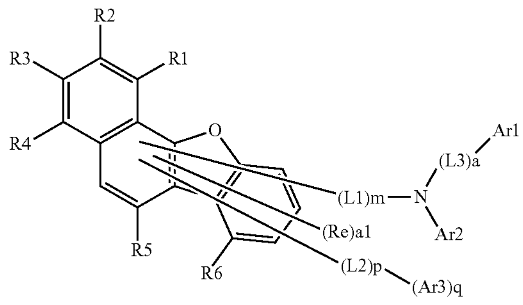

In Chemical Formula 1,

R1 to R6 and Re are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(═O)RR'; —SiRR'R" and —NRR', or two or more groups adjacent to each other bond to each other to form a substituted or unsubstituted C6 to C60 aliphatic or aromatic hydrocarbon ring or a substituted or unsubstituted C2 to C60 aliphatic or aromatic heteroring, L1 to L3 are the same as or different from each other, and each independently a direct bond; a substituted or unsubstituted C6 to C60 arylene group; or a substituted or unsubstituted C2 to C60 heteroarylene group, Ar1 to Ar3 are the same as or different from each other, and each independently selected from the group consisting of a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(═O)RR'; —SiRR'R" and —NRR', R, R' and R" are the same as or different from each other, and each independently a substituted or unsubstituted C1 to C60 alkyl group; a substituted or unsubstituted C6 to C60 aryl group; or a substituted or unsubstituted C2 to C60 heteroaryl group, q is an integer of 1 to 4, a1 is an integer of 0 to 2, p, a and m are an integer of 0 to 4, and when q, p, a and m are an integer of 2 or greater or a1 is an integer of 2, substituents in the parentheses are the same as or different from each other.

In addition, one embodiment of the present application provides an organic light emitting device including a first electrode; a second electrode provided opposite to the first electrode; and one or more organic material layers provided between the first electrode and the second electrode, wherein one or more layers of the organic material layers include the heterocyclic compound represented by Chemical Formula 1.

In addition, in the organic light emitting device provided in one embodiment of the present application, the organic material layer including the heterocyclic compound of Chemical Formula 1 further includes a heterocyclic compound represented by the following Chemical Formula A or a heterocyclic compound represented by the following Chemical Formula B.

[Chemical Formula A]

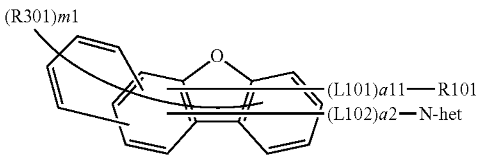

[Chemical Formula B]

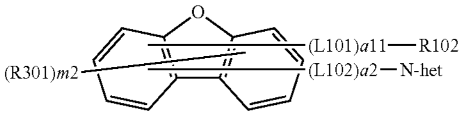

In Chemical Formulae A and B,

L101 and L102 are the same as or different from each other, and each independently a direct bond; a substituted or unsubstituted C6 to C60 arylene group; or a substituted or unsubstituted C2 to C60 heteroarylene group, N-het is a monocyclic or polycyclic heterocyclic group substituted or unsubstituted and including one or more Ns, R101 is a substituted or unsubstituted C1 to C60 alkyl group; a substituted or unsubstituted C6 to C60 aryl group; a substituted or unsubstituted C2 to C60 heteroaryl group; or —NR103R104, R102 is hydrogen; deuterium; a substituted or unsubstituted C1 to C60 alkyl group; a substituted or unsubstituted C6 to C60 aryl group; a substituted or unsubstituted C2 to C60 heteroaryl group; or —NR103R104, R301 is selected from the group consisting of hydrogen; deuterium; halogen; a cyano group; a substituted or unsubstituted C1 to C60 alkyl group; a substituted or unsubstituted C6 to C60 aryl group; and a substituted or unsubstituted C2 to C60 heteroaryl group, R103 and R104 are the same as or different from each other, and each independently a substituted or unsubstituted C1 to C60 alkyl group; a substituted or unsubstituted C6 to C60 aryl group; or a substituted or unsubstituted C2 to C60 heteroaryl group, m1 is an integer of 0 to 8, m2 is an integer of 0 to 6, and a11 and a2 are an integer of 0 to 4, and when m1, m2, a11 and a2 are 2 or greater, substituents in the parentheses are the same as or different from each other.

In addition, another embodiment of the present application provides a composition for an organic material layer of an organic light emitting device, the composition including the heterocyclic compound represented by Chemical Formula 1; and the heterocyclic compound represented by Chemical Formula A or the heterocyclic compound represented by Chemical Formula B.

Lastly, one embodiment of the present application provides a method for manufacturing an organic light emitting device, the method including preparing a substrate; forming a first electrode on the substrate; forming one or more organic material layers on the first electrode; and forming a second electrode on the organic material layers, wherein the forming of organic material layers includes forming one or more organic material layers using the composition for an organic material layer according to one embodiment of the present application.

Advantageous Effects

A compound described in the present specification can be used as a material of an organic material layer of an organic light emitting device. The compound is capable of performing a role of a hole injection material, a hole transfer material, a light emitting material, an electron transfer material, an electron injection material, an electron blocking material, a hole blocking material or the like in an organic light emitting device. Particularly, the compound can be used as a light emitting material of an organic light emitting device.

Particularly, the heterocyclic compound according to Chemical Formula 1 of the present application has an amine-based substituent and a -(L2)p-(Ar3)q substituent in the naphthobenzofuran structure, a core structure, and, by strengthening hole properties in the naphthobenzofuran skeleton, a core structure, is capable of adjusting a wide band gap and a T1 value, and accordingly, excellent efficiency is obtained when using the compound as a light emitting material of an organic light emitting device.

In addition, the heterocyclic compound represented by Chemical Formula 1, and the heterocyclic compound represented by Chemical Formula A or Chemical Formula B can be used as a material of a light emitting layer of an organic light emitting device at the same time. In this case, a driving voltage of the device can be lowered, light efficiency can be enhanced, and lifetime properties of the device can be particularly enhanced by thermal stability of the compound.

DESCRIPTION OF DRAWINGS

FIG. 1 to FIG. 3 are diagrams each schematically illustrating a lamination structure of an organic light emitting device according to one embodiment of the present application.

MODE FOR DISCLOSURE

Hereinafter, the present application will be described in detail.

In the present specification, a "case of a substituent being not indicated in a chemical formula or compound structure" means that a hydrogen atom bonds to a carbon atom. However, since deuterium ($^2H$) is an isotope of hydrogen, some hydrogen atoms may be deuterium.

In one embodiment of the present application, a "case of a substituent being not indicated in a chemical formula or compound structure" may mean that positions that may come as a substituent may all be hydrogen or deuterium. In other words, since deuterium is an isotope of hydrogen, some hydrogen atoms may be deuterium that is an isotope, and herein, a content of the deuterium may be from 0% to 100%.

In one embodiment of the present application, in a "case of a substituent being not indicated in a chemical formula or compound structure", hydrogen and deuterium may be mixed in compounds when deuterium is not explicitly excluded such as a deuterium content being 0%, a hydrogen content being 100% or substituents being all hydrogen.

In one embodiment of the present application, deuterium is one of isotopes of hydrogen, is an element having deuteron formed with one proton and one neutron as a nucleus, and may be expressed as hydrogen-2, and the elemental symbol may also be written as D or $^2H$.

In one embodiment of the present application, an isotope means an atom with the same atomic number (Z) but with a different mass number (A), and may also be interpreted as an element with the same number of protons but with a different number of neutrons.

In one embodiment of the present application, a meaning of a content T % of a specific substituent may be defined as T2/T1×100=T % when the total number of substituents that a basic compound may have is defined as T1, and the number of specific substituents among these is defined as T2.

In other words, in one example, having a deuterium content of 20% in a phenyl group represented by

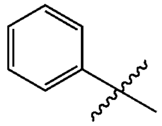 [SMILES: *c1ccccc1]

means that the total number of substituents that the phenyl group may have is 5 (T1 in the formula), and the number of deuterium among these is 1 (T2 in the formula). In other words, having a deuterium content of 20% in a phenyl group may be represented by the following structural formulae.

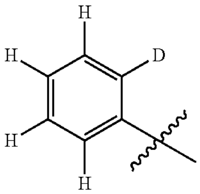
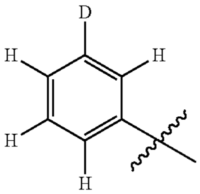
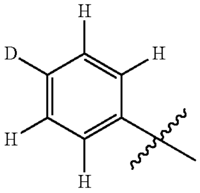
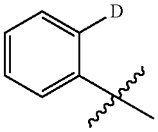
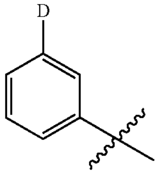
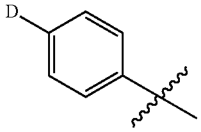

In addition, in one embodiment of the present application, "a phenyl group having a deuterium content of 0%" may mean a phenyl group that does not include a deuterium atom, that is, a phenyl group that has 5 hydrogen atoms.

In the present specification, the halogen may be fluorine, chlorine, bromine or iodine.

In the present specification, the alkyl group includes linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group includes linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl) vinyl-1-yl group, a 2,2-bis(diphenyl-1-yl) vinyl-1-yl group, a stilbenyl group, a styrenyl group and the like, but are not limited thereto.

In the present specification, the alkynyl group includes linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group includes monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may include a cyclopropyl group, a cyclobutyl group, a cyclopentyl group, 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group includes O, S, Se, N or Si as a heteroatom, includes monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group includes monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The number of carbon atoms of the aryl group may be from 6 to 60, specifically from 6 to 40 and more specifically from 6 to 25. Specific examples of the aryl group may include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, an indenyl group, an acenaphthylenyl group, a 2,3-dihydro-1H-indenyl group, a fused ring group thereof, and the like, but are not limited thereto.

In the present specification, a fluorenyl group may be substituted, and adjacent substituents may bond to each other to form a ring.

When the fluorenyl group is substituted, the following structural formulae may be included, however, the structure is not limited thereto.

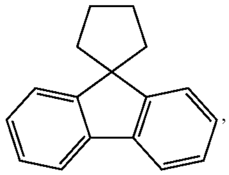,
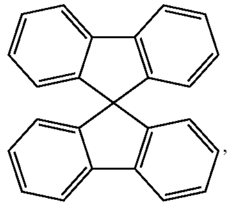,
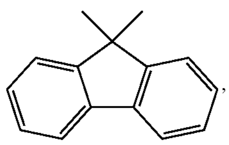,
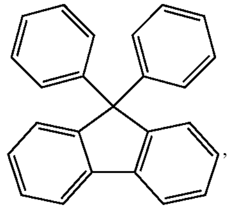,

-continued

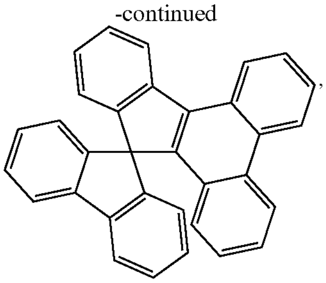,

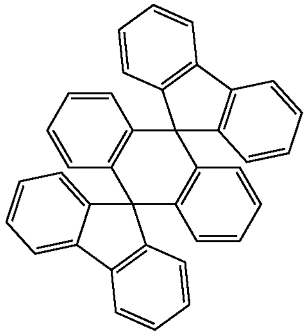

In the present specification, the heteroaryl group includes S, O, Se, N or Si as a heteroatom, includes monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi (dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido

[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. The descriptions on the aryl group provided above may be applied thereto except for those that are each a divalent group. In addition, the heteroarylene group means the heteroaryl group having two bonding sites, that is, a divalent group. The descriptions on the heteroaryl group provided above may be applied thereto except for those that are each a divalent group.

In the present specification, the phosphine oxide group is represented by —P(═O) R201R202, and R201 and R202 are the same as or different from each other and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the phosphine oxide may include a diphenylphosphine oxide group, a dinaphthylphosphine oxide group and the like, but are not limited thereto.

In the present specification, the silyl group is a substituent including Si, having the Si atom directly linked as a radical, and is represented by —SiR204R205R206. R204 to R206 are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the "adjacent" group may mean a substituent substituting an atom directly linked to an atom substituted by the corresponding substituent, a substituent sterically closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

As the aliphatic or aromatic hydrocarbon ring or heteroring that adjacent groups may form, the structures illustrated as the cycloalkyl group, the cycloheteroalkyl group, the aryl group and the heteroaryl group described above may be used except for those that are not a monovalent group.

In the present specification, the term "substitution" means a hydrogen atom bonding to a carbon atom of a compound being changed to another substituent, and the position of substitution is not limited as long as it is a position at which the hydrogen atom is substituted, that is, a position at which a substituent is capable of substituting, and when two or more substituents substitute, the two or more substituents may be the same as or different from each other.

In the present specification, "substituted or unsubstituted" means being substituted with one or more substituents selected from the group consisting of deuterium; a halogen group; a cyano group; C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(═O)RR'; C1 to C20 alkylamine; C6 to C60 monocyclic or polycyclic arylamine; and C2 to C60 monocyclic or polycyclic heteroarylamine or being unsubstituted, or being substituted with a substituent linking two or more substituents selected from among the substituents illustrated above or being unsubstituted, and R, R' and R" are the same as or different from each other, and each independently a substituted or unsubstituted C1 to C60 alkyl group; a substituted or unsubstituted C6 to C60 aryl group; or a substituted or unsubstituted C2 to C60 heteroaryl group.

One embodiment of the present application provides compound represented by Chemical Formula 1.

In one embodiment of the present application, the heterocyclic compound represented by Chemical Formula 1 may have a deuterium content of greater than or equal to 0% and less than or equal to 100%, preferably greater than or equal to 20% and less than or equal to 100%, and more preferably greater than or equal to 40% and less than or equal to 100%.

Particularly, in Chemical Formula 1, those not indicated as substituents may be hydrogen or deuterium.

The heterocyclic compound of Chemical Formula 1 of the present application has an amine-based substituent and a -(L2)p-(Ar3)q substituent having hole properties, and when used as a hole transfer layer, a hole transfer auxiliary layer or a light emitting layer of an organic light emitting device later, the unshared electron pair of the amine substituent improves the flow of holes enhancing a hole transfer ability of the hole transfer layer, and when used as an electron blocking layer, deterioration of a hole transfer material caused by electrons invading the hole transfer layer may be suppressed.

In addition, by the -(L2)p-(Ar3)q substituent with strengthened hole properties and the amine part of the amine-based substituent bonding to each other, planarity and glass transition temperature of the amine derivative increase, which increases thermal stability of the heterocyclic compound, and as a result, a lifetime of an organic light emitting device including the same is improved as well.

In addition, a band gap and a T1 value are readily adjusted, a hole transfer ability is enhanced, thermal stability is superior by readily adjusting a decomposition temperature as well, and molecular stability also increases, and as a result, a driving voltage of the device may be lowered, light efficiency may be enhanced, and lifetime properties of the device may be enhanced by thermal stability of the compound.

In one embodiment of the present application, Chemical Formula 1 may be represented by the following Chemical Formula 2 or 3.

[Chemical Formula 2]

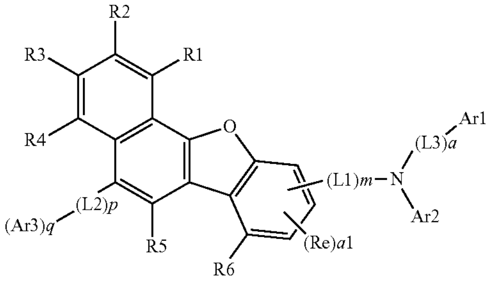

[Chemical Formula 3]

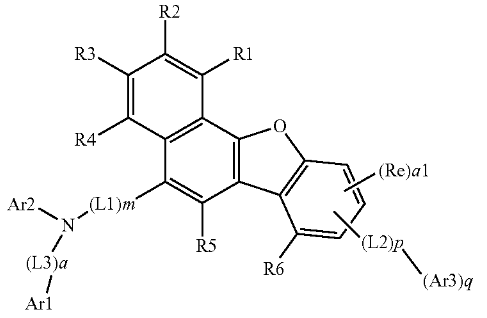

In Chemical Formulae 2 and 3,

R1 to R6, Re, L1 to L3, Ar1 to Ar3, a1, p, q, m and a have the same definitions as in Chemical Formula 1.

In one embodiment of the present application, Chemical Formula 2 may be represented by any one of the following Chemical Formulae 2-1 to 2-3.

[Chemical Formula 2-1]

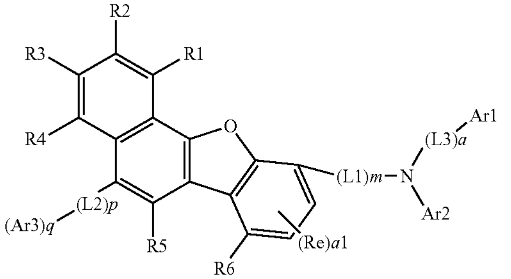

[Chemical Formula 2-2]

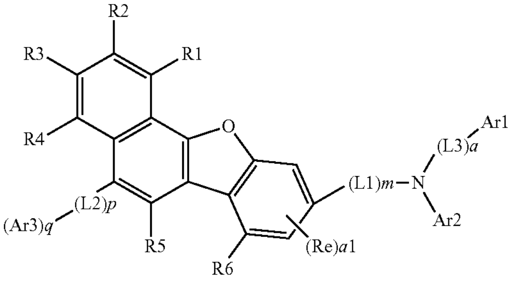

-continued

[Chemical Formula 2-3]

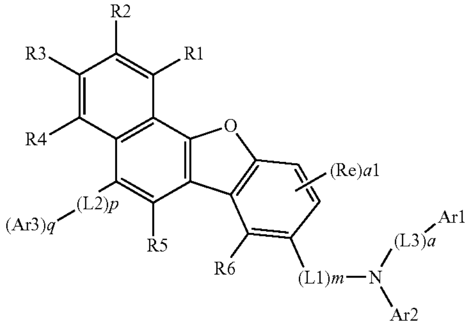

In Chemical Formulae 2-1 to 2-3,

R1 to R6, Re, L1 to L3, Ar1 to Ar3, a1, p, q, m and a have the same definitions as in Chemical Formula 2.

In one embodiment of the present application, Chemical Formula 3 may be represented by any one of the following Chemical Formulae 3-1 to 3-3.

[Chemical Formula 3-1]

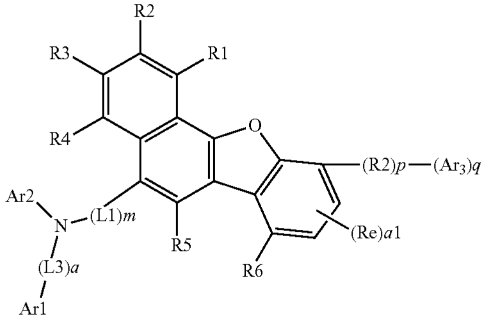

[Chemical Formula 3-2]

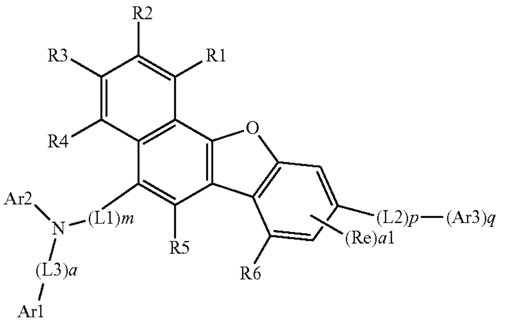

[Chemical Formula 3-3]

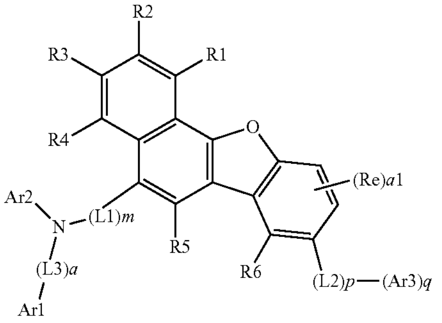

In Chemical Formulae 3-1 to 3-3,

R1 to R6, Re, L1 to L3, Ar1 to Ar3, a1, p, q, m and a have the same definitions as in Chemical Formula 3.

In one embodiment of the present application, R1 to R6 and Re are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(═O)RR'; —SiRR'R" and —NRR', or two or more groups adjacent to each other may bond to each other to form a substituted or unsubstituted C6 to C60 aliphatic or aromatic hydrocarbon ring or a substituted or unsubstituted C2 to C60 aliphatic or aromatic heteroring.

In another embodiment, R1 to R6 and Re are the same as or different from each other, and each independently selected from the group consisting of hydrogen; deuterium; a substituted or unsubstituted C1 to C60 alkyl group; a substituted or unsubstituted C6 to C60 aryl group; and a substituted or unsubstituted C2 to C60 heteroaryl group, or two or more groups adjacent to each other may bond to each other to form a substituted or unsubstituted C6 to C60 aromatic hydrocarbon ring or a substituted or unsubstituted C2 to C60 aromatic heteroring.

In another embodiment, R1 to R6 and Re are the same as or different from each other, and each independently selected from the group consisting of hydrogen; deuterium; a C1 to C60 alkyl group; a C6 to C60 aryl group; and a C2 to C60 heteroaryl group, or two or more groups adjacent to each other may bond to each other to form a C6 to C60 aromatic hydrocarbon ring or a C2 to C60 aromatic heteroring.

In another embodiment, R1 to R6 and Re are the same as or different from each other, and each independently selected from the group consisting of hydrogen; deuterium; a C1 to C40 alkyl group; a C6 to C40 aryl group; and a C2 to C40 heteroaryl group, or two or more groups adjacent to each other may bond to each other to form a C6 to C40 aromatic hydrocarbon ring or a C2 to C40 aromatic heteroring.

In another embodiment, R1 to R6 and Re are the same as or different from each other, and each independently selected from the group consisting of hydrogen; deuterium; a C1 to C30 alkyl group; a C6 to C30 aryl group; and a C2 to C30 heteroaryl group, or two or more groups adjacent to each other may bond to each other to form a C6 to C30 aromatic hydrocarbon ring or a C2 to C30 aromatic heteroring.

In another embodiment, R1 to R6 and Re are the same as or different from each other, and may be each independently hydrogen; or deuterium.

In another embodiment, R1 to R6 and Re may be hydrogen.

In one embodiment of the present application, L1 to L3 are the same as or different from each other, and may be each independently a direct bond; a substituted or unsubstituted C6 to C60 arylene group; or a substituted or unsubstituted C2 to C60 heteroarylene group.

In another embodiment, L1 to L3 are the same as or different from each other, and may be each independently a direct bond; a substituted or unsubstituted C6 to C40 arylene group; or a substituted or unsubstituted C2 to C40 heteroarylene group.

In another embodiment, L1 to L3 are the same as or different from each other, and may be each independently a direct bond; a C6 to C40 arylene group; or a C2 to C40 heteroarylene group.

In another embodiment, L1 to L3 are the same as or different from each other, and may be each independently a direct bond; or a C6 to C40 arylene group.

In another embodiment, L1 to L3 are the same as or different from each other, and may be each independently a direct bond; or a C6 to C40 monocyclic or polycyclic arylene group.

In another embodiment, L1 to L3 are the same as or different from each other, and may be each independently a direct bond; a C6 to C10 monocyclic arylene group; or a C10 to C40 polycyclic arylene group.

In another embodiment, L1 to L3 are the same as or different from each other, and may be each independently a direct bond; a phenylene group; a biphenylene group; or a naphthalene group.

In one embodiment of the present application, L1 may be a direct bond; a phenylene group; or a naphthalene group.

In one embodiment of the present application, L2 may be a direct bond; a phenylene group; or a biphenylene group.

In one embodiment of the present application, L3 may be a direct bond; a phenylene group; a naphthalene group; or a biphenylene group.

In one embodiment of the present application, L1 to L3 may be unsubstituted or substituted with deuterium.

In one embodiment of the present application, L1 to L3 may have a deuterium content of greater than or equal to 0% and less than or equal to 100%, preferably greater than or equal to 20% and less than or equal to 1008, and more preferably greater than or equal to 40% and less than or equal to 100%.

In one embodiment of the present application, Ar1 to Ar3 are the same as or different from each other, and may be each independently selected from the group consisting of a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(═O)RR'; —SiRR'R" and —NRR'.

In another embodiment, Ar1 to Ar3 are the same as or different from each other, and may be each independently selected from the group consisting of a substituted or unsubstituted C6 to C60 aryl group; and a substituted or unsubstituted C2 to C60 heteroaryl group.

In another embodiment, Ar1 to Ar3 are the same as or different from each other, and may be each independently selected from the group consisting of a substituted or unsubstituted C6 to C40 aryl group; and a substituted or unsubstituted C2 to C40 heteroaryl group.

In another embodiment, Ar1 to Ar3 are the same as or different from each other, and may be each independently selected from the group consisting of a C6 to C40 aryl group unsubstituted or substituted with one or more substituents selected from the group consisting of a C1 to C20 alkyl group, a C6 to C40 aryl group and a C2 to C40 heteroaryl group; and a C2 to C40 heteroaryl group unsubstituted or substituted with a C6 to C40 aryl group.

In another embodiment, Ar1 to Ar3 are the same as or different from each other, and may be each independently selected from the group consisting of a C6 to C20 aryl group unsubstituted or substituted with one or more substituents selected from the group consisting of a C1 to C10 alkyl group, a C1 to C10 haloalkyl group, a C6 to C20 aryl group and a C2 to C20 heteroaryl group; and a C2 to C20 heteroaryl group unsubstituted or substituted with a C6 to C20 aryl group.

In another embodiment, Ar1 to Ar3 are the same as or different from each other, and may be each independently a phenyl group unsubstituted or substituted with a t-butyl group or $CF_3$; a biphenyl group unsubstituted or substituted with a phenyl group; a terphenyl group; a naphthyl group; a triphenylenyl group; a phenanthrenyl group; a fluoranthenyl group; a dimethylfluorenyl group unsubstituted or substituted with a phenyl group; a diphenylfluorenyl group; a spirobifluorenyl group; a dibenzofuran group; a dibenzothiophene group; a carbazole group unsubstituted or substituted with a phenyl group; a benzene ring-fused dibenzofuran group; a benzene ring-fused dibenzothiophene group; or a benzene ring-fused dimethylfluorenyl group.

In one embodiment of the present application, Ar3 may be a phenyl group unsubstituted or substituted with a t-butyl group or $CF_3$; a biphenyl group unsubstituted or substituted with a phenyl group; a terphenyl group; a naphthyl group; a dimethylfluorenyl group; a diphenylfluorenyl group; a spirobifluorenyl group; a dibenzofuran group; a dibenzothiophene group; or a carbazole group unsubstituted or substituted with a phenyl group.

In one embodiment of the present application, Ar1 to Ar3 may be unsubstituted or substituted with deuterium.

In one embodiment of the present application, Ar1 to Ar3 may have a deuterium content of greater than or equal to 0% and less than or equal to 100%, preferably greater than or equal to 20% and less than or equal to 100%, and more preferably greater than or equal to 40% and less than or equal to 100%.

In one embodiment of the present application, the benzene ring-fused dibenzofuran group may mean the following structures.

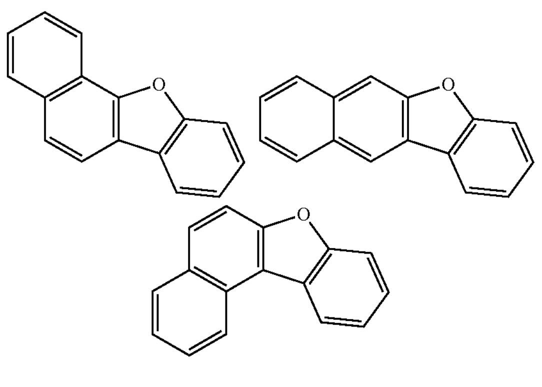

In the structural formulae, positions substitutable with a substituent may all be linked to a substituent.

In one embodiment of the present application, the benzene ring-fused dibenzothiophene group may mean the following structures.

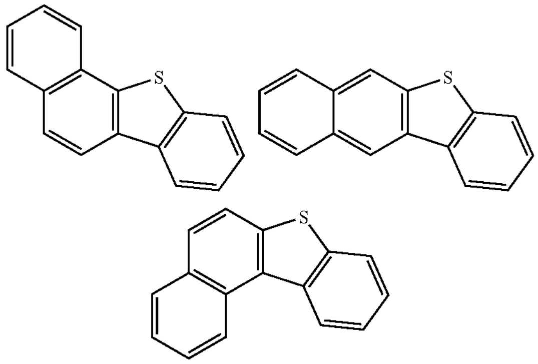

In the structural formulae, positions substitutable with a substituent may all be linked to a substituent.

In one embodiment of the present application, the benzene ring-fused dimethylfluorenyl group may mean the following structures.

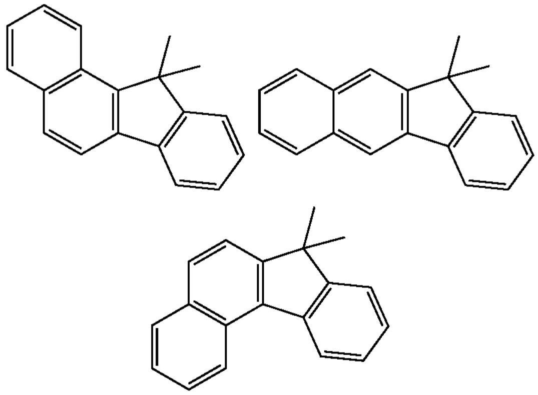

In the structural formulae, positions substitutable with a substituent may all be linked to a substituent.

In one embodiment of the present application,

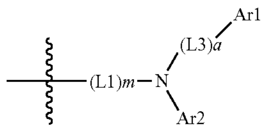

may be represented by any one of the following Chemical Formulae 1-1 to 1-4.

[Chemical Formula 1-1]

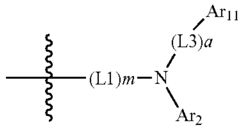

-continued

[Chemical Formula 1-2]

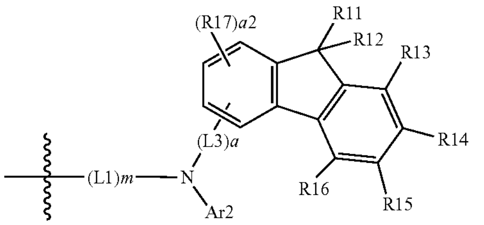

[Chemical Formula 1-3]

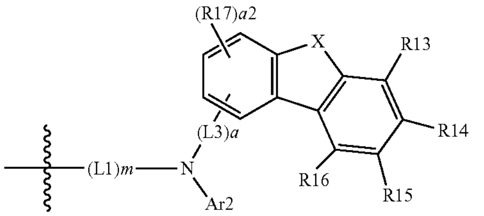

[Chemical Formula 1-4]

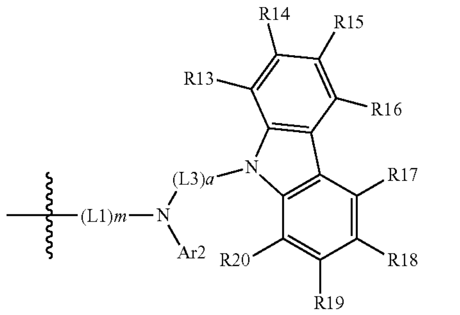

In Chemical Formulae 1-1 to 1-4,

L1, m, L3, a and Ar2 have the same definitions as in Chemical Formula 1,

Ar11 is a substituted or unsubstituted C6 to C20 aryl group,

X is O; S; or NRa,

R11 and R12 are the same as or different from each other, and each independently a substituted or unsubstituted C1 to C60 alkyl group; a substituted or unsubstituted C6 to C60 aryl group; or a substituted or unsubstituted C2 to C60 heteroaryl group, or two groups adjacent to each other bond to each other to form a substituted or unsubstituted C6 to C60 aromatic hydrocarbon ring, R13 to R20 and Ra are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or group; a substituted or unsubstituted C2 to C60 alkynyl unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(=O)RR'; —SiRR'R" and —NRR', or two or more groups adjacent to each other bond to each other to form a substituted or unsubstituted C6 to C60 aliphatic or aromatic hydrocarbon ring or a substituted or unsubstituted C2 to C60 aliphatic or aromatic heteroring, a2 is an integer of 0 to 3, and when a2 is 2 or greater, substituents in the parentheses are the same as or different from each other, and R, R' and R" have the same definitions as in Chemical Formula 1.

In one embodiment of the present application X may be O.

In one embodiment of the present application X may be S.

In one embodiment of the present application X may be NRa.

In one embodiment of the present application, Ar11 may be a substituted or unsubstituted C6 to C20 aryl group.

In another embodiment, Ar11 may be a C6 to C20 aryl group unsubstituted or substituted with a C6 to C10 aryl group.

In another embodiment, Ar11 may be a phenyl group; a biphenyl group unsubstituted or substituted with a phenyl group; a terphenyl group; a naphthyl group; a triphenylenyl group; a phenanthrenyl group; or a fluoranthenyl group.

In one embodiment of the present application, R11 and R12 are the same as or different from each other, and each independently a substituted or unsubstituted C1 to C60 alkyl group; a substituted or unsubstituted C6 to C60 aryl group; or a substituted or unsubstituted C2 to C60 heteroaryl group, or two groups adjacent to each other may bond to each other to form a substituted or unsubstituted C6 to C60 aromatic hydrocarbon ring.

In another embodiment, R11 and R12 are the same as or different from each other, and each independently a substituted or unsubstituted C1 to C40 alkyl group; a substituted or unsubstituted C6 to C40 aryl group; or a substituted or unsubstituted C2 to C40 heteroaryl group, or two groups adjacent to each other may bond to each other to form a substituted or unsubstituted C6 to C40 aromatic hydrocarbon ring.

In another embodiment, R11 and R12 are the same as or different from each other, and each independently a C1 to C40 alkyl group; a C6 to C40 aryl group; or a C2 to C40 heteroaryl group, or two groups adjacent to each other may bond to each other to form a C6 to C40 aromatic hydrocarbon ring.

In another embodiment, R11 and R12 are the same as or different from each other, and each independently a C1 to C20 alkyl group; a C6 to C20 aryl group; or a C2 to C20 heteroaryl group, or two groups adjacent to each other may bond to each other to form a C6 to C20 aromatic hydrocarbon ring.

In another embodiment, R11 and R12 are the same as or different from each other, and each independently a methyl group; or a phenyl group, or two groups adjacent to each other may bond to each other to form a fluorenyl ring.

In one embodiment of the present application, R11 and R12 may be unsubstituted or substituted with deuterium.

In one embodiment of the present application, R13 to R20 and Ra are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(=O)RR'; —SiRR'R" and —NRR', or two or more groups adjacent to each other may bond to each other to form a substituted or unsubstituted C6 to C60 aliphatic or aromatic hydrocarbon ring or a substituted or unsubstituted C2 to C60 aliphatic or aromatic heteroring.

In another embodiment, R13 to R20 and Ra are the same as or different from each other, and each independently selected from the group consisting of hydrogen; deuterium; a substituted or unsubstituted C6 to C60 aryl group; and a substituted or unsubstituted C2 to C60 heteroaryl group, or two or more groups adjacent to each other may bond to each other to form a substituted or unsubstituted C6 to C60 aromatic hydrocarbon ring.

In another embodiment, R13 to R20 and Ra are the same as or different from each other, and each independently selected from the group consisting of hydrogen; deuterium; a substituted or unsubstituted C6 to C40 aryl group; and a substituted or unsubstituted C2 to C40 heteroaryl group, or two or more groups adjacent to each other may bond to each other to form a substituted or unsubstituted C6 to C40 aromatic hydrocarbon ring.

In another embodiment, R13 to R20 and Ra are the same as or different from each other, and each independently selected from the group consisting of hydrogen; deuterium; a C6 to C40 aryl group; and a C2 to C40 heteroaryl group, or two or more groups adjacent to each other may bond to each other to form a C6 to C40 aromatic hydrocarbon ring.

In another embodiment, R13 to R20 and Ra are the same as or different from each other, and each independently hydrogen; deuterium; or a phenyl group, or two or more groups adjacent to each other may bond to each other to form a benzene ring.

In one embodiment of the present application, Ra may be a phenyl group.

In one embodiment of the present application, R13 to R20 are the same as or different from each other, and each independently hydrogen; deuterium; or a phenyl group, or two or more groups adjacent to each other may bond to each other to form a benzene ring.

In one embodiment of the present application, R, R' and R" are the same as or different from each other, and may be each independently a substituted or unsubstituted C1 to C60 alkyl group; a substituted or unsubstituted C6 to C60 aryl group; or a substituted or unsubstituted C2 to C60 heteroaryl group.

In another embodiment, R, R' and R" are the same as or different from each other, and may be each independently a substituted or unsubstituted C6 to C60 aryl group.

In another embodiment, R, R' and R" are the same as or different from each other, and may be each independently a substituted or unsubstituted C6 to C60 monocyclic or polycyclic aryl group.

In another embodiment, R, R' and R" are the same as or different from each other, and may be each independently a substituted or unsubstituted C6 to C40 monocyclic aryl group.

In another embodiment, R, R' and R" are the same as or different from each other, and may be each independently a C6 to C20 monocyclic aryl group.

In another embodiment, R, R' and R" may be a phenyl group.

According to one embodiment of the present application, Chemical Formula 1 may be represented by any one of the following compounds, but is not limited thereto.

1-1

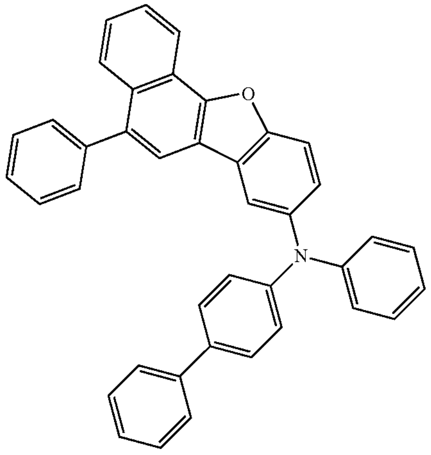

1-2

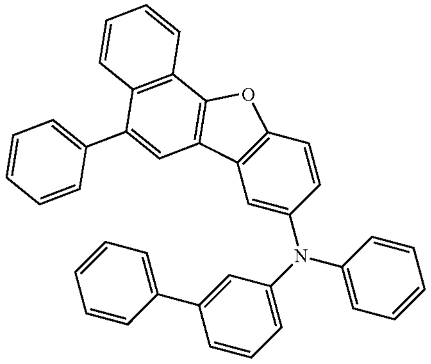

1-3

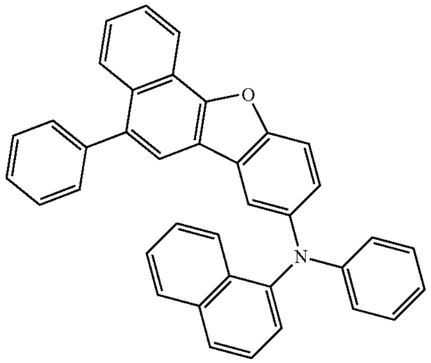

1-4

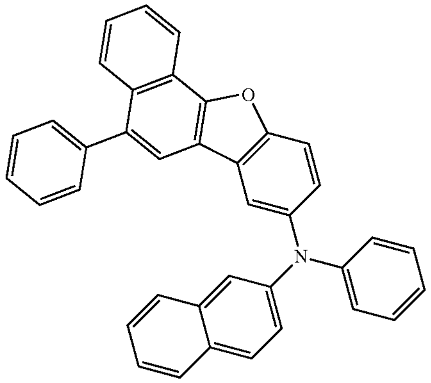

-continued
1-5
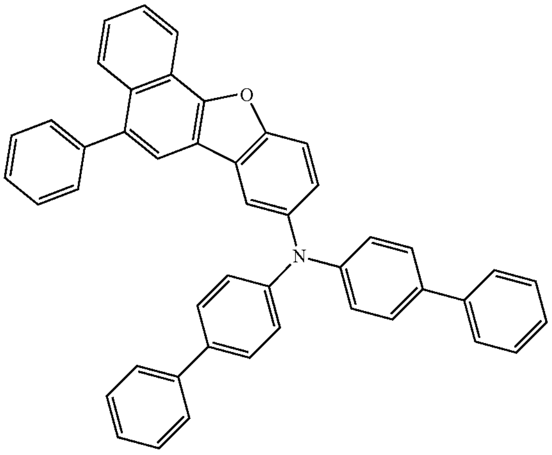
1-6
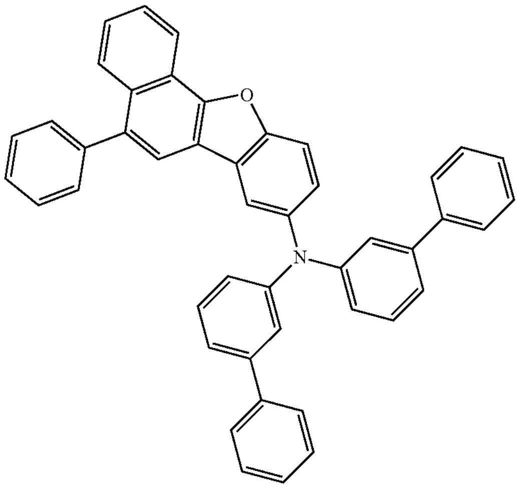
1-7
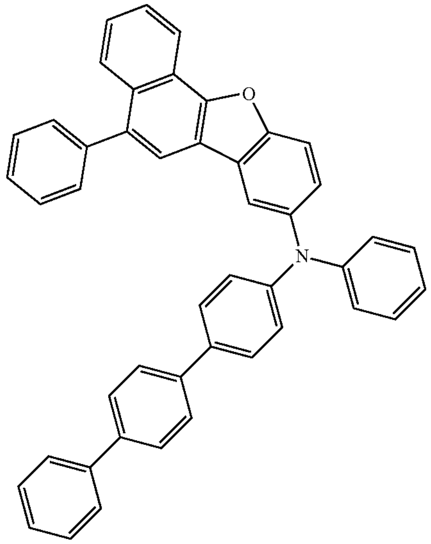
-continued
1-8
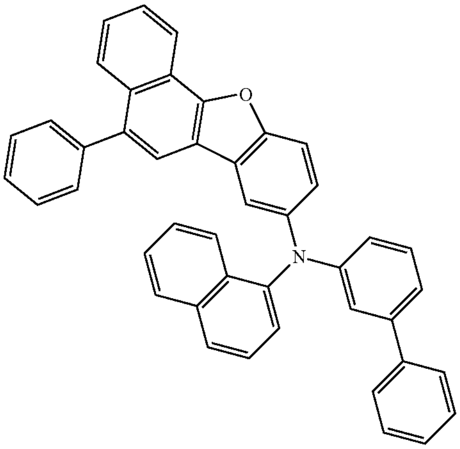
1-9
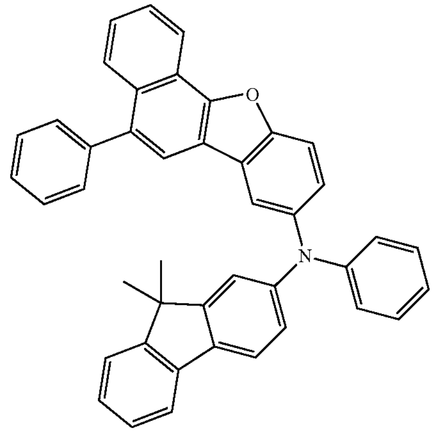
1-10
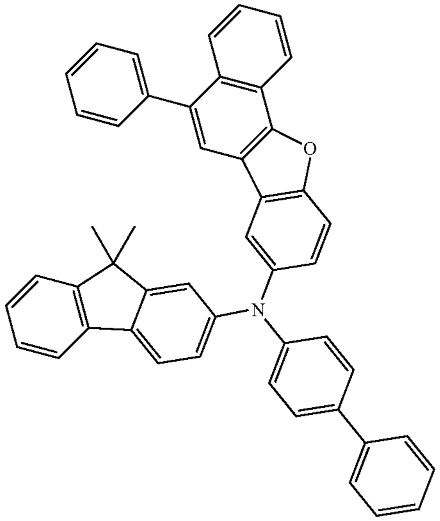

-continued
1-11
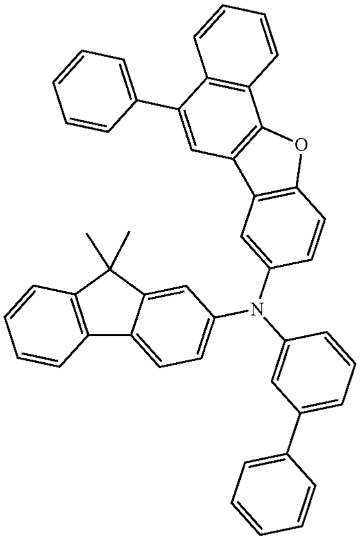
1-12
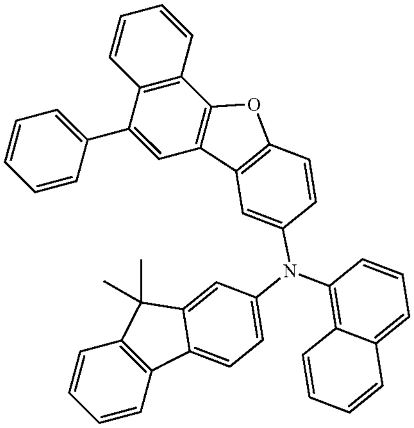
1-13
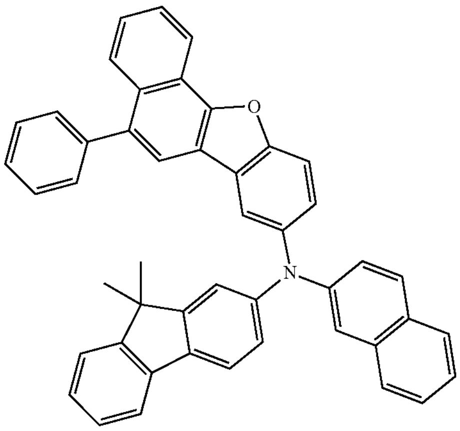
-continued
1-14
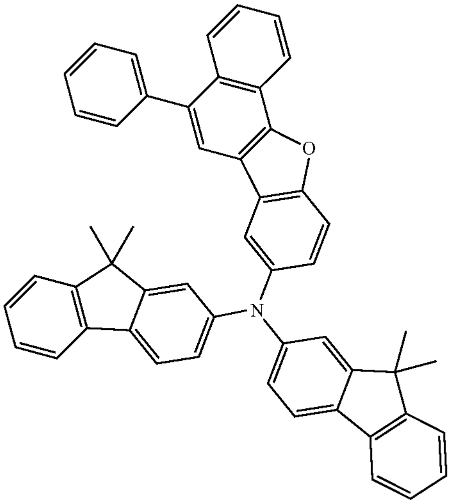
1-15
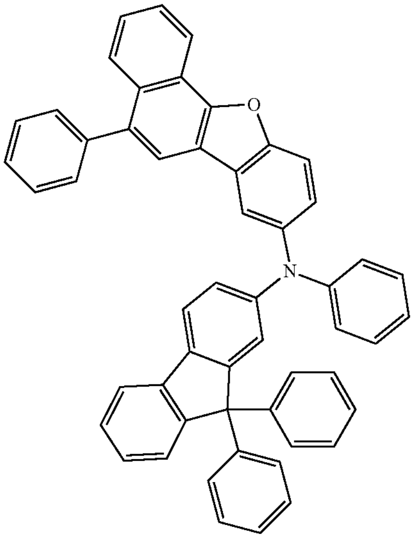
1-16
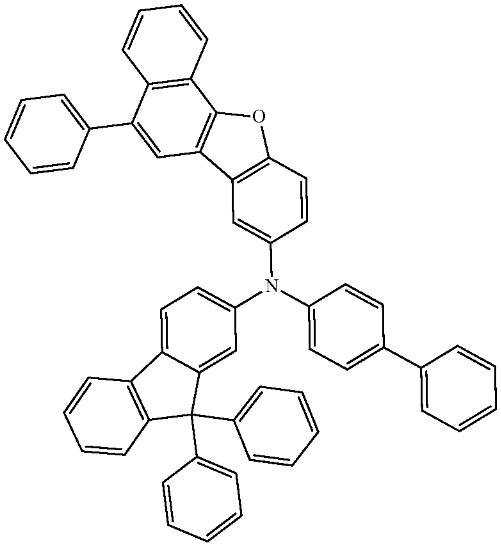

-continued
1-17
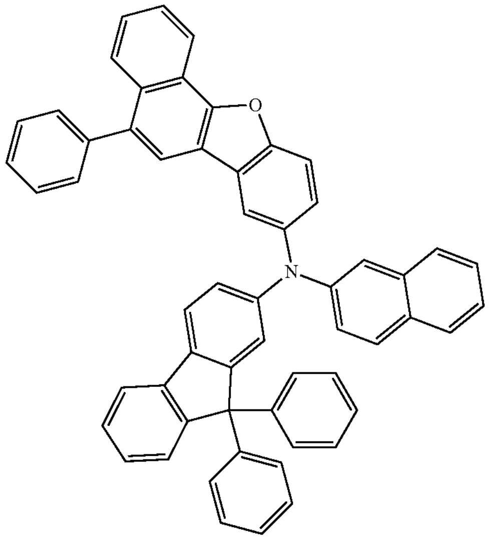
1-18
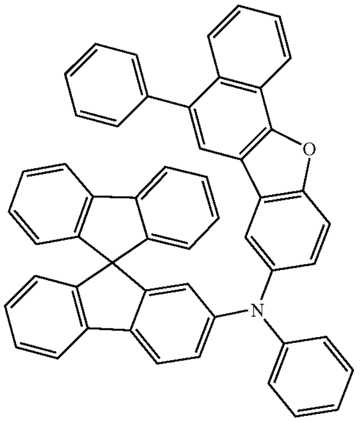
1-19
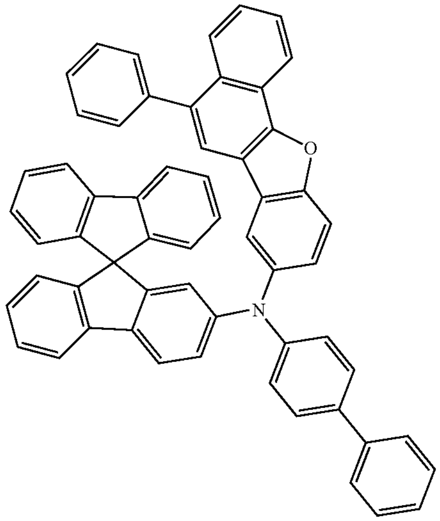
-continued
1-20
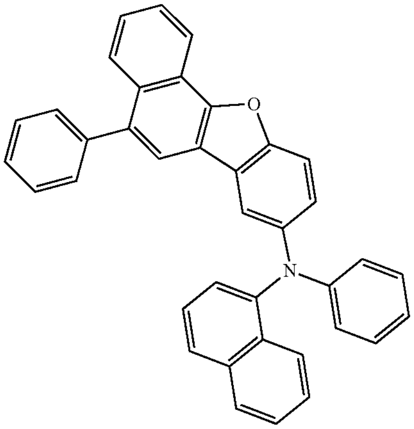
1-21
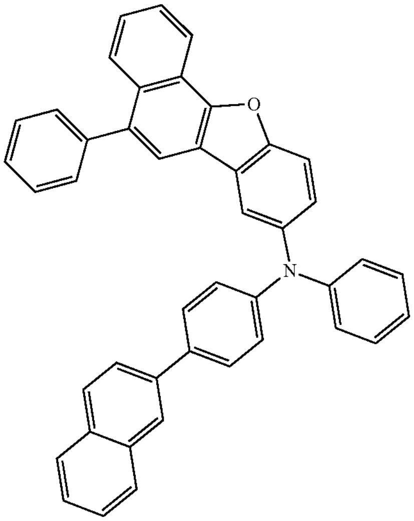
1-22
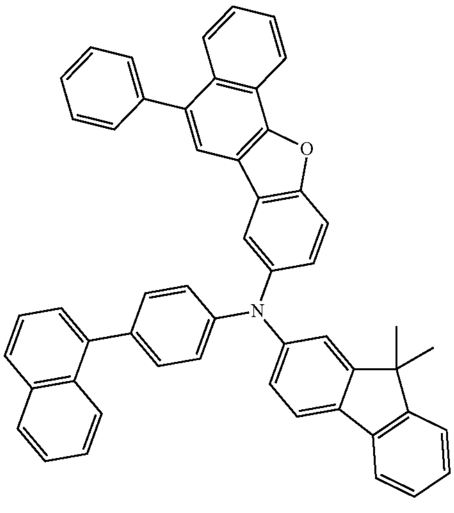

-continued
1-23
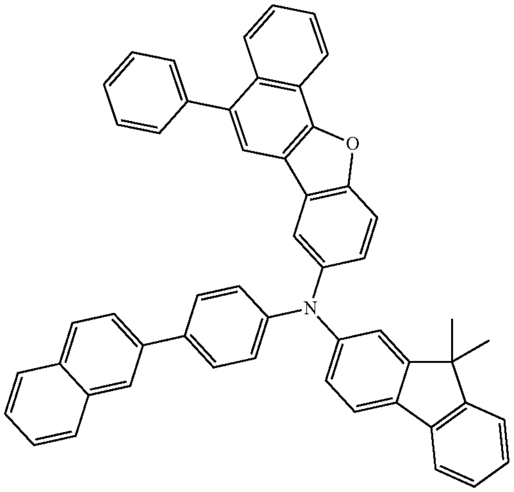
1-24
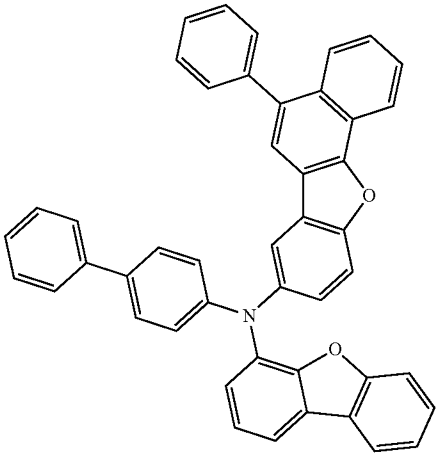
1-25
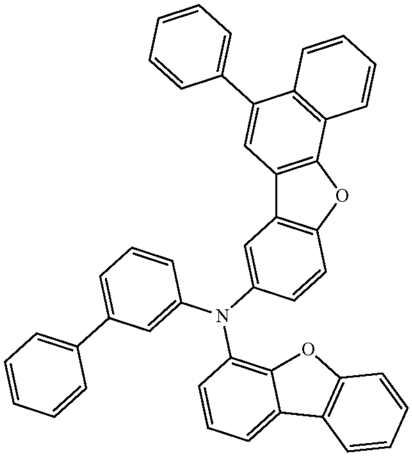
-continued
1-26
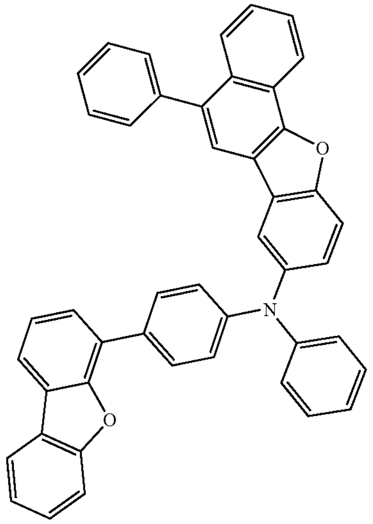
1-27
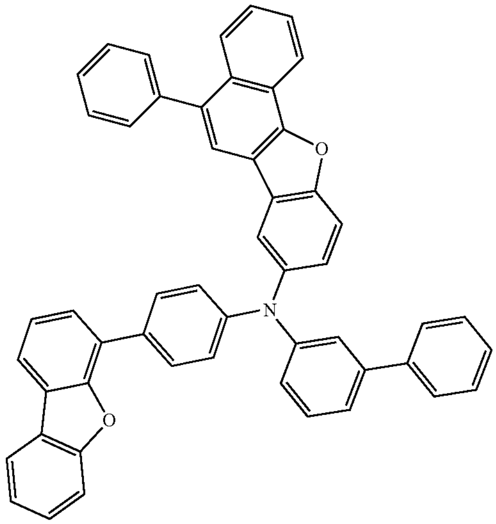
1-28
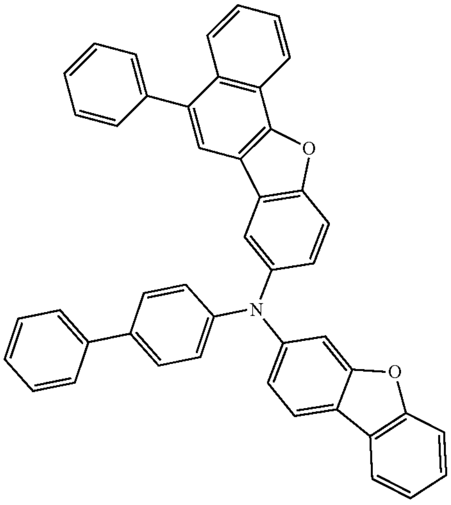

-continued
1-29
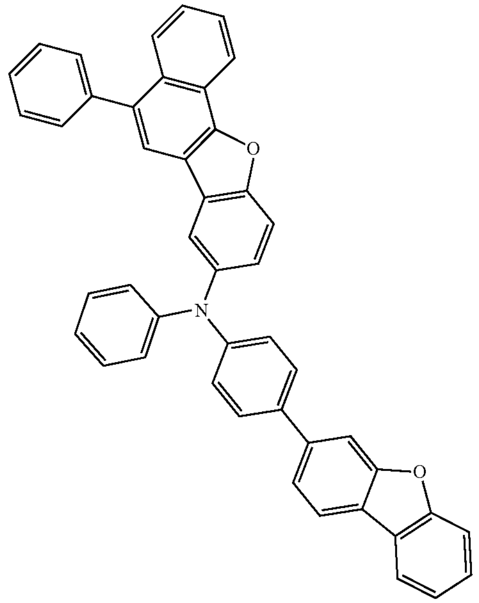
1-30
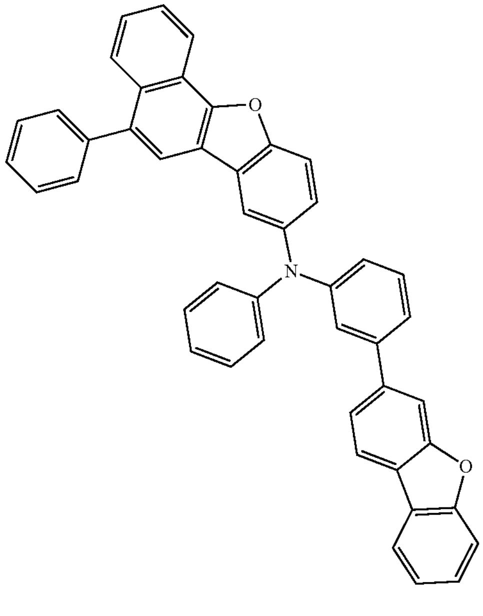
-continued
1-31
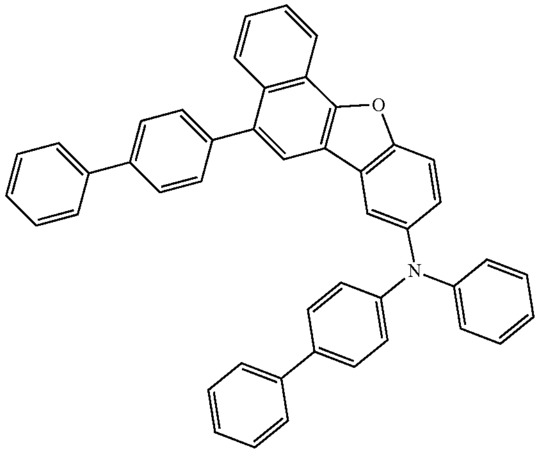
1-32
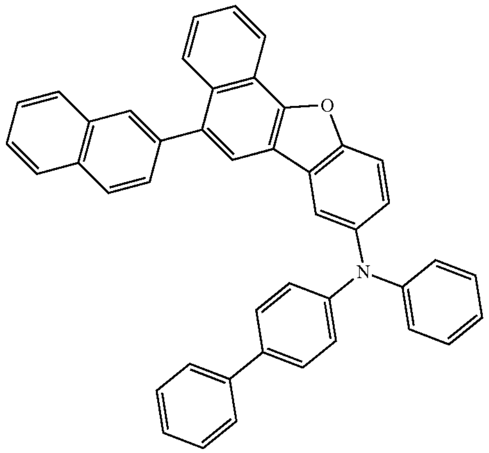
1-33
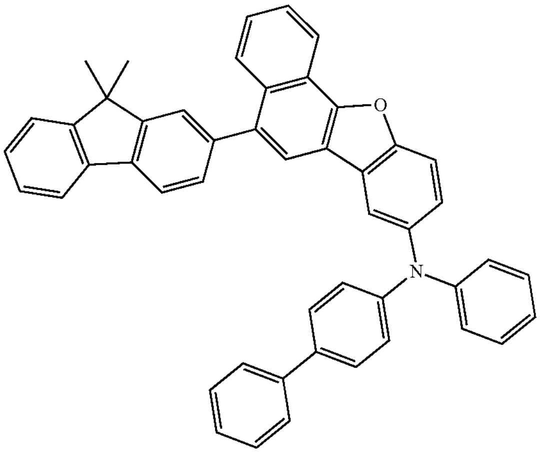

-continued
1-34
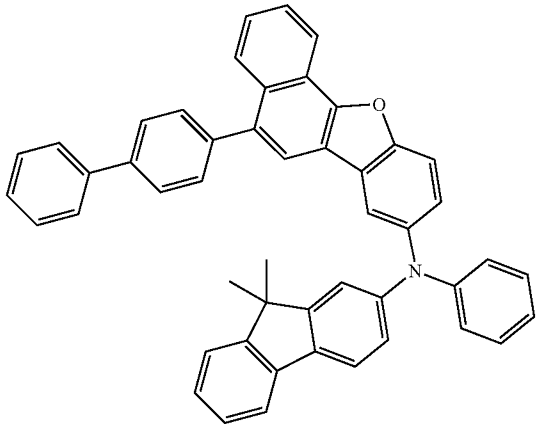
1-35
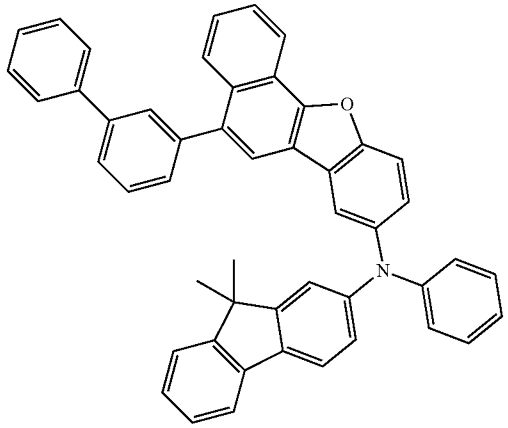
1-36
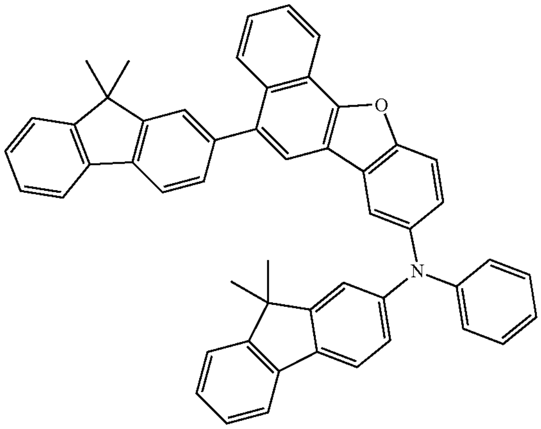
-continued
1-37
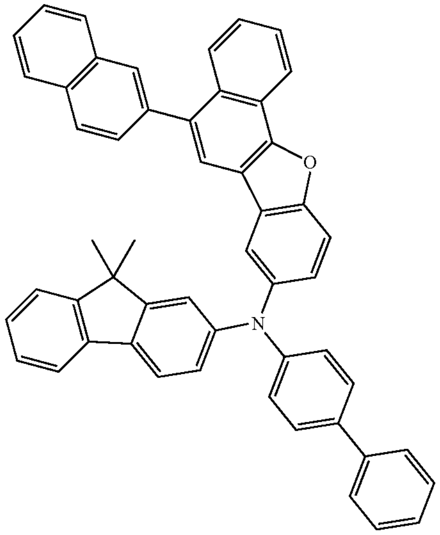
1-38
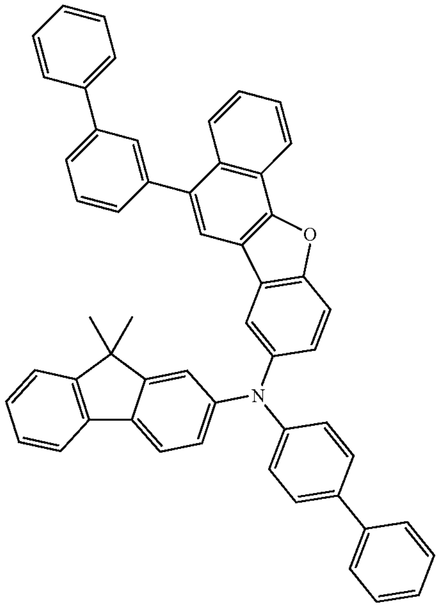

-continued
1-39
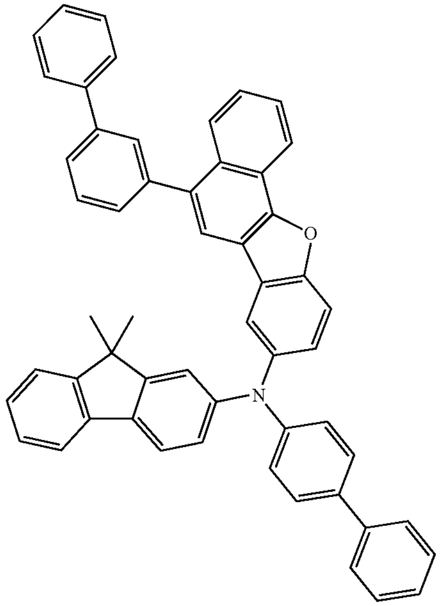
1-40
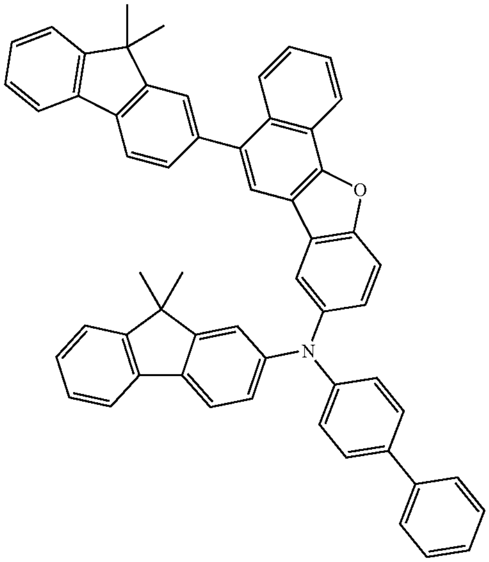
-continued
1-41
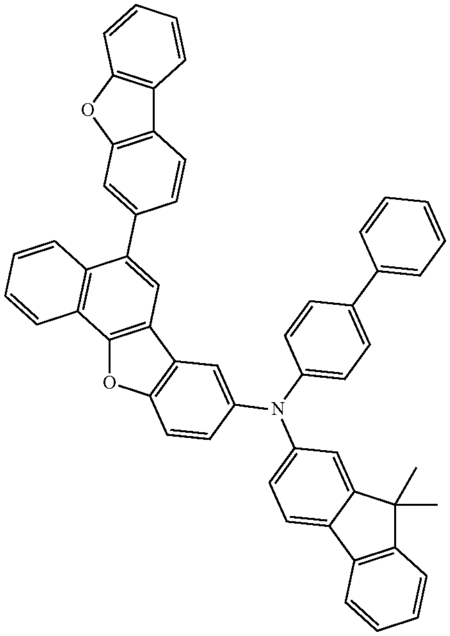
1-42
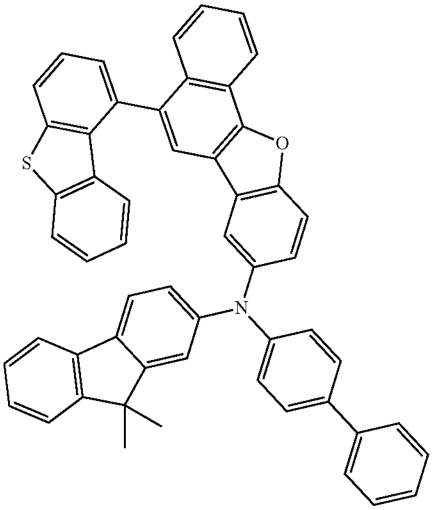

-continued
1-43
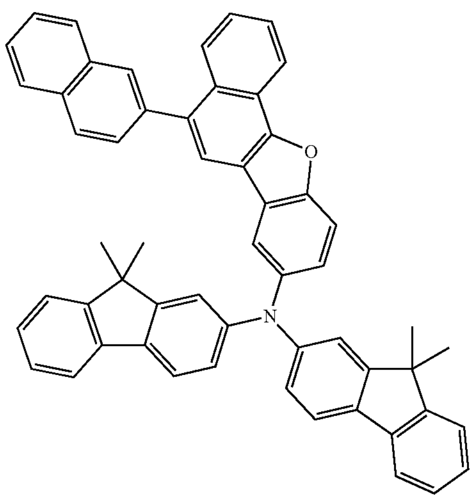
1-44
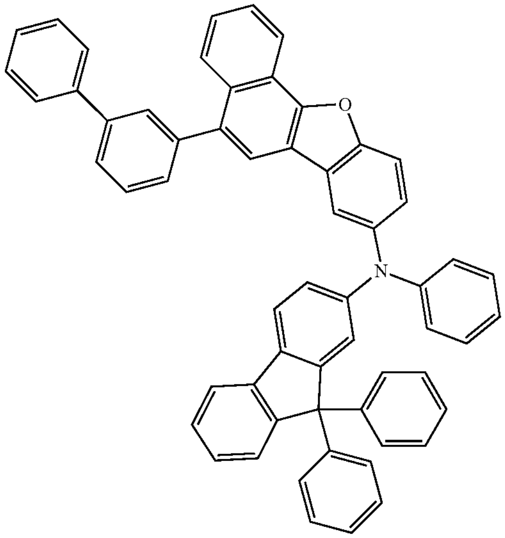
1-45
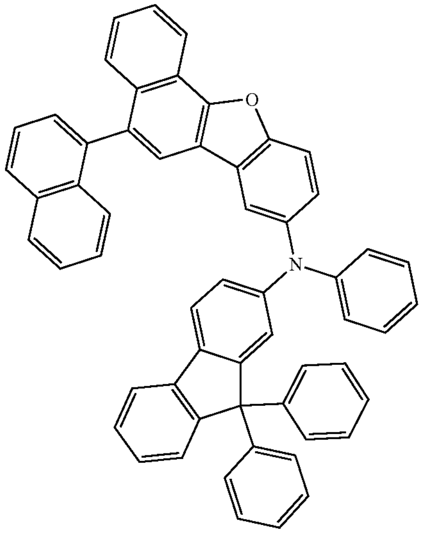
-continued
1-46
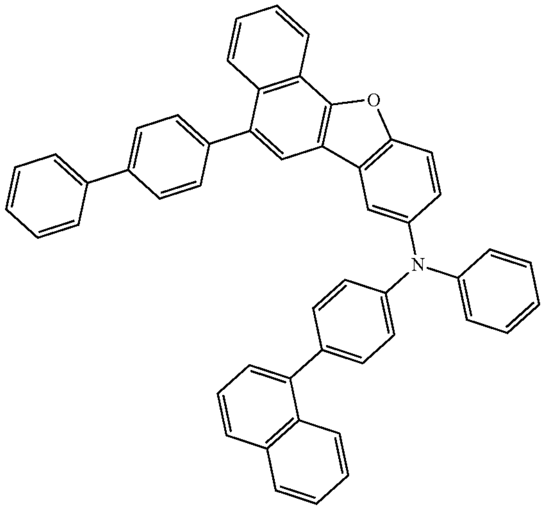
1-47
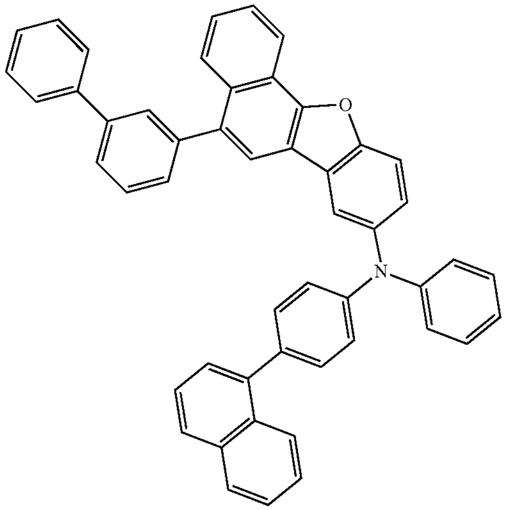
1-48
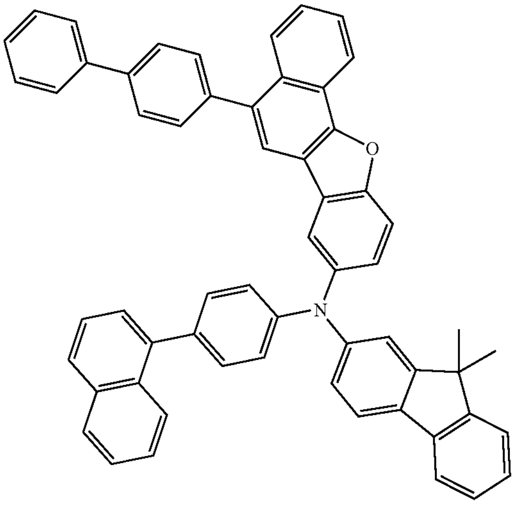

-continued
1-49
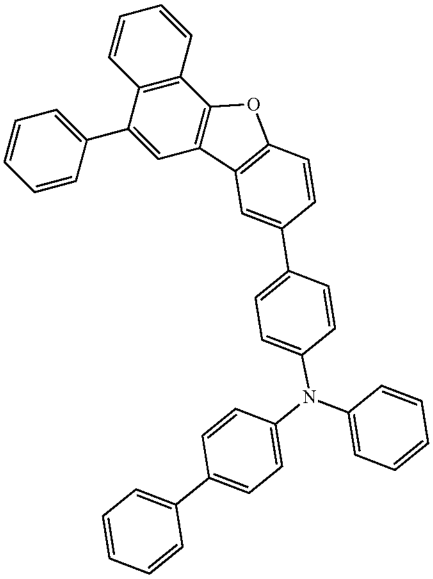
1-50
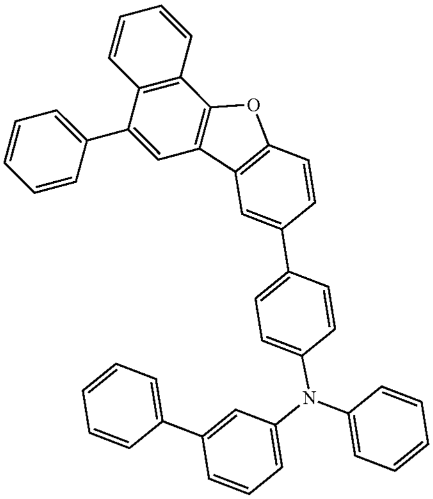
1-51
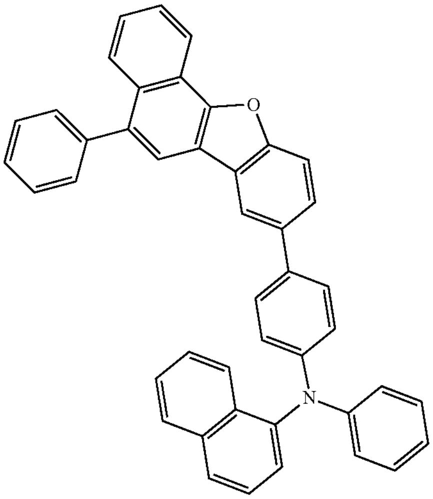
-continued
1-52
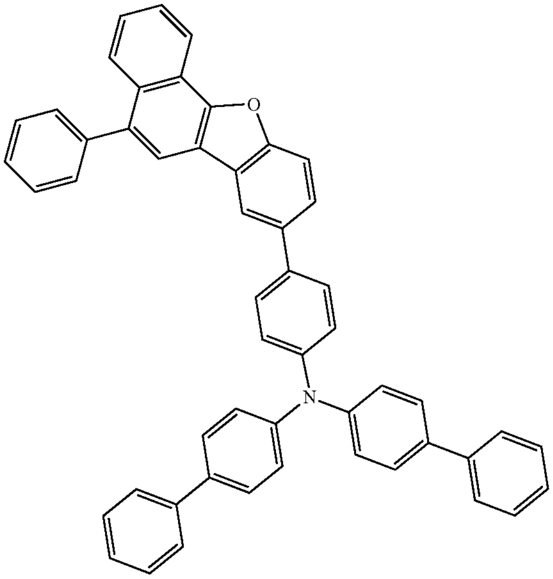
1-53
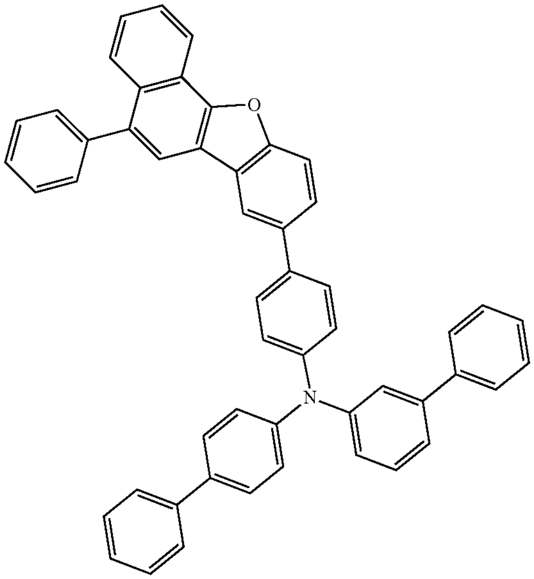

-continued
1-54
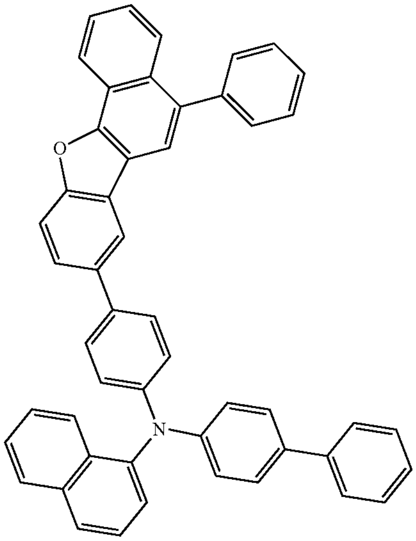
1-55
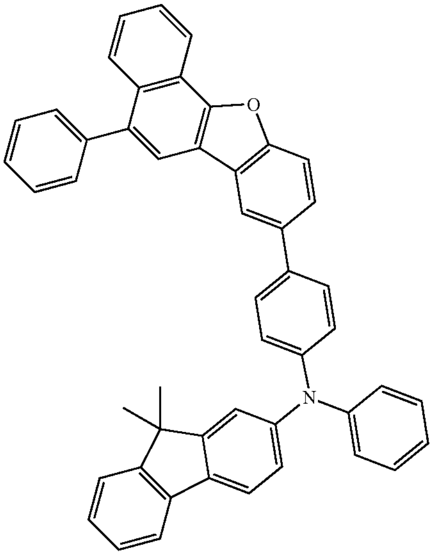
-continued
1-56
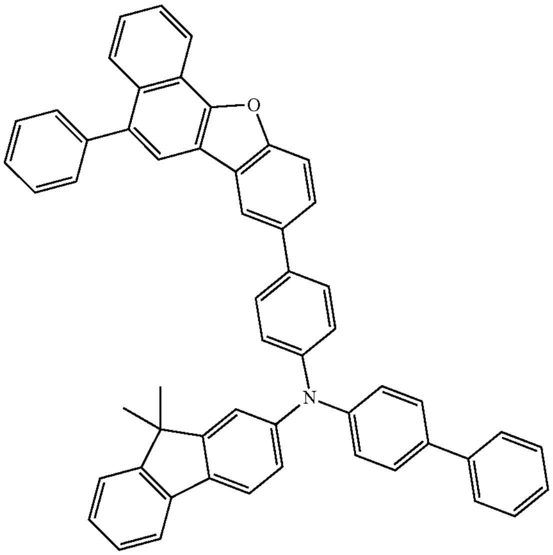
1-57
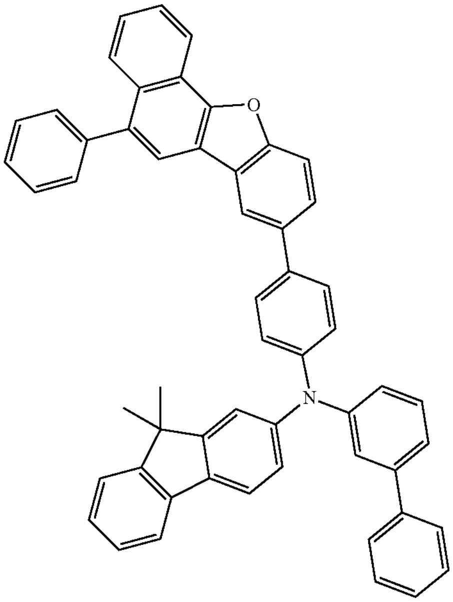

-continued
1-58
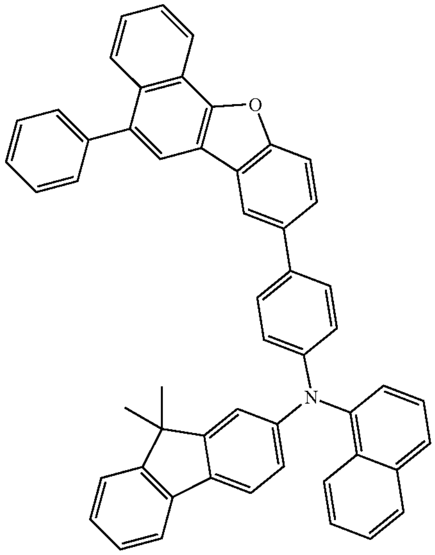
1-59
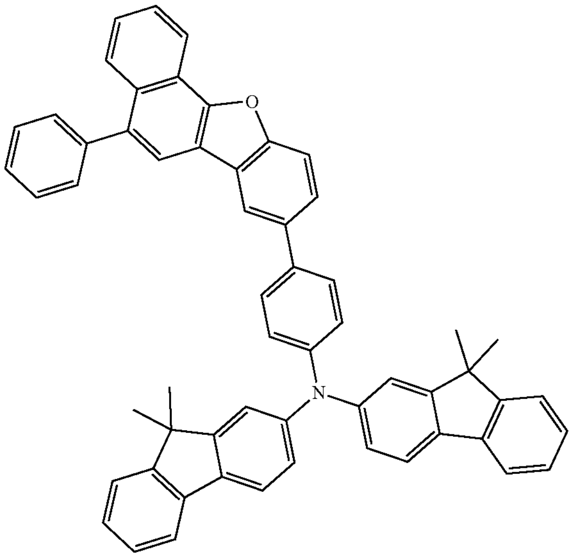
-continued
1-60
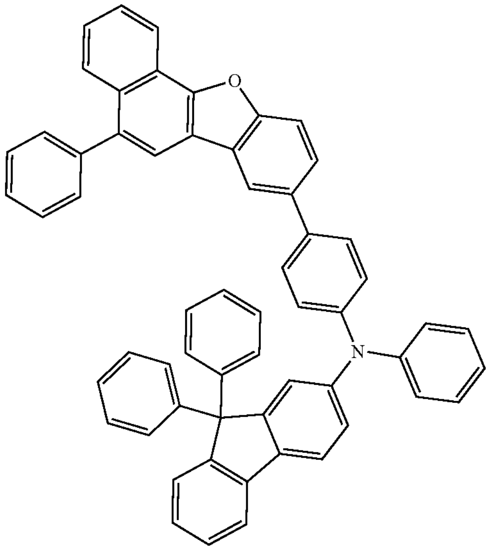
1-61
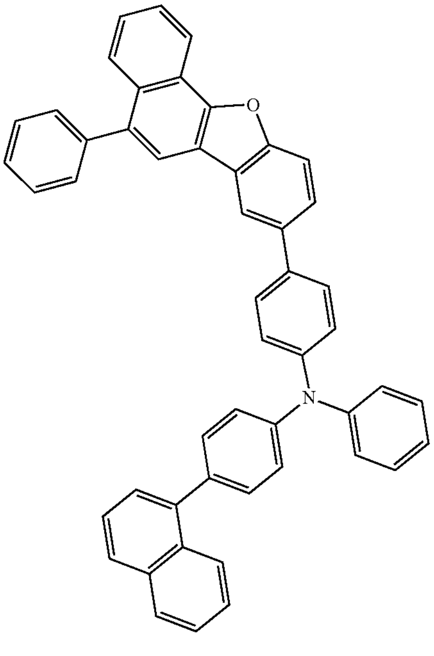

-continued
1-62
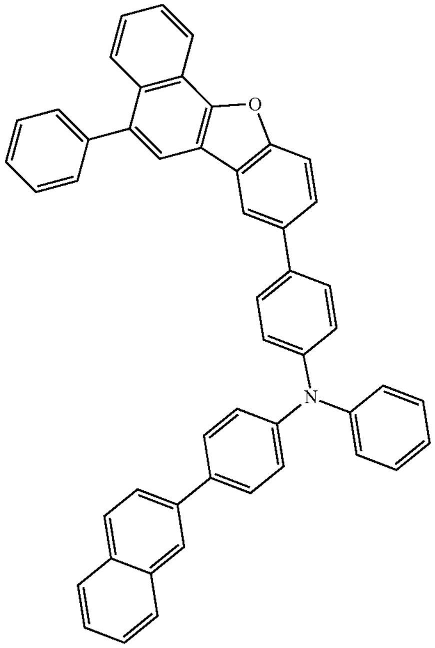
-continued
1-64
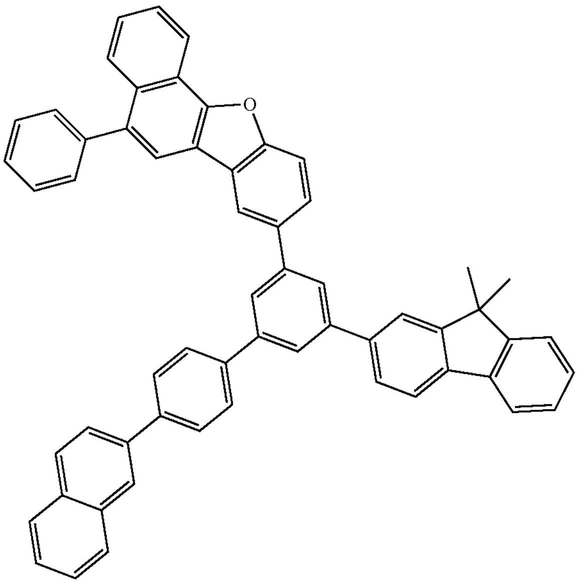
1-63
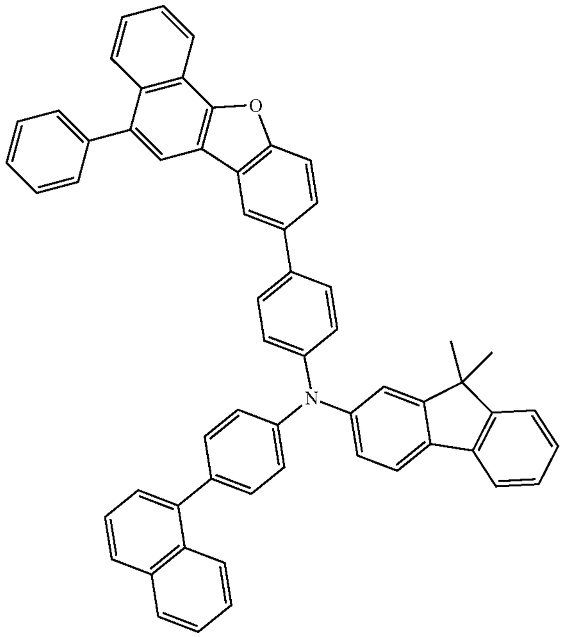
1-65
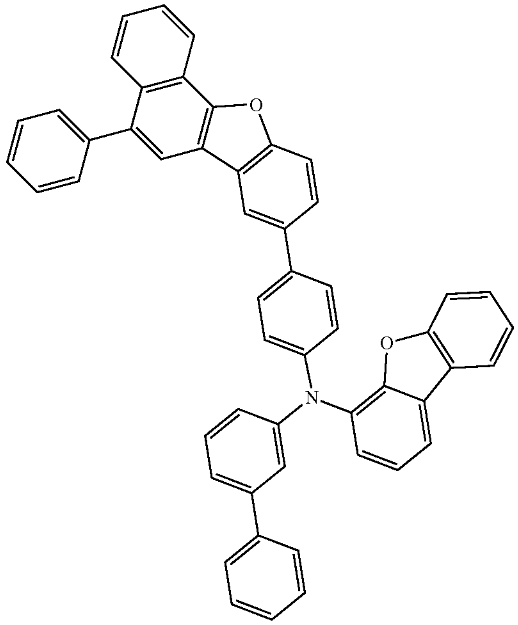

-continued
1-66
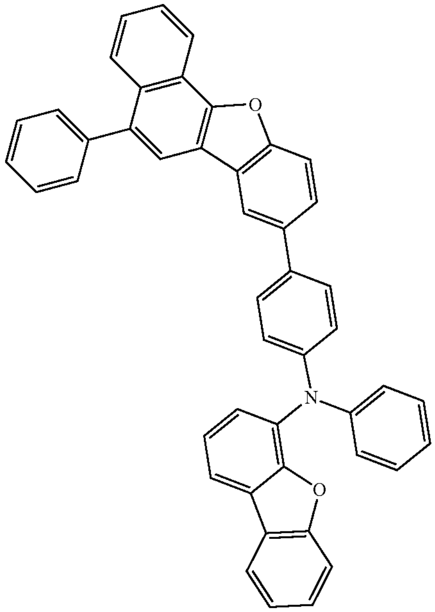
1-67
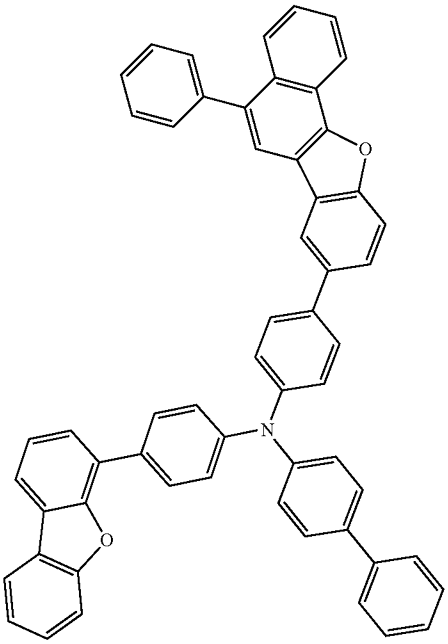
-continued
1-68
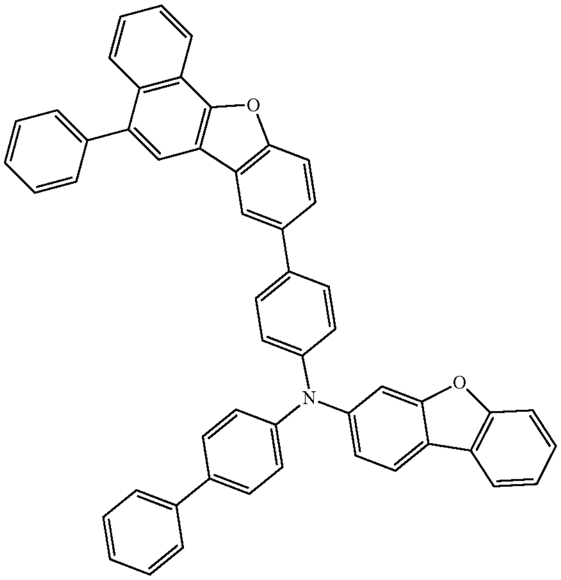
1-69
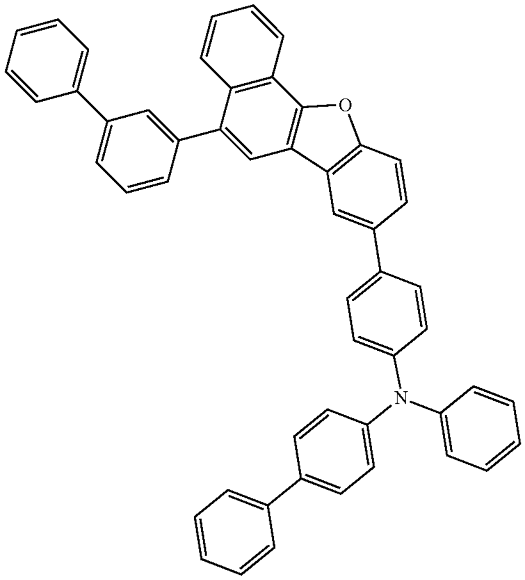

1-70
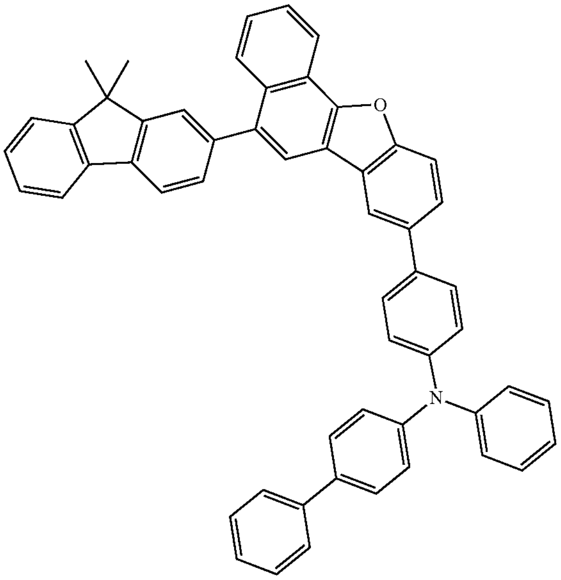
1-71
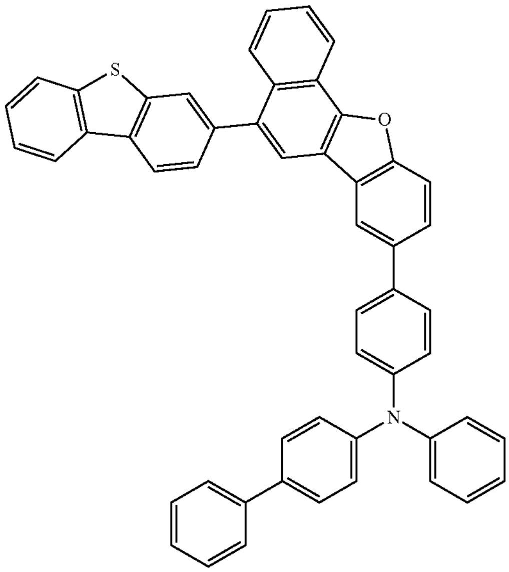
1-72
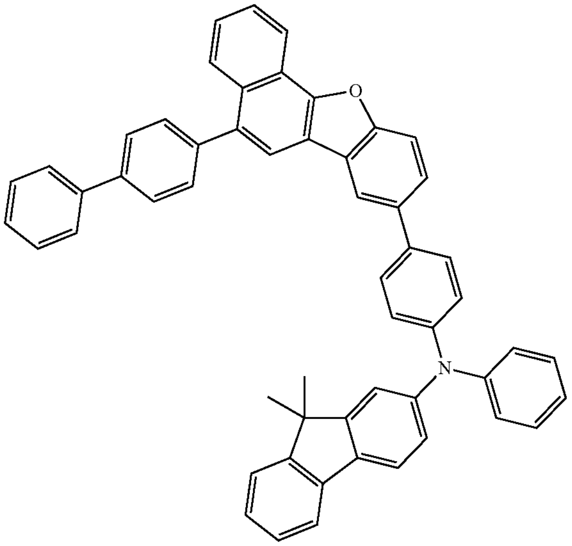
1-73
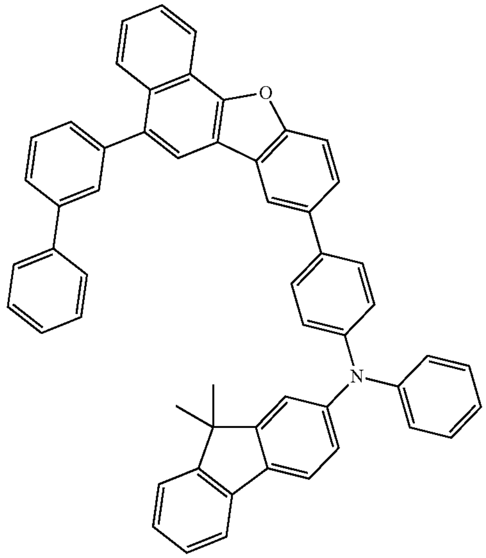

1-74
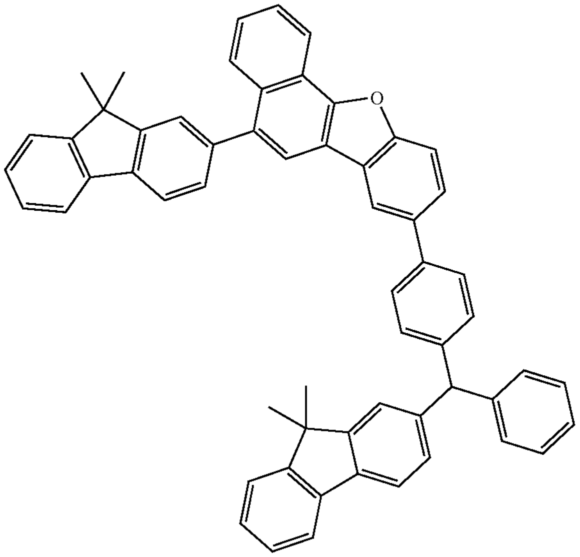
1-75
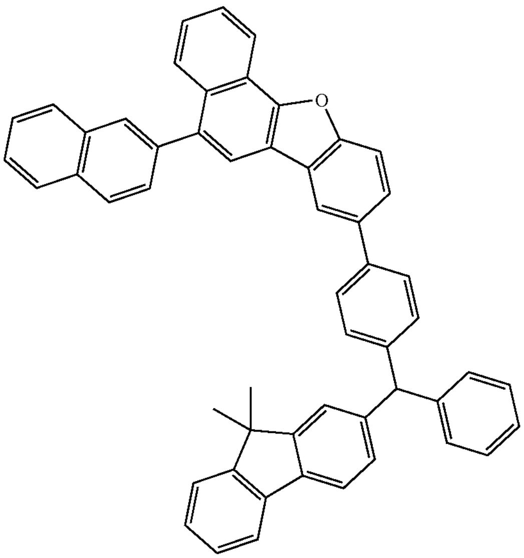
1-76
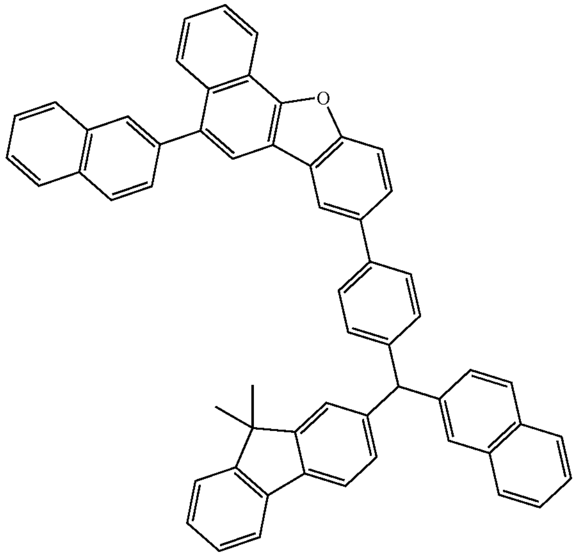
1-77
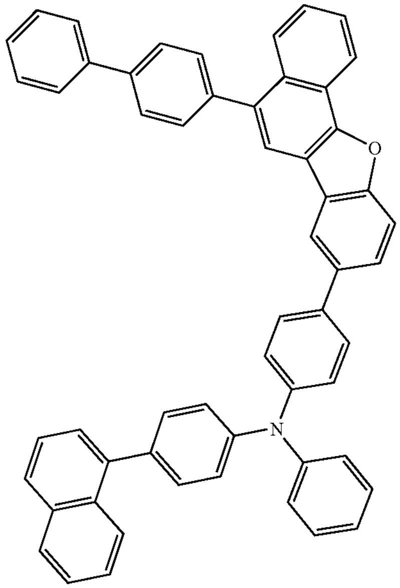

-continued
1-78
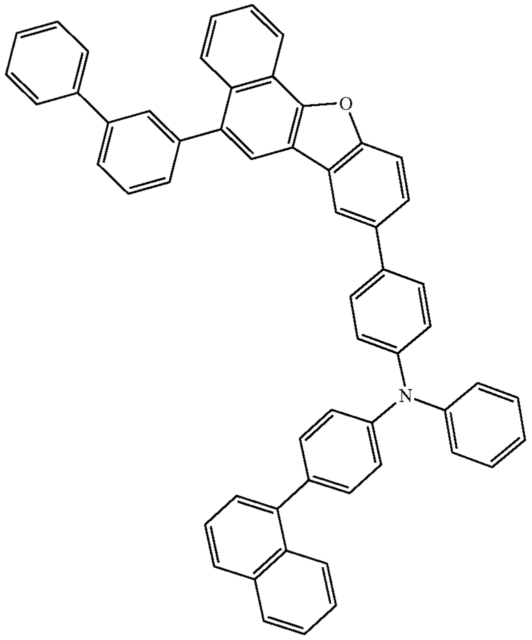
1-79
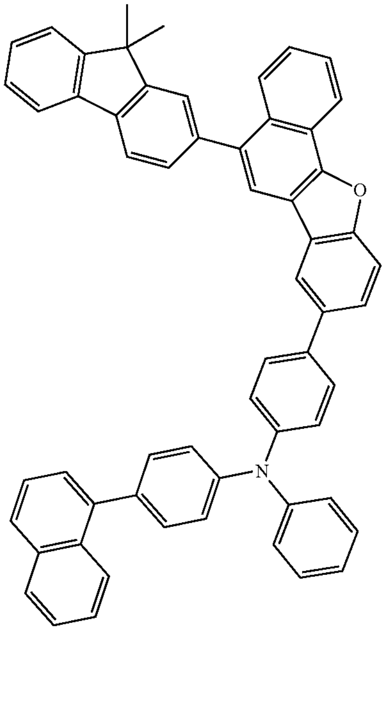
-continued
1-80
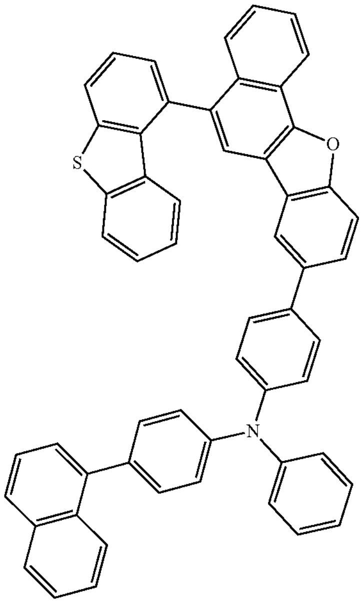
1-81
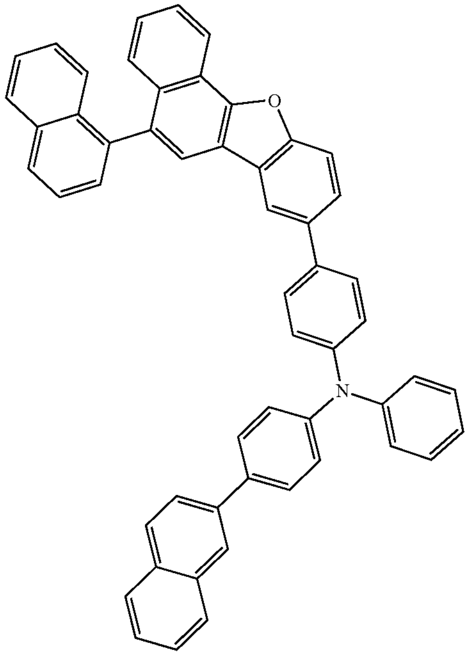

-continued
1-82
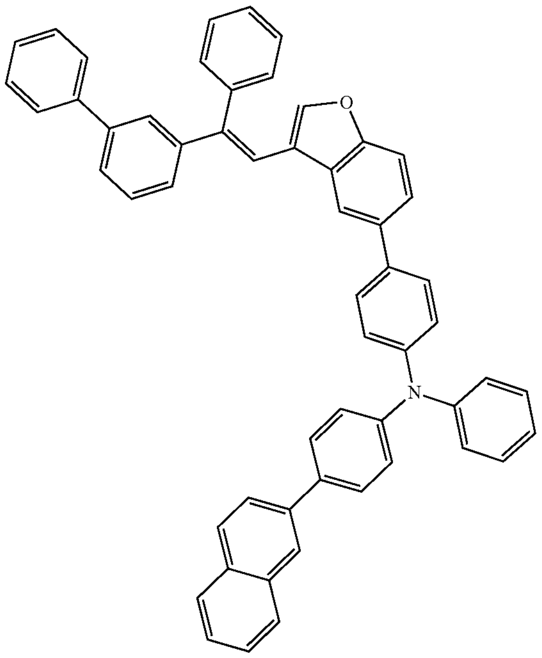
1-83
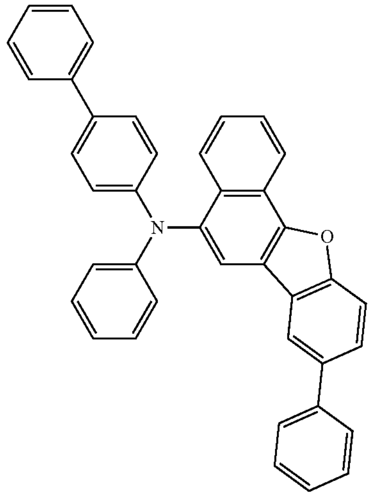
1-84
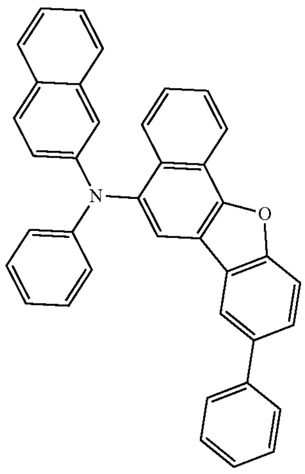
-continued
1-85
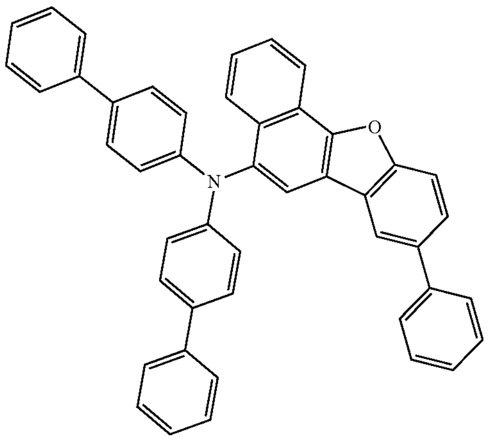
1-86
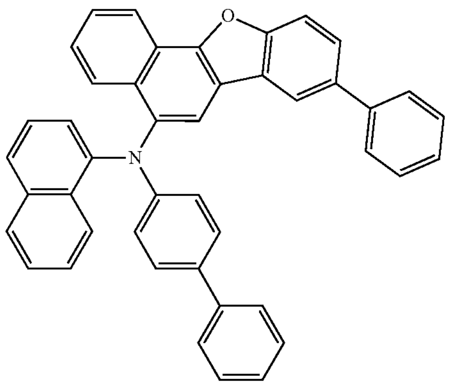
1-87
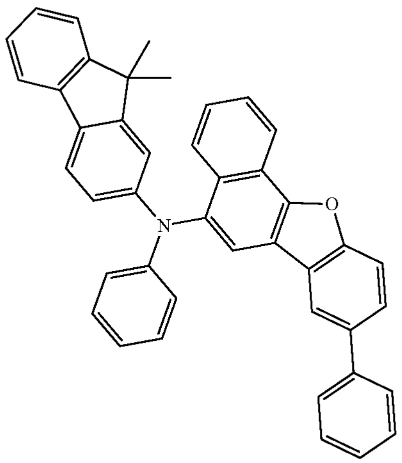

-continued
1-88
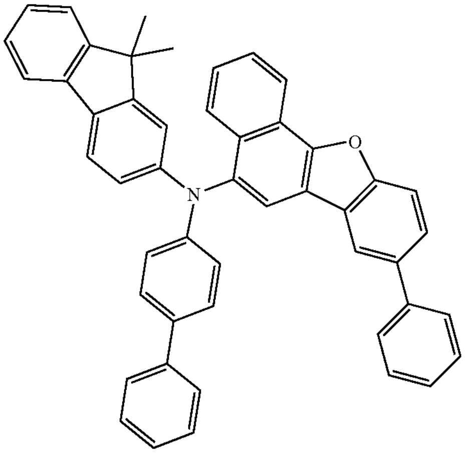
1-89
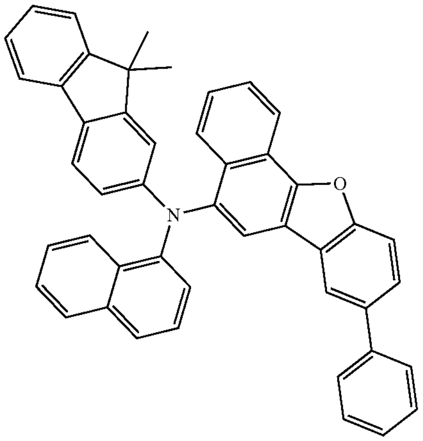
1-90
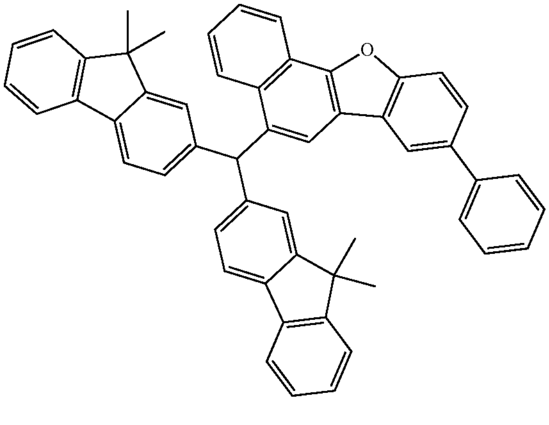
-continued
1-91
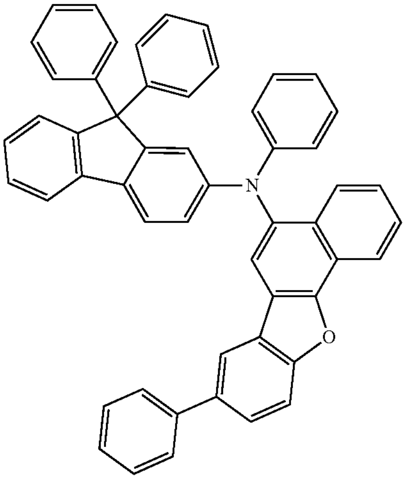
1-92
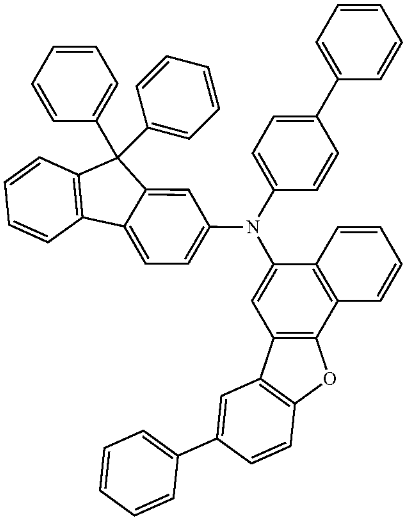
1-93
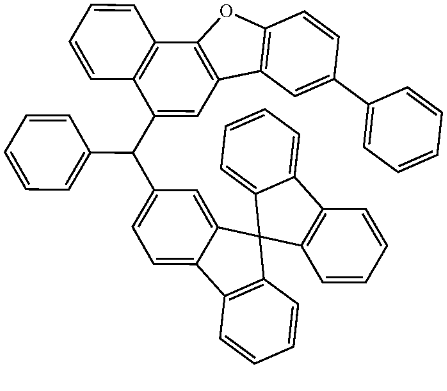

-continued
1-94
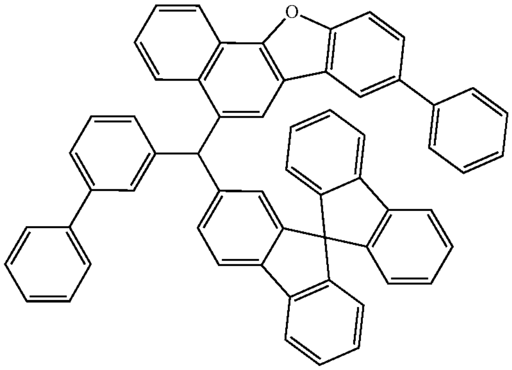
1-95
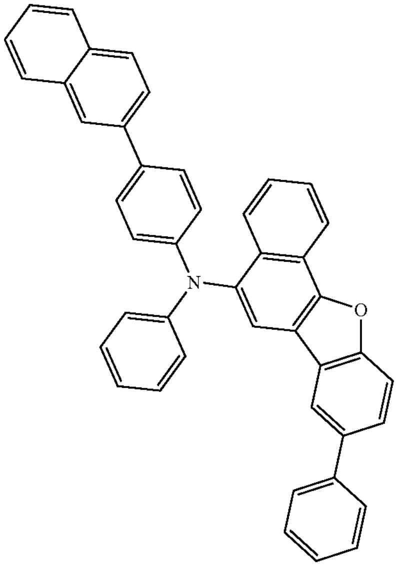
1-96
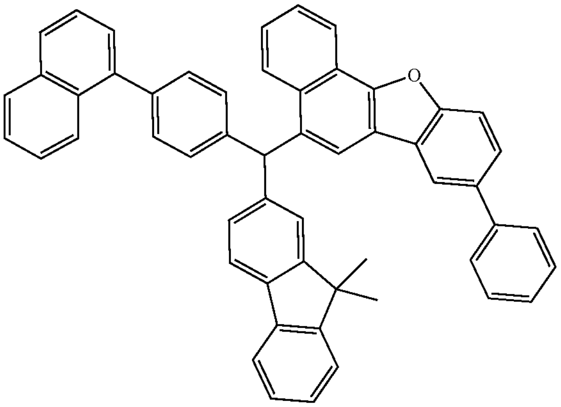
-continued
1-97
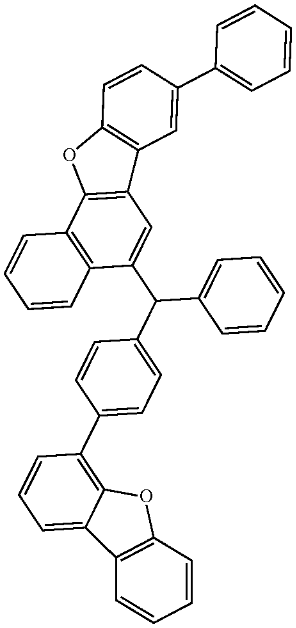
1-98
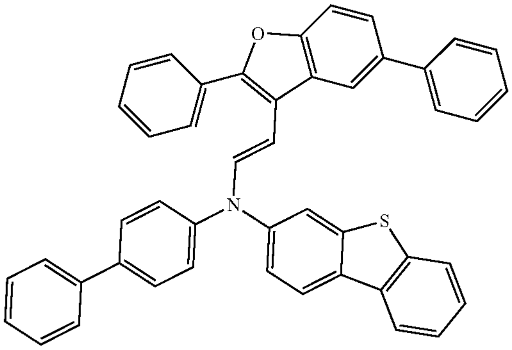
1-99
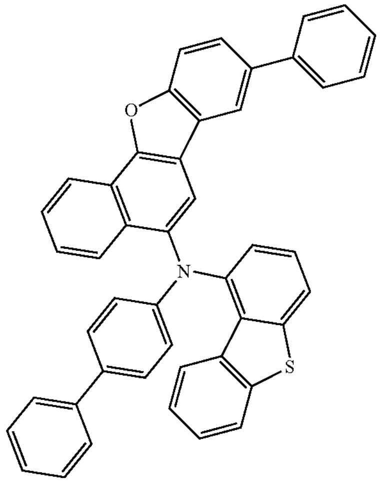

-continued
1-100
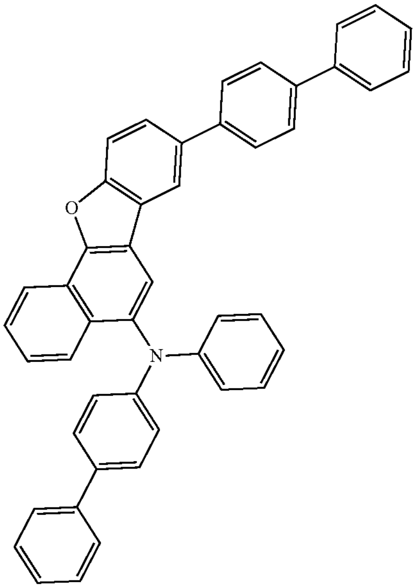
1-101
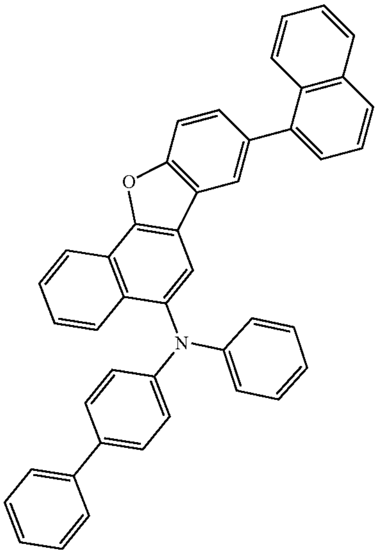
-continued
1-102
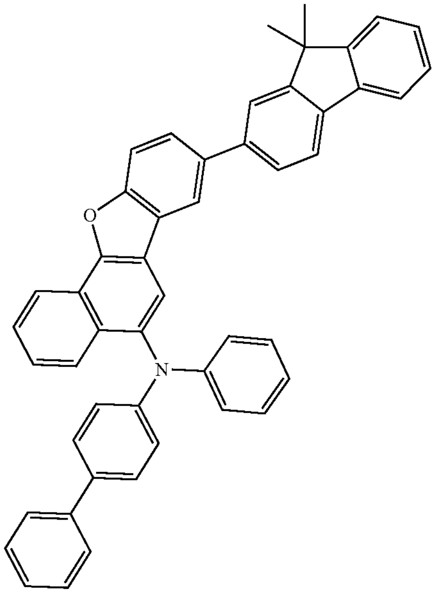
1-103
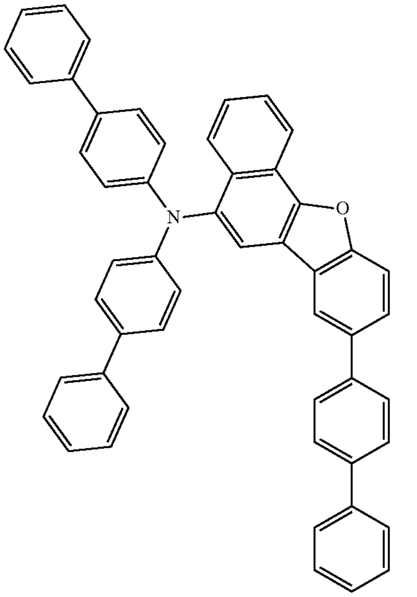

-continued
1-104
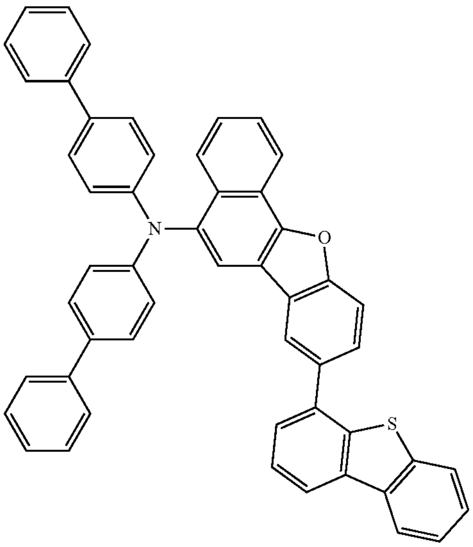
1-105
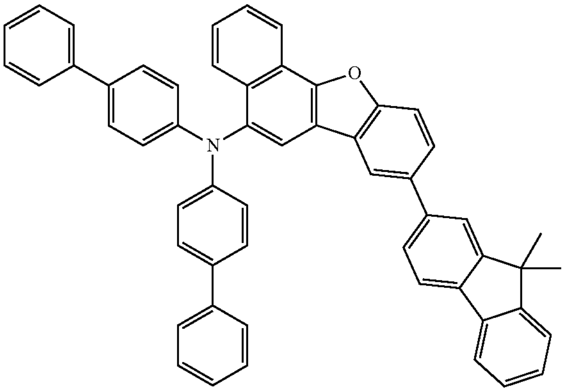
1-106
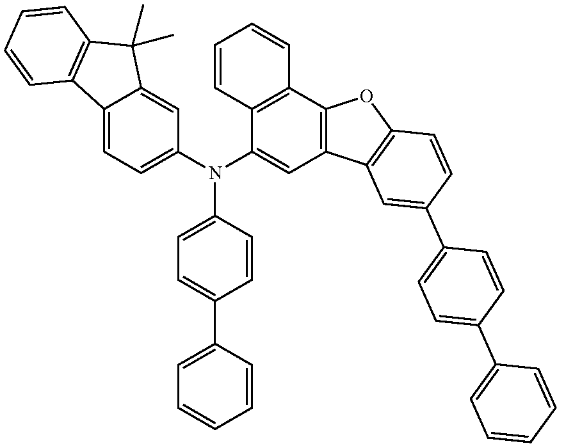
-continued
1-107
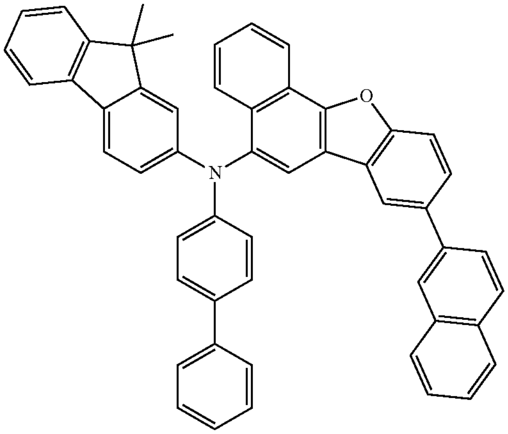
1-108
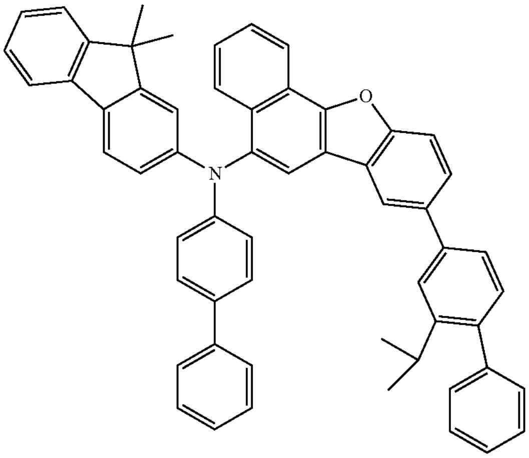
1-109
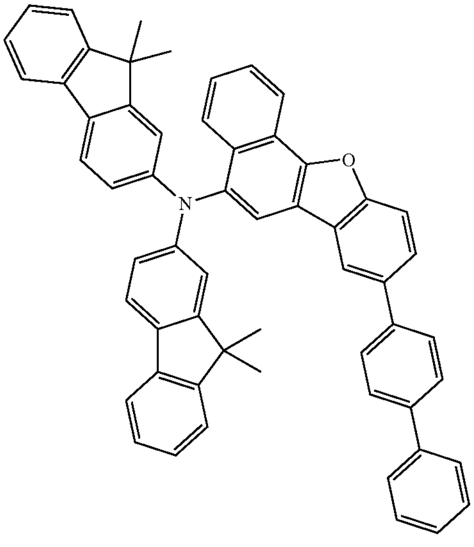

-continued
1-110
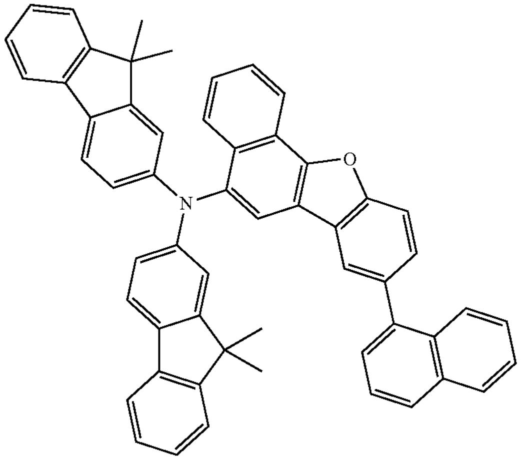
1-111
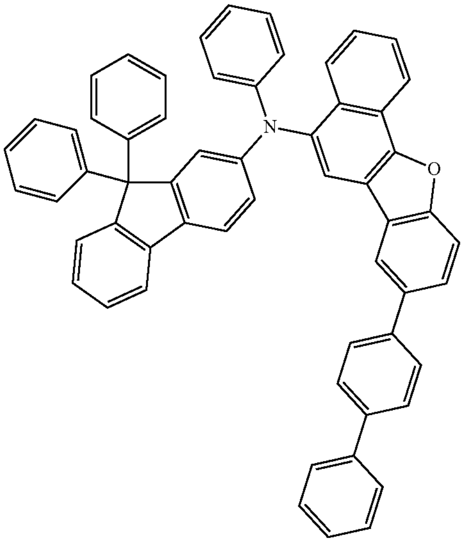
1-112
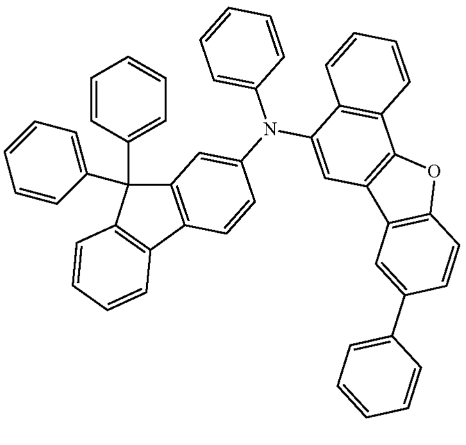
-continued
1-113
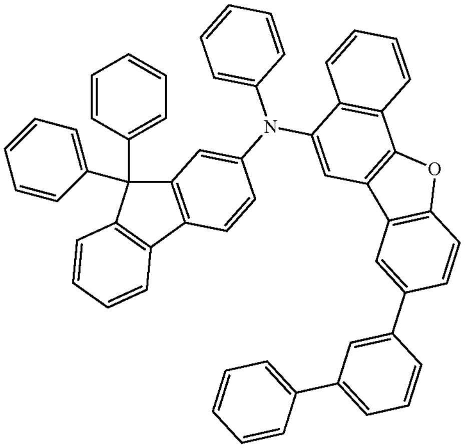
1-114
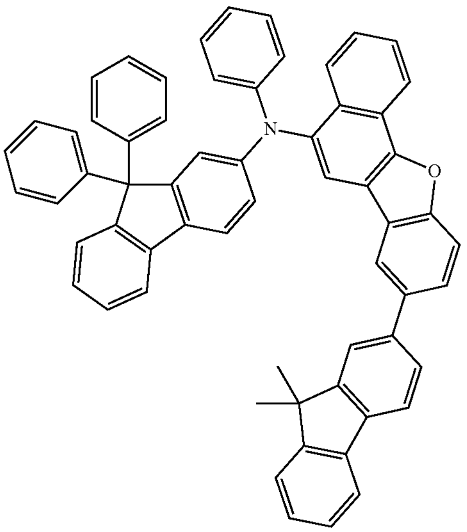
1-115
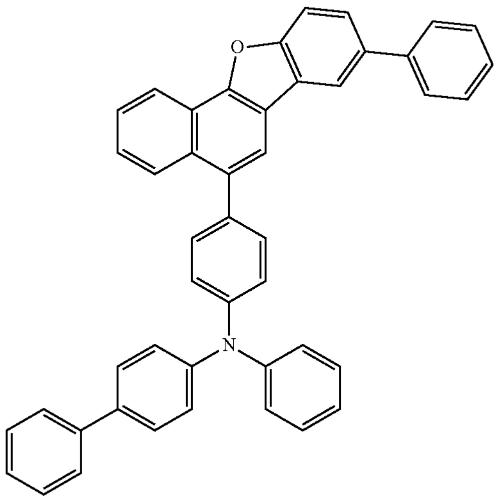

-continued
1-116
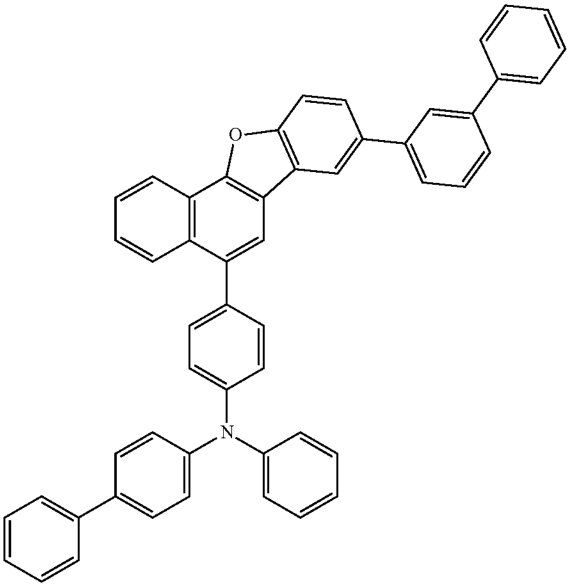
1-117
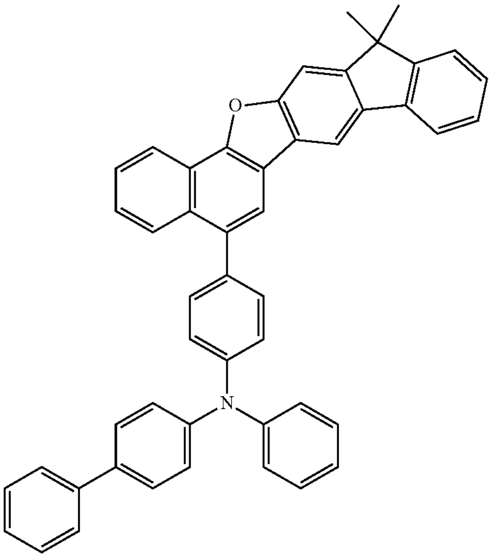
-continued
1-118
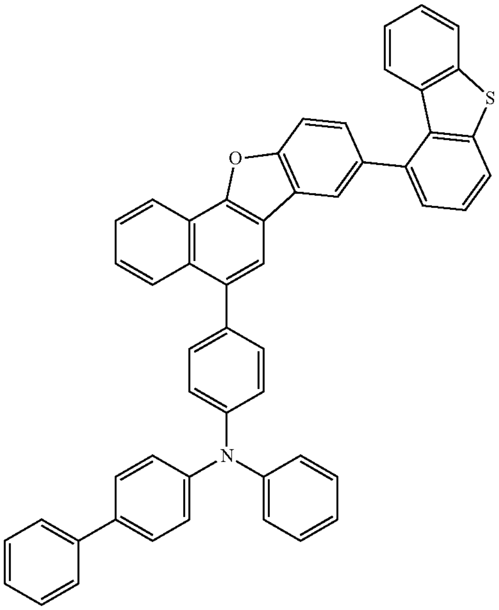
1-119
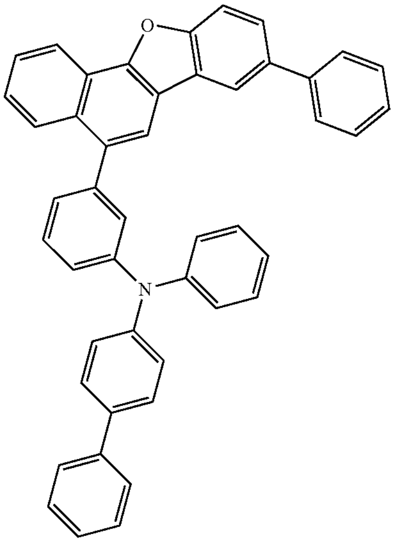

-continued
1-120
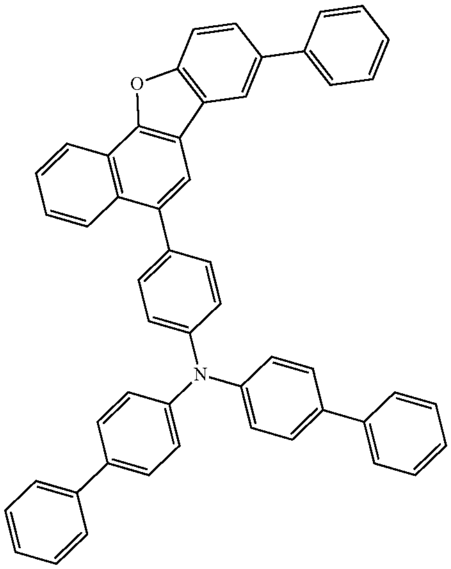
1-121
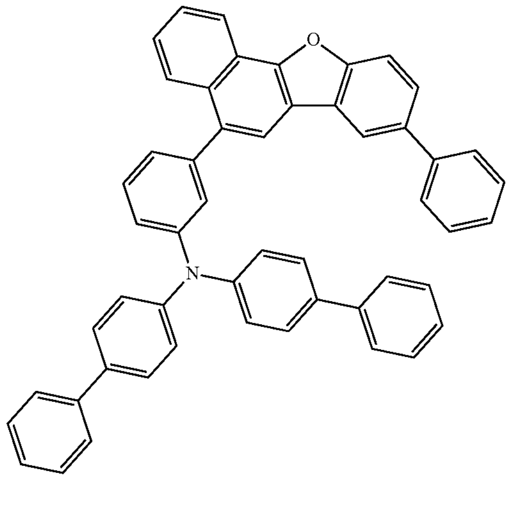
-continued
1-122
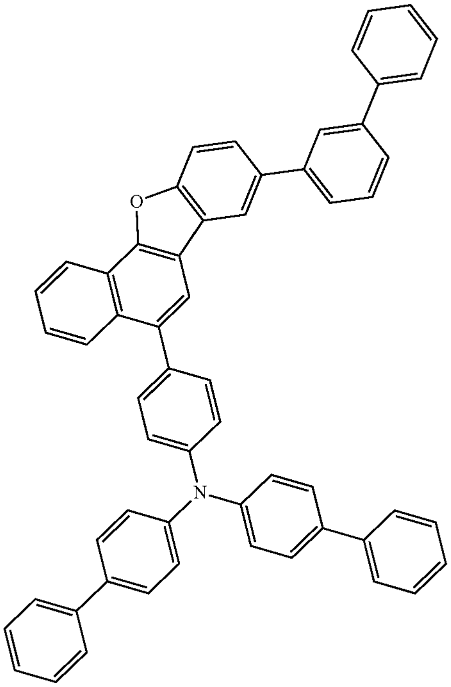
1-123
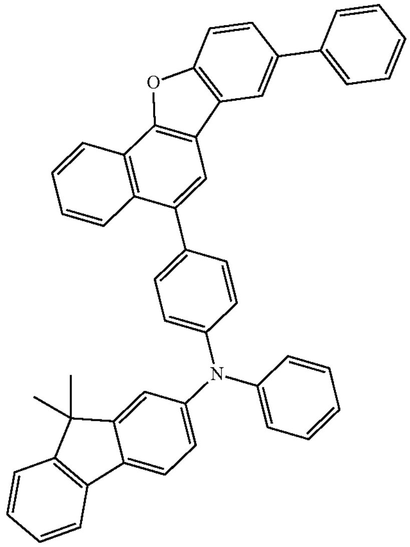

-continued
1-124
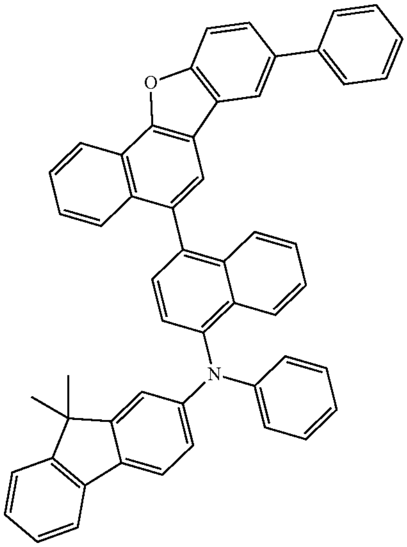
1-125
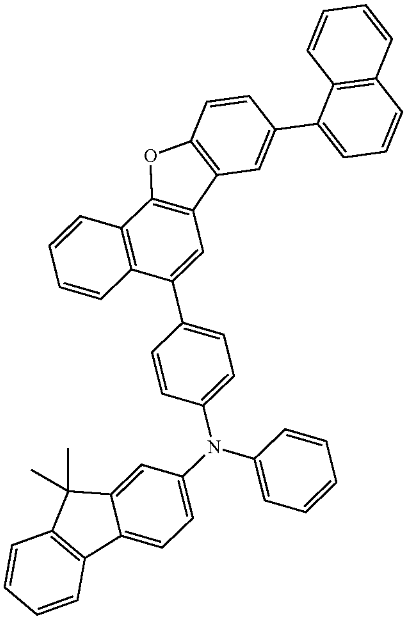
-continued
1-126
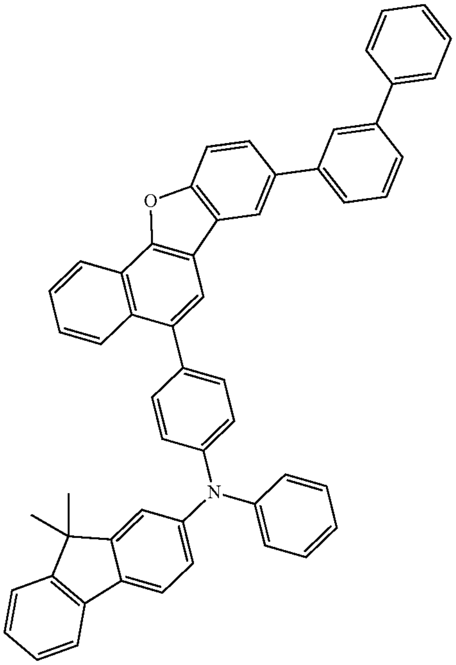
1-127
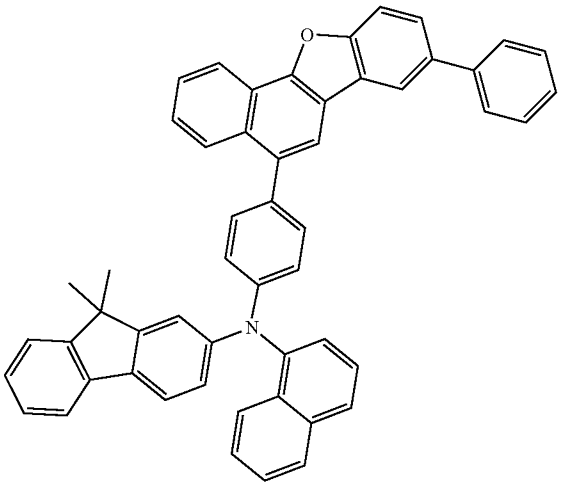
1-128
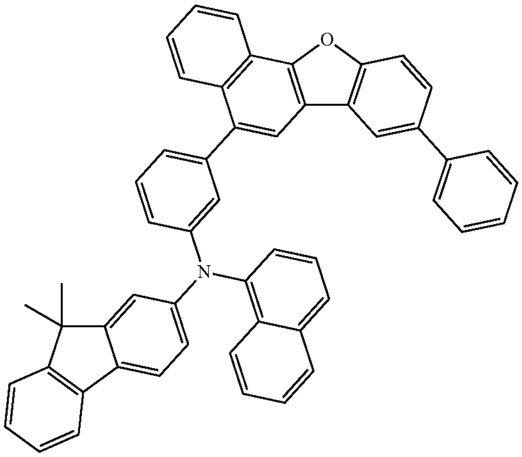

-continued
1-129
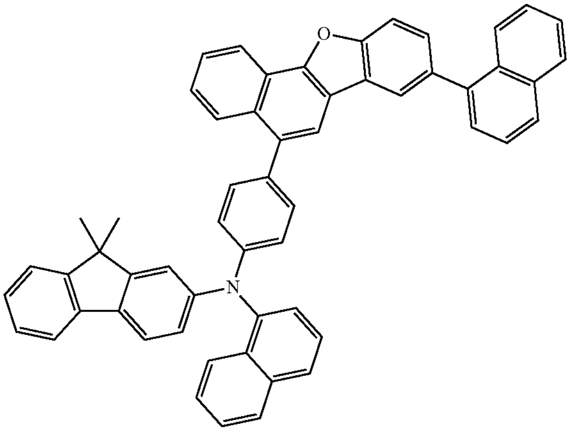
1-130
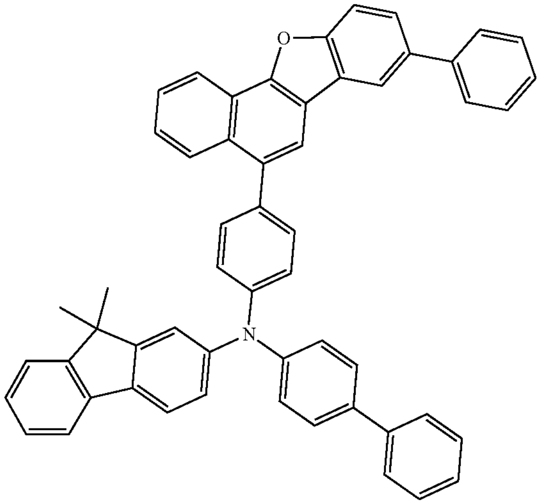
1-131
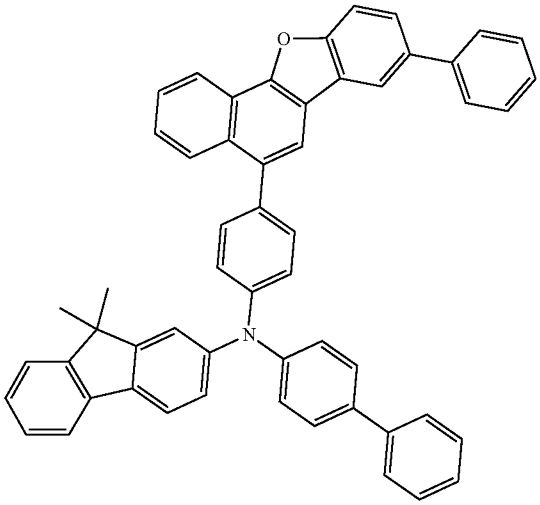
-continued
1-132
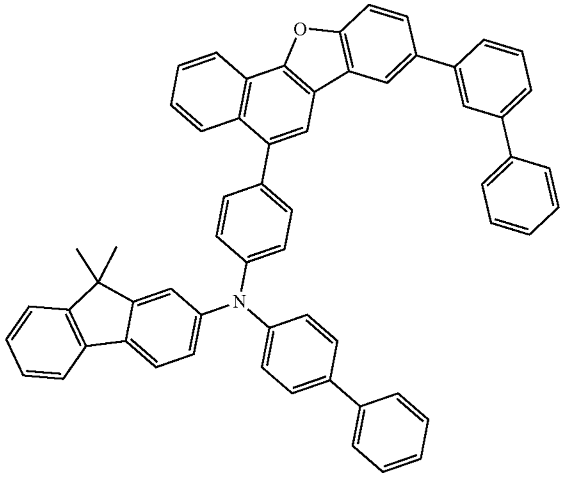
1-133
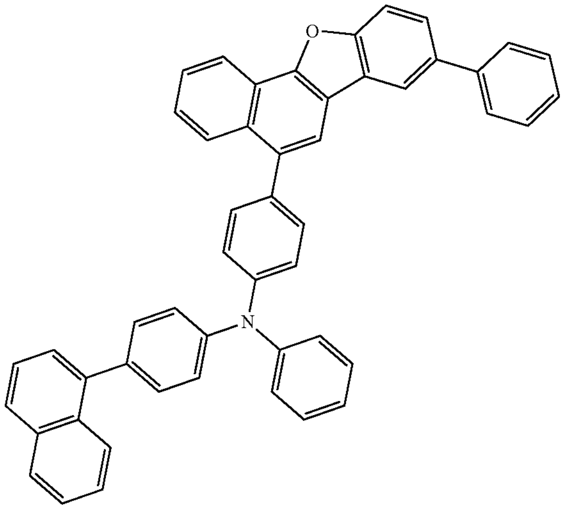
1-134
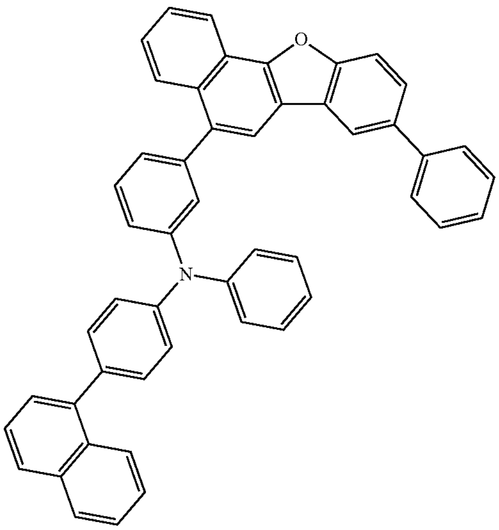

-continued
1-135
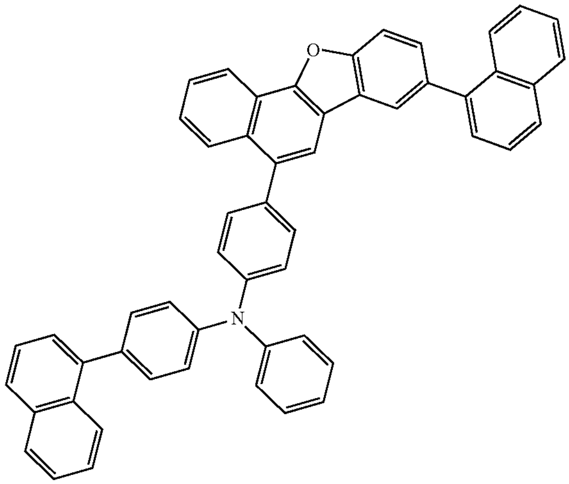
1-136
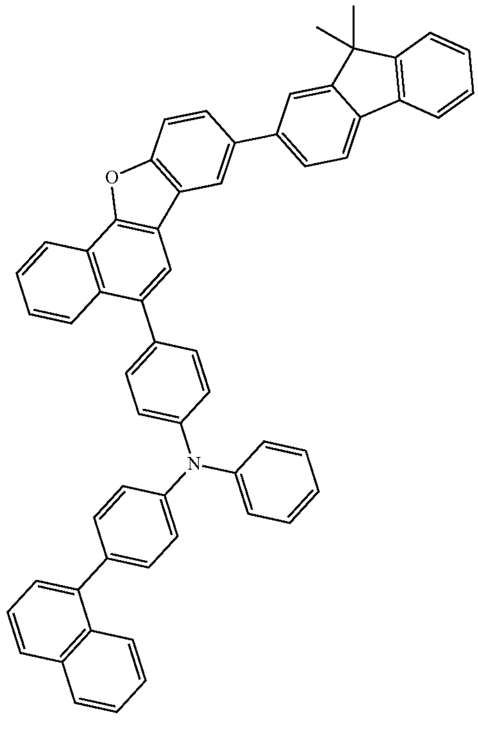
-continued
1-137
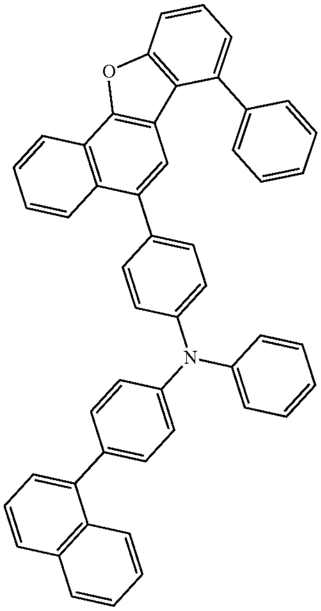
1-138
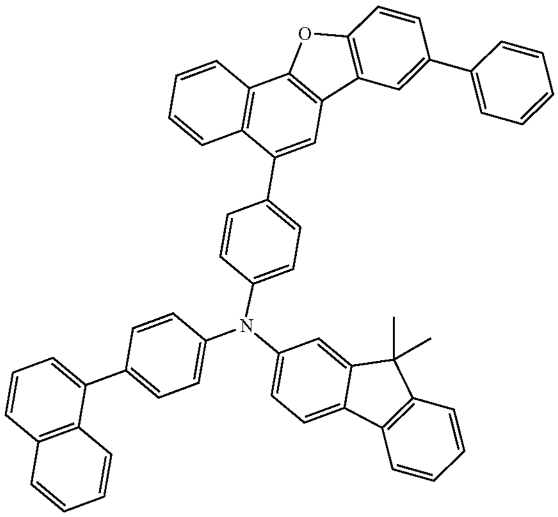
1-139
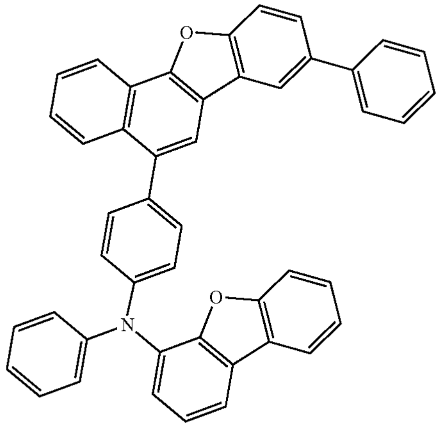

-continued
1-140
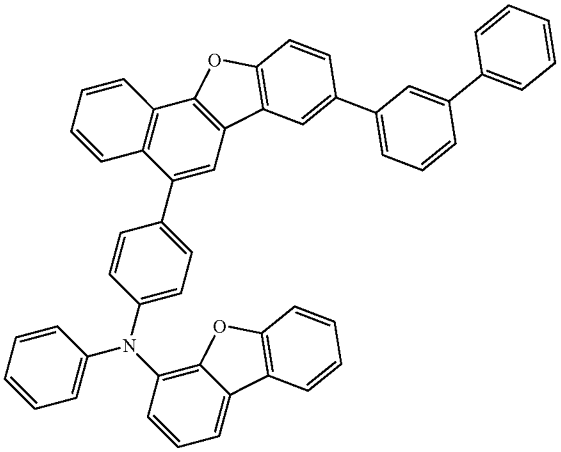
1-141
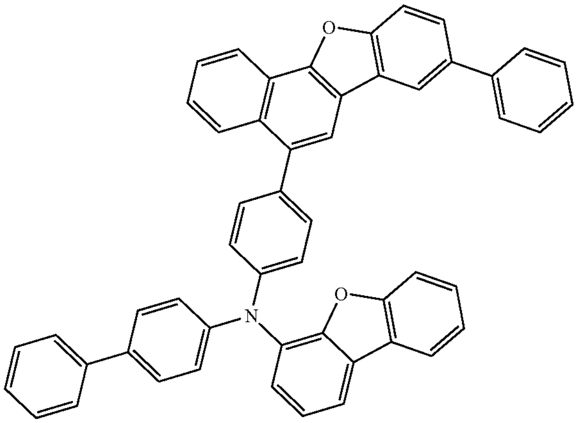
1-142
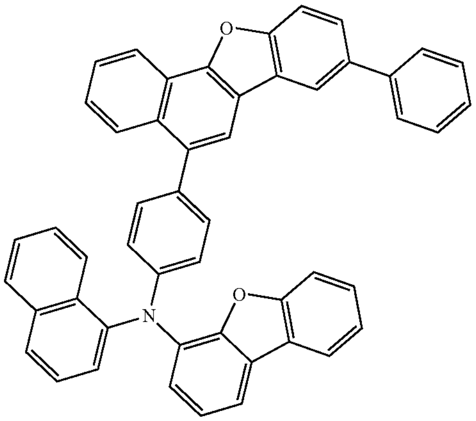
-continued
1-143
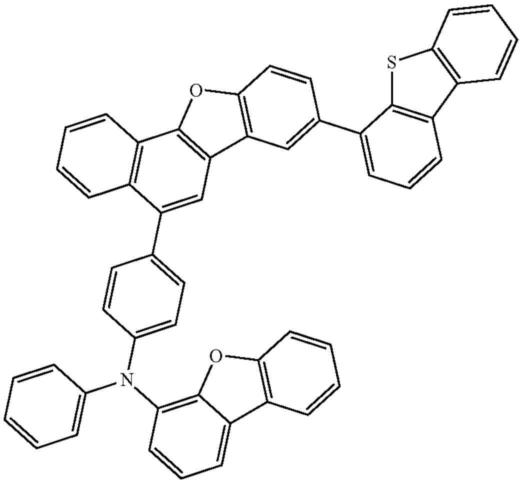
1-144
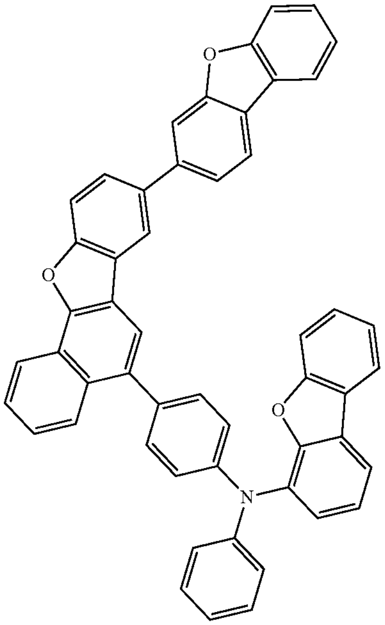

-continued
1-145
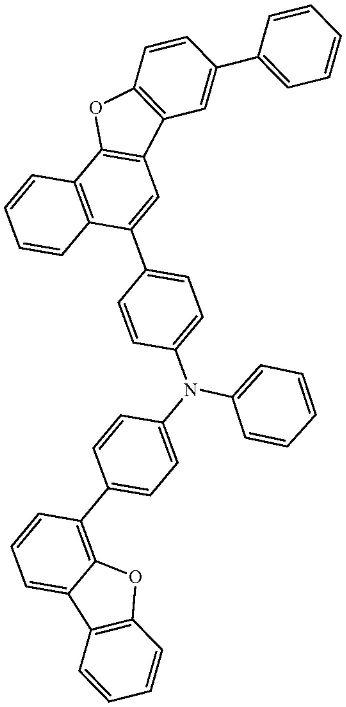
1-146
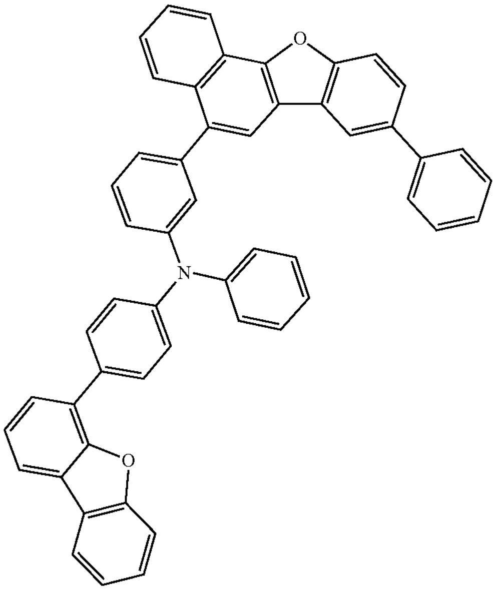
-continued
1-147
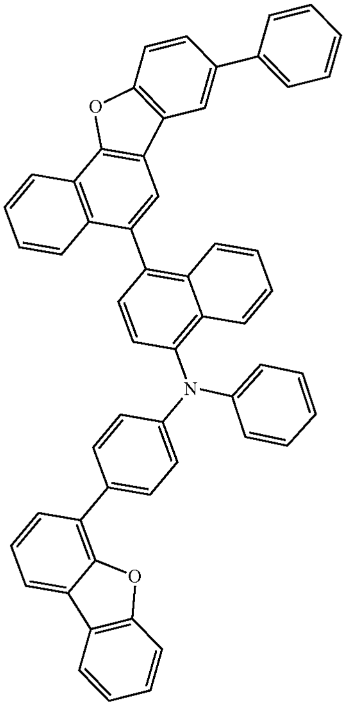
1-148
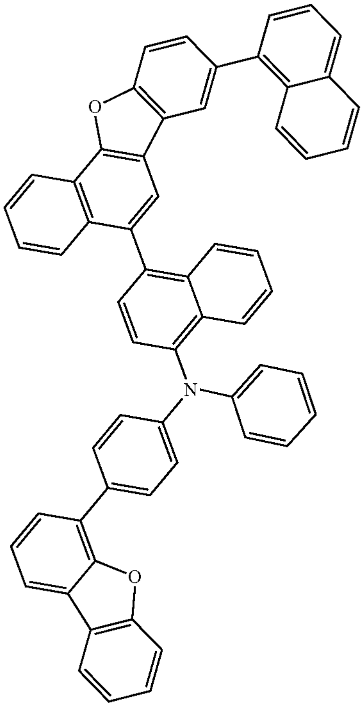

-continued
1-149
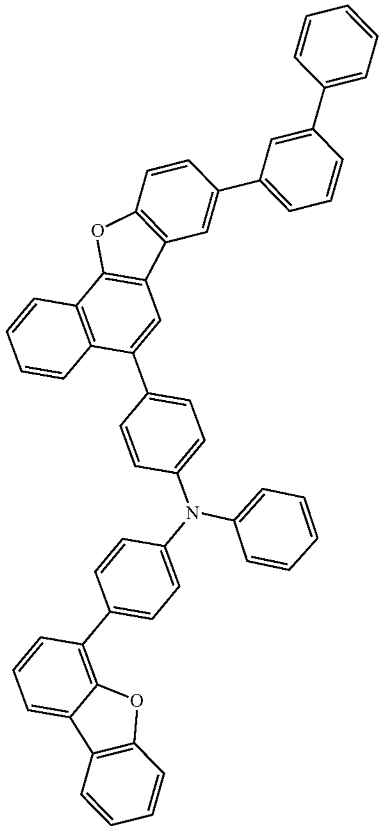
1-150
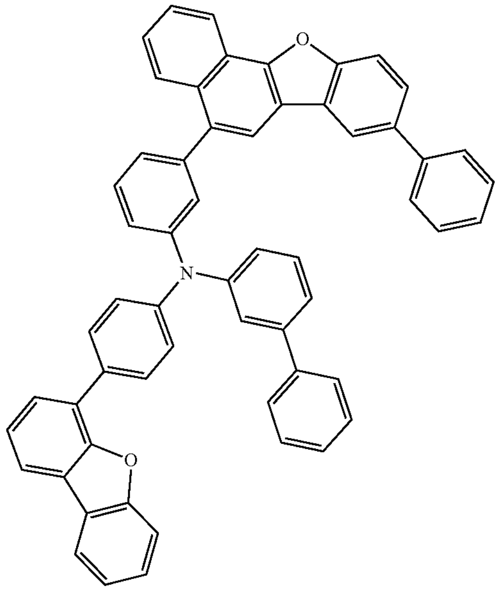
-continued
1-151
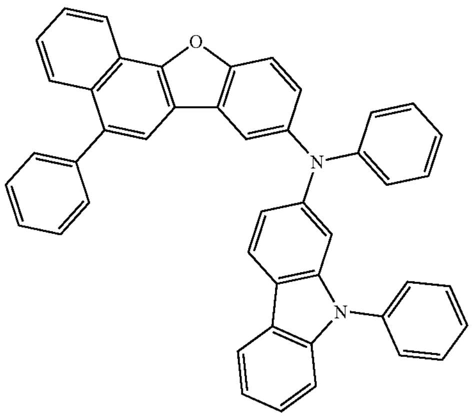
1-152
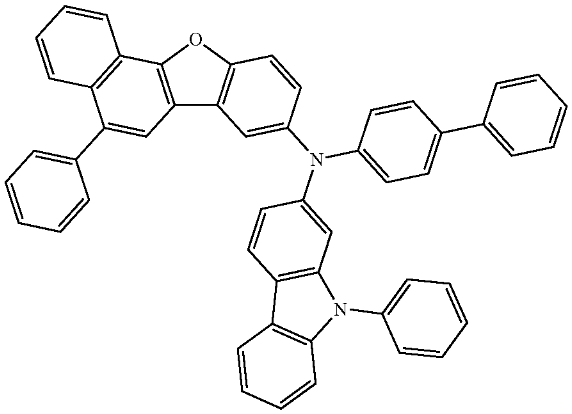
1-153
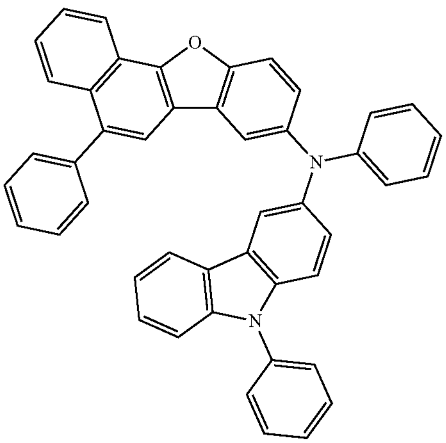

-continued
1-154
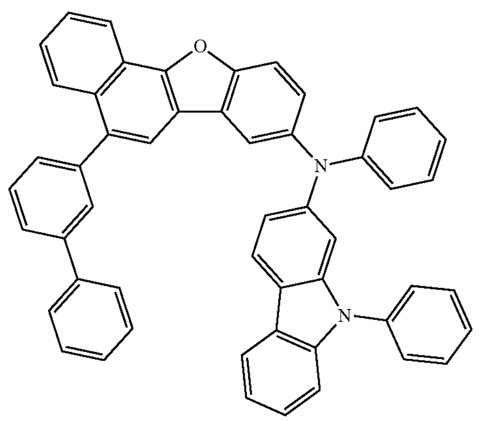
1-155
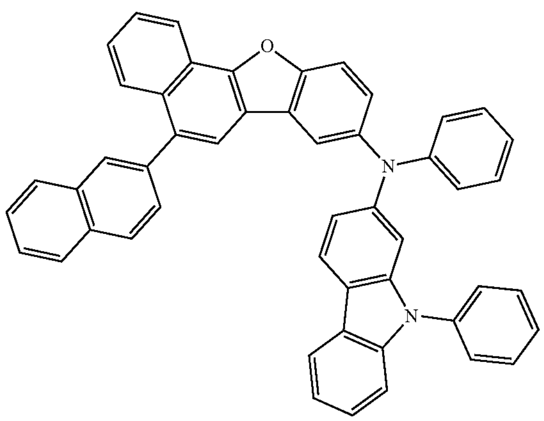
1-156
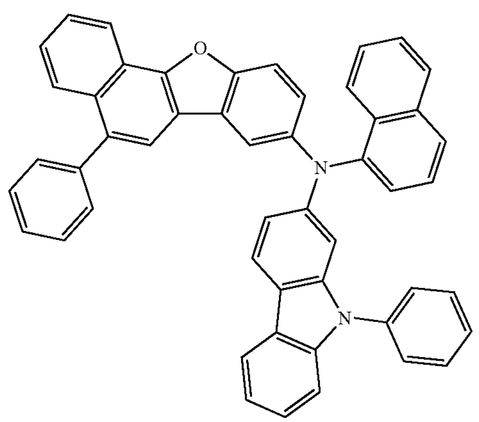
-continued
1-157
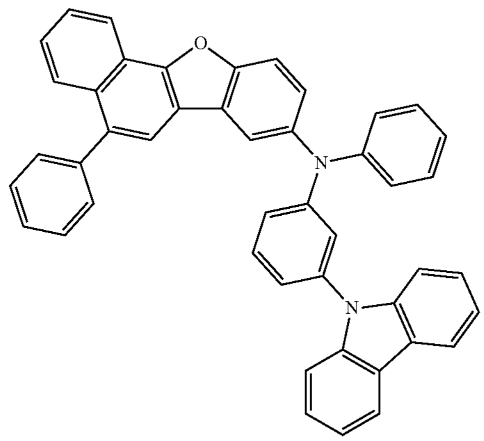
1-158
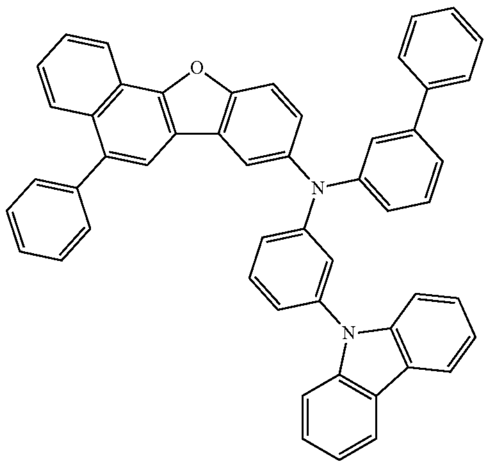
1-159
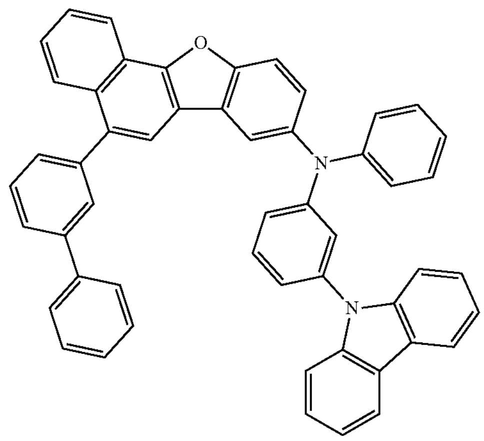

-continued
1-160
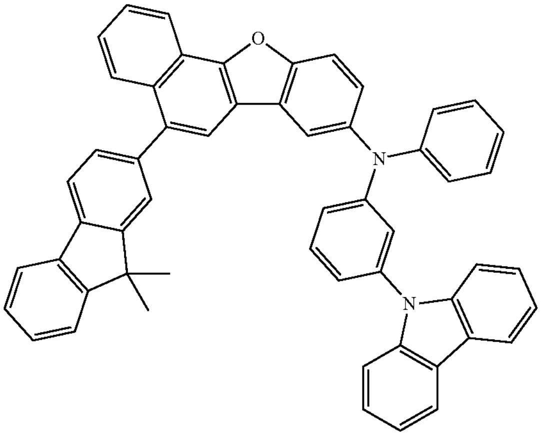
1-161
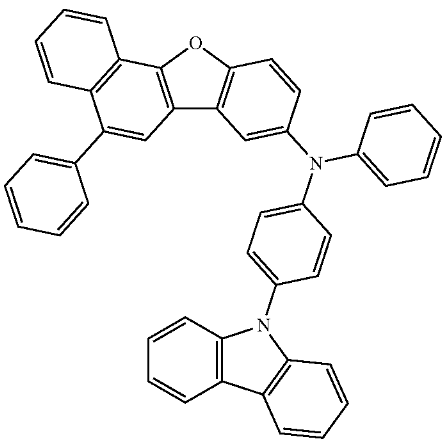
1-162
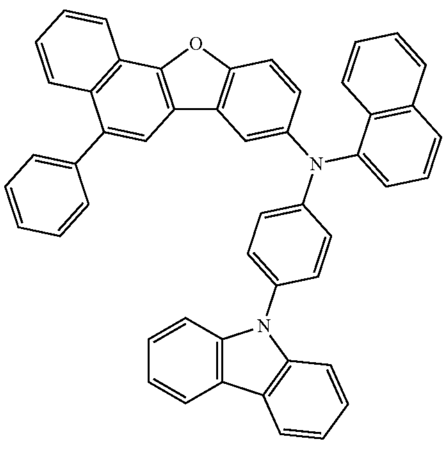
-continued
1-163
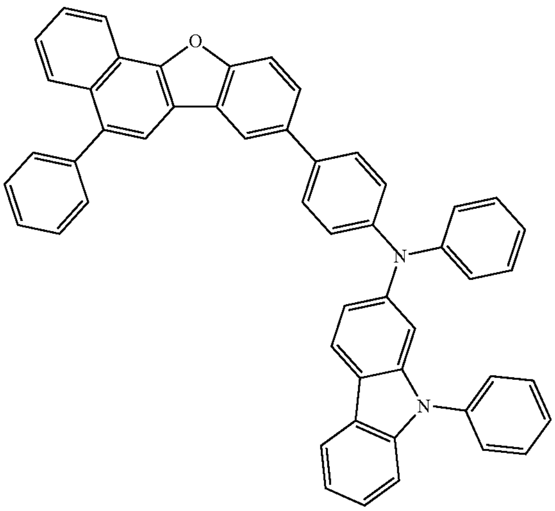
1-164
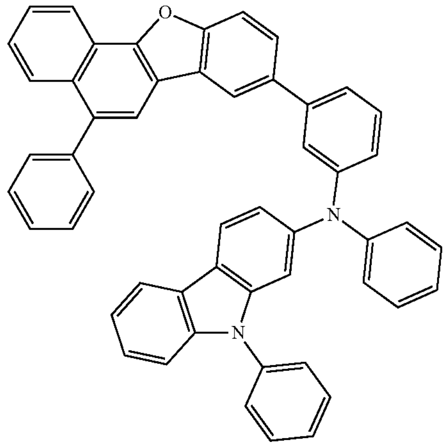
1-165
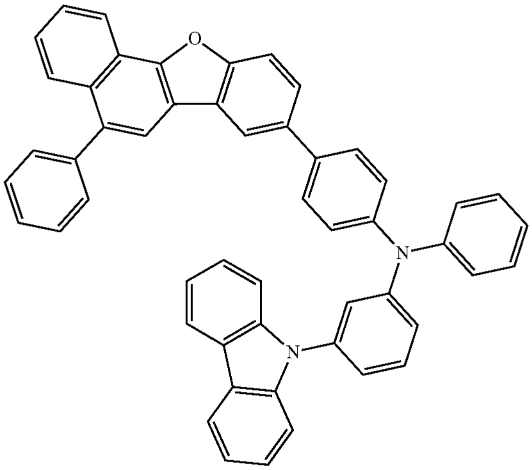

-continued
1-166
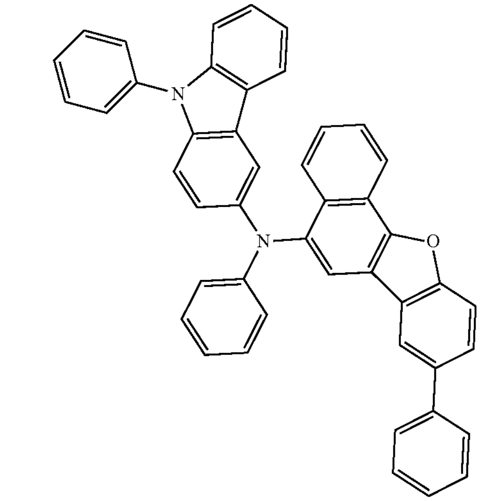
1-167
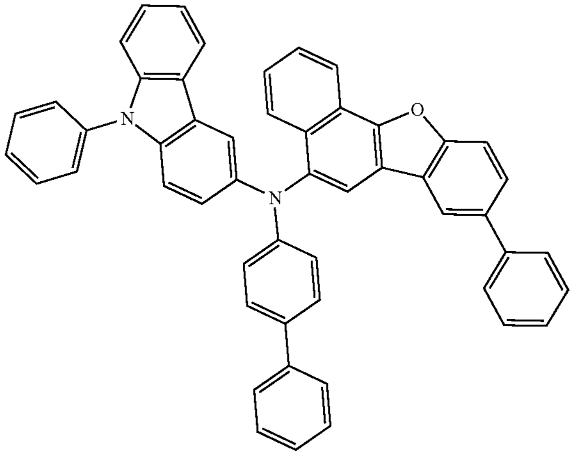
1-168
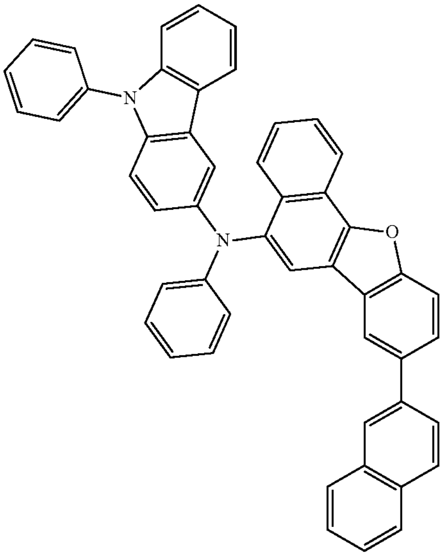
-continued
1-169
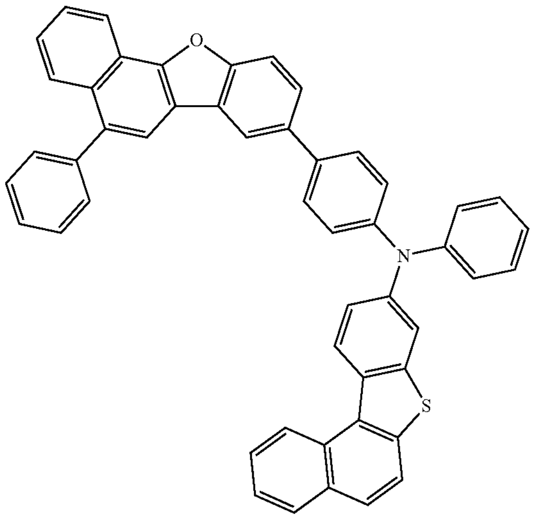
1-170
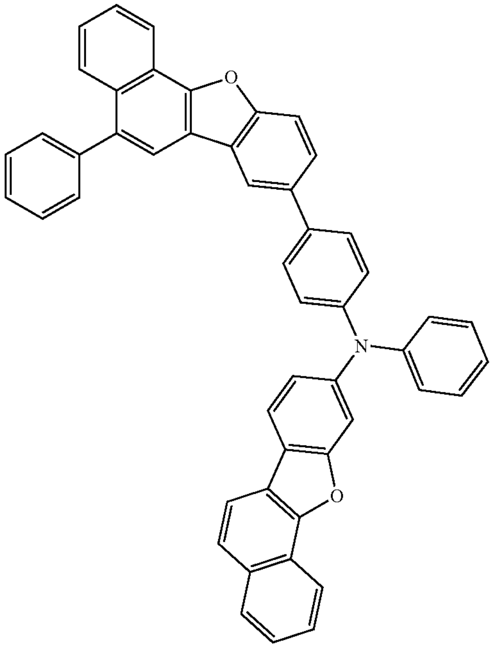

-continued
1-171
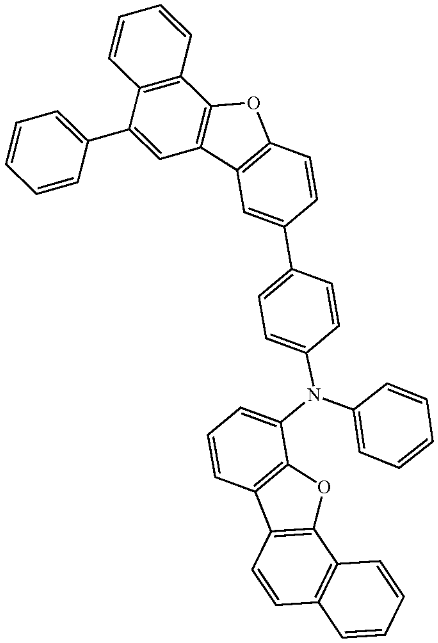
1-172
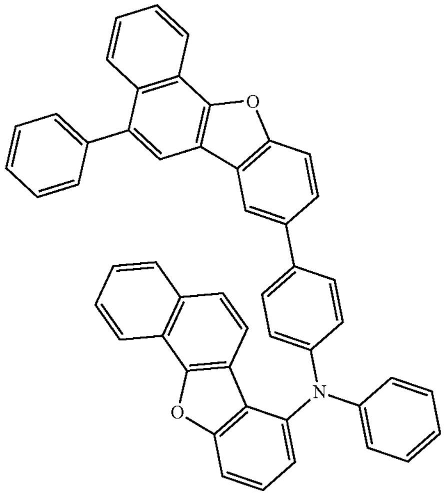
1-173
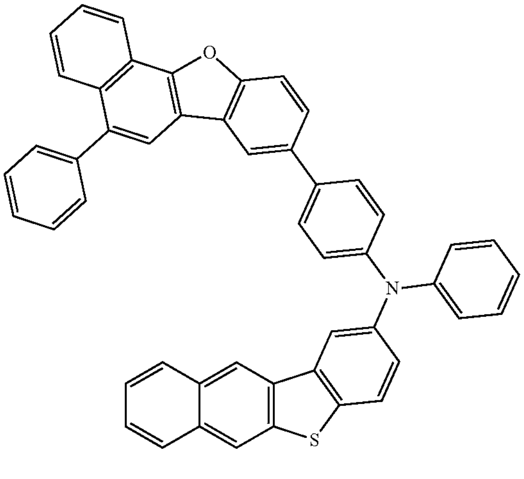
-continued
1-174
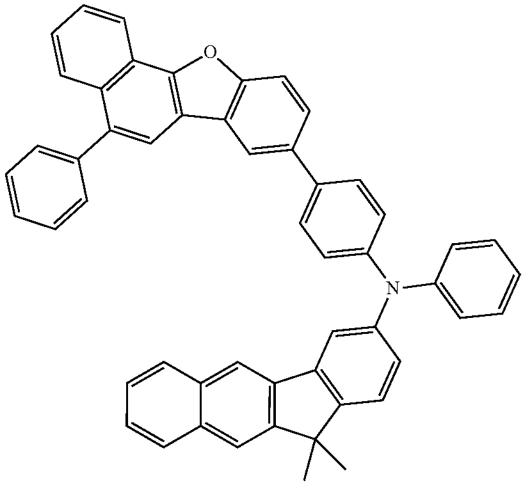
1-175
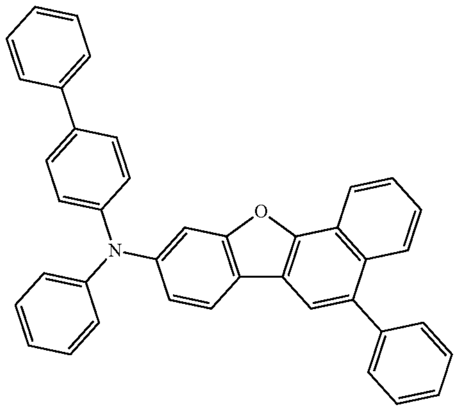
1-176
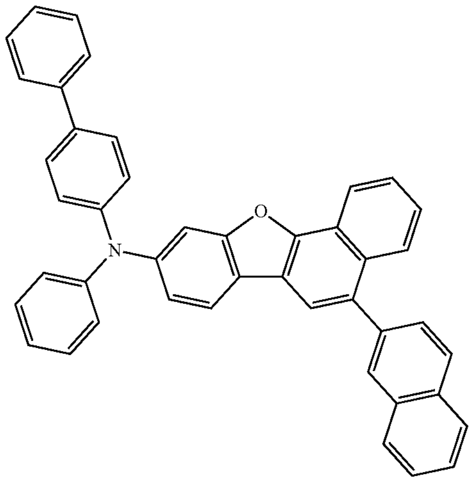

-continued
1-177
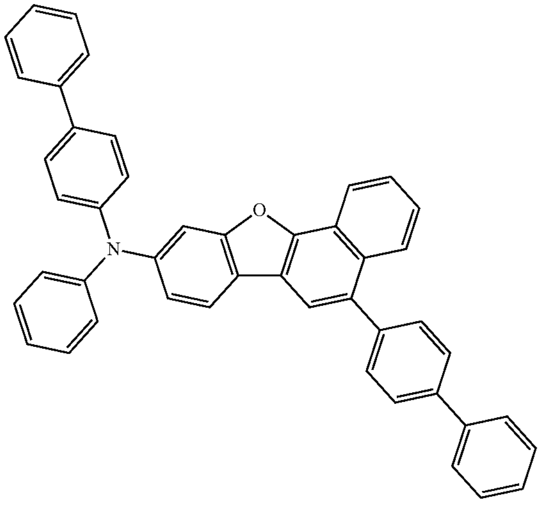
1-178
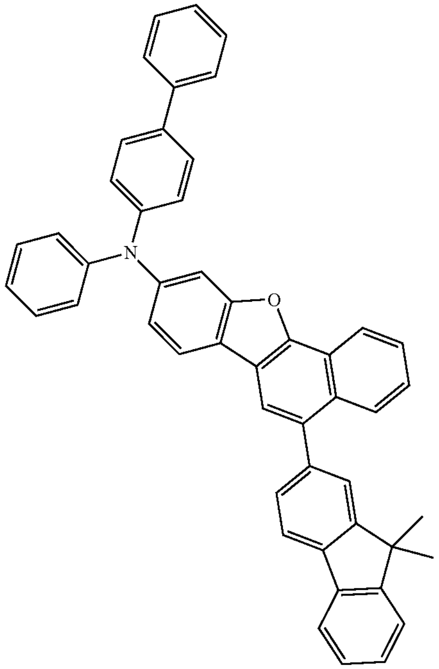
-continued
1-179
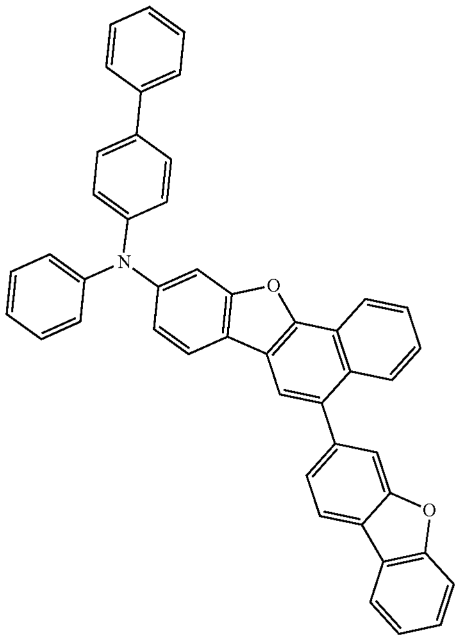
1-180
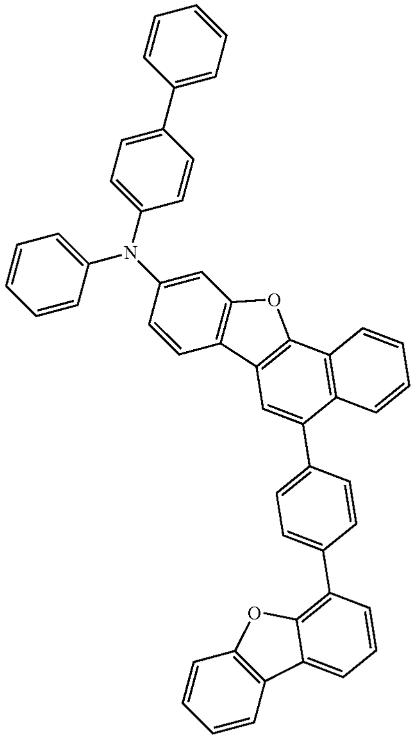

-continued
1-181
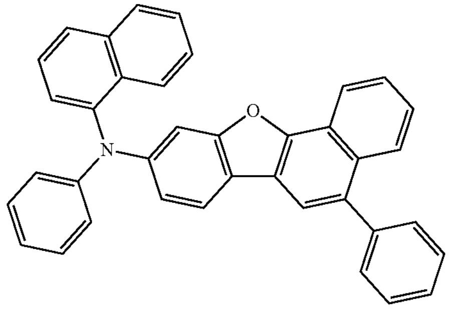
1-182
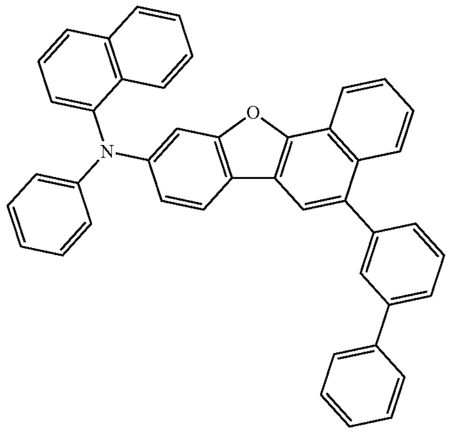
1-183
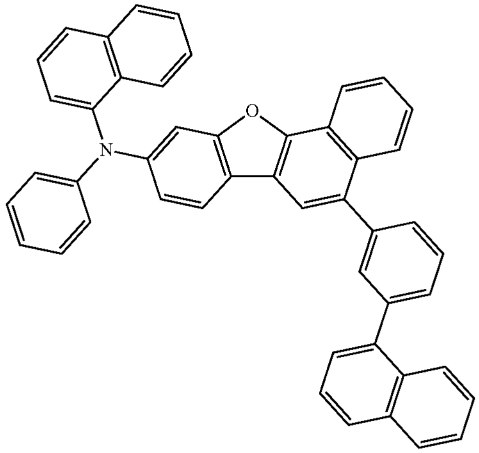
1-184
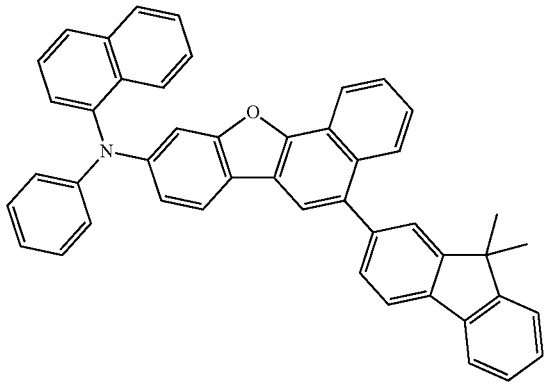
-continued
1-185
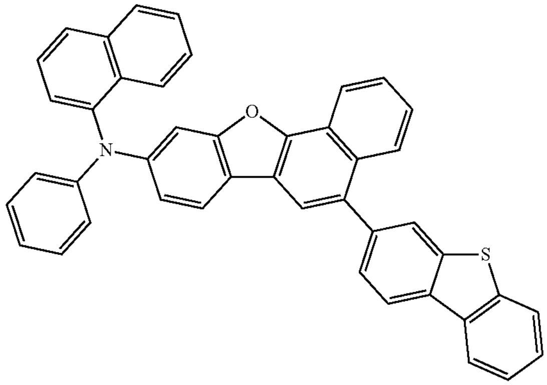
1-186
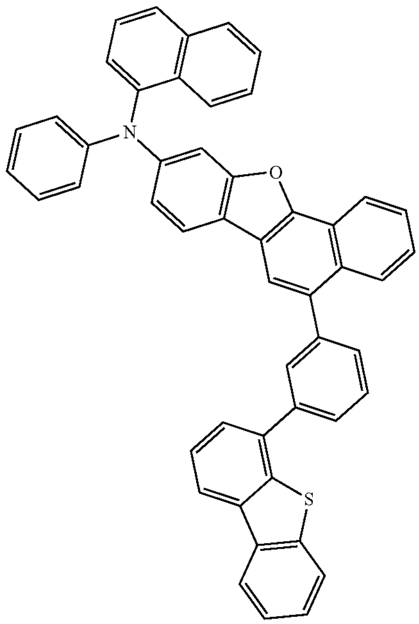
1-187
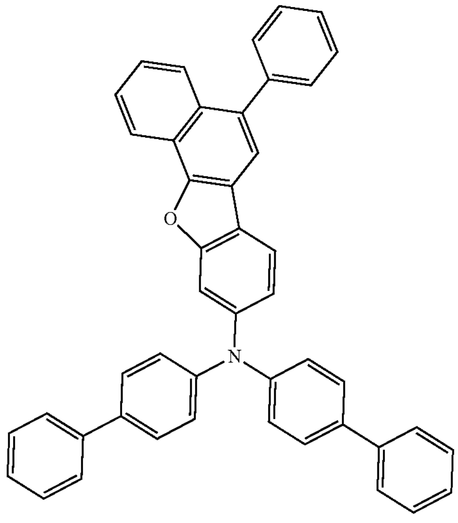

-continued
1-188
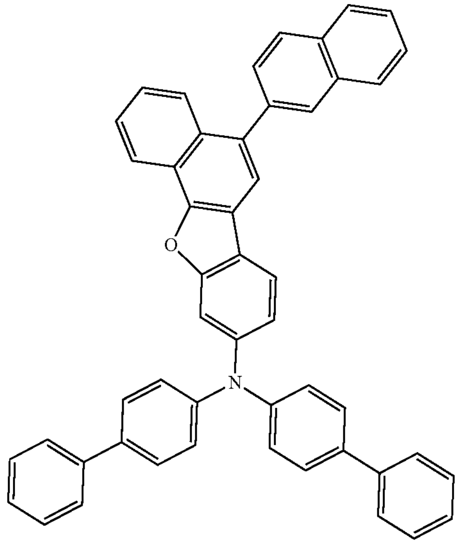
1-189
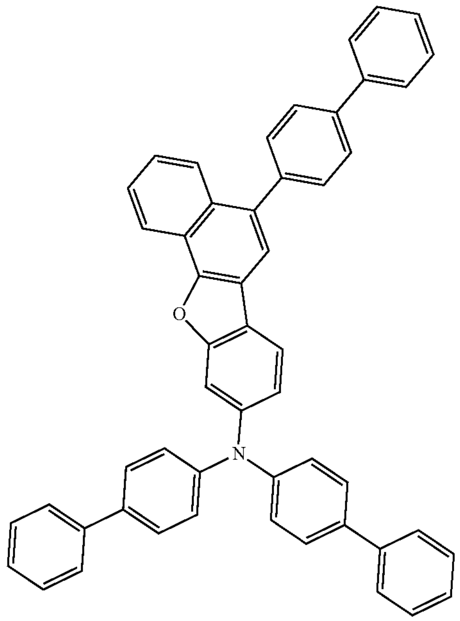
-continued
1-190
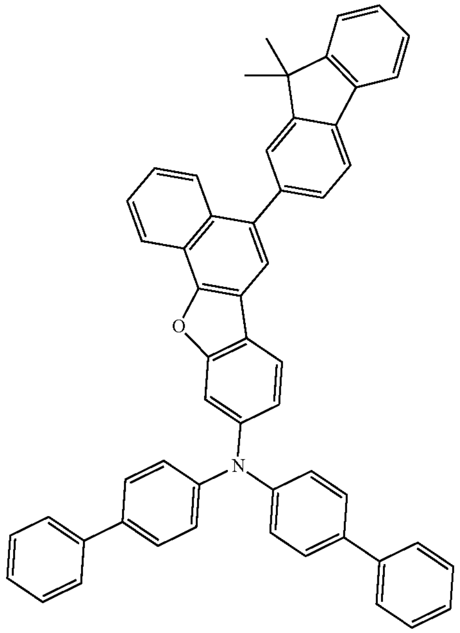
1-191
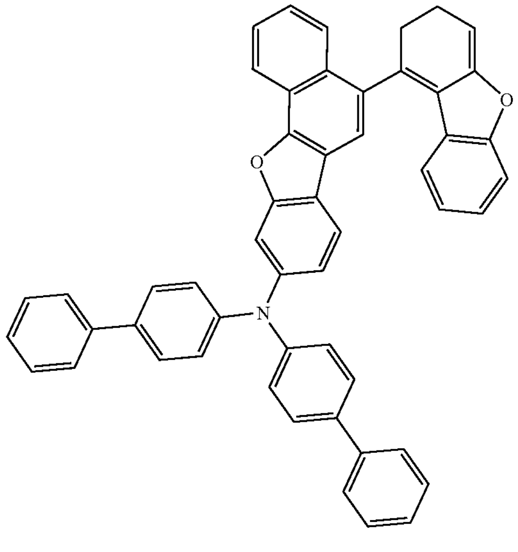

-continued
1-192
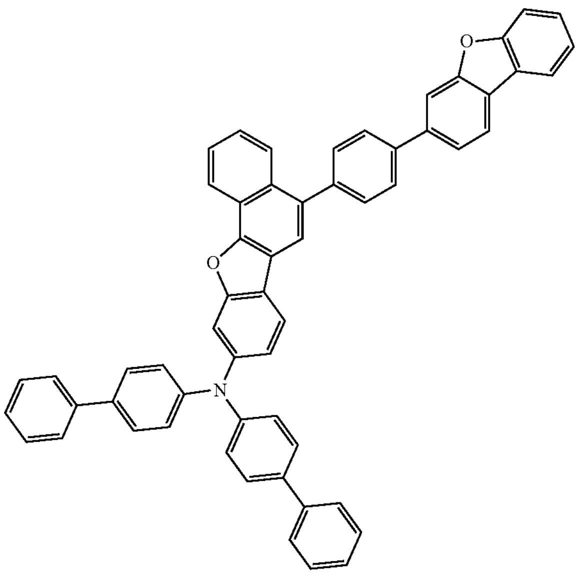
1-193
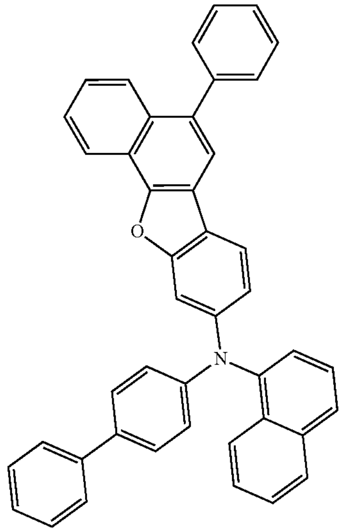
1-194
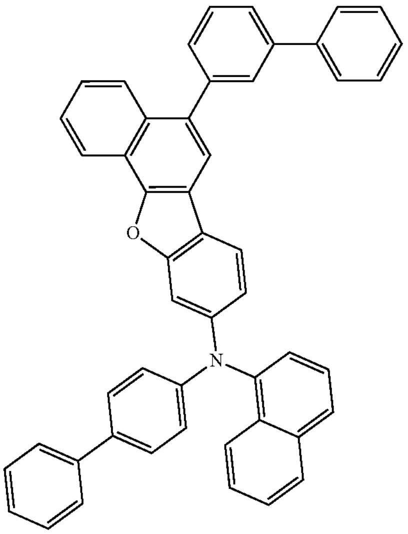
-continued
1-195
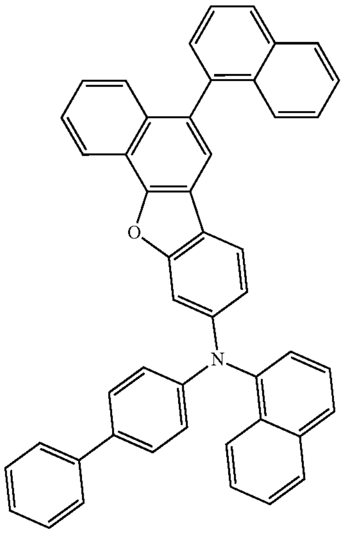
1-196
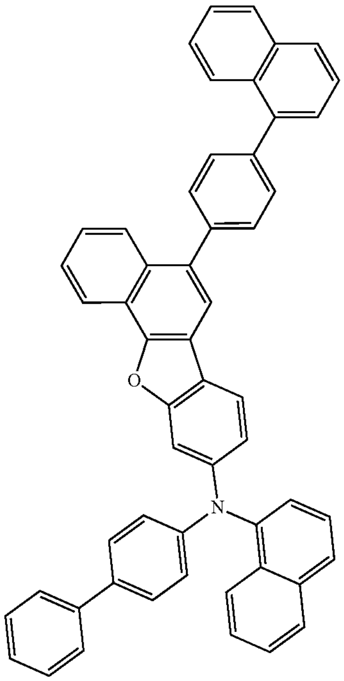

-continued
1-197
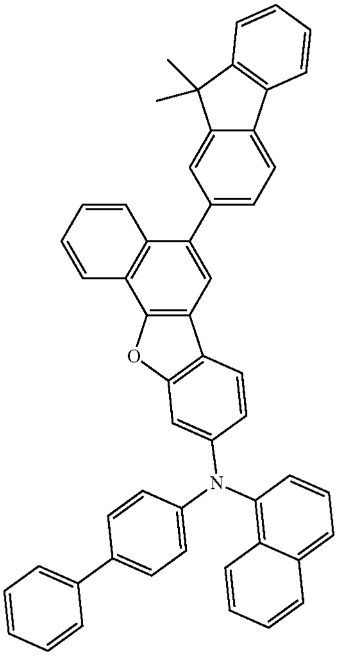
1-198
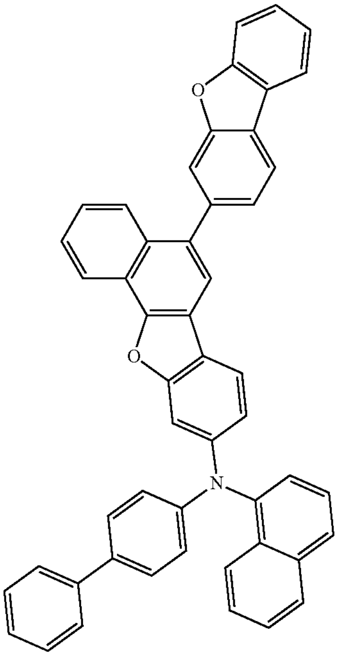
-continued
1-199
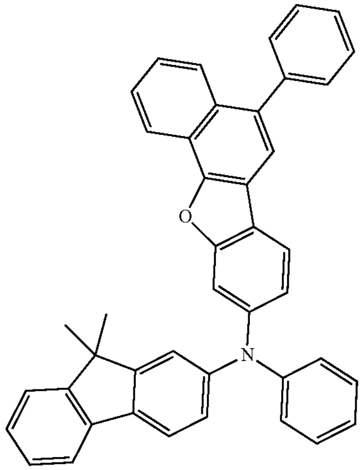
1-200
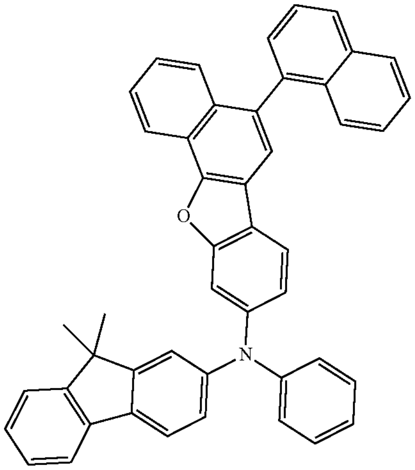
1-201
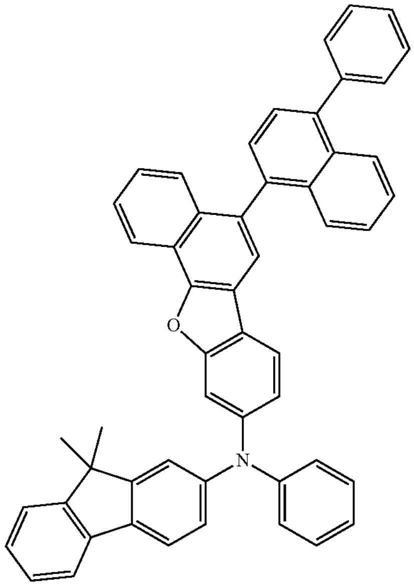

-continued
1-202
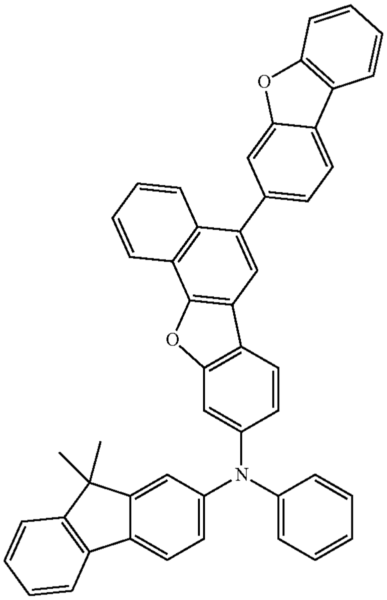
1-203
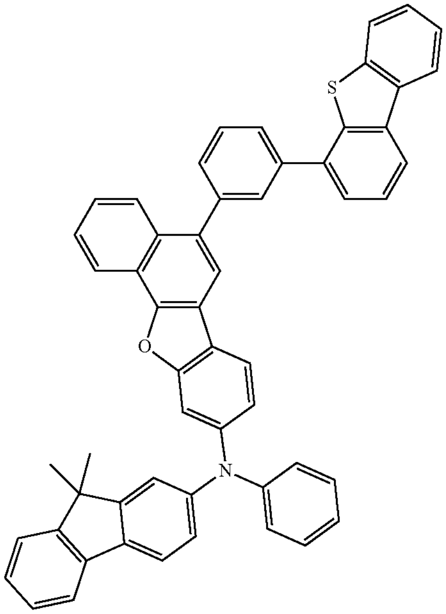
-continued
1-204
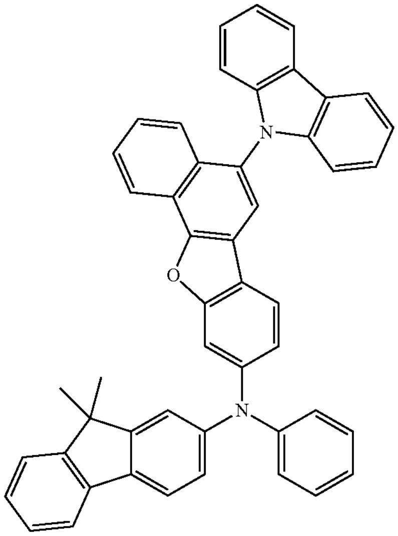
1-205
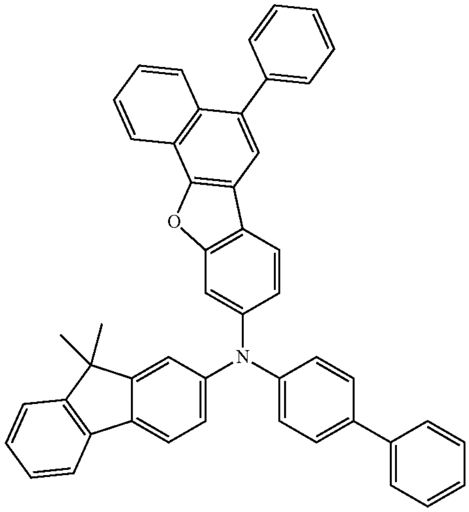
1-206
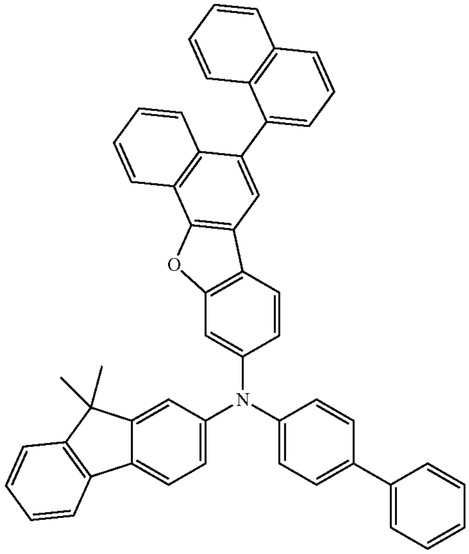

-continued
1-207
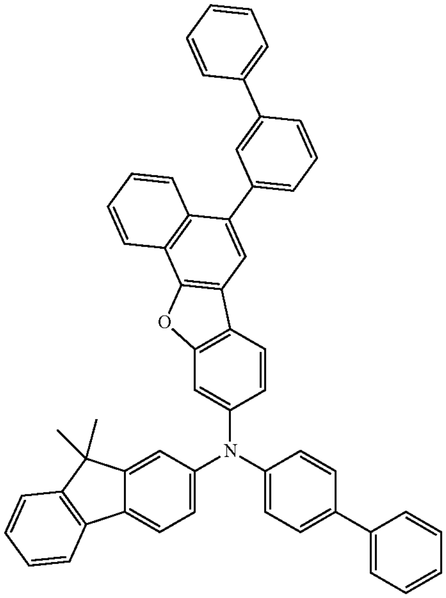
1-208
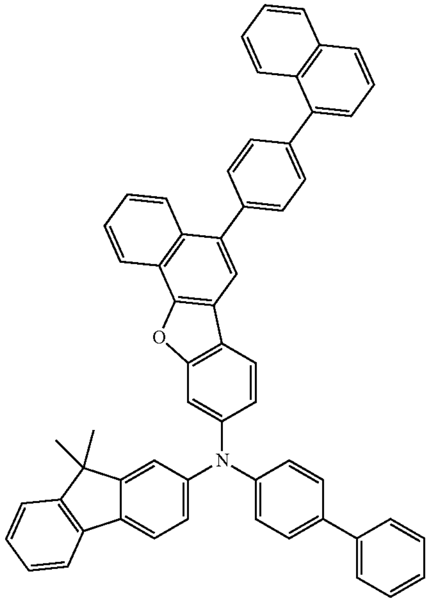
-continued
1-209
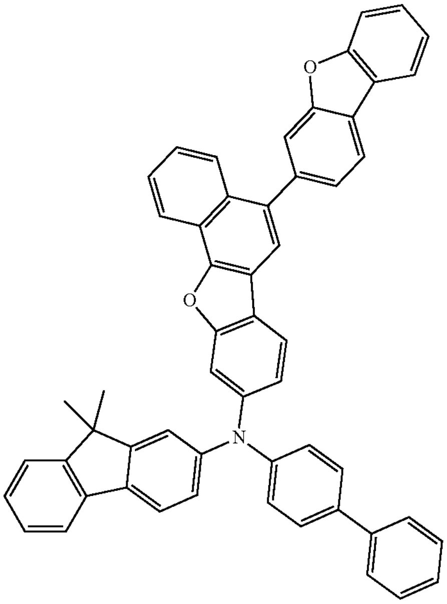
1-210
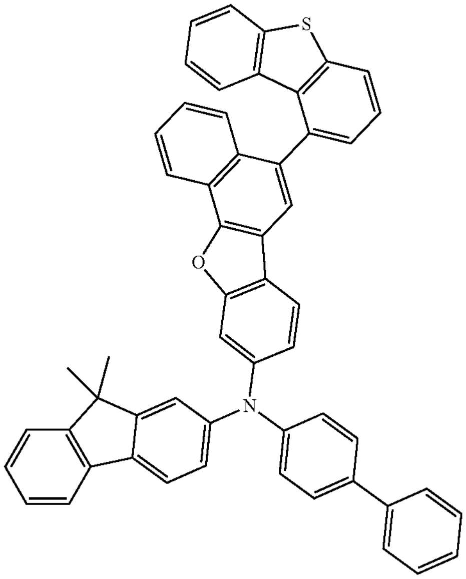

-continued
1-211
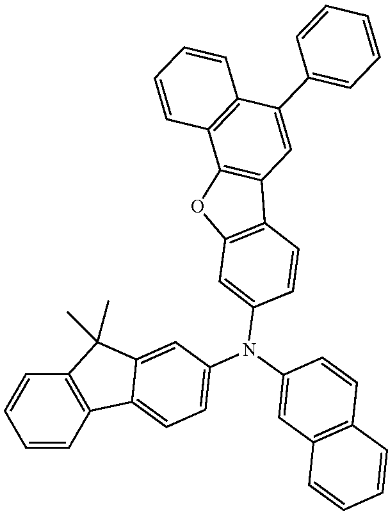
1-212
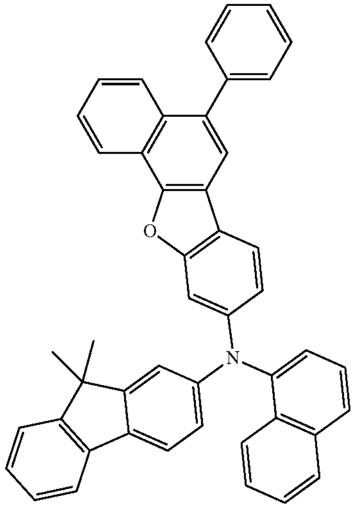
1-213
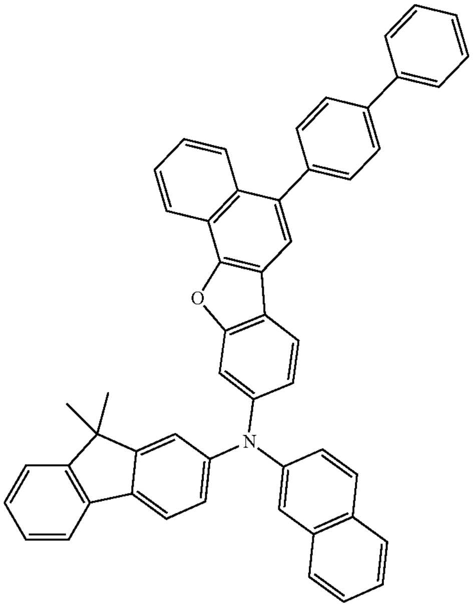
-continued
1-214
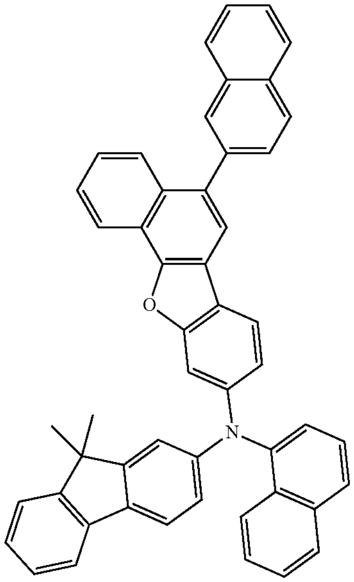
1-215
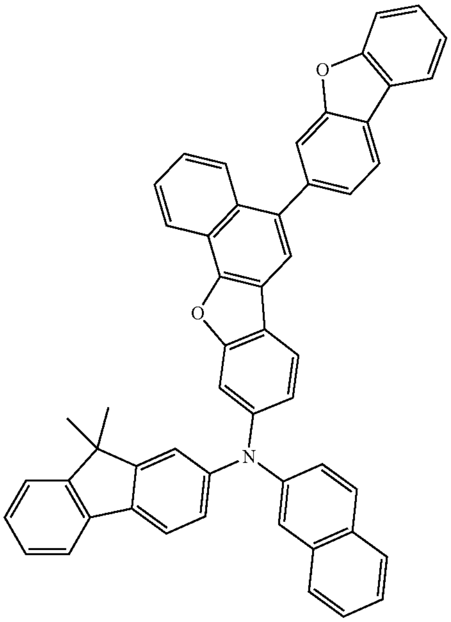

-continued
1-216
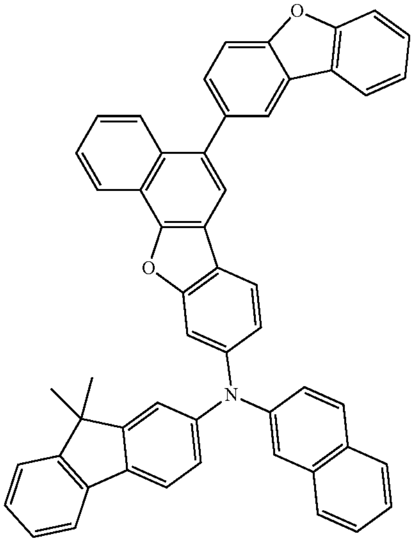
1-217
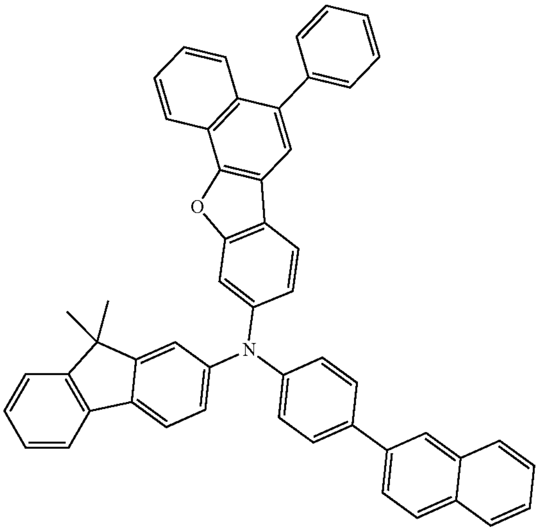
1-218
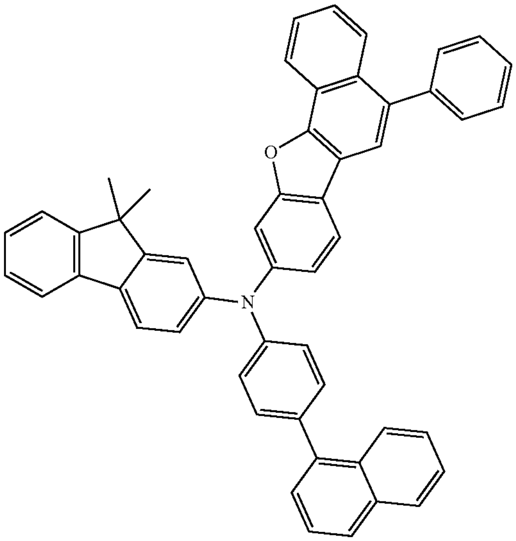
-continued
1-219
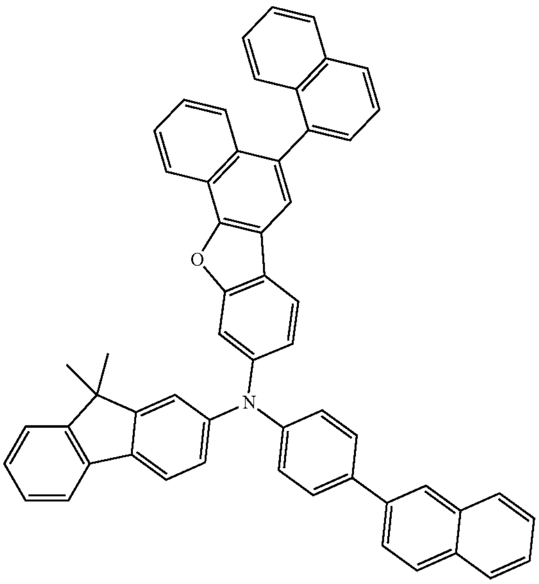
1-220
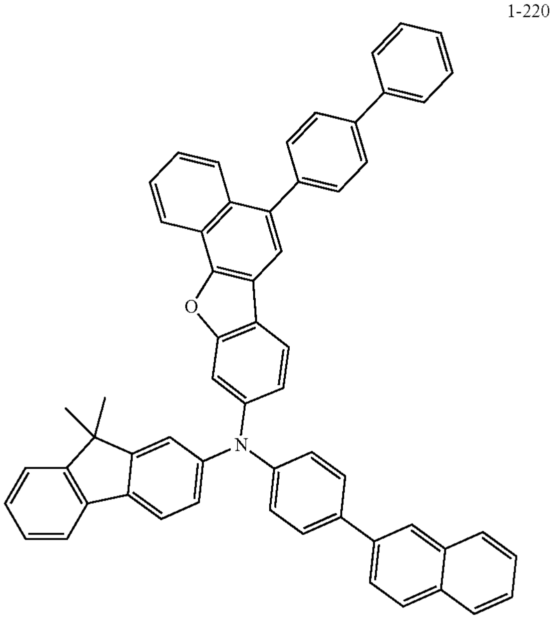

-continued
1-221
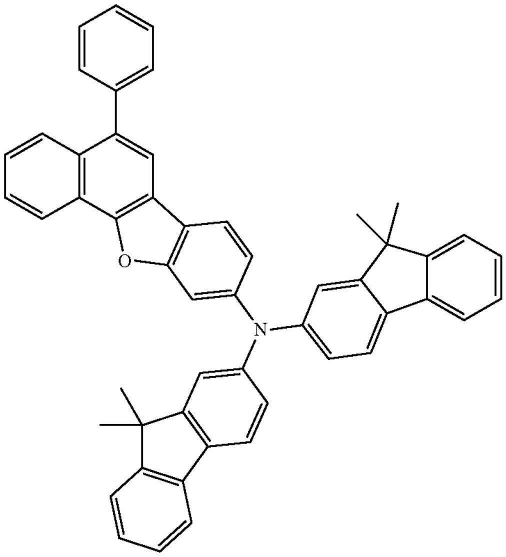
1-222
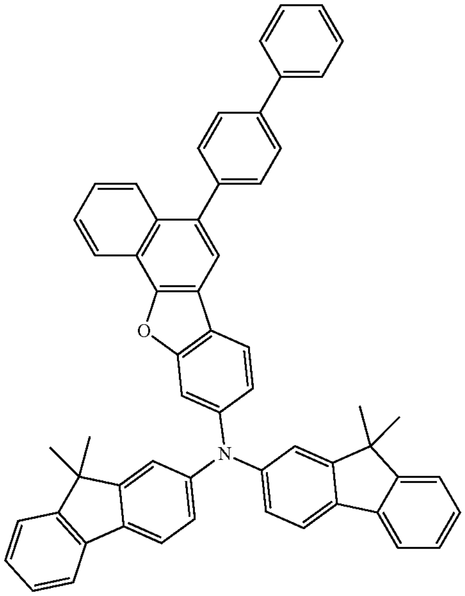
1-223
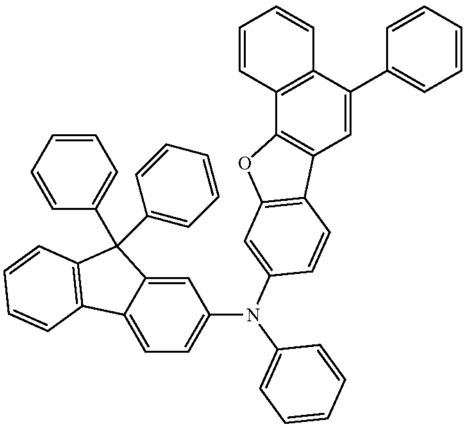
-continued
1-224
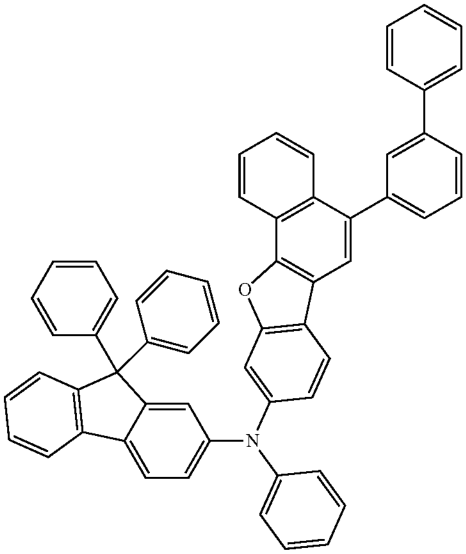
1-225
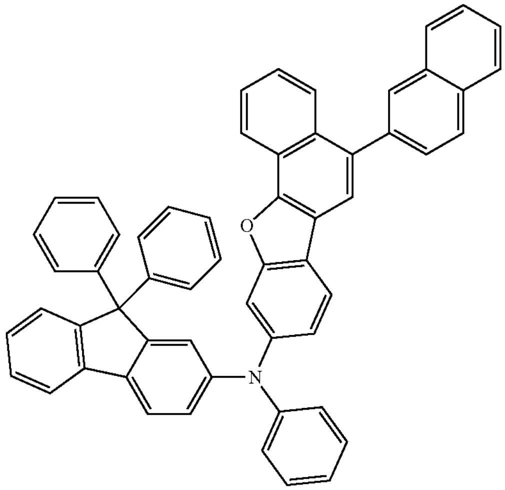
1-226
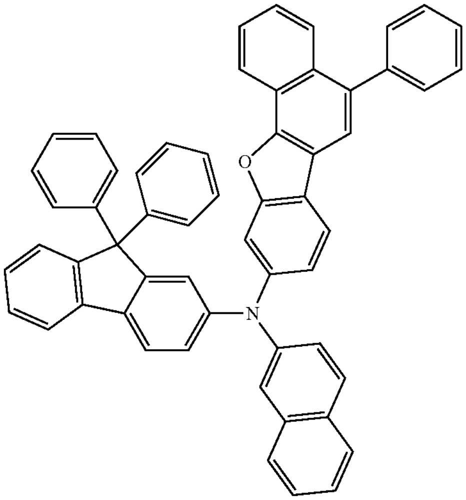

-continued
1-227
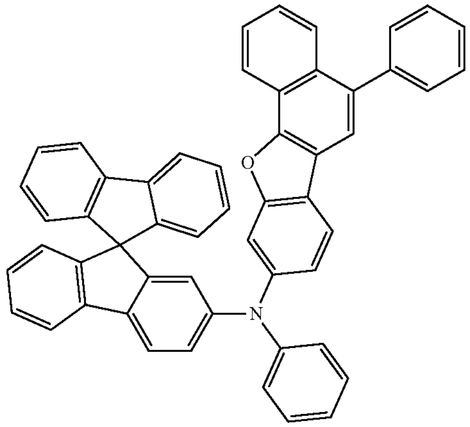
1-228
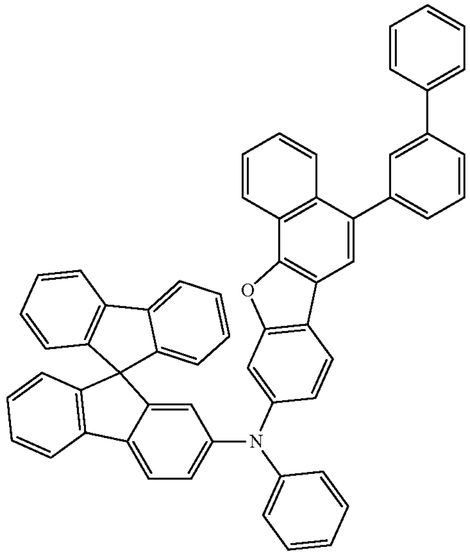
1-229
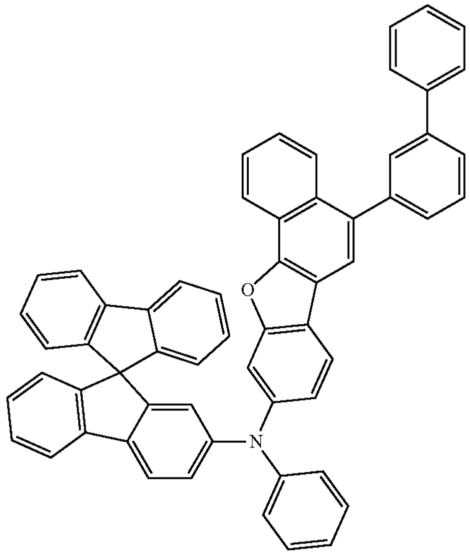
-continued
1-230
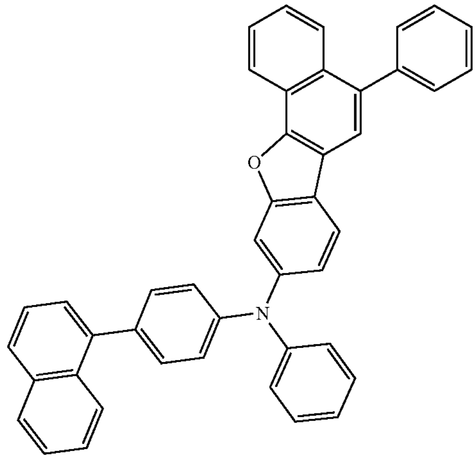
1-231
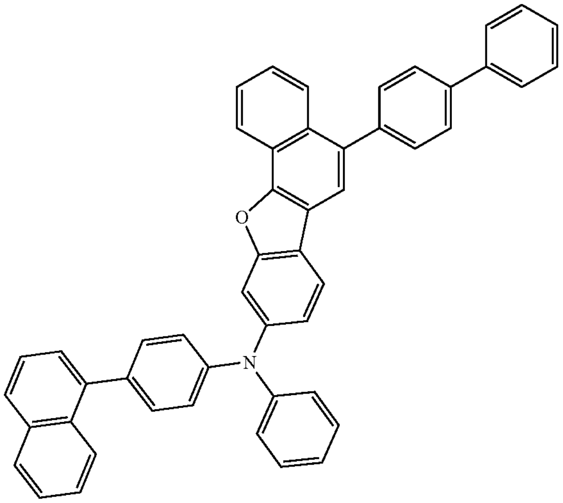
1-232
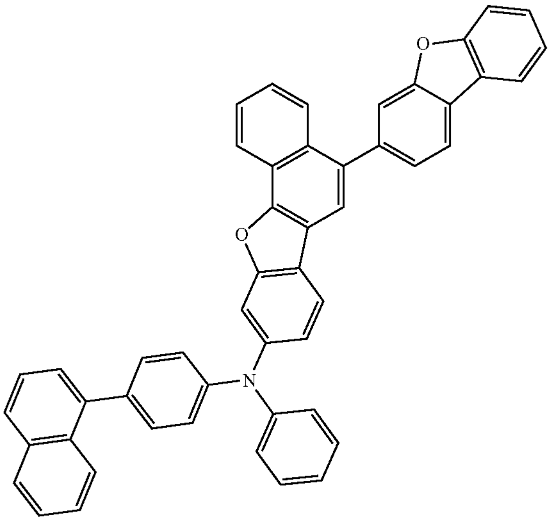

-continued
1-233
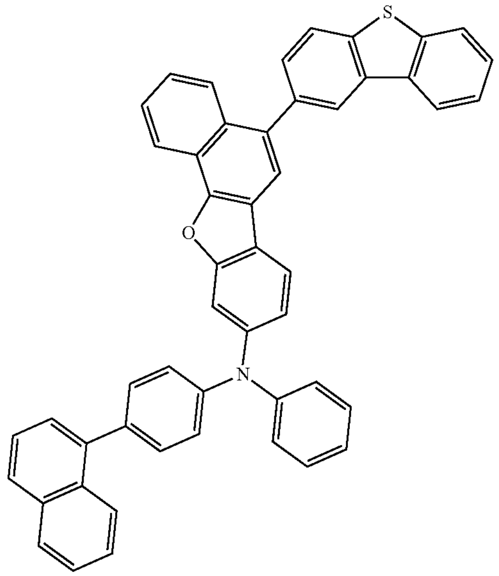
1-235
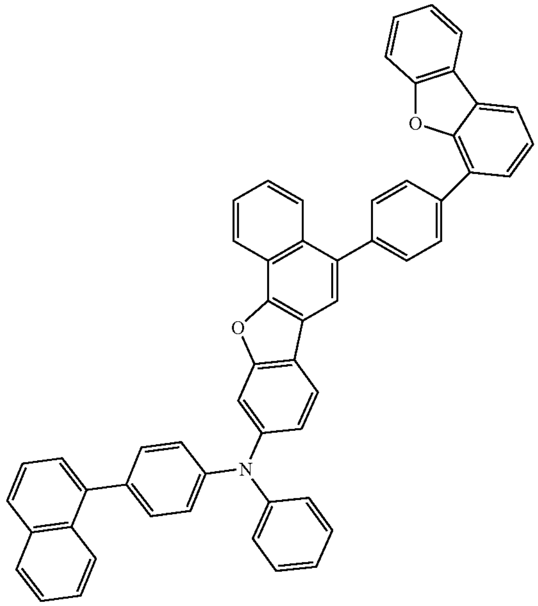
1-234
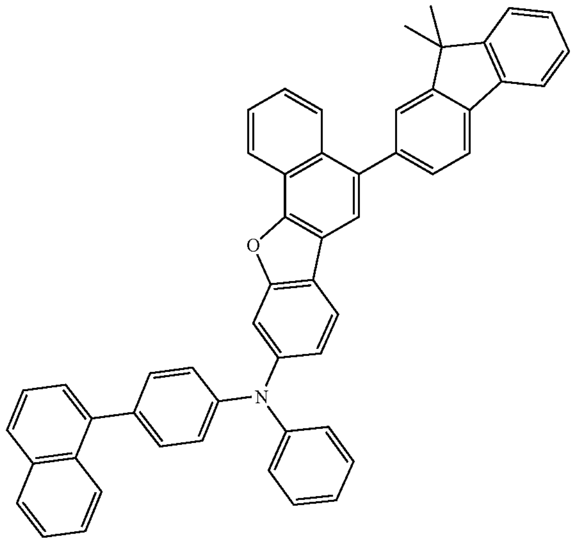
1-236
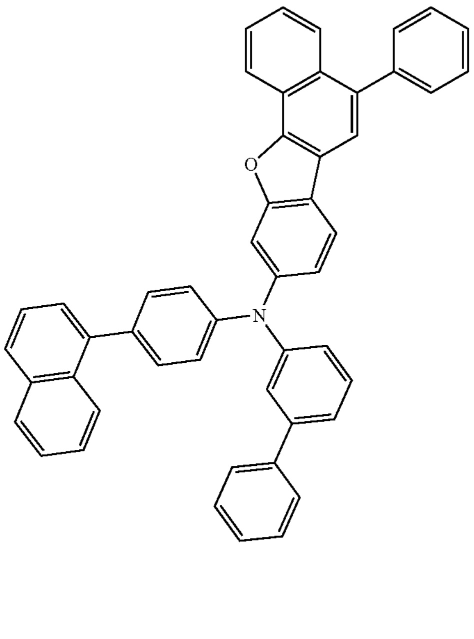

-continued
1-237
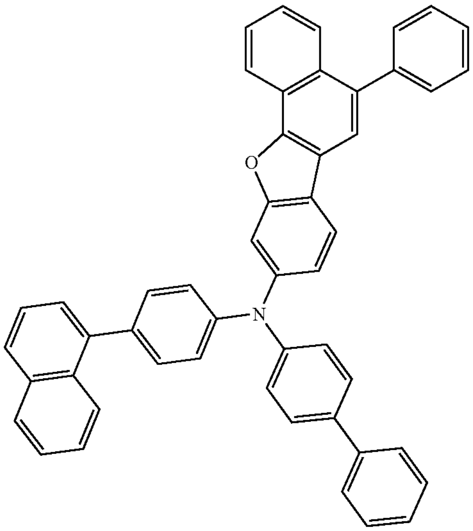
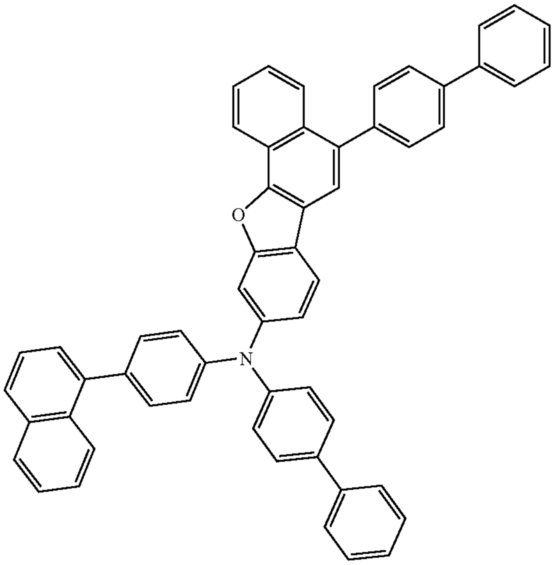
1-239
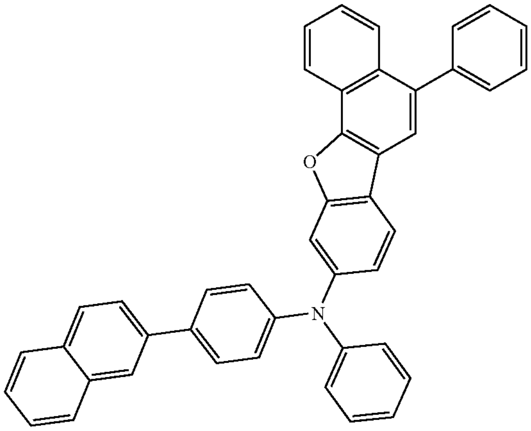
-continued
1-240
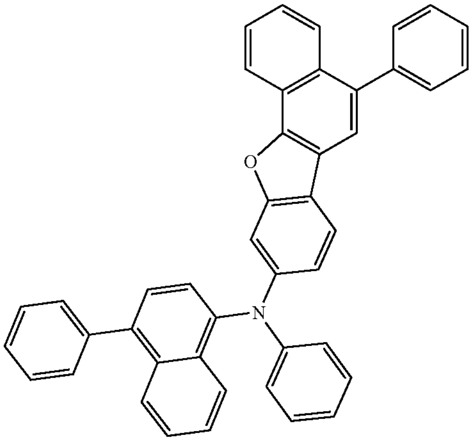
1-241
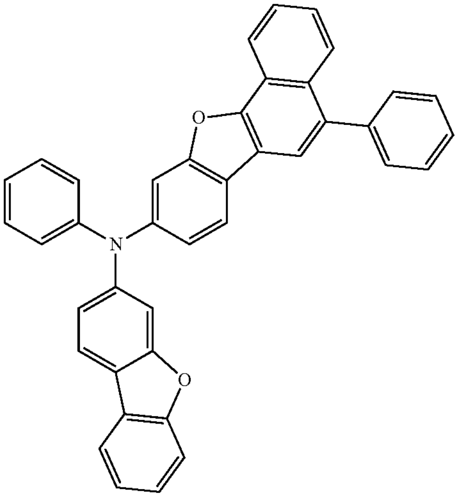
1-242
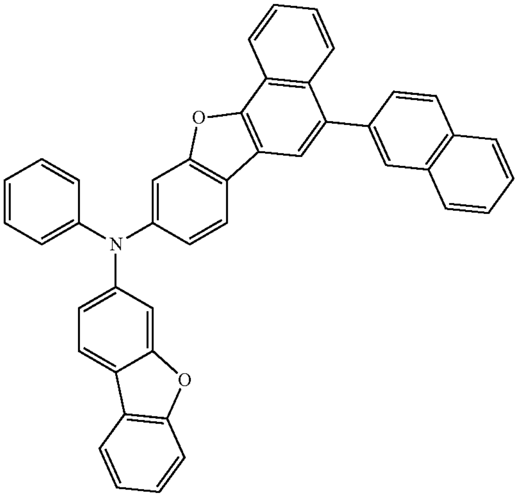

-continued
1-243
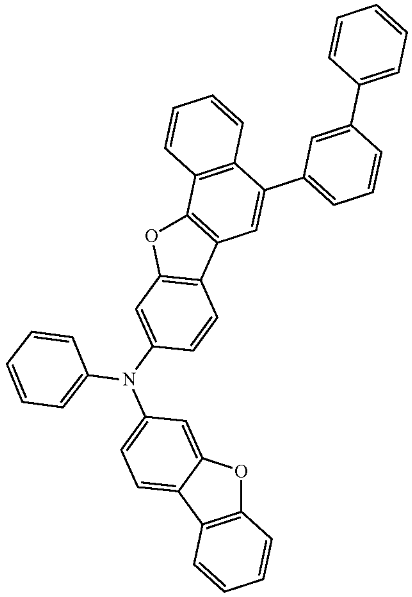
1-244
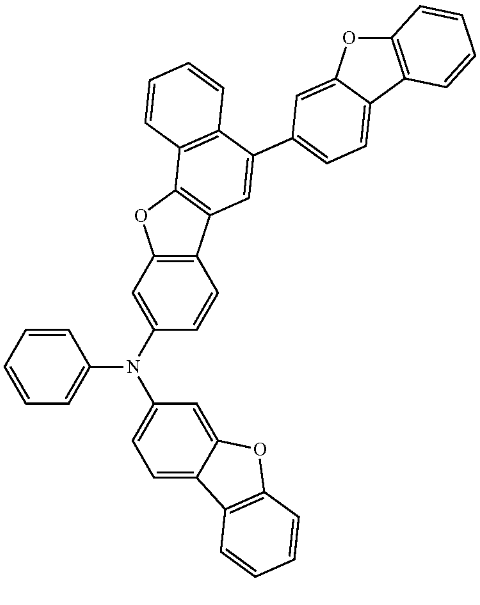
-continued
1-245
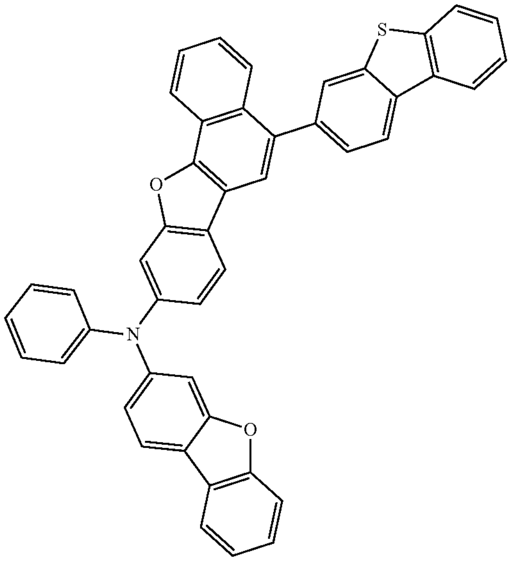
1-246
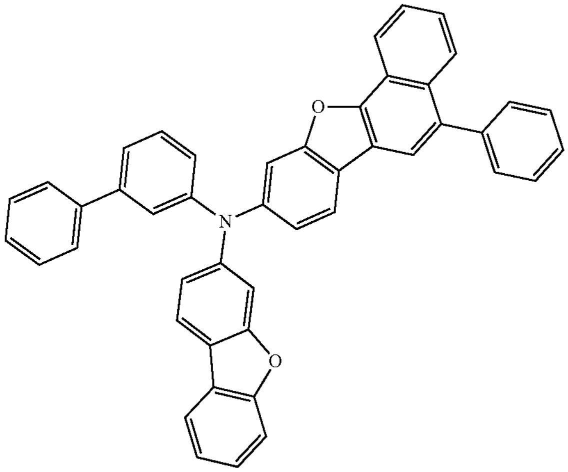
1-247
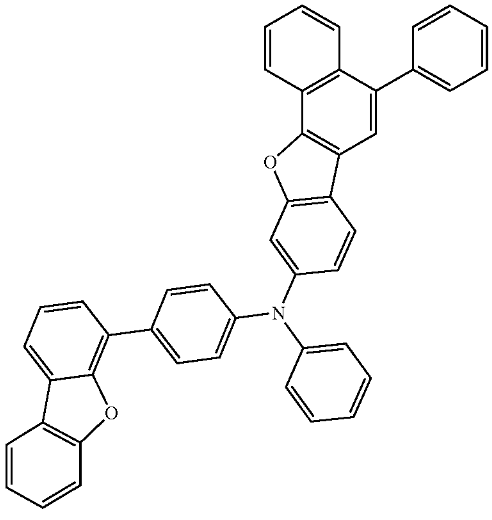

-continued
1-248
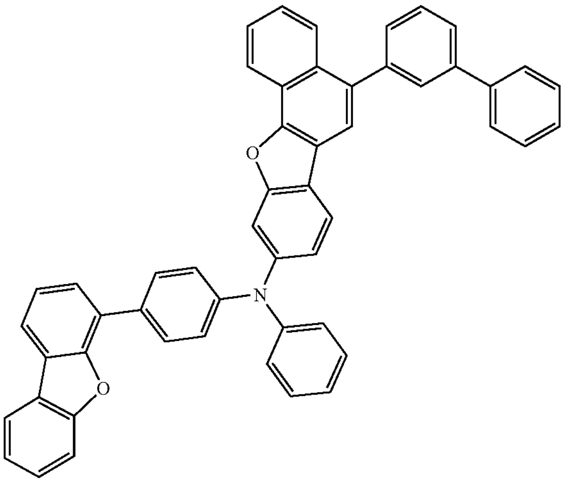
1-249
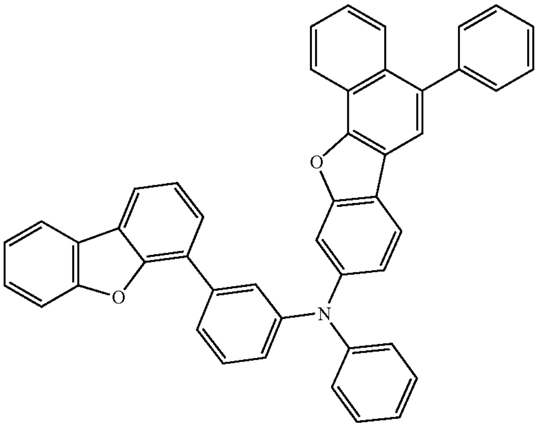
1-250
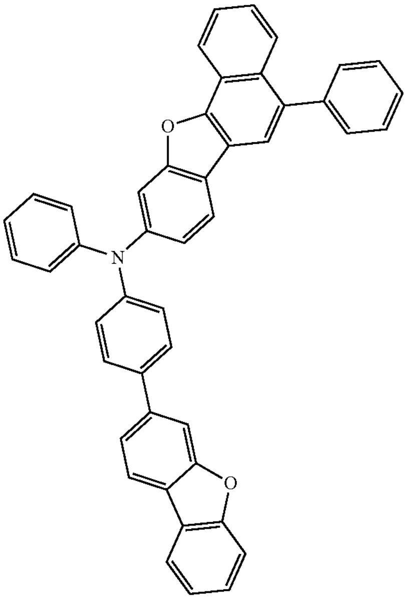
-continued
1-251
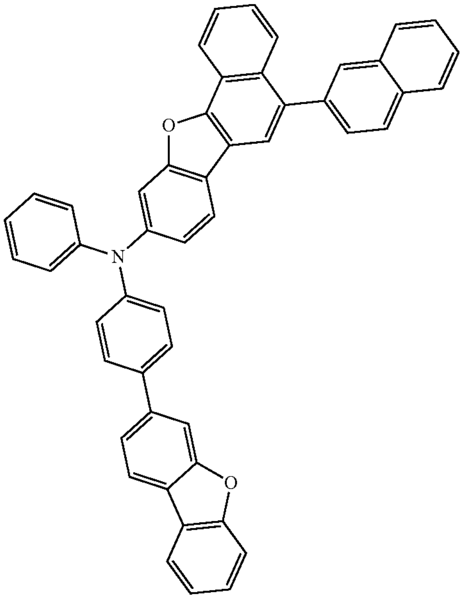
1-252
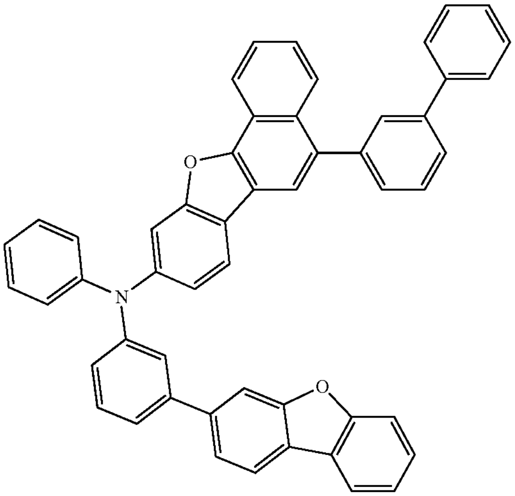

1-253
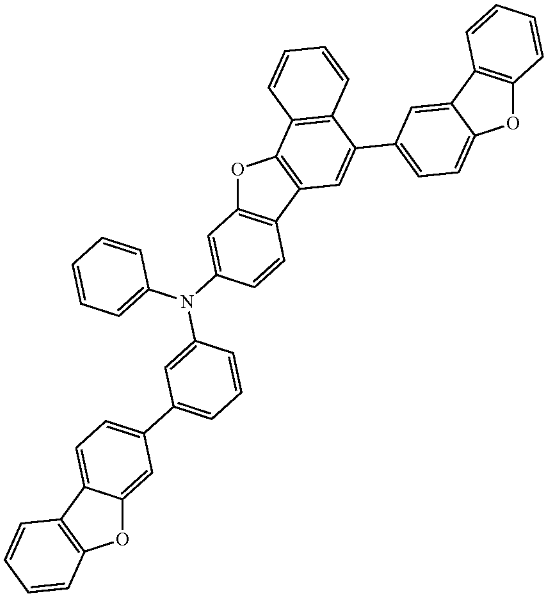
1-254
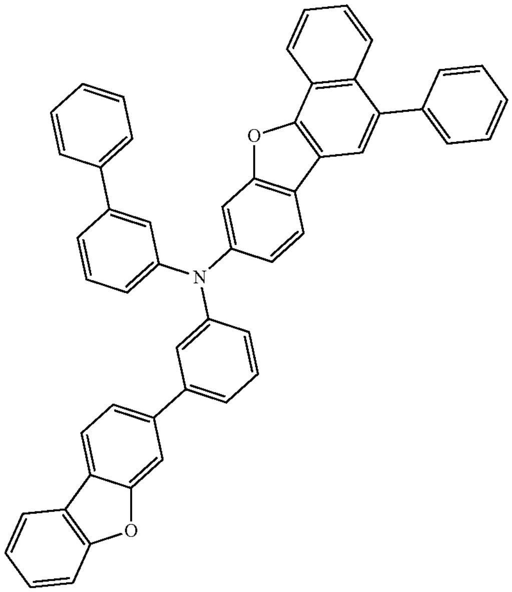
1-255
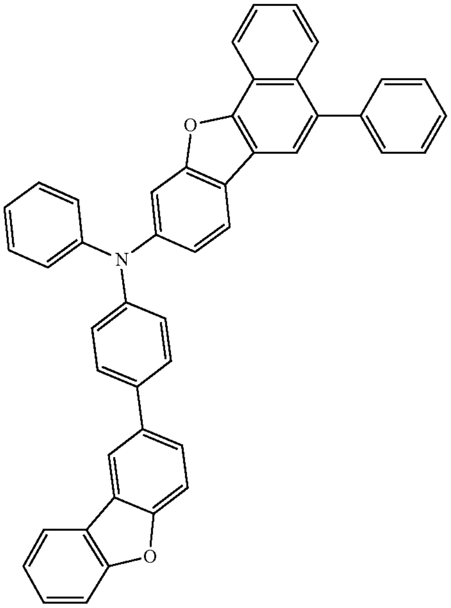
1-256
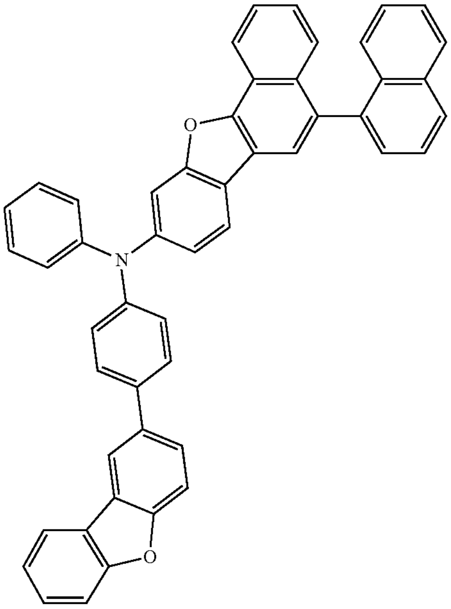

-continued
1-257
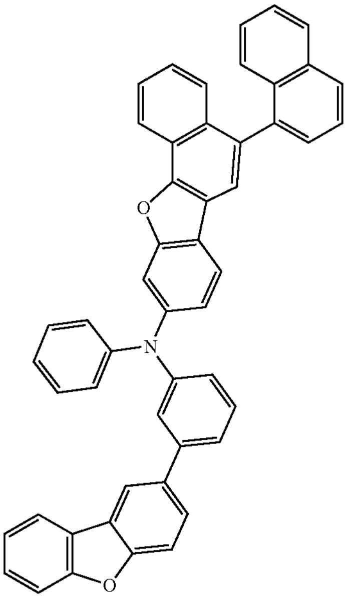
1-258
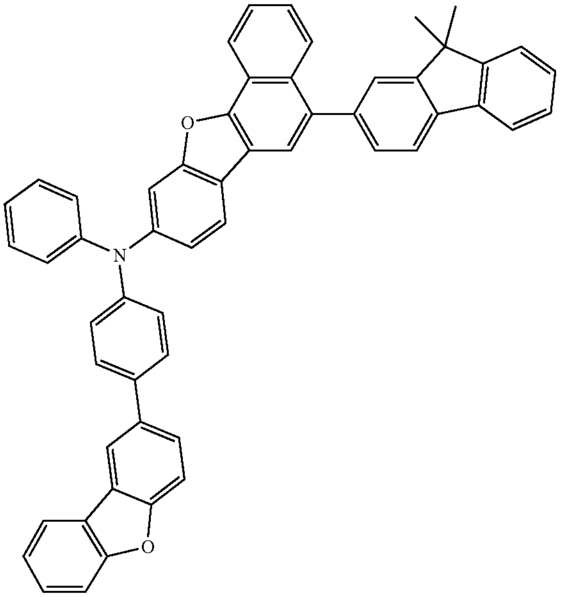
-continued
1-259
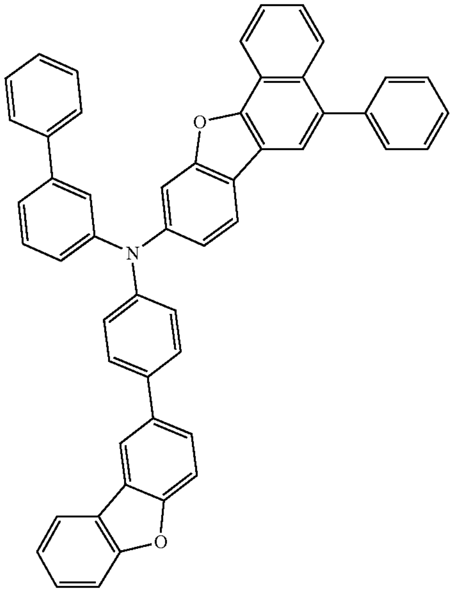
1-260
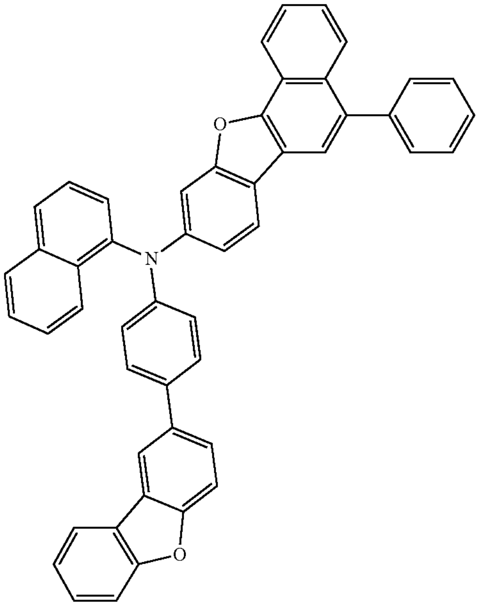

-continued
1-261
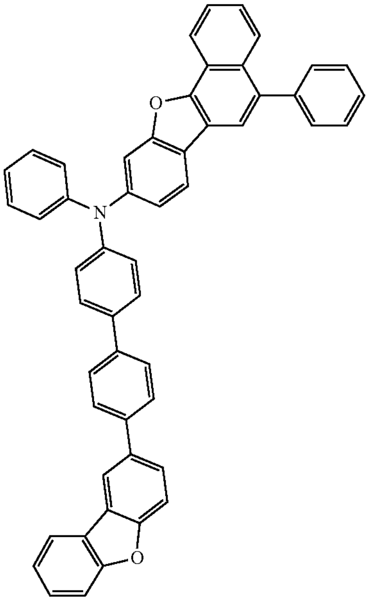
1-262
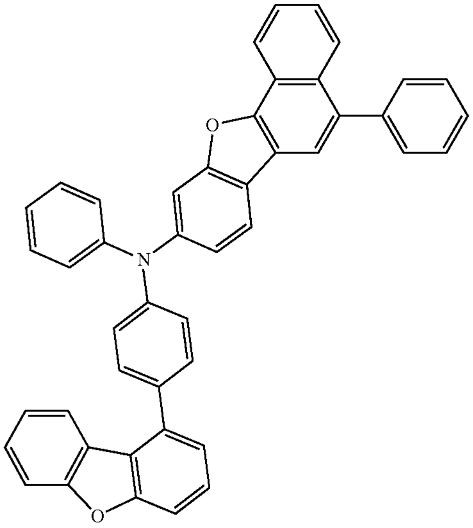
-continued
1-263
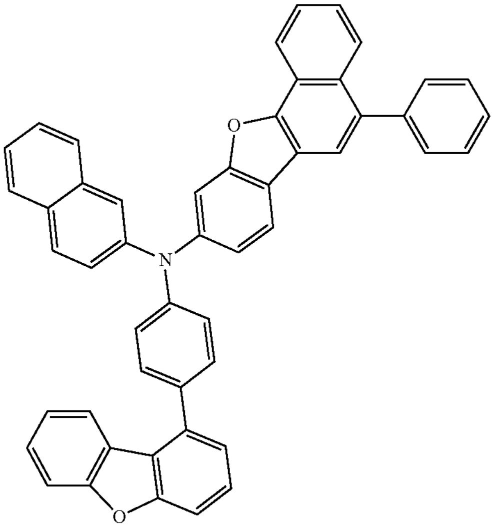
1-264
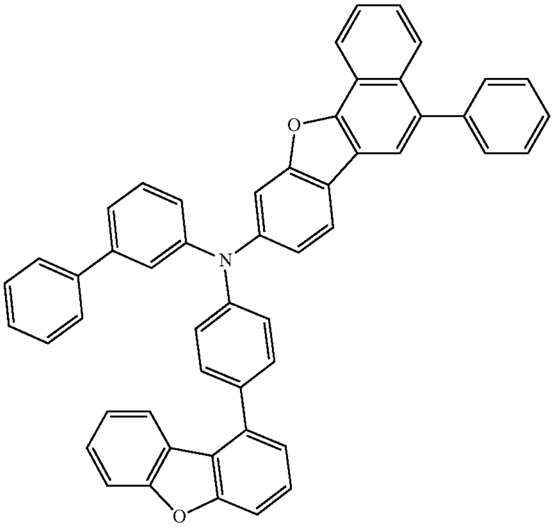
1-265
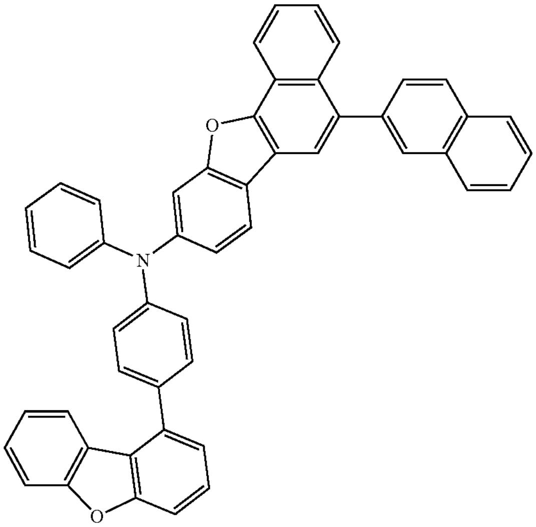

1-266
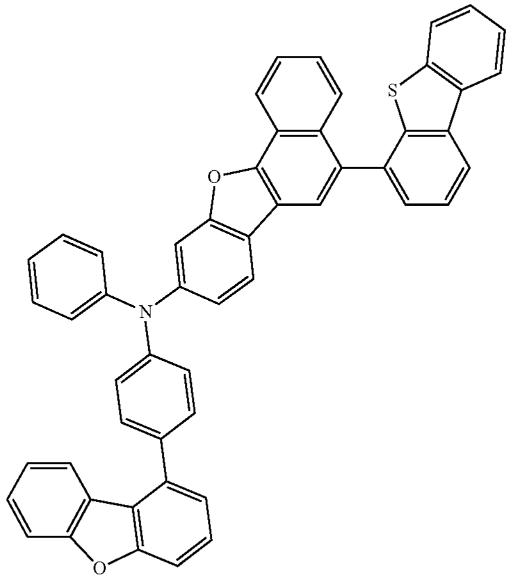
1-267
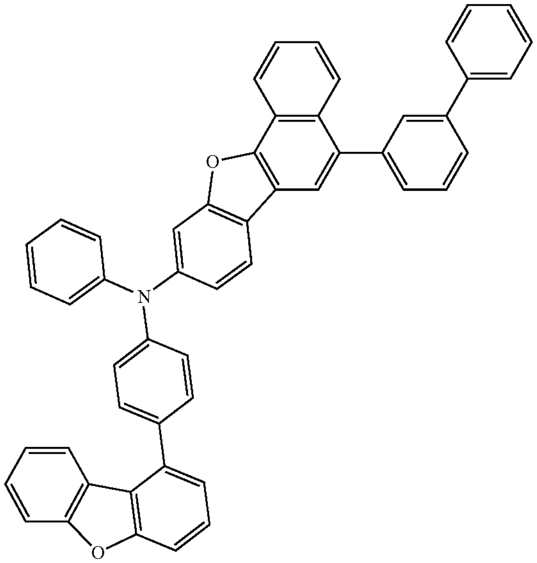
1-268
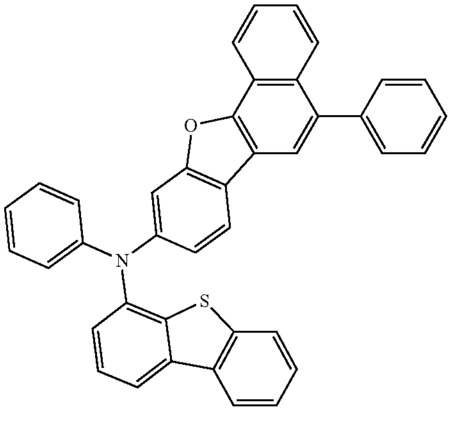
1-269
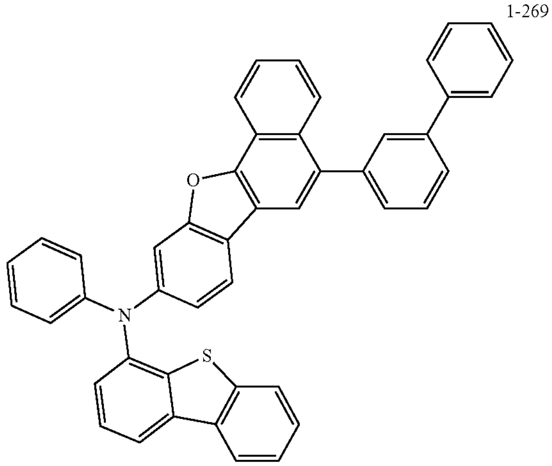
1-270
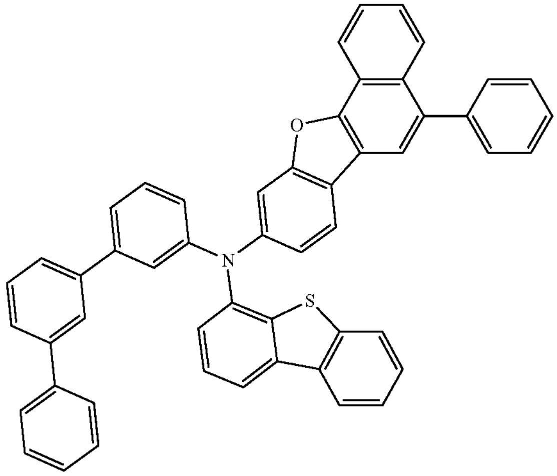
1-271
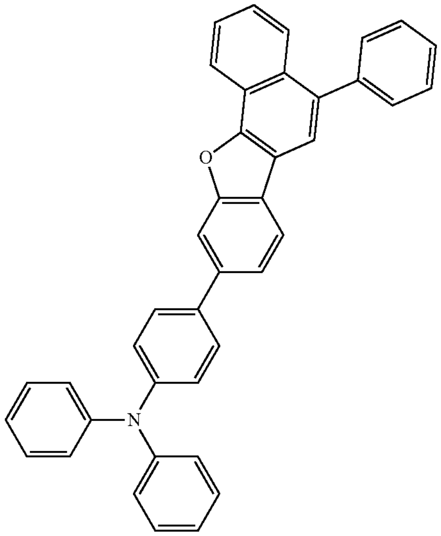

-continued
1-272
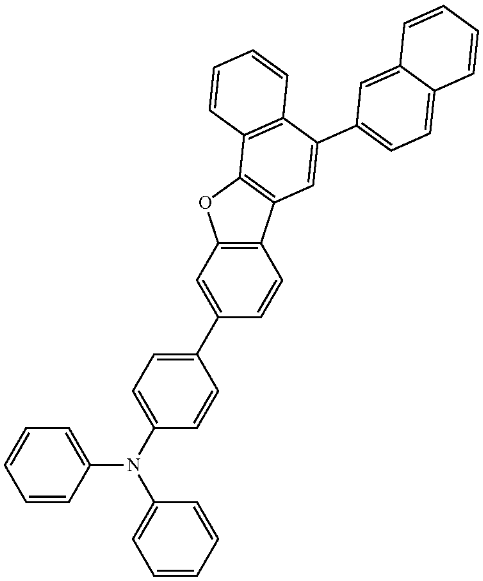
1-273
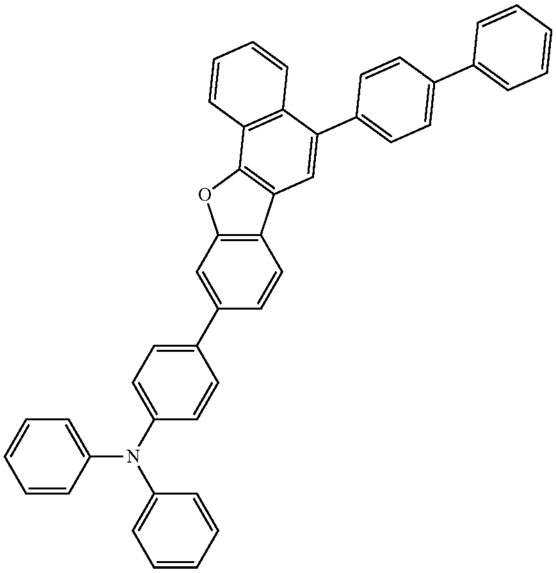
-continued
1-274
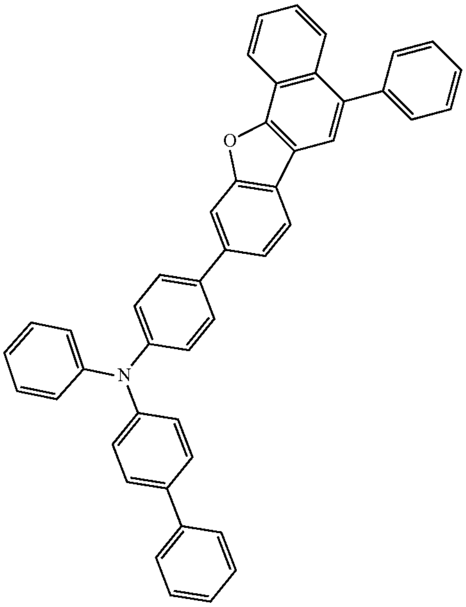
1-275
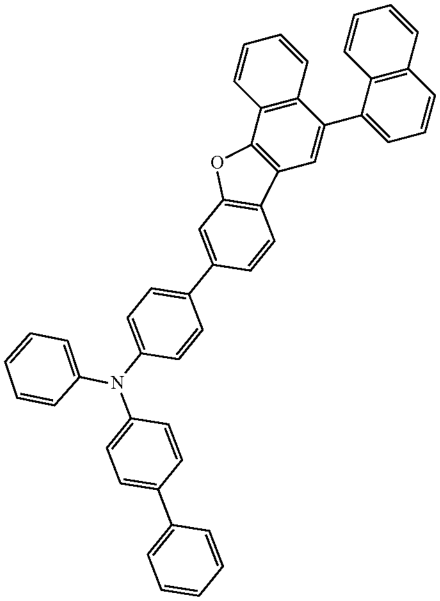

-continued
1-276
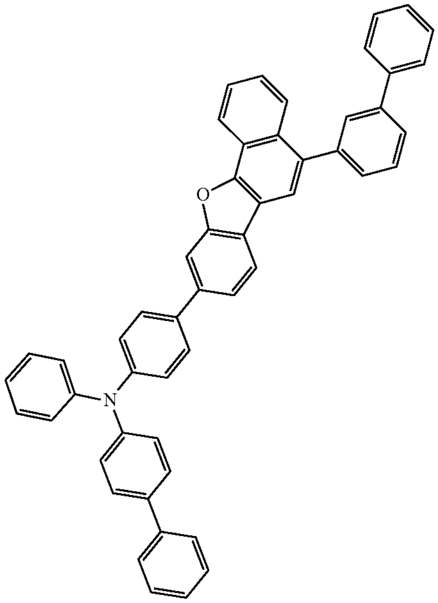
1-277
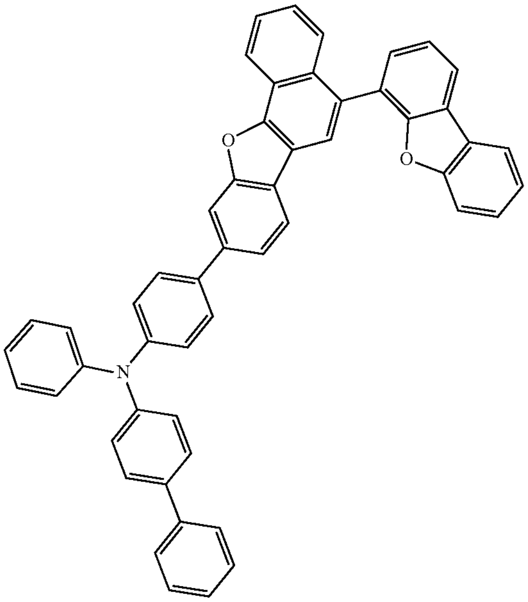
-continued
1-278
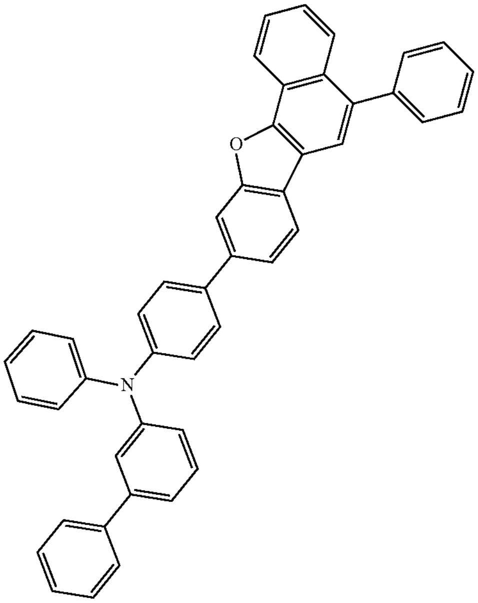
1-279
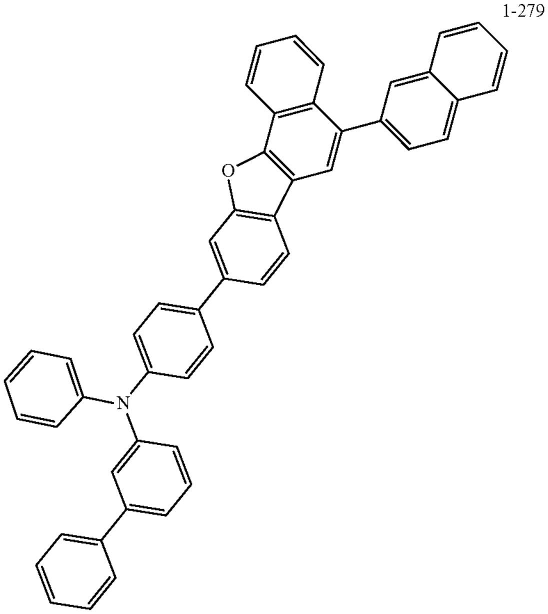

-continued
1-280
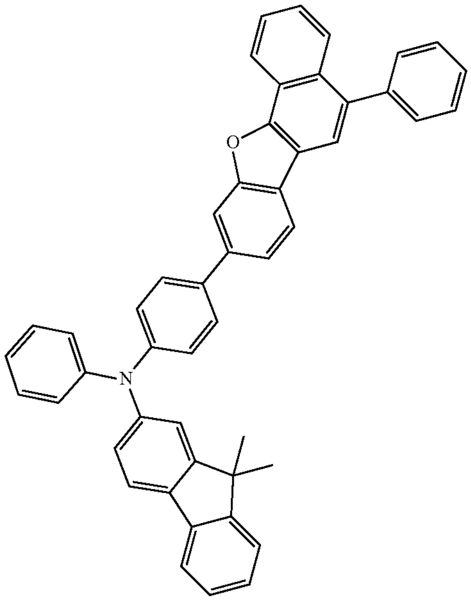
1-281
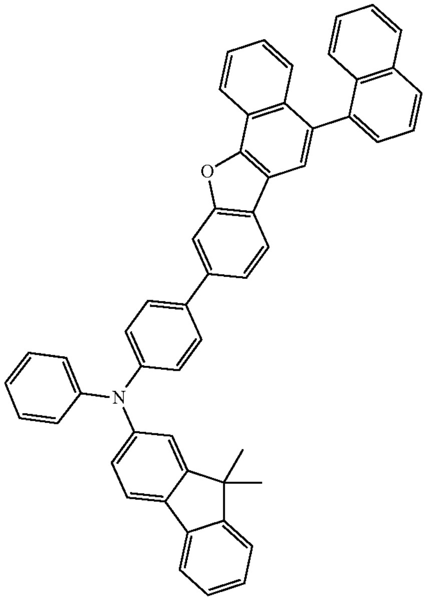
-continued
1-282
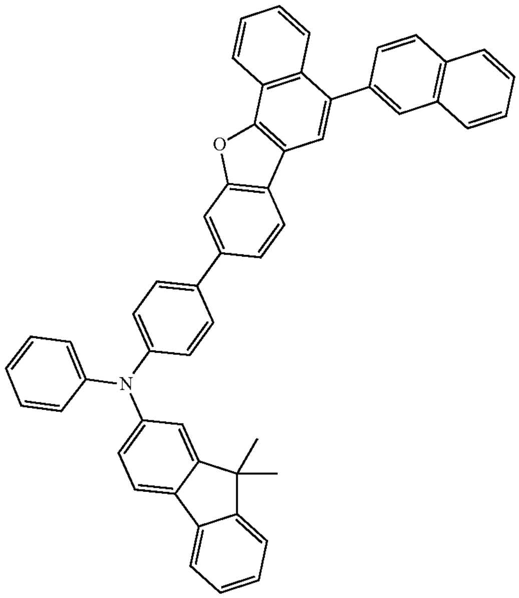
1-283
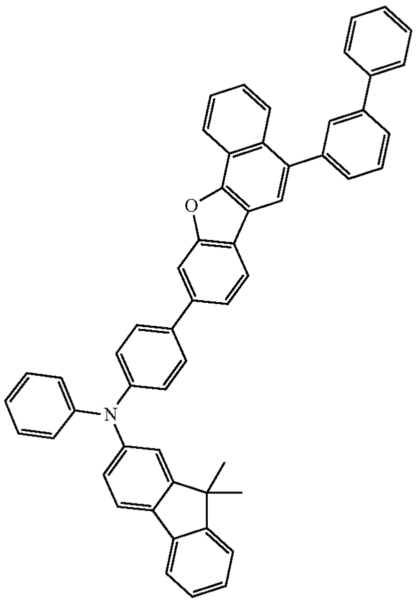

-continued
1-284
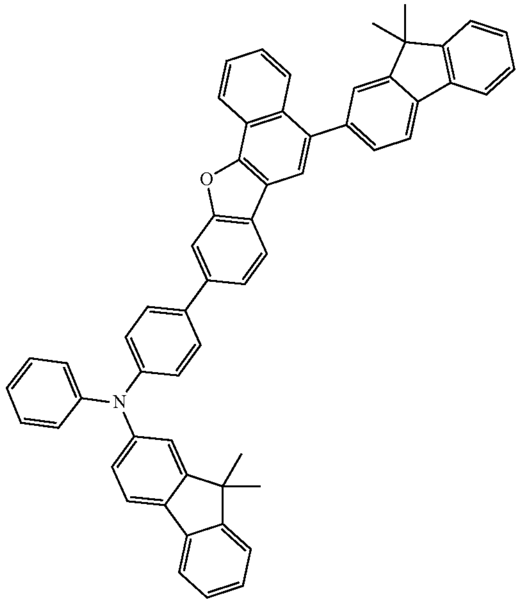
1-285
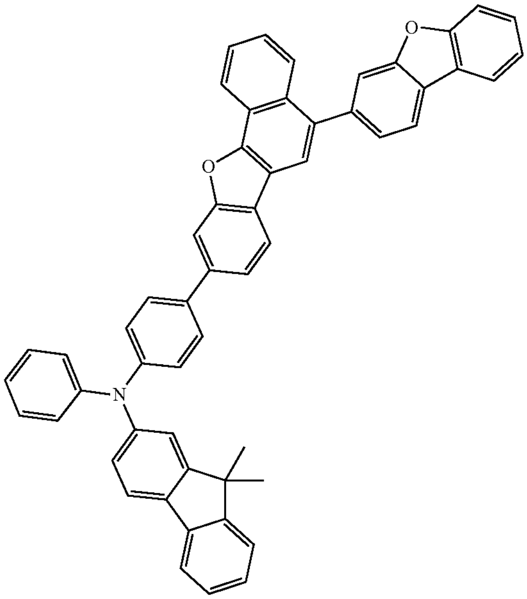
-continued
1-286
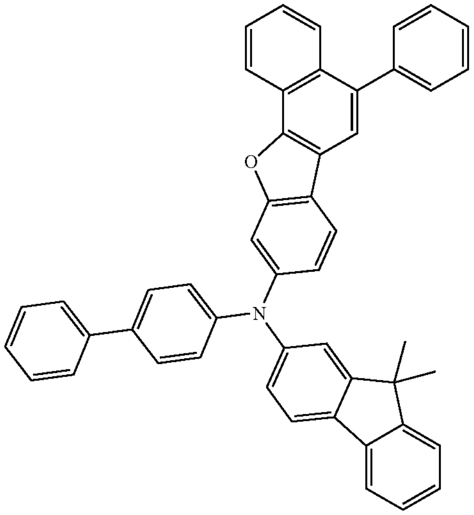
1-287
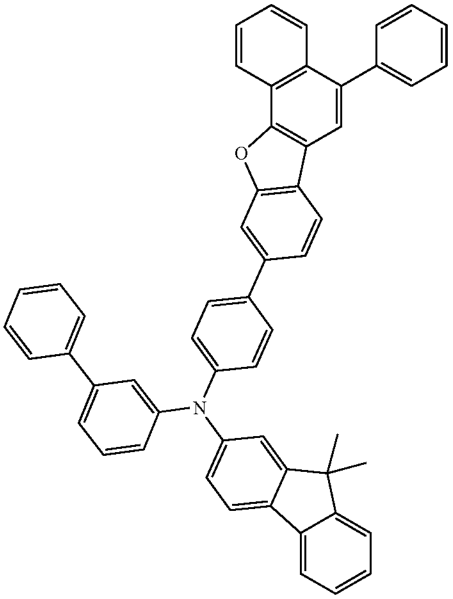

-continued
1-288
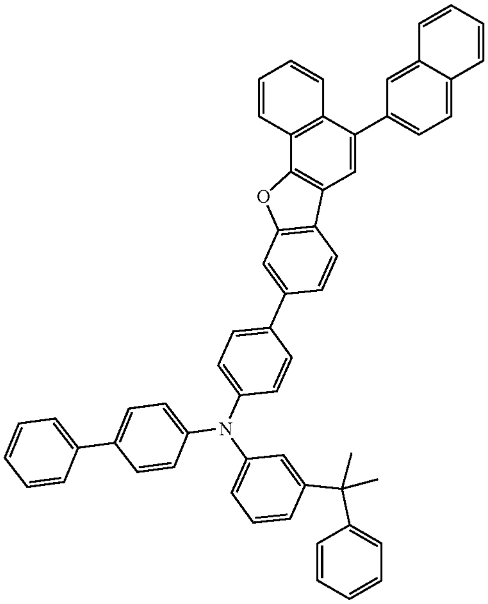
1-289
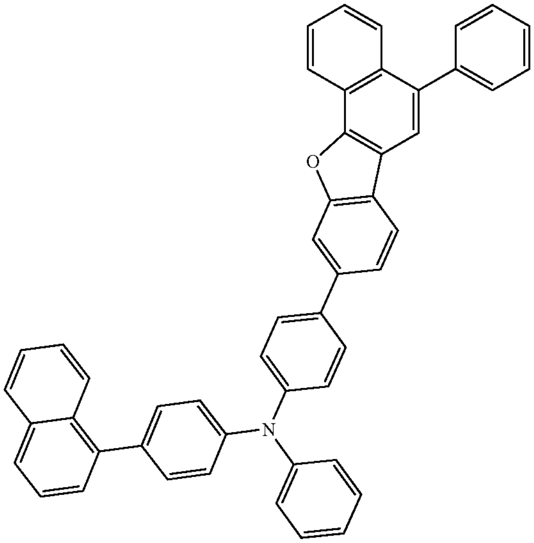
-continued
1-290
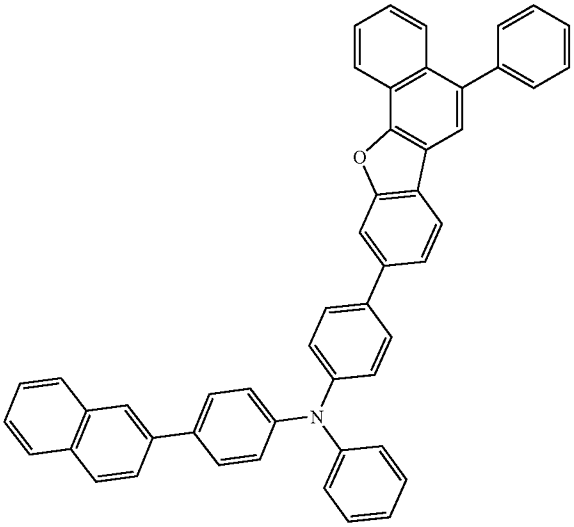
1-291
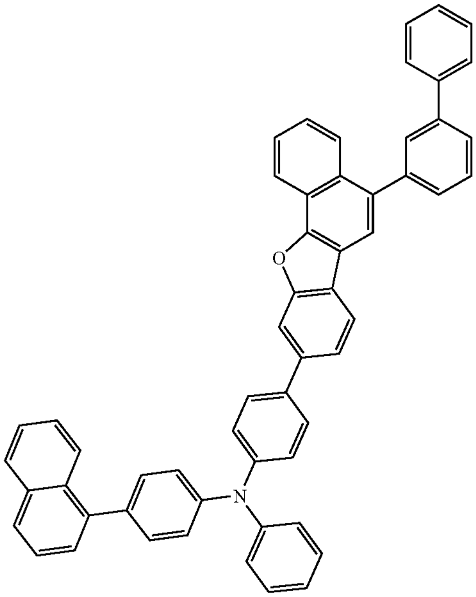

-continued
1-292
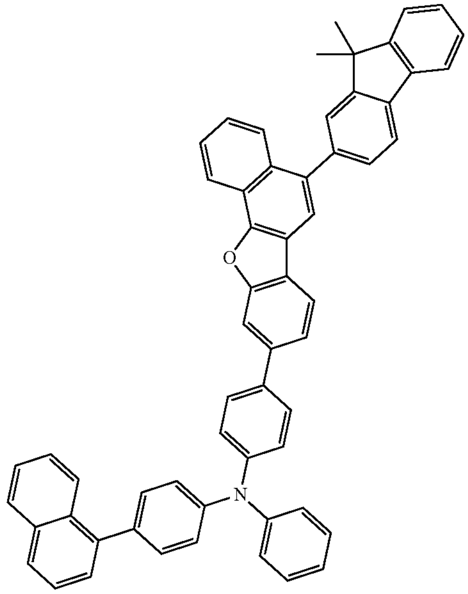
1-293
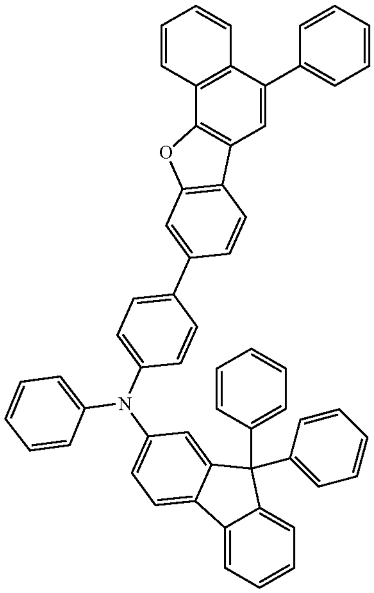
-continued
1-294
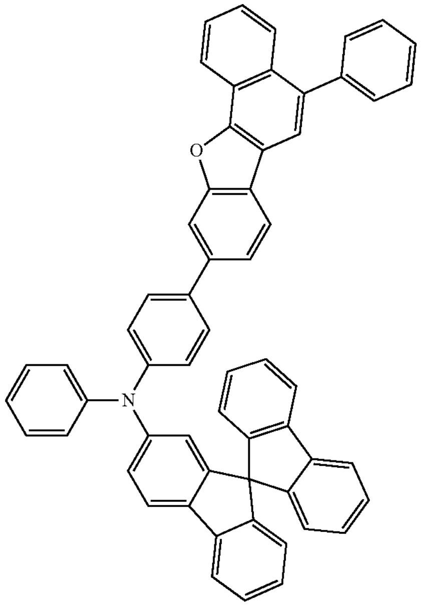
1-295
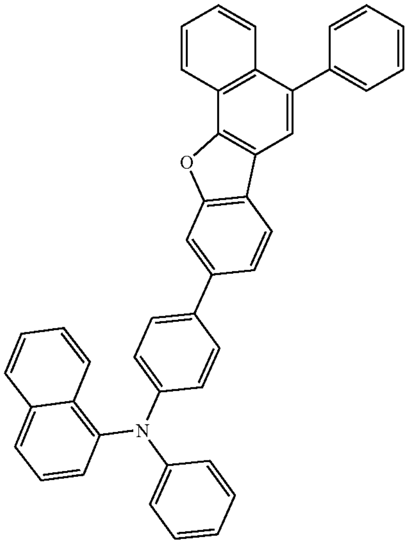

-continued
1-296
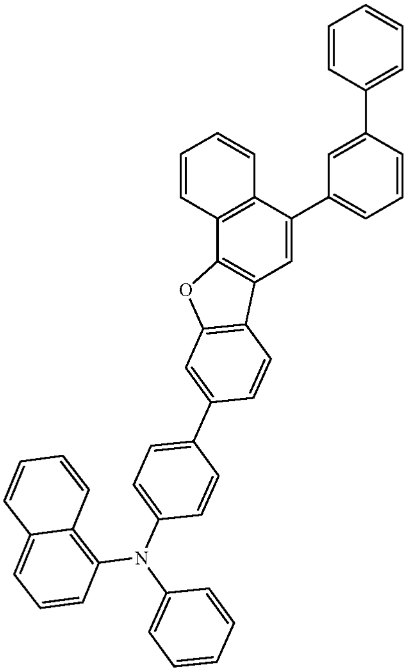
1-297
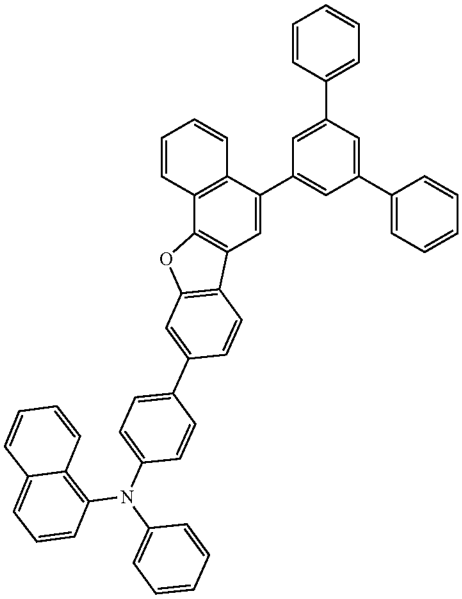
-continued
1-298
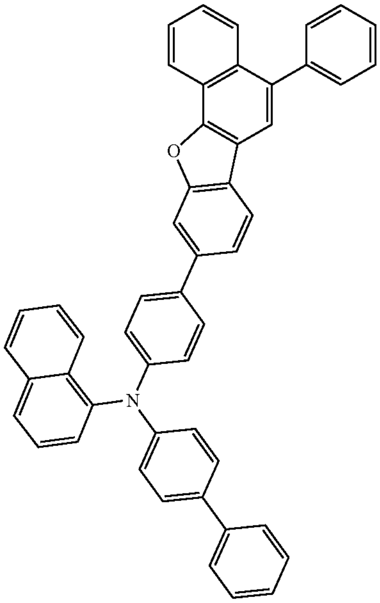
1-299
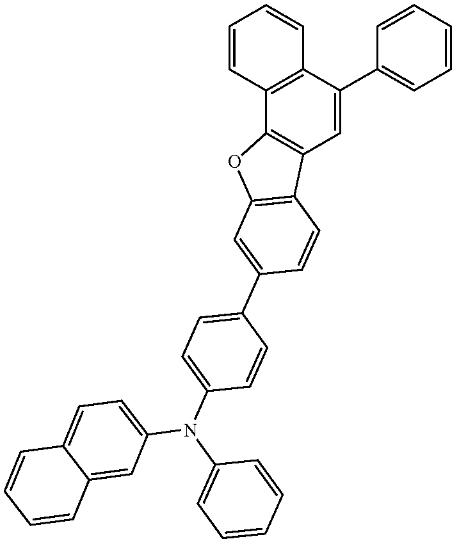

-continued
1-300
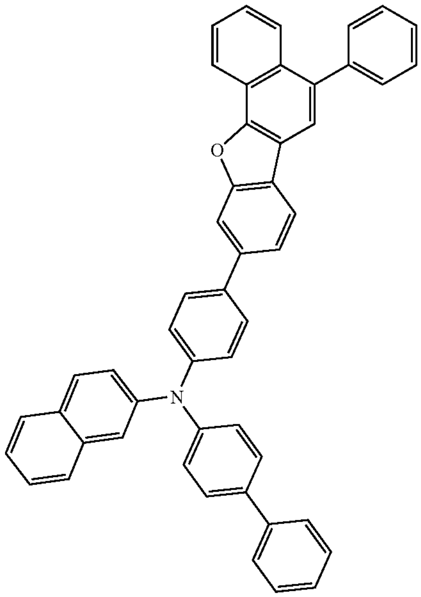
1-301
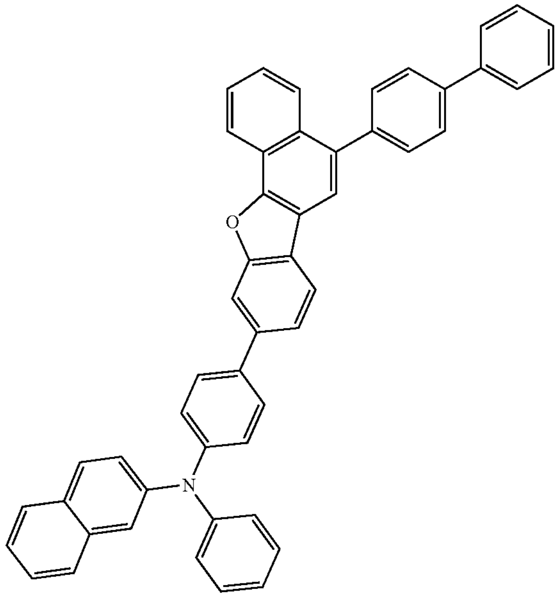
-continued
1-302
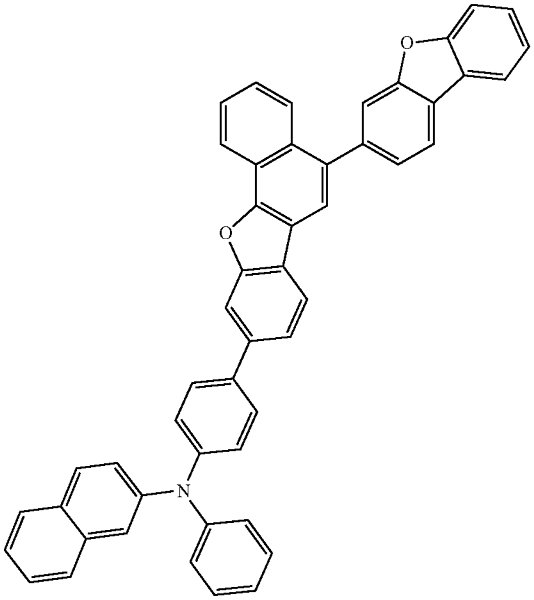
1-303
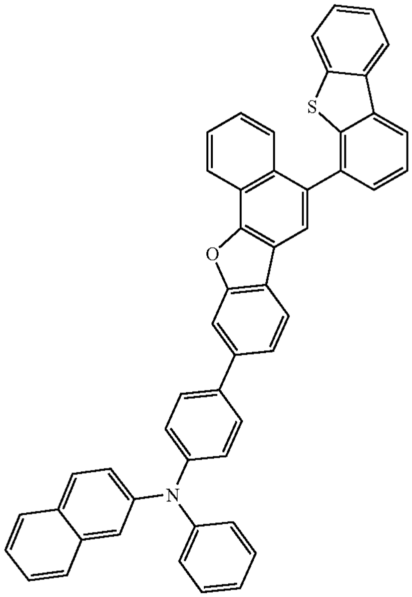

-continued
1-304
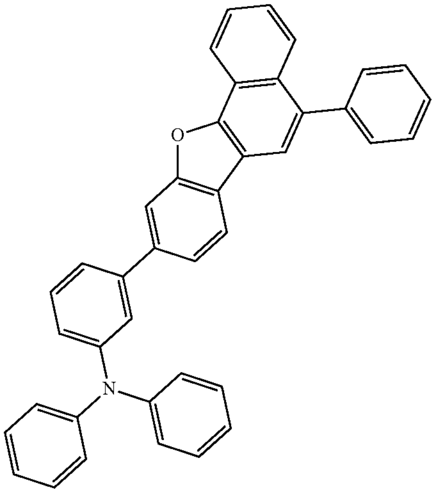
1-305
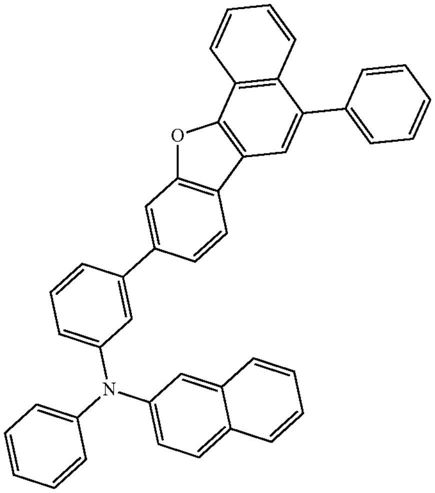
1-306
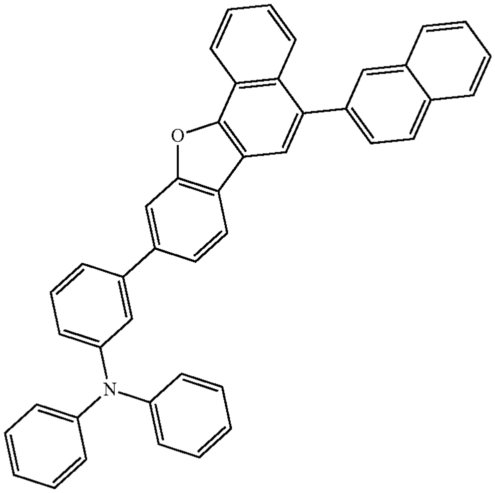
-continued
1-307
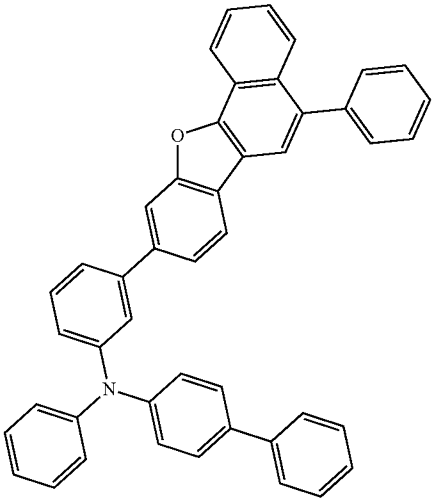
1-308
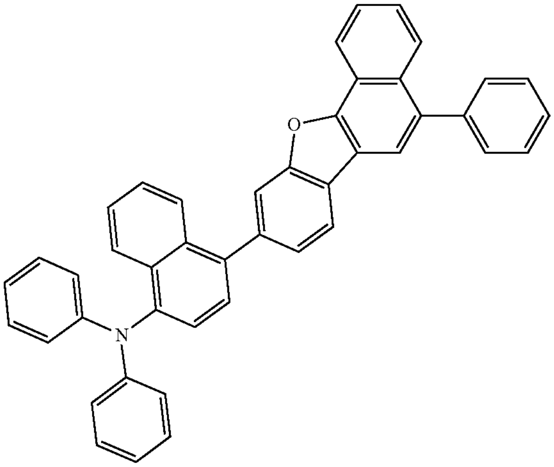
1-309
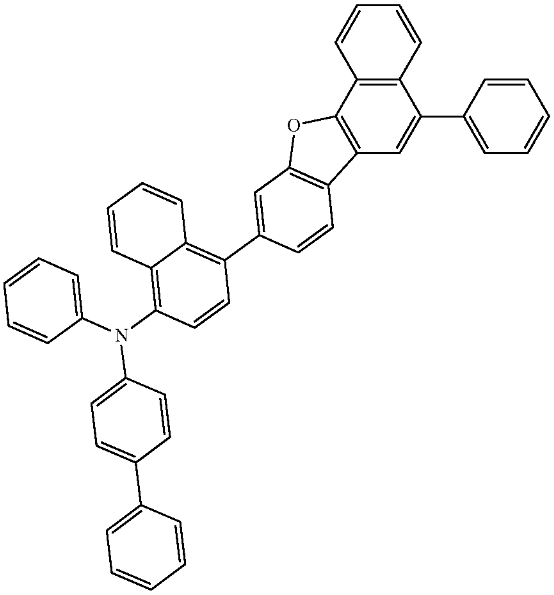

-continued
1-310
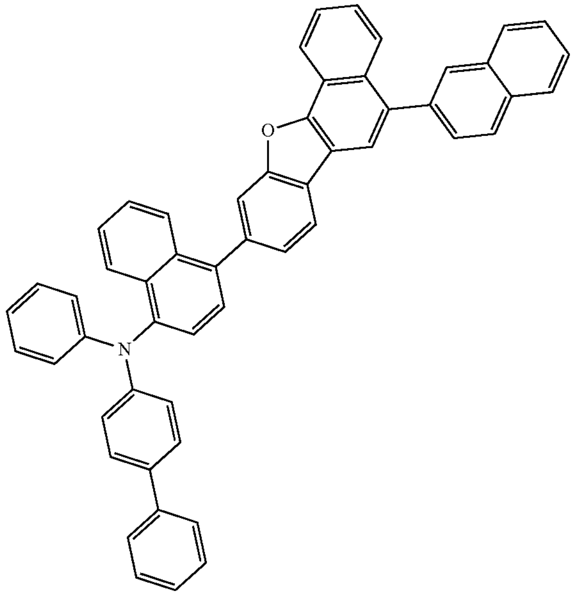
1-311
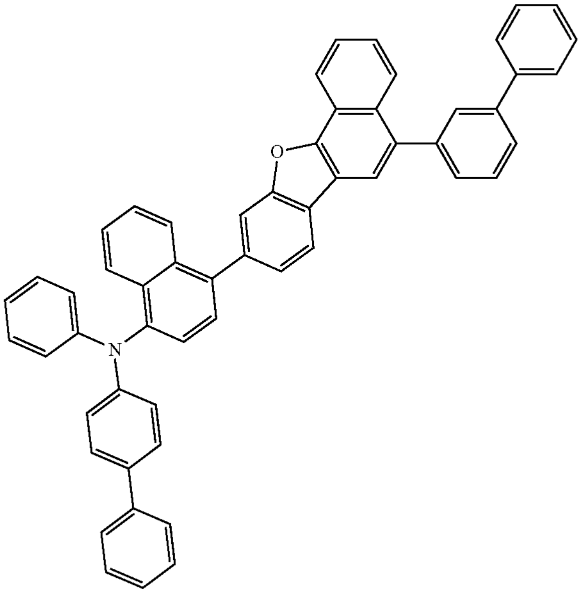
-continued
1-312
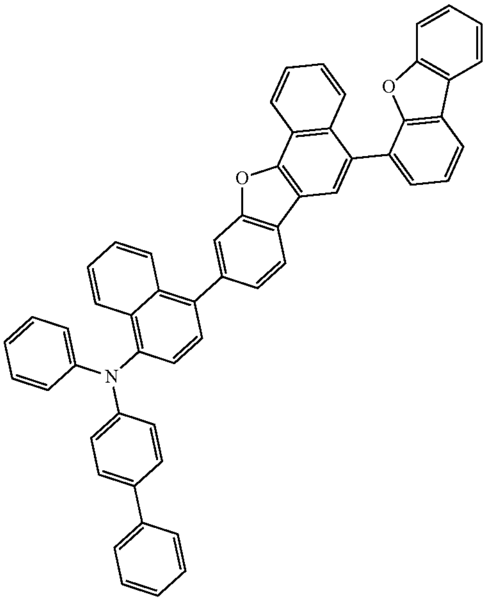
1-313
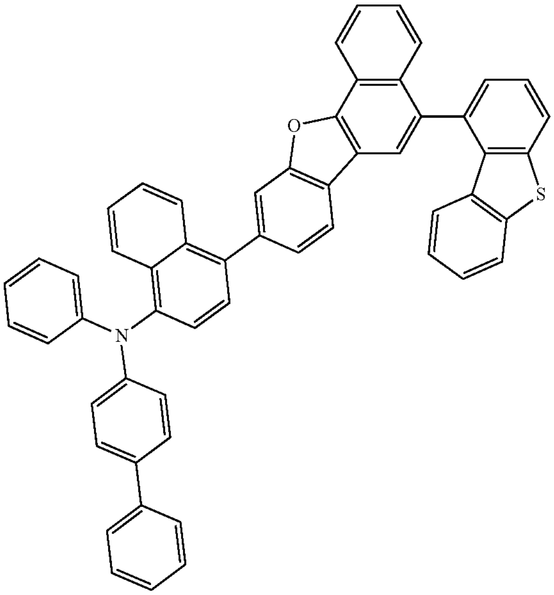

-continued
1-314
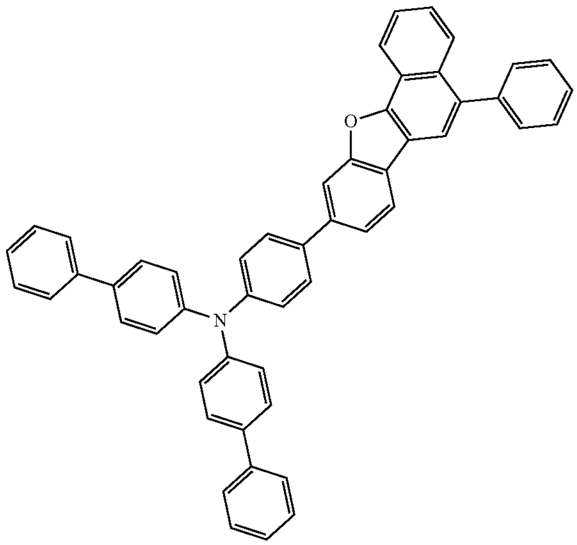
1-315
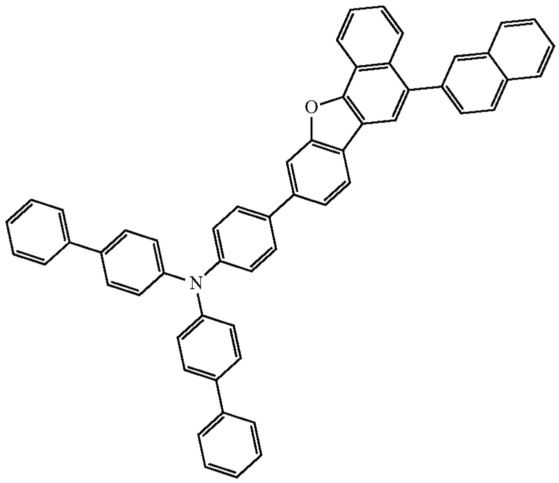
1-316
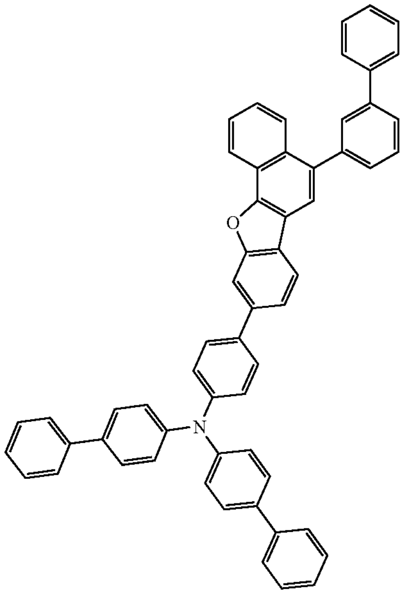
-continued
1-317
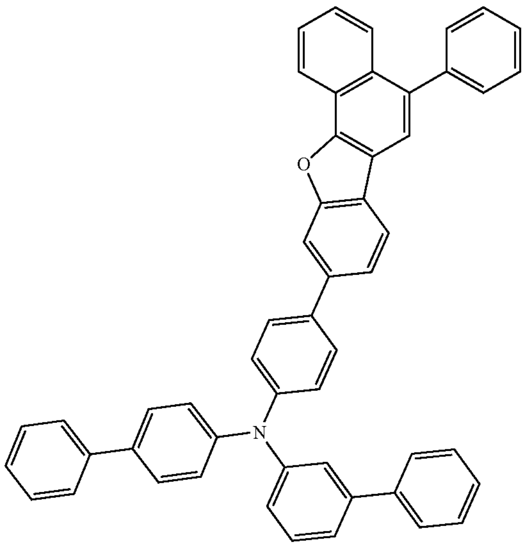
1-318
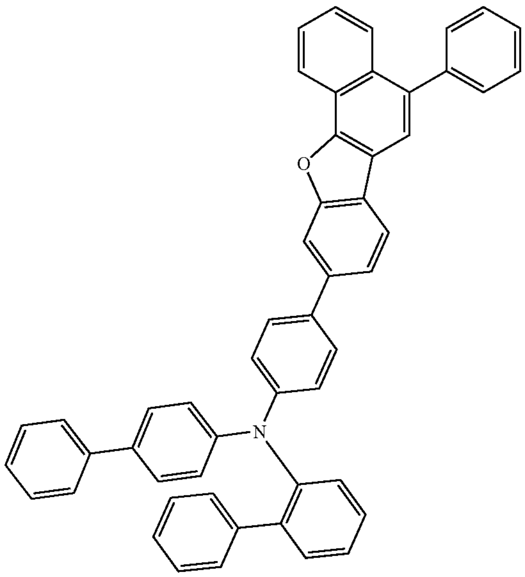

-continued
1-319
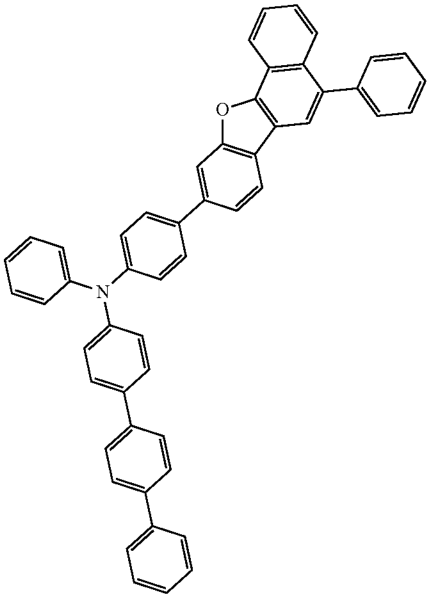
1-320
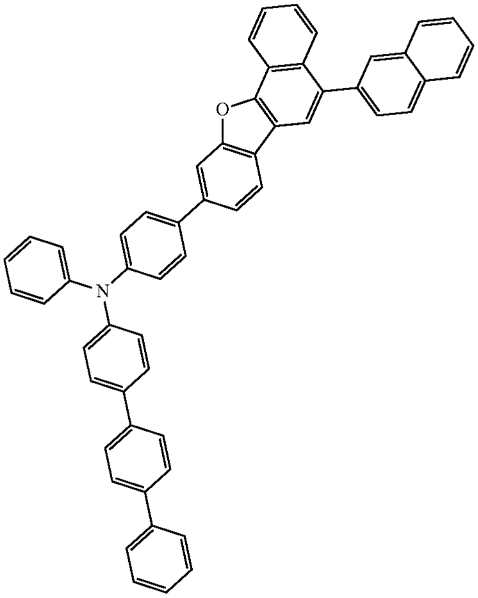
-continued
1-321
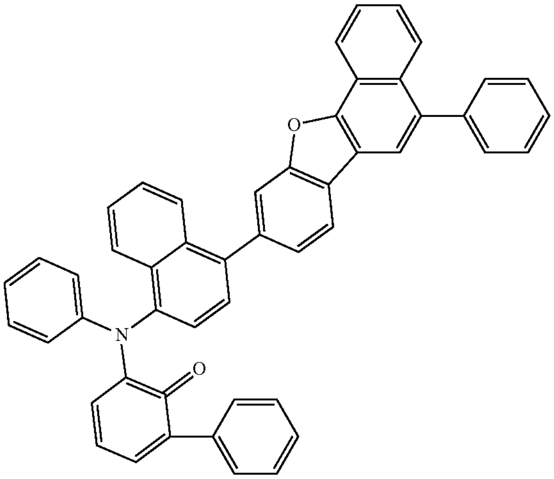
1-322
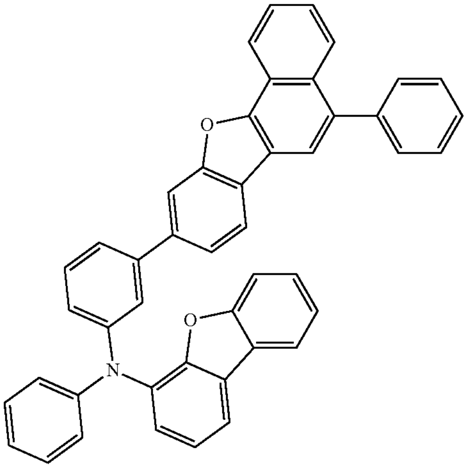
1-323
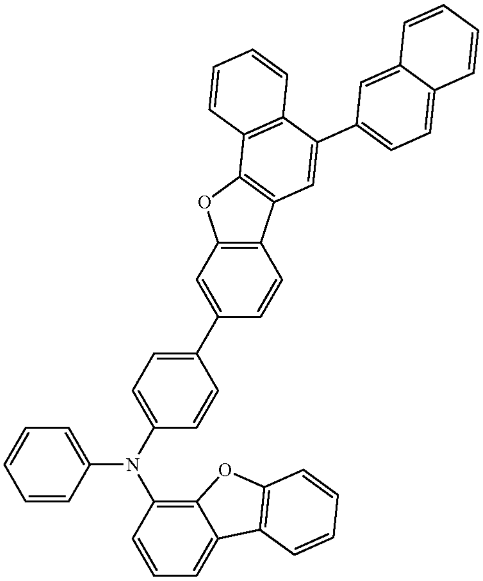

-continued
1-324
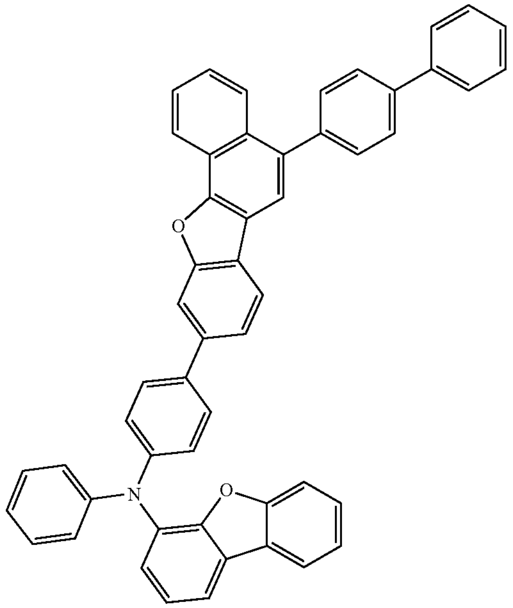
-continued
1-326
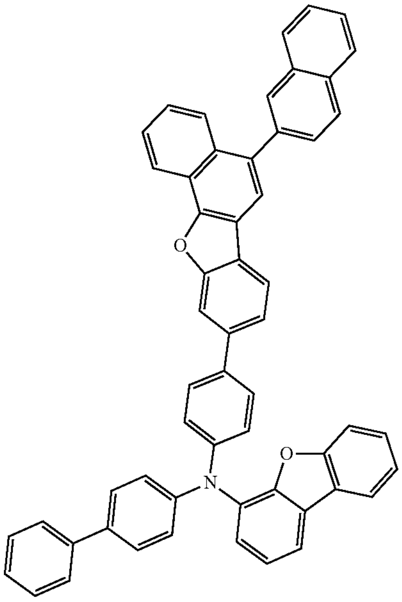
1-325
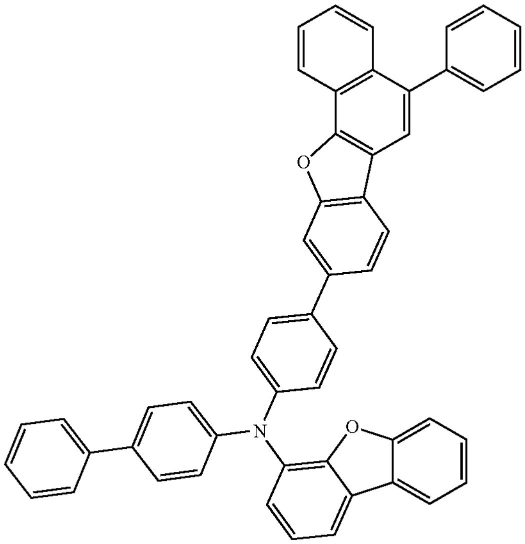
1-327
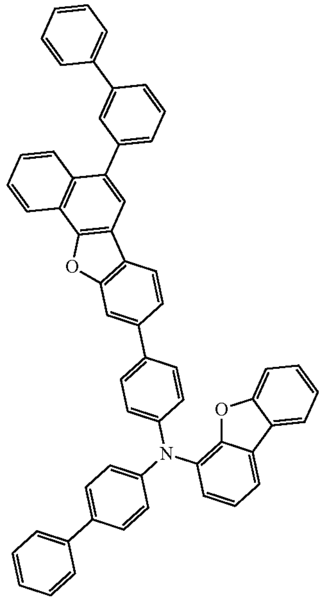

-continued
1-328
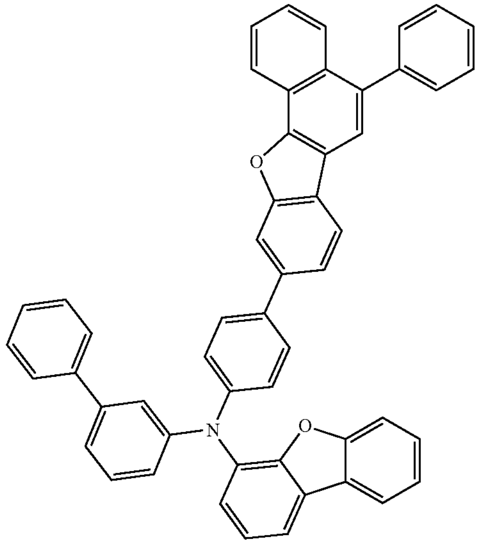
1-329
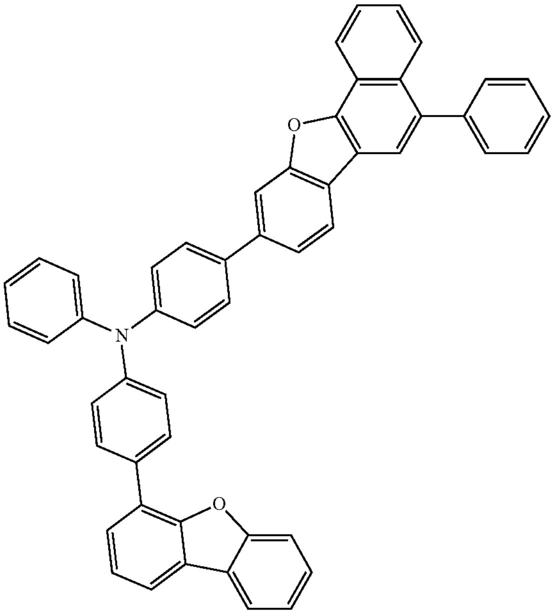
-continued
1-330
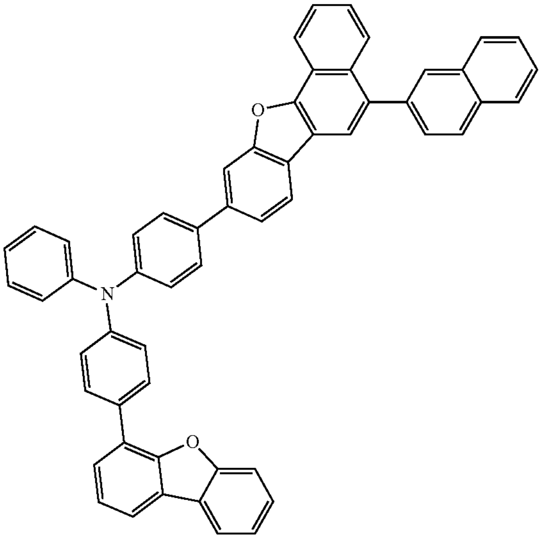
1-331
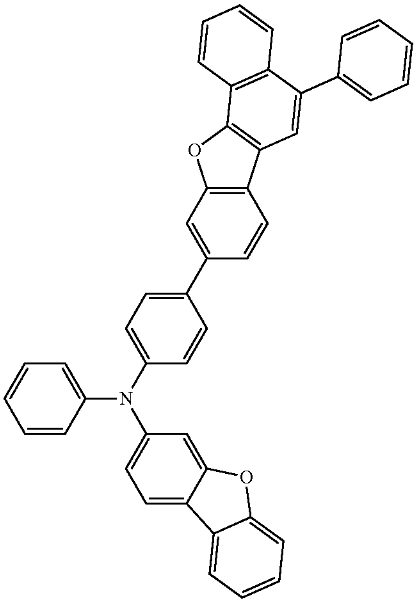

-continued
1-332
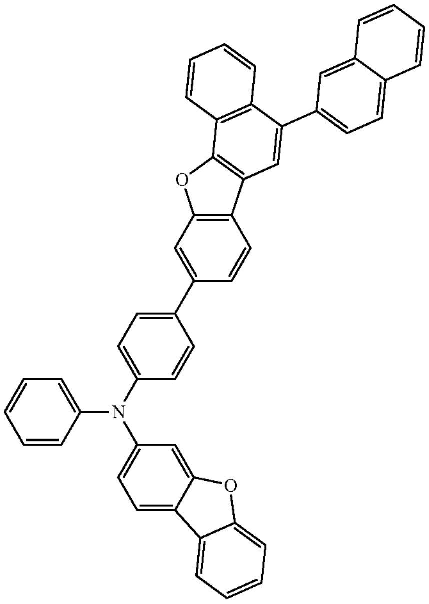
1-333
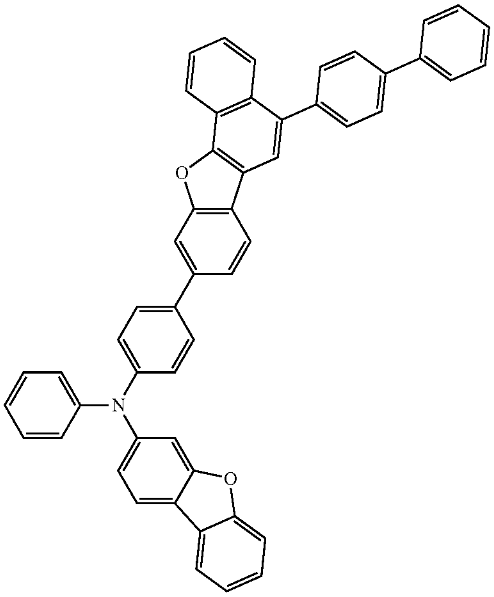
-continued
1-334
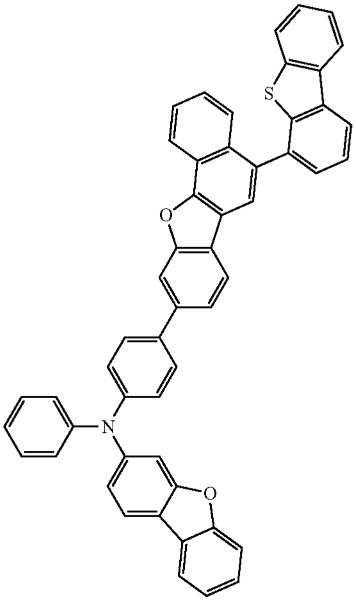
1-335
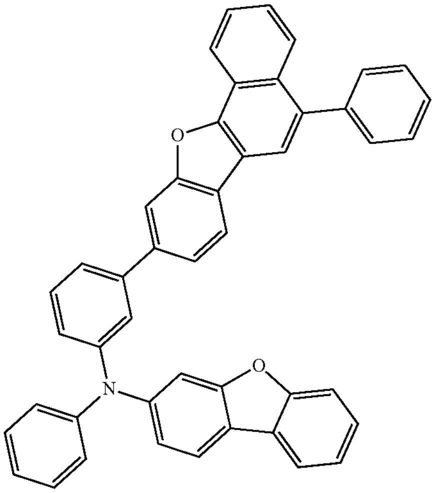
1-336
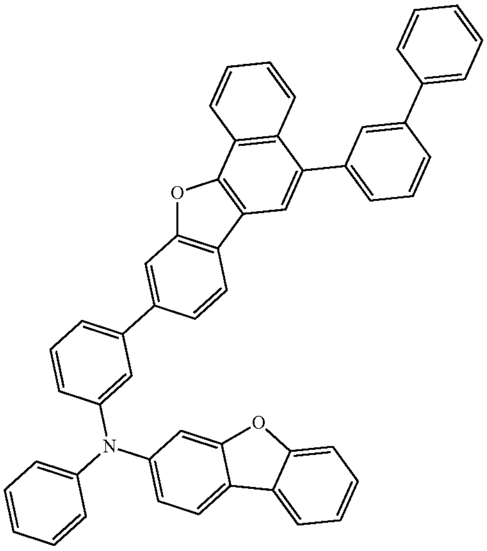

-continued
1-337
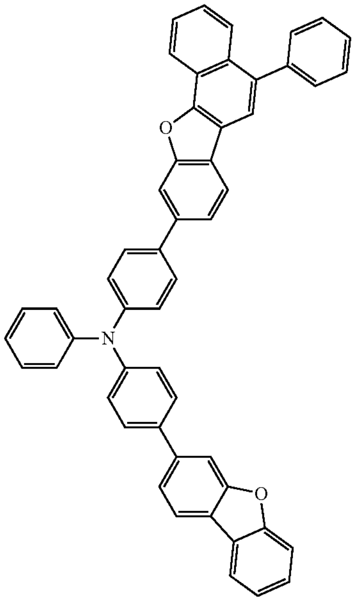
1-338
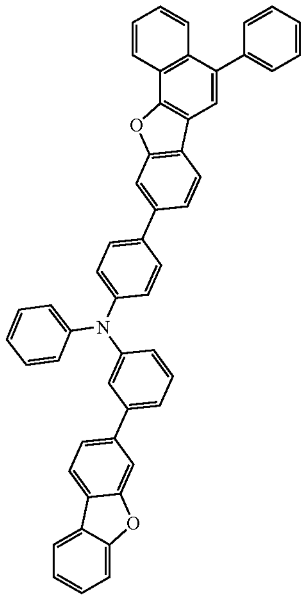
-continued
1-339
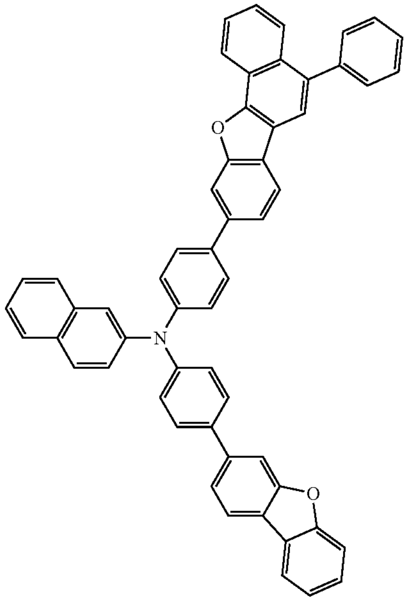
1-340
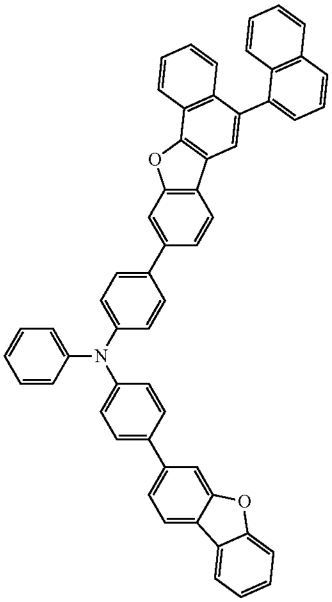

-continued
1-341
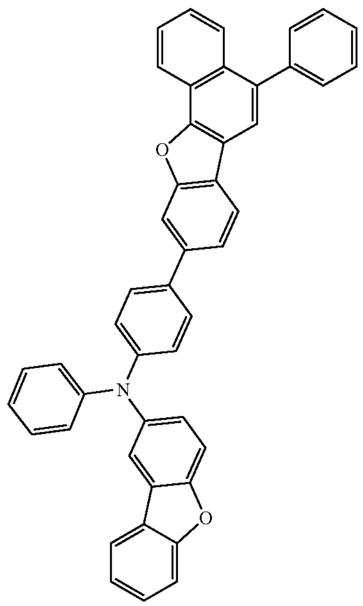
1-342
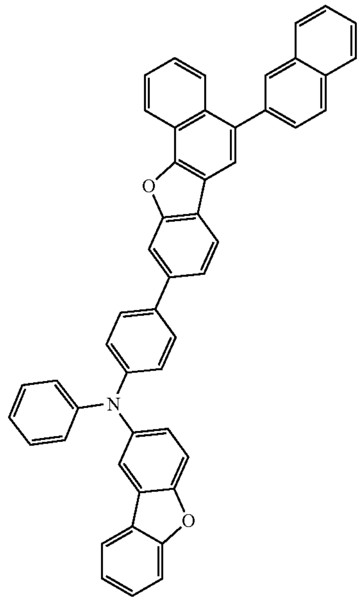
-continued
1-343
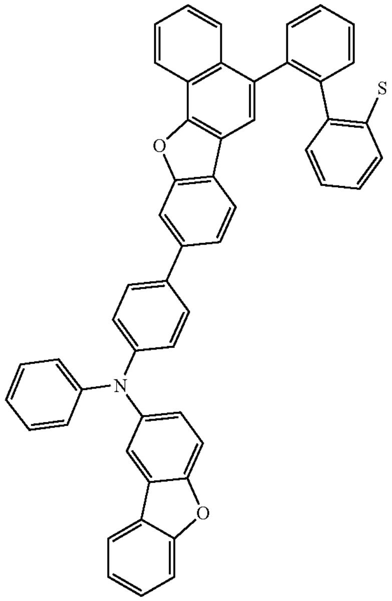
1-344
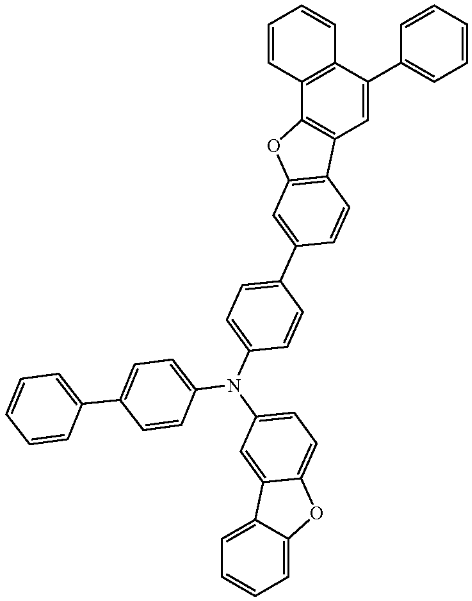

-continued
1-345
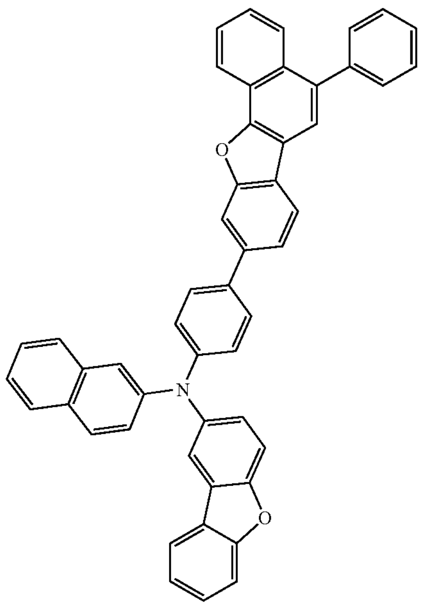
1-346
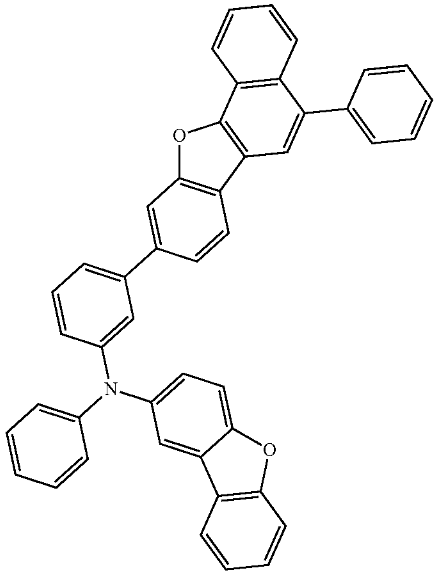
-continued
1-347
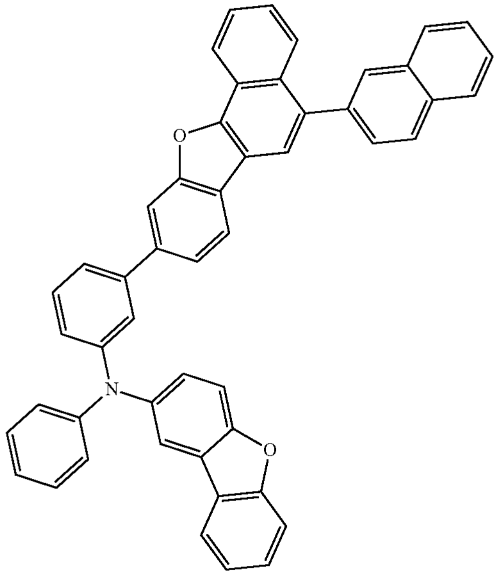
1-348
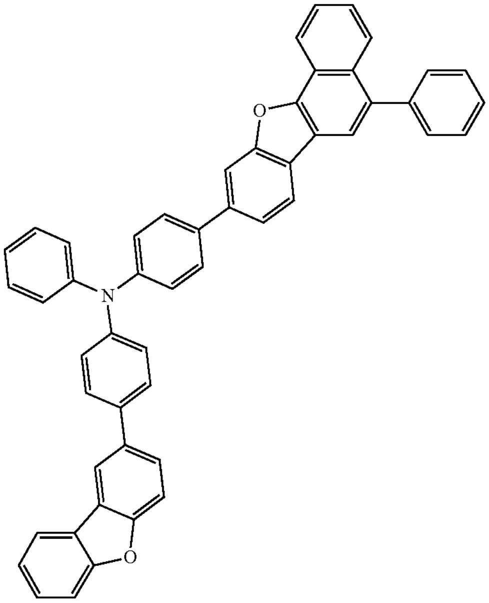

-continued
1-349
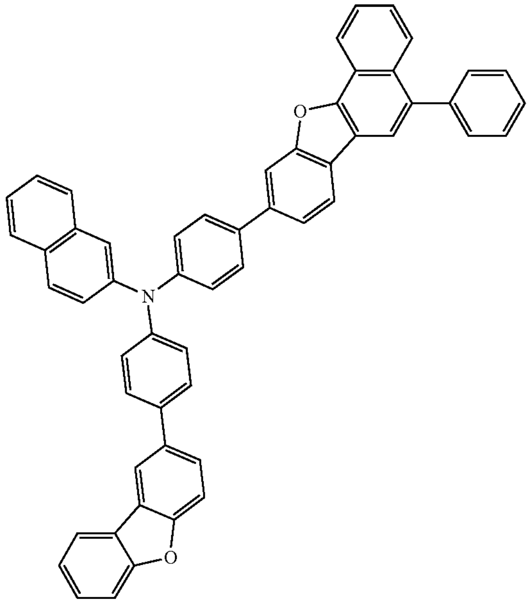
1-350
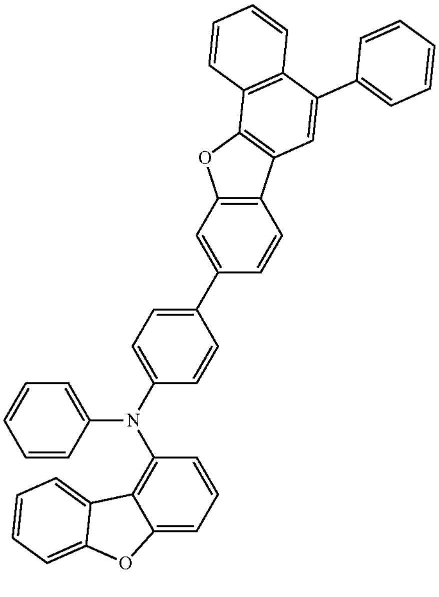
-continued
1-351
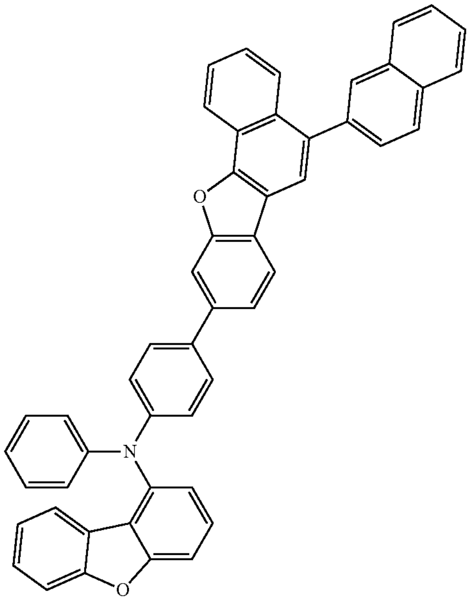
1-352
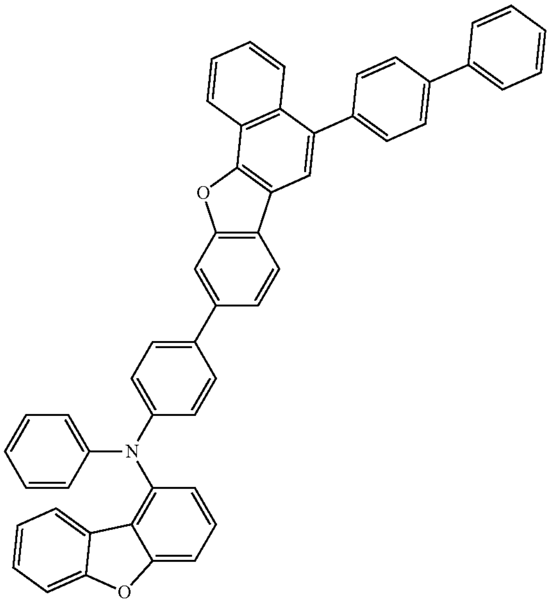

-continued
1-353
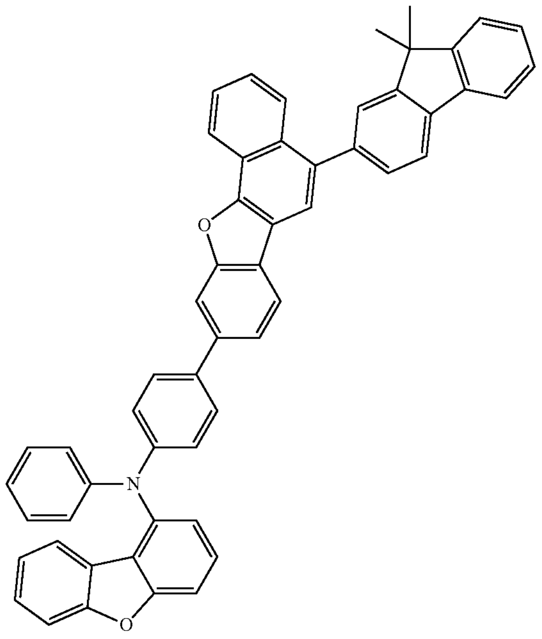
1-354
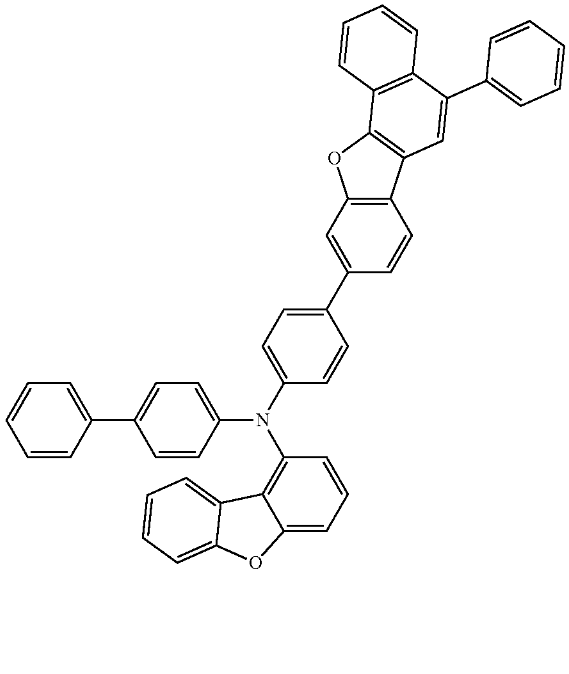
-continued
1-355
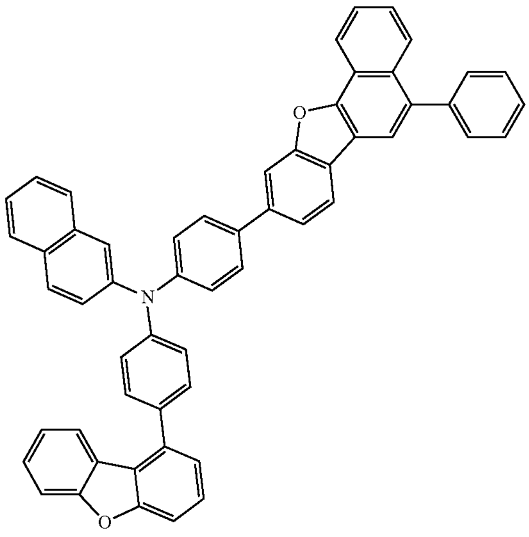
1-356
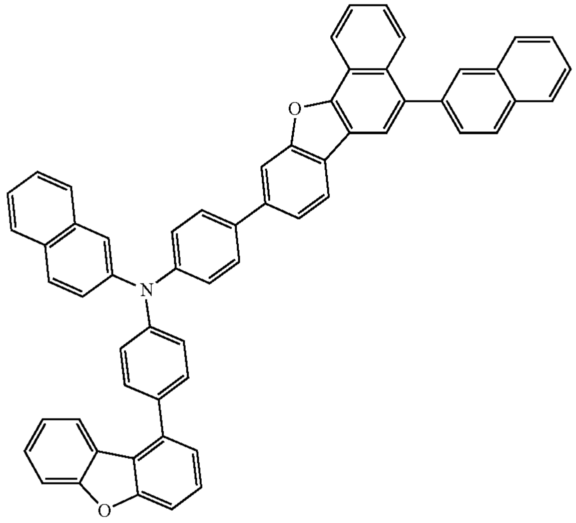
1-357
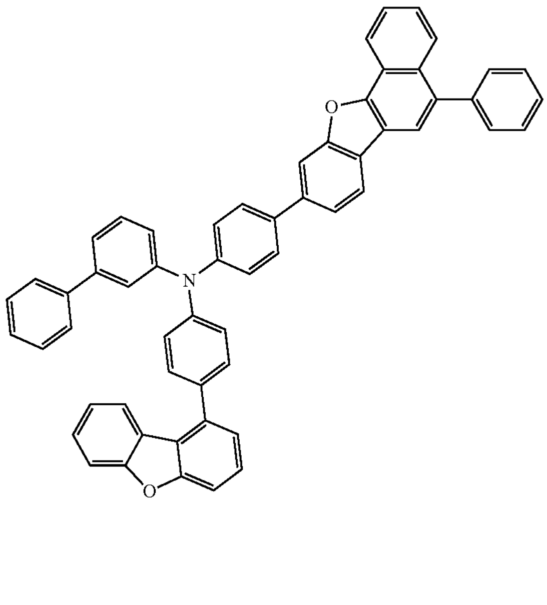

1-358
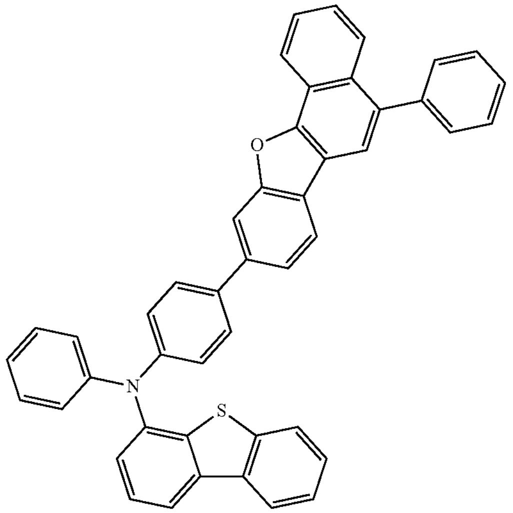
1-359
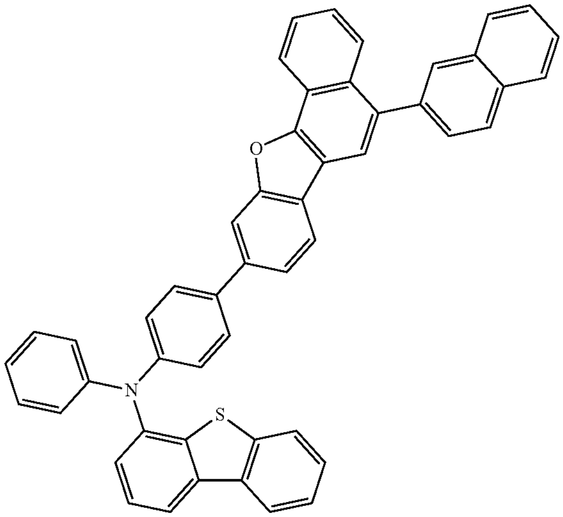
1-360
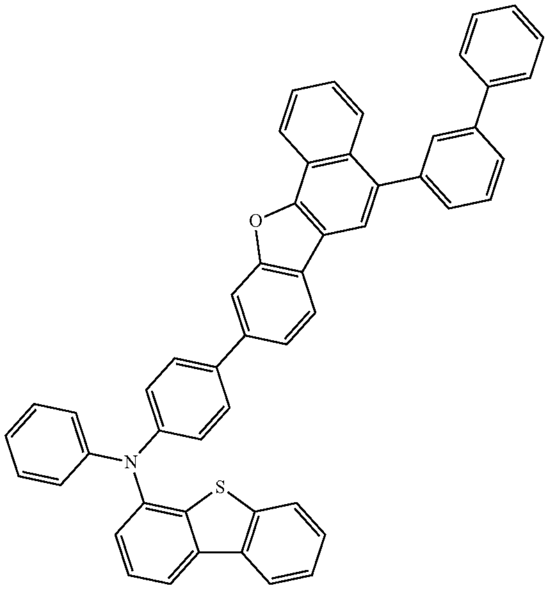
1-361
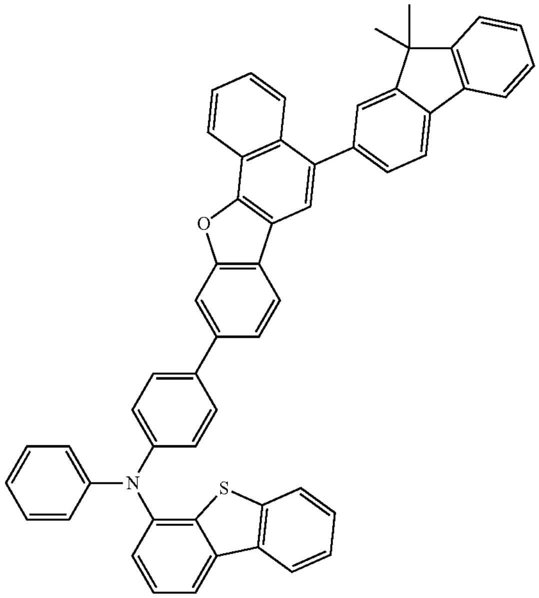

-continued
1-362
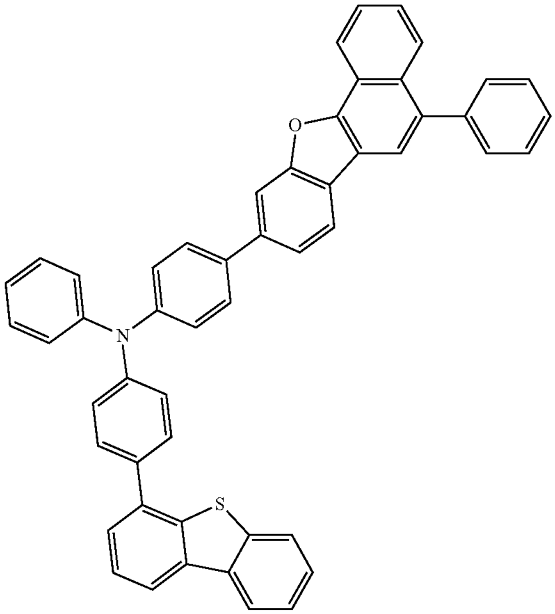
1-363
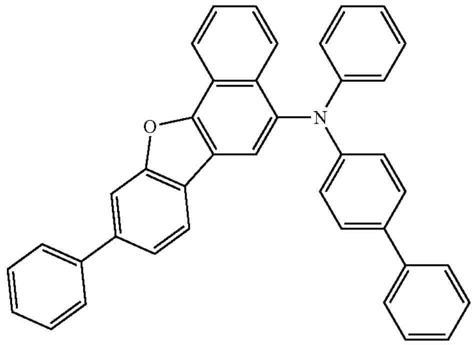
1-364
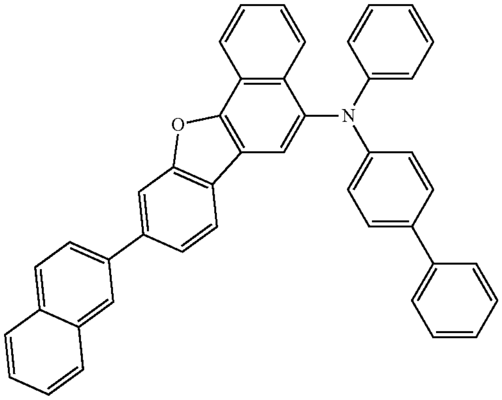
-continued
1-365
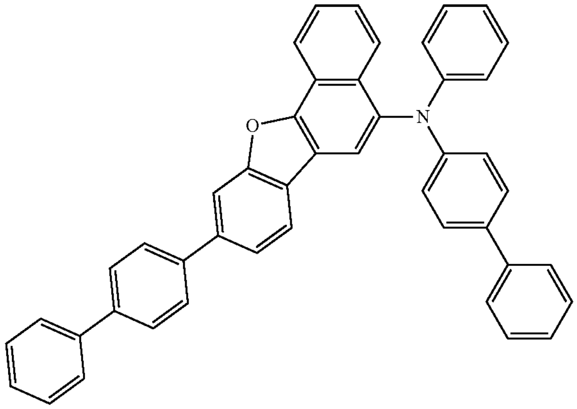
1-366
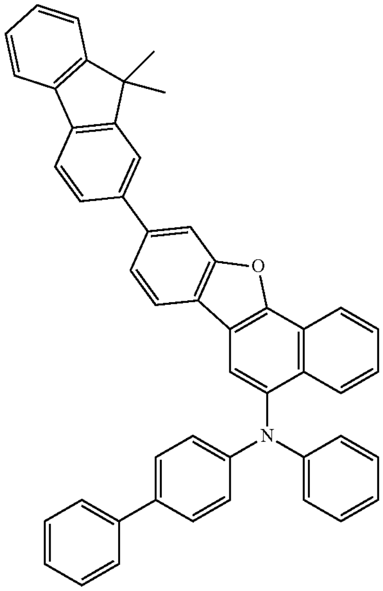
1-367
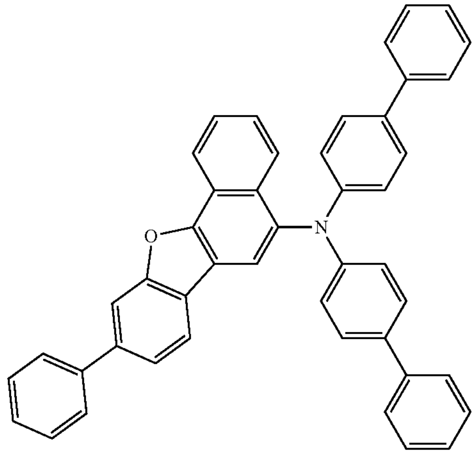

-continued
1-368
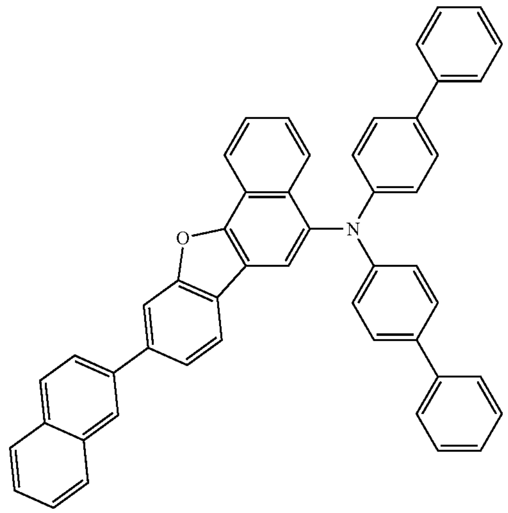
1-369
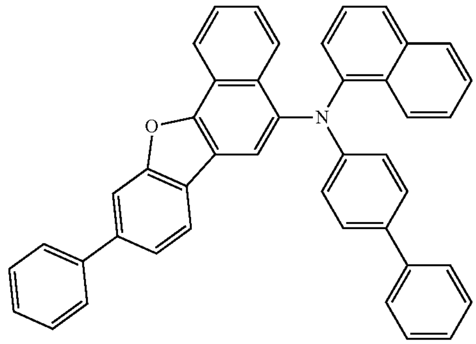
1-370
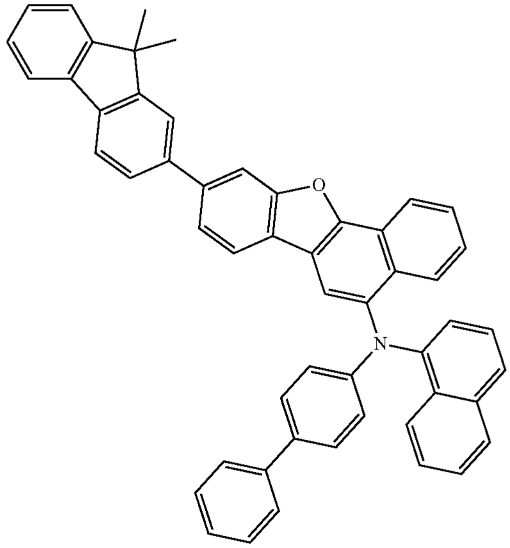
-continued
1-371
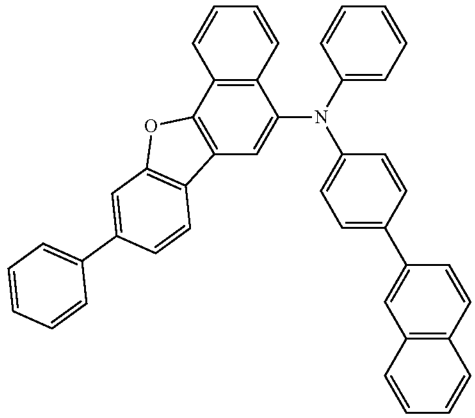
1-372
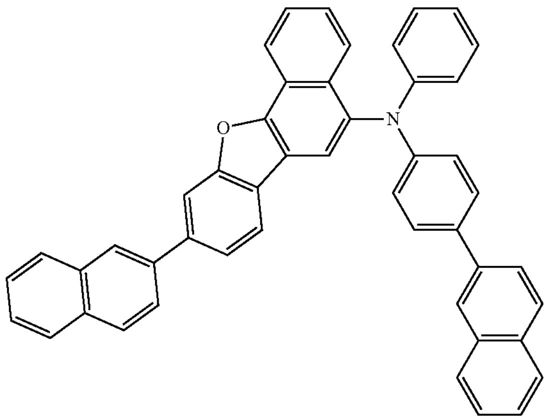
1-373
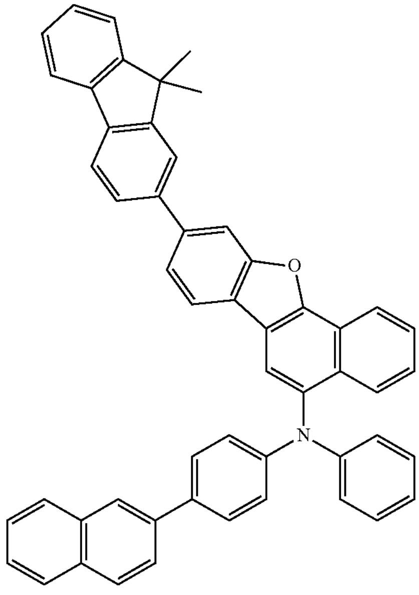

-continued
1-374
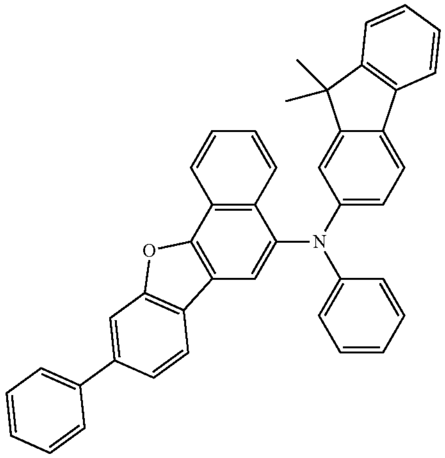
1-375
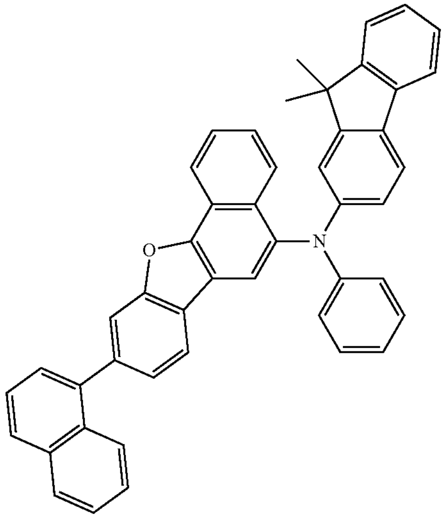
1-376
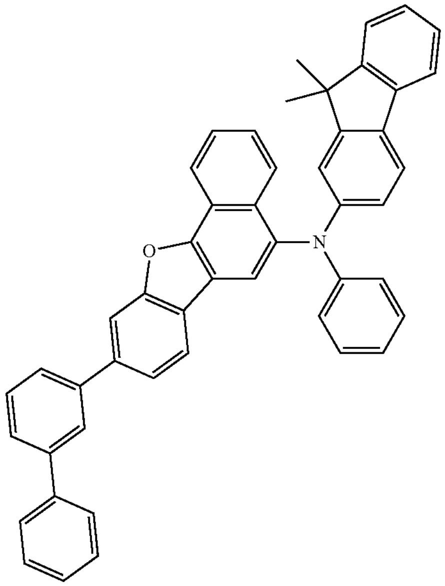
-continued
1-377
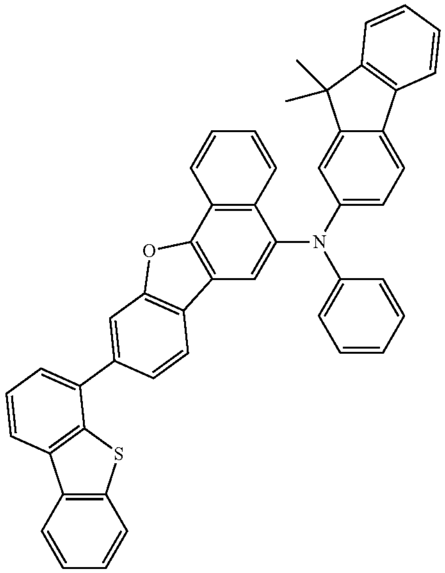
1-378
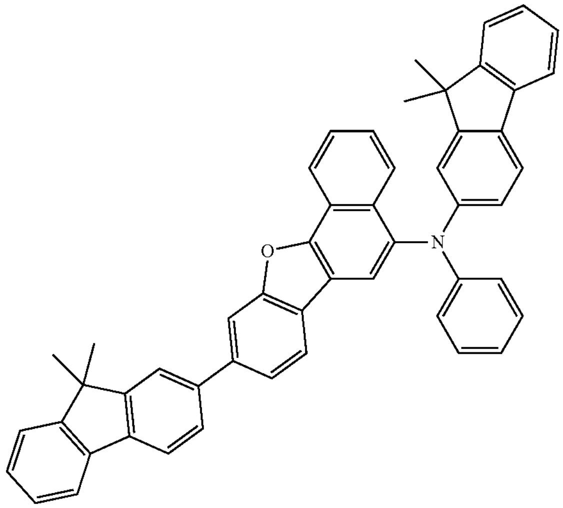
1-379
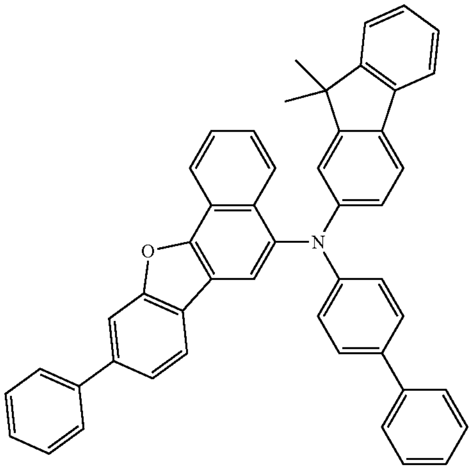

-continued
1-380
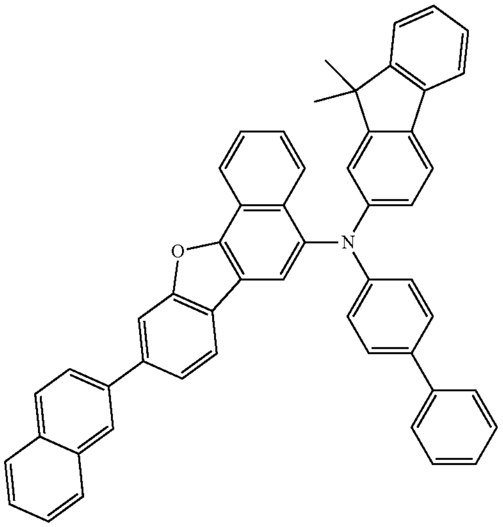
1-381
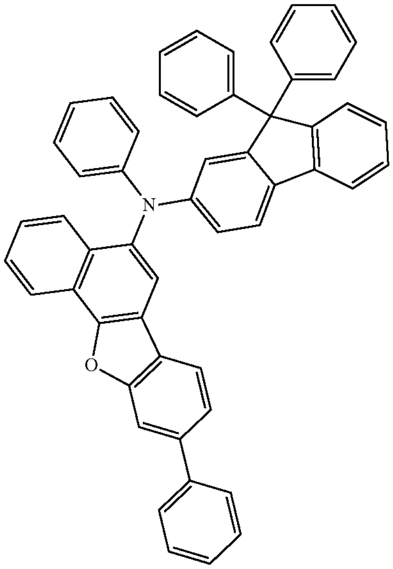
-continued
1-382
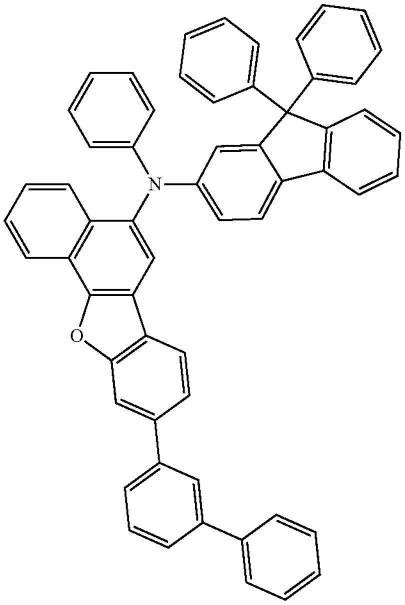
1-383
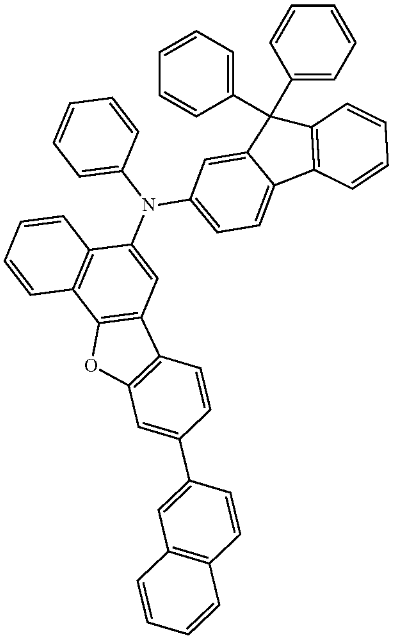

-continued
1-384
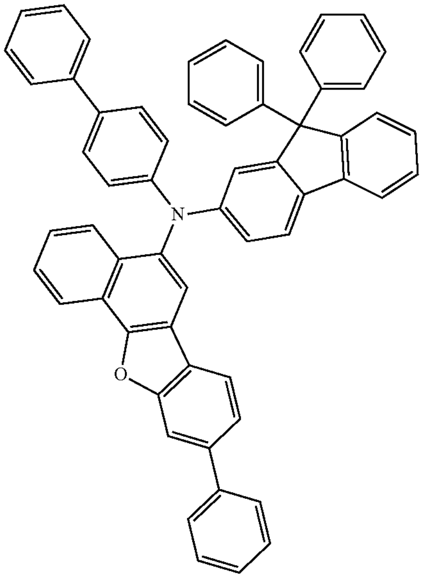
1-385
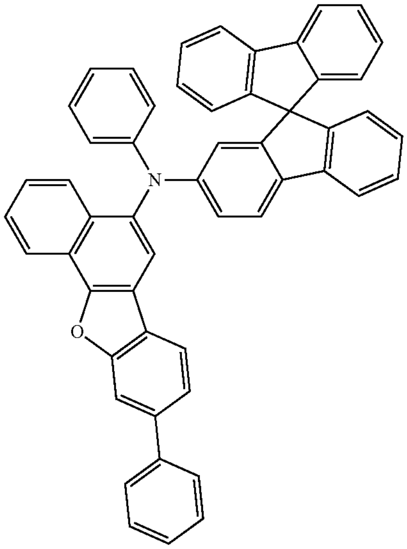
-continued
1-386
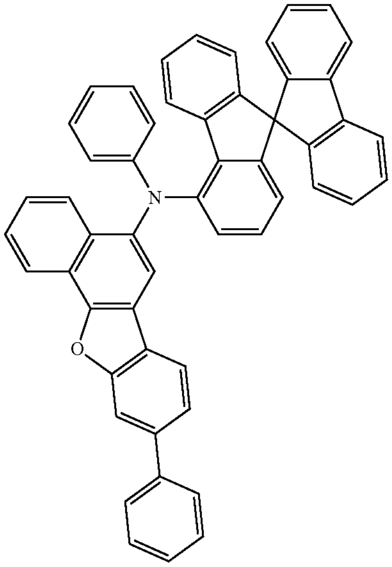
1-387
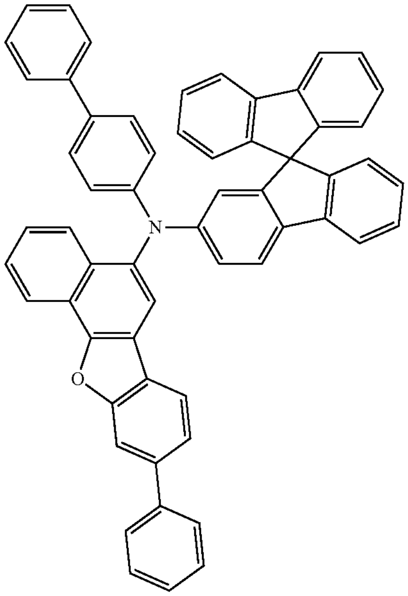

-continued
1-388
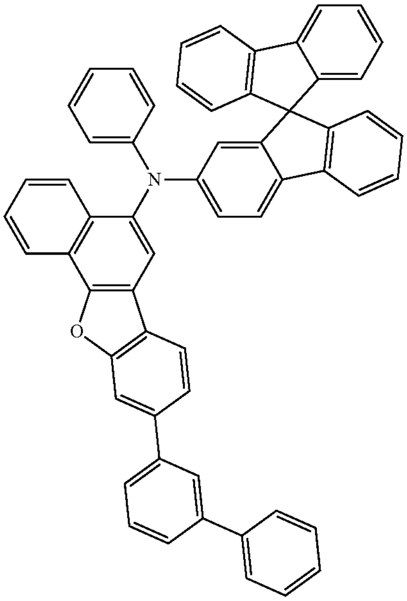
1-389
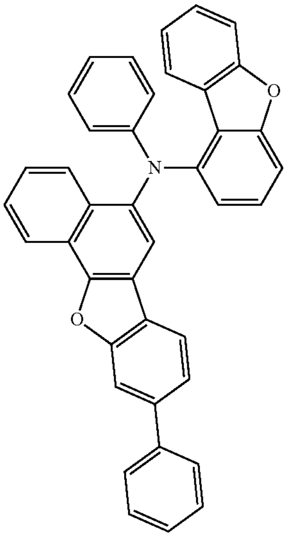
-continued
1-390
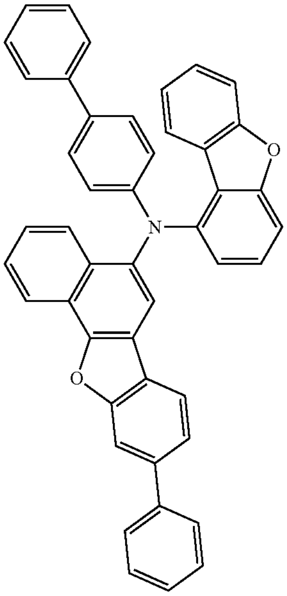
1-391
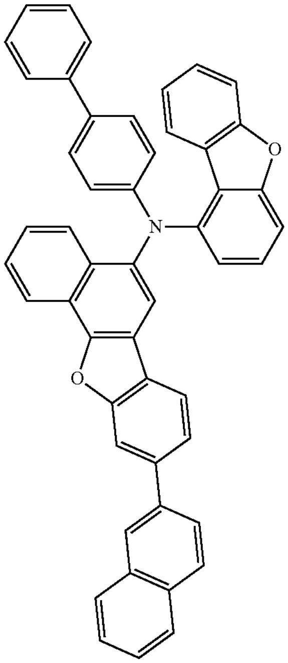

-continued
1-392
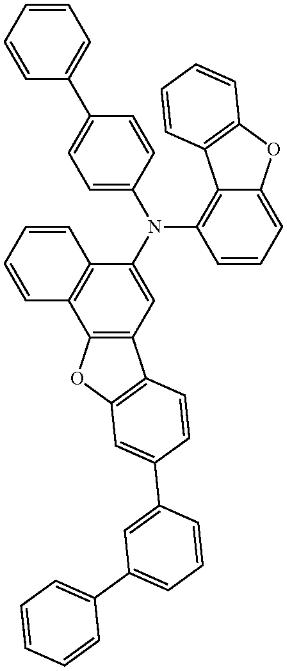
1-393
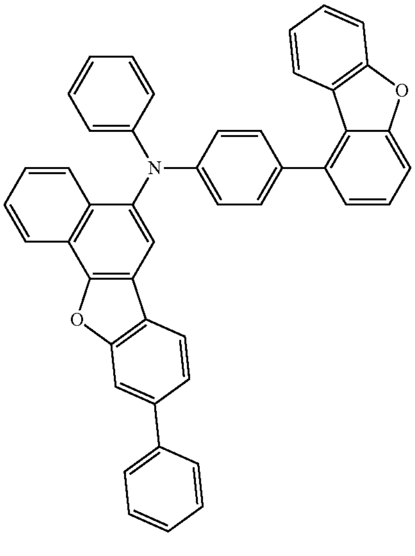
-continued
1-394
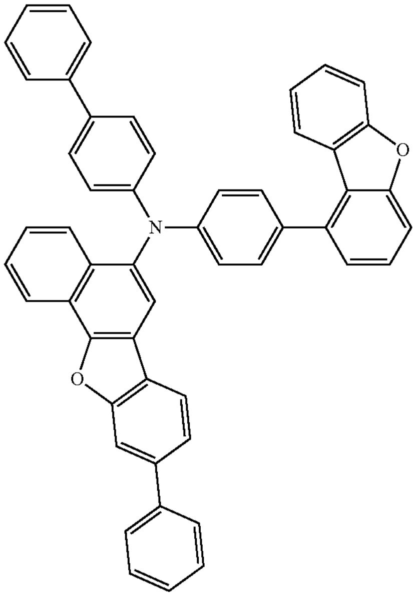
1-395
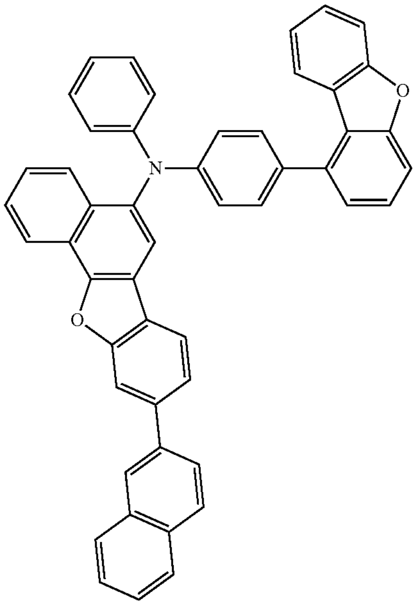

-continued
1-396
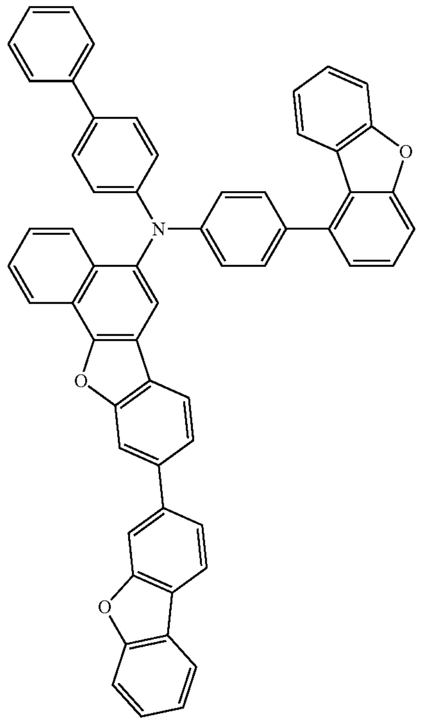
1-397
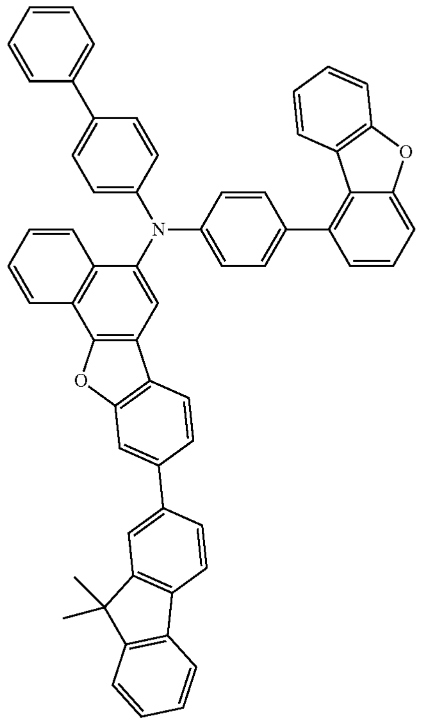
-continued
1-398
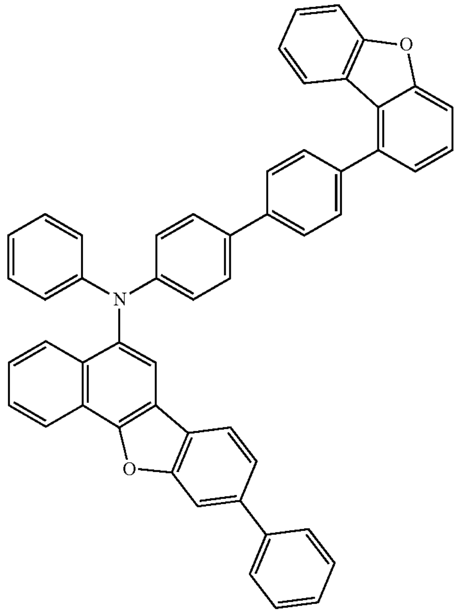
1-399
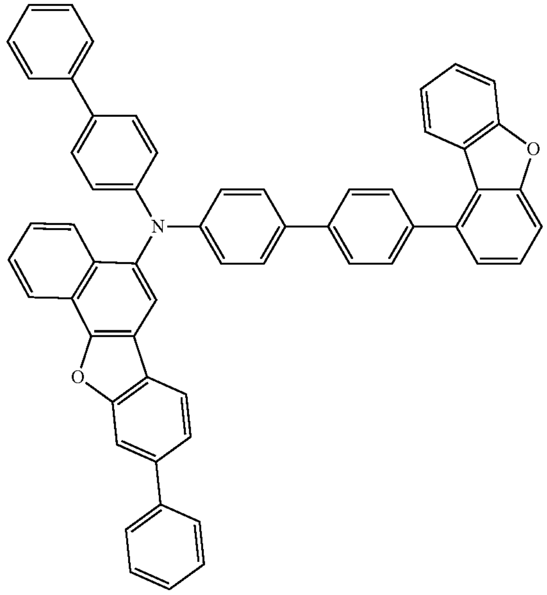

-continued
1-400
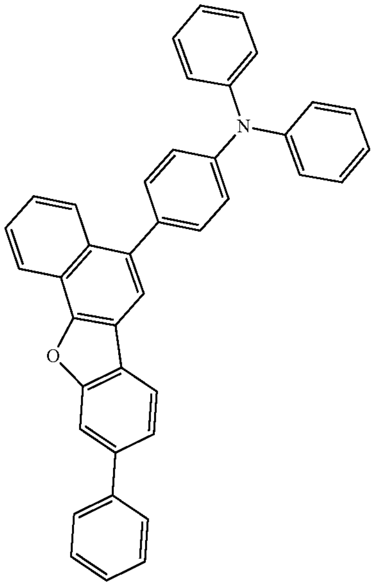
1-401
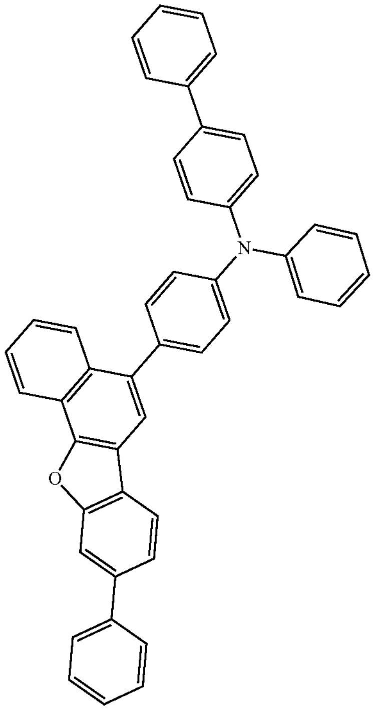
-continued
1-402
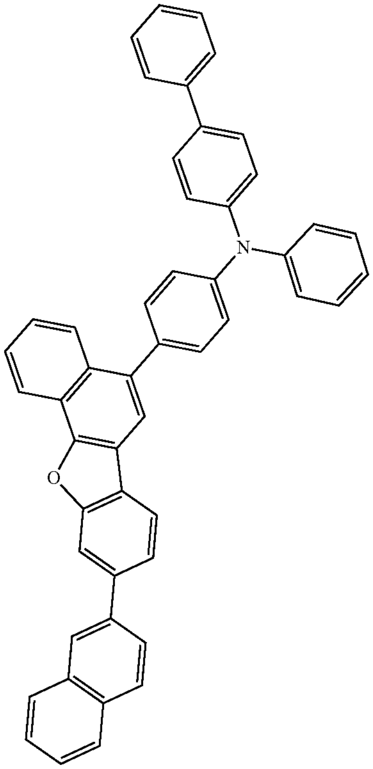
1-403
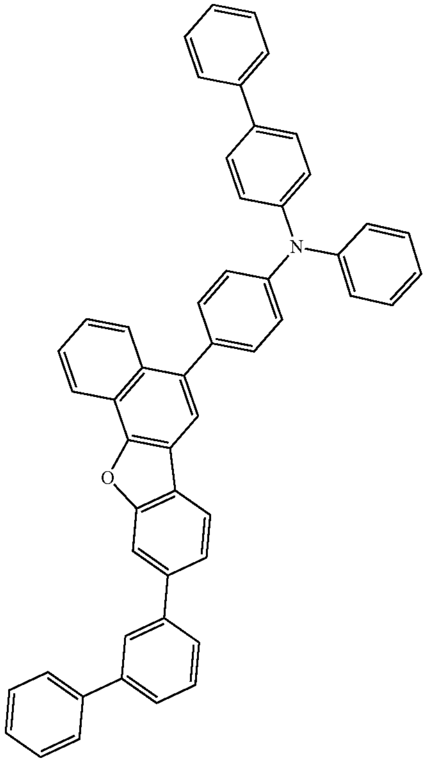

-continued
1-404
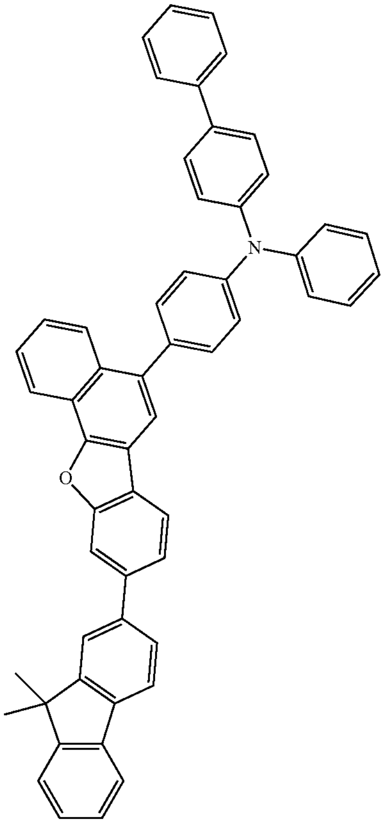
1-405
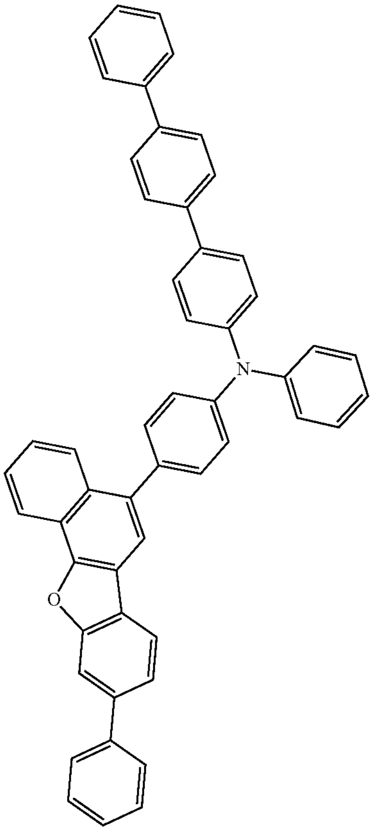
-continued
1-406
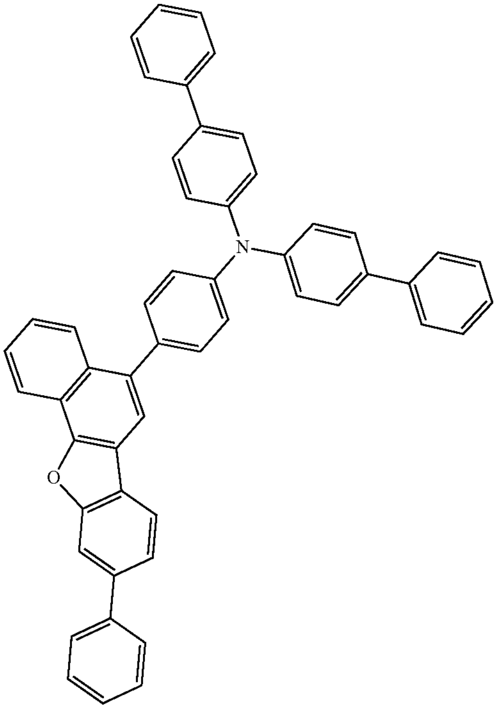
1-407
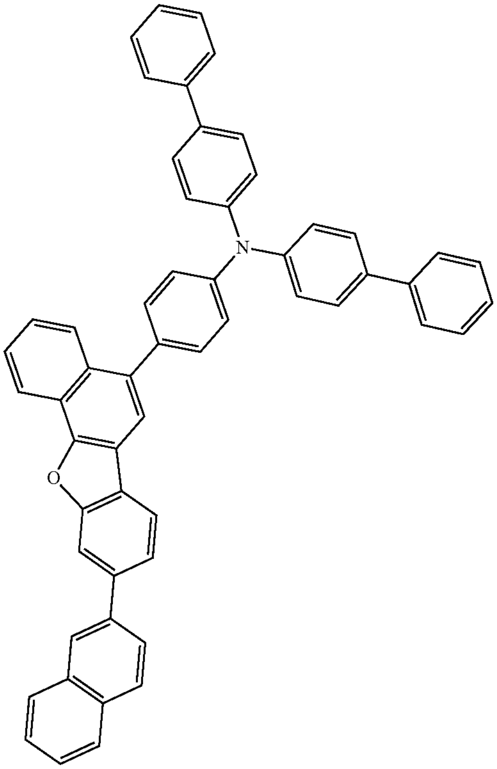

-continued
1-408
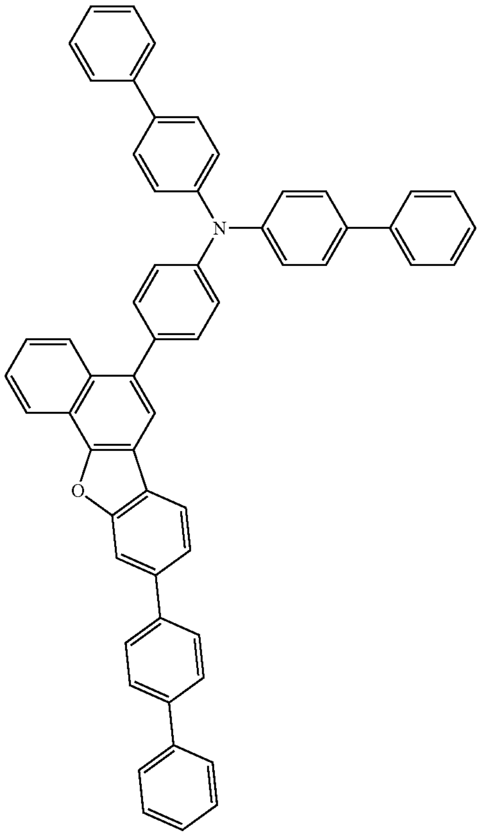
1-409
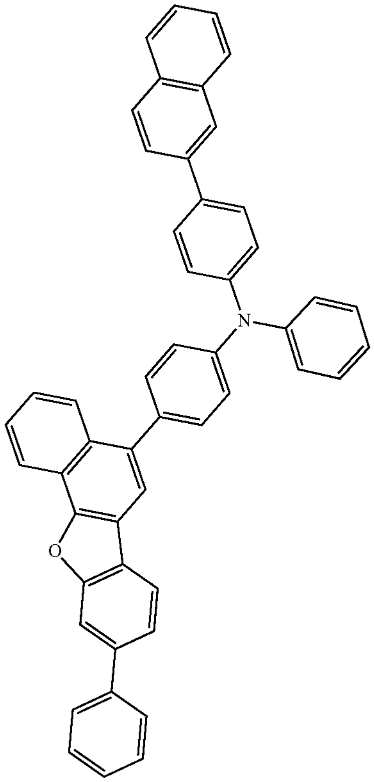
-continued
1-410
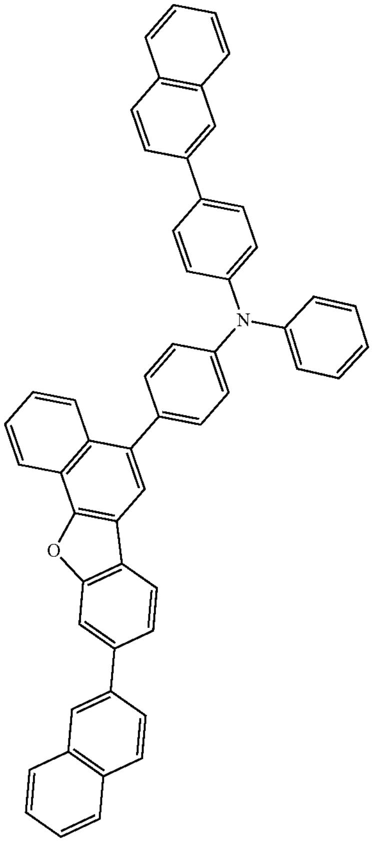

-continued
1-411
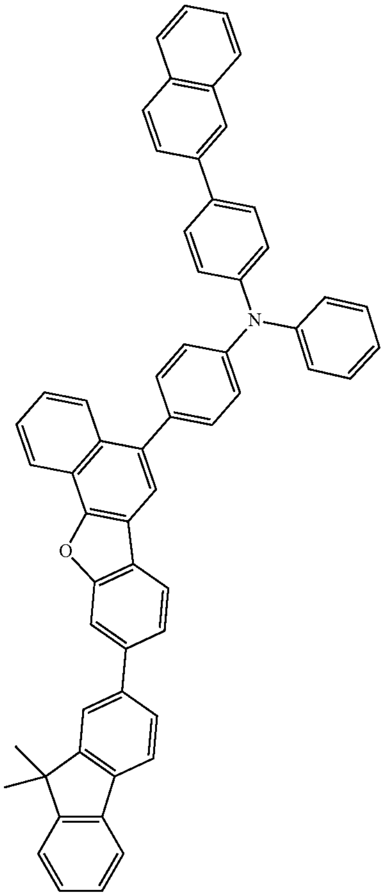
1-412
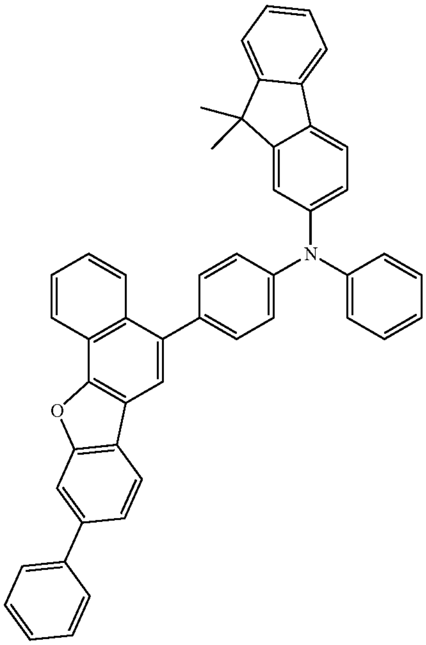
-continued
1-413
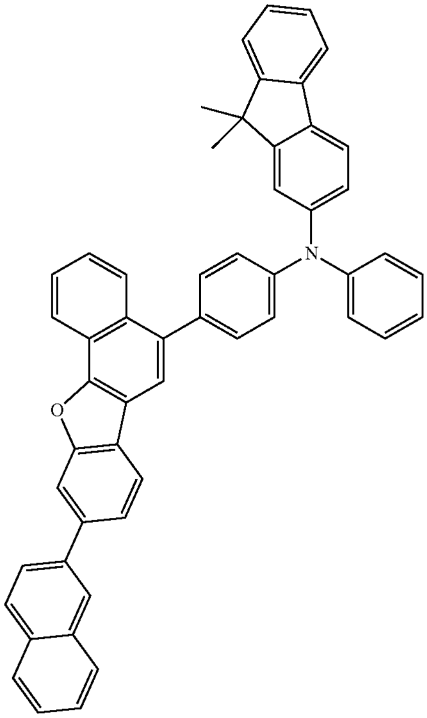
1-414
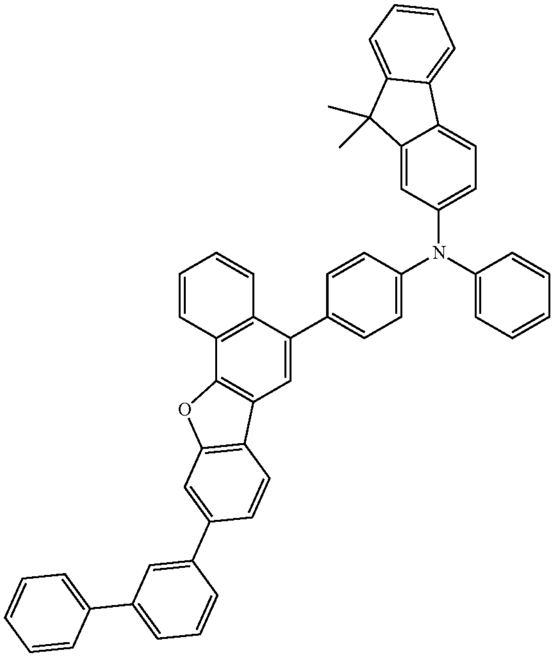

-continued
1-415
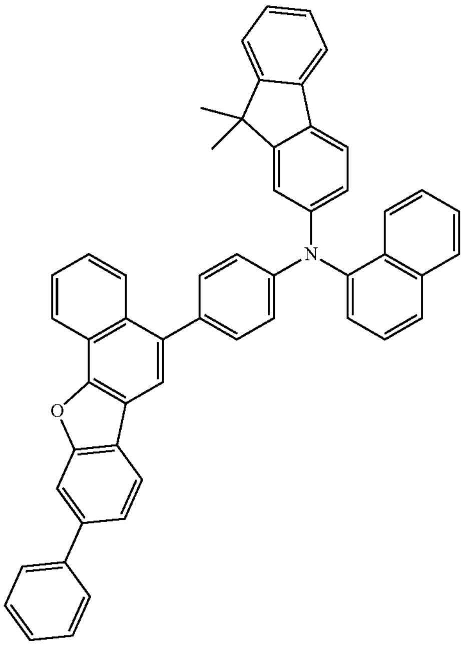
1-416
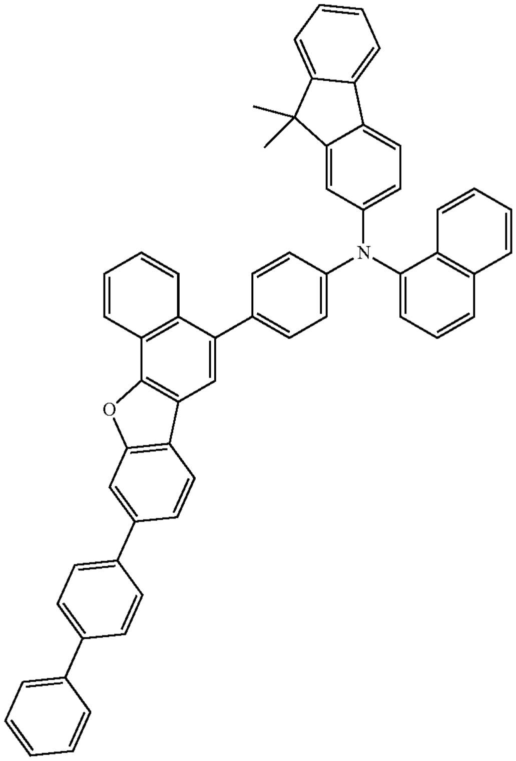
-continued
1-417
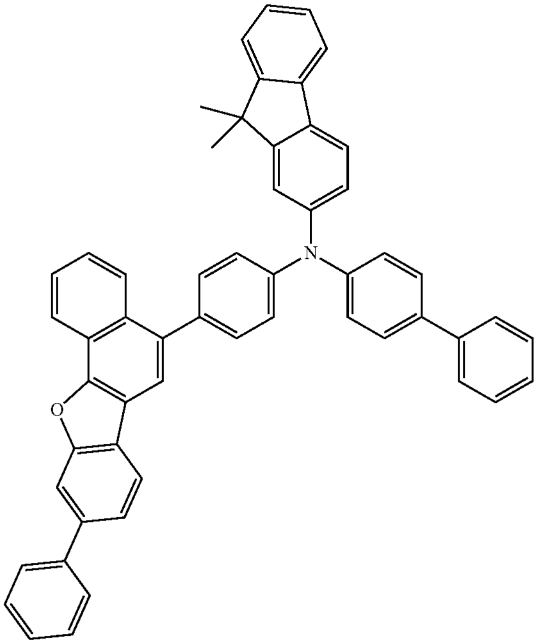
1-418
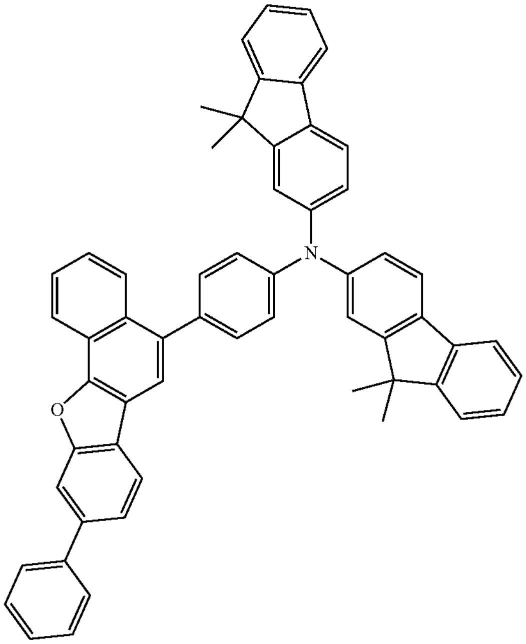

-continued
1-419
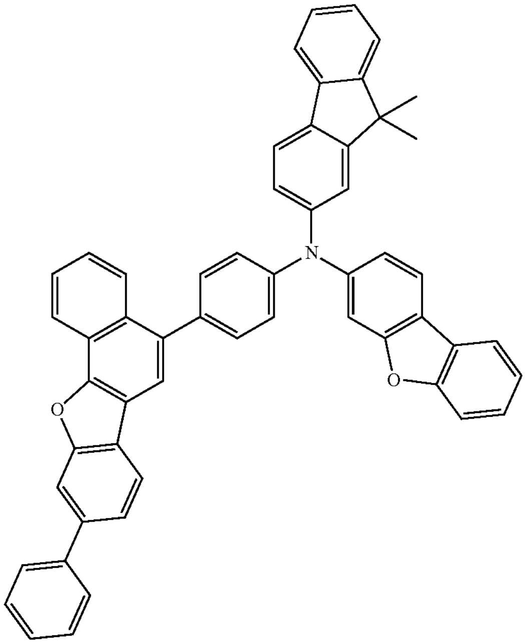
1-420
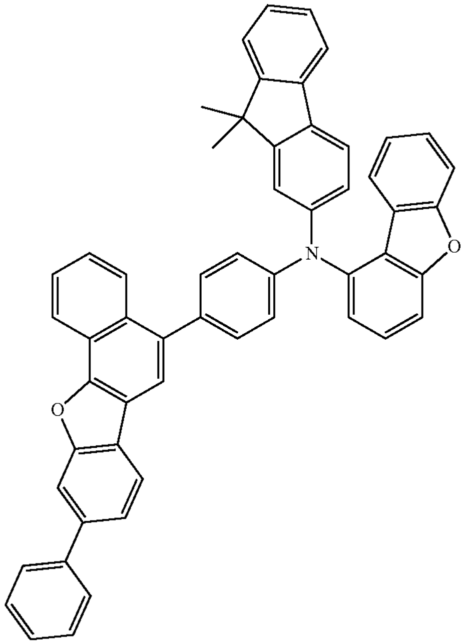
-continued
1-421
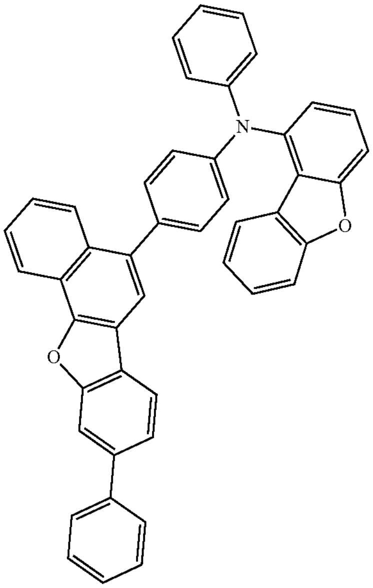
1-422
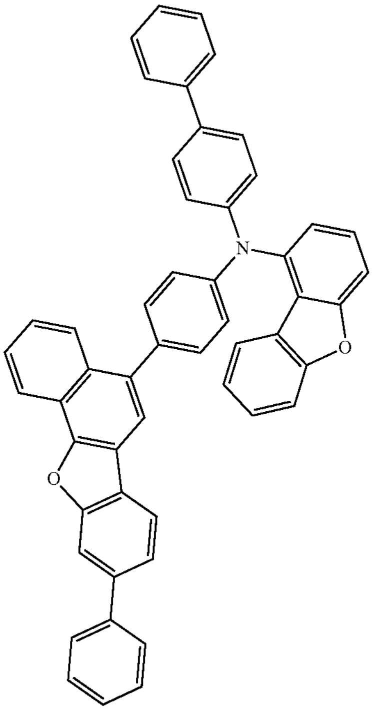

-continued
1-423
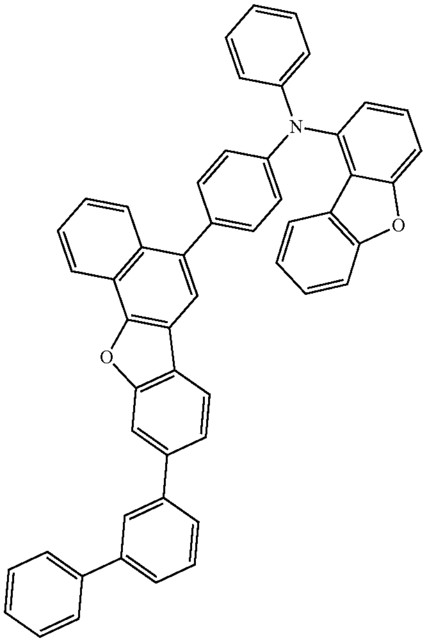
-continued
1-425
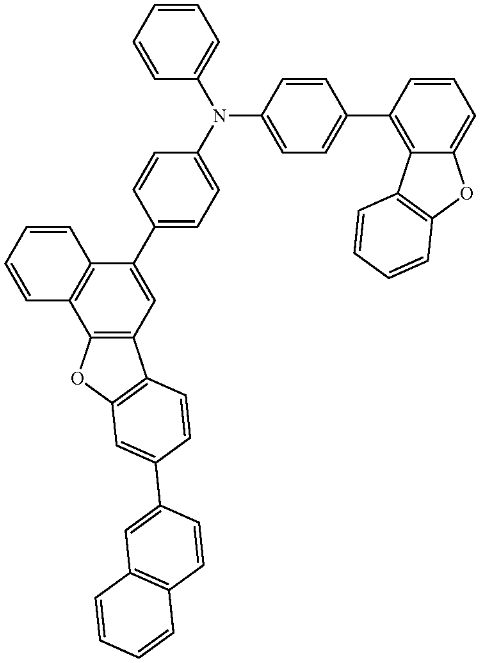
1-424
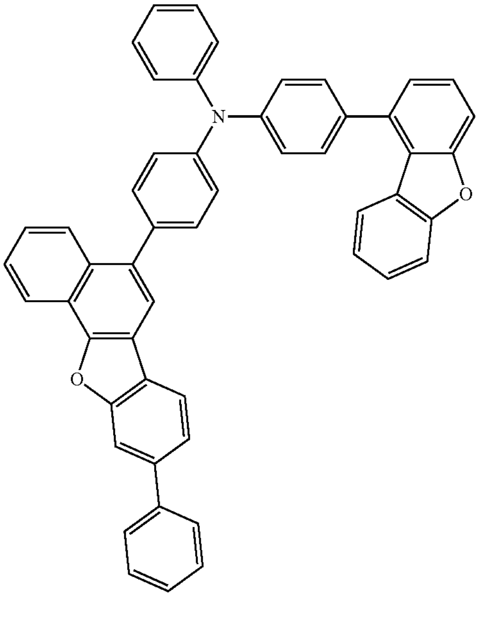
1-426
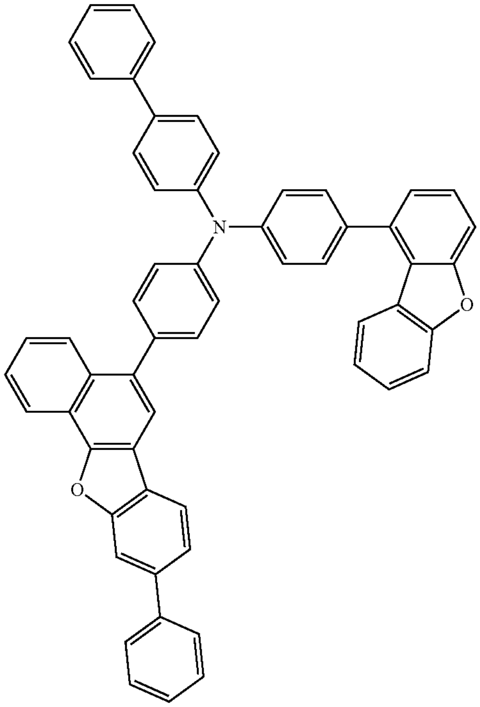

1-427
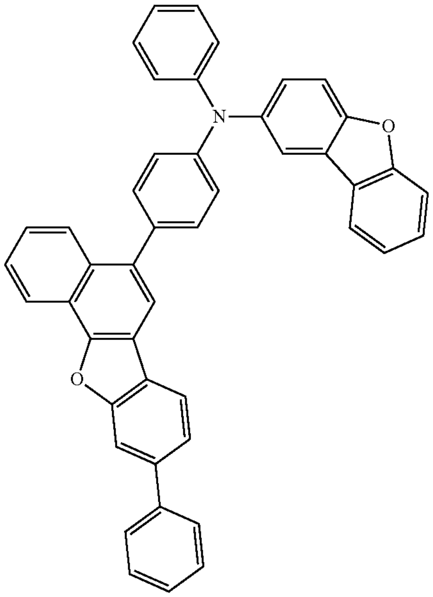
1-428
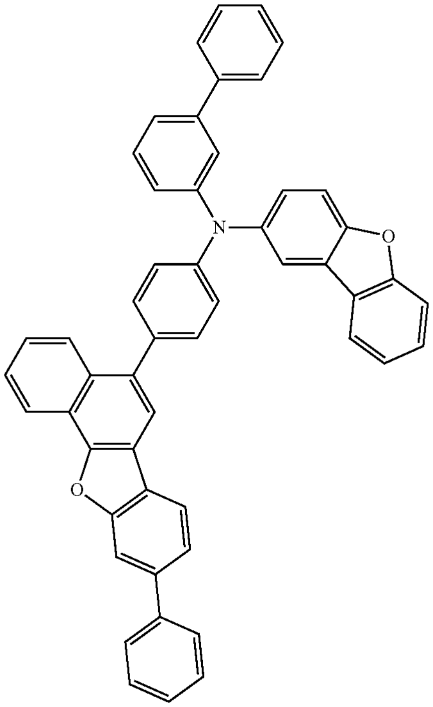
1-429
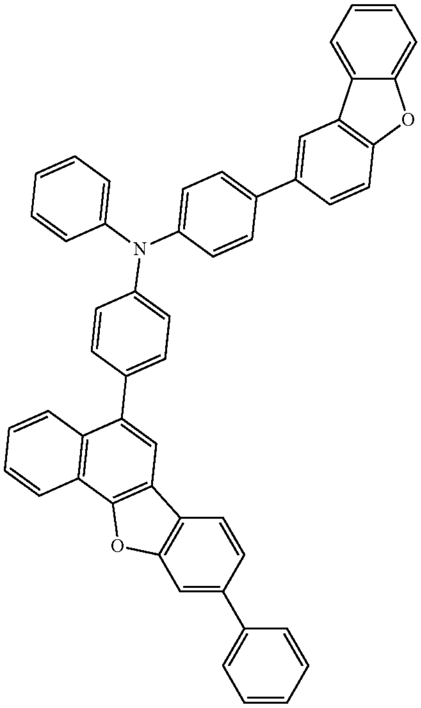
1-430
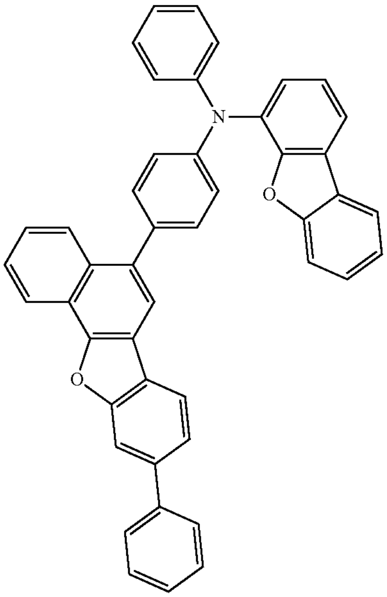

-continued
1-431
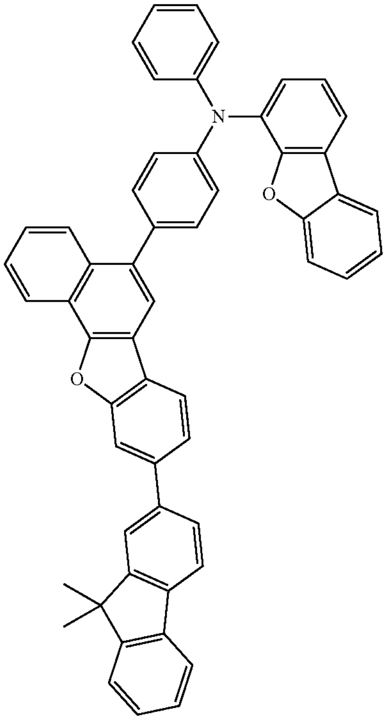
1-432
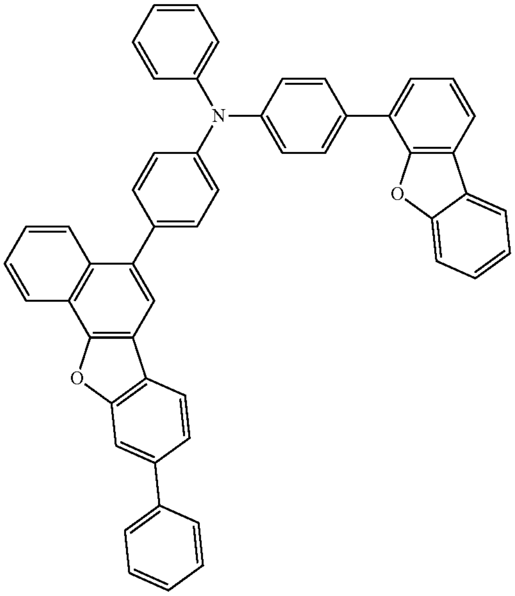
-continued
1-433
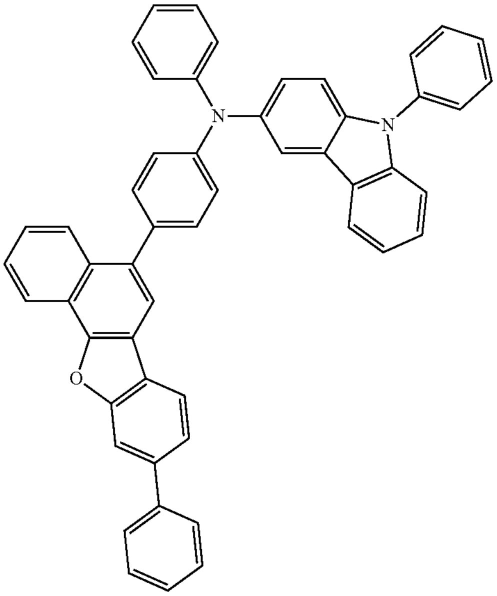
1-434
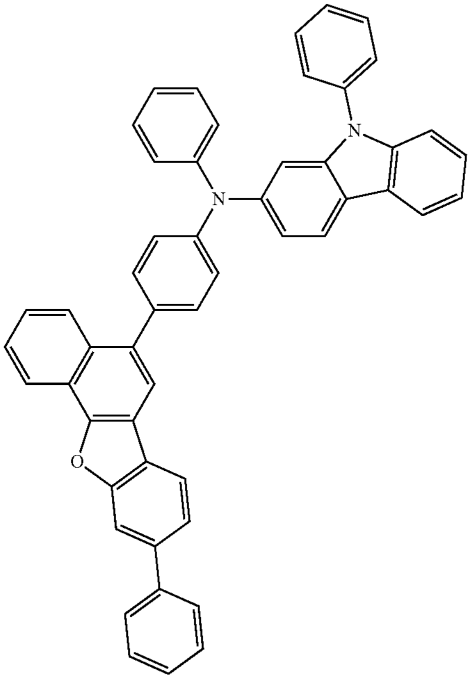

-continued
1-435
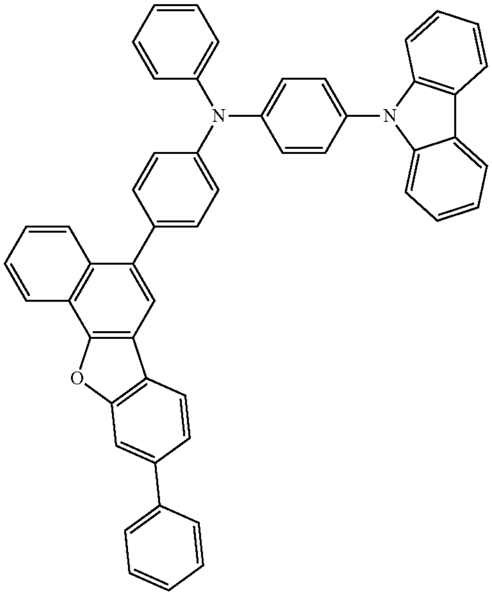
1-436
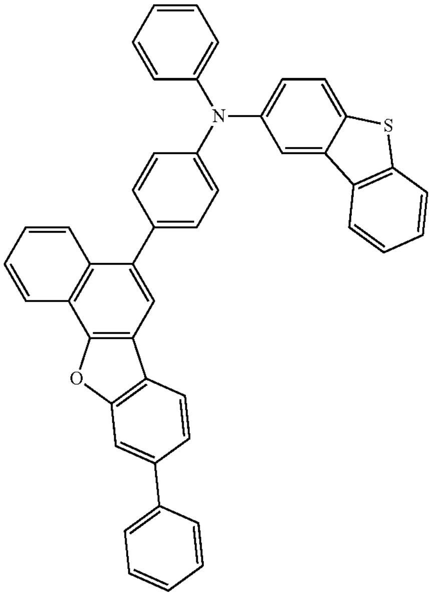
-continued
1-437
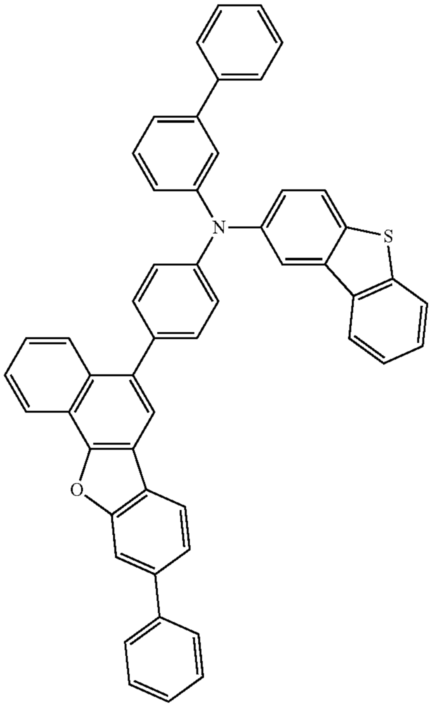
1-438
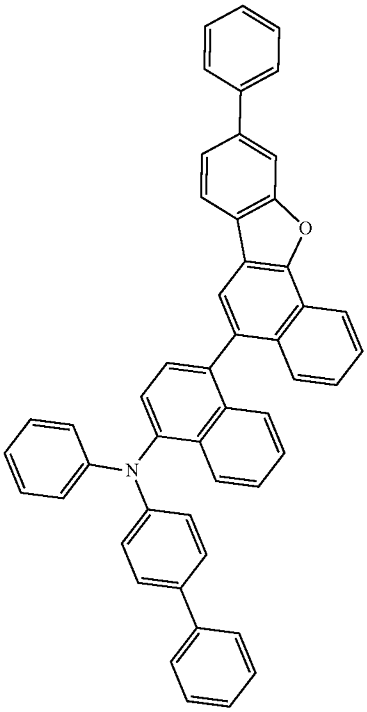

-continued
1-439
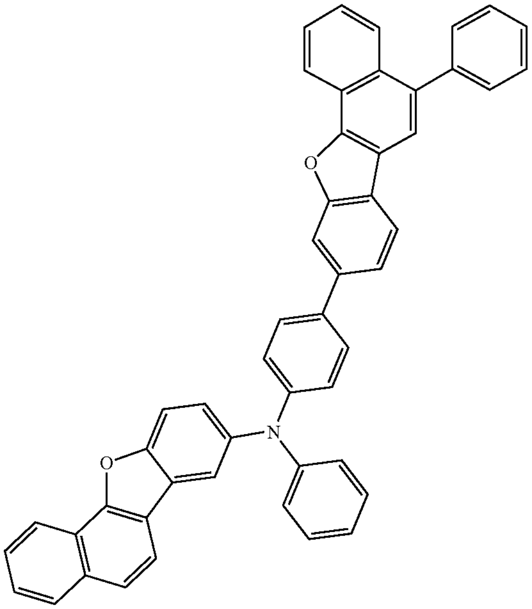
1-440
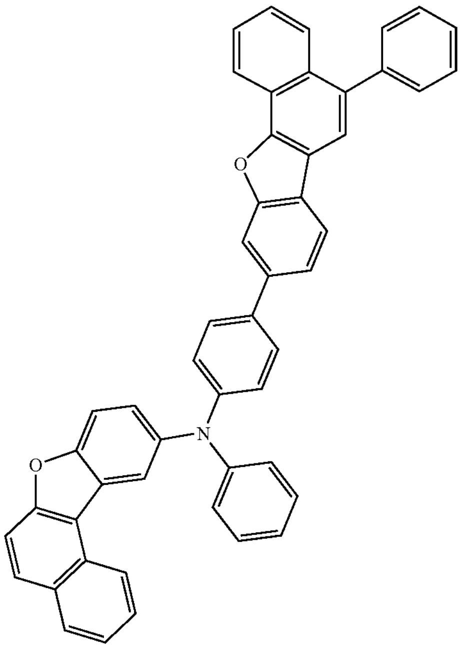
-continued
1-441
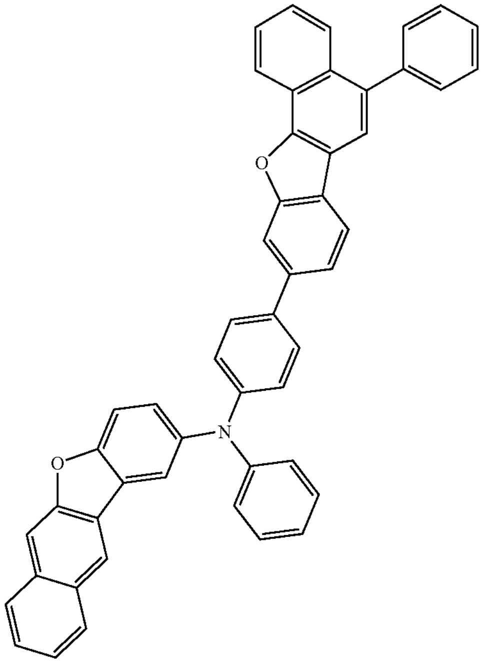
1-442
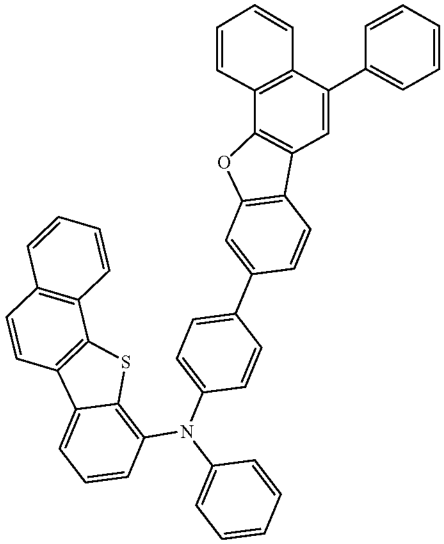

-continued
1-443
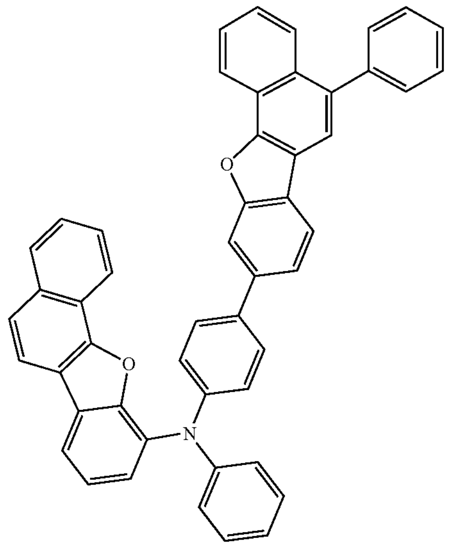
1-444
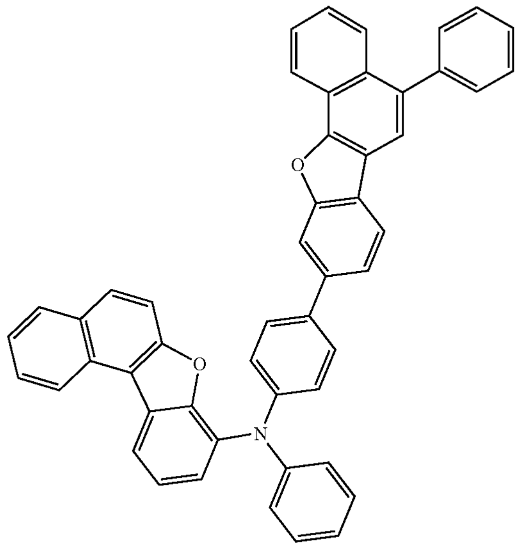
-continued
1-445
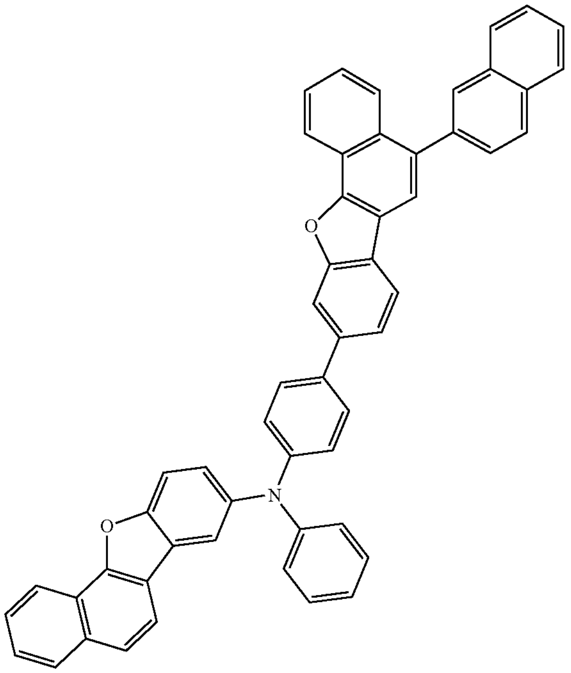
1-446
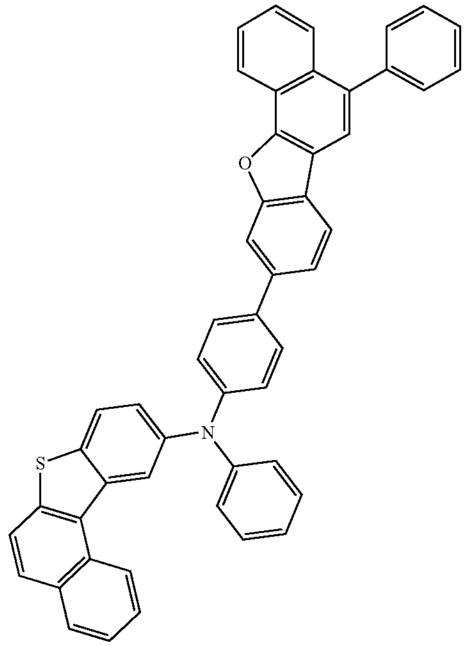

-continued
1-447
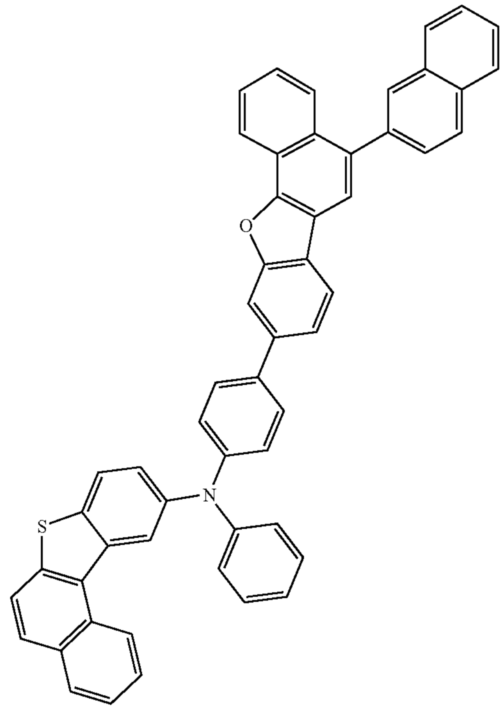
1-448
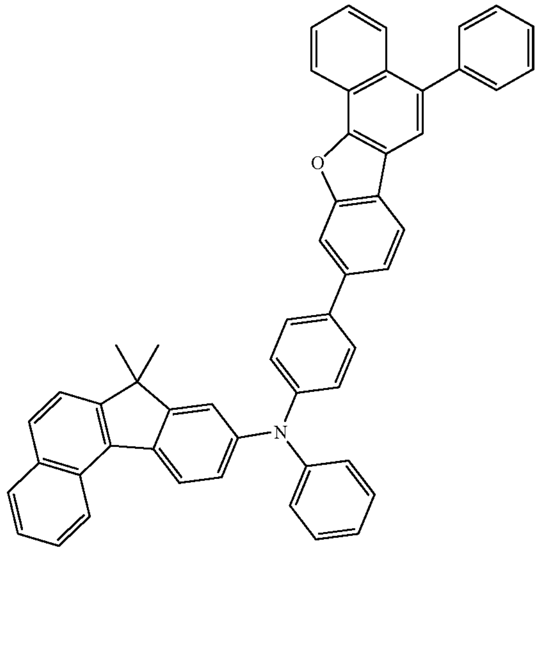
-continued
1-449
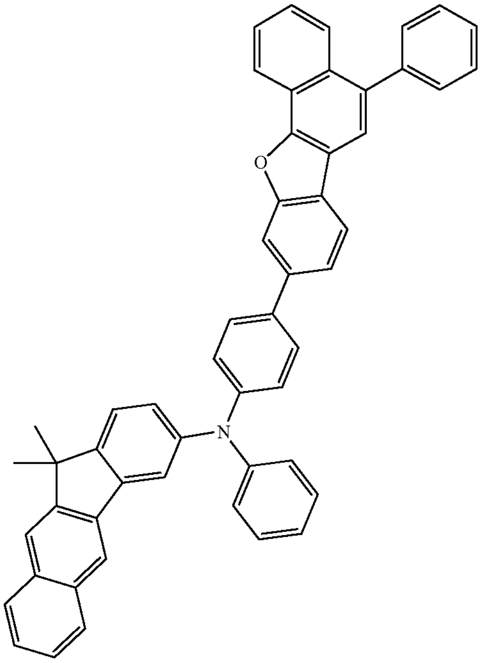
1-450
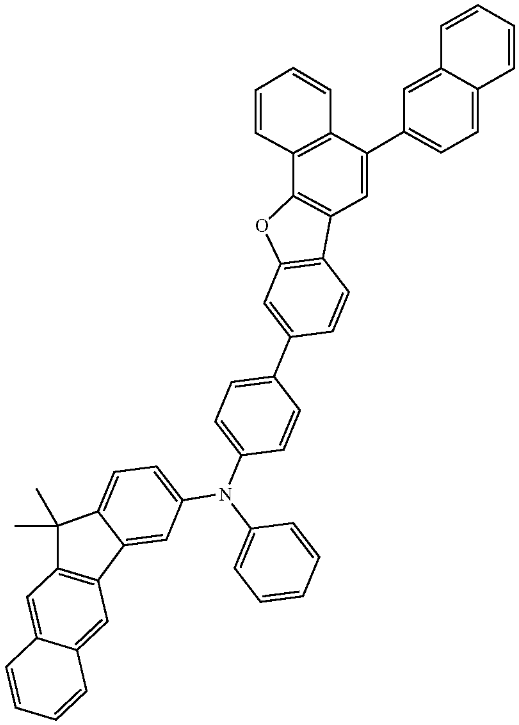

-continued
1-451
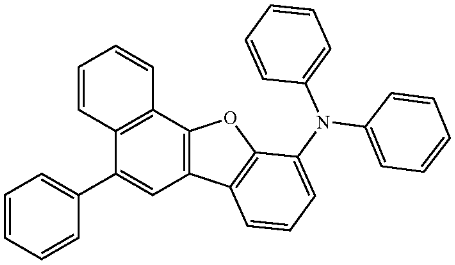
1-452
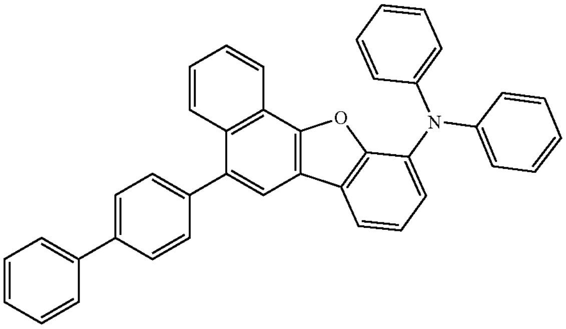
1-453
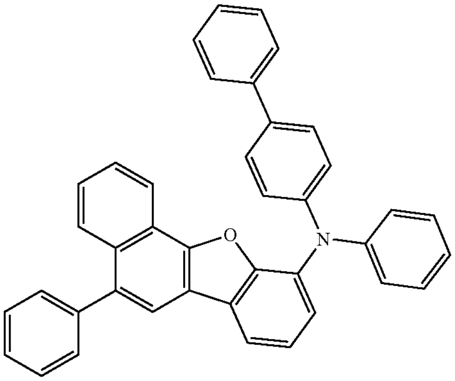
1-454
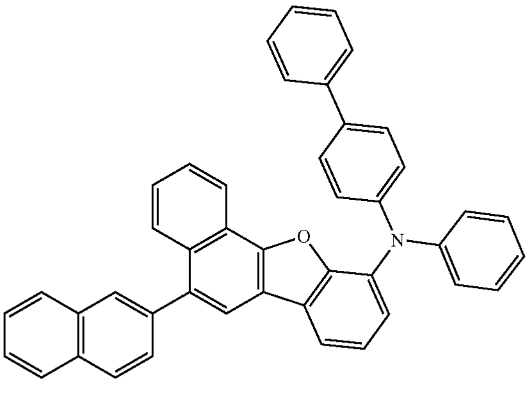
-continued
1-455
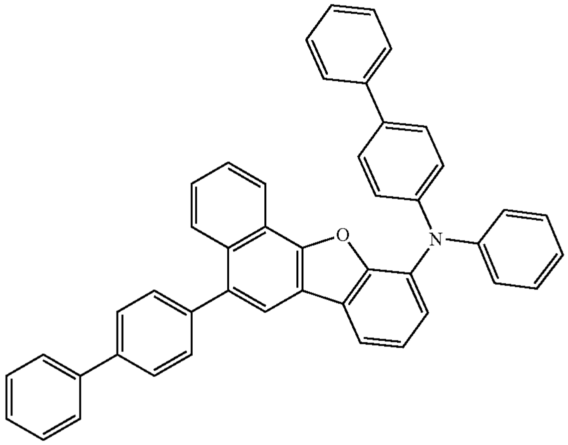
1-456
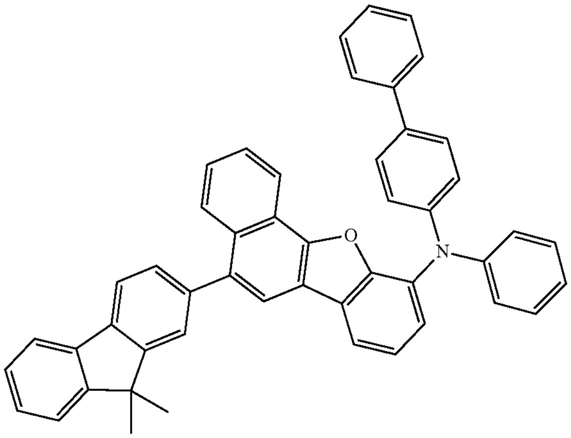
1-457
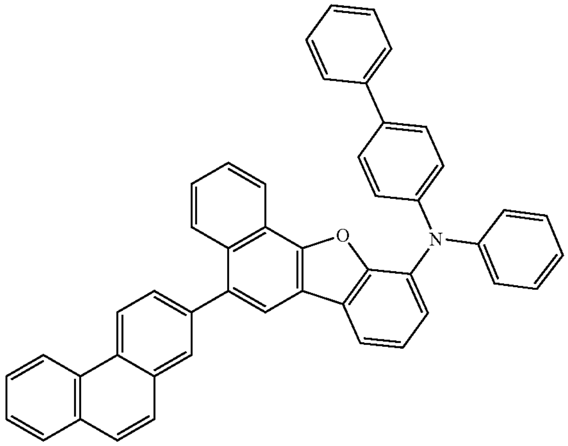

-continued
1-458
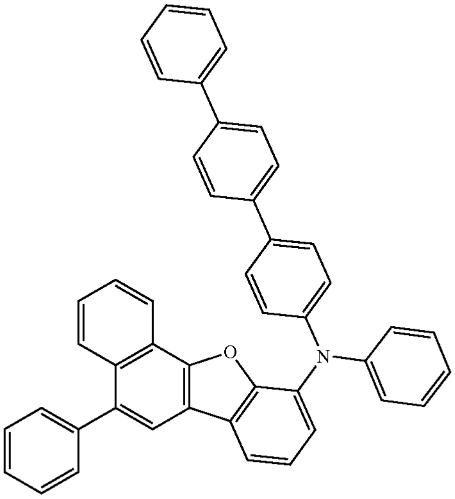
1-459
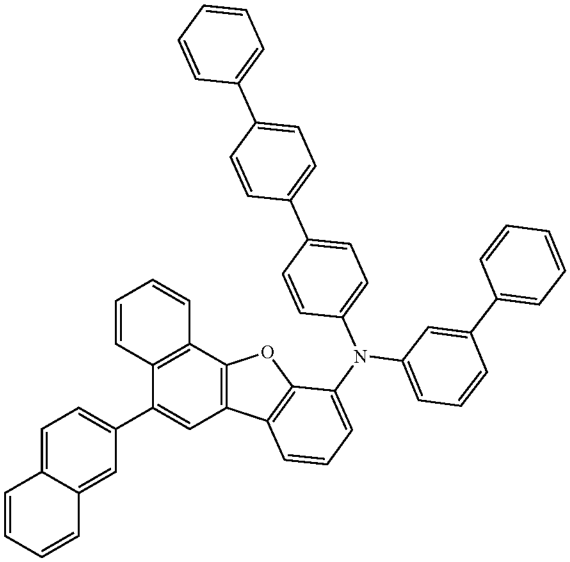
1-460
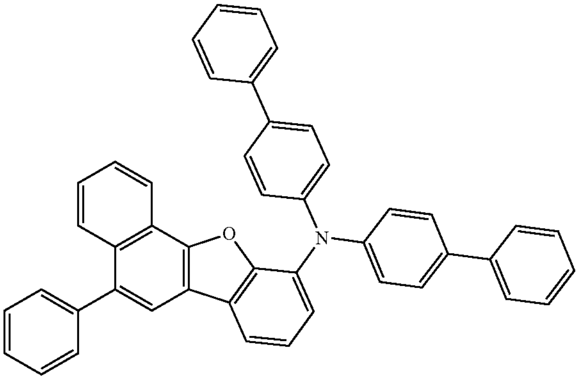
-continued
1-461
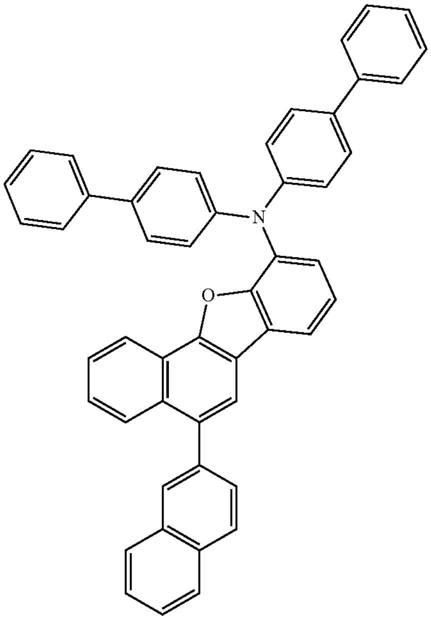
1-462
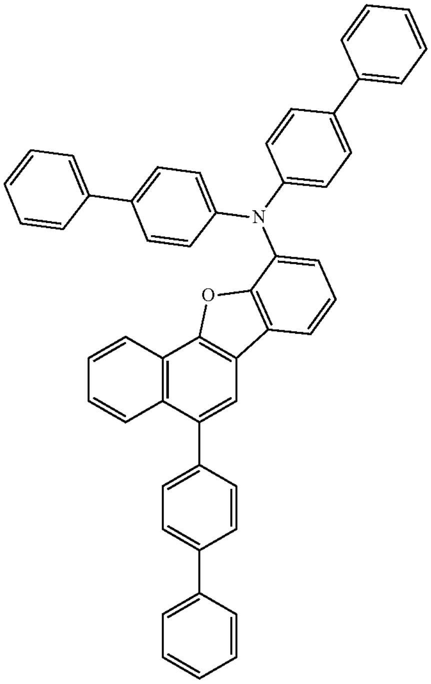

-continued
1-463
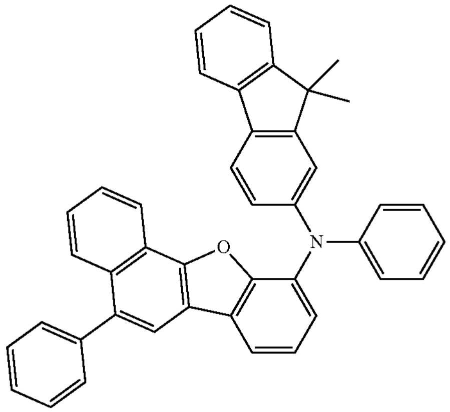
1-464
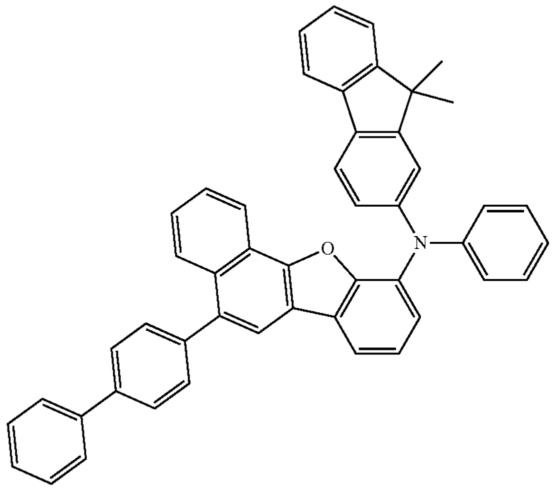
1-465
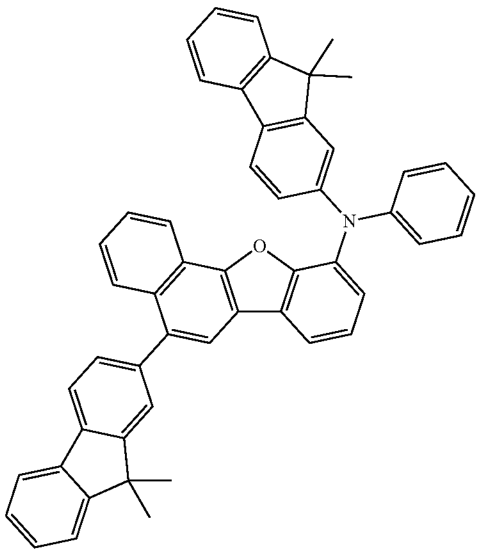
-continued
1-466
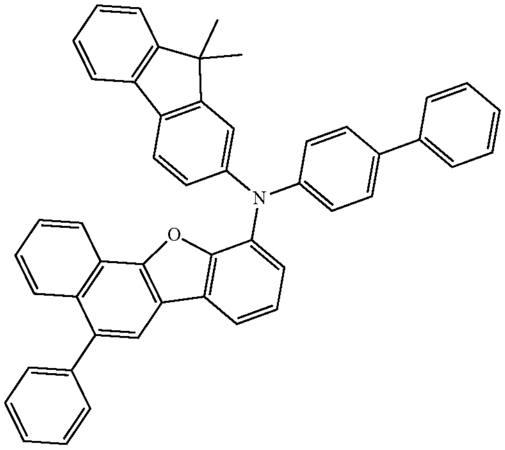
1-467
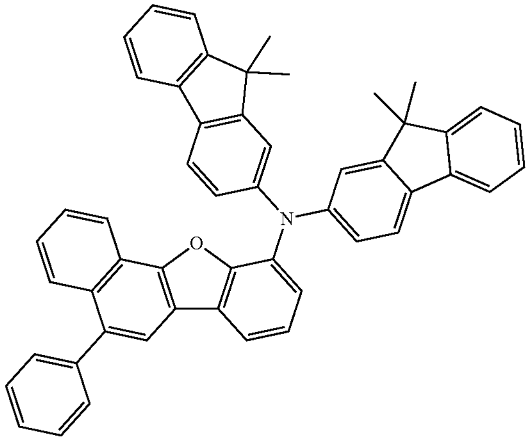
1-468
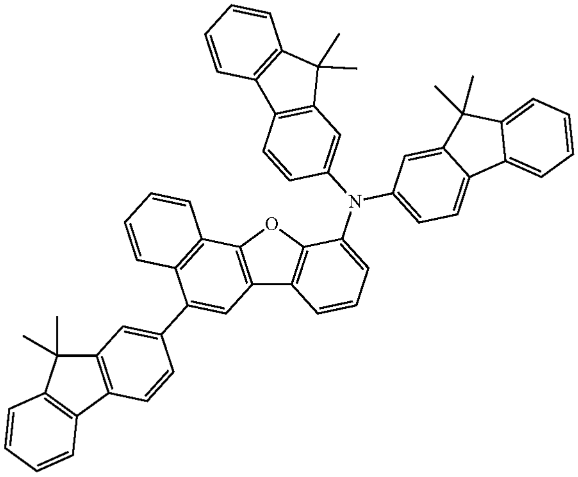

-continued
1-469
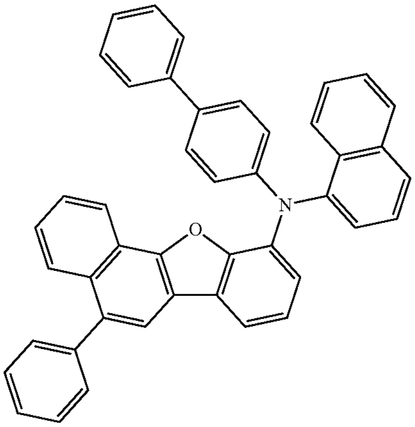
1-470
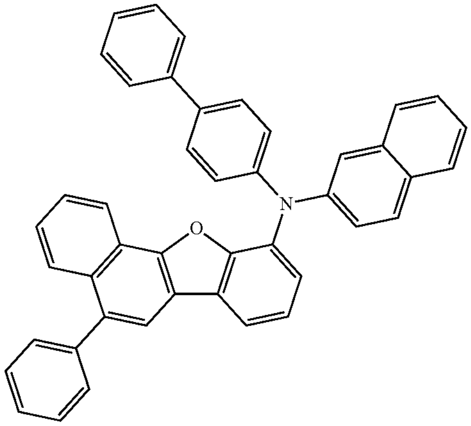
1-471
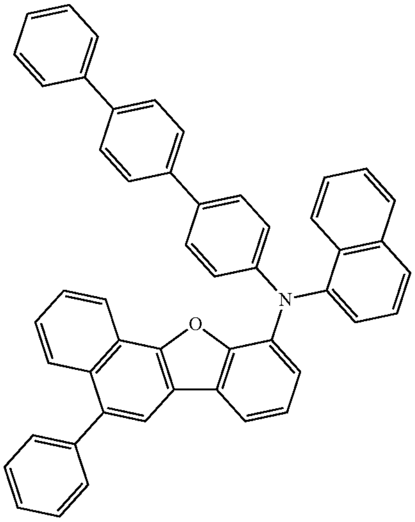
-continued
1-472
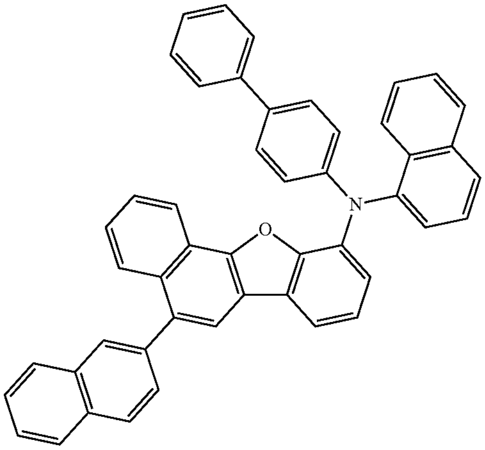
1-473
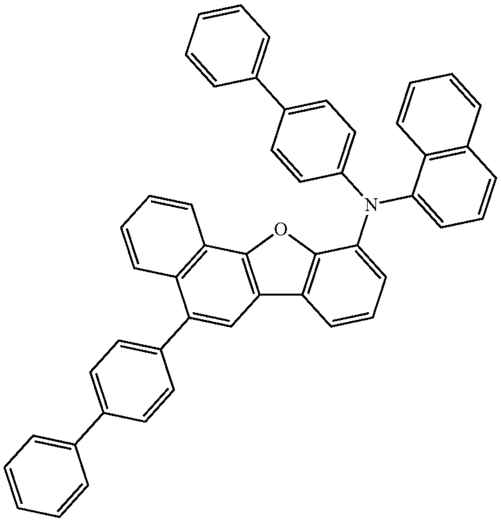
1-474
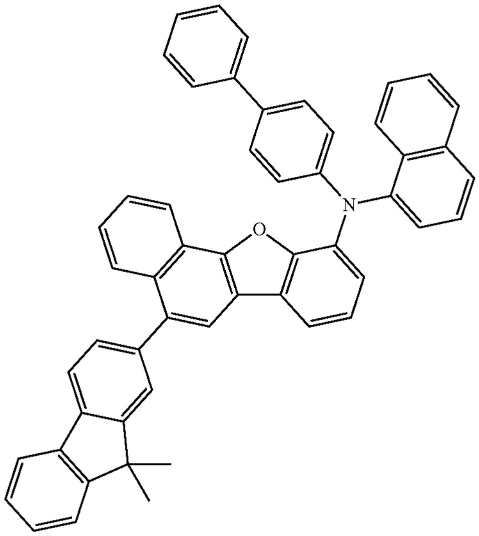

-continued
1-475
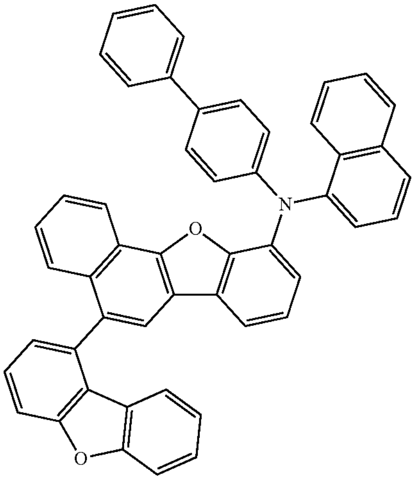
1-476
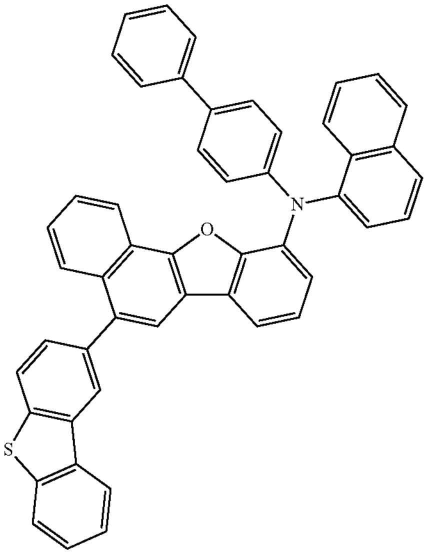
1-477
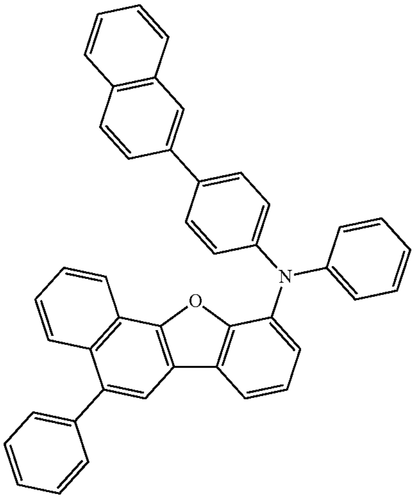
-continued
1-478
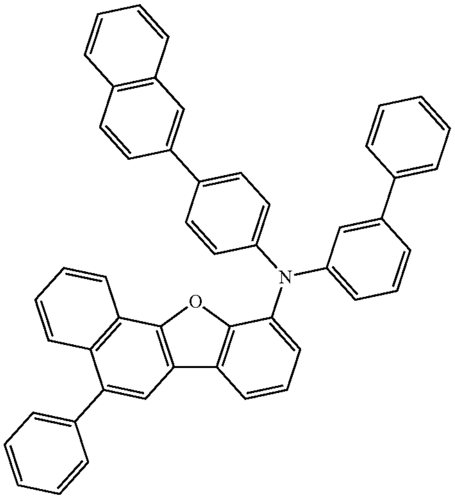
1-479
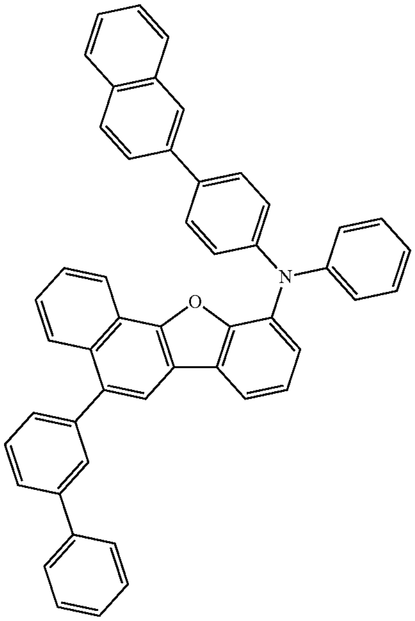

-continued
1-480
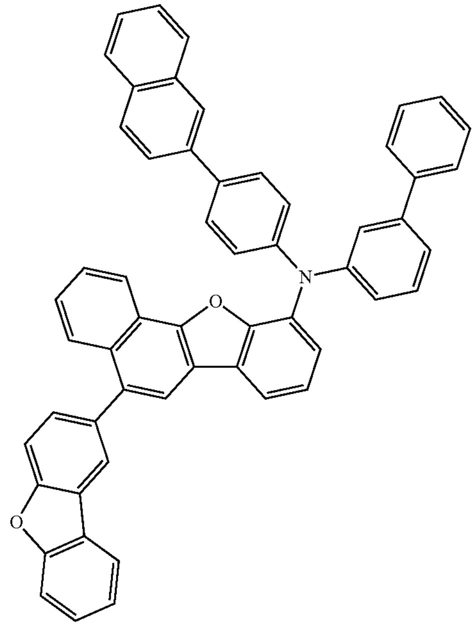
1-481
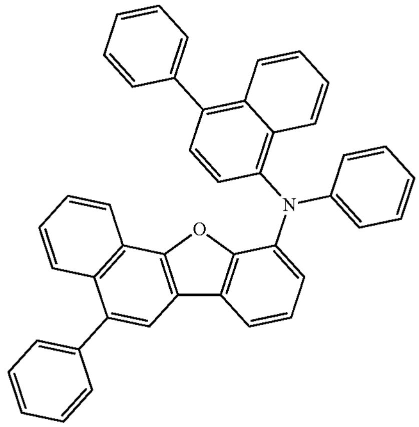
1-482
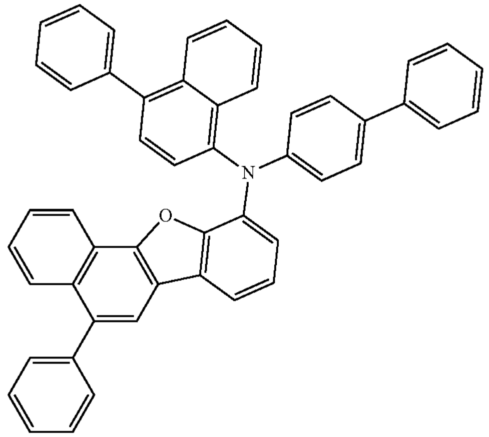
-continued
1-483
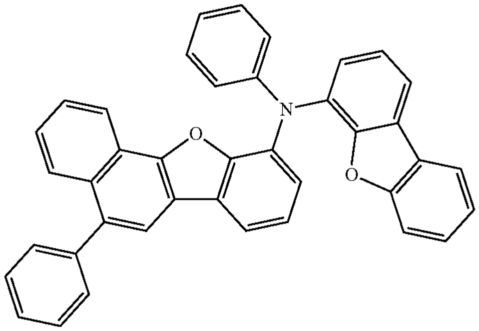
1-484
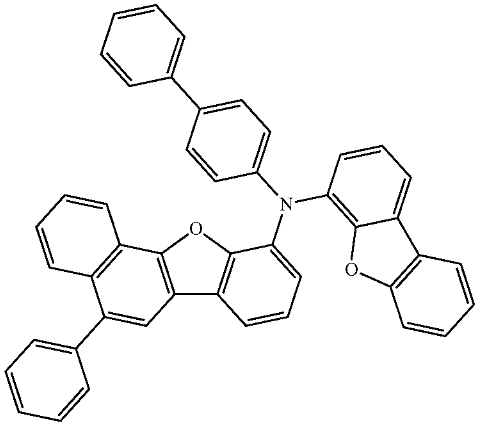
1-485
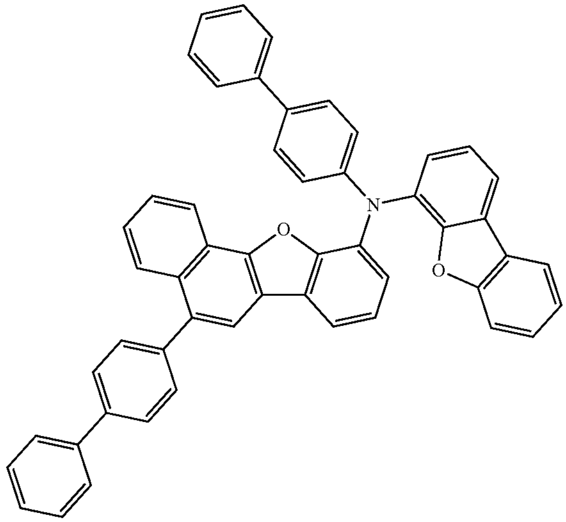

-continued
1-486
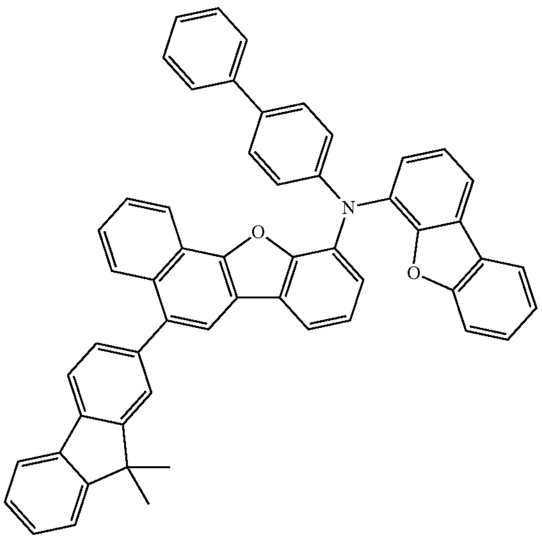
1-487
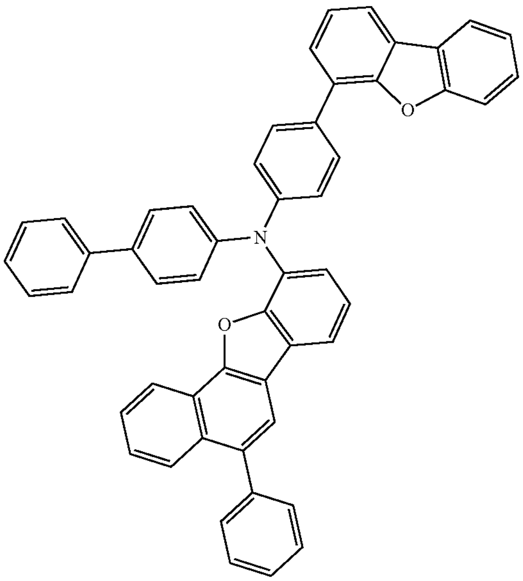
-continued
1-488
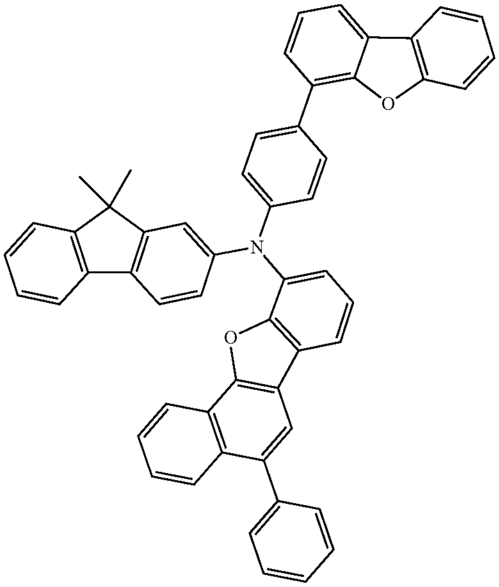
1-489
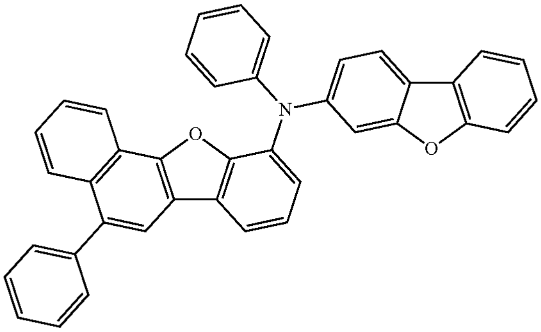
1-490
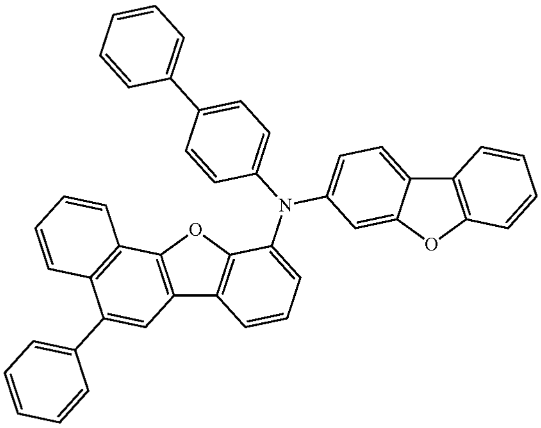

-continued
1-491
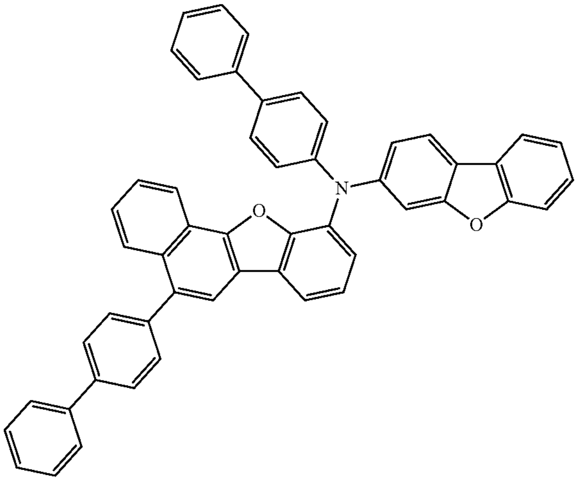
1-492
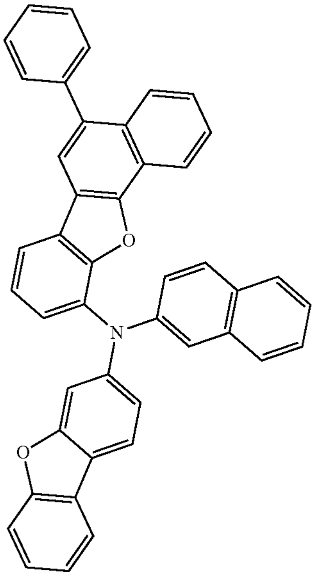
-continued
1-493
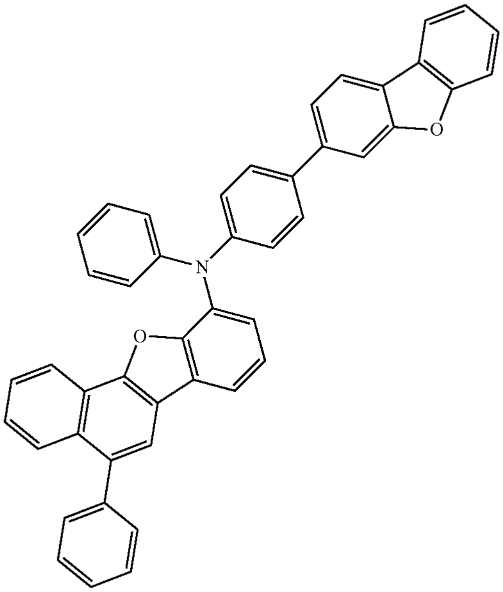
1-494
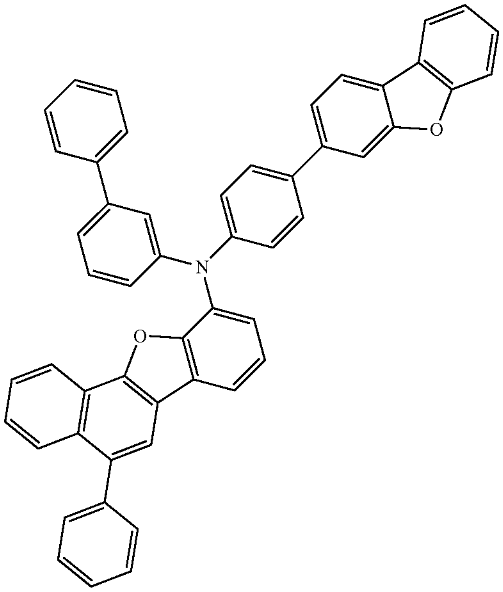

-continued
1-495
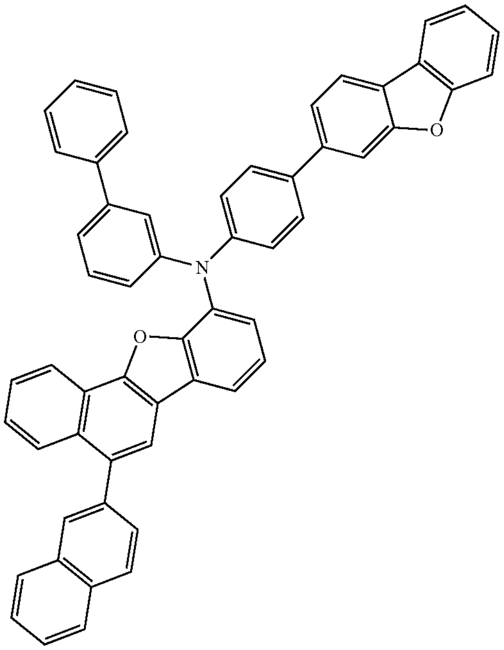
1-496
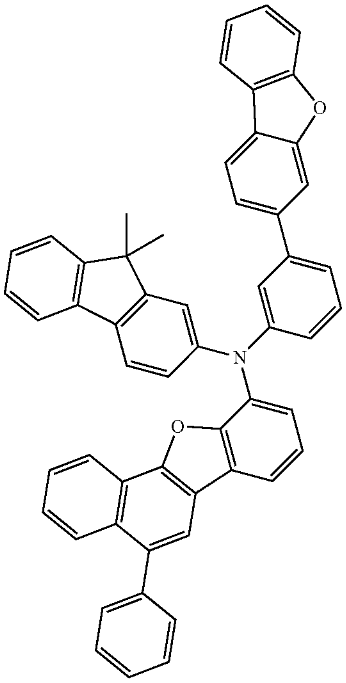
-continued
1-497
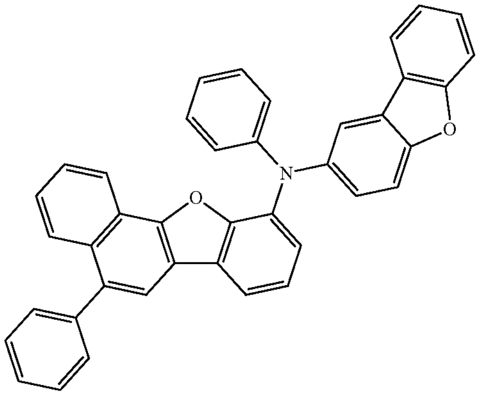
1-498
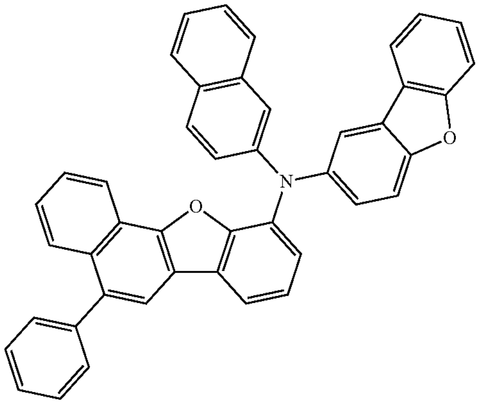
1-499
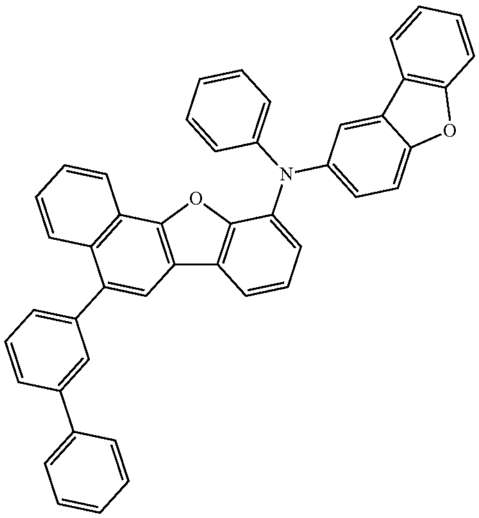

-continued
1-500
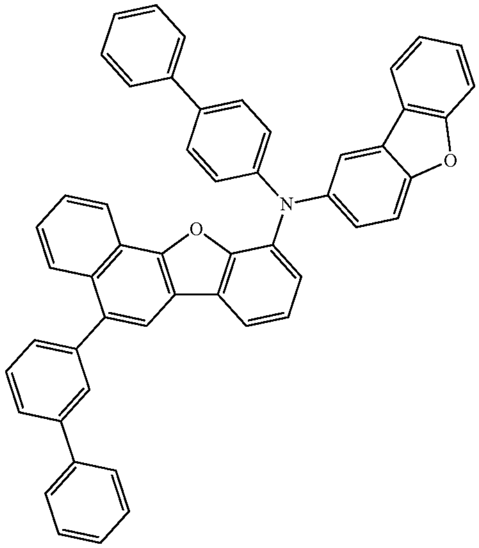
1-501
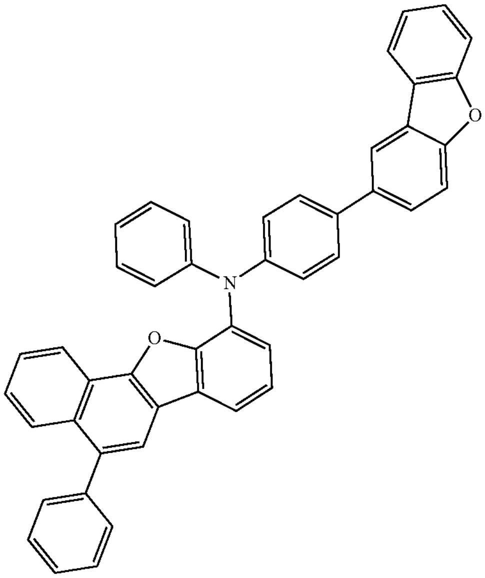
-continued
1-502
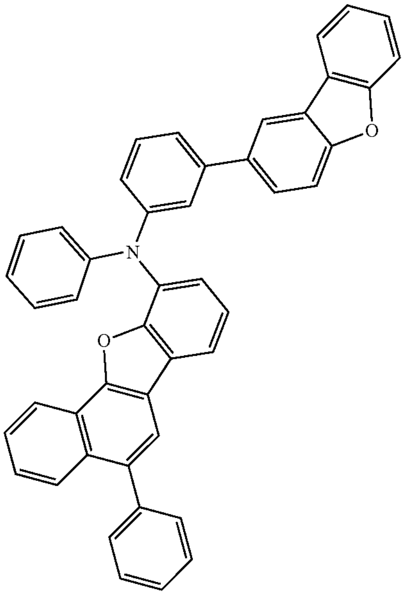
1-503
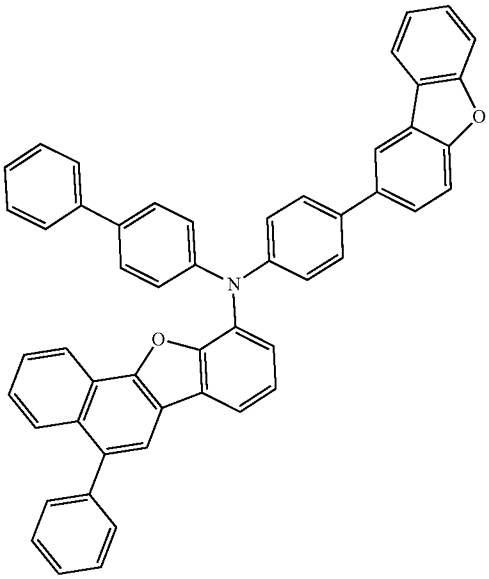

-continued
1-504
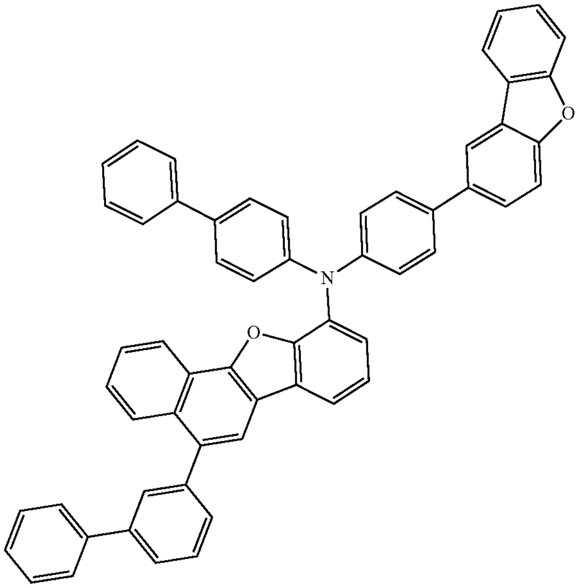
1-505
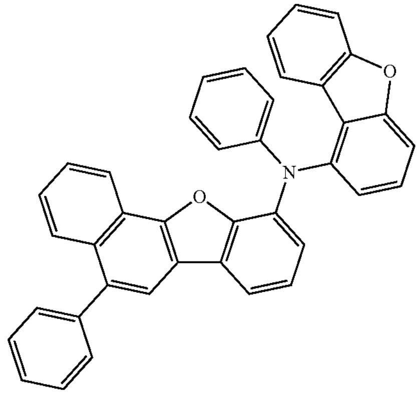
1-506
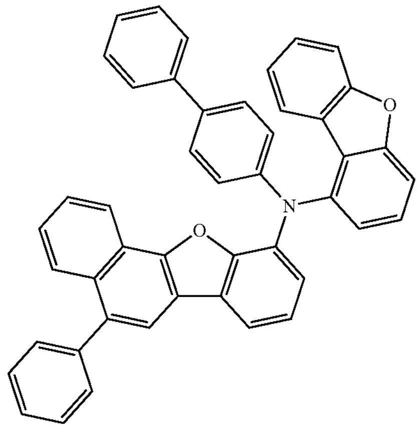
-continued
1-507
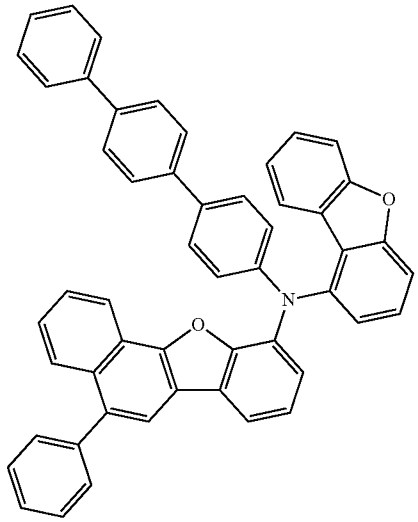
1-508
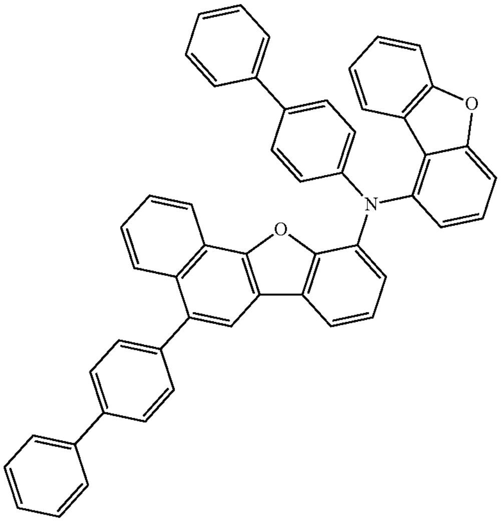
1-509
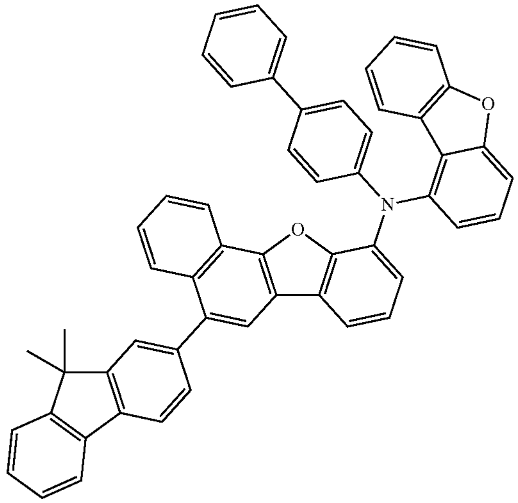

-continued
1-510
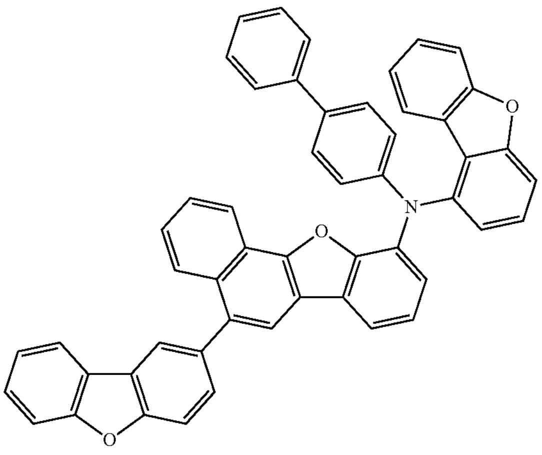
1-511
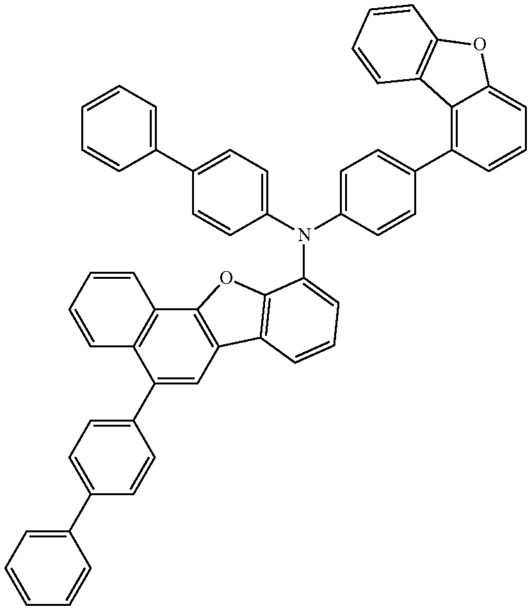
1-512
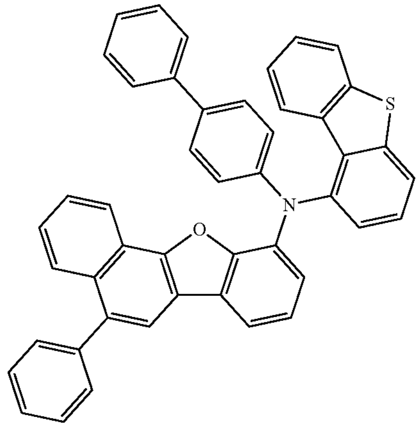
-continued
1-513
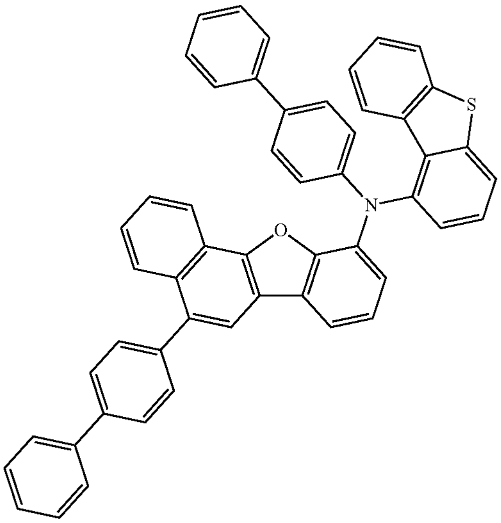
1-514
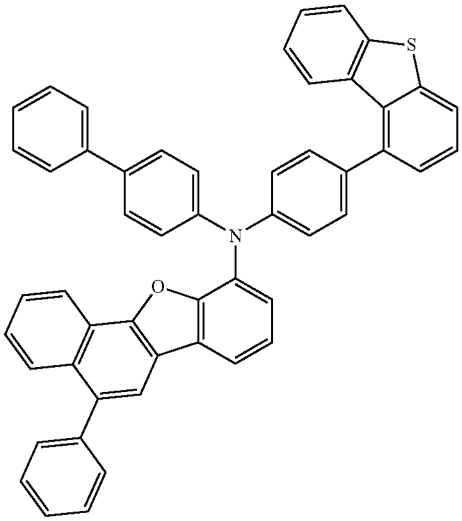
1-515
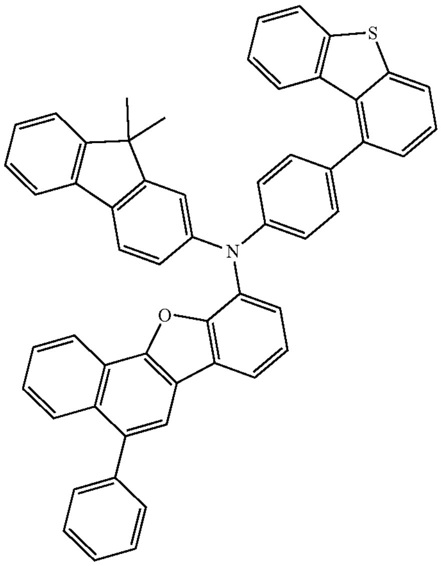

-continued
1-516
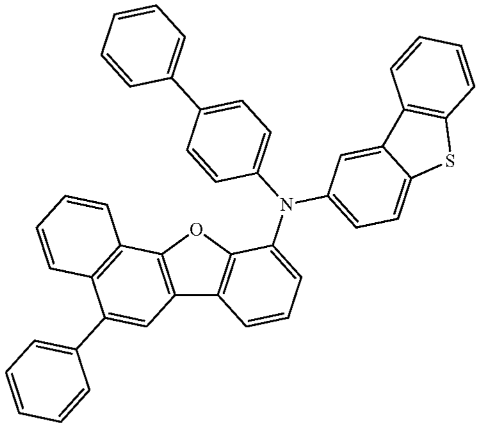
1-517
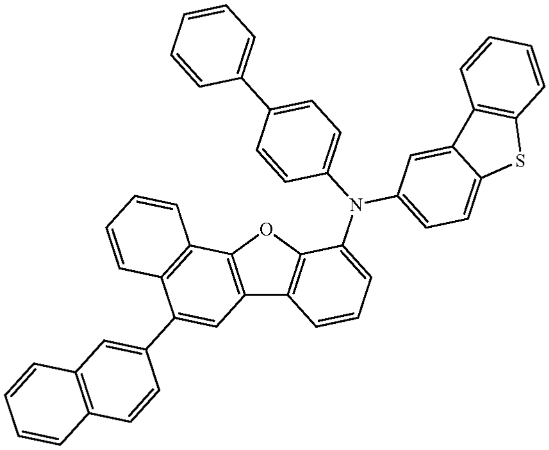
1-518
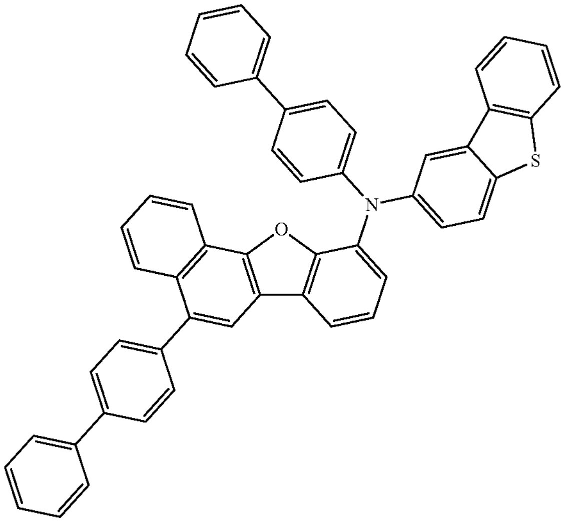
-continued
1-519
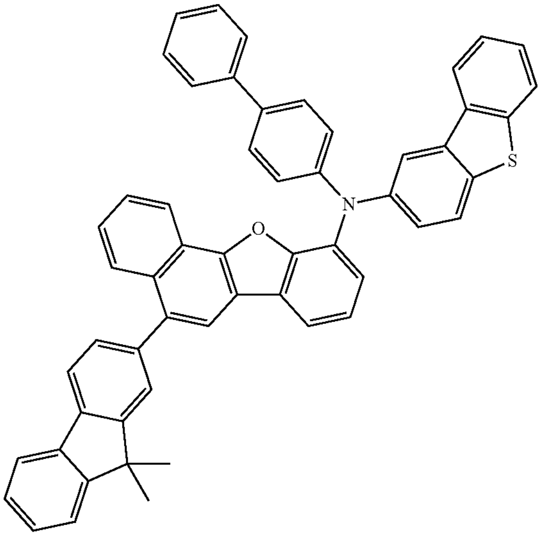
1-520
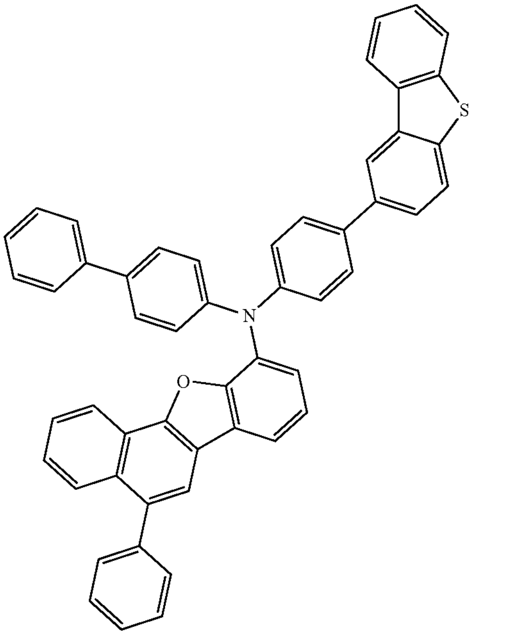
1-521
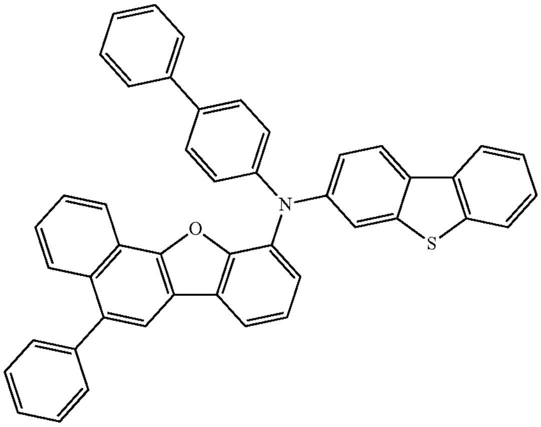

-continued
1-522
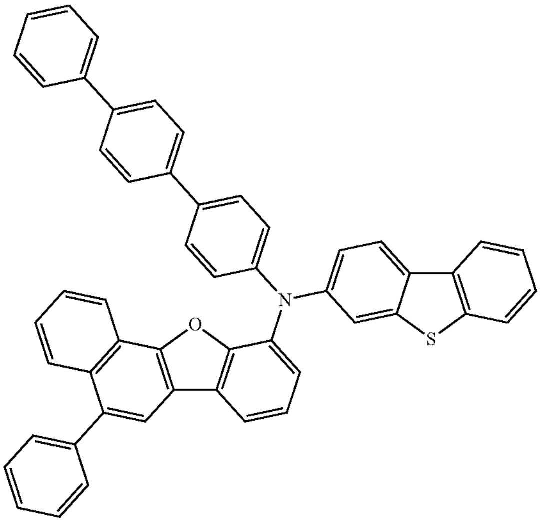
1-523
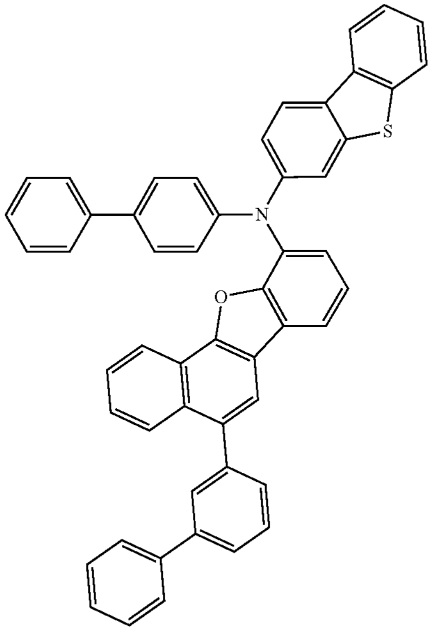
1-524
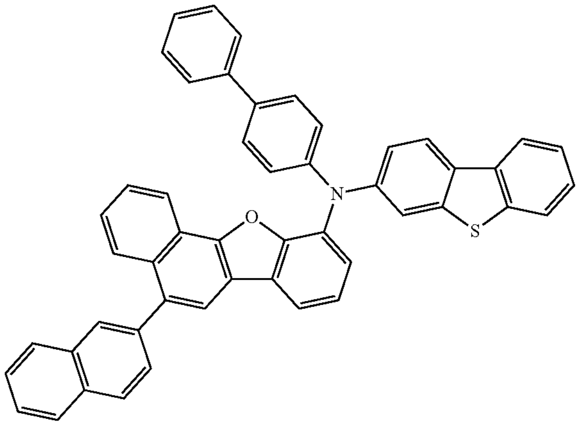
-continued
1-525
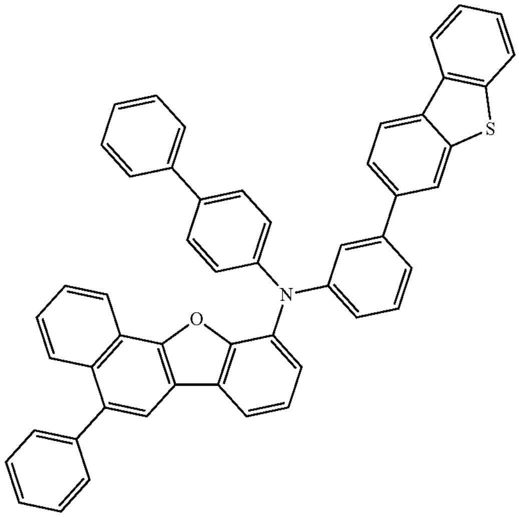
1-526
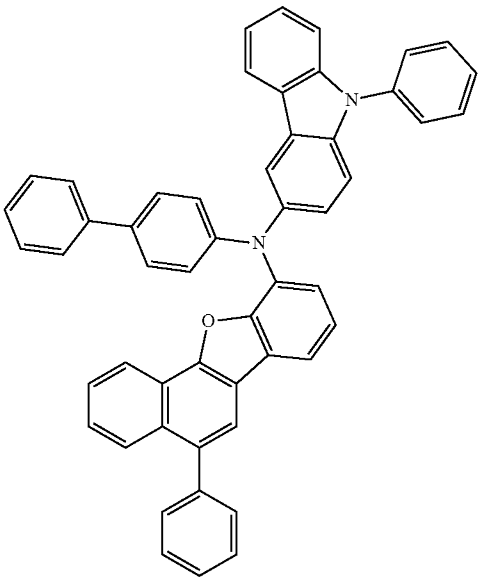

-continued
1-527
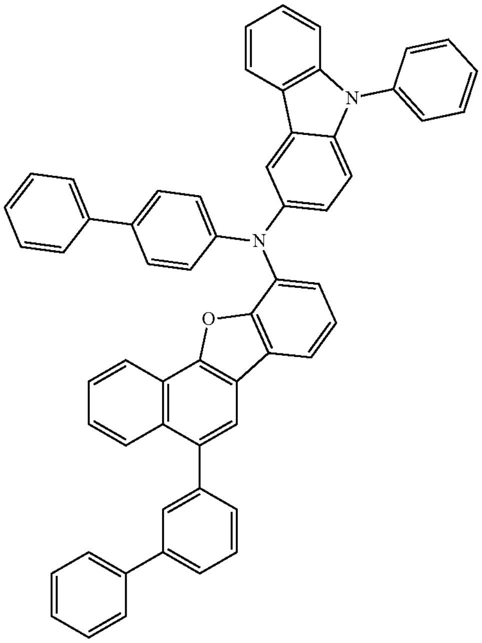
1-528
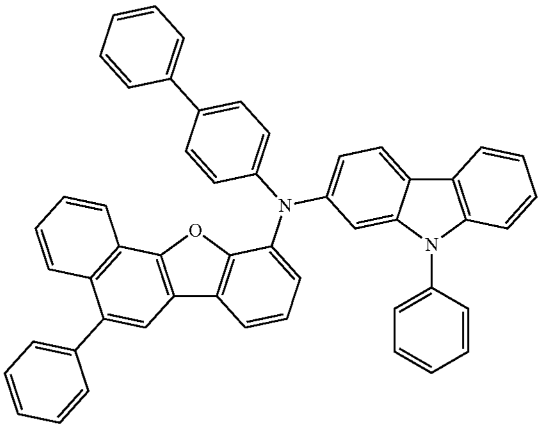
-continued
1-529
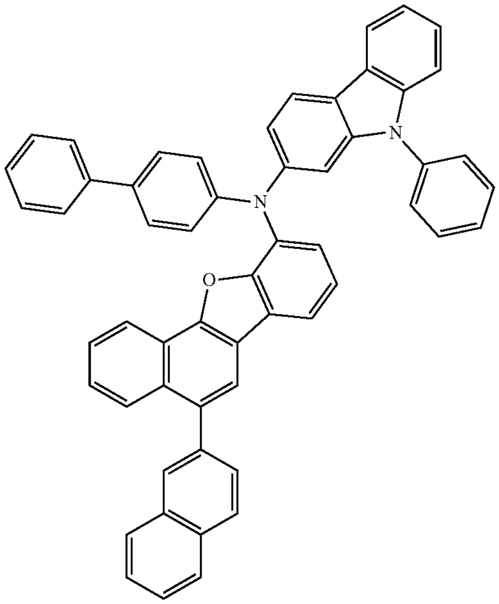
1-530
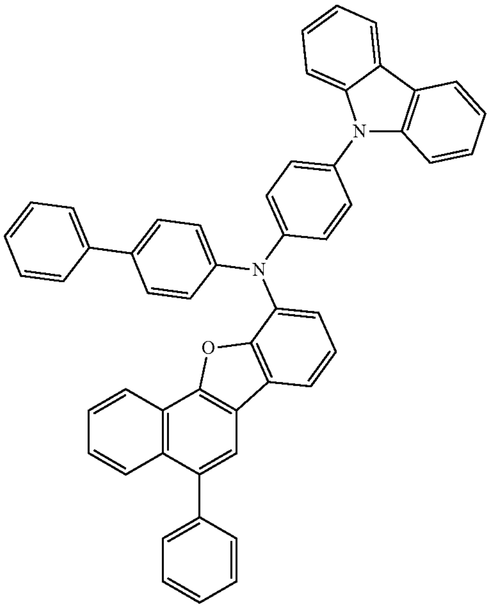

1-531
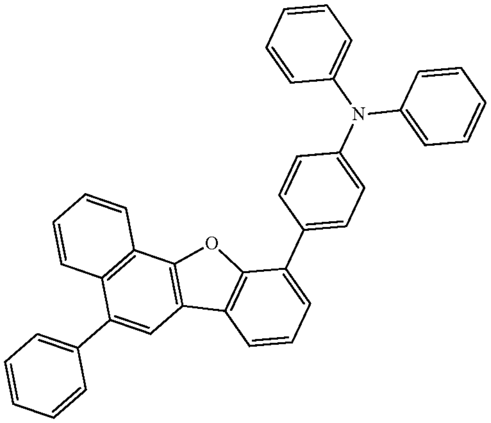
1-532
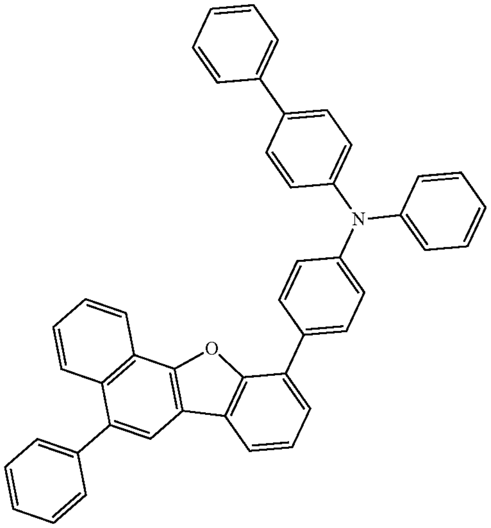
1-533
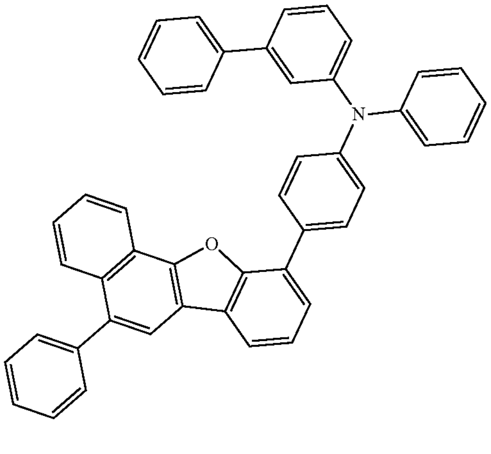
1-534
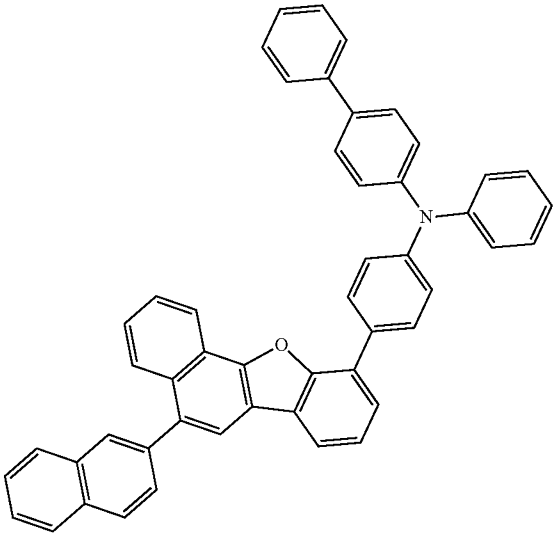
1-535
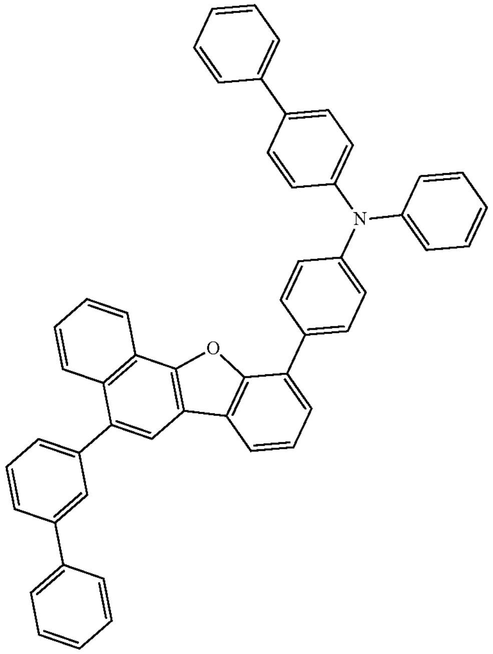

-continued
1-536
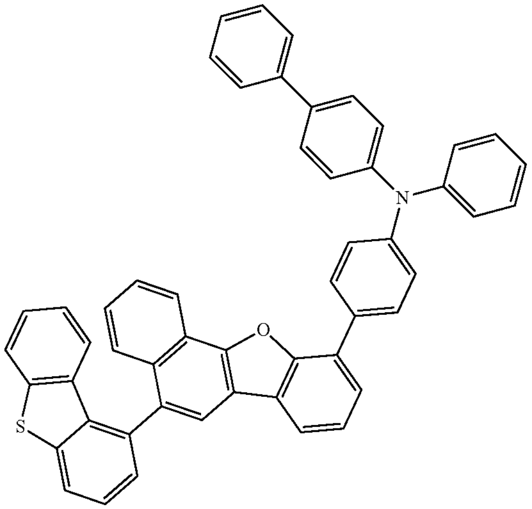
1-537
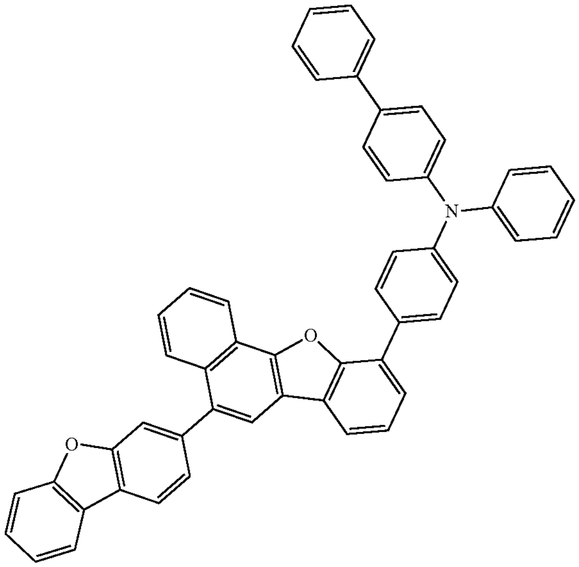
-continued
1-538
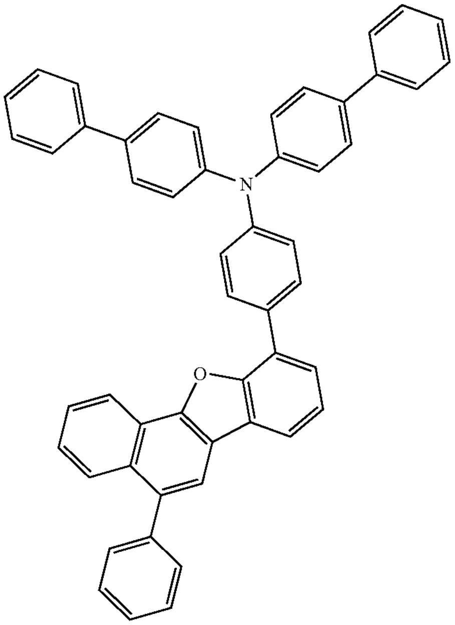
1-539
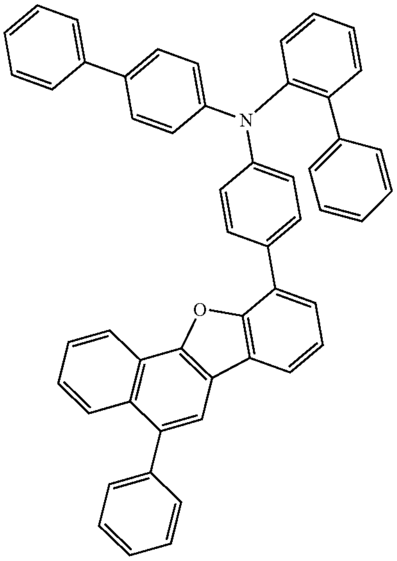

-continued
1-540
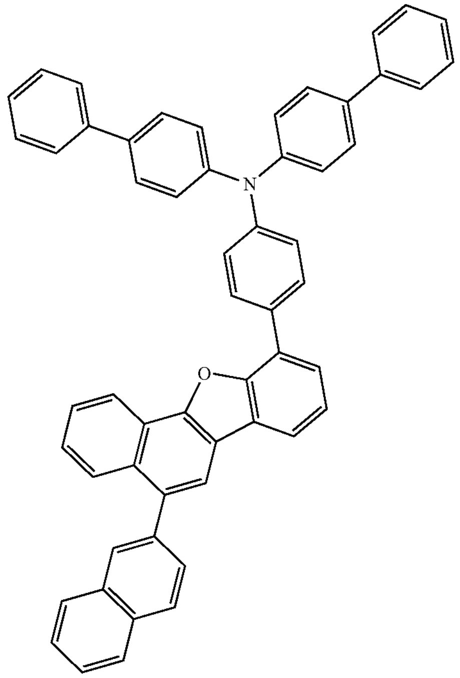
1-541
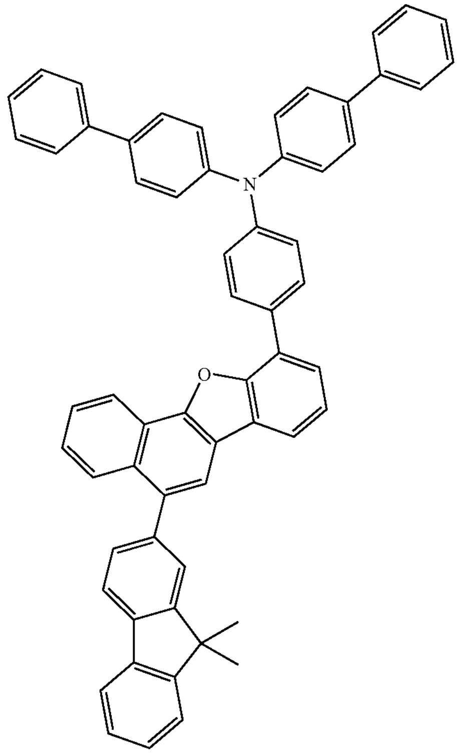
-continued
1-542
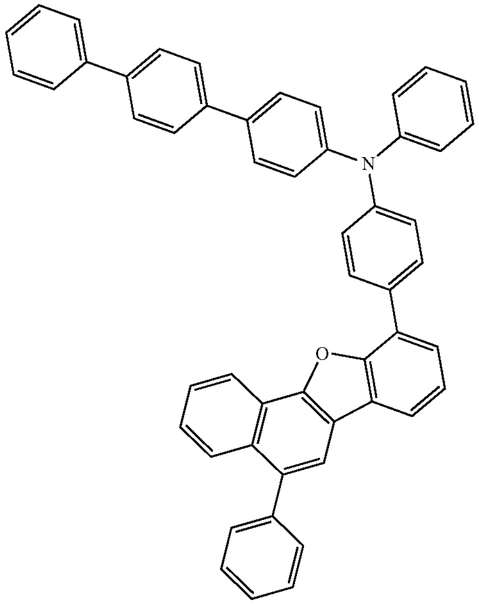
1-543
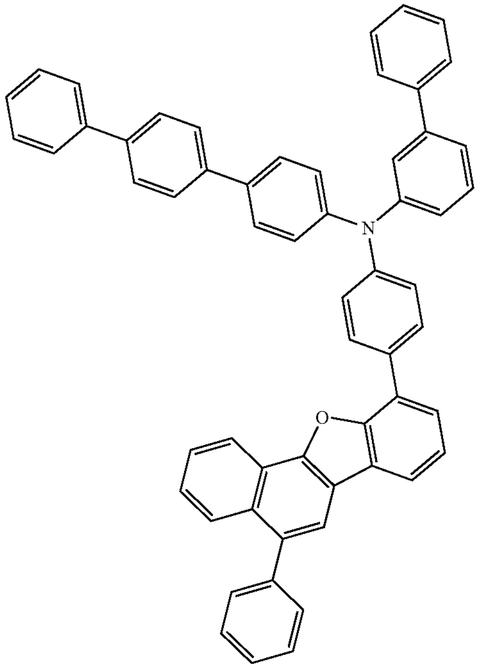

-continued
1-544
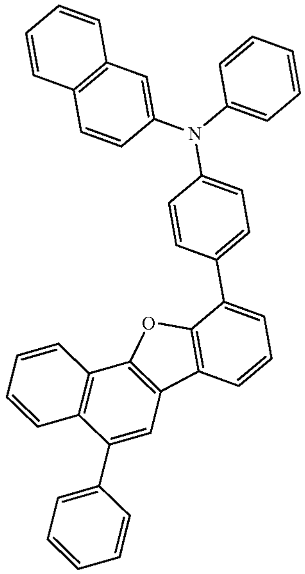
1-545
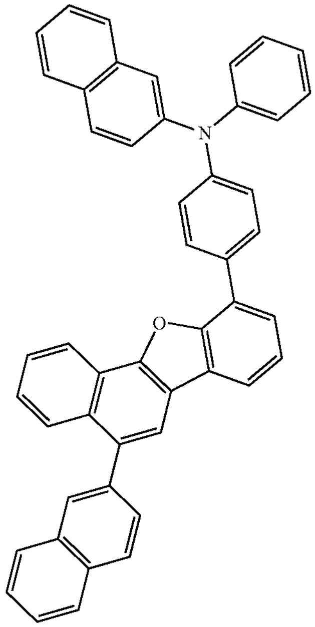
-continued
1-546
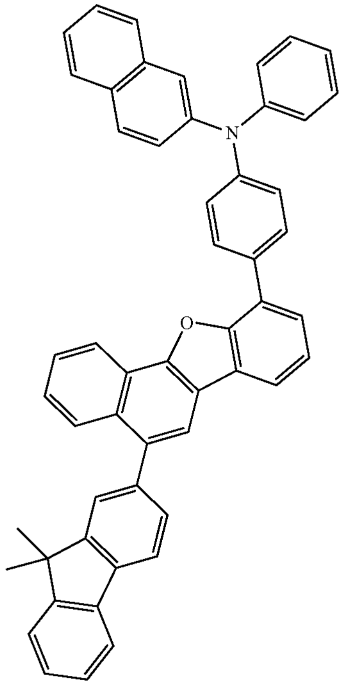
1-547
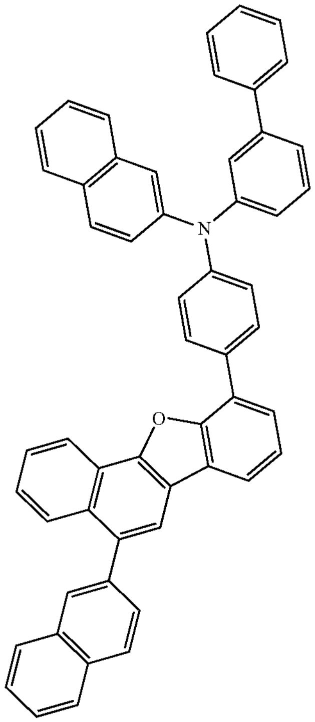

-continued
1-548
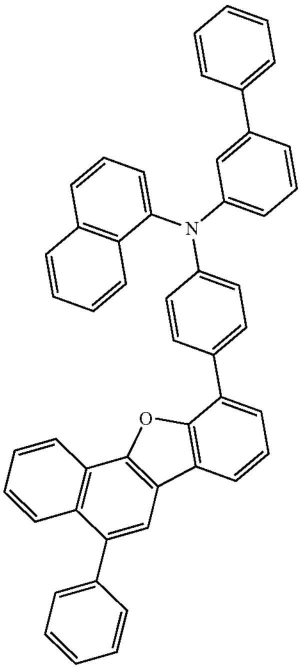
1-549
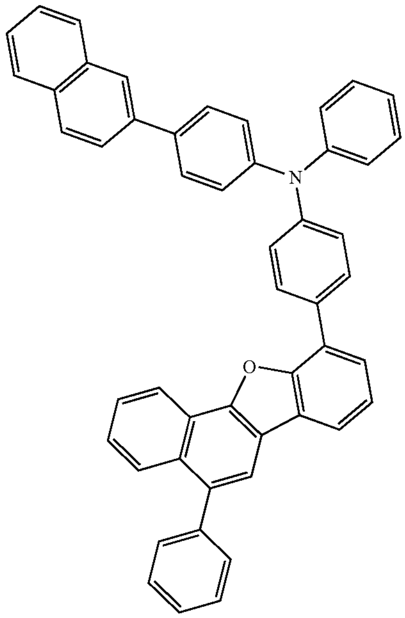
-continued
1-550
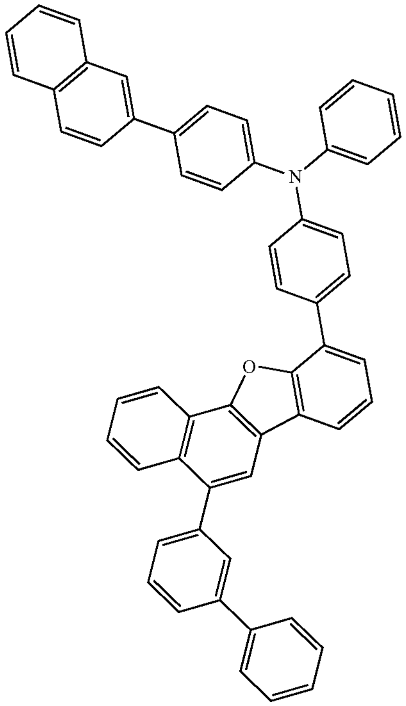
1-551
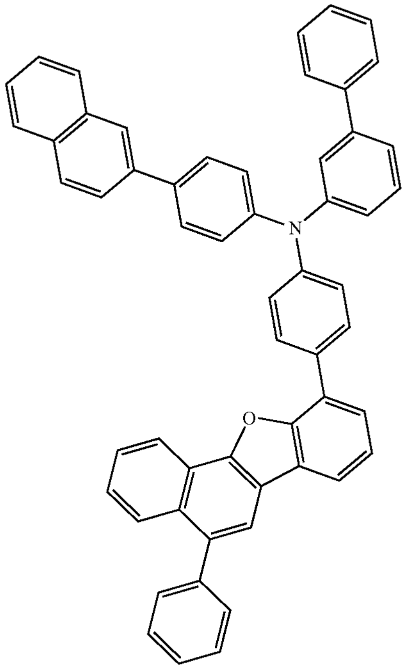

1-552
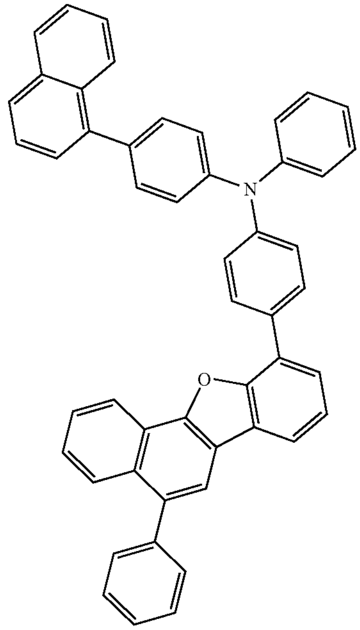
1-553
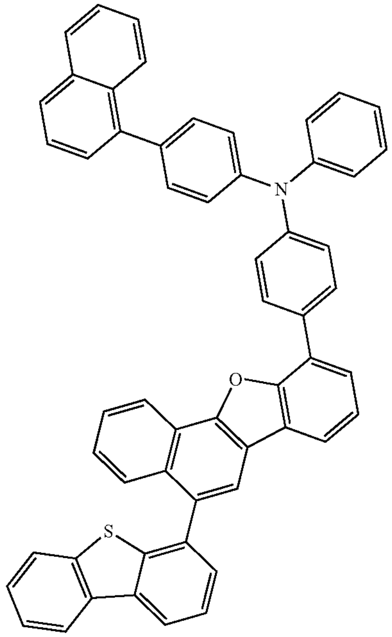
1-554
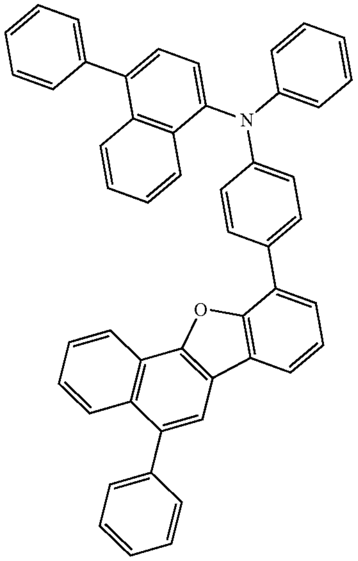
1-555
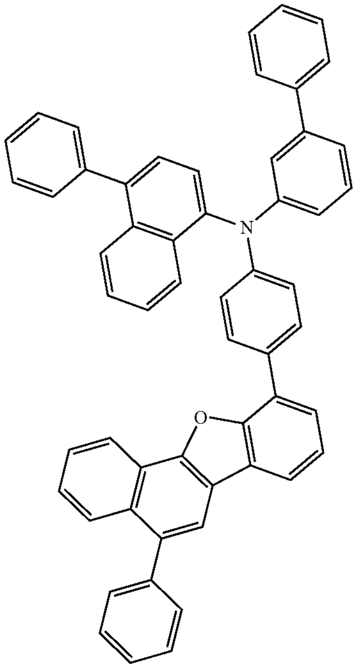

-continued
1-556
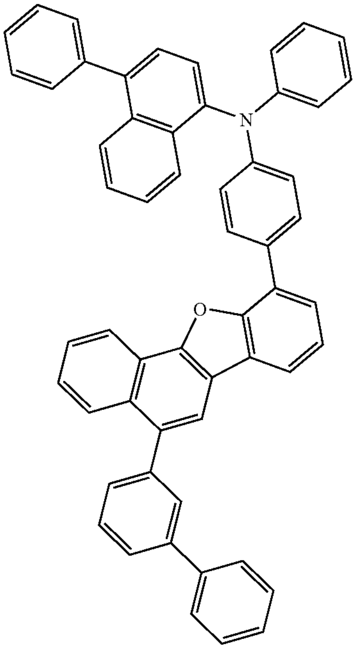
1-557
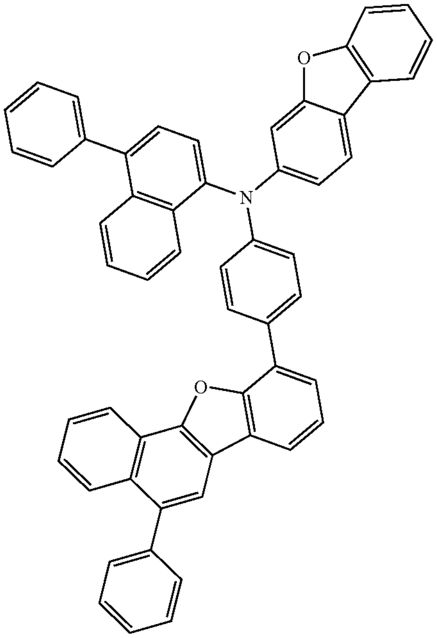
-continued
1-558
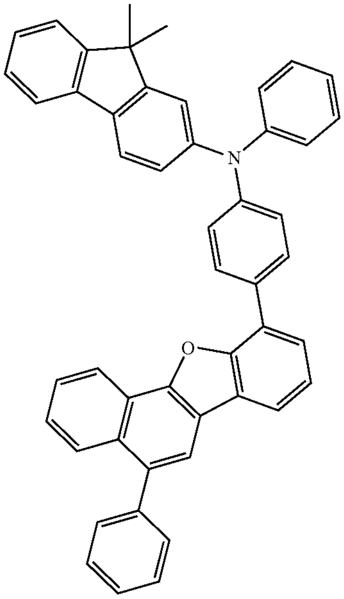
1-559
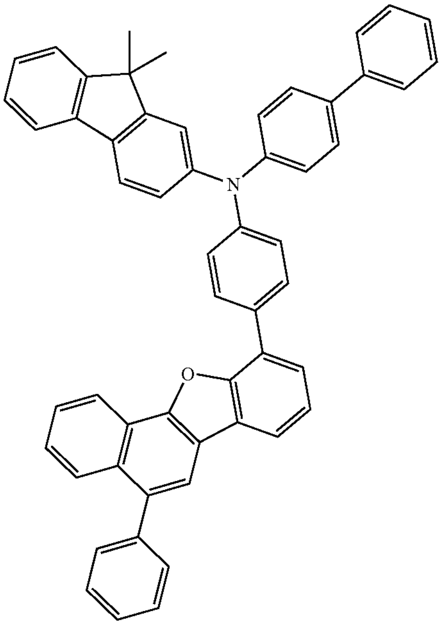

-continued
1-560
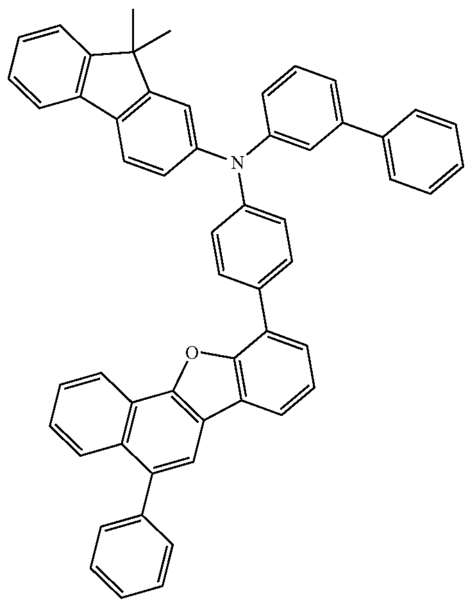
1-561
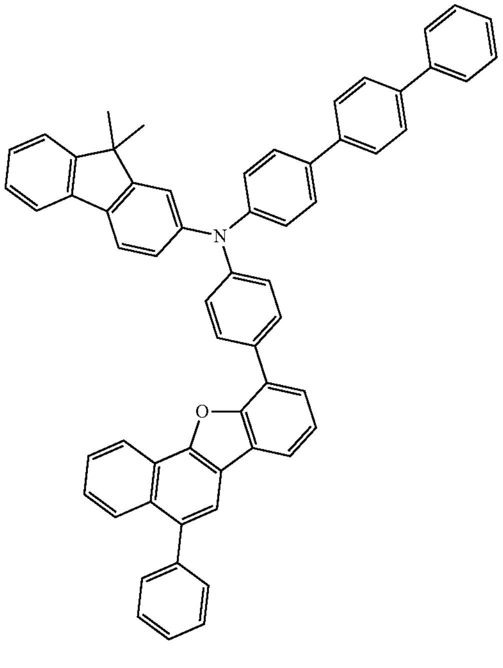
-continued
1-562
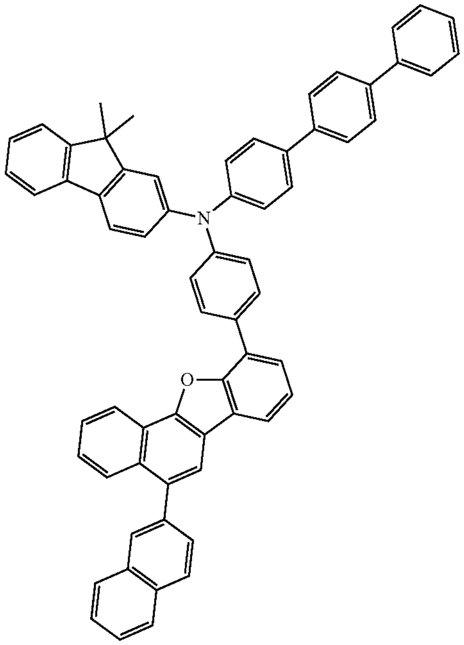
1-563
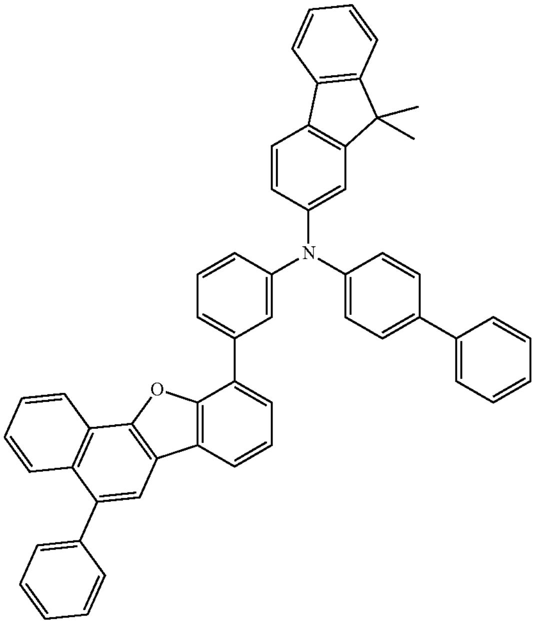

1-564
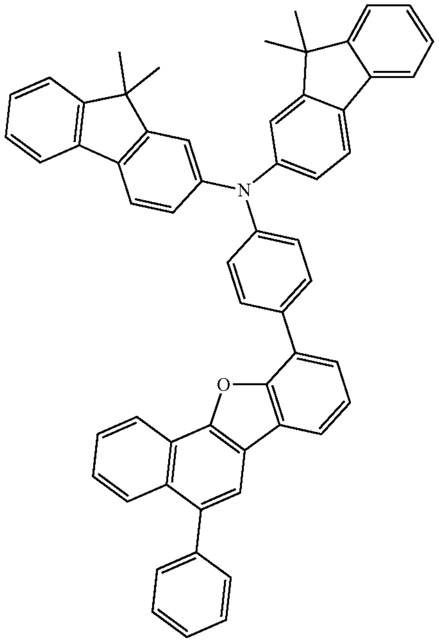
1-565
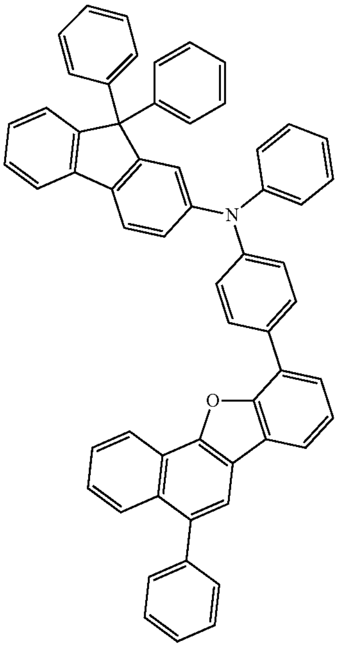
1-566
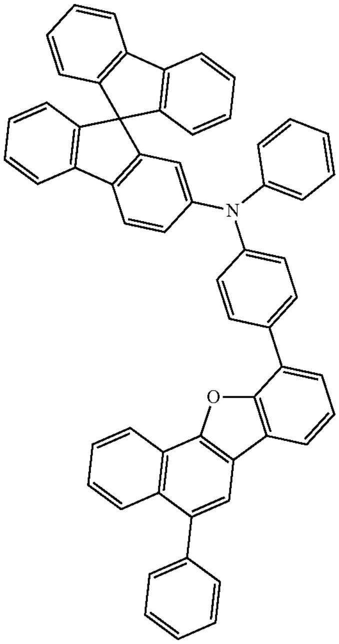
1-567
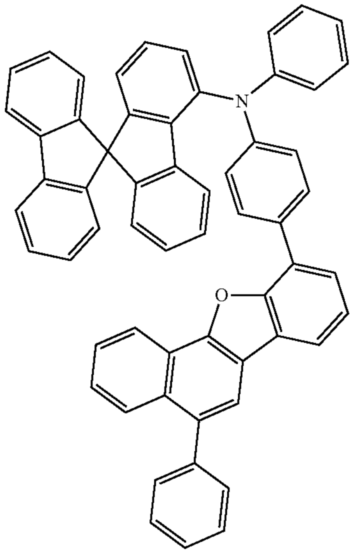

-continued
1-568
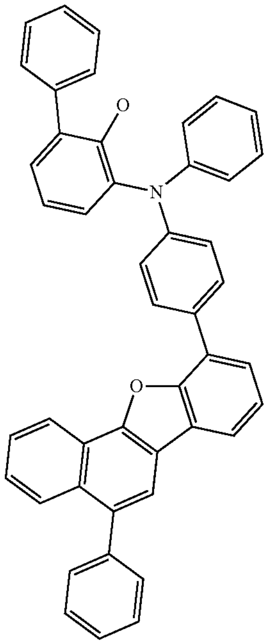
1-569
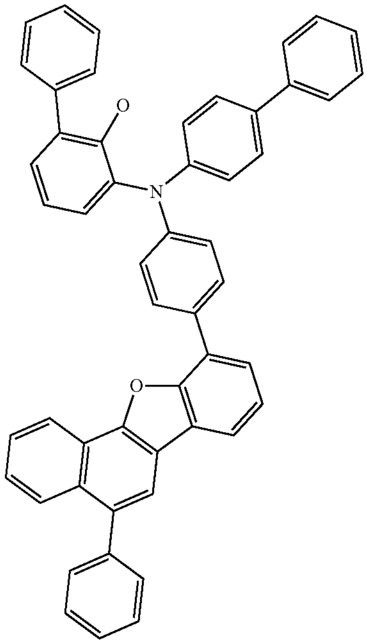
-continued
1-570
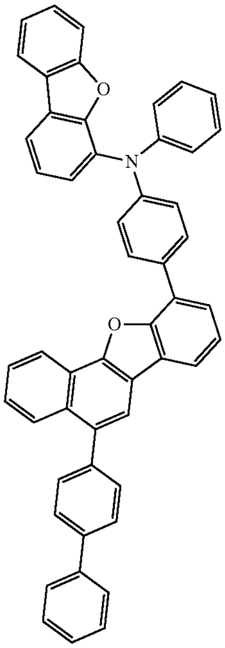
1-571
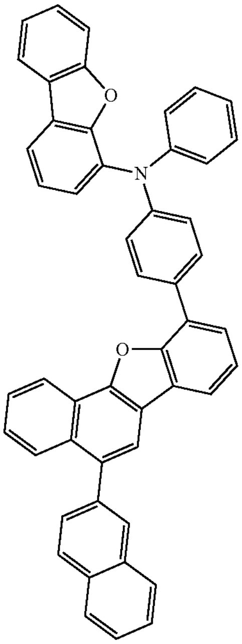

1-572
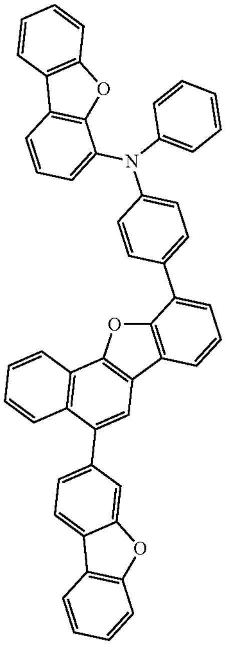
1-573
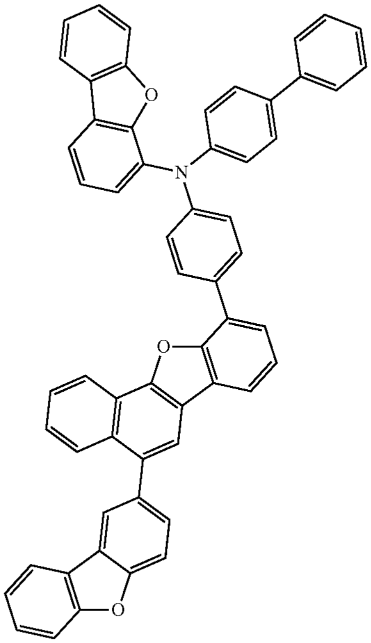
1-574
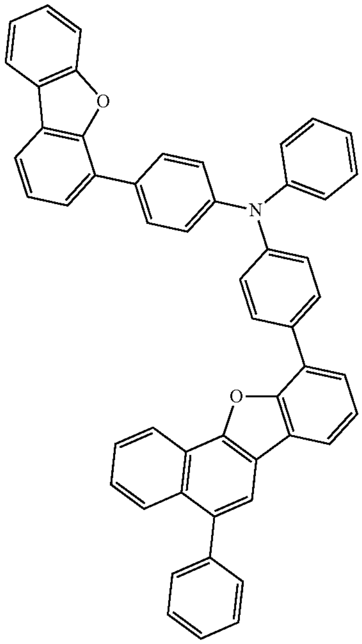
1-575
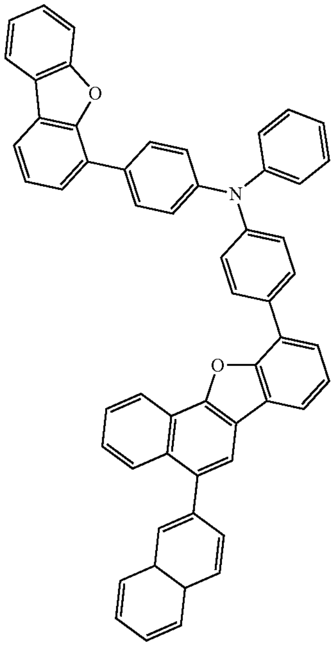

-continued
1-576
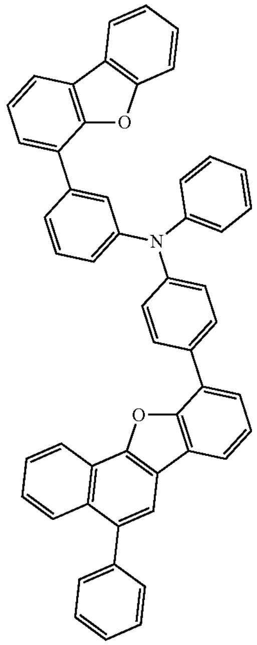
1-577
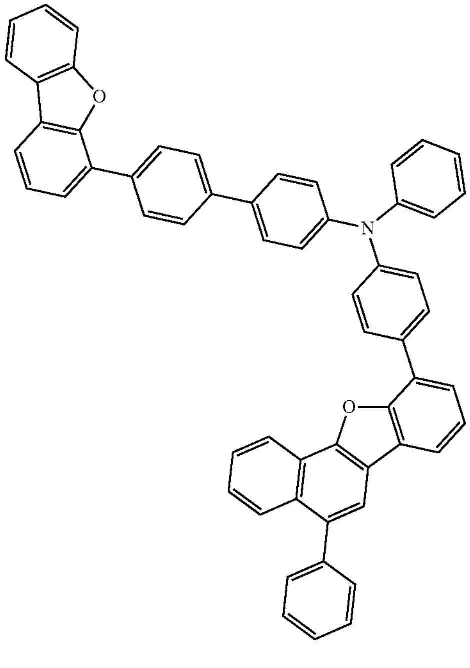
-continued
1-578
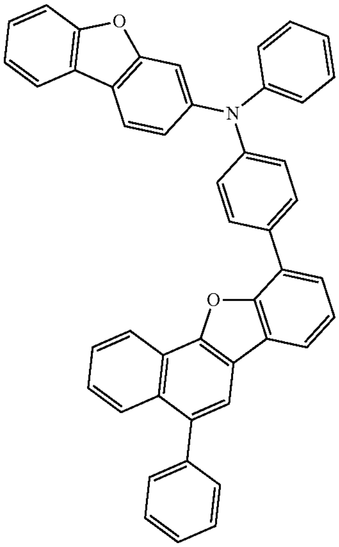
1-579
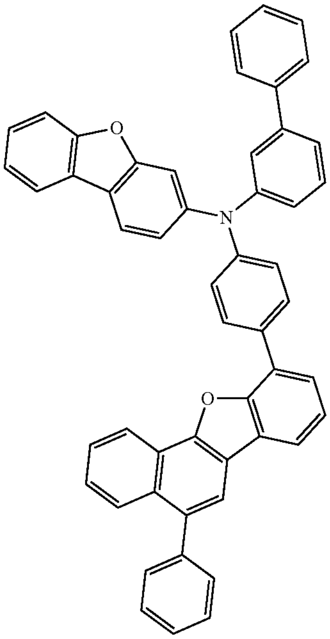

-continued
1-580
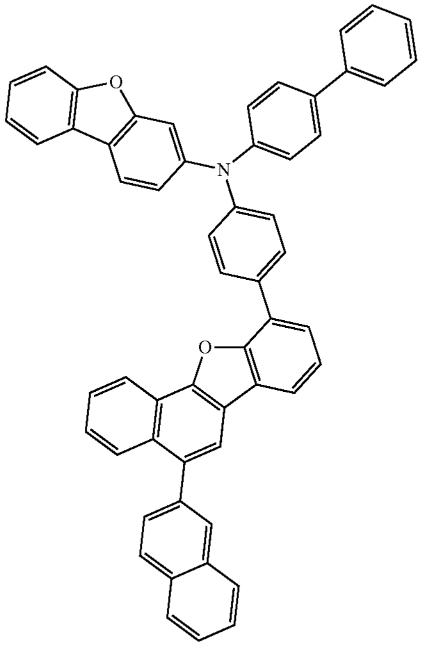
1-581
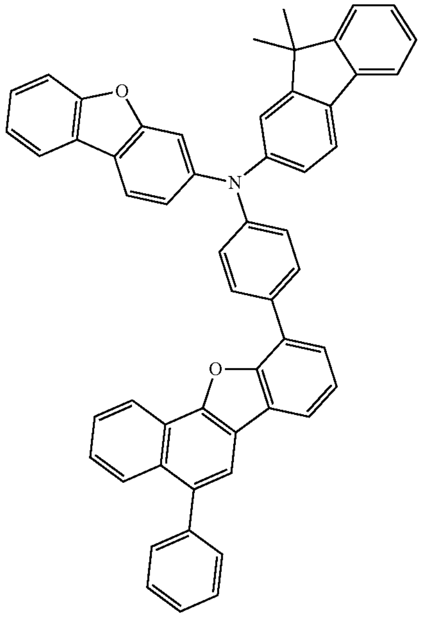
-continued
1-582
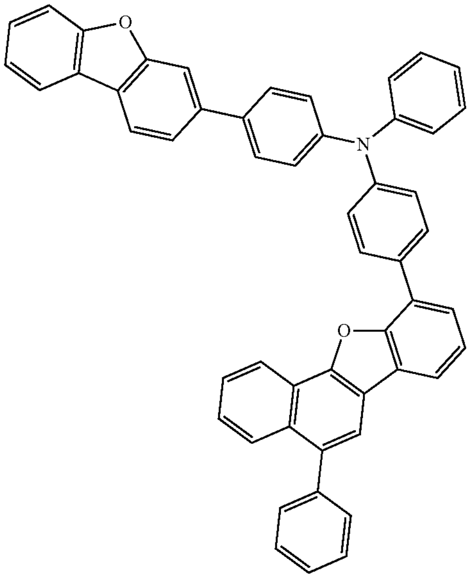
1-583
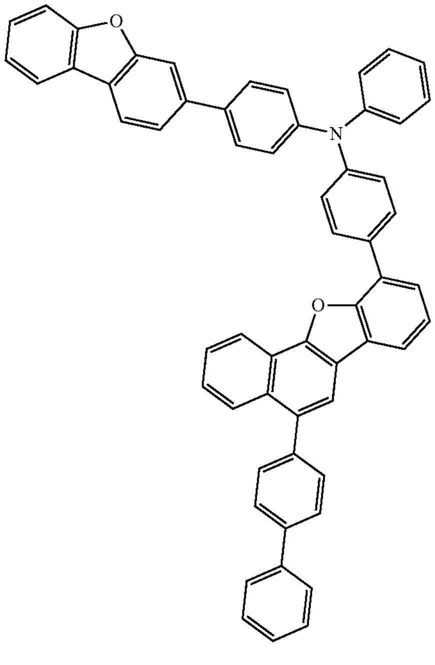

-continued
1-584
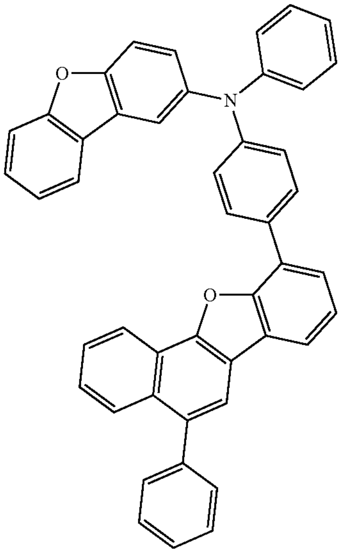
1-585
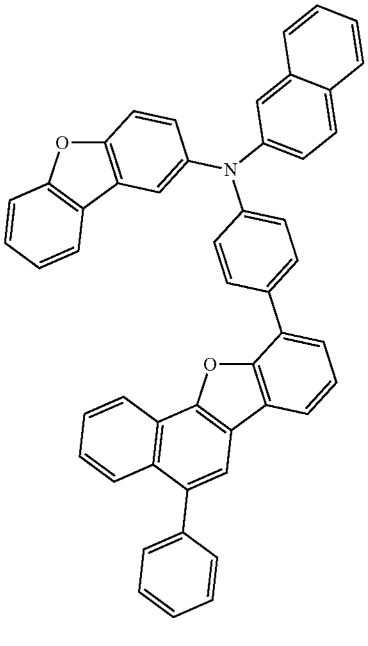
-continued
1-586
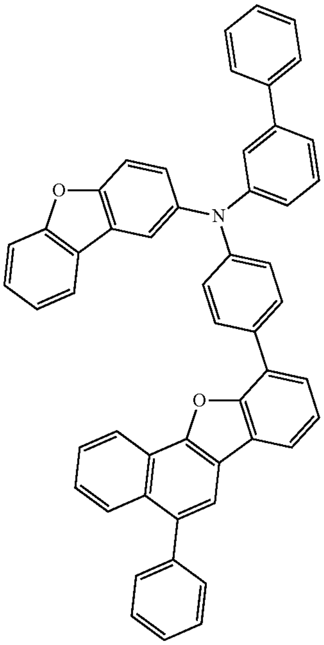
1-587
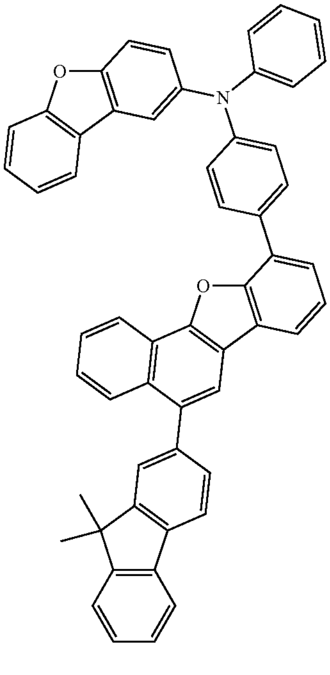

-continued
1-588
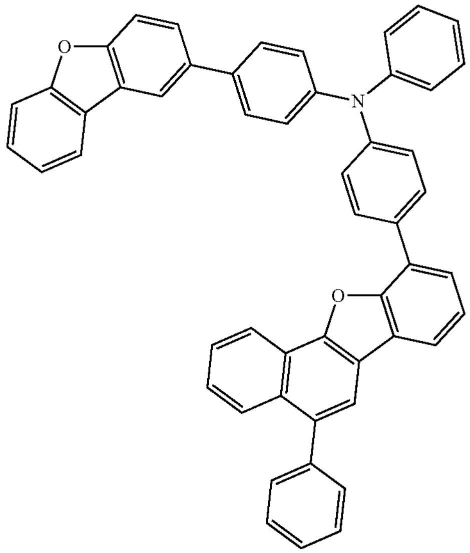
1-589
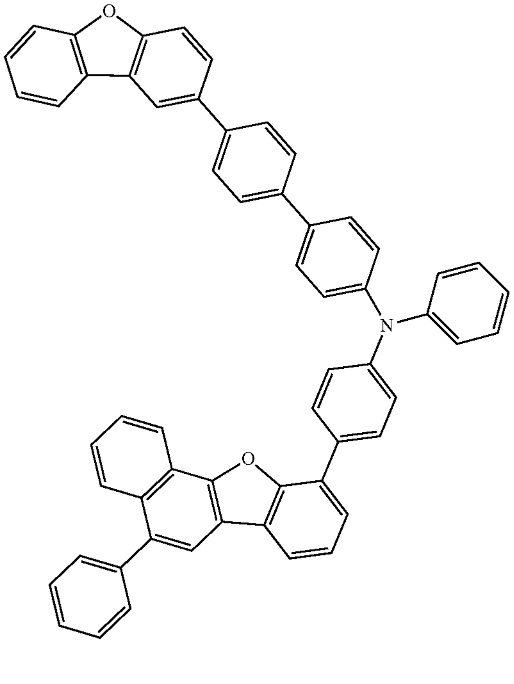
-continued
1-590
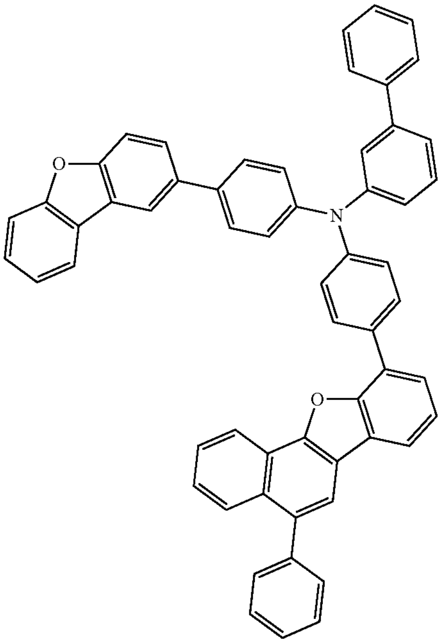
1-591
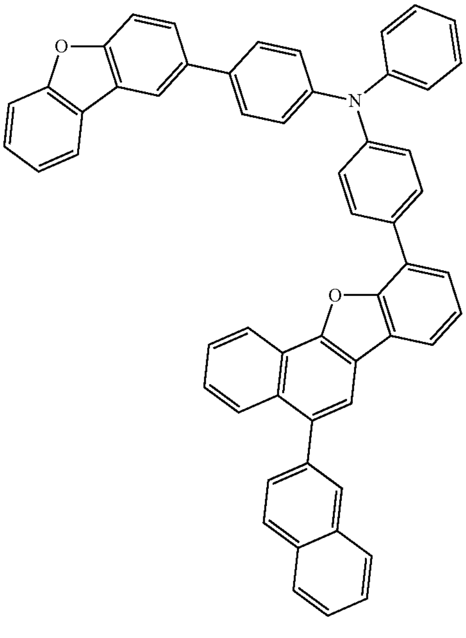

-continued
1-592
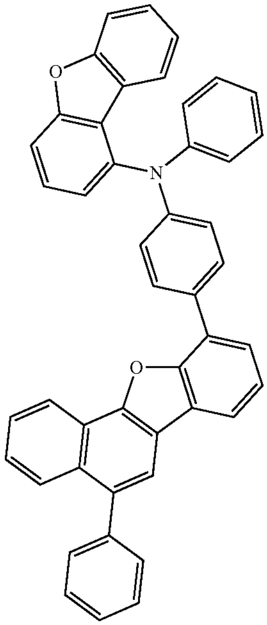
1-593
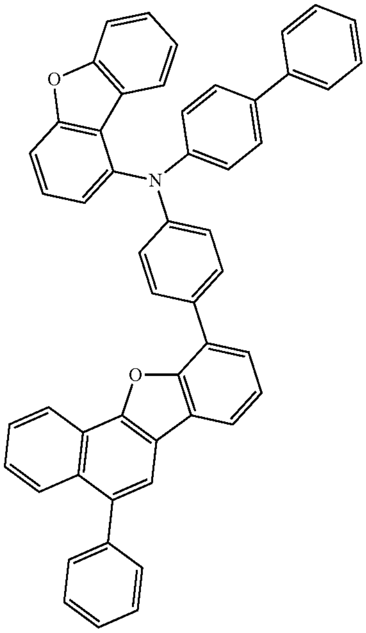
-continued
1-594
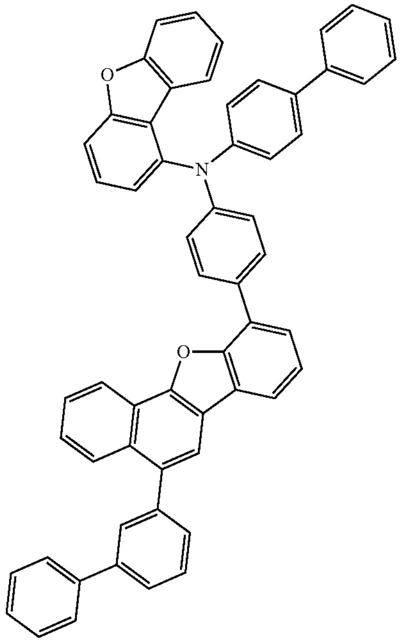
1-595
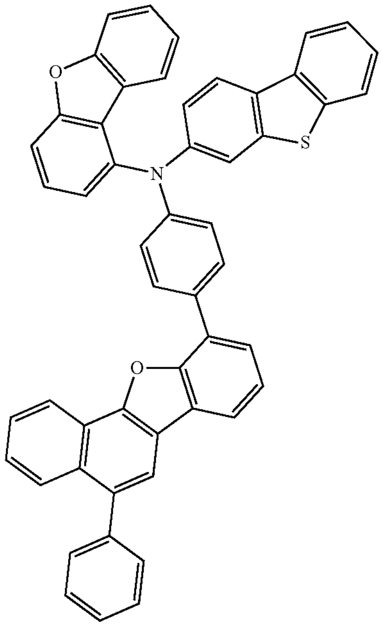

-continued
1-596
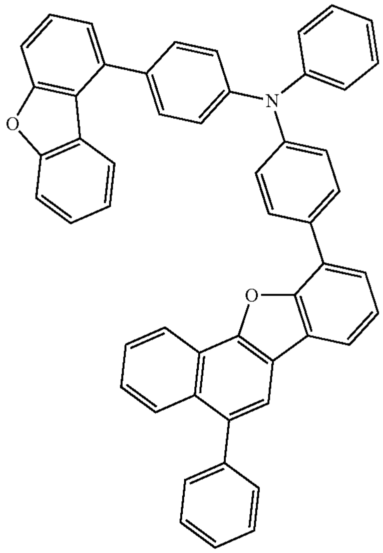
1-597
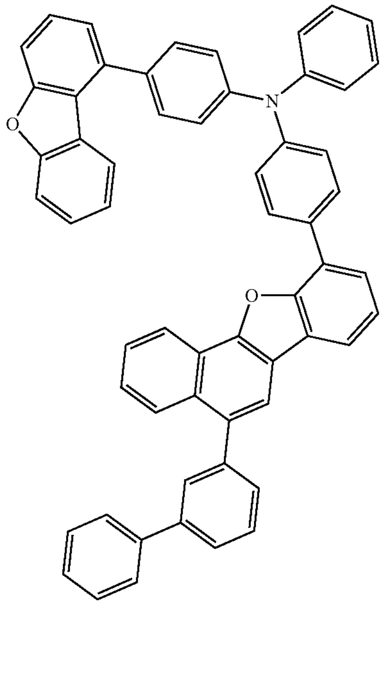
-continued
1-598
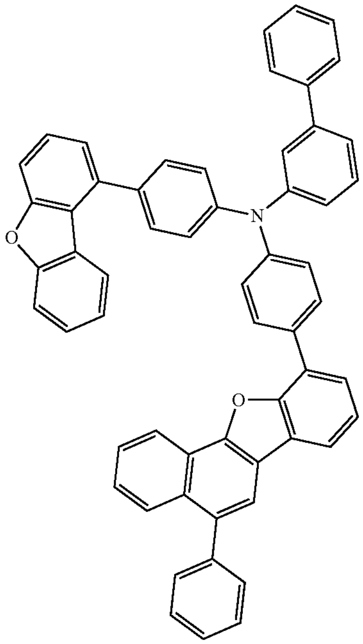
1-599
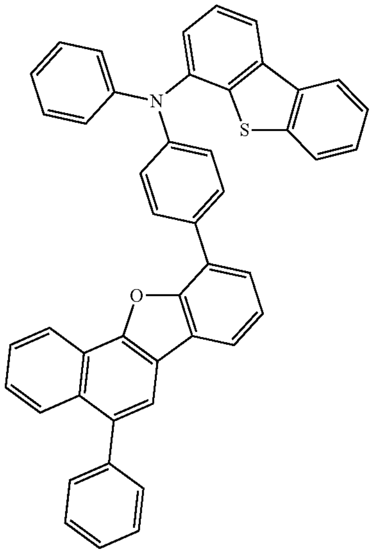

-continued
1-600
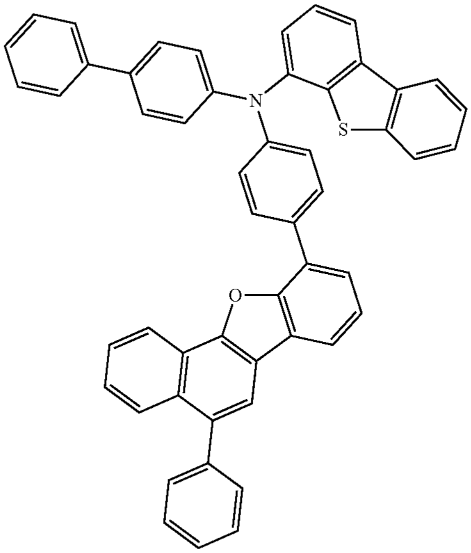
1-601
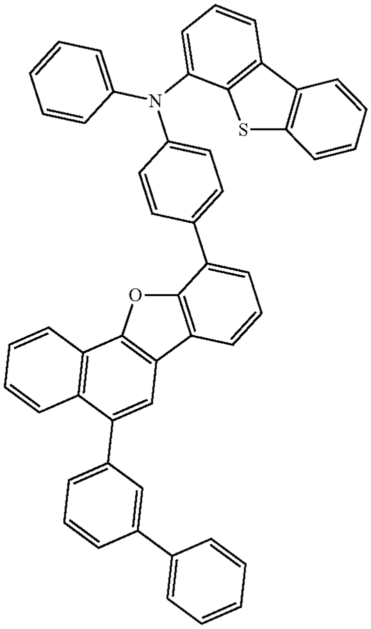
-continued
1-602
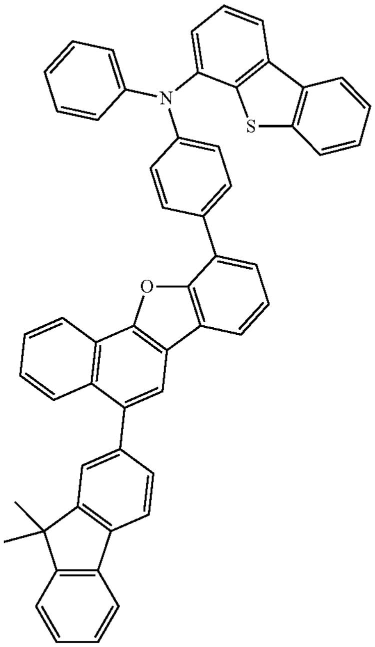
1-603
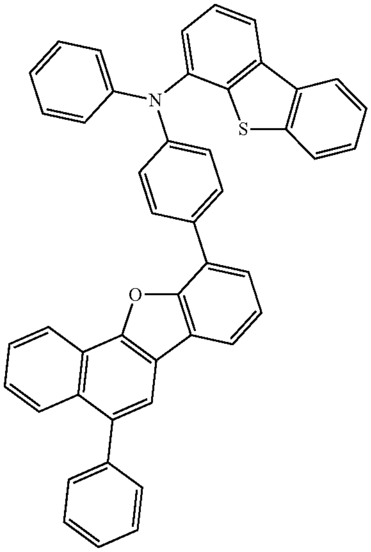

-continued
1-604
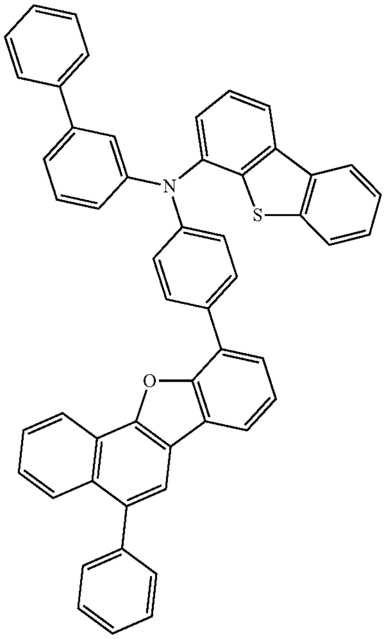
1-605
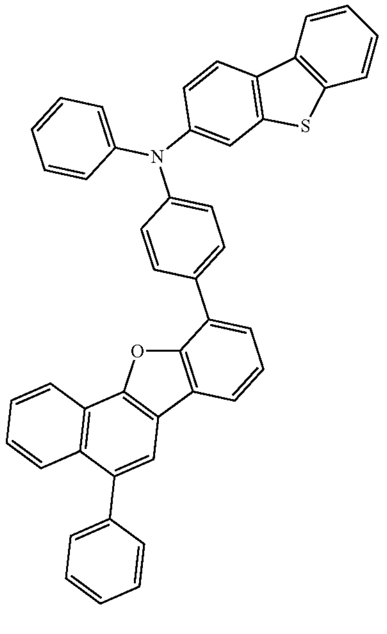
-continued
1-606
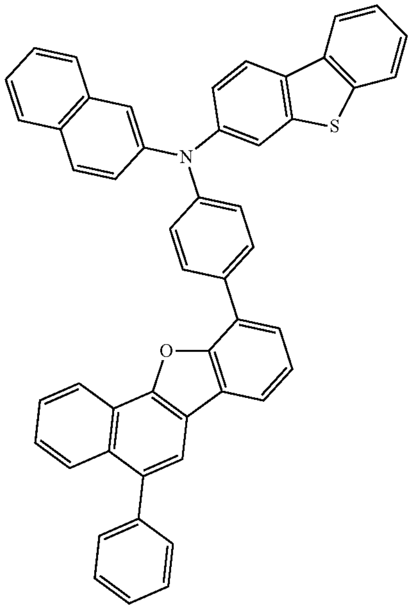
1-607
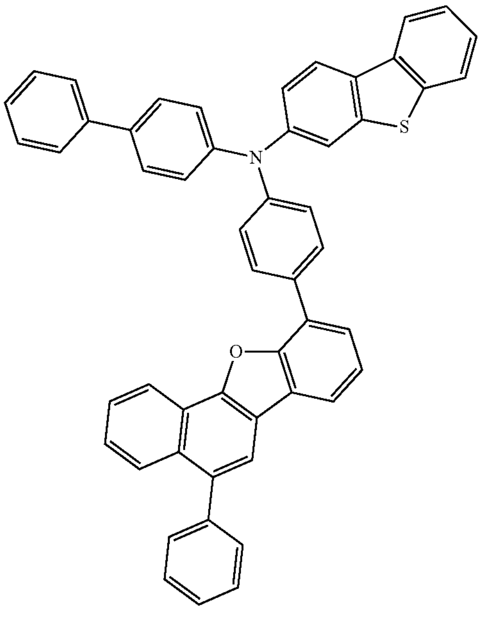

1-608
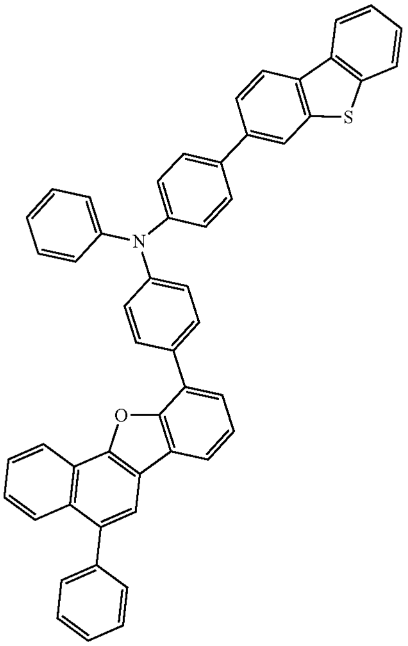
1-609
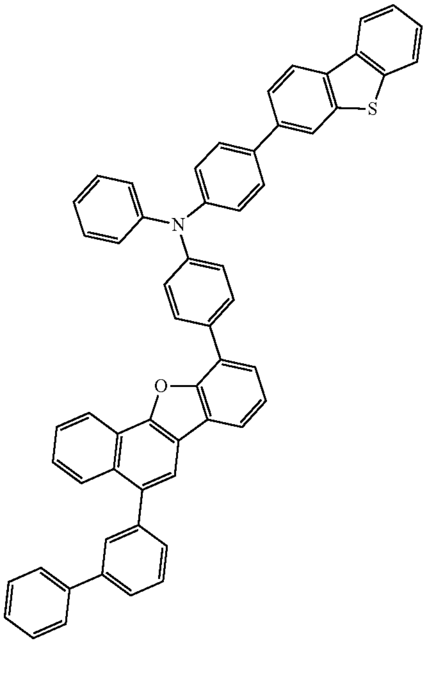
1-610
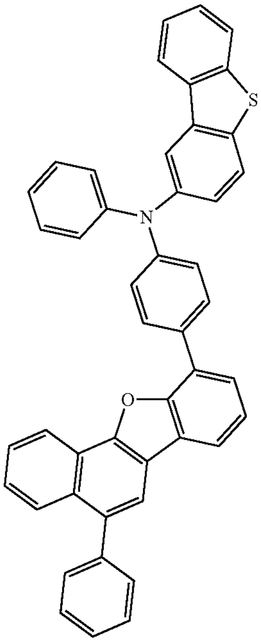
1-611
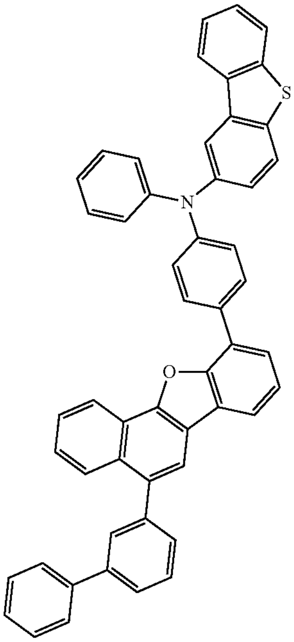

-continued
1-612
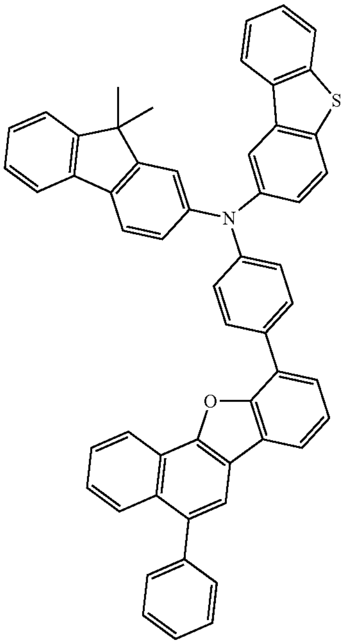
1-613
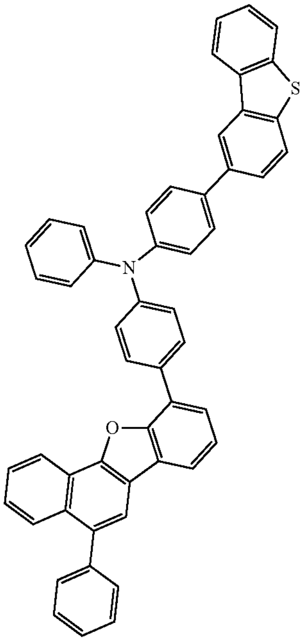
-continued
1-614
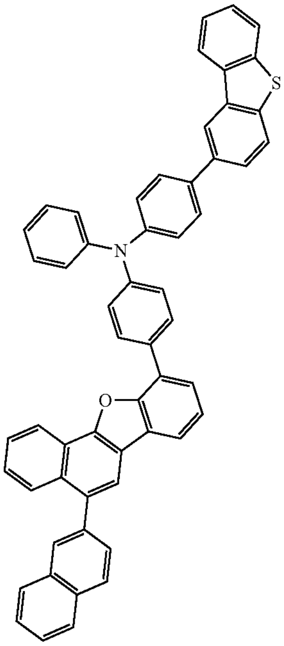
1-615
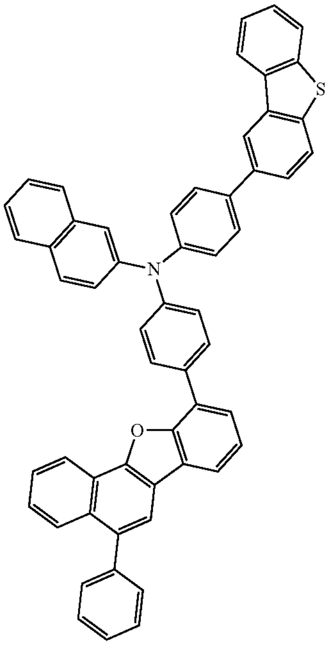

-continued
1-616
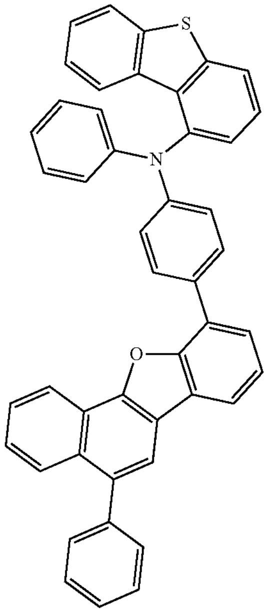
1-618
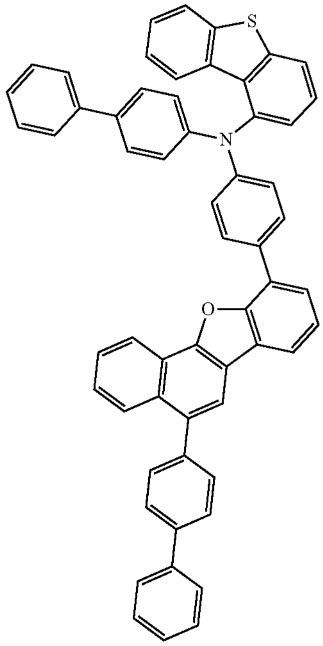
1-617
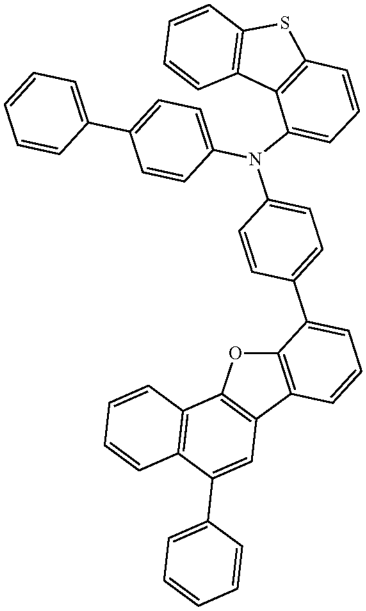
1-619
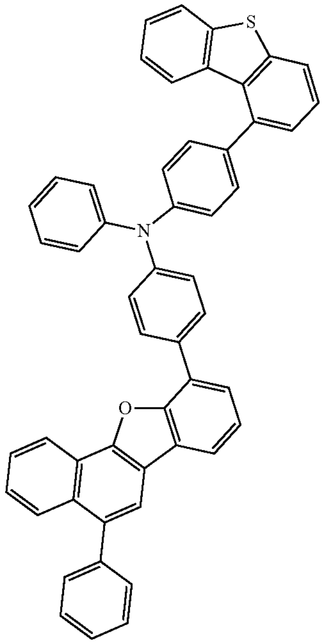

-continued
1-620
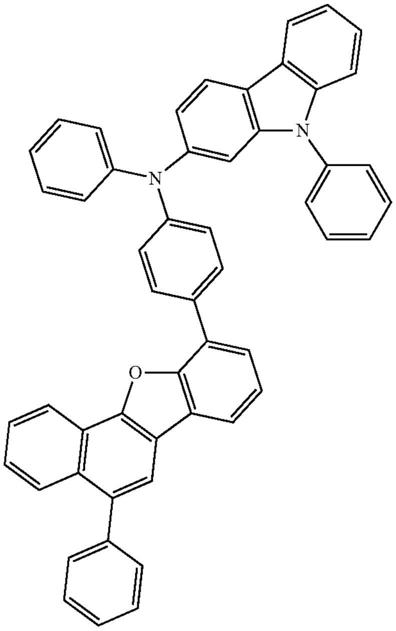
1-621
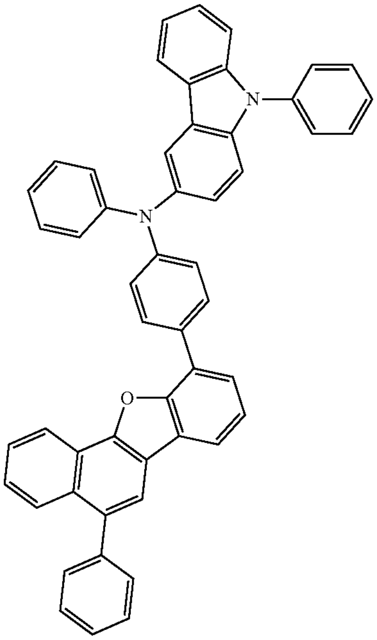
-continued
1-622
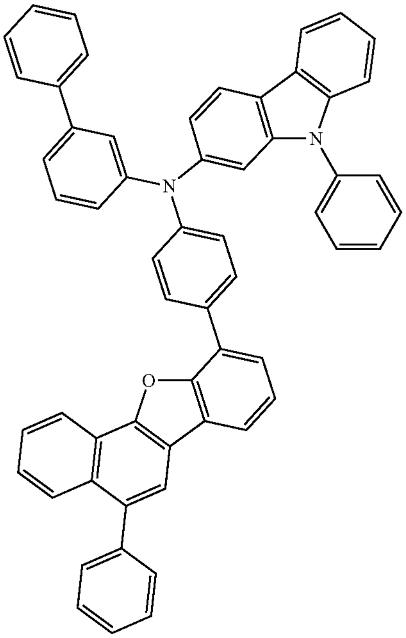
1-623
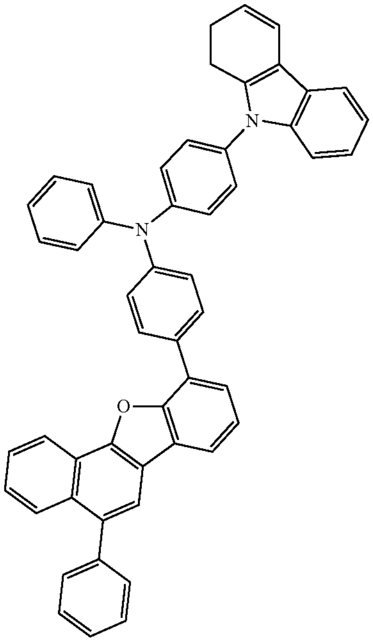

-continued
1-624
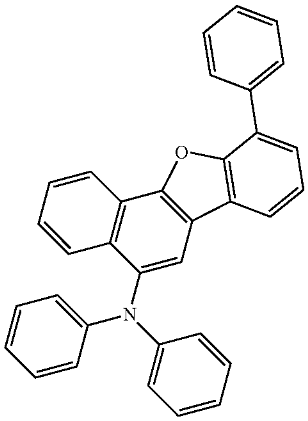
1-625
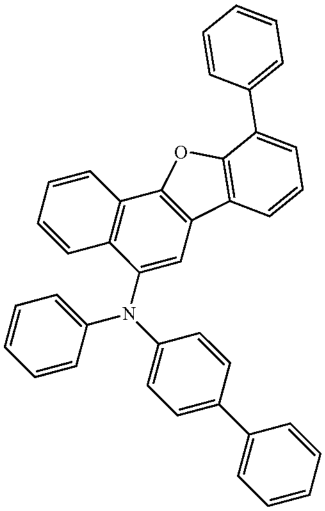
1-626
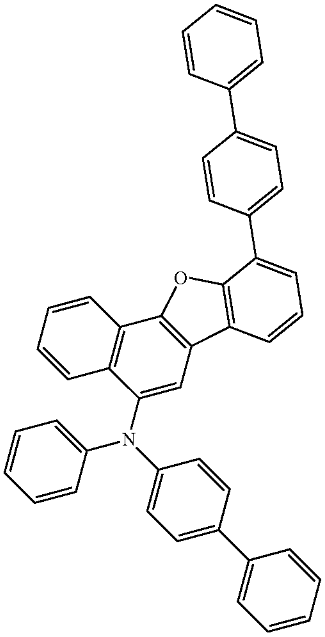
-continued
1-627
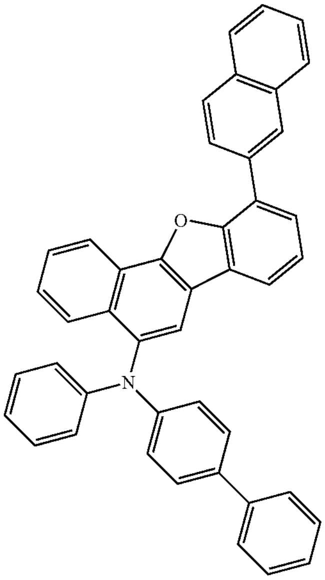
1-628
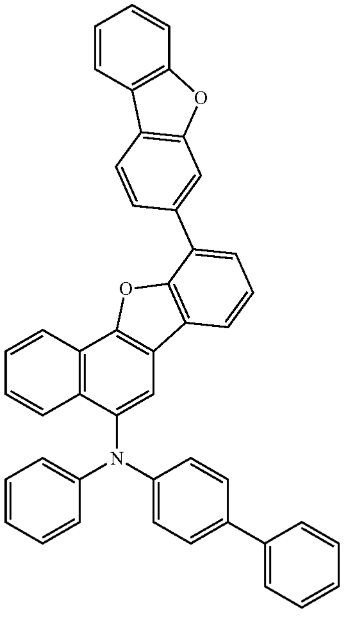

-continued
1-629
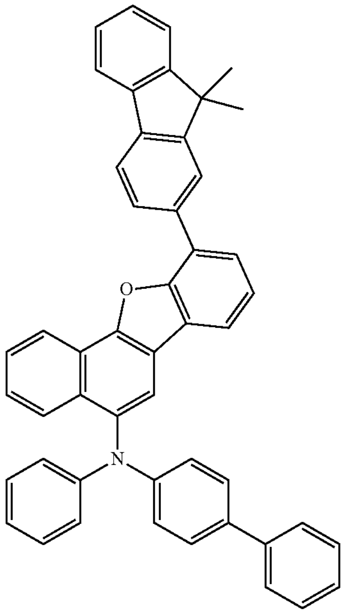
1-630
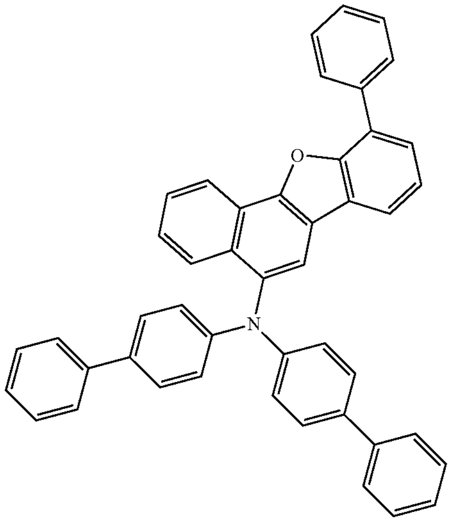
-continued
1-631
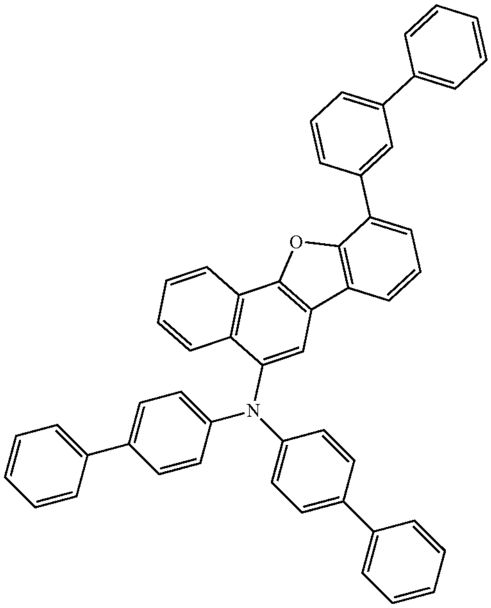
1-632
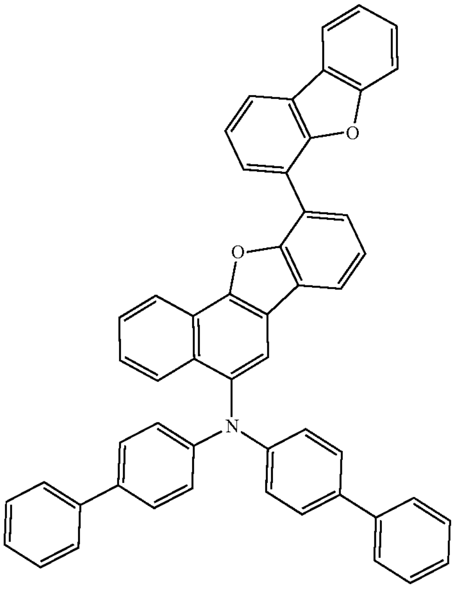

-continued
1-633
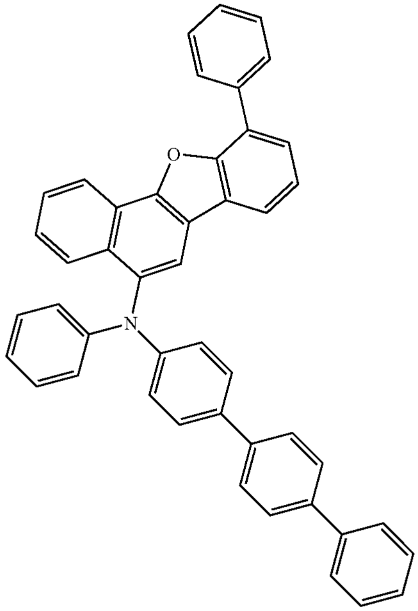
1-634
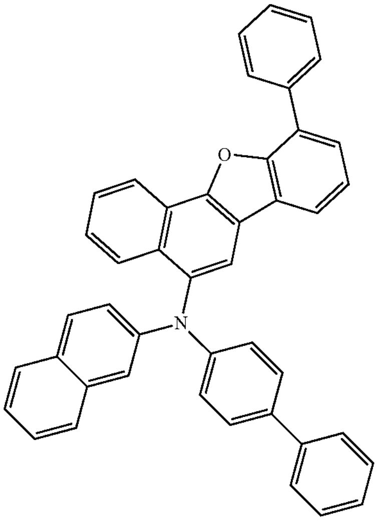
-continued
1-635
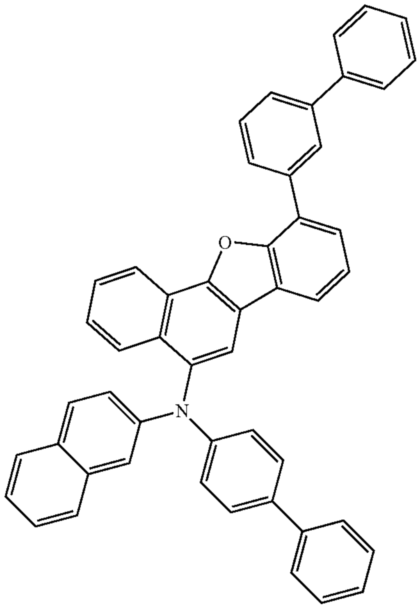
1-636
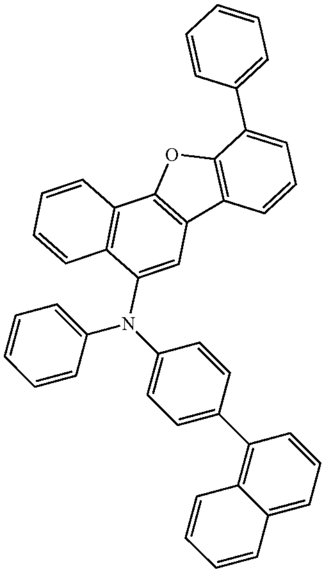

-continued
1-637
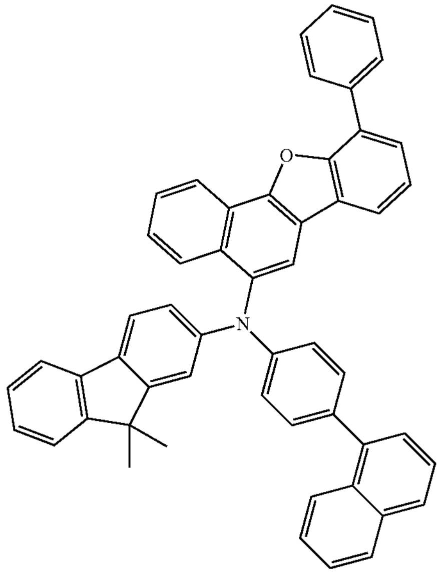
1-638
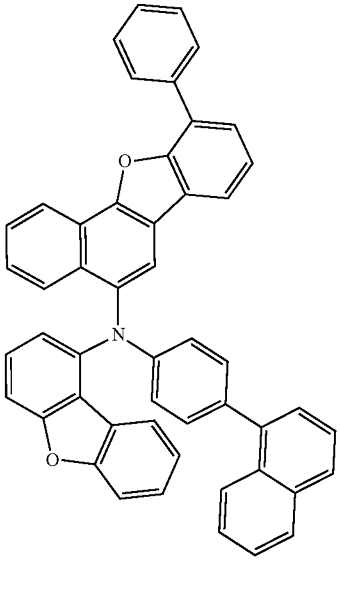
-continued
1-639
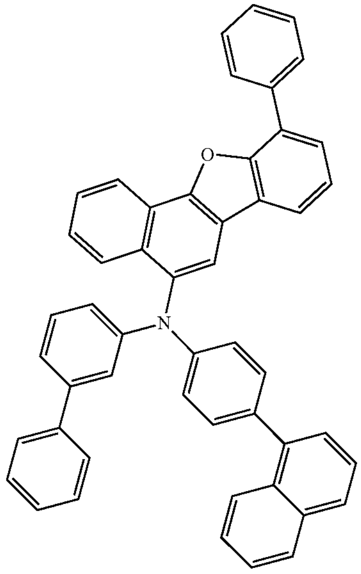
1-640
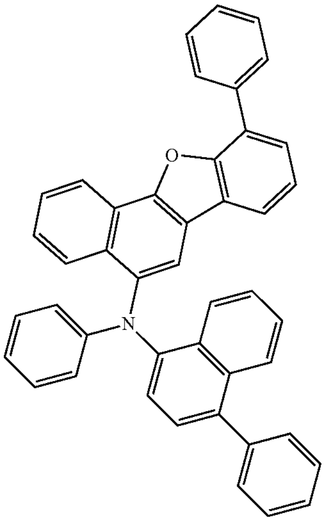

-continued
1-641
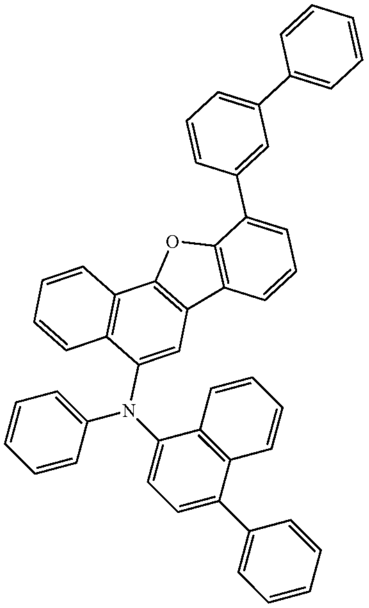
1-642
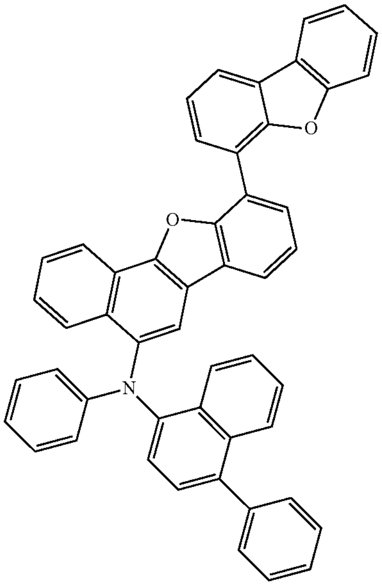
1-643
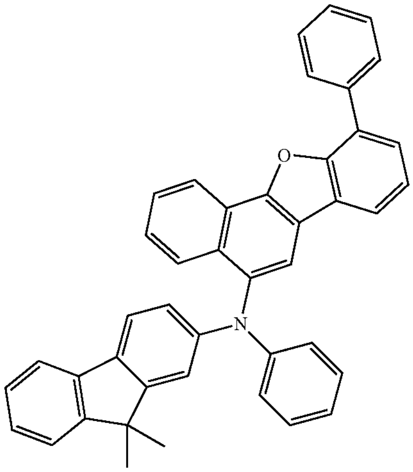
-continued
1-644
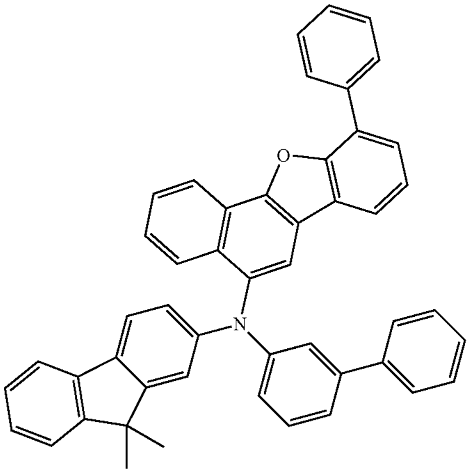
1-645
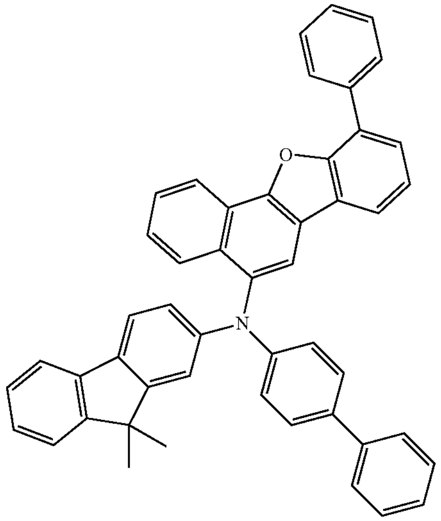
1-646
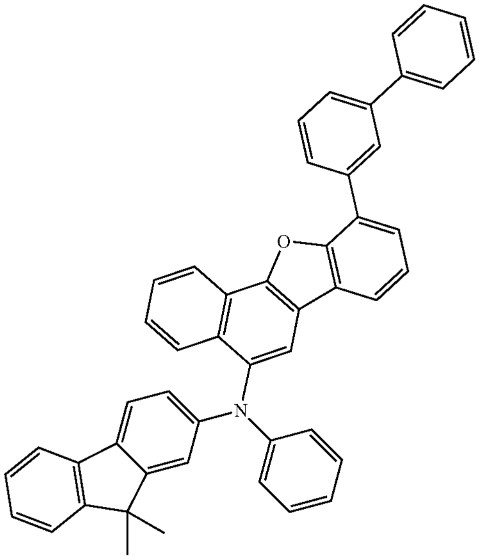

-continued
1-647
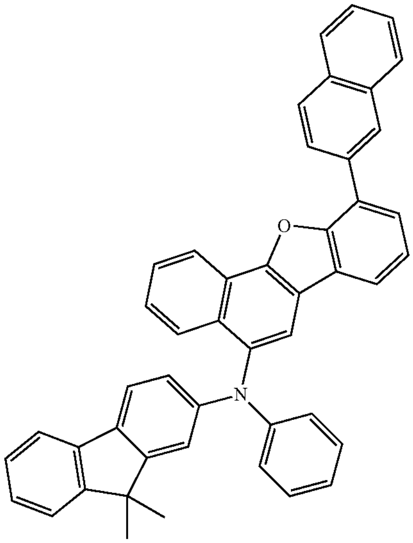
1-648
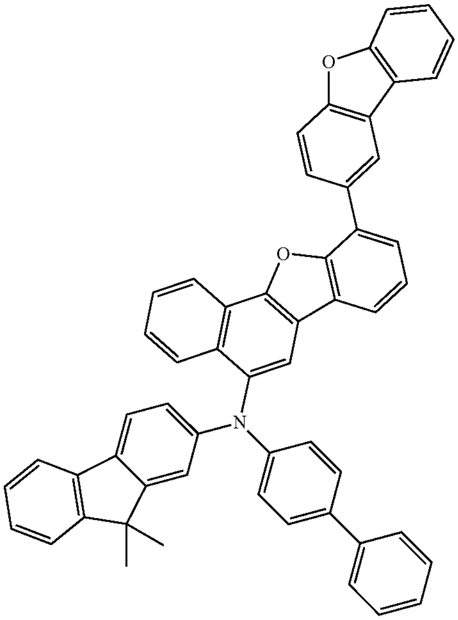
-continued
1-649
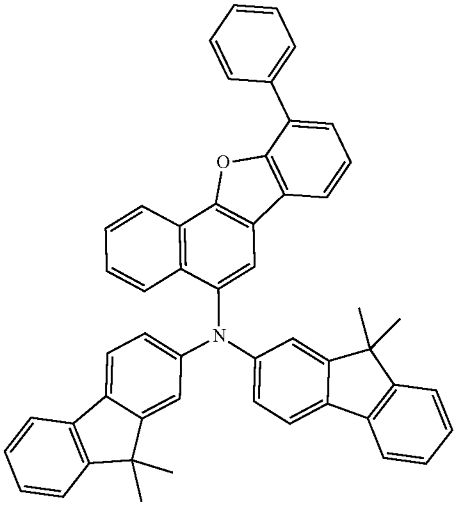
1-650
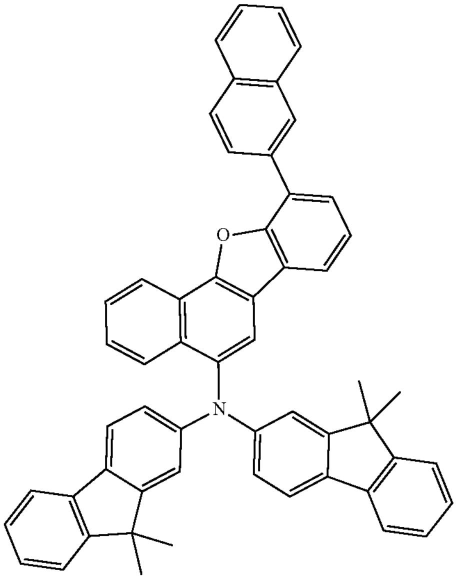

-continued
1-651
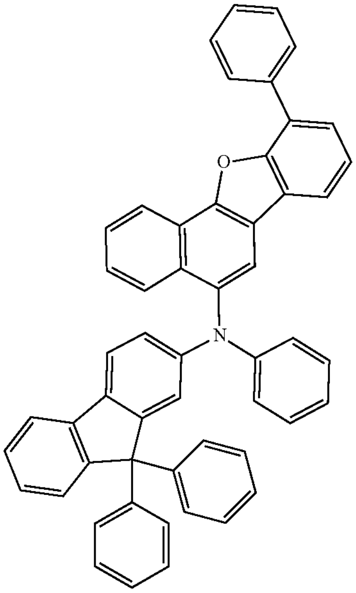
1-652
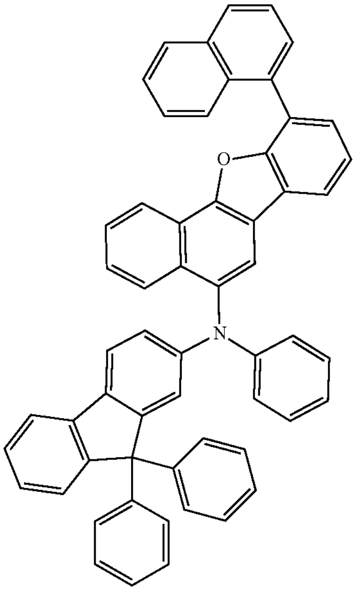
-continued
1-653
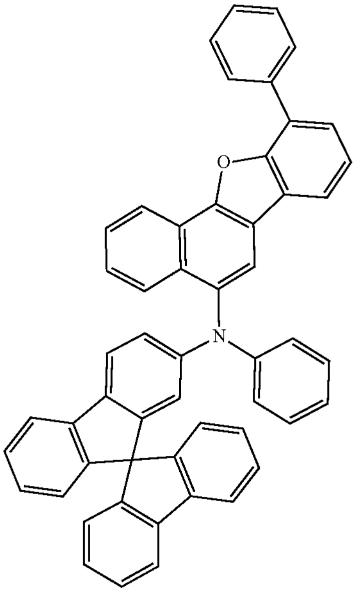
1-654
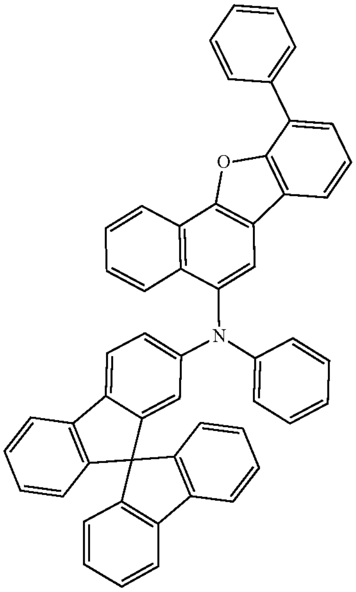

-continued
1-655
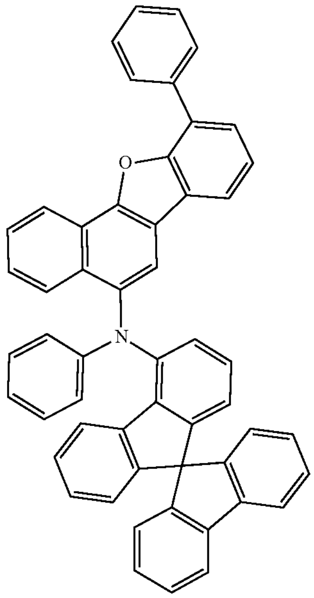
1-656
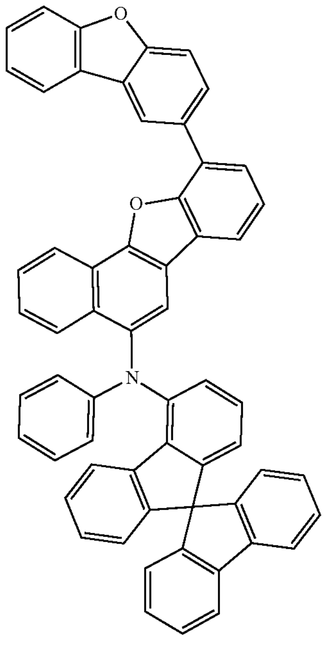
-continued
1-657
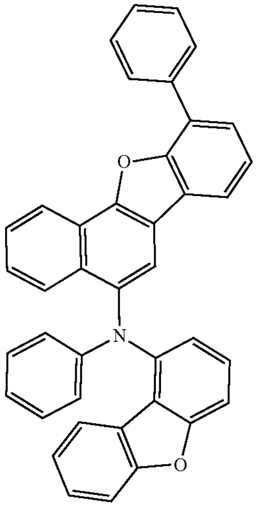
1-658
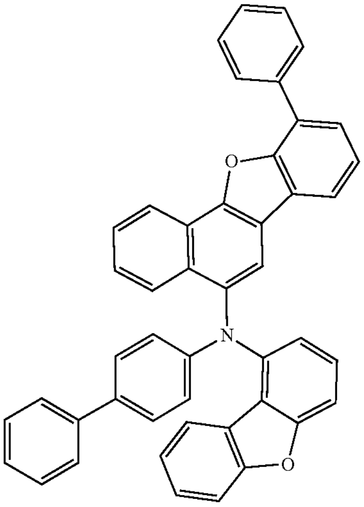
1-659
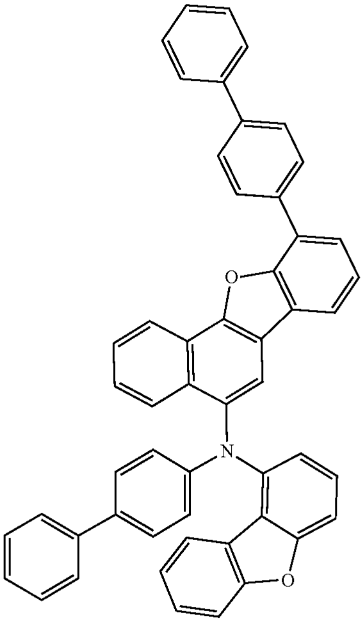

-continued
1-660
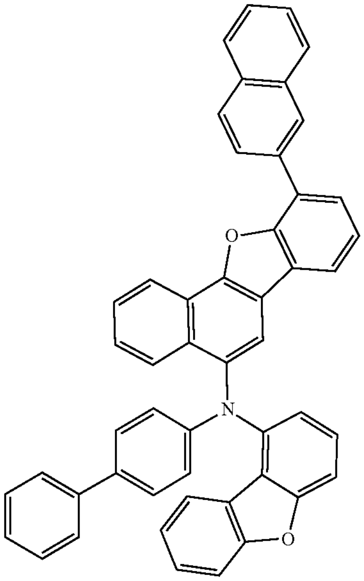
1-661
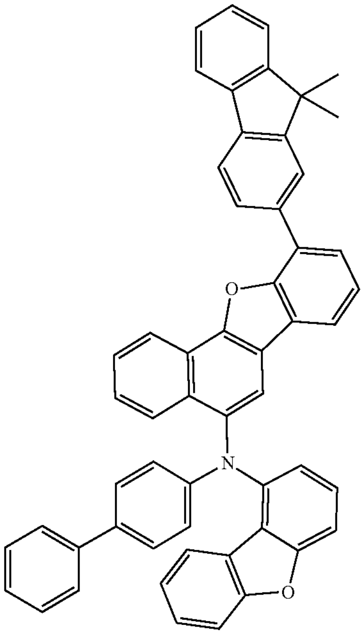
-continued
1-662
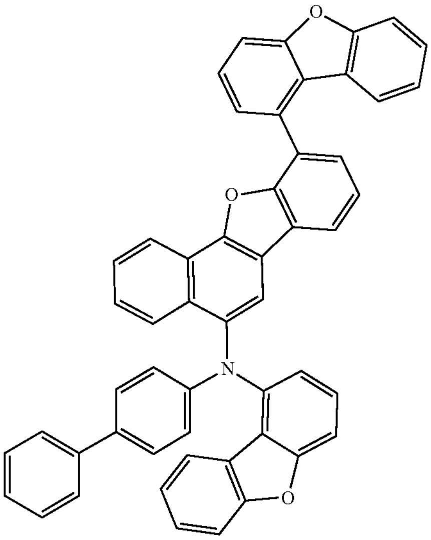
1-663
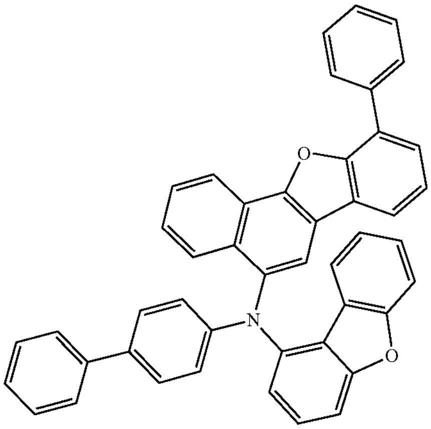
1-664
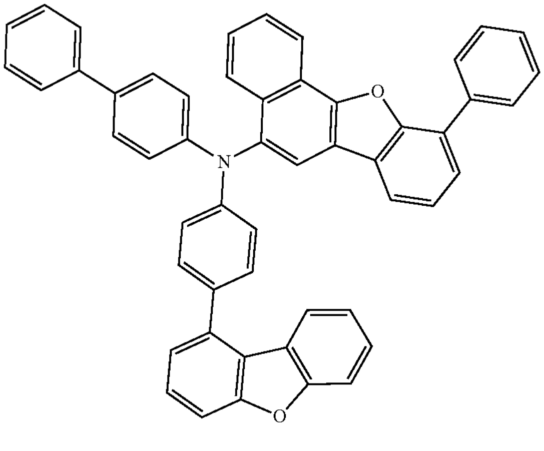

-continued
1-665
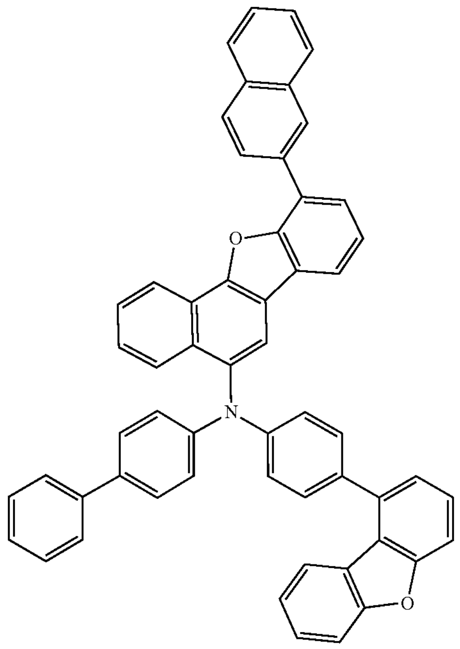
1-666
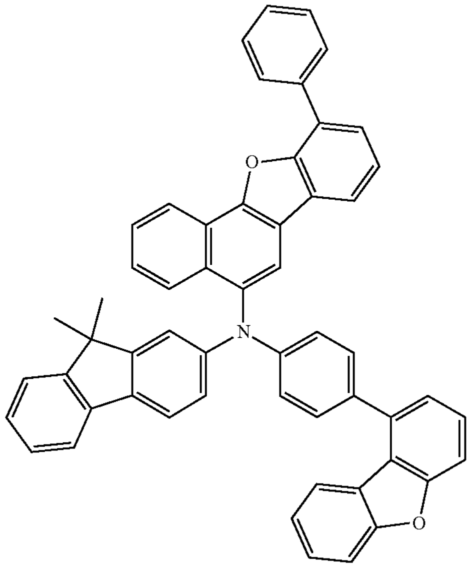
-continued
1-667
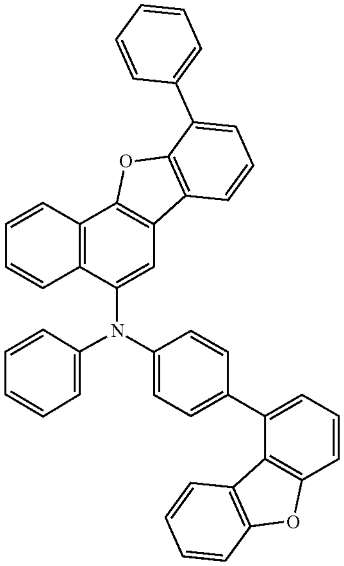
1-668
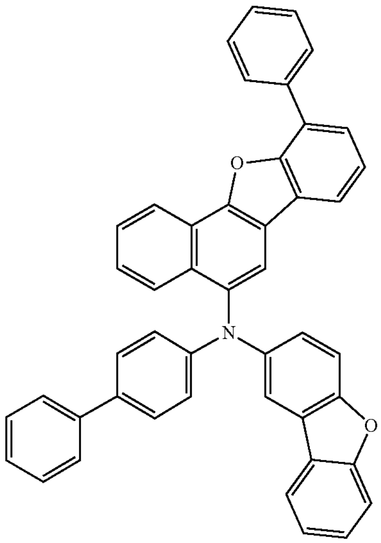

-continued
1-669
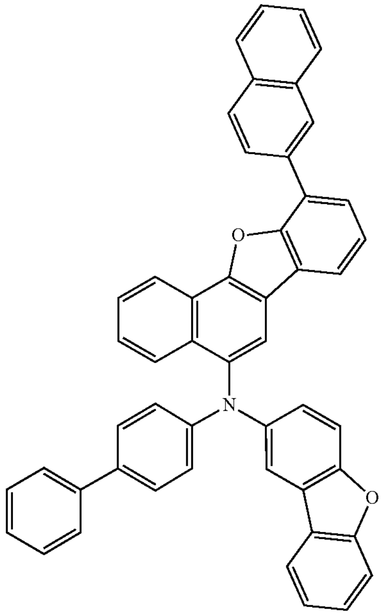
1-670
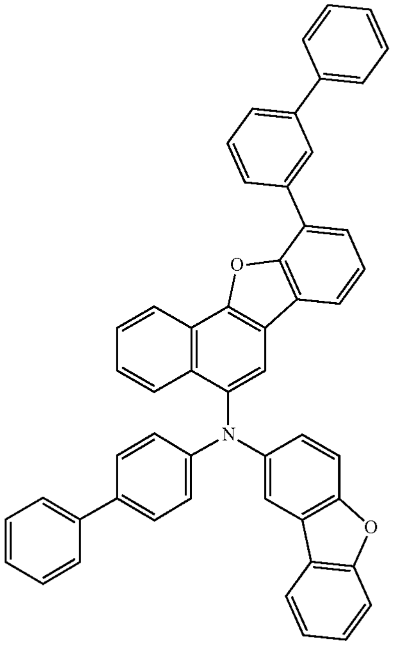
-continued
1-671
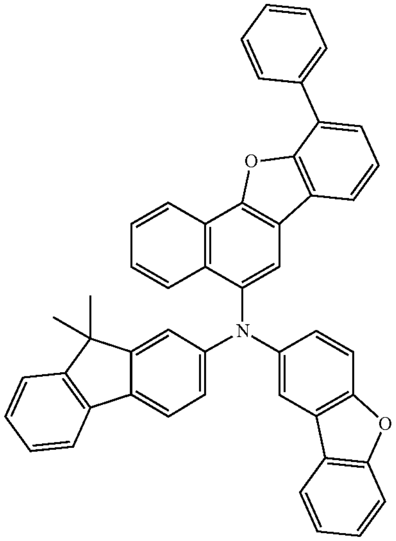
1-672
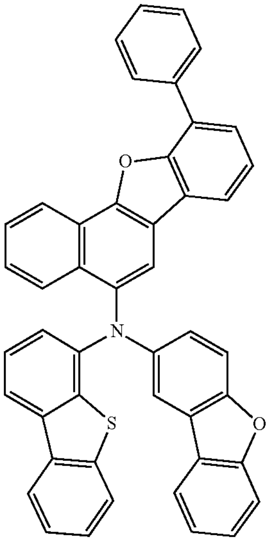

-continued
1-673
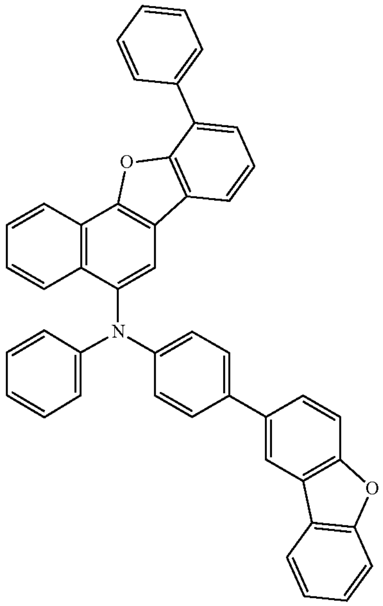
1-674
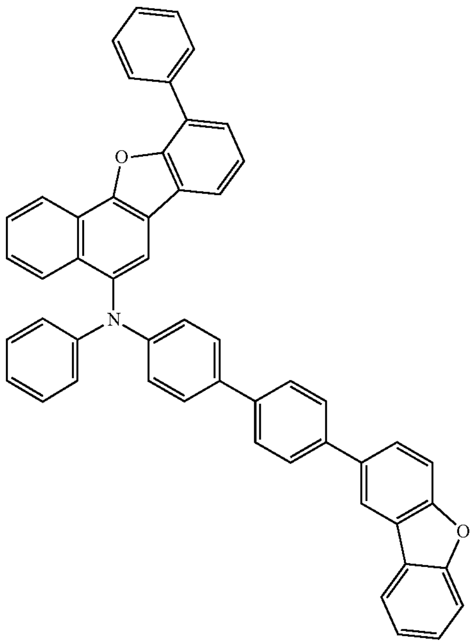
-continued
1-675
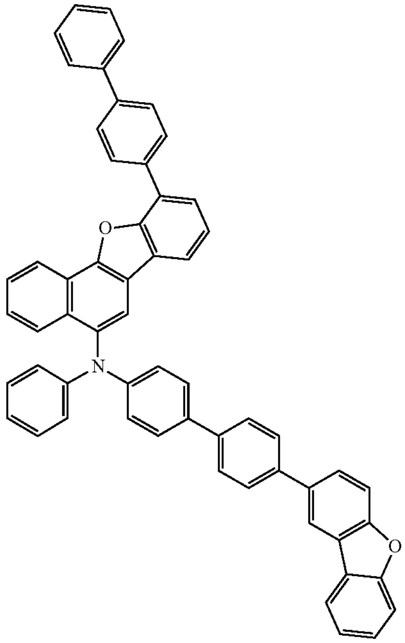
1-676
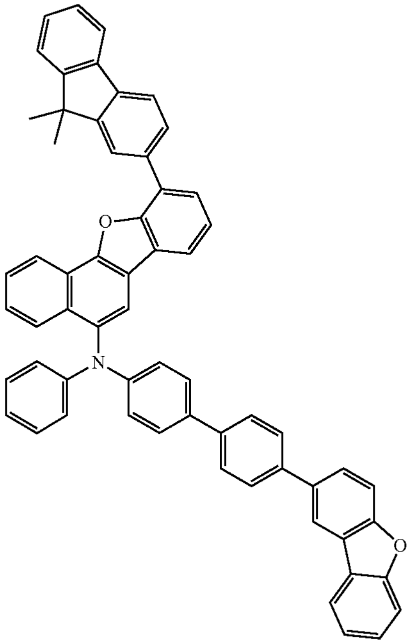

-continued
1-677
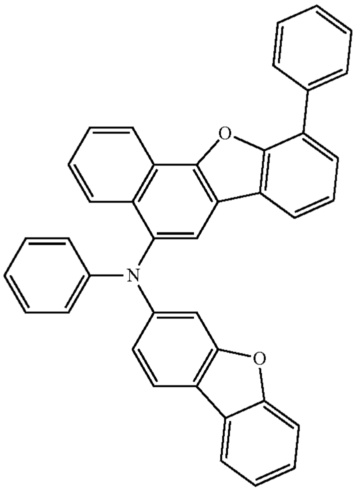
1-678
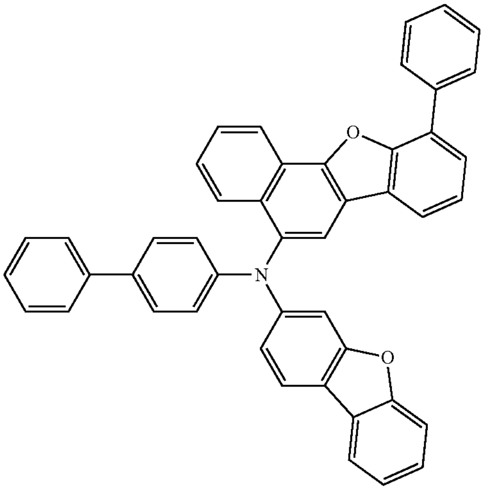
1-679
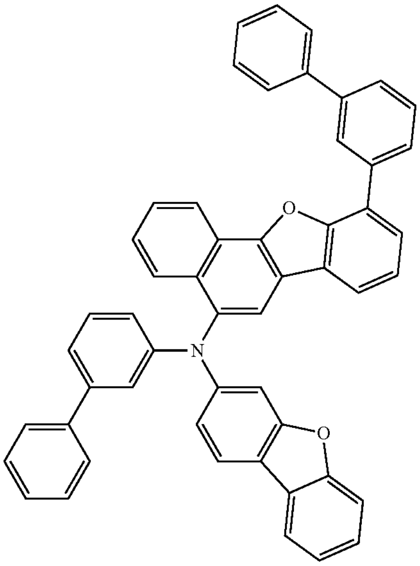
-continued
1-680
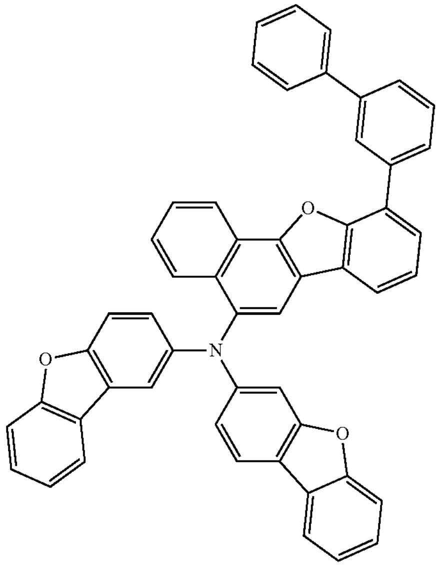
1-681
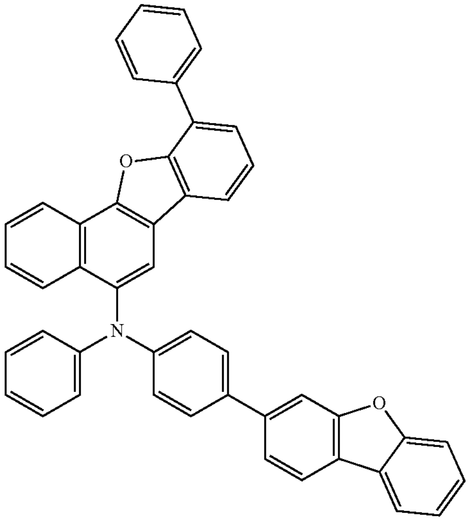

-continued
1-682
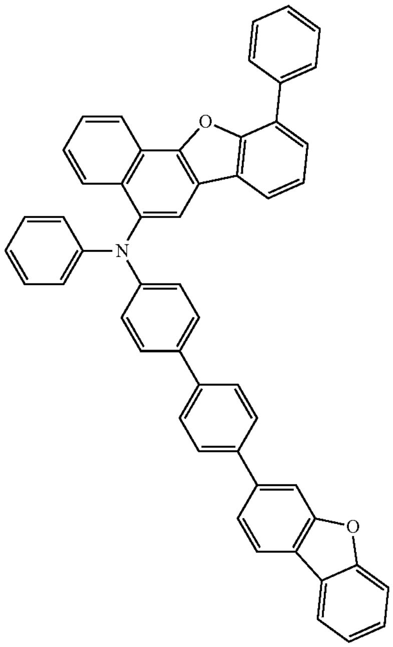
1-683
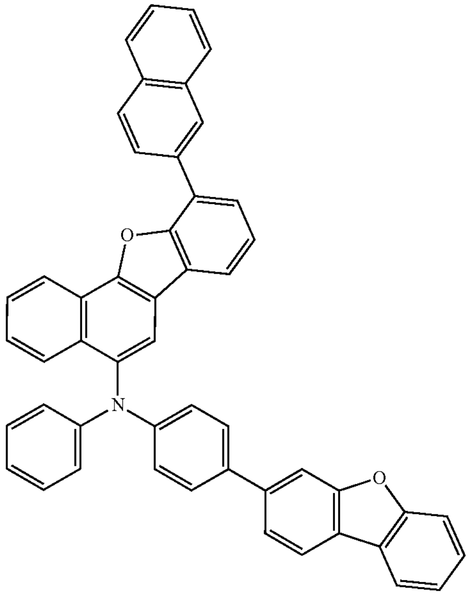
-continued
1-684
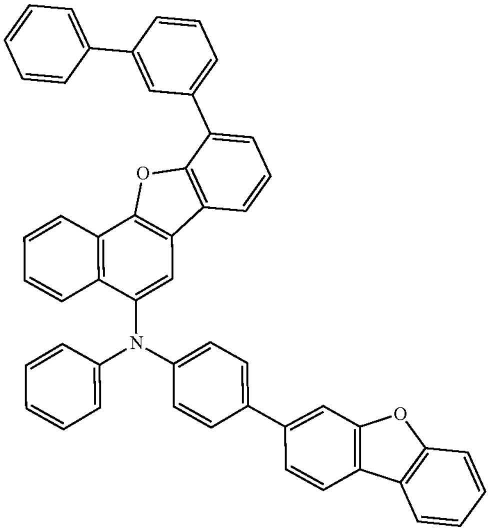
1-685
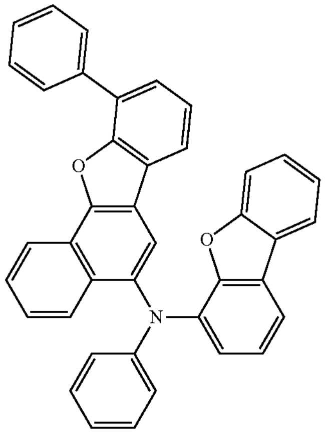
1-686
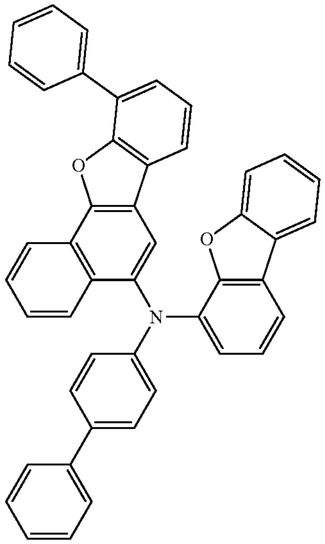

-continued
1-687
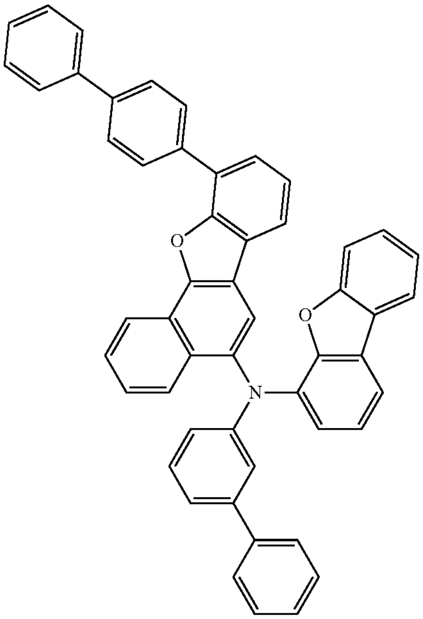
1-688
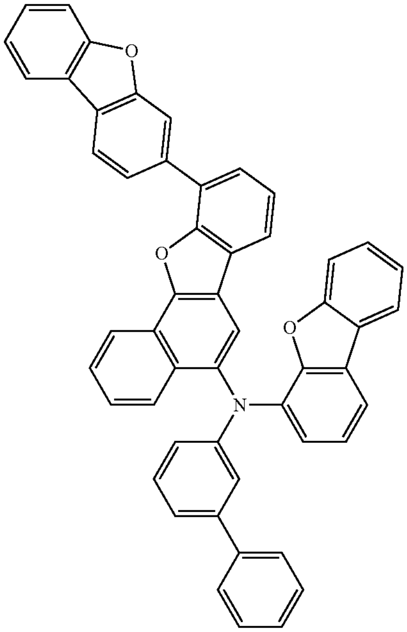
-continued
1-689
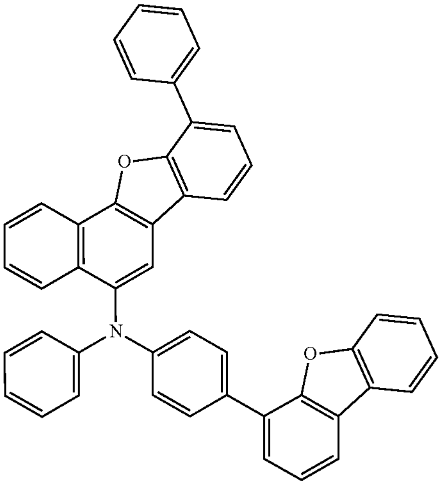
1-690
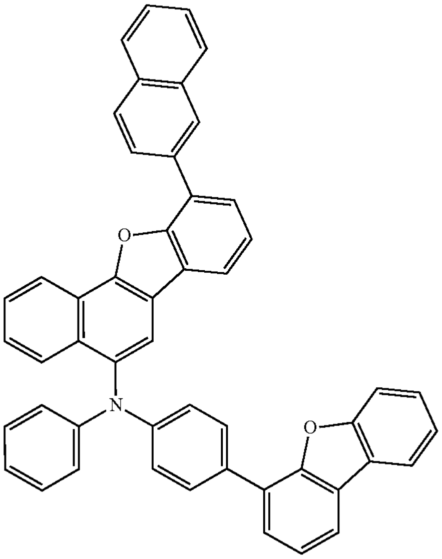

-continued
1-691
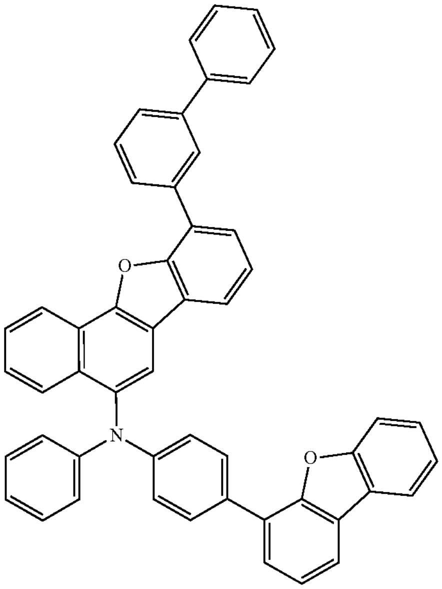
1-692
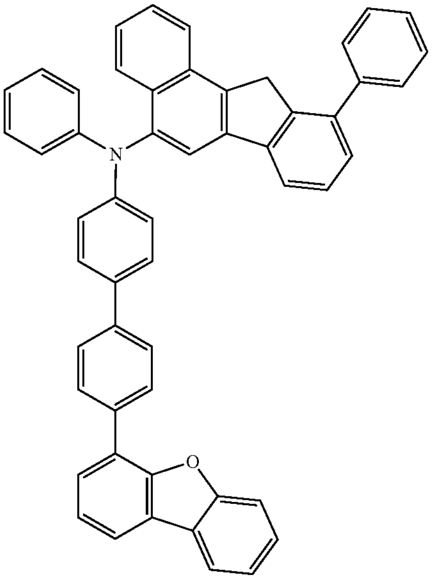
1-693
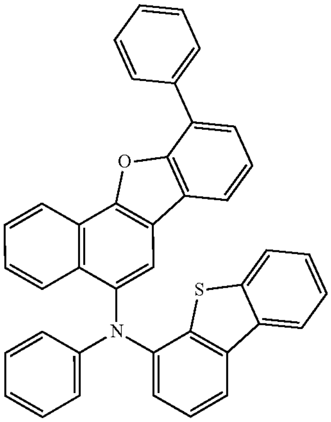
-continued
1-694
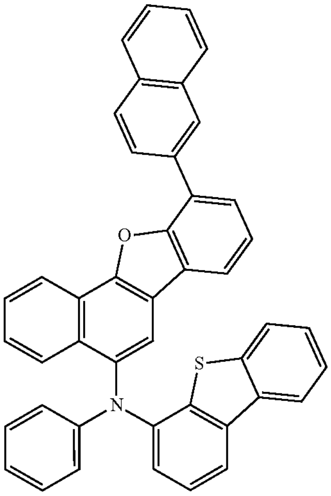
1-695
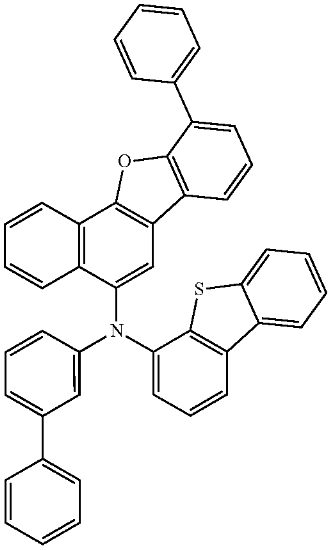
1-696
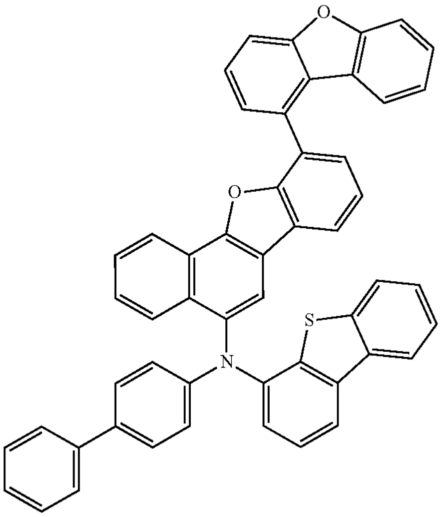

-continued
1-697
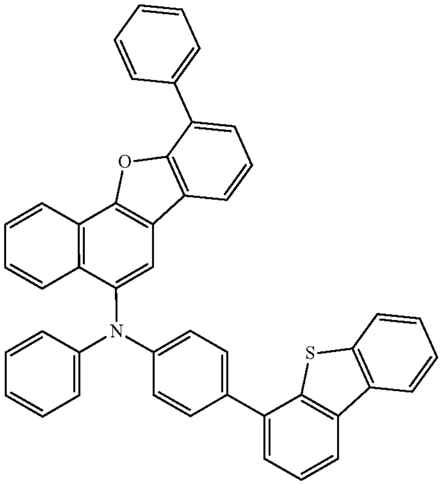
1-698
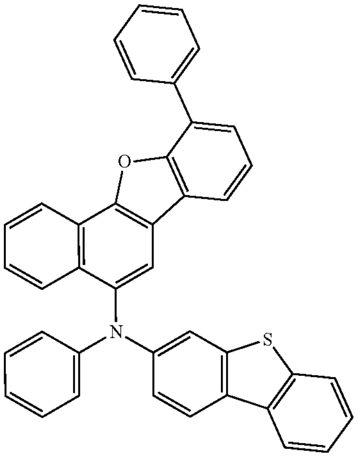
1-699
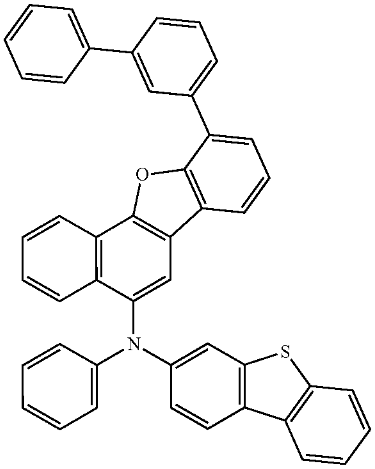
-continued
1-700
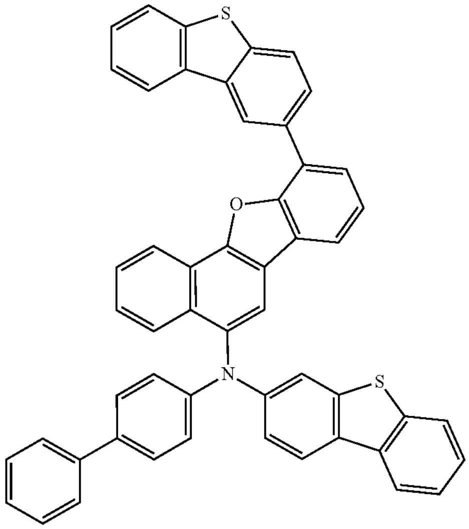
1-701
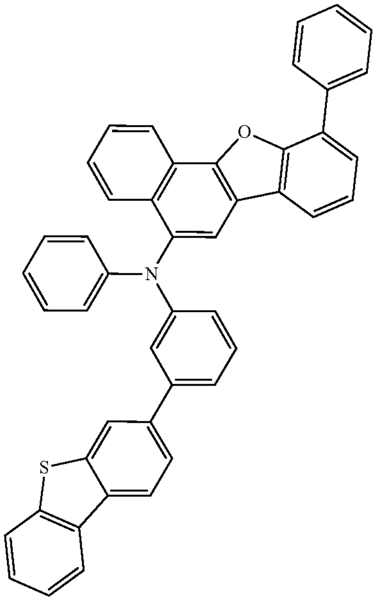

-continued
1-702
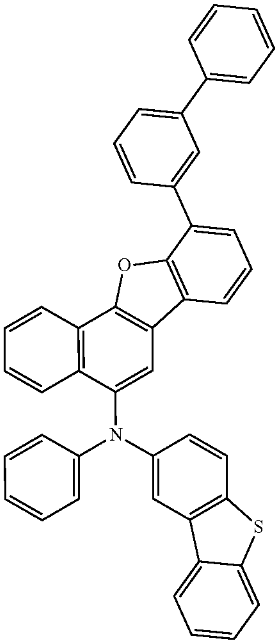
1-703
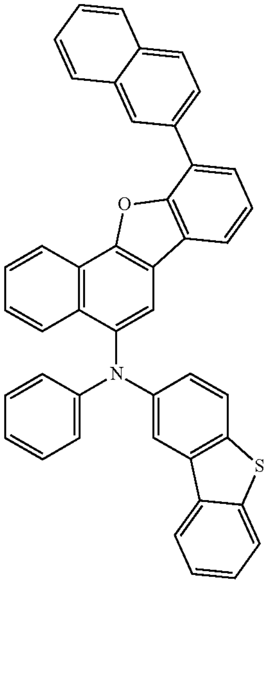
-continued
1-704
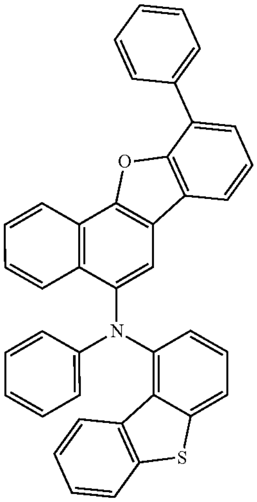
1-705
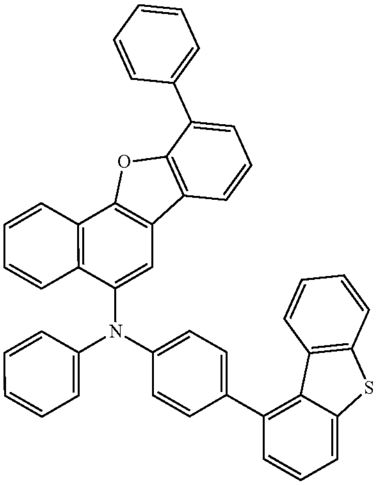
1-706
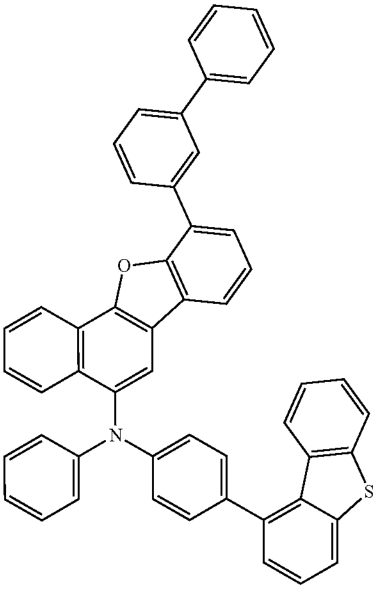

-continued
1-707
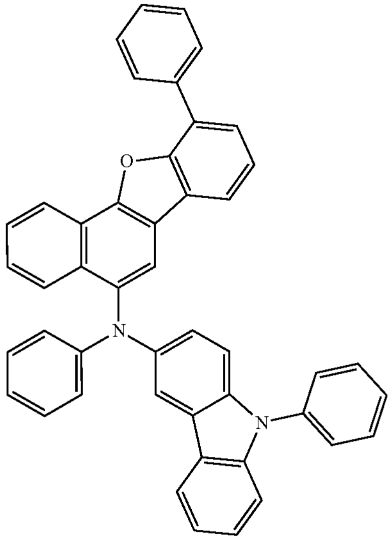
1-708
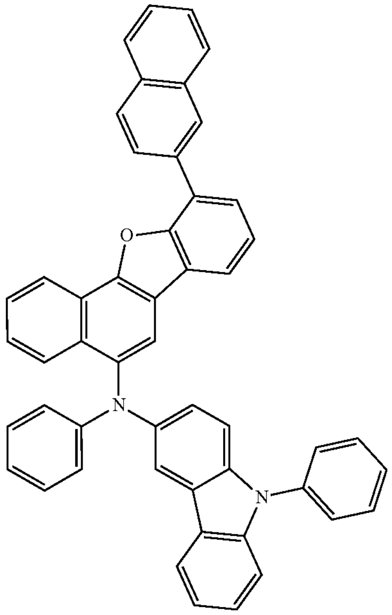
-continued
1-709
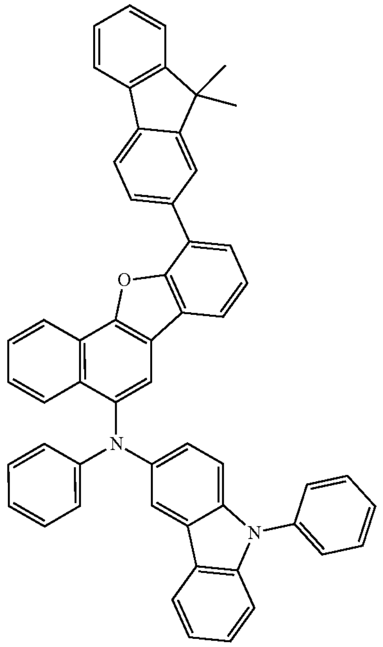
1-710
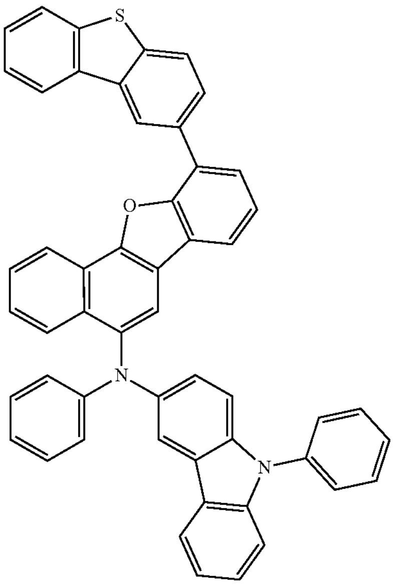

-continued
1-711
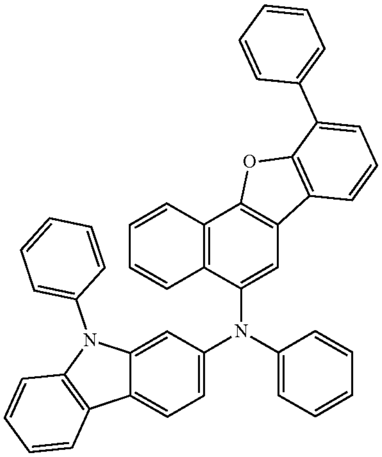
1-712
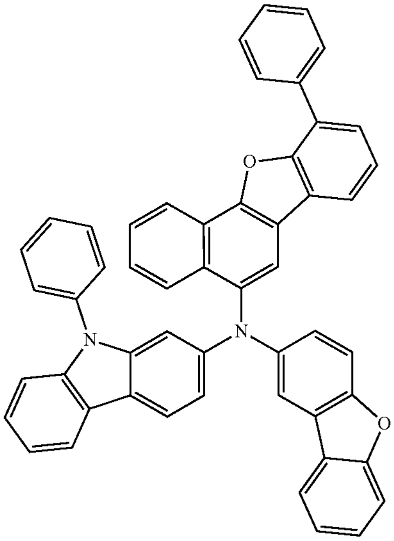
1-713
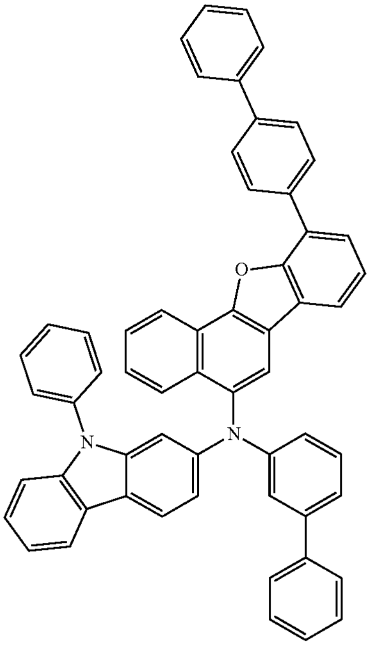
-continued
1-714
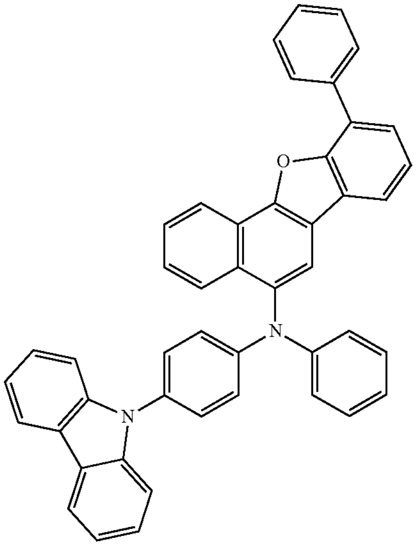
1-715
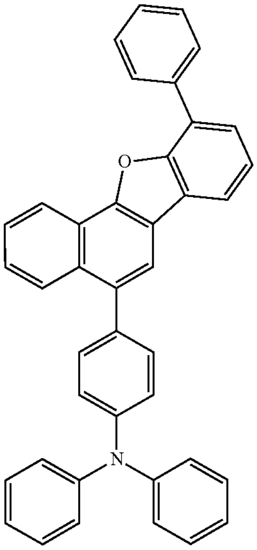

-continued
1-716
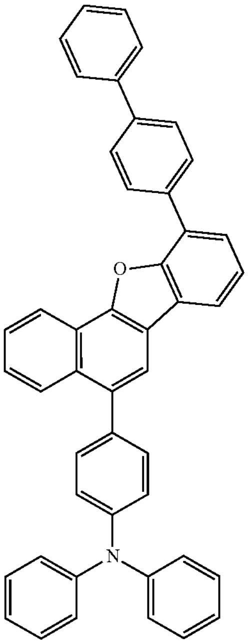
1-717
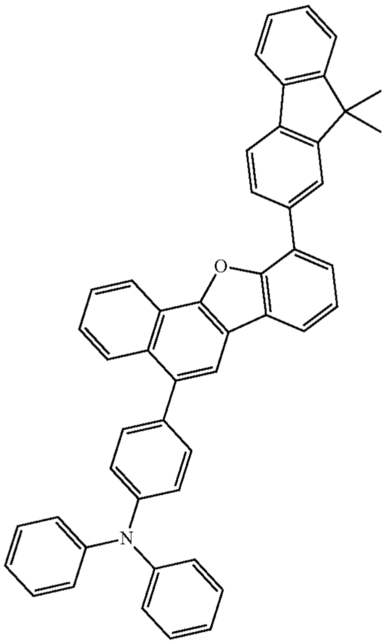
-continued
1-718
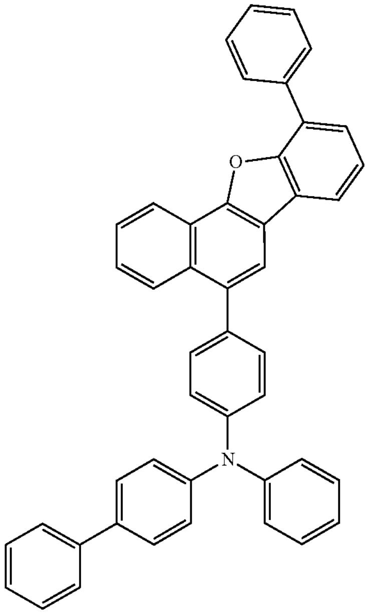
1-719
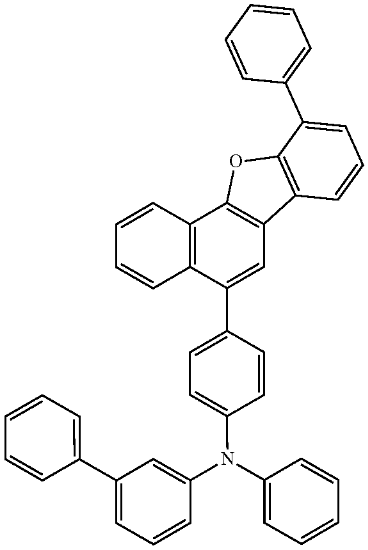

-continued
1-720
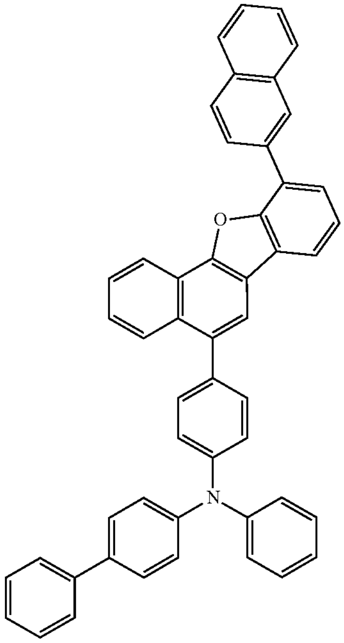
1-721
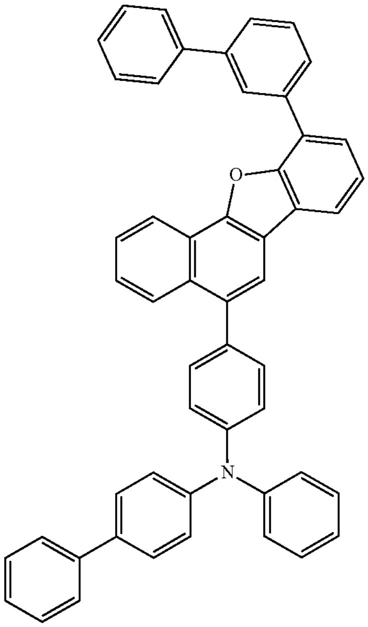
-continued
1-722
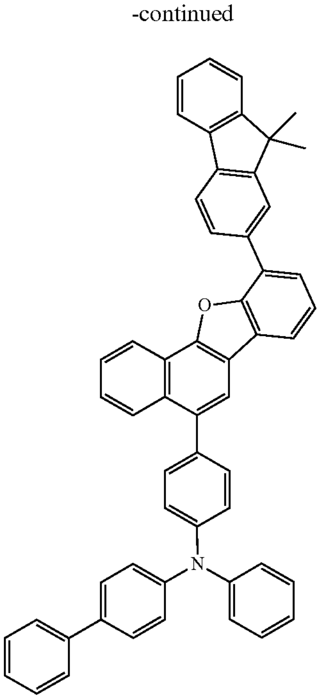
1-723
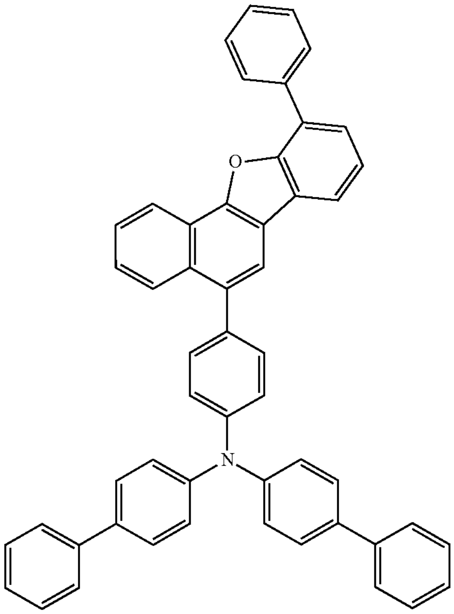

-continued
1-724
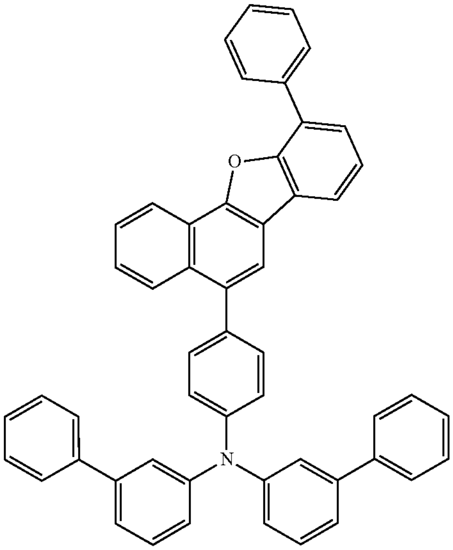
1-725
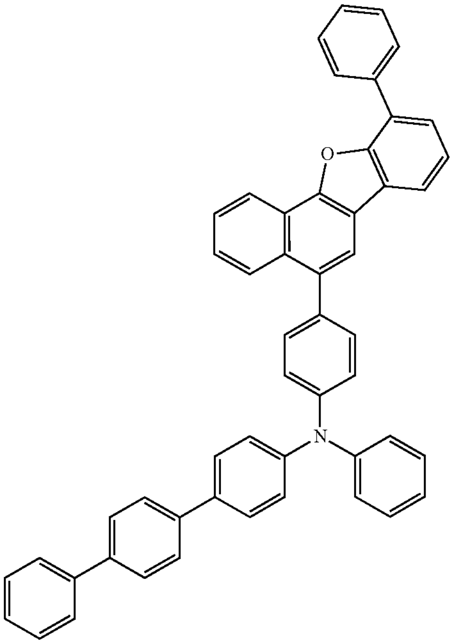
-continued
1-726
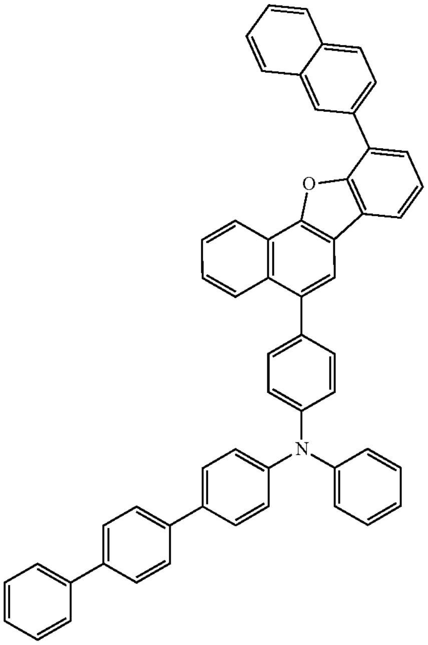
1-727
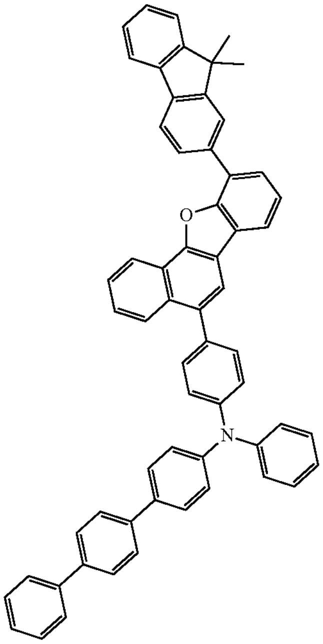

1-728
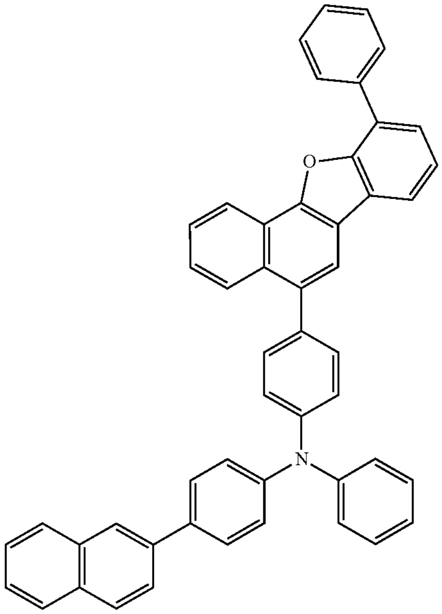
1-729
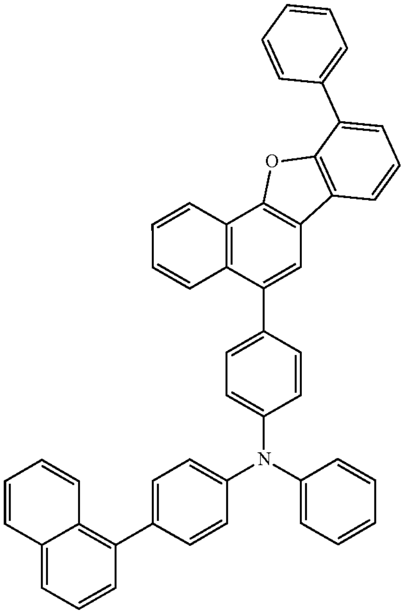
1-730
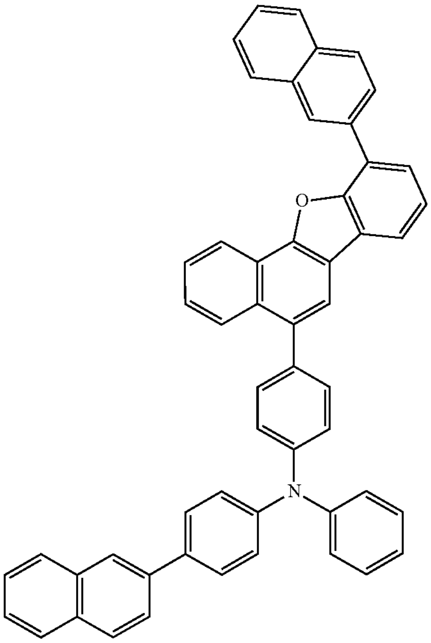
1-731
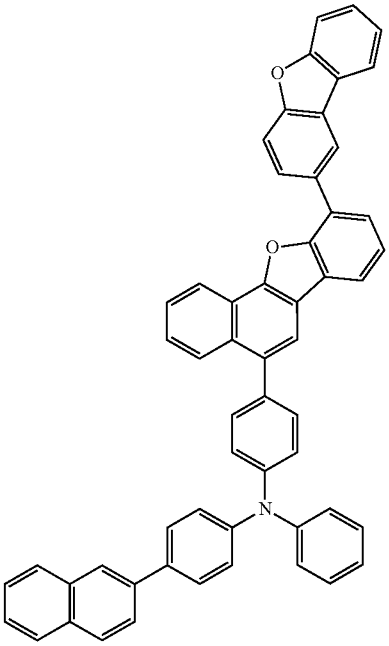

-continued
1-732
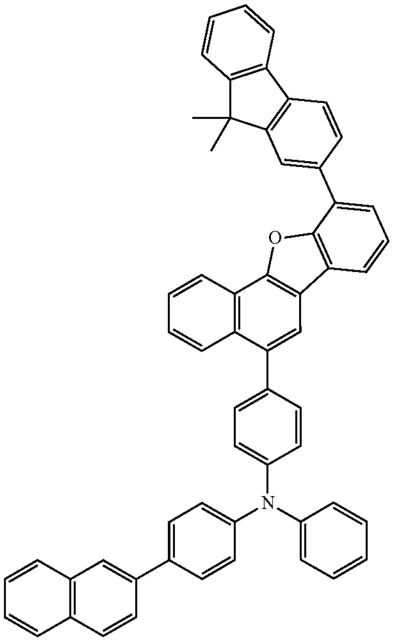
1-733
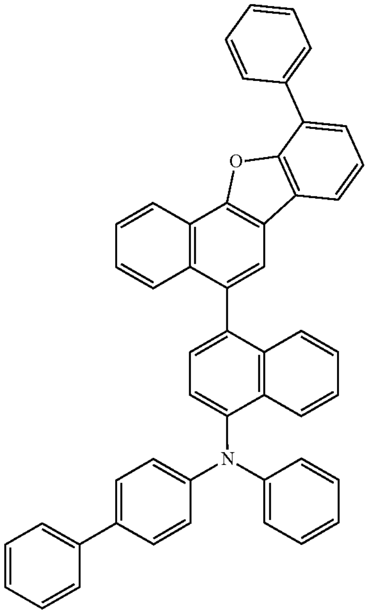
-continued
1-734
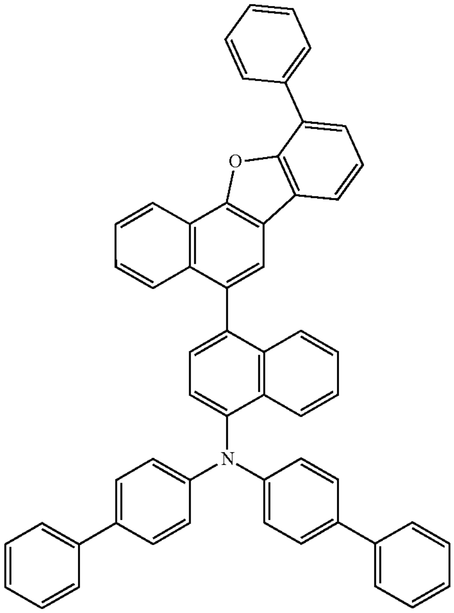
1-735
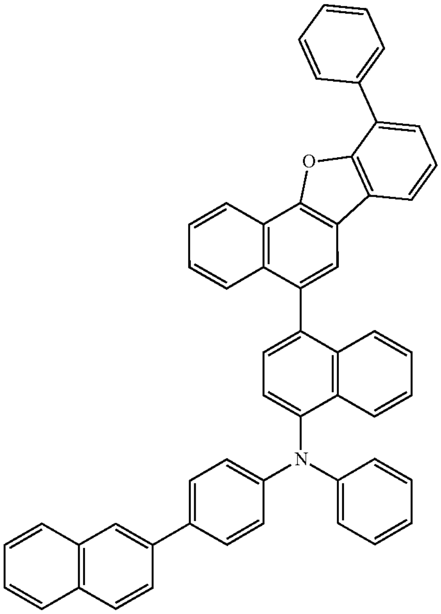

-continued
1-736
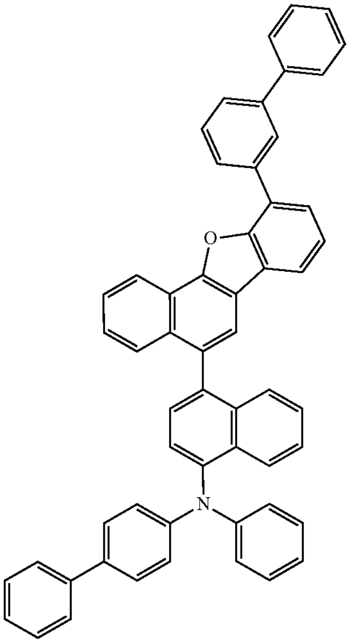
1-737
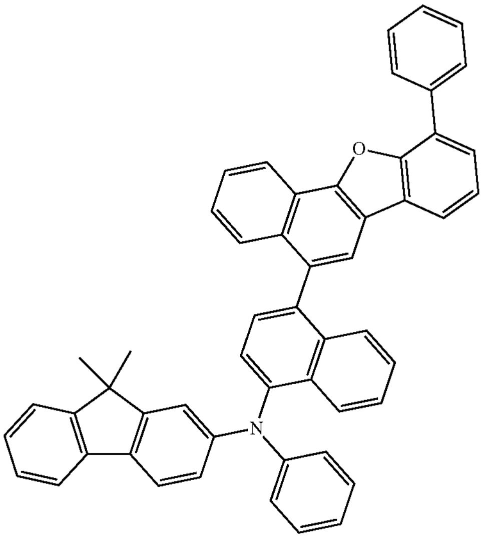
-continued
1-738
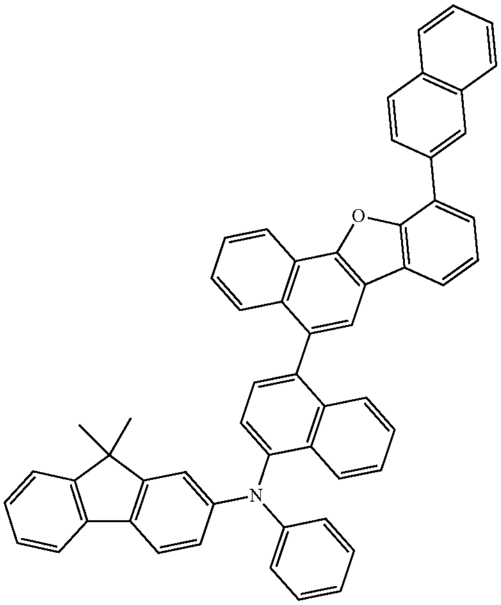
1-739
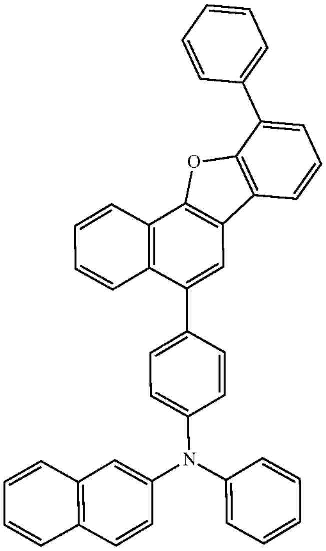

-continued
1-740
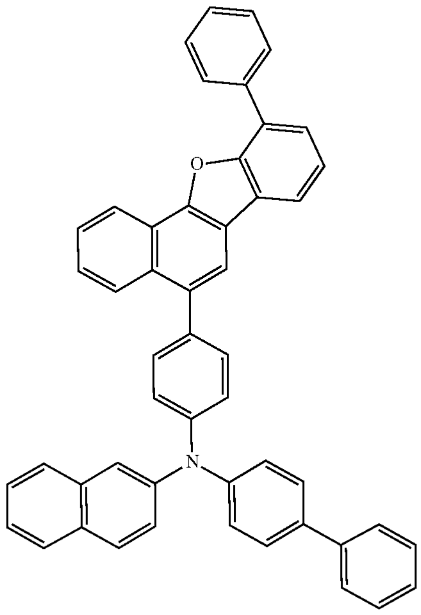
1-741
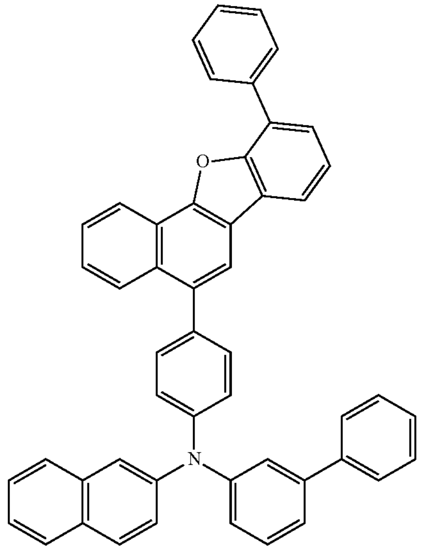
1-742
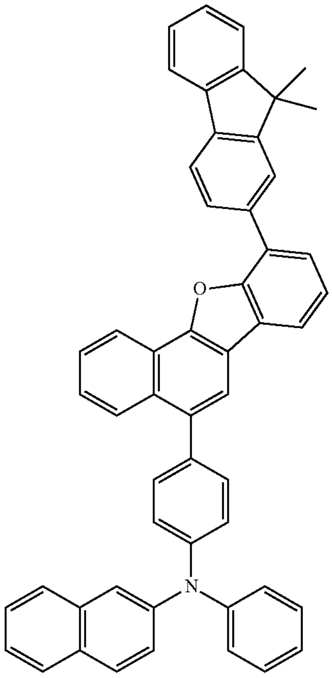

-continued
1-743
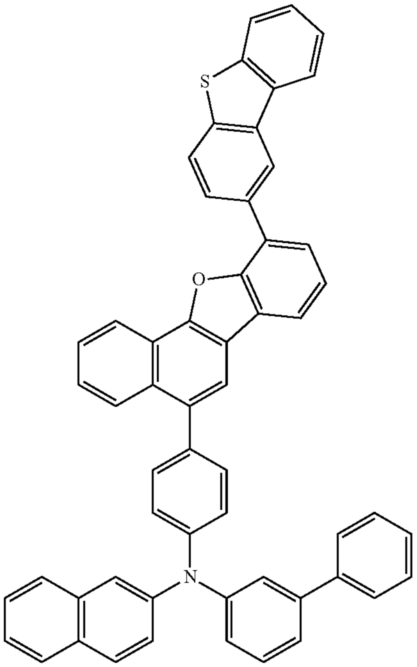
1-744
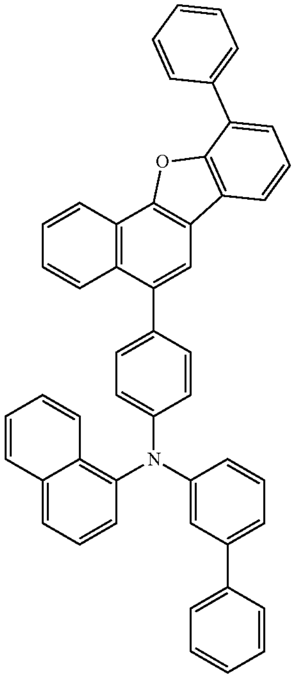
1-745
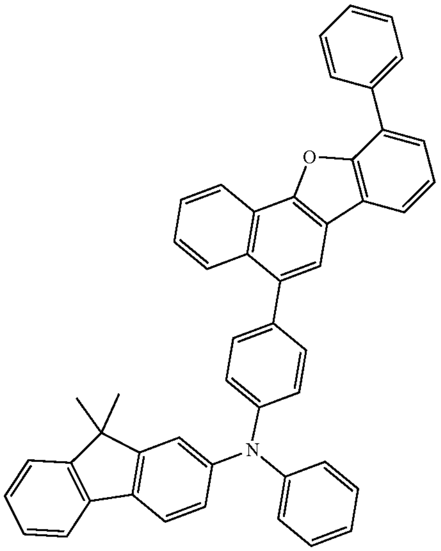
1-746
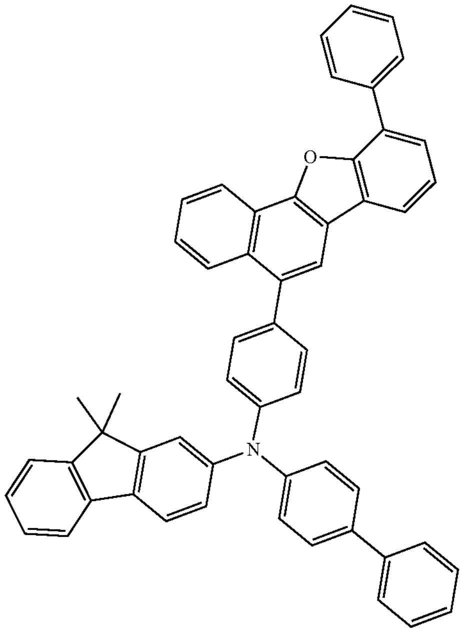

-continued
1-747
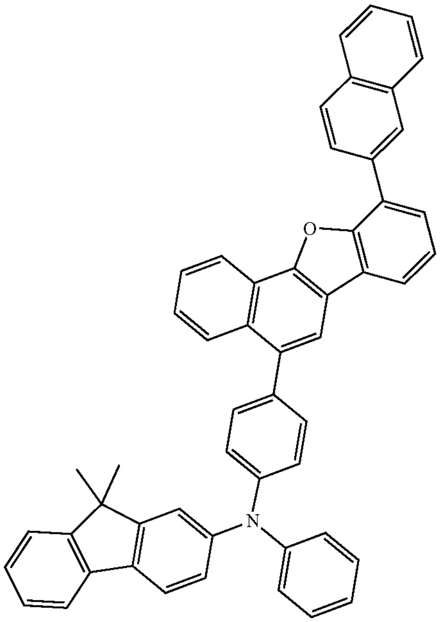
1-748
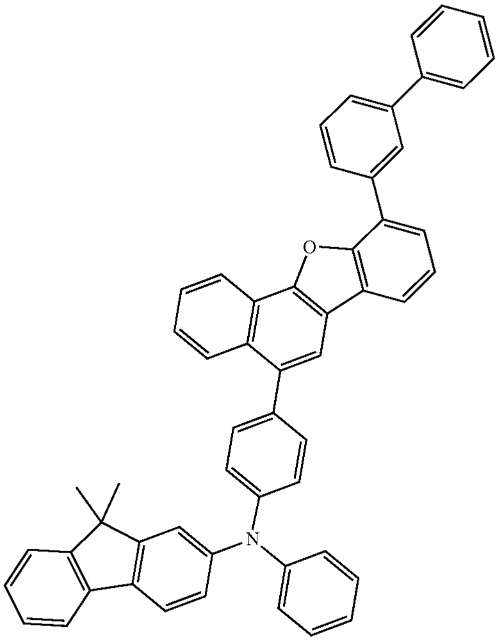
1-749
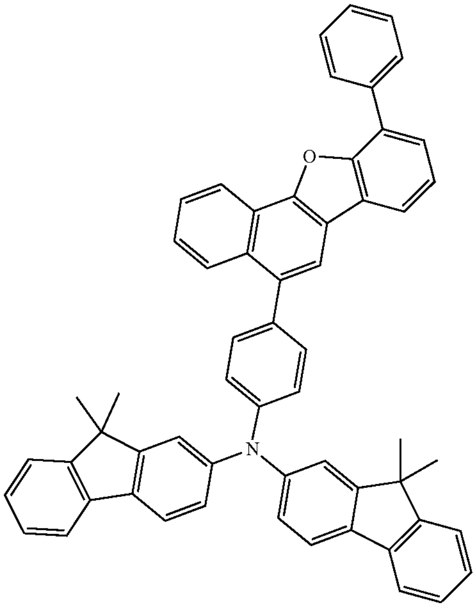
1-750
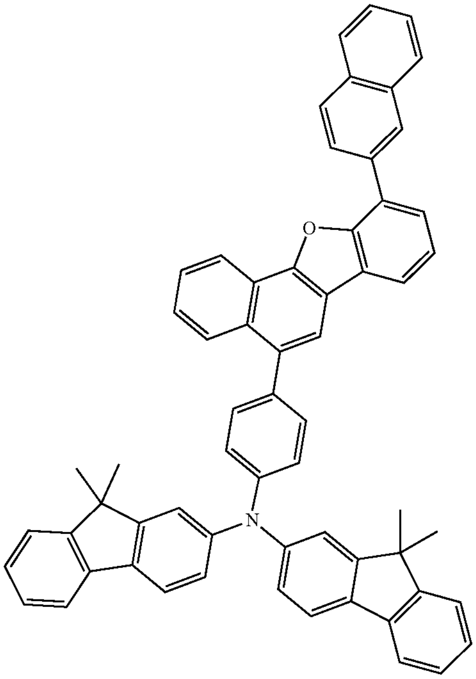

-continued
1-751
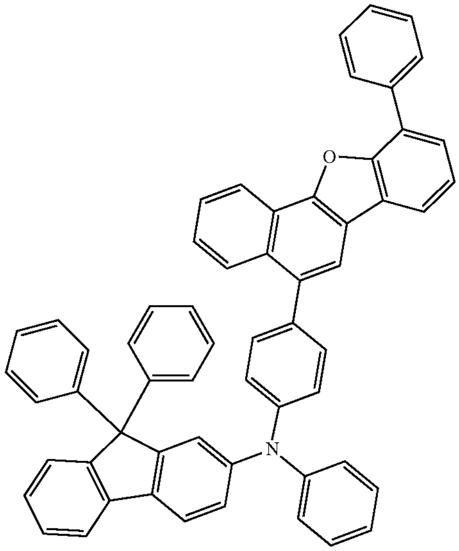
1-752
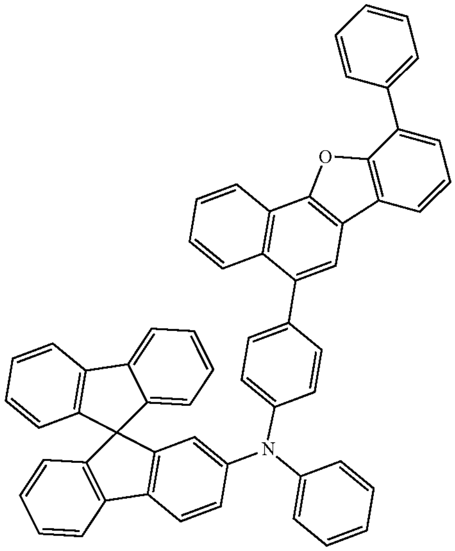
1-753
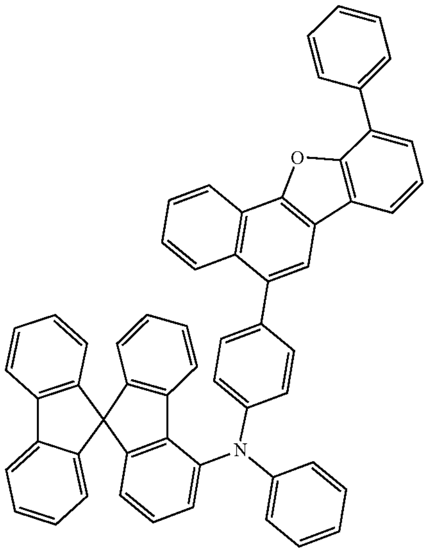
1-754
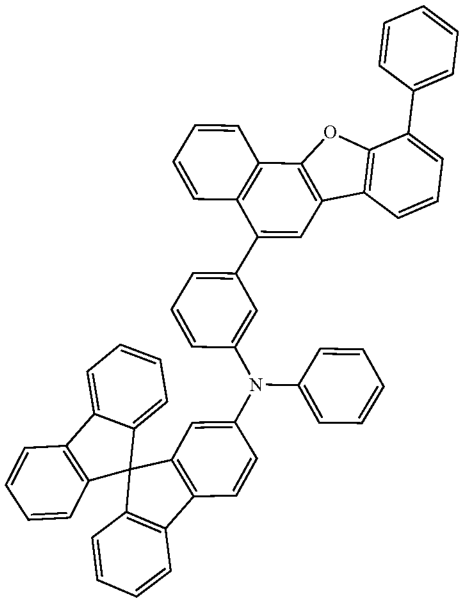

-continued
1-755
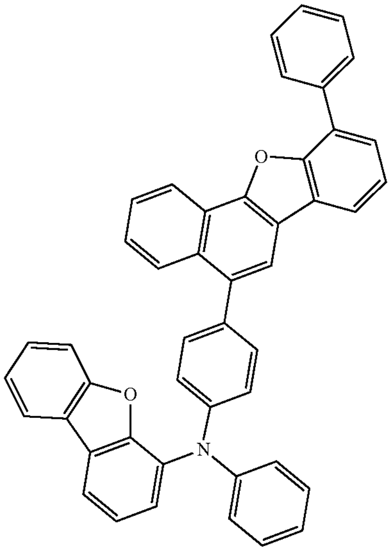
1-756
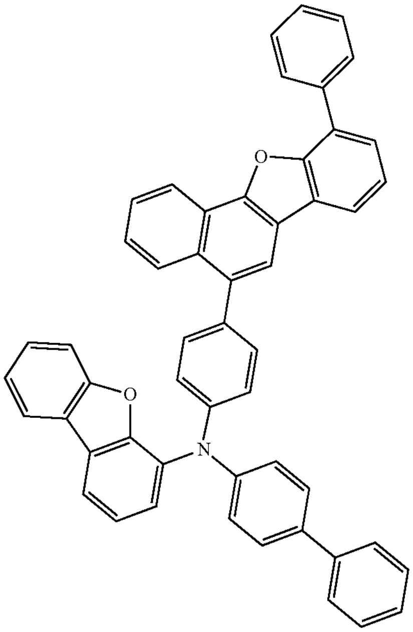
1-757
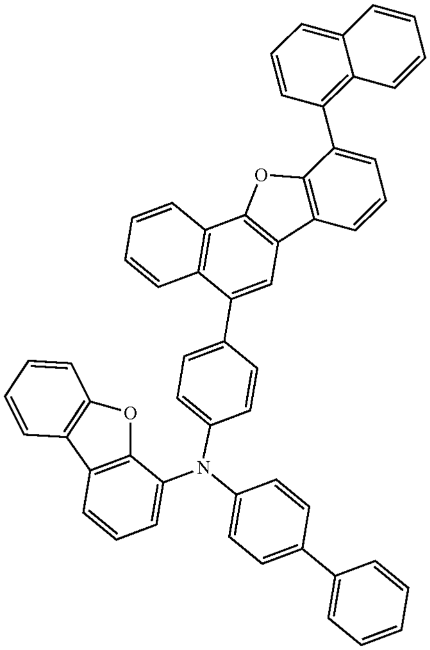
1-758
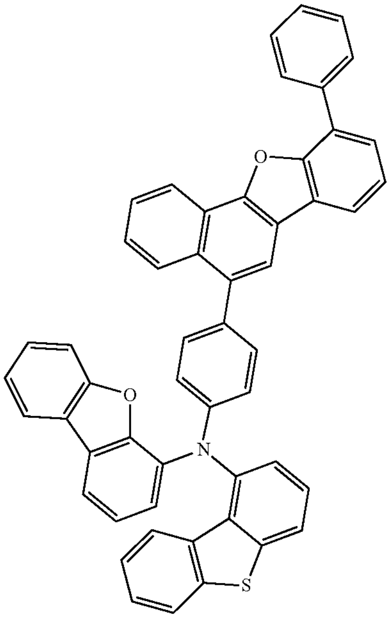

-continued
1-759
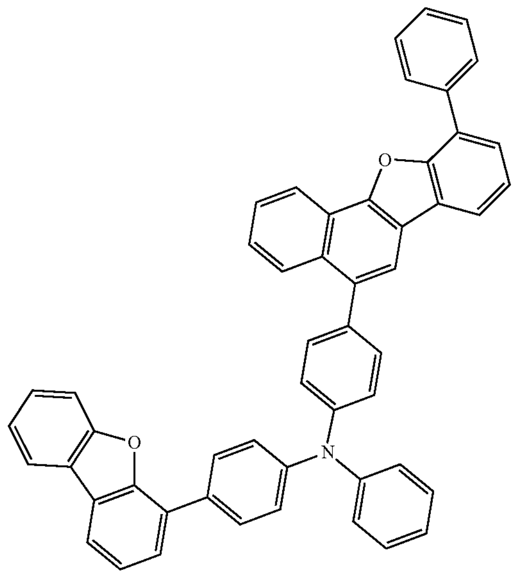
1-760
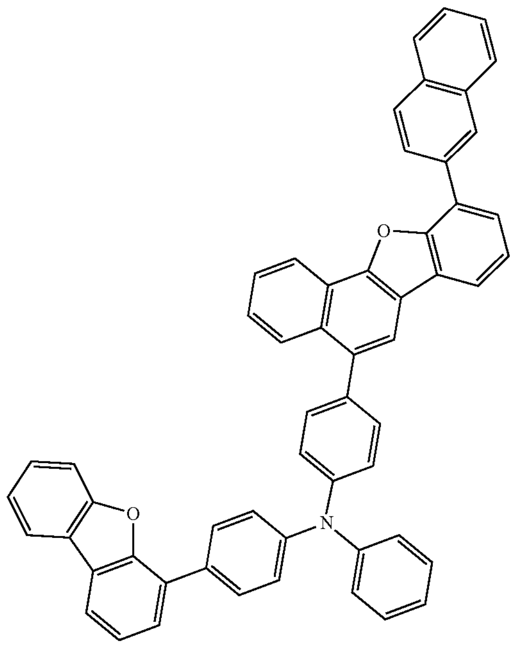
1-761
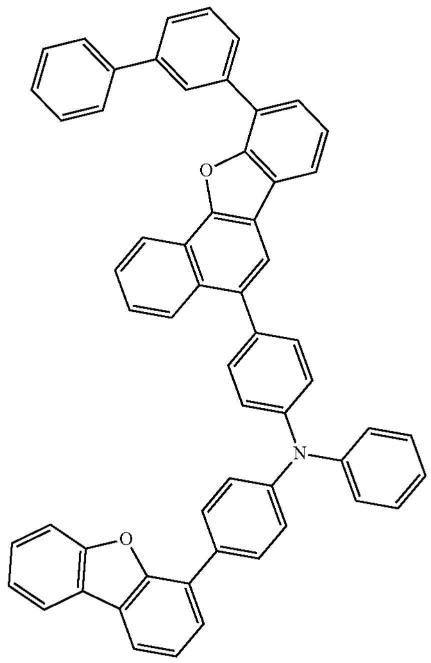
1-762
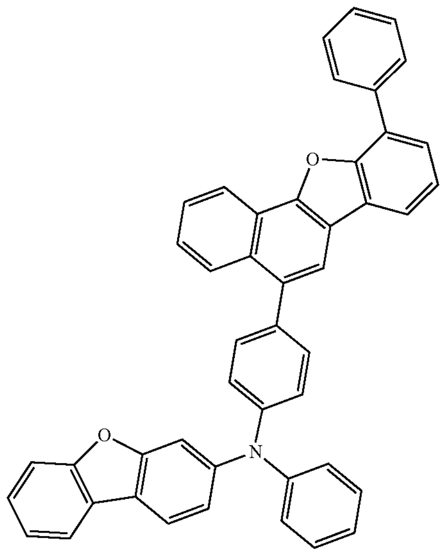

-continued
1-763
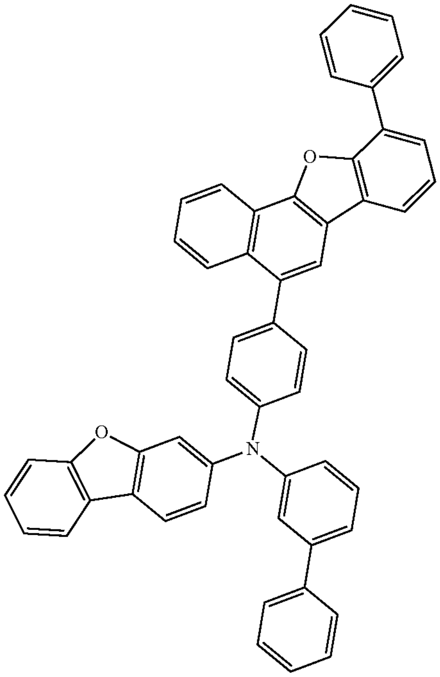
1-764
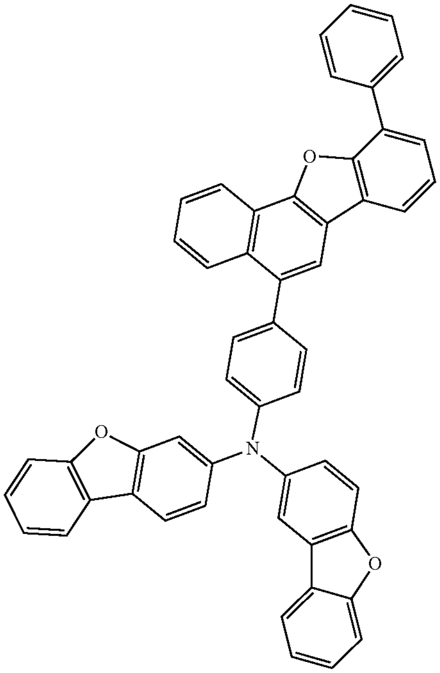
1-765
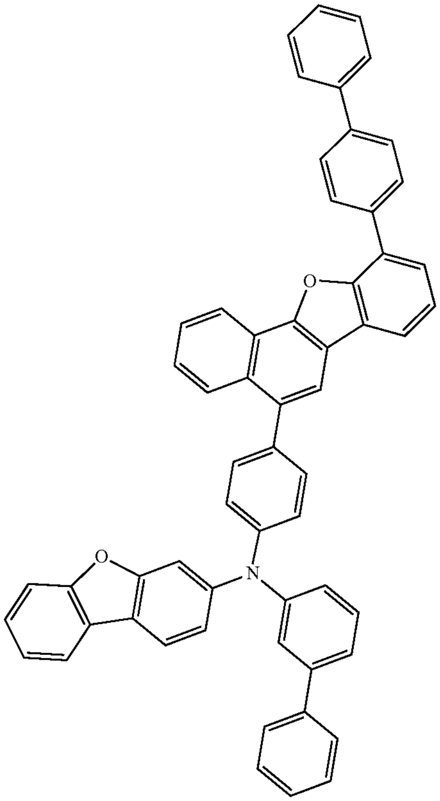
1-766
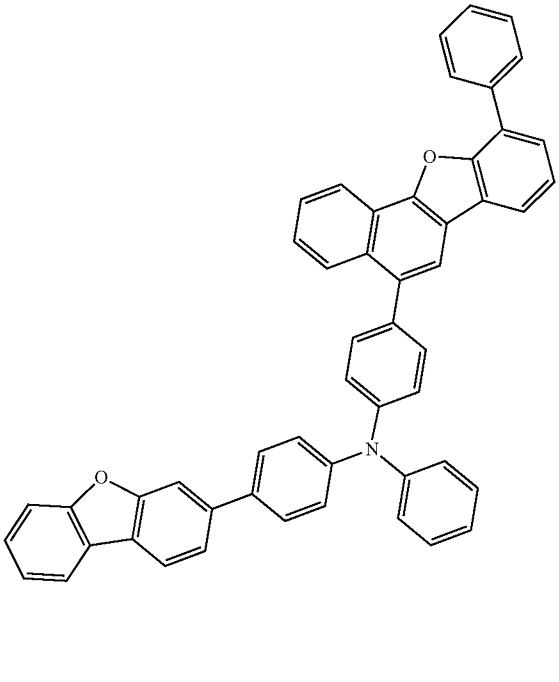

-continued
1-767
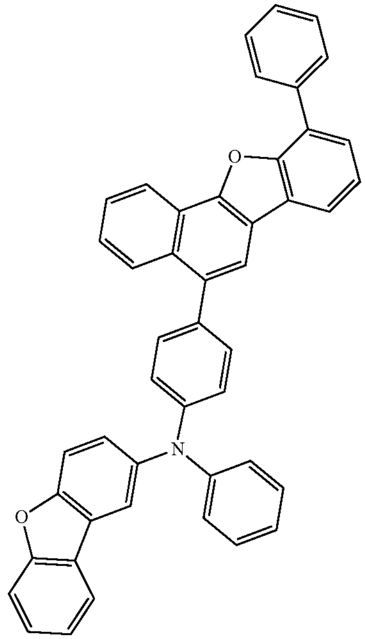
1-768
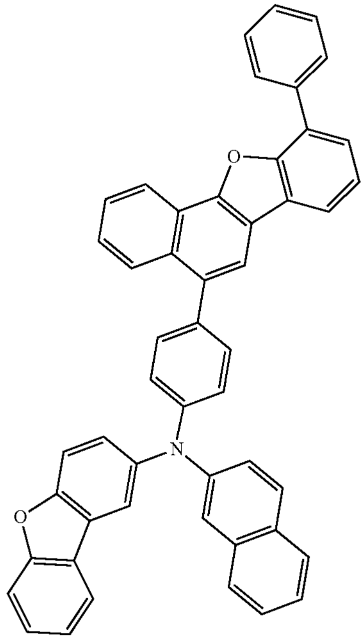
1-769
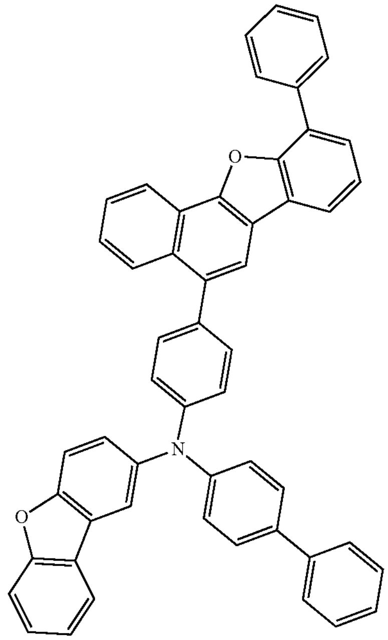
1-770
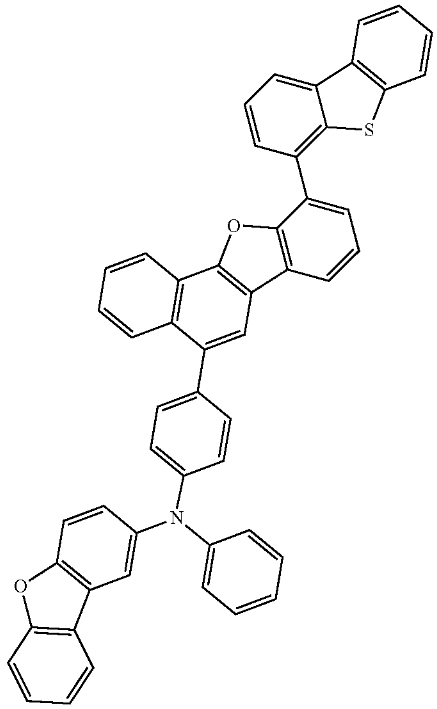

-continued
1-771
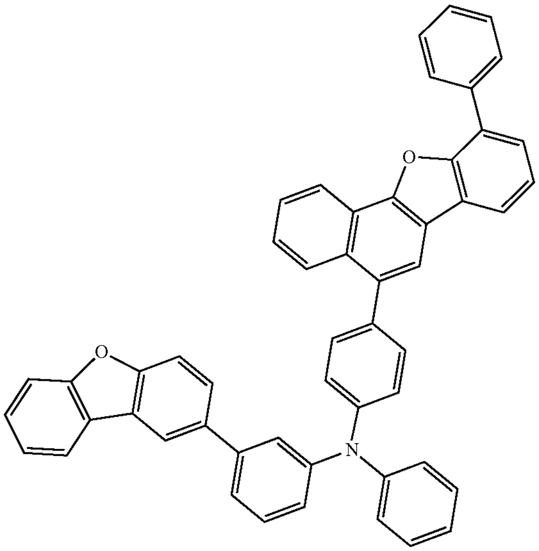
1-772
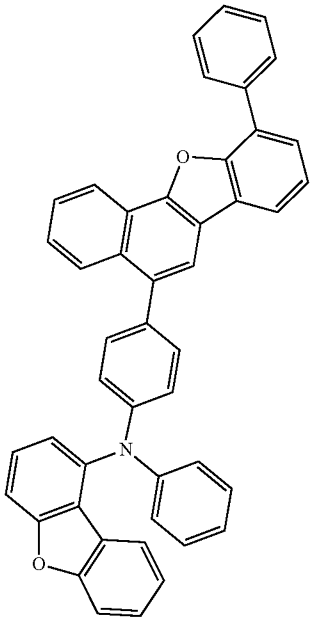
1-773
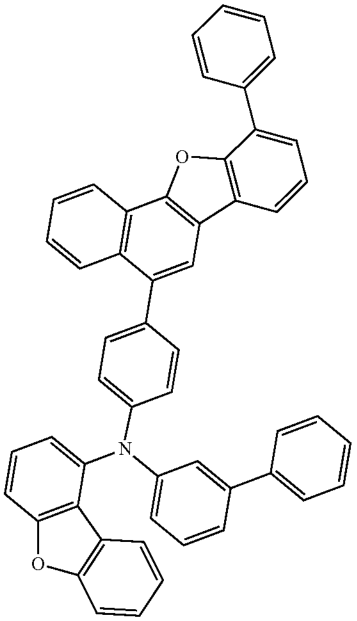
1-774
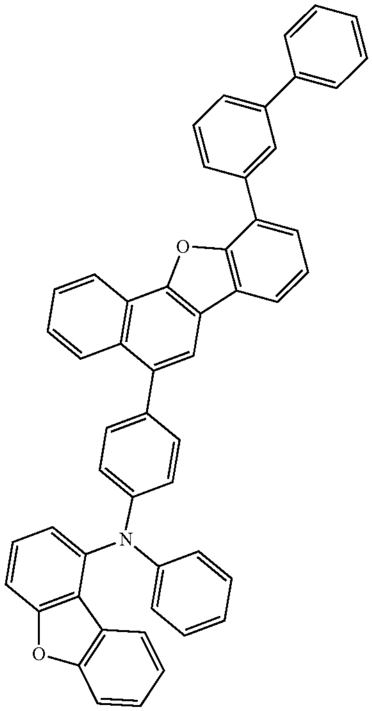

-continued
1-775
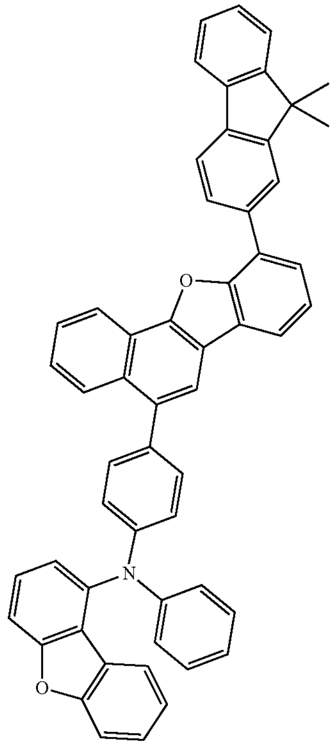
1-776
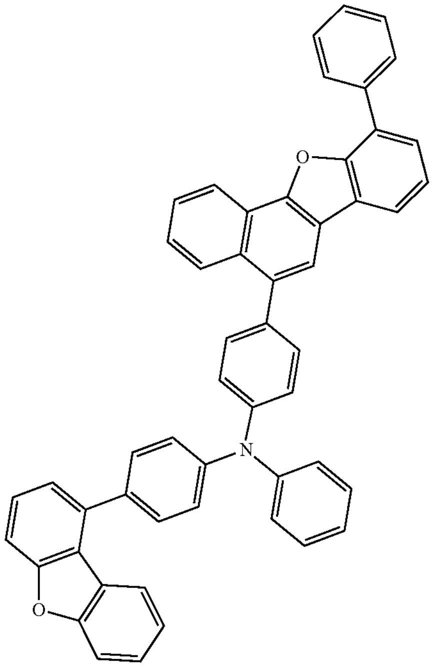
1-777
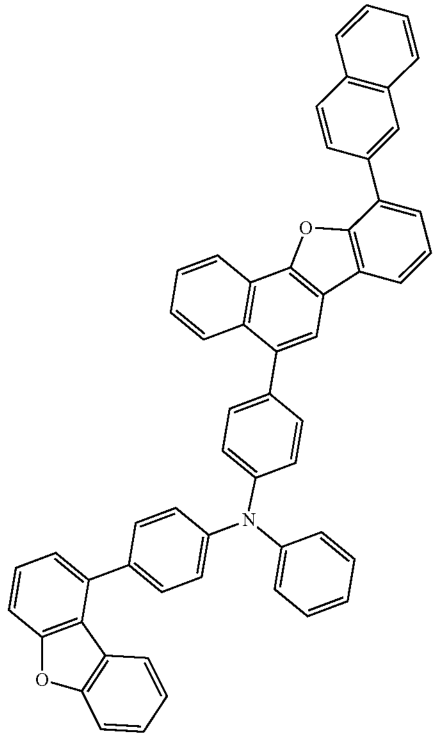
1-778
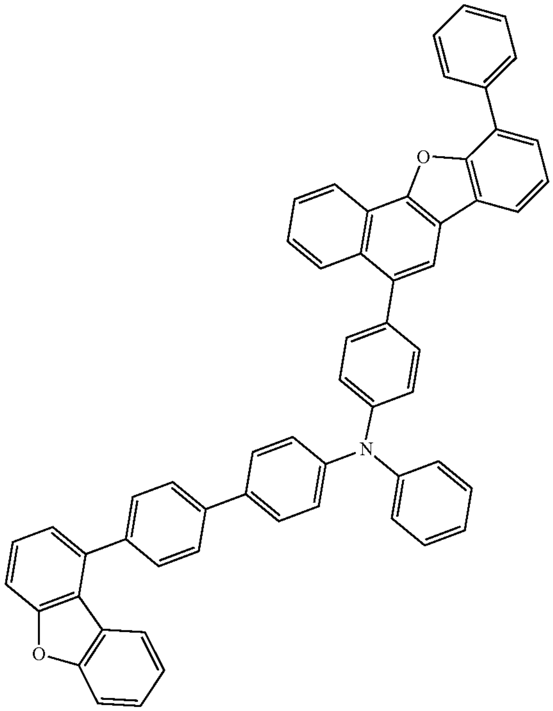

-continued
1-779
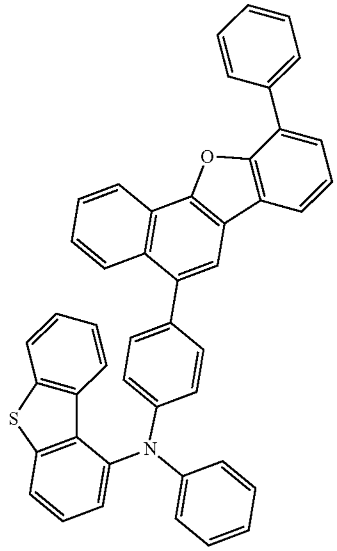
1-780
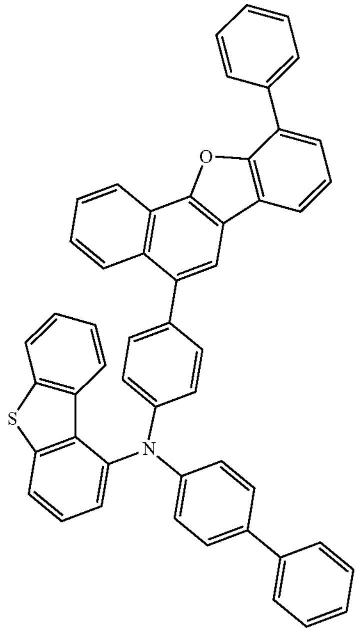
1-781
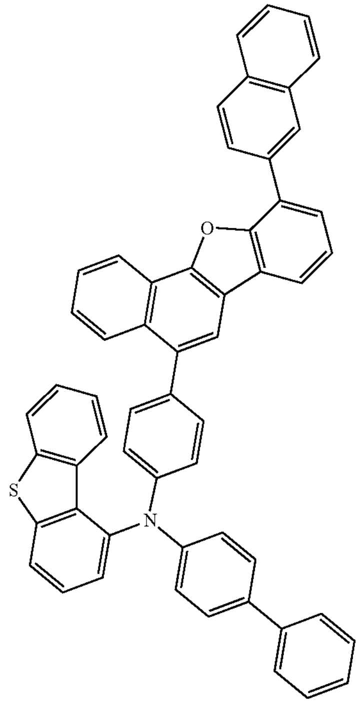
1-782
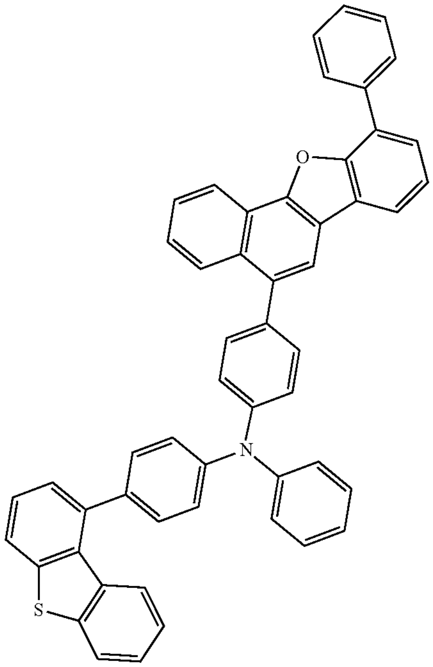

-continued
1-783
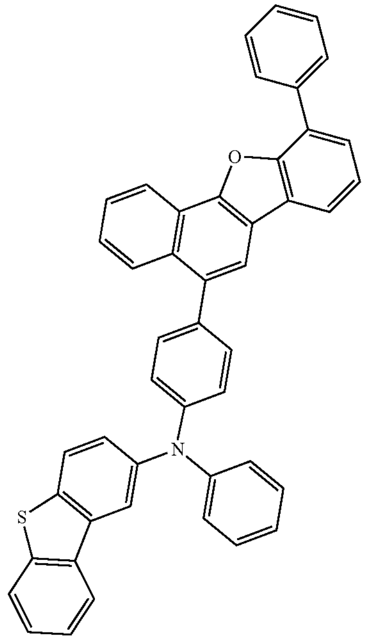
1-784
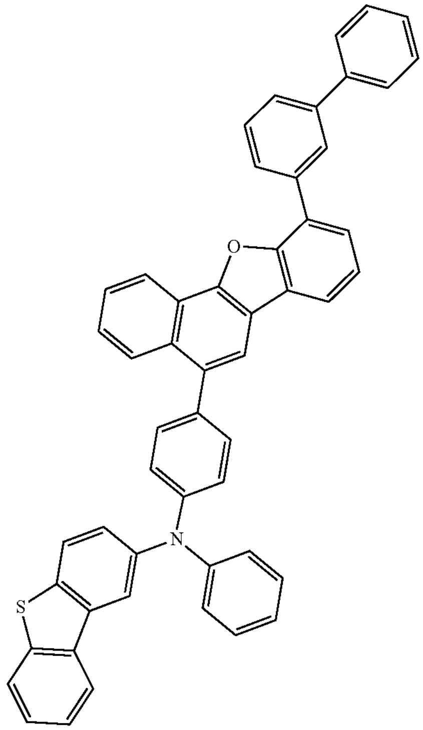
1-785
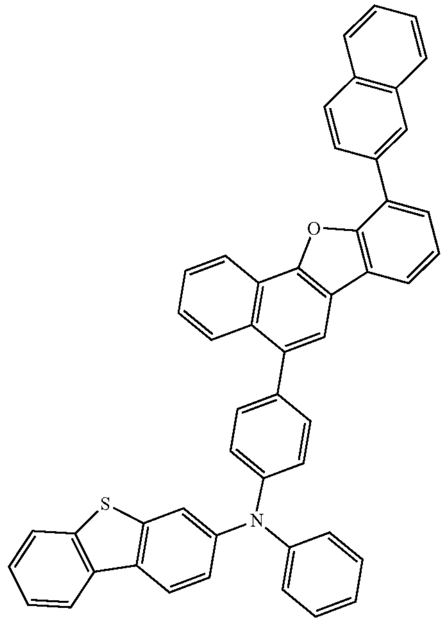
1-786
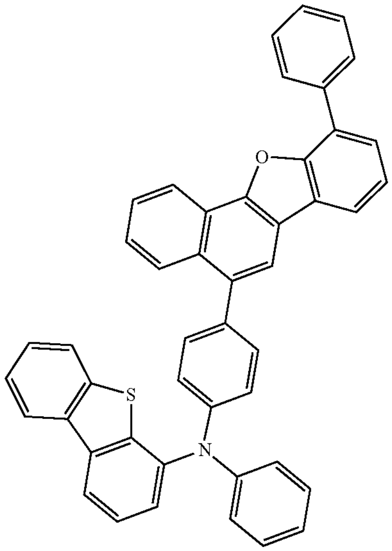

-continued
1-787
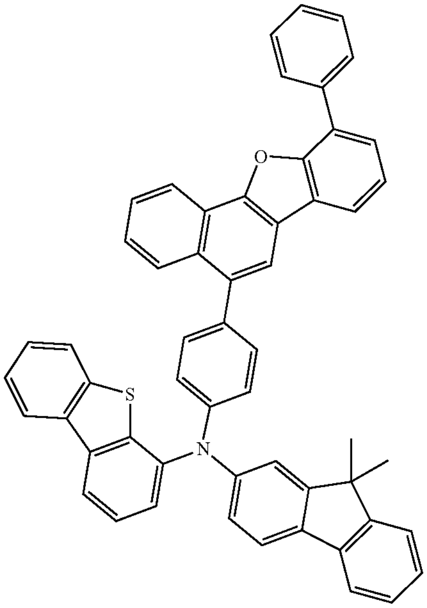
1-788
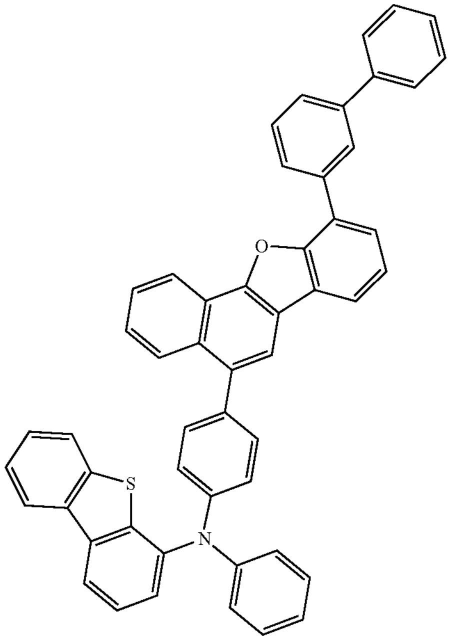
1-789
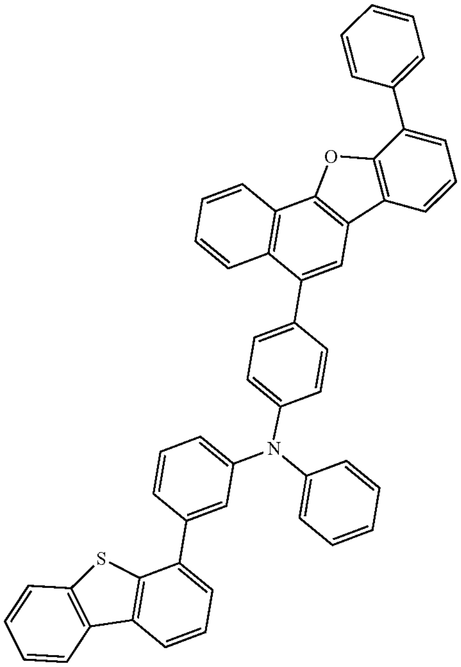
1-790
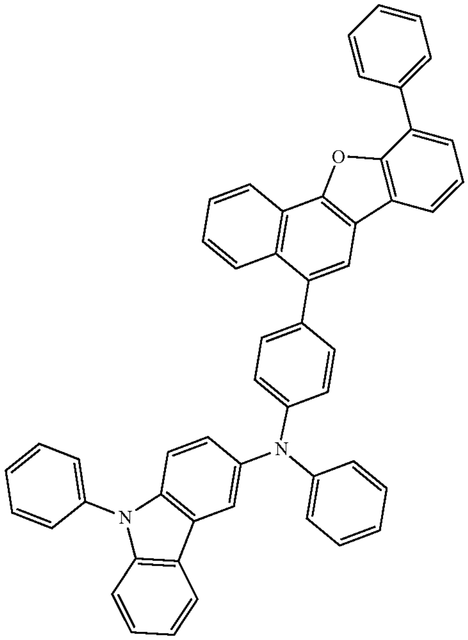

-continued
1-791
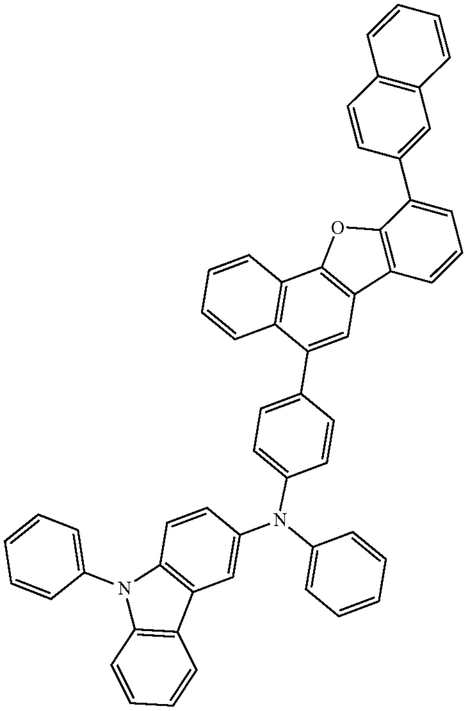
1-792
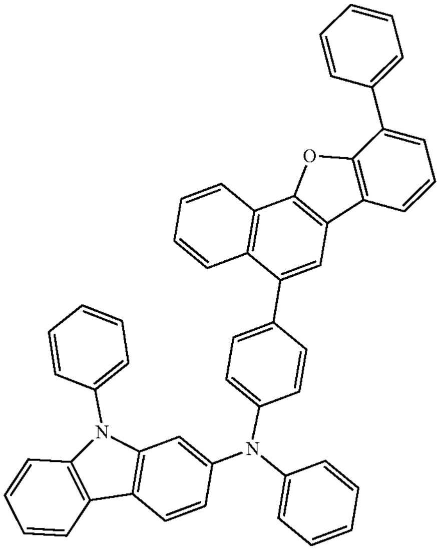
1-793
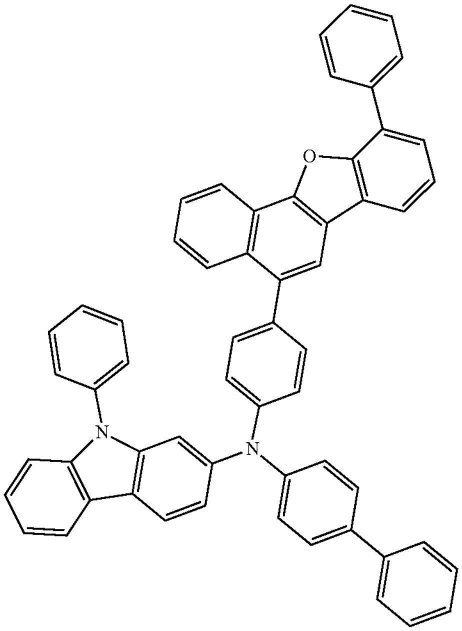
1-794
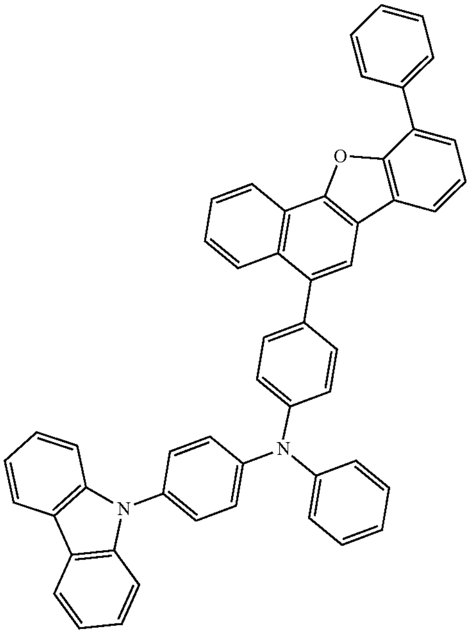

-continued
1-795
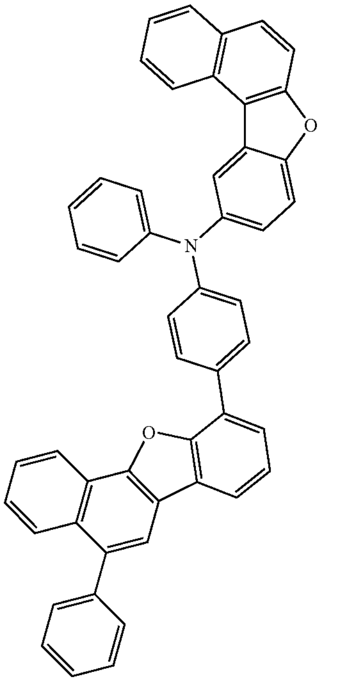
1-796
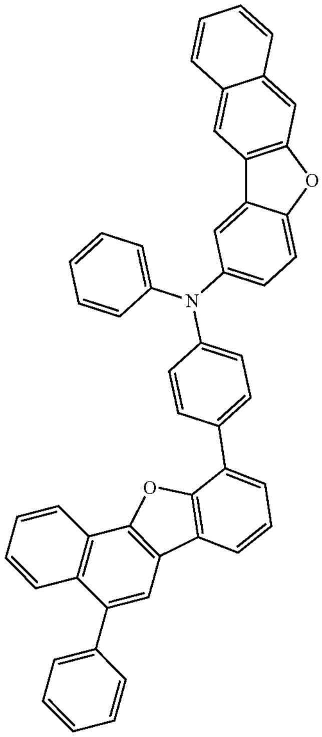
1-797
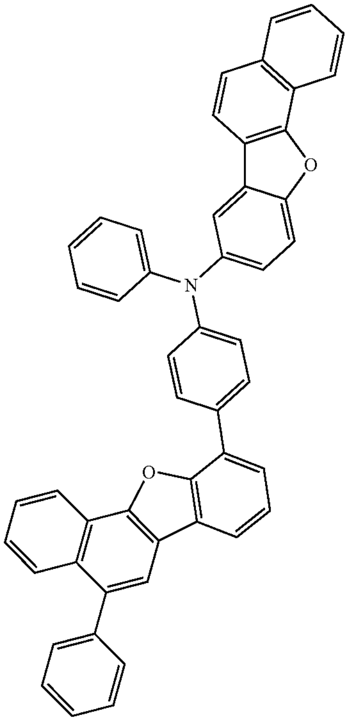
1-798
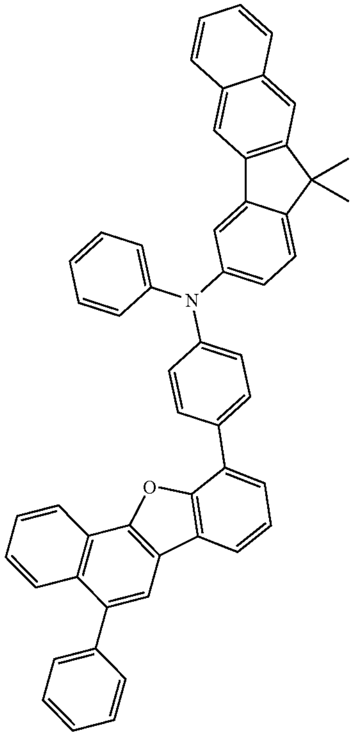

-continued
1-799
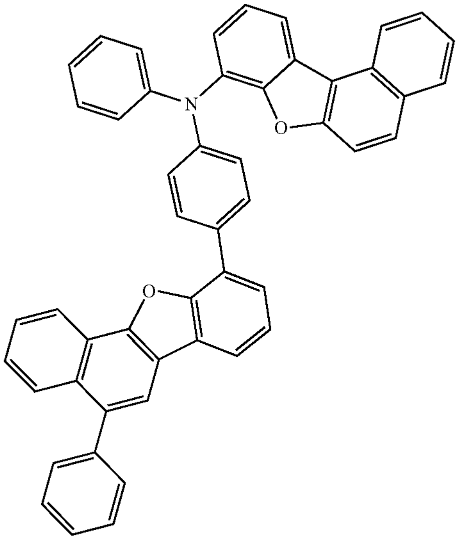
1-800
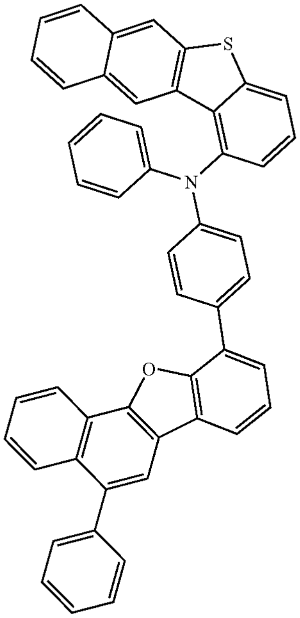
1-801
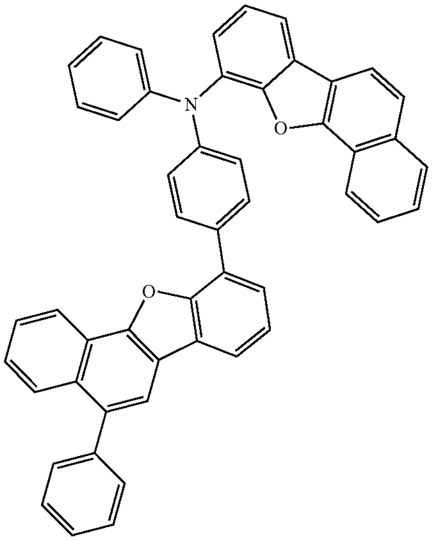
1-802
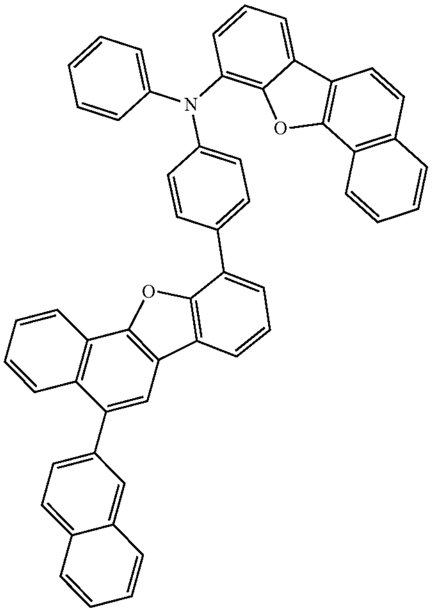

-continued
1-803
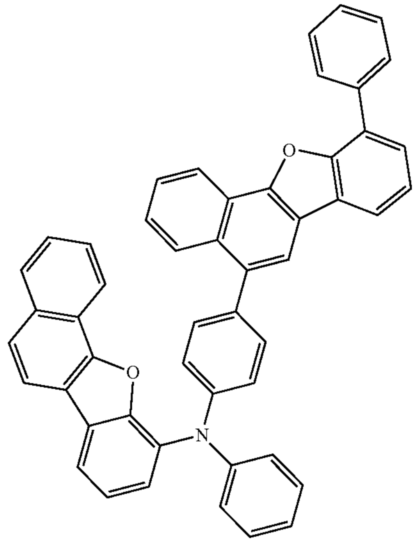
1-804
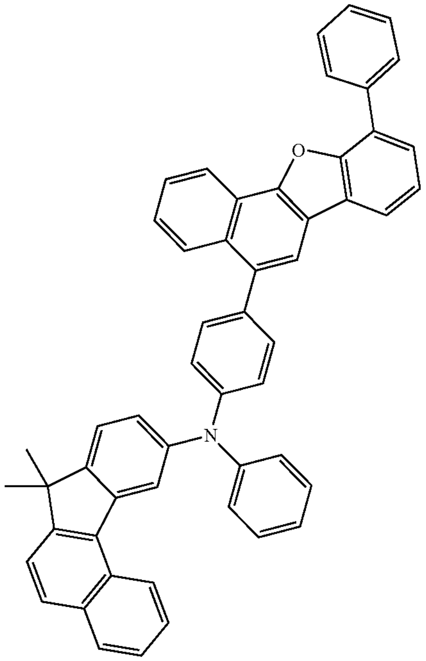
1-805
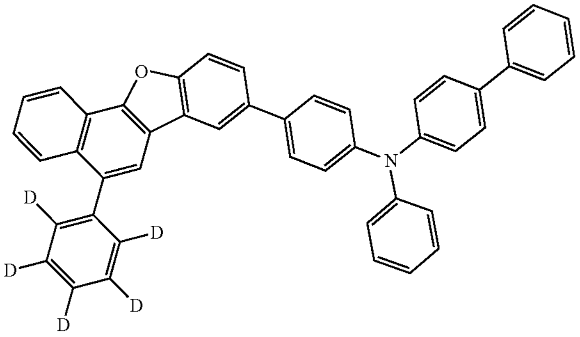
1-806
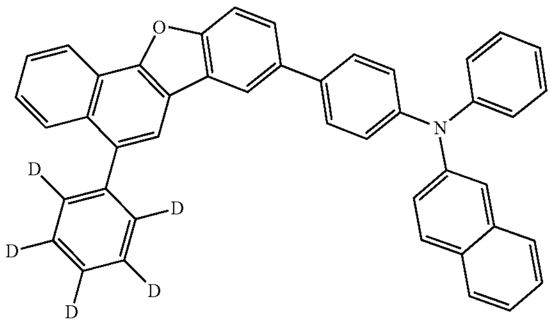
1-807
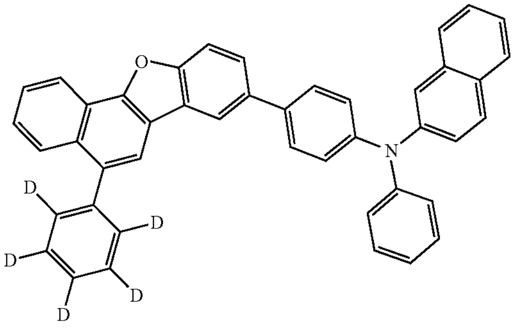
1-808
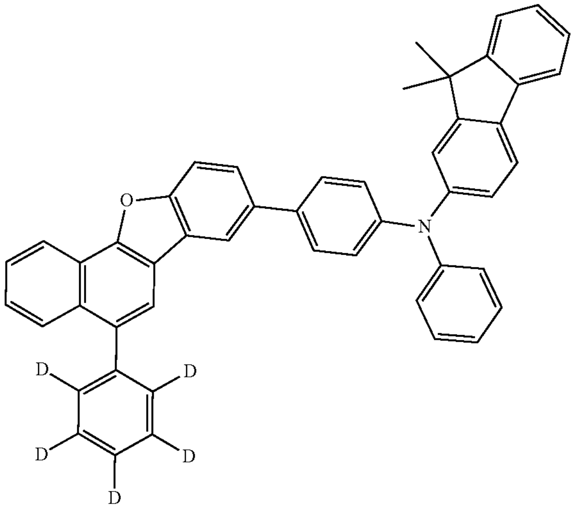

-continued
1-809
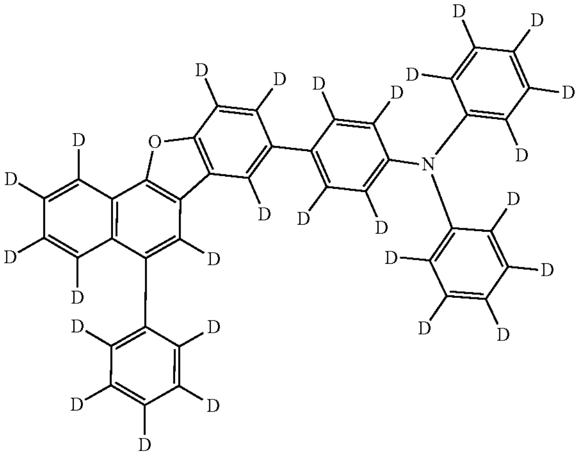
1-810
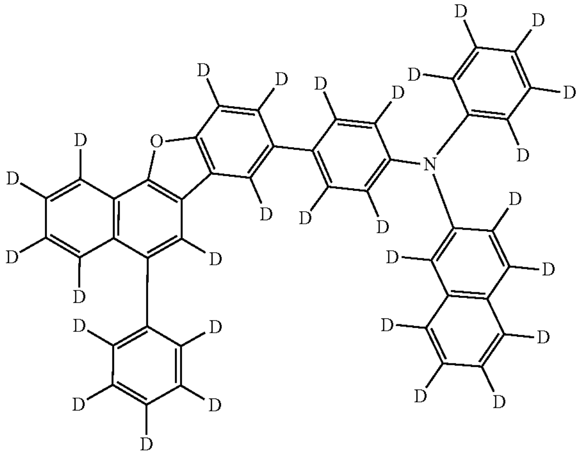
1-811
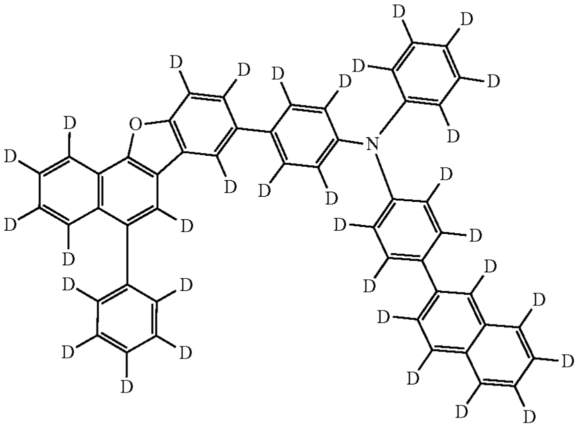
1-812
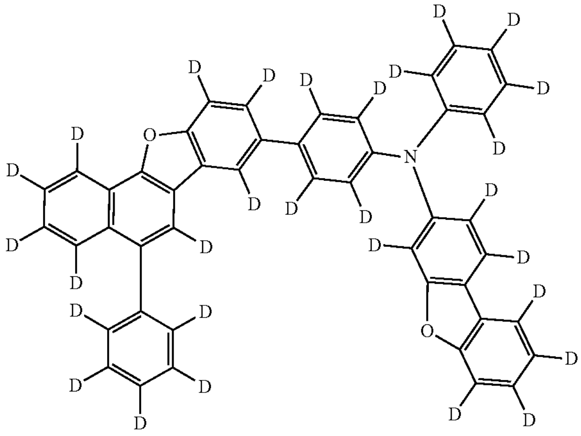
1-813
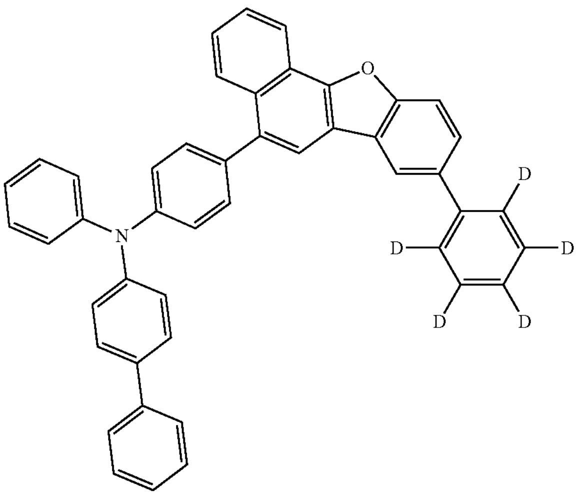

-continued
1-814
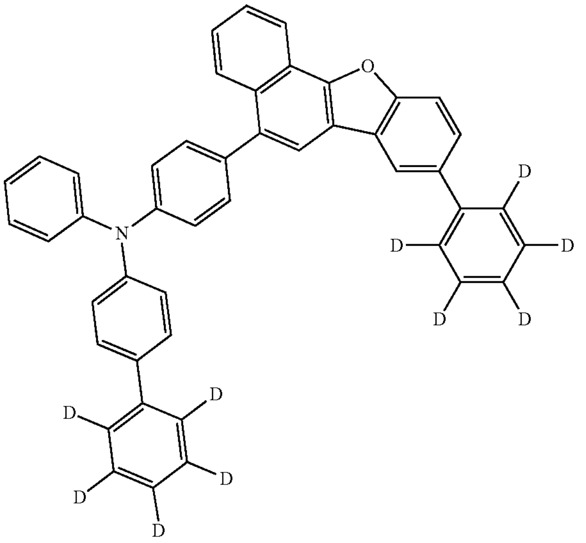
1-815
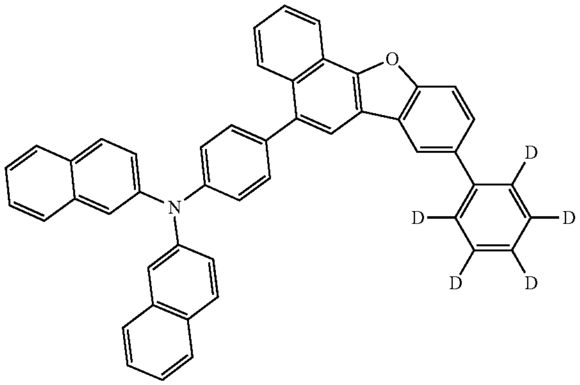
1-816
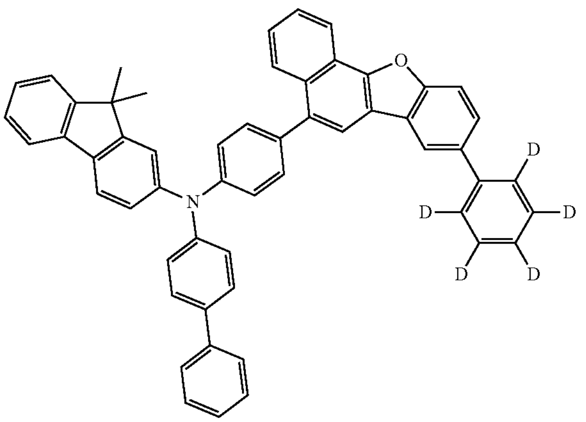
1-817
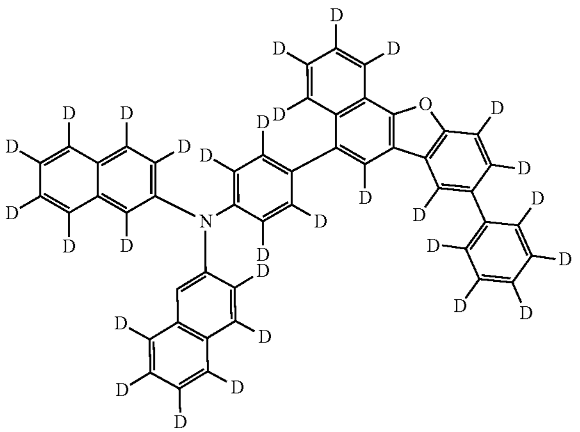
1-818
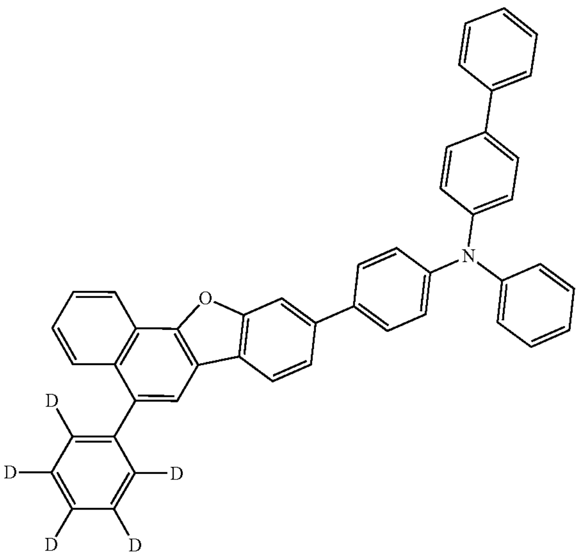
1-819
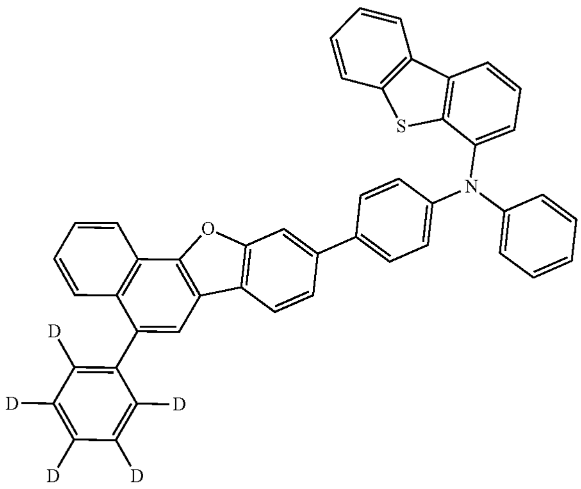

-continued
1-820
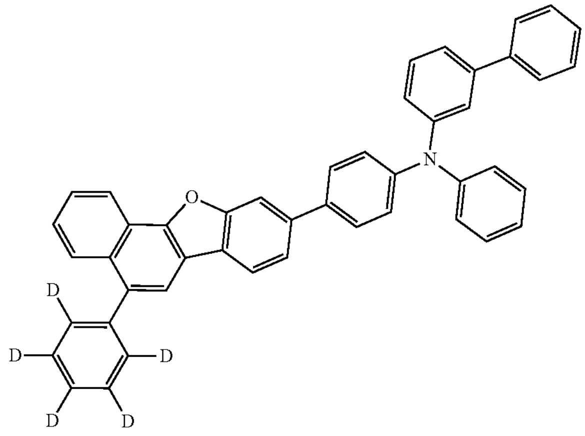
1-821
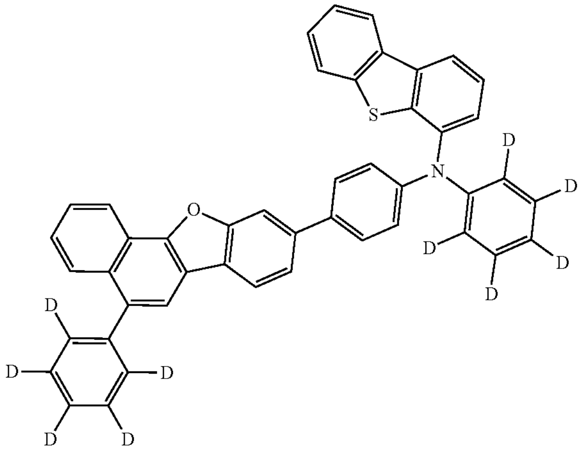
1-822
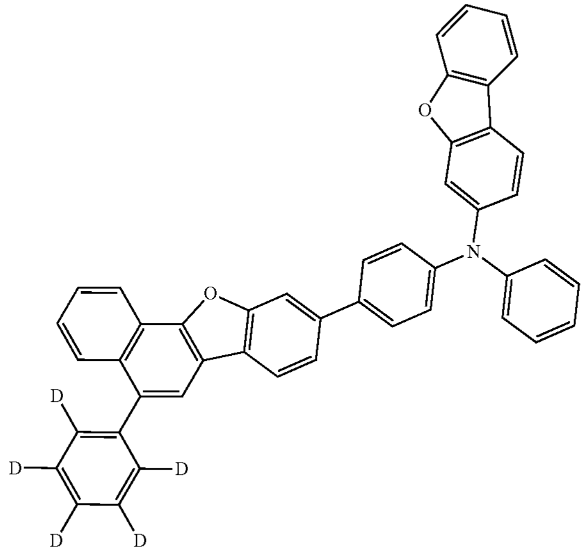
1-823
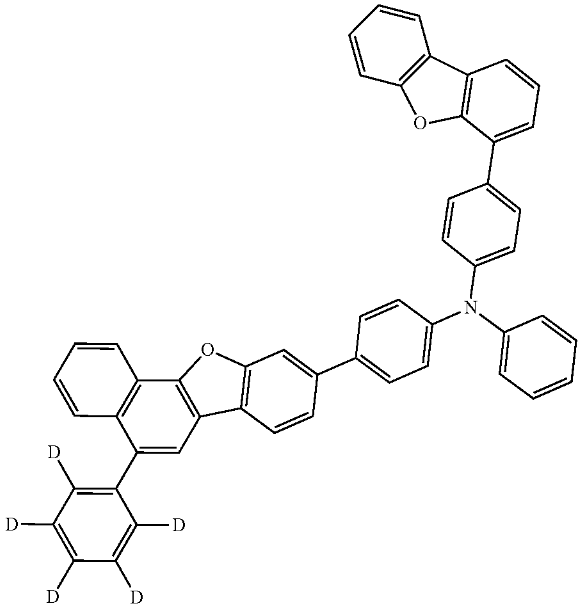

-continued
1-824
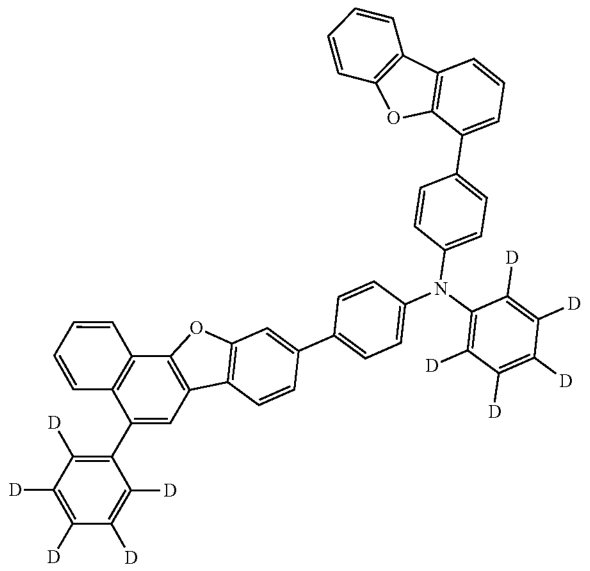
1-825
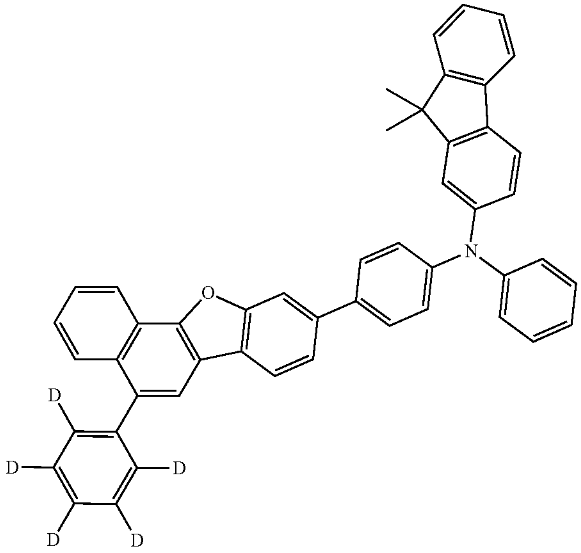
1-826
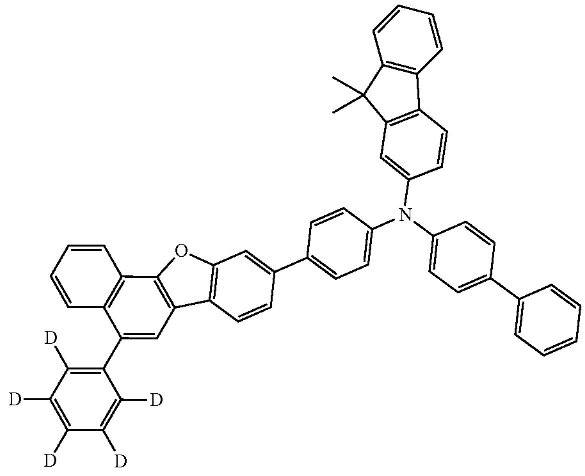
1-827
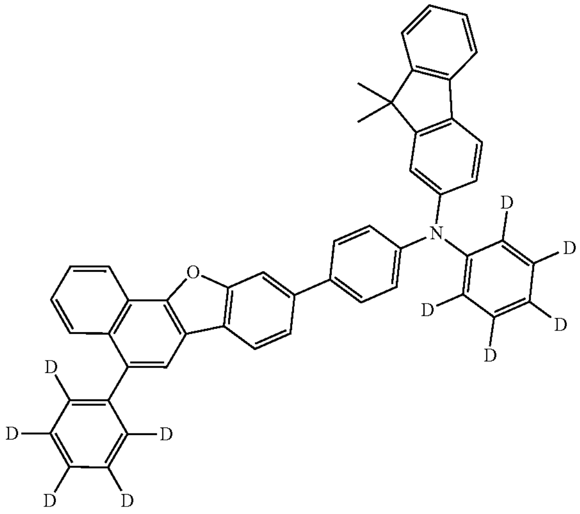

-continued
1-828
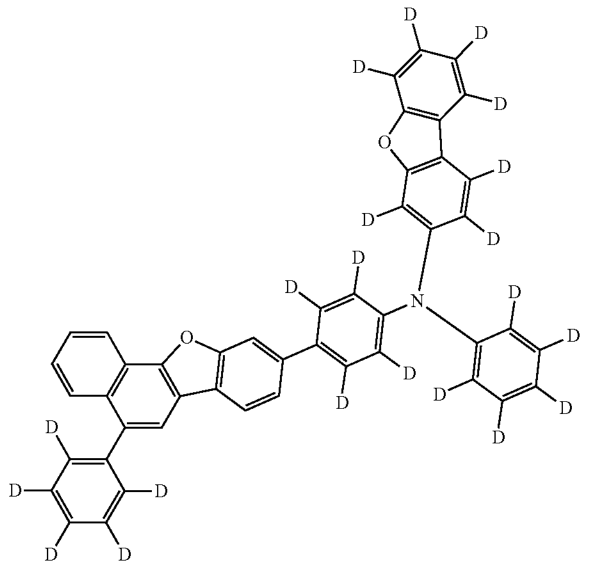
1-829
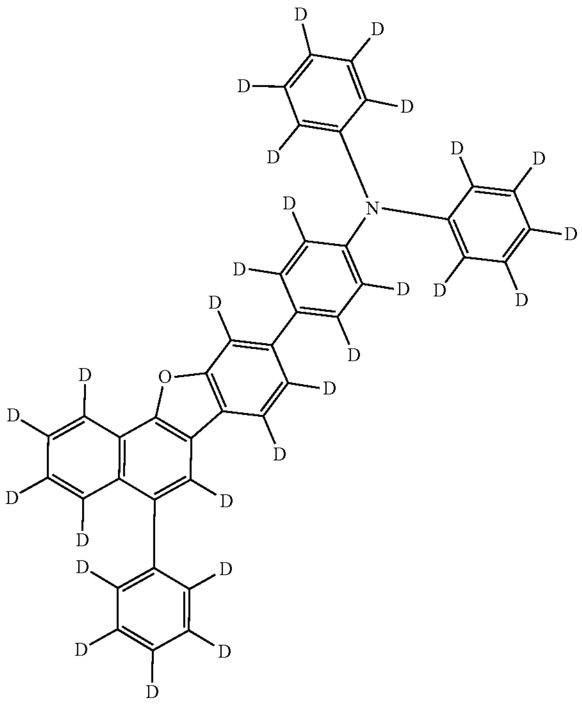
1-830
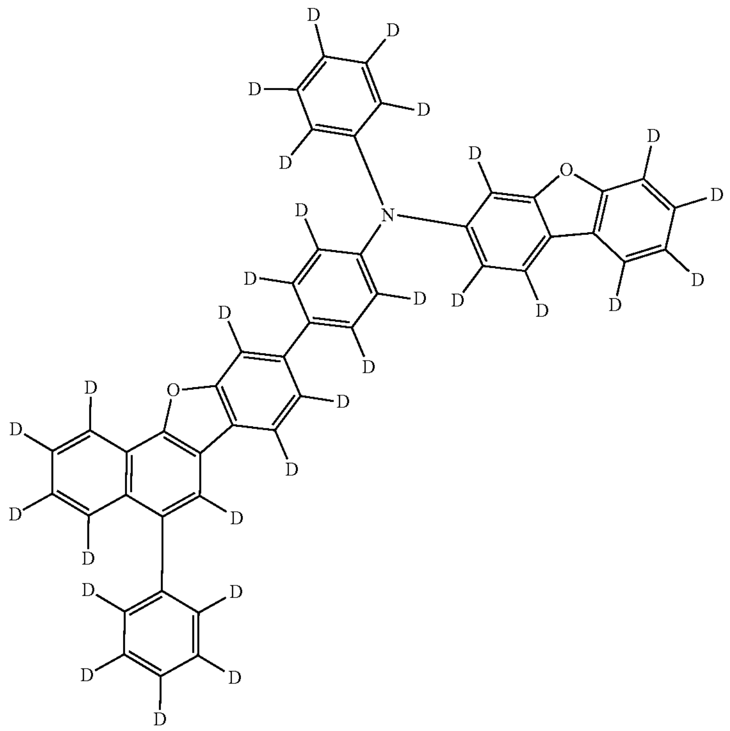

-continued
1-831
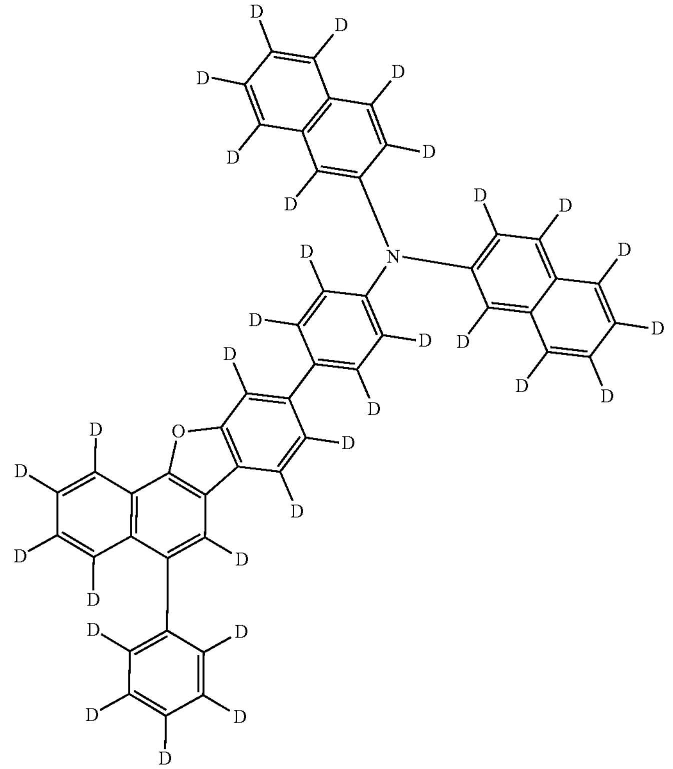
1-832
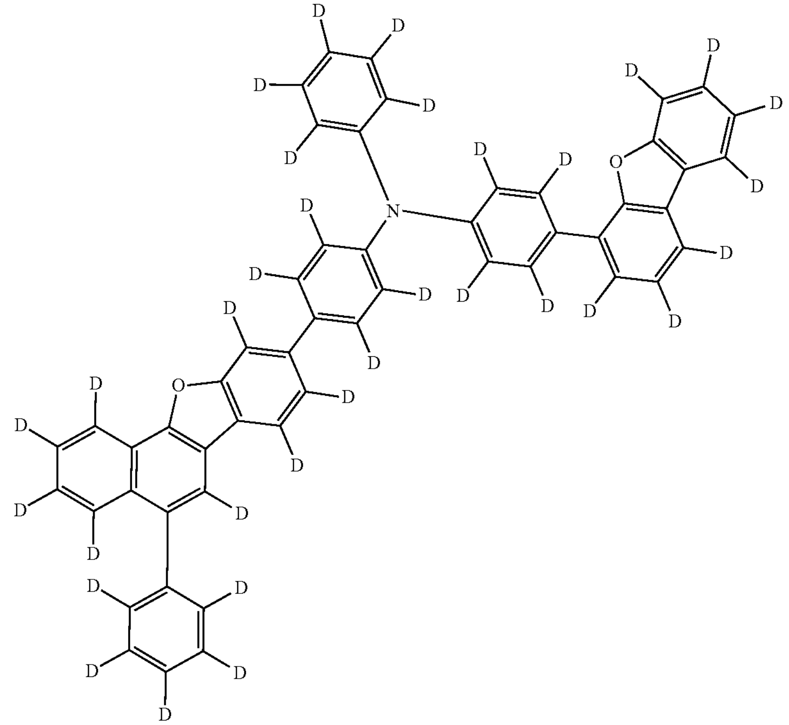

-continued
1-833
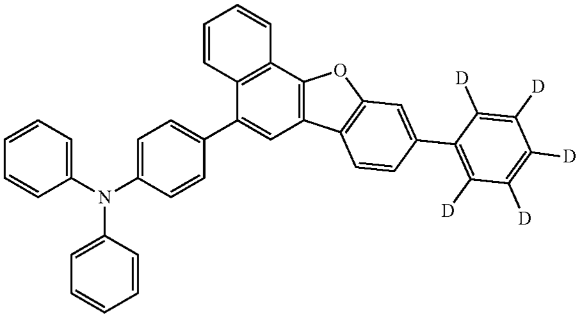
1-834
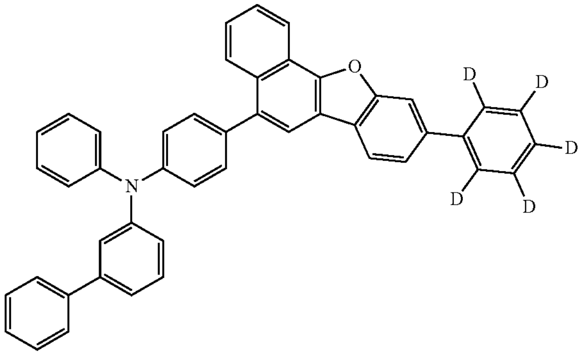
1-835
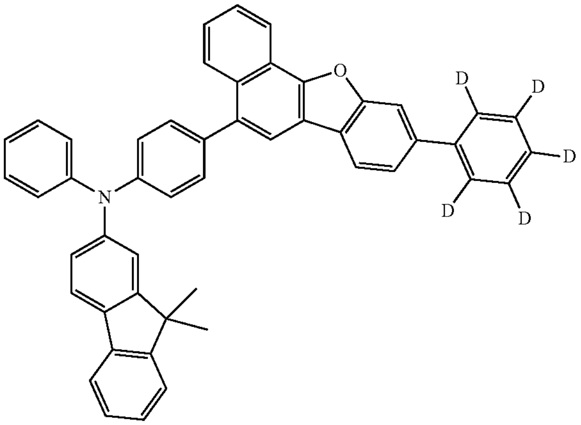
1-836
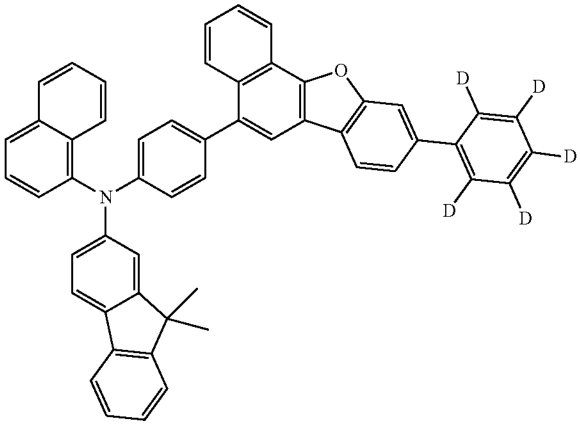
1-837
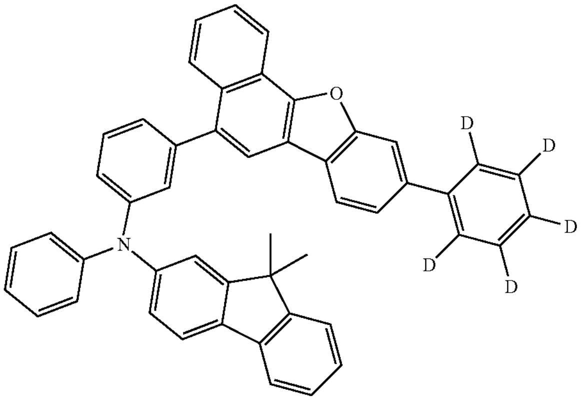
1-838
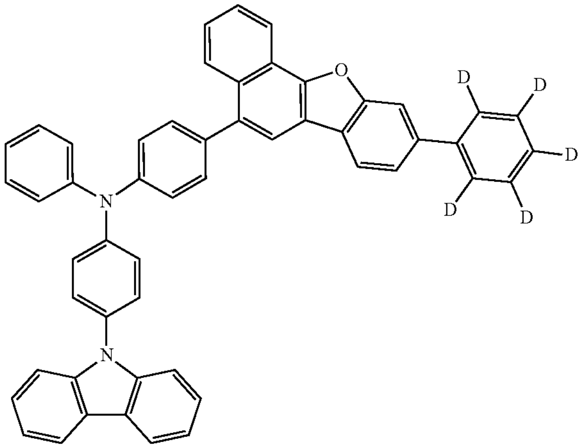

-continued
1-839
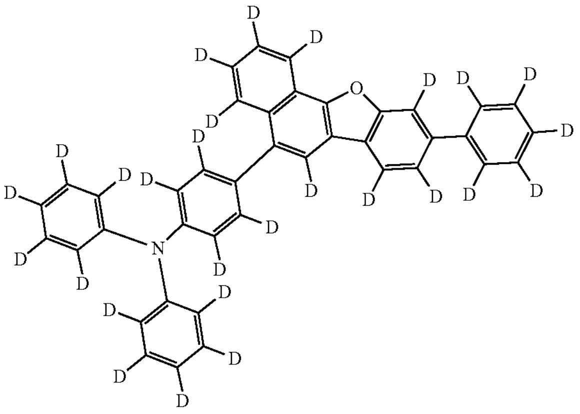
1-840
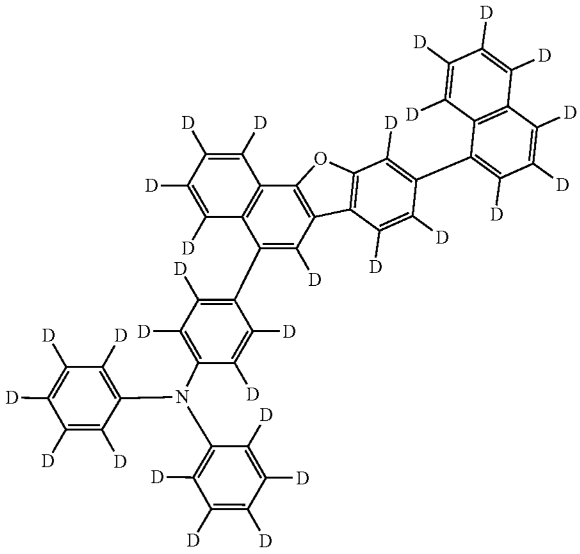
1-841
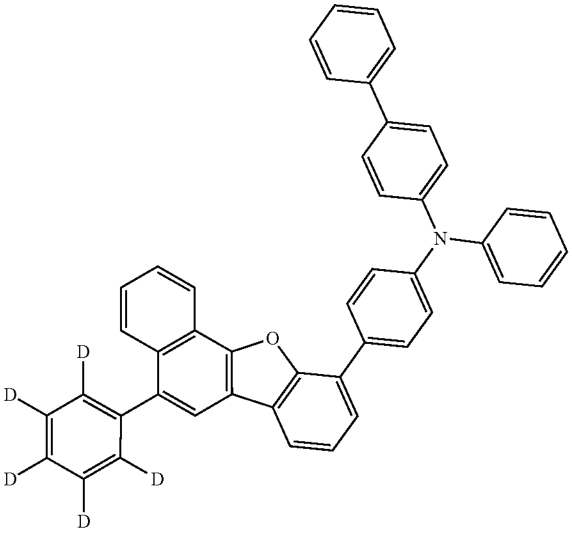
1-842
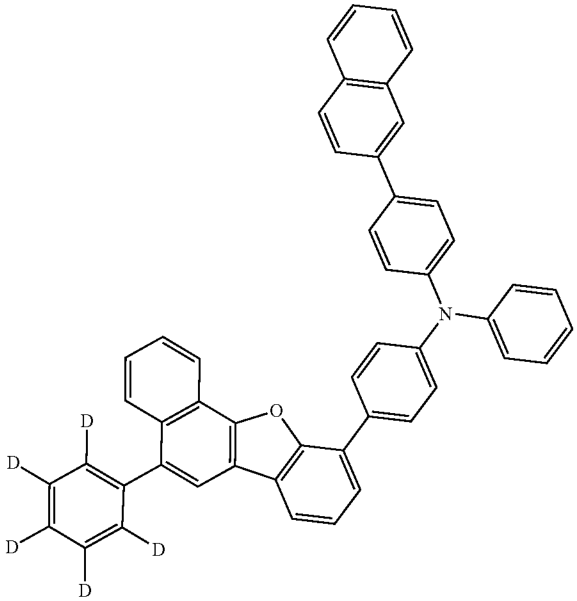

-continued
1-843
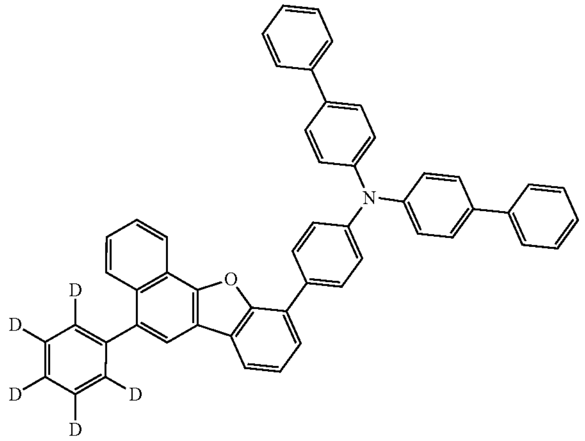
1-844
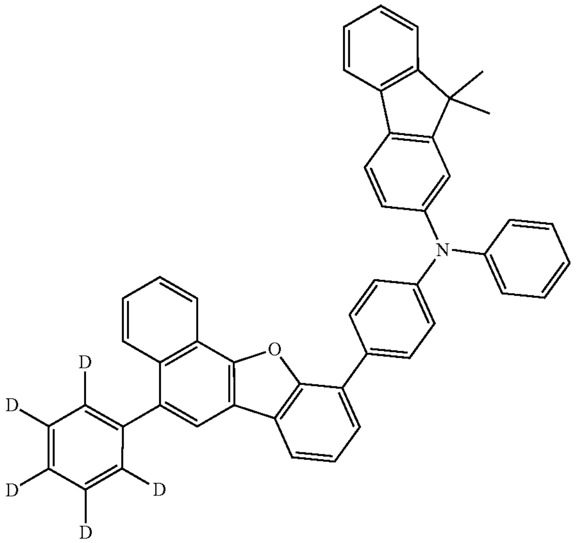
1-845
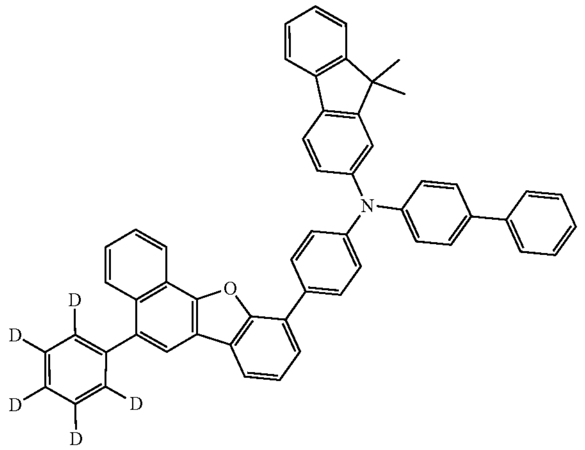
1-846
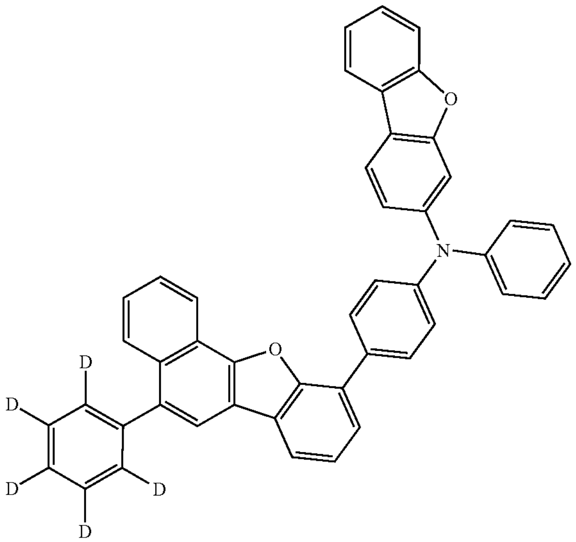

-continued
1-847
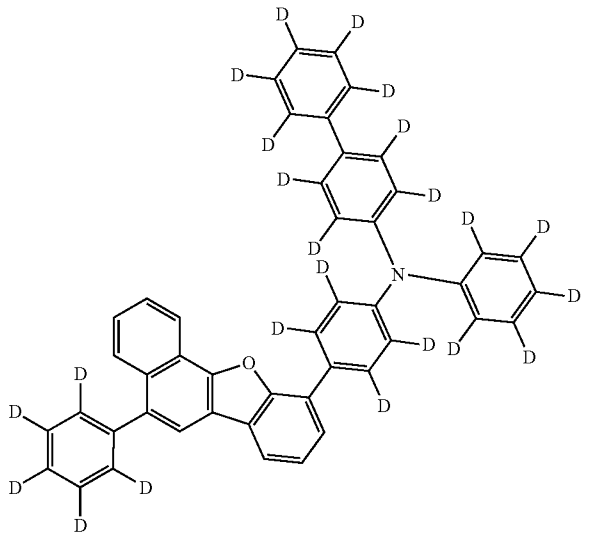
1-848
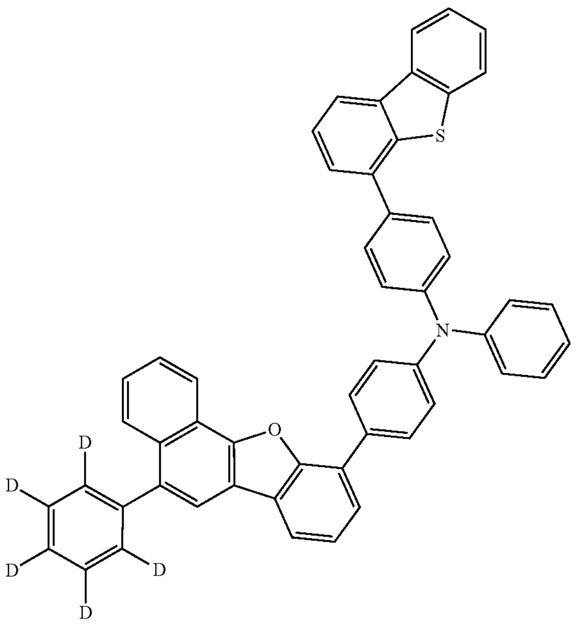
1-849
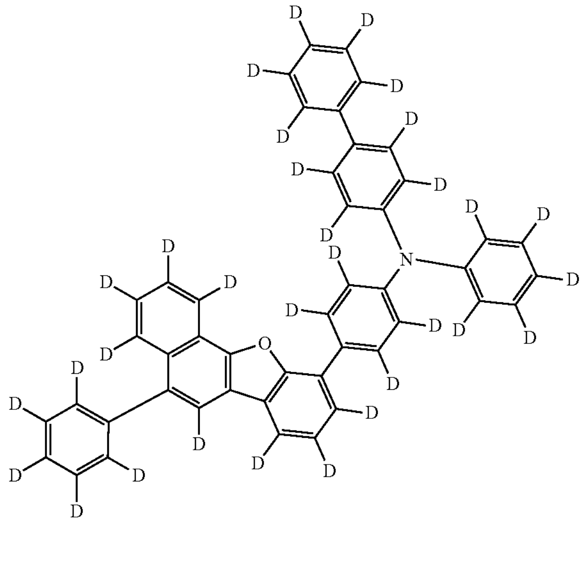
1-850
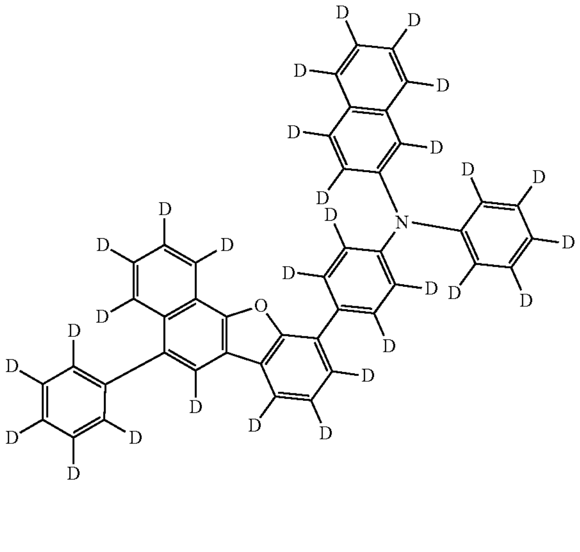

-continued
1-851
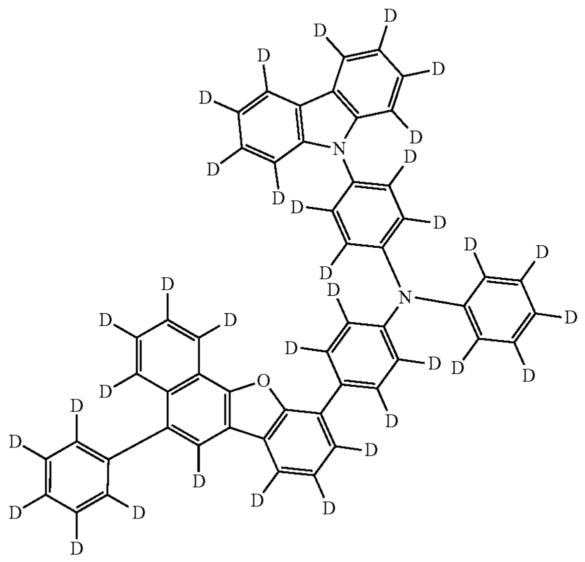
1-852
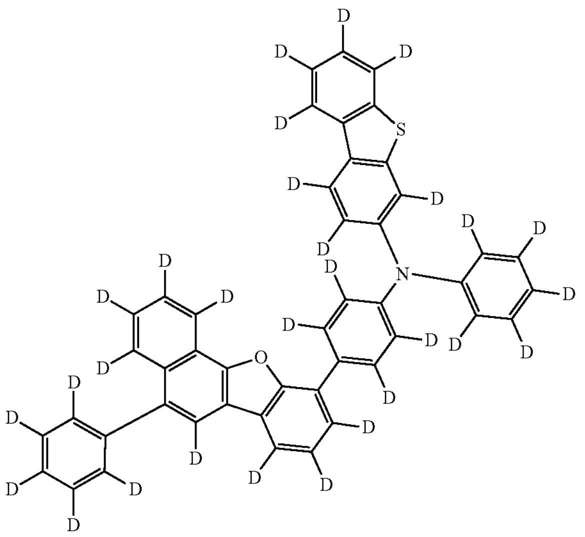
1-853
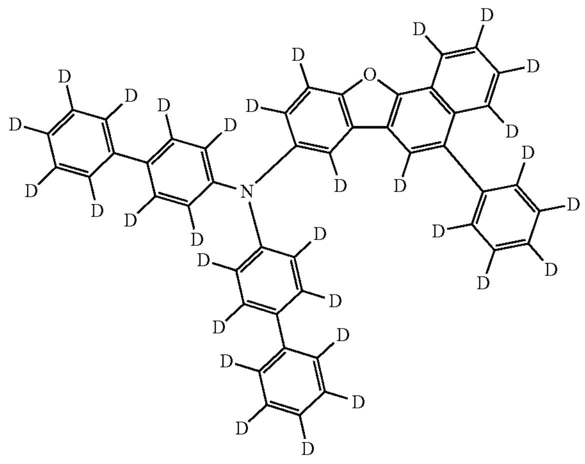
1-854
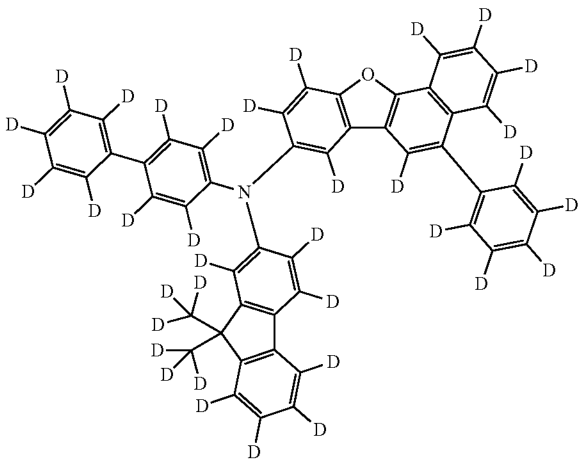

-continued
1-855
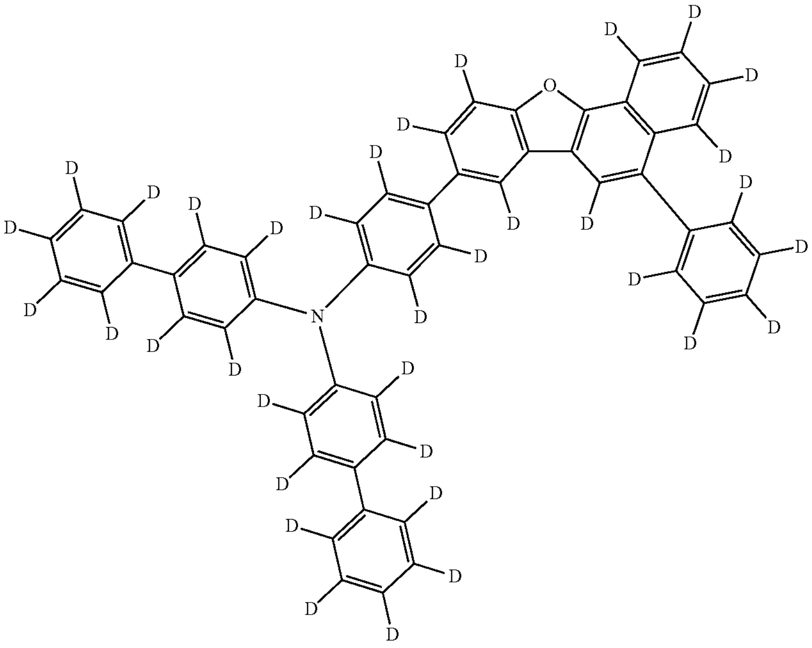
1-856
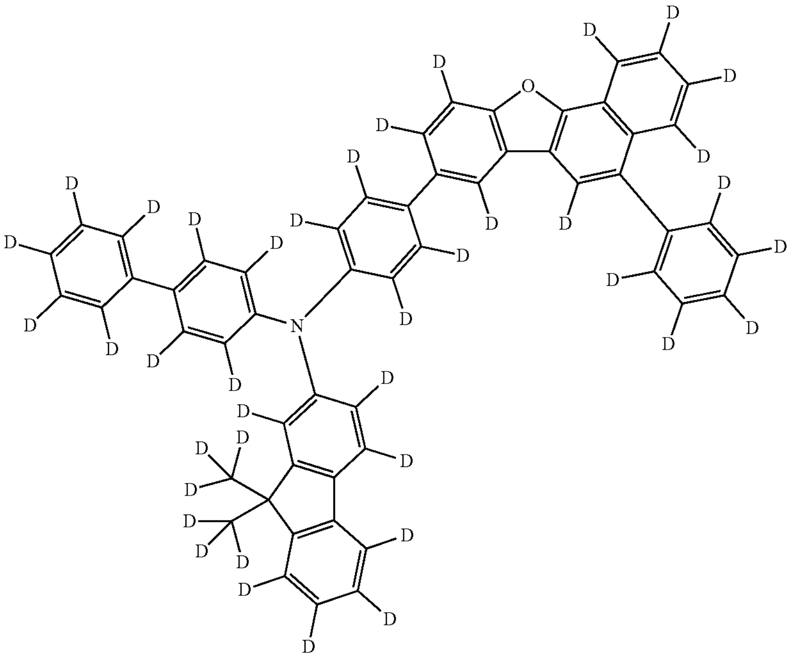

-continued
1-857
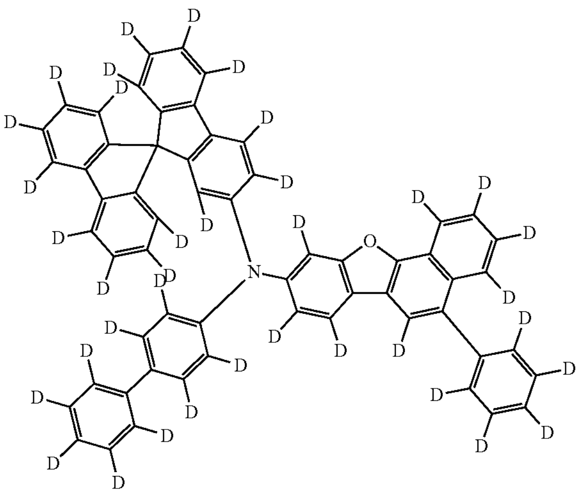
1-858
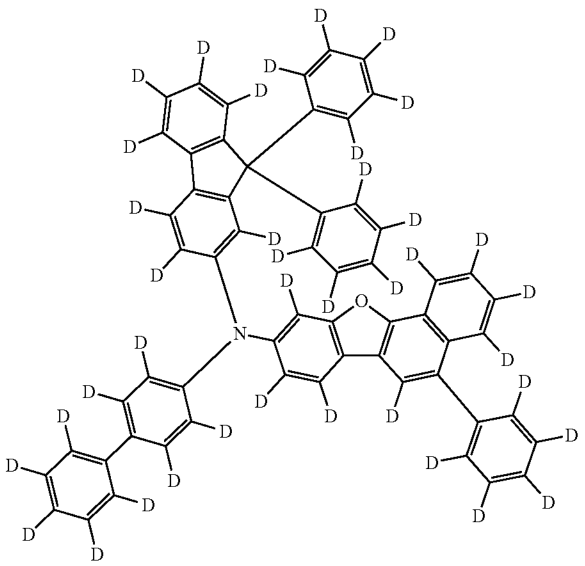
1-859
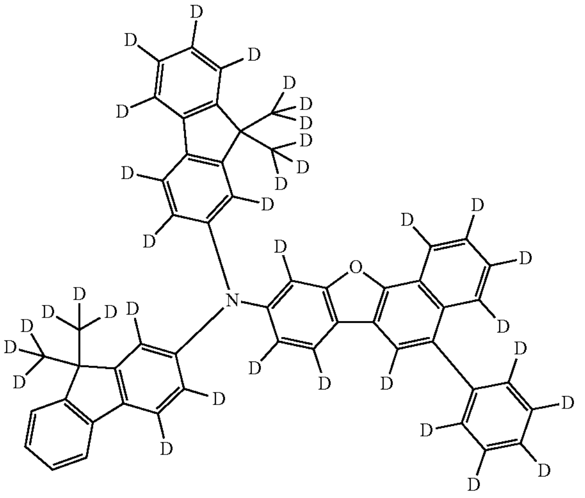
1-860
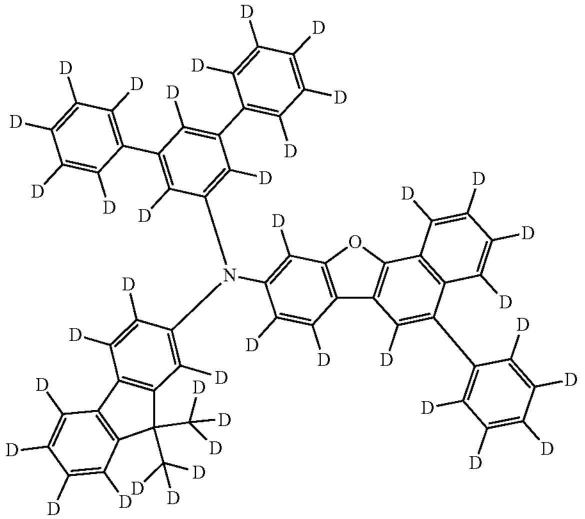
1-861
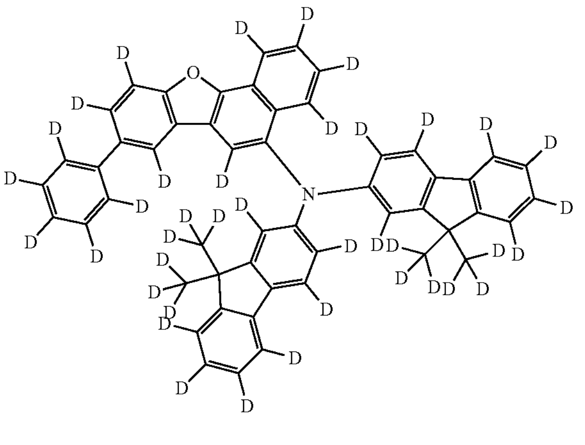
1-862
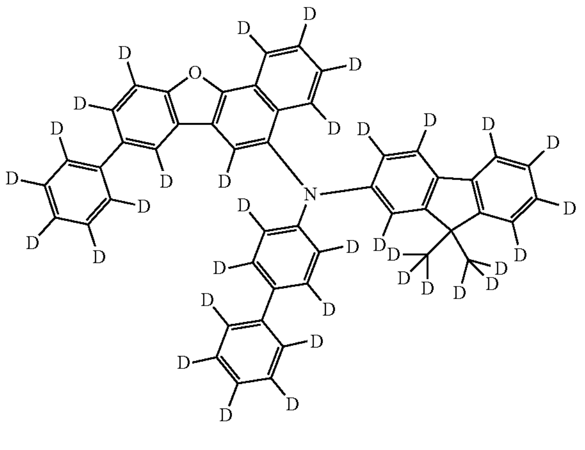

-continued
1-863
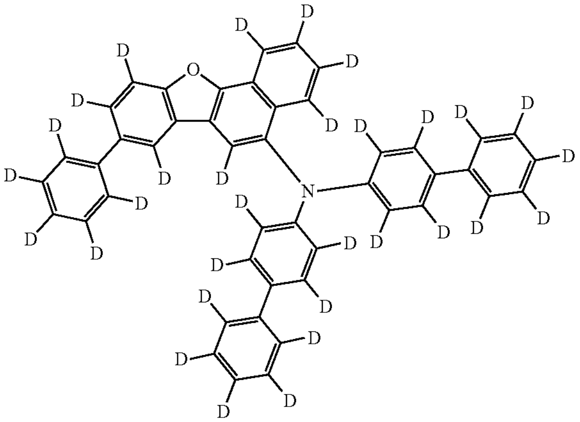
1-864
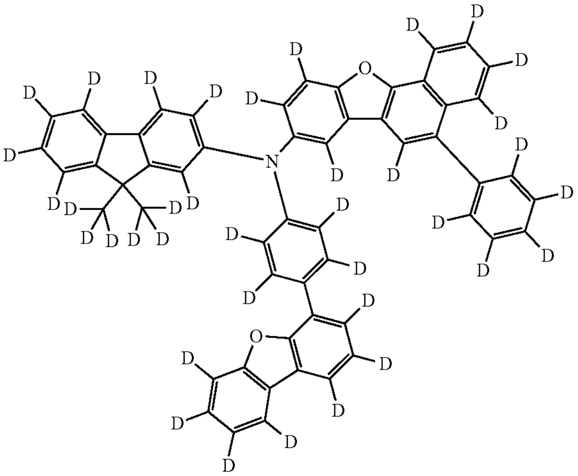
1-865
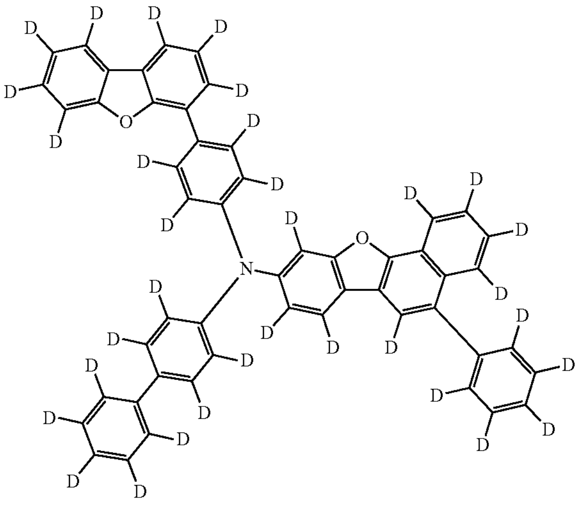
1-866
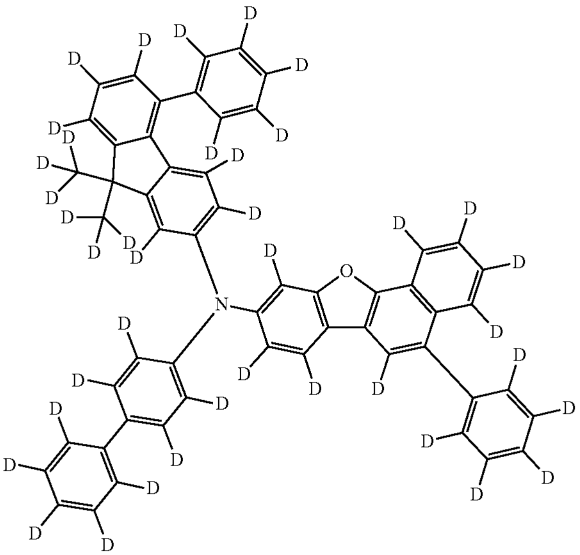

-continued
1-867
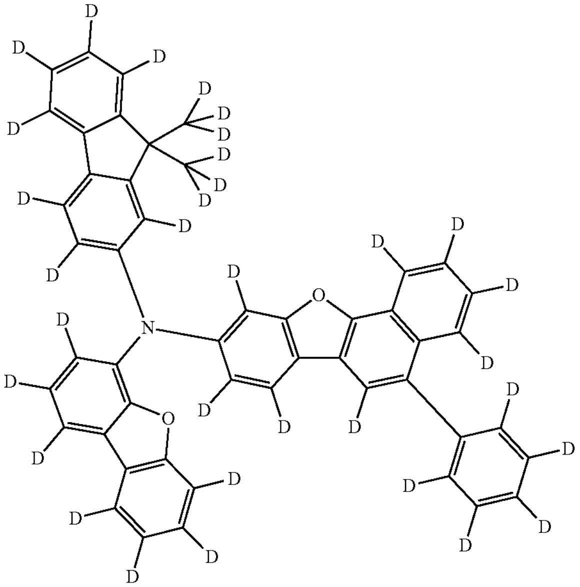
1-868
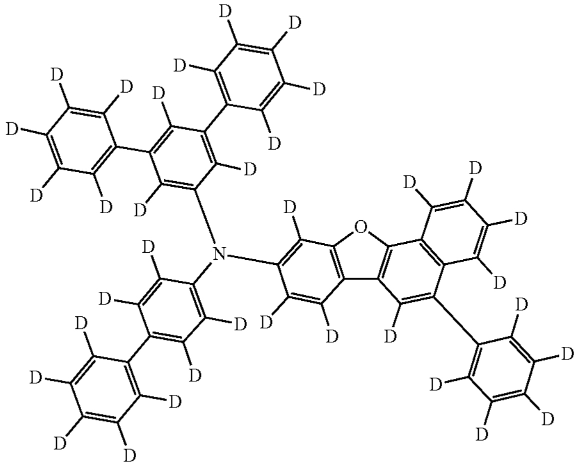
1-869
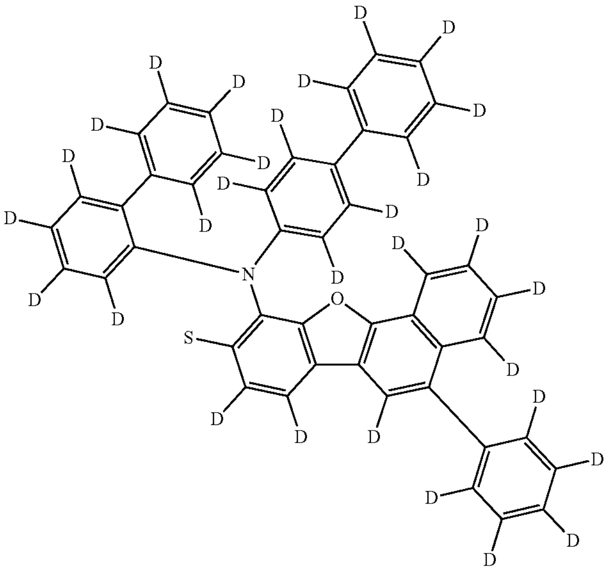

-continued
1-870
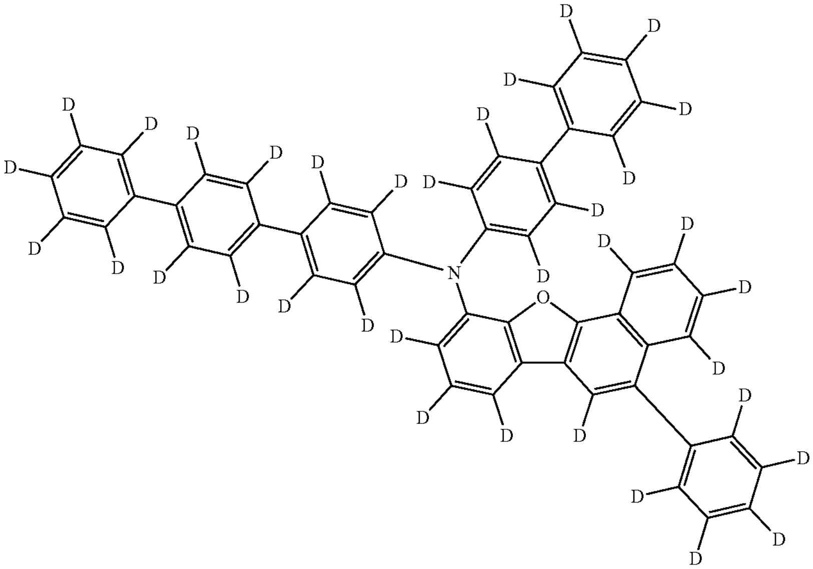
1-871
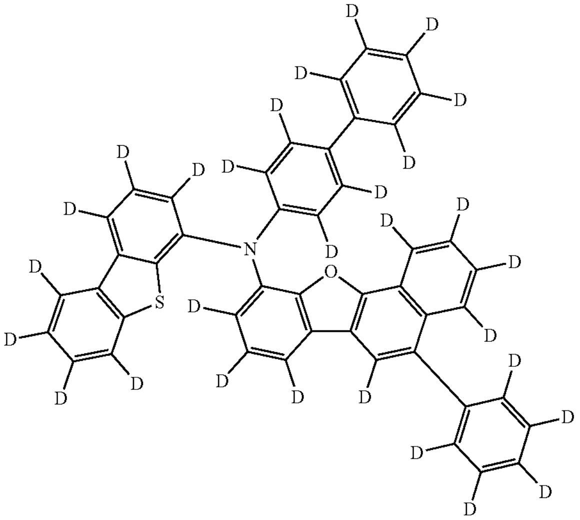
1-872
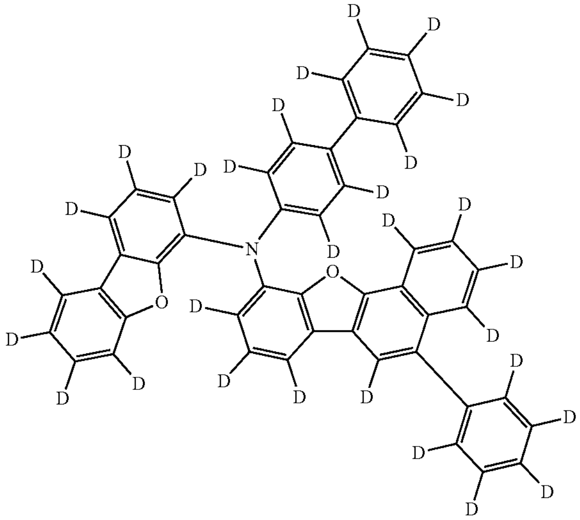
1-873
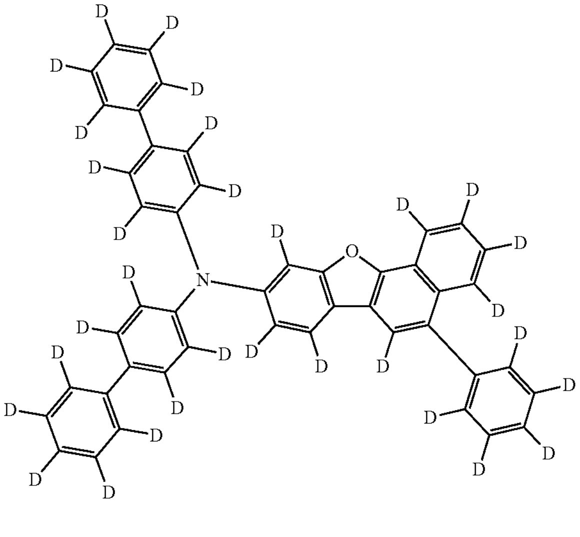
1-874
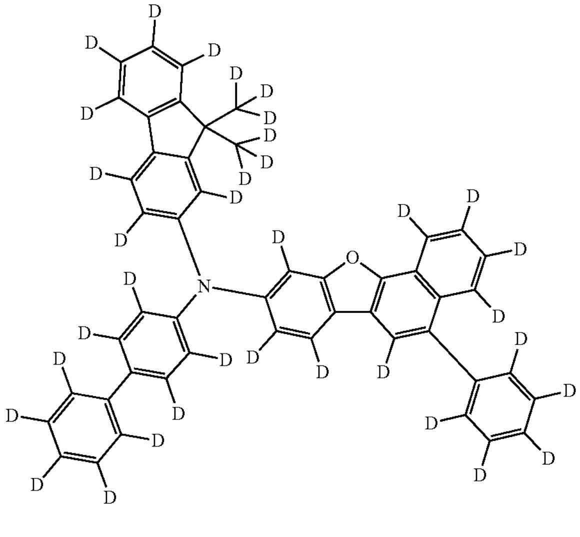

-continued
1-875
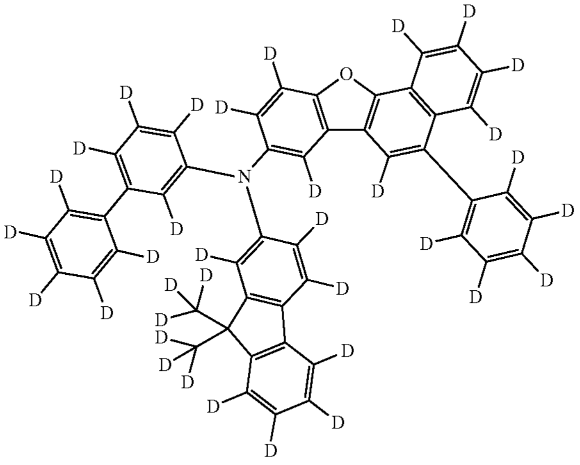
1-876
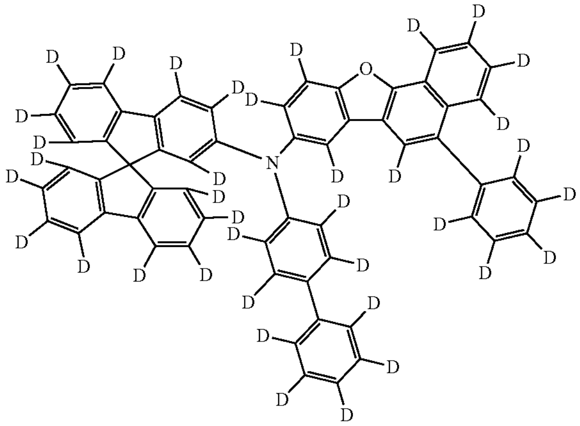
1-877
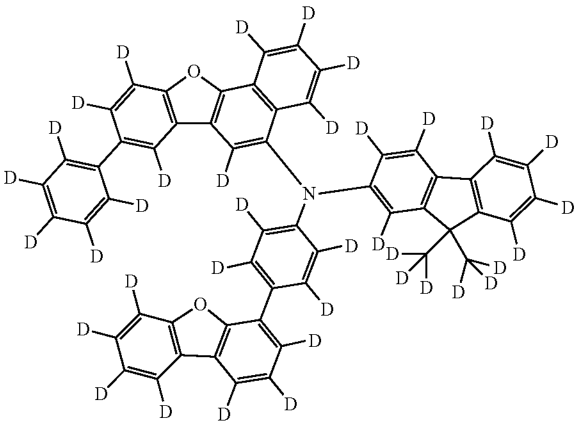
1-878
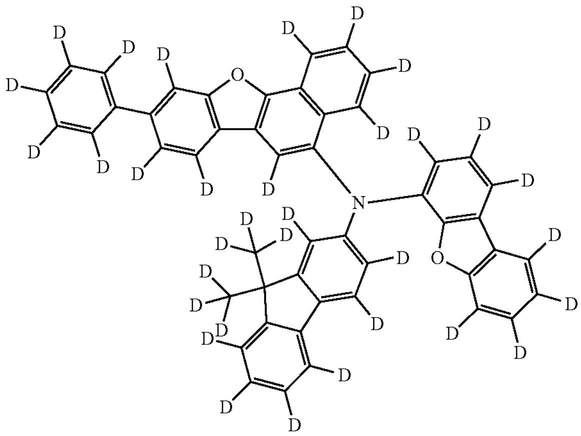
1-879
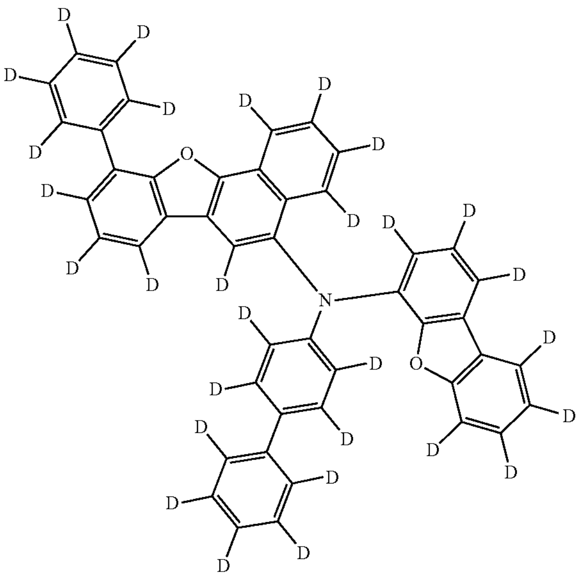
1-880
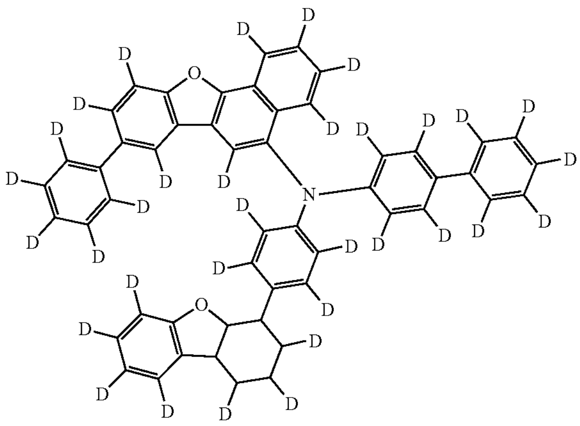

-continued
1-881
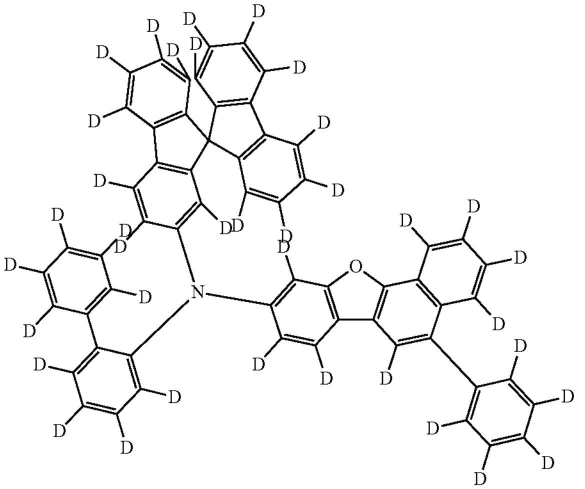
1-882
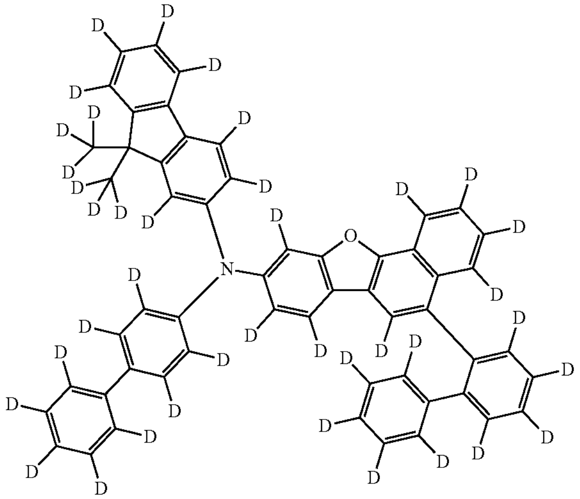
1-883
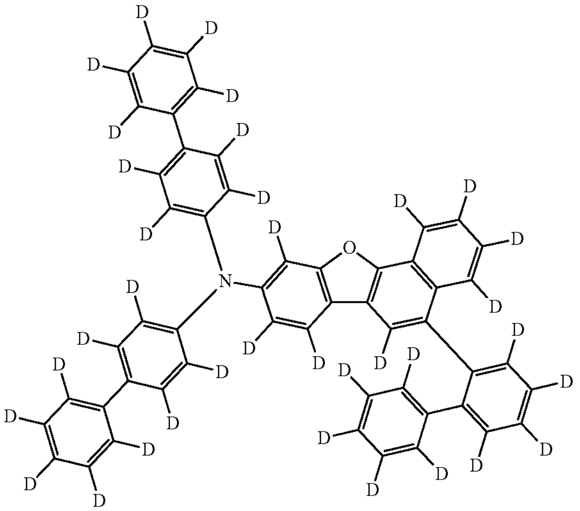
1-884
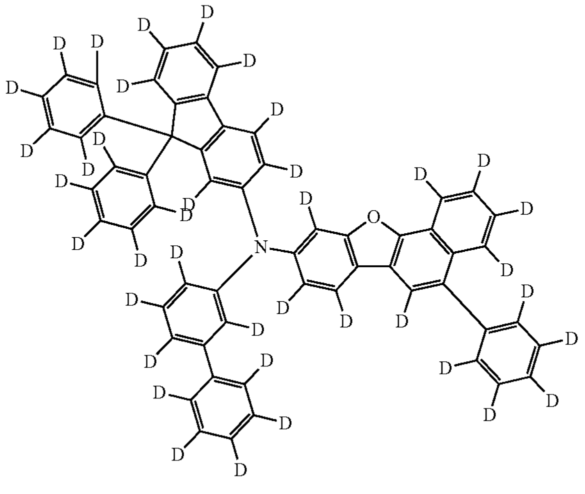
1-885
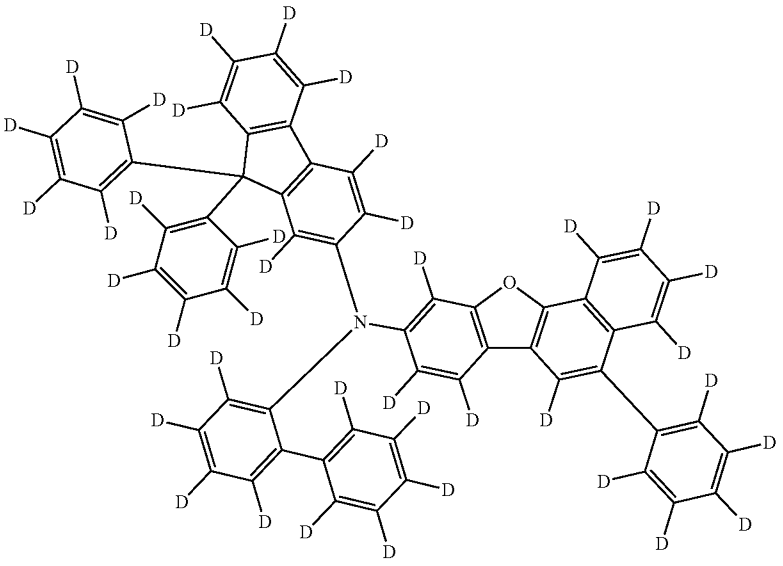

-continued
1-886
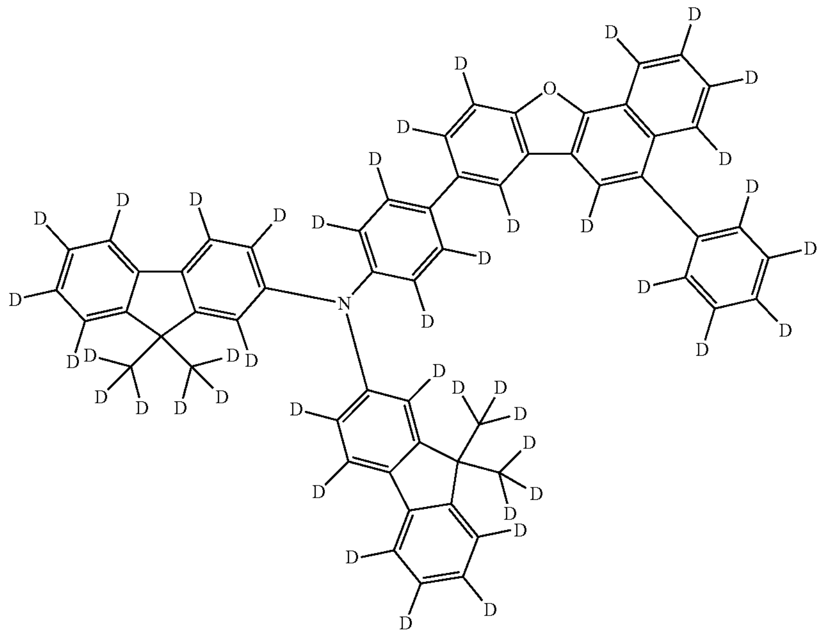
1-887
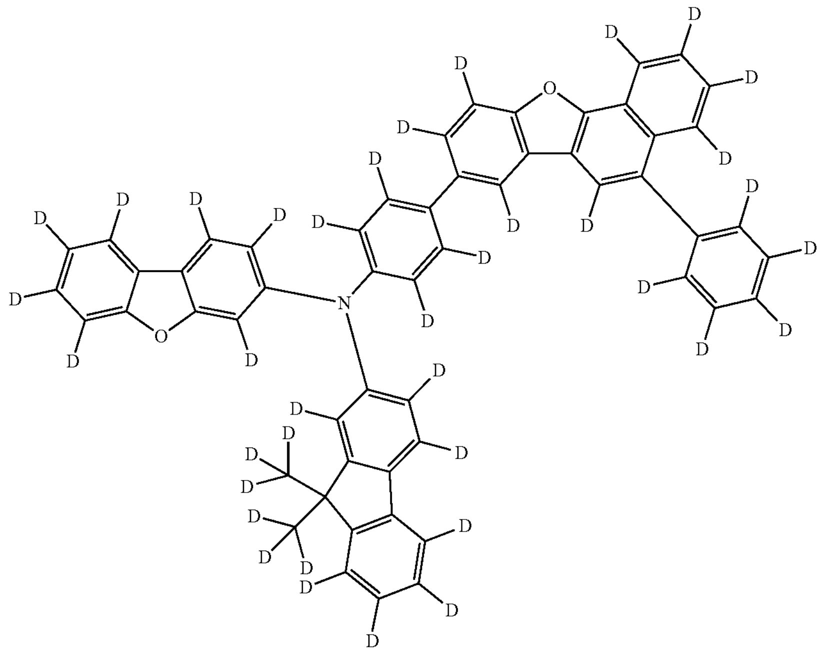

-continued
1-888
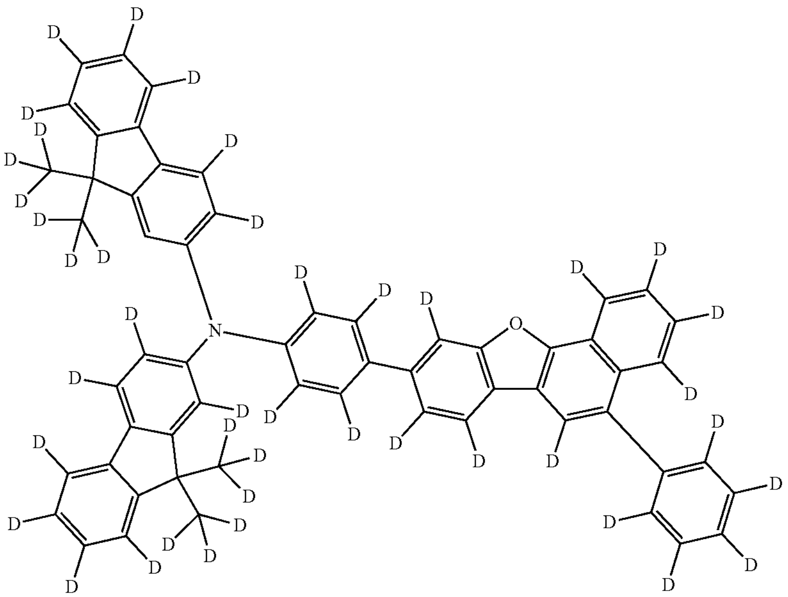
1-889
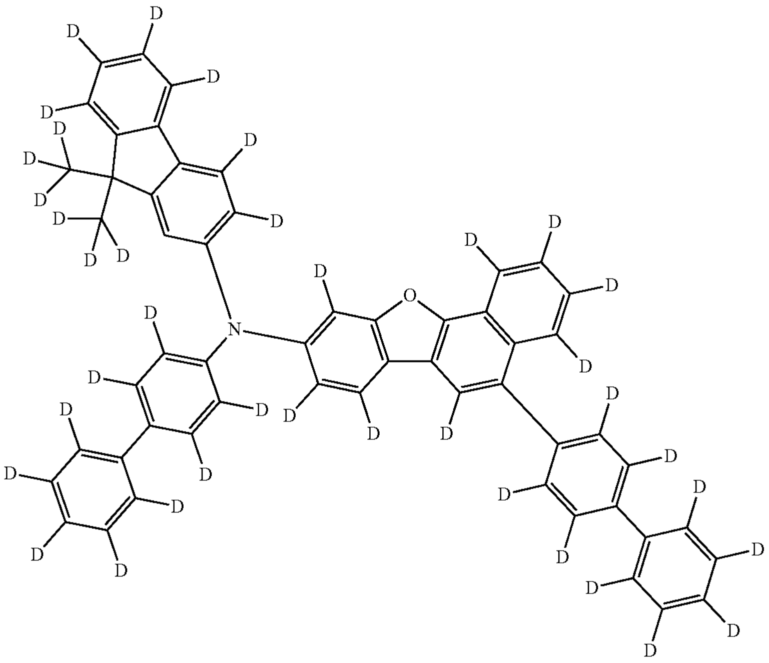

-continued
1-890
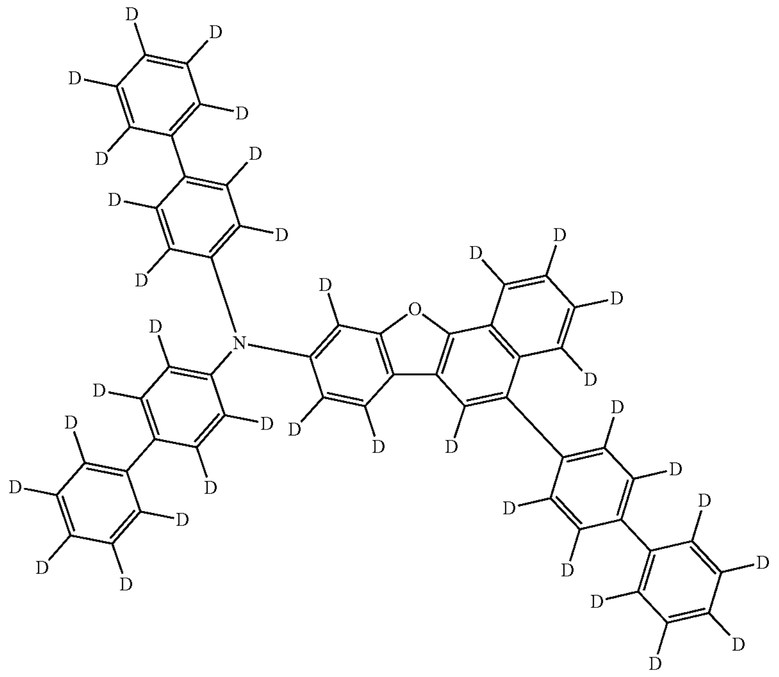
1-891
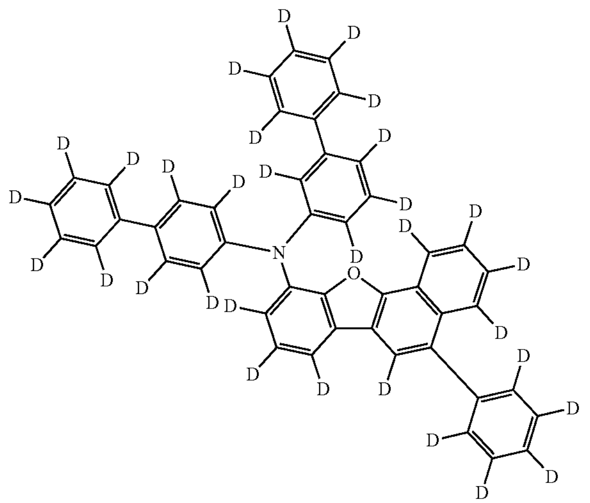
1-892
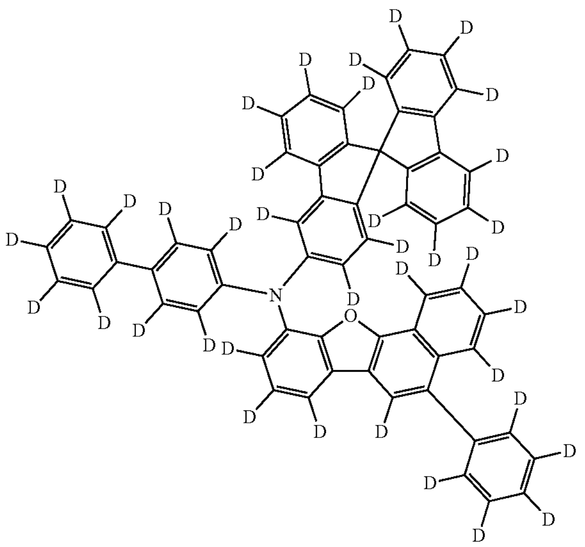

1-893
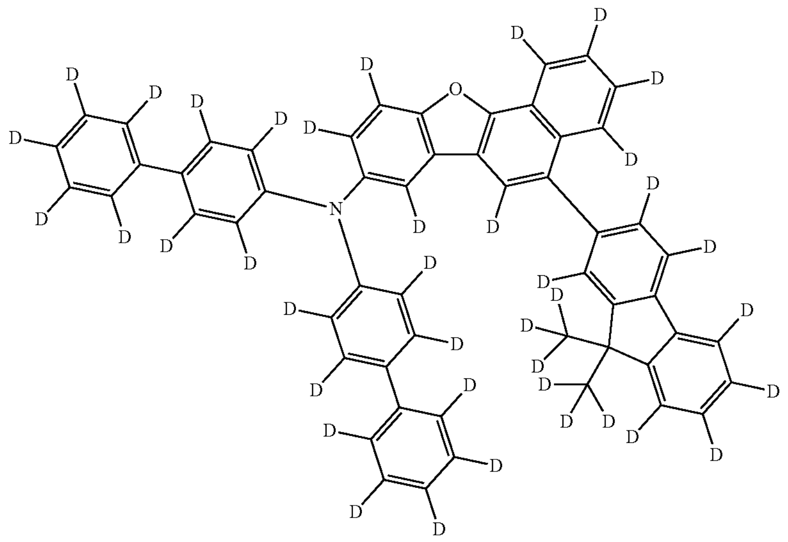
1-894
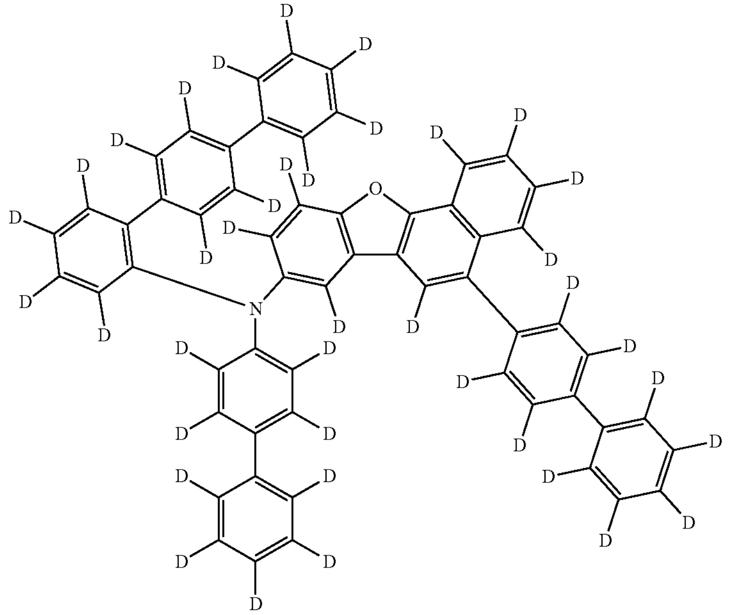

-continued
1-895
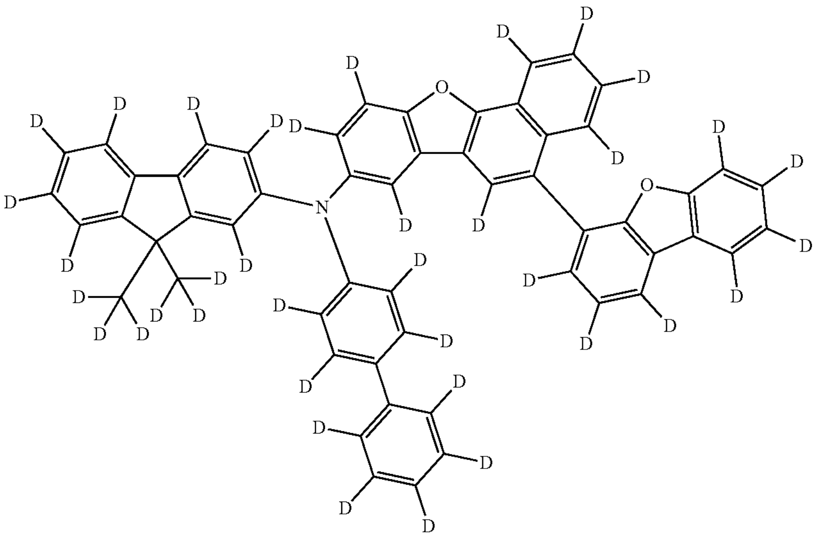
1-896
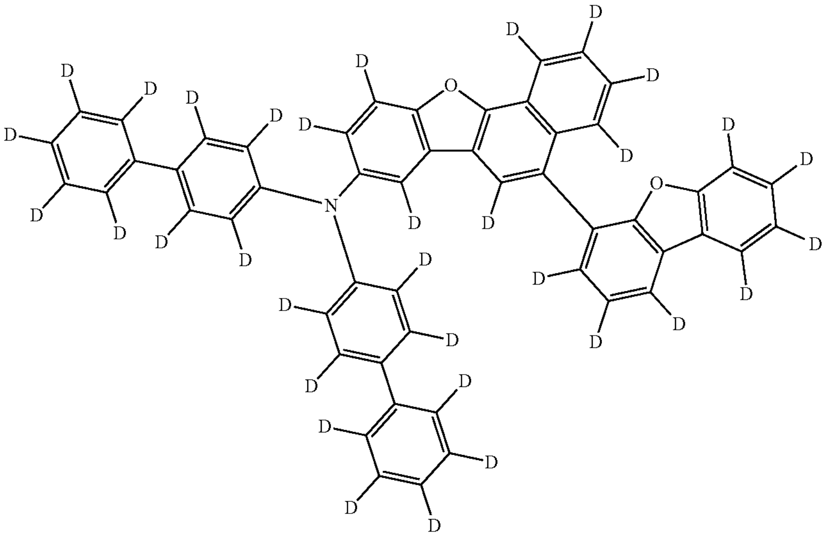
1-897
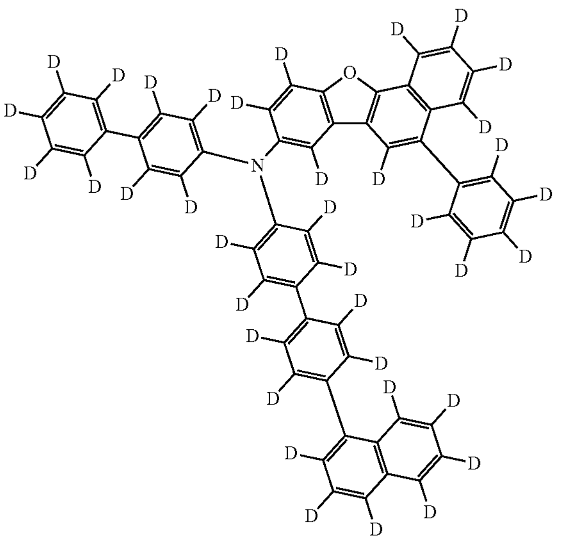
1-898
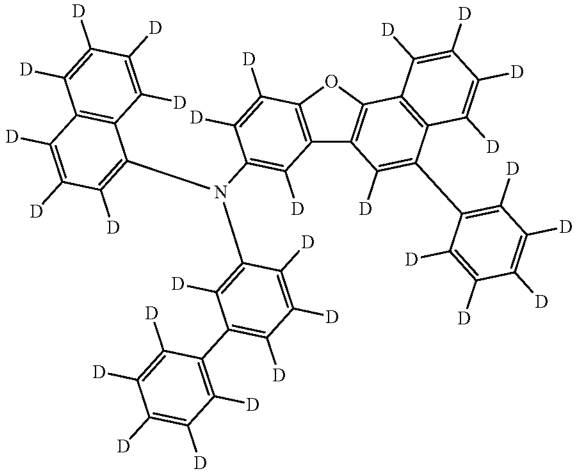

-continued
1-899
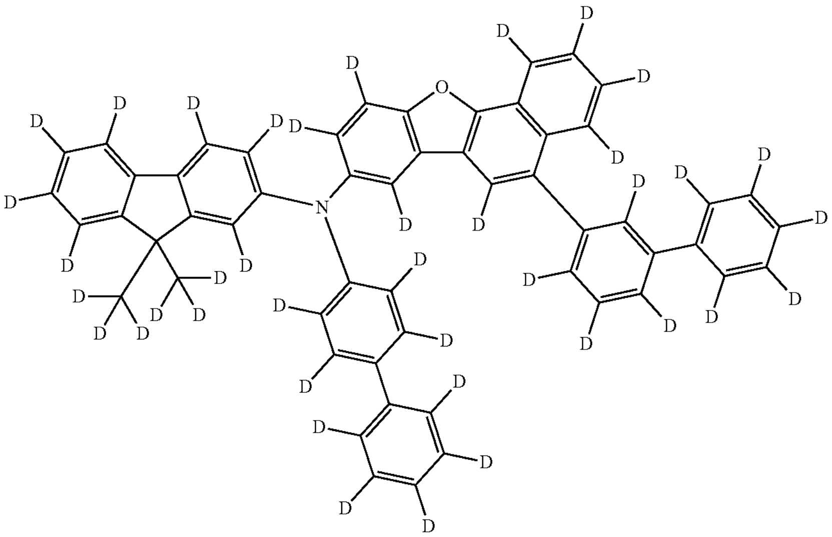
1-900
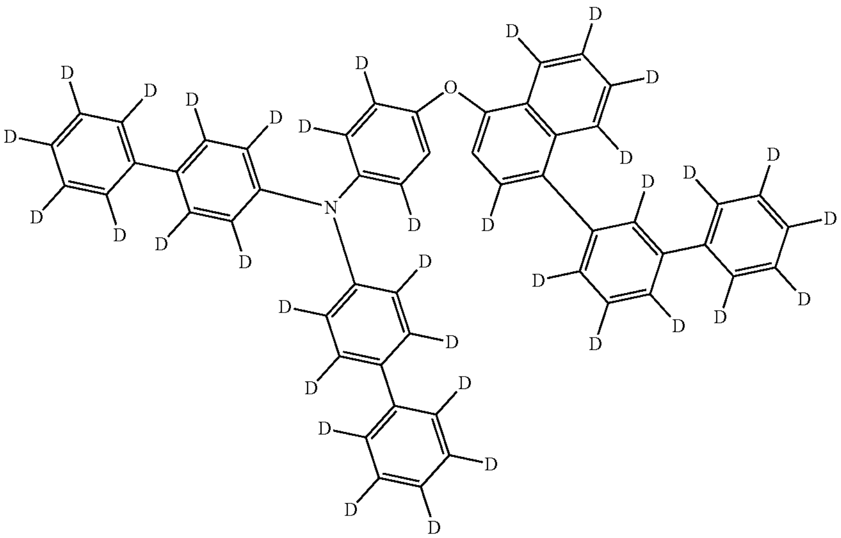
1-901
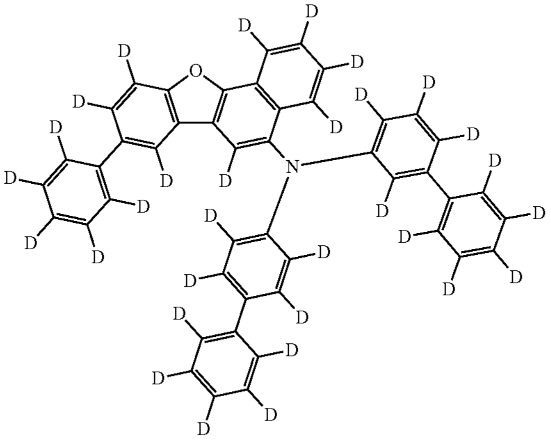
1-902
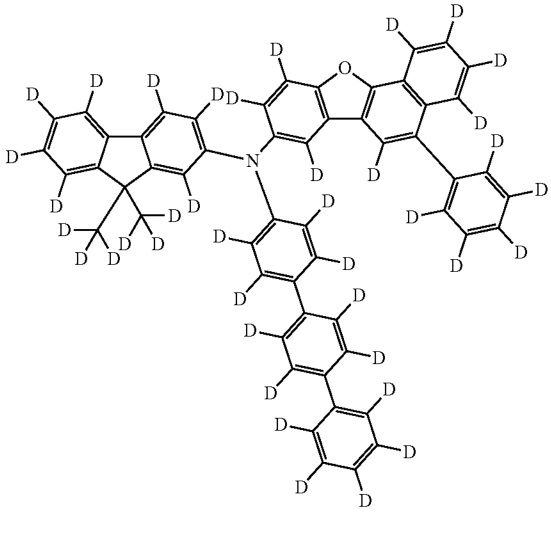

-continued
1-903
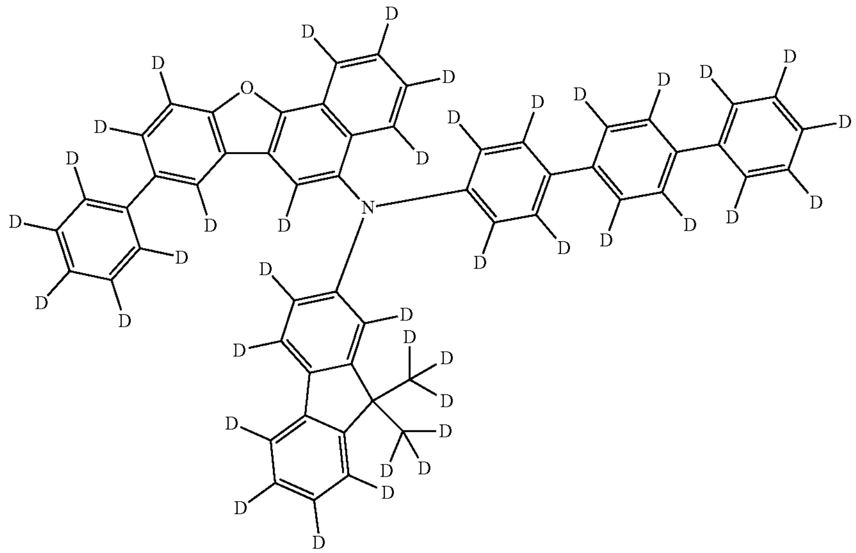
1-904
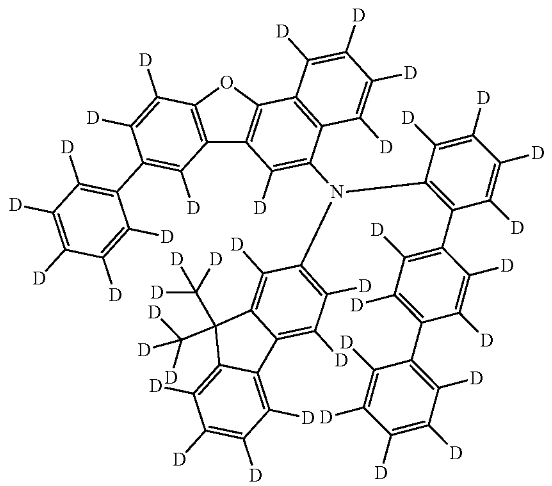
1-905
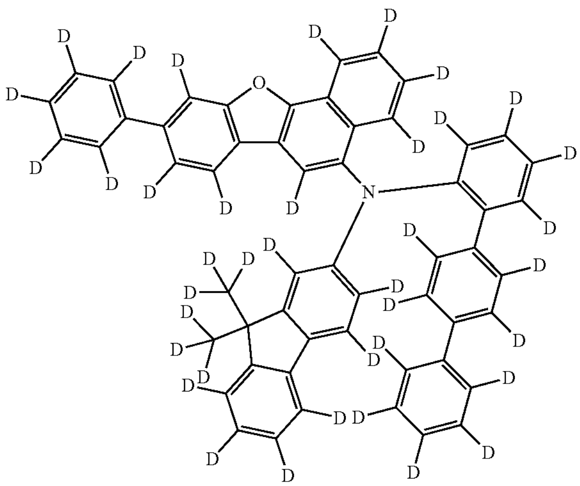
1-906
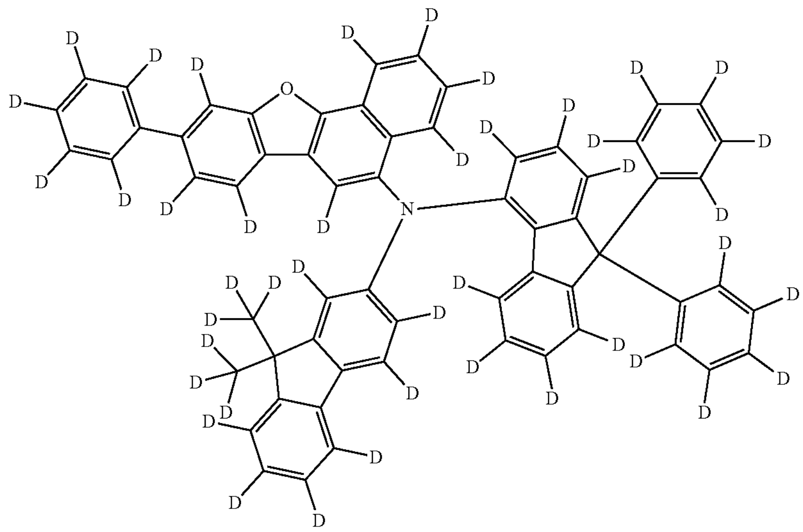

-continued
1-907
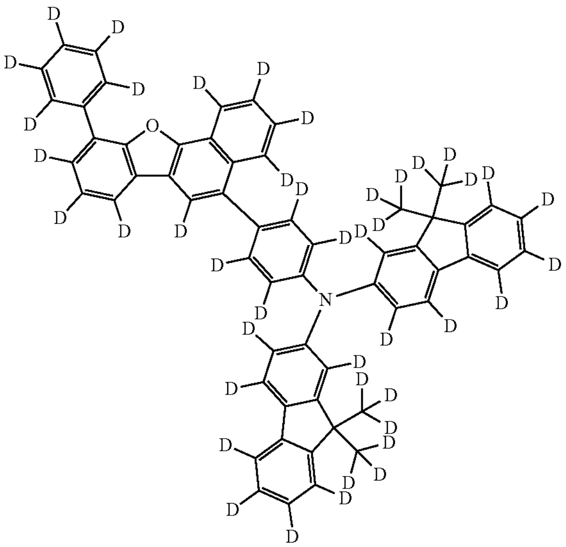
1-908
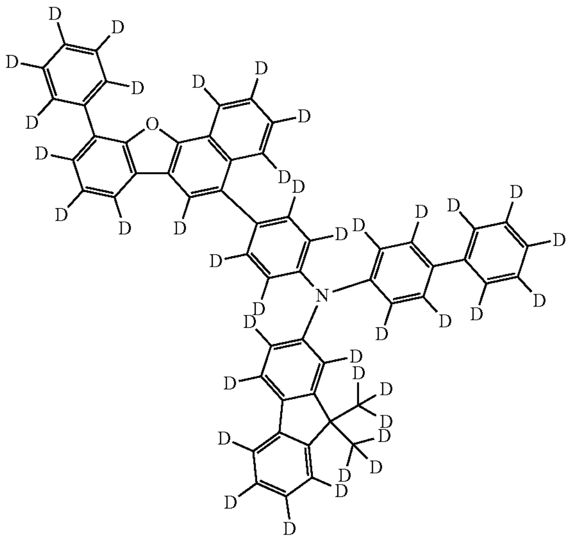
1-909
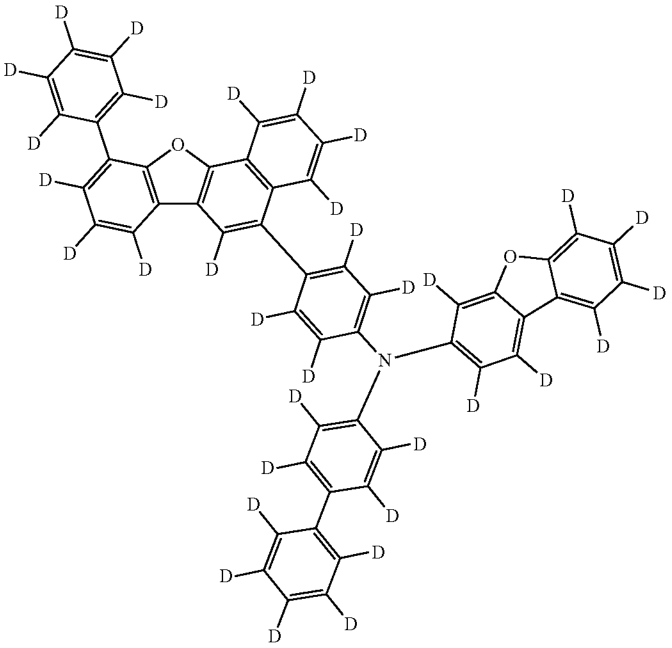

-continued
1-910
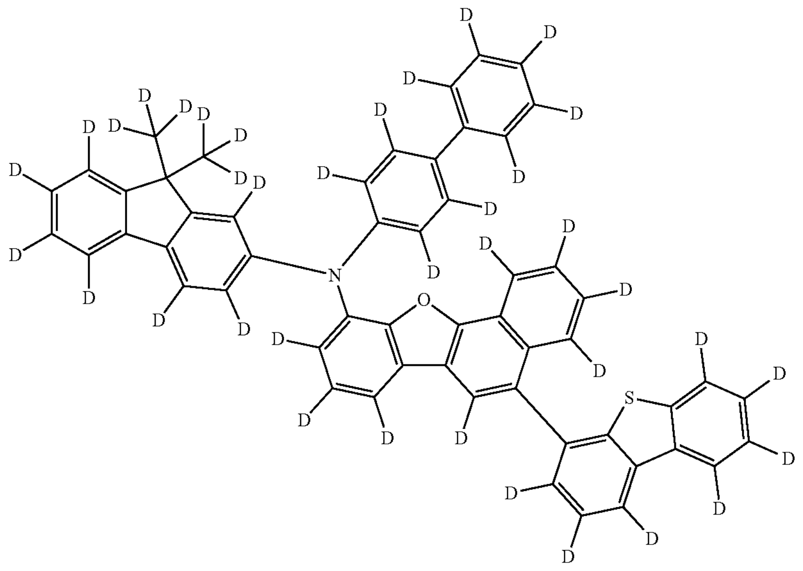
1-911
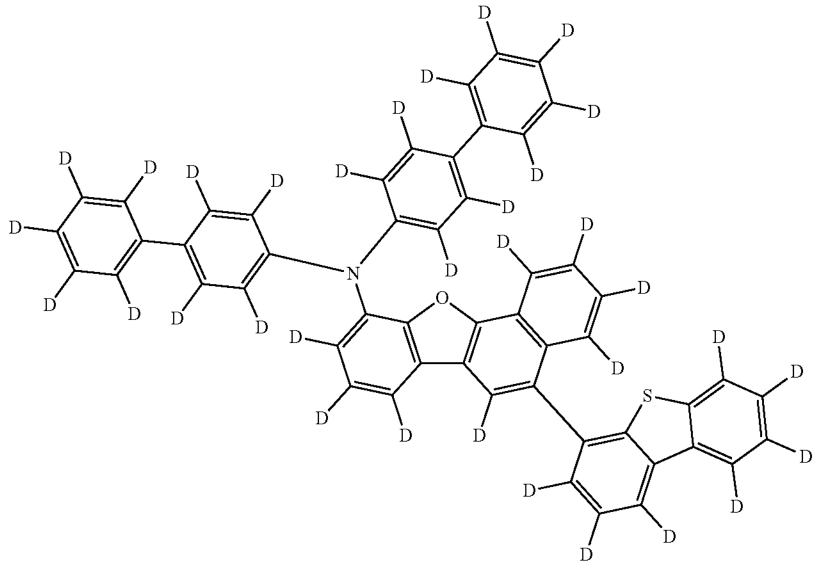

-continued
1-912
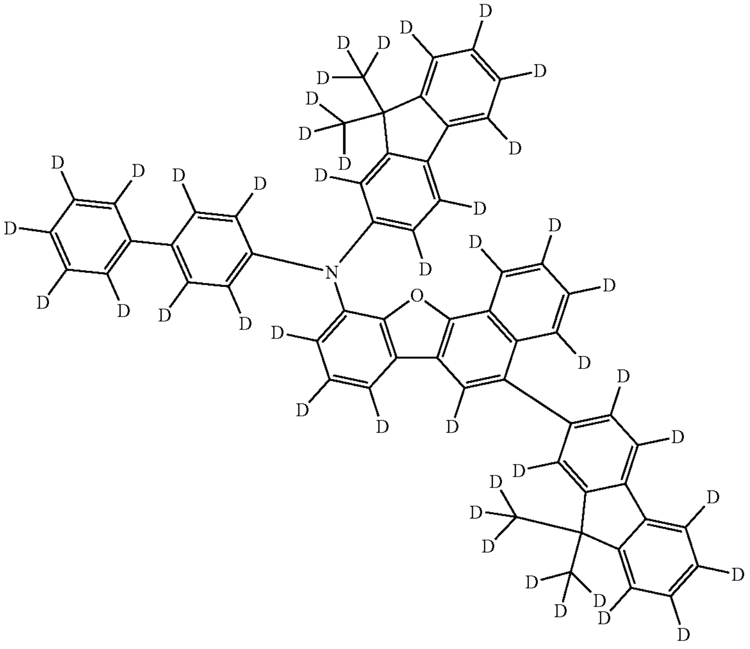
1-913
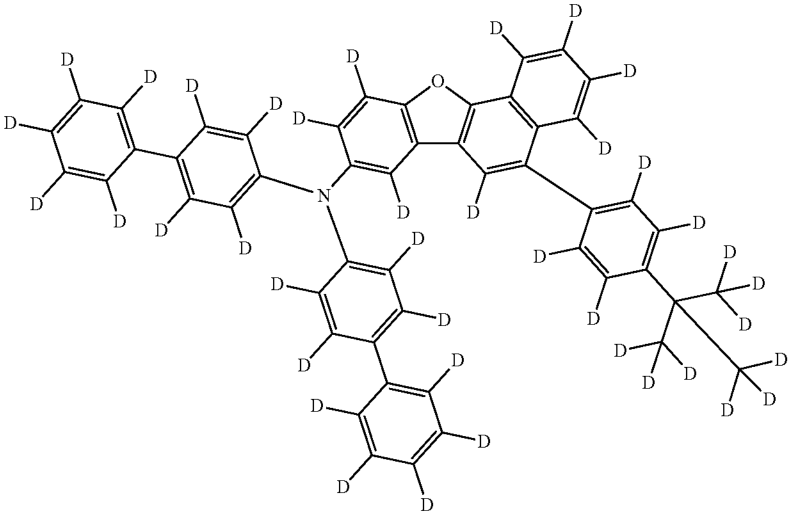

-continued
1-914
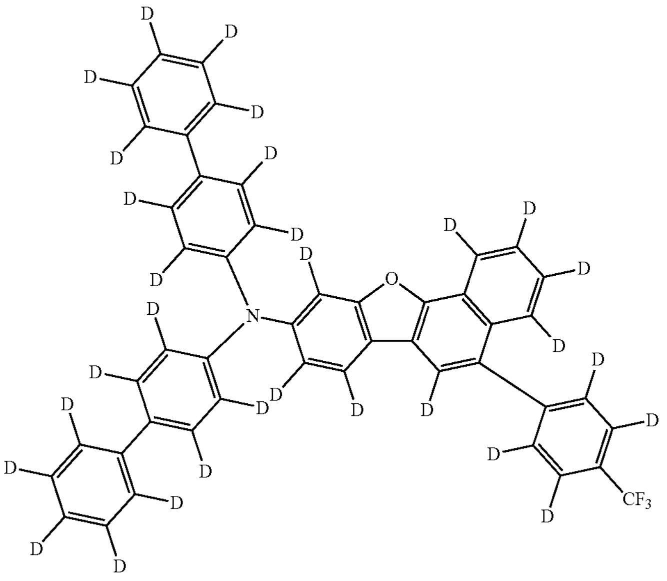
1-915
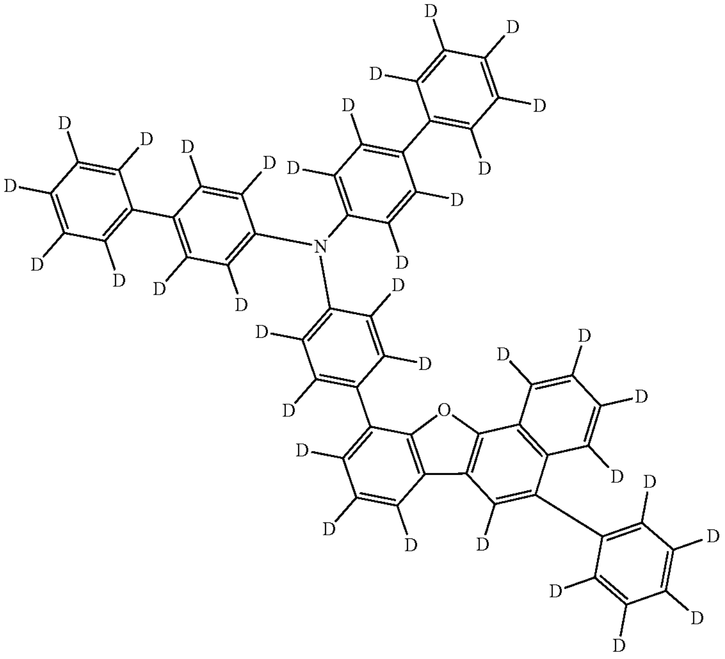

-continued
1-916
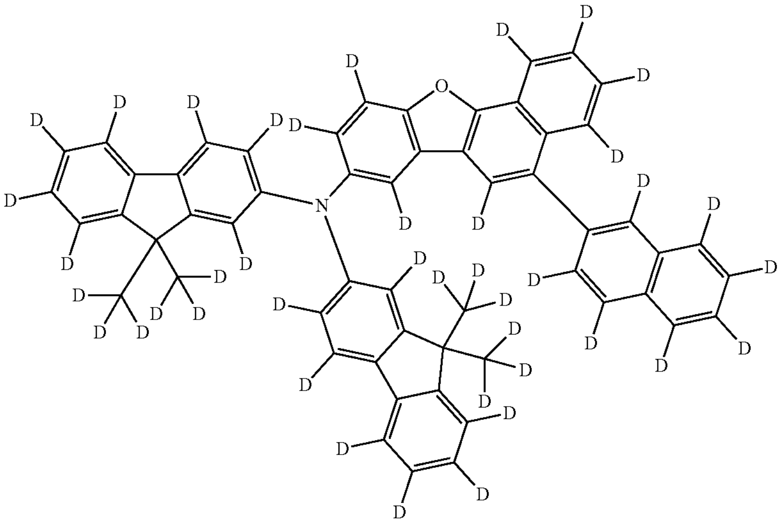
1-917
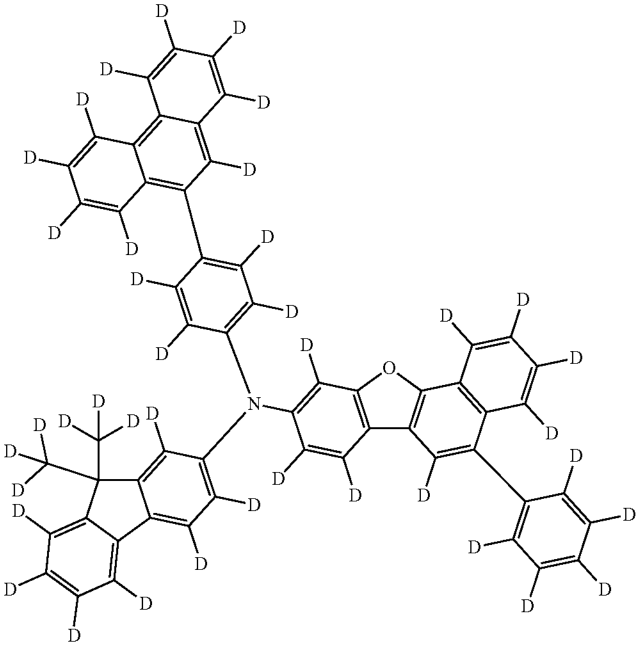

-continued
1-918
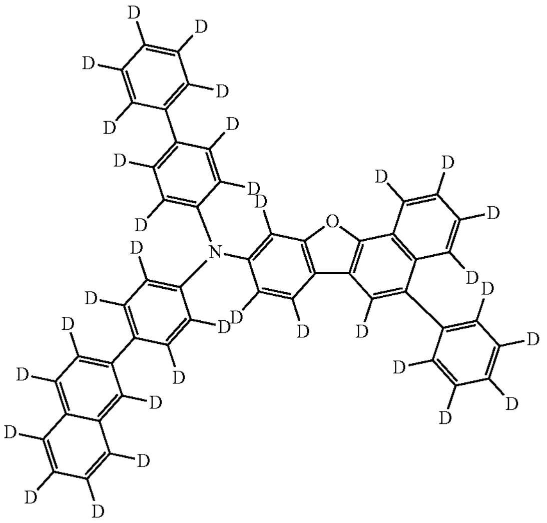
1-919
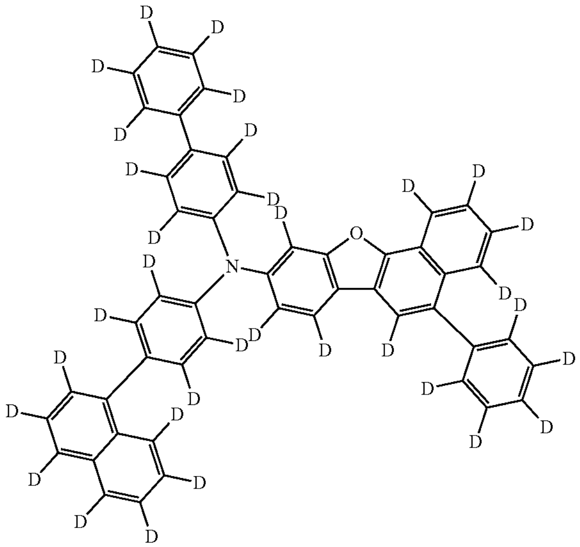
1-920
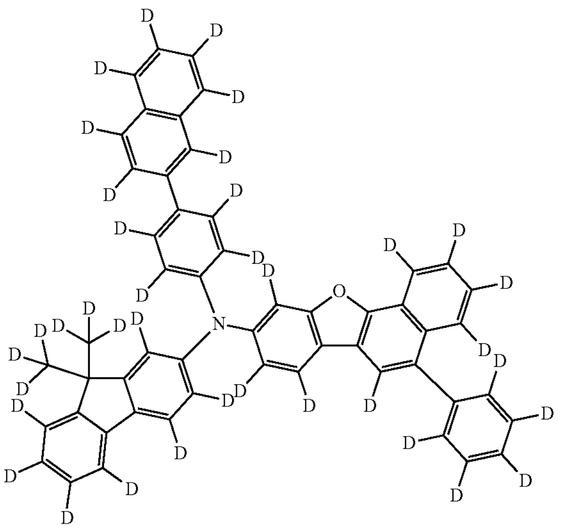
1-921
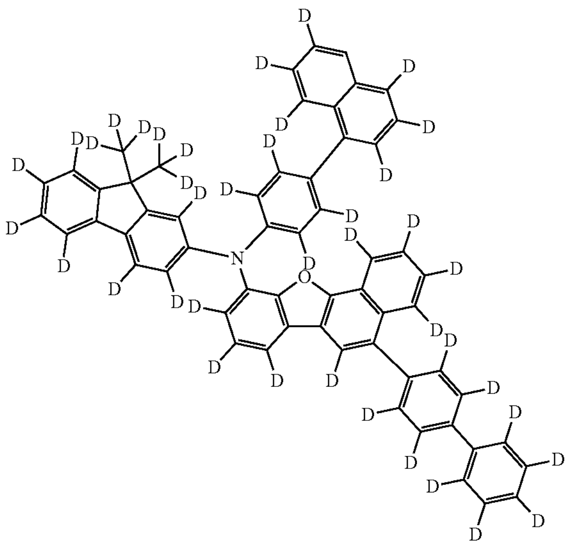
1-922
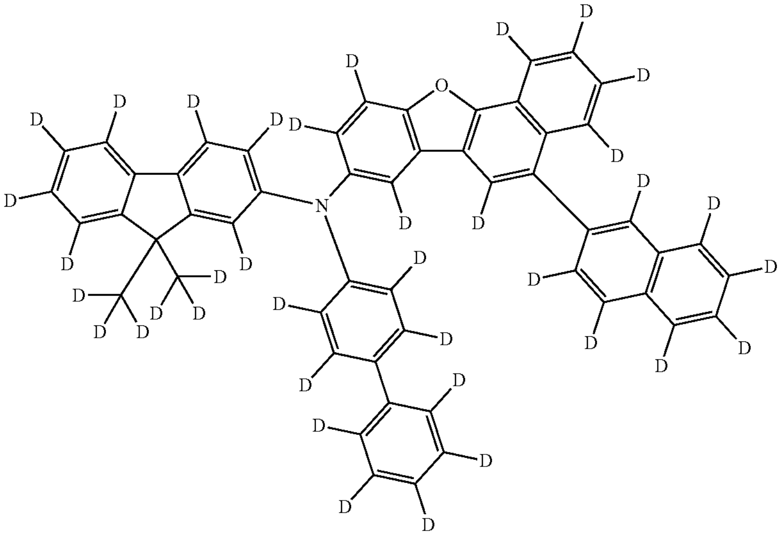

-continued
1-923
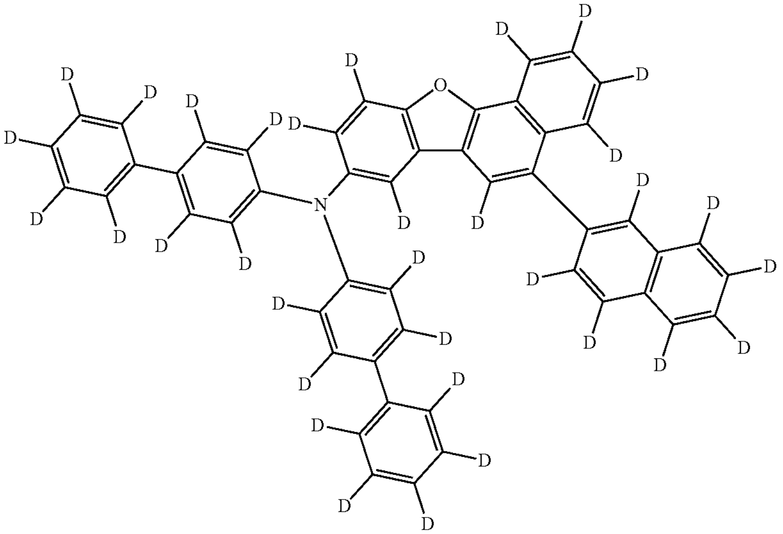
1-924
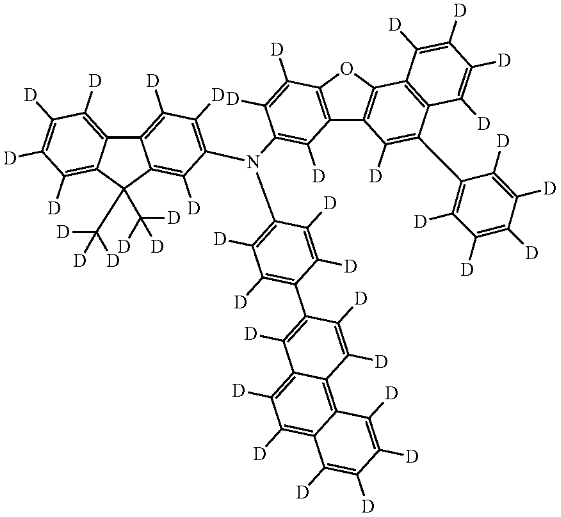
1-925
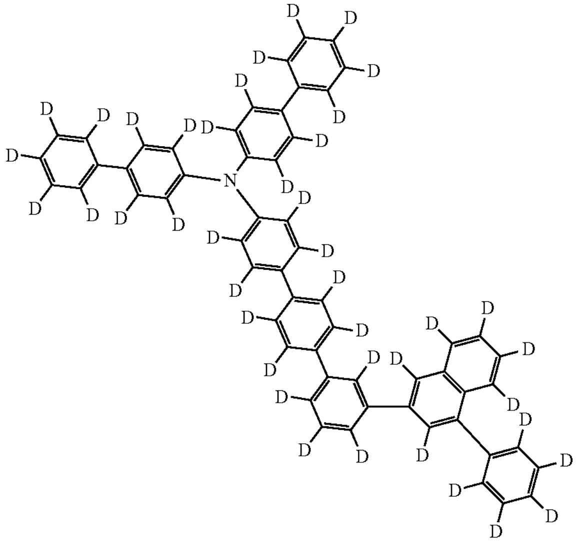
1-926
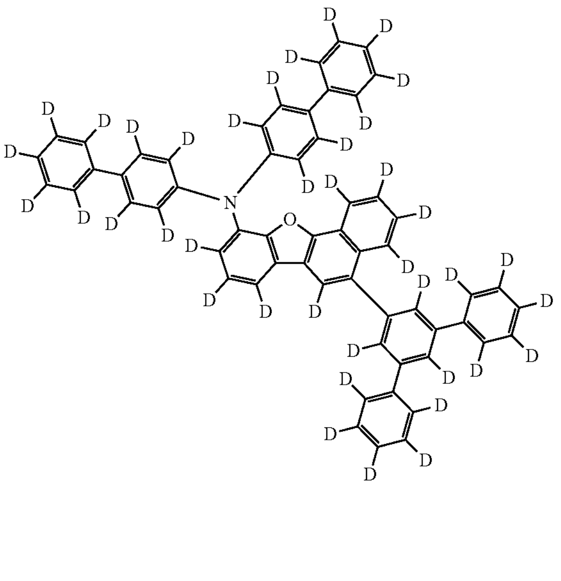

-continued
1-927
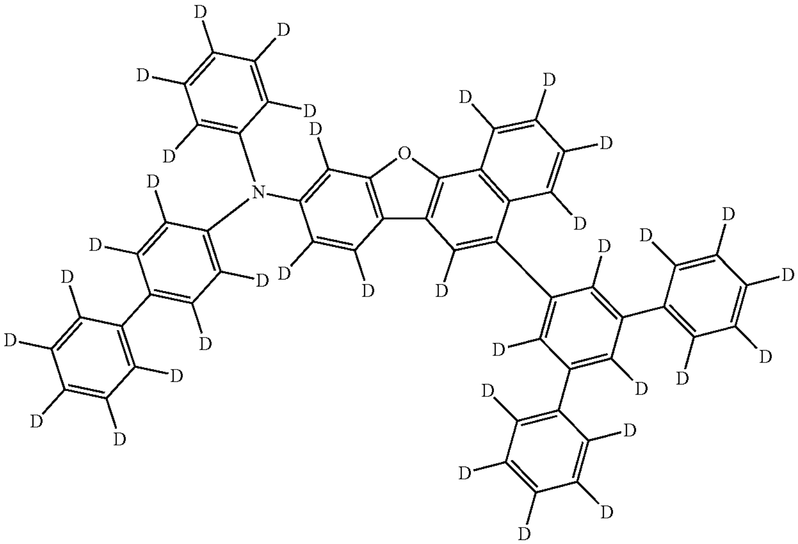
1-928
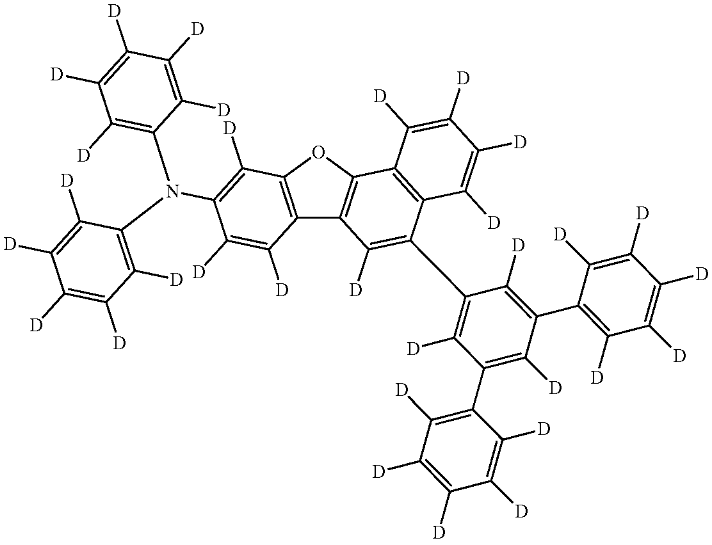
1-929
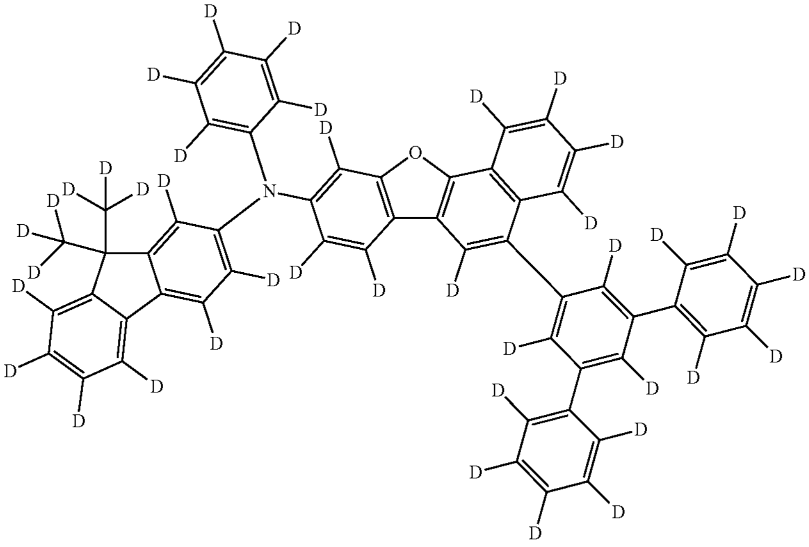

-continued
1-930
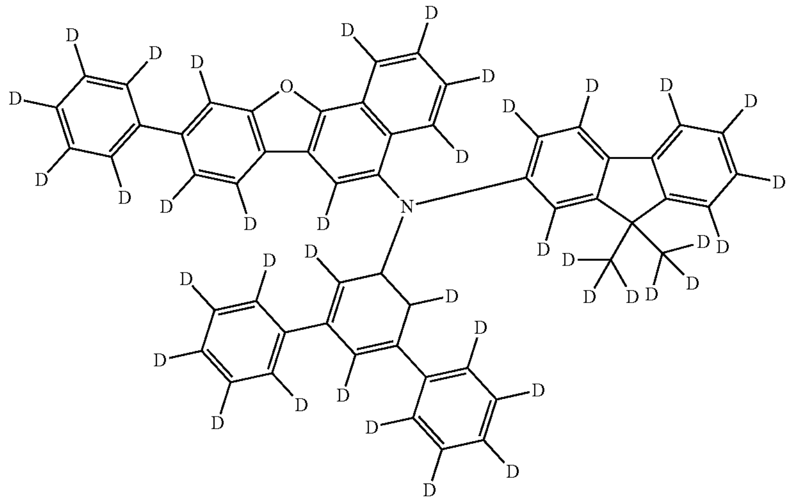
1-931
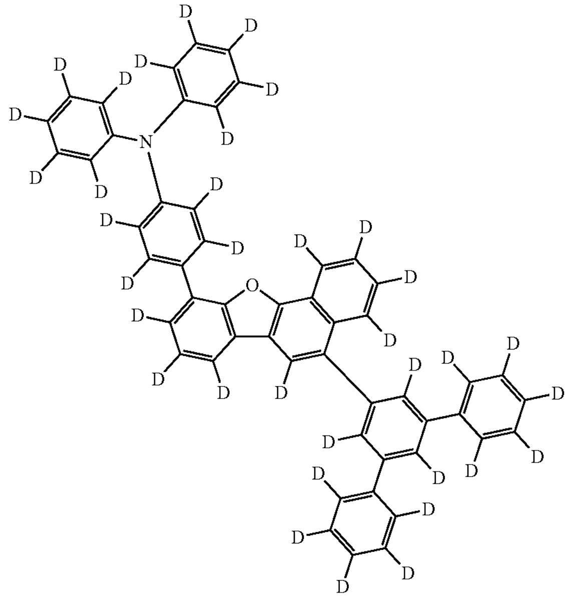
1-932
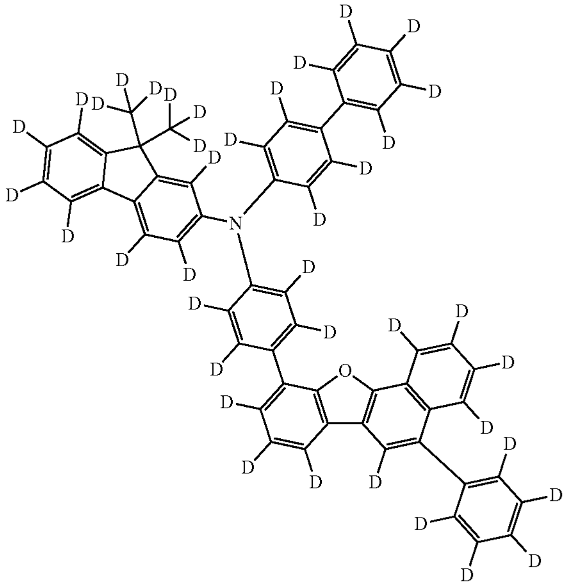
1-933
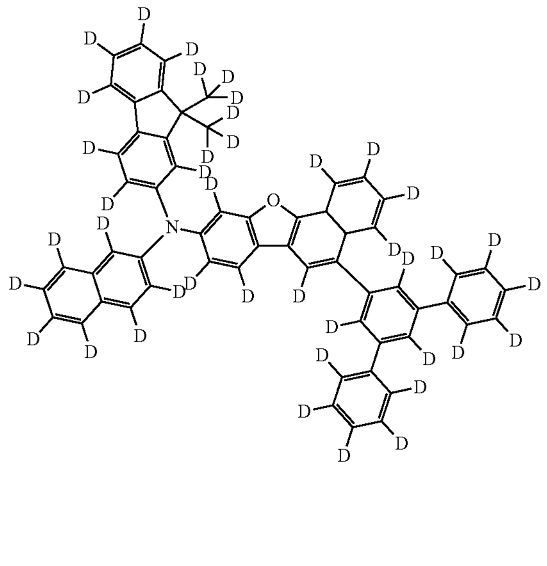
1-934
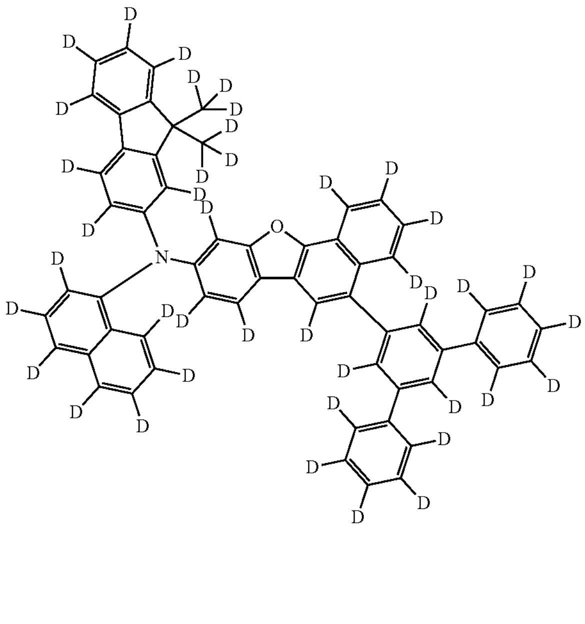

-continued
1-935
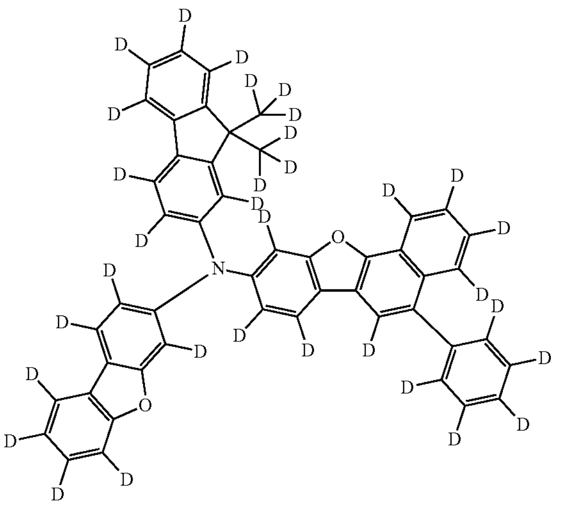
1-936
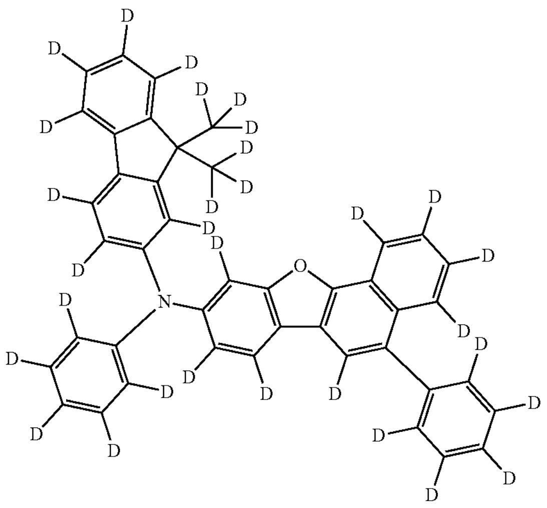
1-937
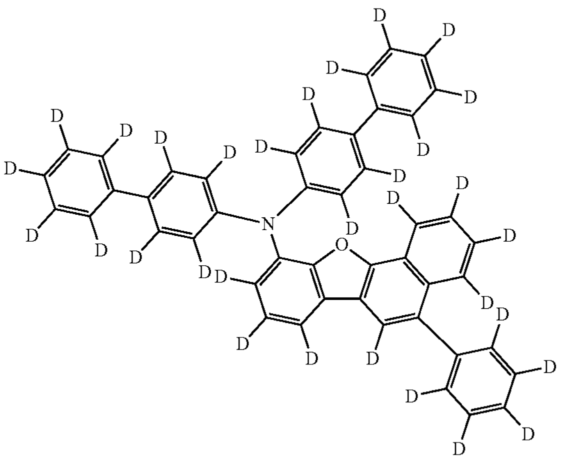
1-938
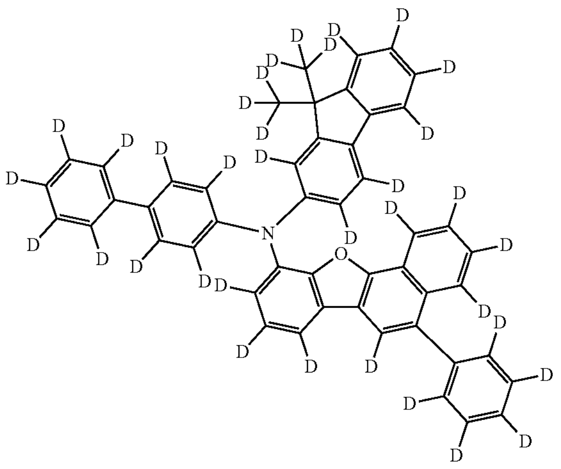
1-939
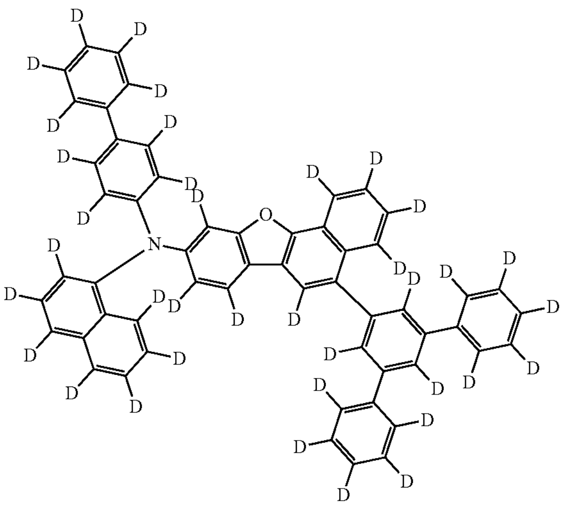

-continued
1-940
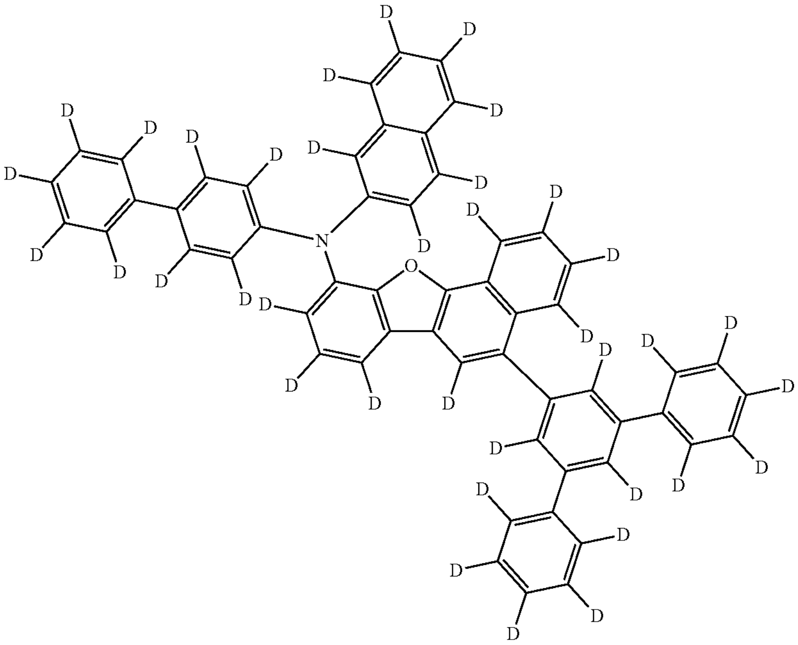
1-941
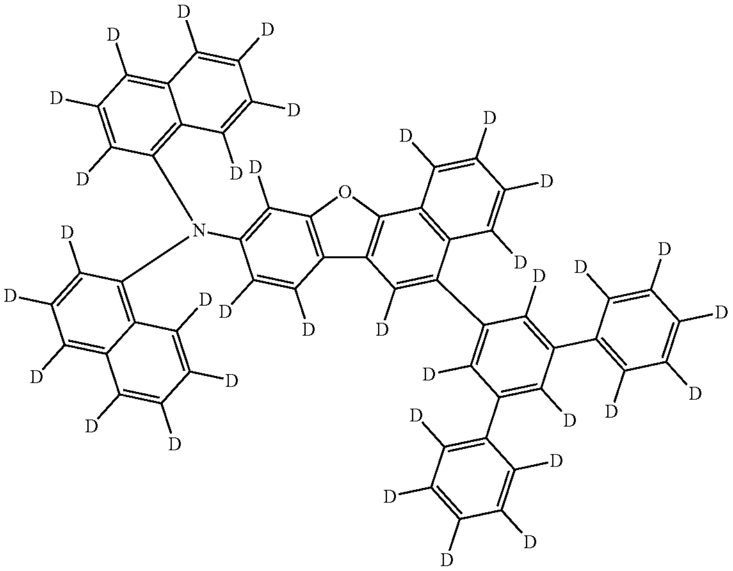

-continued
1-942
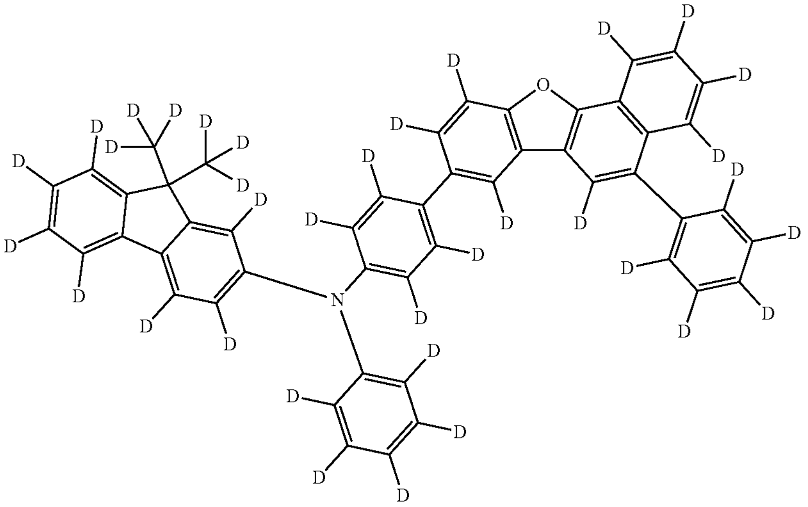
1-943
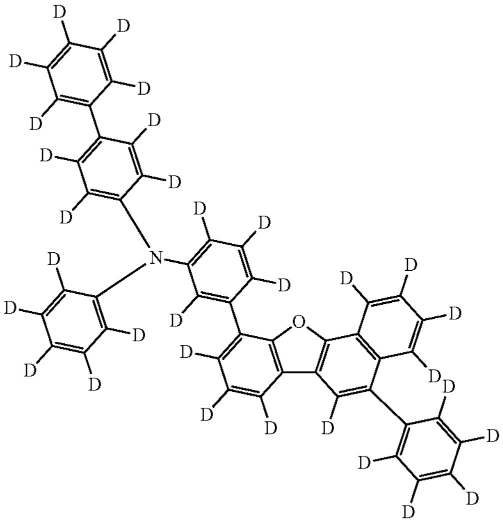
1-944
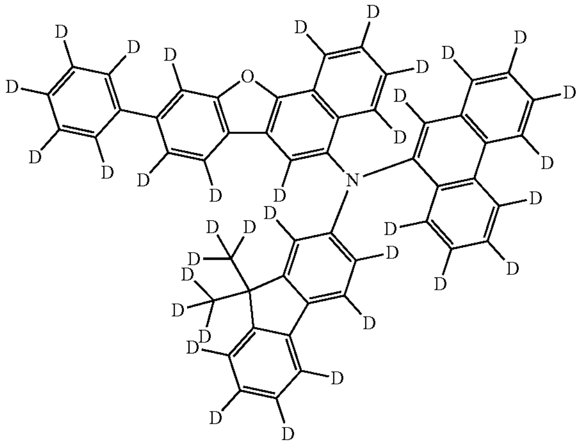
1-945
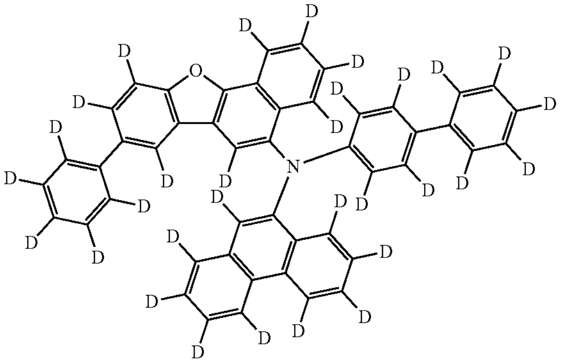
1-946
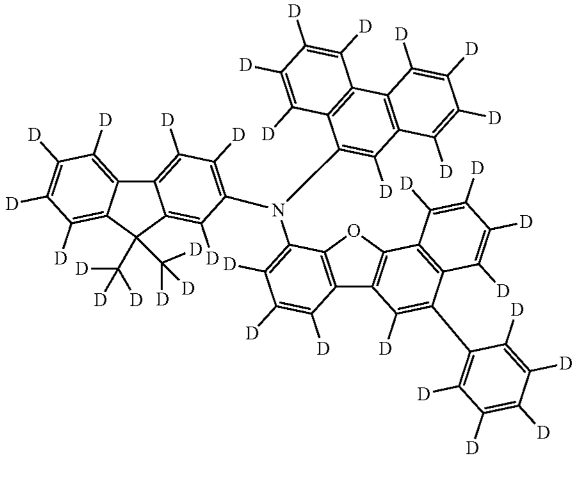

-continued
1-947
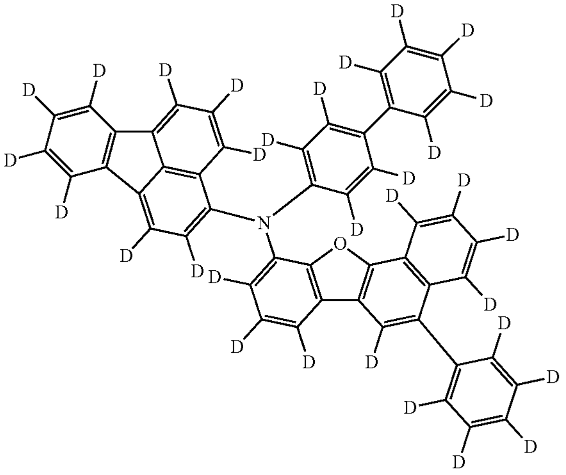
1-948
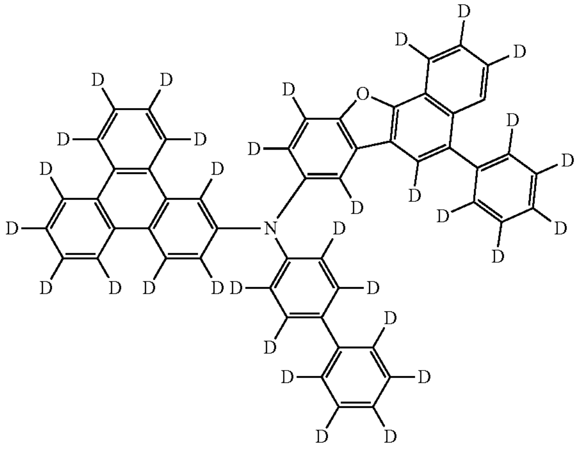
1-949
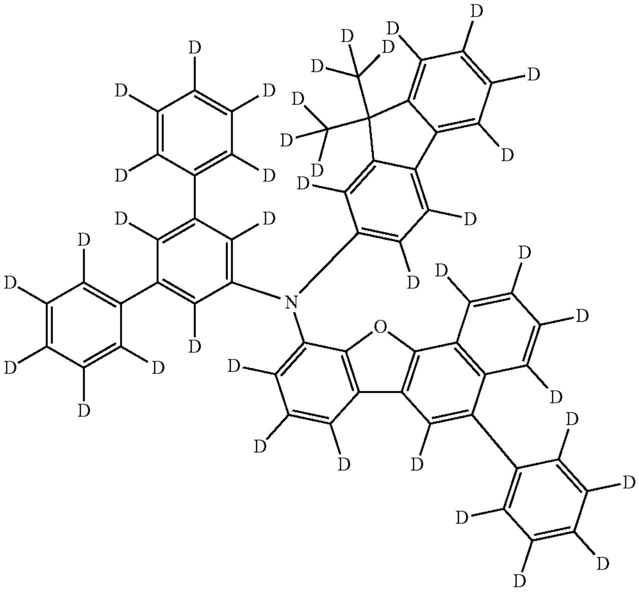

-continued
1-950
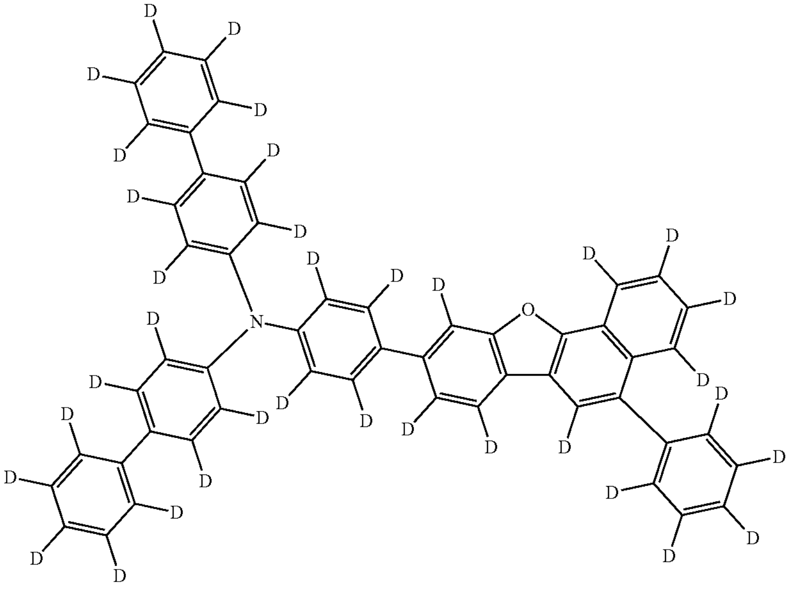
1-951
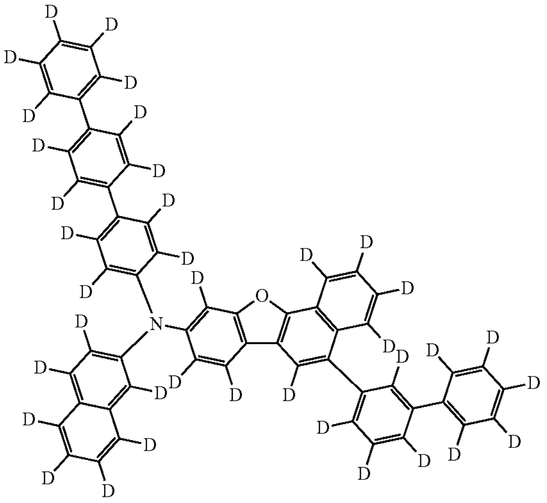
1-952
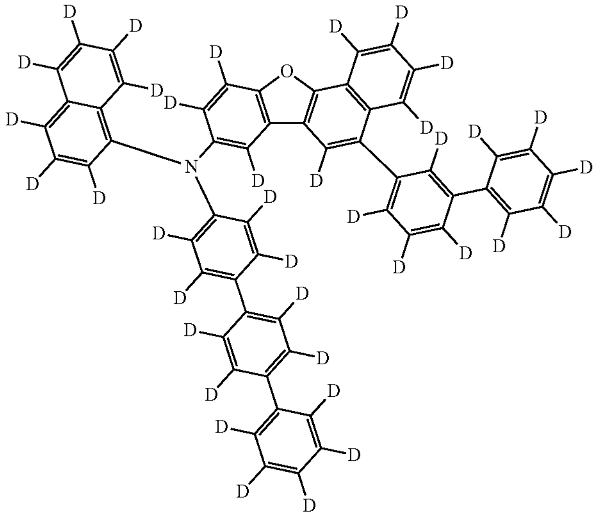

-continued
1-953
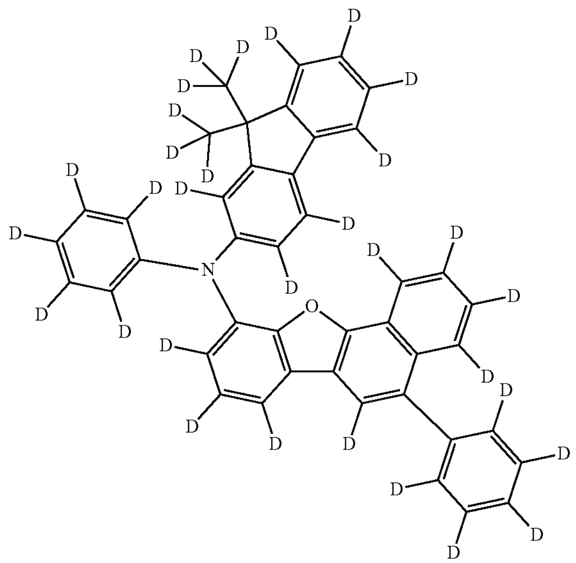
1-954
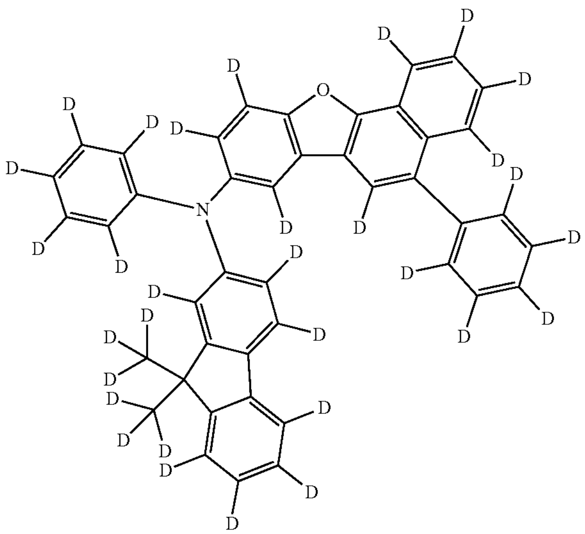
1-955
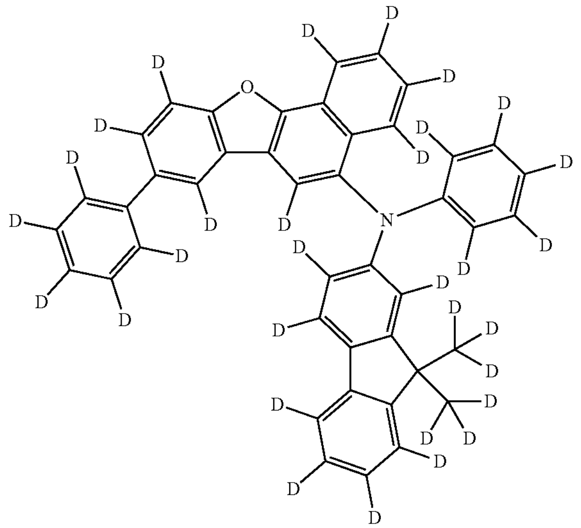
1-956
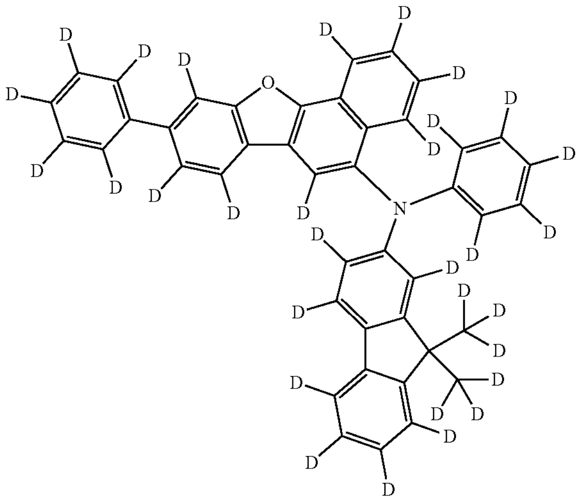
1-957
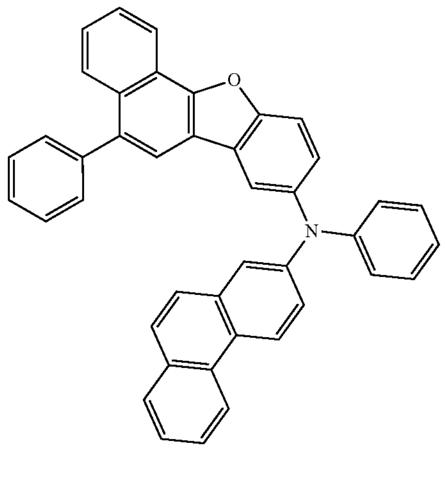
1-958
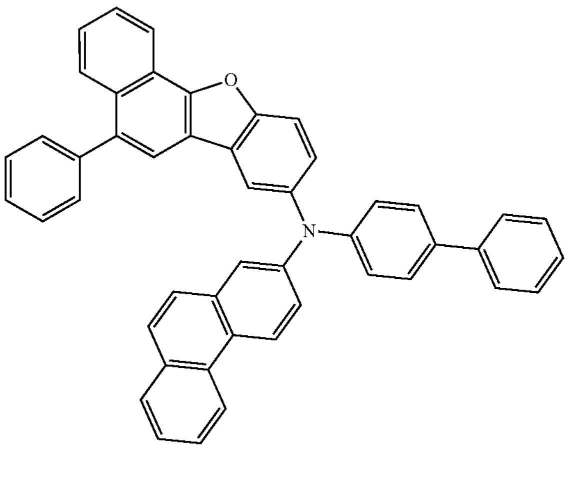

-continued
1-959
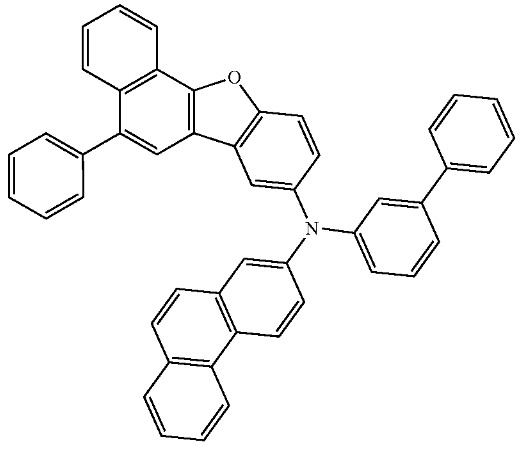
1-960
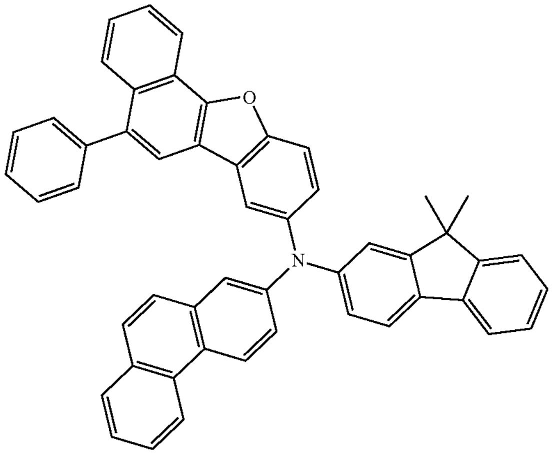
1-961
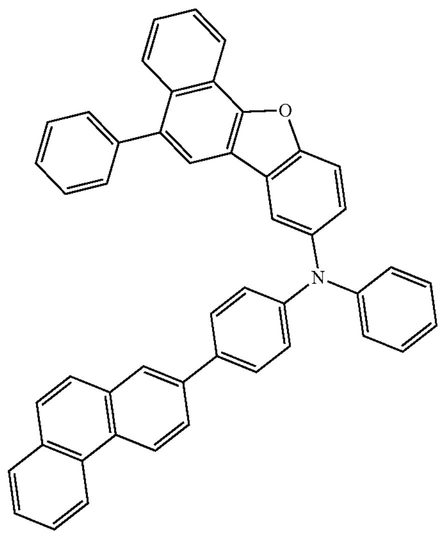
1-962
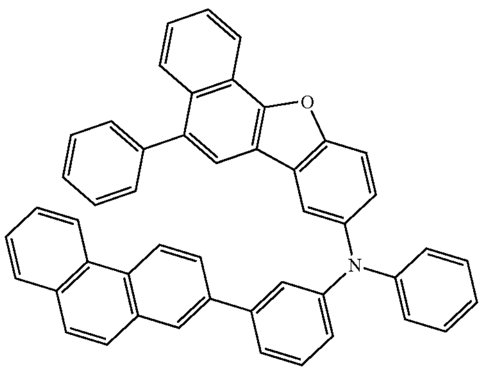
1-963
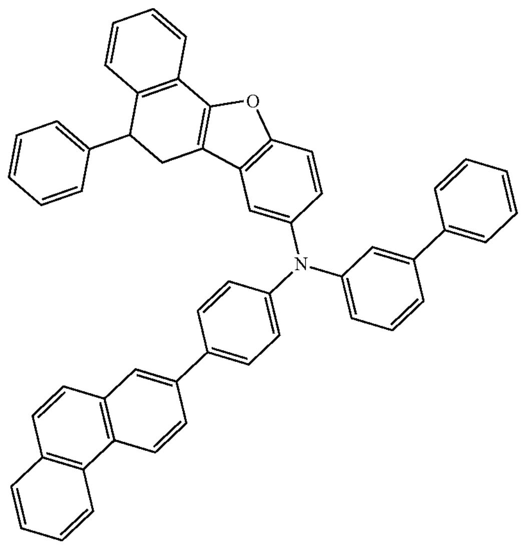
1-964
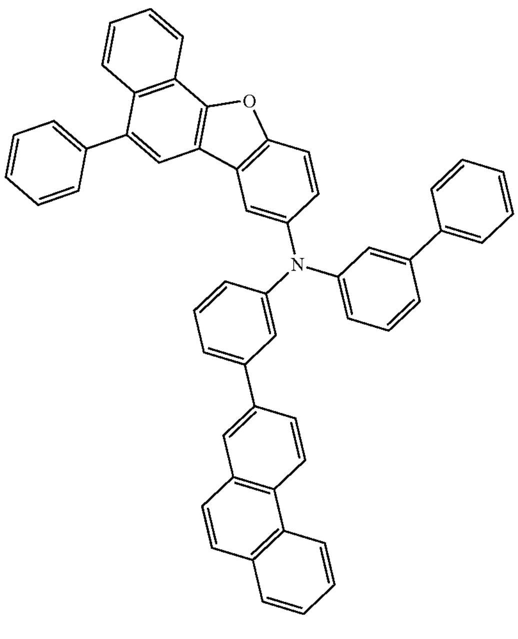

-continued
1-965
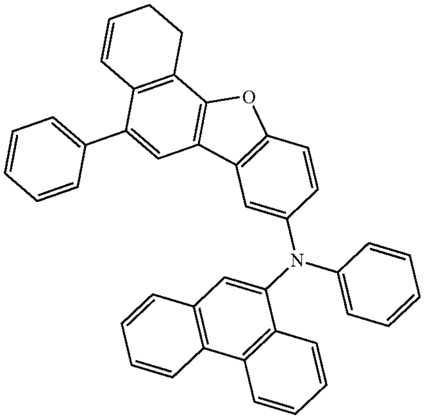
1-966
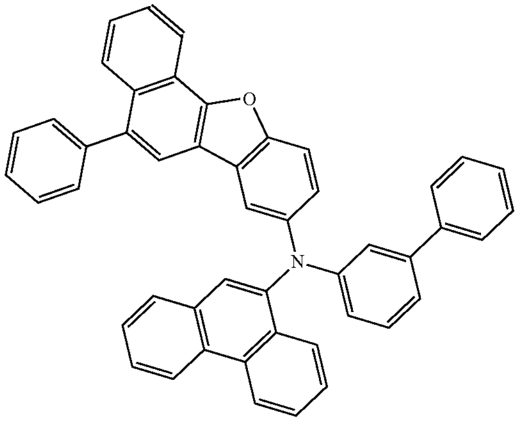
1-967
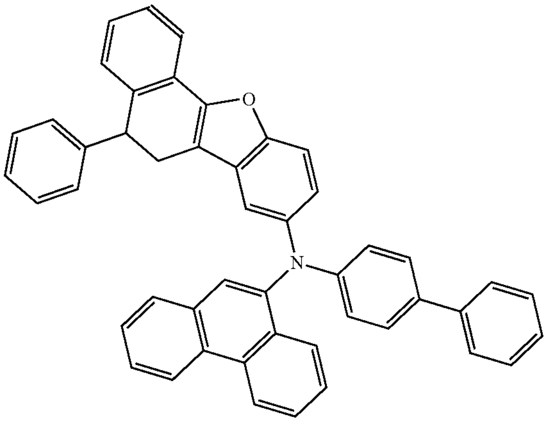
1-968
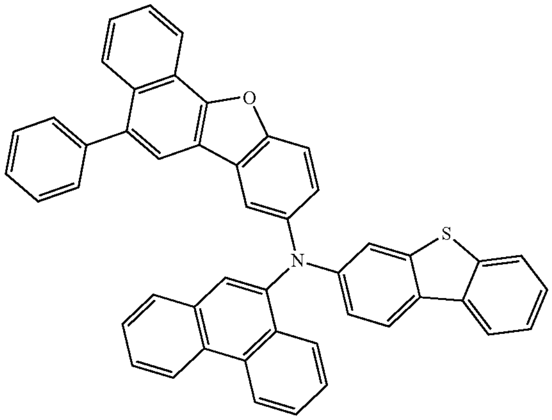
1-969
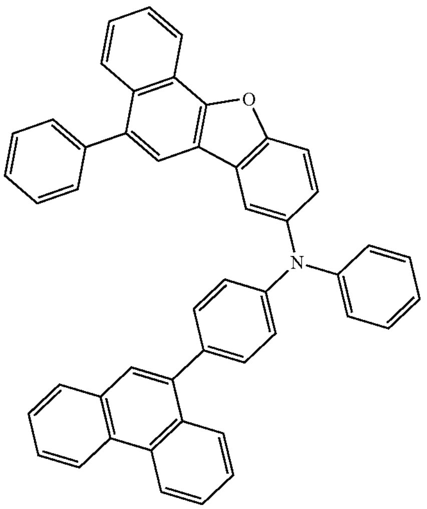
1-970
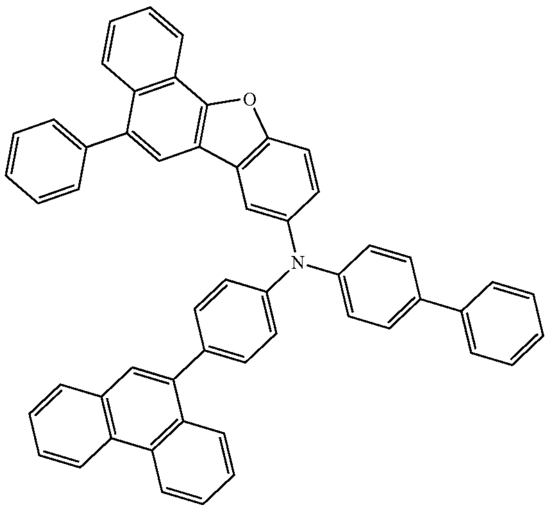

-continued
1-971
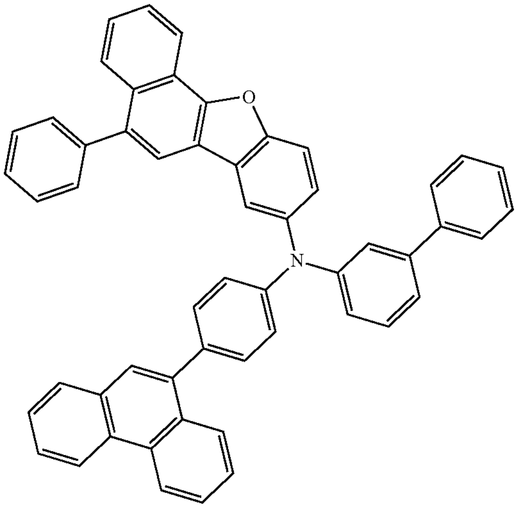
1-972
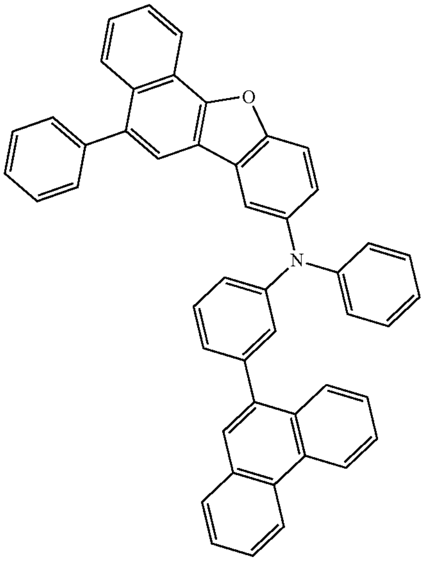
1-973
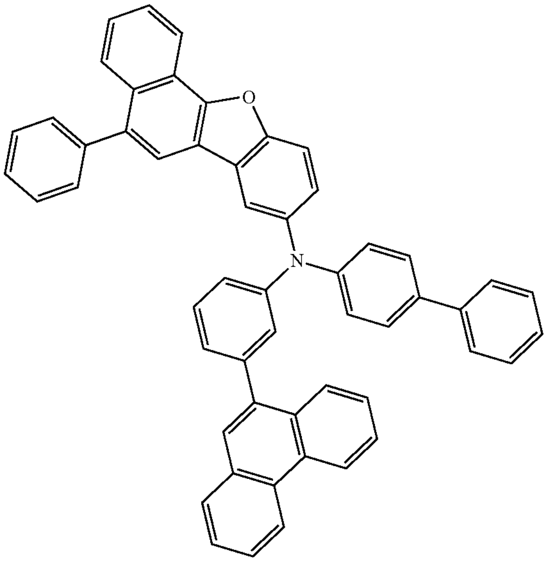
1-974
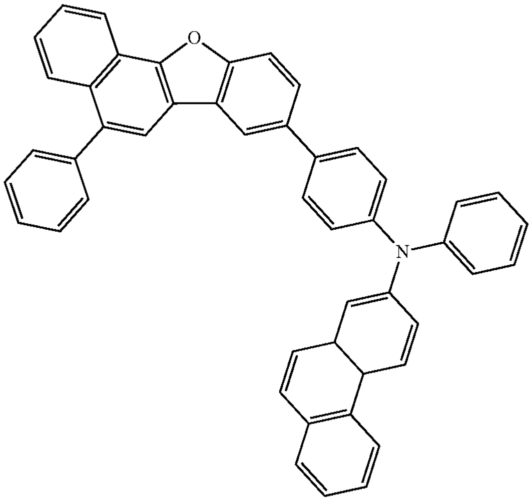

-continued
1-975
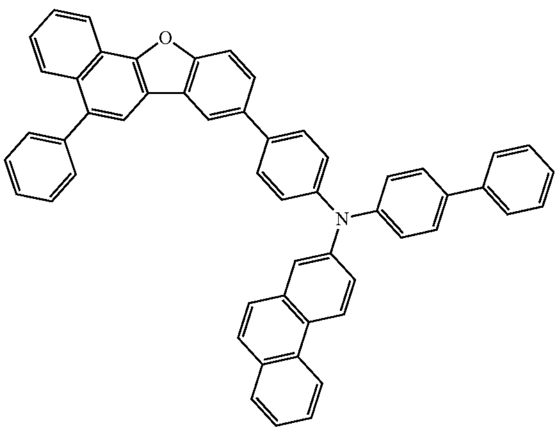
1-976
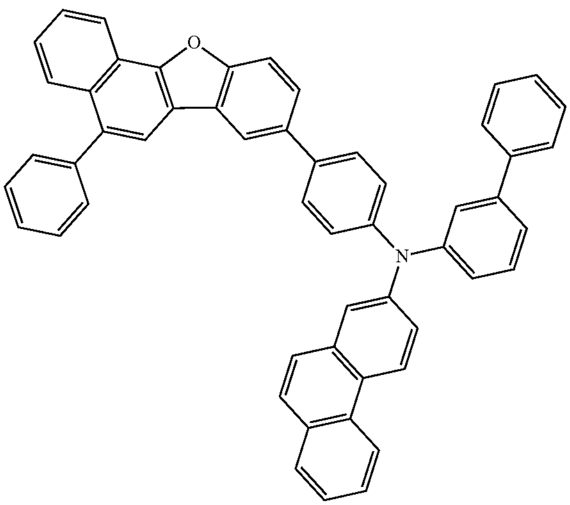
1-977
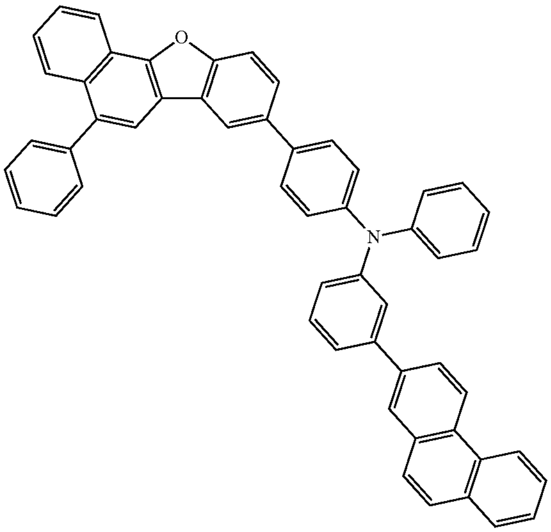
1-978
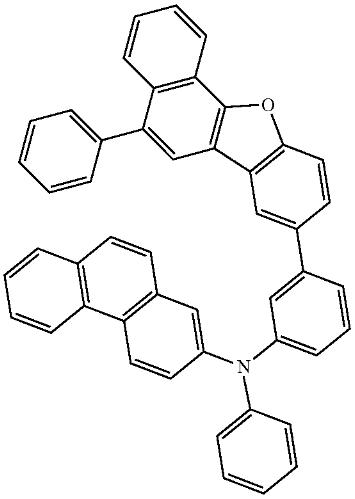

-continued
1-979
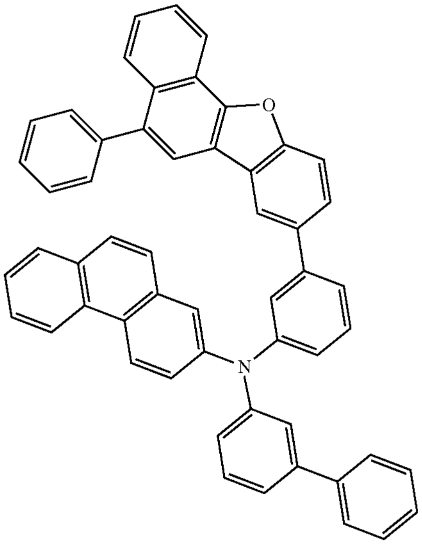
1-980
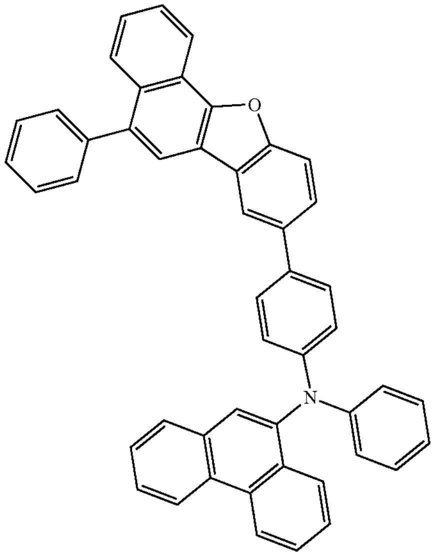
1-981
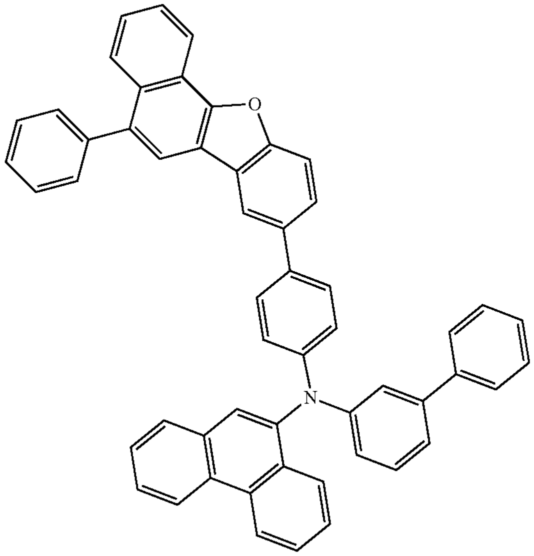
1-982
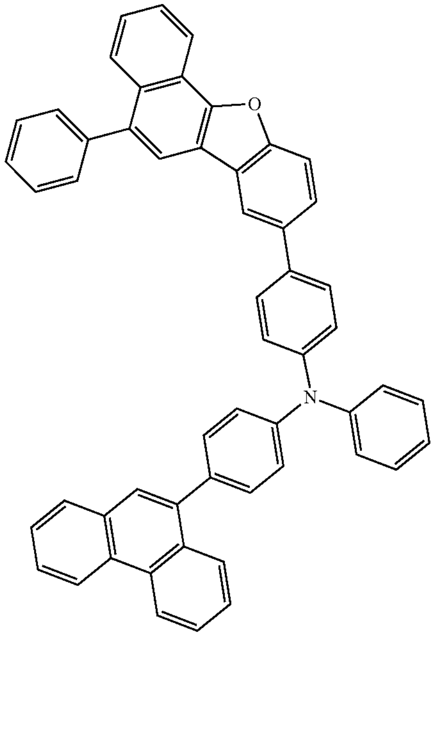

-continued
1-983
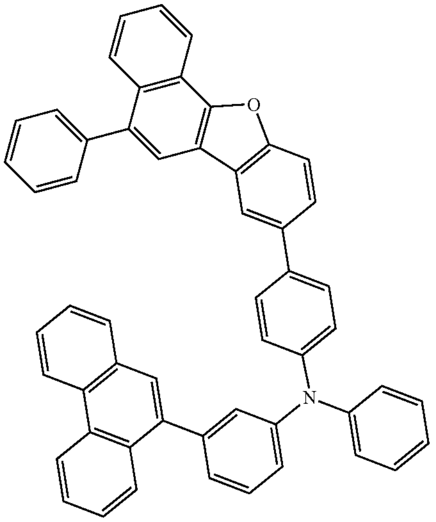
1-984
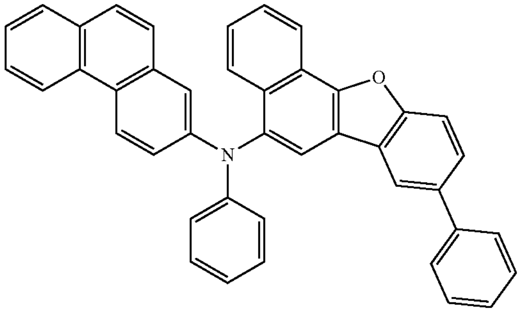
1-985
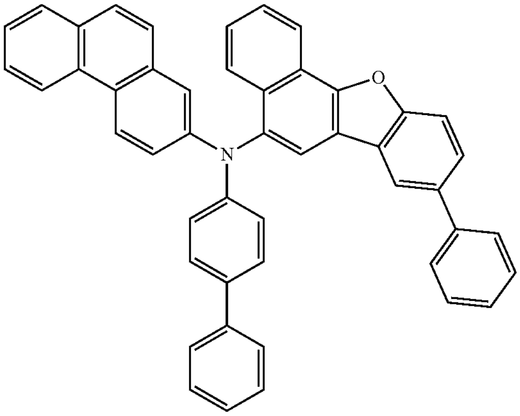
1-986
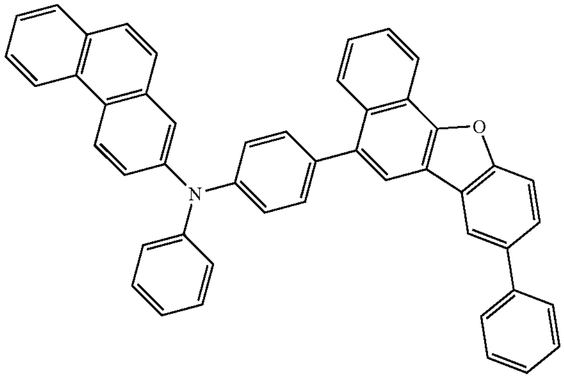
1-987
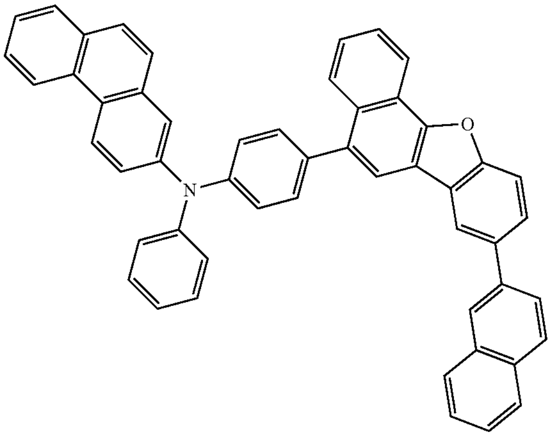
1-988
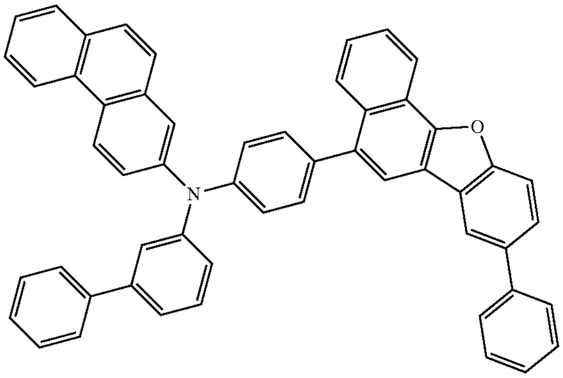

-continued
1-989
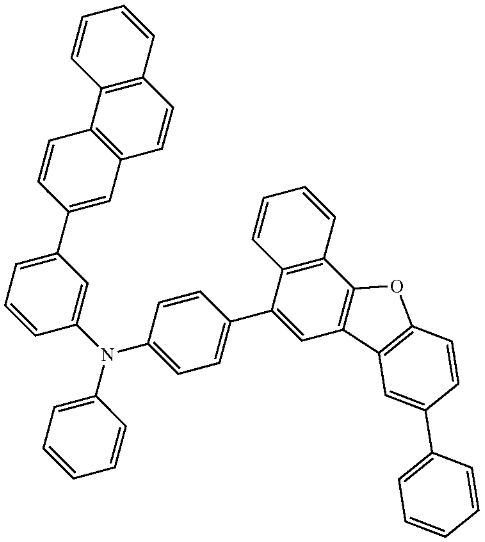
1-990
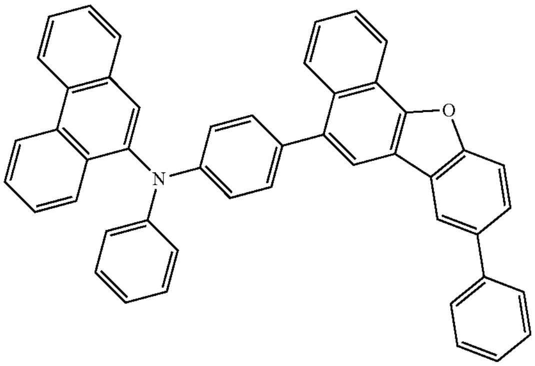
1-991
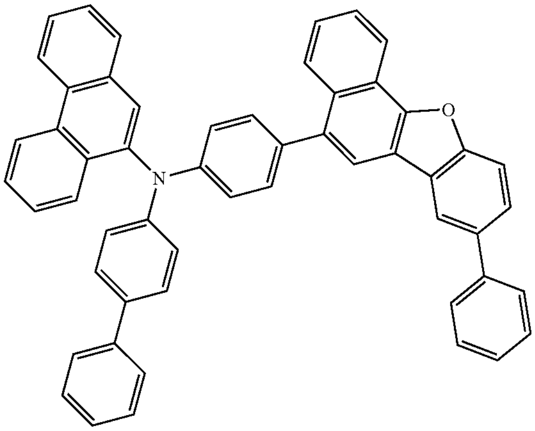
1-992
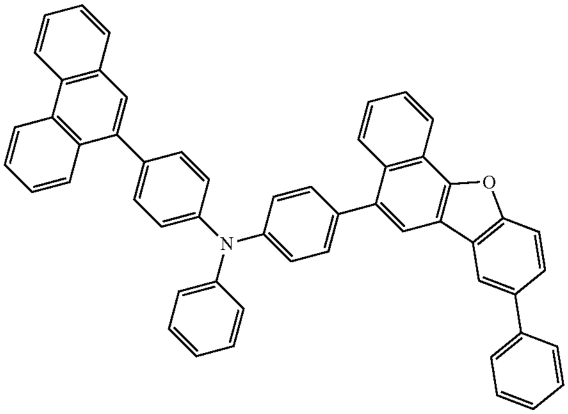
1-993
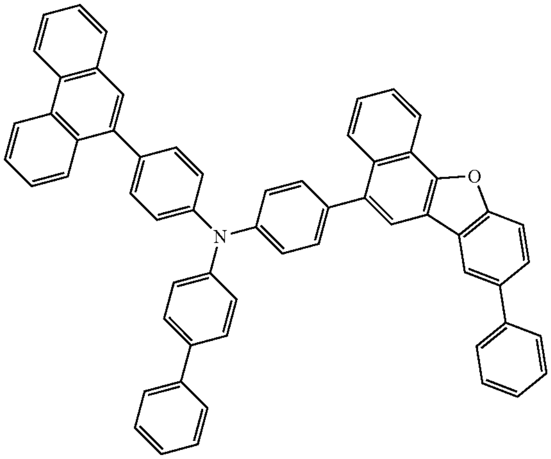
1-994
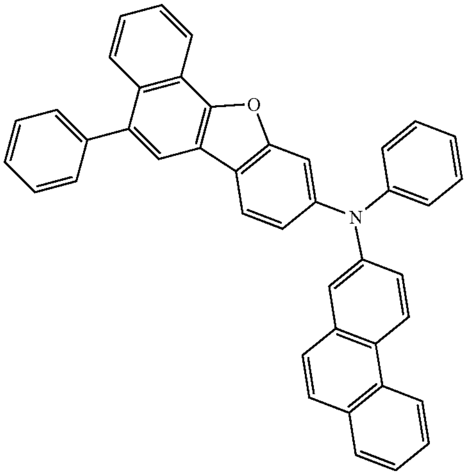

-continued
1-995
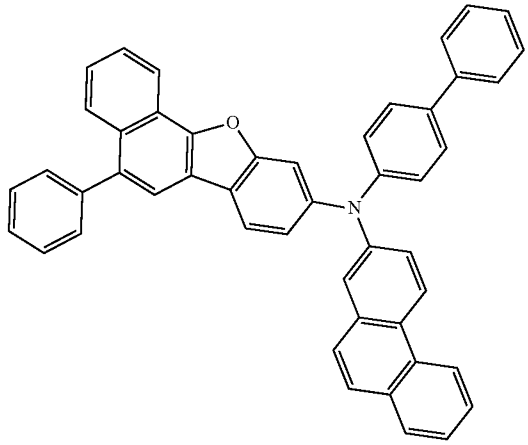
1-996
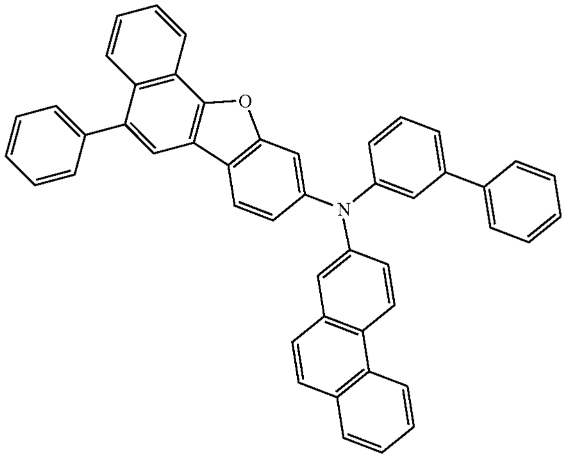
1-997
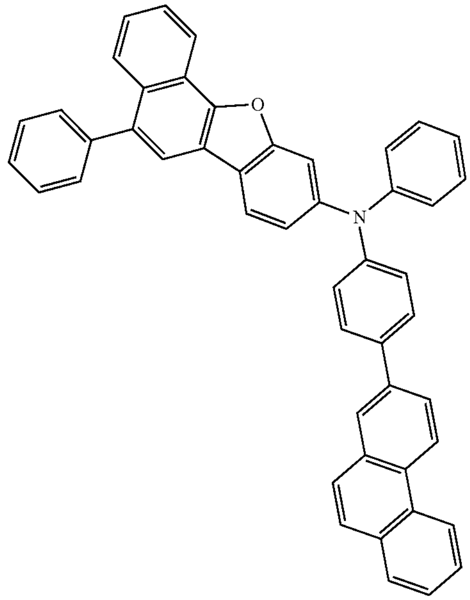
1-998
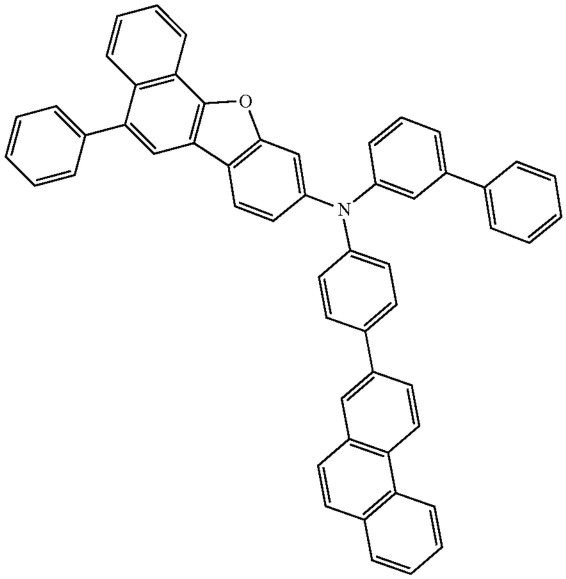
1-999
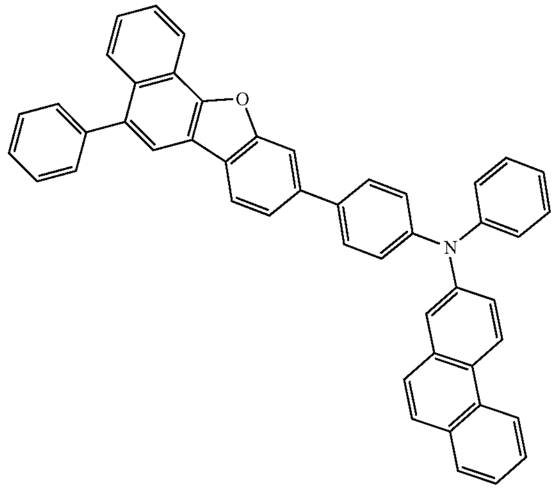
1-1000
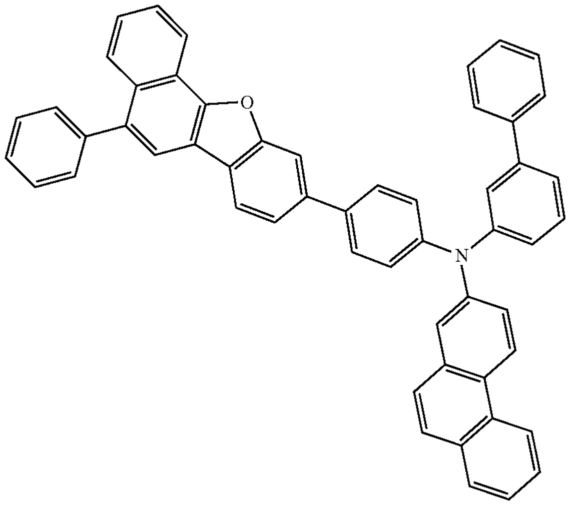

-continued
1-1001
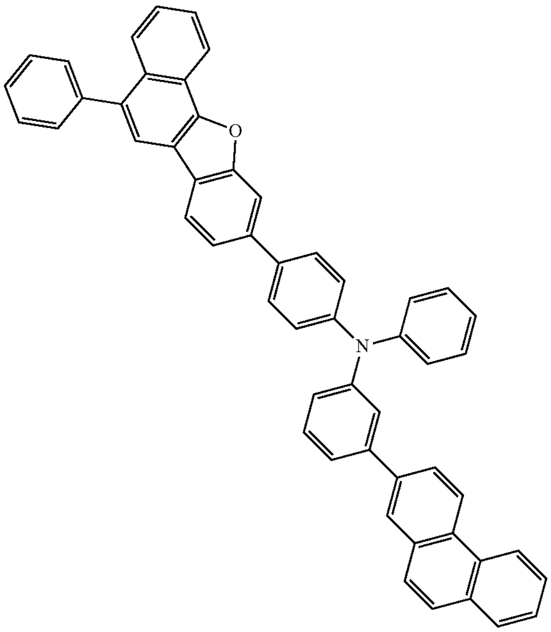
1-1002
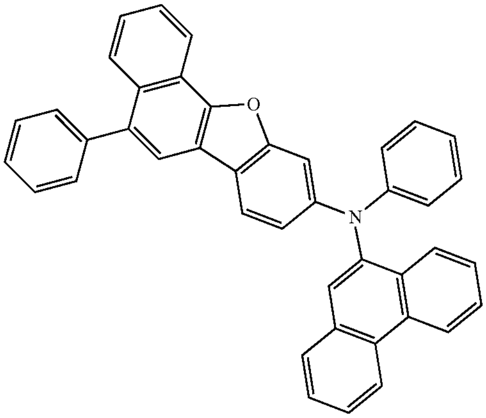
1-1003
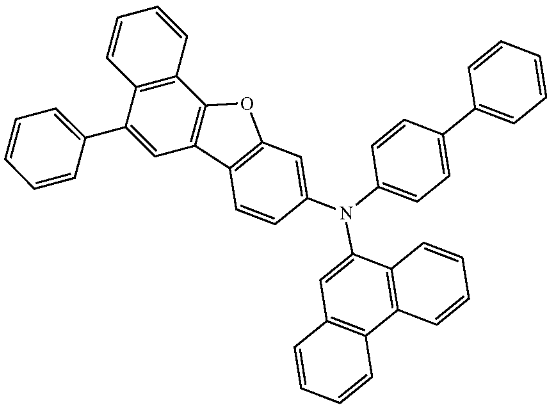
1-1004
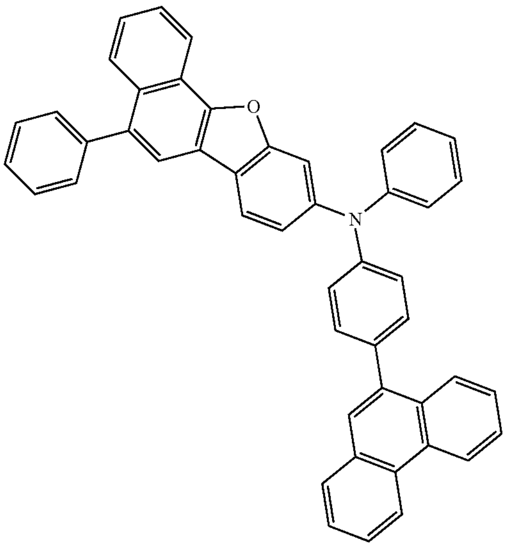

-continued
1-1005
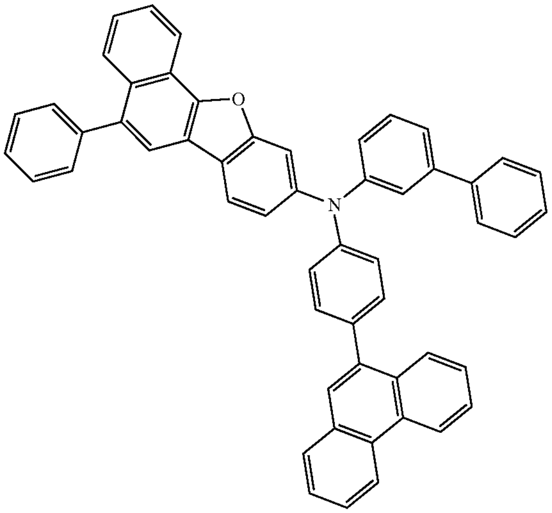
1-1006
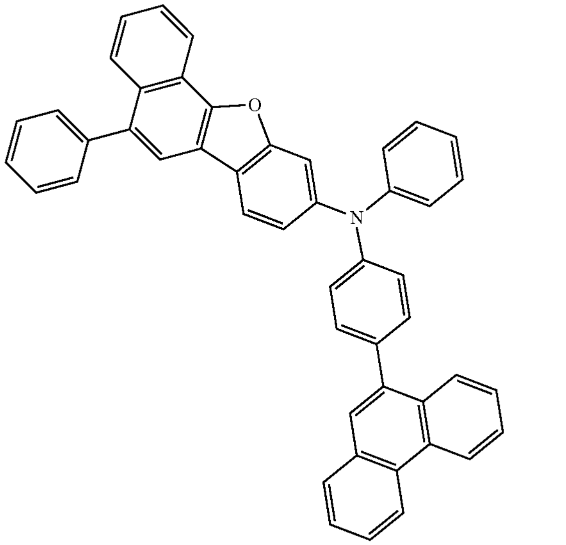
1-1007
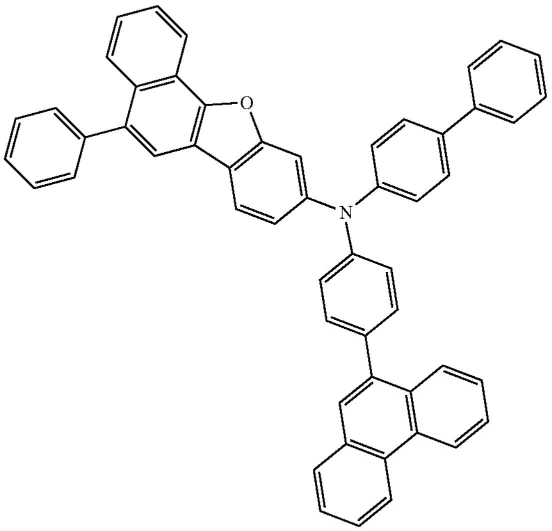
1-1008
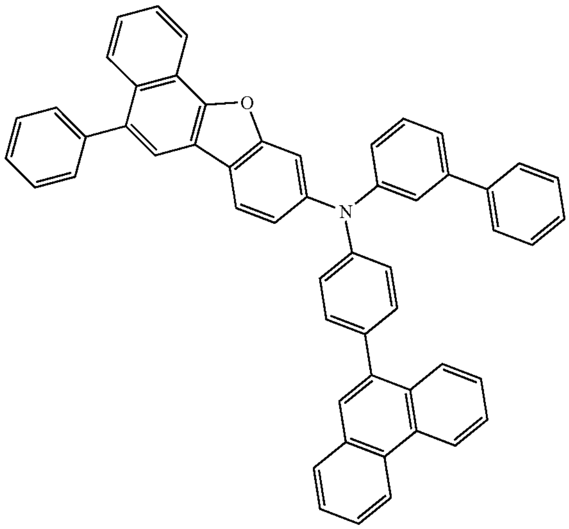
1-1009
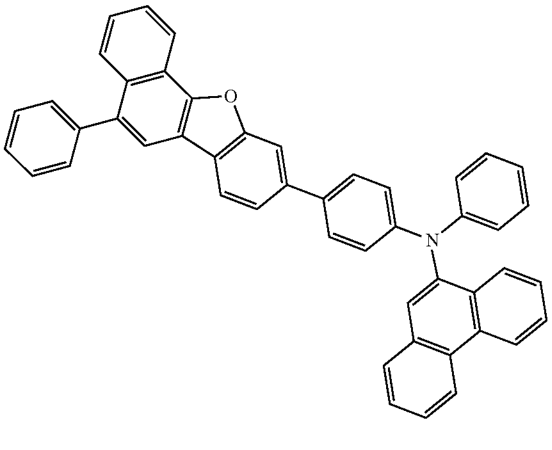
1-1010
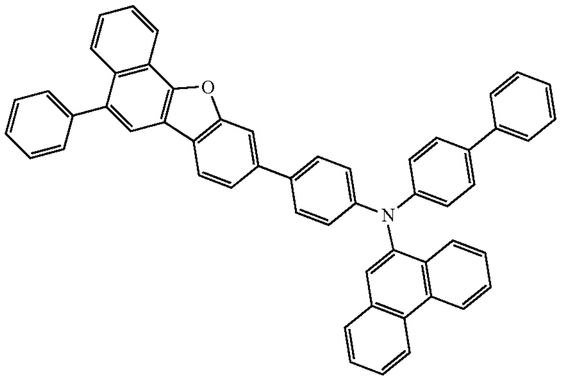

-continued
1-1011
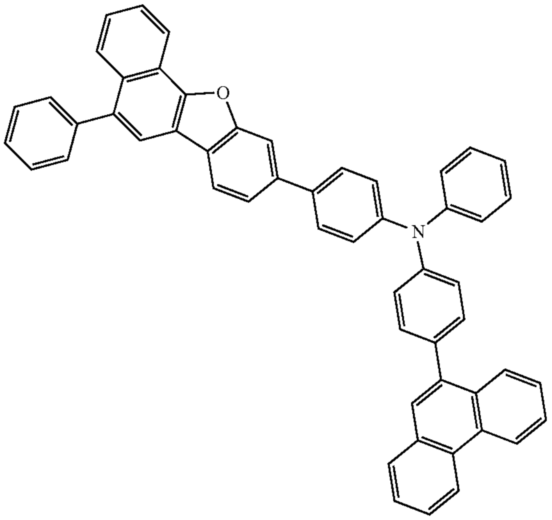
1-1012
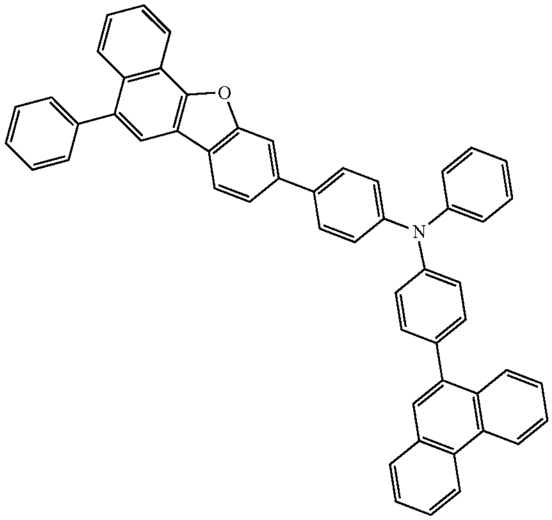
1-1013
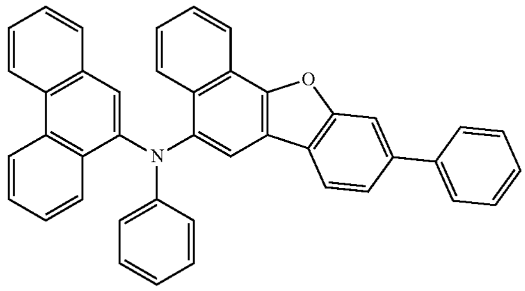
1-1014
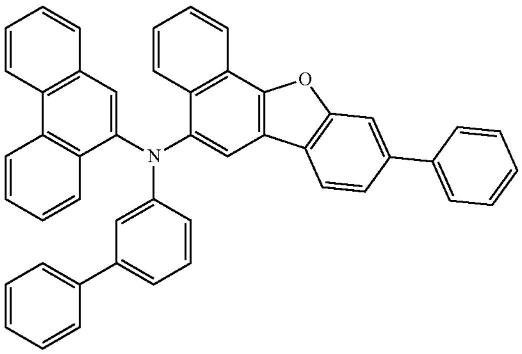
1-1015
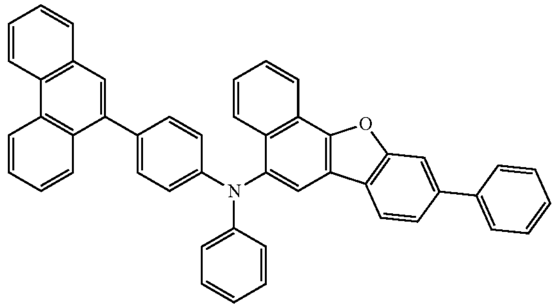
1-1016
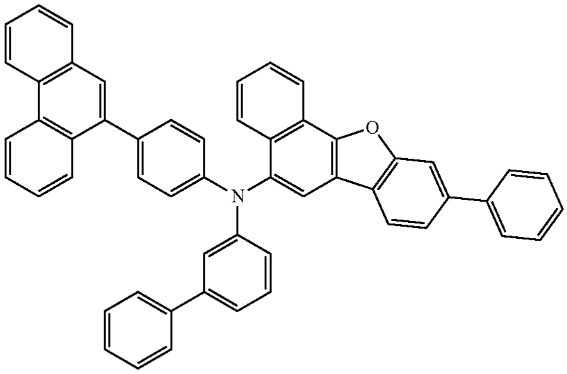
1-1017
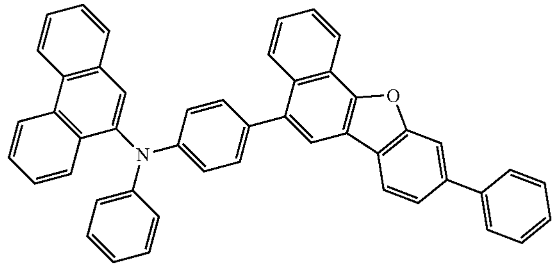
1-1018
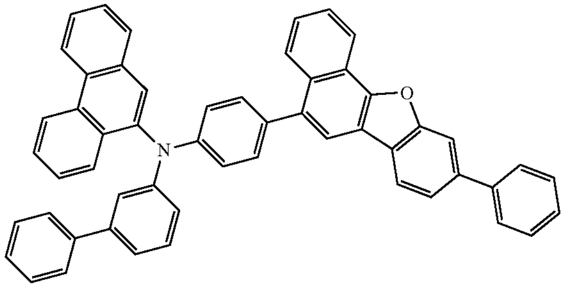

-continued
1-1019
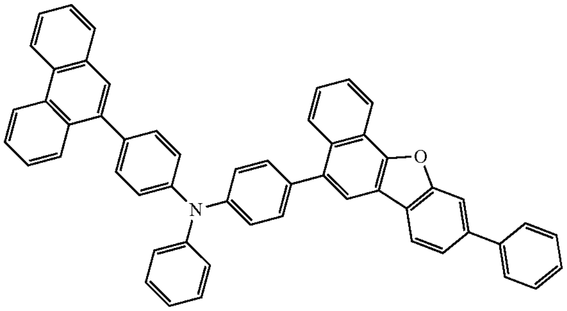
1-1020
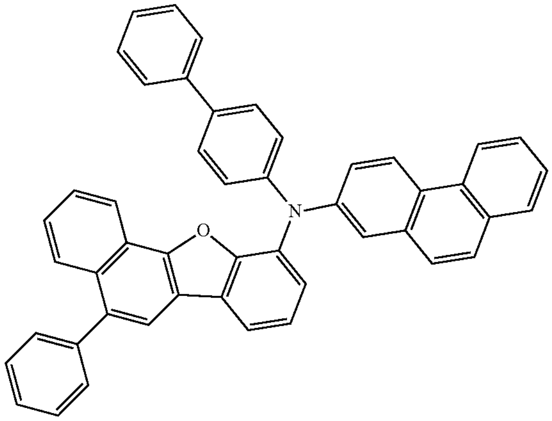
1-1021
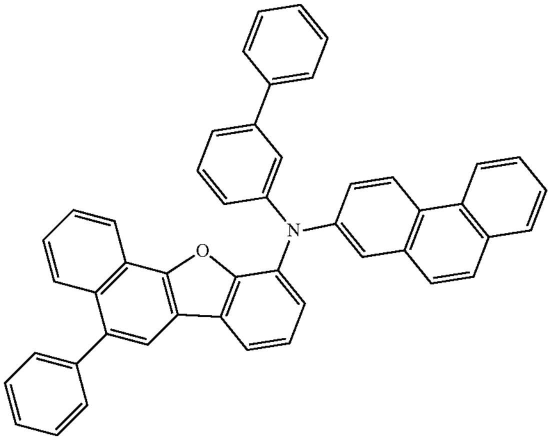
1-1022
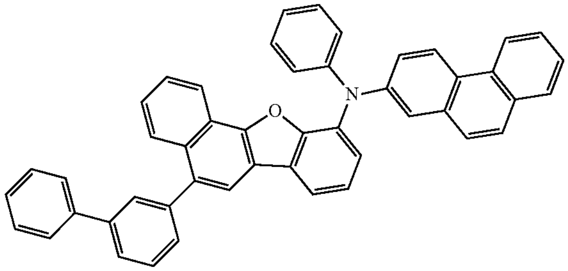
1-1023
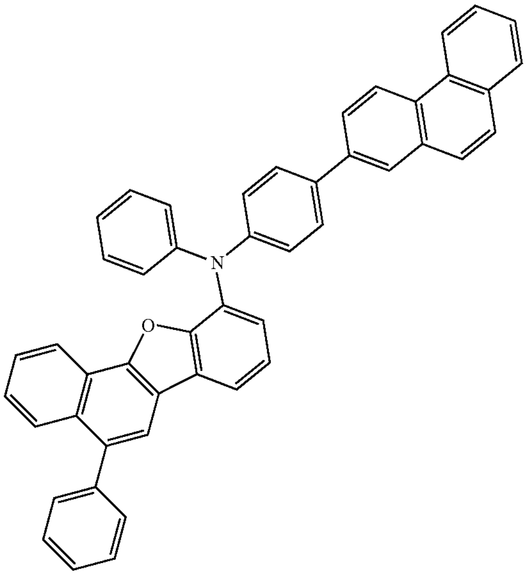
1-1024
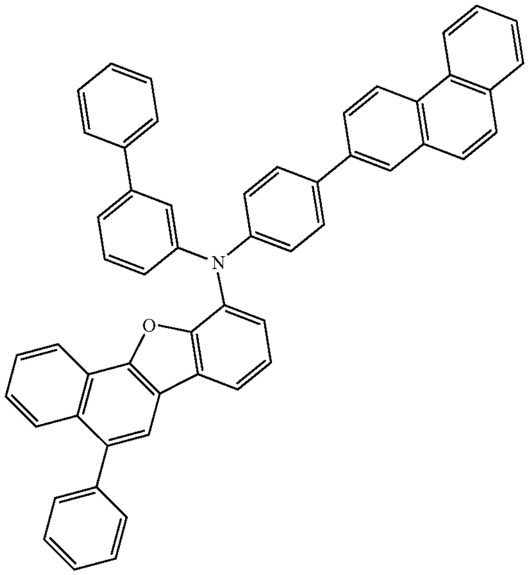

-continued
1-1025
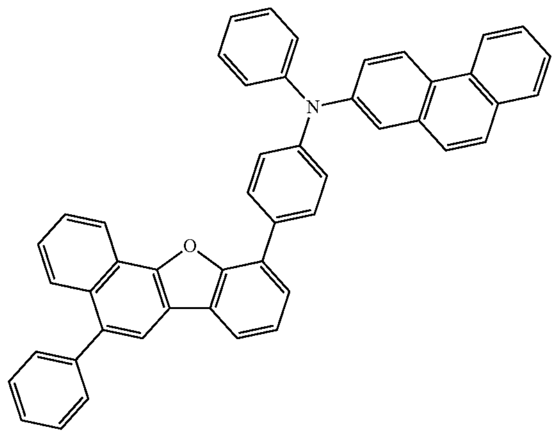
1-1026
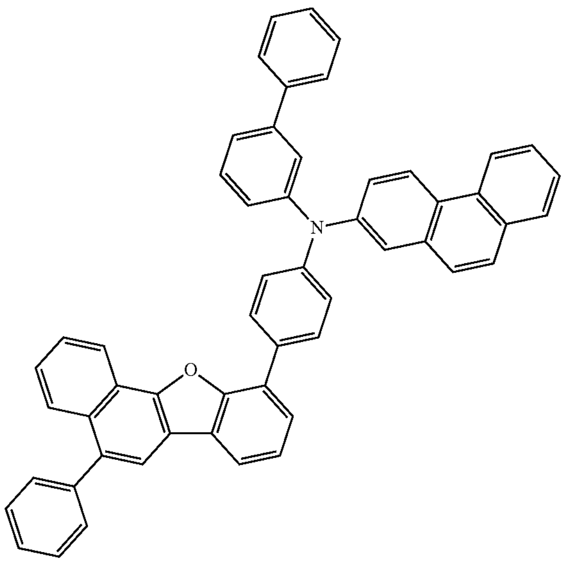
1-1027
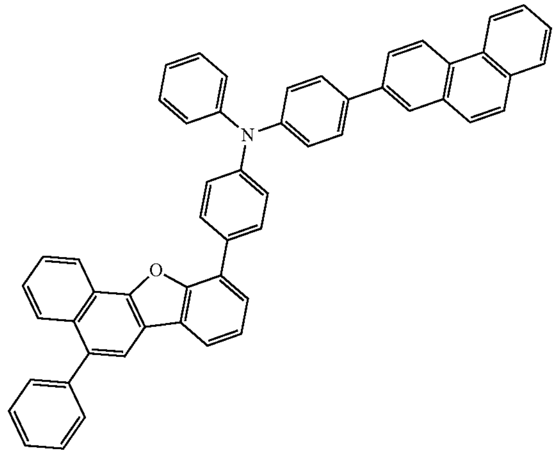
1-1028
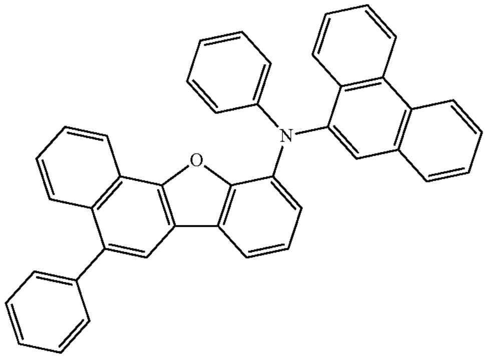
1-1029
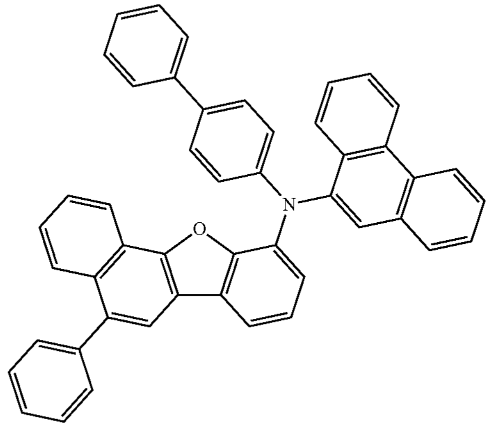
1-1030
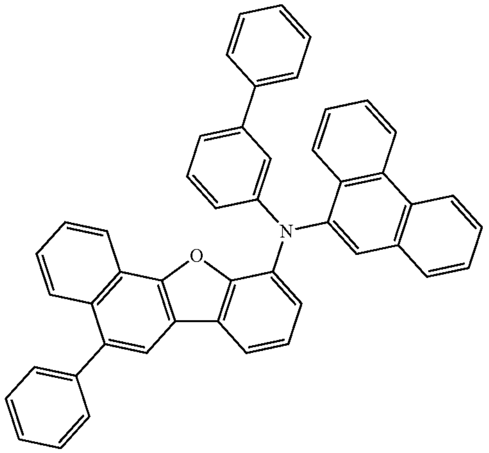

-continued
1-1031
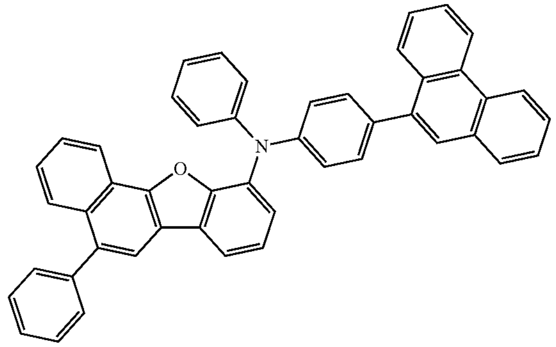
1-1032
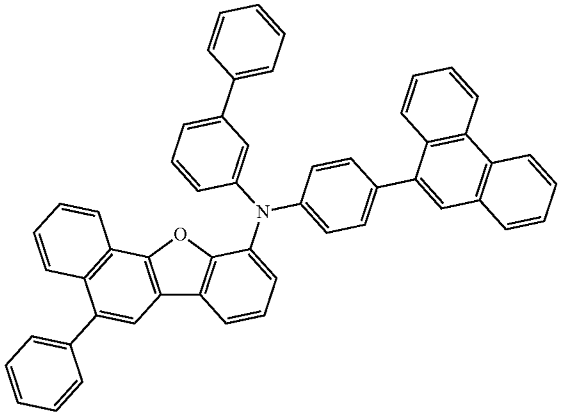
1-1033
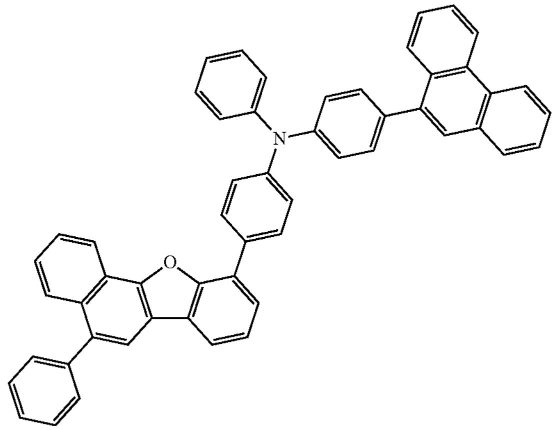
1-1034
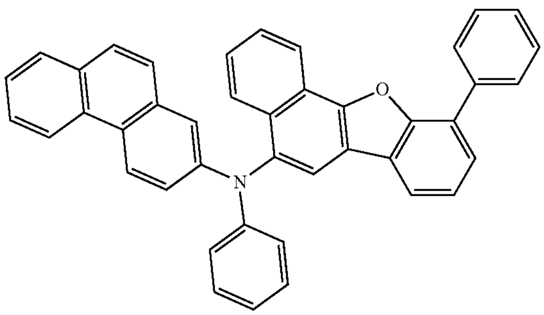
1-1035
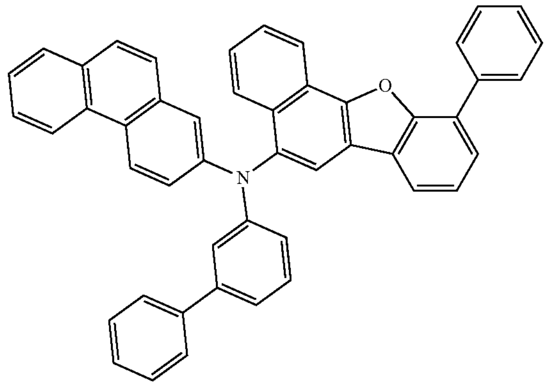
1-1036
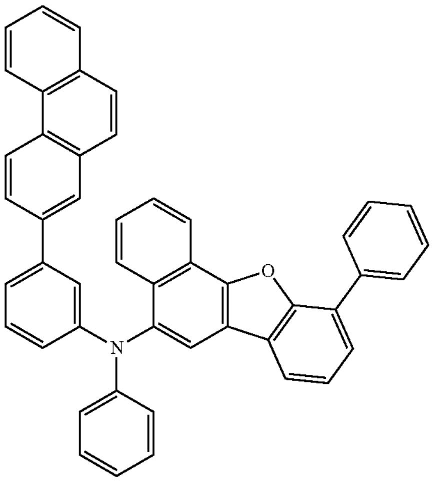

-continued
1-1037
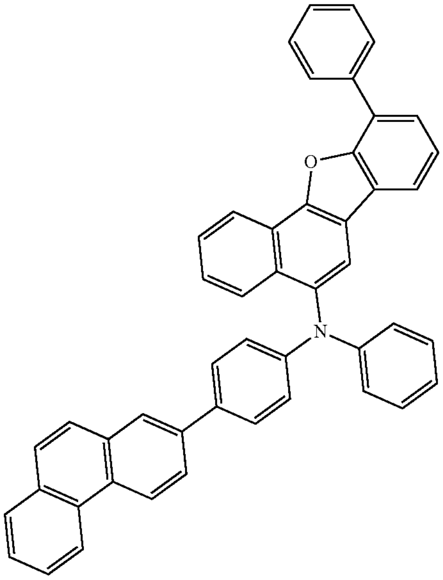
1-1038
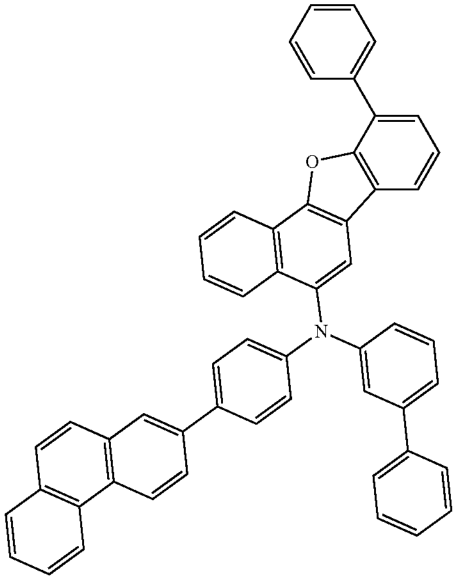
1-1039
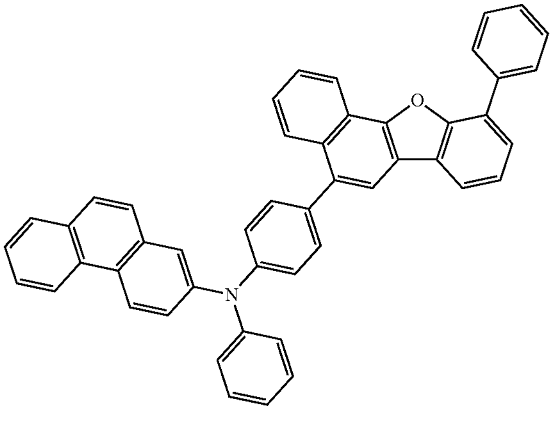
1-1040
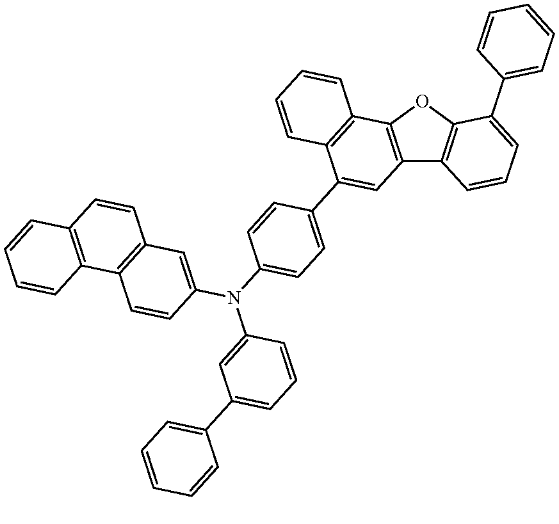

-continued
1-1041
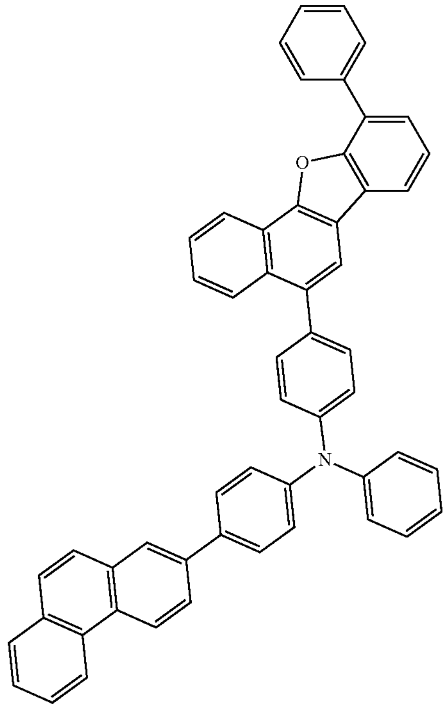
1-1042
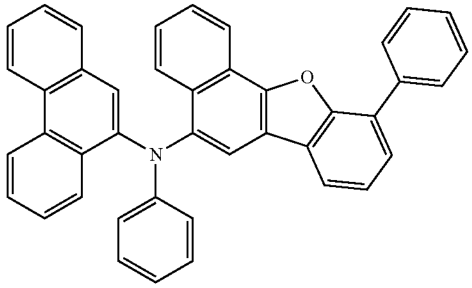
1-1043
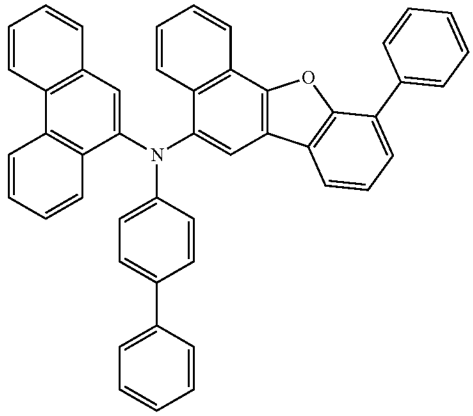
1-1044
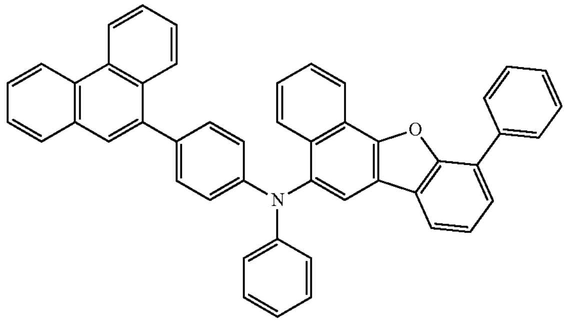
1-1045
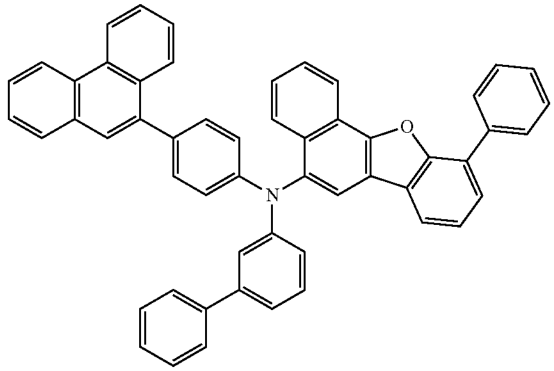
1-1046
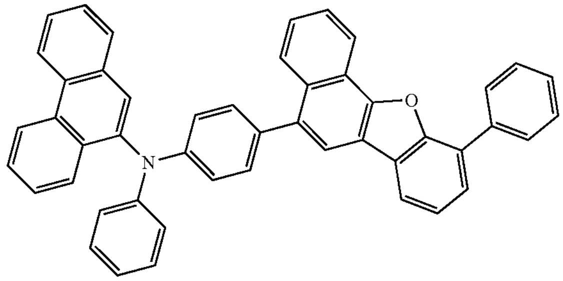

-continued
1-1047
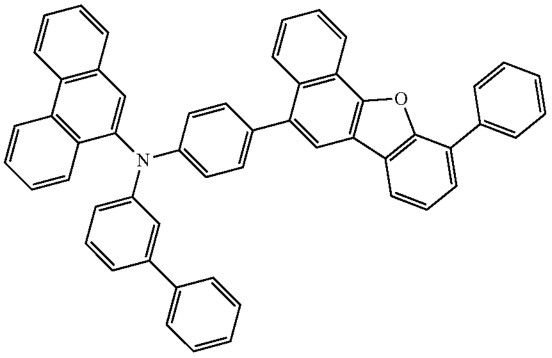
1-1048
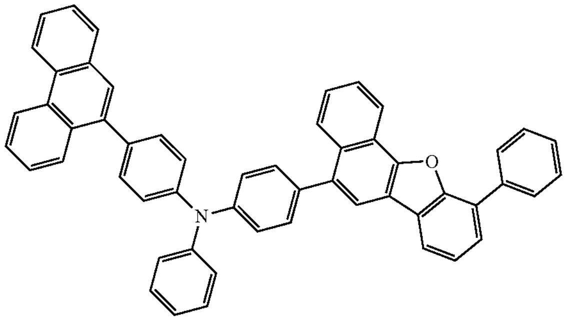
1-1049
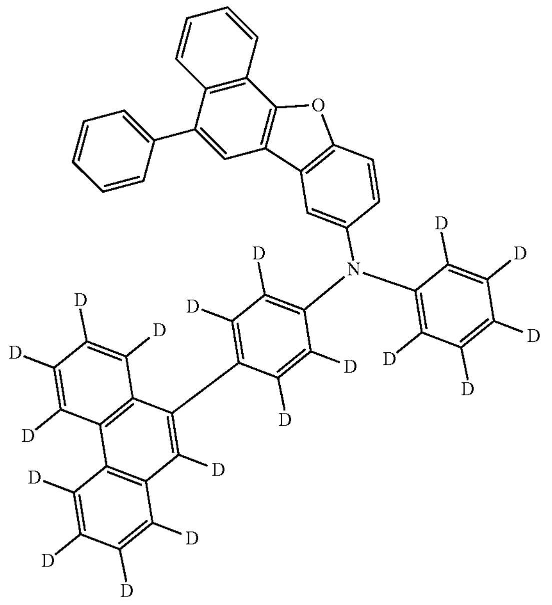
1-1050
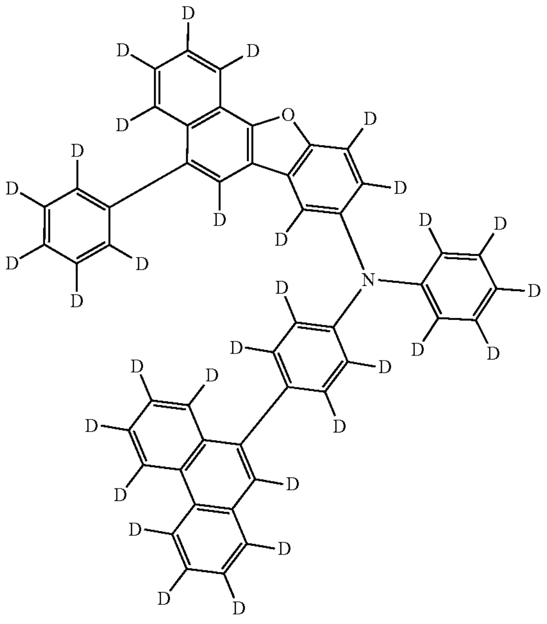

-continued
1-1051
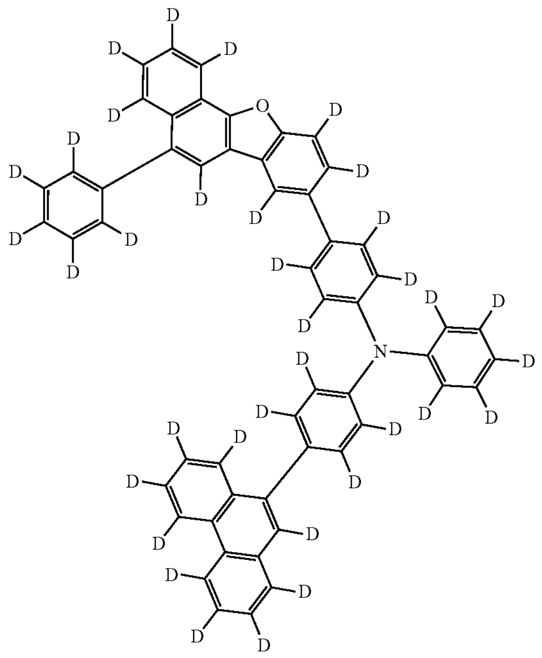
1-1052
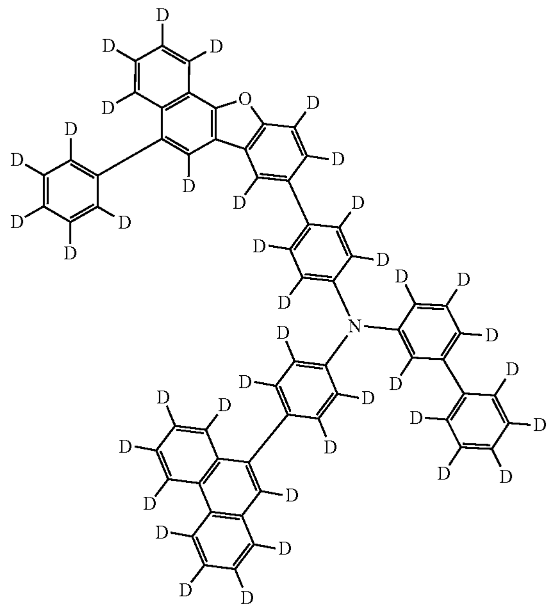
1-1053
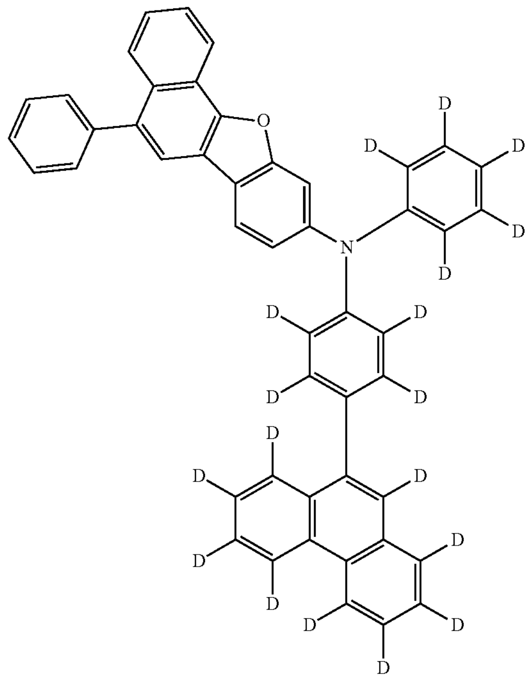
1-1054
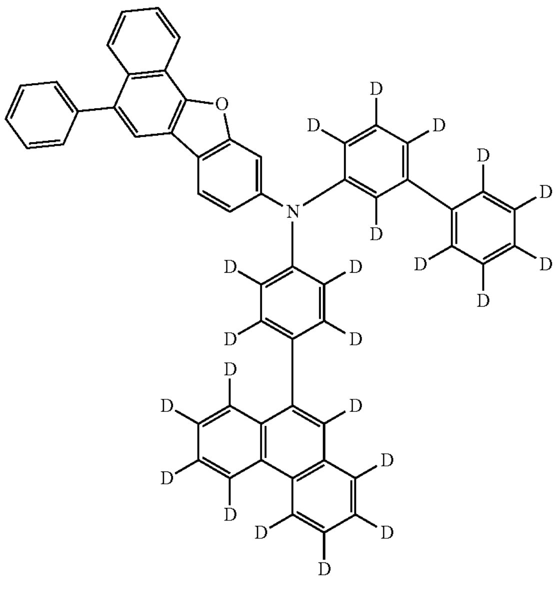

-continued 1-1055

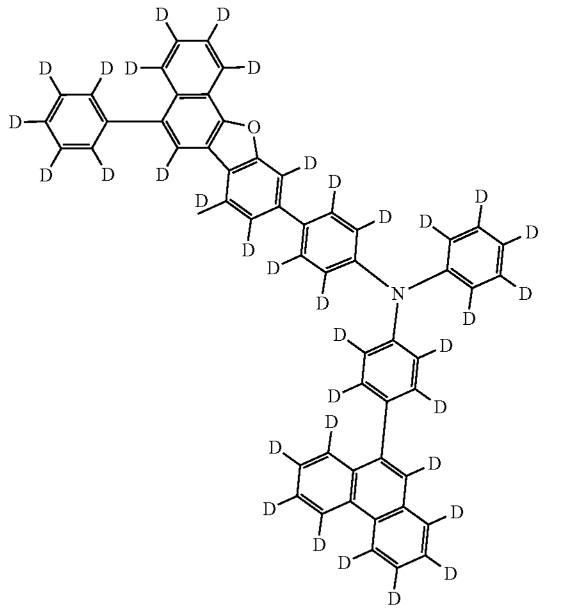

1-1056

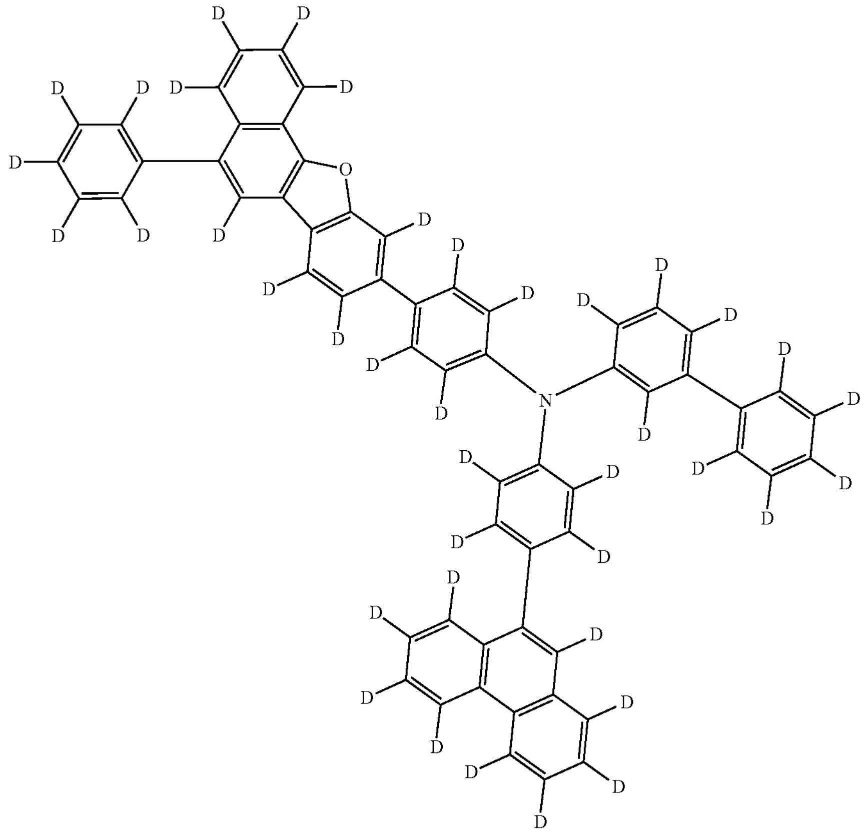

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

In addition, one embodiment of the present application provides an organic light emitting device including a first electrode; a second electrode provided opposite to the first electrode; and one or more organic material layers provided between the first electrode and the second electrode, wherein one or more layers of the organic material layers include the heterocyclic compound represented by Chemical Formula 1.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound represented by Chemical Formula 1 may be used as a material of the green organic light emitting device.

In one embodiment of the present application, the organic light emitting device may be a red organic light emitting device, and the heterocyclic compound represented by Chemical Formula 1 may be used as a material of the red organic light emitting device.

In one embodiment of the present application, the organic light emitting device may be a blue organic light emitting device, and the heterocyclic compound according to Chemical Formula 1 may be used as a light emitting layer material of the blue organic light emitting device.

In one embodiment of the present application, the organic light emitting device may be a green organic light emitting device, and the heterocyclic compound represented by Chemical Formula 1 may be used as a light emitting layer material of the green organic light emitting device.

In one embodiment of the present application, the organic light emitting device may be a red organic light emitting device, and the heterocyclic compound represented by Chemical Formula 1 may be used as a light emitting layer material of the red organic light emitting device.

Specific details on the heterocyclic compound represented by Chemical Formula 1 are the same as the descriptions provided above.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include a smaller number of organic material layers.

In the organic light emitting device of the present disclosure, the organic material layer includes a light emitting layer, and the light emitting layer may include the heterocyclic compound of Chemical Formula 1.

In the organic light emitting device of the present disclosure, the organic material layer includes a light emitting layer, and the light emitting layer may include the heterocyclic compound of Chemical Formula 1 as a light emitting layer host.

In the organic light emitting device provided in one embodiment of the present application, the organic material layer including the heterocyclic compound represented by Chemical Formula 1 further includes a heterocyclic compound represented by the following Chemical Formula A; or a heterocyclic compound represented by the following Chemical Formula B.

[Chemical Formula A]

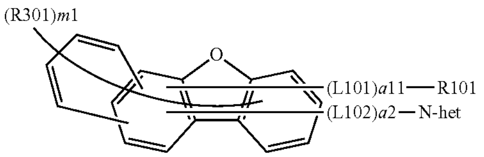

[Chemical Formula B]

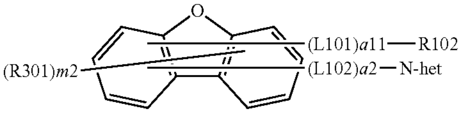

In Chemical Formulae A and B,

L101 and L102 are the same as or different from each other, and each independently a direct bond; a substituted or unsubstituted C6 to C60 arylene group; or a substituted or unsubstituted C2 to C60 heteroarylene group, N-het is a monocyclic or polycyclic heterocyclic group substituted or unsubstituted and including one or more Ns, R101 is a substituted or unsubstituted C1 to C60 alkyl group; a substituted or unsubstituted C6 to C60 aryl group; a substituted or unsubstituted C2 to C60 heteroaryl group; or —NR103R104, R102 is hydrogen; deuterium; a substituted or unsubstituted C1 to C60 alkyl group; a substituted or unsubstituted C6 to C60 aryl group; a substituted or unsubstituted C2 to C60 heteroaryl group; or —NR103R104, R301 is selected from the group consisting of hydrogen; deuterium; halogen; a cyano group; a substituted or unsubstituted C1 to C60 alkyl group; a substituted or unsubstituted C6 to C60 aryl group; and a substituted or unsubstituted C2 to C60 heteroaryl group, R103 and R104 are the same as or different from each other, and each independently a substituted or unsubstituted C1 to C60 alkyl group; a substituted or unsubstituted C6 to C60 aryl group; or a substituted or unsubstituted C2 to C60 heteroaryl group, m1 is an integer of 0 to 8, m2 is an integer of 0 to 6, and a11 and a2 are an integer of 0 to 4, and when m1, m2, a11 and a2 are 2 or greater, substituents in the parentheses are the same as or different from each other.

Effects of more superior efficiency and lifetime are obtained when including the heterocyclic compound of Chemical Formula 1 and the heterocyclic compound of Chemical Formula A or Chemical Formula B in the organic material layer of the organic light emitting device. Such results may lead to a forecast that an exciplex phenomenon occurs when including the two compounds at the same time.

The exciplex phenomenon is a phenomenon of releasing energy having sizes of a donor (p-host) HOMO level and an acceptor (n-host) LUMO level due to electron exchanges between two molecules. When the exciplex phenomenon occurs between two molecules, reverse intersystem crossing (RISC) occurs, and as a result, internal quantum efficiency of fluorescence may increase up to 100%. When a donor (p-host) having a favorable hole transfer ability and an acceptor (n-host) having a favorable electron transfer ability are used as a host of a light emitting layer, holes are injected to the p-host and electrons are injected to the n-host, and therefore, a driving voltage may be lowered, which resultantly helps with enhancement in the lifetime.

In one embodiment of the present application, Chemical Formula A may be represented by any one of the following Chemical Formulae A-1 to A-3.

[Chemical Formula A-1[

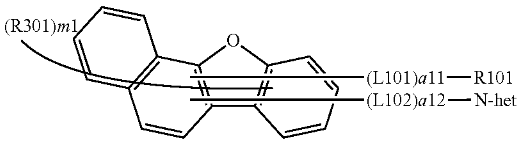

[Chemical Formula A-2]

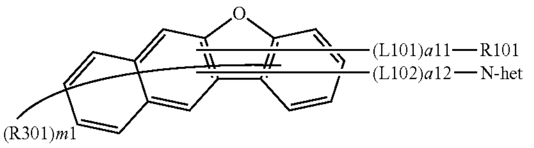

[Chemical Formula A-3]

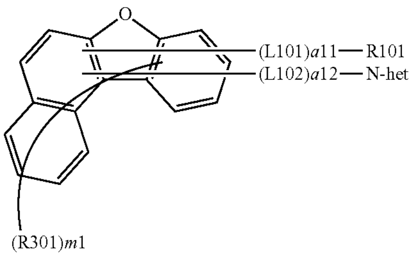

In Chemical Formulae A-1 to A-3, each substituent has the same definition as in Chemical Formula A.

In one embodiment of the present application, Chemical Formula B may be represented by the following Chemical Formula B-1 or B-2.

[Chemical Formula B-1]

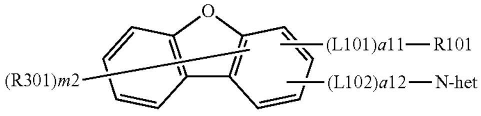

[Chemical Formula B-2]

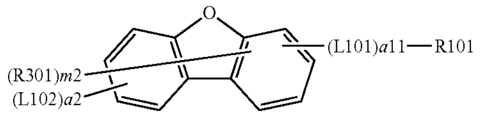

In Chemical Formulae B-1 and B-2, each substituent has the same definition as in Chemical Formula B.

In one embodiment of the present application, L101 and L102 are the same as or different from each other, and may be each independently a direct bond; a substituted or unsubstituted C6 to C60 arylene group; or a substituted or unsubstituted C2 to C60 heteroarylene group.

In another embodiment, L101 and L102 are the same as or different from each other, and may be each independently a direct bond; or a substituted or unsubstituted C6 to C60 arylene group.

In another embodiment, L101 and L102 are the same as or different from each other, and may be each independently a direct bond; or a substituted or unsubstituted C6 to C40 arylene group.

In another embodiment, L101 and L102 are the same as or different from each other, and may be each independently a direct bond; or a C6 to C40 arylene group.

In another embodiment, L101 and L102 are the same as or different from each other, and may be each independently a direct bond; or a C6 to C20 arylene group.

In another embodiment, L101 and L102 are the same as or different from each other, and may be each independently a direct bond; a phenylene group; a naphthalene group; or a biphenylene group.

In one embodiment of the present application, L101 and L102 may be further substituted with deuterium.

In one embodiment of the present application, N-het may be a monocyclic or polycyclic heterocyclic group substituted or unsubstituted and including one or more Ns.

In another embodiment, N-het may be a monocyclic or polycyclic heterocyclic group unsubstituted or substituted with one or more substituents selected from the group consisting of a C6 to C60 aryl group and a C2 to C60 heteroaryl group, and including one or more and three or less Ns.

In another embodiment, N-het may be a substituted or unsubstituted pyridine group; a substituted or unsubstituted pyrimidine group; a substituted or unsubstituted triazine group; a substituted or unsubstituted quinazoline group; a substituted or unsubstituted quinoxaline group; a substituted or unsubstituted benzofuro[3,2-d]pyrimidine group; or a substituted or unsubstituted benzo[4,5]thieno[3,2-d]pyrimidine group.

In one embodiment of the present application, N-het may be unsubstituted or substituted with one or more substituents selected from the group consisting of a C1 to C60 alkyl group; a C6 to C60 aryl group; and a C2 to C60 heteroaryl group, or a substituent linking the substituents.

In one embodiment of the present application, N-het may be unsubstituted or substituted with one or more substituents selected from the group consisting of a phenyl group; a biphenyl group; a naphthyl group; a phenanthrenyl group; a chrysenyl group; a dibenzofuran group; a dibenzothiophene group; a dimethylfluorenyl group; a terphenyl group; and a triphenylenyl group, or a substituent linking the substituents.

In one embodiment of the present application, N-het may be further substituted with deuterium.

In one embodiment of the present application, R101 may be a substituted or unsubstituted C1 to C60 alkyl group; a substituted or unsubstituted C6 to C60 aryl group; a substituted or unsubstituted C2 to C60 heteroaryl group; or —NR103R104.

In another embodiment, R101 may be a substituted or unsubstituted C6 to C60 aryl group; a substituted or unsubstituted C2 to C60 heteroaryl group; or —NR102R103.

In another embodiment, R101 may be a substituted or unsubstituted C6 to C40 aryl group; a substituted or unsubstituted C2 to C40 heteroaryl group; or —NR103R104.

In another embodiment, R101 may be a C6 to C40 aryl group unsubstituted or substituted with a C6 to C40 aryl group; a C2 to C40 heteroaryl group unsubstituted or substituted with a C6 to C40 aryl group; or —NR103R104.

In another embodiment, R101 may be a substituted or unsubstituted phenyl group; a substituted or unsubstituted biphenyl group; a substituted or unsubstituted naphthyl group; a substituted or unsubstituted terphenyl group; a substituted or unsubstituted anthracenyl group; a substituted or unsubstituted dibenzofuran group; a substituted or unsubstituted dibenzothiophene group; a substituted or unsubstituted carbazole group; a substituted or unsubstituted benzocarbazole group; or —NR103R104.

In another embodiment, R101 may be a phenyl group; a biphenyl group; a naphthyl group; a terphenyl group; an anthracenyl group; a dibenzofuran group; a dibenzothiophene group; a carbazole group unsubstituted or substituted with a phenyl group; a benzocarbazole group; or —NR103R104.

In one embodiment of the present application, R102 may be hydrogen; deuterium; a substituted or unsubstituted C1 to C60 alkyl group; a substituted or unsubstituted C6 to C60 aryl group; a substituted or unsubstituted C2 to C60 heteroaryl group; or —NR102R103.

In another embodiment, R101 may be a substituted or unsubstituted C6 to C60 aryl group; a substituted or unsubstituted C2 to C60 heteroaryl group; or —NR103R104.

In another embodiment, R102 may be hydrogen; deuterium; a substituted or unsubstituted C6 to C40 aryl group; a substituted or unsubstituted C2 to C40 heteroaryl group; or —NR103R104.

In another embodiment, R102 may be hydrogen; deuterium; a C6 to C40 aryl group unsubstituted or substituted with a C6 to C40 aryl group; a C2 to C40 heteroaryl group unsubstituted or substituted with a C6 to C40 aryl group; or —NR103R104. In another embodiment, R102 may be hydrogen; deuterium; a substituted or unsubstituted phenyl group; a substituted or unsubstituted biphenyl group; a substituted or unsubstituted naphthyl group; a substituted or unsubstituted terphenyl group; a substituted or unsubstituted anthracenyl group; a substituted or unsubstituted dibenzofuran group; a substituted or unsubstituted dibenzothiophene group; a substituted or unsubstituted carbazole group; a substituted or unsubstituted benzocarbazole group; or —NR103R104.

In another embodiment, R102 may be hydrogen; deuterium; a phenyl group; a biphenyl group; a naphthyl group; a terphenyl group; an anthracenyl group; a dibenzofuran group; a dibenzothiophene group; a carbazole group unsubstituted or substituted with a phenyl group; a benzocarbazole group; or —NR103R104.

In one embodiment of the present application, R101 and R102 may be further substituted with deuterium.

In one embodiment of the present application, R103 and R104 are the same as or different from each other, and may be each independently a substituted or unsubstituted C1 to C60 alkyl group; a substituted or unsubstituted C6 to C60 aryl group; or a substituted or unsubstituted C2 to C60 heteroaryl group.

In another embodiment, R103 and R104 are the same as or different from each other, and may be each independently a C6 to C60 aryl group unsubstituted or substituted with a C1 to C60 alkyl group or a C6 to C60 aryl group; or a C2 to C60 heteroaryl group.

In another embodiment, R103 and R104 are the same as or different from each other, and may be each independently a C6 to C40 aryl group unsubstituted or substituted with a C1 to C40 alkyl group or a C6 to C40 aryl group; or a C2 to C40 heteroaryl group.

In another embodiment, R103 and R104 are the same as or different from each other, and may be each independently a phenyl group unsubstituted or substituted with a naphthyl group; a biphenyl group; a naphthyl group; a dimethylfluorenyl group; a dibenzofuran group; or a dibenzothiophene group.

In one embodiment of the present application, R301 may be hydrogen; or deuterium.

In one embodiment of the present application, Chemical Formula A may have a deuterium content of 0% to 100%.

In another embodiment, Chemical Formula A may have a deuterium content of 08; or 30% to 100%.

In another embodiment, Chemical Formula A may have a deuterium content of 08, or 35% to 100%, 40% to 100%, 45% to 100% or 50% to 100%.

In one embodiment of the present application, Chemical Formula B may have a deuterium content of 0% to 100%.

In another embodiment, Chemical Formula B may have a deuterium content of 08; or 10% to 100%.

In another embodiment, Chemical Formula B may have a deuterium content of 0%, or 10% to 1008, 15% to 100%, 20% to 100% or 25% to 100%.

In one embodiment of the present application, the heterocyclic compound of Chemical Formula A may be represented by any one of the following compounds.

-continued
2-1
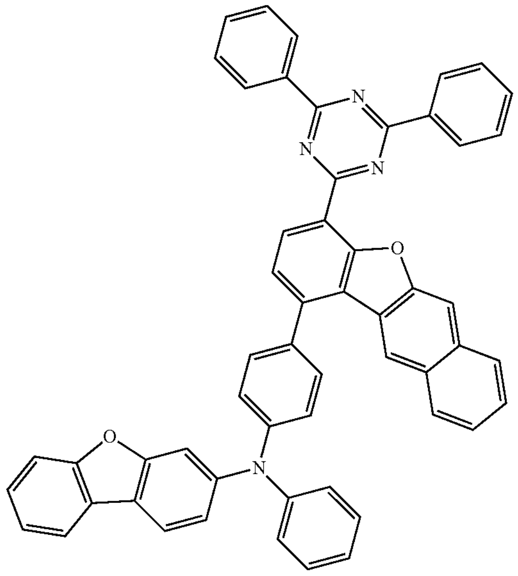
2-2
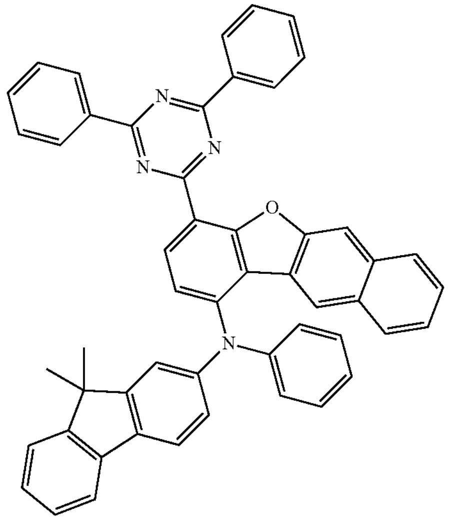
2-3
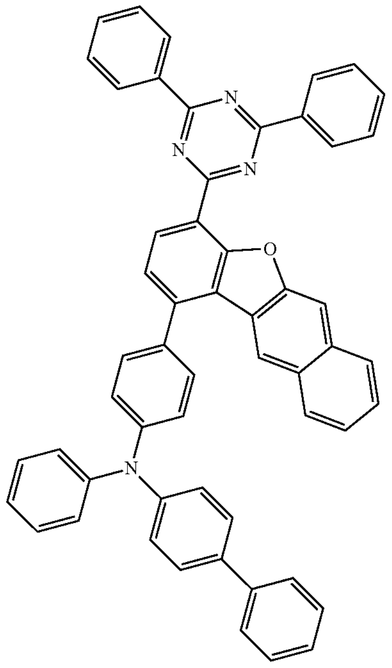
2-4
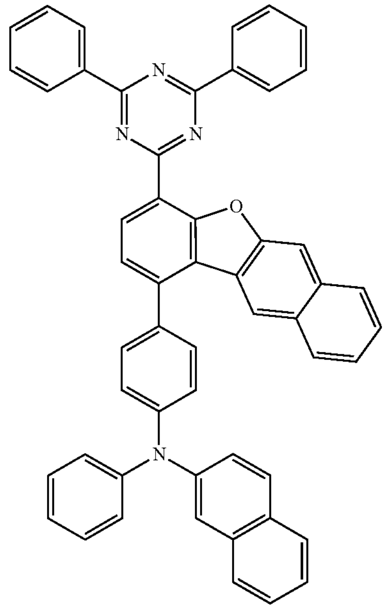

-continued
2-5
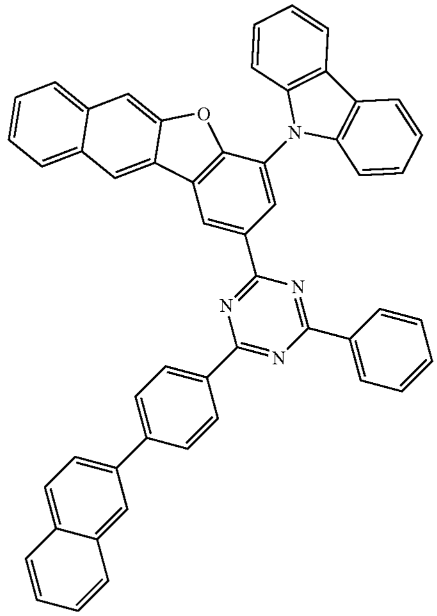
2-6
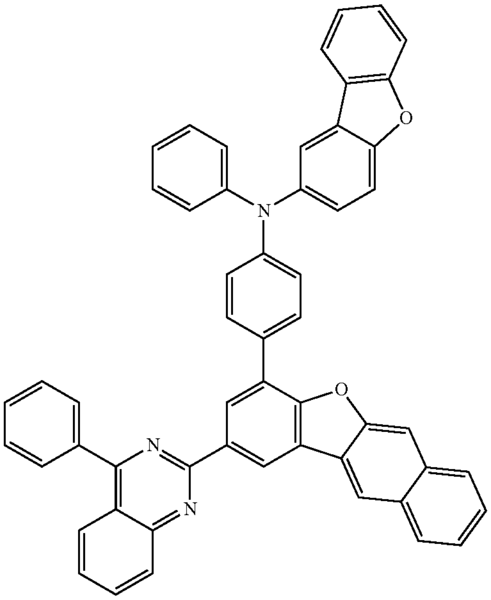
-continued
2-7
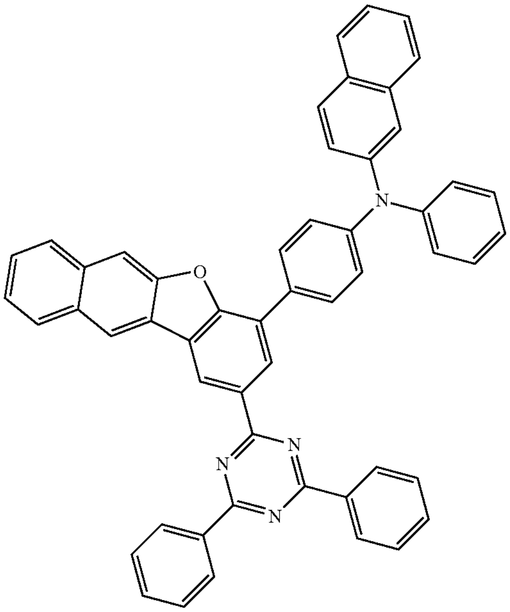
2-8
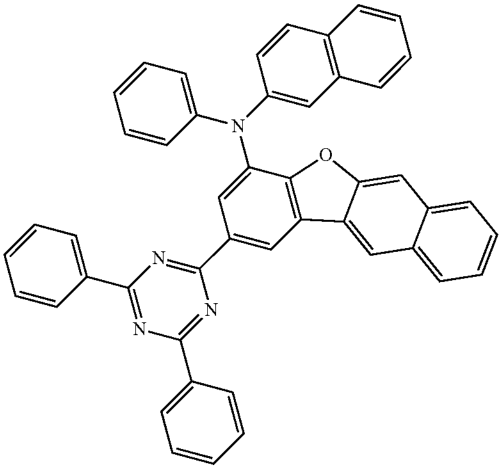
2-9
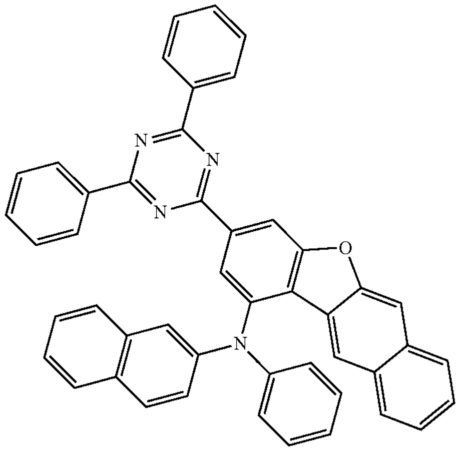

-continued
2-10
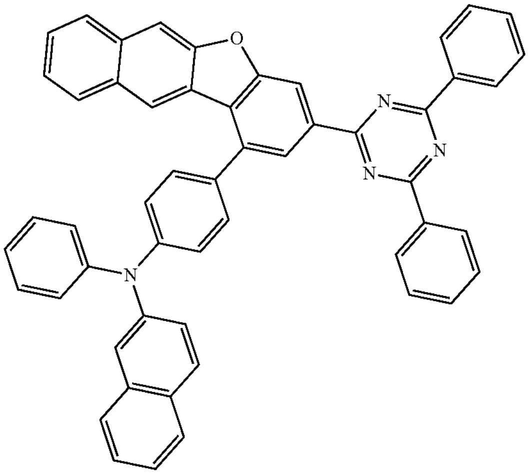
2-11
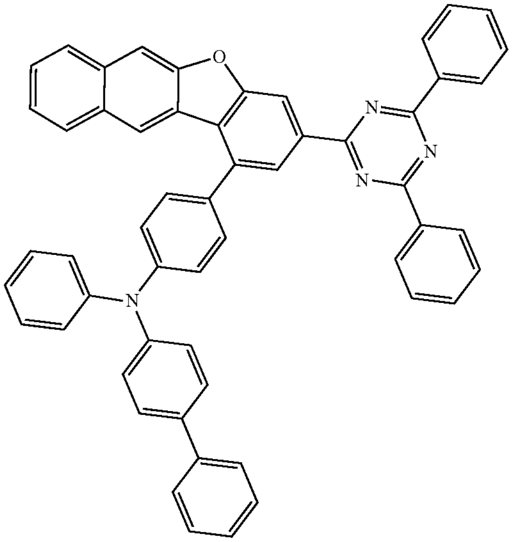
2-12
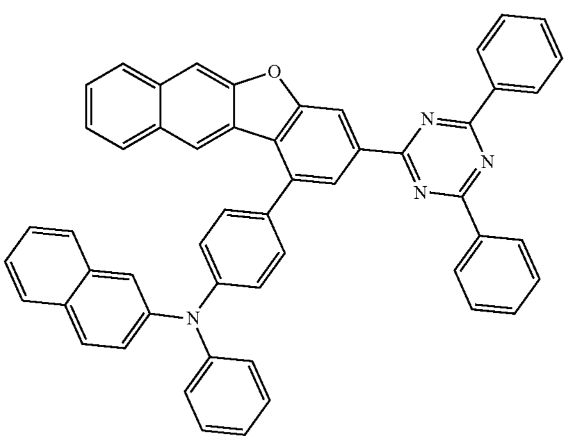
-continued
2-13
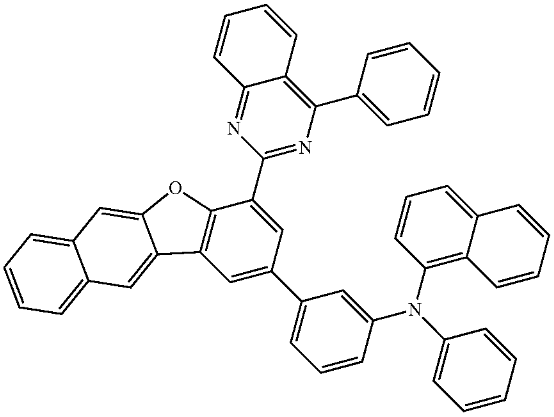
2-14
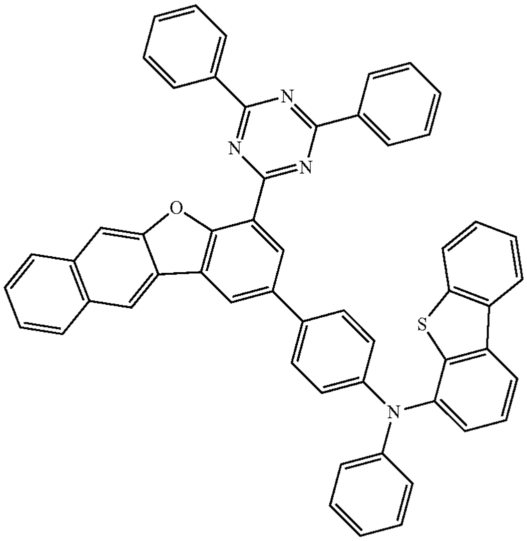
2-15
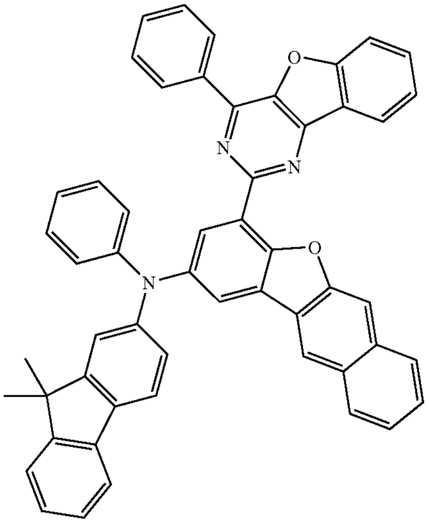

-continued
2-16
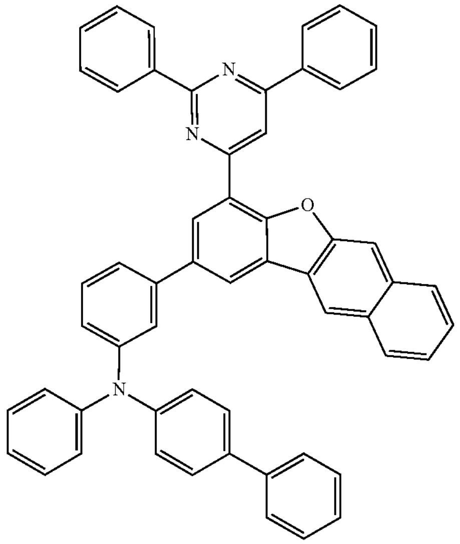
2-17
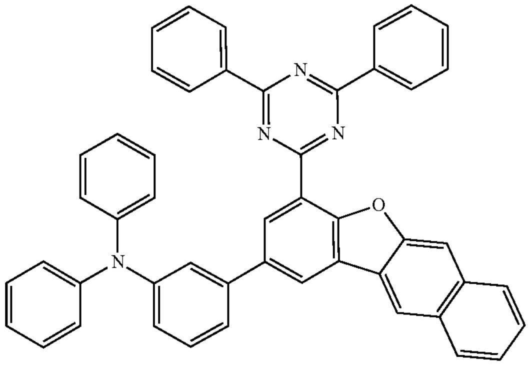
2-18
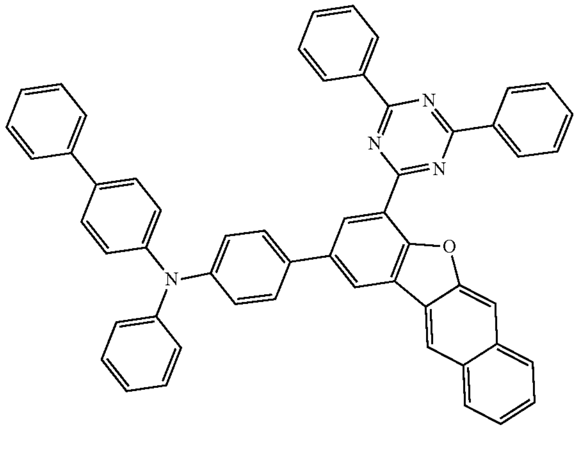
-continued
2-19
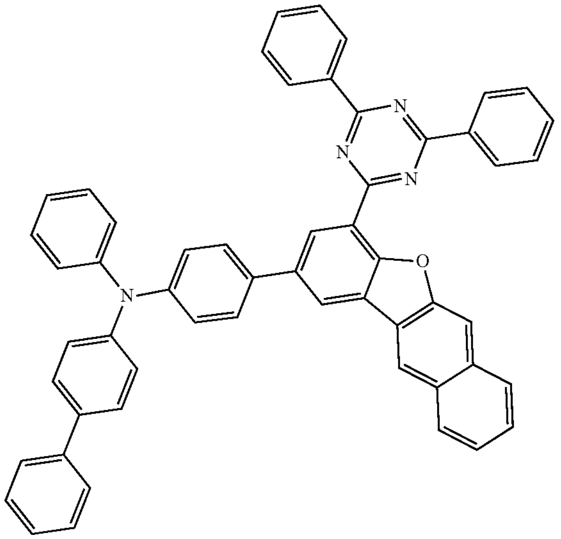
2-20
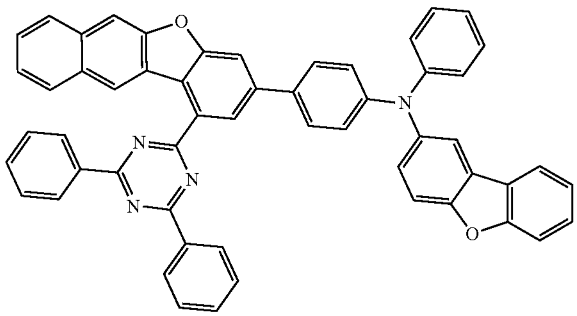
2-21
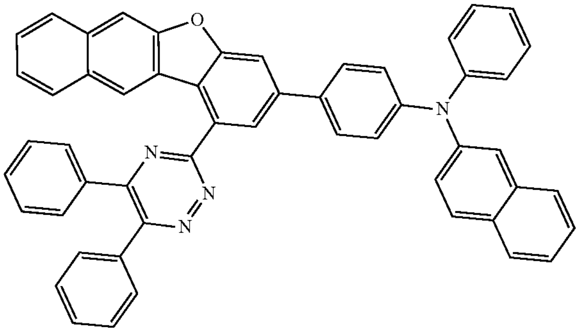

-continued
2-22
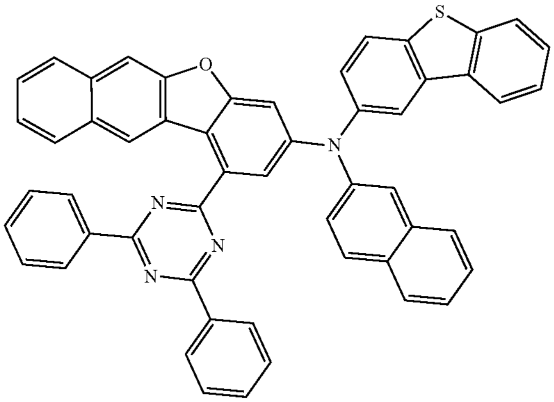
2-23
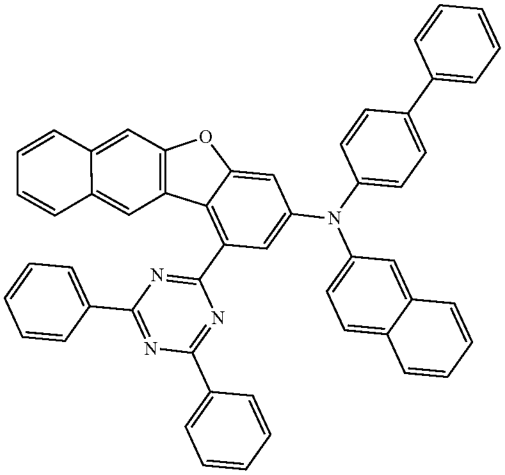
2-24
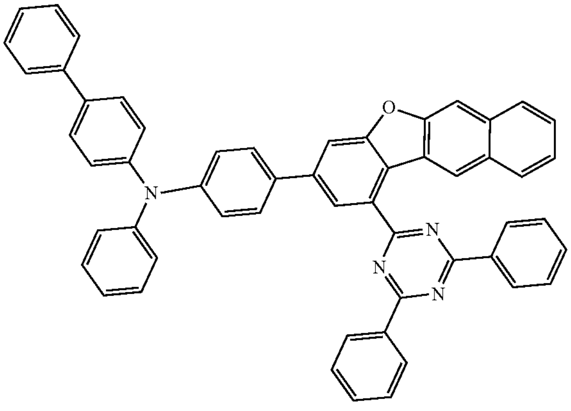
-continued
2-25
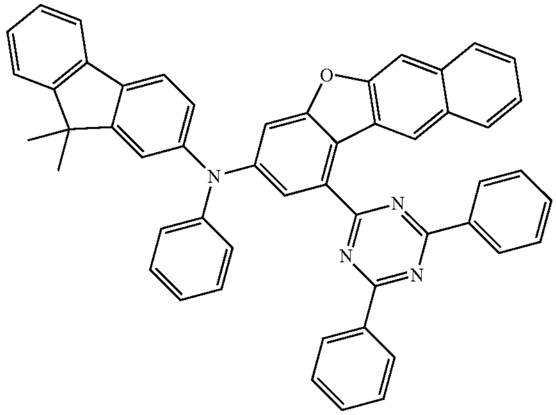
2-26
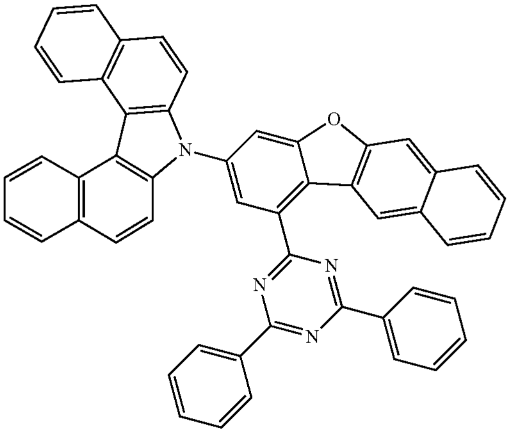
2-27
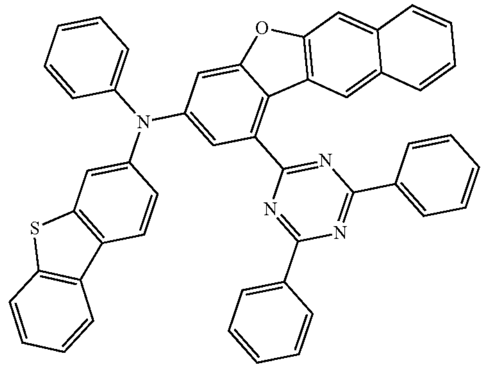
2-28
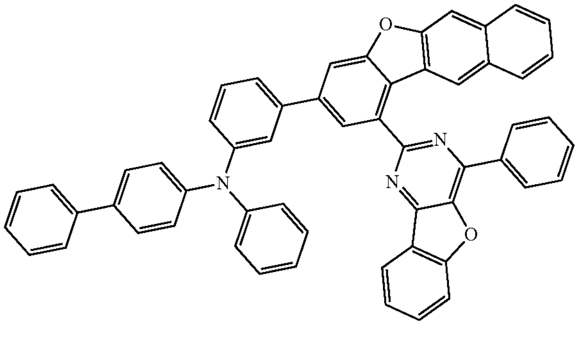

-continued
2-29
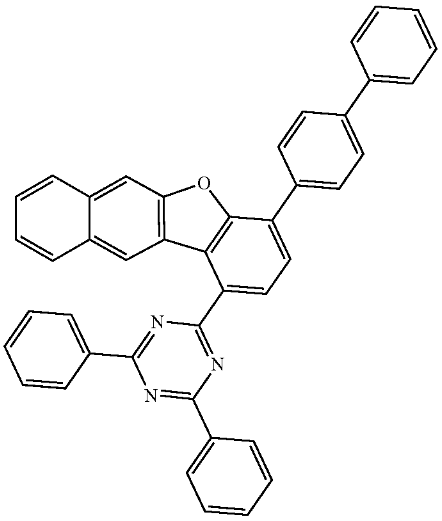
2-30
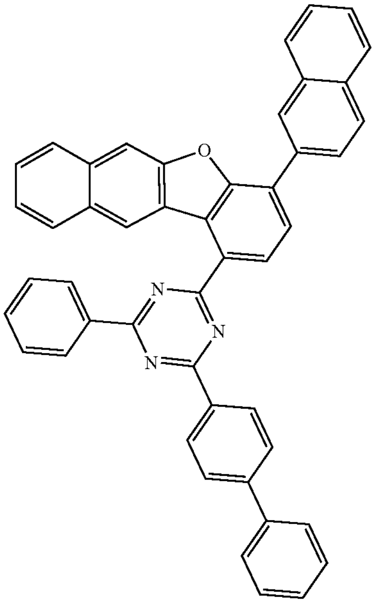
-continued
2-31
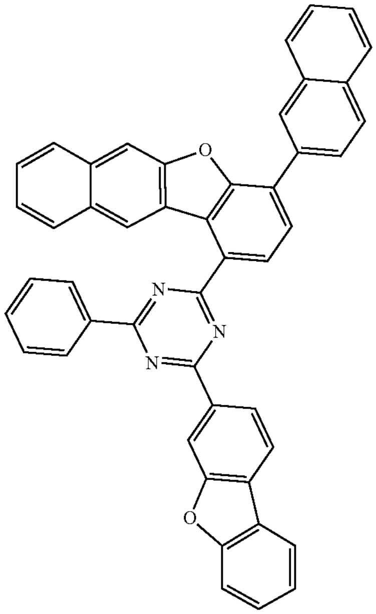
2-32
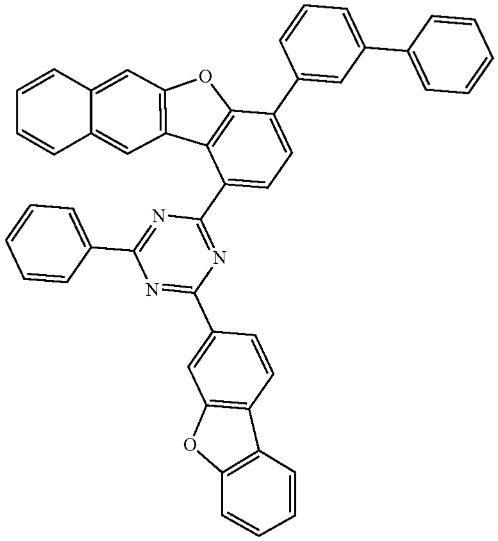

-continued
2-33
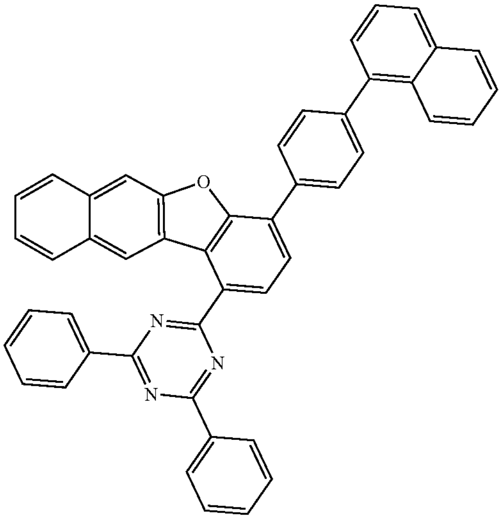
2-34
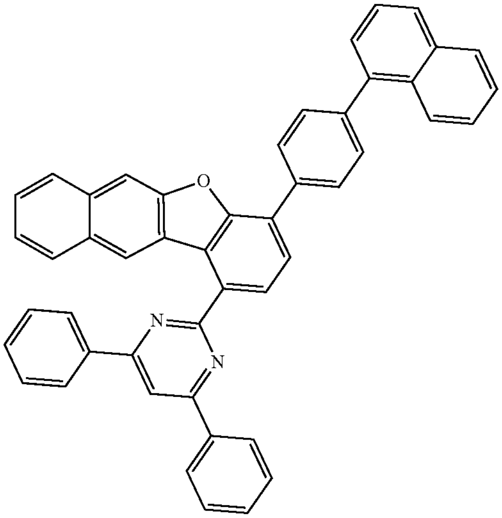
2-35
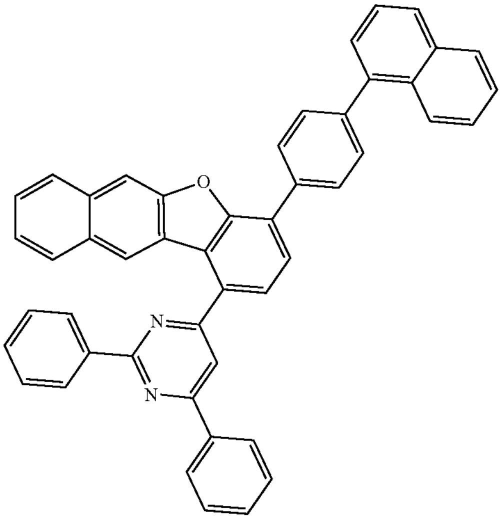
-continued
2-36
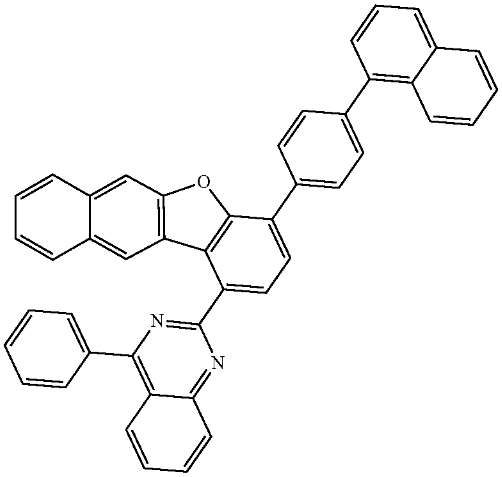
2-37
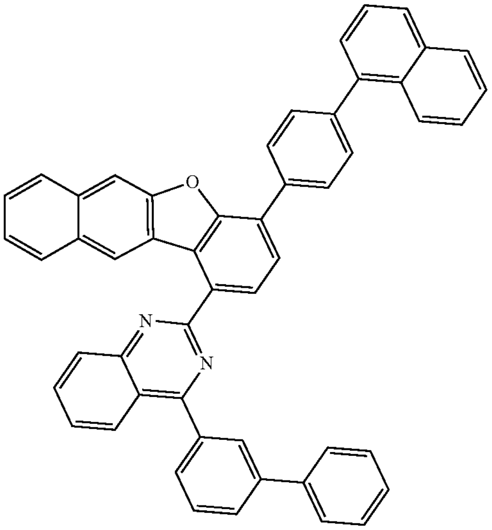
2-38
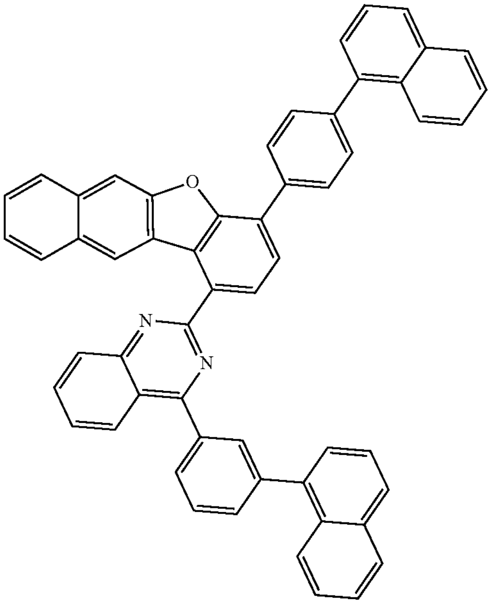

-continued
2-39
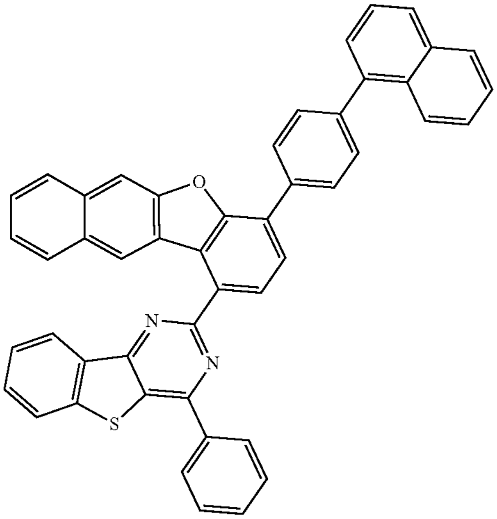
2-40
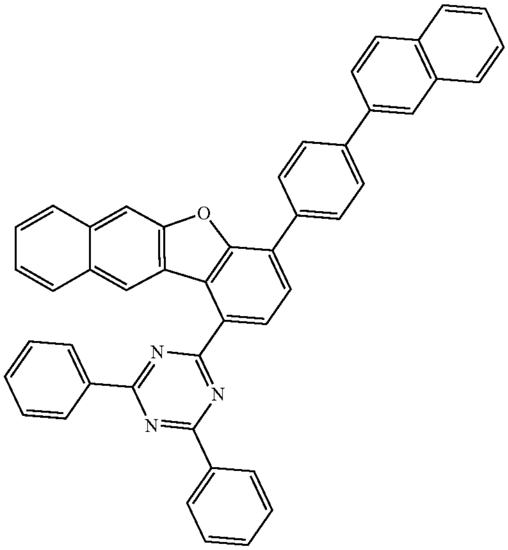
2-41
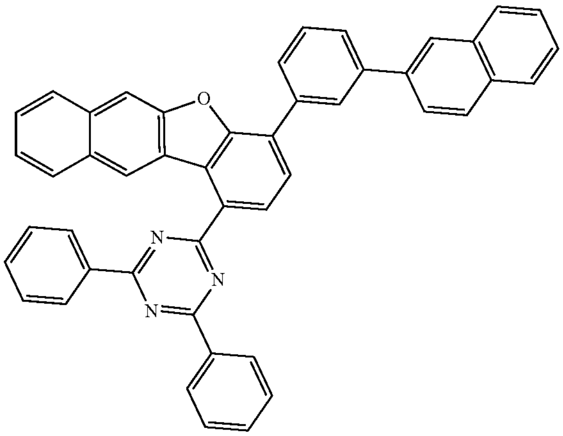
-continued
2-42
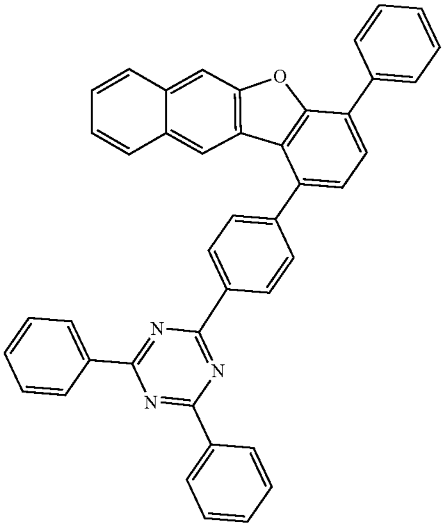
2-43
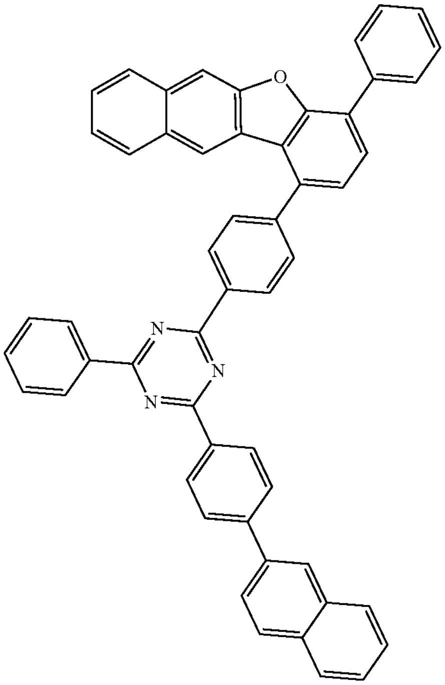

-continued
2-44
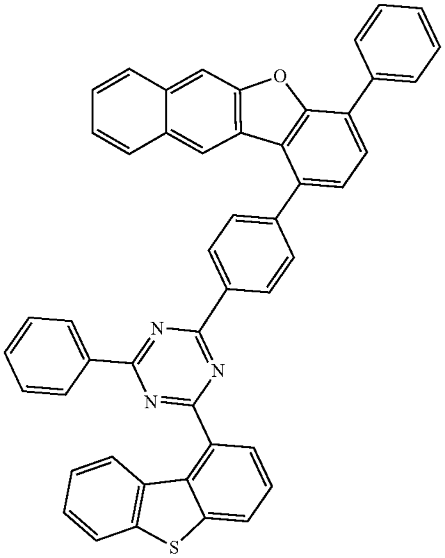
2-45
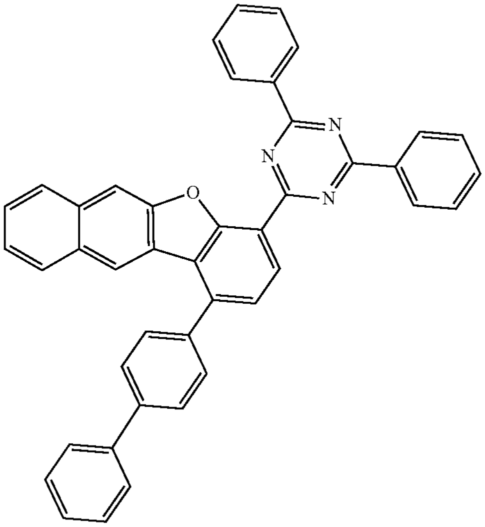
-continued
2-46
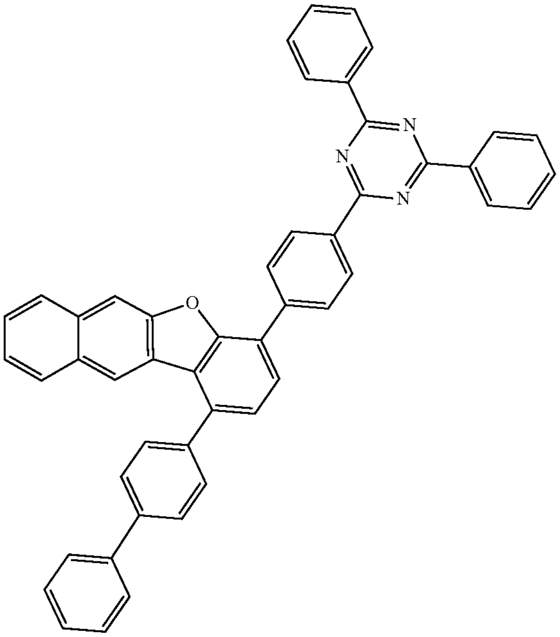
2-47
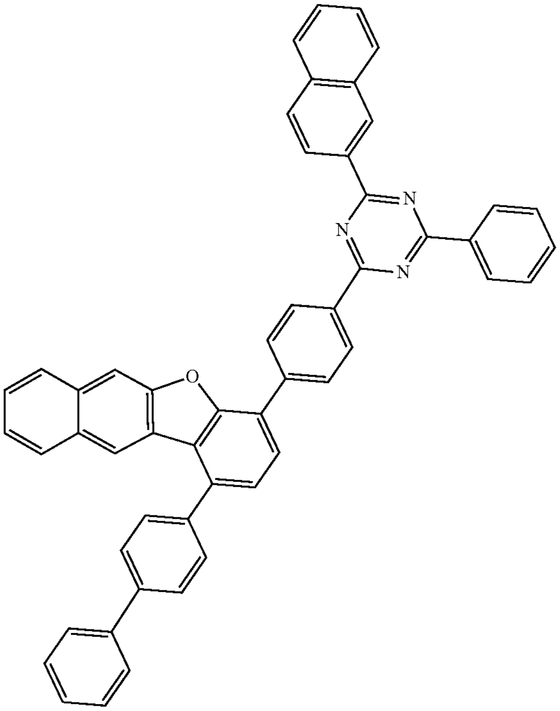

-continued
2-48
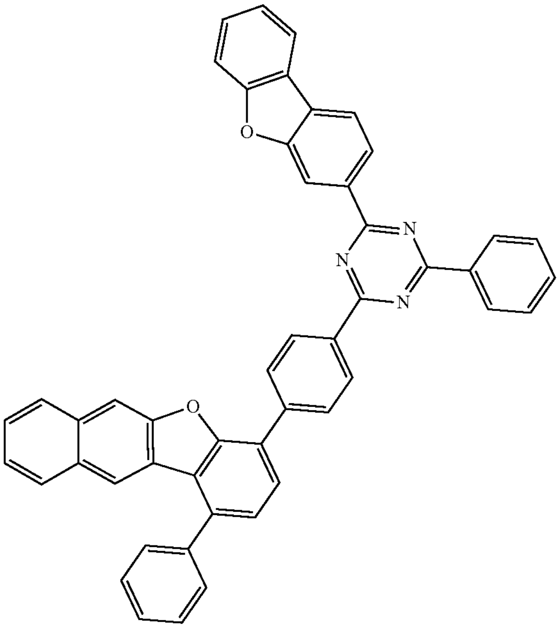
2-49
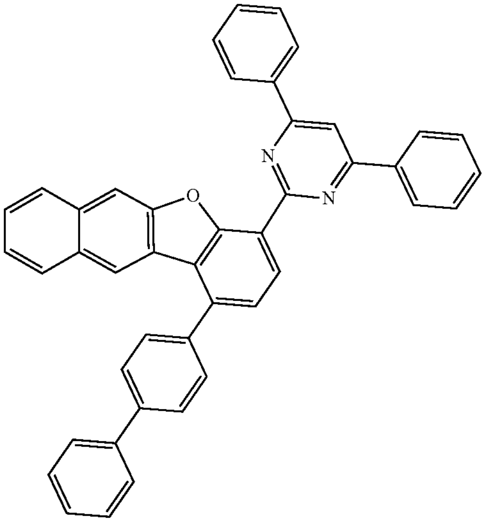
-continued
2-50
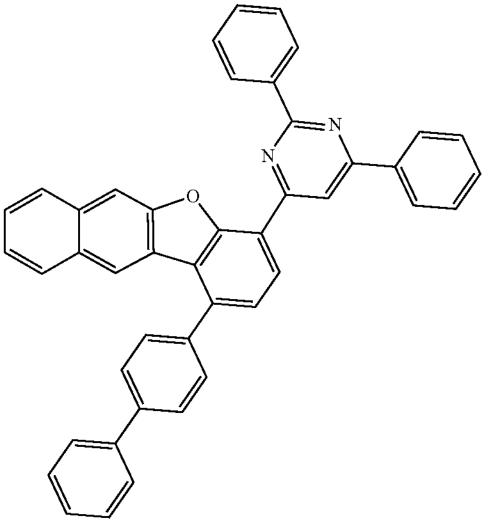
2-51
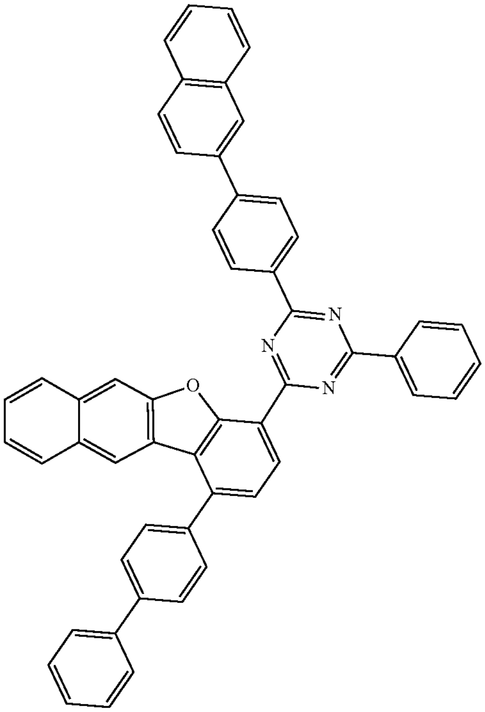

-continued
2-52
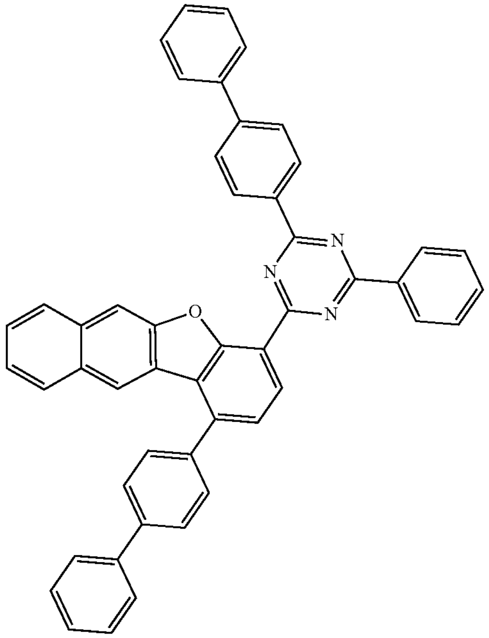
2-53
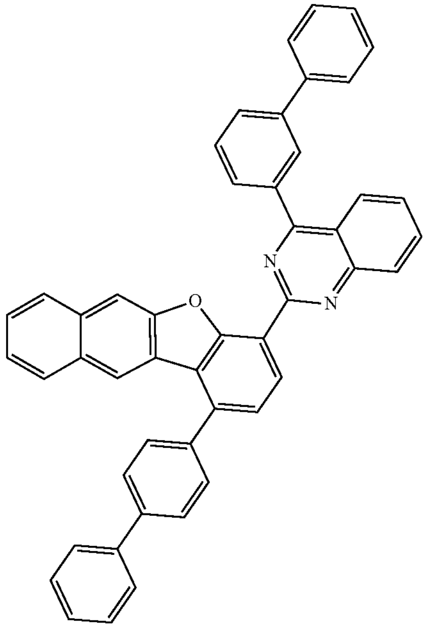
-continued
2-54
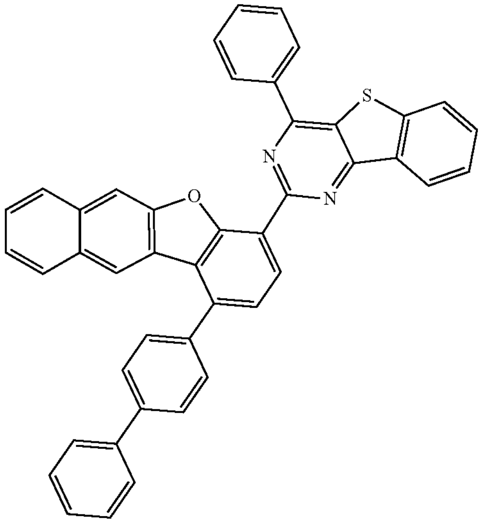
2-55
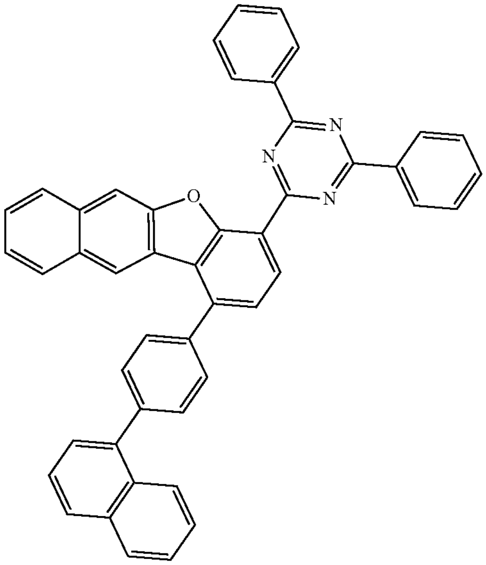
2-56
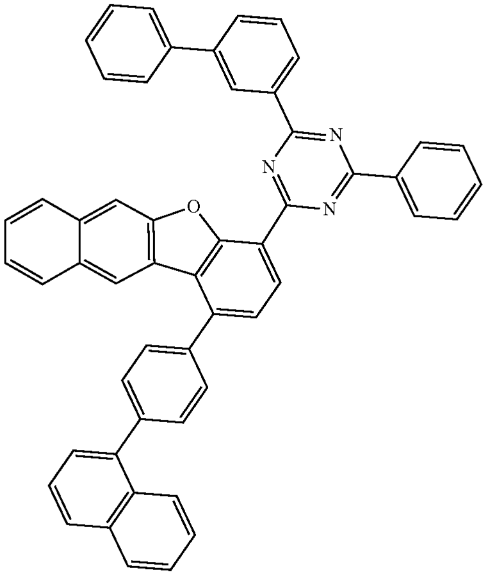

-continued
2-57
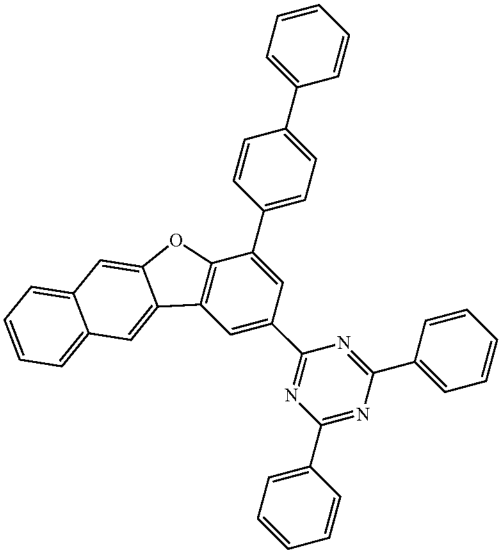
2-58
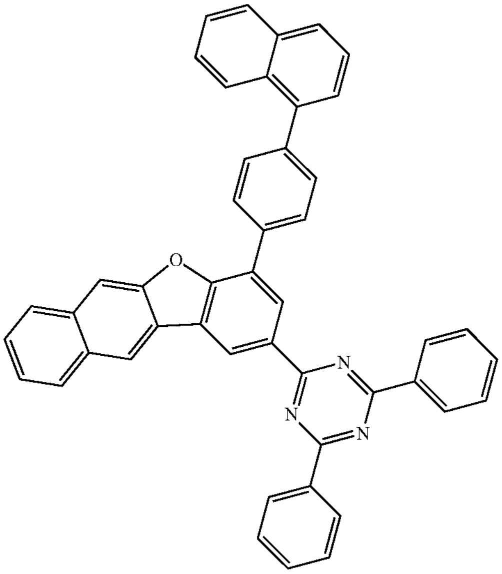
-continued
2-59
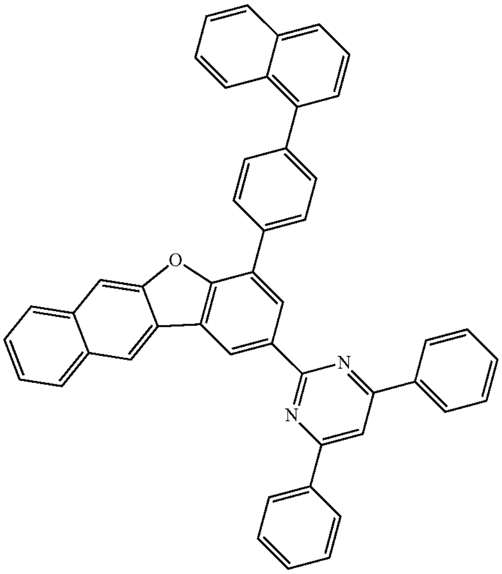
2-60
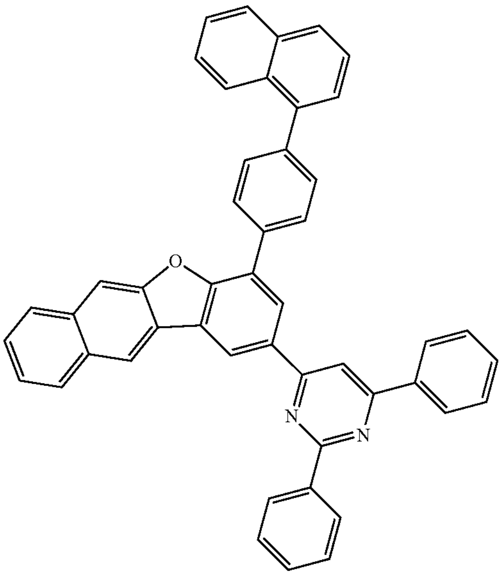

-continued
2-61
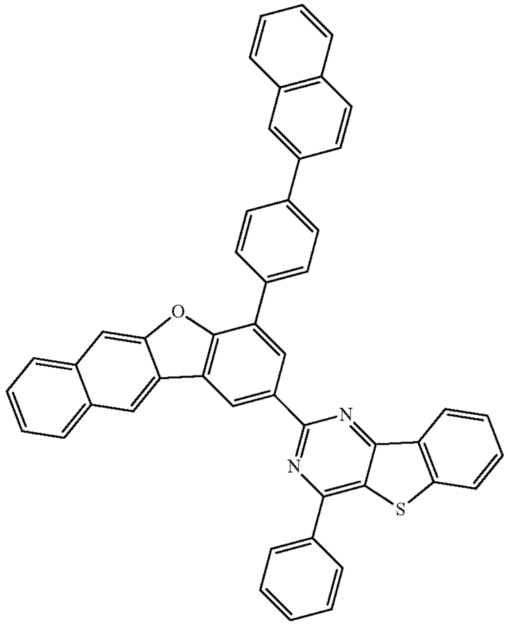
2-62
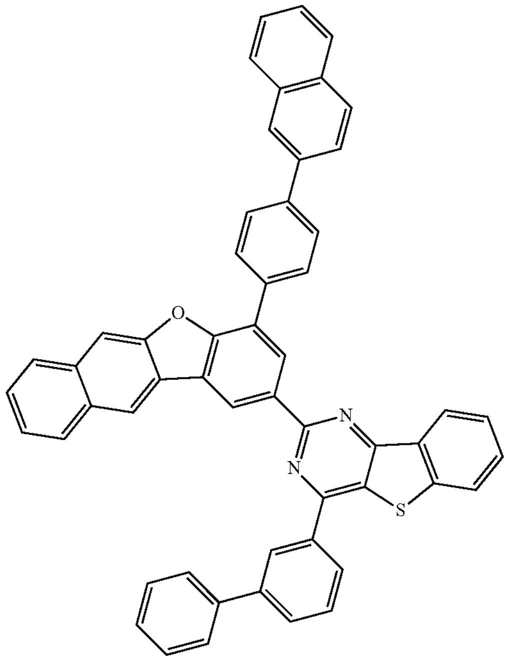
-continued
2-63
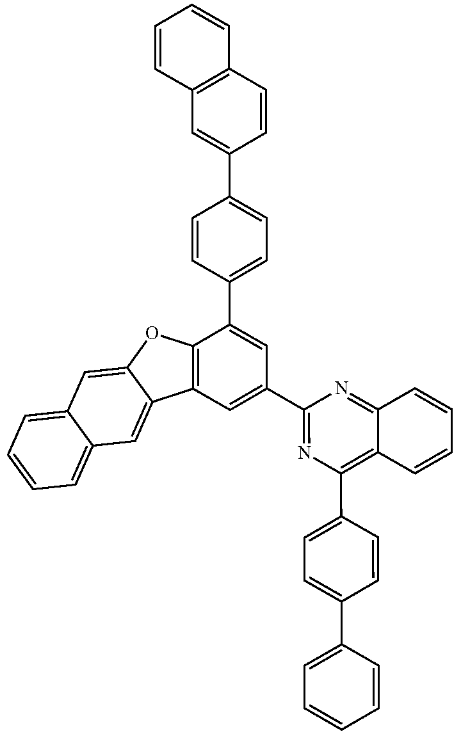
2-64
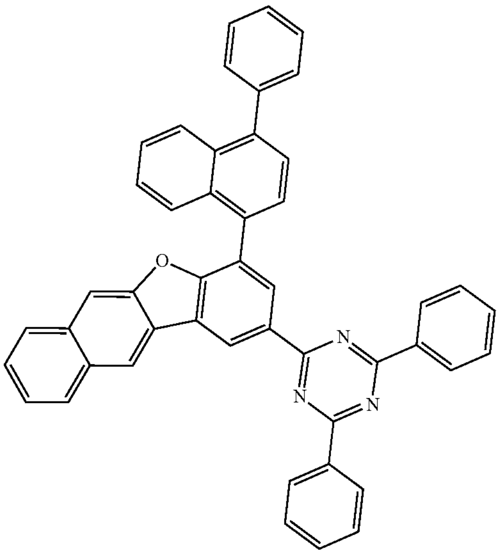

-continued
2-65
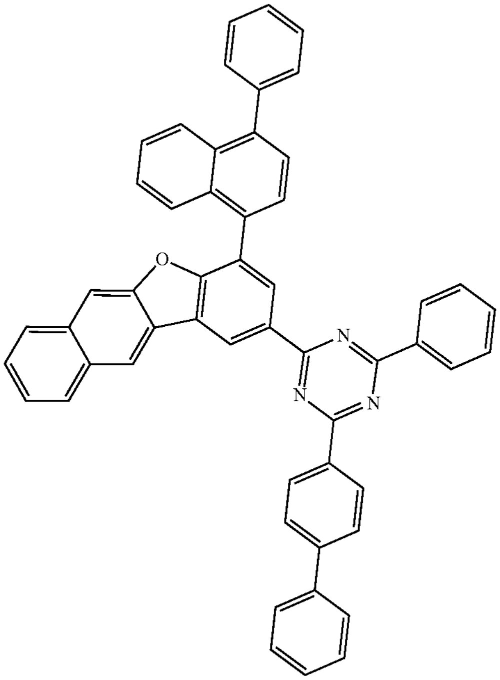
2-66
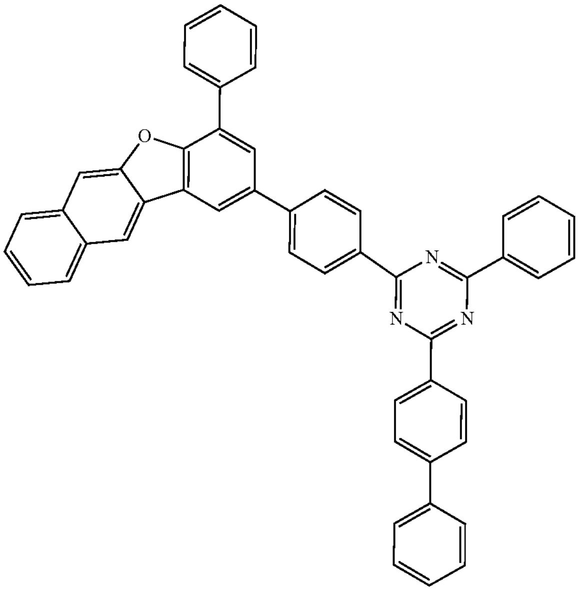
-continued
2-67
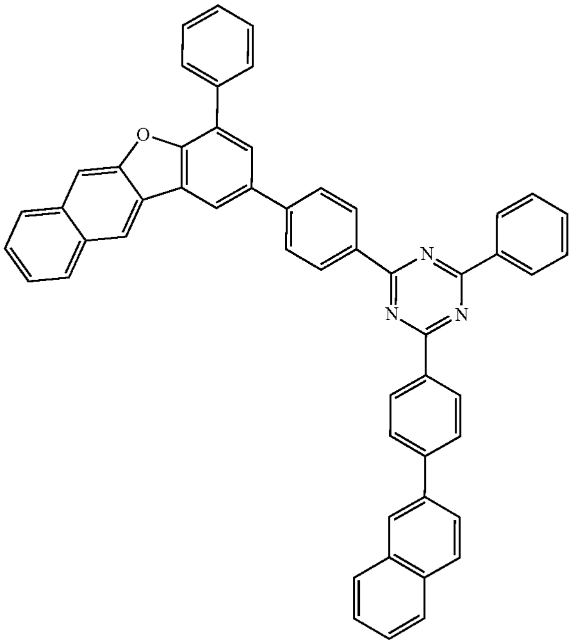
2-68
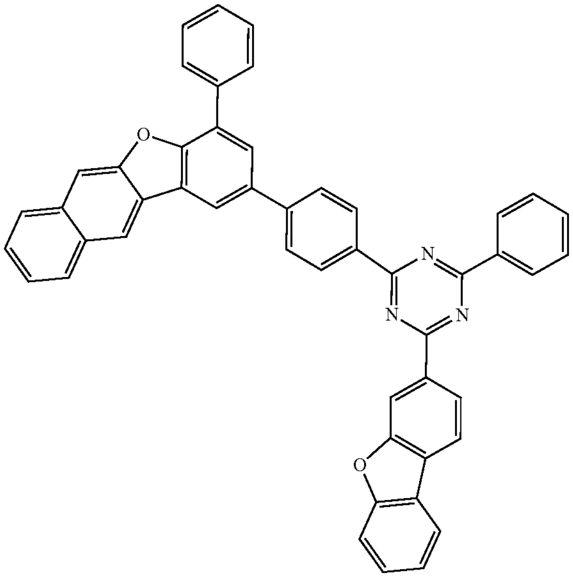

-continued
2-69
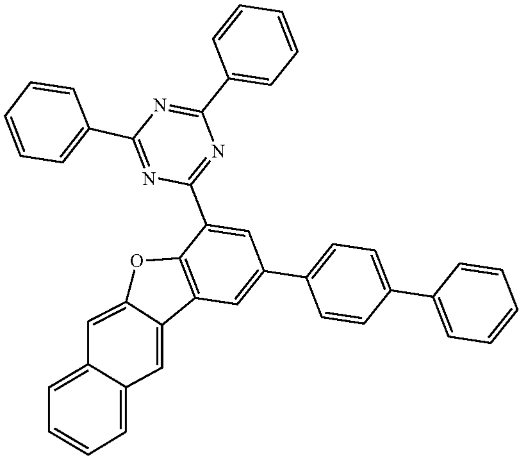
2-70
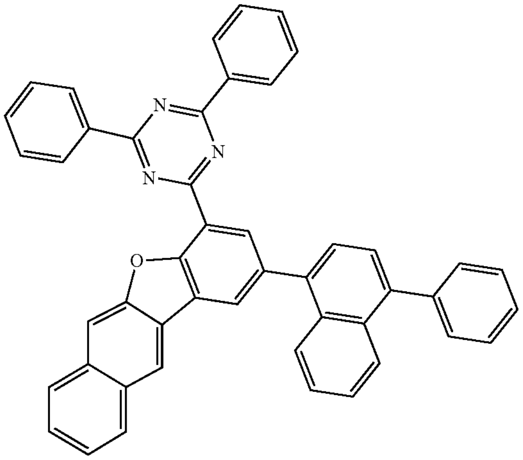
2-71
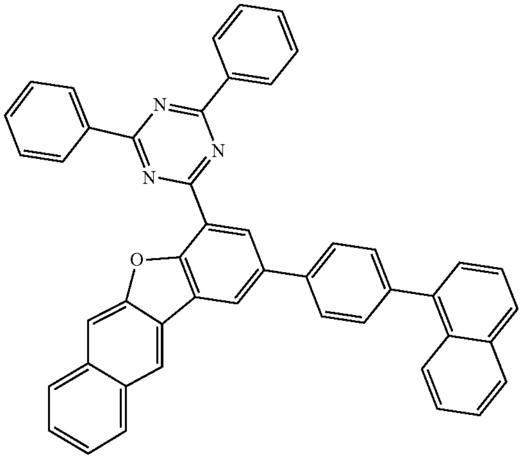
-continued
2-72
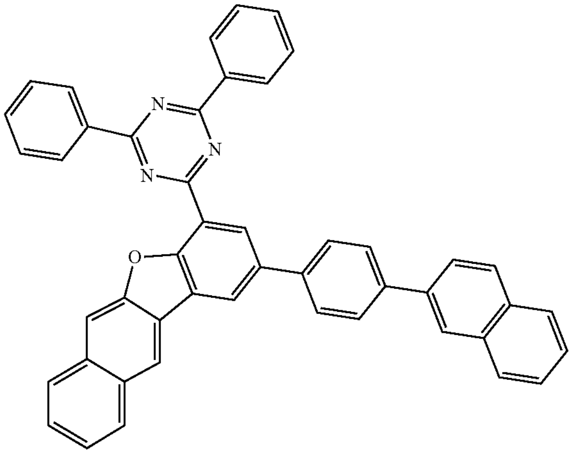
2-73
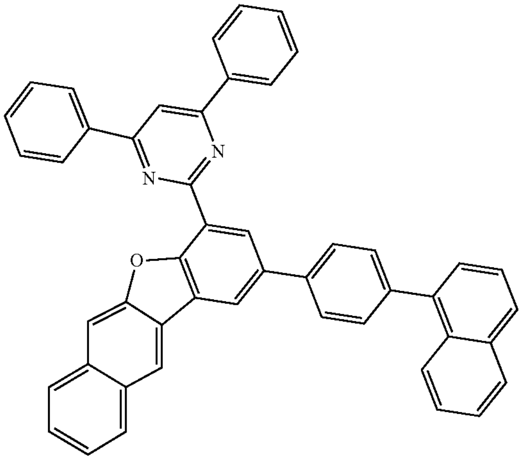
2-74
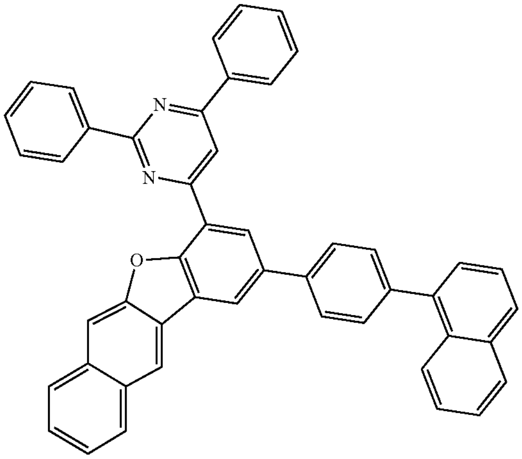

-continued
2-75
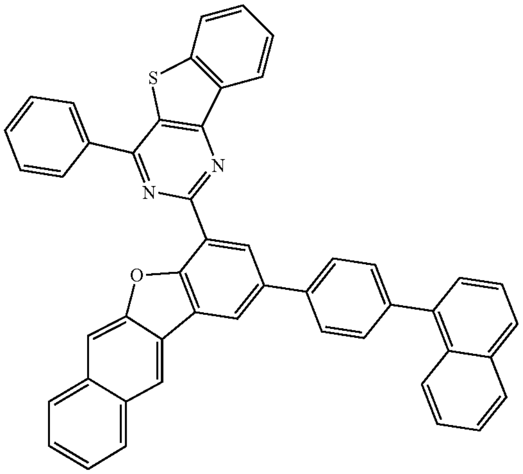
2-76
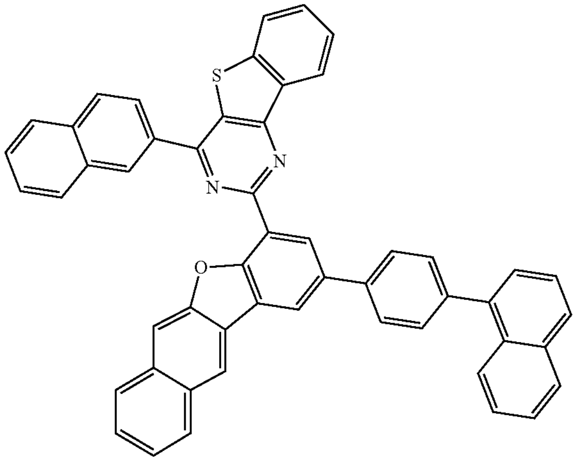
2-77
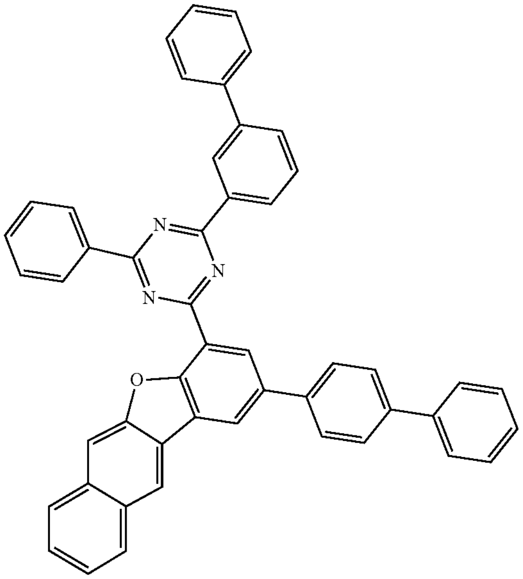
-continued
2-78
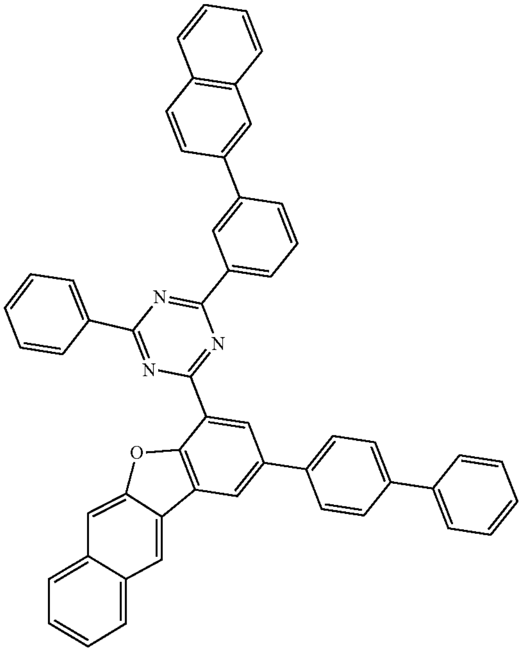
2-79
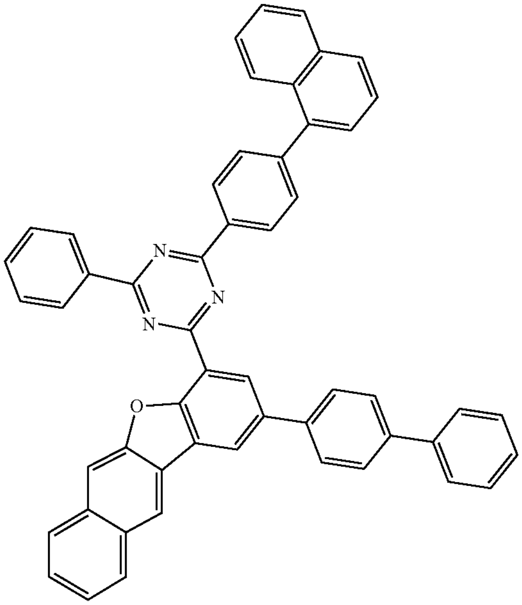

-continued
2-80
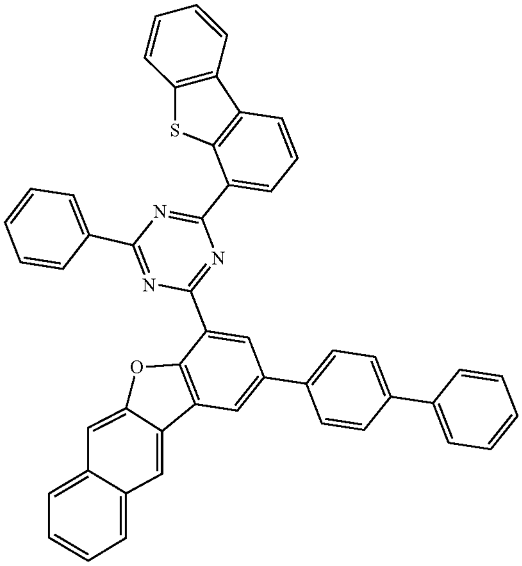
2-81
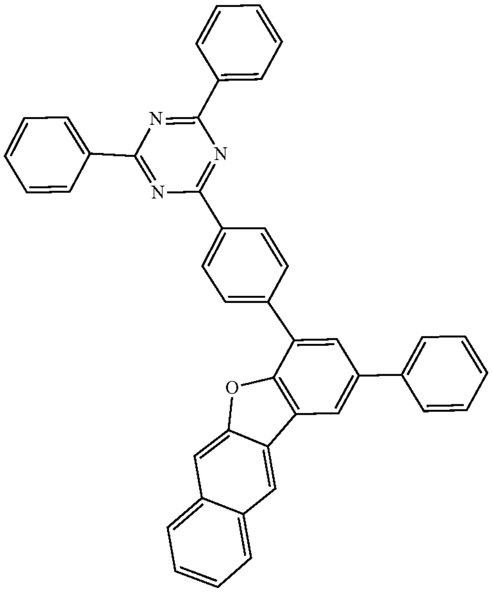
-continued
2-82
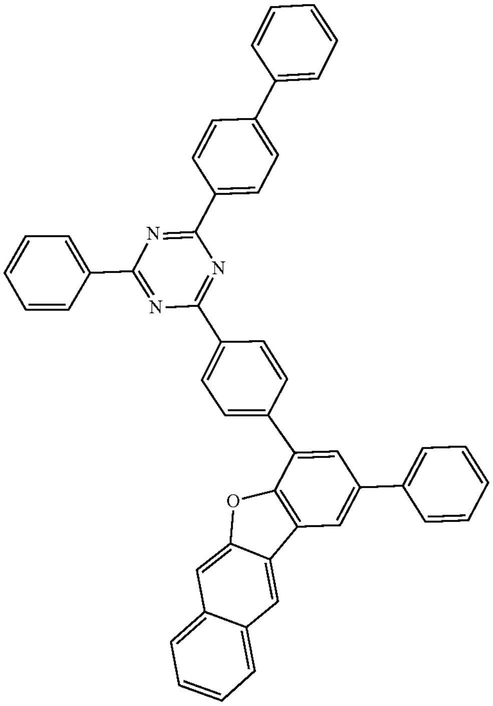
2-83
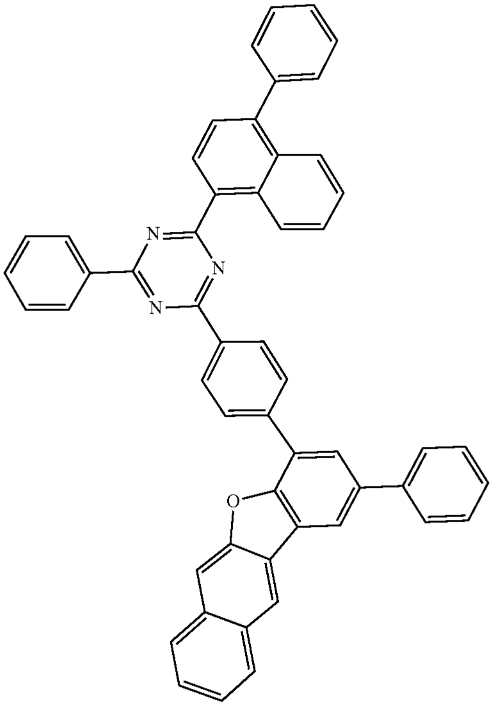

-continued
2-84
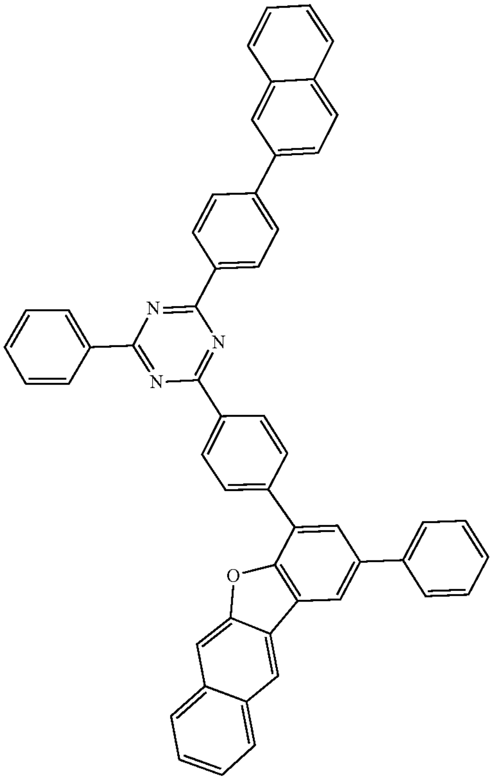
2-85
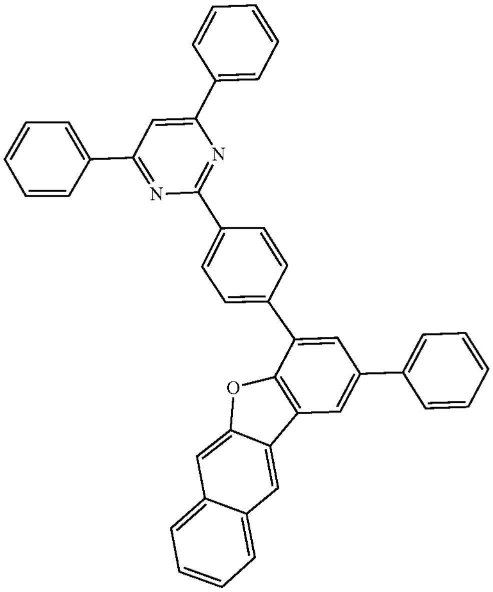
-continued
2-86
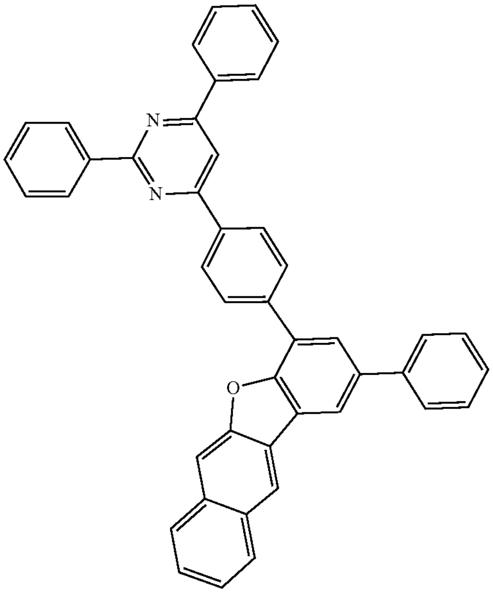
2-87
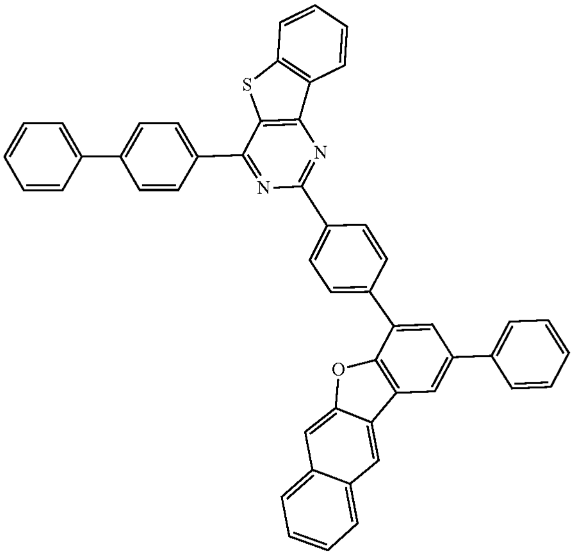

-continued
2-88
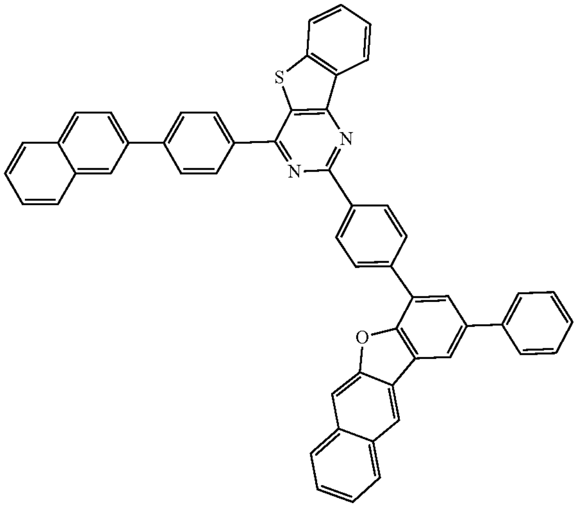
2-89
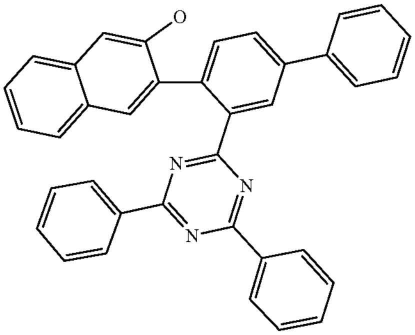
2-90
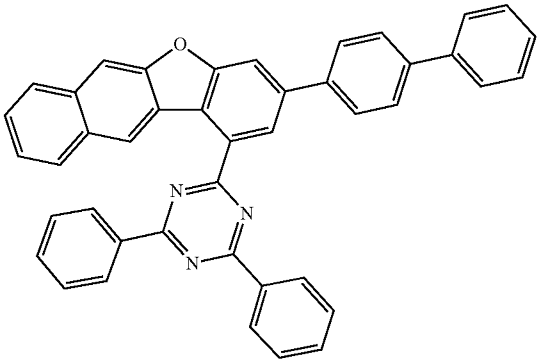
-continued
2-91
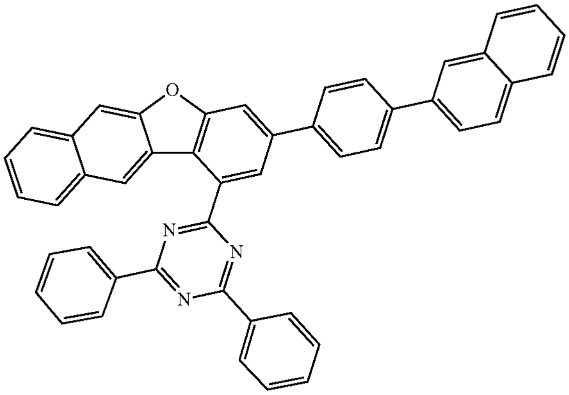
2-92
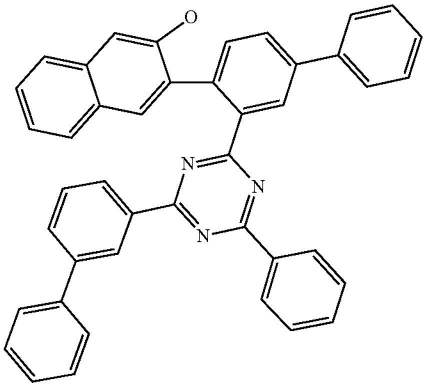
2-93
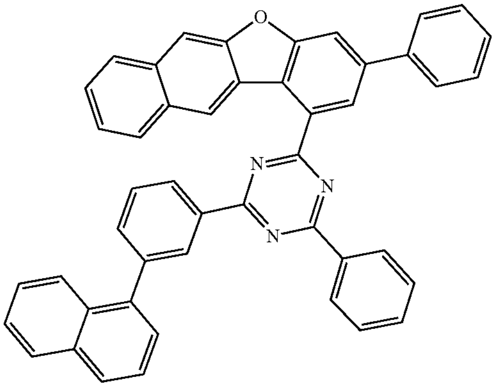
2-94
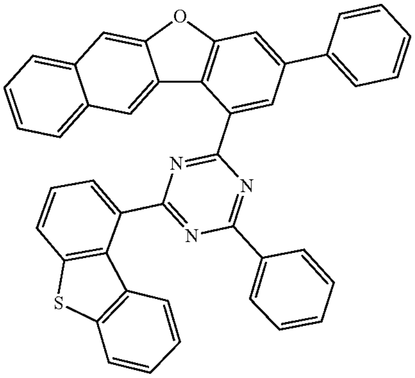

-continued
2-95
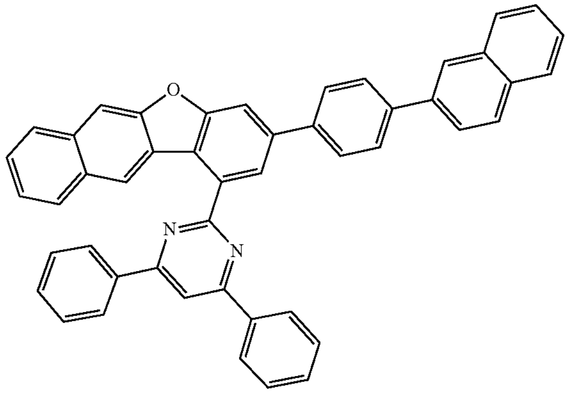
2-96
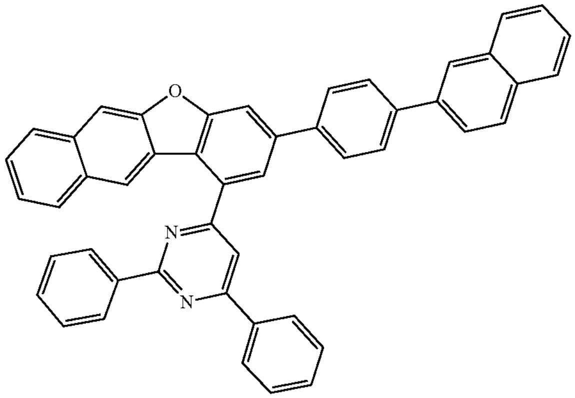
2-97
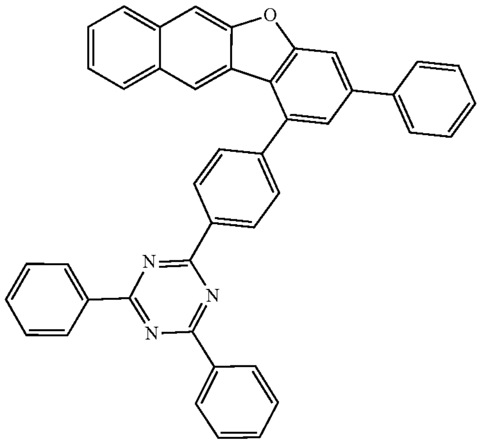
-continued
2-98
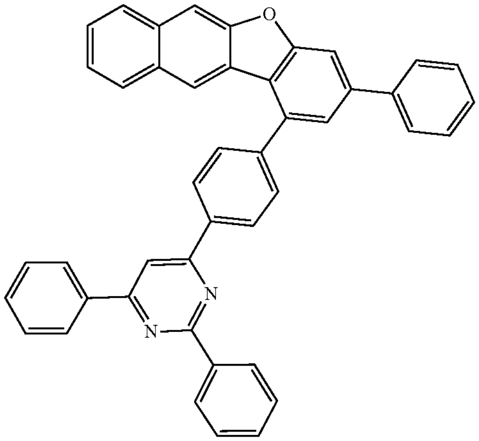
2-99
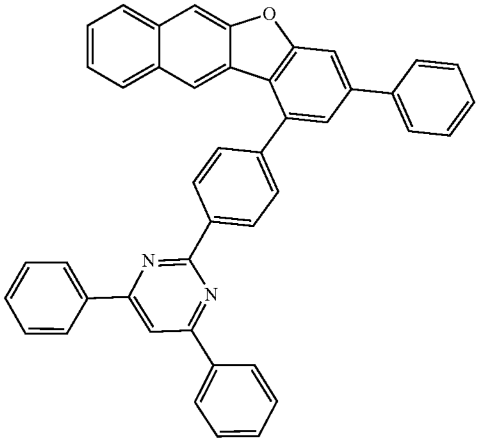
2-100
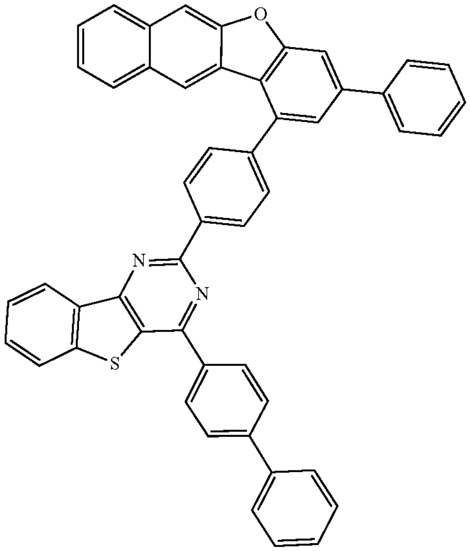

-continued
2-101
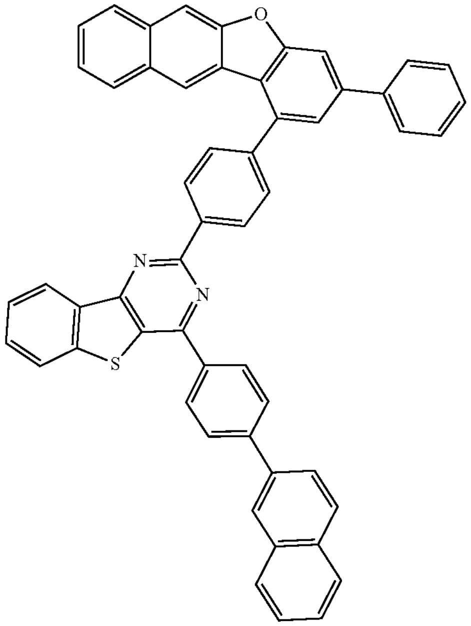
2-102
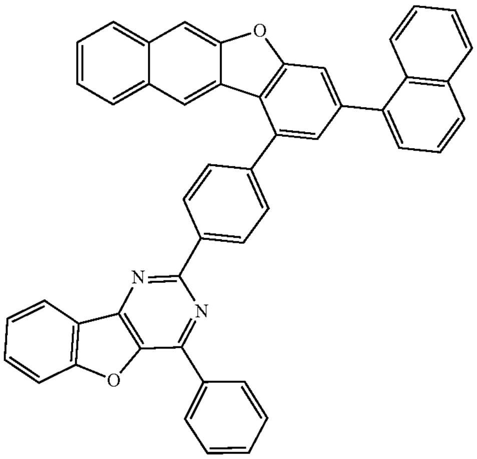
2-103
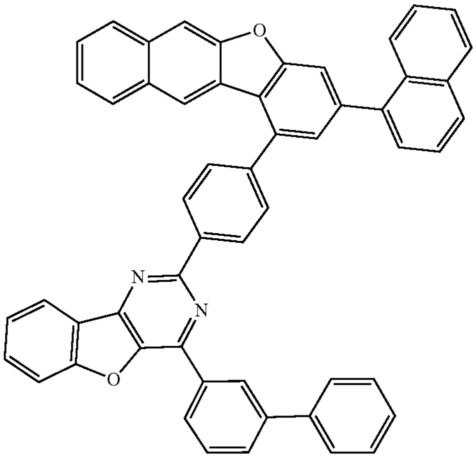
-continued
2-104
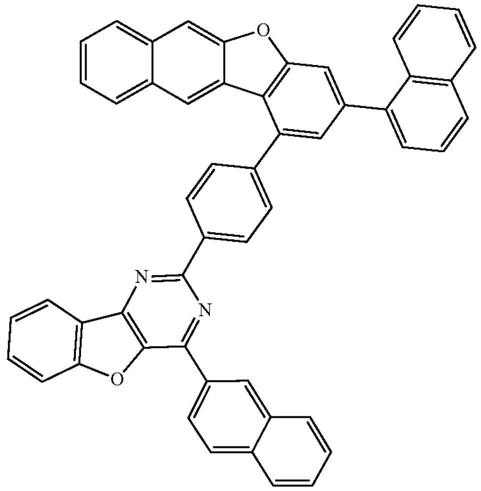
2-105
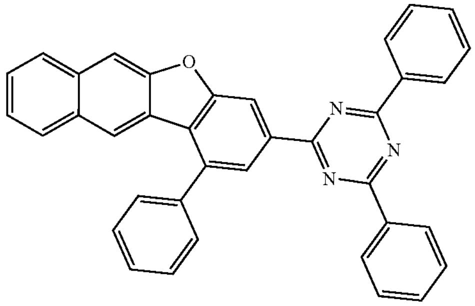
2-106
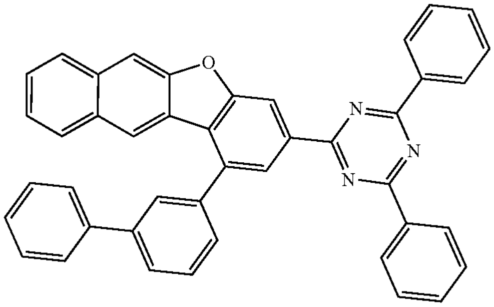
2-107
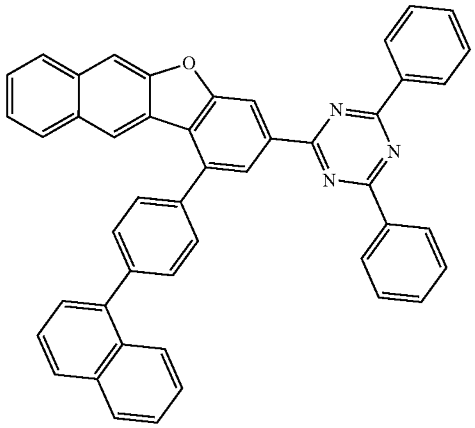

-continued
2-108
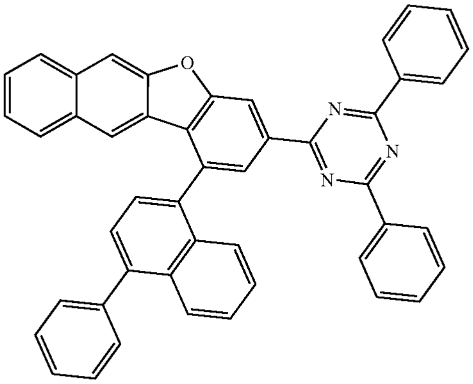
2-109
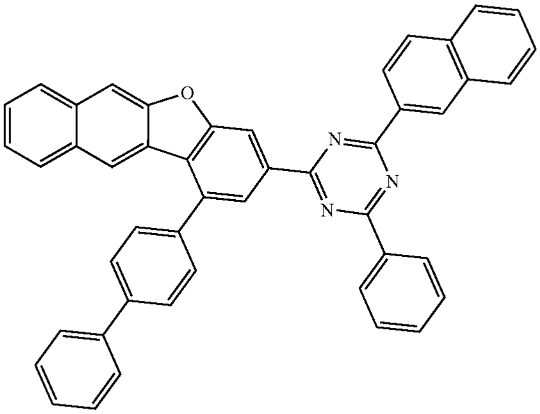
2-110
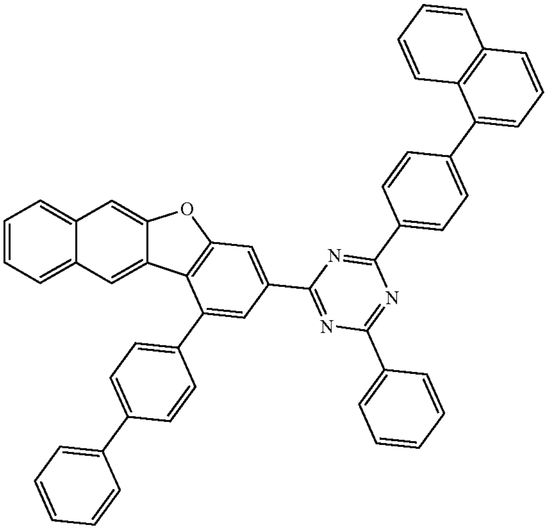
-continued
2-111
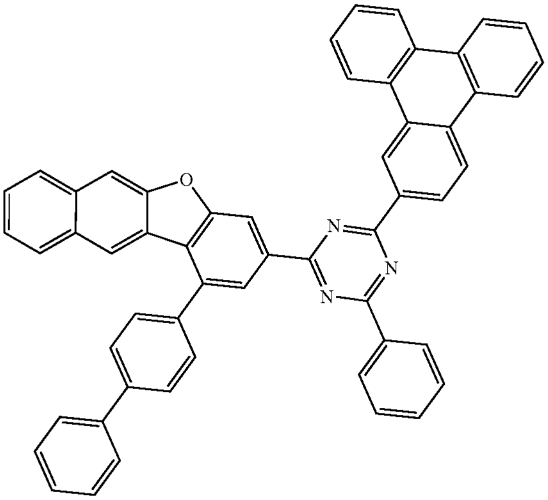
2-112
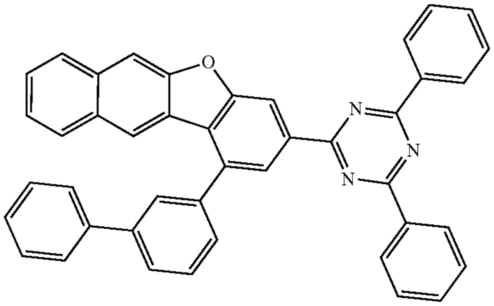
2-113
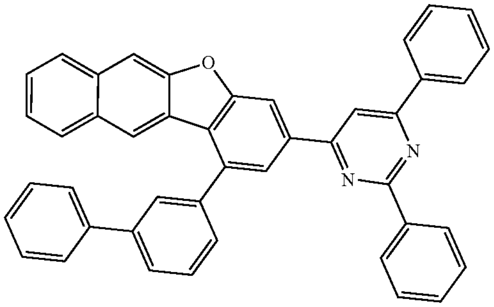
2-114
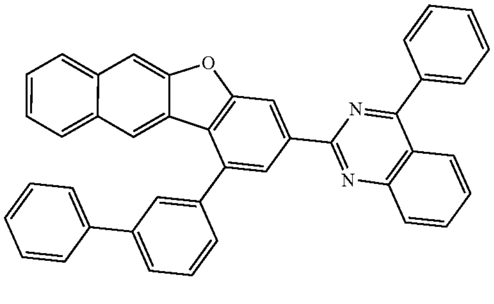

-continued
2-115
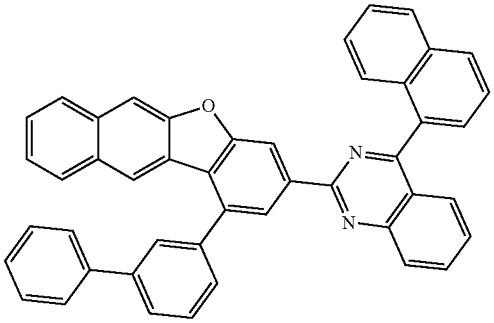
2-116
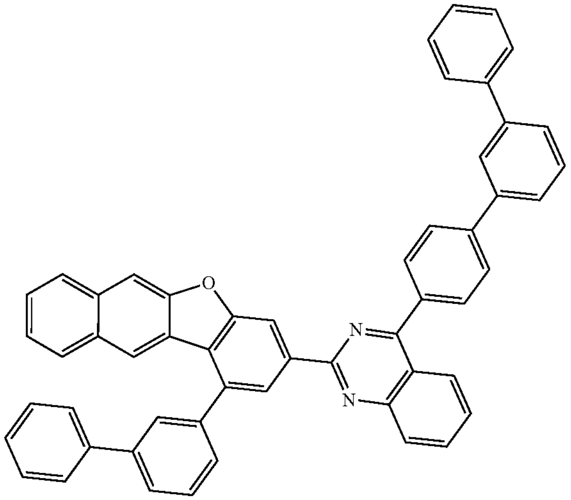
2-117
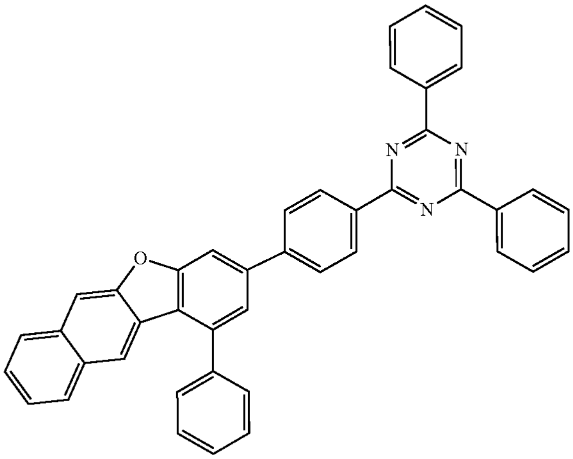
-continued
2-118
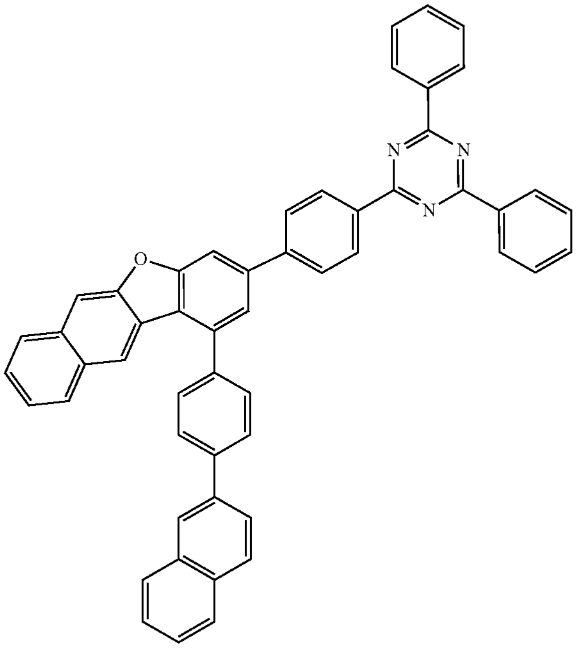
2-119
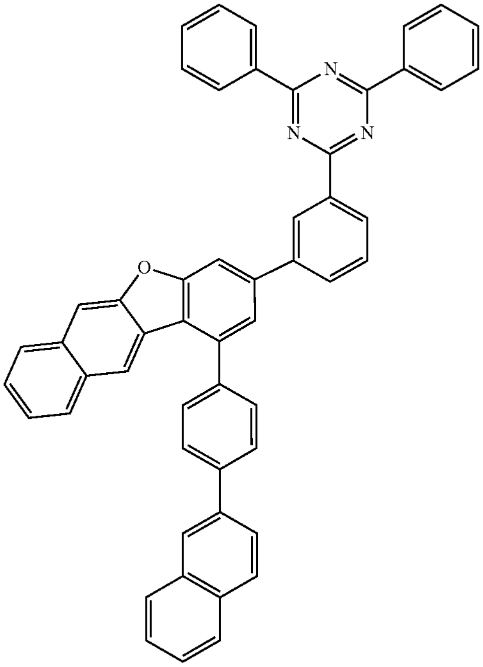

-continued
2-120
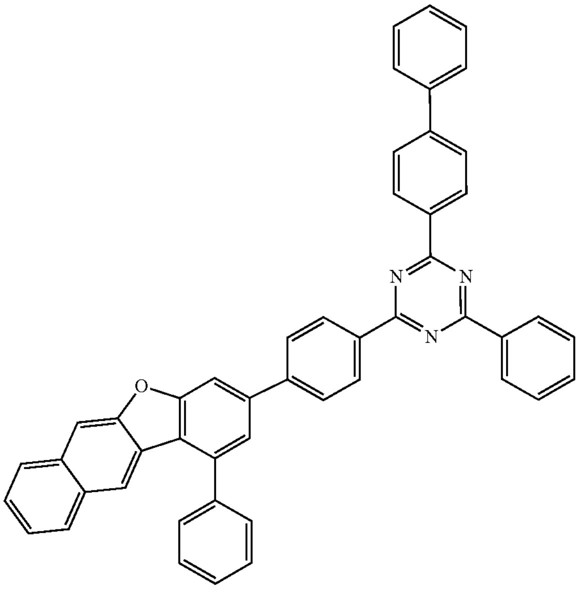
2-121
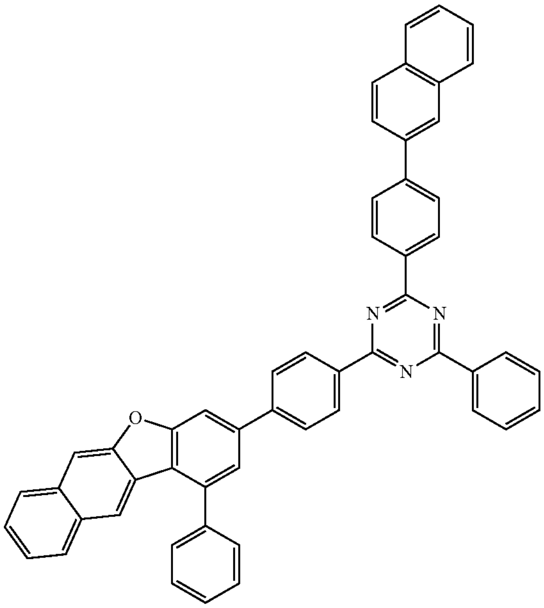
-continued
2-122
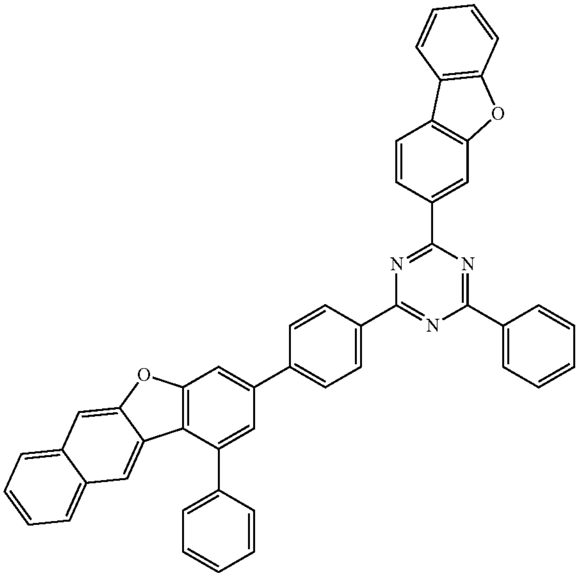
2-123
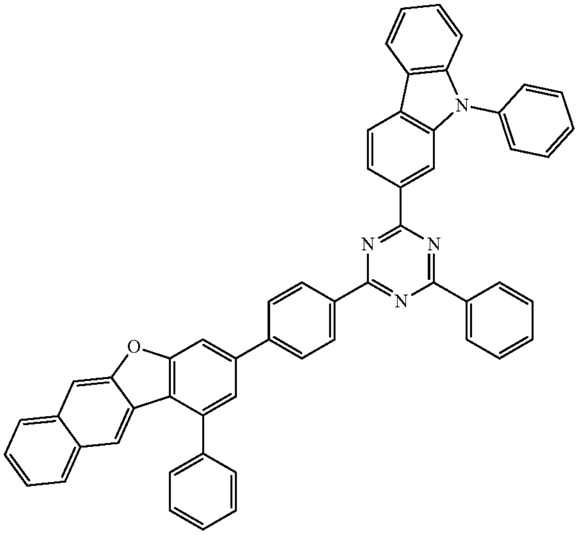
2-124
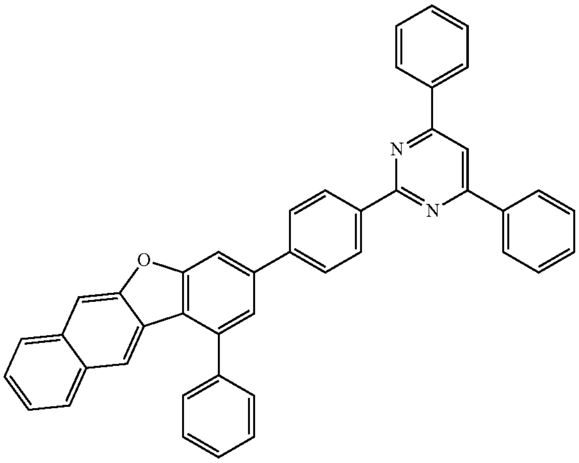

-continued
2-125
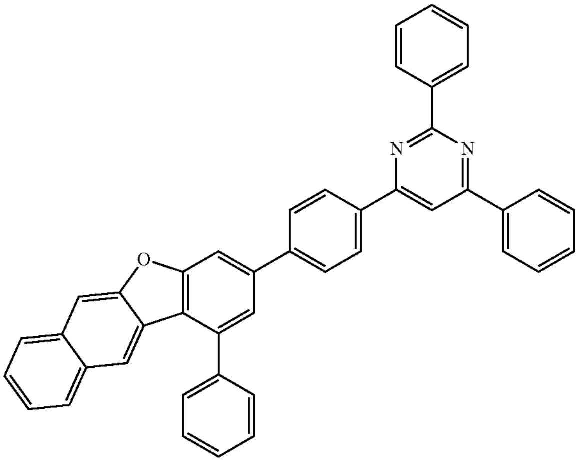
2-126
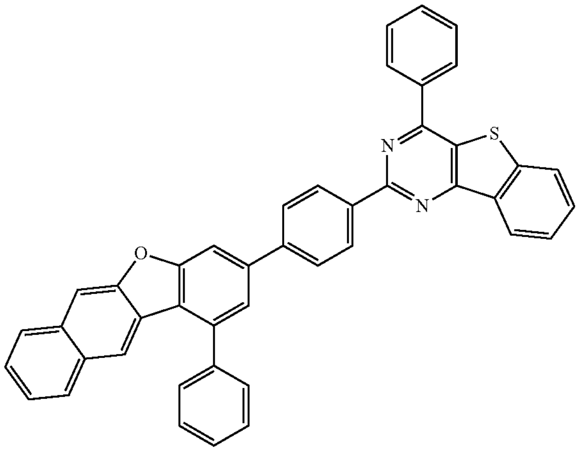
2-127
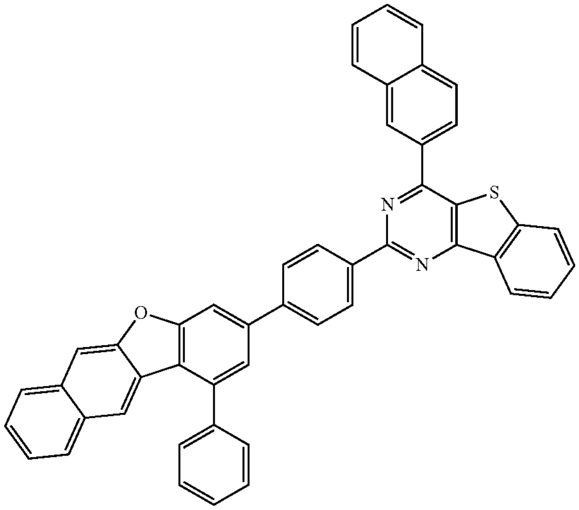
-continued
2-128
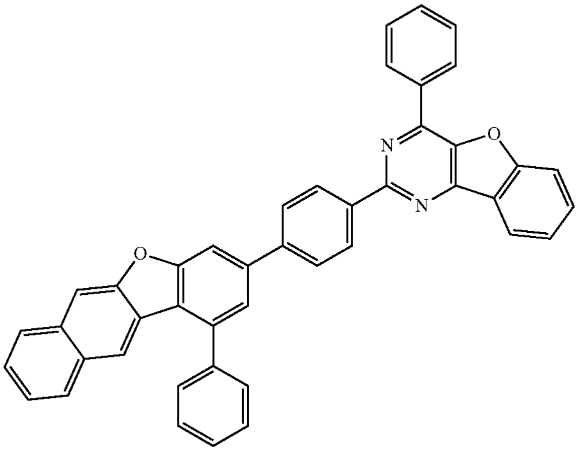
2-129
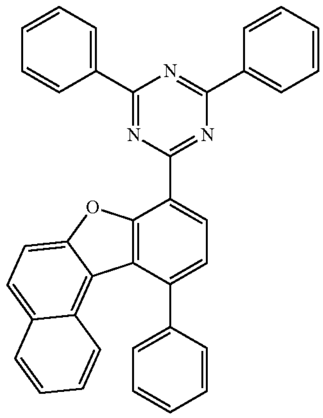
2-130
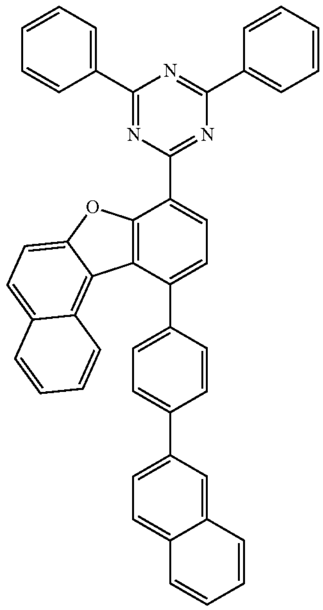

-continued
2-131
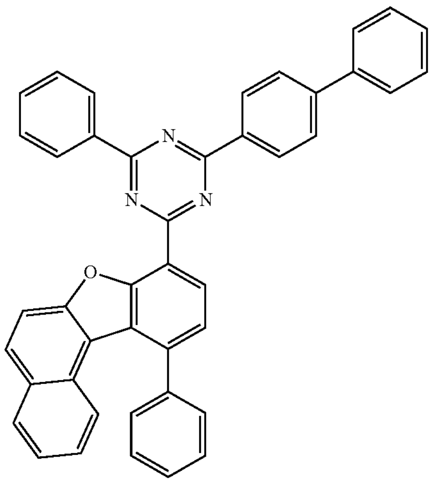
2-132
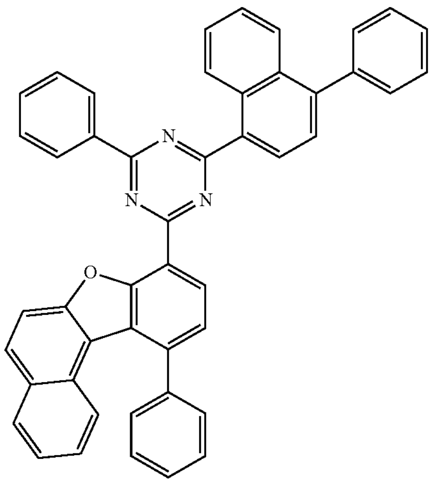
2-133
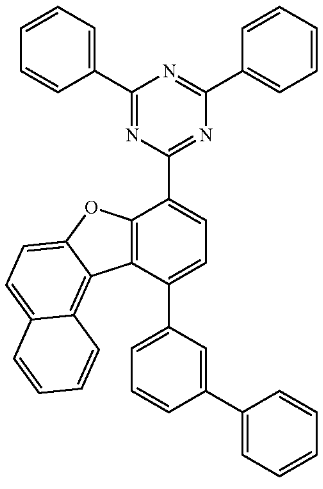
-continued
2-134
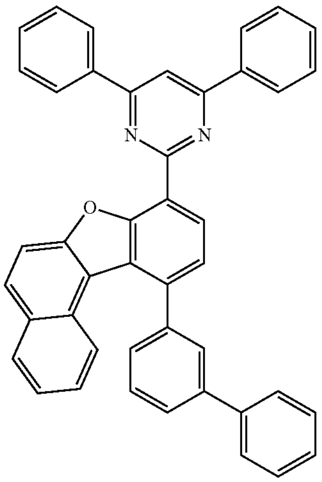
2-135
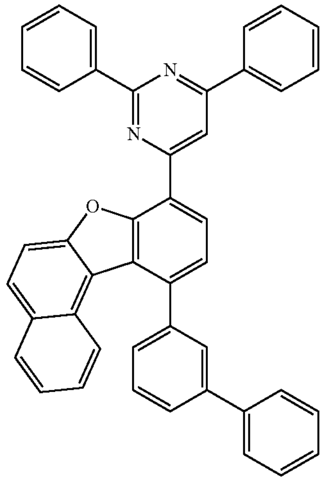
2-136
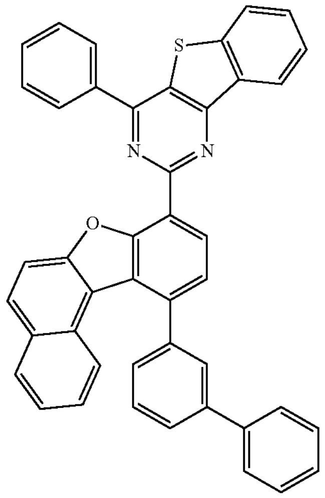

-continued
2-137
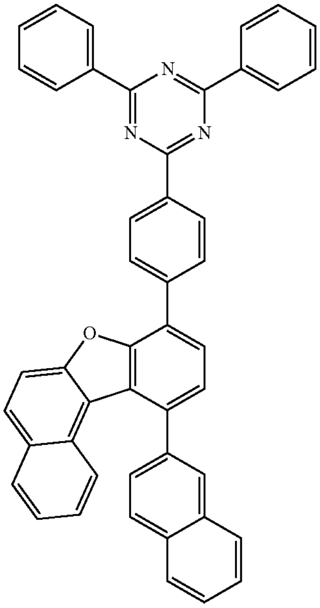
2-138
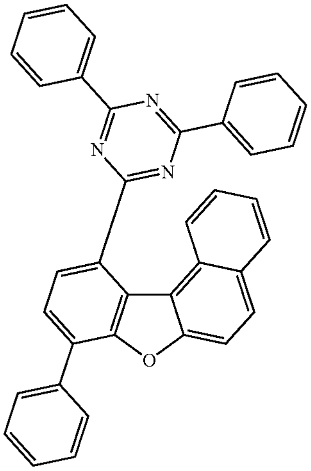
-continued
2-139
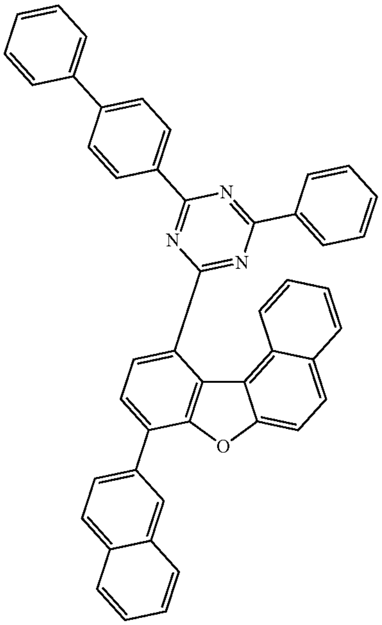
2-140
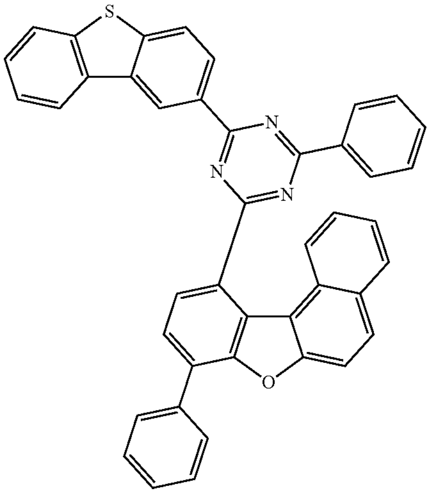

-continued
2-141
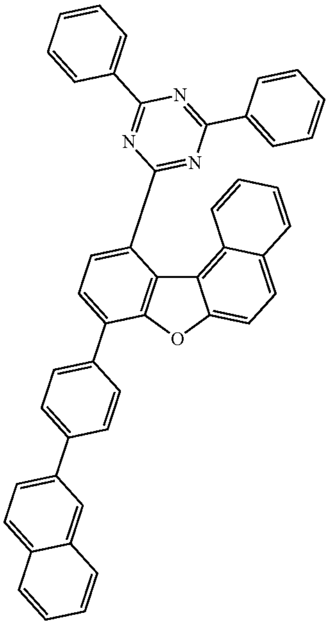
2-142
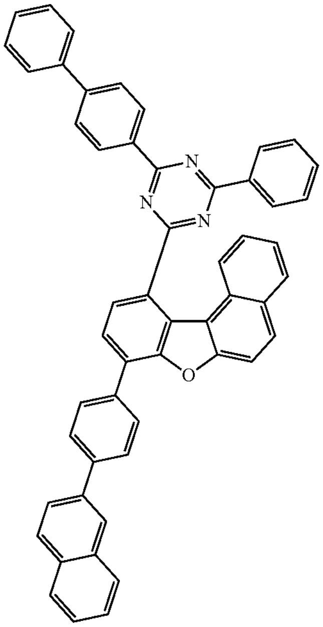
-continued
2-143
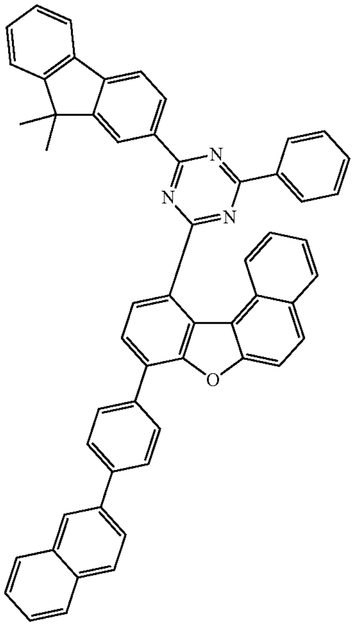
2-144
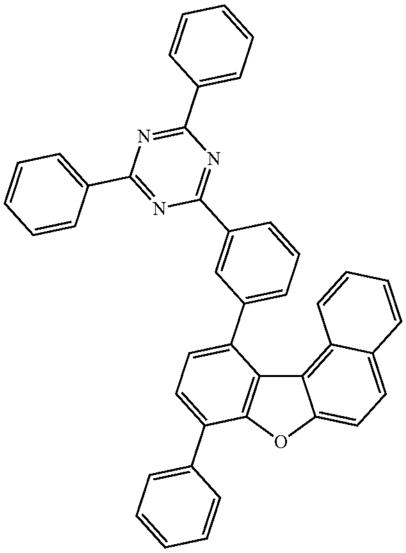
2-145
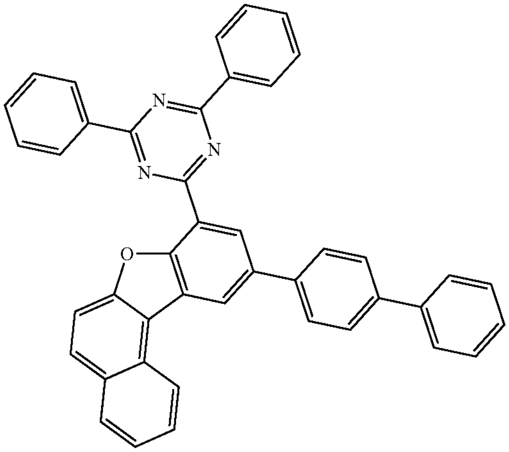

-continued
2-146
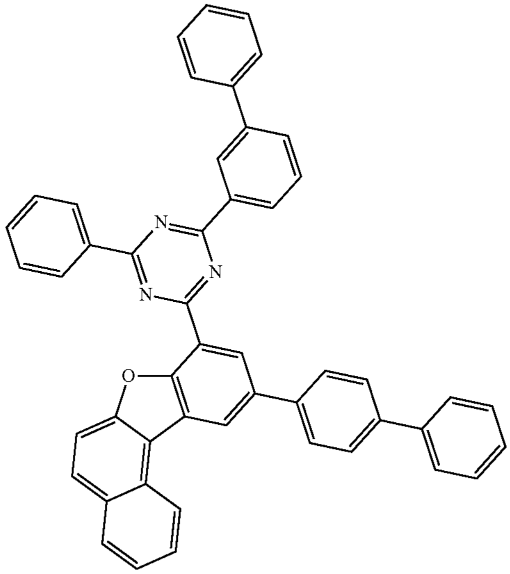
2-147
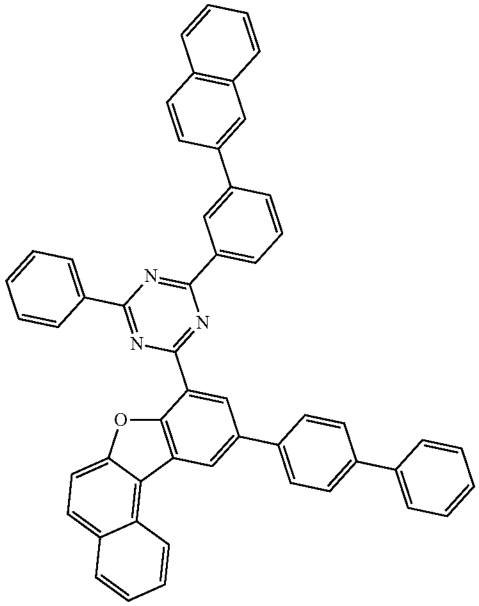
-continued
2-148
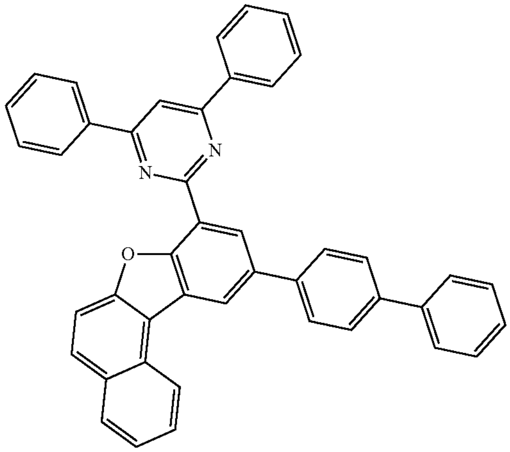
2-149
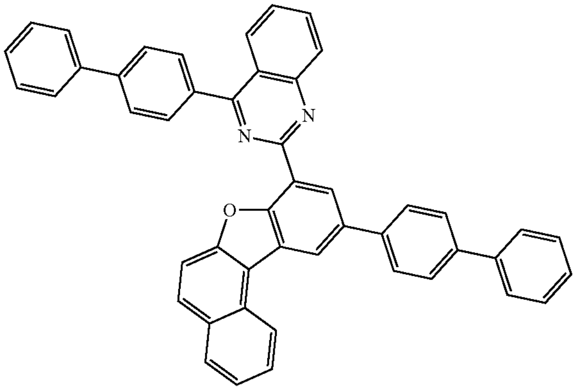
2-150
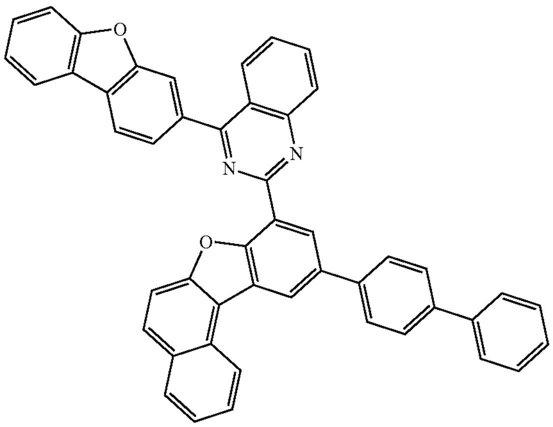

-continued
2-151
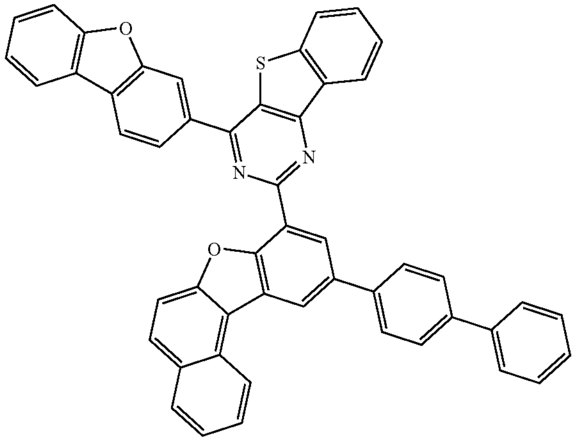
2-152
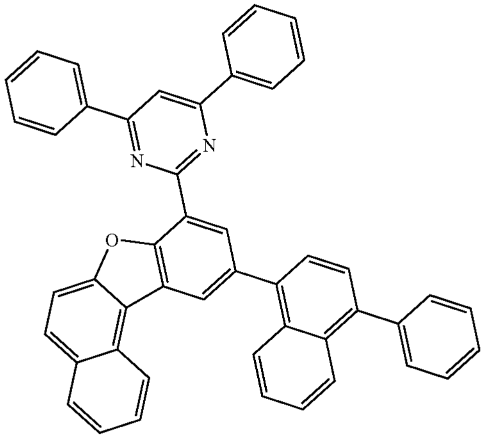
2-153
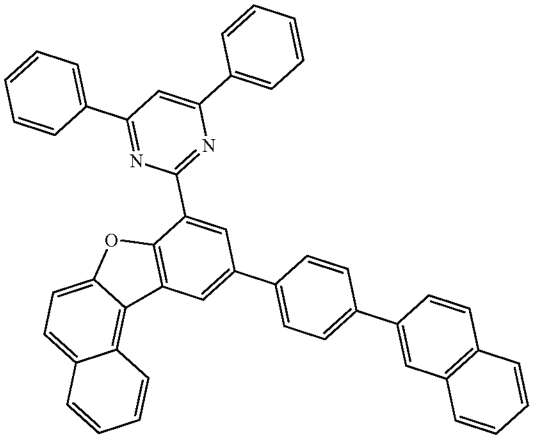
-continued
2-154
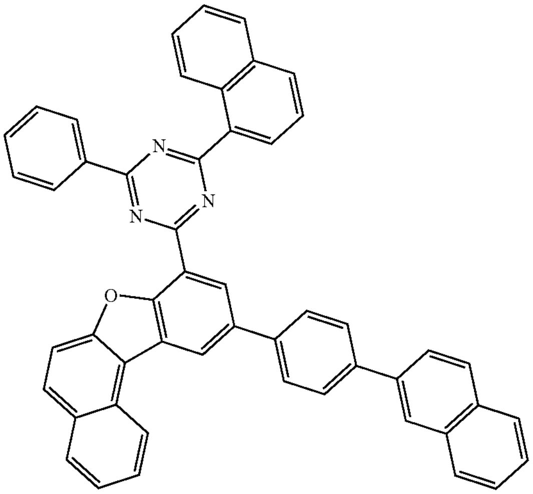
2-155
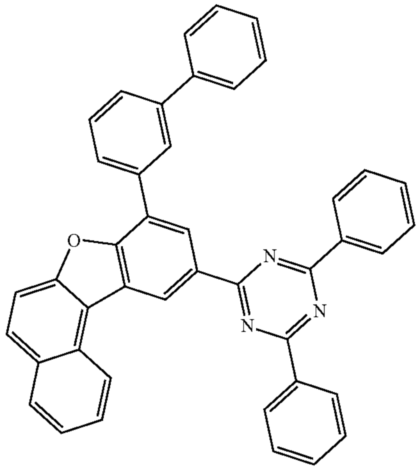
2-156
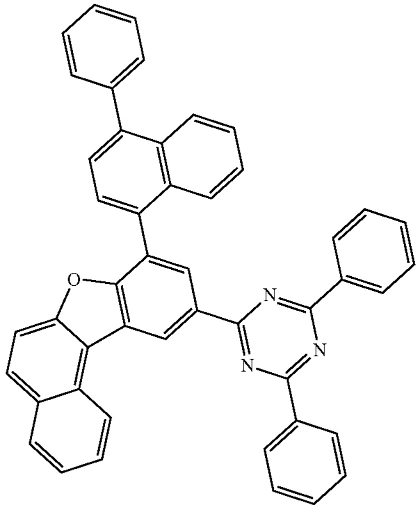

-continued
2-157
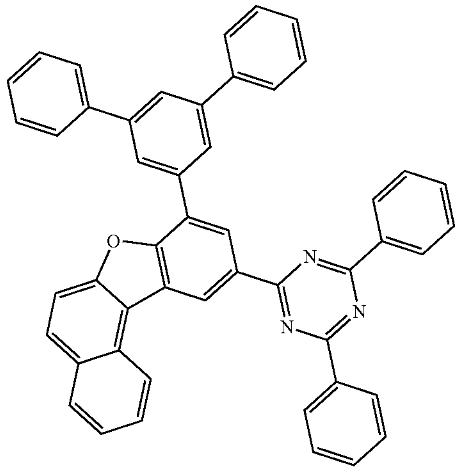
2-158
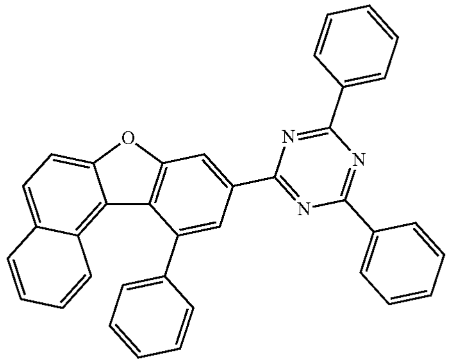
2-159
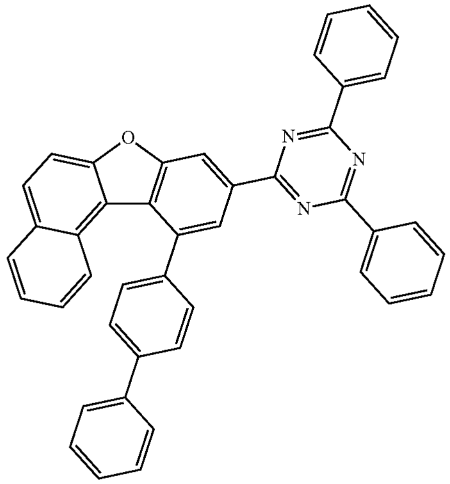
-continued
2-160
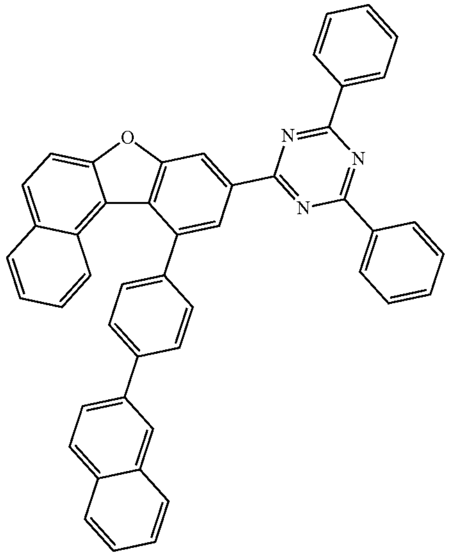
2-161
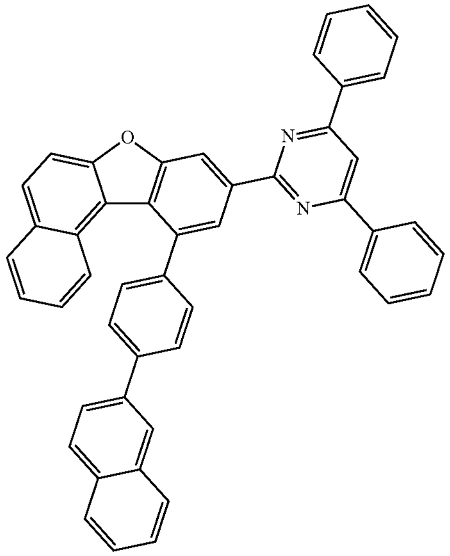
2-162
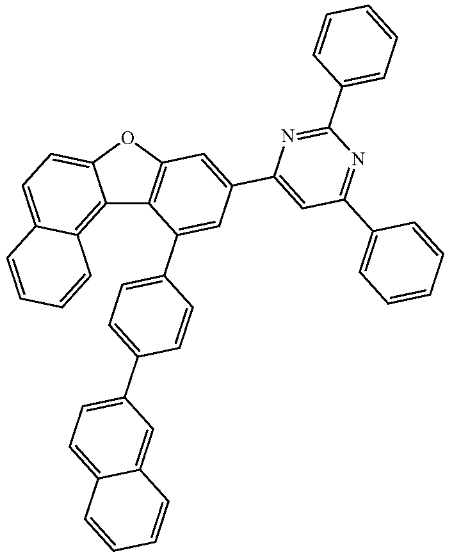

-continued
2-163
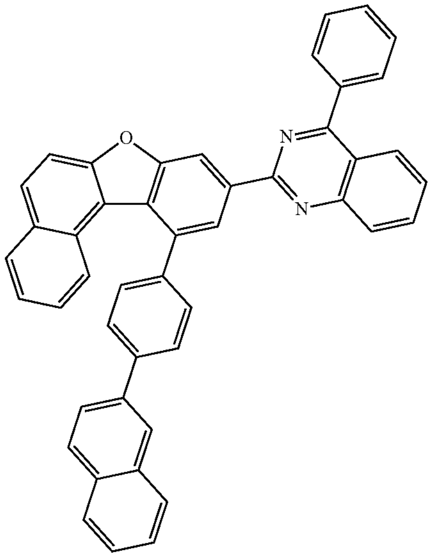
2-164
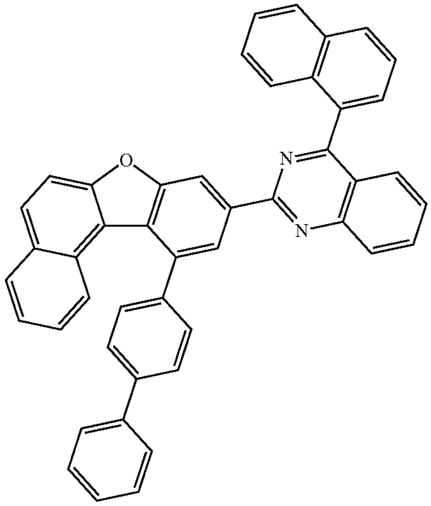
2-165
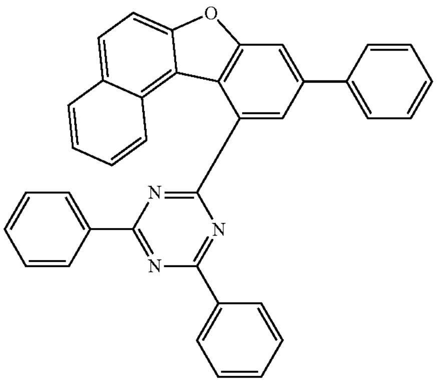
-continued
2-166
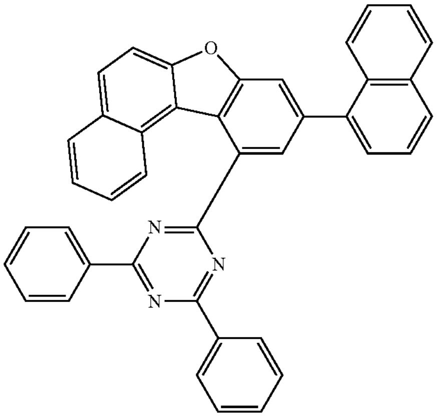
2-167
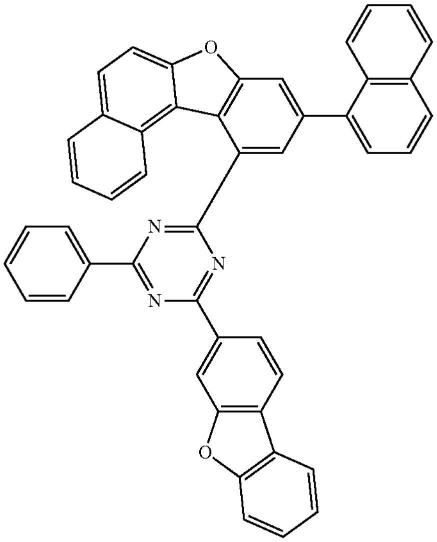
2-168
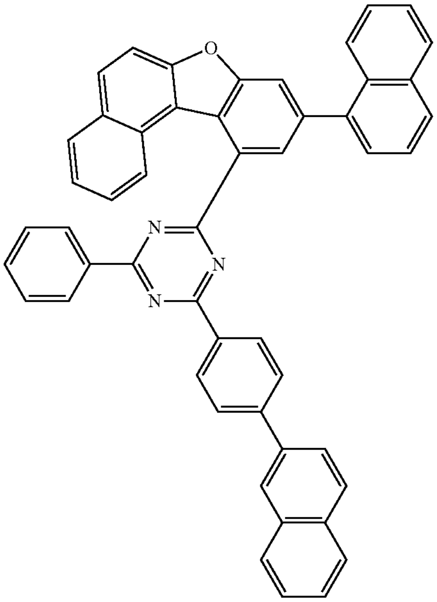

-continued
2-169
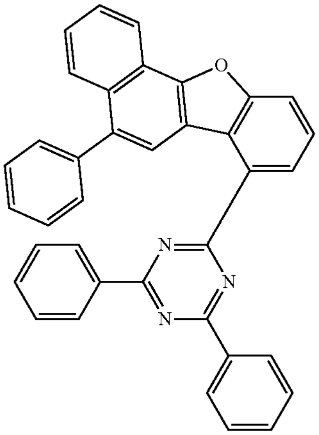
2-170
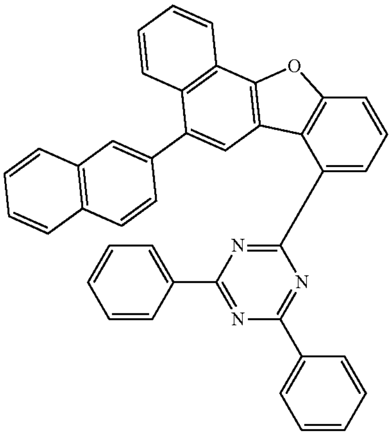
2-171
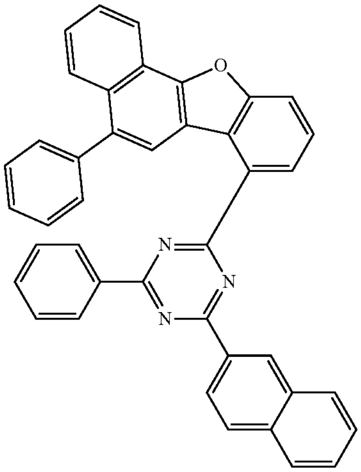
-continued
2-172
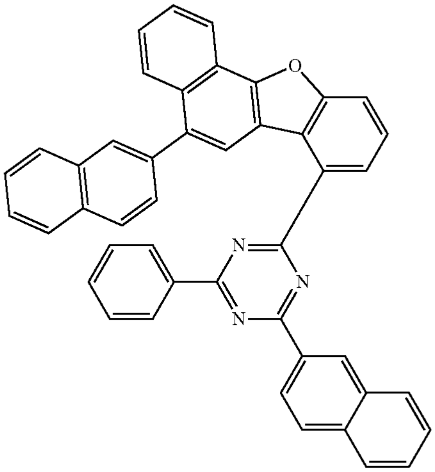
2-173
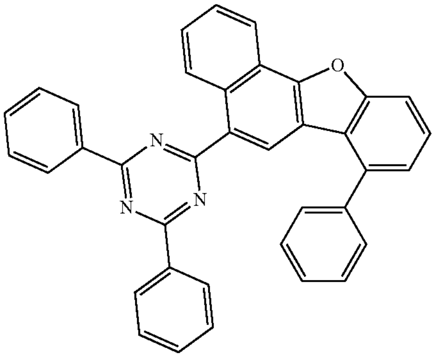
2-174
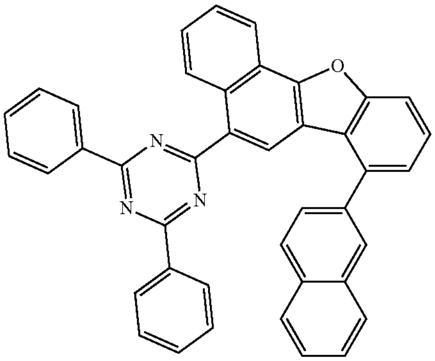
2-175
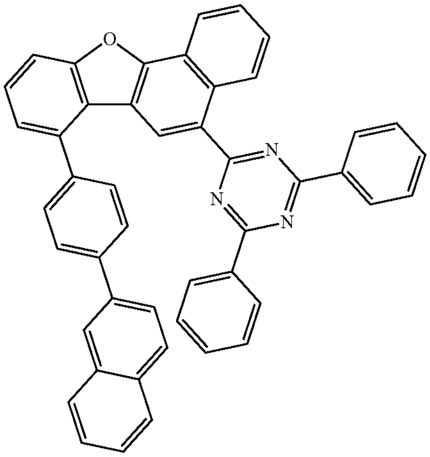

2-176
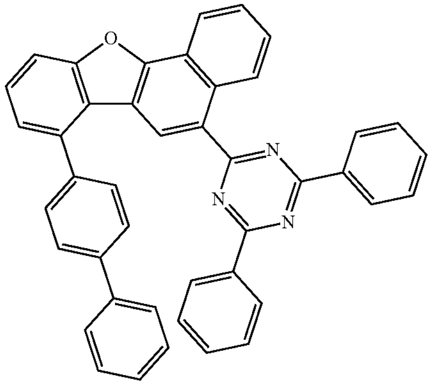
2-177
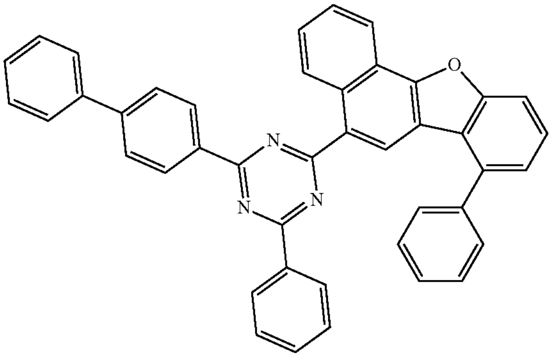
2-178
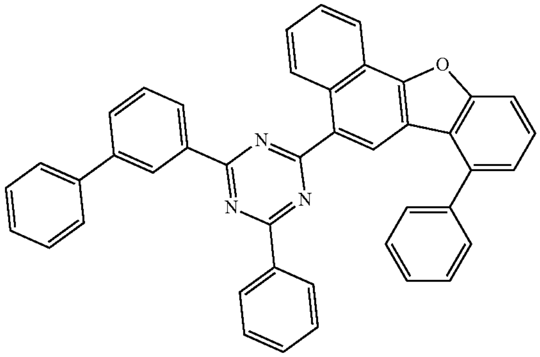
2-179
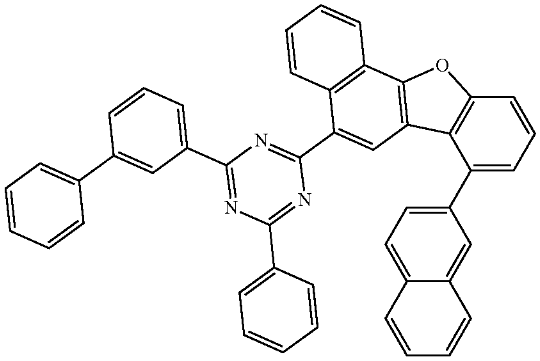
2-180
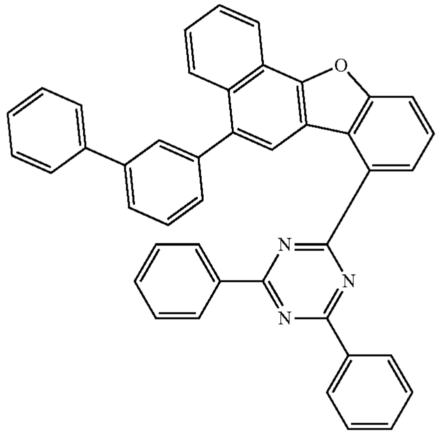
2-181
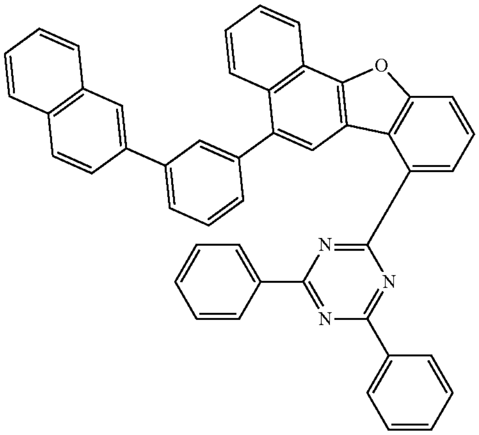
2-182
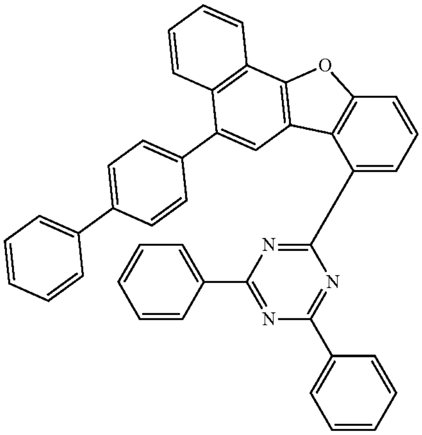

-continued
2-183
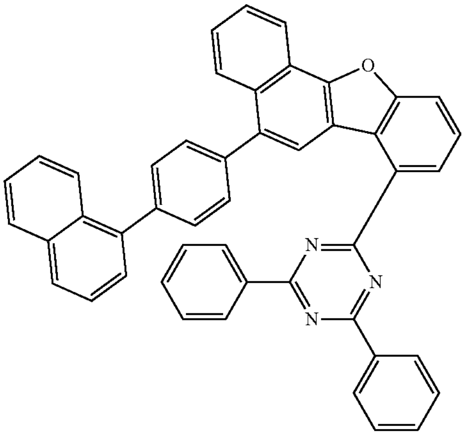
2-184
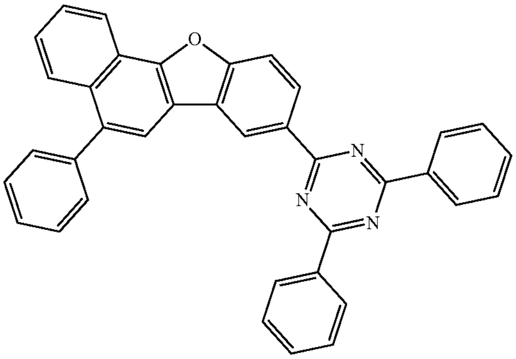
2-185
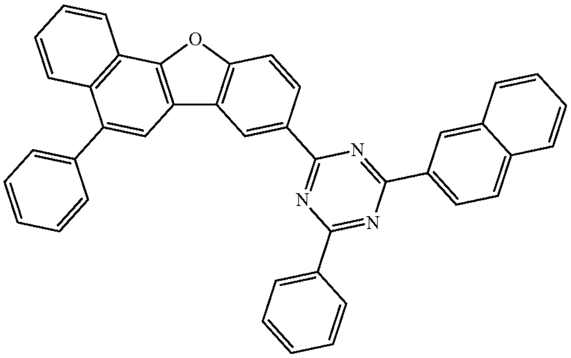
2-186
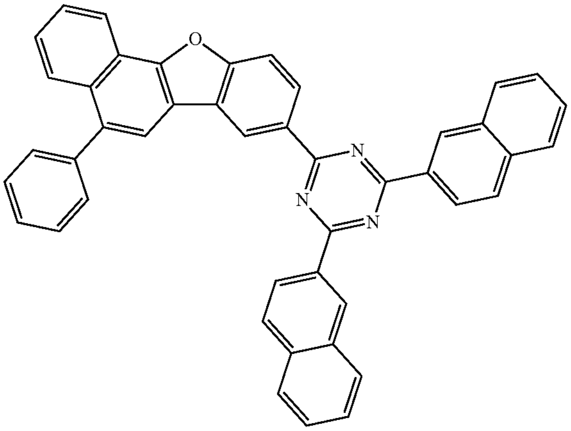
-continued
2-187
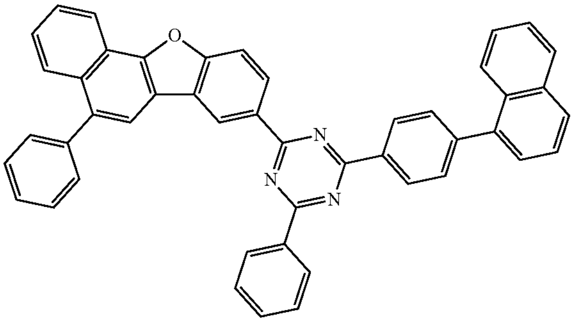
2-188
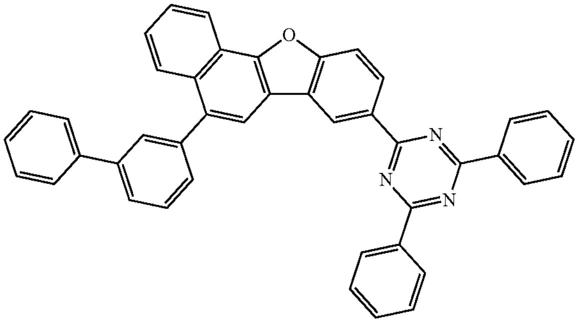
2-189
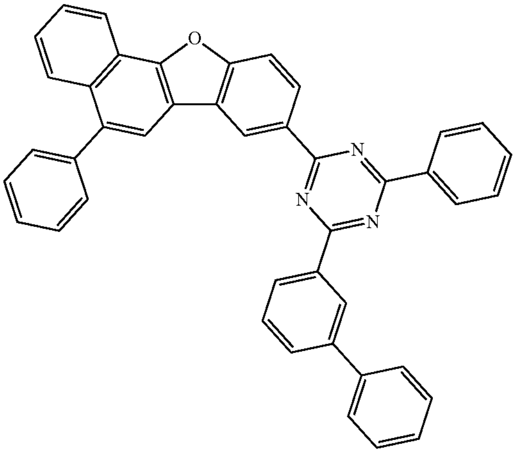
2-190
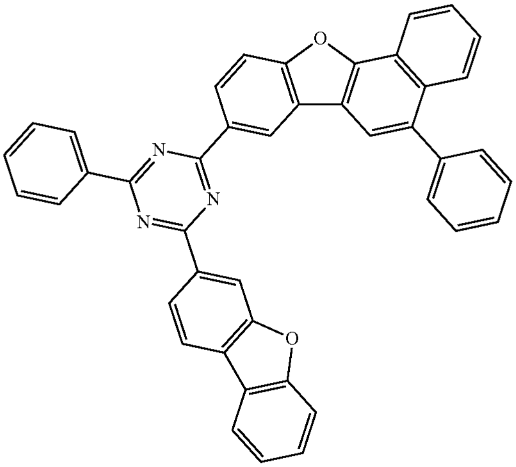

-continued
2-191
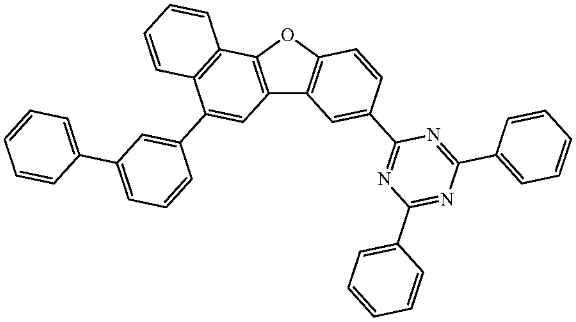
2-192
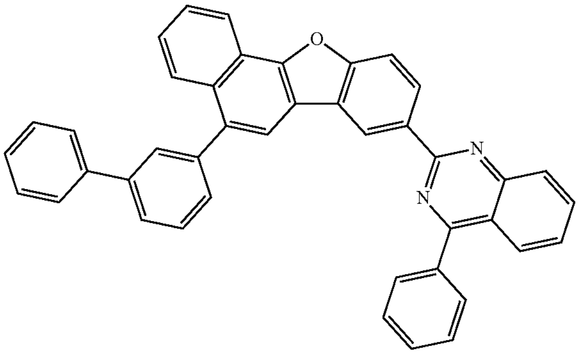
2-193
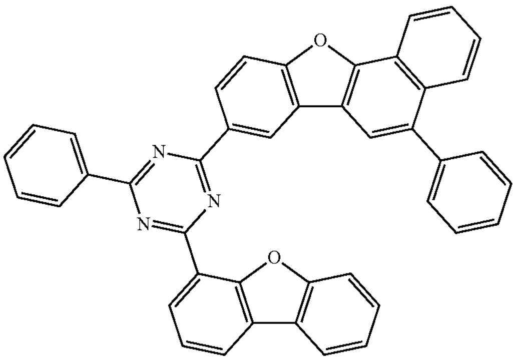
2-194
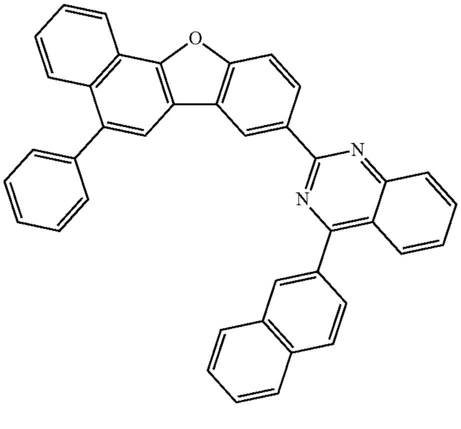
-continued
2-195
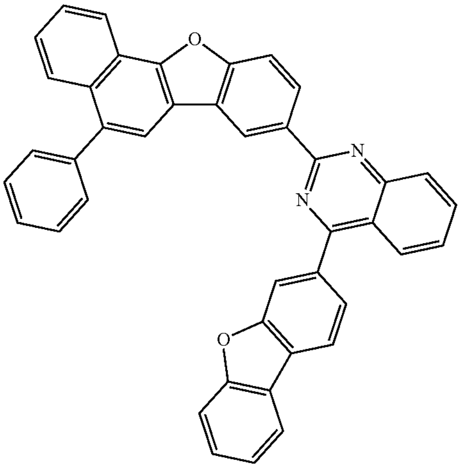
2-196
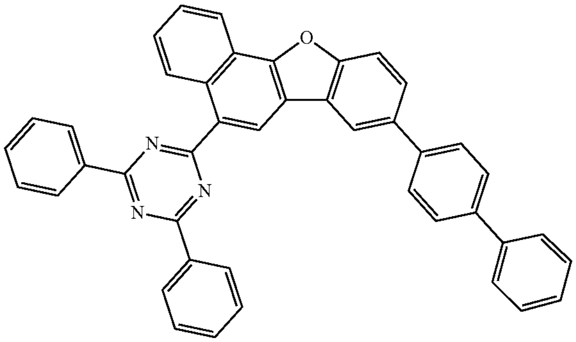
2-197
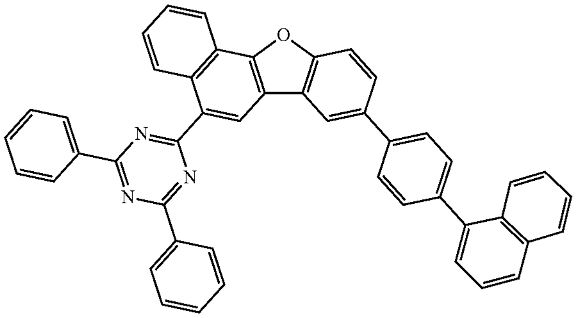
2-198
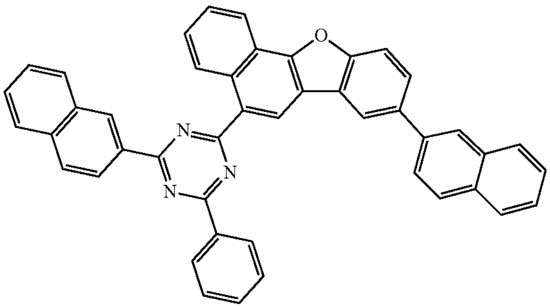

-continued
2-199
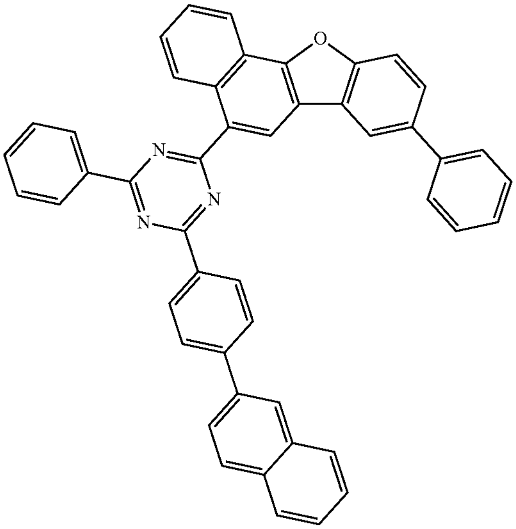
2-200
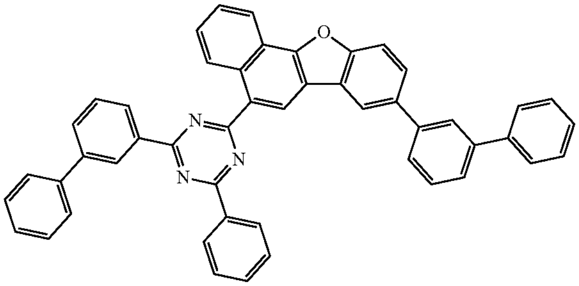
2-201
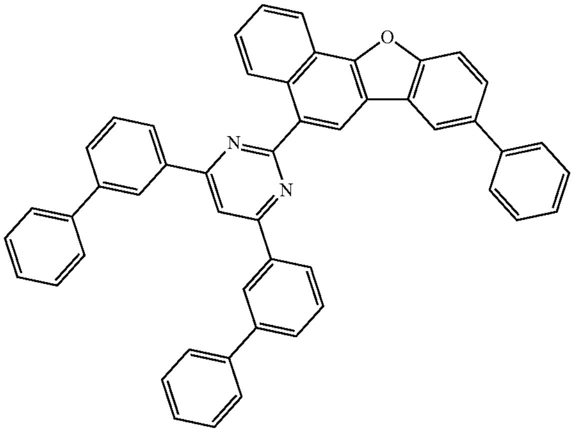
-continued
2-202
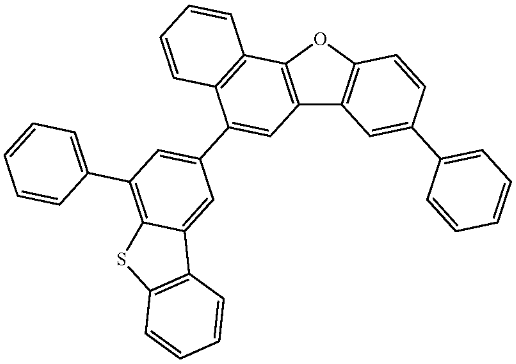
2-203
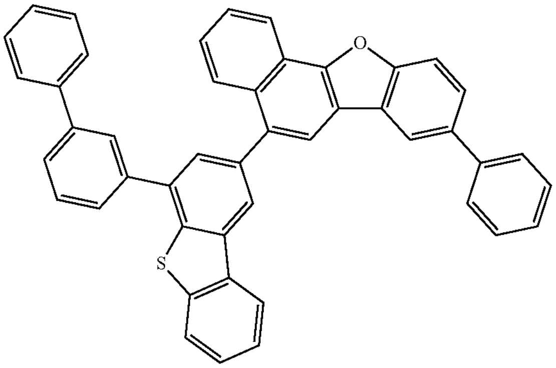
2-204
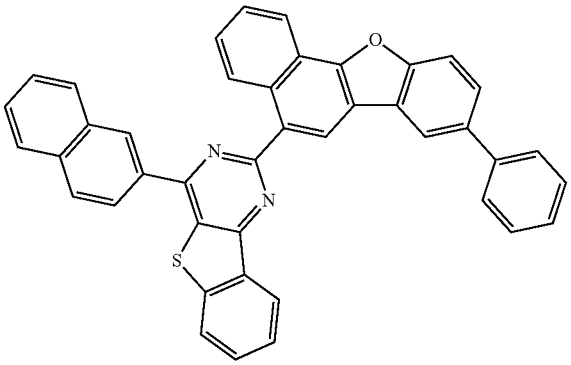
2-205
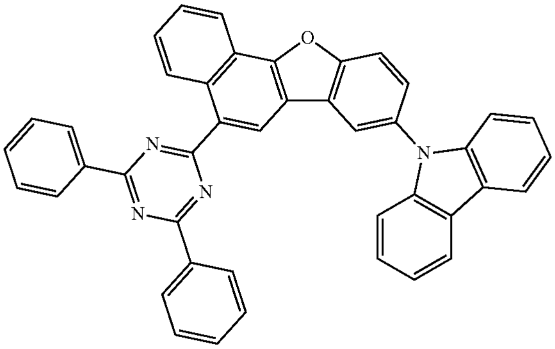

-continued
2-206
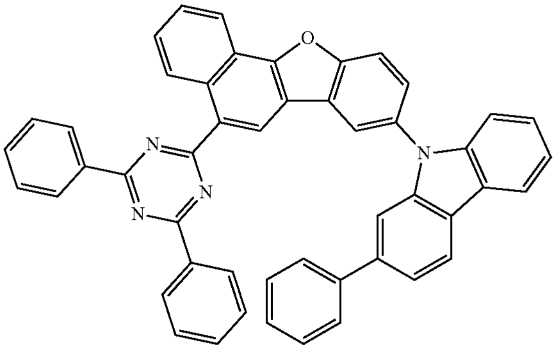
2-207
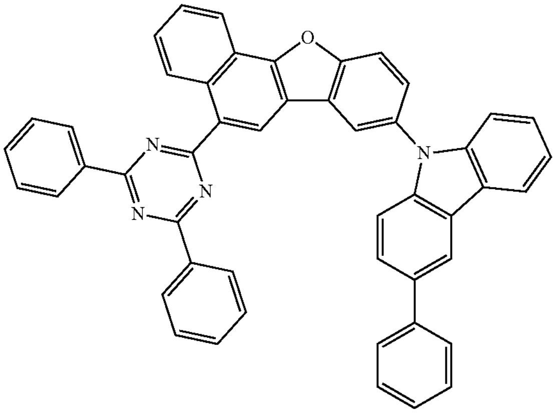
2-208
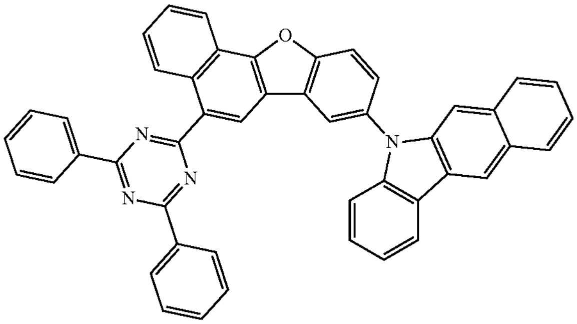
2-209
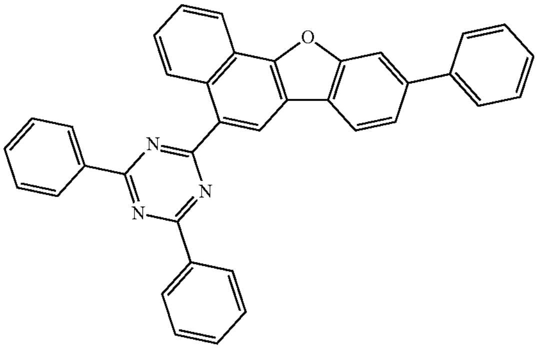
-continued
2-210
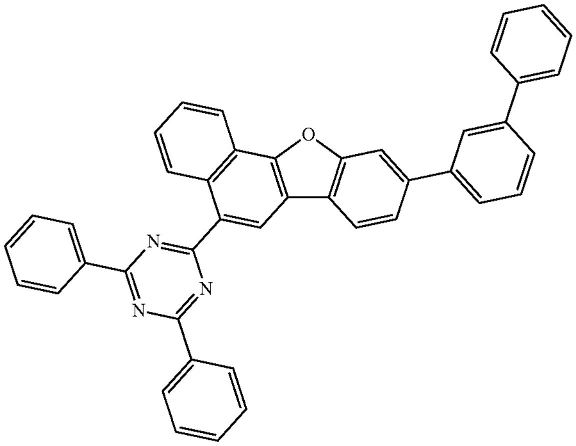
2-211
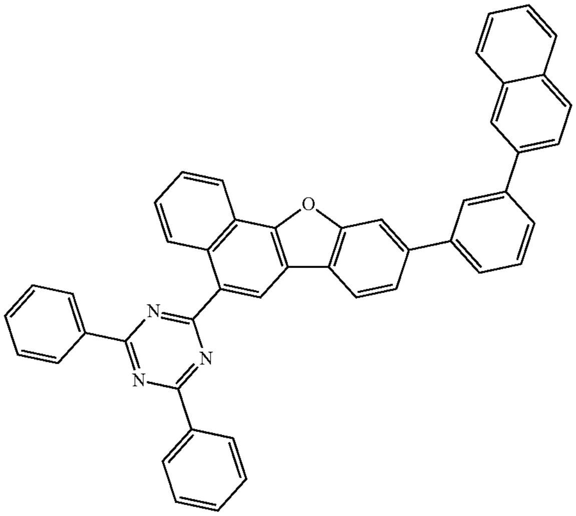
2-212
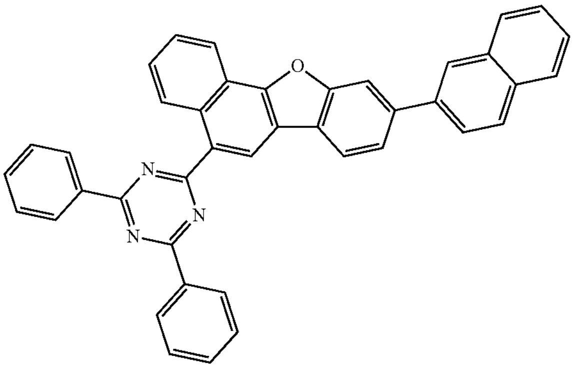

-continued
2-213
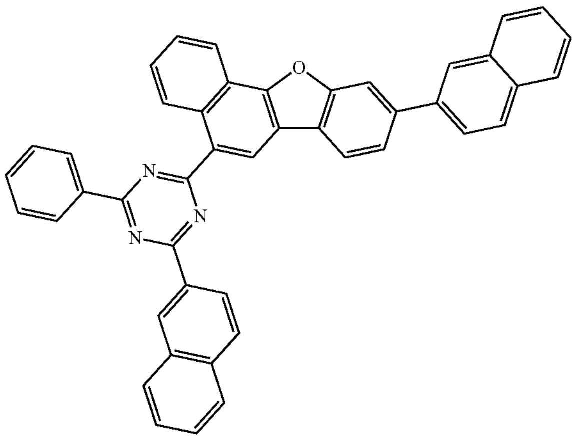
2-214
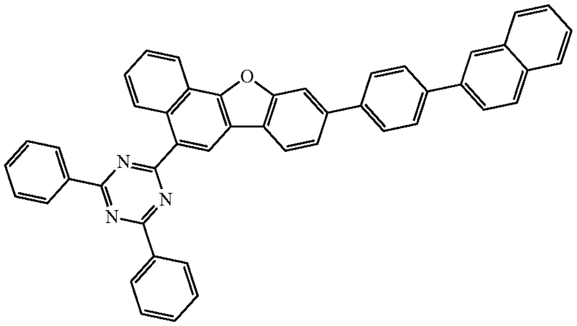
2-215
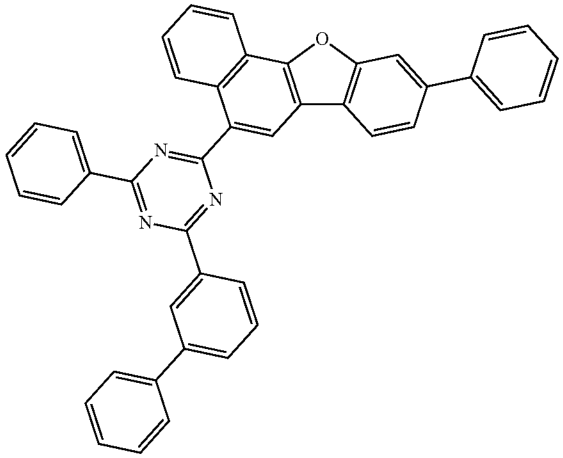
2-216
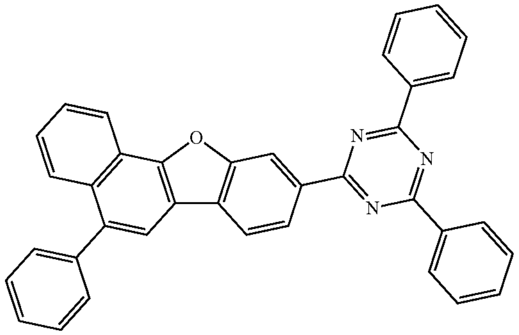
-continued
2-217
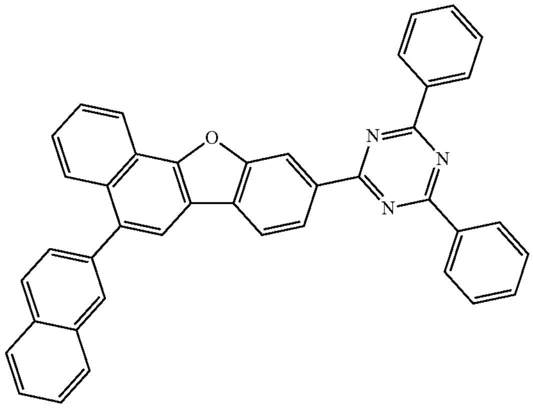
2-218
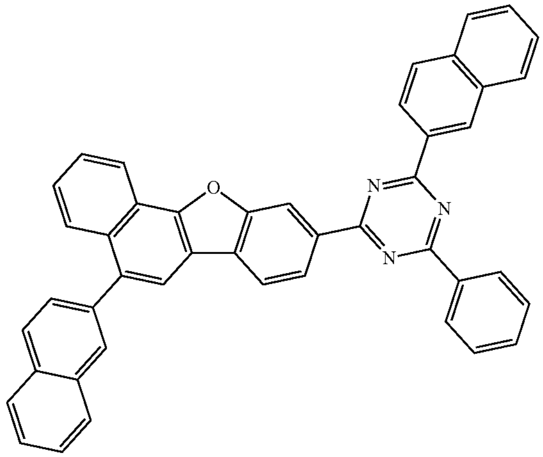
2-219
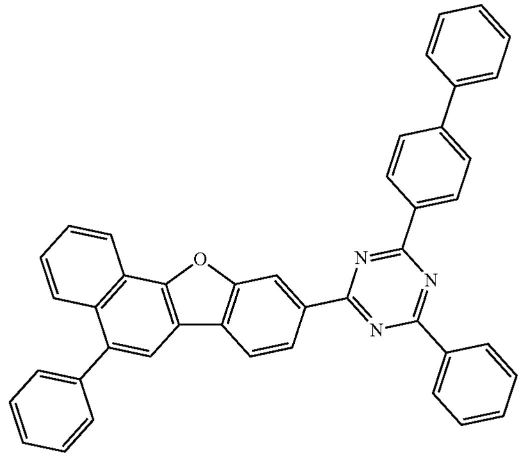

2-220
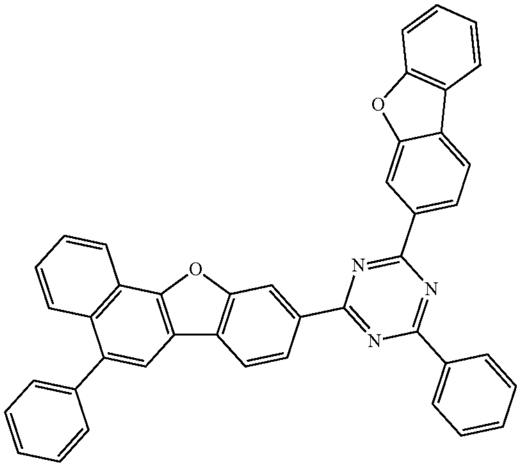
2-221
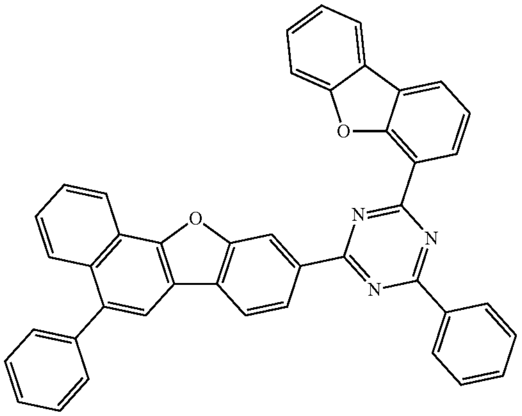
2-222
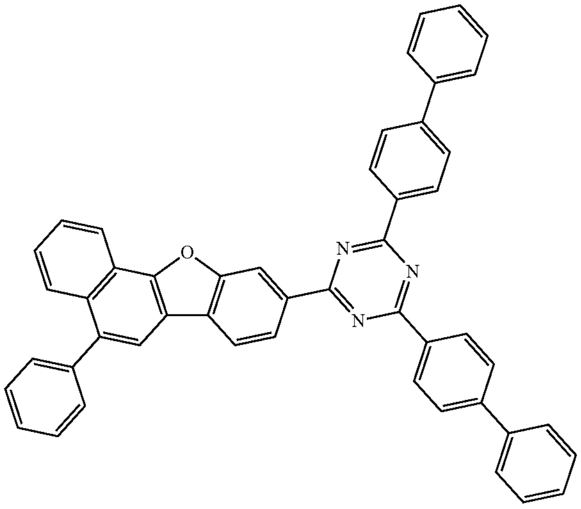
2-223
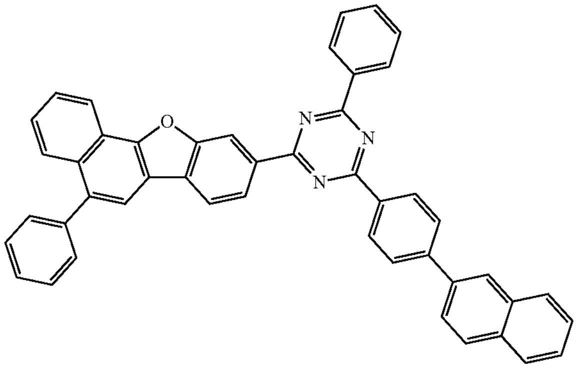
2-224
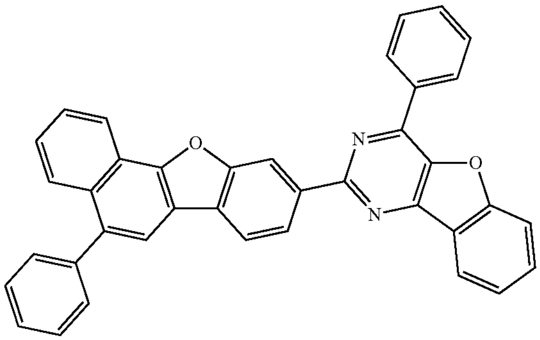
2-225
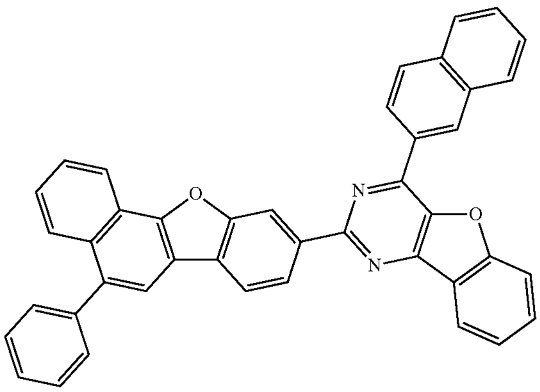
2-226
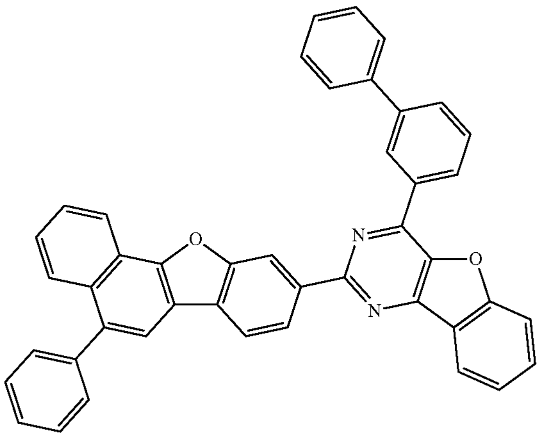

-continued
2-227
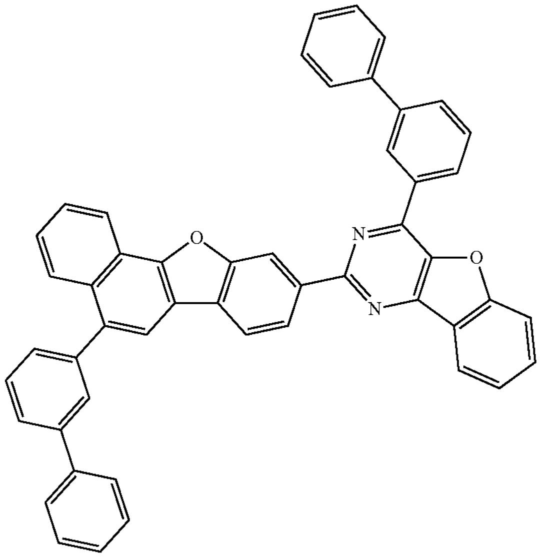
2-228
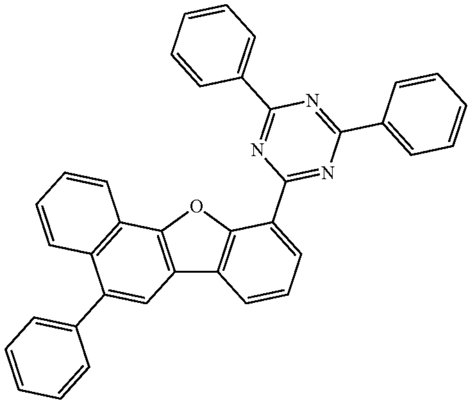
2-229
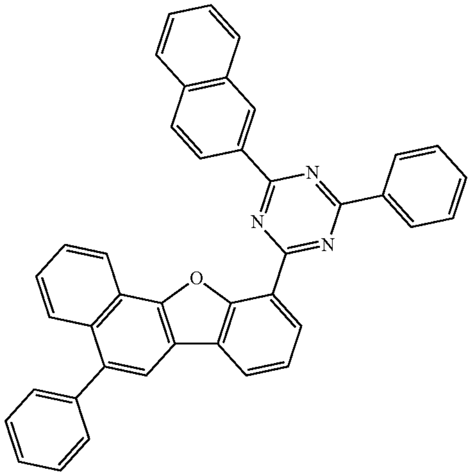
-continued
2-230
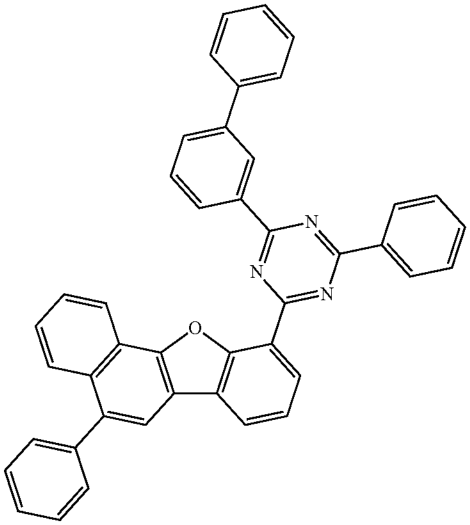
2-231
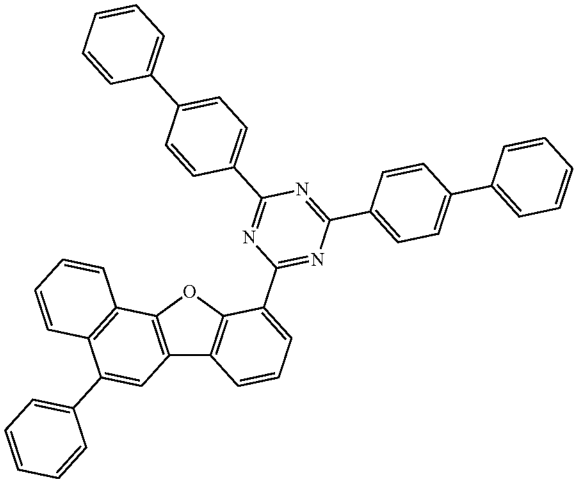
2-232
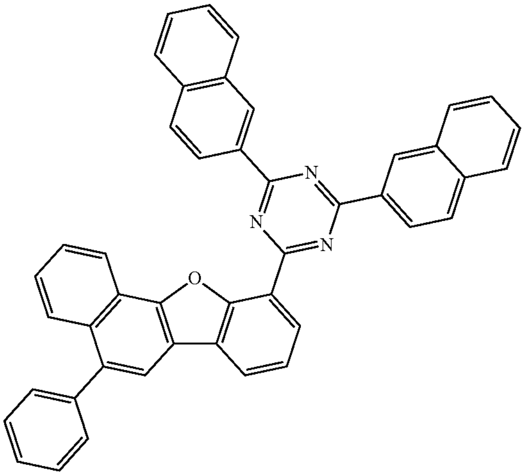

-continued
2-233
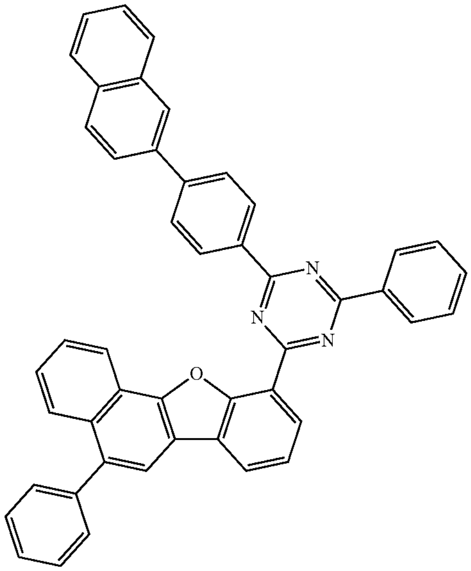
2-234
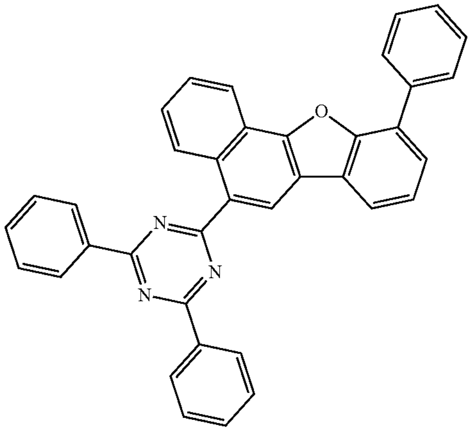
2-235
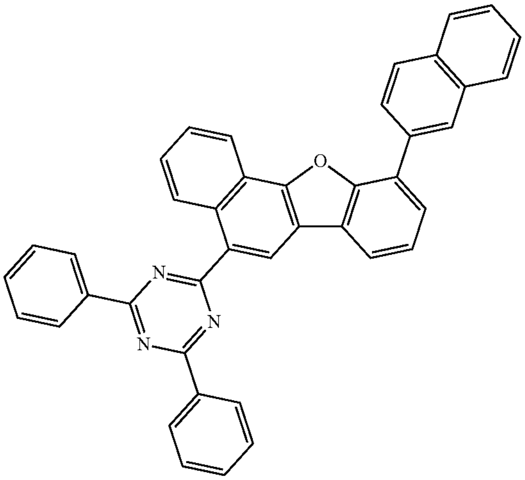
-continued
2-236
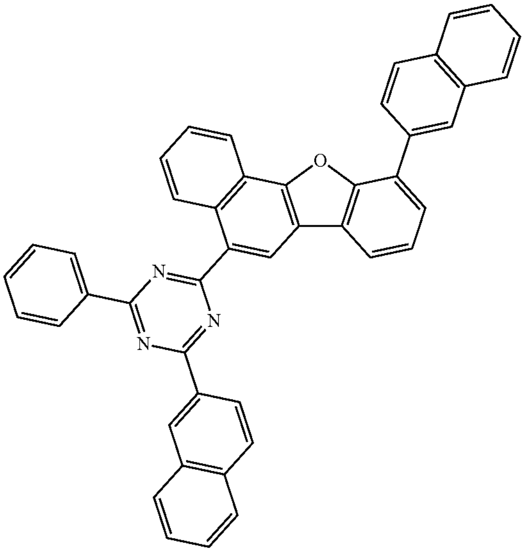
2-237
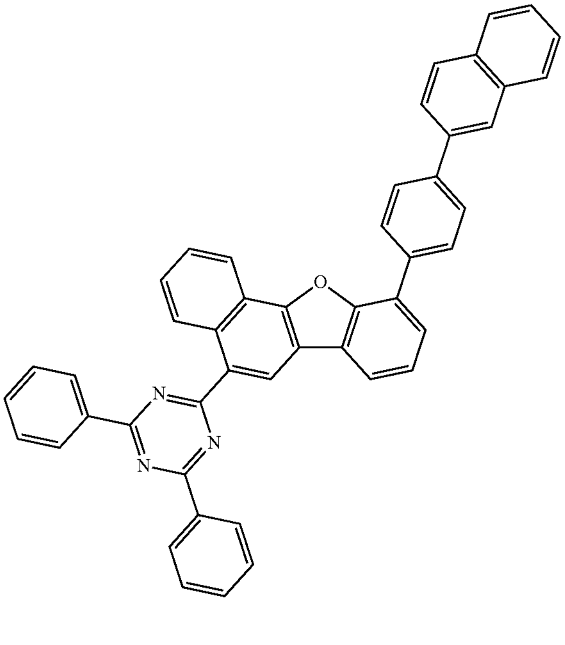

-continued
2-238
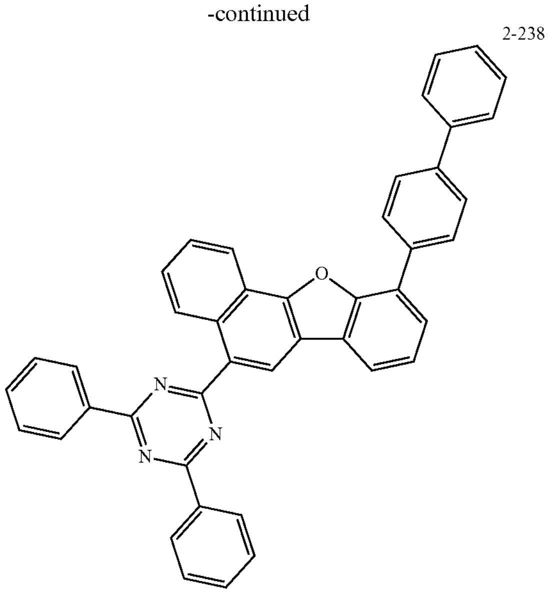
2-239
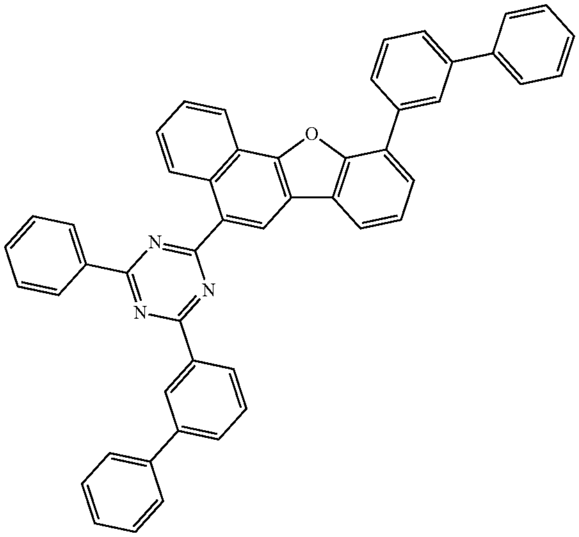
2-240
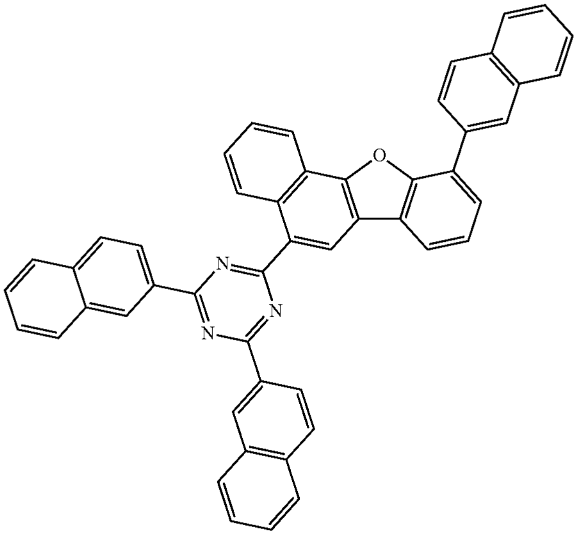
-continued
2-241
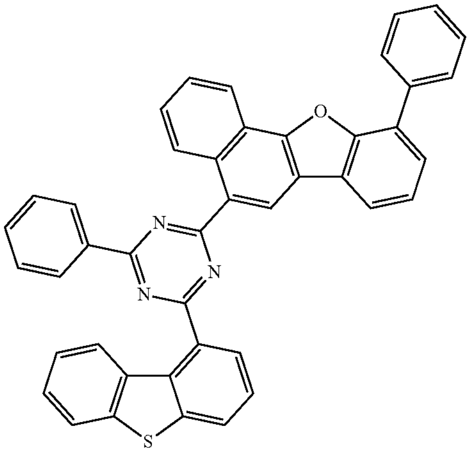
2-242
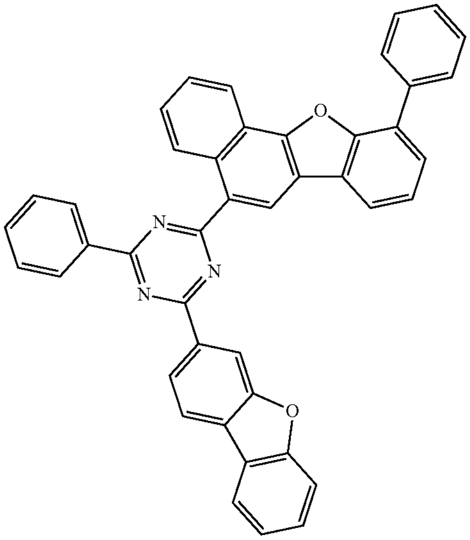
2-243
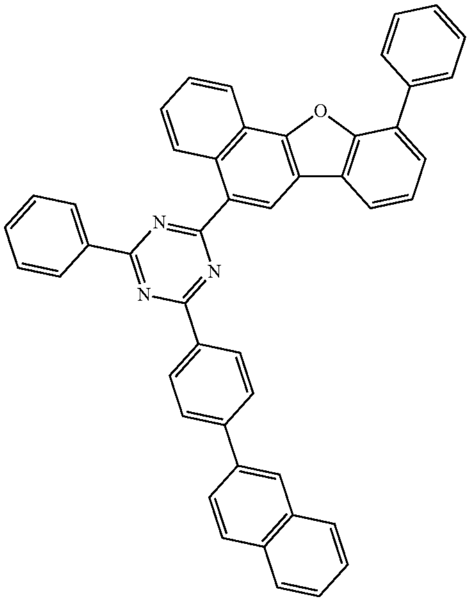

-continued
2-244
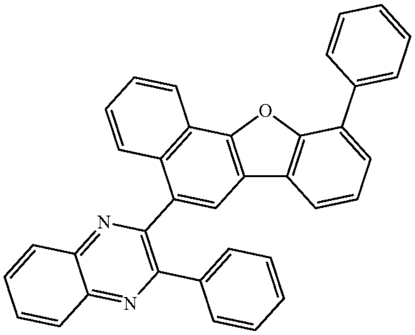
2-245
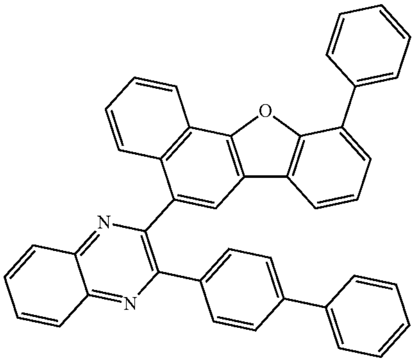
2-246
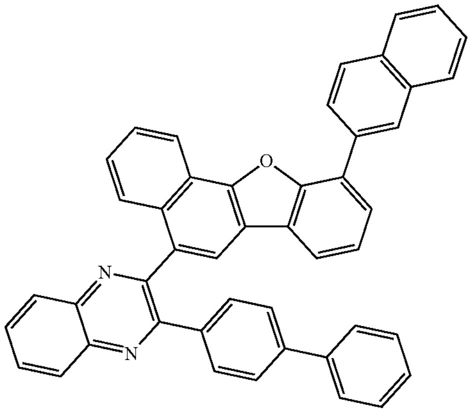
2-247
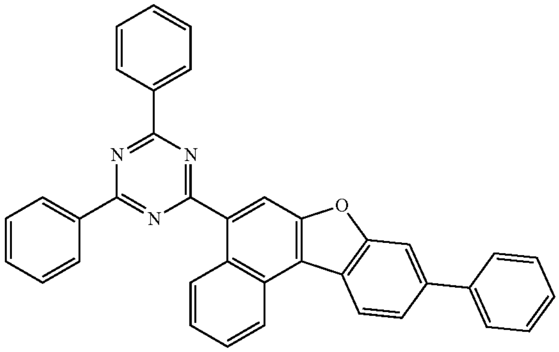
-continued
2-248
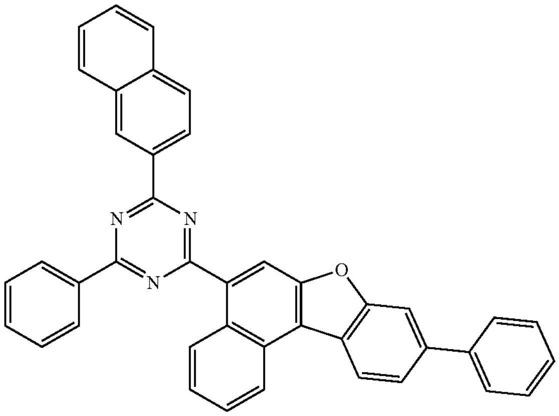
2-249
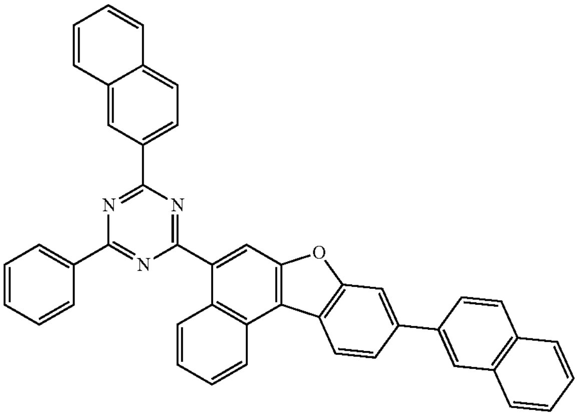
2-250
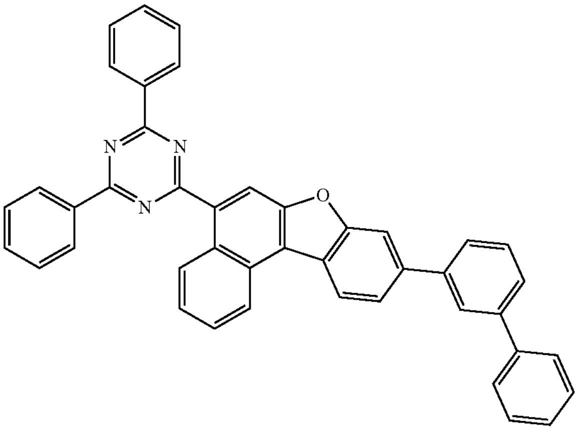
2-251
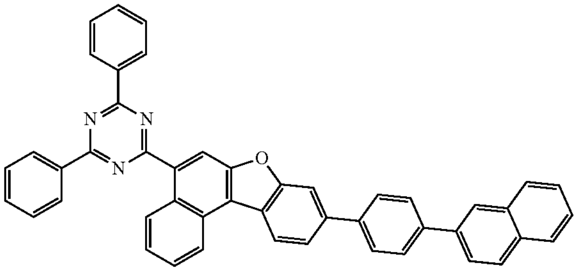

-continued
2-252
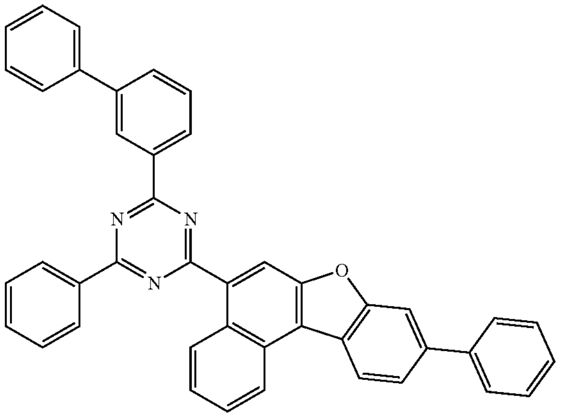
2-253
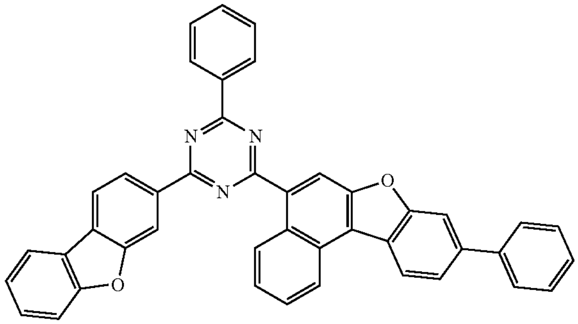
2-254
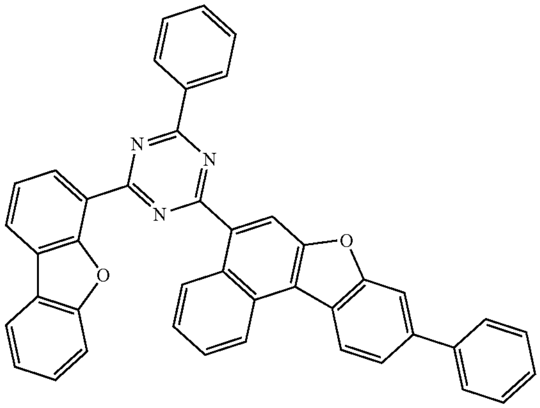
-continued
2-255
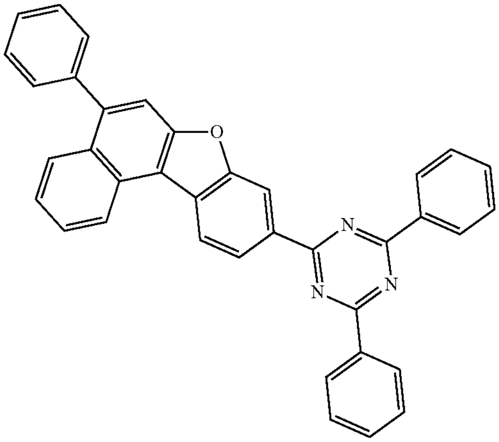
2-256
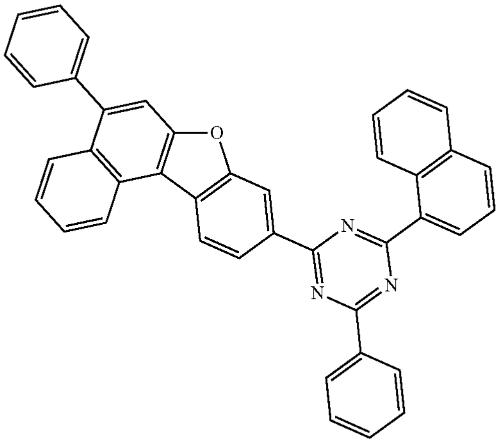
2-257
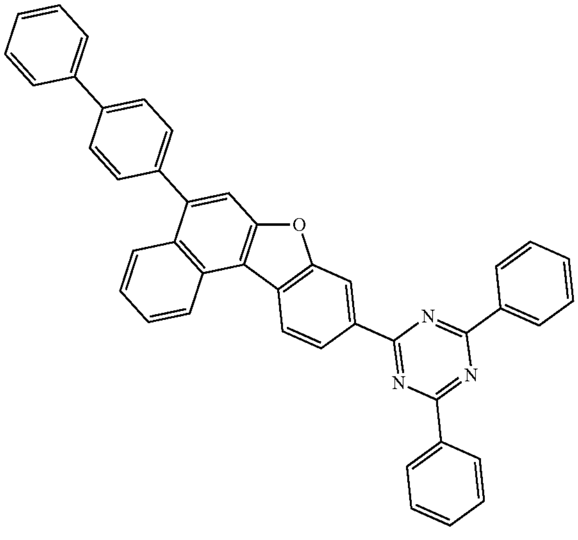

-continued
2-258
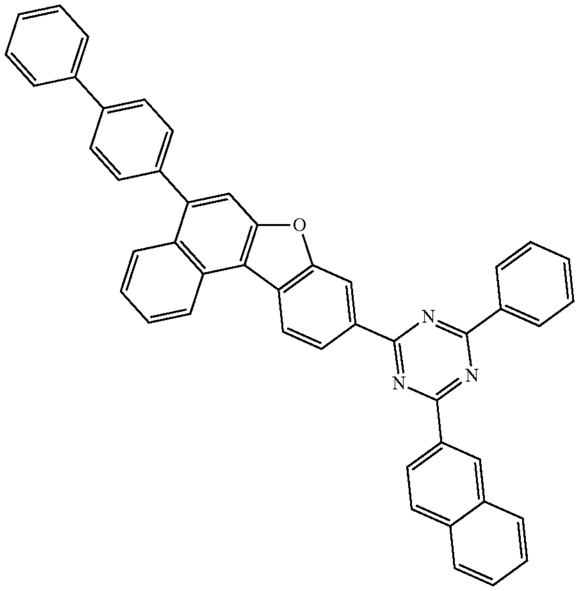
2-259
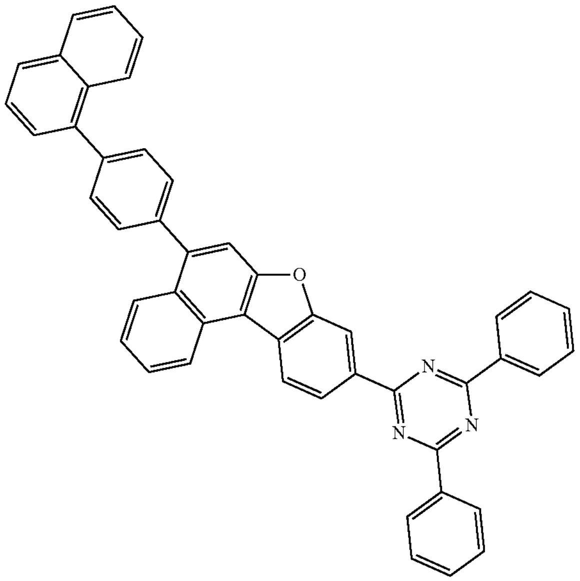
2-260
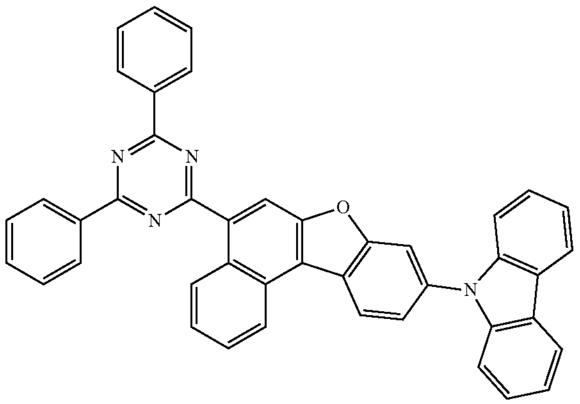
-continued
2-261
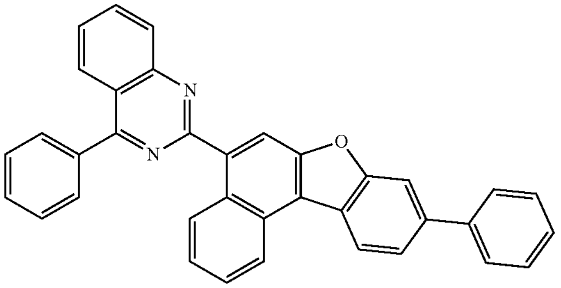
2-262
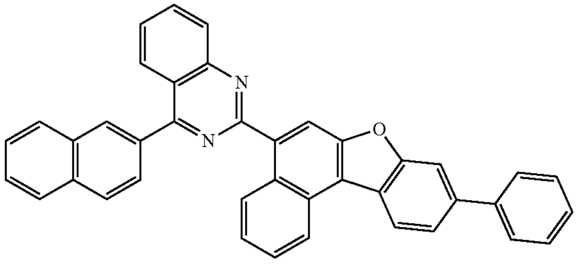
2-263
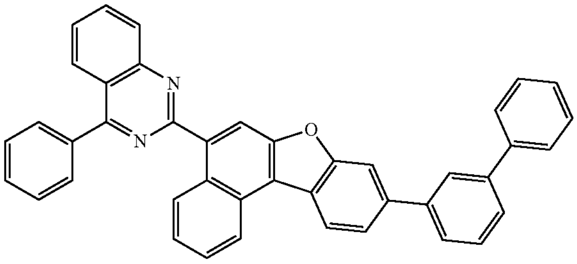
2-264
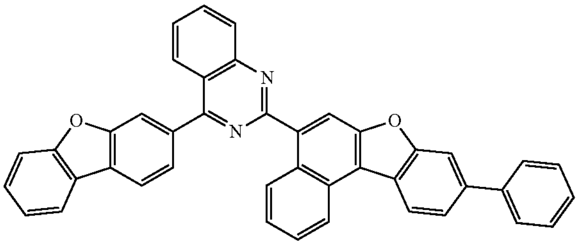
2-265
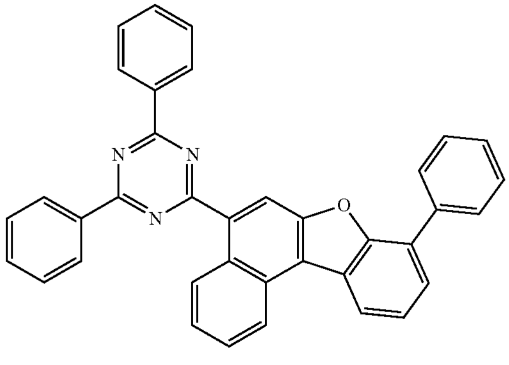

-continued
2-266
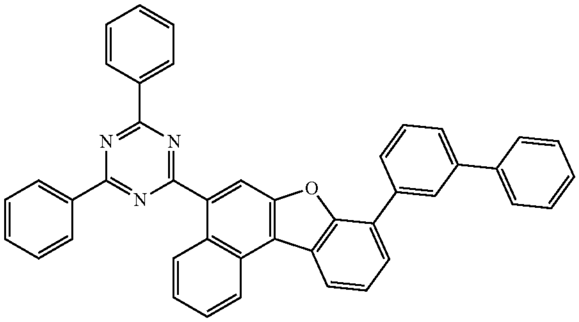
2-267
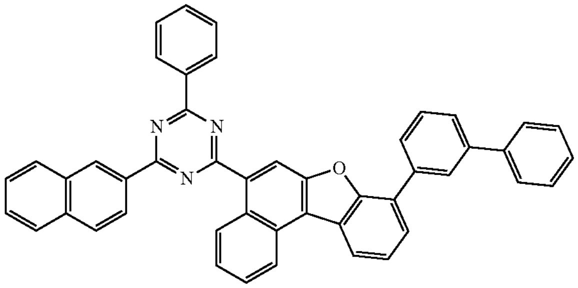
2-268
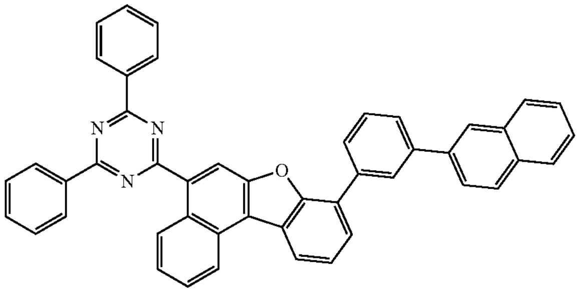
2-269
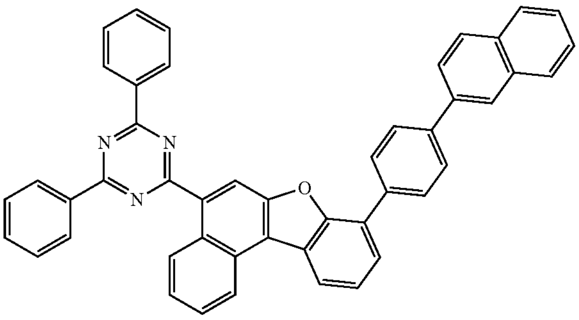
-continued
2-270
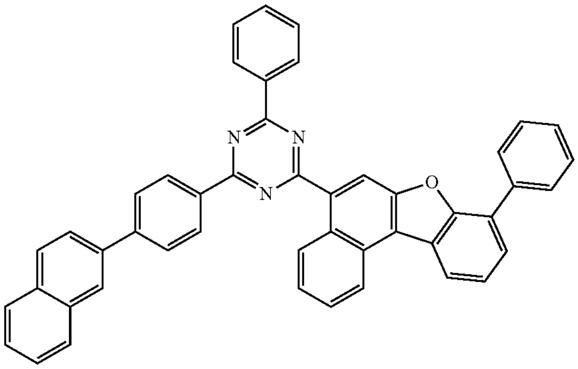
2-271
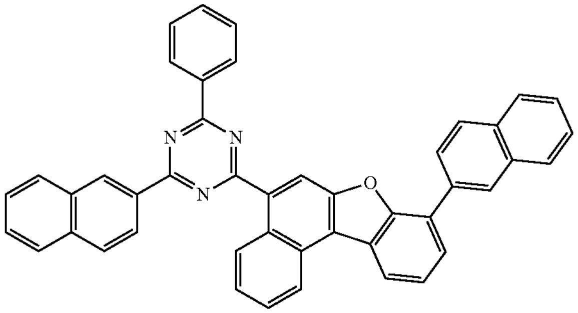
2-272
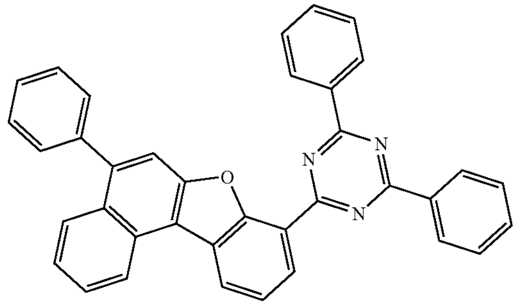
2-273
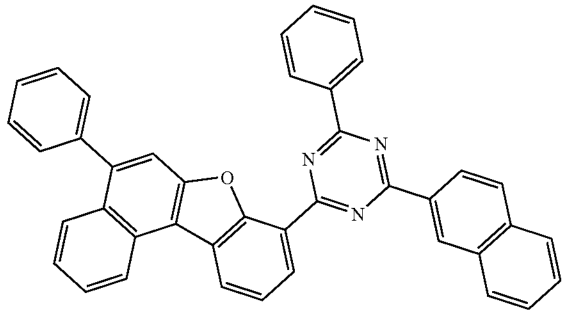

-continued
2-274
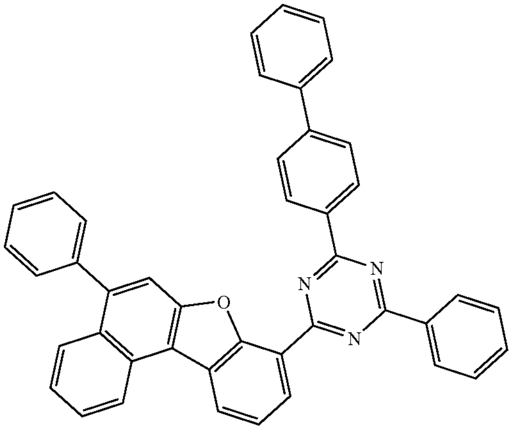
2-275
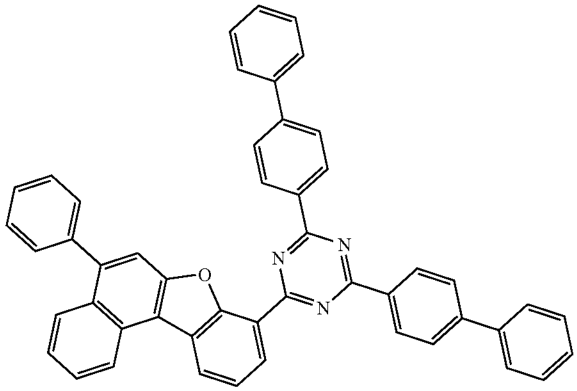
2-276
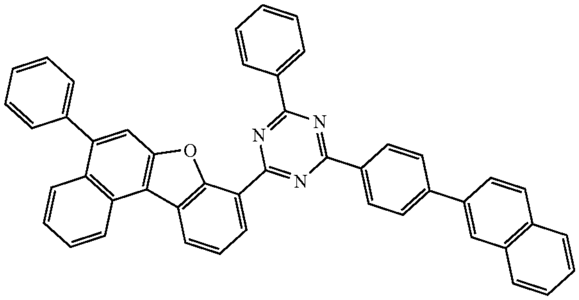
2-277
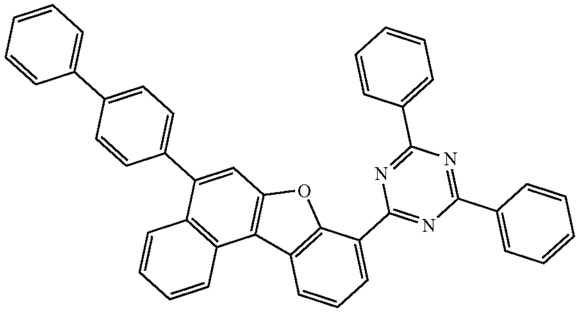
-continued
2-278
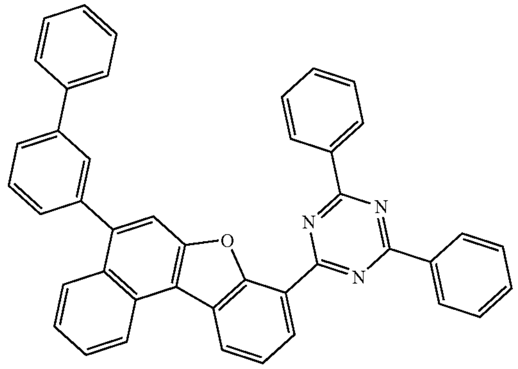
2-279
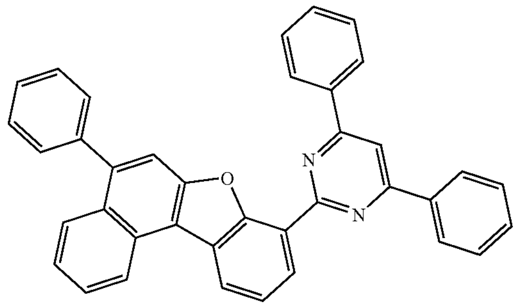
2-280
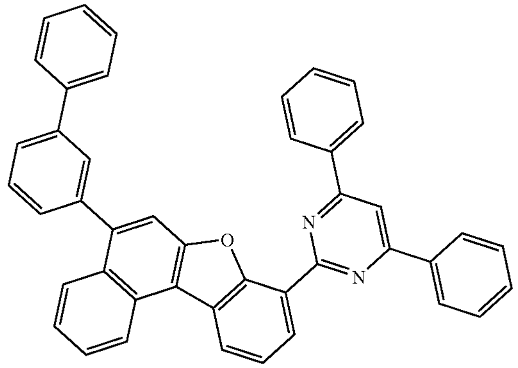
2-281
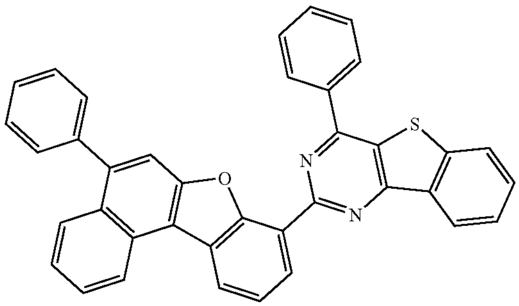

-continued
2-282
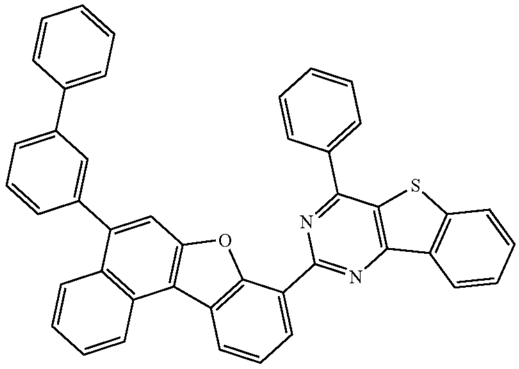
2-283
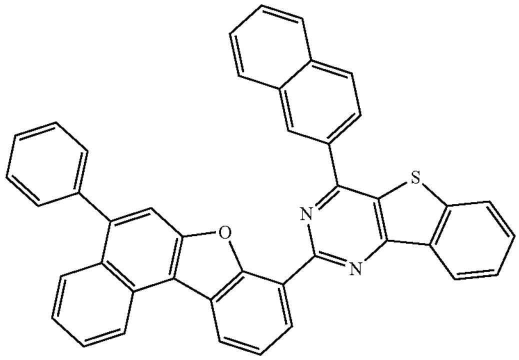
2-284
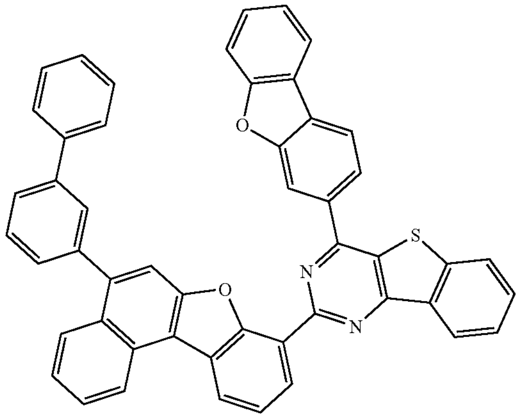
-continued
2-285
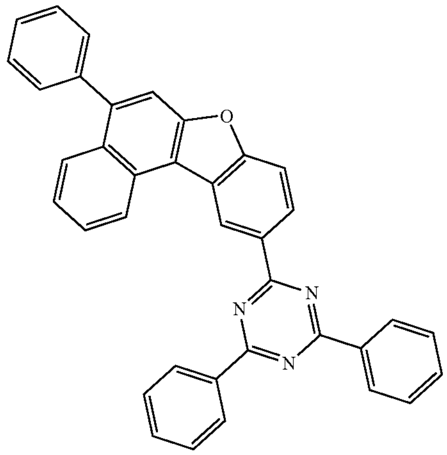
2-286
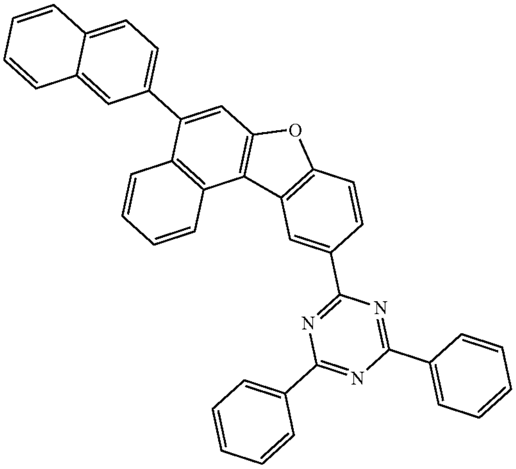
2-287
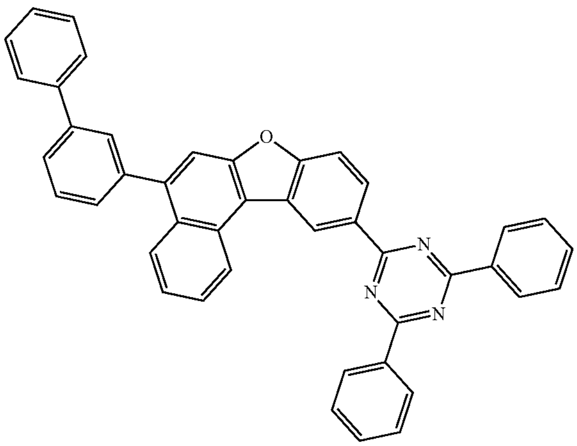

-continued
2-288
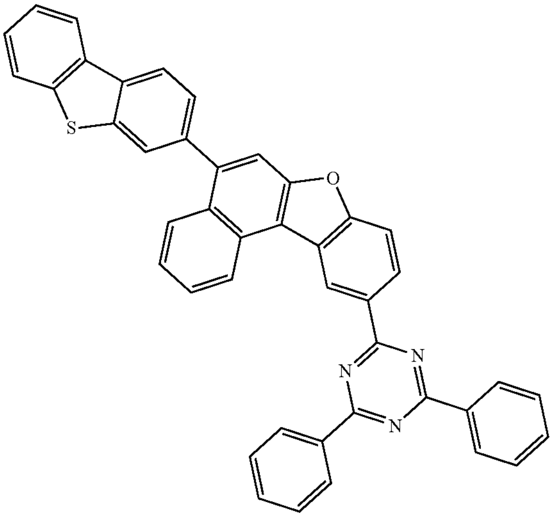
2-289
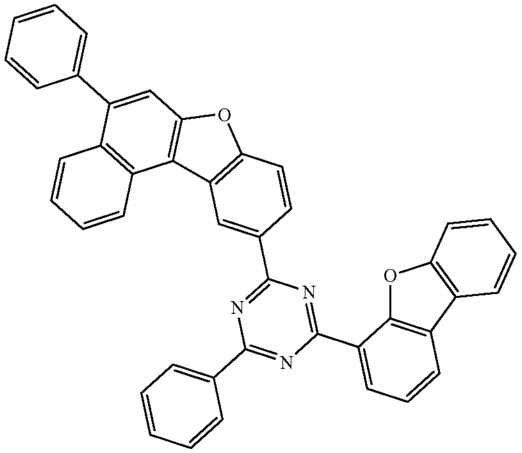
2-290
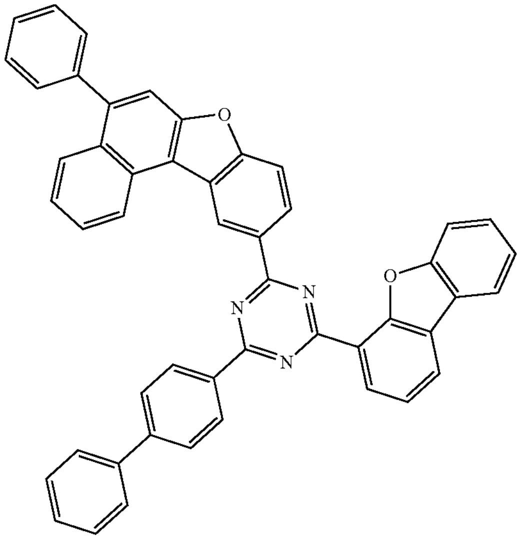
-continued
2-291
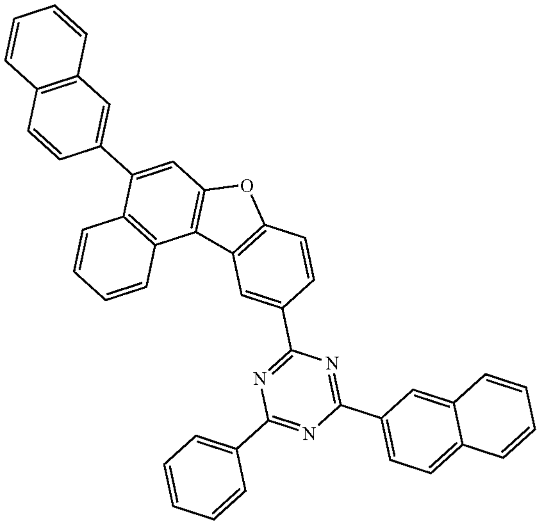
2-292
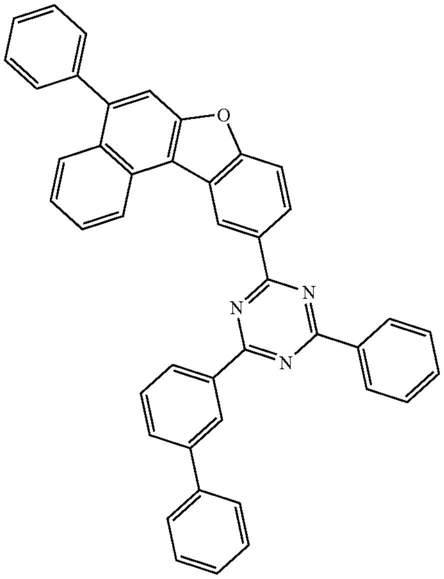
2-293
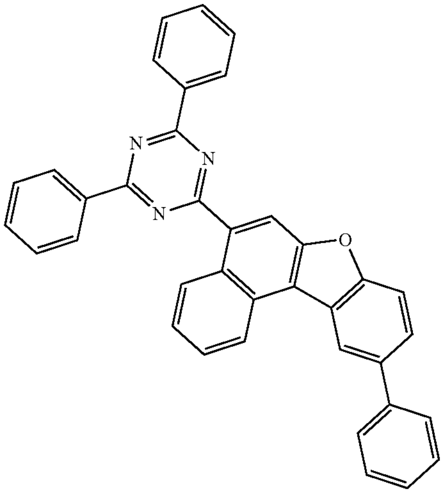

-continued
2-294
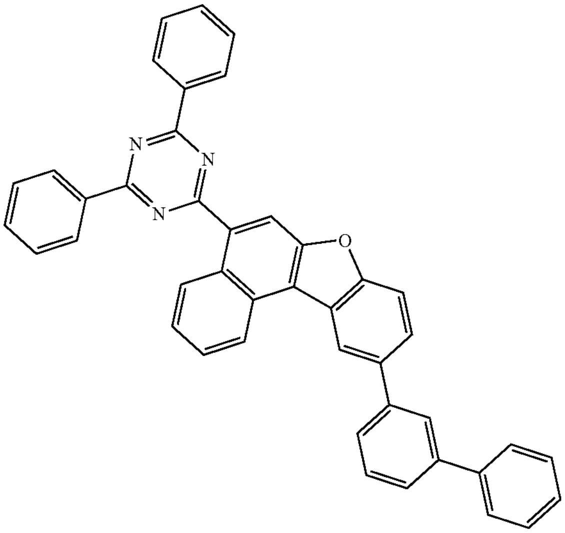
2-295
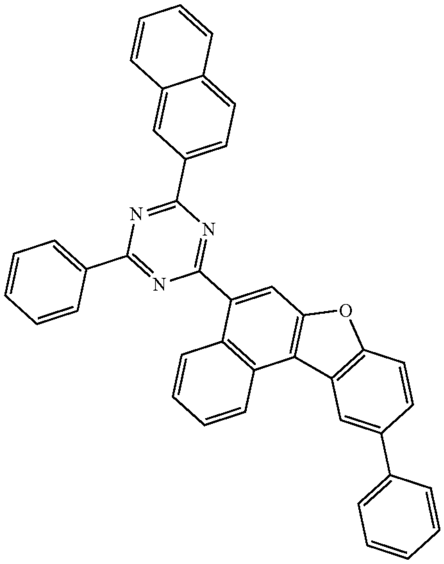
-continued
2-296
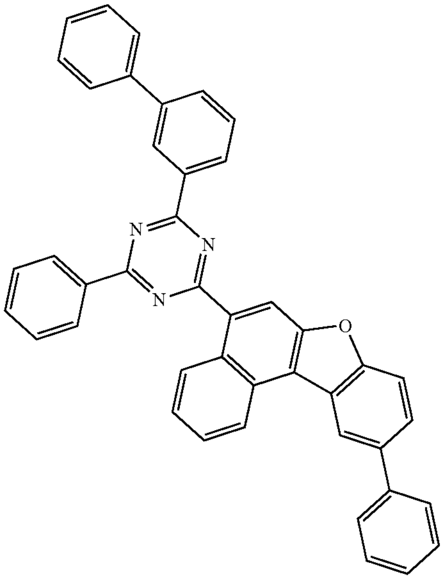
2-297
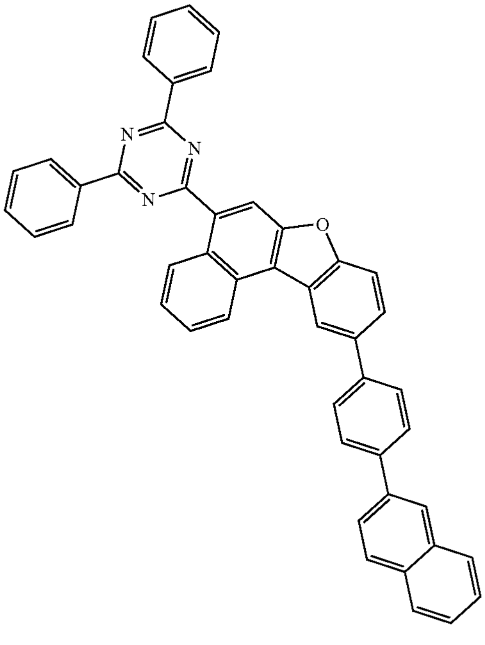

-continued
2-298
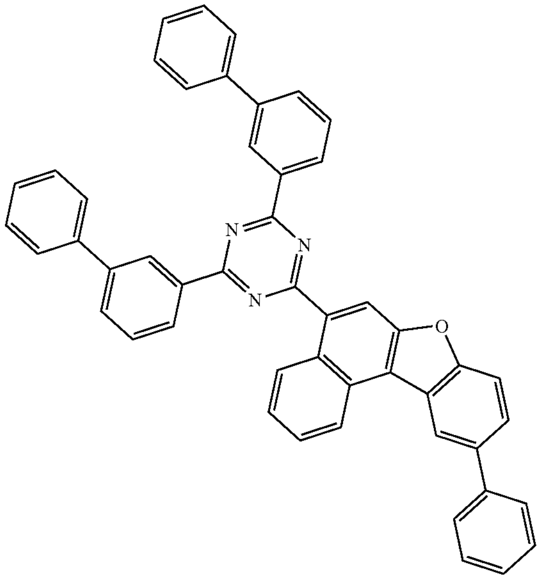
2-299
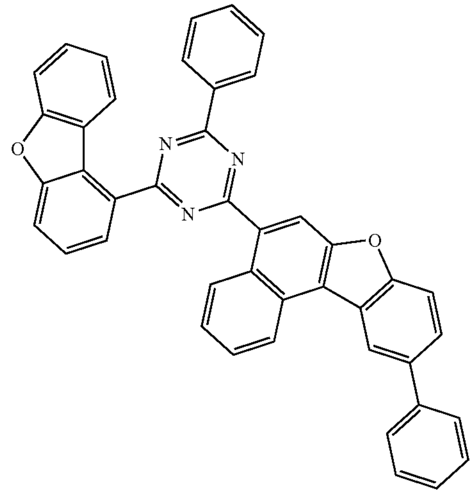
2-300
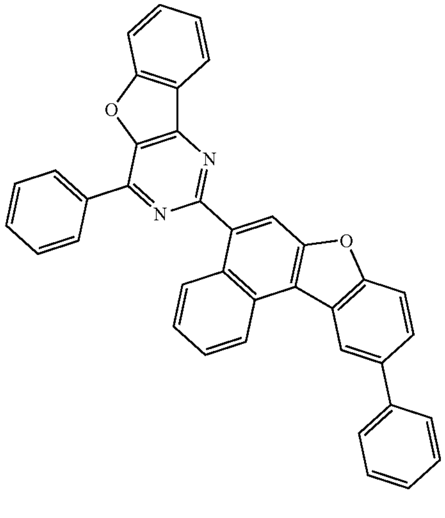
2-301
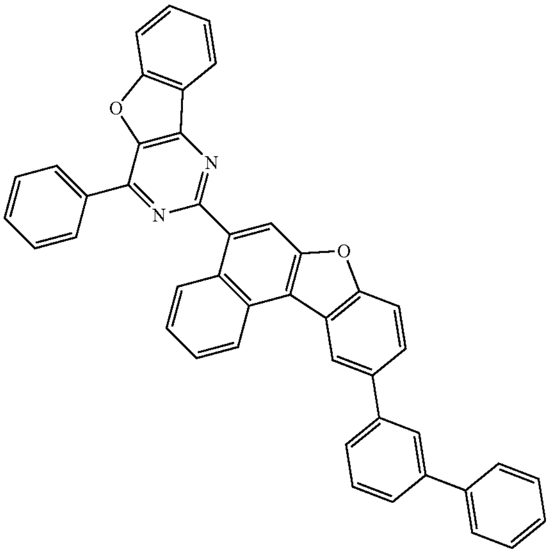
2-302
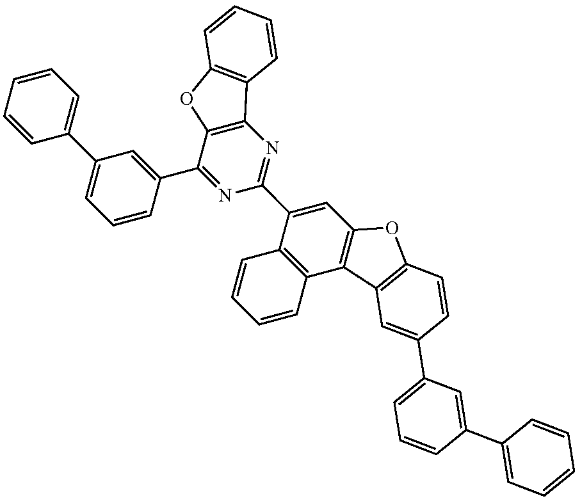
2-303
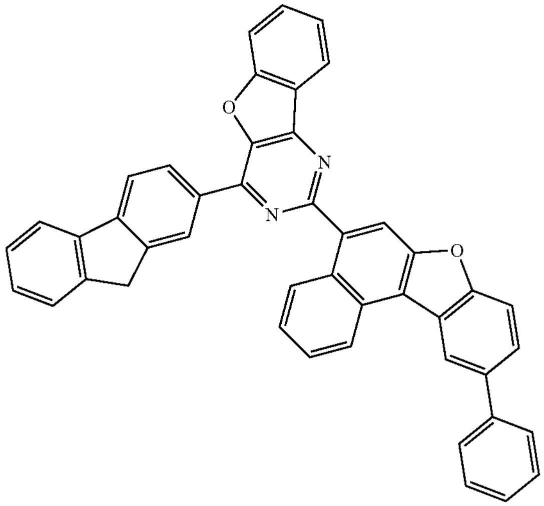

-continued
2-304
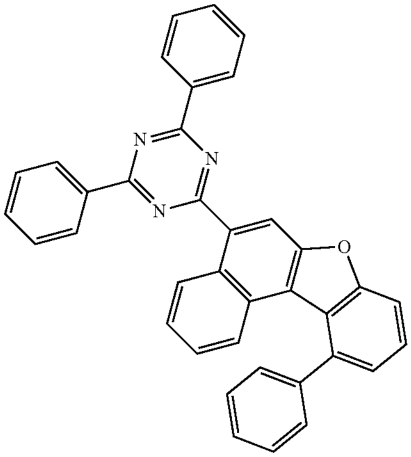
2-305
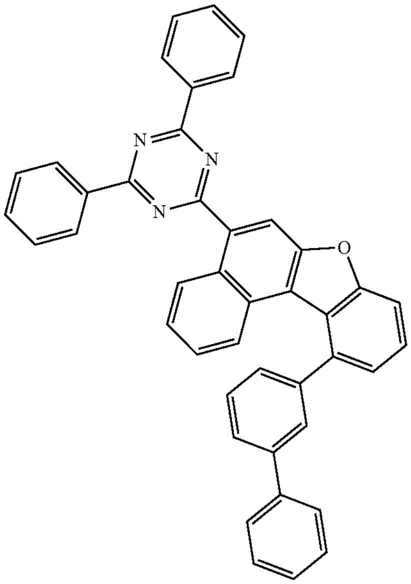
2-306
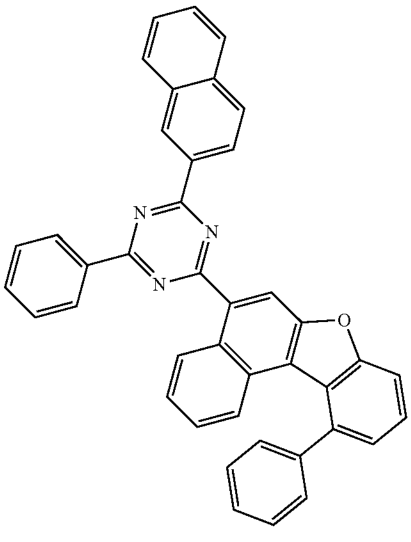
-continued
2-307
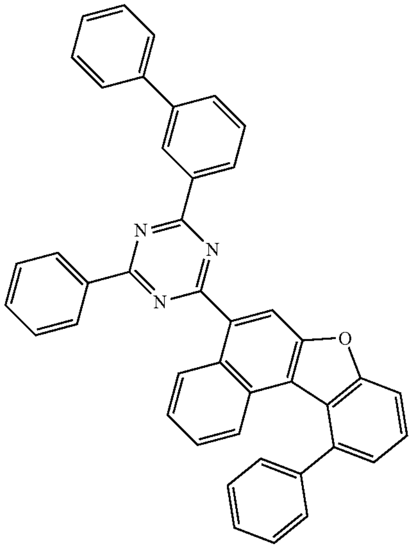
2-308
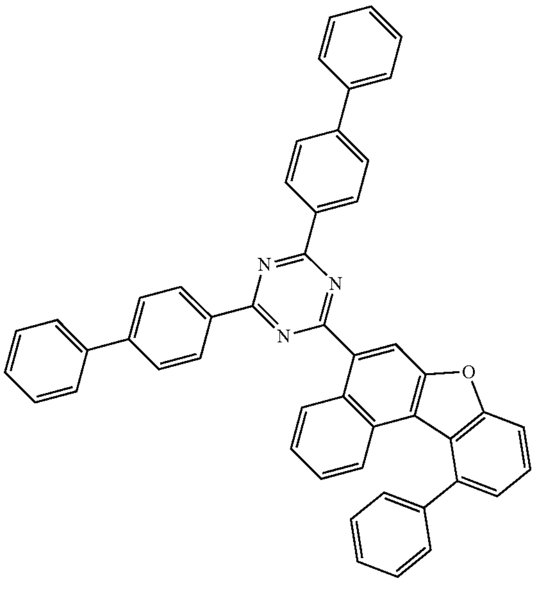

-continued
2-309
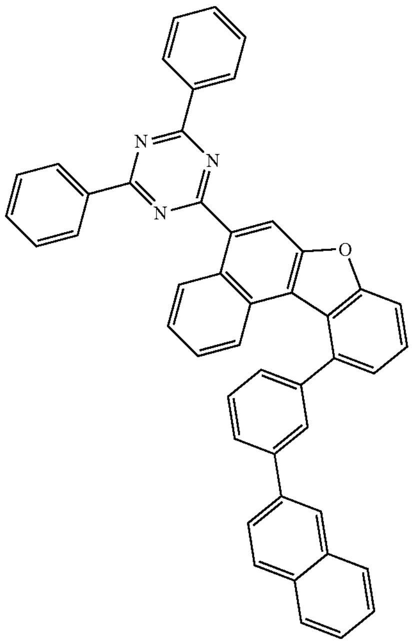
2-310
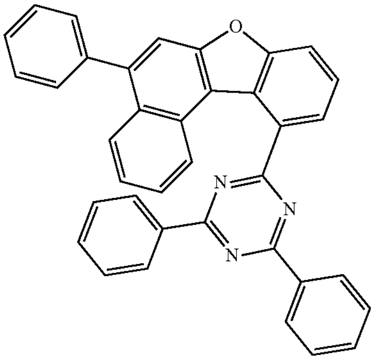
2-311
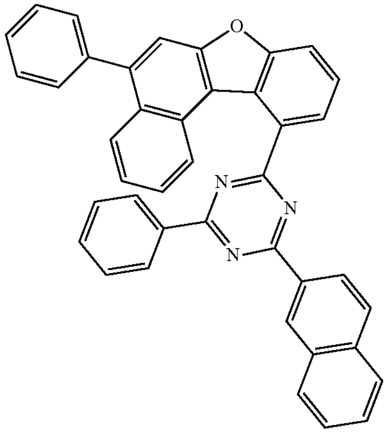
-continued
2-312
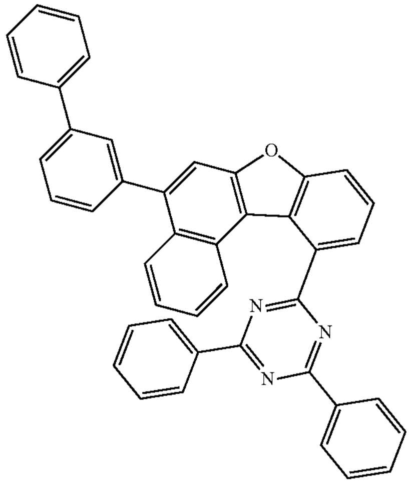
2-313
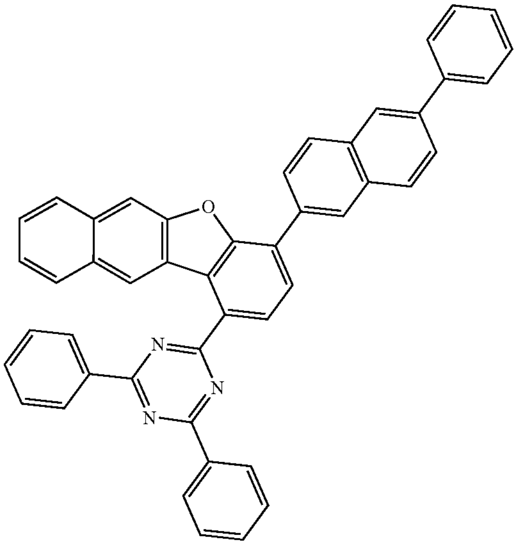
2-314
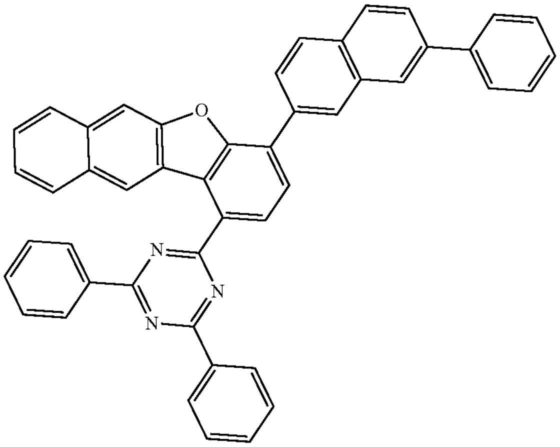

-continued
2-315
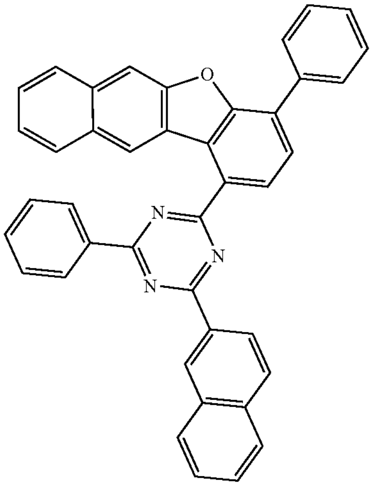
2-316
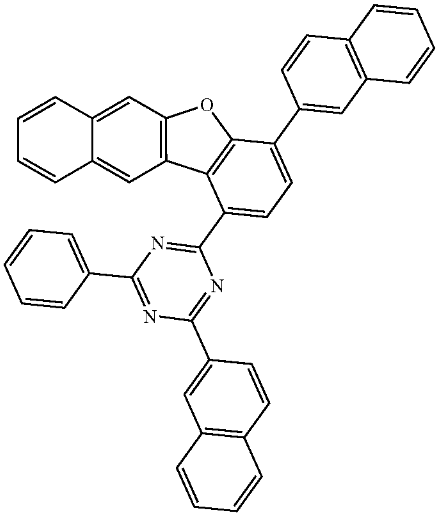
2-317
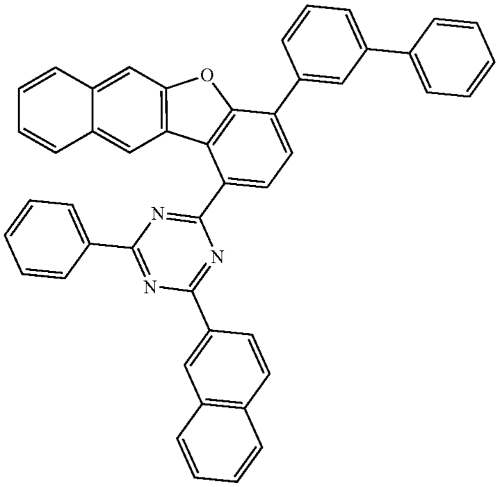
-continued
2-318
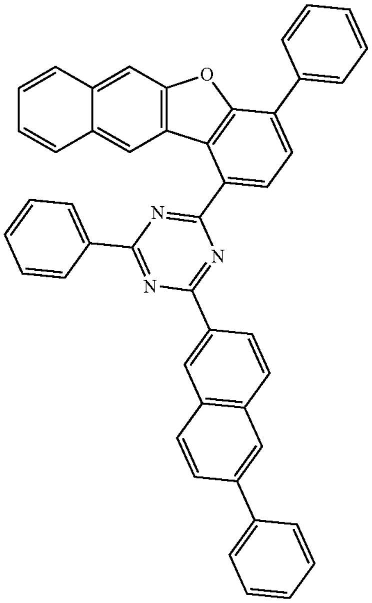
2-319
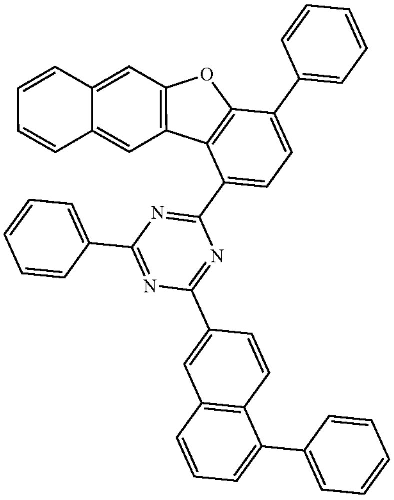

-continued
2-320
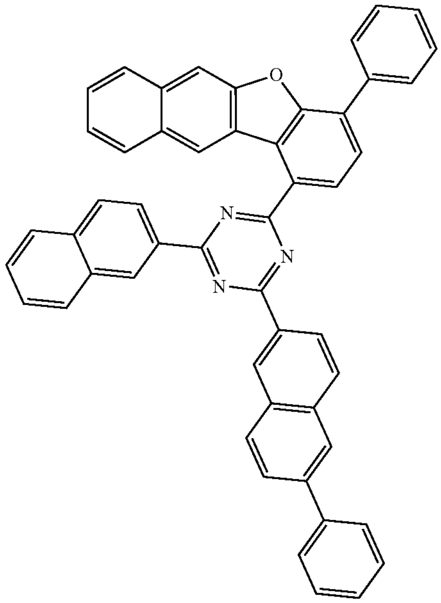
2-321
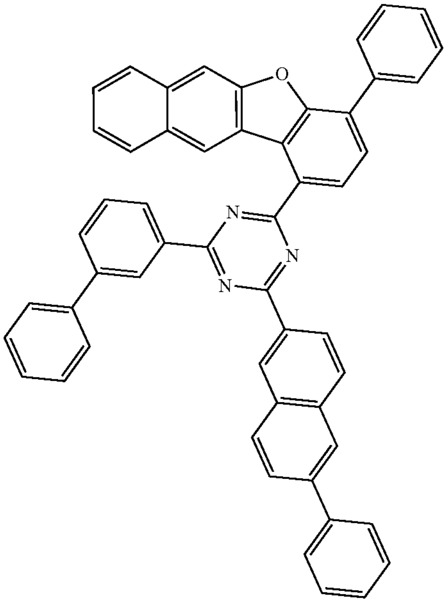
-continued
2-322
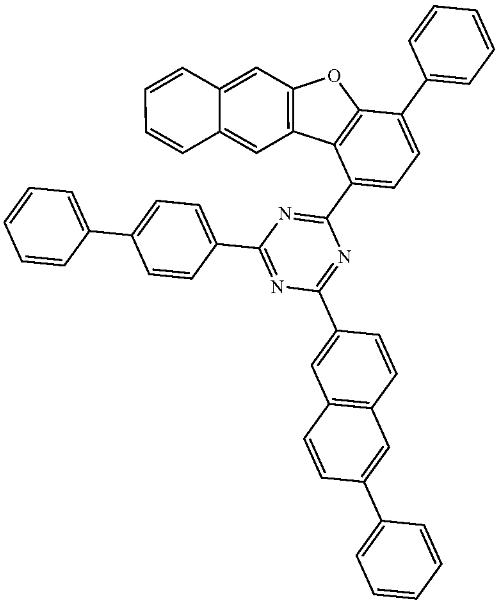
2--323
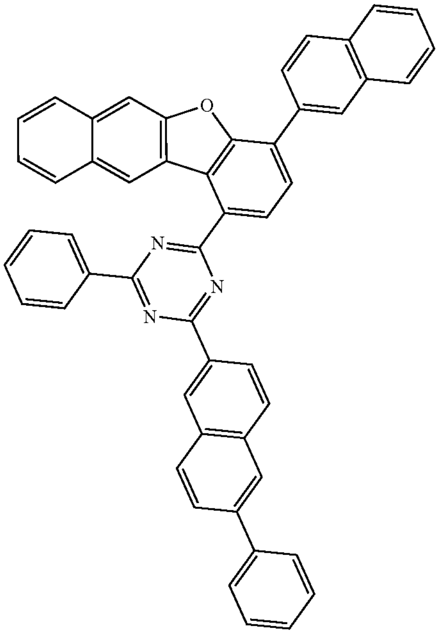

-continued
2-324
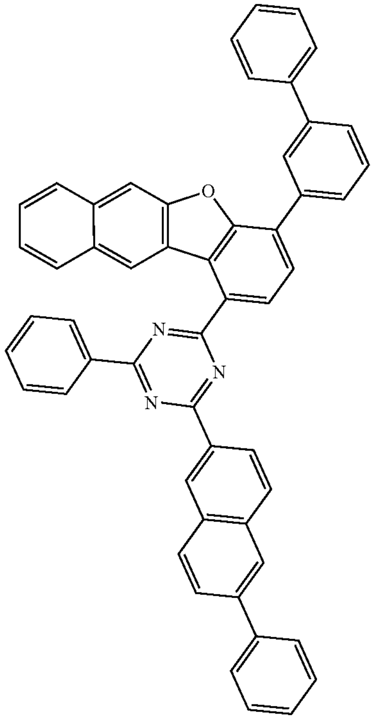
2-325
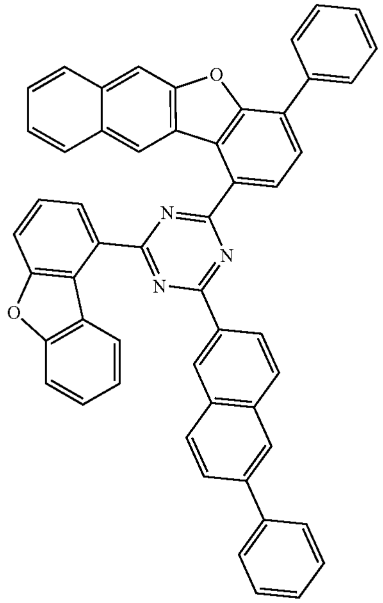
-continued
2-326
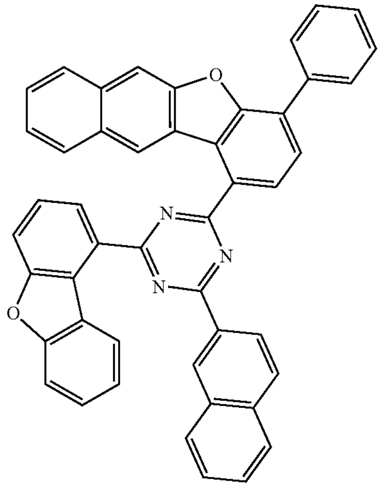
2-327
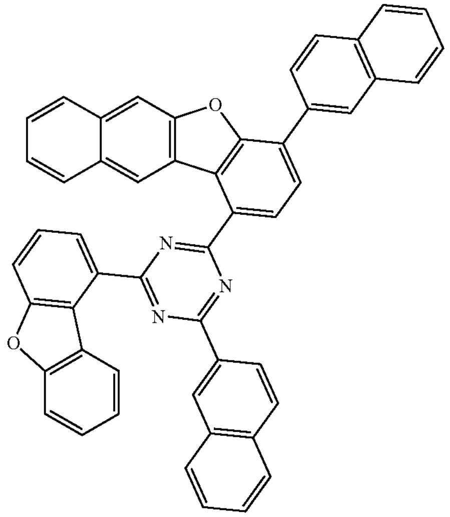
2-328
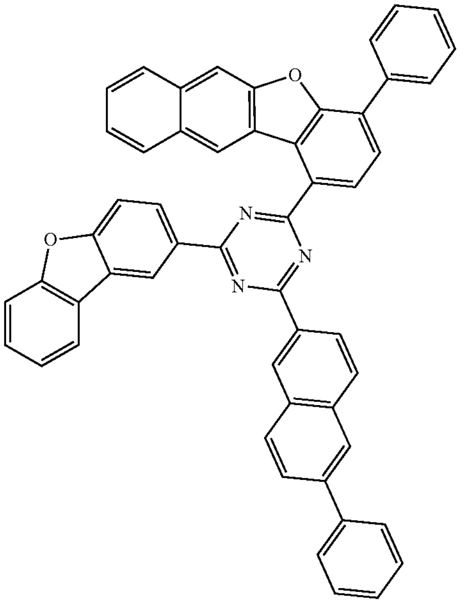

-continued
2-329
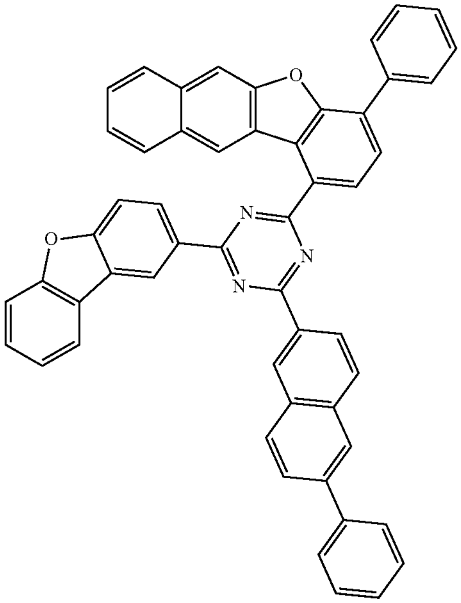
2-330
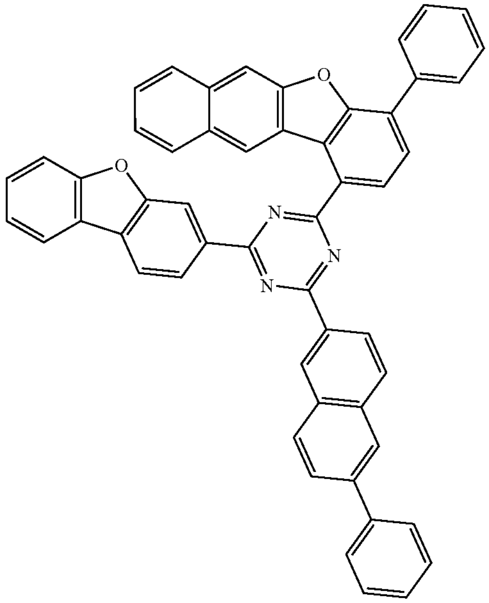
-continued
2-331
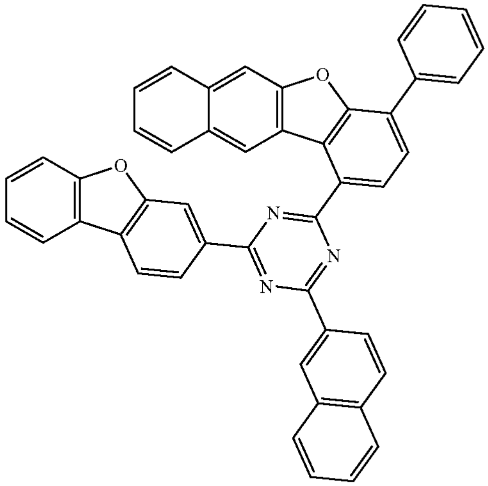
2-332
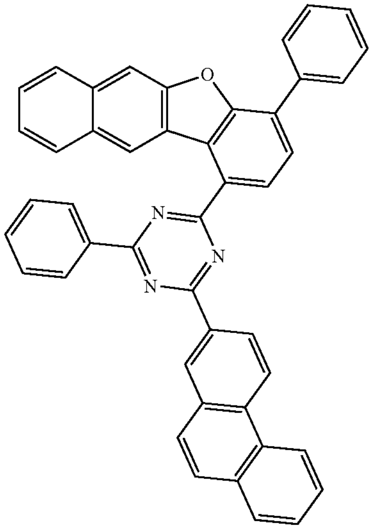
2-333
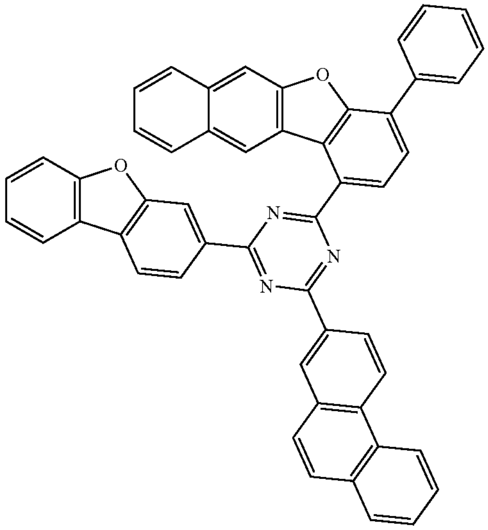

-continued
2-334
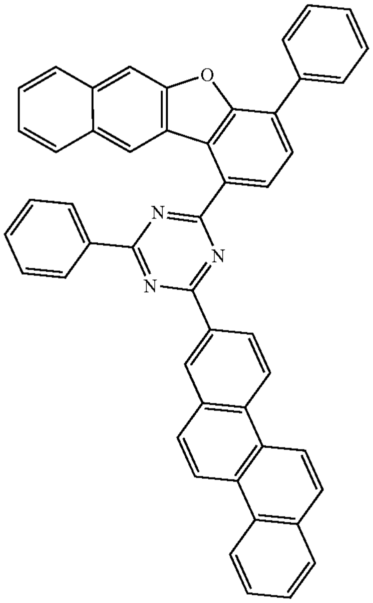
2-335
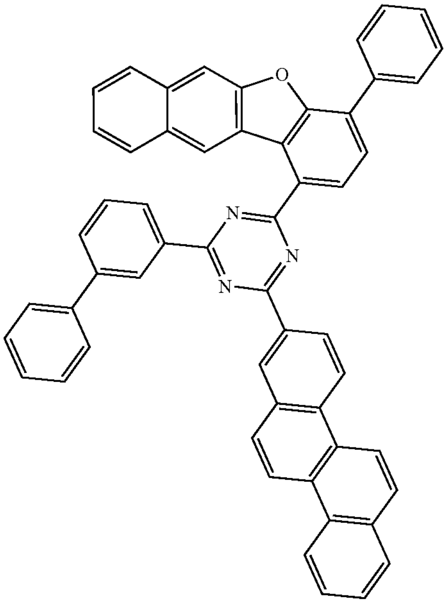
-continued
2-336
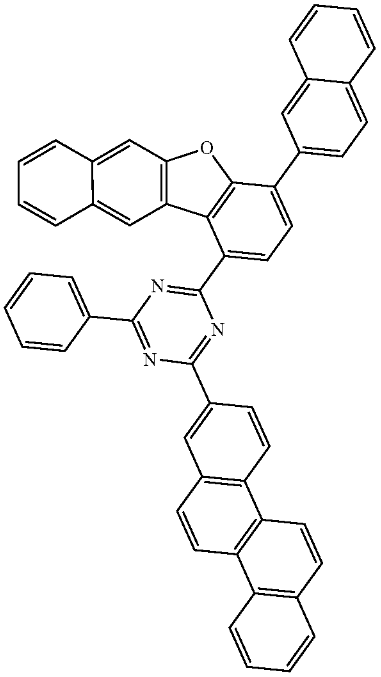
2-337
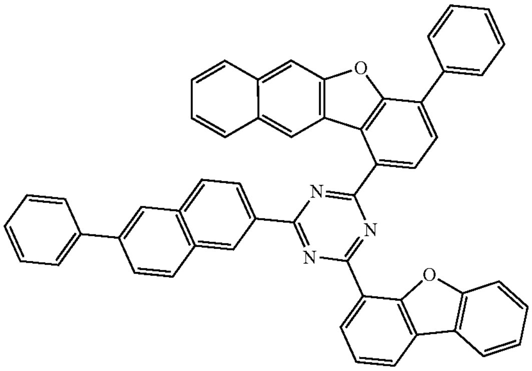
2-338
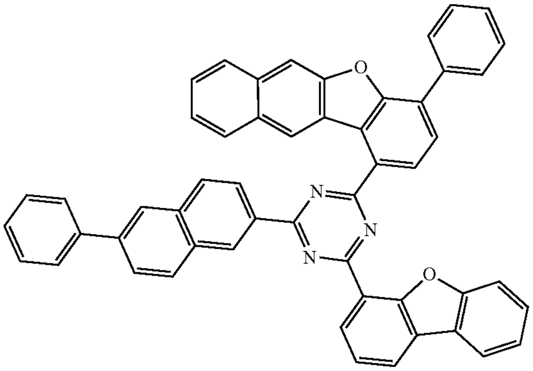

-continued
2-339
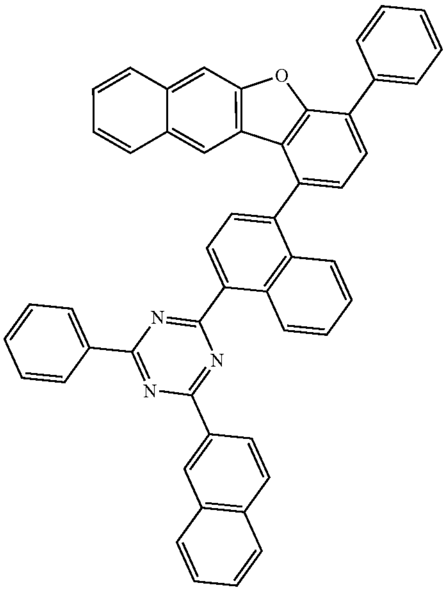
2-340
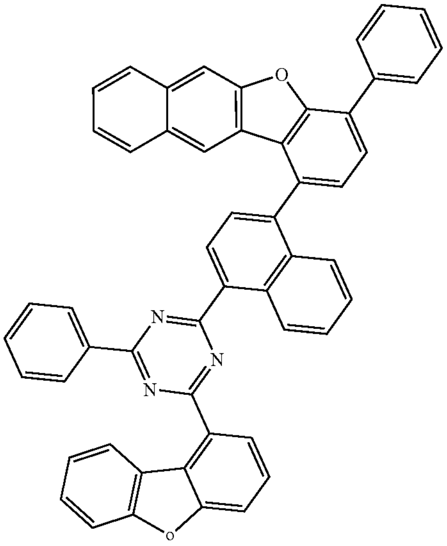
2-341
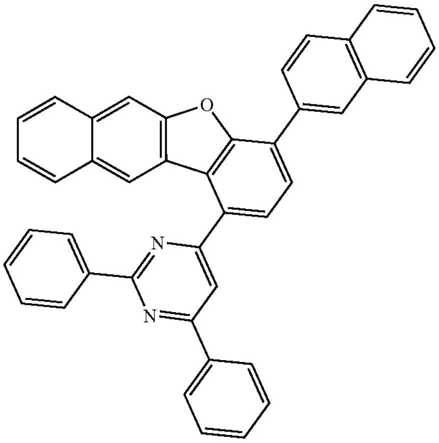
-continued
2-342
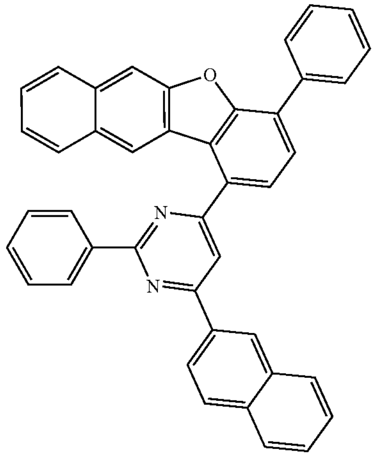
2-343
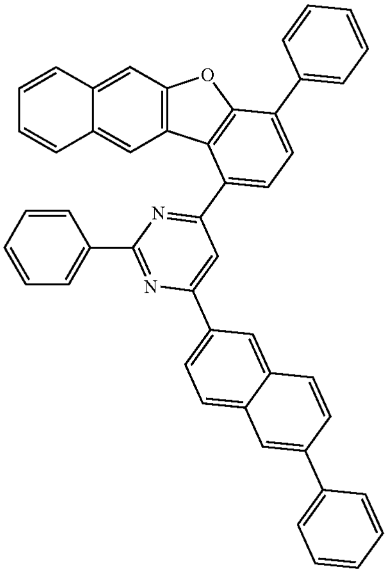
2-344
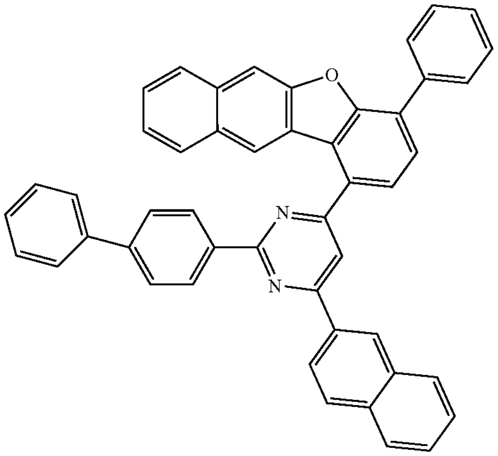

-continued
2-345
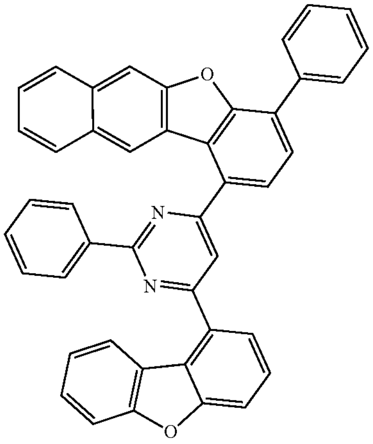
2-346
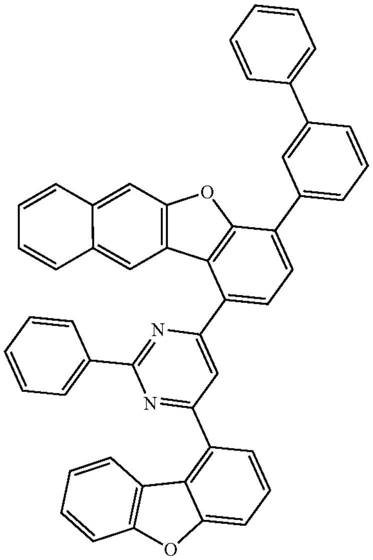
2-347
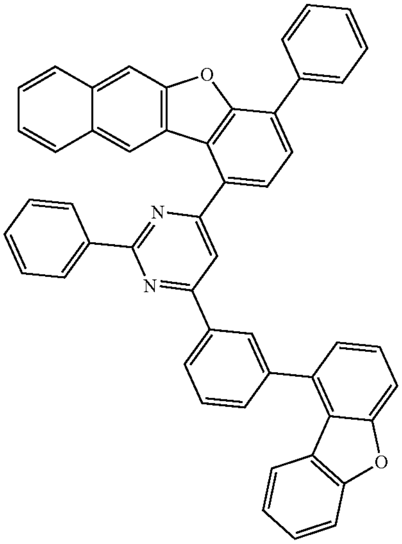
-continued
2-348
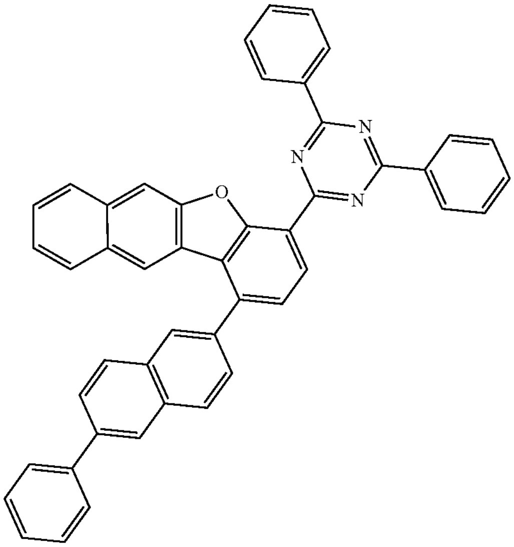
2-349
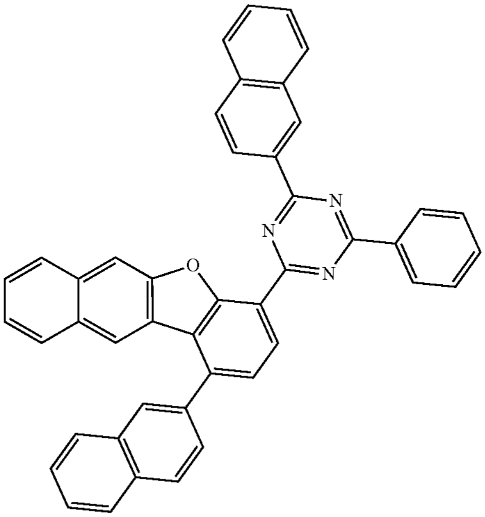
2-350
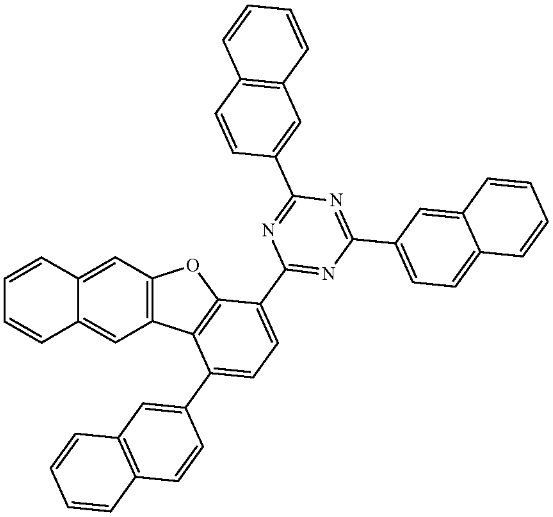

-continued
2-351
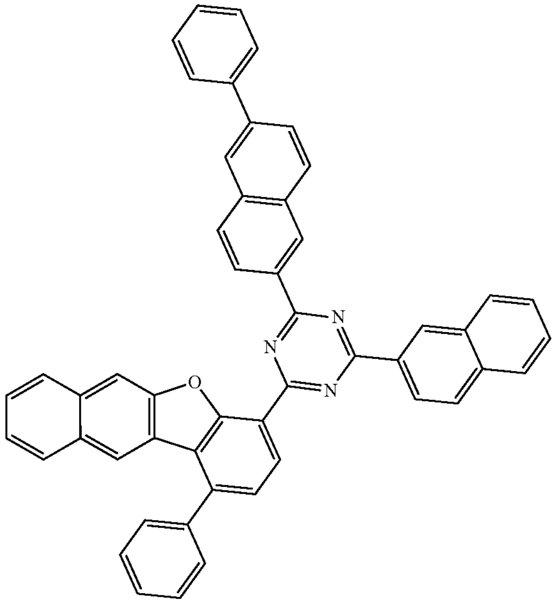
2-352
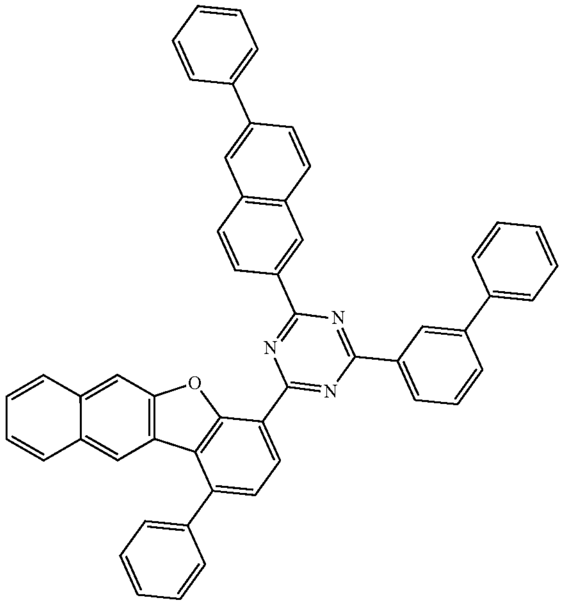
-continued
2-353
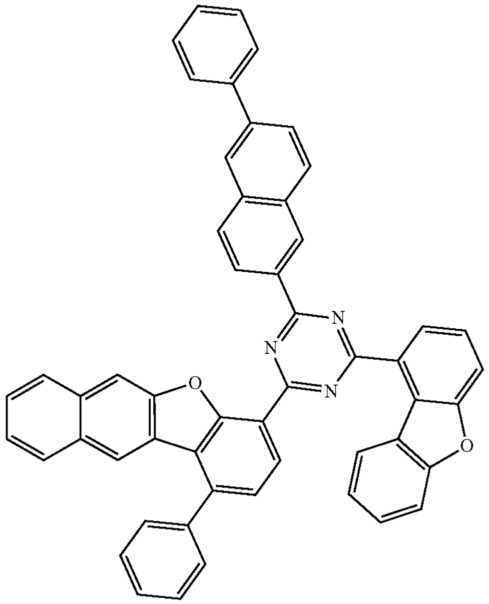
2-354
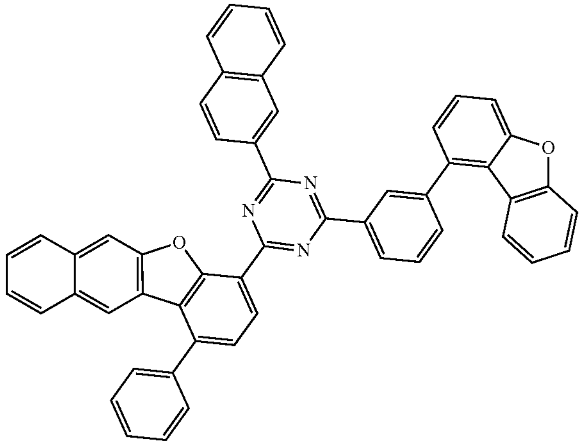
2-355
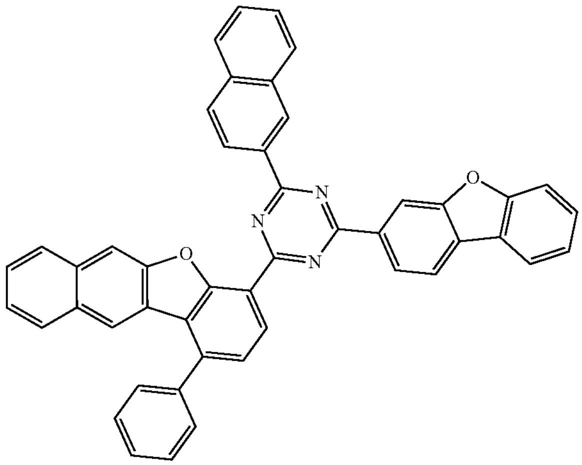

-continued
2-356
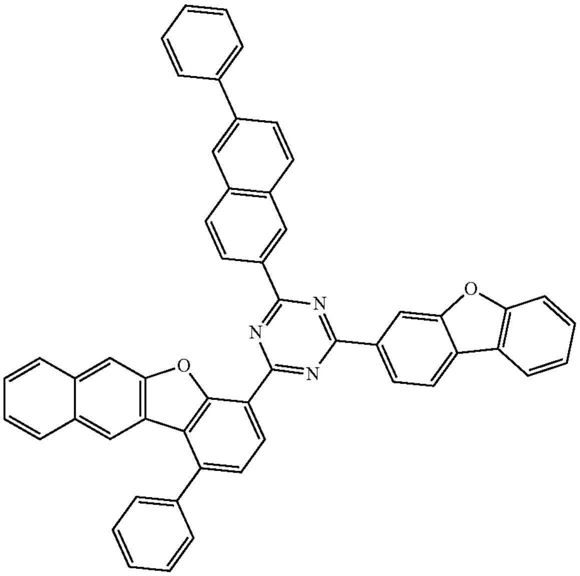
2-357
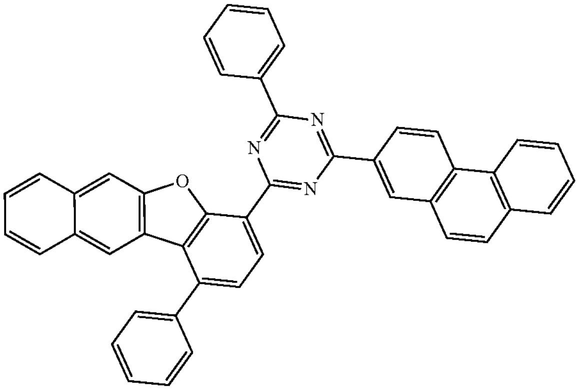
2-358
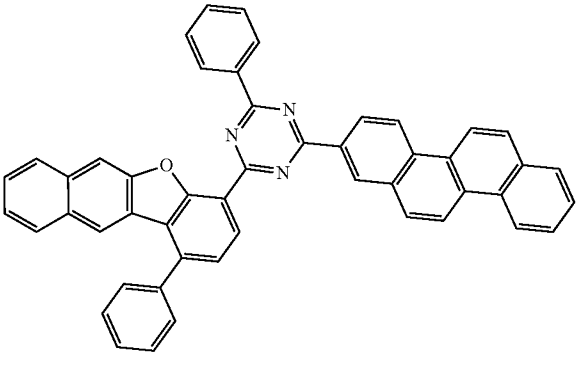
-continued
2-359
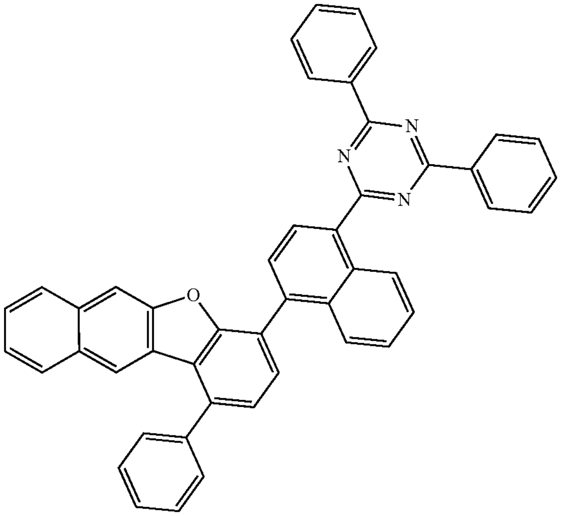
2-360
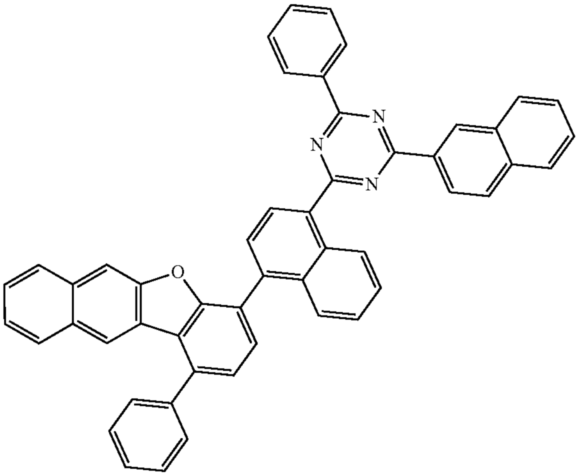
2-361
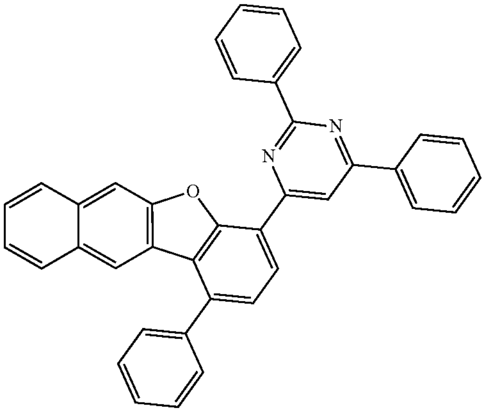

-continued
2-362
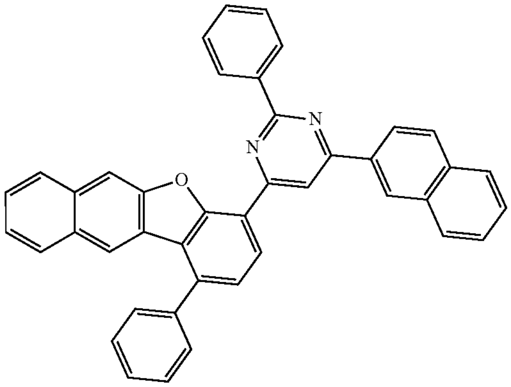
2-363
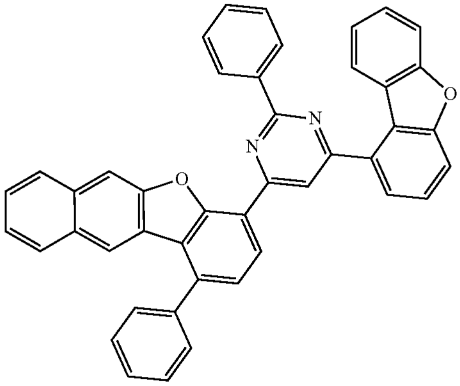
2-364
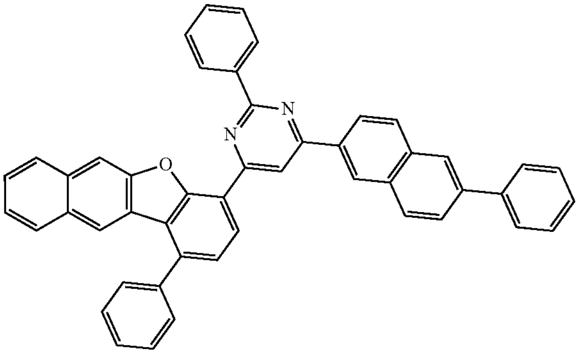
2-365
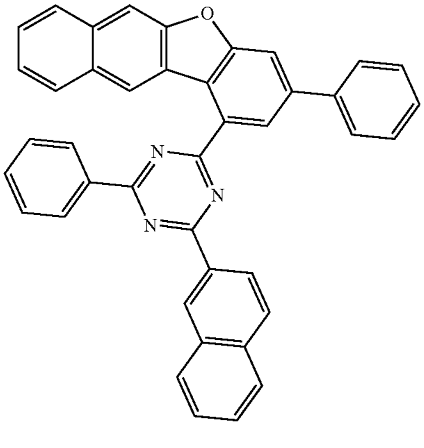
-continued
2-366
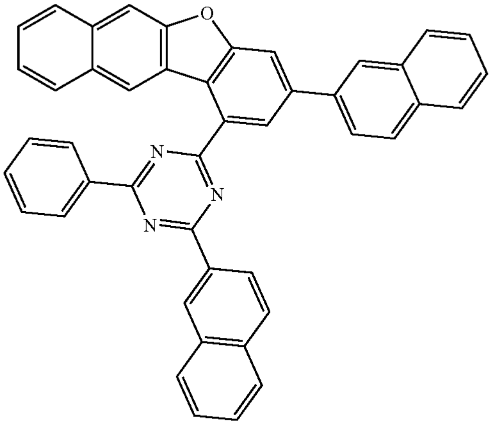
2-367
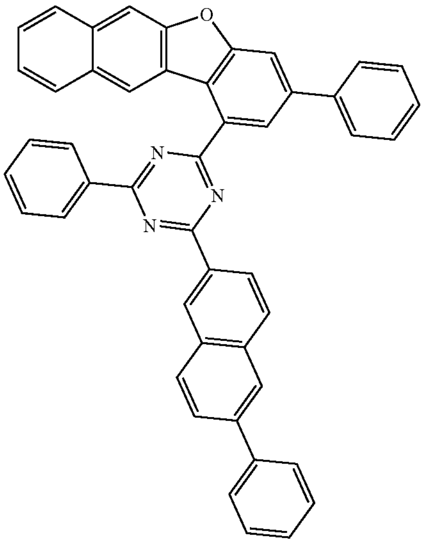
2-368
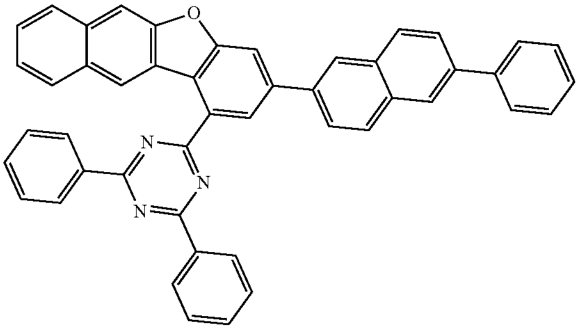

-continued
2-369
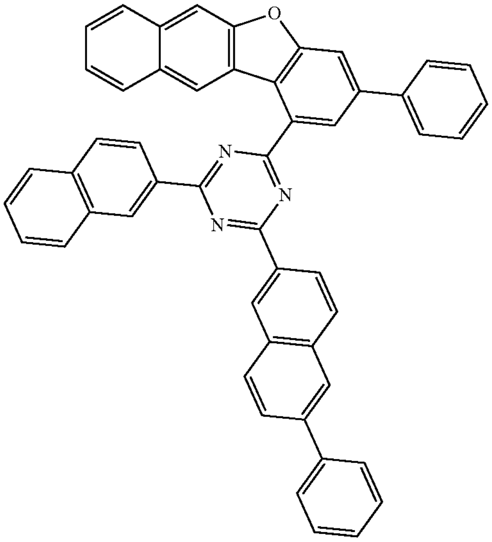
2-370
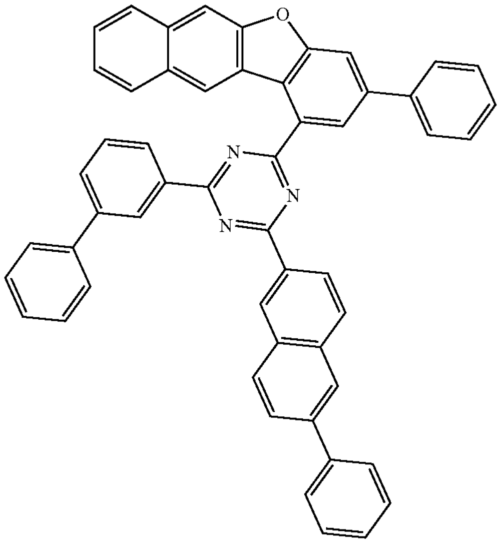
2-371
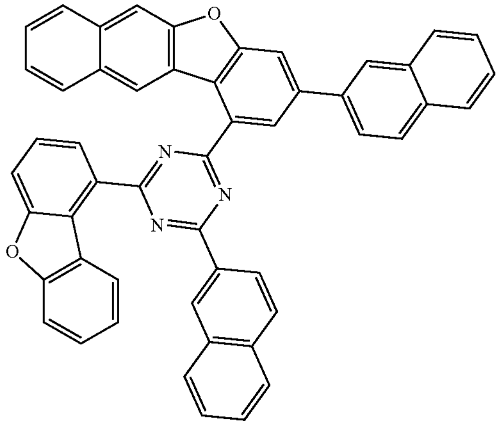
-continued
2-372
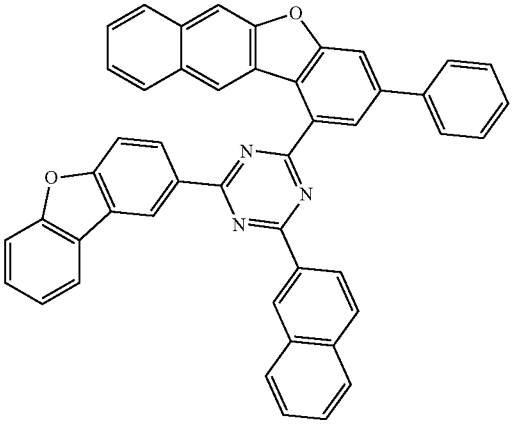
2-373
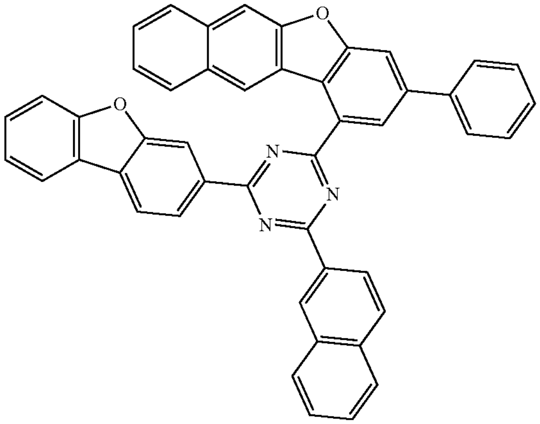
2-374
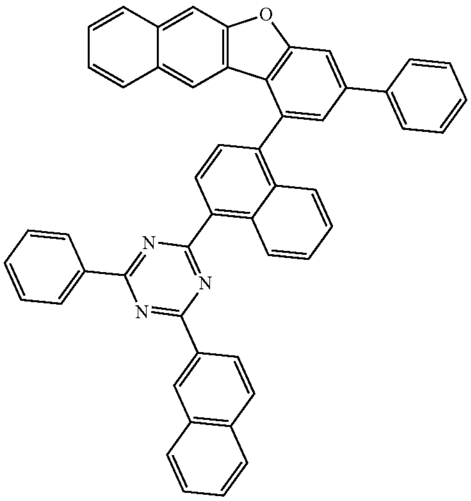

-continued
2-375
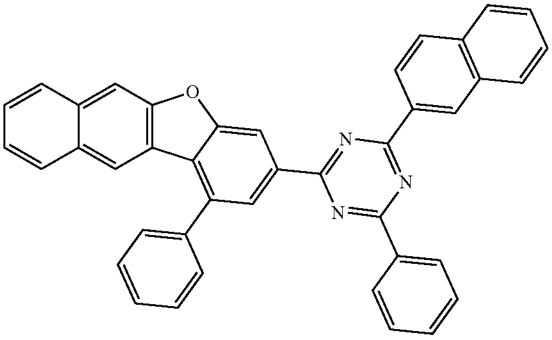
2-376
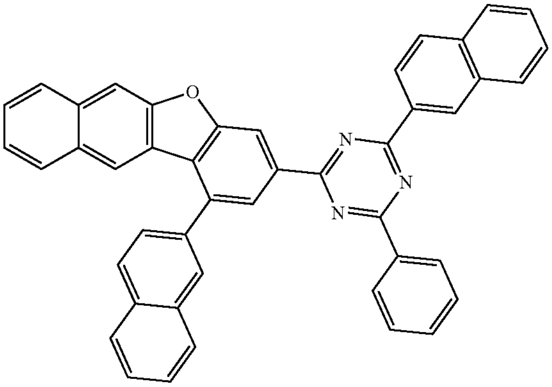
2--377
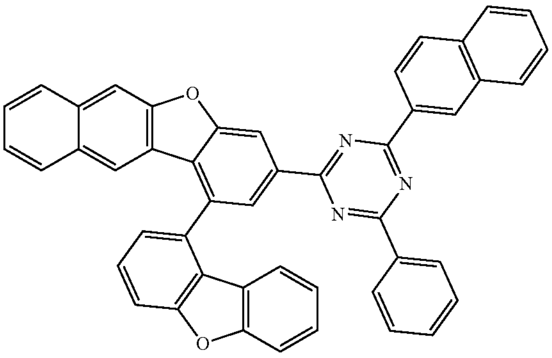
2-378
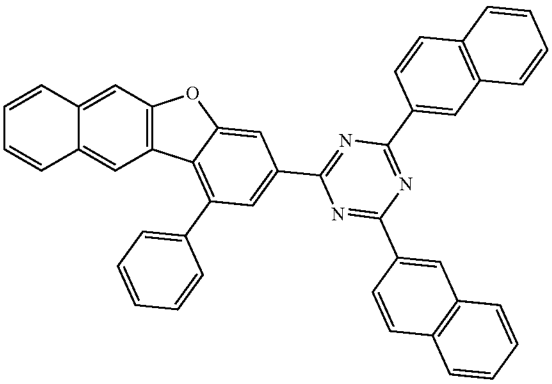
-continued
2-379
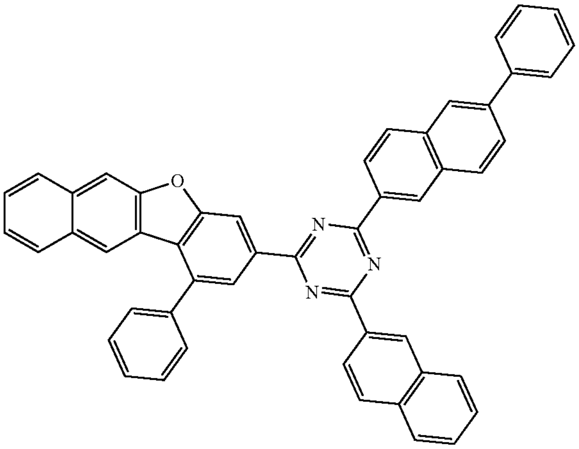
2-380
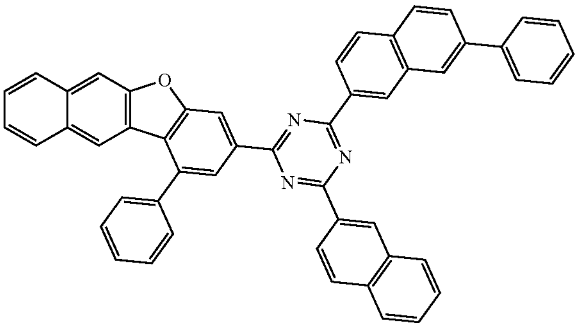
2-381
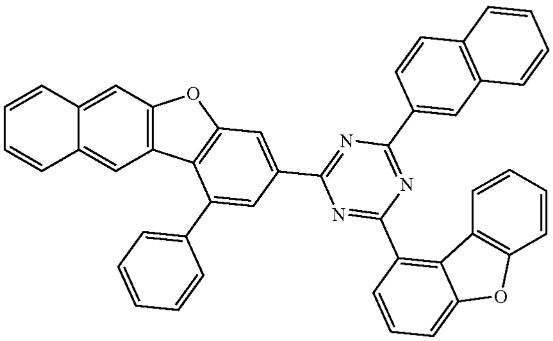
2-382
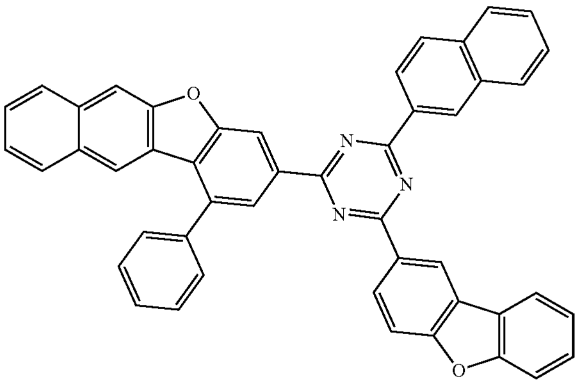

-continued
2-383
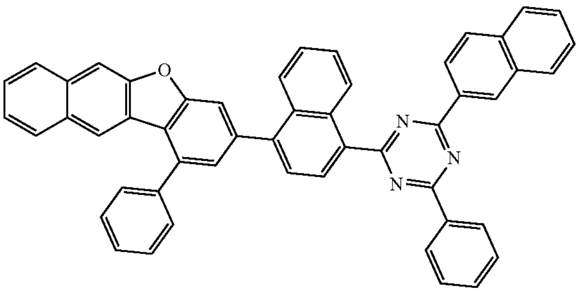
2-384
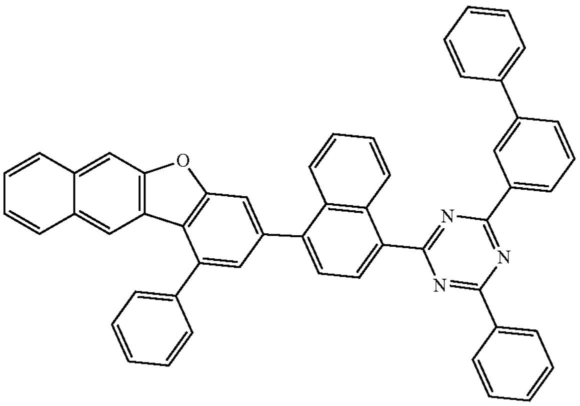
2-385
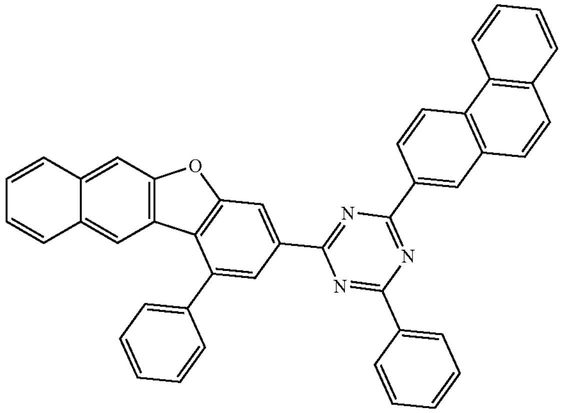
2-386
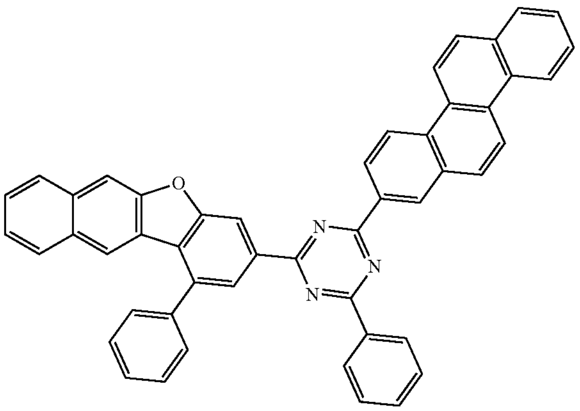
-continued
2-387
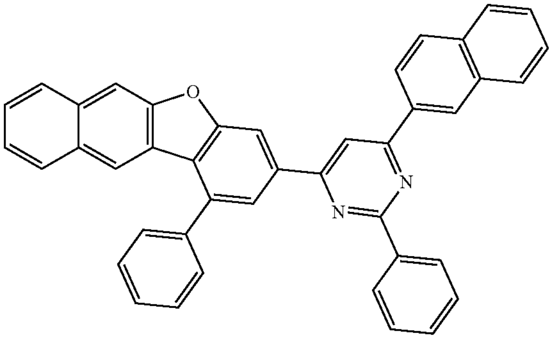
2-388
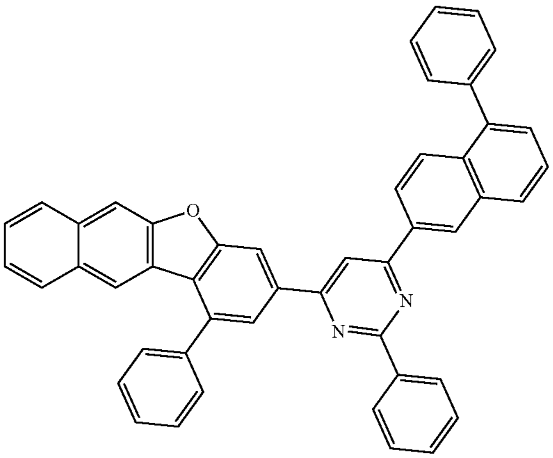
2-389
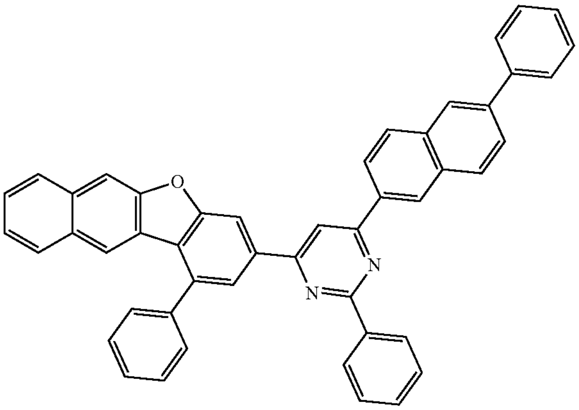
2-390
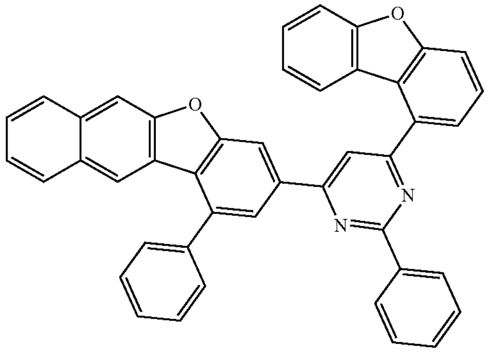

2-391
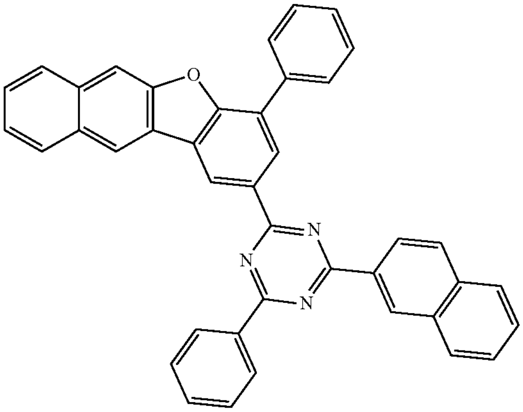
2-392
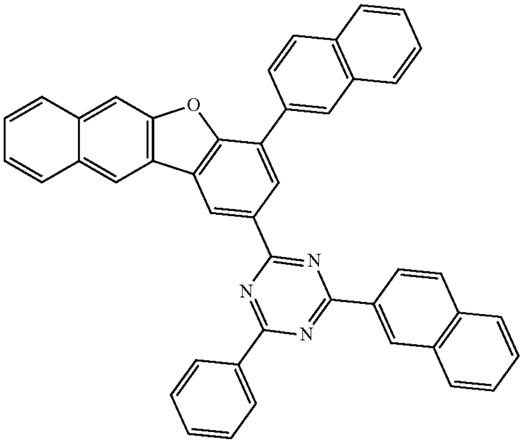
2-393
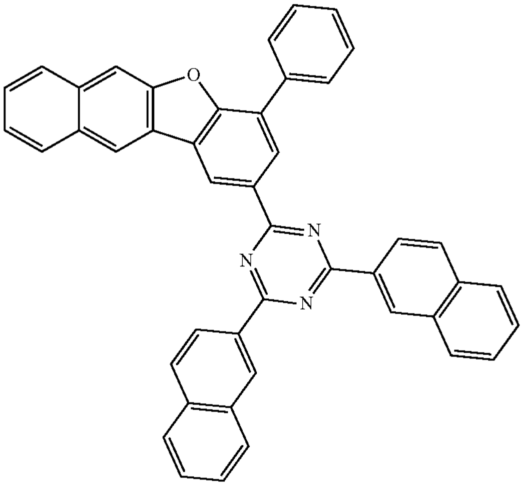
2-394
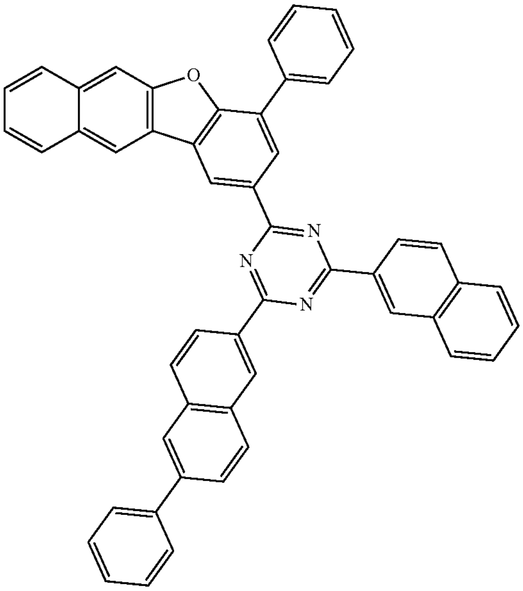
2-395
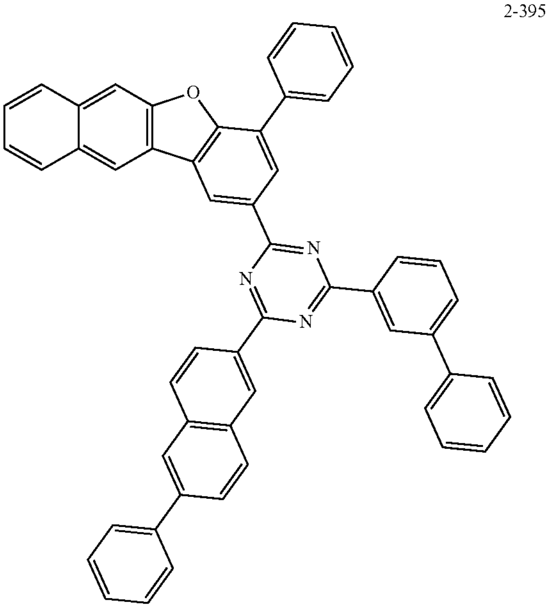

-continued
2-396
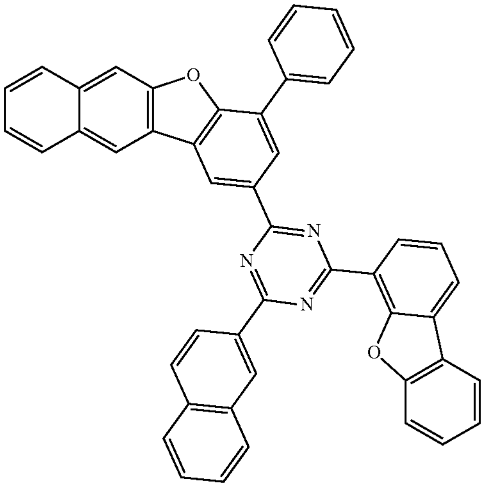
2-397
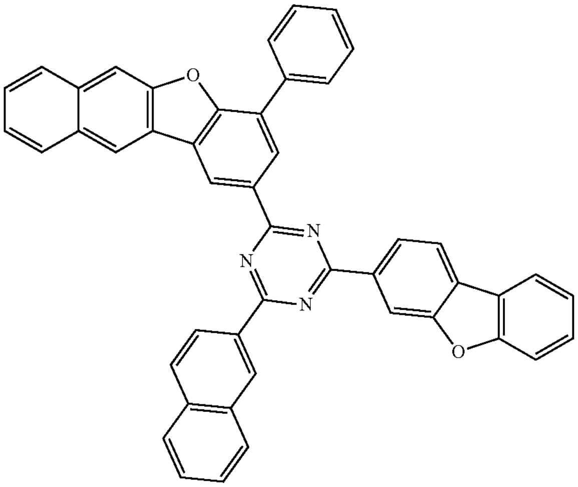
2-398
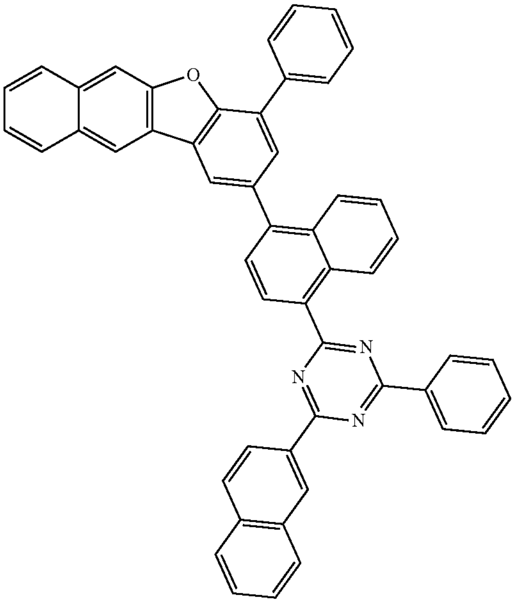
-continued
2-399
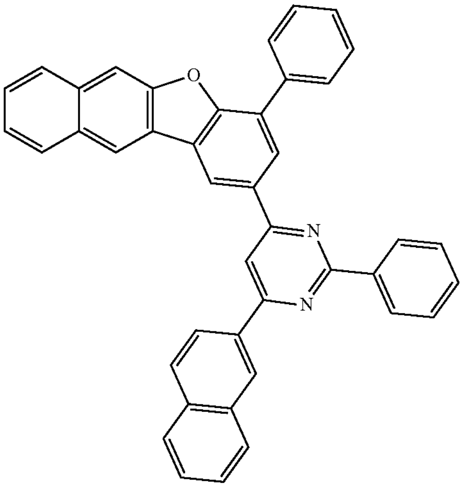
2-400
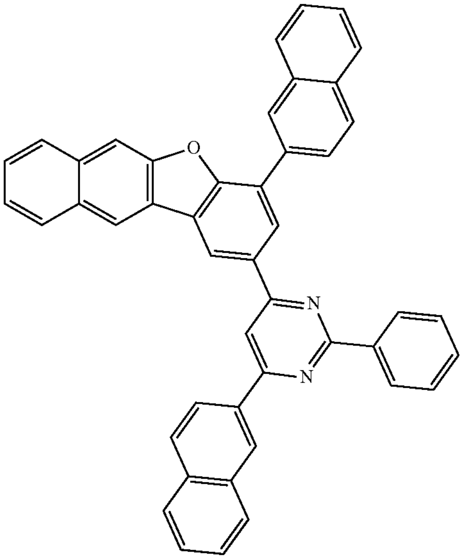
2-401
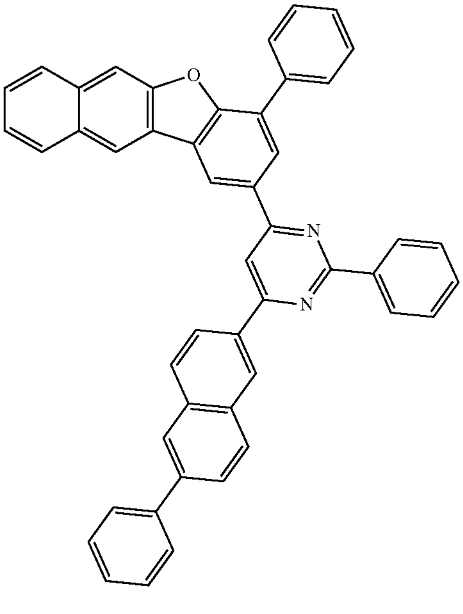

-continued
2-402
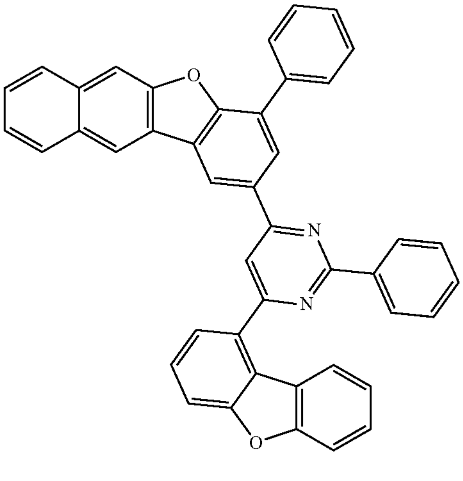
2-403
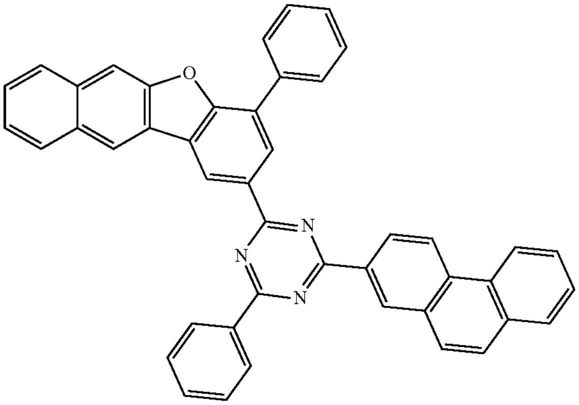
2-404
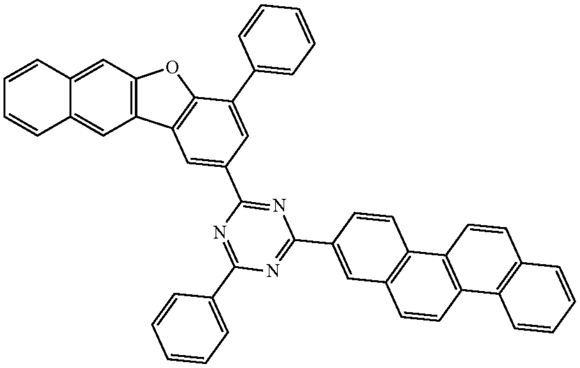
-continued
2-405
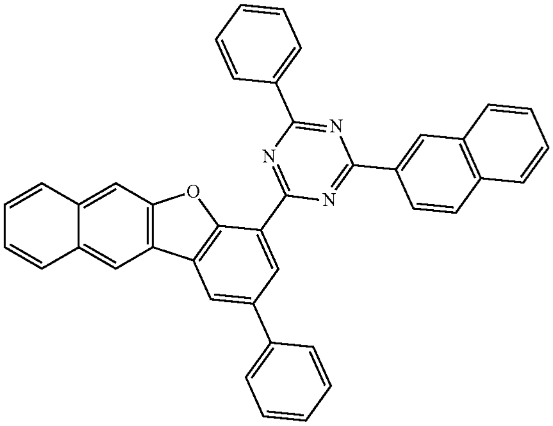
2-406
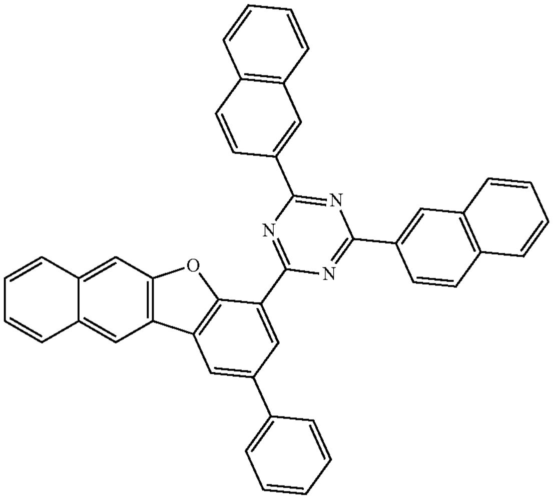
2-407
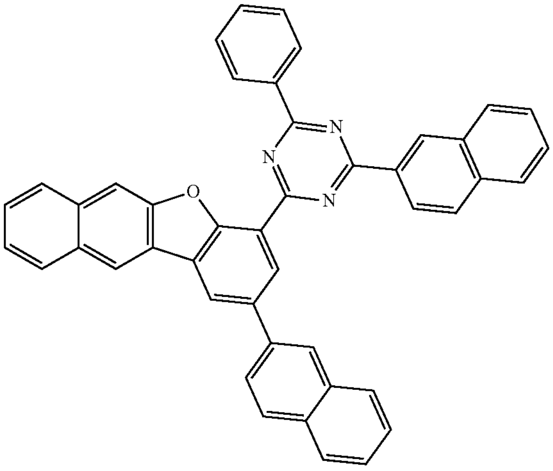

-continued
2-408
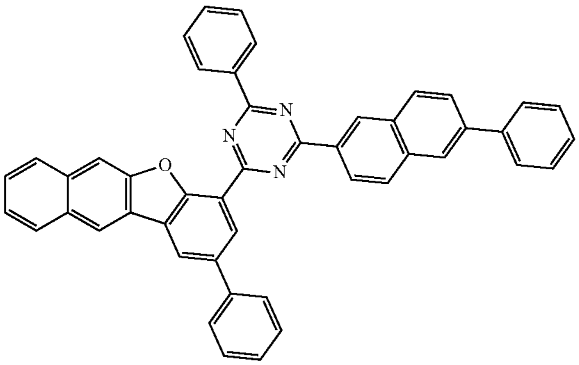
2-409
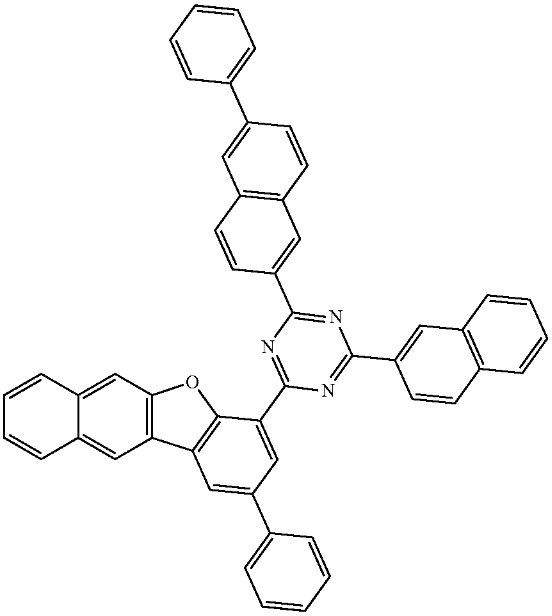
2-410
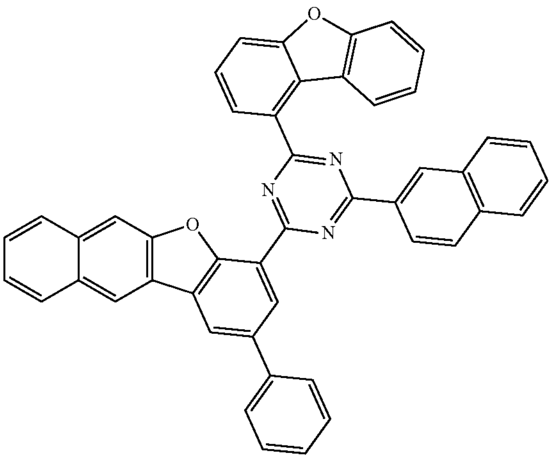
-continued
2-411
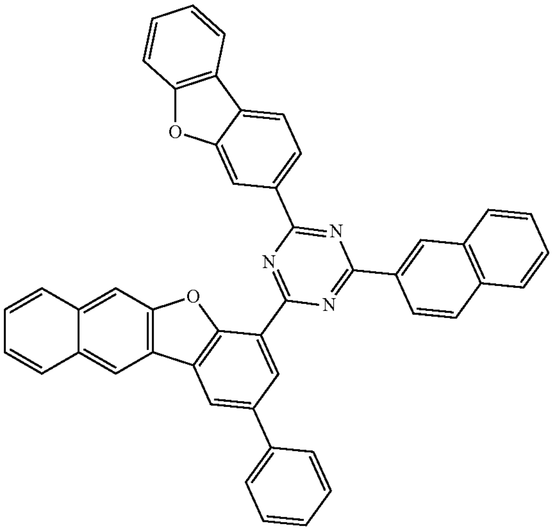
2-412
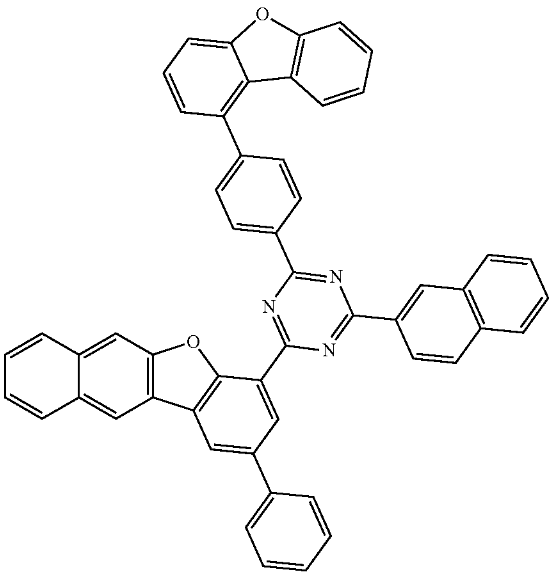

-continued
2-413
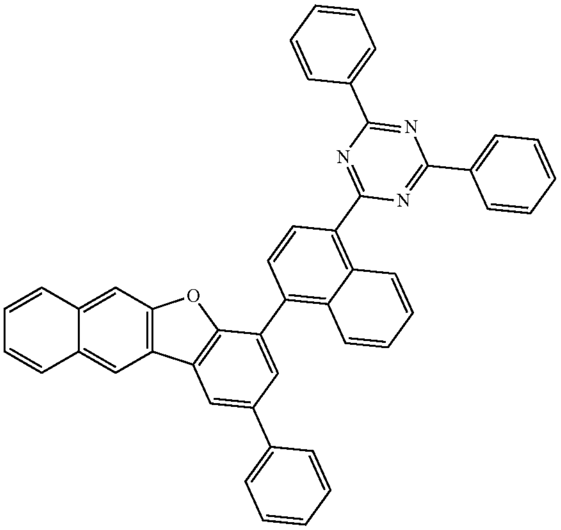
2-414
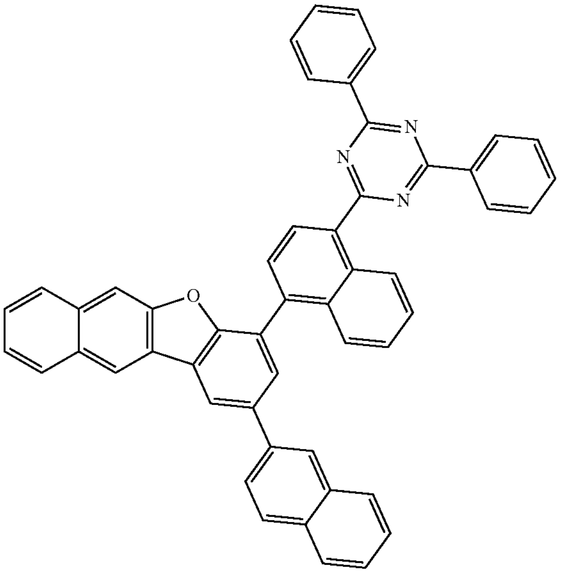
2-415
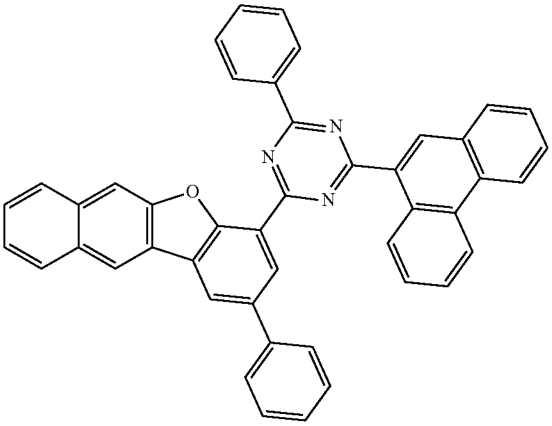
-continued
2-416
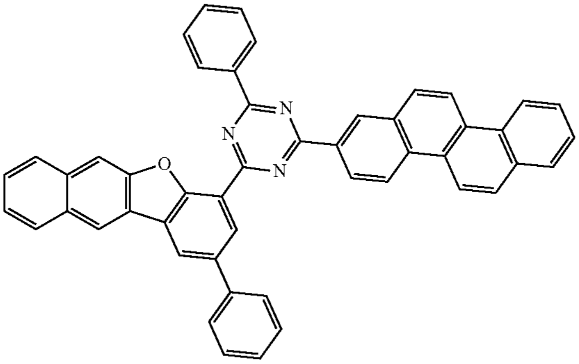
2-417
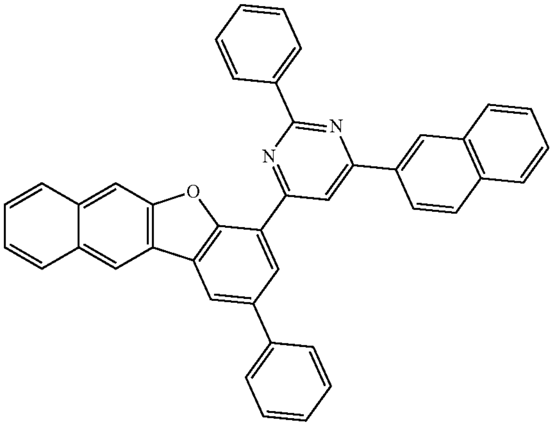
2-418
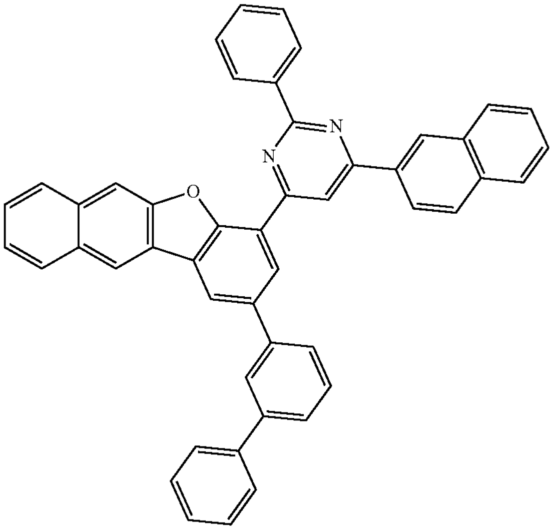

-continued
2-419
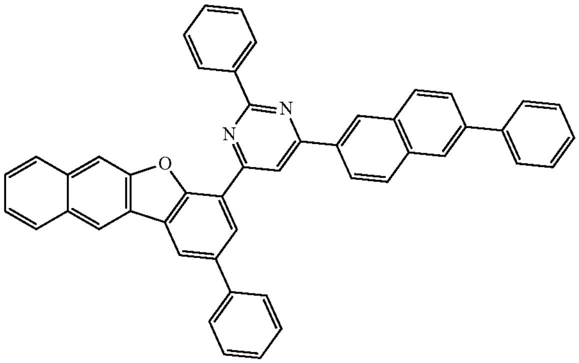
2-420
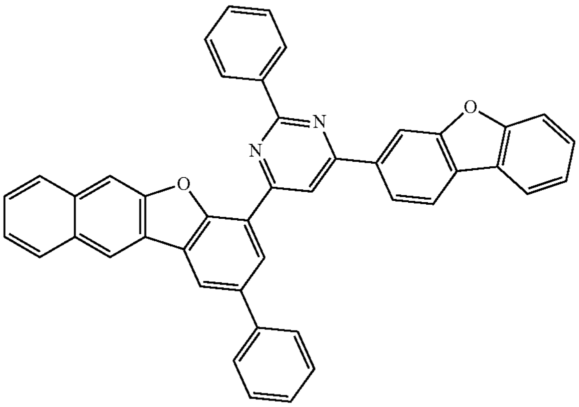
2-421
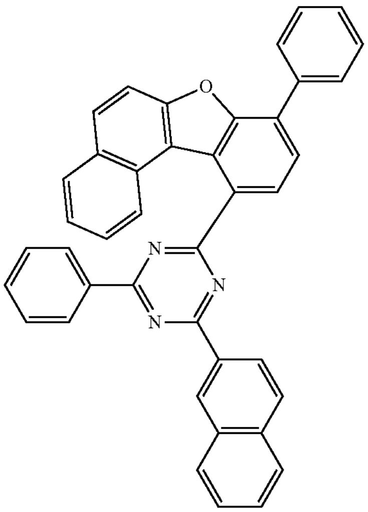
-continued
2-422
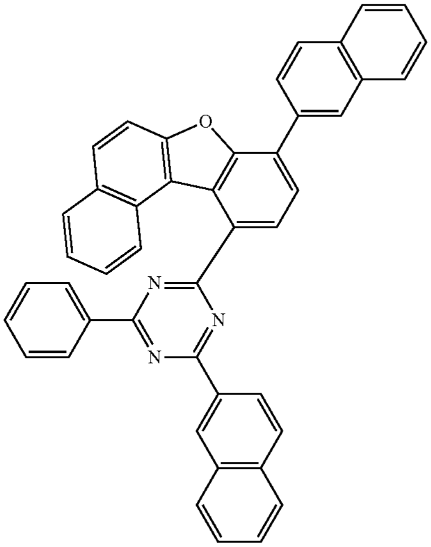
2-423
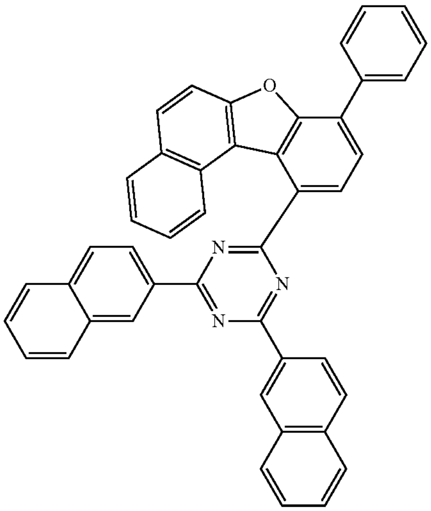

-continued
2-424
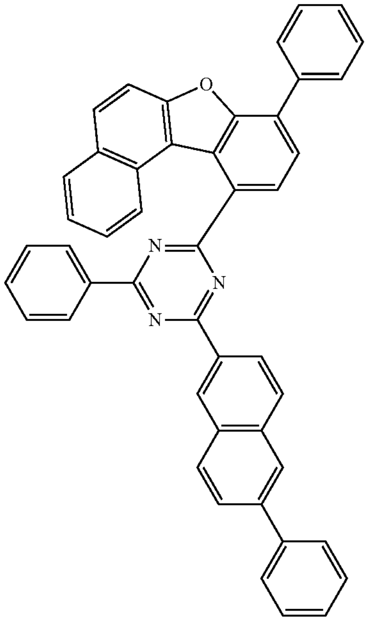
2-425
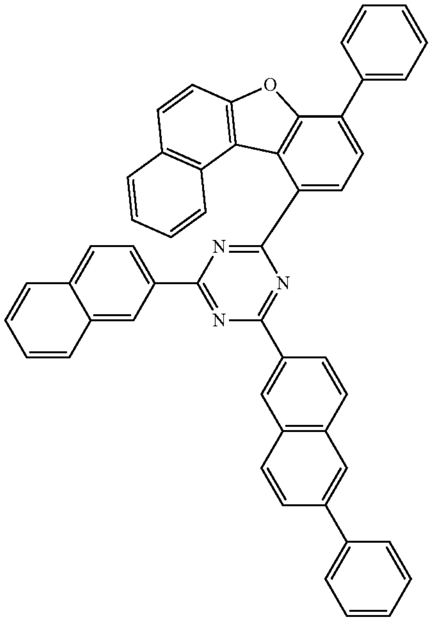
-continued
2-426
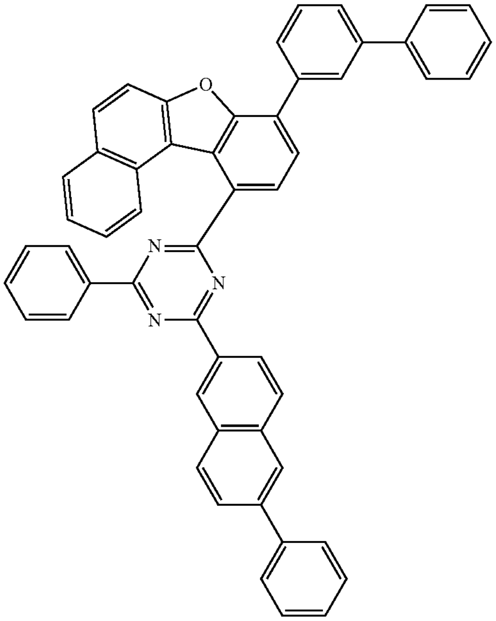
2-427
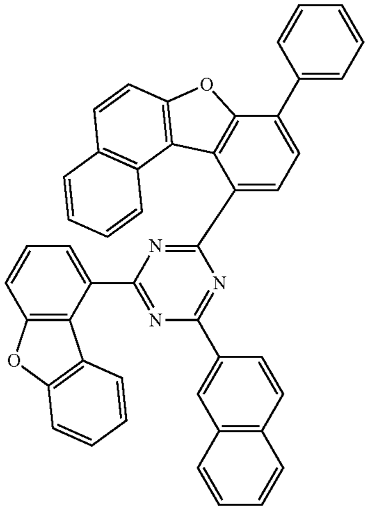

-continued
2-428
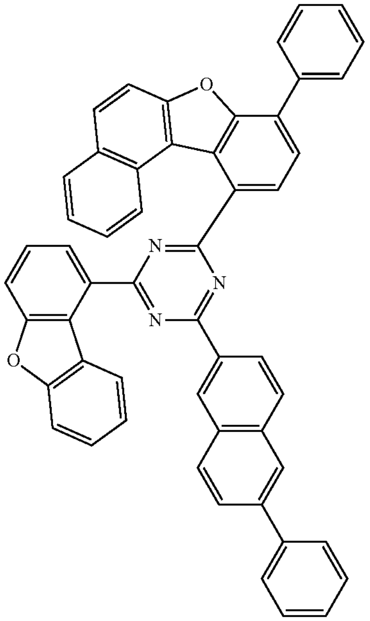
2-429
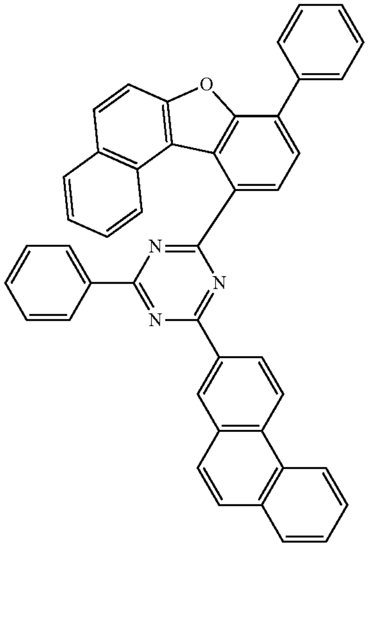
-continued
2-430
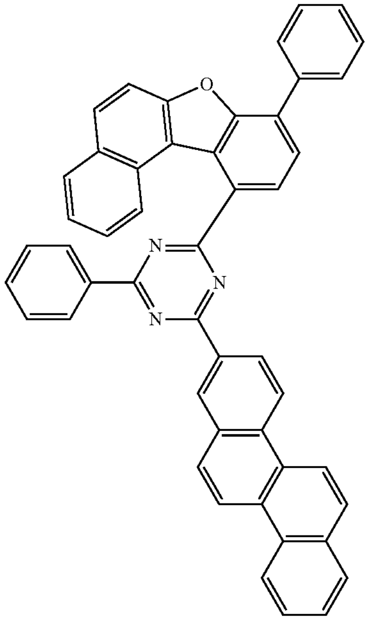
2-431
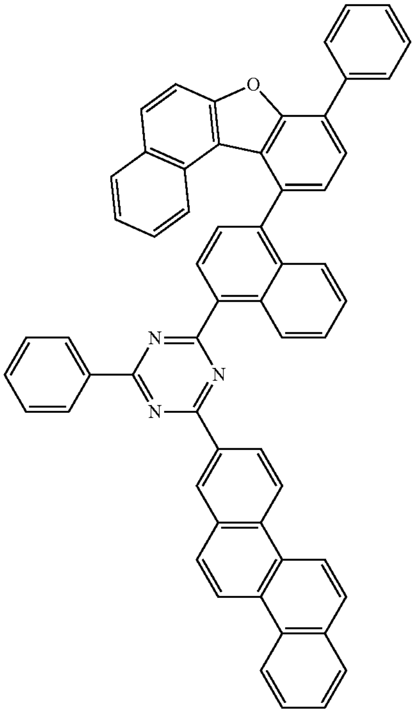

-continued
2-432
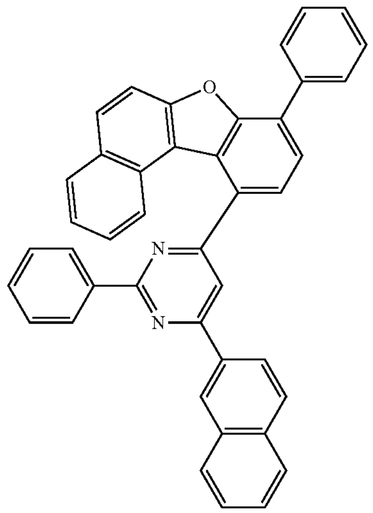
2-433
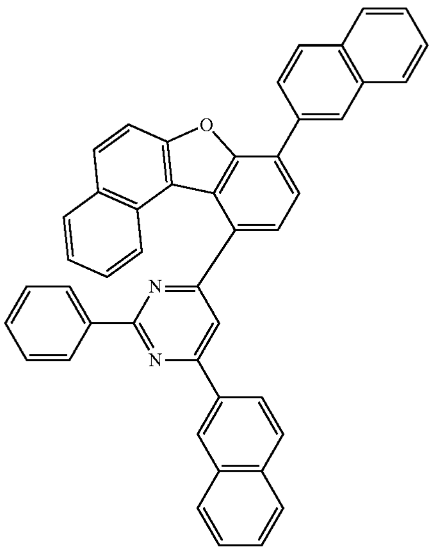
-continued
2-434
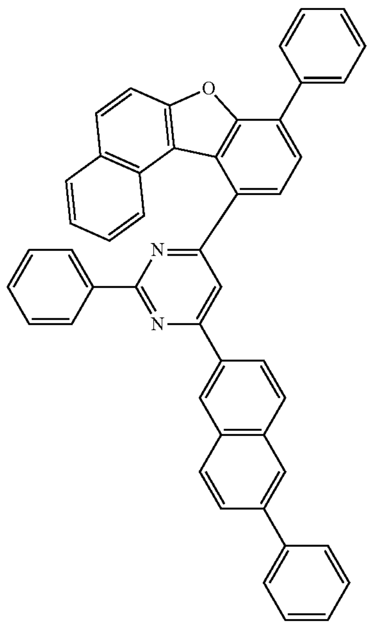
2-435
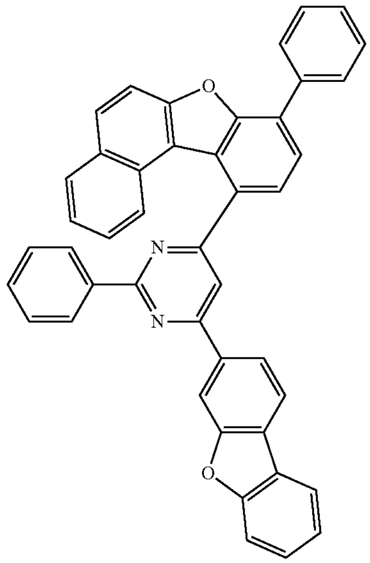
2-436
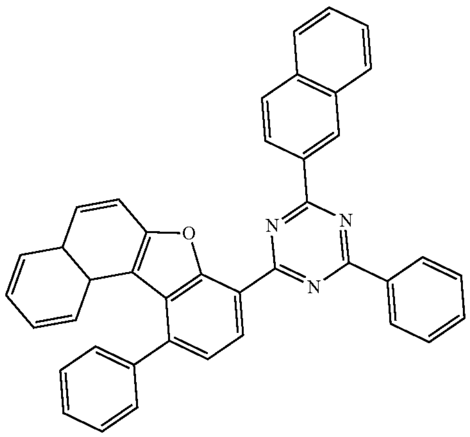

-continued
2-437
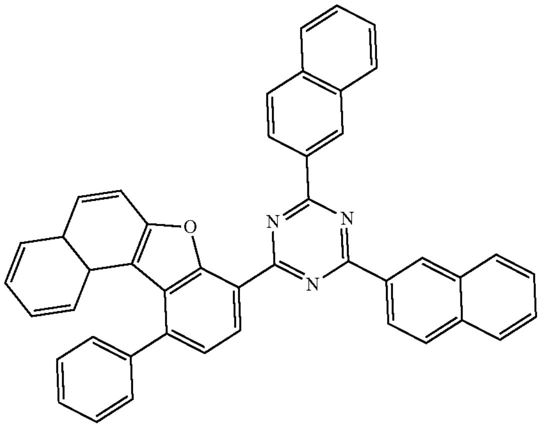
2-438
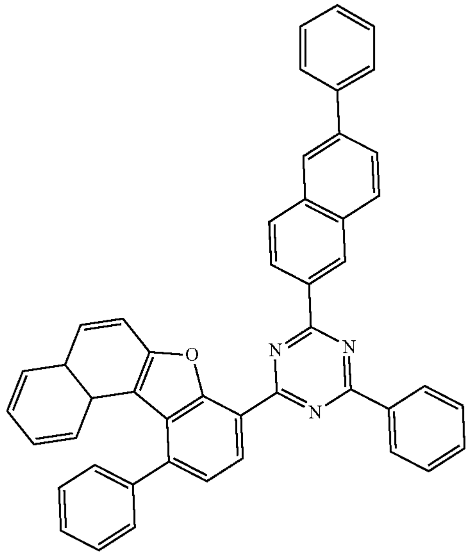
2-439
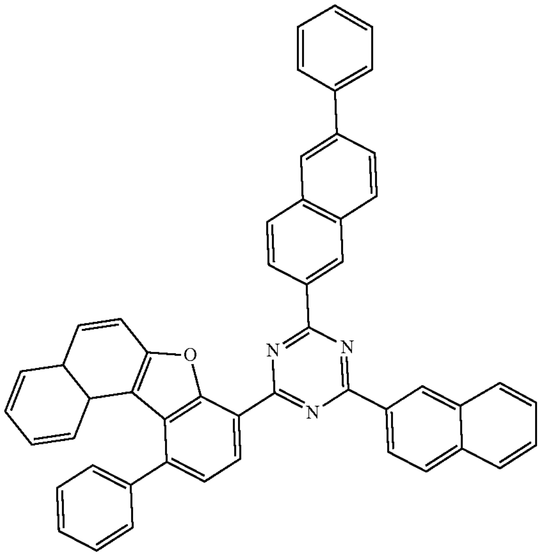
-continued
2-440
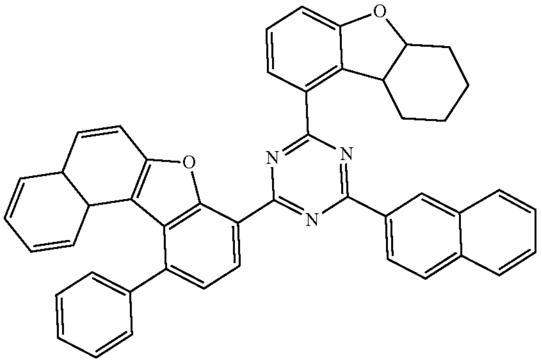
2-441
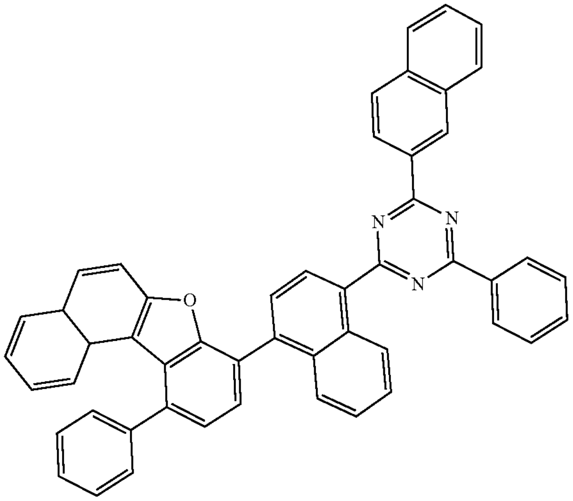
2-442
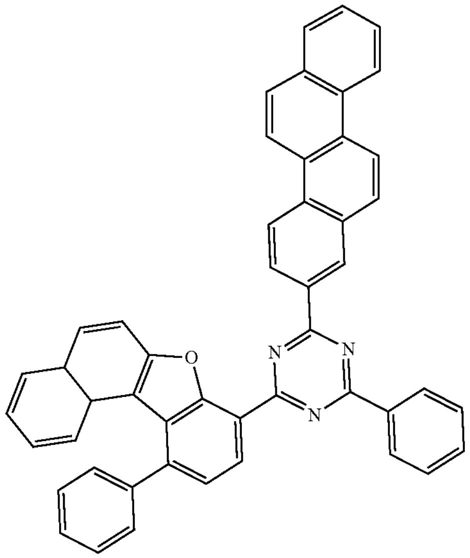

2-443
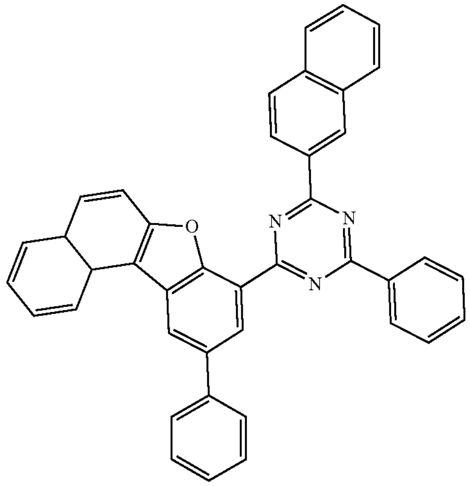
2-444
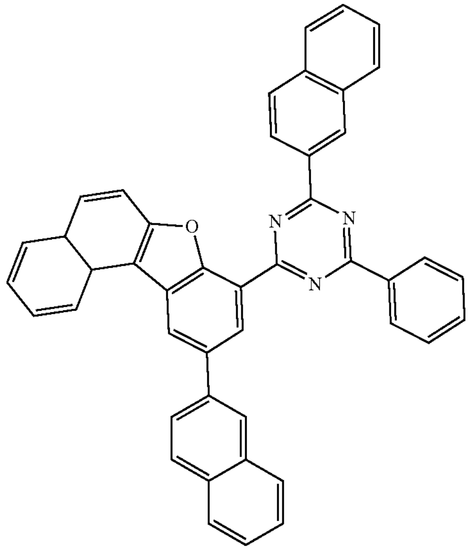
2-445
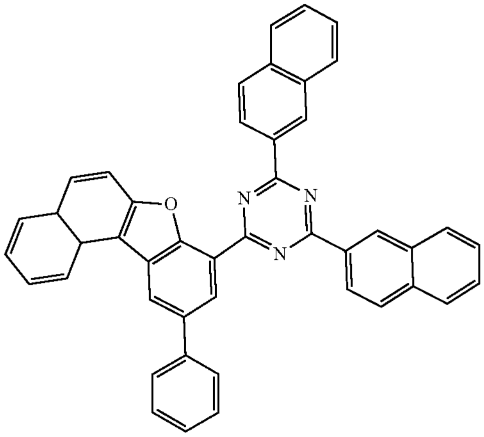
2-446
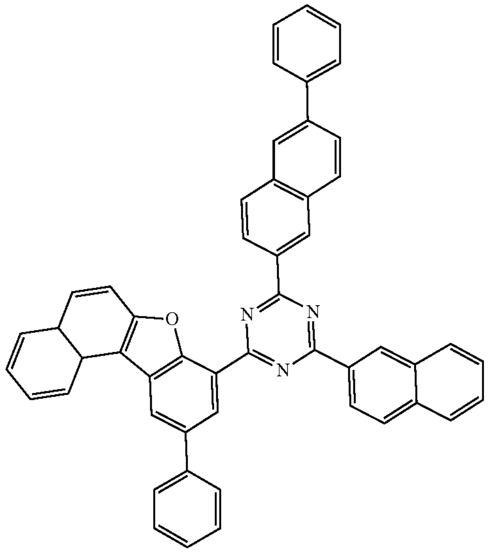
2-447
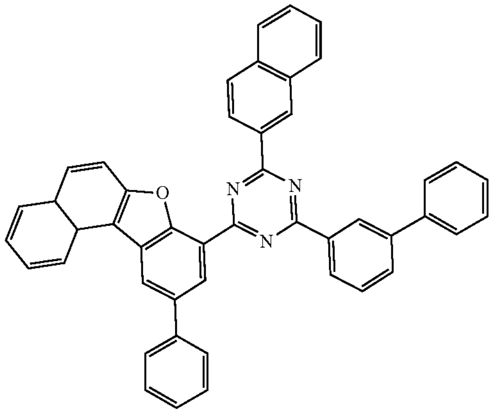
2-448
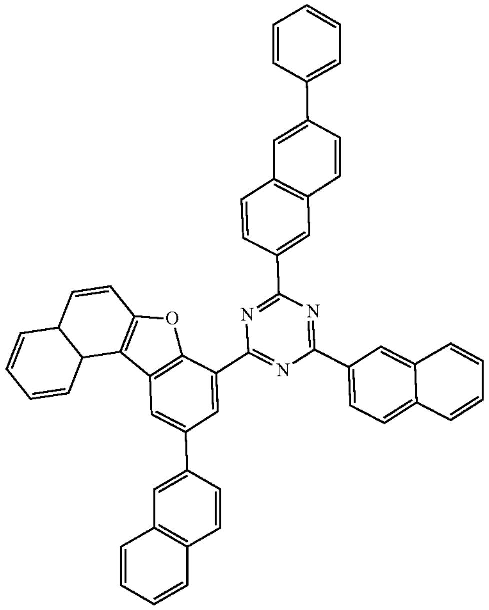

-continued
2-449
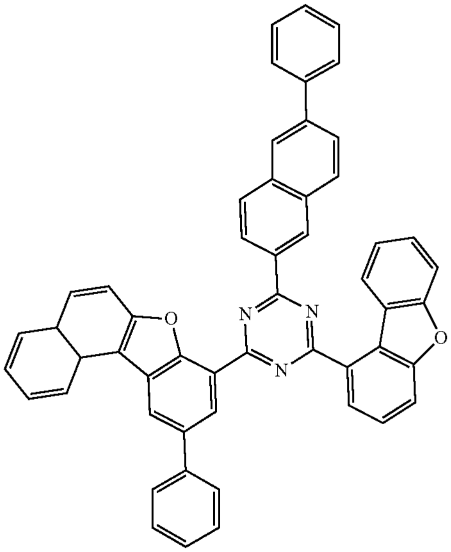
2-450
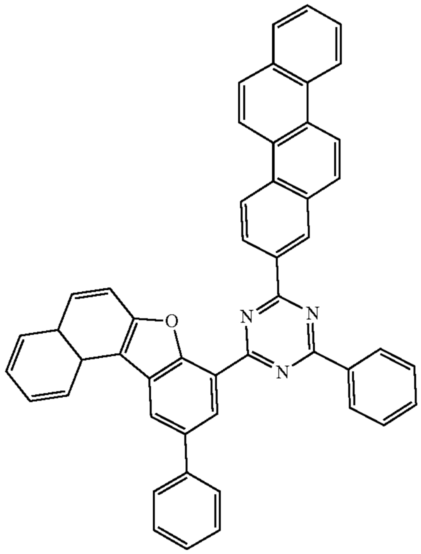
2-451
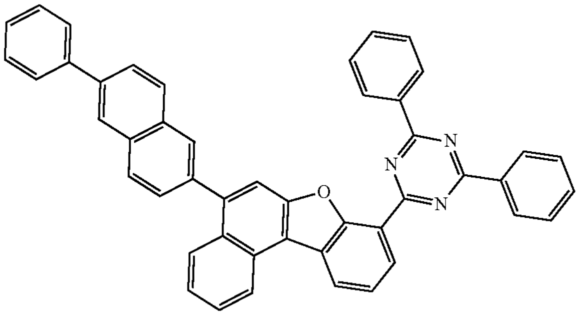
-continued
2-452
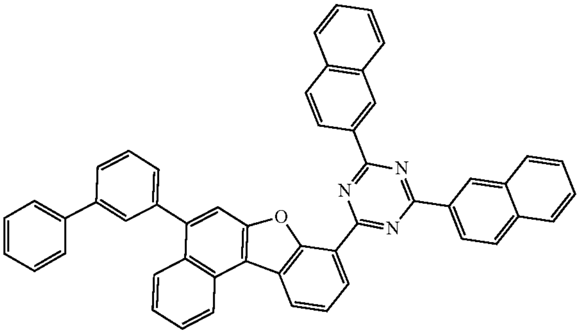
2-453
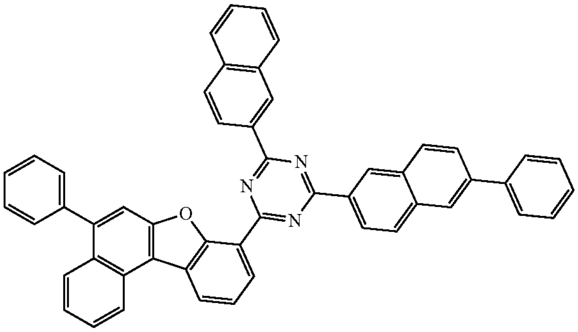
2-454
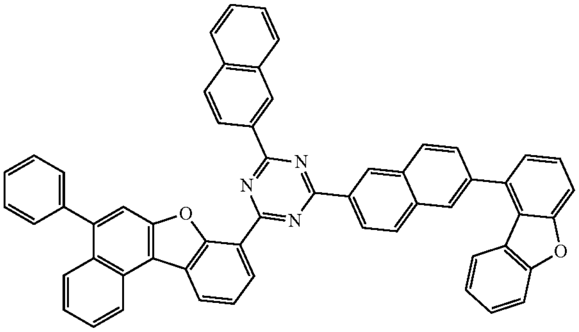
2-455
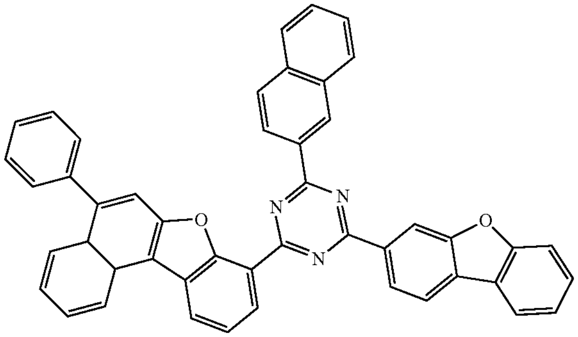

-continued
2-456
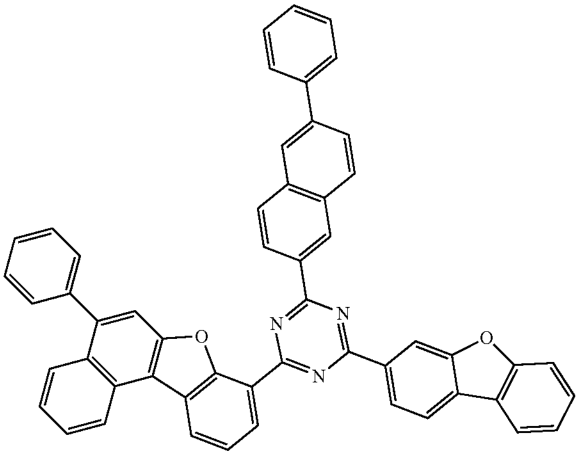
2-457
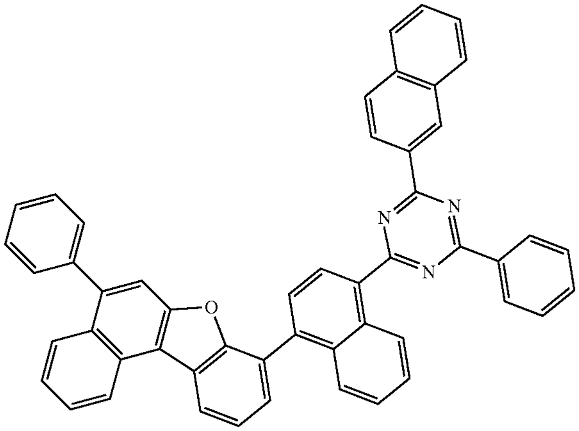
2-458
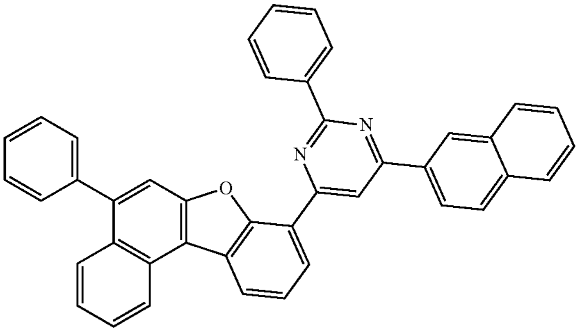
2-459
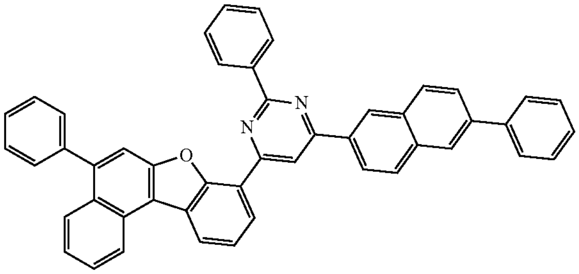
-continued
2-460
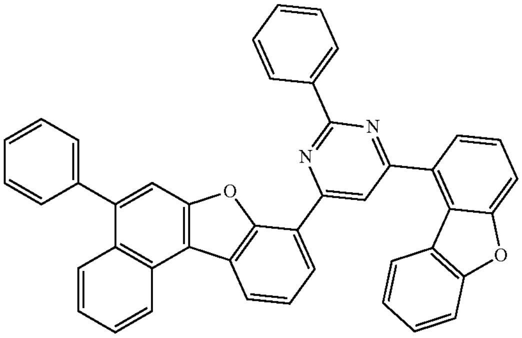
2-461
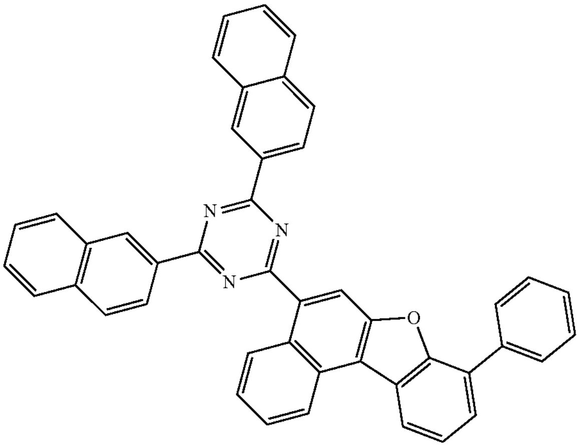
2-462
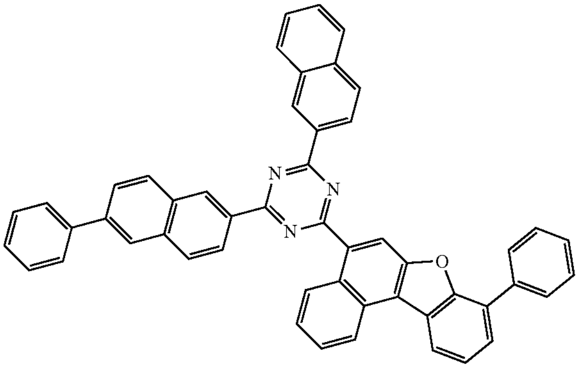

-continued
2-463
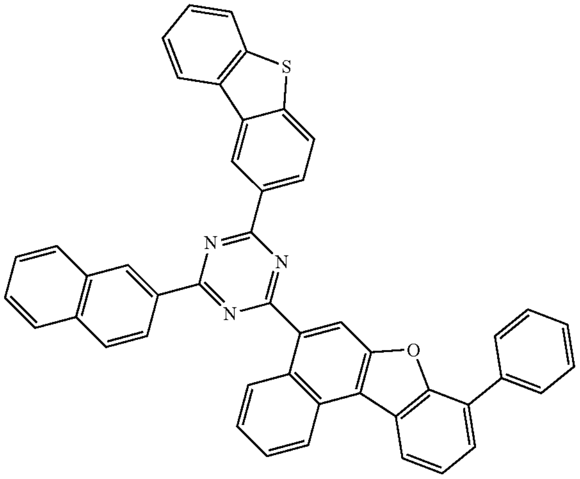
2-464
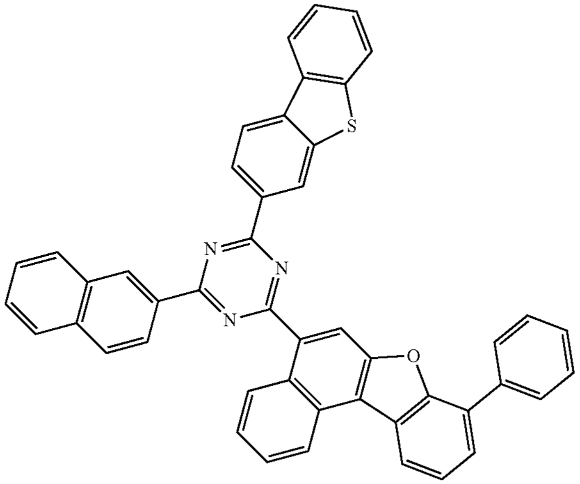
2-465
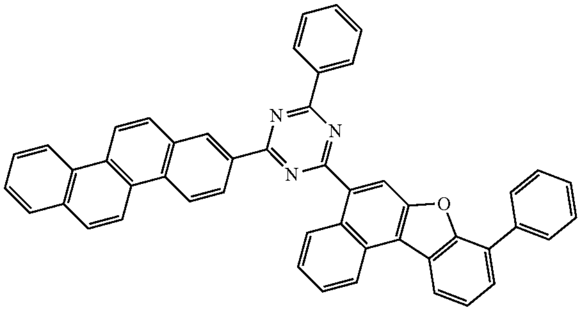
-continued
2-466
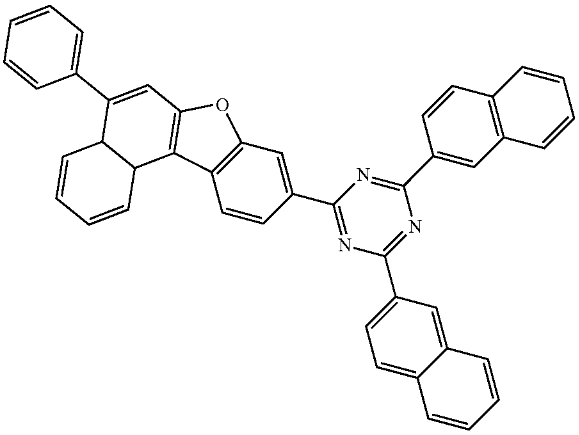
2-467
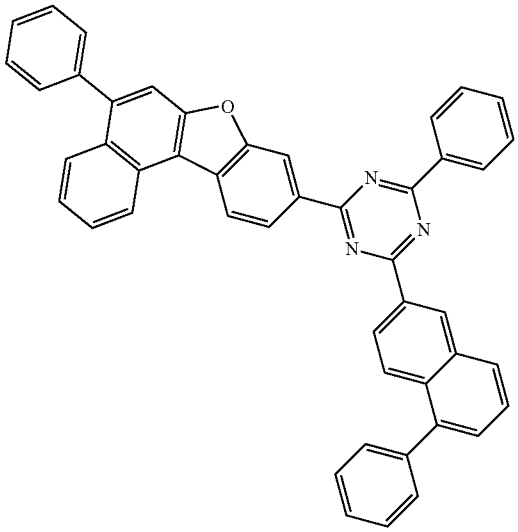
2-468
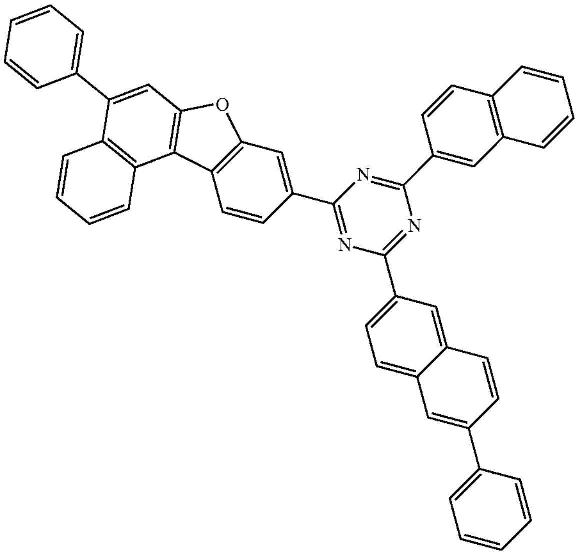

-continued
2-469
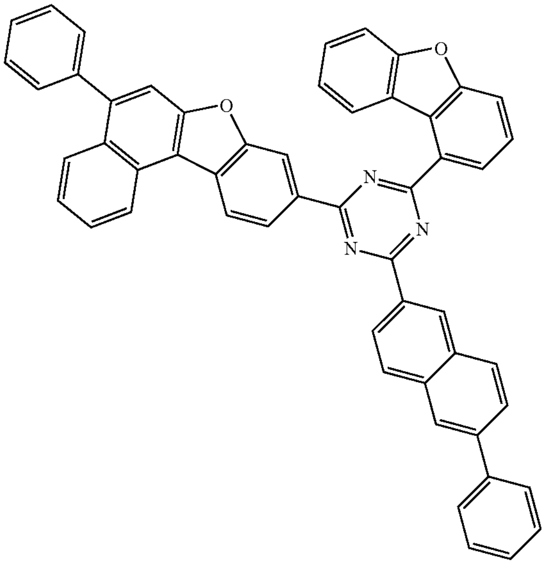
2-470
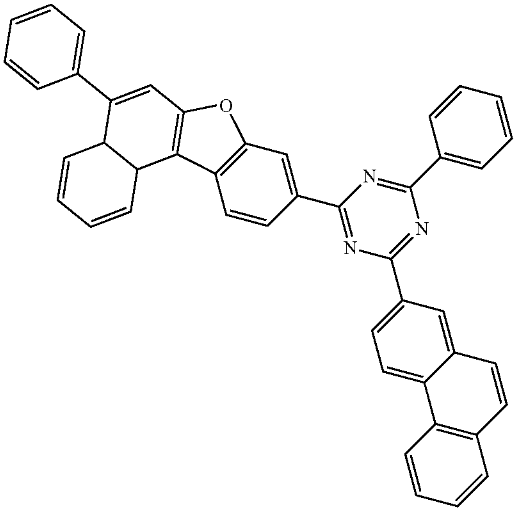
-continued
2-471
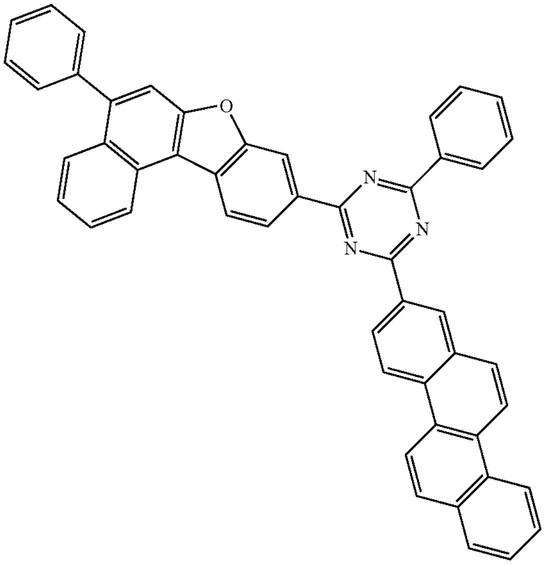
2-472
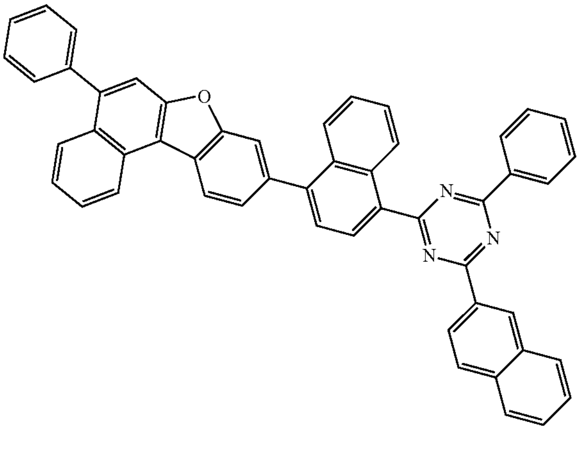
2-473
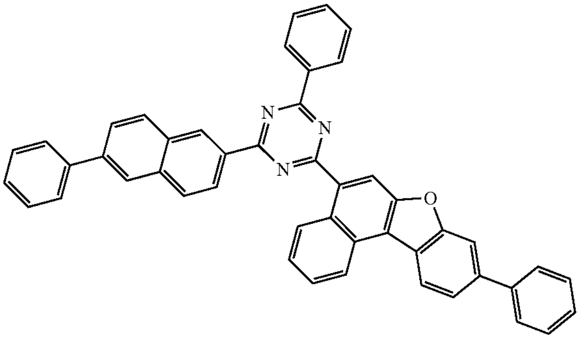

-continued
2-474
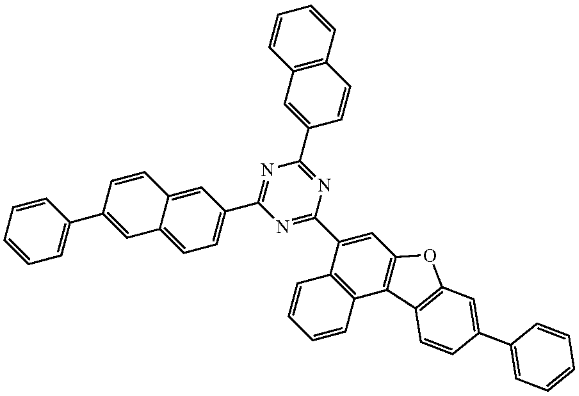
2-475
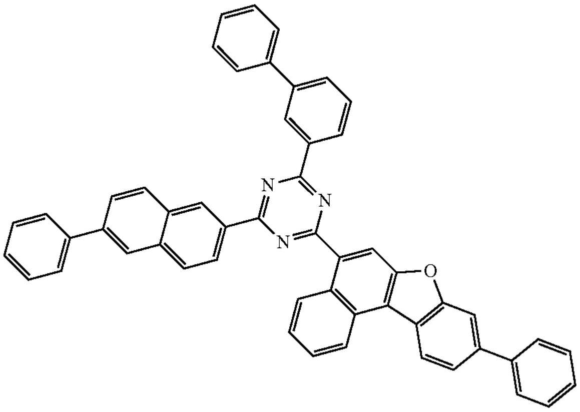
2-476
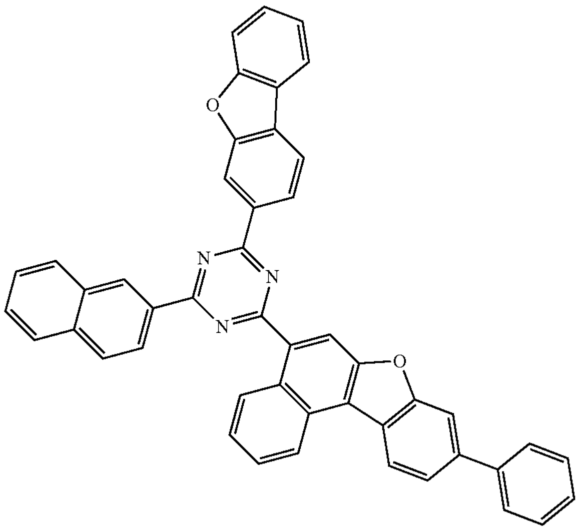
-continued
2-477
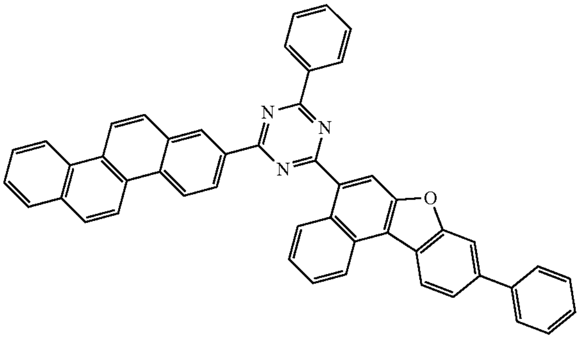
2-478
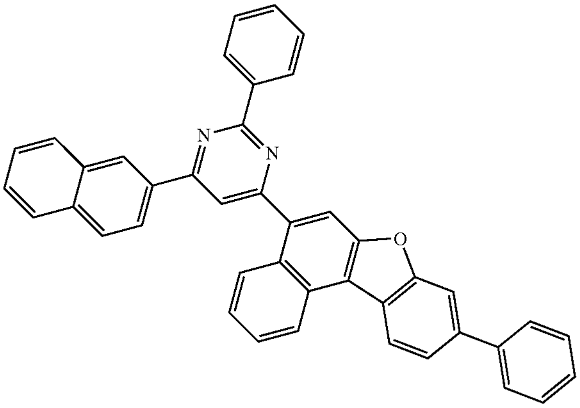
2-479
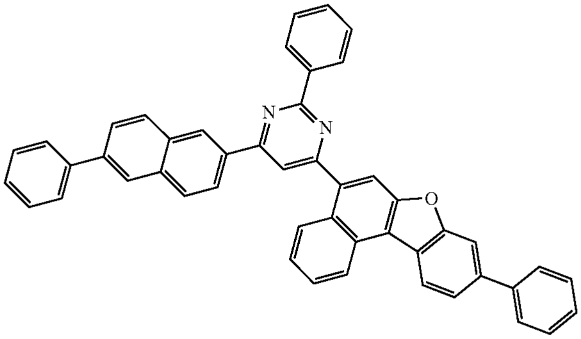

2-480
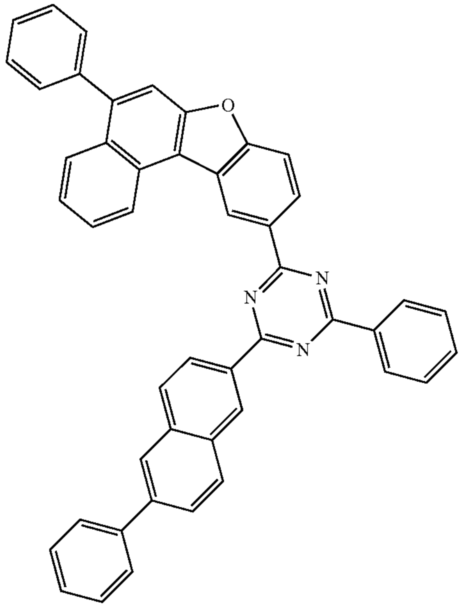
2-481
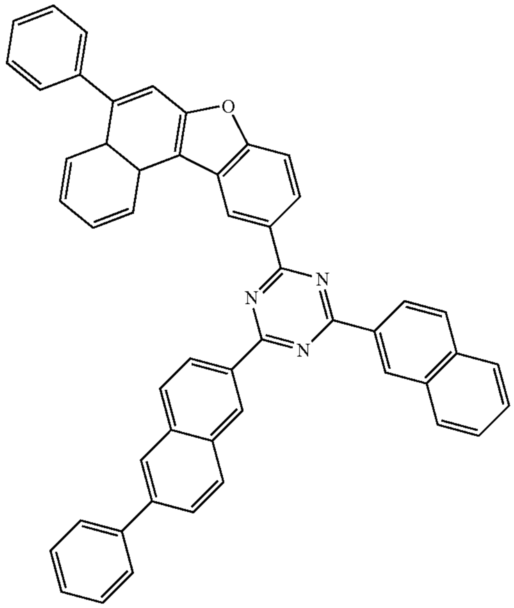
2-482
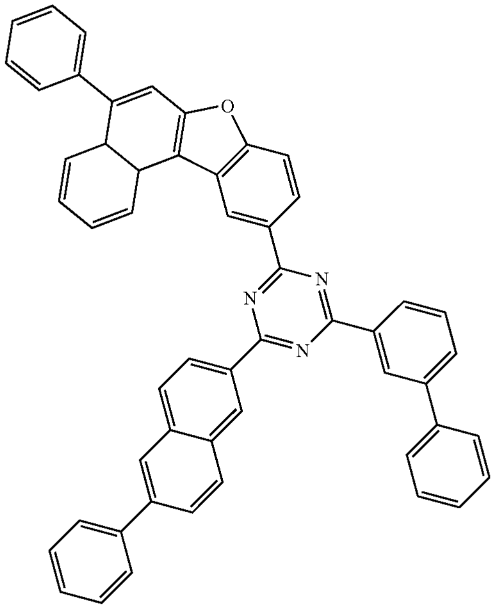
2-483
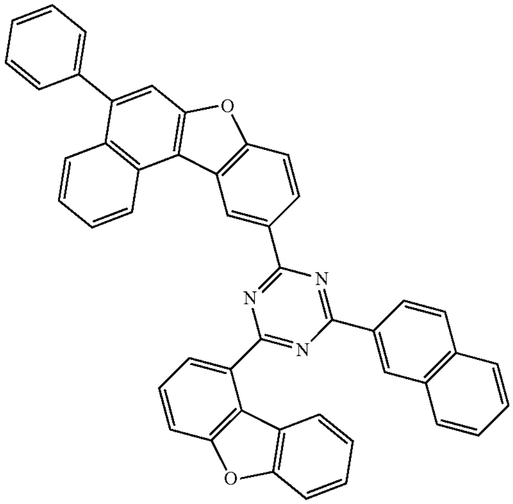

-continued
2-484
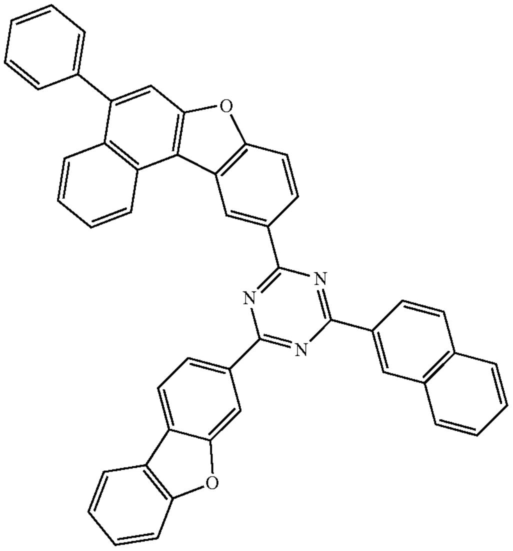
2-485
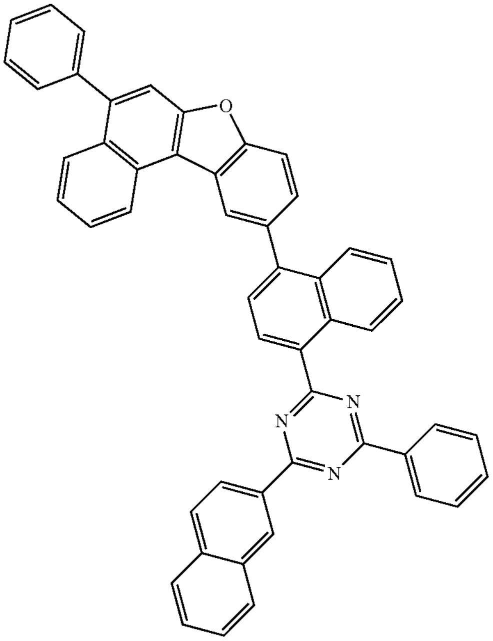
-continued
2-486
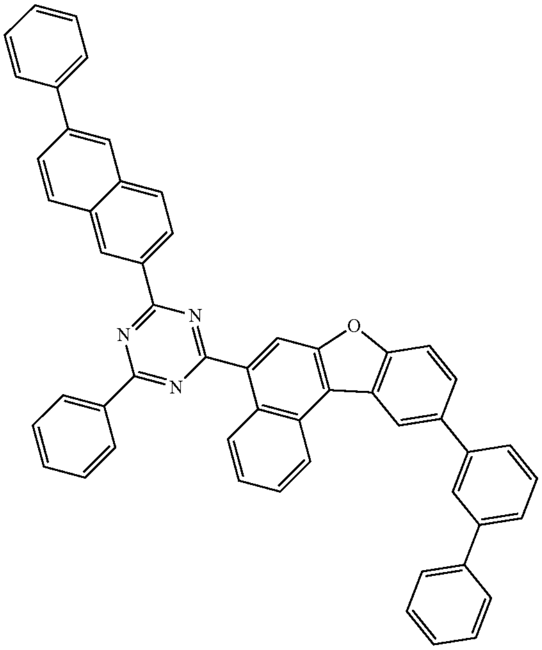
2-487
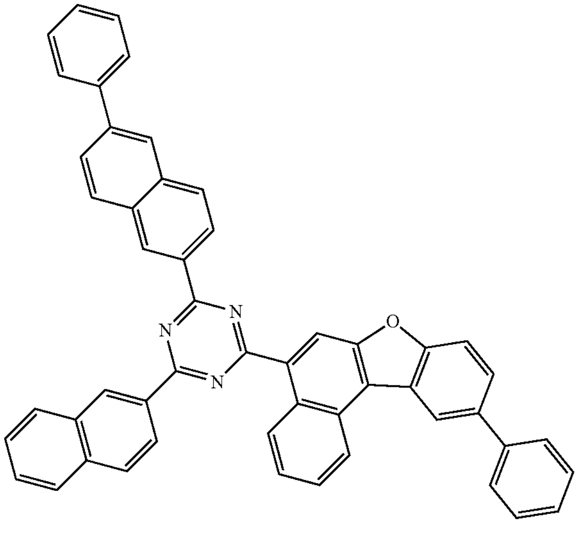

-continued
2-488
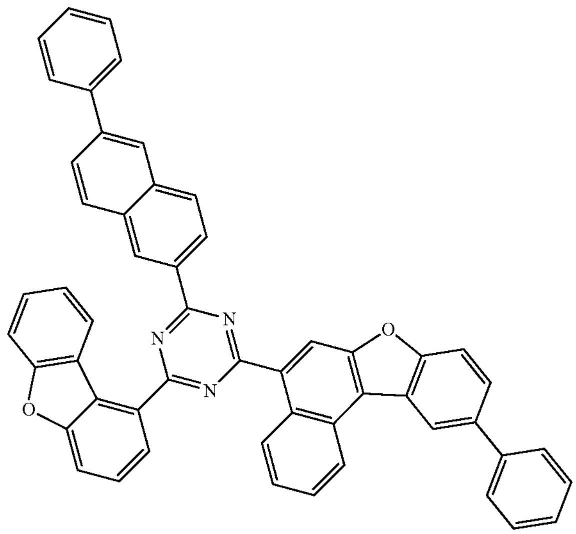
2-489
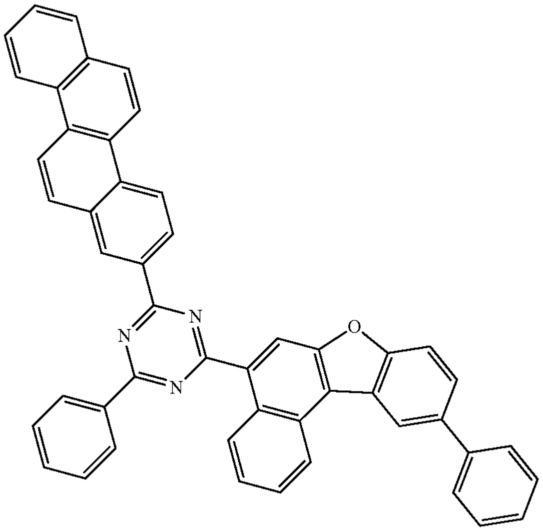
2-490
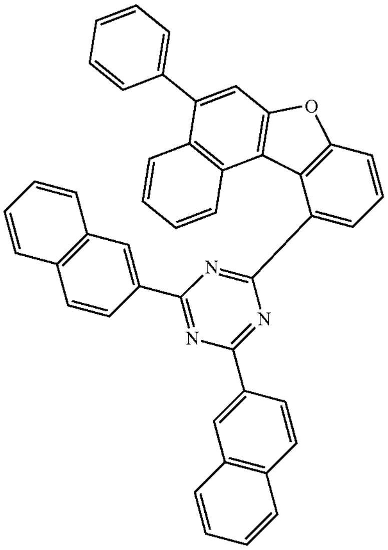
-continued
2-491
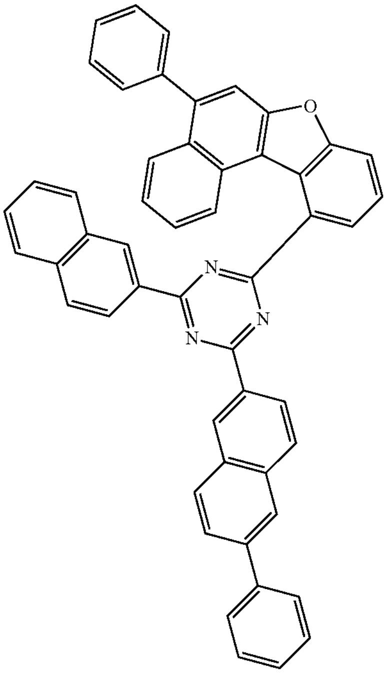
2-492
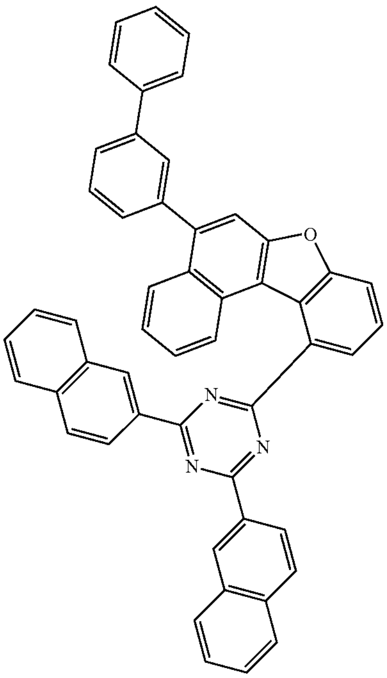

-continued
2-493
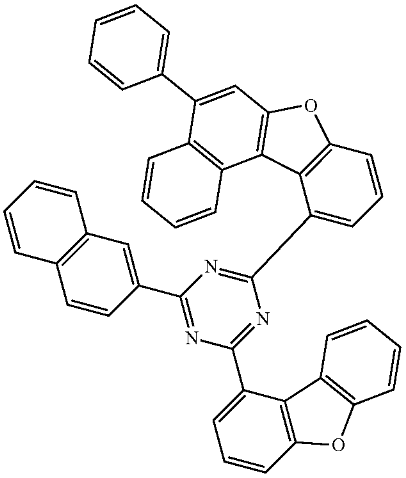
2-94
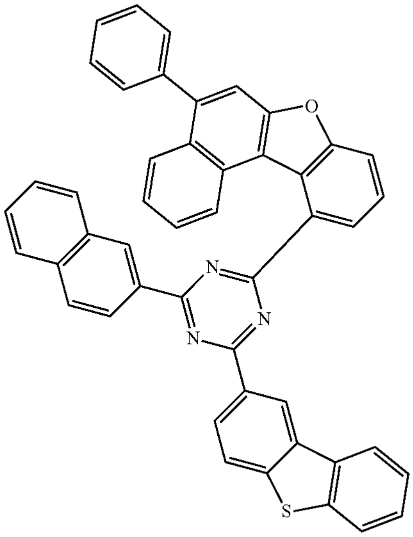
-continued
2-495
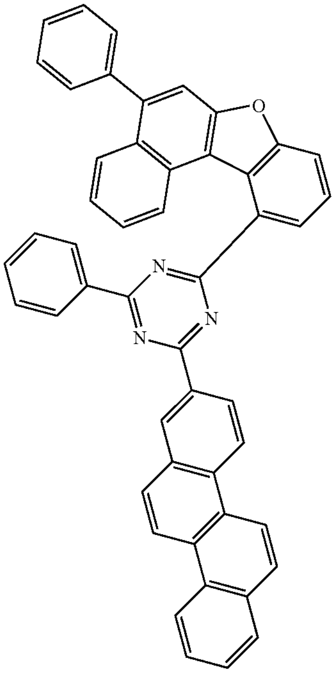
2-496
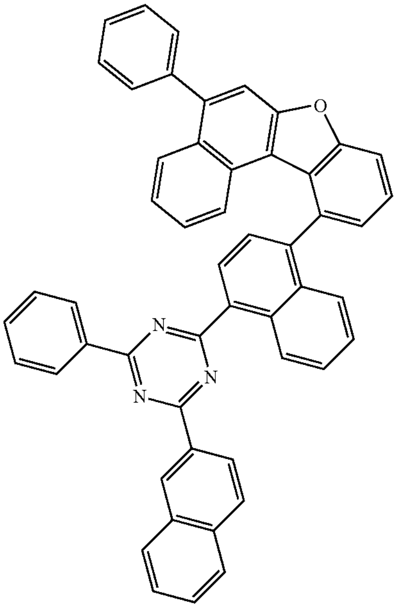

-continued
2-497
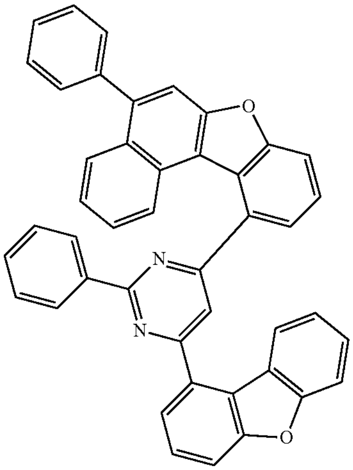
2-498
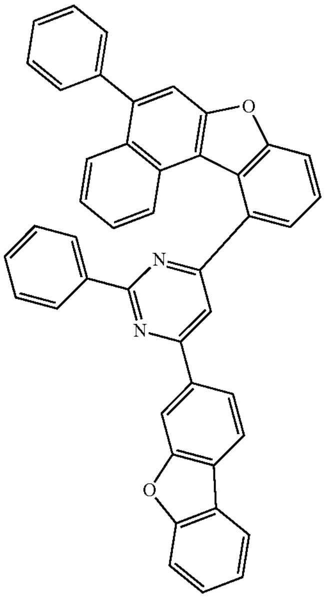
2-499
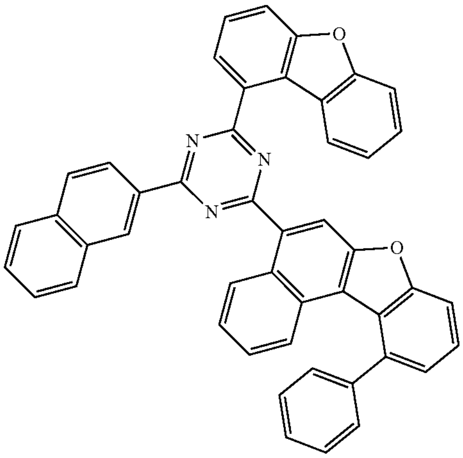
-continued
2-500
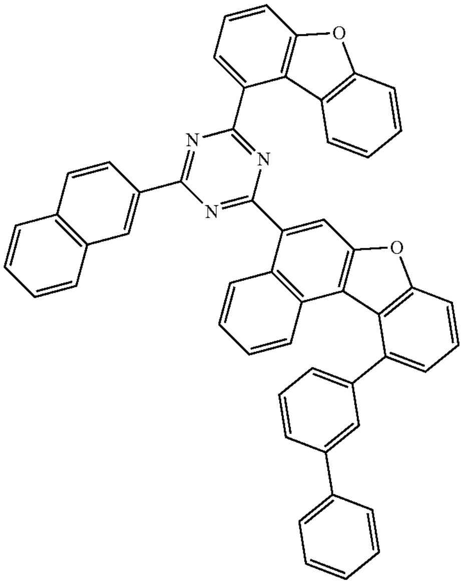
2-501
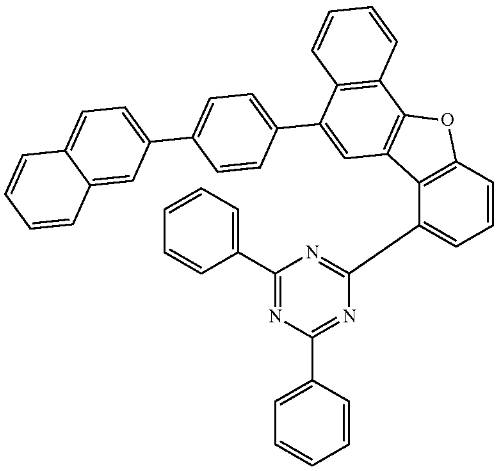

-continued
2-502
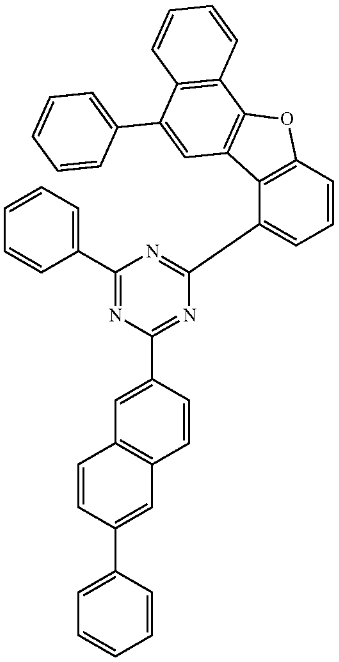
2-503
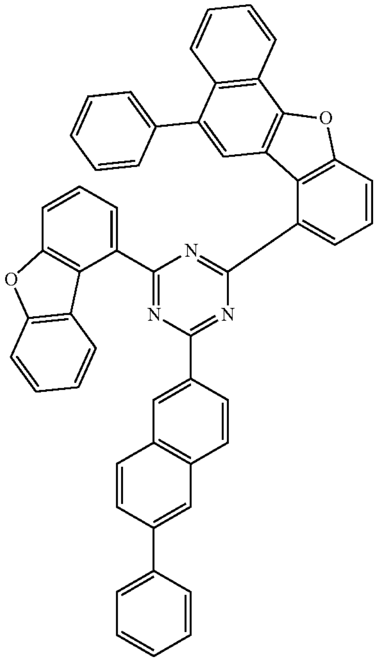
-continued
2-504
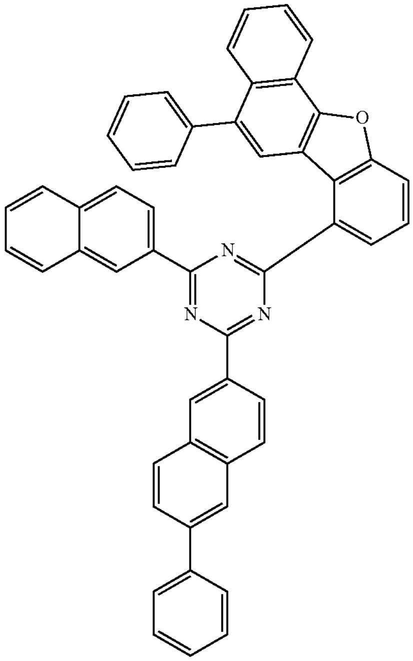
2-505
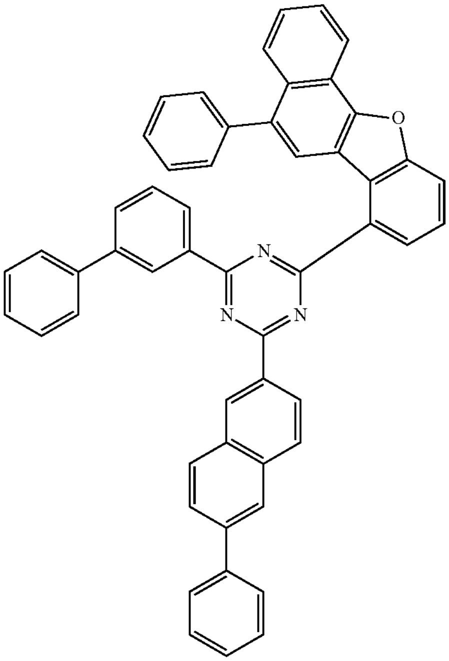

-continued
2-506
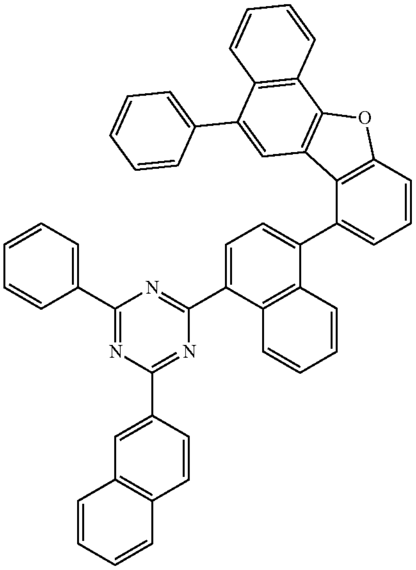
2-507
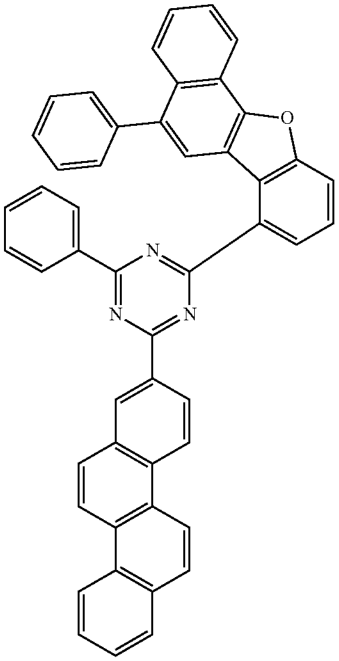
-continued
2-508
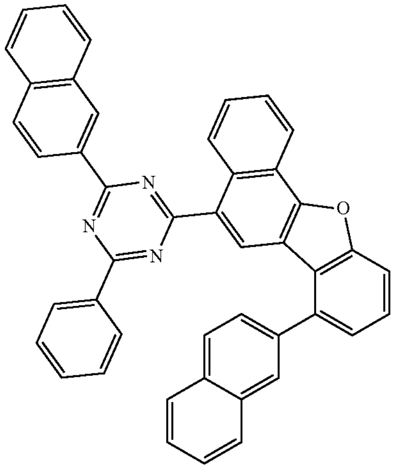
2-509
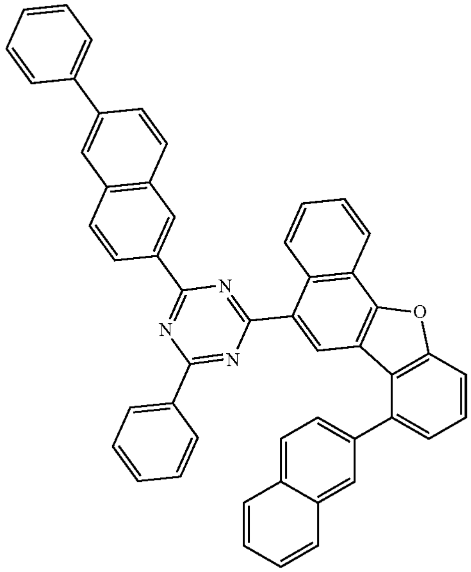
2-510
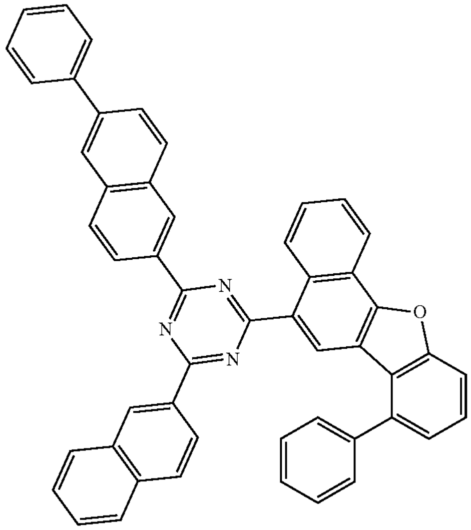

-continued
2-511
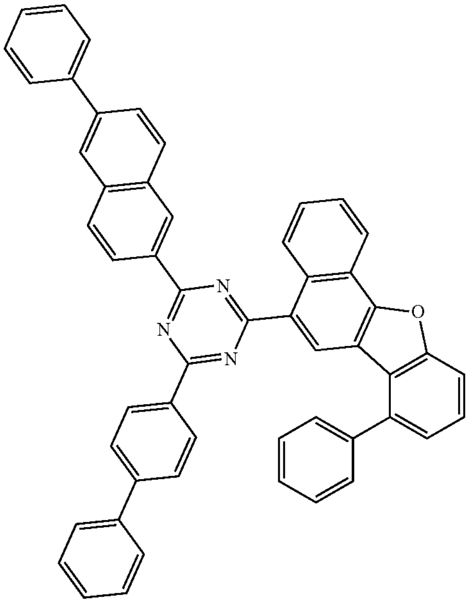
2-512
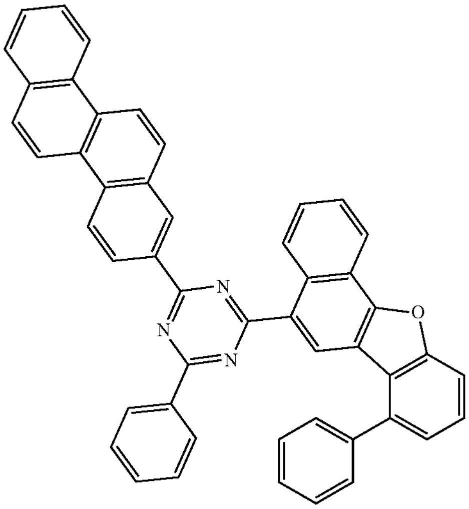
-continued
2-513
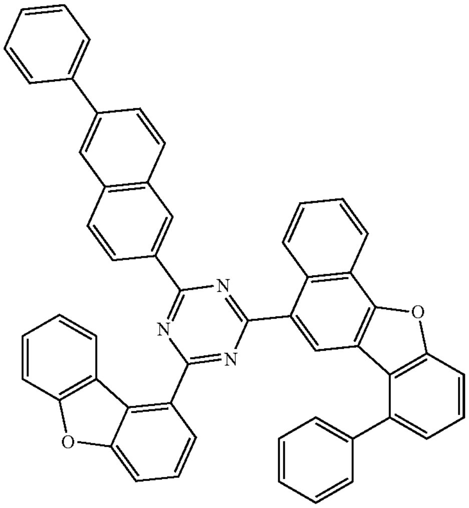
2-514
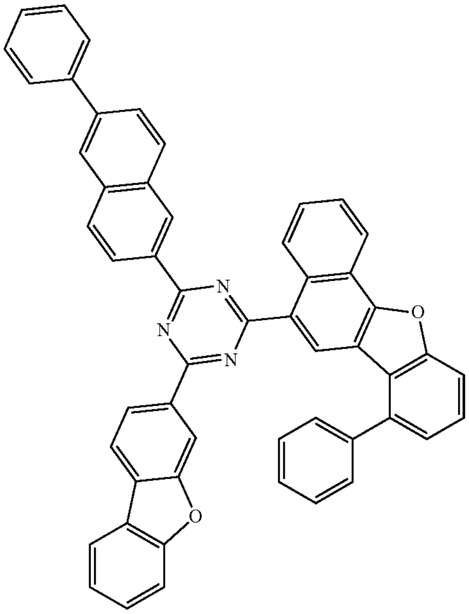
2-515
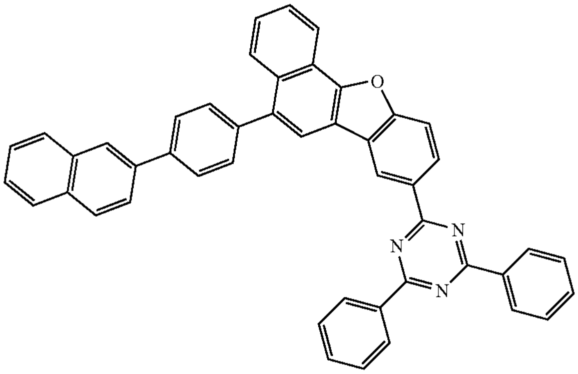

-continued
2-516
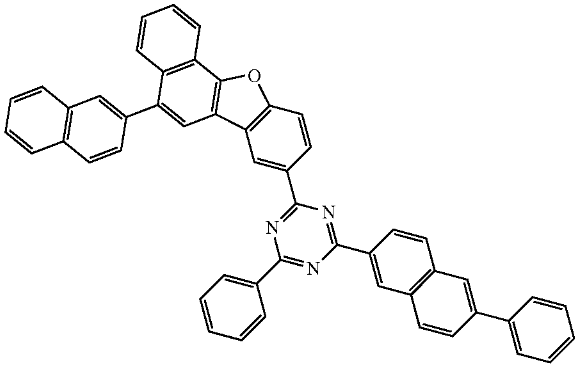
2-517
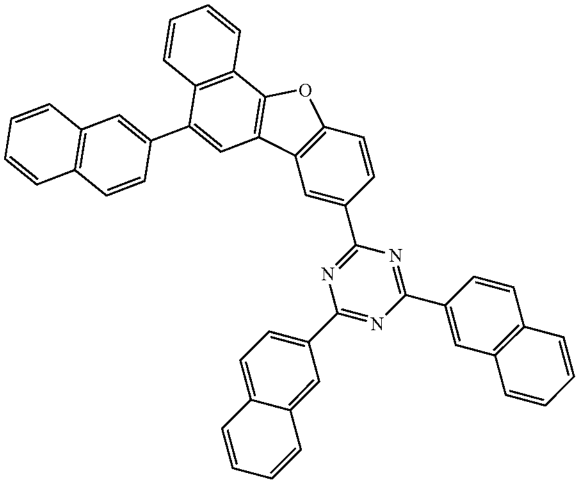
2-518
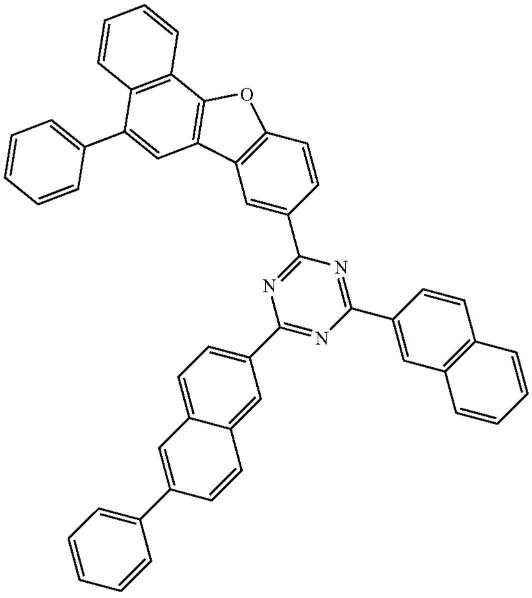
-continued
2-519
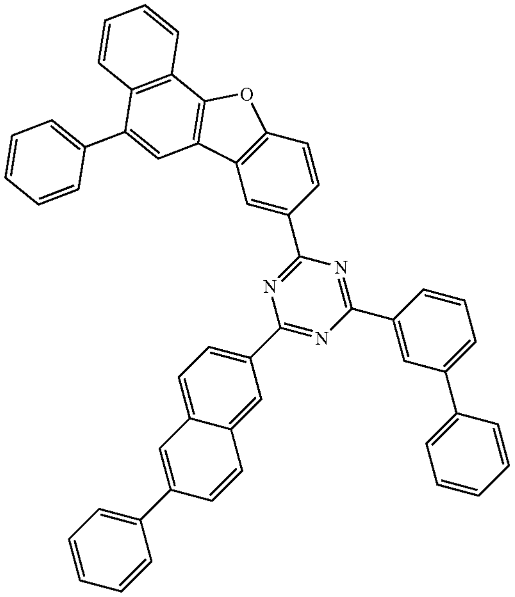
2-520
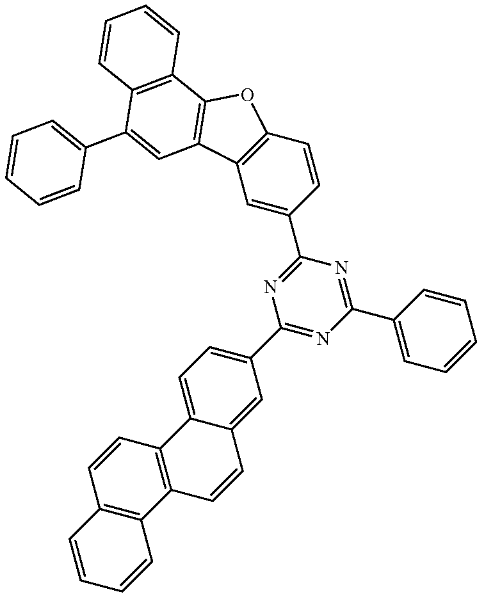

-continued
2-521
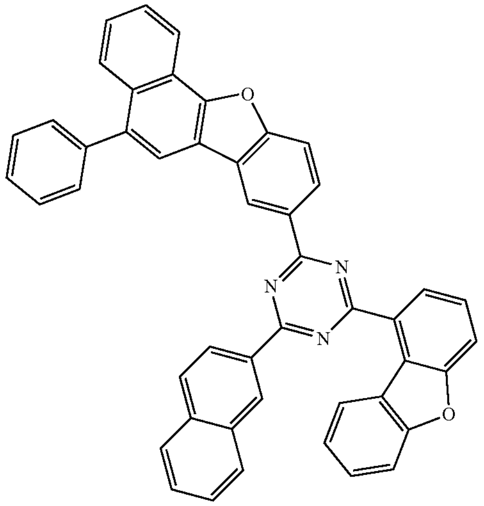
2-522
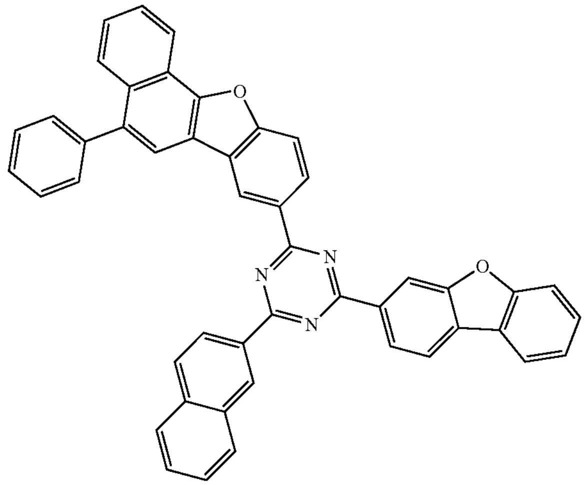
-continued
2-523
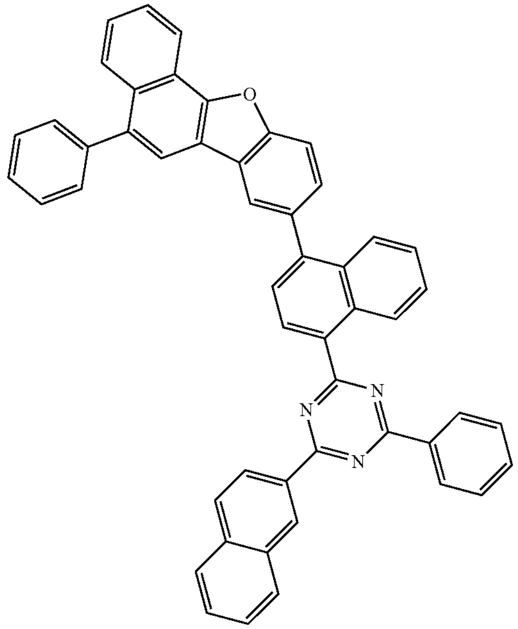
2-524
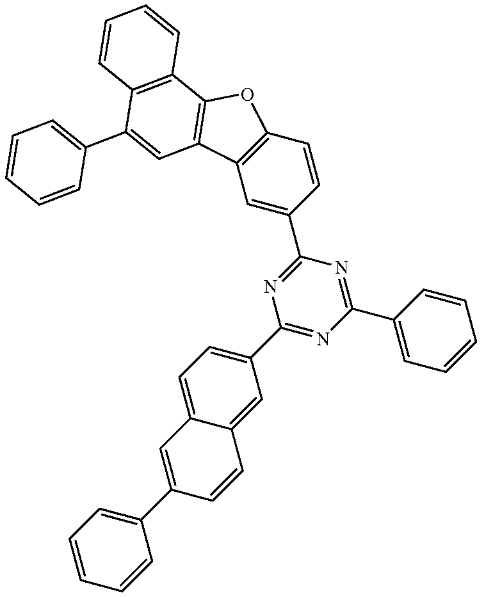

-continued
2-525
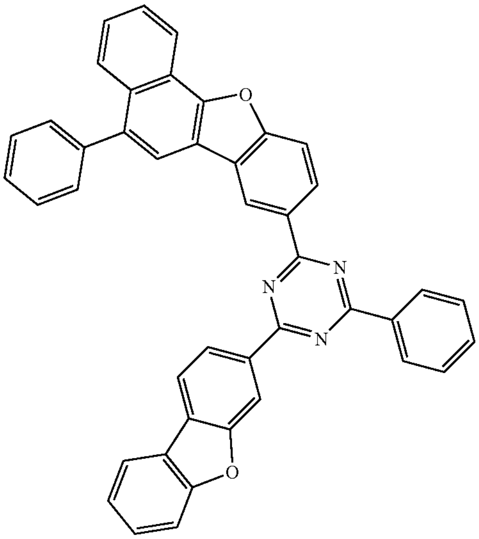
2-526
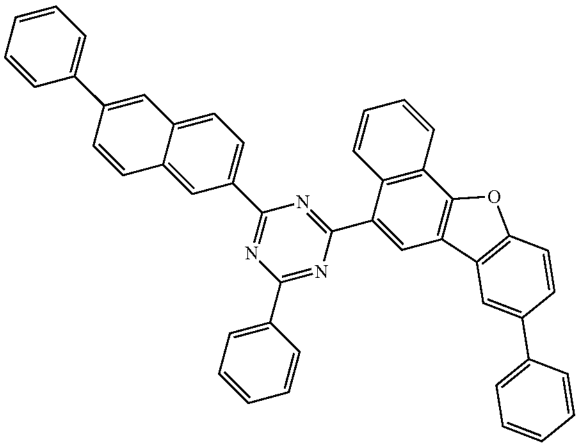
2-527
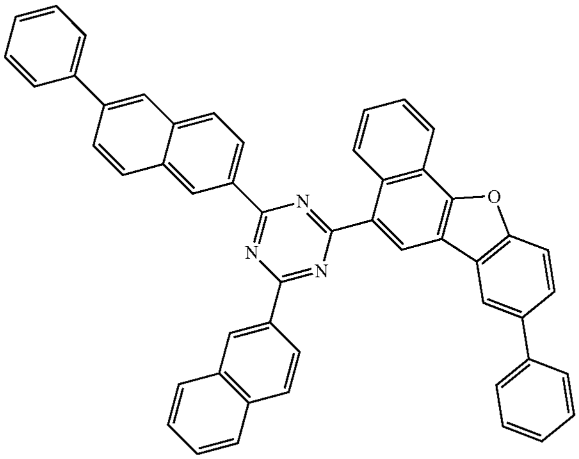
-continued
2-528
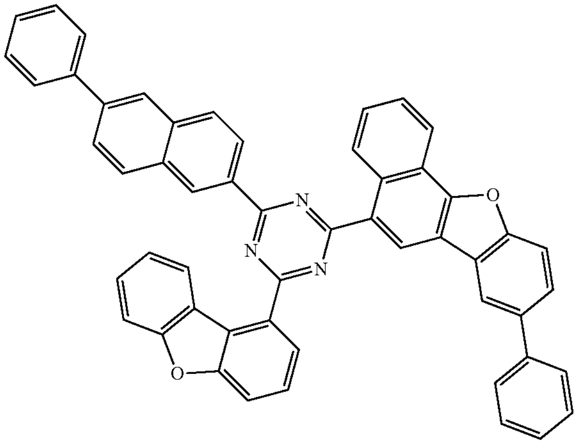
2-529
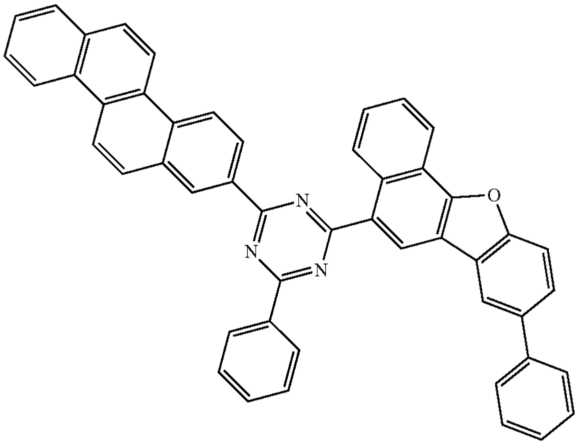
2-530
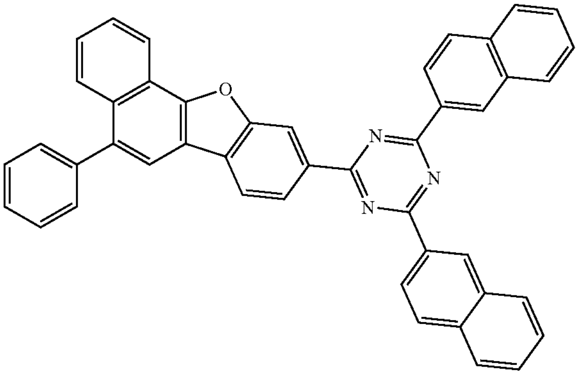

-continued
2-531
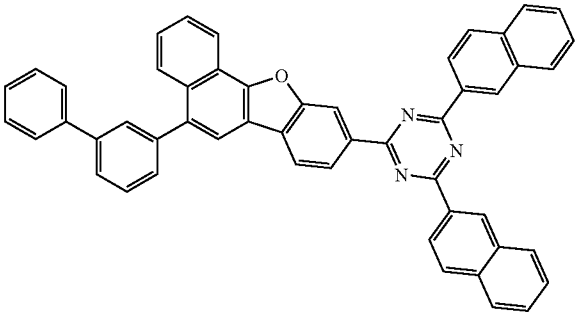
2-532
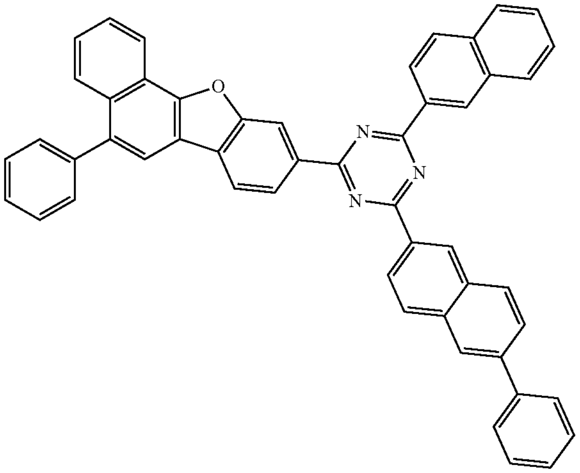
2-533
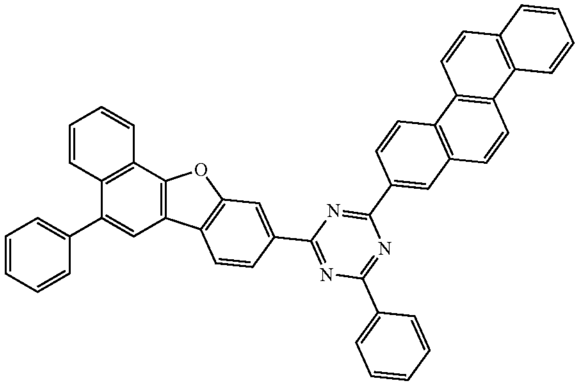
2-534
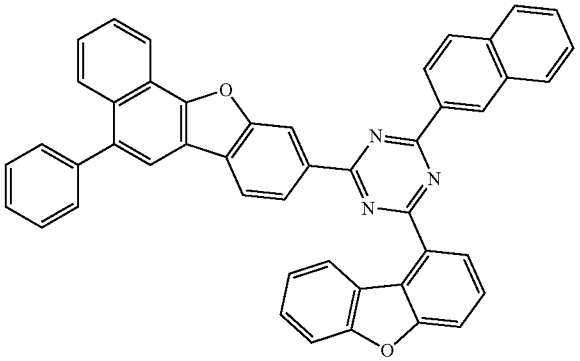
-continued
2-535
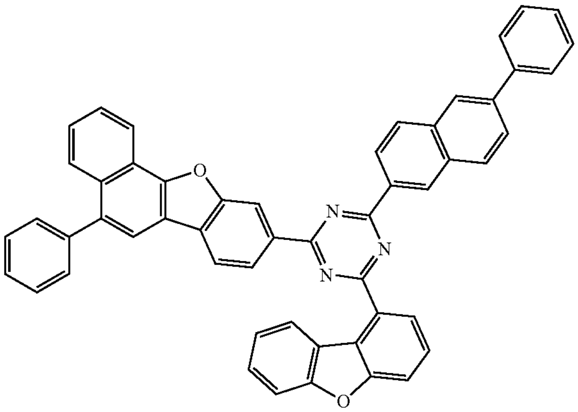
2-536
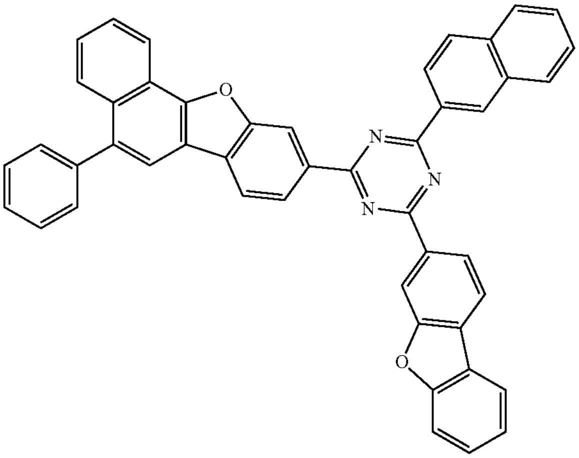
2-537
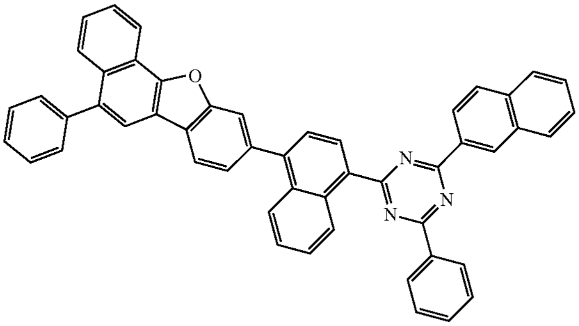
2-538
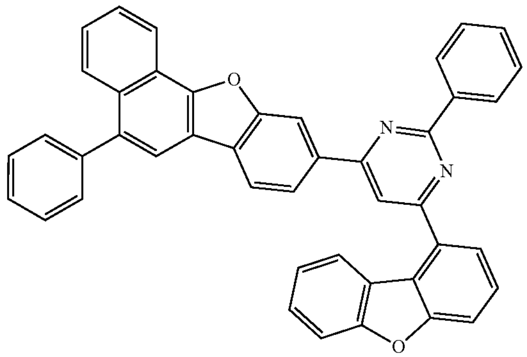

-continued
2-539
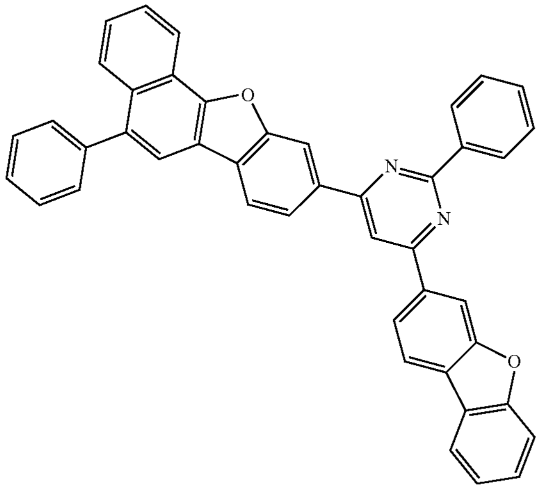
2-540
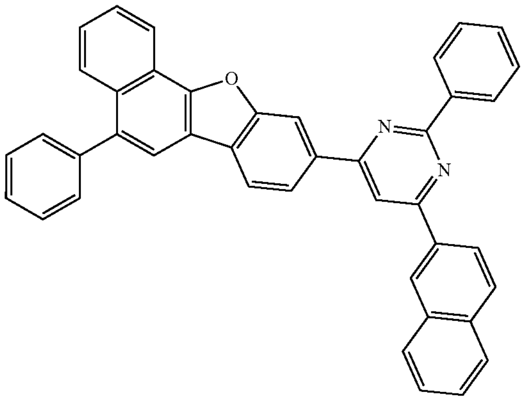
2-541
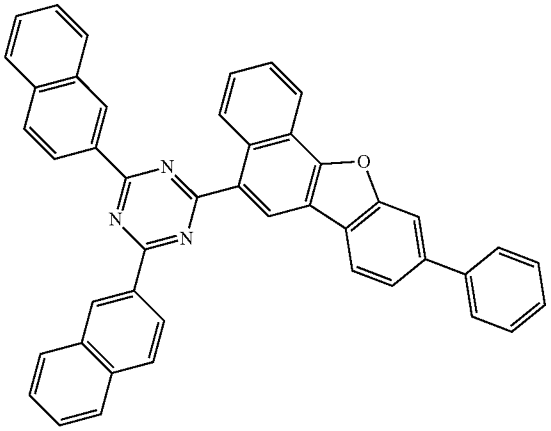
-continued
2-542
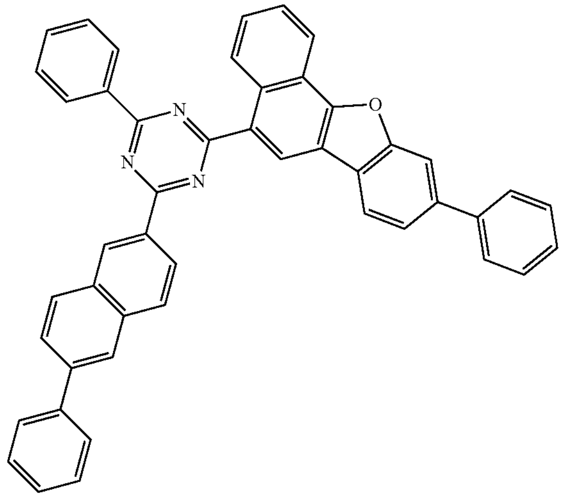
2-543
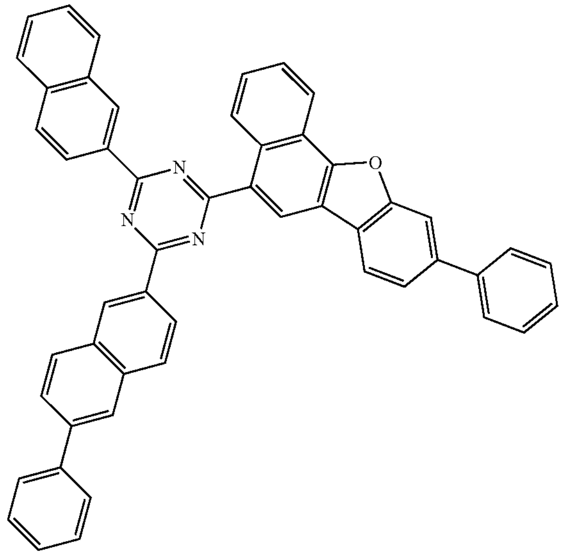
2-544
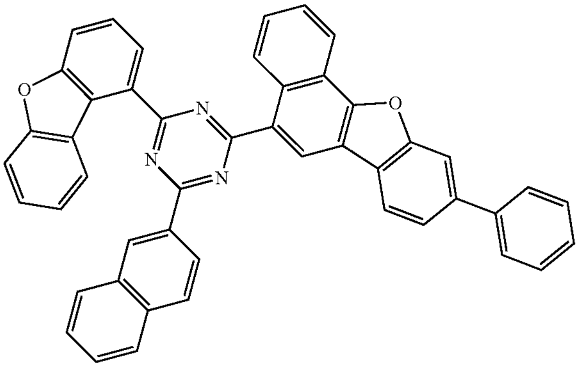

-continued
2-545
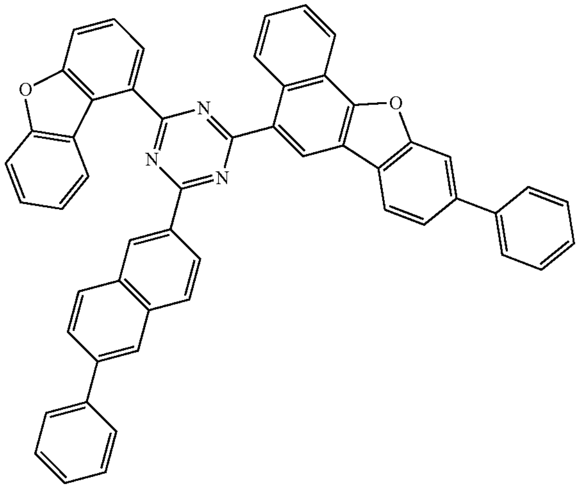
2-546
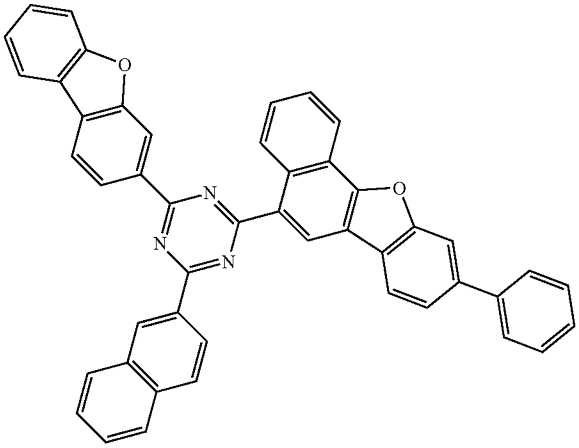
2-547
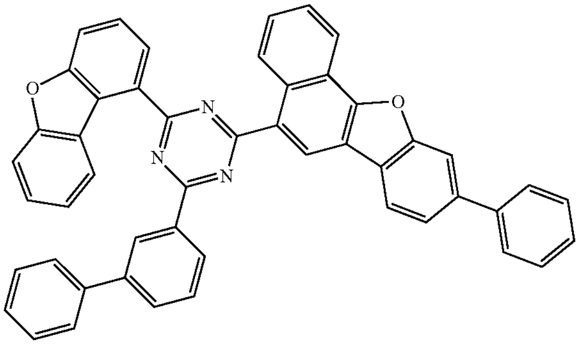
-continued
2-548
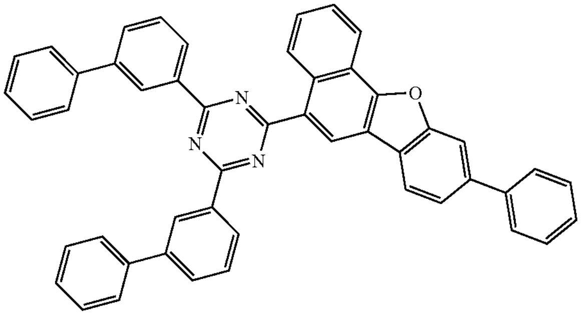
2-549
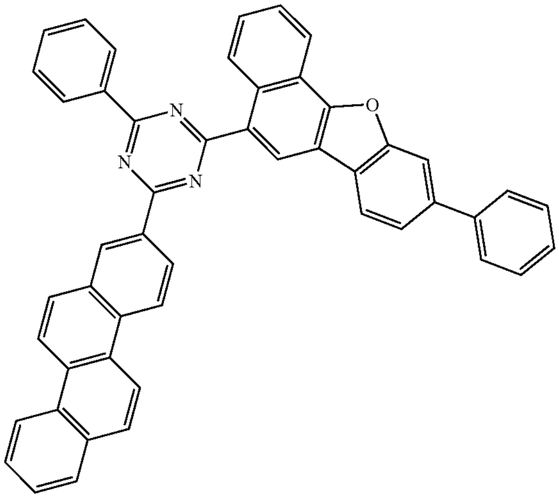
2-550
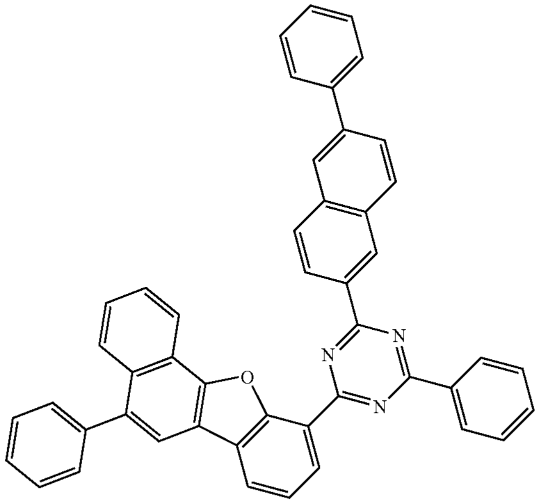

-continued
2-551
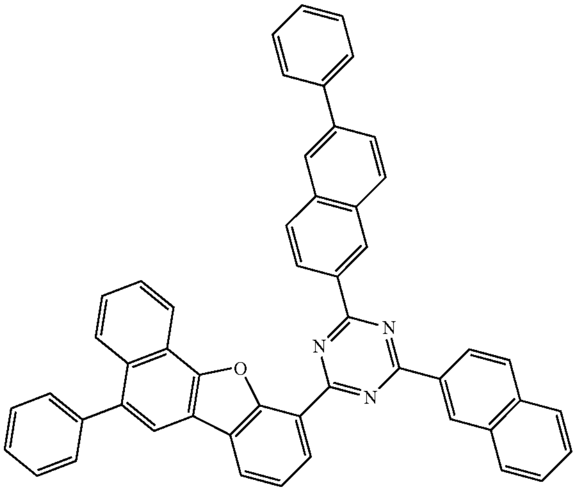
2-552
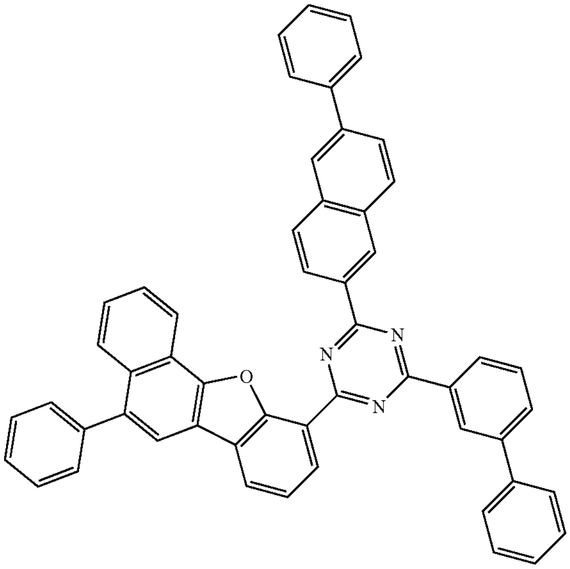
-continued
2-553
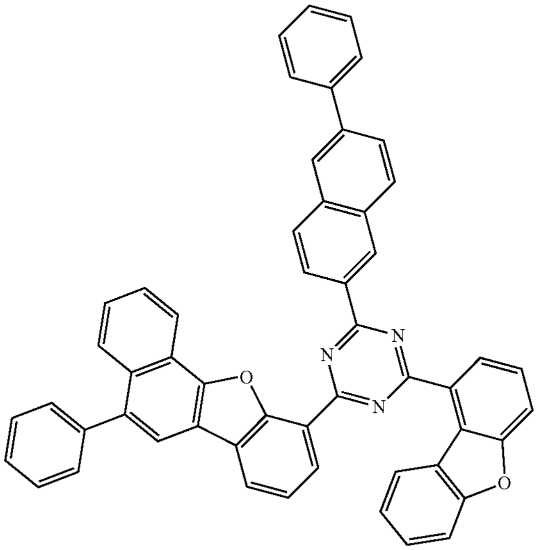
2-554
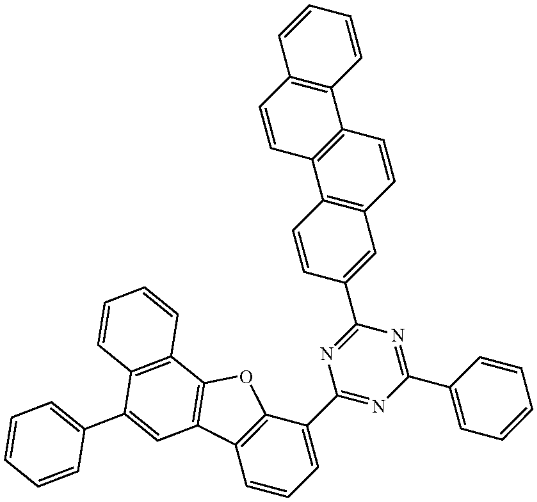
2-554
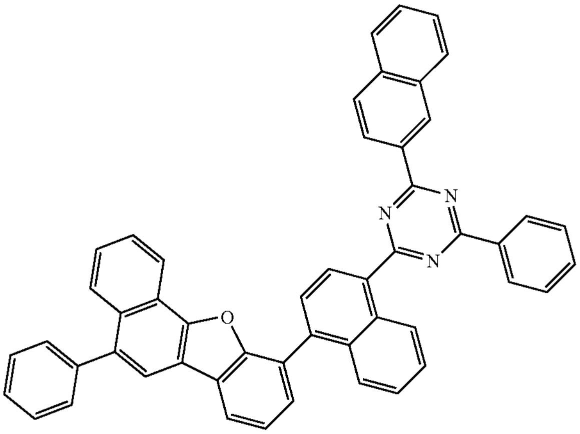

-continued
2-555
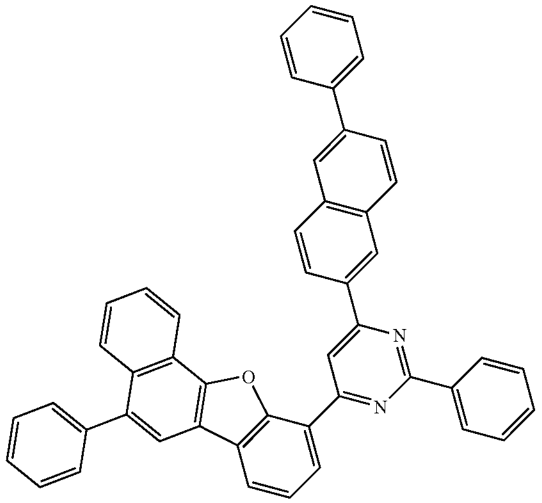
2-557
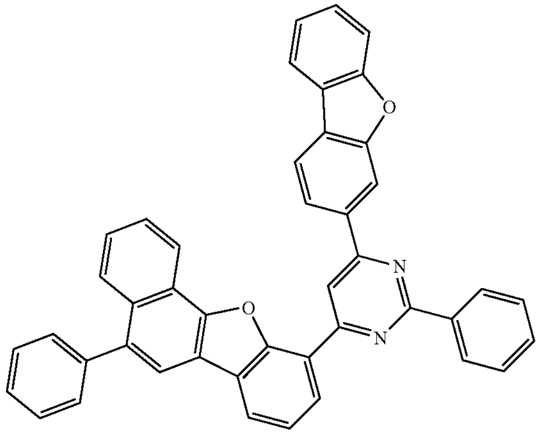
2-558
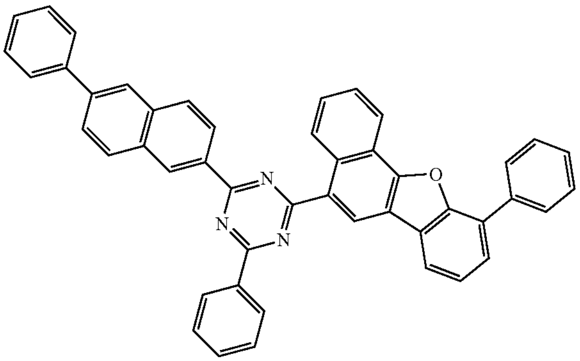
-continued
2-559
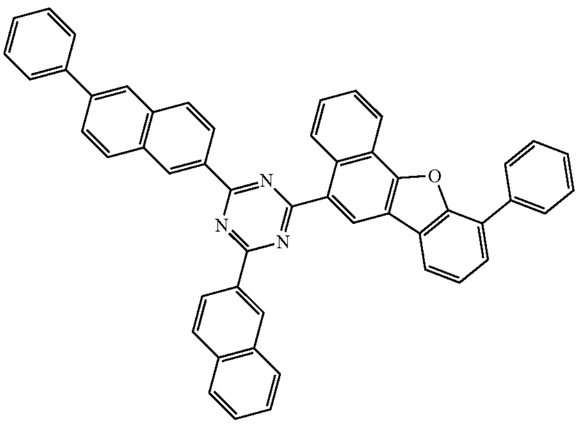
2-560
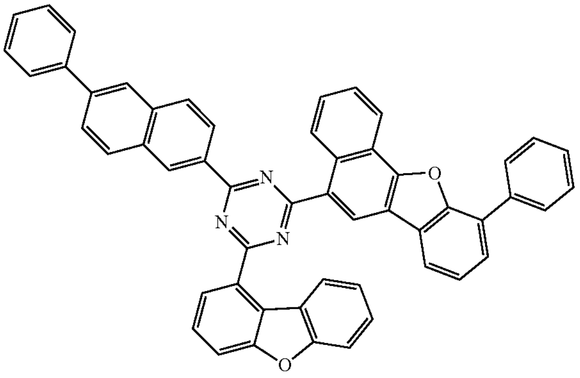
2-561
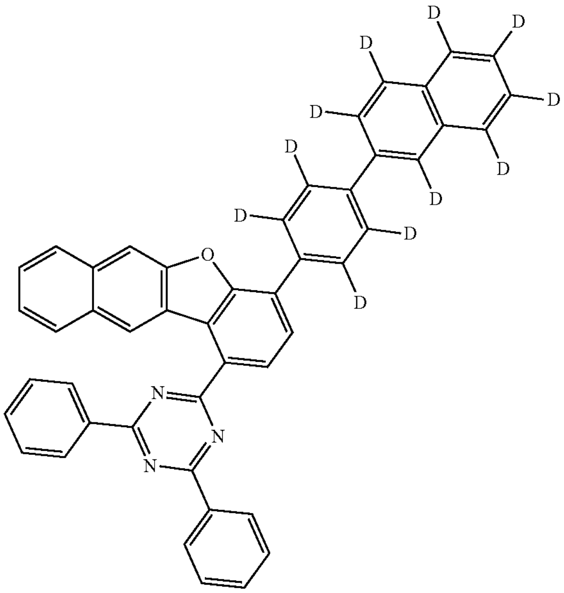

2-562
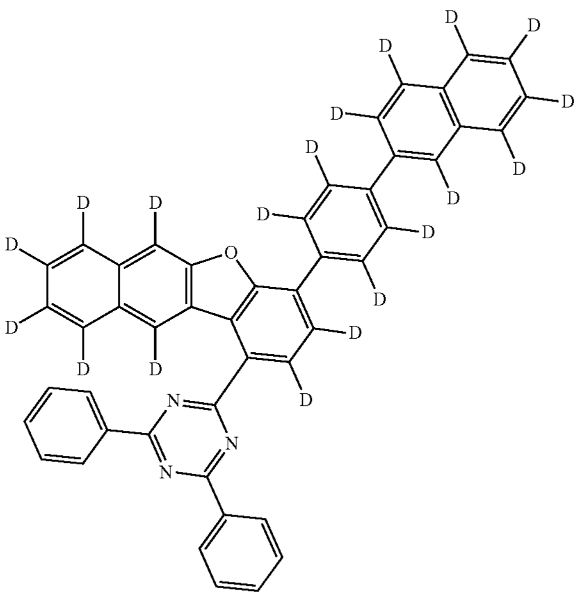
2-563
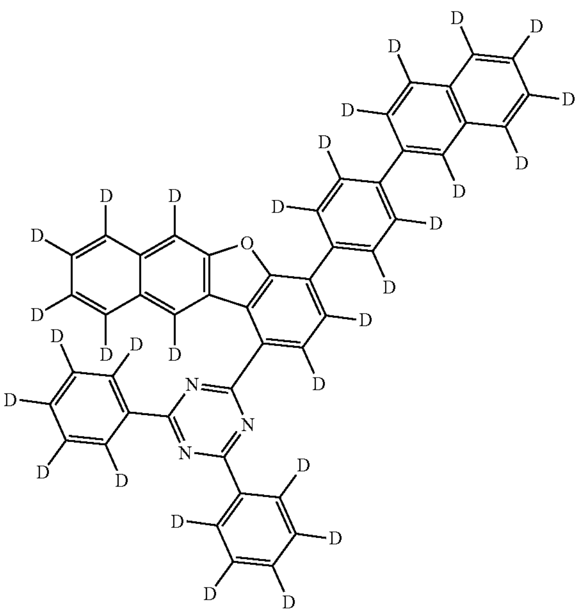
2-564
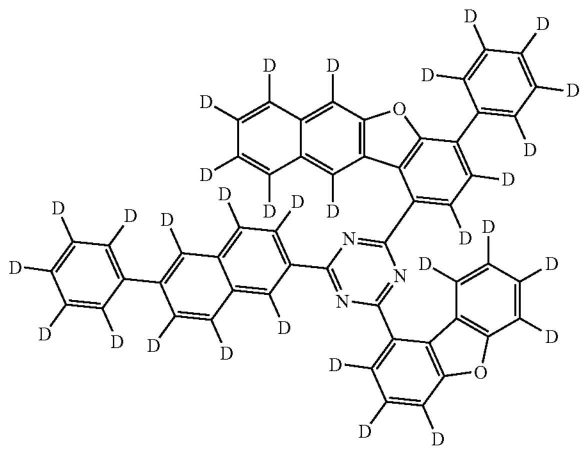
2-565
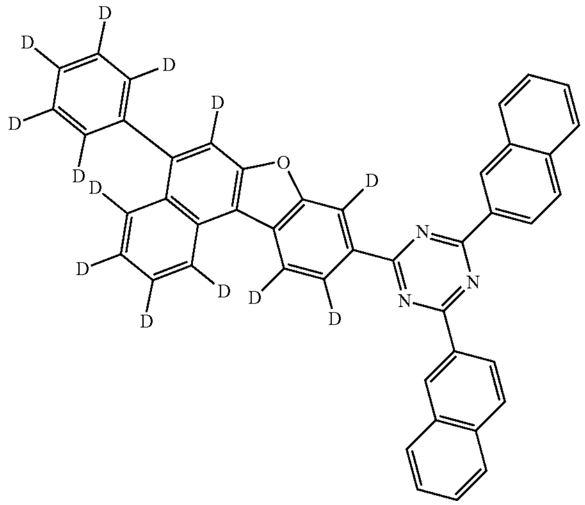
2-566
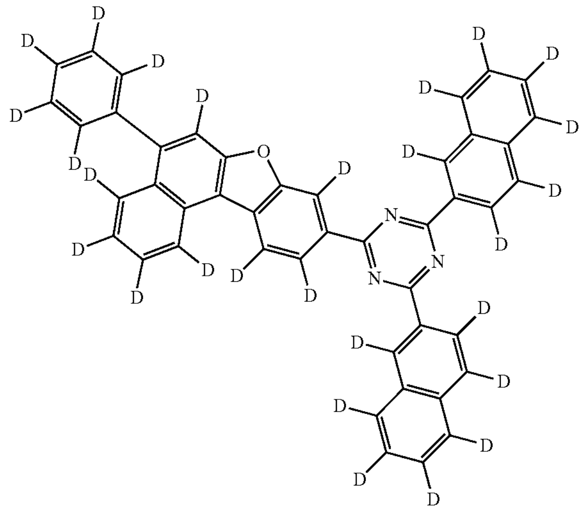

-continued
2-567
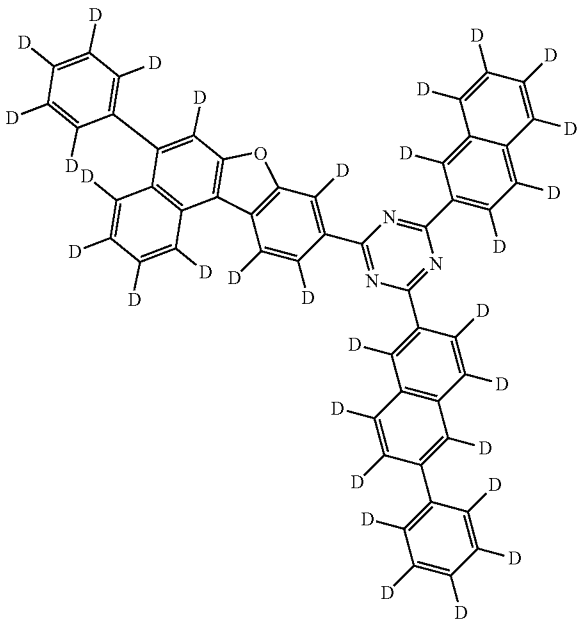
2-568
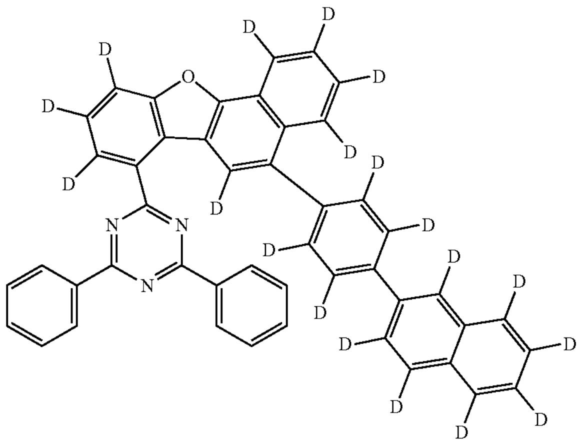
-continued
2-569
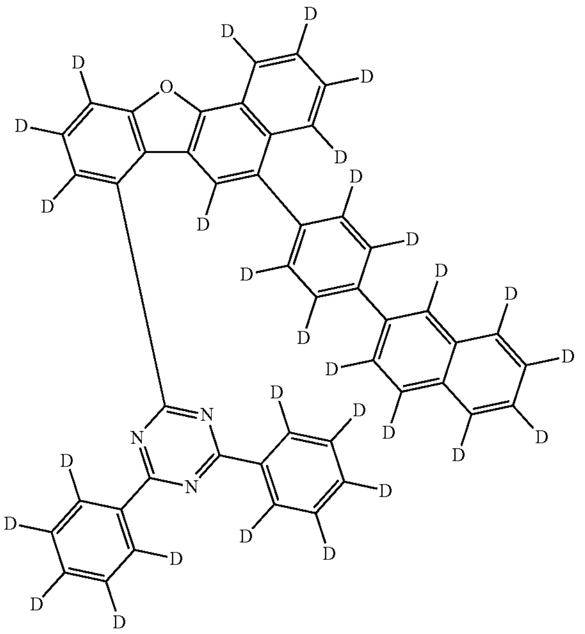
2-570
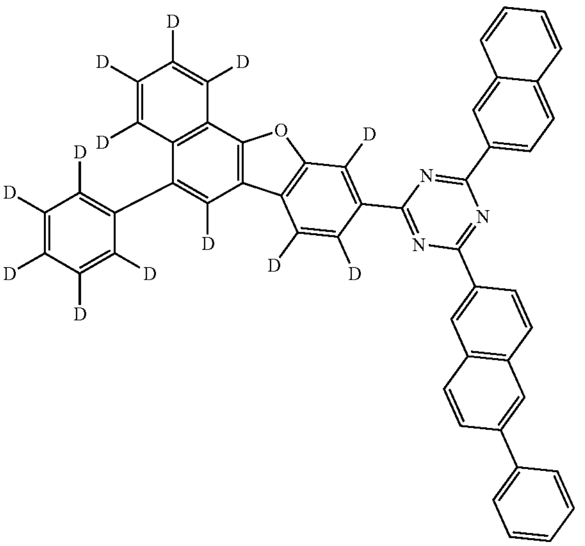

-continued
2-571
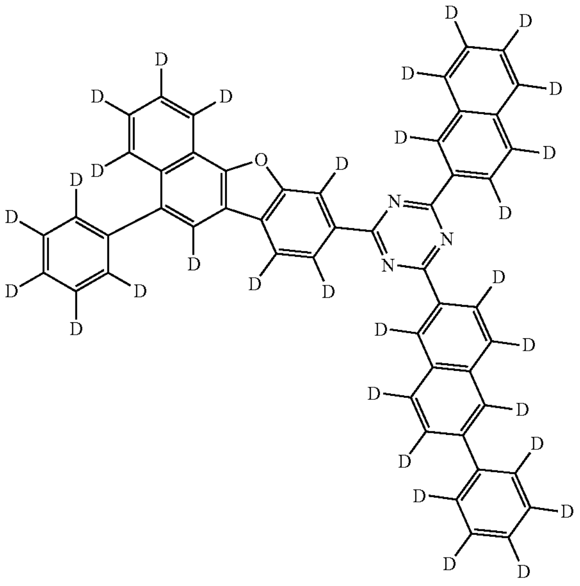
2-572
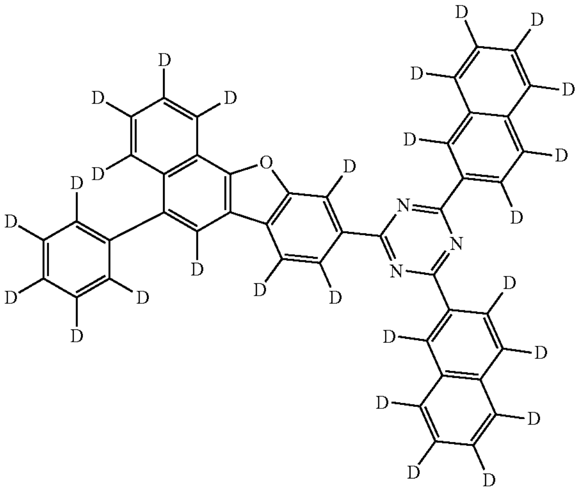
In one embodiment of the present application, the heterocyclic compound of Chemical Formula B may be represented by any one of the following compounds.
3-1
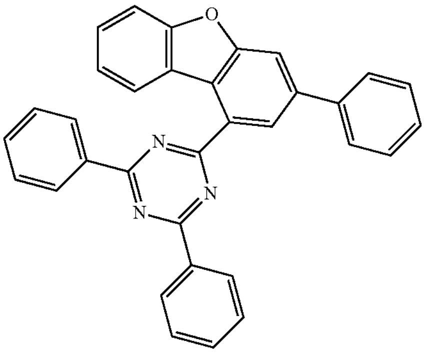
-continued
3-2
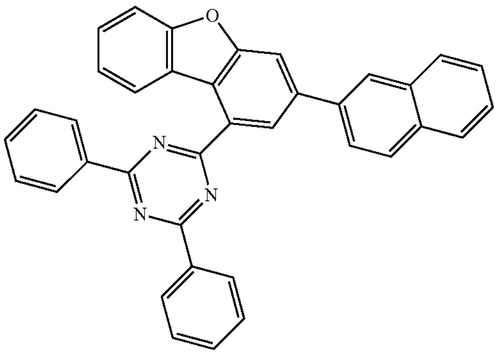
3-3
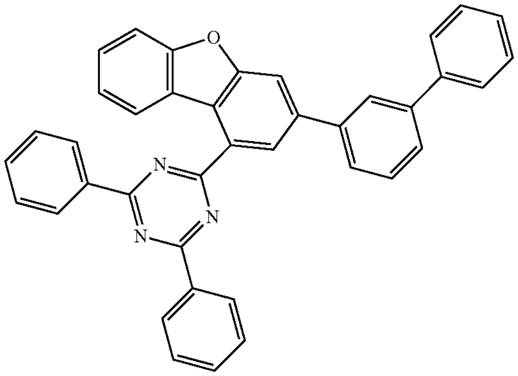
3-4
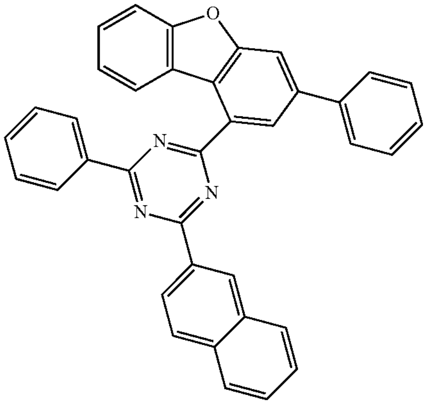
3-5
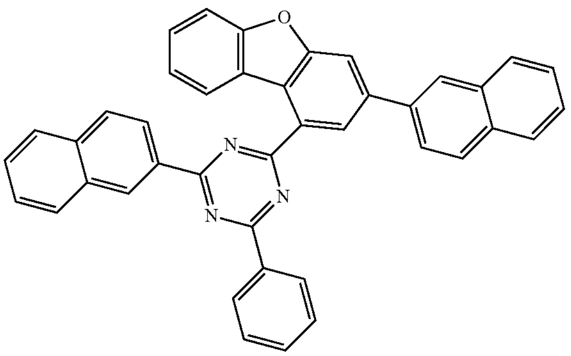

-continued
3-6
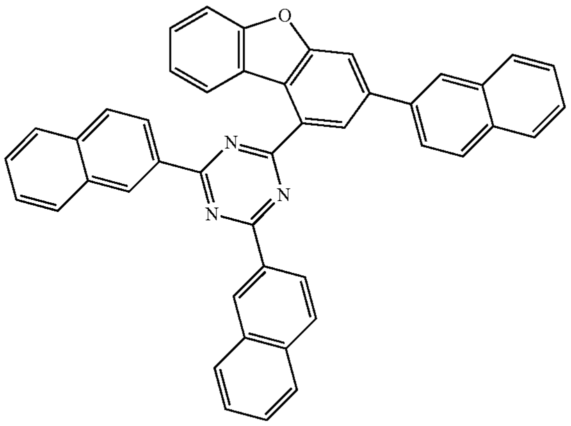
3-7
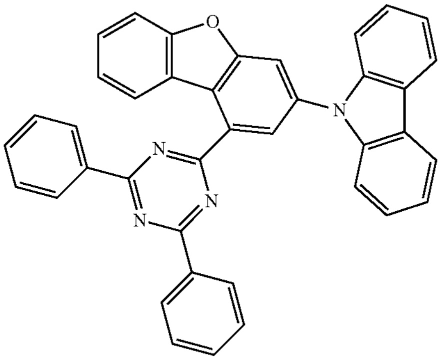
3-8
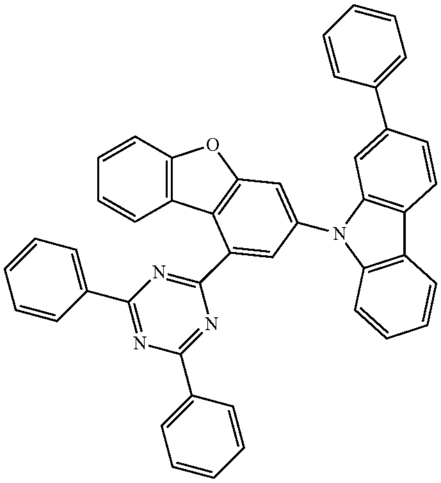
3-9
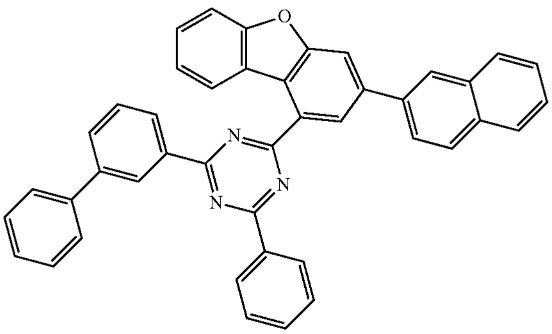
-continued
3-10
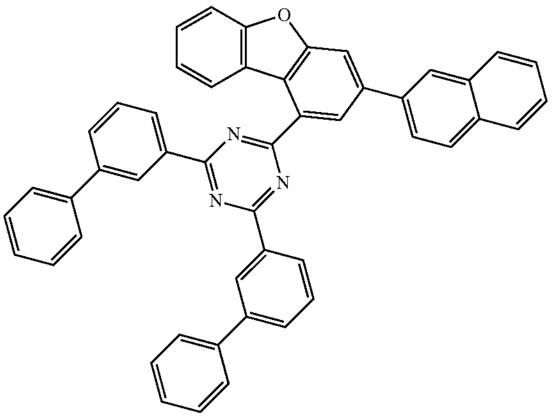
3-11
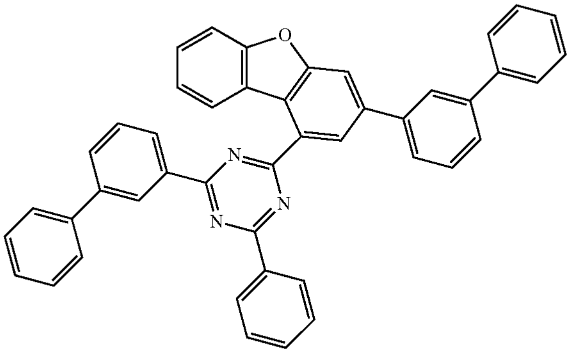
3-12
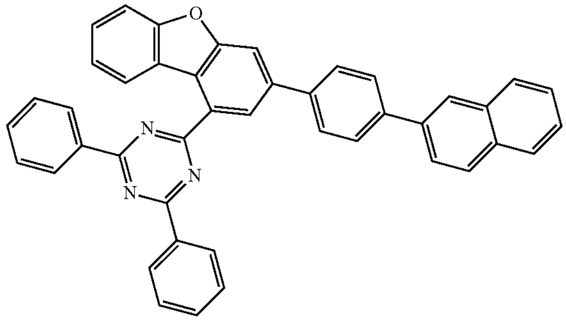

-continued
3-13
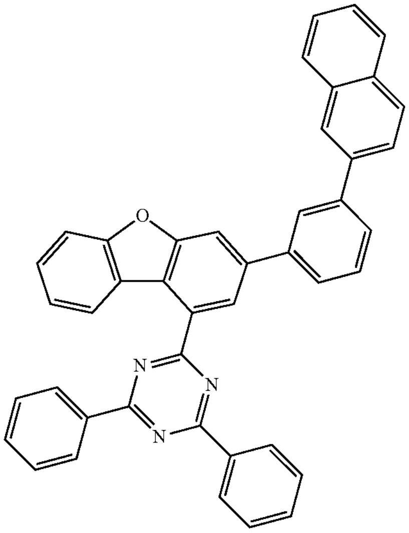
3-14
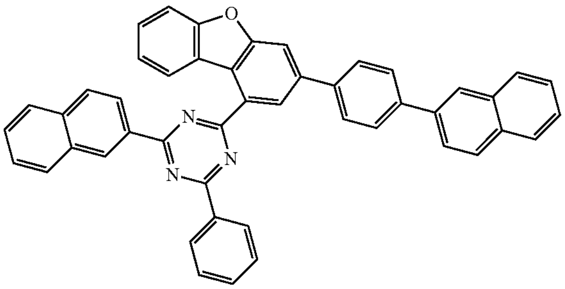
3-15
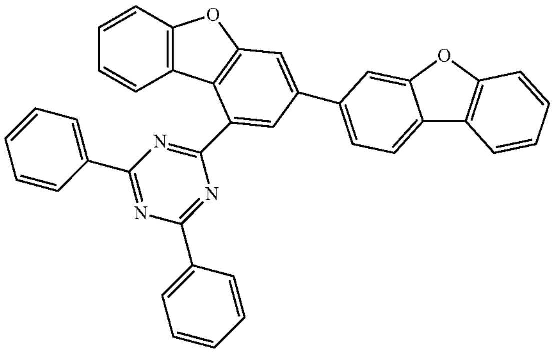
3-16
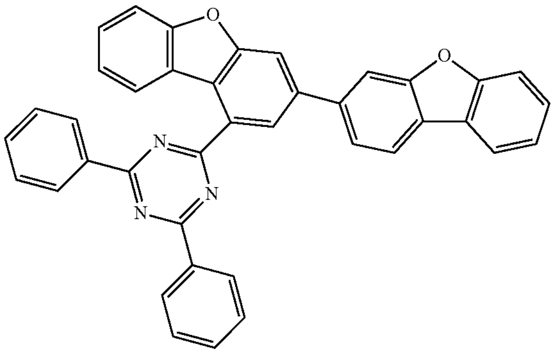
-continued
3-17
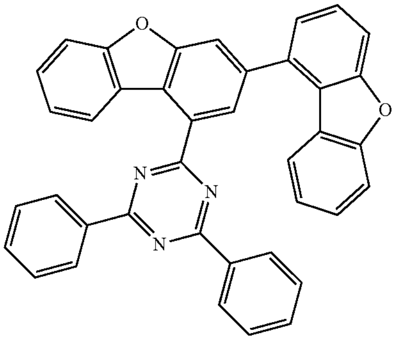
3-18
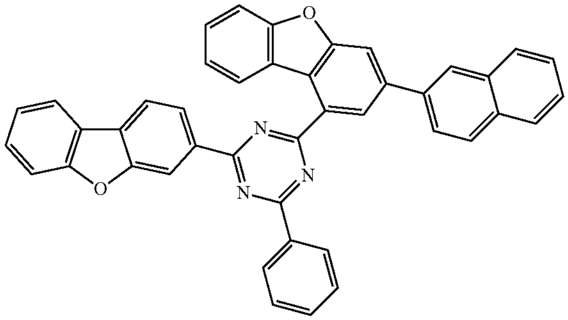
3-19
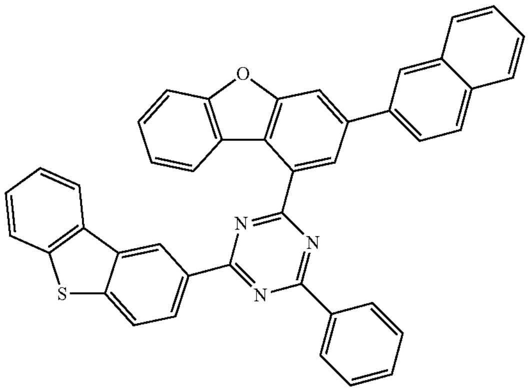
3-20
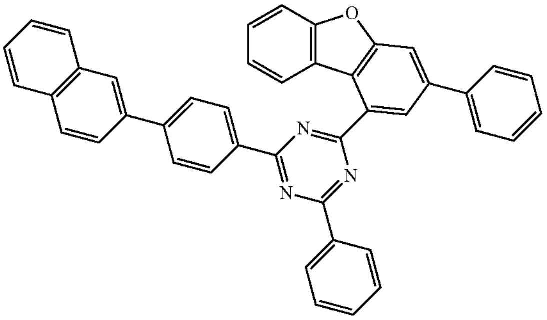

-continued
3-21
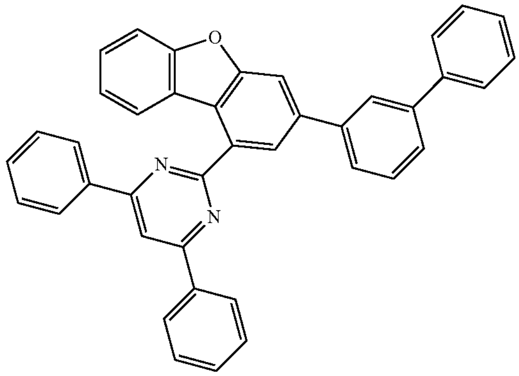
3-22
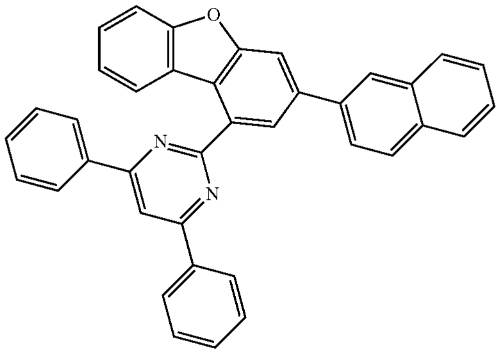
3-23
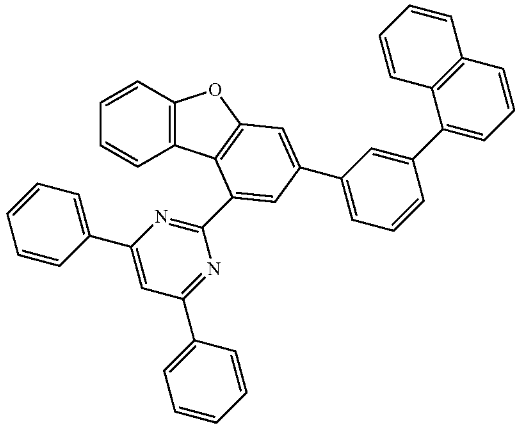
3-24
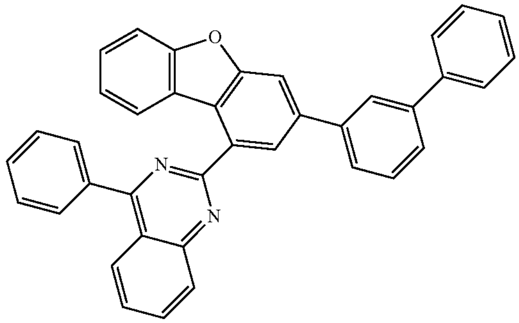
-continued
3-25
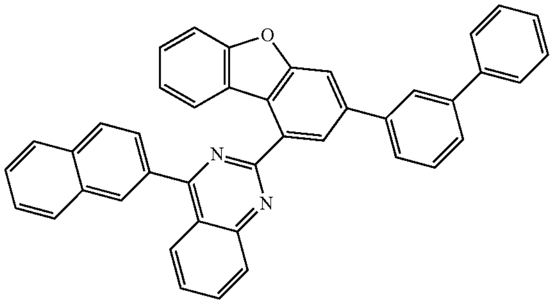
3-26
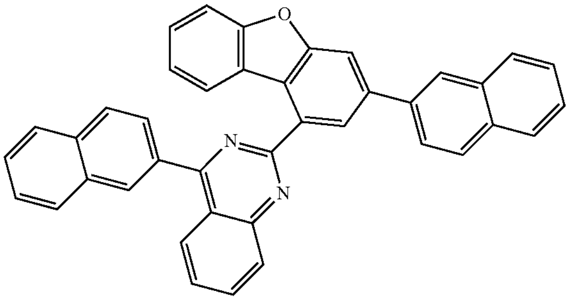
3-27
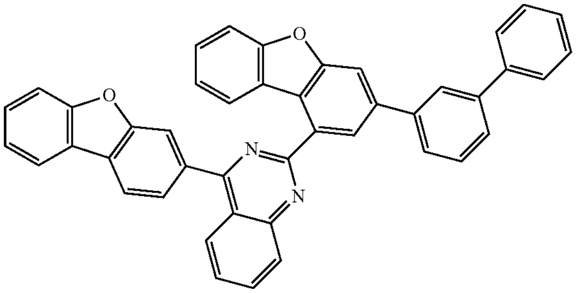
3-28
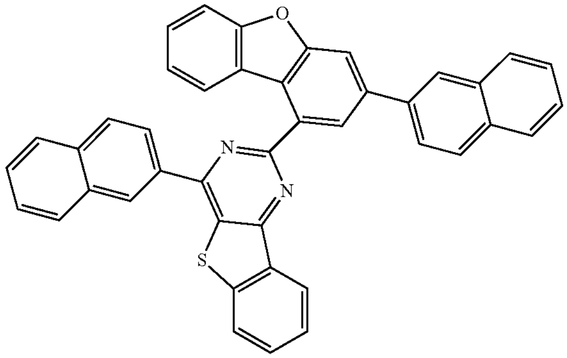

-continued
3-29
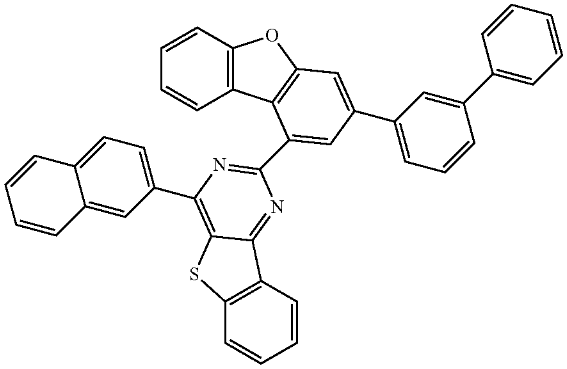
3-30
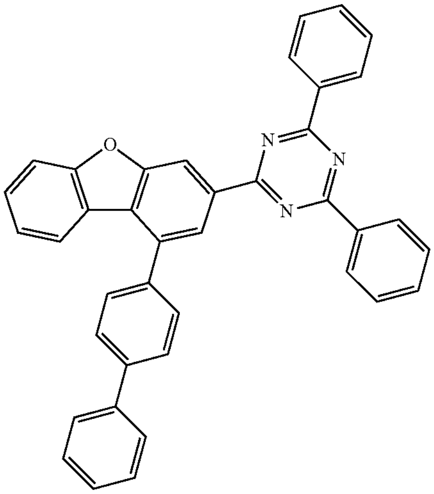
3-31
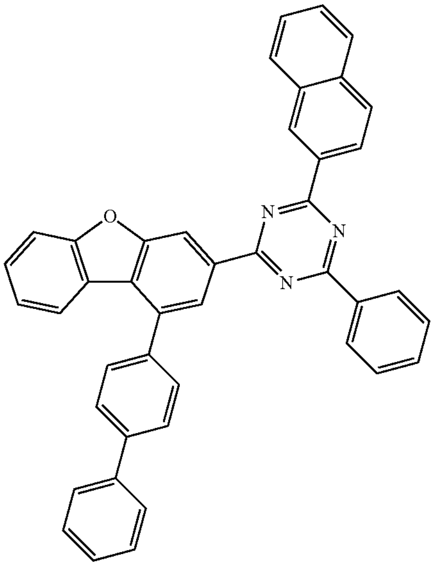
-continued
3-32
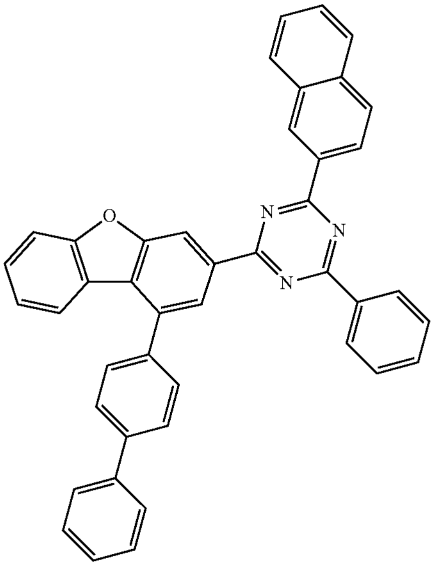
3-33
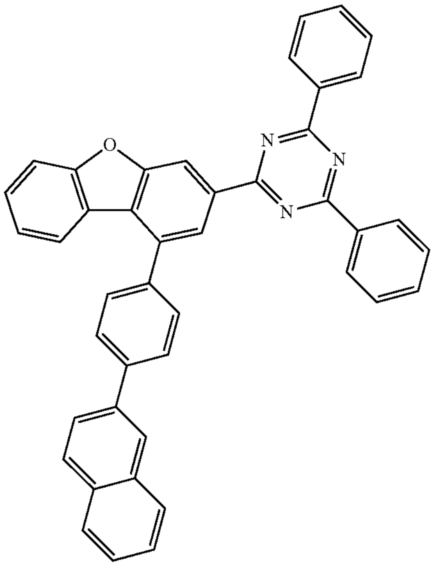

-continued
3-34
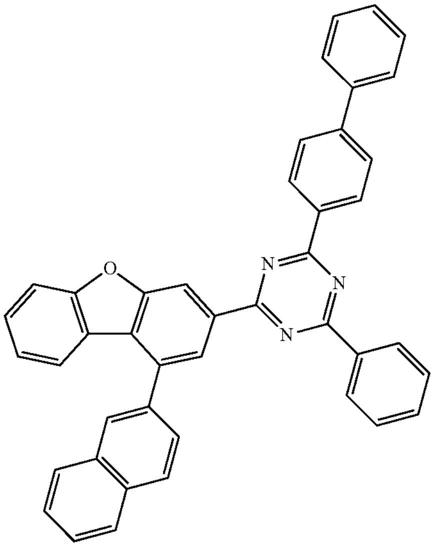
3-35
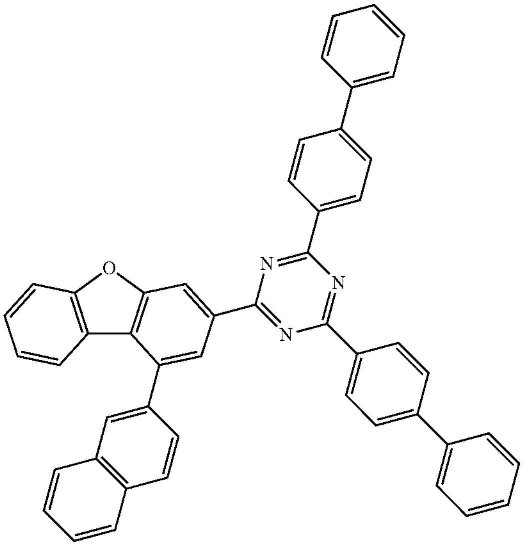
3-36
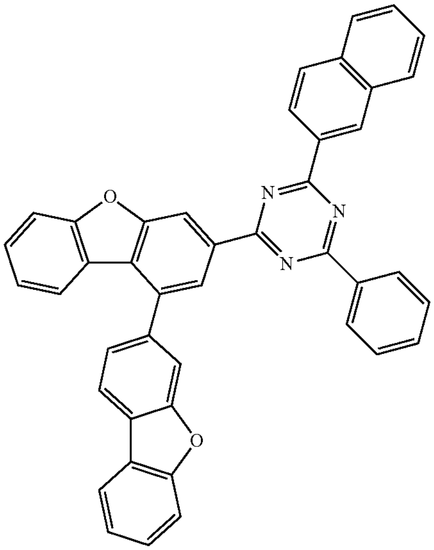
-continued
3-37
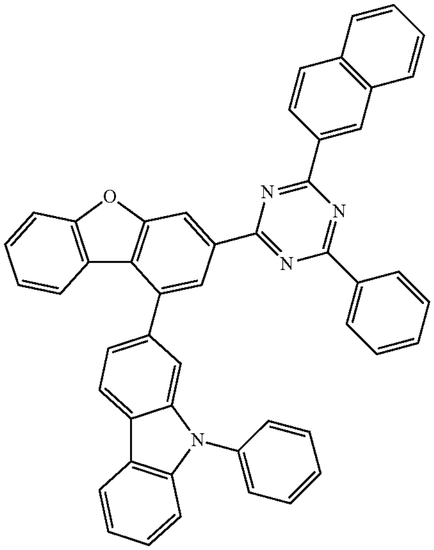
3-38
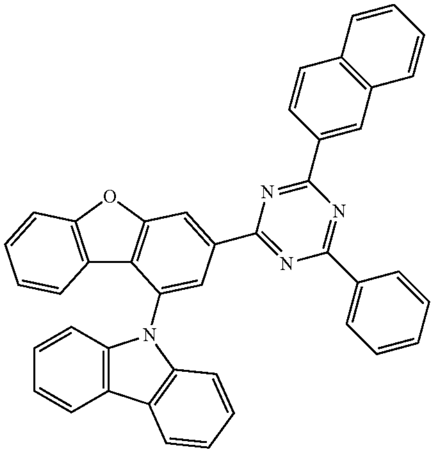
3-39
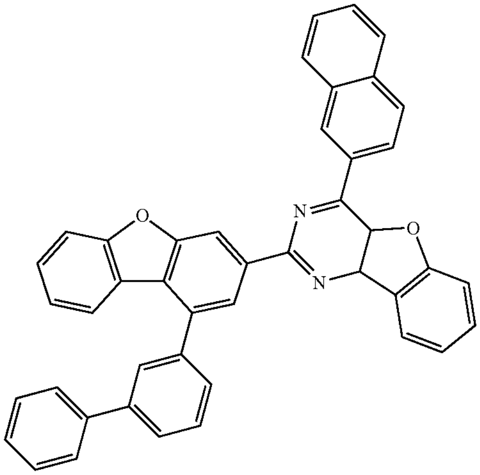

-continued
3-40
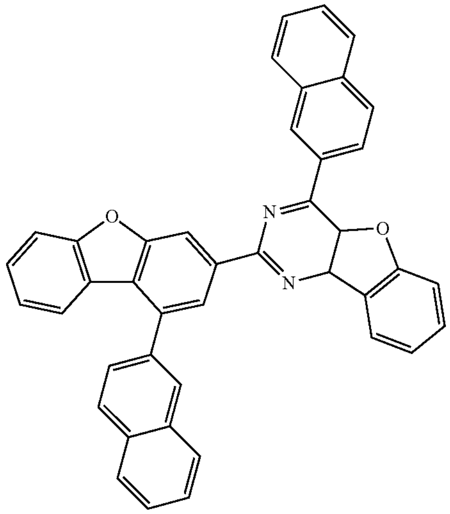
3-41
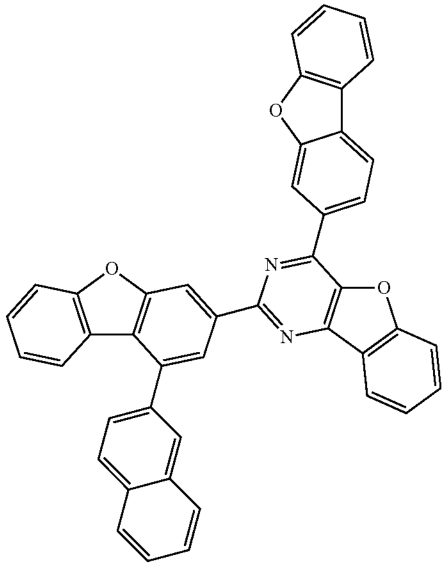
3-42
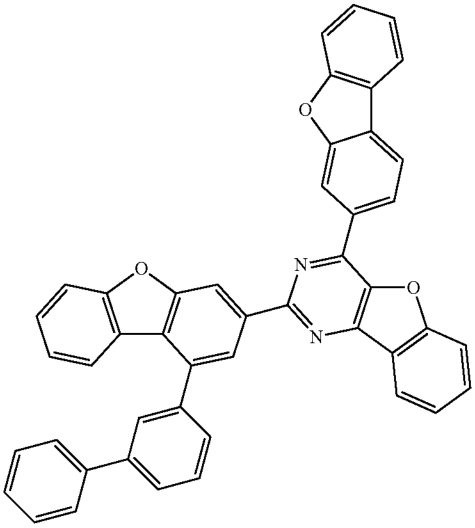
-continued
3-43
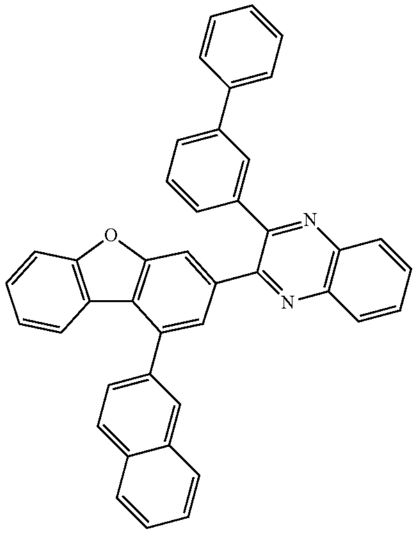
3-44
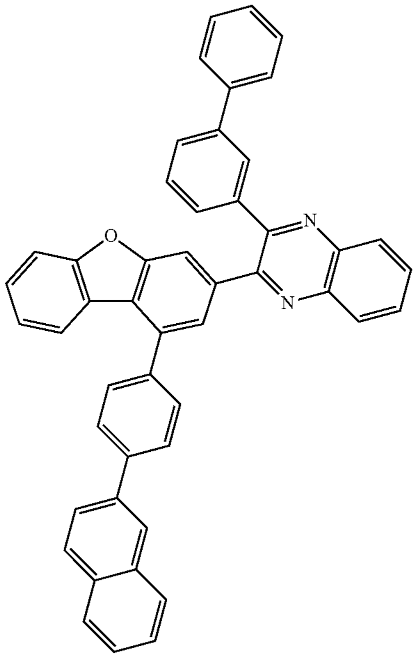
3-5
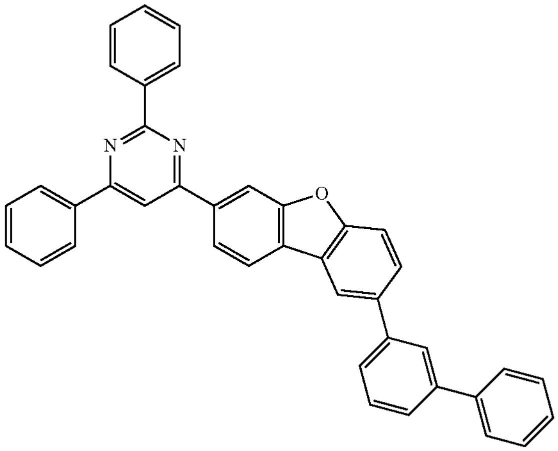

3-46
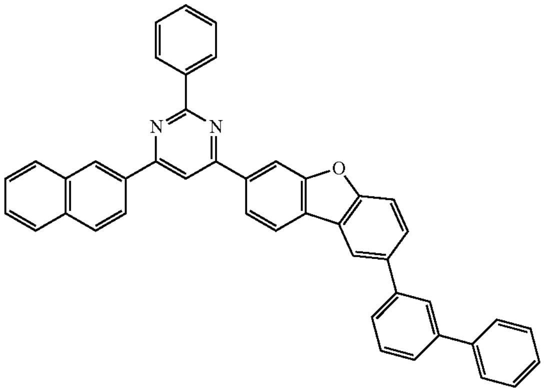
3-47
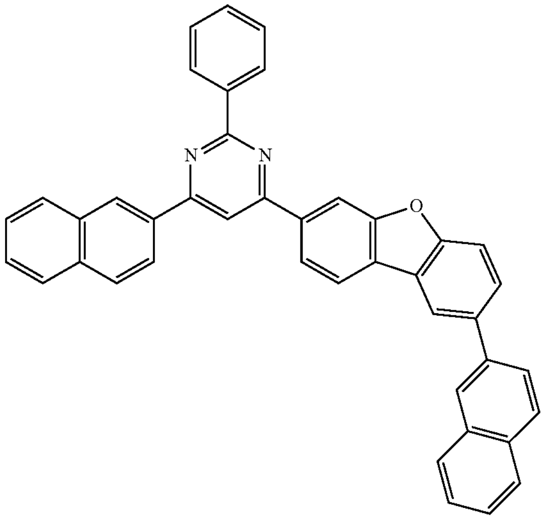
3-48
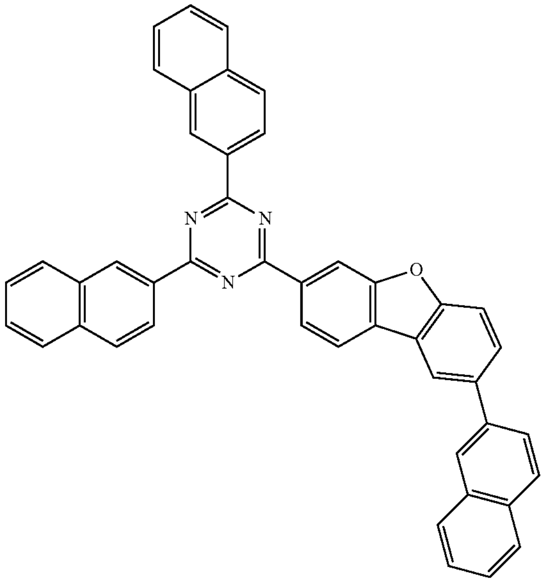
3-49
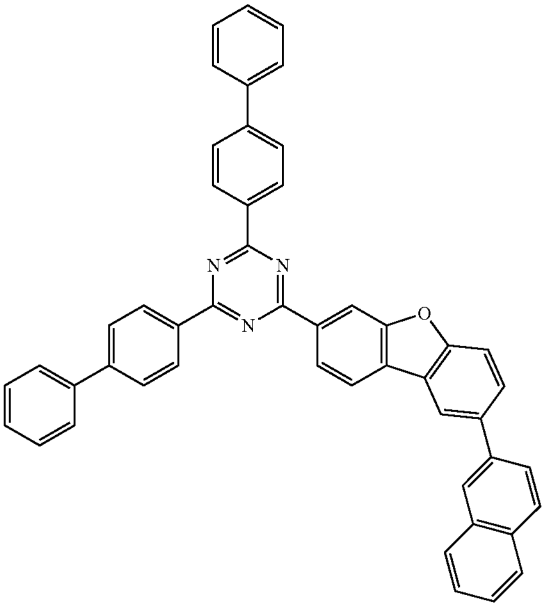
3-50
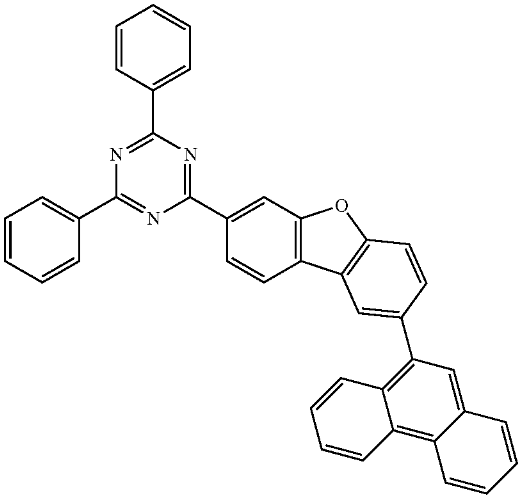

-continued
3-51
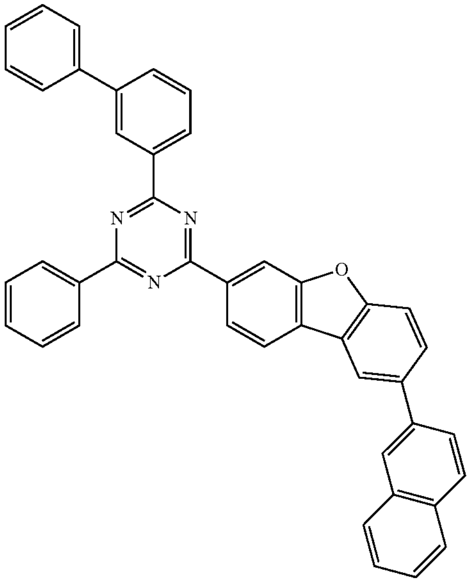
3-52
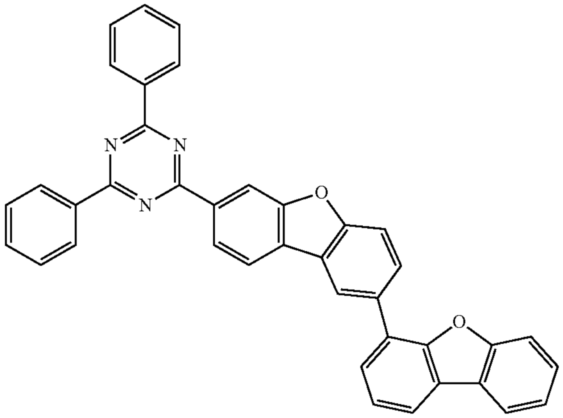
3-53
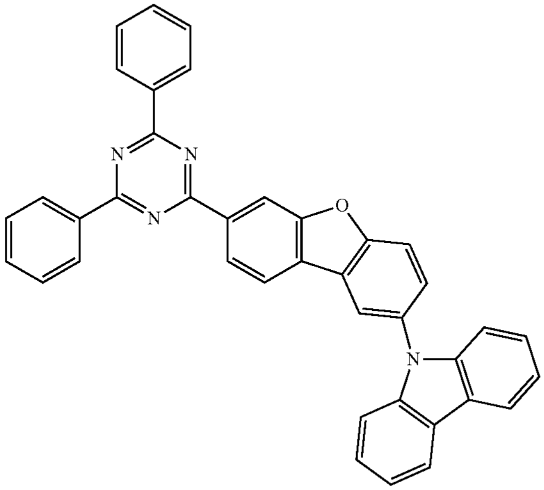
-continued
3-54
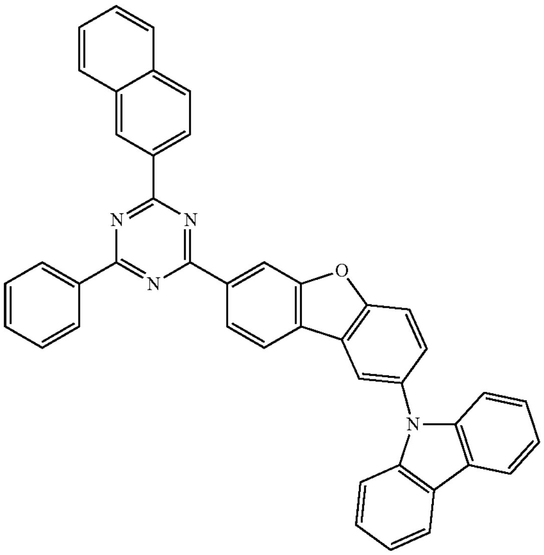
3-55
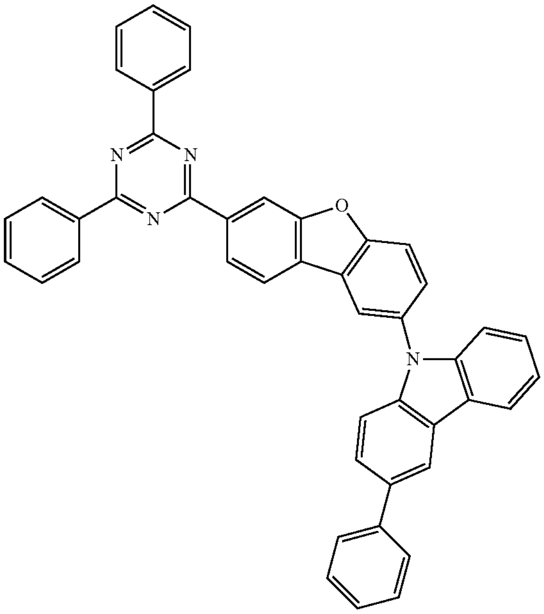

3-56
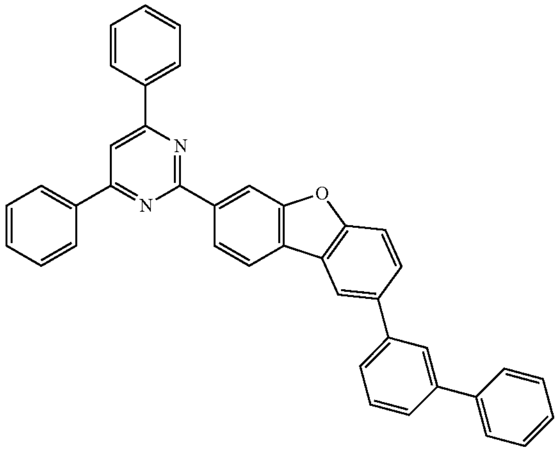
3-57
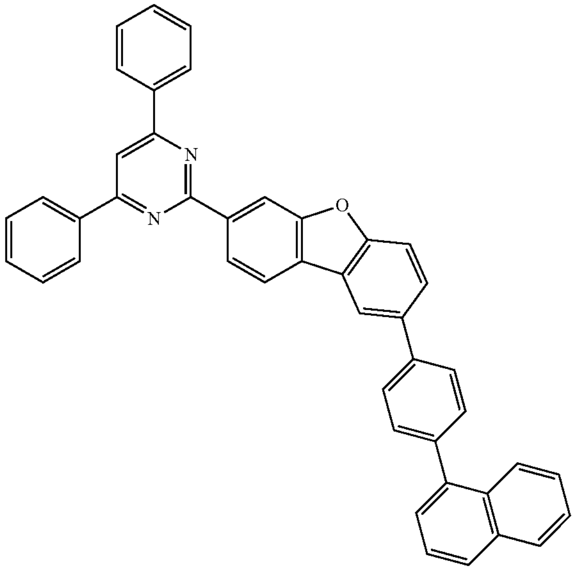
3-58
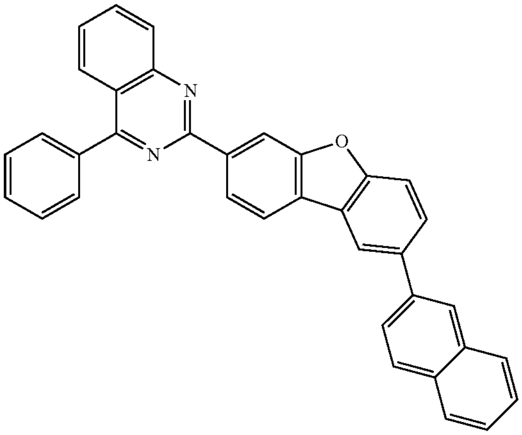
3-59
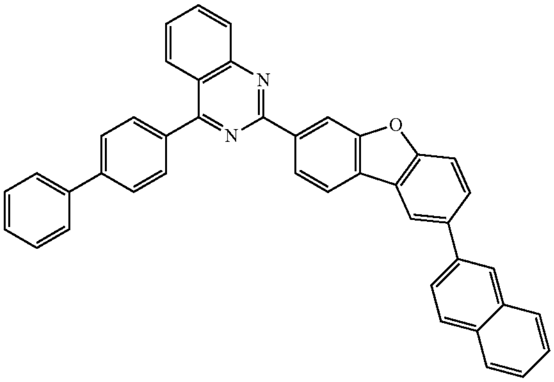
3-60
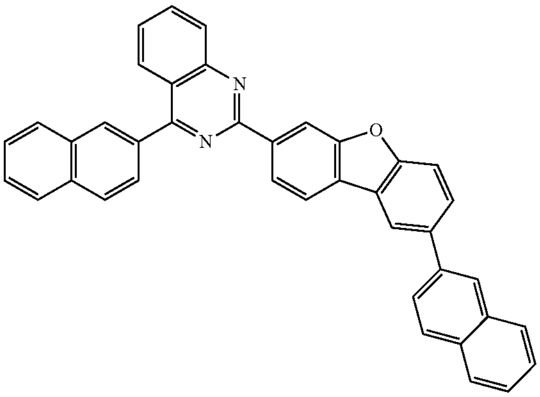
3-61
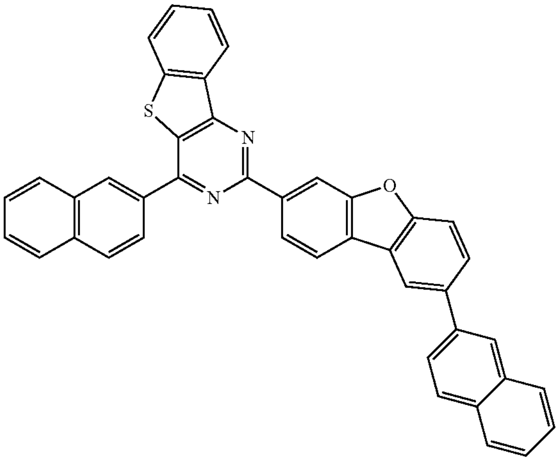

-continued
3-62
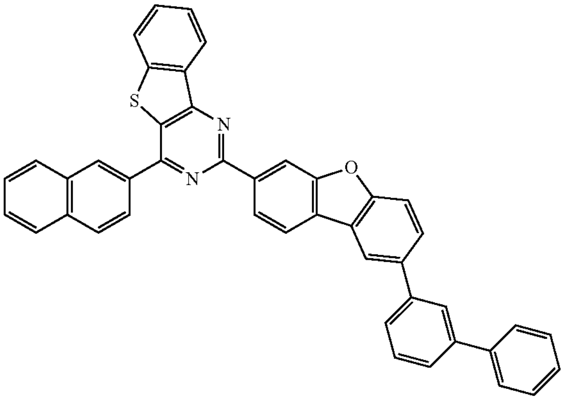
3-63
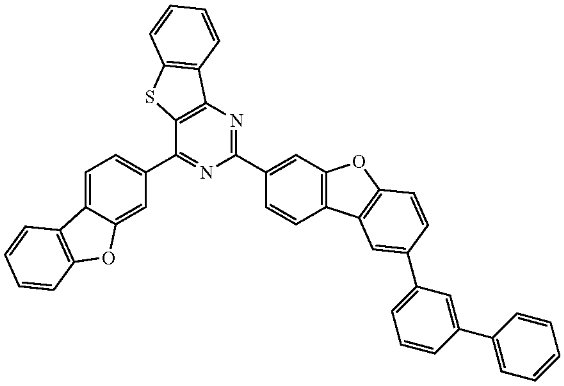
3-64
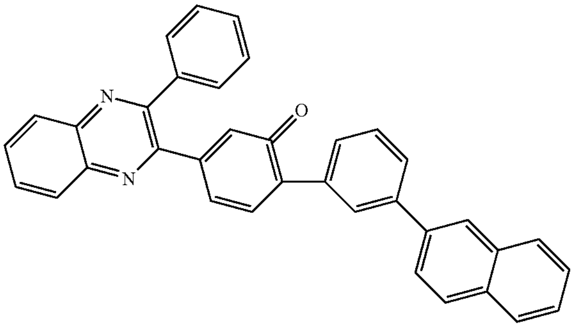
3-65
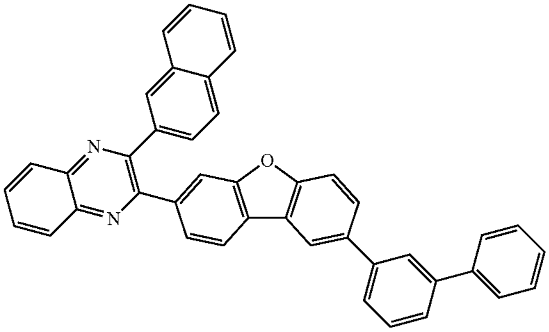
-continued
3-66
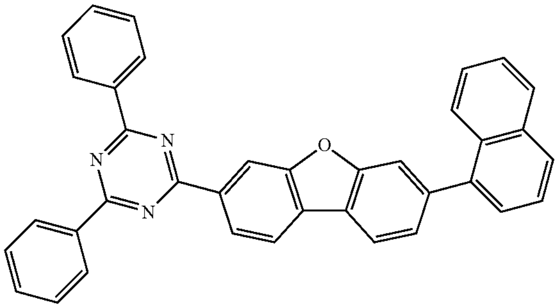
3-67
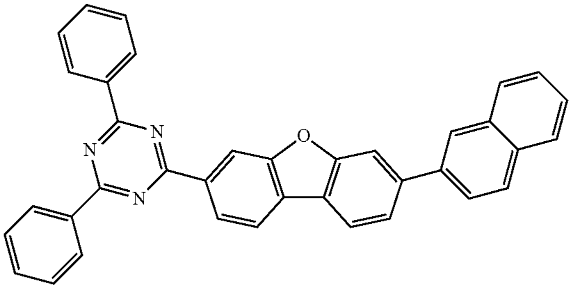
3-68
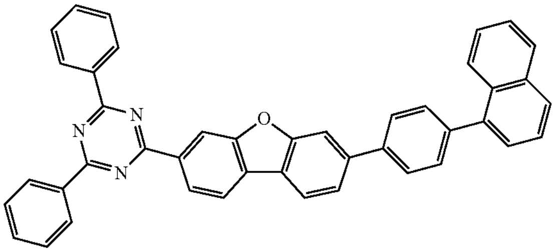
3-69
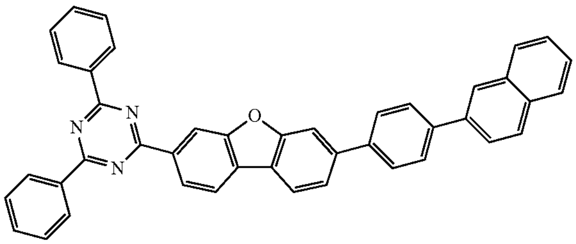
3-70
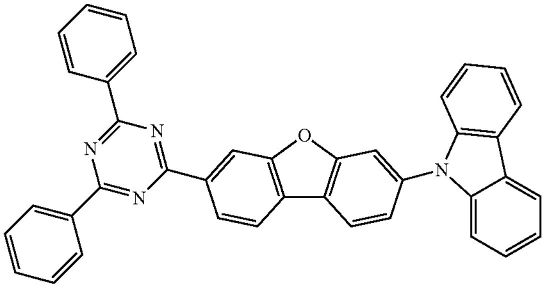

-continued
3-71
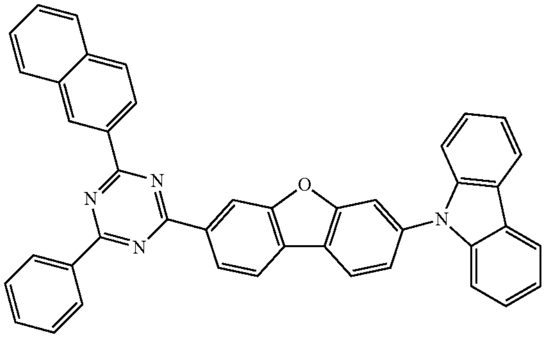
3-72
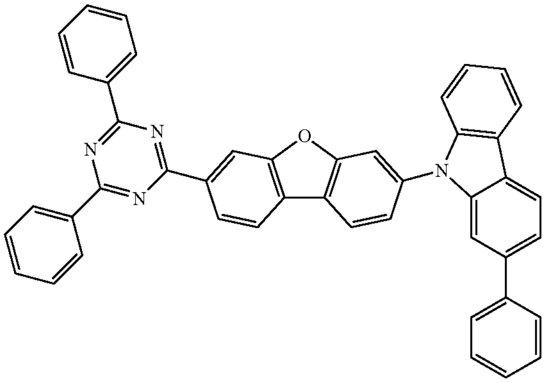
3-73
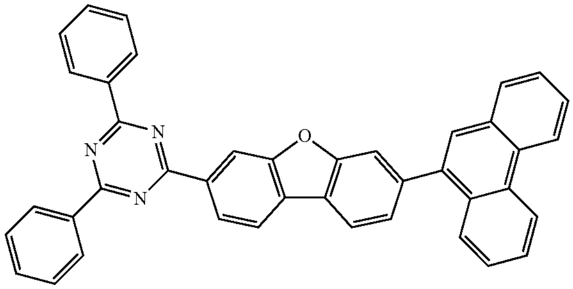
3-74
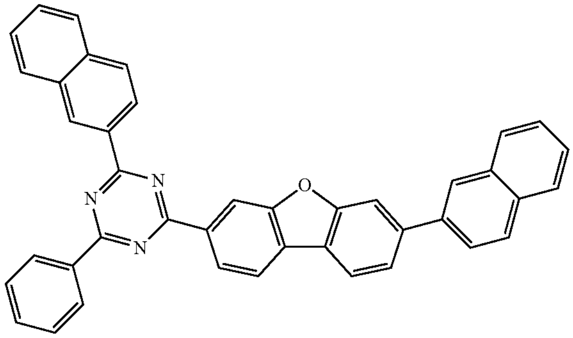
-continued
3-75
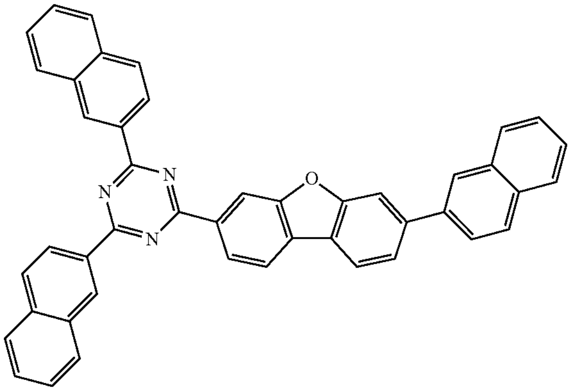
3-76
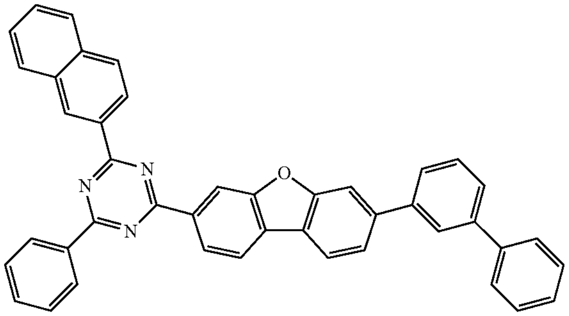
3-77
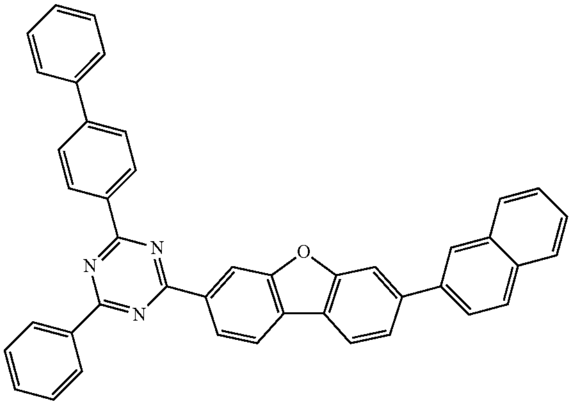
3-78
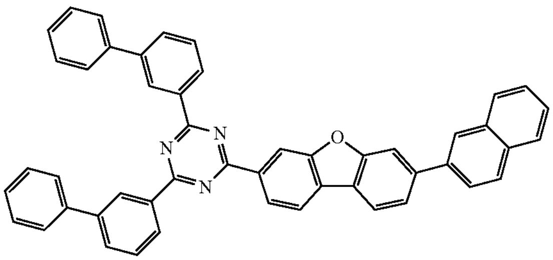

-continued
3-79
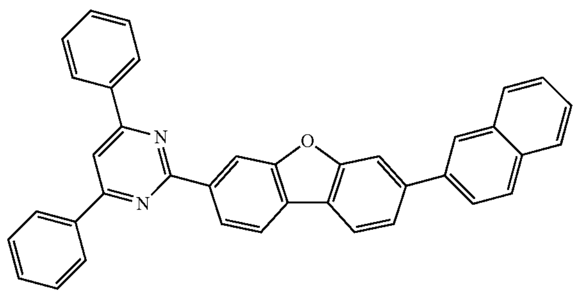
3-80
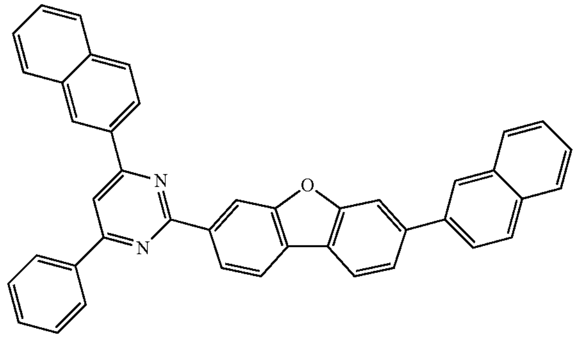
3-81
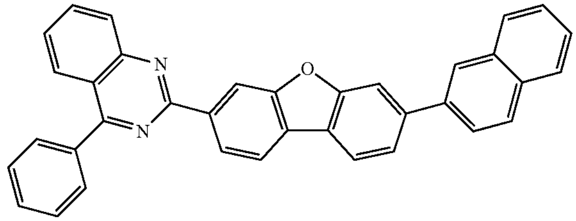
3-82
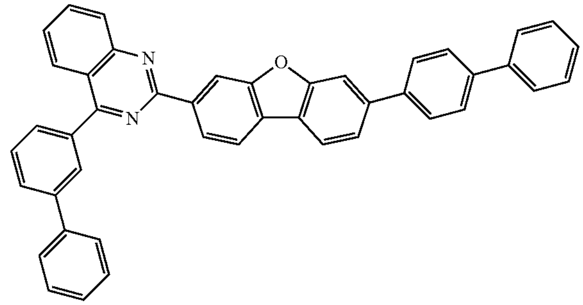
3-83
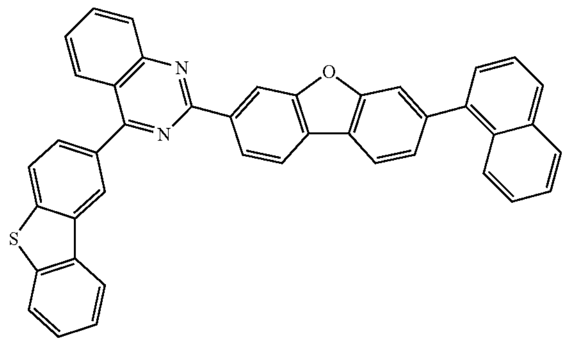
-continued
3-84
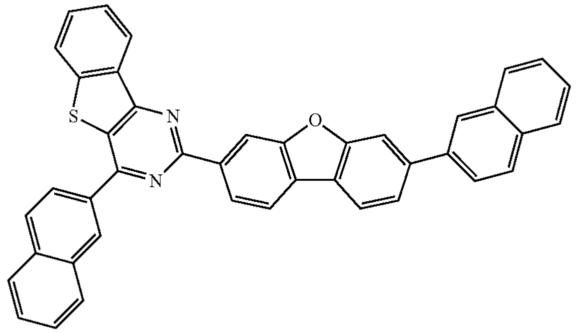
3-85
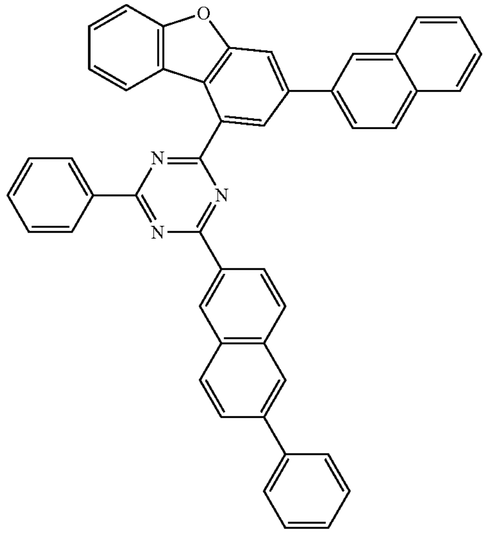
3-86
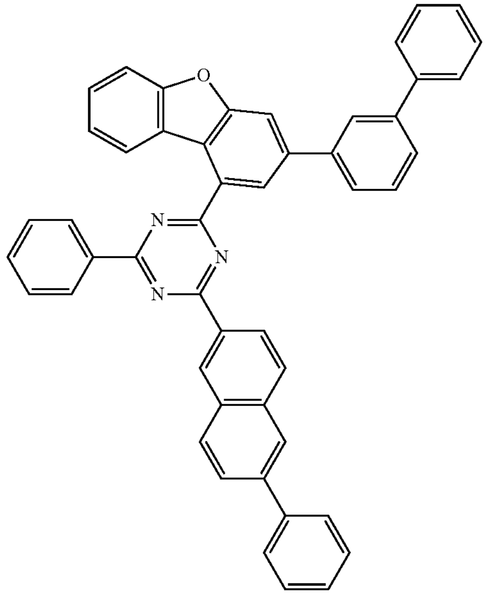

-continued
3-87
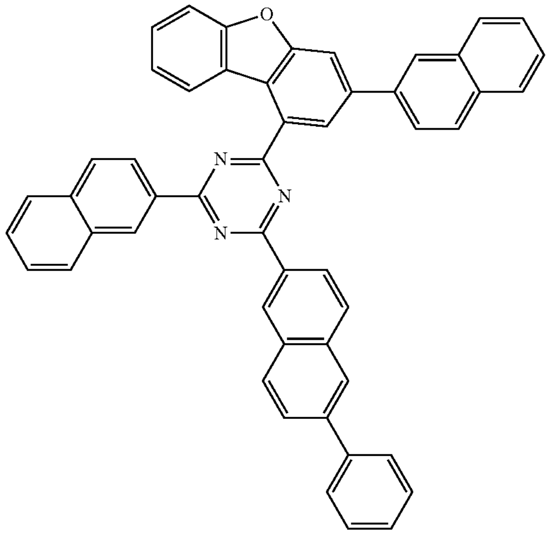
3-88
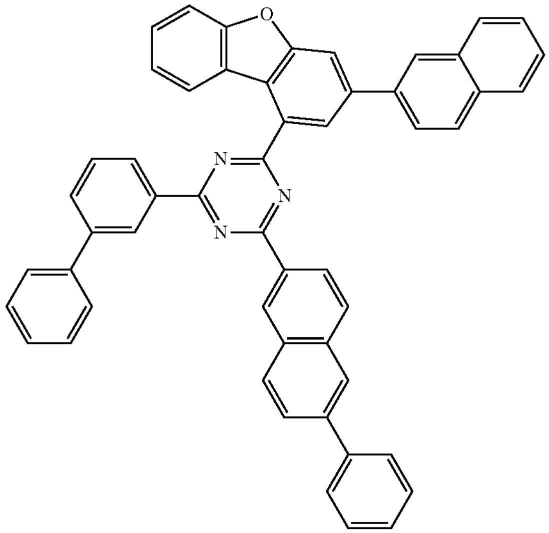
3-89
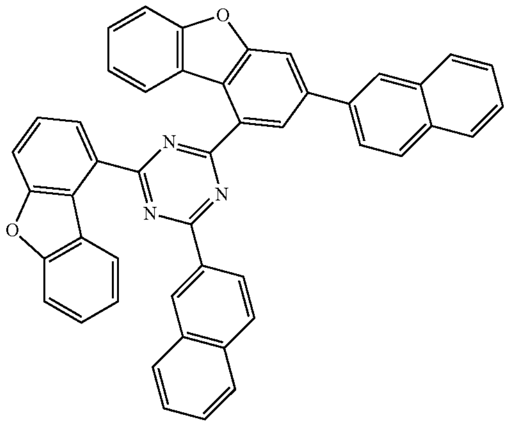
-continued
3-90
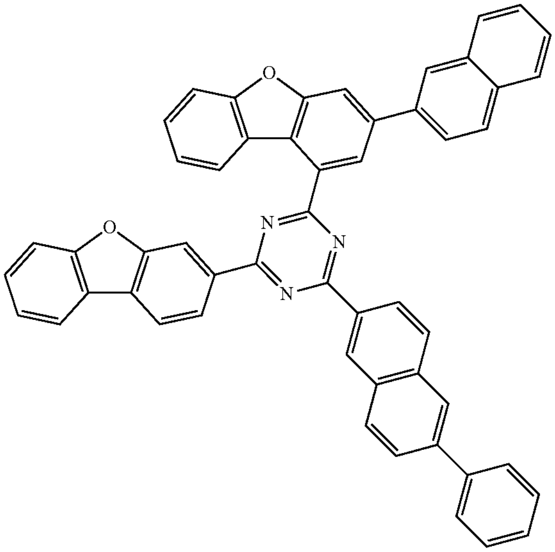
3-91
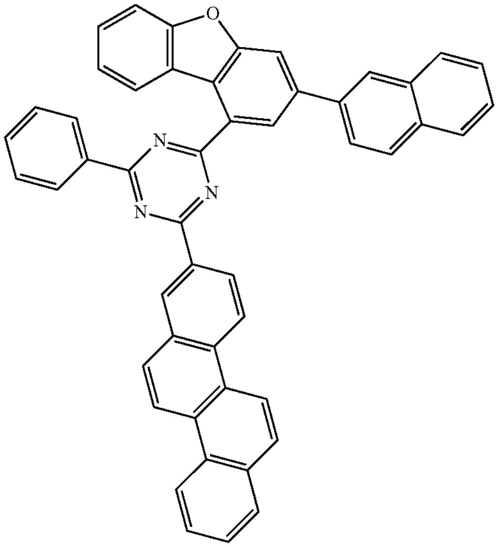
3-92
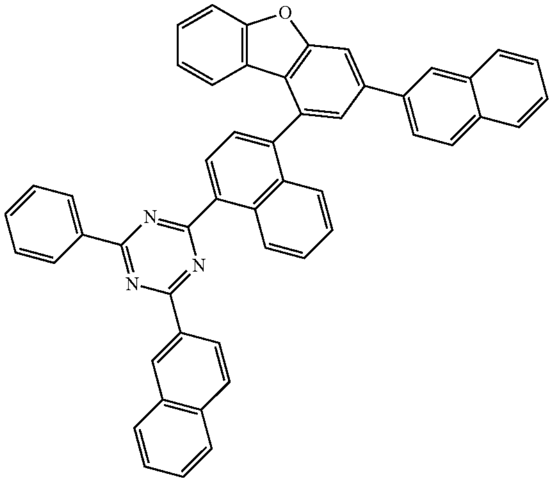

-continued
3-93
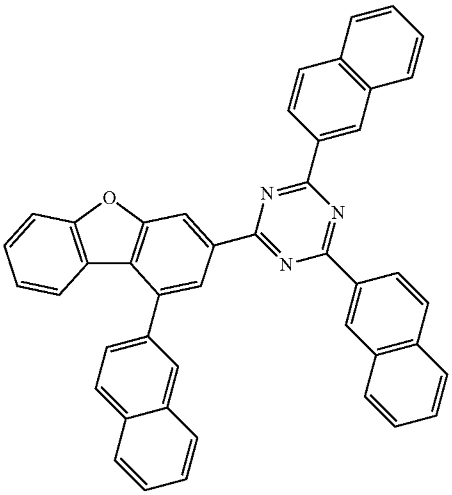
3-94
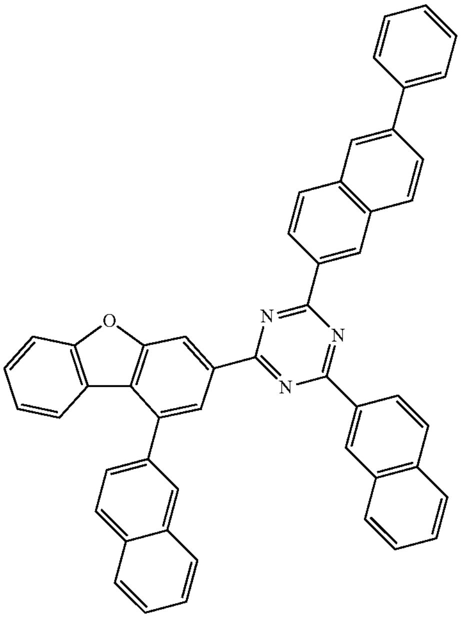
-continued
3-95
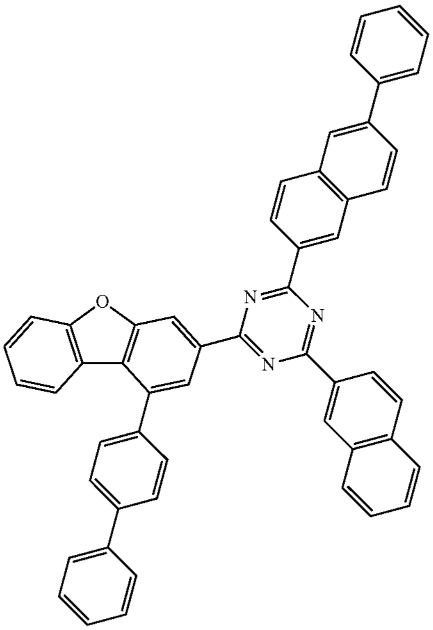
3-96
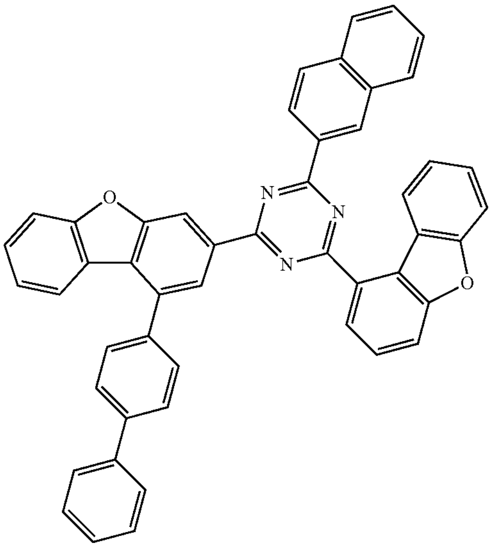

-continued
3-97
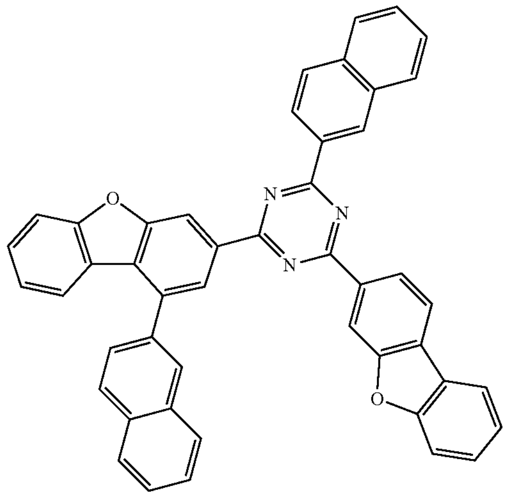
3-98
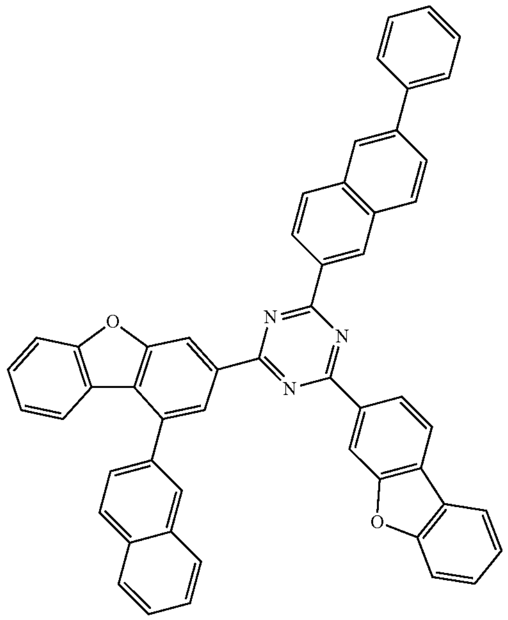
-continued
3-99
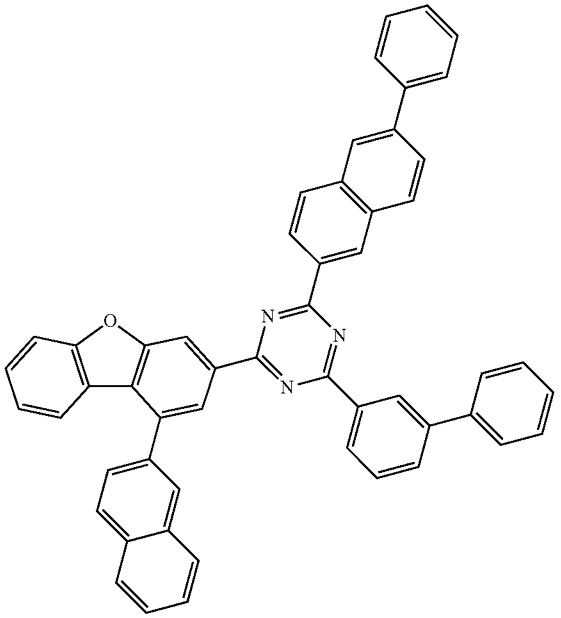
3-100
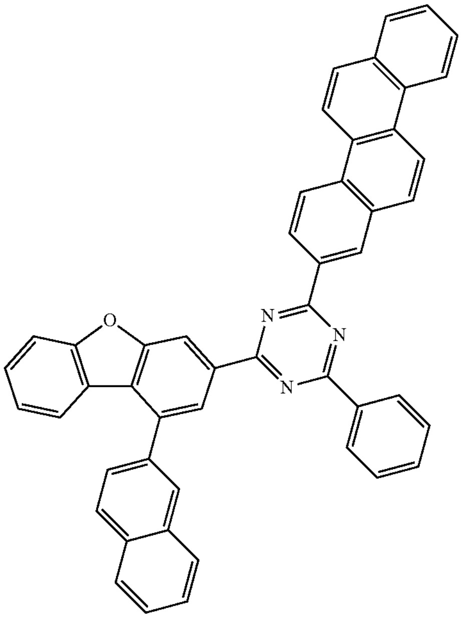

-continued
3-101
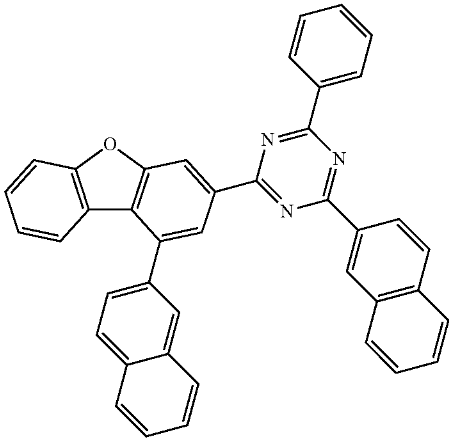
3-102
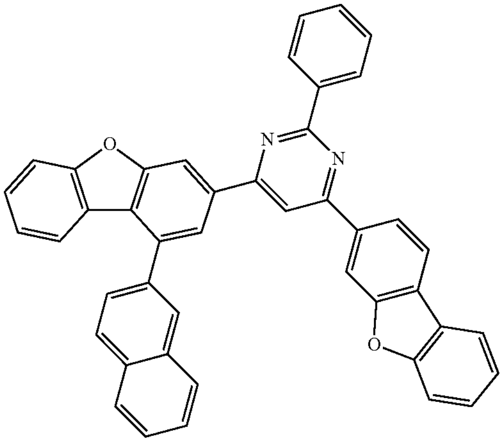
3-103
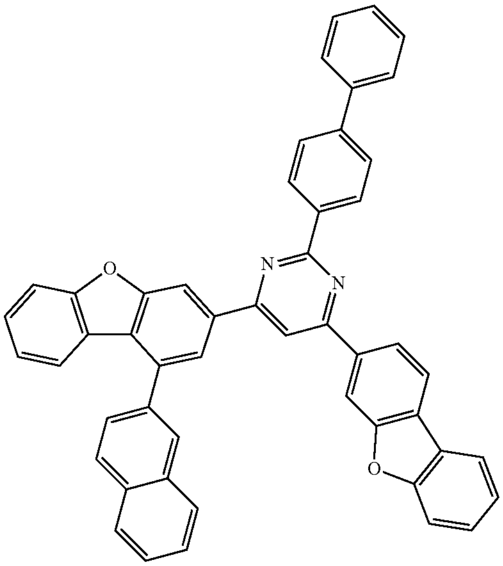
-continued
3-104
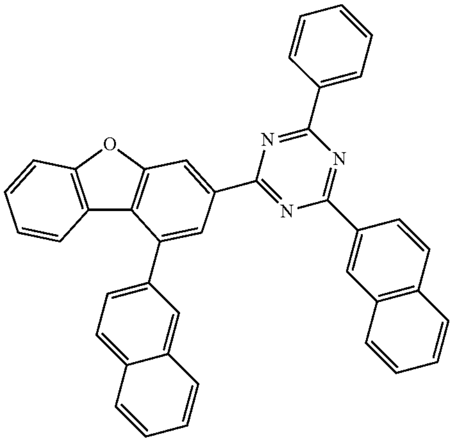
3-105
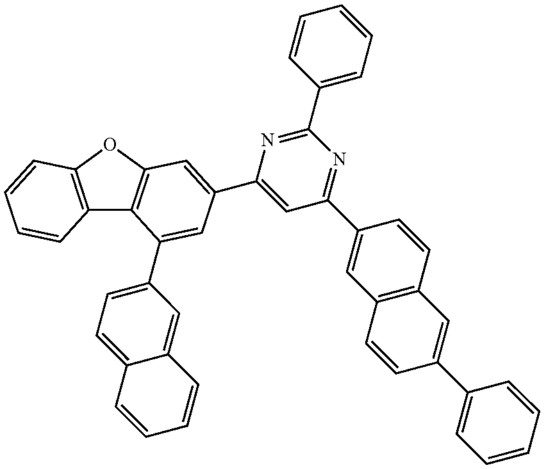
3-106
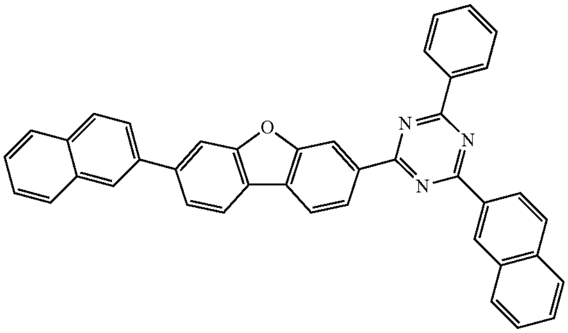
3-107
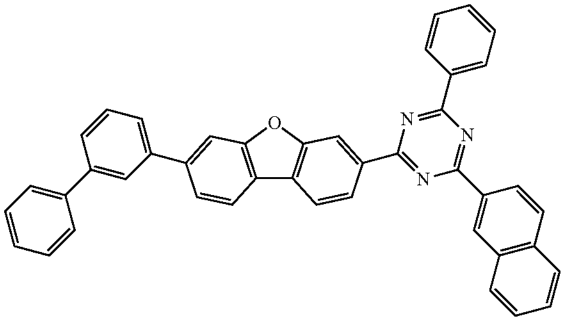

-continued
3-108
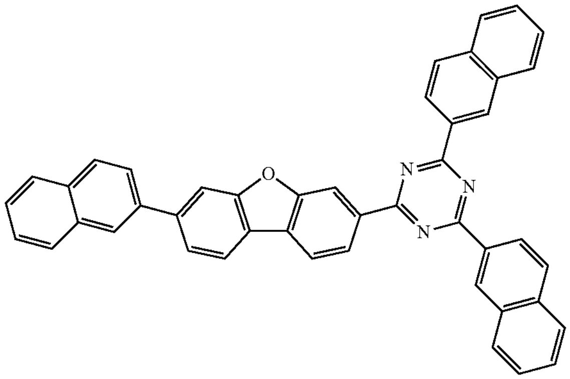
3-109
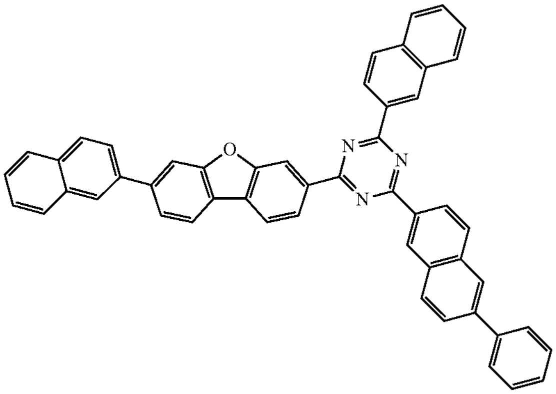
3-110
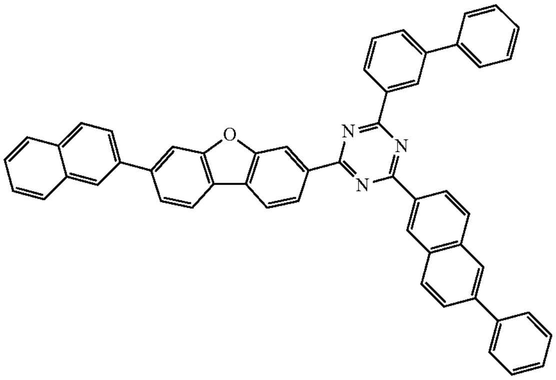
3-111
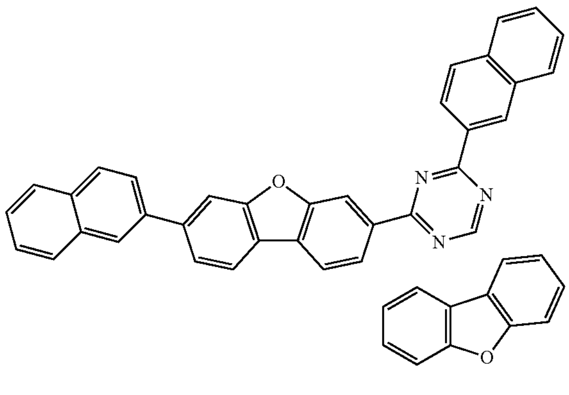
-continued
3-112
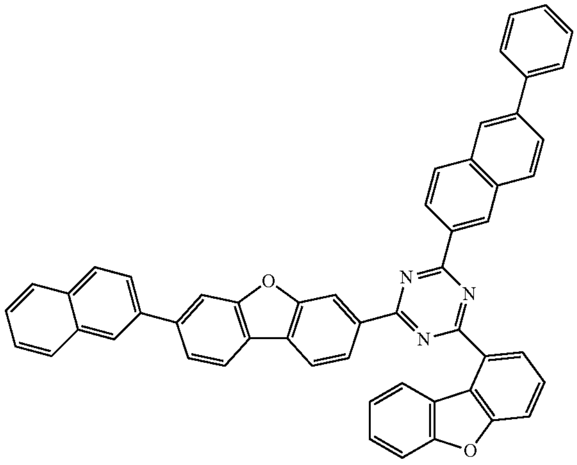
3-113
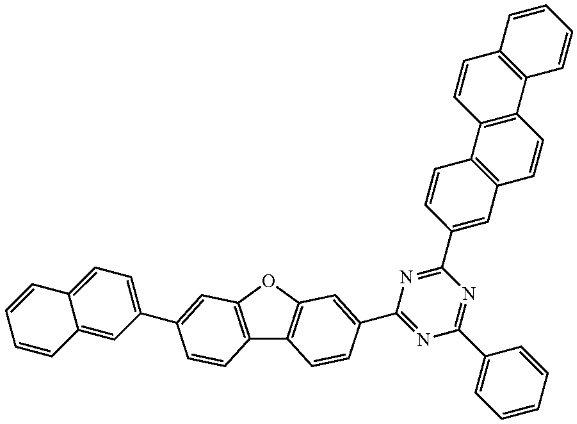
3-114
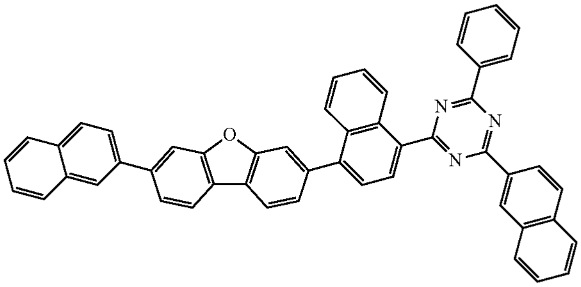
3-115
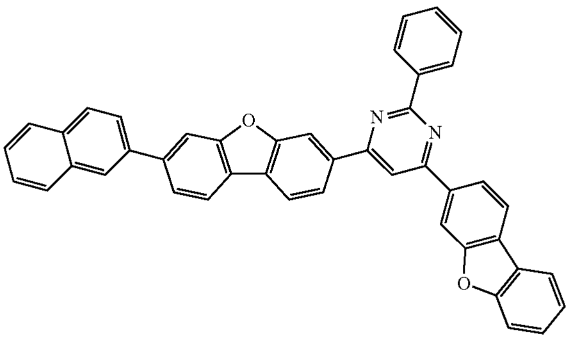

-continued
3-116
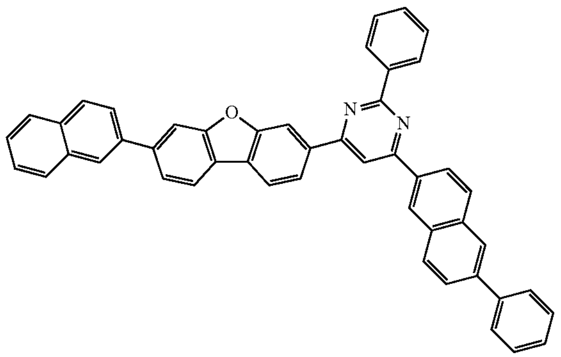
3-117
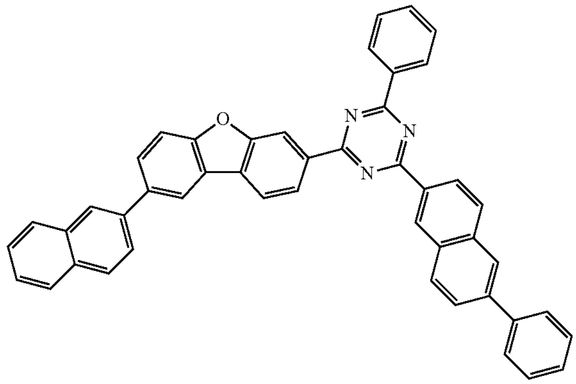
3-118
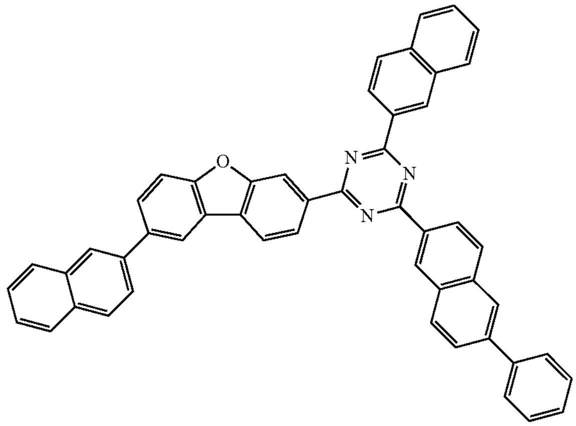
3-119
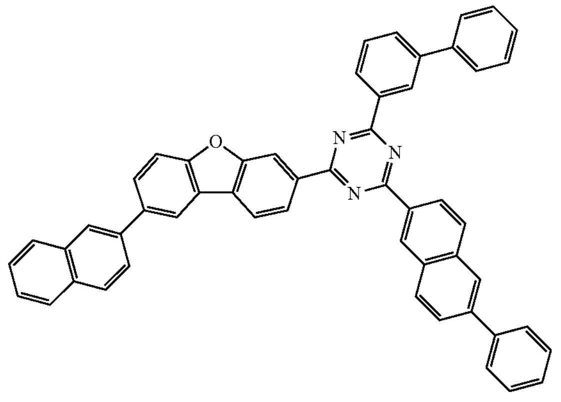
-continued
3-120
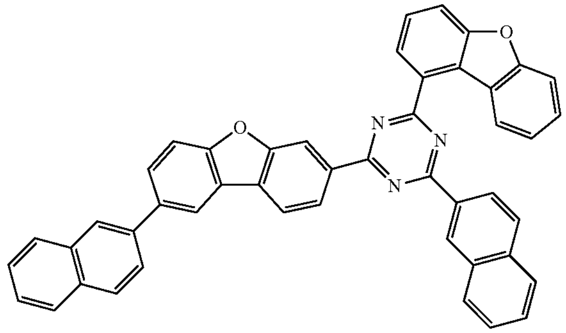
3-121
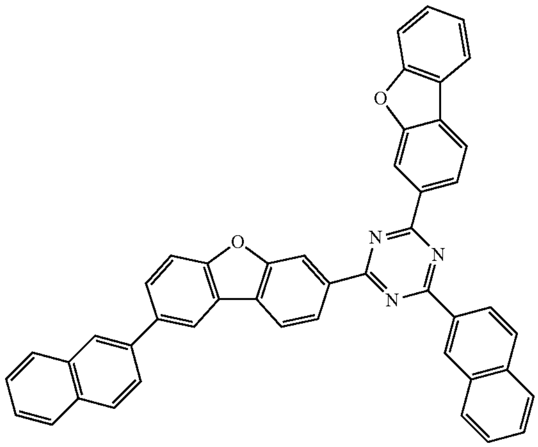
3-122
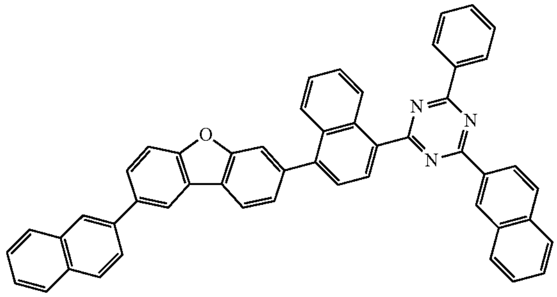
3-123
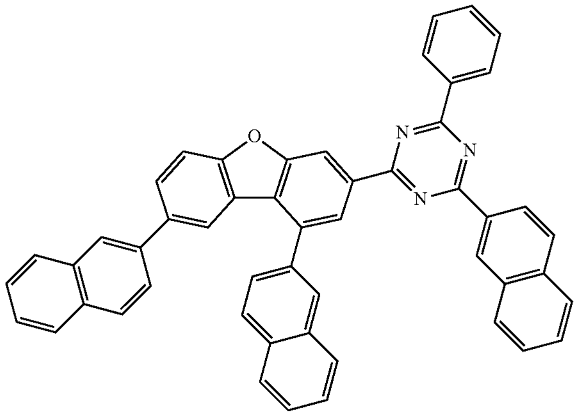

-continued
3-124
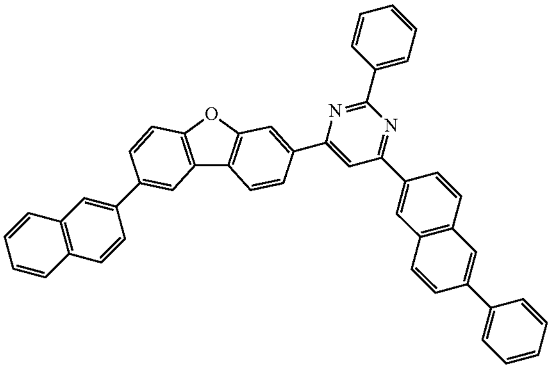
3-125
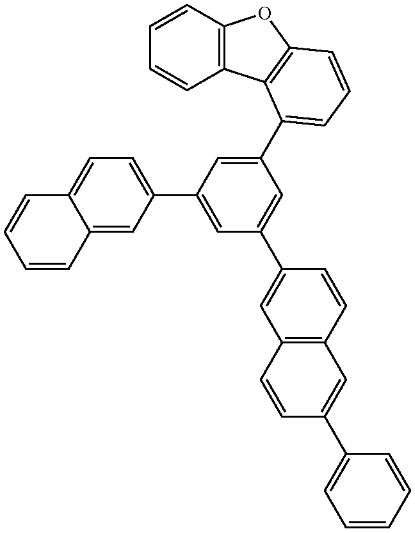
3-126
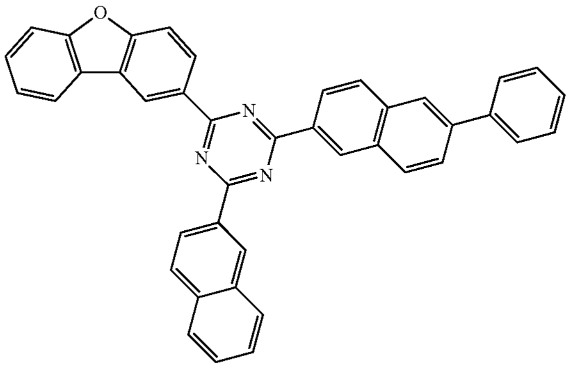
-continued
3-127
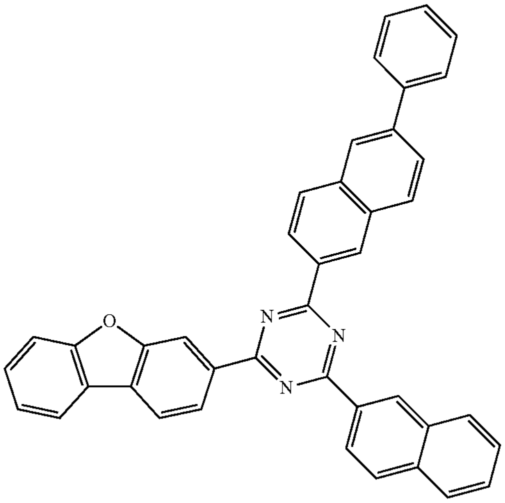
3-128
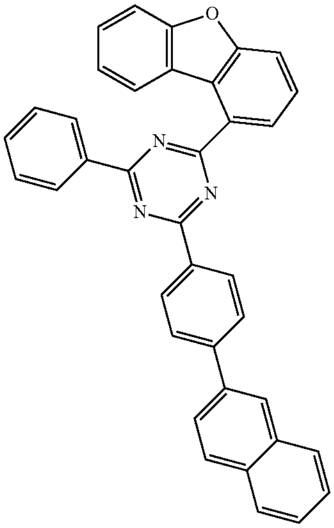
3-129
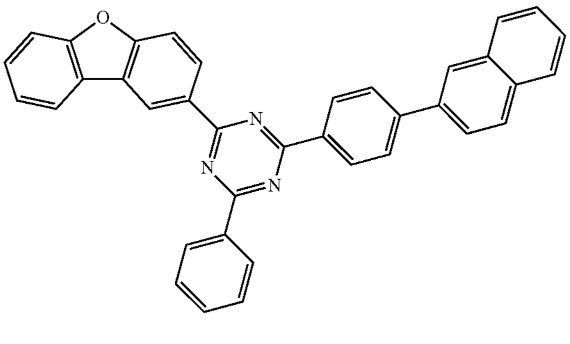

-continued
3-130
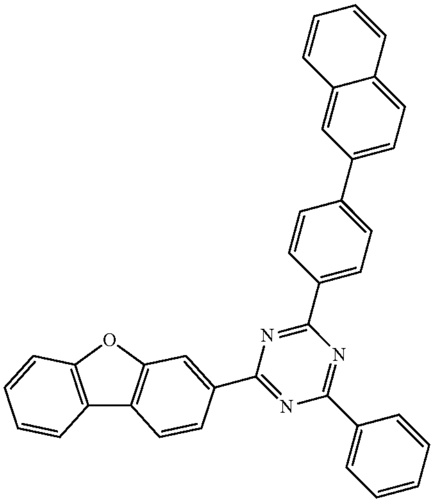
3-131
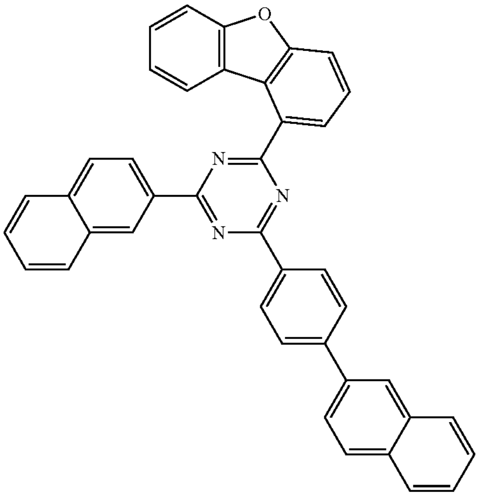
3-132
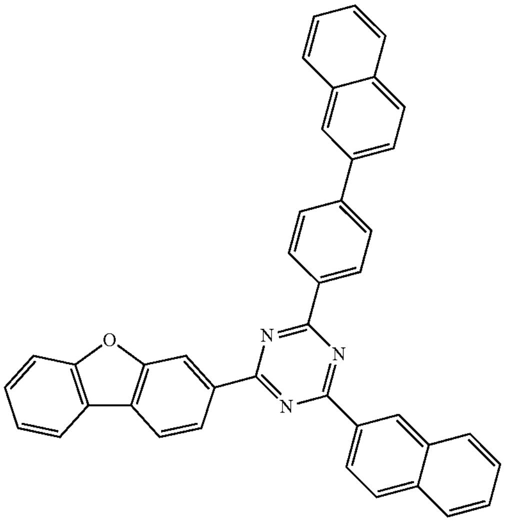
-continued
3-133
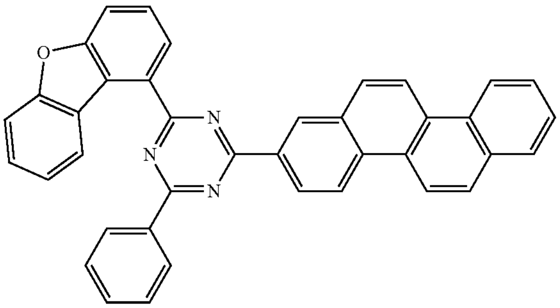
3-134
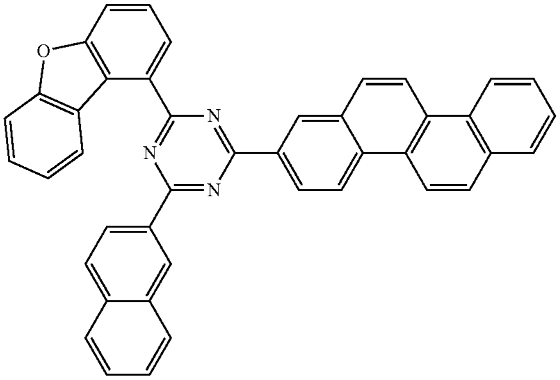
3-135
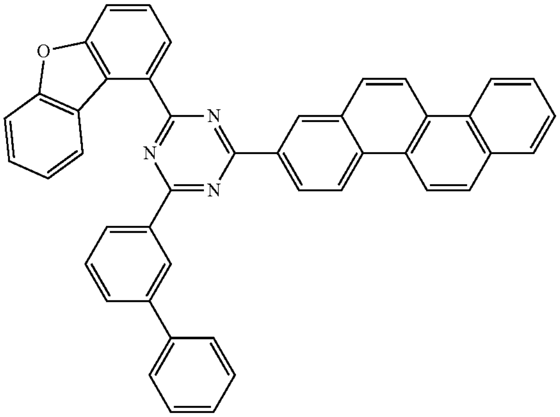
3-136
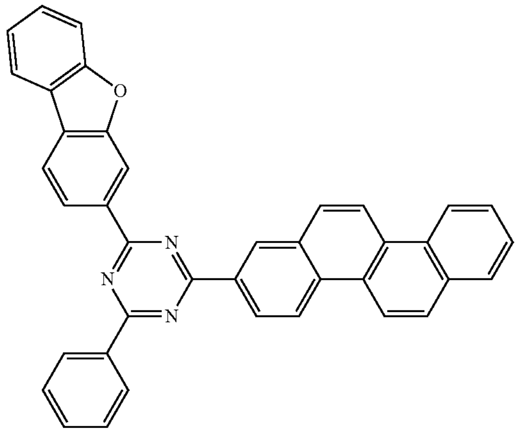

-continued
3-137
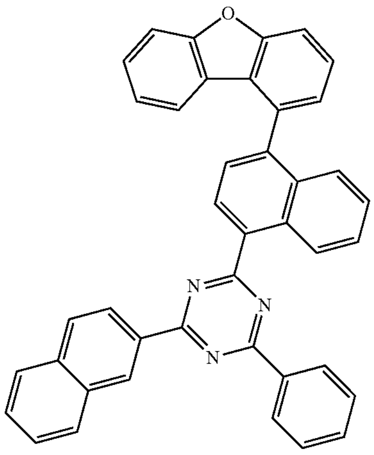
3-138
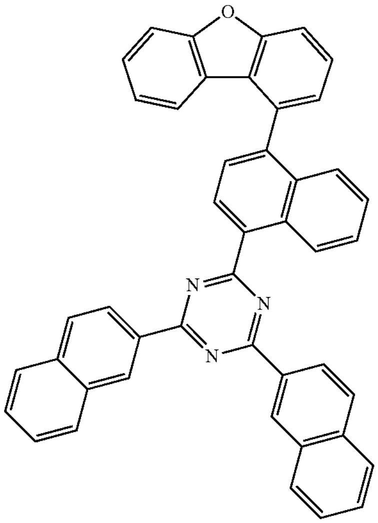
3-139
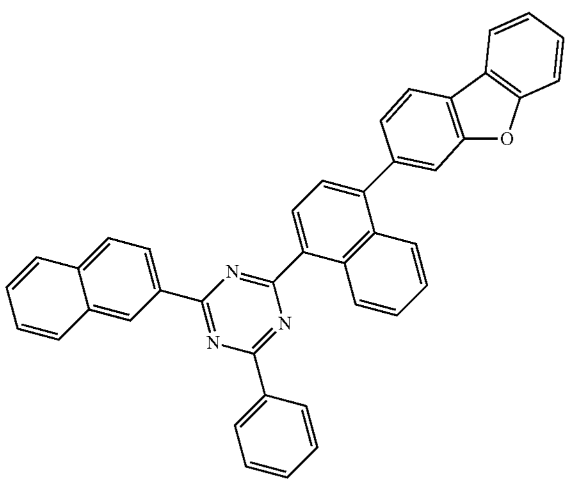
-continued
3-140
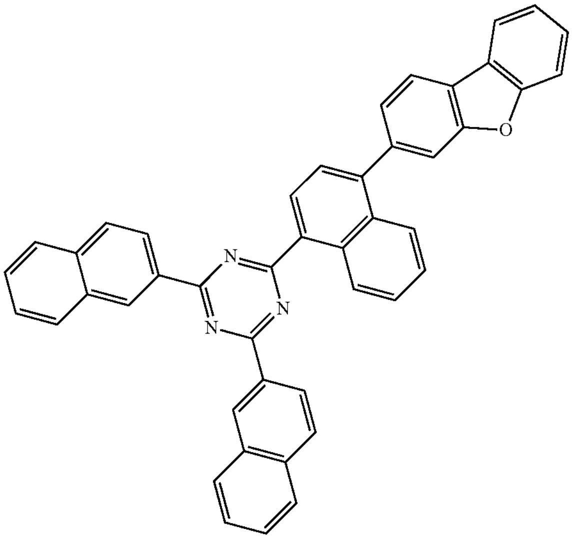
3-141
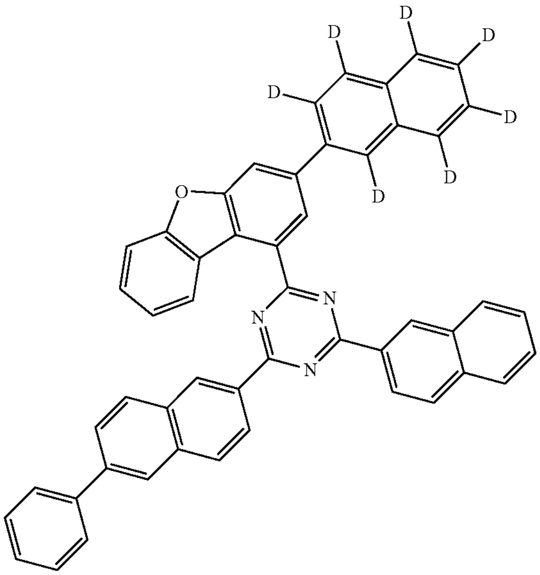

-continued
3.-142
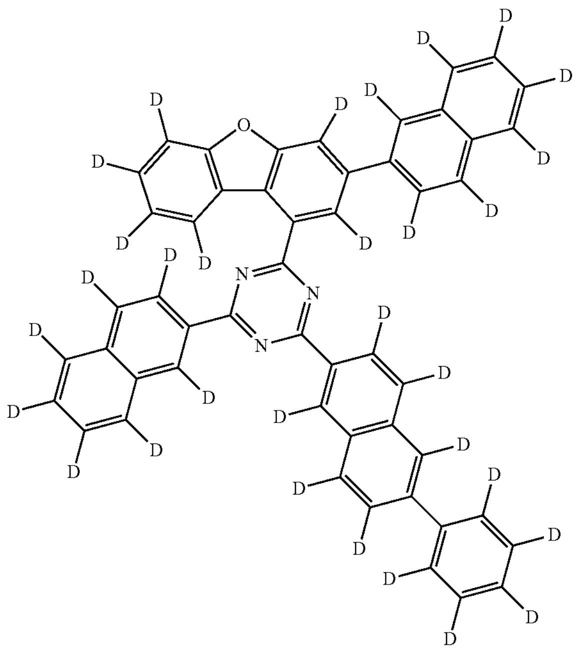
3-143
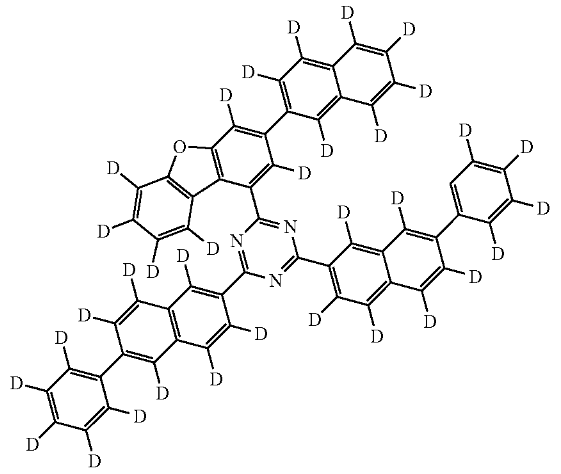
3-144
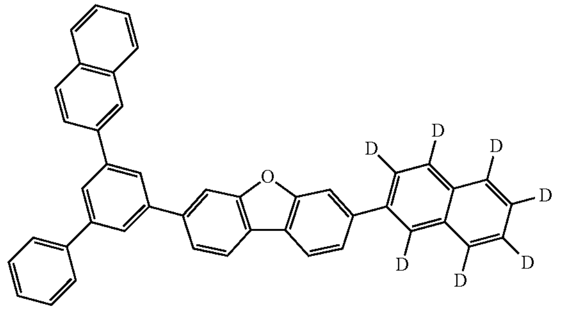
-continued
3-145
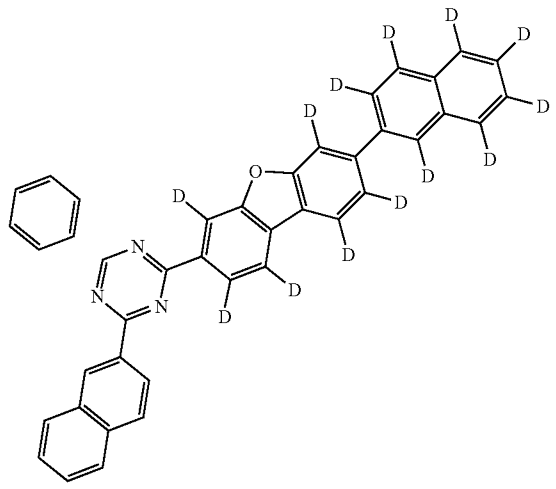
3-146
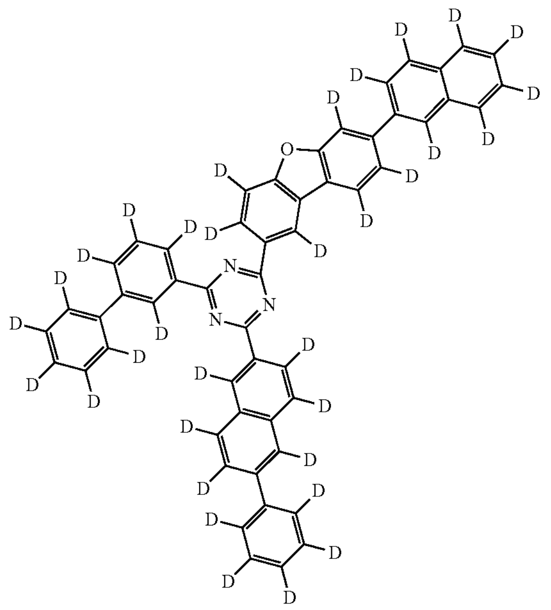

-continued 3-147

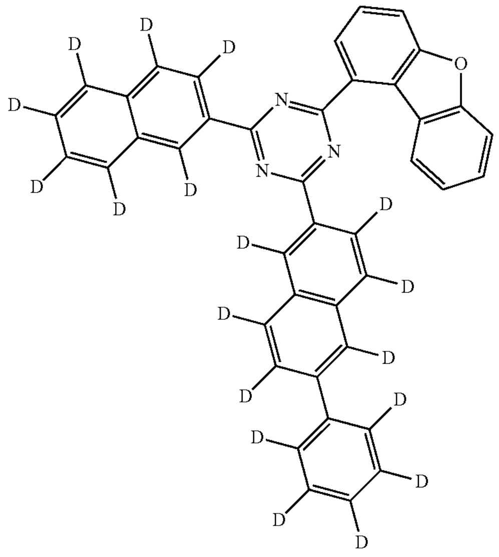

3-148

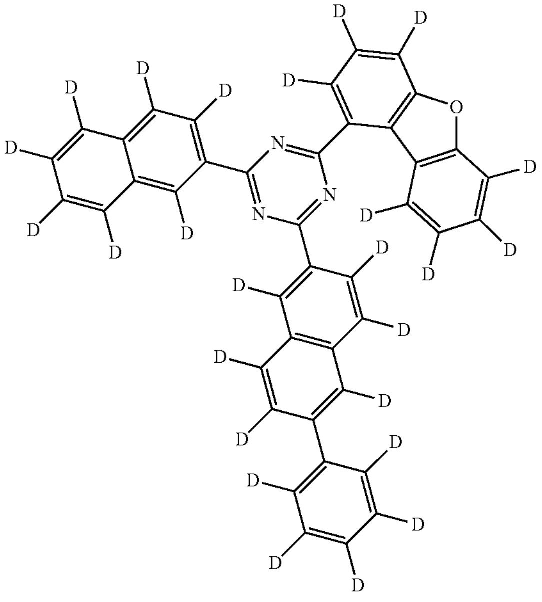

Another embodiment of the present application provides a composition for an organic material layer of an organic light emitting device, the composition including the heterocyclic compound represented by Chemical Formula 1; and the heterocyclic compound represented by Chemical Formula A or Chemical Formula B.

Specific descriptions on the heterocyclic compound represented by Chemical Formula 1, the heterocyclic compound represented by Chemical Formula A and the heterocyclic compound represented by Chemical Formula B are the same as the descriptions provided above.

In the composition, the heterocyclic compound represented by Chemical Formula 1: the heterocyclic compound represented by Chemical Formula A or Chemical Formula B may have a weight ratio of 1:10 to 10:1, 1:8 to 8:1, 1:5 to 5:1 or 1:2 to 2:1, however, the weight ratio is not limited thereto.

The composition may be used when forming an organic material of an organic light emitting device, and may be more preferably used when forming a host of a light emitting layer.

In one embodiment of the present application, the organic material layer includes the heterocyclic compound represented by Chemical Formula 1; and the heterocyclic compound represented by Chemical Formula A or Chemical Formula B, and a phosphorescent dopant may be used therewith.

In one embodiment of the present application, the organic material layer includes the heterocyclic compound represented by Chemical Formula 1; and the heterocyclic compound represented by Chemical Formula A or Chemical Formula B, and an iridium-based dopant may be used therewith.

As a material of the phosphorescent dopant, those known in the art may be used.

For example, phosphorescent dopant materials represented by LL'MX', LL'L"M, LMX'X", $L_2MX'$ and $L_3M$ may be used, however, the scope of the present disclosure is not limited to these examples.

Herein, L, L', L", X' and X" are a bidentate ligand different from each other, and M is a metal forming an octahedral complex.

M may be iridium, platinum, osmium or the like.

L is an anionic bidentate ligand coordinated to M as the iridium-based dopant by sp2 carbon and heteroatom, and X may function to trap electrons or holes. Nonlimiting examples of L may include 2-(1-naphthyl)benzoxazole, (2-phenylbenzoxazole), (2-phenylbenzothiazole), (2-phenylbenzothiazole), (7,8-benzoquinoline), (thiophene group pyrizine), phenylpyridine, benzothiophene group pyrizine, 3-methoxy-2-phenylpyridine, thiophene group pyrizine, tolylpyridine and the like. Nonlimiting examples of X' and X" may include acetylacetonate (acac), hexafluoroacetylacetonate, salicylidene, picolinate, 8-hydroxyquinolinate and the like.

More specific examples thereof are described below, however, the phosphorescent dopant is not limited to these examples.

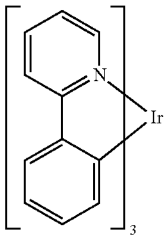
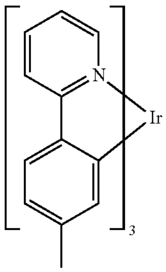
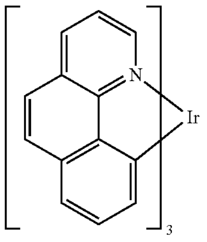

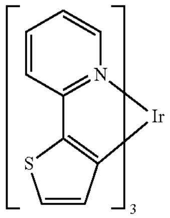
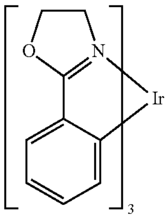
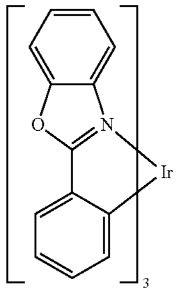

-continued

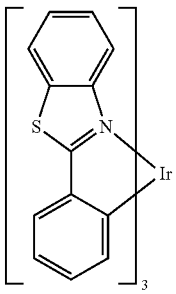

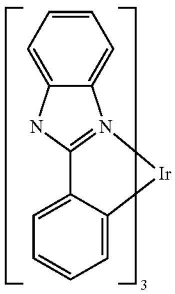

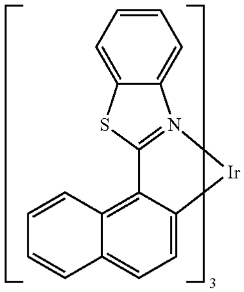

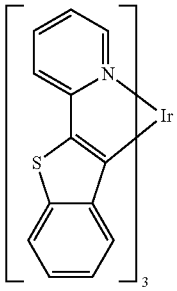

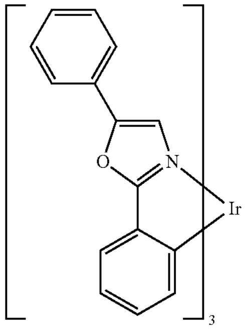

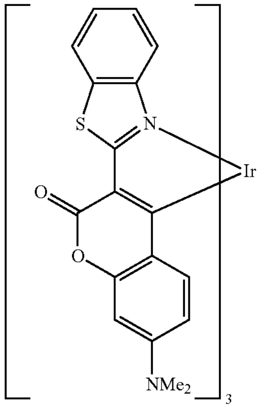

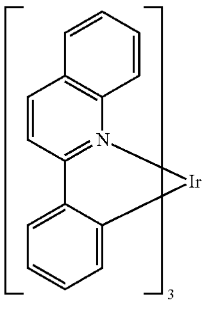

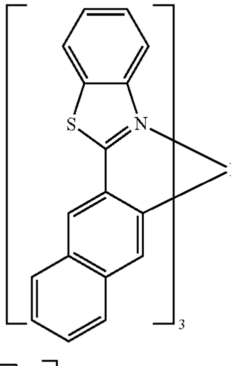

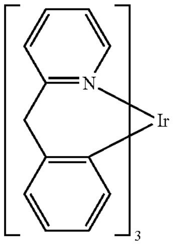

In one embodiment of the present application, as the iridium-based dopant, $Ir(ppy)_3$ may be used as a green phosphorescent dopant.

In one embodiment of the present application, a content of the dopant may be from 1% to 15%, preferably from 3% to 10% and more preferably from 5% to 10% based on the whole light emitting layer.

The content may mean a weight ratio.

In the organic light emitting device of the present disclosure, the organic material layer includes an electron injection layer or an electron transfer layer, and the electron injection layer or the electron transfer layer may include the heterocyclic compound.

In another organic light emitting device, the organic material layer includes an electron blocking layer or a hole blocking layer, and the electron blocking layer or the hole blocking layer may include the heterocyclic compound.

In another organic light emitting device, the organic material layer includes an electron transfer layer, a light emitting layer or a hole blocking layer, and the electron transfer layer, the light emitting layer or the hole blocking layer may include the heterocyclic compound.

The organic light emitting device of the present disclosure may further include one, two or more layers selected from the group consisting of a light emitting layer, a hole injection layer, a hole transfer layer, an electron injection layer, an electron transfer layer, an electron blocking layer and a hole blocking layer.

FIG. 1 to FIG. 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 includes a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further added.

One embodiment of the present application provides a method for manufacturing an organic light emitting device, the method including preparing a substrate; forming a first electrode on the substrate; forming one or more organic material layers on the first electrode; and forming a second electrode on the organic material layer, wherein the forming of organic material layers includes forming one or more organic material layers using the composition for an organic material layer according to one embodiment of the present application.

In the method for manufacturing an organic light emitting device provided in one embodiment of the present application, the forming of organic material layers is forming the heterocyclic compound of Chemical Formula 1; and the heterocyclic compound of Chemical Formula A or Chemical Formula B using a thermal vacuum deposition method after pre-mixing.

The pre-mixing means first mixing the heterocyclic compound of Chemical Formula 1 and the heterocyclic compound of Chemical Formula A or Chemical Formula B in one source of supply before depositing on the organic material layer.

The pre-mixed material may be referred to as the composition for an organic material layer according to one embodiment of the present application.

The organic material layer including Chemical Formula 1 may further include other materials as necessary.

The organic material layer including Chemical Formula 1; and Chemical Formula A or Chemical Formula B at the same time may further include other materials as necessary.

In the organic light emitting device according to one embodiment of the present application, materials other than the compounds of Chemical Formula 1, Chemical Formula A and Chemical Formula B are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being pre-mixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device including an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

[Preparation Example 1] Preparation of Compound 1-1

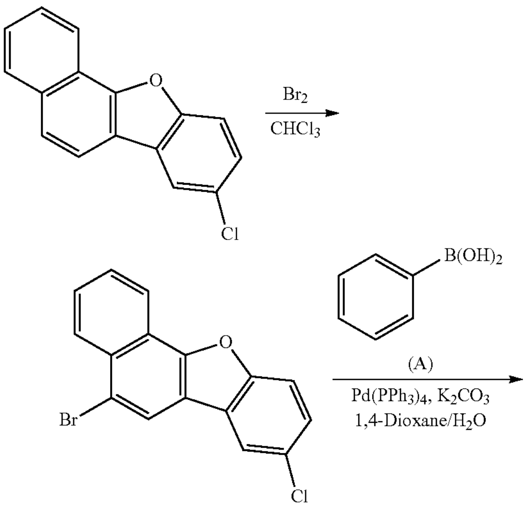

1-2-1

-continued

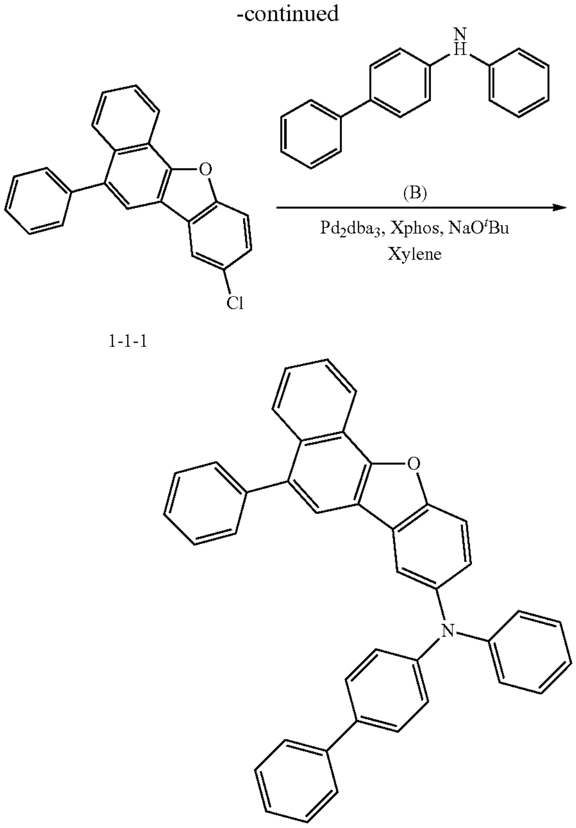

1-1-1

1-1

1-1. Synthesis Method of Compound 1-2-1

8-Chloronaphtho[1,2-b]benzofuran (60.0 g, 237.5 mM) and bromine (38.0 g, 237.5 mM) were dissolved in chloroform (600 mL), and stirred for 1 hour. After the reaction was completed, methanol (300 ml) was introduced thereto to terminate the reaction. Target Compound 1-2-1 (69.4 g, 88.1%) was obtained.

1-2. Synthesis Method of Compound 1-1-1

1-2-1 (50 g, 150.8 mM), phenylboronic acid (23.9 g, 196.0 mM), $Pd(PPh_3)_4$ (8.7 g, 7.5 mM) and $K_2CO_3$ (62.5 g, 452.4 mM) were dissolved in 1,4-dioxane/$H_2O$ (600 ml/120 ml), and refluxed for 3 hours. After r the reaction was terminated, the result was extracted with dichloromethane/$H_2O$ at room temperature. The reaction material was purified by column chromatography (DCM:Hex=1:5), and recrystallized with methanol to obtain target Compound 1-1-1 (45.1 g, 91.0%).

1-3. Synthesis Method of Compound 1-1

1-1-1 (10.0 g, 30.4 mM), N-phenyl-[1,1'-biphenyl]-4-amine (7.5 g, 30.4 mM), $Pd_2dba_3$ (1.4 g, 1.5 mM), xphos (1.4 g, 3.0 mM) and NaOtBu (8.8 g, 91.2 mM) were dissolved in xylene (150 ml), and refluxed for 1 hour. After the reaction was completed, the result was celite filtered at t room temperature, and then concentrated. The reaction material was purified by column chromatography (DCM: Hex=1:1), and recrystallized with methanol to obtain target Compound 1-1 (14.9 g, 91.1%).

Target compounds were synthesized in the same manner as in Preparation Example 1 except that Intermediate A and Intermediate B of the following Table 1 were used.

TABLE 1

| Compound No. | Intermediate A | Intermediate B | Target Compound | Yield |
|---|---|---|---|---|
| 1-1 | 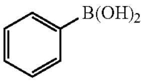 | 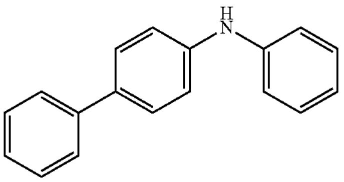 [SMILES: c1ccc(Nc2ccc(-c3ccccc3)cc2)cc1] | 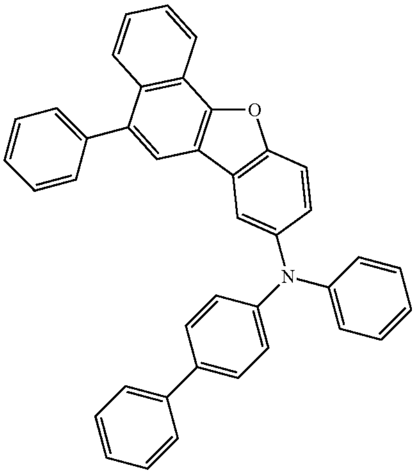 [SMILES: c1ccc(-c2ccc(N(c3ccccc3)c3ccc4oc5c6ccccc6c(-c6ccccc6)cc5c4c3)cc2)cc1] | 91.1% |

TABLE 1-continued
| Compound No. | Intermediate A | Intermediate B | Target Compound | Yield |
|---|---|---|---|---|
| 1-4 | | 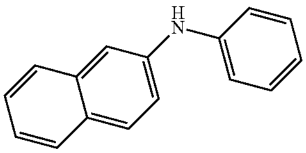 [SMILES: c1ccc(Nc2ccc3ccccc3c2)cc1] | 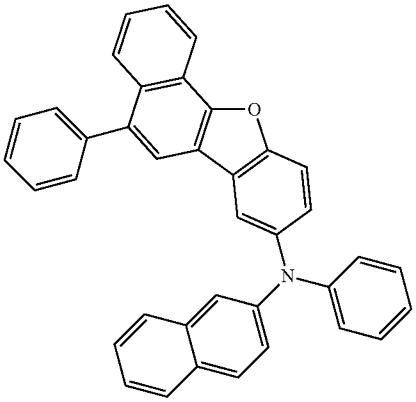 [SMILES: c1ccc(-c2cc3c4cc(N(c5ccccc5)c5ccc6ccccc6c5)ccc4oc3c3ccccc23)cc1] | 91.8% |
| 1-10 | | 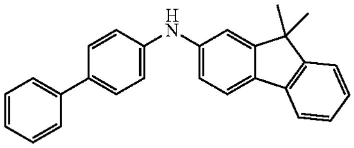 [SMILES: CC1(C)c2ccccc2-c2ccc(Nc3ccc(-c4ccccc4)cc3)cc21] | 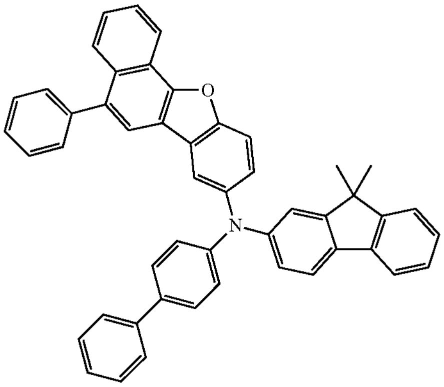 [SMILES: CC1(C)c2ccccc2-c2ccc(N(c3ccc(-c4ccccc4)cc3)c3ccc4oc5c6ccccc6c(-c6ccccc6)cc5c4c3)cc21] | 90.5% |
| 1-22 | | 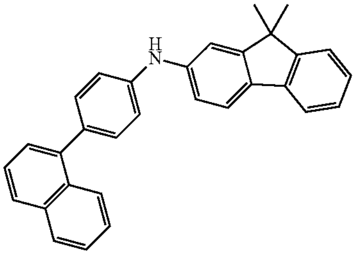 [SMILES: CC1(C)c2ccccc2-c2ccc(Nc3ccc(-c4cccc5ccccc45)cc3)cc21] | 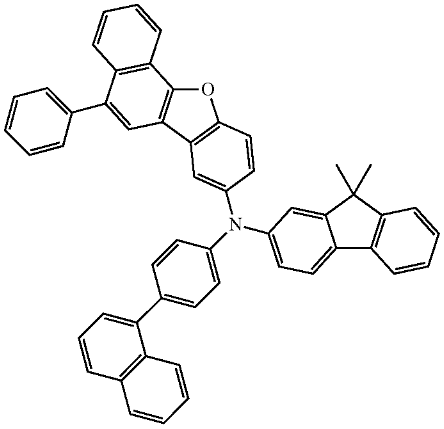 [SMILES: CC1(C)c2ccccc2-c2ccc(N(c3ccc(-c4cccc5ccccc45)cc3)c3ccc4oc5c6ccccc6c(-c6ccccc6)cc5c4c3)cc21] | 85.5% |

TABLE 1-continued
| Compound No. | Intermediate A | Intermediate B | Target Compound | Yield |
| --- | --- | --- | --- | --- |
| 1-24 | | 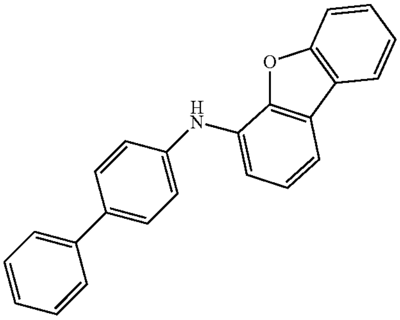 [SMILES: c1ccc(-c2ccc(Nc3cccc4c3oc3ccccc34)cc2)cc1] | 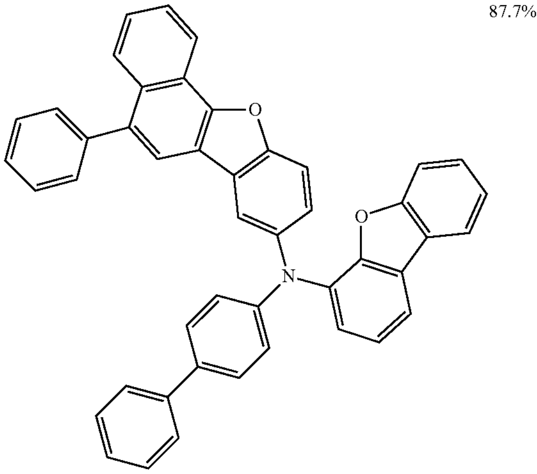 | 87.7% |
| 1-175 | | 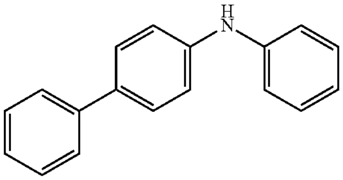 [SMILES: c1ccc(Nc2ccc(-c3ccccc3)cc2)cc1] | 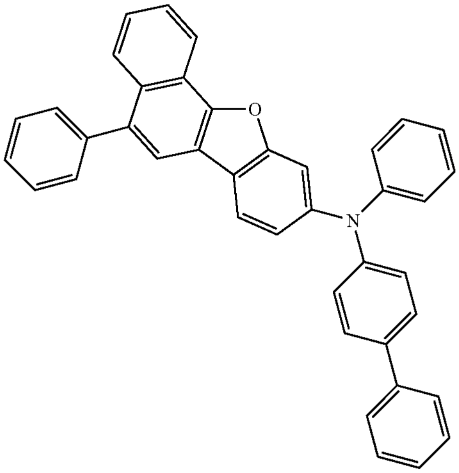 [SMILES: c1ccc(-c2ccc(N(c3ccccc3)c3ccc4c(c3)oc3c5ccccc5c(-c5ccccc5)cc43)cc2)cc1] | 85.5% |
| 1-460 | | 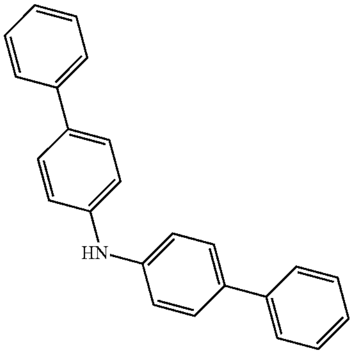 [SMILES: c1ccc(-c2ccc(Nc3ccc(-c4ccccc4)cc3)cc2)cc1] | 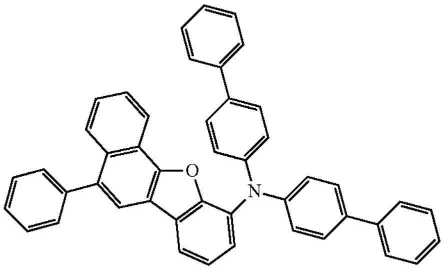 [SMILES: c1ccc(-c2ccc(N(c3ccc(-c4ccccc4)cc3)c3cccc4c3oc3c5ccccc5c(-c5ccccc5)cc43)cc2)cc1] | 80.1% |

[Preparation Example 2] Preparation of Compound 1-49

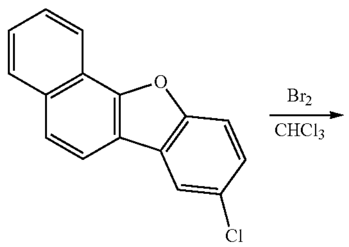

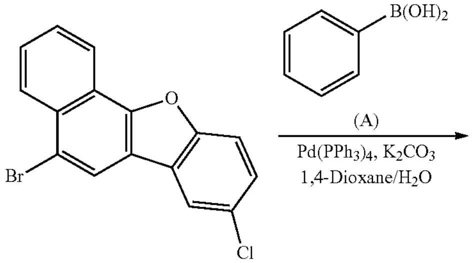

1-2-1

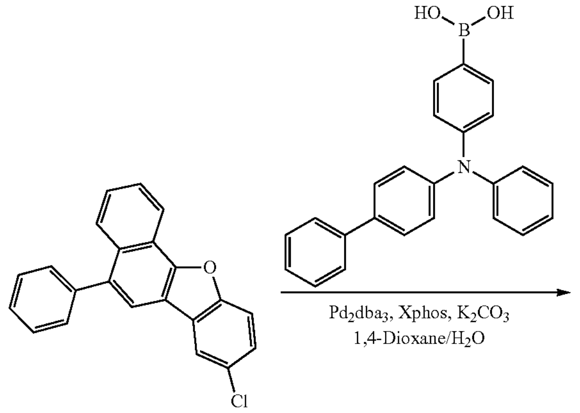

1-1-1

-continued

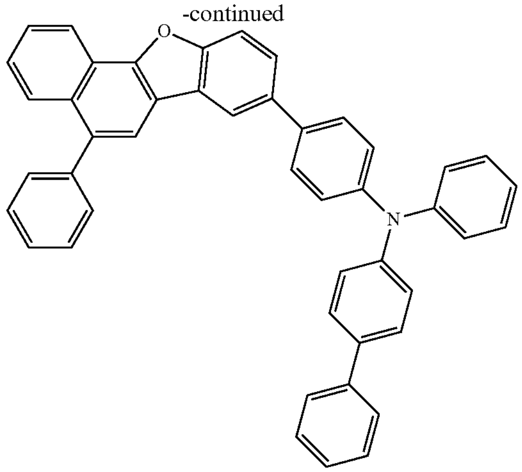

1-49

1-1-1 (10.0 g, 30.4 mM) in Preparation Example 1, (4-([1,1'-biphenyl]-4-yl(phenyl)amino)phenyl)boronic acid (11.1 g, 30.4 mM), $Pd_2dba_3$ (1.4 g, 1.5 mM), xphos (1.4 g, 3.0 mM) and $K_2CO_3$ (12.6 g, 91.2 mM) were dissolved in 1,4-dioxane/$H_2O$ (120 ml/24 ml), and refluxed for 1 hour. After the reaction was terminated, the result was extracted with dichloromethane/$H_2O$ at room temperature. The reaction material was purified by column chromatography (DCM:Hex=1:1), and recrystallized with methanol to obtain target Compound 1-49 (15.5 g, 83.2%).

Target compounds were synthesized in the same manner as in Preparation Example 2 except that Intermediate A and Intermediate B of the following Table 2 were used.

TABLE 2
| Compound No. | Intermediate A | Intermediate B | Target Compound | Yield |
|---|---|---|---|---|
| 1-49 | 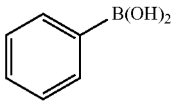 | 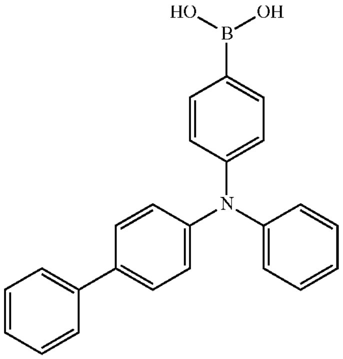 [SMILES: OB(O)c1ccc(N(c2ccccc2)c2ccc(-c3ccccc3)cc2)cc1] | 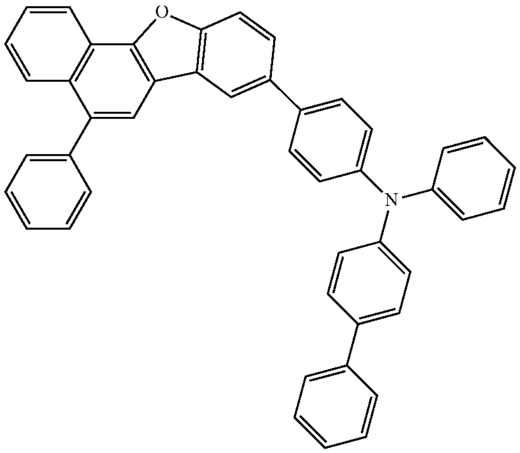 [SMILES: c1ccc(-c2ccc(N(c3ccccc3)c3ccc(-c4ccc5oc6c7ccccc7c(-c7ccccc7)cc6c5c4)cc3)cc2)cc1] | 83.2% |
| 1-52 | | 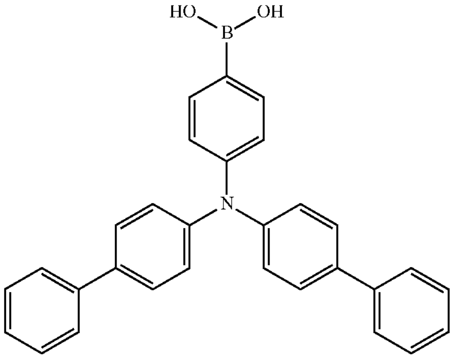 [SMILES: OB(O)c1ccc(N(c2ccc(-c3ccccc3)cc2)c2ccc(-c3ccccc3)cc2)cc1] | 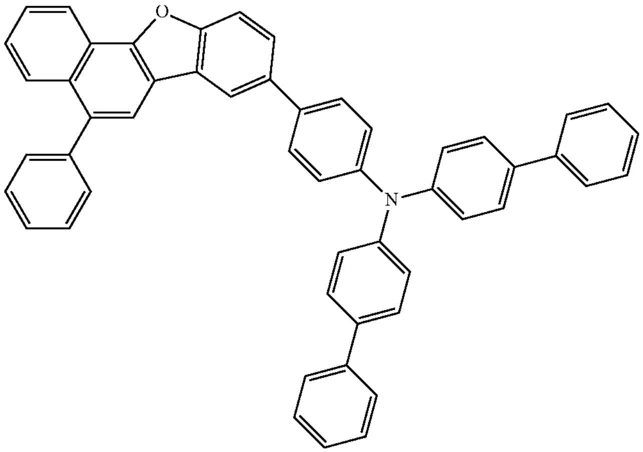 [SMILES: c1ccc(-c2ccc(N(c3ccc(-c4ccccc4)cc3)c3ccc(-c4ccc5oc6c7ccccc7c(-c7ccccc7)cc6c5c4)cc3)cc2)cc1] | 85.5% |

TABLE 2-continued
| Compound No. | Intermediate A | Intermediate B | Target Compound | Yield |
| --- | --- | --- | --- | --- |
| 1-55 | | 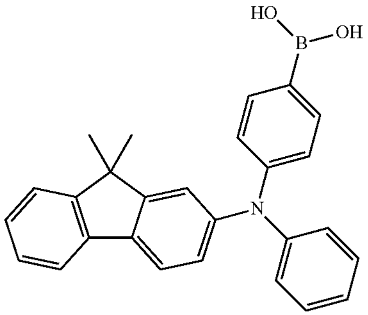 [SMILES: CC1(C)c2ccccc2-c2ccc(N(c3ccccc3)c3ccc(B(O)O)cc3)cc21] | 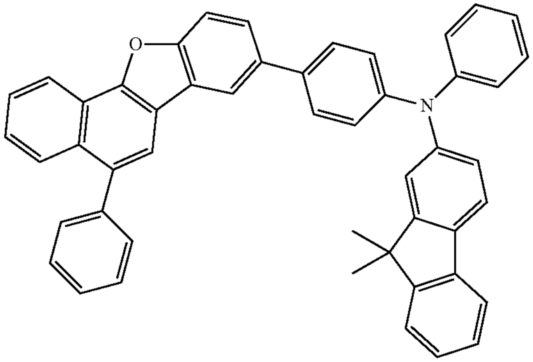 [SMILES: CC1(C)c2ccccc2-c2ccc(N(c3ccccc3)c3ccc(-c4ccc5oc6c7ccccc7c(-c7ccccc7)cc6c5c4)cc3)cc21] | 80.1% |
| 1-56 | | 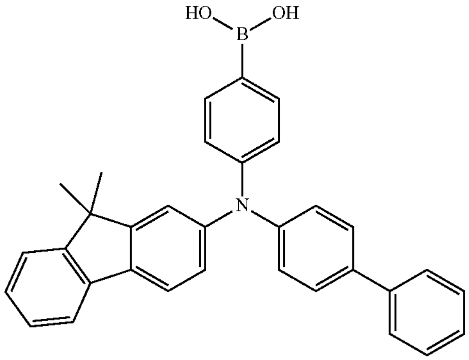 [SMILES: CC1(C)c2ccccc2-c2ccc(N(c3ccc(B(O)O)cc3)c3ccc(-c4ccccc4)cc3)cc21] | 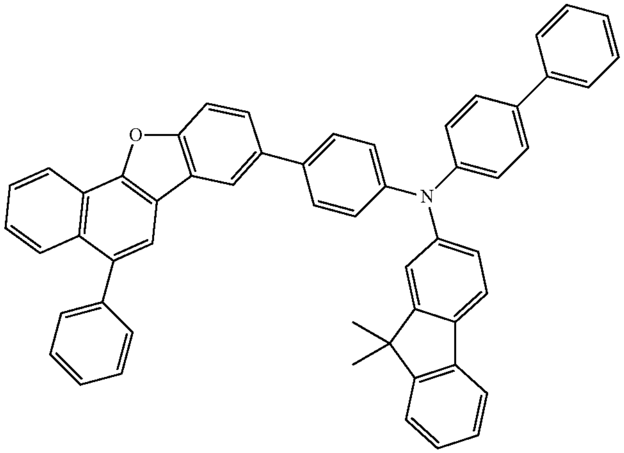 [SMILES: CC1(C)c2ccccc2-c2ccc(N(c3ccc(-c4ccccc4)cc3)c3ccc(-c4ccc5oc6c7ccccc7c(-c7ccccc7)cc6c5c4)cc3)cc21] | 80.3% |

TABLE 2-continued
| Compound No. | Intermediate A | Intermediate B | Target Compound | Yield |
|---|---|---|---|---|
| 1-60 | | 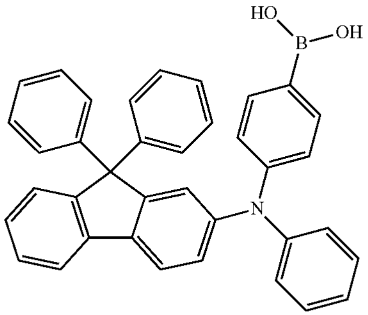 [SMILES: OB(O)c1ccc(N(c2ccccc2)c2ccc3c(c2)C(c2ccccc2)(c2ccccc2)c2ccccc2-3)cc1] | 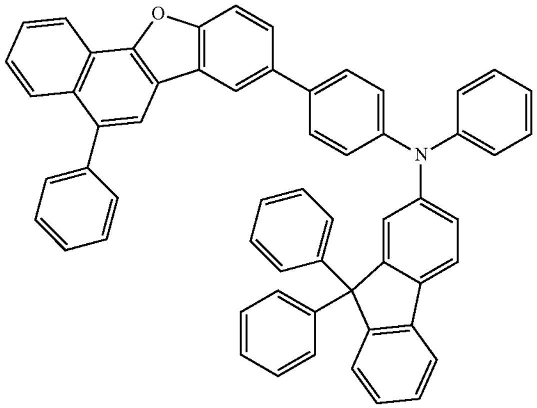 [SMILES: c1ccc(-c2cc3c4cc(-c5ccc(N(c6ccccc6)c6ccc7c(c6)C(c6ccccc6)(c6ccccc6)c6ccccc6-7)cc5)ccc4oc3c3ccccc23)cc1] | 80.0% |
| 1-66 | | 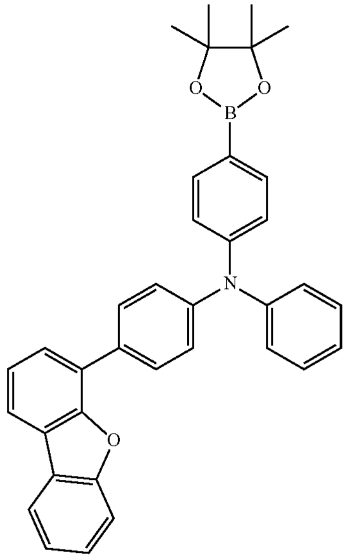 [SMILES: CC1(C)OB(c2ccc(N(c3ccccc3)c3ccc(-c4cccc5c4oc4ccccc45)cc3)cc2)OC1(C)C] | 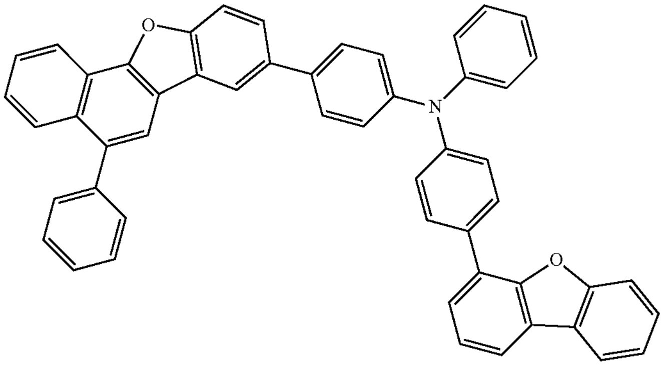 [SMILES: c1ccc(-c2cc3c4cc(-c5ccc(N(c6ccccc6)c6ccc(-c7cccc8c7oc7ccccc78)cc6)cc5)ccc4oc3c3ccccc23)cc1] | 78.3% |

TABLE 2-continued
| Compound No. | Intermediate A | Intermediate B | Target Compound | Yield |
|---|---|---|---|---|
| 1-274 | | 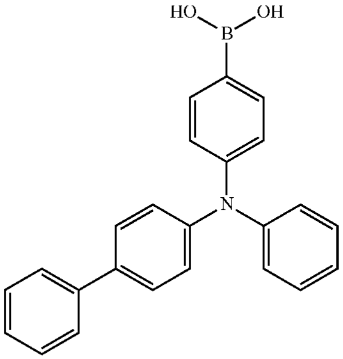 [SMILES: OB(O)c1ccc(N(c2ccccc2)c2ccc(-c3ccccc3)cc2)cc1] | 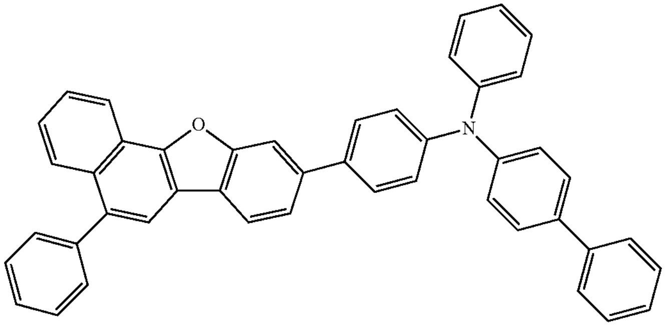 [SMILES: c1ccc(-c2ccc(N(c3ccccc3)c3ccc(-c4ccc5c(c4)oc4c6ccccc6c(-c6ccccc6)cc54)cc3)cc2)cc1] | 75.8% |
| 1-275 | 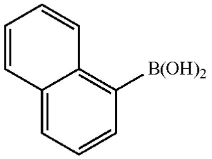 [SMILES: OB(O)c1cccc2ccccc12] | | 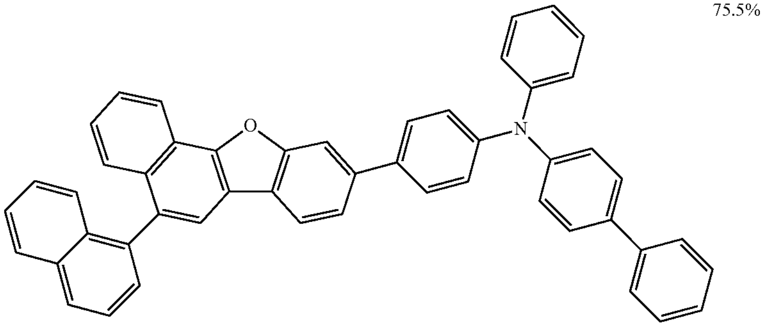 | 75.5% |

TABLE 2-continued
| Compound No. | Intermediate A | Intermediate B | Target Compound | Yield |
| --- | --- | --- | --- | --- |
| 1-280 | 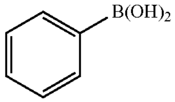 | 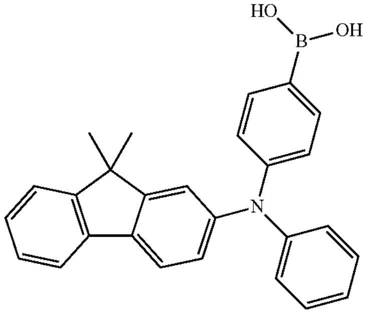 [SMILES: CC1(C)c2ccccc2-c2ccc(N(c3ccccc3)c3ccc(B(O)O)cc3)cc21] | 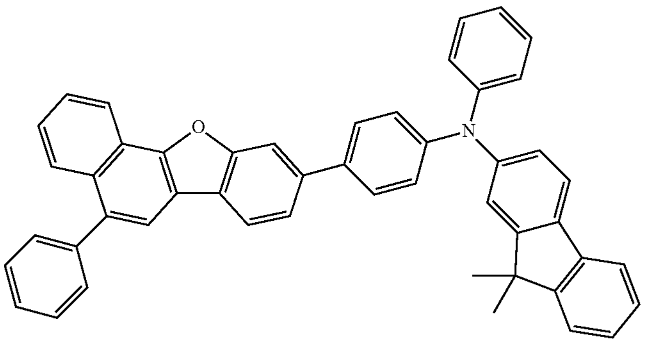 [SMILES: CC1(C)c2ccccc2-c2ccc(N(c3ccccc3)c3ccc(-c4ccc5c(c4)oc4c6ccccc6c(-c6ccccc6)cc54)cc3)cc21] | 71.5% |
| 1-290 | | 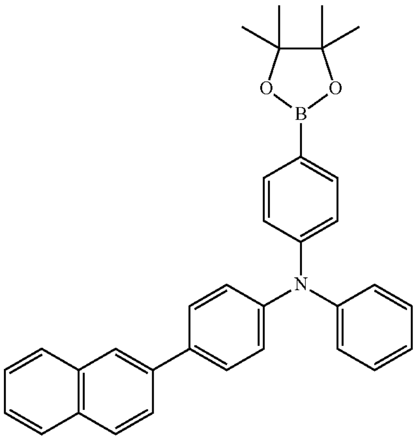 [SMILES: CC1(C)OB(c2ccc(N(c3ccccc3)c3ccc(-c4ccc5ccccc5c4)cc3)cc2)OC1(C)C] | 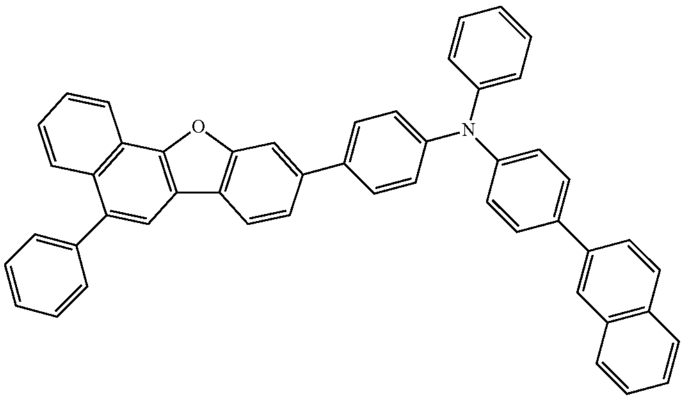 [SMILES: c1ccc(-c2cc3c4ccc(-c5ccc(N(c6ccccc6)c6ccc(-c7ccc8ccccc8c7)cc6)cc5)cc4oc3c3ccccc23)cc1] | 71.9% |

TABLE 2-continued
| Compound No. | Intermediate A | Intermediate B | Target Compound | Yield |
|---|---|---|---|---|
| 1-300 | | 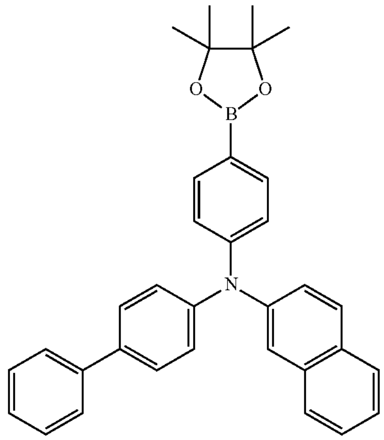 [SMILES: CC1(C)OB(c2ccc(N(c3ccc(-c4ccccc4)cc3)c3ccc4ccccc4c3)cc2)OC1(C)C] | 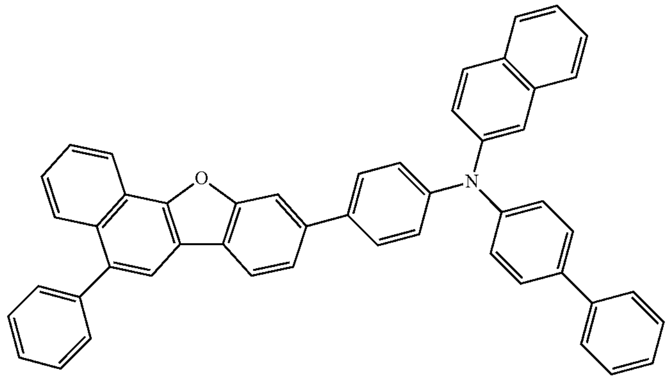 [SMILES: c1ccc(-c2ccc(N(c3ccc(-c4ccc5c(c4)oc4c6ccccc6c(-c6ccccc6)cc54)cc3)c3ccc4ccccc4c3)cc2)cc1] | 70.8% |
| 1-532 | | 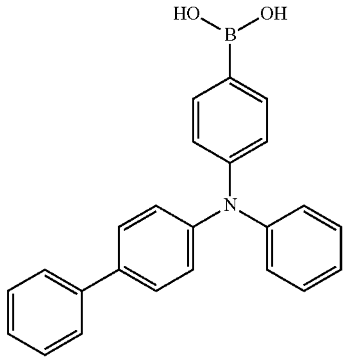 [SMILES: OB(O)c1ccc(N(c2ccccc2)c2ccc(-c3ccccc3)cc2)cc1] | 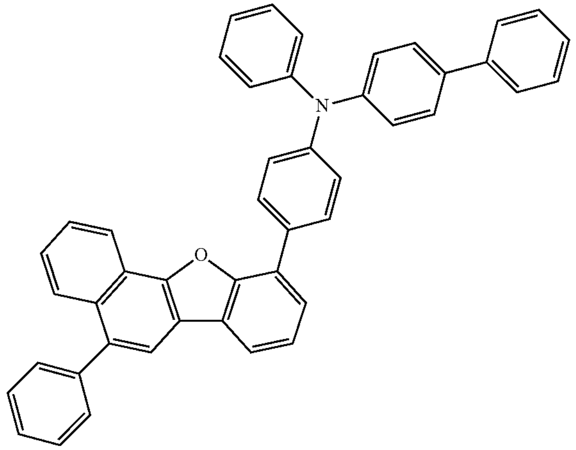 [SMILES: c1ccc(-c2ccc(N(c3ccccc3)c3ccc(-c4cccc5c4oc4c6ccccc6c(-c6ccccc6)cc54)cc3)cc2)cc1] | 70.5% |

TABLE 2-continued
| Compound No. | Intermediate A | Intermediate B | Target Compound | Yield |
|---|---|---|---|---|
| 1-538 | | 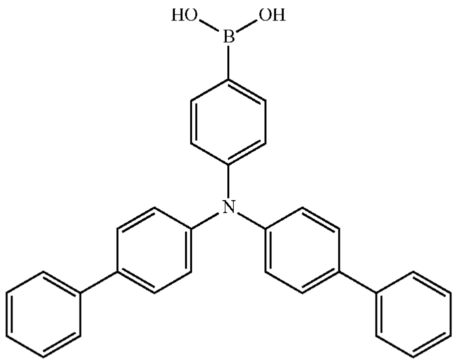 [SMILES: OB(O)c1ccc(N(c2ccc(-c3ccccc3)cc2)c2ccc(-c3ccccc3)cc2)cc1] | 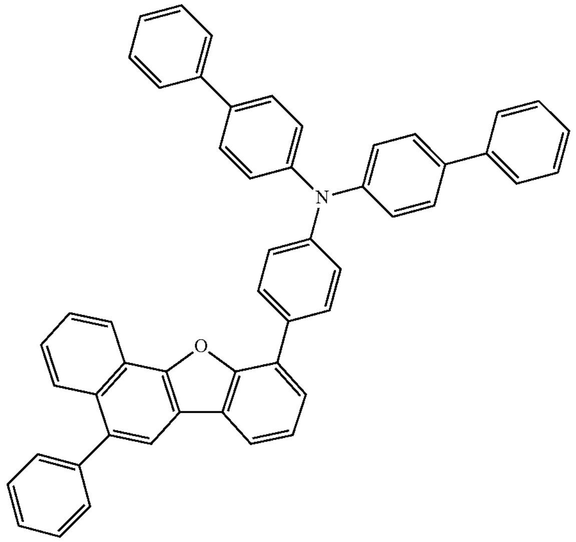 [SMILES: c1ccc(-c2ccc(N(c3ccc(-c4ccccc4)cc3)c3ccc(-c4cccc5c4oc4c6ccccc6c(-c6ccccc6)cc54)cc3)cc2)cc1] | 70.1% |

TABLE 2-continued
| Compound No. | Intermediate A | Intermediate B | Target Compound | Yield |
|---|---|---|---|---|
| 1-545 | 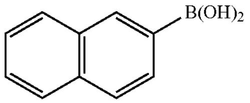 [SMILES: OB(O)c1ccc2ccccc2c1] | 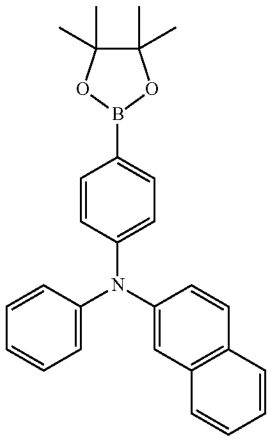 [SMILES: CC1(C)OB(c2ccc(N(c3ccccc3)c3ccc4ccccc4c3)cc2)OC1(C)C] | 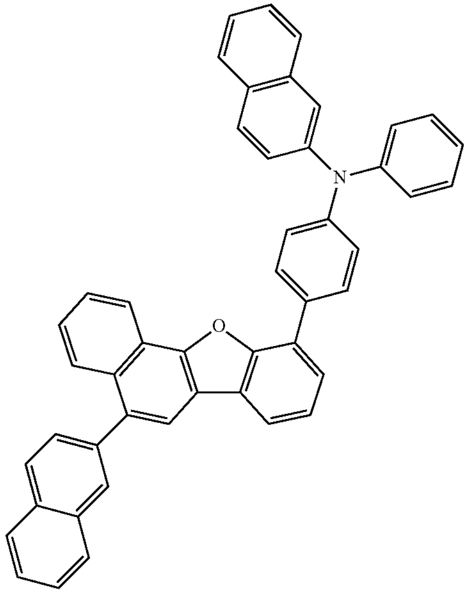 [SMILES: c1ccc(N(c2ccc(-c3cccc4c3oc3c5ccccc5c(-c5ccc6ccccc6c5)cc43)cc2)c2ccc3ccccc3c2)cc1] | 70.3% |

TABLE 2-continued
| Compound No. | Intermediate A | Intermediate B | Target Compound | Yield |
| --- | --- | --- | --- | --- |
| 1-549 | 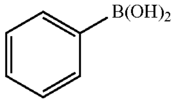 | 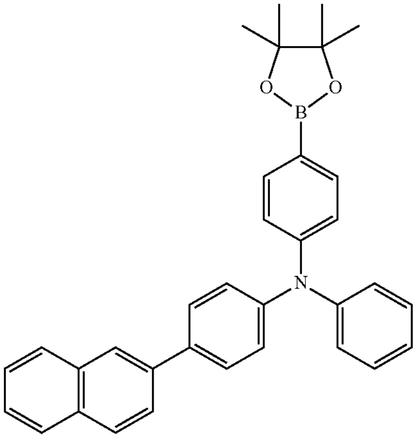 [SMILES: CC1(C)OB(c2ccc(N(c3ccccc3)c3ccc(-c4ccc5ccccc5c4)cc3)cc2)OC1(C)C] | 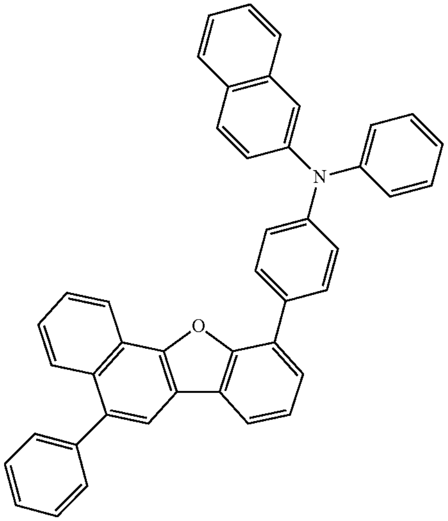 [SMILES: c1ccc(-c2cc3c4cccc(-c5ccc(N(c6ccccc6)c6ccc7ccccc7c6)cc5)c4oc3c3ccccc23)cc1] | 70.4% |
| 1-554 | | 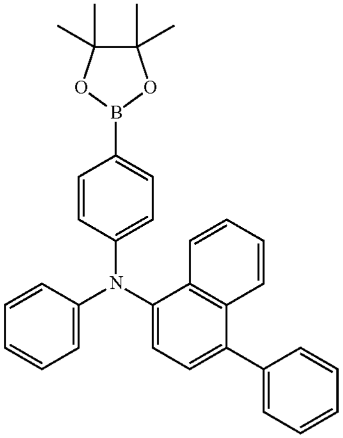 [SMILES: CC1(C)OB(c2ccc(N(c3ccccc3)c3ccc(-c4ccccc4)c4ccccc34)cc2)OC1(C)C] | 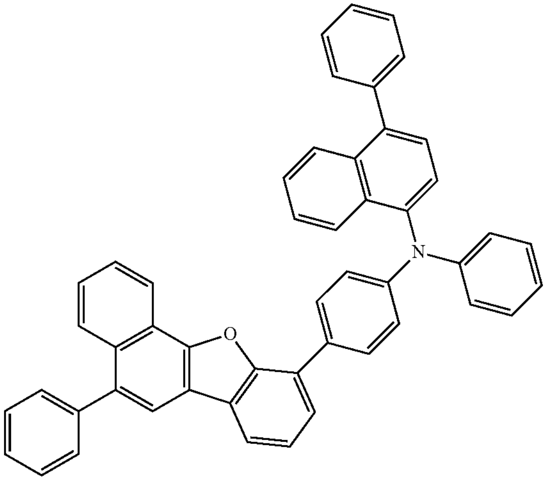 [SMILES: c1ccc(-c2ccc(N(c3ccccc3)c3ccc(-c4cccc5c4oc4c6ccccc6c(-c6ccccc6)cc54)cc3)c3ccccc23)cc1] | 70.9% |

TABLE 2-continued
| Compound No. | Intermediate A | Intermediate B | Target Compound | Yield |
|---|---|---|---|---|
| 1-558 | | 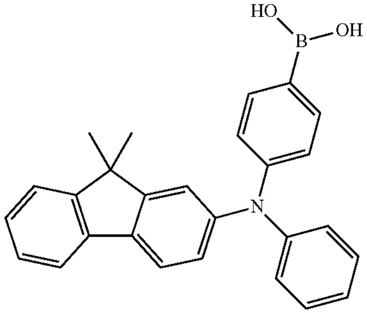 [SMILES: CC1(C)c2ccccc2-c2ccc(N(c3ccccc3)c3ccc(B(O)O)cc3)cc21] | 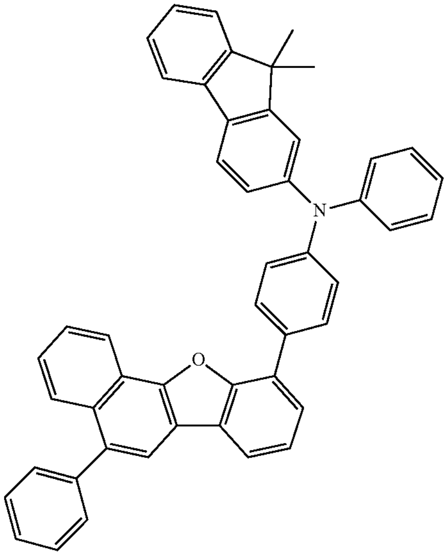 [SMILES: CC1(C)c2ccccc2-c2ccc(N(c3ccccc3)c3ccc(-c4cccc5c4oc4c6ccccc6c(-c6ccccc6)cc54)cc3)cc21] | 71.5% |

TABLE 2-continued
| Compound No. | Intermediate A | Intermediate B | Target Compound | Yield |
|---|---|---|---|---|
| 1-559 | | 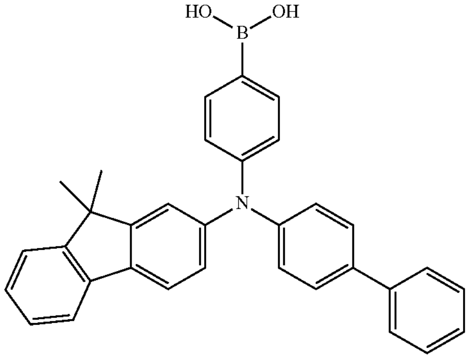 [SMILES: CC1(C)c2ccccc2-c2ccc(N(c3ccc(B(O)O)cc3)c3ccc(-c4ccccc4)cc3)cc21] | 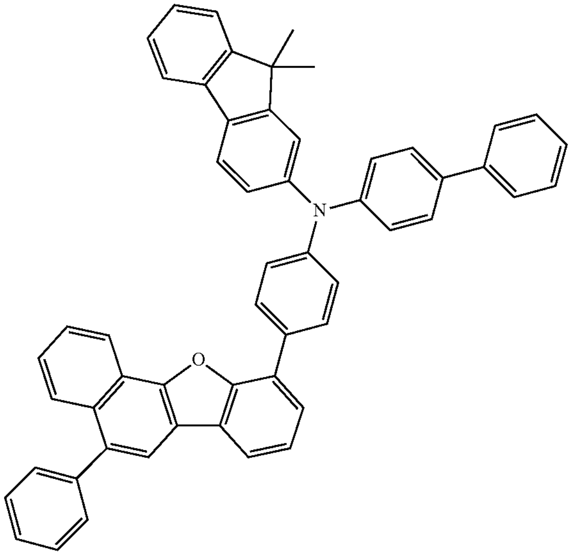 [SMILES: CC1(C)c2ccccc2-c2ccc(N(c3ccc(-c4ccccc4)cc3)c3ccc(-c4cccc5c4oc4c6ccccc6c(-c6ccccc6)cc54)cc3)cc21] | 71.3% |

TABLE 2-continued
| Compound No. | Intermediate A | Intermediate B | Target Compound | Yield |
|---|---|---|---|---|
| 1-572 | 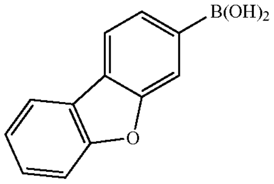 [SMILES: OB(O)c1ccc2c(c1)oc1ccccc12] | 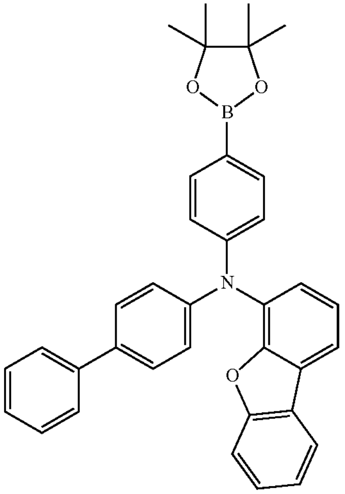 [SMILES: CC1(C)OB(c2ccc(N(c3ccc(-c4ccccc4)cc3)c3cccc4c3oc3ccccc34)cc2)OC1(C)C] | 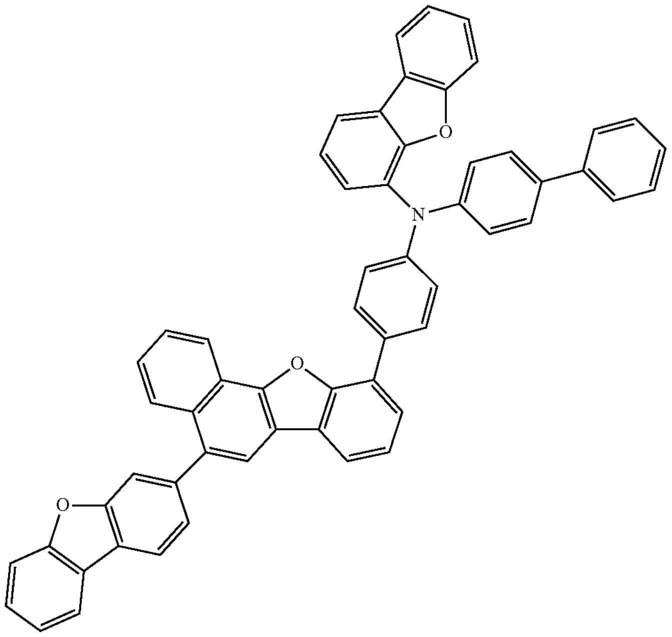 [SMILES: c1ccc(-c2ccc(N(c3ccc(-c4cccc5c4oc4c6ccccc6c(-c6ccc7c(c6)oc6ccccc67)cc54)cc3)c3cccc4c3oc3ccccc34)cc2)cc1] | 70.1% |

TABLE 2-continued
| Compound No. | Intermediate A | Intermediate B | Target Compound | Yield |
|---|---|---|---|---|
| 1-577 | 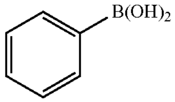 | 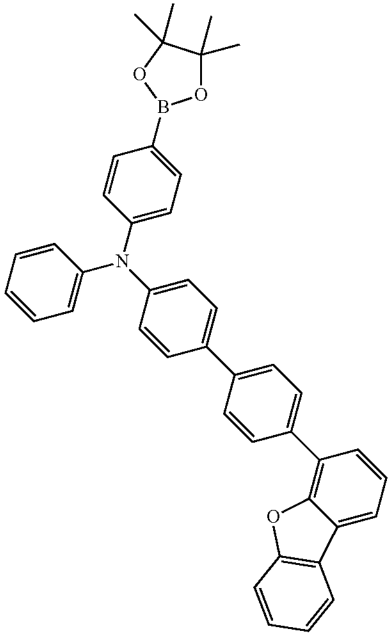 [SMILES: CC1(C)OB(c2ccc(N(c3ccccc3)c3ccc(-c4ccc(-c5cccc6c5oc5ccccc56)cc4)cc3)cc2)OC1(C)C] | 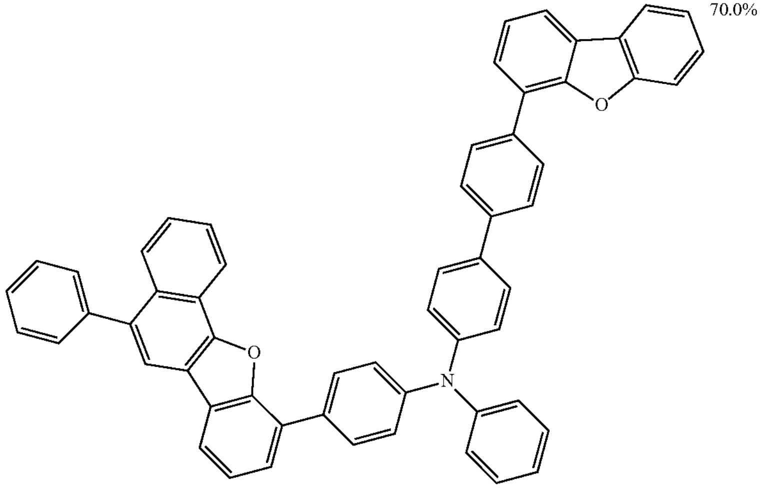 | 70.0% |

TABLE 2-continued
| Compound No. | Intermediate A | Intermediate B | Target Compound | Yield |
|---|---|---|---|---|
| 1-805 | 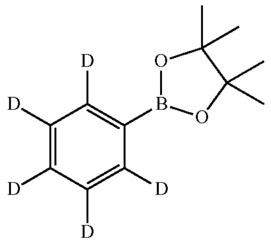 [SMILES: [2H]c1c([2H])c([2H])c(B2OC(C)(C)C(C)(C)O2)c([2H])c1[2H]] | 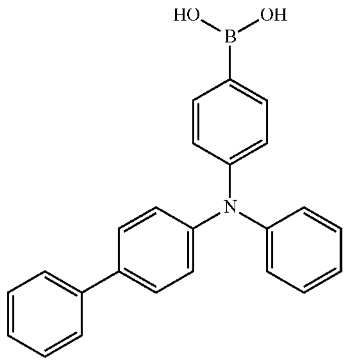 [SMILES: OB(O)c1ccc(N(c2ccccc2)c2ccc(-c3ccccc3)cc2)cc1] | 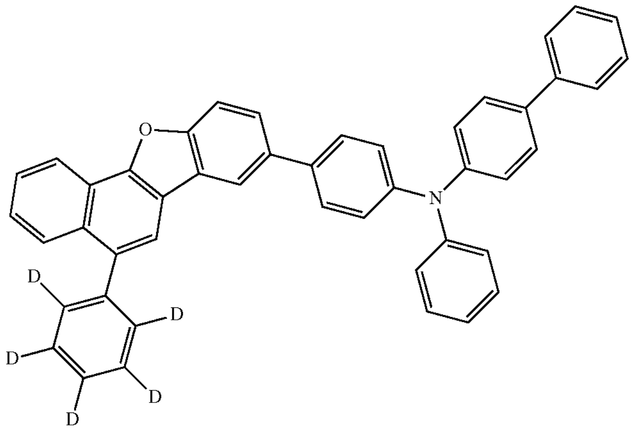 [SMILES: [2H]c1c([2H])c([2H])c(-c2cc3c4cc(-c5ccc(N(c6ccccc6)c6ccc(-c7ccccc7)cc6)cc5)ccc4oc3c3ccccc23)c([2H])c1[2H]] | 80.3% |
| 1-841 | | | 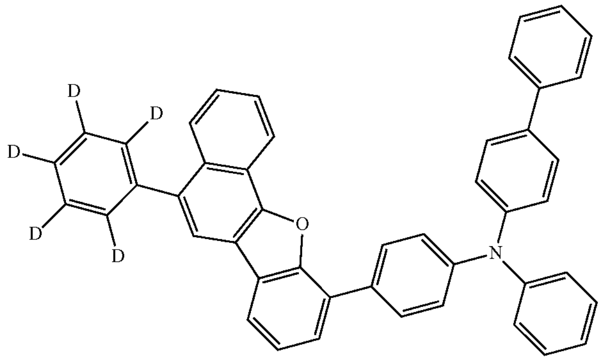 [SMILES: [2H]c1c([2H])c([2H])c(-c2cc3c4cccc(-c5ccc(N(c6ccccc6)c6ccc(-c7ccccc7)cc6)cc5)c4oc3c3ccccc23)c([2H])c1[2H]] | 75.1% |

TABLE 2-continued
| Compound No. | Intermediate A | Intermediate B | Target Compound | Yield |
| --- | --- | --- | --- | --- |
| 1-845 | | 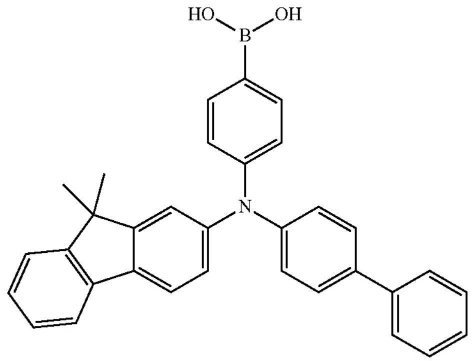 [SMILES: CC1(C)c2ccccc2-c2ccc(N(c3ccc(B(O)O)cc3)c3ccc(-c4ccccc4)cc3)cc21] | 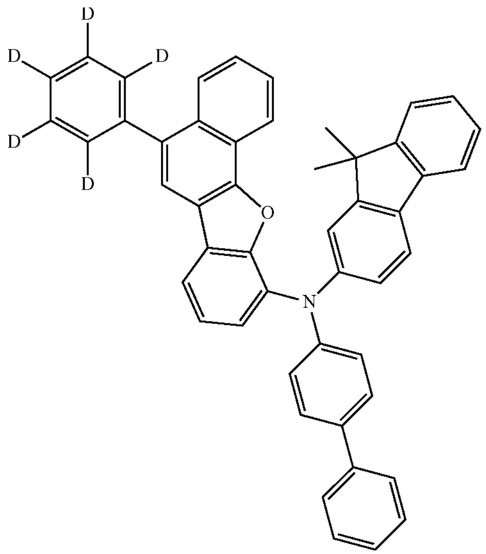 [SMILES: [2H]c1c([2H])c([2H])c(-c2cc3c4cccc(N(c5ccc(-c6ccccc6)cc5)c5ccc6c(c5)C(C)(C)c5ccccc5-6)c4oc3c3ccccc23)c([2H])c1[2H]] | 75.4% |

[Preparation Example 3] Preparation of Compound 1-401

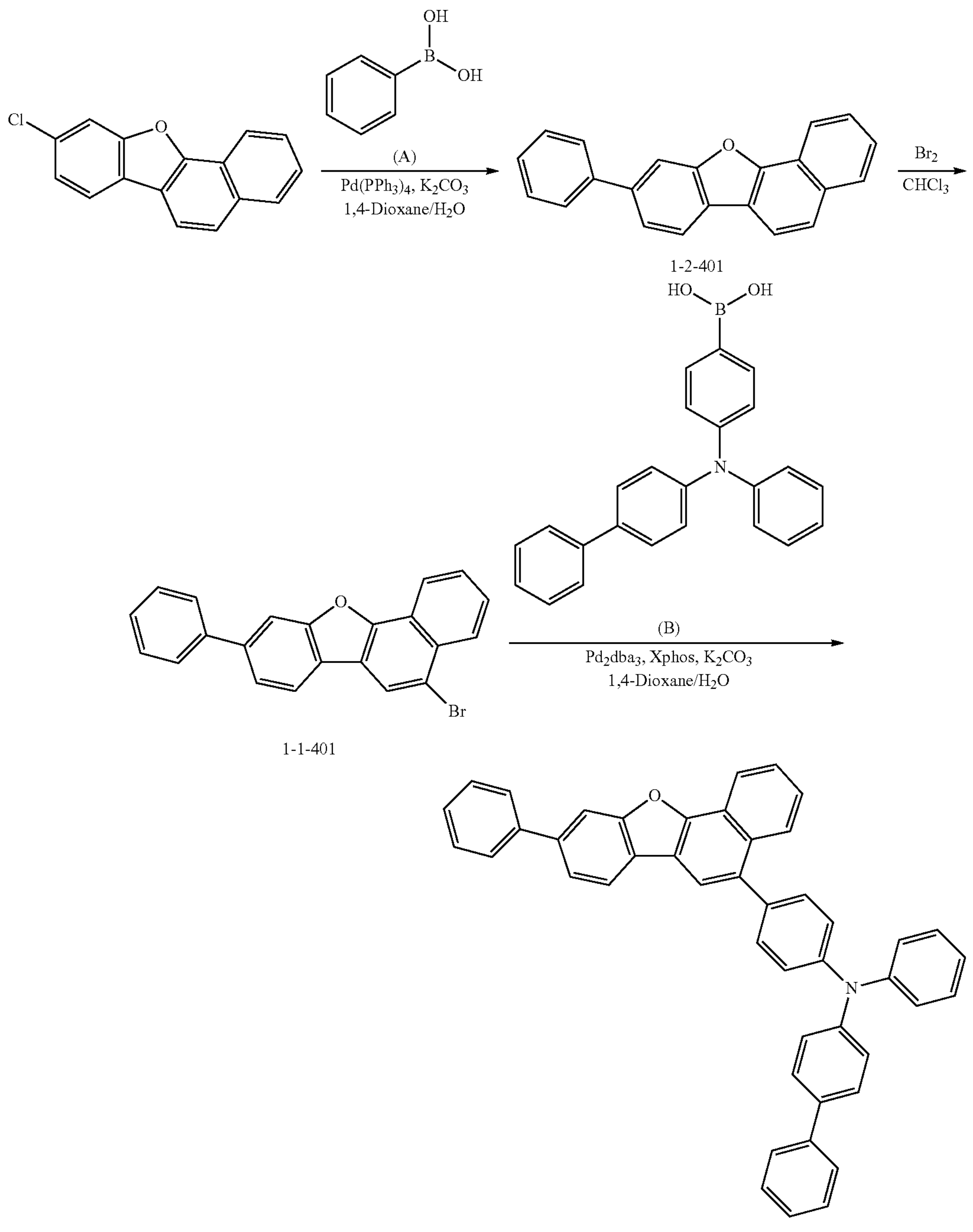

1-2-401

1-1-401

1-401

3-1. Synthesis Method of Compound 1-2-401

9-Chloronaphtho[1,2-b]benzofuran (60.0 g, 237.4 mM), phenylboronic acid (37.6 g, 308.6 mM), $Pd(PPh_3)_4$ (13.8 g, 11.9 mM) and $K_2CO_3$ (82.0 g, 593.5 mM) were dissolved in 1,4-dioxane/$H_2O$ (600 ml/120 ml), and refluxed for 3 hours. After the reaction was terminated, the result was extracted with dichloromethane/$H_2O$ at room temperature. The reaction material was purified by column chromatography (DCM:Hex=1:5), and recrystallized with methanol to obtain target Compound 1-2-401 (59.5 g, 85.1%).

3-2. Synthesis Method of Compound 1-1-401

1-2-401 (59 g, 200.4 mM) and bromine (32.0 g, 200.4 mM) were dissolved in chloroform (600 ml), and stirred for 1 hour. After the reaction was completed, methanol (300 ml) was introduced thereto to terminate the reaction. Target Compound 1-1-401 (65.3 g, 87.3%) was obtained.

3-3. Synthesis Method of Compound 1-401

1-1-401 (10.0 g, 26.8 mM), (4-([1,1'-biphenyl]-4-yl(phenyl)amino) phenyl)boronic acid (9.8 g, 26.8 mM), $Pd_2dba_3$ (1.2 g, 1.3 mM), xphos (1.3 g, 2.7 mM) and $K_2CO_3$ (11.1 g, 80.4 mM) were dissolved in 1,4-dioxane/$H_2O$ (120 ml/24 ml), and refluxed for 1 hour. After the reaction was terminated, the result was extracted with dichloromethane/$H_2O$ at room temperature. The reaction material was purified by column chromatography (DCM:Hex=1:1), and recrystallized with methanol to obtain target Compound 1-401 (15.5 g, 94.4%).

Target compounds were synthesized in the same manner as in Preparation Example 3 except that Intermediate A and Intermediate B of the following Table 3 were used.

TABLE 3

| Compound No. | Intermediate A | Intermediate B | Target Compound | Yield |
|---|---|---|---|---|
| 1-401 | 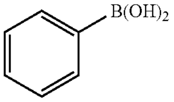 | 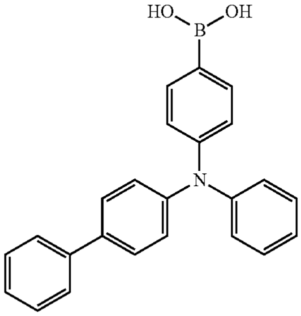 [SMILES: OB(O)c1ccc(N(c2ccccc2)c2ccc(-c3ccccc3)cc2)cc1] | 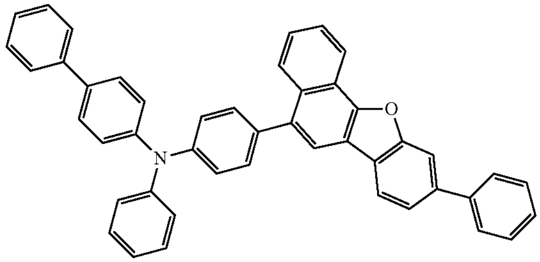 [SMILES: c1ccc(-c2ccc(N(c3ccccc3)c3ccc(-c4cc5c6ccc(-c7ccccc7)cc6oc5c5ccccc45)cc3)cc2)cc1] | 94.4% |
| 1-402 | 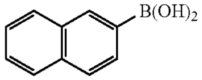 | | 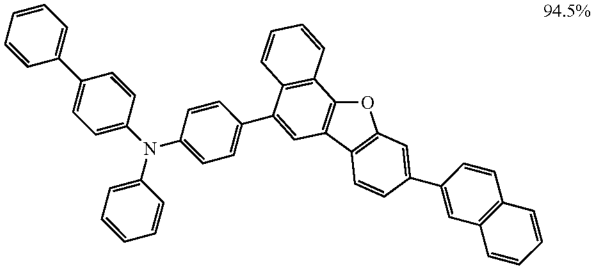 | 94.5% |
| 1-409 | 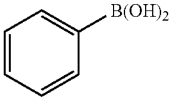 | 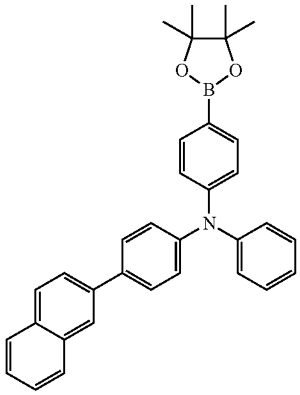 [SMILES: CC1(C)OB(c2ccc(N(c3ccccc3)c3ccc(-c4ccc5ccccc5c4)cc3)cc2)OC1(C)C] | 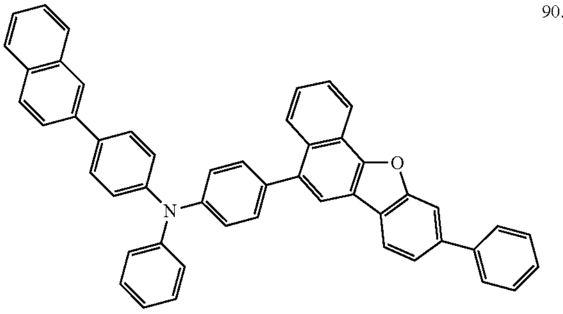 | 90.8% |
| 1-412 | | 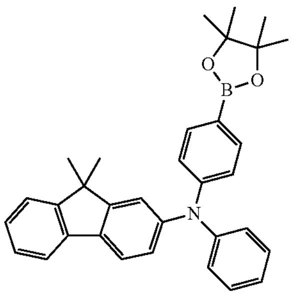 [SMILES: CC1(C)c2ccccc2-c2ccc(N(c3ccccc3)c3ccc(B4OC(C)(C)C(C)(C)O4)cc3)cc21] | 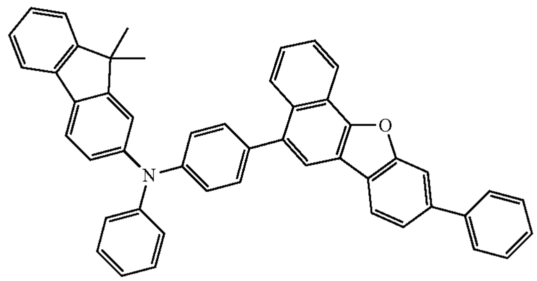 [SMILES: CC1(C)c2ccccc2-c2ccc(N(c3ccccc3)c3ccc(-c4cc5c6ccc(-c7ccccc7)cc6oc5c5ccccc45)cc3)cc21] | 91.1% |

[Preparation Example 4] Preparation of Compound 1-811

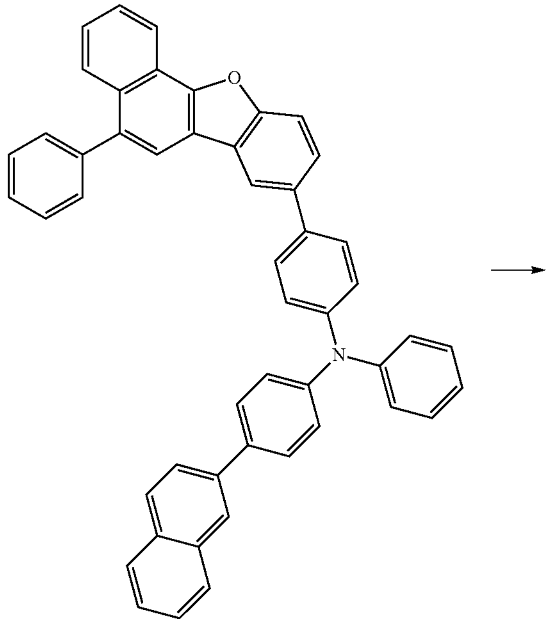

1-62

-continued

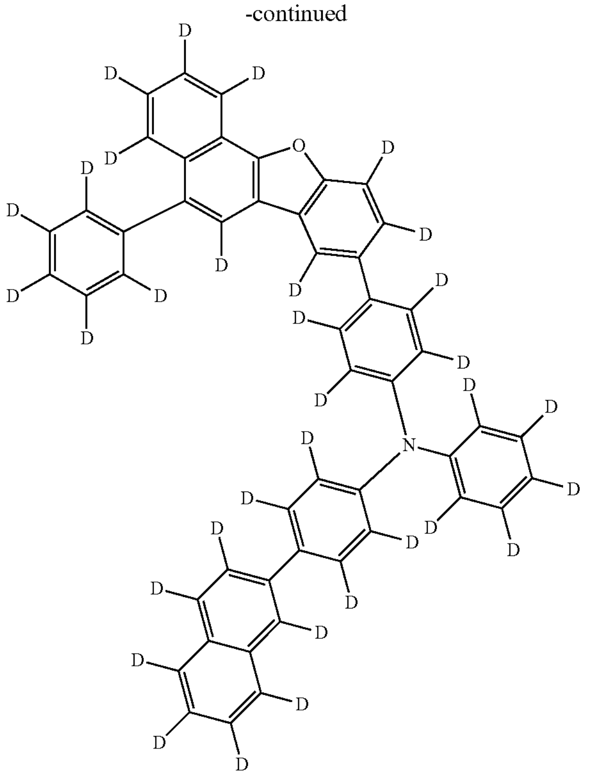

1-811

1-62 (10.0 g, 15.1 mM) and trifluoromethanesulfonic acid (15.4 g, 102.7 mM) were dissolved in D6 benzene (100 ml), and stirred for 1 hour at 60° C. After the reaction was terminated, the result was neutralized with an aqueous $K_3PO_4$ solution at room temperature and then extracted with dichloromethane/$H_2O$. The reaction material was purified by column chromatography (DCM:Hex=1:1), and recrystallized with methanol to obtain target Compound 1-811 (7.5 g, 71.5%).

[Preparation Example 5] Preparation of Compound 1-849

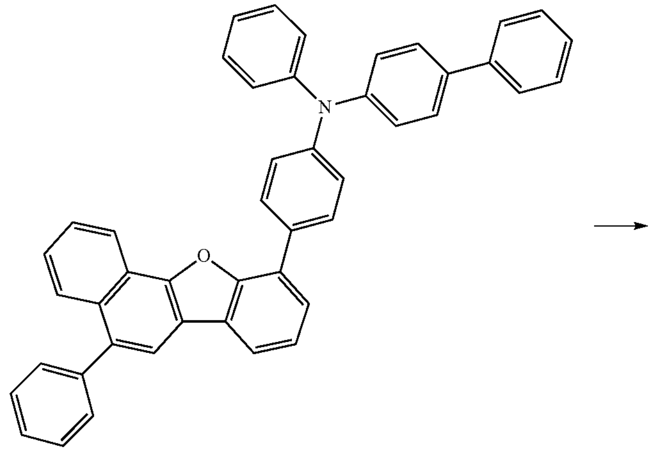

1-532

-continued

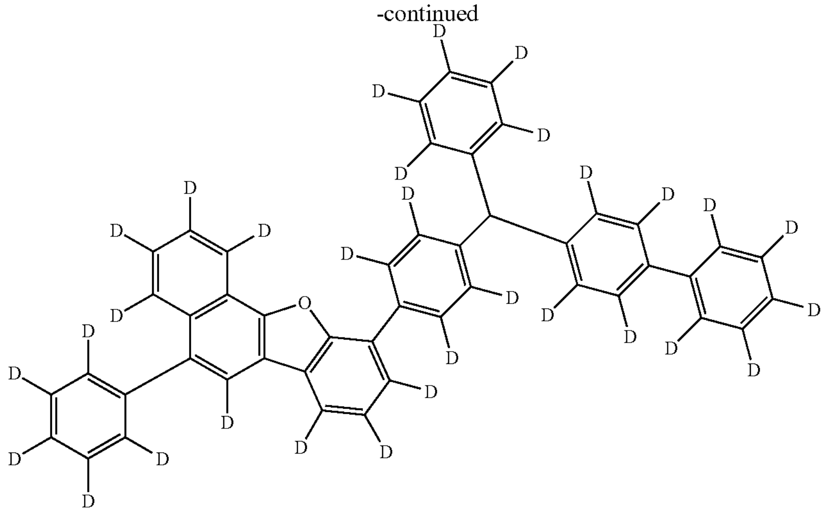

1-849

1-532 (15.0 g, 24.4 mM) and trifluoromethanesulfonic acid (24.9 g, 165.9 mM) were dissolved in D6 benzene (150 ml), and stirred for 1 hour at 60° C. After the reaction was terminated, the result was neutralized with an aqueous $K_3PO_4$ solution at room temperature and then extracted with dichloromethane/$H_2O$. The reaction material was purified by column chromatography (DCM:Hex=1:1), and recrystallized with methanol to obtain target Compound 1-849 (11.5 g, 73.0%).

[Preparation Example 6] Preparation of Compound 1-853

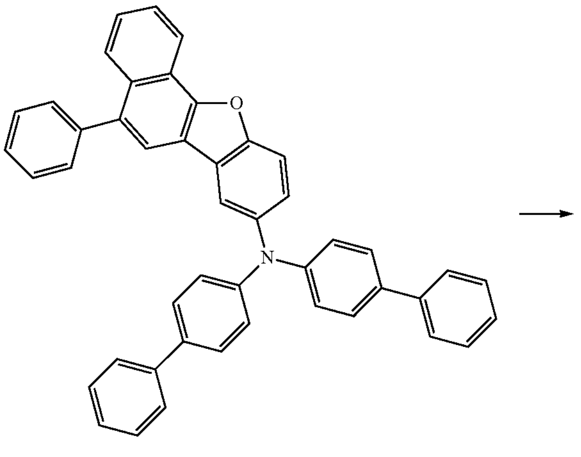

1-5

-continued

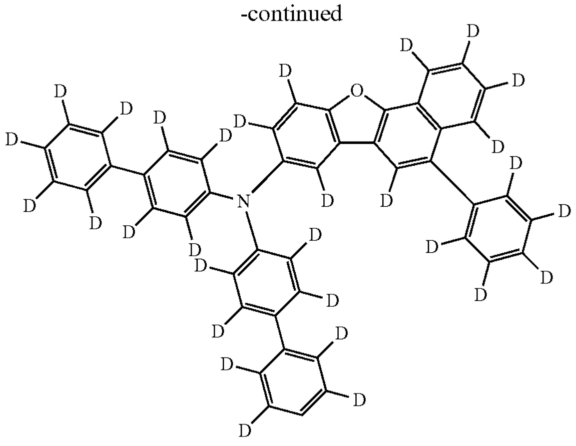

1-853

Compound 1 (4 g, 6.52) and trifluoromethanesulfonic acid (4.07 mL, 45.62 mmol) were dissolved in D6-benzene (40 ml), and stirred for 4 hours at 60° C. After the reaction was terminated, the result was neutralized with an aqueous $K_3PO_4$ solution at room temperature and then extracted with dichloromethane (DCM) and water ($H_2O$).

The reaction material extracted once again was purified by column chromatography (dichloromethane:hexane=1:1 volume ratio), recrystallized with methanol, and extracted with dichloromethane/$H_2O$. The reaction material was purified by column chromatography (DCM:Hex=1:1), and recrystallized with methanol to obtain target Compound 1-853 (4 g, 6.2 mmol, 95% yield).

[Preparation Example 7] Preparation of Compound 2-337

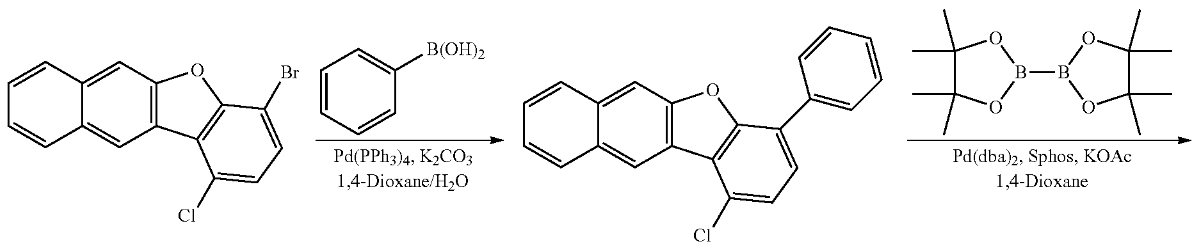

2-2-337

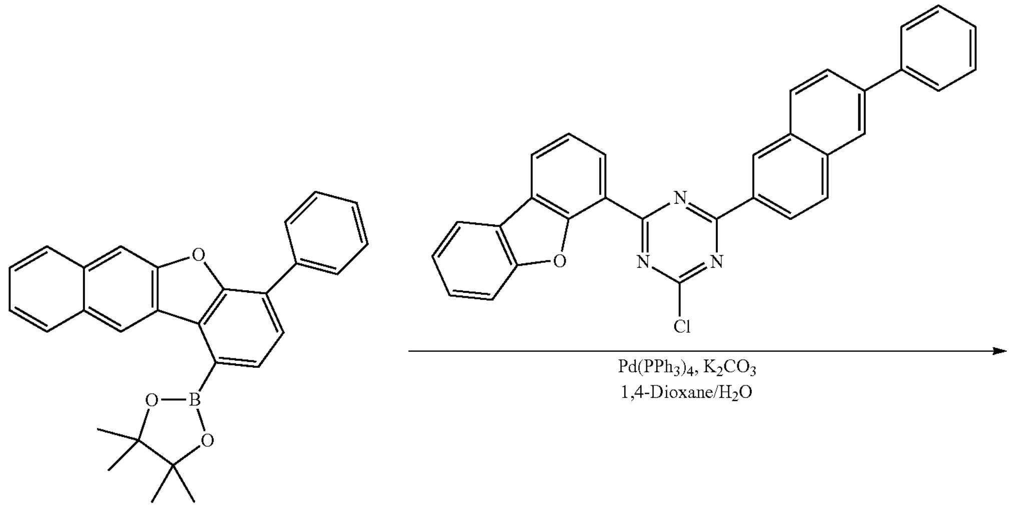

2-1-337

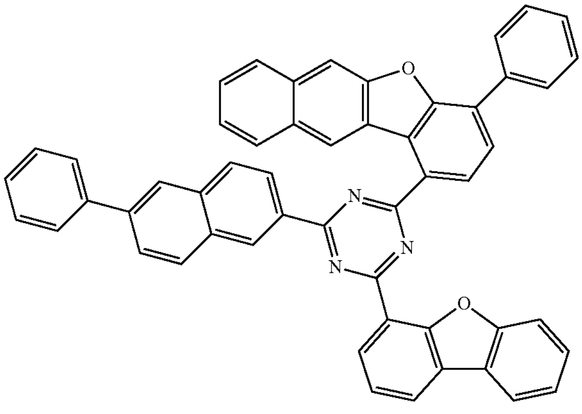

2-337

Preparation of Compound 2-2-337

4-Bromo-1-chloronaphtho[2,3-b]benzofuran (30.0 g, 90.5 mM), phenylboronic acid (14.4 g, 117.7 mM), $Pd(PPh_3)_4$ (5.2 g, 4.5 mM) and $K_2CO_3$ (31.3 g, 226.3 mM) were dissolved in 1,4-dioxane/$H_2O$ (300 ml/60 ml), and refluxed for 1 hour. The reaction material was purified by column chromatography (DCM:Hex=1:1), and recrystallized with methanol to obtain target Compound 2-2-337 (25.3 g, 85.0%).

Preparation of Compound 2-1-337

2-2-337 (25.0 g, 76.0 mM), 4,4,4',4',5,5,5',5'-octamethyl-2,2'-bi(1,3,2-dioxaborolane) (28.9 g, 114.0 mM), $Pd(dba)_2$ (2.2 g, 3.8 mM), Sphos (3.1 g, 7.6 mM) and KOAc (14.9 g, 152.0 mM) were dissolved in 1,4-dioxane (250 ml), and refluxed for 1 hour. The reaction material was purified by column chromatography (DCM:Hex=1:1), and recrystallized with methanol to obtain target Compound 2-1-337 (25.5 g, 79.9%).

Preparation of Compound 2-337

2-1-337 (15.0 g, 35.7 mM), 2-chloro-4-(dibenzo[b,d]furan-4-yl)-6-(6-phenylnaphthalen-2-yl)-1,3,5-triazine (17.3 g, 35.7 mM), $Pd(PPh_3)_4$ (2.1 g, 1.8 mM) and $K_2CO_3$ (14.8 g, 107.1 mM) were dissolved in 1,4-dioxane/$H_2O$ (200 ml/40 ml), and refluxed for 3 hours. The reaction material was recrystallized with methanol to obtain target Compound 2-337 (21.5 g, 81.2%).

Target compounds were synthesized in the same manner as in Preparation Example 7 except that Intermediate A of the following Table 4 was used instead of phenylboronic acid, and Intermediate B of the following Table 4 was used instead of 2-chloro-4-(dibenzo[b,d]furan-4-yl)-6-(6-phenylnaphthalen-2-yl)-1,3,5-triazine.

TABLE 4
| Compound No. | Intermediate A | Intermediate B | Target Compound | Yield |
|---|---|---|---|---|
| 2-337 | 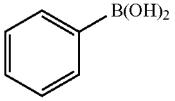 | 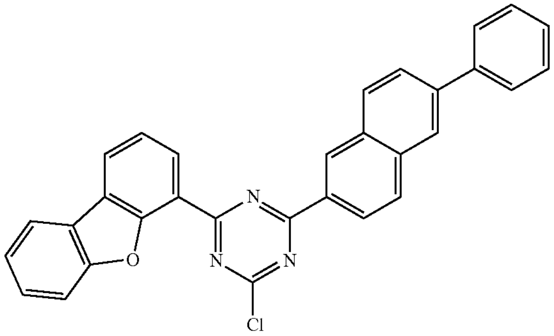 [SMILES: Clc1nc(-c2ccc3cc(-c4ccccc4)ccc3c2)nc(-c2cccc3c2oc2ccccc23)n1] | 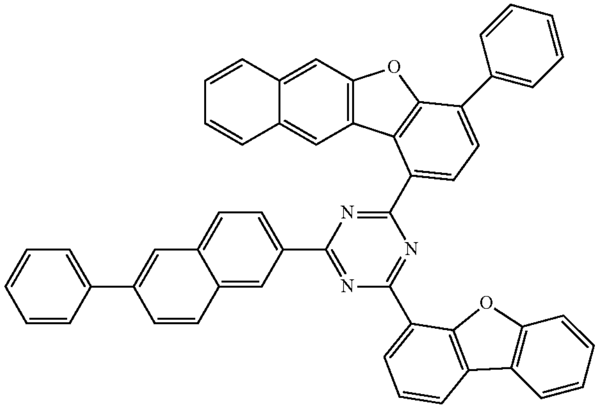 [SMILES: c1ccc(-c2ccc3cc(-c4nc(-c5cccc6c5oc5ccccc56)nc(-c5ccc(-c6ccccc6)c6oc7cc8ccccc8cc7c56)n4)ccc3c2)cc1] | 81.2% |
| 2-339 | | 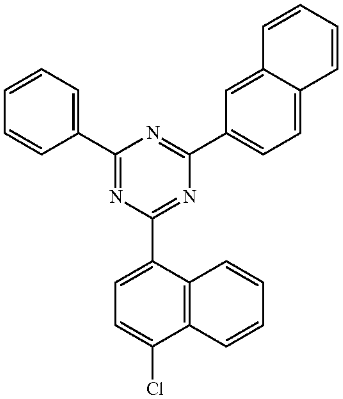 [SMILES: Clc1ccc(-c2nc(-c3ccccc3)nc(-c3ccc4ccccc4c3)n2)c2ccccc12] | 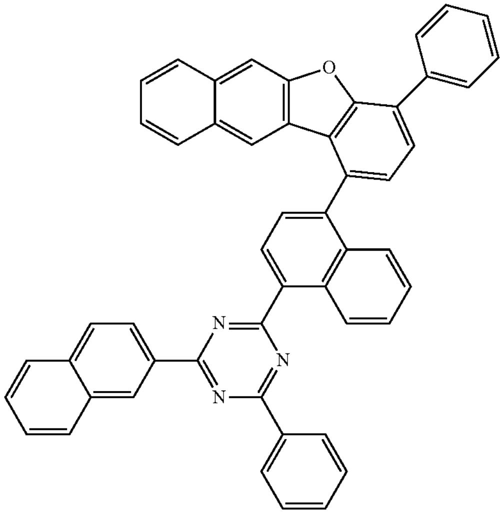 [SMILES: c1ccc(-c2nc(-c3ccc4ccccc4c3)nc(-c3ccc(-c4ccc(-c5ccccc5)c5oc6cc7ccccc7cc6c45)c4ccccc34)n2)cc1] | 80.5% |

TABLE 4-continued
| Compound No. | Intermediate A | Intermediate B | Target Compound | Yield |
|---|---|---|---|---|
| 2-348 | 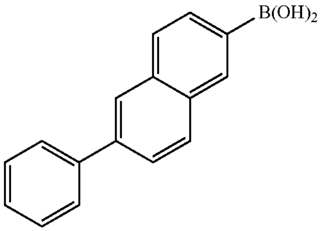 [SMILES: OB(O)c1ccc2cc(-c3ccccc3)ccc2c1] | 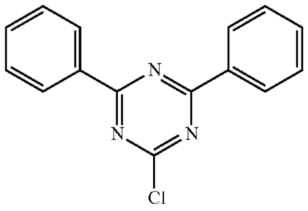 [SMILES: Clc1nc(-c2ccccc2)nc(-c2ccccc2)n1] | 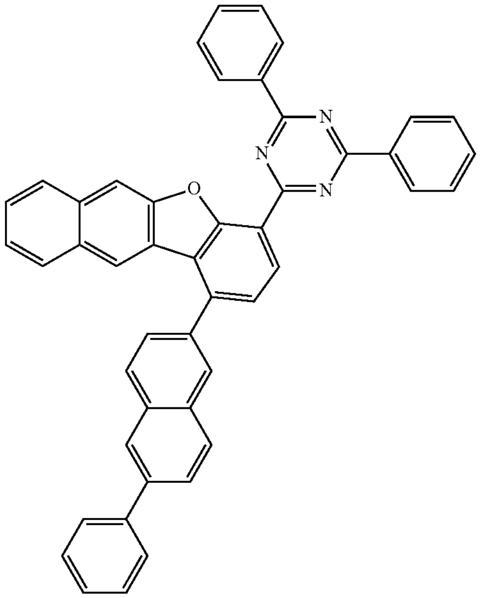 [SMILES: c1ccc(-c2ccc3cc(-c4ccc(-c5nc(-c6ccccc6)nc(-c6ccccc6)n5)c5oc6cc7ccccc7cc6c45)ccc3c2)cc1] | 80.1% |

TABLE 4-continued
| Compound No. | Intermediate A | Intermediate B | Target Compound | Yield |
|---|---|---|---|---|
| 2-351 | 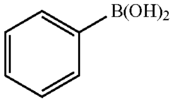 | 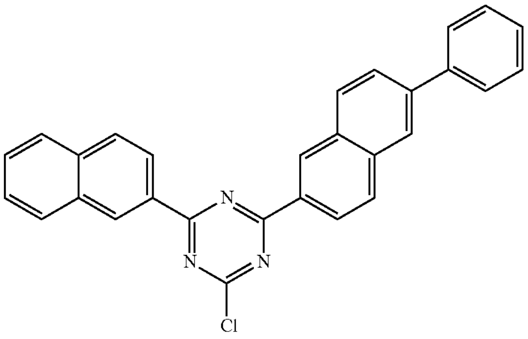 [SMILES: Clc1nc(-c2ccc3ccccc3c2)nc(-c2ccc3cc(-c4ccccc4)ccc3c2)n1] | 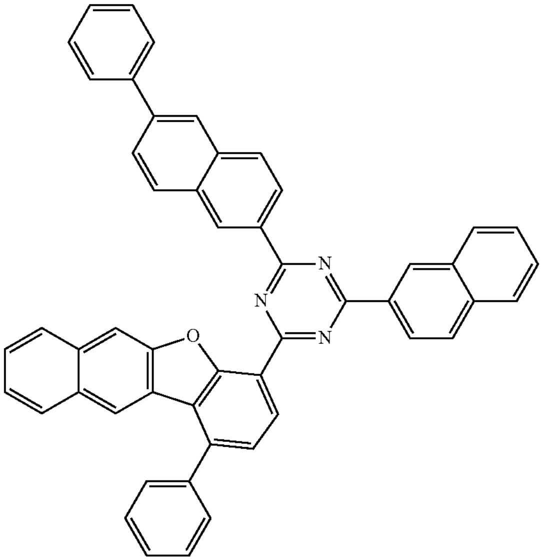 [SMILES: c1ccc(-c2ccc3cc(-c4nc(-c5ccc6ccccc6c5)nc(-c5ccc(-c6ccccc6)c6c5oc5cc7ccccc7cc56)n4)ccc3c2)cc1] | 80.3% |

TABLE 4-continued
| Compound No. | Intermediate A | Intermediate B | Target Compound | Yield |
|---|---|---|---|---|
| 2-369 | | 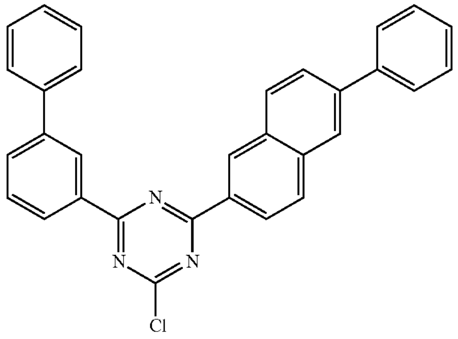 [SMILES: Clc1nc(-c2cccc(-c3ccccc3)c2)nc(-c2ccc3cc(-c4ccccc4)ccc3c2)n1] | 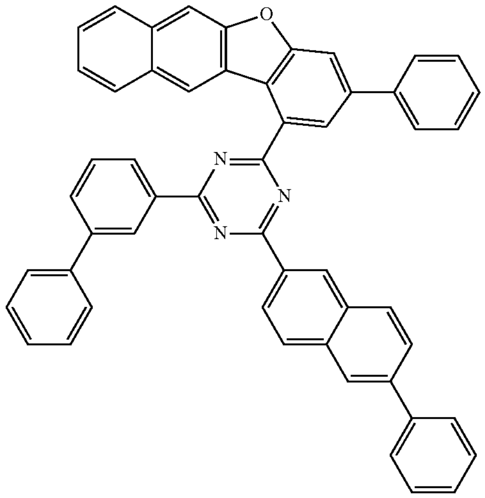 [SMILES: c1ccc(-c2cccc(-c3nc(-c4ccc5cc(-c6ccccc6)ccc5c4)nc(-c4cc(-c5ccccc5)cc5oc6cc7ccccc7cc6c45)n3)c2)cc1] | 80.7% |
| 2-466 | | 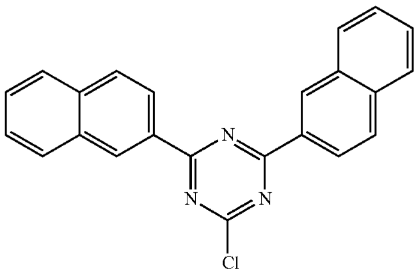 [SMILES: Clc1nc(-c2ccc3ccccc3c2)nc(-c2ccc3ccccc3c2)n1] | 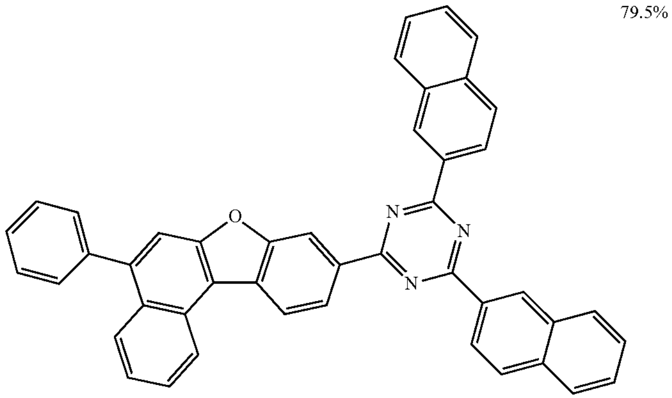 | 79.5% |

TABLE 4-continued
| Compound No. | Intermediate A | Intermediate B | Target Compound | Yield |
| --- | --- | --- | --- | --- |
| 2-468 | | 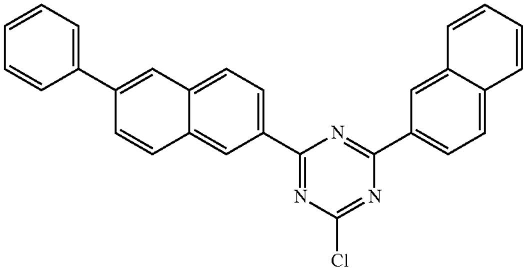 [SMILES: Clc1nc(-c2ccc3ccccc3c2)nc(-c2ccc3cc(-c4ccccc4)ccc3c2)n1] | 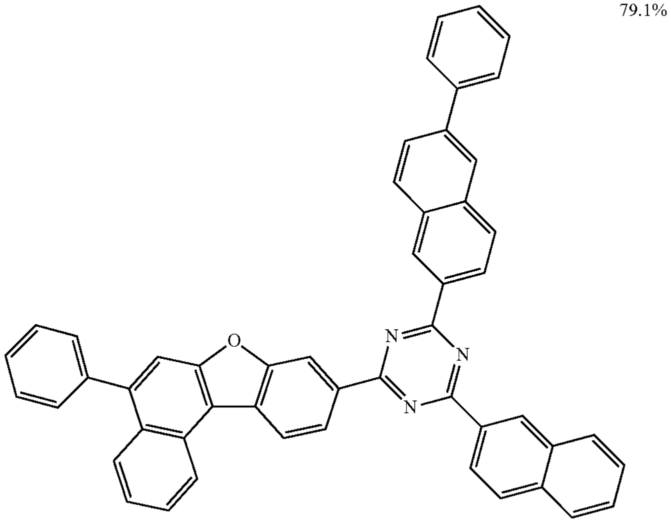 | 79.1% |
| 2-472 | | 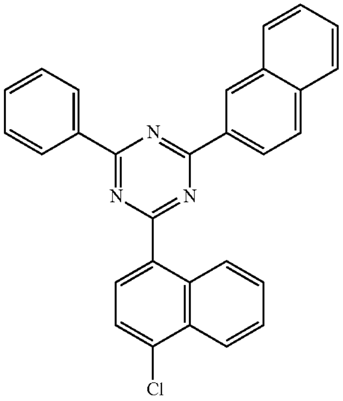 [SMILES: Clc1ccc(-c2nc(-c3ccccc3)nc(-c3ccc4ccccc4c3)n2)c2ccccc12] | 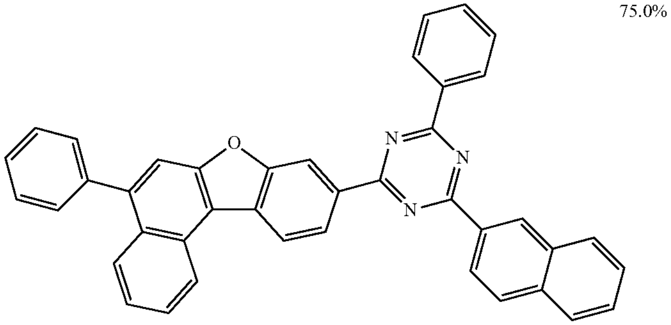 | 75.0% |

TABLE 4-continued
| Compound No. | Intermediate A | Intermediate B | Target Compound | Yield |
|---|---|---|---|---|
| 2-490 | | 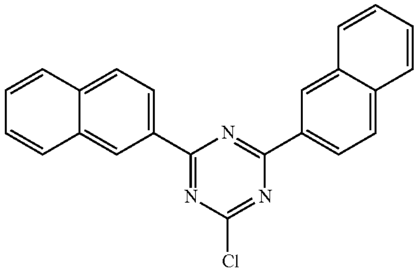 [SMILES: Clc1nc(-c2ccc3ccccc3c2)nc(-c2ccc3ccccc3c2)n1] | 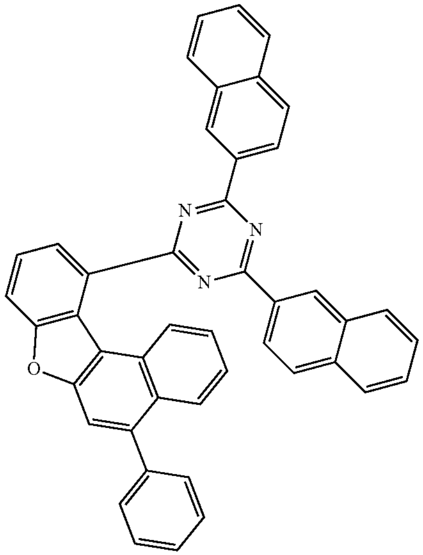 [SMILES: c1ccc(-c2cc3oc4cccc(-c5nc(-c6ccc7ccccc7c6)nc(-c6ccc7ccccc7c6)n5)c4c3c3ccccc23)cc1] | 70.5% |

TABLE 4-continued
| Compound No. | Intermediate A | Intermediate B | Target Compound | Yield |
| --- | --- | --- | --- | --- |
| 2-491 | | 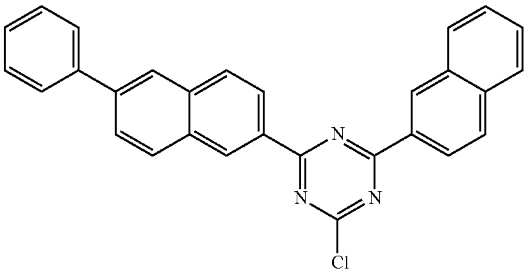 [SMILES: Clc1nc(-c2ccc3ccccc3c2)nc(-c2ccc3cc(-c4ccccc4)ccc3c2)n1] | 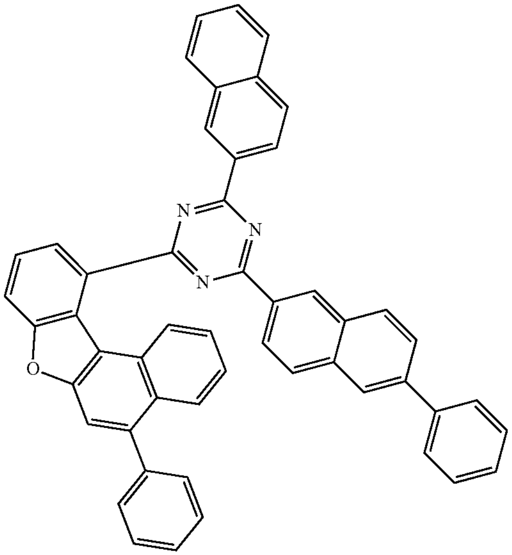 [SMILES: c1ccc(-c2ccc3cc(-c4nc(-c5ccc6ccccc6c5)nc(-c5cccc6oc7cc(-c8ccccc8)c8ccccc8c7c56)n4)ccc3c2)cc1] | 69.8% |
| 2-501 | 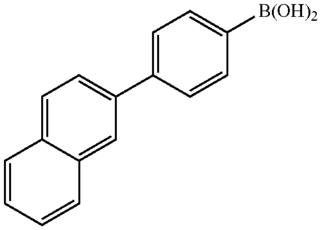 [SMILES: OB(O)c1ccc(-c2ccc3ccccc3c2)cc1] | 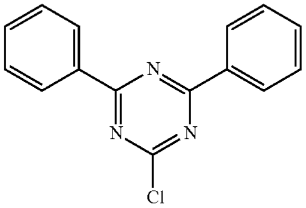 [SMILES: Clc1nc(-c2ccccc2)nc(-c2ccccc2)n1] | 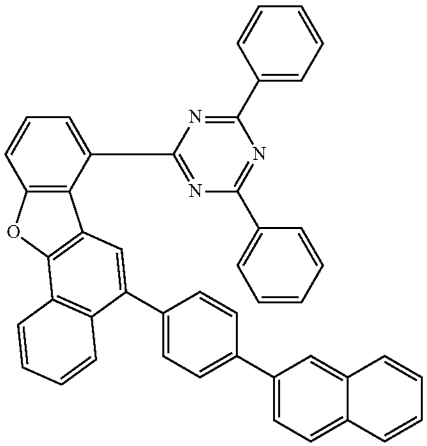 [SMILES: c1ccc(-c2nc(-c3ccccc3)nc(-c3cccc4oc5c6ccccc6c(-c6ccc(-c7ccc8ccccc8c7)cc6)cc5c34)n2)cc1] | 73.8% |

TABLE 4-continued
| Compound No. | Intermediate A | Intermediate B | Target Compound | Yield |
| --- | --- | --- | --- | --- |
| 2-504 | 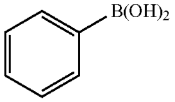 | 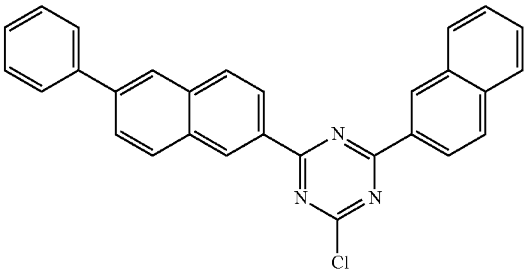 [SMILES: Clc1nc(-c2ccc3ccccc3c2)nc(-c2ccc3cc(-c4ccccc4)ccc3c2)n1] | 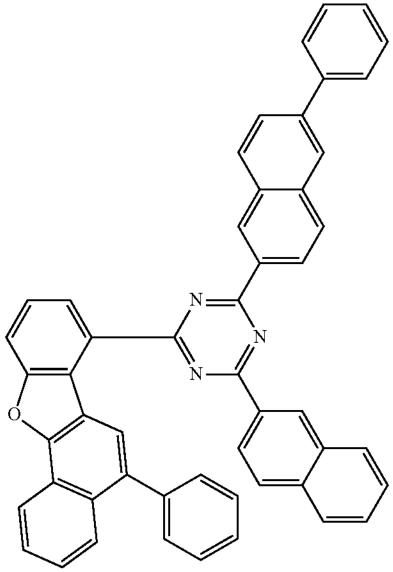 [SMILES: c1ccc(-c2ccc3cc(-c4nc(-c5ccc6ccccc6c5)nc(-c5cccc6oc7c8ccccc8c(-c8ccccc8)cc7c56)n4)ccc3c2)cc1] | 75.1% |
| 2-506 | | 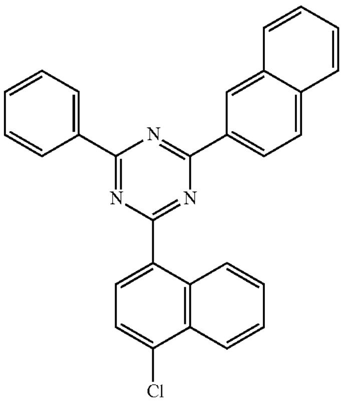 [SMILES: Clc1ccc(-c2nc(-c3ccccc3)nc(-c3ccc4ccccc4c3)n2)c2ccccc12] | 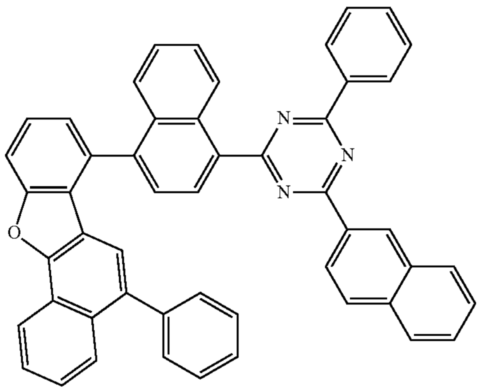 [SMILES: c1ccc(-c2nc(-c3ccc4ccccc4c3)nc(-c3ccc(-c4cccc5oc6c7ccccc7c(-c7ccccc7)cc6c45)c4ccccc34)n2)cc1] | 68.5% |

TABLE 4-continued
| Compound No. | Intermediate A | Intermediate B | Target Compound | Yield |
| --- | --- | --- | --- | --- |
| 2-530 | | 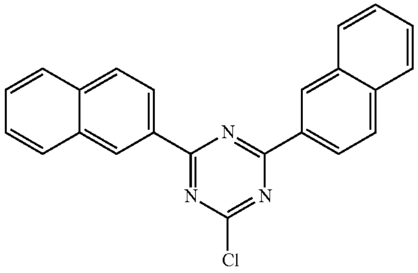 [SMILES: Clc1nc(-c2ccc3ccccc3c2)nc(-c2ccc3ccccc3c2)n1] | 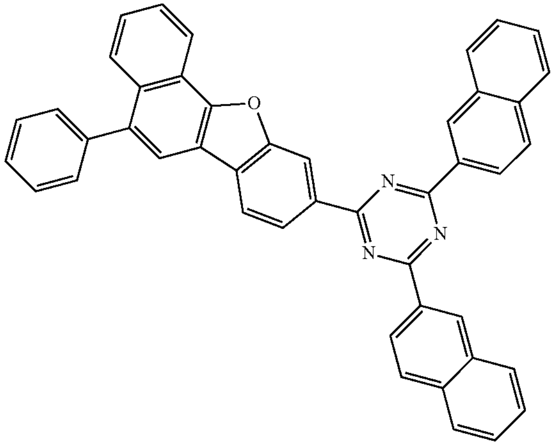 [SMILES: c1ccc(-c2cc3c4ccc(-c5nc(-c6ccc7ccccc7c6)nc(-c6ccc7ccccc7c6)n5)cc4oc3c3ccccc23)cc1] | 80.5% |
| 2-532 | | 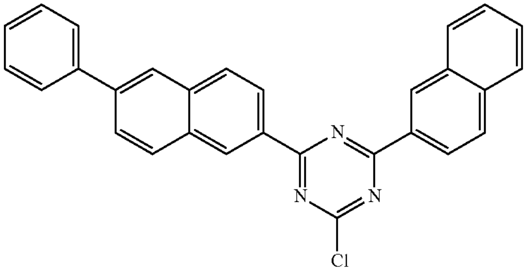 [SMILES: Clc1nc(-c2ccc3ccccc3c2)nc(-c2ccc3cc(-c4ccccc4)ccc3c2)n1] | 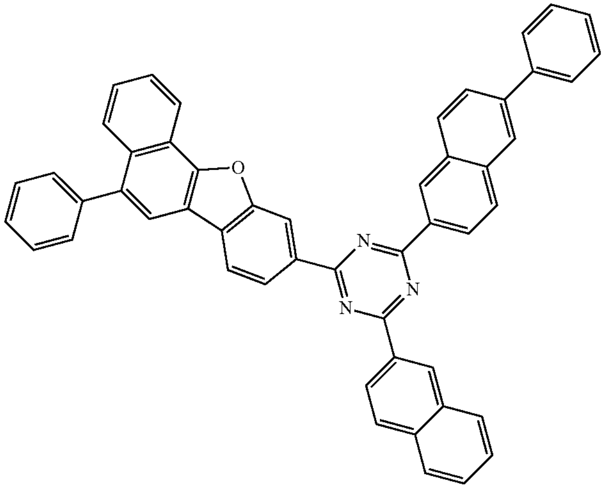 [SMILES: c1ccc(-c2ccc3cc(-c4nc(-c5ccc6ccccc6c5)nc(-c5ccc6c(c5)oc5c7ccccc7c(-c7ccccc7)cc65)n4)ccc3c2)cc1] | 80.3% |

TABLE 4-continued
| Compound No. | Intermediate A | Intermediate B | Target Compound | Yield |
|---|---|---|---|---|
| 3-87 | 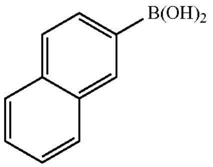 [SMILES: OB(O)c1ccc2ccccc2c1] | 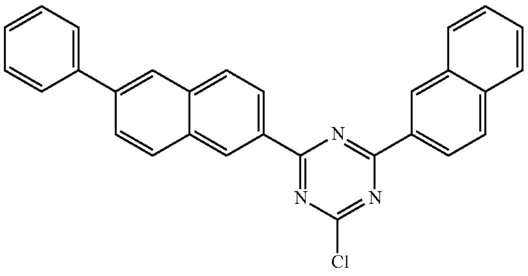 [SMILES: Clc1nc(-c2ccc3ccccc3c2)nc(-c2ccc3cc(-c4ccccc4)ccc3c2)n1] | 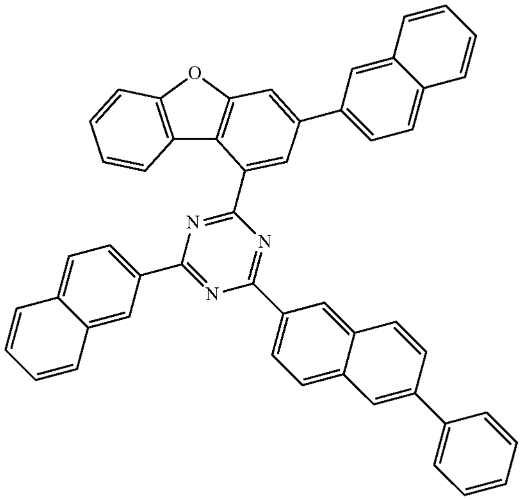 [SMILES: c1ccc(-c2ccc3cc(-c4nc(-c5ccc6ccccc6c5)nc(-c5cc(-c6ccc7ccccc7c6)cc6oc7ccccc7c56)n4)ccc3c2)cc1] | 85.1% |
| 3-110 | | 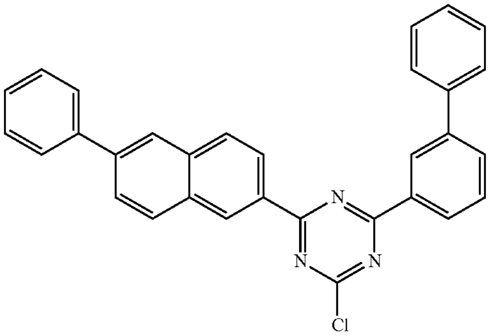 [SMILES: Clc1nc(-c2cccc(-c3ccccc3)c2)nc(-c2ccc3cc(-c4ccccc4)ccc3c2)n1] | 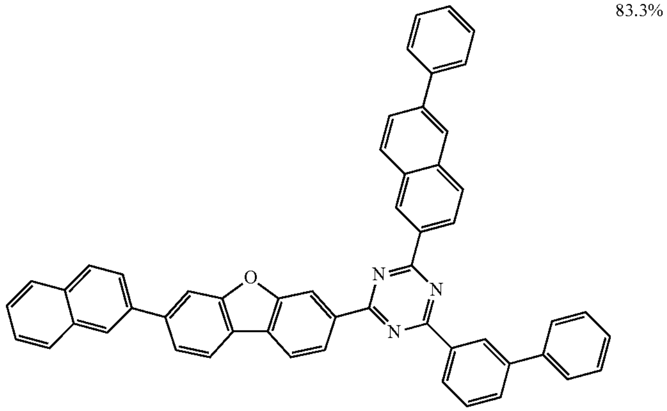 | 83.3% |

[Preparation Example 8] Preparation of Compound 2-542
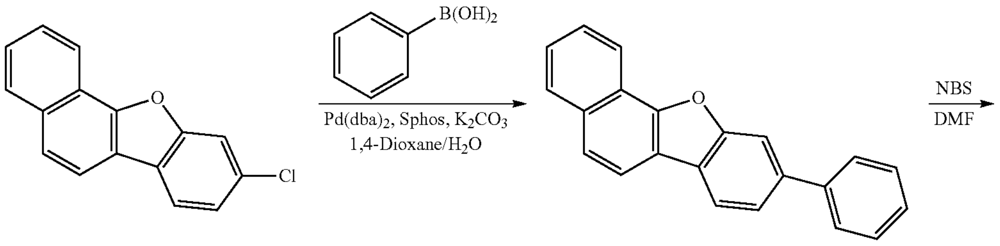
2-3-542
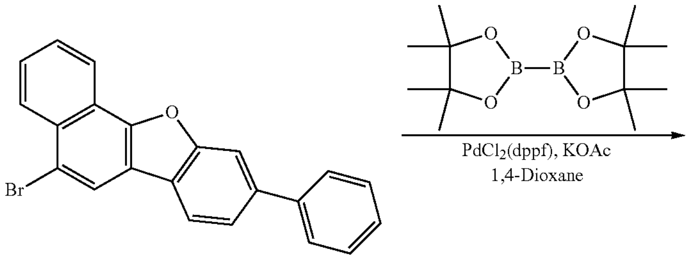
2-2-542
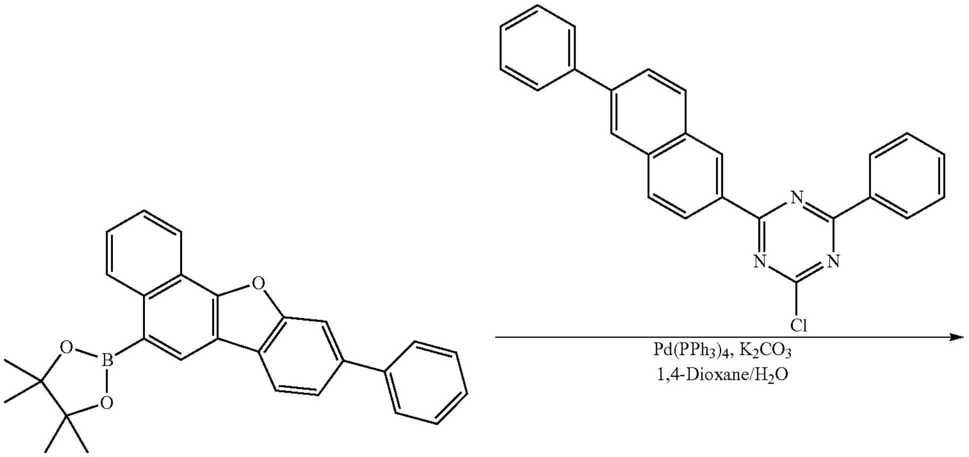
2-1-542

-continued

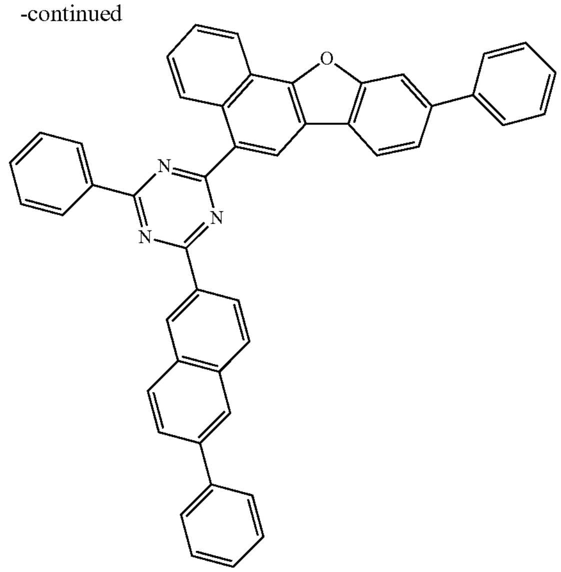

2-542

Preparation of Compound 2-3-542

9-Chloronaphtho[1,2-b]benzofuran (30.0 g, 118.7 mM), phenylboronic acid (18.8 g, 154.3 mM), Pd(dba) 2 (3.4 g, 5.9 mM), Sphos (4.9 g, 11.9 mM) and $K_2CO_3$ (32.8 g, 237.4 mM) were dissolved in 1,4-dioxane/$H_2O$ (300 ml/60 ml), and refluxed for 1 hour. The reaction material was purified by column chromatography (DCM:Hex-1:1), and recrystallized with methanol to obtain target Compound 2-3-542 (28.5 g, 81.6%).

Preparation of Compound 2-2-542

2-3-542 (28.0 g, 95.1 mM) was dissolved in DMF (300 ml), and after slowly introducing N-bromosuccinimide (17.8 g, 99.9 mM) thereto, the mixture was stirred for 1 hour at 80° C. $H_2O$ (200 ml) was introduced thereto to terminate the reaction, and the result was recrystallized with methanol to obtain target Compound 2-2-542 (32.1 g, 90.4%).

Preparation of Compound 2-1-542

2-2-542 (32.0 g, 85.7 mM), 4,4,4',4',5,5,5',5'-octamethyl-2,2'-bi(1,3,2-dioxaborolane) (32.7 g, 128.6 mM), $PdCl_2$(dppf) (3.1 g, 4.3 mM) and KOAc (21.0 g, 214.3 mM) were dissolved in 1,4-dioxane (350 ml), and refluxed for 1 hour. The reaction material was purified by column chromatography (DCM:Hex=1:1), and recrystallized with methanol to obtain target Compound 2-1-542 (27.0 g, 74.9%).

Preparation of Compound 2-542

2-1-337 (15.0 g, 35.7 mM), 2-chloro-4-phenyl-6-(6-phenylnaphthalen-2-yl)-1,3,5-triazine (14.1 g, 35.7 mM), $Pd(PPh_3)_4$ (2.1 g, 1.8 mM) and $K_2CO_3$ (14.8 g, 107.1 mM) were dissolved in 1,4-dioxane/$H_2O$ (200 ml/40 ml), and refluxed for 3 hours. The reaction material was recrystallized with methanol to obtain target Compound 2-542 (19.3 g, 82.9%).

[Preparation Example 9] Preparation of Compound 3-125

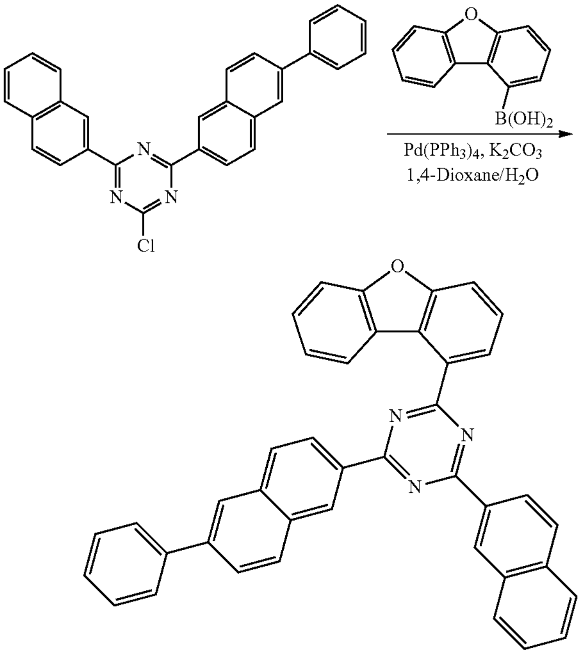

3-125

2-Chloro-4-(naphthalen-2-yl)-6-(6-phenylnaphthalen-2-yl)-1,3,5-triazine (10.0 g, 22.5 mM), dibenzo[b,d]furan-1-ylboronic acid (4.8 g, 22.5 mm), $Pd(PPh_3)_4$ (1.3 g, 1.1 mM) and $K_2CO_3$ (9.3 g, 67.5 mM) were dissolved in 1,4-dioxane/$H_2O$ (150 ml/30 ml), and refluxed for 3 hours. The reaction material was recrystallized with methanol to obtain target Compound 3-125 (10.4 g, 80.4%).

Target compounds were synthesized in the same manner as in Preparation Example 9 except that Intermediate A of the following Table 5 was used instead of 2-chloro-4-(naphthalen-2-yl)-6-(6-phenylnaphthalen-2-yl)-1,3,5-triazine, and Intermediate B of the following Table 5 was used instead of dibenzo[b,d]furan-1-ylboronic acid.
TABLE 5
| Compound No. | Intermediate A | Intermediate B | Target Compound | Yield |
|---|---|---|---|---|
| 3-125 | 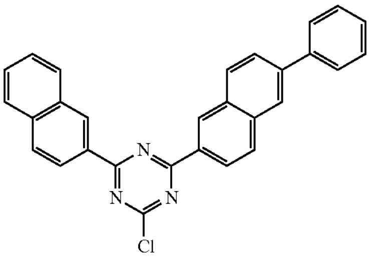 [SMILES: Clc1nc(-c2ccc3ccccc3c2)nc(-c2ccc3cc(-c4ccccc4)ccc3c2)n1] | 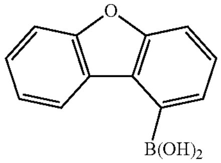 [SMILES: OB(O)c1cccc2oc3ccccc3c12] | 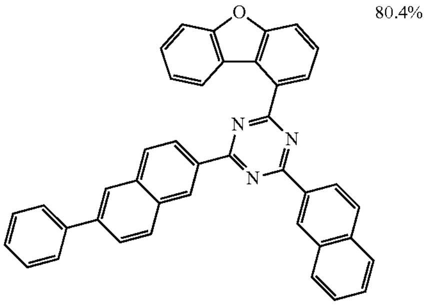 | 80.4% |
| 3-130 | 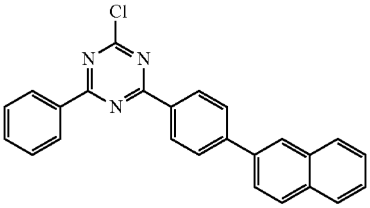 [SMILES: Clc1nc(-c2ccccc2)nc(-c2ccc(-c3ccc4ccccc4c3)cc2)n1] | 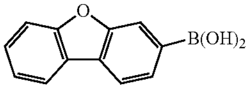 [SMILES: OB(O)c1ccc2c(c1)oc1ccccc12] | 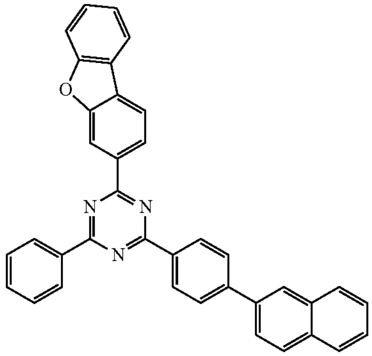 [SMILES: c1ccc(-c2nc(-c3ccc(-c4ccc5ccccc5c4)cc3)nc(-c3ccc4c(c3)oc3ccccc34)n2)cc1] | 79.1% |
| 3-138 | 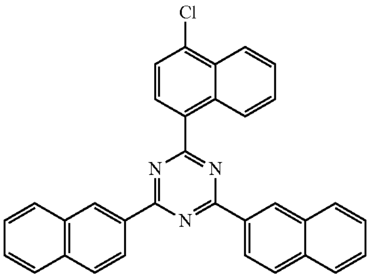 [SMILES: Clc1ccc(-c2nc(-c3ccc4ccccc4c3)nc(-c3ccc4ccccc4c3)n2)c2ccccc12] | 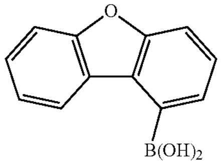 [SMILES: OB(O)c1cccc2oc3ccccc3c12] | 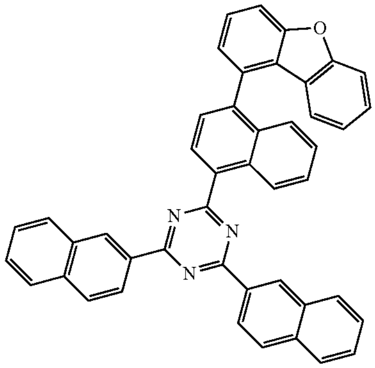 [SMILES: c1ccc2cc(-c3nc(-c4ccc5ccccc5c4)nc(-c4ccc(-c5cccc6oc7ccccc7c56)c5ccccc45)n3)ccc2c1] | 75.0% |

[Preparation Example 10] Preparation of Compound 2-561
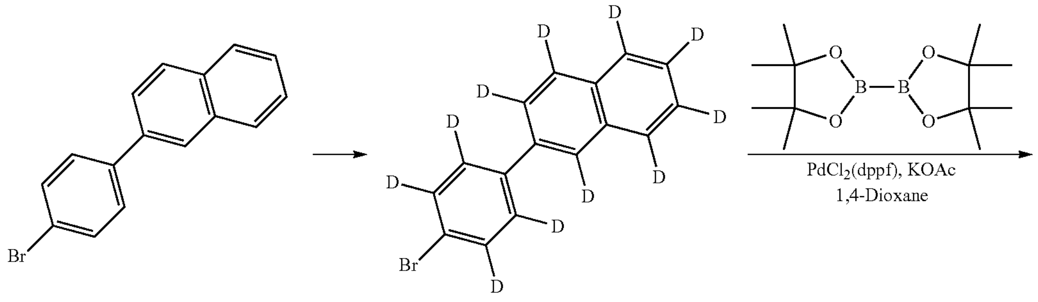
2-C1-561
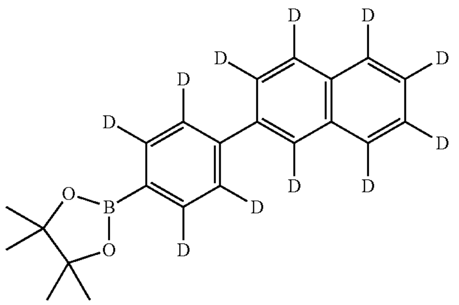
2-C-561
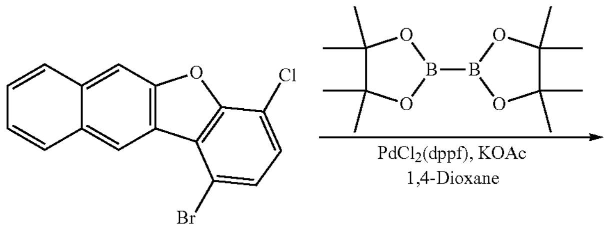
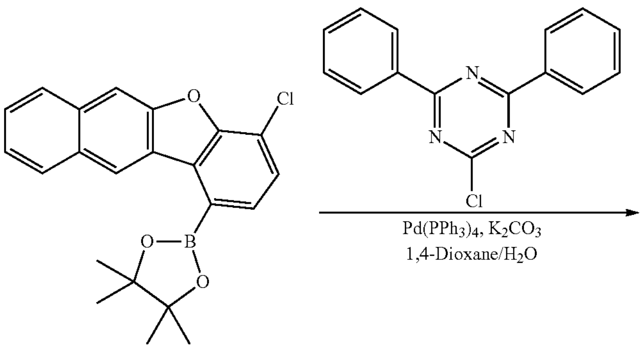
2-2-561

-continued

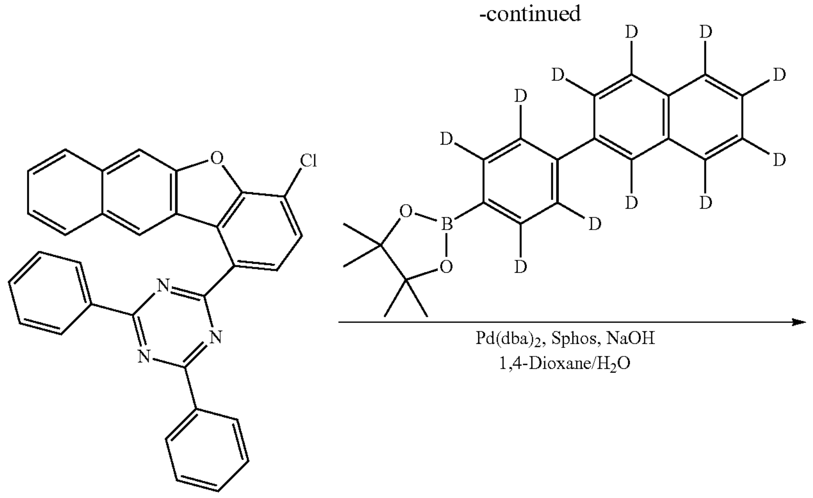

2-1-561

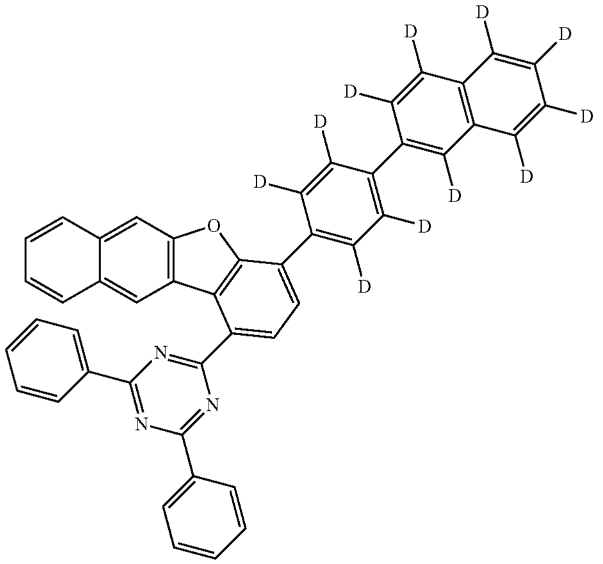

2-561

Preparation of Compound 2-C1-561

2-(4-Bromophenyl) naphthalene (30.0 g, 105.9 mM) and trifluoromethanesulfonic acid (60.8 ml, 688.4 mM) were dissolved in benzene-d6 (300 ml), and stirred for 1 hour at 60° C. Methanol (200 ml) was slowly added thereto to terminate the reaction, and the result was vacuum filtered. Target Compound 2-C1-561 (28.3 g, 90.8%) was obtained.

Preparation of Compound 2-C-561

2-C-561 (28.0 g, 95.2 mM), 4,4,4',4',5,5,5',5'-octamethyl-2,2'-bi(1,3,2-dioxaborolane) (36.3 g, 142.8 mM), $PdCl_2$ (dppf) (3.5 g, 4.8 mM) and KOAc (23.4 g, 238.0 mM) were dissolved in 1,4-dioxane (300 ml), and refluxed for 1 hour. The reaction material was purified by column chromatography (DCM:Hex=1:1), and recrystallized with methanol to obtain target Compound 2-C-561 (24.5 g, 75.4%).

Preparation of Compound 2-2-561

1-Bromo-4-chloronaphtho[2,3-b]benzofuran (30.0 g, 90.5 mM), 4,4,4',4',5,5,5',5'-octamethyl-2,2'-bi(1,3,2-dioxaborolane) (34.5 g, 135.8 mM), $PdCl_2$ (dppf) (3.3 g, 4.5 mM) and KOAc (22.2 g, 226.3 mM) were dissolved in 1,4-dioxane (300 ml), and refluxed for 1 hour. The reaction material was purified by column chromatography (DCM:Hex=1:1), and recrystallized with methanol to obtain target Compound 2-2-561 (27.8 g, 81.1%).

Preparation of Compound 2-1-561

2-2-561 (27.0 g, 71.3 mM), 2-chloro-4,6-diphenyl-1,3,5-triazine (21.0 g, 78.4 mM), $Pd(PPh_3)_4$ (4.2 g, 3.6 mM) and $K_2CO_3$ (24.6 g, 178.3 mM) were dissolved in 1,4-dioxane/$H_2O$ (300 ml/60 ml), and refluxed for 3 hours. The reaction material was recrystallized with methanol to obtain target Compound 2-1-561 (29.7 g, 86.1%).

Preparation of Compound 2-561

2-1-561 (15.0 g, 31.0 mM), 2-C-561 (11.1 g, 32.6 mM), Pd(dba) 2 (0.9 g, 1.6 mM), Sphos (1.3 g, 3.1 mM) and NaOH (3.7 g, 93.0 mM) were dissolved in 1,4-dioxane/$H_2O$ (200 ml/40 ml), and refluxed for 3 hours. The reaction material was recrystallized with methanol to obtain target Compound 2-561 (17.6 g, 85.8%).

[Preparation Example 11] Preparation of Compound 2-562
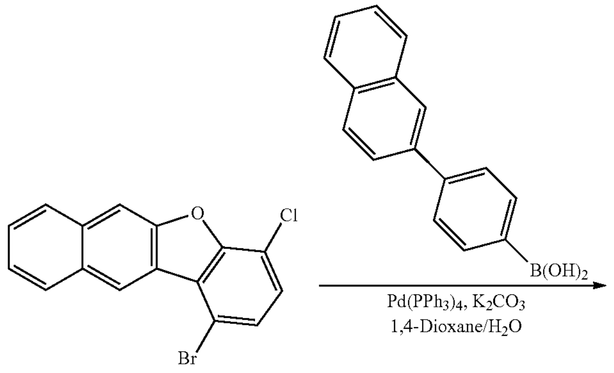
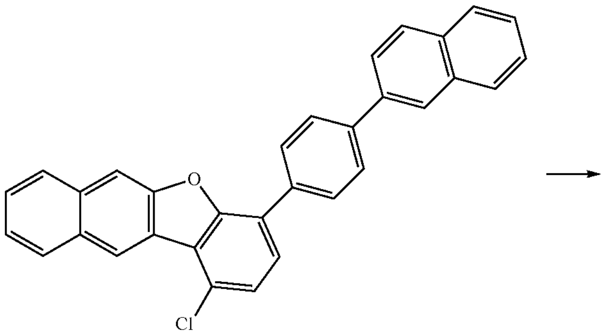
2-3-562
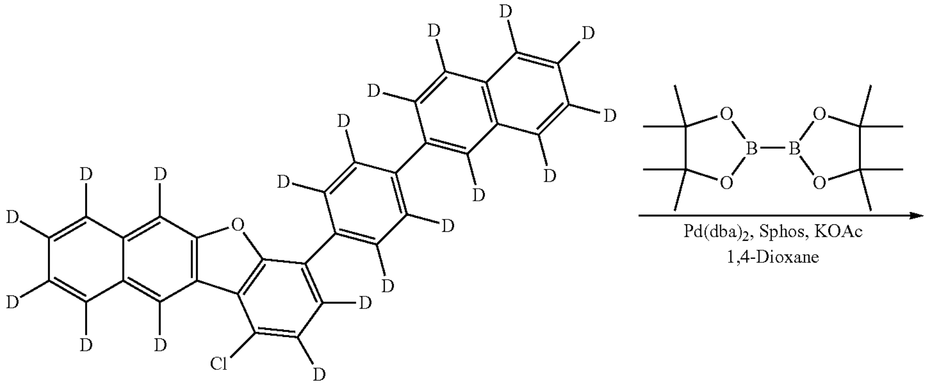
2-2-562

-continued

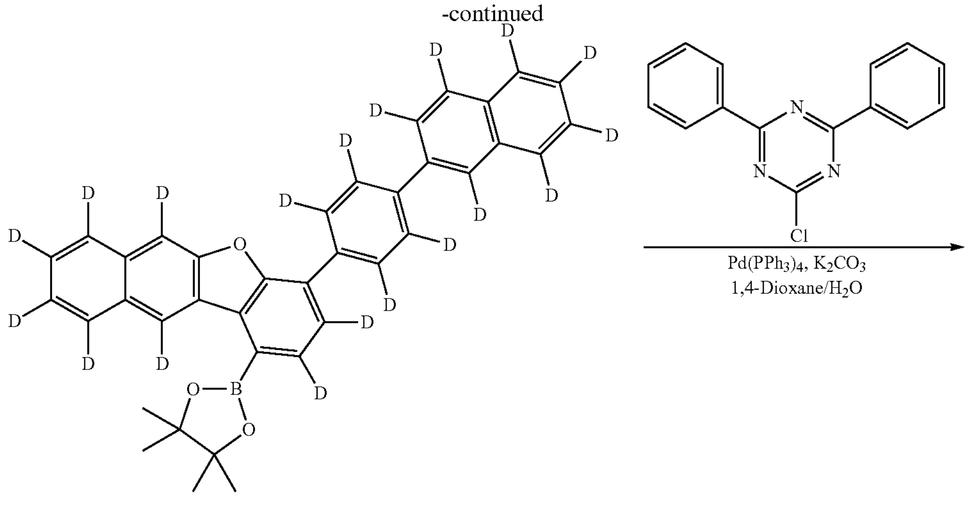

2-1-562

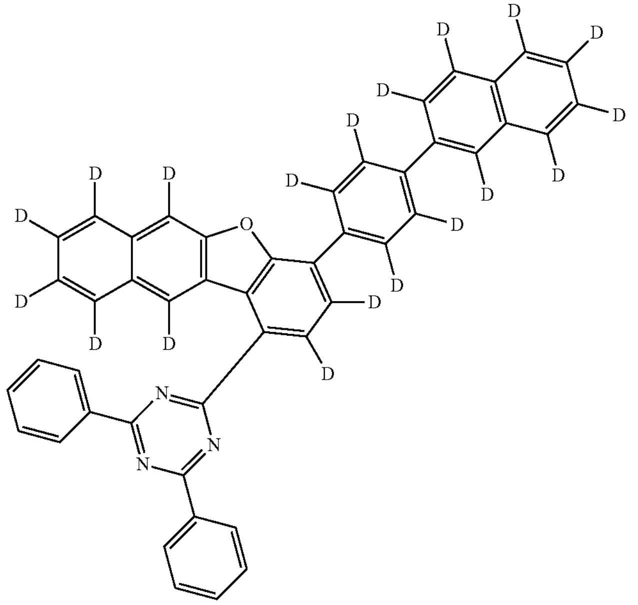

2-562

Preparation of Compound 2-3-562

4-Bromo-1-chloronaphtho[2,3-b]benzofuran (30.0 g, 90.5 mM), (4-(naphthalen-2-yl)phenyl)boronic acid (29.2 g, 117.7 mM), $Pd(PPh_3)_4$ (5.2 g, 4.5 mM) and $K_2CO_3$ (31.3 g, 226.3 mM) were dissolved in 1,4-dioxane/$H_2O$ (300 ml/60 ml), and refluxed for 3 hours. The reaction material was recrystallized with methanol to obtain target Compound 2-3-562 (35.5 g, 86.2%).

Preparation of Compound 2-2-562

2-3-562 (30.0 g, 65.9 mM) and trifluoromethanesulfonic acid (37.8 ml, 428.4 mM) were dissolved in benzene-d6 (300 ml), and stirred for 1 hour at 60° C. Methanol (200 ml) was slowly added thereto to terminate the reaction, and the result was vacuum filtered. Target Compound 2-2-562 (28.4 g, 90.9%) was obtained.

Preparation of Compound 2-1-562

2-2-562 (15.0 g, 31.6 mM), 4,4,4',4',5,5,5',5'-octamethyl-2,2'-bi(1,3,2-dioxaborolane) (12.0 g, 47.4 mM), Pd(dba) 2 (0.9 g, 1.6 mM), Sphos (1.3 g, 3.2 mM) and KOAc (7.8 g, 79.0 mM) were dissolved in 1,4-dioxane (150 ml), and refluxed for 1 hour. The reaction material was purified by column chromatography (DCM:Hex=1:1), and recrystallized with methanol to obtain target Compound 2-1-562 (13.5 g, 75.6%).

Preparation of Compound 2-562

2-1-562 (13.0 g, 23.0 mM), 2-chloro-4,6-diphenyl-1,3,5-triazine (6.2 g, 23.0 mM), $Pd(PPh_3)_4$ (1.4 g, 1.2 mM) and $K_2CO_3$ (9.5 g, 69.0 mM) were dissolved in 1,4-dioxane/$H_2O$ (200 ml/40 ml), and refluxed for 3 hours. The reaction material was recrystallized with methanol to obtain target Compound 2-562 (12.3 g, 79.6%).

[Preparation Example 12] Preparation of Compound 2-563

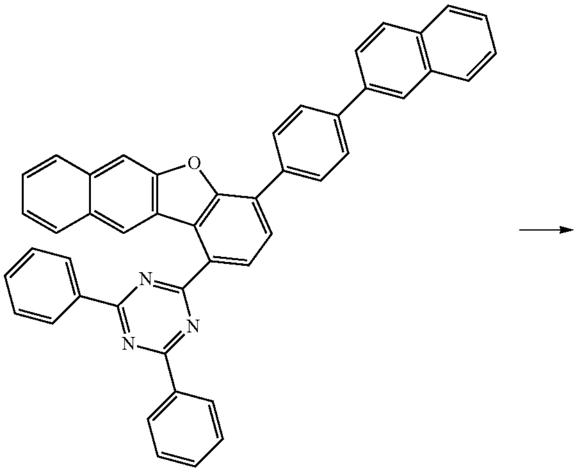

2-40

-continued

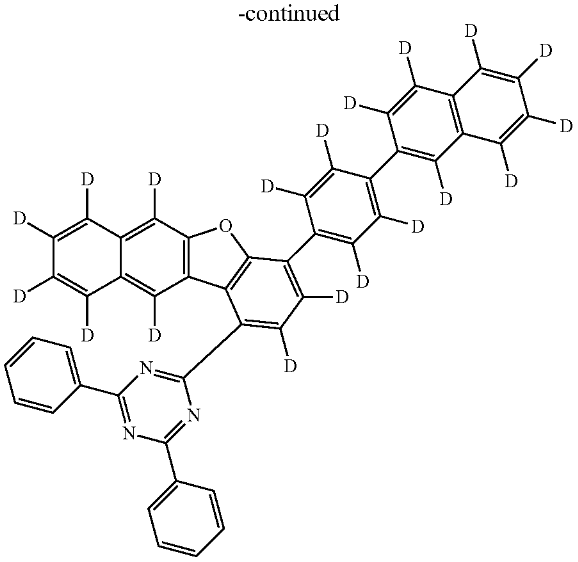

2-563

2-40 (10.0 g, 15.3 mM) and trifluoromethanesulfonic acid (8.8 ml, 99.5 mM) were dissolved in benzene-d6 (100 ml), and stirred for 1 hour at 60° C. Methanol (200 ml) was slowly added thereto to terminate the reaction, and the result was vacuum filtered. Target Compound 2-563 (9.3 g, 90.8%) was obtained.

Synthesis identification data for the compounds prepared above are as described in the following Tables 6 and 7.

TABLE 6

| Compound | FD-Mass | Compound | FD-Mass |
|---|---|---|---|
| 1-1 | m/z = 537.6620 (C40H27NO, 537.2093) | 1-2 | m/z = 537.6620 (C40H27NO, 537.2093) |
| 1-3 | m/z = 511.6240 (C38H25NO, 511.1936) | 1-4 | m/z = 511.6240 (C38H25NO, 511.1936) |
| 1-5 | m/z = 613.7600 (C46H31NO, 613.2406) | 1-6 | m/z = 613.7600 (C46H31NO, 613.2406) |
| 1-7 | m/z = 613.7600 (C46H31NO, 613.2406) | 1-8 | m/z = 587.7220 (C44H29NO, 587.2249) |
| 1-9 | m/z = 577.7270 (C43H31NO, 577.2406) | 1-10 | m/z = 653.8250 (C49H35NO, 653.2719) |
| 1-11 | m/z = 653.8250 (C49H35NO, 653.2719) | 1-12 | m/z = 627.7870 (C47H33NO, 627.2562) |
| 1-13 | m/z = 627.7870 (C47H33NO, 627.2562) | 1-14 | m/z = 693.8900 (C52H39NO, 693.3032) |
| 1-15 | m/z = 701.8690 (C53H35NO, 701.2719) | 1-16 | m/z = 777.9670 (C59H39NO, 777.3032) |
| 1-17 | m/z = 751.9290 (C57H37NO, 751.2875) | 1-18 | m/z = 699.8530 (C53H33NO, 699.2562) |
| 1-19 | m/z = 775.9510 (C59H37NO, 775.2875) | 1-20 | m/z = 587.7220 (C44H29NO, 587.2249) |
| 1-21 | m/z = 587.7220 (C44H29NO, 587.2249) | 1-22 | m/z = 703.8850 (C53H37NO, 703.2875) |
| 1-23 | m/z = 703.8850 (C53H37NO, 703.2875) | 1-24 | m/z = 627.7430 (C46H29NO2, 627.2198) |
| 1-25 | m/z = 627.7430 (C46H29NO2, 627.2198) | 1-26 | m/z = 627.7430 (C46H29NO2, 627.2198) |
| 1-27 | m/z = 703.8410 (C52H33NO2, 703.2511) | 1-28 | m/z = 627.7430 (C46H29NO2, 627.2198) |
| 1-29 | m/z = 627.7430 (C46H29NO2, 627.2198) | 1-30 | m/z = 627.7430 (C46H29NO2, 627.2198) |
| 1-31 | m/z = 613.7600 (C46H31NO, 613.2406) | 1-32 | m/z = 587.7220 (C44H29NO, 587.2249) |
| 1-33 | m/z = 653.8250 (C49H35NO, 653.2719) | 1-34 | m/z = 653.8250 (C49H35NO, 653.2719) |
| 1-35 | m/z = 653.8250 (C49H35NO, 653.2719) | 1-36 | m/z = 693.8900 (C52H39NO, 693.3032) |
| 1-37 | m/z = 703.8850 (C53H37NO, 703.2875) | 1-38 | m/z = 729.9230 (C55H39NO, 729.3032) |
| 1-39 | m/z = 729.9230 (C55H39NO, 729.3032) | 1-40 | m/z = 769.9880 (C58H43NO, 769.3345) |
| 1-41 | m/z = 743.9060 (C55H37NO2, 743.2824) | 1-42 | m/z = 759.9670 (C55H37NOS, 759.2596) |
| 1-43 | m/z = 743.9500 (C56H41NO, 743.3188) | 1-44 | m/z = 777.9670 (C59H39NO, 777.3032) |
| 1-45 | m/z = 751.9290 (C57H37NO, 751.2875) | 1-46 | m/z = 663.8200 (C50H33NO, 663.2562) |
| 1-47 | m/z = 663.8200 (C50H33NO, 663.2562) | 1-48 | m/z = 779.9830 (C59H41NO, 779.3188) |
| 1-49 | m/z = 613.7600 (C46H31NO, 613.2406) | 1-50 | m/z = 613.7600 (C46H31NO, 613.2406) |
| 1-51 | m/z = 587.7220 (C44H29NO, 587.2249) | 1-52 | m/z = 689.8580 (C52H35NO, 689.2719) |
| 1-53 | m/z = 689.8580 (C52H35NO, 689.2719) | 1-54 | m/z = 663.8200 (C50H33NO, 663.2562) |
| 1-55 | m/z = 653.8250 (C49H35NO, 653.2719) | 1-56 | m/z = 729.9230 (C55H39NO, 729.3032) |
| 1-57 | m/z = 729.9230 (C55H39NO, 729.3032) | 1-58 | m/z = 703.8850 (C53H37NO, 703.2875) |
| 1-59 | m/z = 769.9880 (C58H43NO, 769.3345) | 1-60 | m/z = 777.9670 (C59H39NO, 777.3032) |
| 1-61 | m/z = 663.8200 (C50H33NO, 663.2562) | 1-62 | m/z = 663.8200 (C50H33NO, 663.2562) |
| 1-63 | m/z = 779.9830 (C59H41NO, 779.3188) | 1-64 | m/z = 779.9830 (C59H41NO, 779.3188) |
| 1-65 | m/z = 703.8410 (C52H33NO2, 703.2511) | 1-66 | m/z = 703.8410 (C52H33NO2, 703.2511) |
| 1-67 | m/z = 779.9390 (C58H37NO2, 779.2824) | 1-68 | m/z = 703.8410 (C52H33NO2, 703.2511) |
| 1-69 | m/z = 689.8580 (C52H35NO, 689.2719) | 1-70 | m/z = 729.9230 (C55H39NO, 729.3032) |
| 1-71 | m/z = 719.9020 (C52H33NOS, 719.2283) | 1-72 | m/z = 729.9230 (C55H39NO, 729.3032) |
| 1-73 | m/z = 729.9230 (C55H39NO, 729.3032) | 1-74 | m/z = 769.9880 (C58H43NO, 769.3345) |

TABLE 6-continued

| Compound | FD-Mass | Compound | FD-Mass |
|---|---|---|---|
| 1-75 | m/z = 703.8850 (C53H37NO, 703.2875) | 1-76 | m/z = 753.9450 (C57H39NO, 753.3032) |
| 1-77 | m/z = 739.9180 (C56H37NO, 739.2875) | 1-78 | m/z = 739.9180 (C56H37NO, 739.2875) |
| 1-79 | m/z = 779.9830 (C59H41NO, 779.3188) | 1-80 | m/z = 769.9620 (C56H35NOS, 769.2439) |
| 1-81 | m/z = 713.8800 (C54H35NO, 713.2719) | 1-82 | m/z = 739.9180 (C56H37NO, 739.2875) |
| 1-83 | m/z = 537.6620 (C40H27NO, 537.2093) | 1-84 | m/z = 511.6240 (C38H25NO, 511.1936) |
| 1-85 | m/z = 613.7600 (C46H31NO, 613.2406) | 1-86 | m/z = 587.7220 (C44H29NO, 587.2249) |
| 1-87 | m/z = 577.7270 (C43H31NO, 577.2406) | 1-88 | m/z = 653.8250 (C49H35NO, 653.2719) |
| 1-89 | m/z = 627.7870 (C47H33NO, 627.2562) | 1-90 | m/z = 693.8900 (C52H39NO, 693.3032) |
| 1-91 | m/z = 701.8690 (C53H35NO, 701.2719) | 1-92 | m/z = 777.9670 (C59H39NO, 777.3032) |
| 1-93 | m/z = 699.8530 (C53H33NO, 699.2562) | 1-94 | m/z = 775.9510 (C59H37NO, 775.2875) |
| 1-95 | m/z = 587.7220 (C44H29NO, 587.2249) | 1-96 | m/z = 703.8850 (C53H37NO, 703.2875) |
| 1-97 | m/z = 627.7430 (C46H29NO2, 627.2198) | 1-98 | m/z = 643.8040 (C46H29NOS, 643.1970) |
| 1-99 | m/z = 643.8040 (C46H29NOS, 643.1970) | 1-100 | m/z = 613.7600 (C46H31NO, 613.2406) |
| 1-101 | m/z = 587.7220 (C44H29NO, 587.2249) | 1-102 | m/z = 653.8250 (C49H35NO, 653.2719) |
| 1-103 | m/z = 689.8580 (C52H35NO, 689.2719) | 1-104 | m/z = 719.9020 (C52H33NOS, 719.2283) |
| 1-105 | m/z = 729.9230 (C55H39NO, 729.3032) | 1-106 | m/z = 729.9230 (C55H39NO, 729.3032) |
| 1-107 | m/z = 703.8850 (C53H37NO, 703.2875) | 1-108 | m/z = 769.9880 (C58H43NO, 769.3345) |
| 1-109 | m/z = 769.9880 (C58H43NO, 769.3345) | 1-110 | m/z = 743.9500 (C56H41NO, 743.3188) |
| 1-111 | m/z = 777.9670 (C59H39NO, 777.3032) | 1-112 | m/z = 701.8690 (C53H35NO, 701.2719) |
| 1-113 | m/z = 777.9670 (C59H39NO, 777.3032) | 1-114 | m/z = 818.0320 (C62H43NO, 817.3345) |
| 1-115 | m/z = 613.7600 (C46H31NO, 613.2406) | 1-116 | m/z = 689.8580 (C52H35NO, 689.2719) |
| 1-117 | m/z = 729.9230 (C55H39NO, 729.3032) | 1-118 | m/z = 719.9020 (C52H33NOS, 719.2283) |
| 1-119 | m/z = 613.7600 (C46H31NO, 613.2406) | 1-120 | m/z = 689.8580 (C52H35NO, 689.2719) |
| 1-121 | m/z = 689.8580 (C52H35NO, 689.2719) | 1-122 | m/z = 765.9560 (C58H39NO, 765.3032) |
| 1-123 | m/z = 653.8250 (C49H35NO, 653.2719) | 1-124 | m/z = 703.8850 (C53H37NO, 703.2875) |
| 1-125 | m/z = 703.8850 (C53H37NO, 703.2875) | 1-126 | m/z = 729.9230 (C55H39NO, 729.3032) |
| 1-127 | m/z = 703.8850 (C53H37NO, 703.2875) | 1-128 | m/z = 703.8850 (C53H37NO, 703.2875) |
| 1-129 | m/z = 753.9450 (C57H39NO, 753.3032) | 1-130 | m/z = 729.9230 (C55H39NO, 729.3032) |
| 1-131 | m/z = 729.9230 (C55H39NO, 729.3032) | 1-132 | m/z = 805.0210 (C61H43NO, 805.3345) |
| 1-133 | m/z = 663.8200 (C50H33NO, 663.2562) | 1-134 | m/z = 663.8200 (C50H33NO, 663.2562) |
| 1-135 | m/z = 713.8800 (C54H35NO, 713.2719) | 1-136 | m/z = 779.9830 (C59H41NO, 779.3188) |
| 1-137 | m/z = 739.9180 (C56H37NO, 739.2875) | 1-138 | m/z = 779.9830 (C59H41NO, 779.3188) |
| 1-139 | m/z = 627.7430 (C46H29NO2, 627.2198) | 1-140 | m/z = 703.8410 (C52H33NO2, 703.2511) |
| 1-141 | m/z = 703.8410 (C52H33NO2, 703.2511) | 1-142 | m/z = 677.8030 (C50H31NO2, 677.2355) |
| 1-143 | m/z = 733.8850 (C52H31NO2S, 733.2075) | 1-144 | m/z = 717.8240 (C52H31NO3, 717.2304) |
| 1-145 | m/z = 703.8410 (C52H33NO2, 703.2511) | 1-146 | m/z = 703.8410 (C52H33NO2, 703.2511) |
| 1-147 | m/z = 753.9010 (C56H35NO2, 753.2668) | 1-148 | m/z = 753.9010 (C56H35NO2, 753.2668) |
| 1-149 | m/z = 779.9390 (C58H37NO2, 779.2824) | 1-150 | m/z = 779.9390 (C58H37NO2, 779.2824) |
| 1-151 | m/z = 626.7590 (C46H30N2O, 626.2358) | 1-152 | m/z = 702.8570 (C52H34N2O, 702.2671) |
| 1-153 | m/z = 626.7590 (C46H30N2O, 626.2358) | 1-154 | m/z = 702.8570 (C52H34N2O, 702.2671) |
| 1-155 | m/z = 676.8190 (C50H32N2O, 676.2515) | 1-156 | m/z = 676.8190 (C50H32N2O, 676.2515) |
| 1-157 | m/z = 626.7590 (C46H30N2O, 626.2358) | 1-158 | m/z = 702.8570 (C52H34N2O, 702.2671) |
| 1-159 | m/z = 702.8570 (C52H34N2O, 702.2671) | 1-160 | m/z = 742.9220 (C55H38N2O, 742.2984) |
| 1-161 | m/z = 626.7590 (C46H30N2O, 626.2358) | 1-162 | m/z = 676.8190 (C50H32N2O, 676.2515) |
| 1-163 | m/z = 702.8570 (C52H34N2O, 702.2671) | 1-164 | m/z = 702.8570 (C52H34N2O, 702.2671) |
| 1-165 | m/z = 702.8570 (C52H34N2O, 702.2671) | 1-166 | m/z = 626.7590 (C46H30N2O, 626.2358) |
| 1-167 | m/z = 702.8570 (C52H34N2O, 702.2671) | 1-168 | m/z = 676.8190 (C50H32N2O, 676.2515) |
| 1-169 | m/z = 693.8640 (C50H31NOS, 693.2126) | 1-170 | m/z = 677.8030 (C50H31NO2, 677.2355) |
| 1-171 | m/z = 677.8030 (C50H31NO2, 677.2355) | 1-172 | m/z = 677.8030 (C50H31NO2, 677.2355) |
| 1-173 | m/z = 693.8640 (C50H31NOS, 693.2126) | 1-174 | m/z = 703.8850 (C53H37NO, 703.2875) |
| 1-175 | m/z = 537.6620 (C40H27NO, 537.2093) | 1-176 | m/z = 587.7220 (C44H29NO, 587.2249) |
| 1-177 | m/z = 613.7600 (C46H31NO, 613.2406) | 1-178 | m/z = 653.8250 (C49H35NO, 653.2719) |
| 1-179 | m/z = 627.7430 (C46H29NO2, 627.2198) | 1-180 | m/z = 703.8410 (C52H33NO2, 703.2511) |
| 1-1S1 | m/z = 511.6240 (C38H25NO, 511.1936) | 1-182 | m/z = 587.7220 (C44H29NO, 587.2249) |
| 1-183 | m/z = 637.7820 (C48H31NO, 637.2406) | 1-184 | m/z = 627.7870 (C47H33NO, 627.2562) |
| 1-135 | m/z = 617.7660 (C44H27NOS, 617.1813) | 1-186 | m/z = 693.8640 (C50H31NOS, 693.2126) |
| 1-187 | m/z = 613.7600 (C46H31NO, 613.2406) | 1-188 | m/z = 663.8200 (C50H33NO, 663.2562) |
| 1-189 | m/z = 689.8580 (C52H35NO, 689.2719) | 1-190 | m/z = 729.9230 (C55H39NO, 729.3032) |
| 1-191 | m/z = 703.8410 (C52H33NO2, 703.2511) | 1-192 | m/z = 779.9390 (C58H37NO2, 779.2824) |
| 1-193 | m/z = 587.7220 (C44H29NO, 587.2249) | 1-194 | m/z = 663.8200 (C50H33NO, 663.2562) |
| 1-195 | m/z = 637.7820 (C48H31NO, 637.2406) | 1-196 | m/z = 713.8800 (C54H35NO, 713.2719) |
| 1-197 | m/z = 703.8850 (C53H37NO, 703.2875) | 1-198 | m/z = 677.8030 (C50H31NO2, 677.2355) |
| 1-199 | m/z = 577.7270 (C43H31NO, 577.2406) | 1-200 | m/z = 627.7870 (C47H33NO, 627.2562) |
| 1-201 | m/z = 703.8850 (C53H37NO, 703.2875) | 1-202 | m/z = 667.8080 (C49H33NO2, 667.2511) |
| 1-203 | m/z = 759.9670 (C55H37NOS, 759.2596) | 1-204 | m/z = 666.8240 (C49H34N2O, 666.2671) |
| 1-205 | m/z = 653.8250 (C49H35NO, 653.2719) | 1-206 | m/z = 703.8850 (C53H37NO, 703.2875) |
| 1-207 | m/z = 729.9230 (C55H39NO, 729.3032) | 1-208 | m/z = 779.9830 (C59H41NO, 779.3188) |
| 1-209 | m/z = 743.9060 (C55H37NO2, 743.2824) | 1-210 | m/z = 759.9670 (C55H37NOS, 759.2596) |
| 1-211 | m/z = 627.7870 (C47H33NO, 627.2562) | 1-212 | m/z = 627.7870 (C47H33NO, 627.2562) |
| 1-213 | m/z = 703.8850 (C53H37NO, 703.2875) | 1-214 | m/z = 677.8470 (C51H35NO, 677.2719) |
| 1-215 | m/z = 717.8680 (C53H35NO2, 717.2668) | 1-216 | m/z = 717.8680 (C53H35NO2, 717.2668) |
| 1-217 | m/z = 703.8850 (C53H37NO, 703.2875) | 1-218 | m/z = 703.8850 (C53H37NO, 703.2875) |
| 1-219 | m/z = 753.9450 (C57H39NO, 753.3032) | 1-220 | m/z = 779.9830 (C59H41NO, 779.3188) |
| 1-221 | m/z = 693.8900 (C52H39NO, 693.3032) | 1-222 | m/z = 769.9880 (C58H43NO, 769.3345) |
| 1-223 | m/z = 701.8690 (C53H35NO, 701.2719) | 1-224 | m/z = 777.9670 (C59H39NO, 777.3032) |
| 1-225 | m/z = 751.9290 (C57H37NO, 751.2875) | 1-226 | m/z = 751.9290 (C57H37NO, 751.2875) |
| 1-227 | m/z = 699.8530 (C53H33NO, 699.2562) | 1-228 | m/z = 775.9510 (C59H37NO, 775.2875) |
| 1-229 | m/z = 749.9130 (C57H35NO, 749.2719) | 1-230 | m/z = 587.7220 (C44H29NO, 587.2249) |

TABLE 6-continued

| Compound | FD-Mass | Compound | FD-Mass |
|---|---|---|---|
| 1-231 | m/z = 663.8200 (C50H33NO, 663.2562) | 1-232 | m/z = 677.8030 (C50H31NO2, 677.2355) |
| 1-233 | m/z = 693.8640 (C50H31NOS, 693.2126) | 1-234 | m/z = 703.8850 (C53H37NO, 703.2875) |
| 1-235 | m/z = 753.9010 (C56H35NO2, 753.2668) | 1-236 | m/z = 663.8200 (C50H33NO, 663.2562) |
| 1-237 | m/z = 663.8200 (C50H33NO, 663.2562) | 1-238 | m/z = 739.9180 (C56H37NO, 739.2875) |
| 1-239 | m/z = 587.7220 (C44H29NO, 587.2249) | 1-240 | m/z = 587.7220 (C44H29NO, 587.2249) |
| 1-241 | m/z = 551.6450 (C40H25NO2, 551.1885) | 1-242 | m/z = 601.7050 (C44H27NO2, 601.2042) |
| 1-243 | m/z = 627.7430 (C46H29NO2, 627.2198) | 1-244 | m/z = 641.7260 (C46H27NO3, 641.1991) |
| 1-245 | m/z = 657.7870 (C46H27NO2S, 657.1762) | 1-246 | m/z = 627.7430 (C46H29NO2, 627.2198) |
| 1-247 | m/z = 627.7430 (C46H29NO2, 627.2198) | 1-248 | m/z = 703.8410 (C52H33NO2, 703.2511) |
| 1-249 | m/z = 627.7430 (C46H29NO2, 627.2198) | 1-250 | m/z = 627.7430 (C46H29NO2, 627.2198) |
| 1-251 | m/z = 677.8030 (C50H31NO2, 677.2355) | 1-252 | m/z = 703.8410 (C52H33NO2, 703.2511) |
| 1-253 | m/z = 717.8240 (C52H31NO3, 717.2304) | 1-254 | m/z = 703.8410 (C52H33NO2, 703.2511) |
| 1-255 | m/z = 627.7430 (C46H29NO2, 627.2198) | 1-256 | m/z = 677.8030 (C50H31NO2, 677.2355) |
| 1-257 | m/z = 677.8030 (C50H31NO2, 677.2355) | 1-258 | m/z = 743.9060 (C55H37NO2, 743.2824) |
| 1-259 | m/z = 703.8410 (C52H33NO2, 703.2511) | 1-260 | m/z = 677.8030 (C50H31NO2, 677.2355) |
| 1-261 | m/z = 703.8410 (C52H33NO2, 703.2511) | 1-262 | m/z = 627.7430 (C46H29NO2, 627.2198) |
| 1-263 | m/z = 677.8030 (C50H31NO2, 677.2355) | 1-264 | m/z = 703.8410 (C52H33NO2, 703.2511) |
| 1-265 | m/z = 677.8030 (C50H31NO2, 677.2355) | 1-266 | m/z = 733.8850 (C52H31NO2S, 733.2075) |
| 1-267 | m/z = 703.8410 (C52H33NO2, 703.2511) | 1-268 | m/z = 567.7060 (C40H25NOS, 567.1657) |
| 1-269 | m/z = 643.8040 (C46H29NOS, 643.1970) | 1-270 | m/z = 719.9020 (C52H33NOS, 719.2283) |
| 1-271 | m/z = 537.6620 (C40H27NO, 537.2093) | 1-272 | m/z = 587.7220 (C44H29NO, 587.2249) |
| 1-273 | m/z = 613.7600 (C46H31NO, 613.2406) | 1-274 | m/z = 613.7600 (C46H31NO, 613.2406) |
| 1-275 | m/z = 663.8200 (C50H33NO, 663.2562) | 1-276 | m/z = 689.8580 (C52H35NO, 689.2719) |
| 1-277 | m/z = 703.8410 (C52H33NO2, 703.2511) | 1-278 | m/z = 613.7600 (C46H31NO, 613.2406) |
| 1-279 | m/z = 663.8200 (C50H33NO, 663.2562) | 1-280 | m/z = 653.8250 (C49H35NO, 653.2719) |
| 1-281 | m/z = 703.8850 (C53H37NO, 703.2875) | 1-282 | m/z = 703.8850 (C53H37NO, 703.2875) |
| 1-283 | m/z = 729.9230 (C55H39NO, 729.3032) | 1-284 | m/z = 769.9880 (C58H43NO, 769.3345) |
| 1-285 | m/z = 743.9060 (C55H37NO2, 743.2824) | 1-286 | m/z = 729.9230 (C55H39NO, 729.3032) |
| 1-287 | m/z = 729.9230 (C55H39NO, 729.3032) | 1-288 | m/z = 779.9830 (C59H41NO, 779.3188) |
| 1-289 | m/z = 663.8200 (C50H33NO, 663.2562) | 1-290 | m/z = 663.8200 (C50H33NO, 663.2562) |
| 1-291 | m/z = 739.9180 (C56H37NO, 739.2875) | 1-292 | m/z = 779.9830 (C59H41NO, 779.3188) |
| 1-293 | m/z = 777.9670 (C59H39NO, 777.3032) | 1-294 | m/z = 775.9510 (C59H37NO, 775.2875) |
| 1-295 | m/z = 587.7220 (C44H29NO, 587.2249) | 1-296 | m/z = 663.8200 (C50H33NO, 663.2562) |
| 1-297 | m/z = 739.9180 (C56H37NO, 739.2875) | 1-298 | m/z = 663.8200 (C50H33NO, 663.2562) |
| 1-299 | m/z = 587.7220 (C44H29NO, 587.2249) | 1-300 | m/z = 663.8200 (C50H33NO, 663.2562) |
| 1-301 | m/z = 663.8200 (C50H33NO, 663.2562) | 1-302 | m/z = 677.8030 (C50H31NO2, 677.2355) |
| 1-303 | m/z = 693.8640 (C50H31NOS, 693.2126) | 1-304 | m/z = 537.6620 (C40H27NO, 537.2093) |
| 1-305 | m/z = 587.7220 (C44H29NO, 587.2249) | 1-306 | m/z = 587.7220 (C44H29NO, 587.2249) |
| 1-307 | m/z = 613.7600 (C46H31NO, 613.2406) | 1-308 | m/z = 587.7220 (C44H29NO, 587.2249) |
| 1-309 | m/z = 663.8200 (C50H33NO, 663.2562) | 1-310 | m/z = 713.8800 (C54H35NO, 713.2719) |
| 1-311 | m/z = 739.9180 (C56H37NO, 739.2875) | 1-312 | m/z = 753.9010 (C56H35NO2, 753.2668) |
| 1-313 | m/z = 769.9620 (C56H35NOS, 769.2439) | 1-314 | m/z = 689.8580 (C52H35NO, 689.2719) |
| 1-315 | m/z = 739.9180 (C56H37NO, 739.2875) | 1-316 | m/z = 765.9560 (C58H39NO, 765.3032) |
| 1-317 | m/z = 689.8580 (C52H35NO, 689.2719) | 1-318 | m/z = 689.8580 (C52H35NO, 689.2719) |
| 1-319 | m/z = 689.8580 (C52H35NO, 689.2719) | 1-320 | m/z = 739.9180 (C56H37NO, 739.2875) |
| 1-321 | m/z = 627.7430 (C46H29NO2, 627.2198) | 1-322 | m/z = 627.7430 (C46H29NO2, 627.2198) |
| 1-323 | m/z = 677.8030 (C50H31NO2, 677.2355) | 1-324 | m/z = 703.8410 (C52H33NO2, 703.2511) |
| 1-325 | m/z = 703.8410 (C52H33NO2, 703.2511) | 1-326 | m/z = 753.9010 (C56H35NO2, 753.2668) |
| 1-327 | m/z = 779.9390 (C58H37NO2, 779.2824) | 1-328 | m/z = 703.8410 (C52H33NO2, 703.2511) |
| 1-329 | m/z = 703.8410 (C52H33NO2, 703.2511) | 1-330 | m/z = 753.9010 (C56H35NO2, 753.2668) |
| 1-331 | m/z = 627.7430 (C46H29NO2, 627.2198) | 1-332 | m/z = 677.8030 (C50H31NO2, 677.2355) |
| 1-333 | m/z = 703.8410 (C52H33NO2, 703.2511) | 1-334 | m/z = 733.8850 (C52H31NO2S, 733.2075) |
| 1-335 | m/z = 627.7430 (C46H29NO2, 627.2198) | 1-336 | m/z = 703.8410 (C52H33NO2, 703.2511) |
| 1-337 | m/z = 703.8410 (C52H33NO2, 703.2511) | 1-338 | m/z = 703.8410 (C52H33NO2, 703.2511) |
| 1-339 | m/z = 753.9010 (C56H35NO2, 753.2668) | 1-340 | m/z = 753.9010 (C56H35NO2, 753.2668) |
| 1-341 | m/z = 627.7430 (C46H29NO2, 627.2198) | 1-342 | m/z = 677.8030 (C50H31NO2, 677.2355) |
| 1-343 | m/z = 733.8850 (C52H31NO2S, 733.2075) | 1-344 | m/z = 703.8410 (C52H33NO2, 703.2511) |
| 1-345 | m/z = 677.8030 (C50H31NO2, 677.2355) | 1-346 | m/z = 627.7430 (C46H29NO2, 627.2198) |
| 1-347 | m/z = 677.8030 (C50H31NO2, 677.2355) | 1-348 | m/z = 703.8410 (C52H33NO2, 703.2511) |
| 1-349 | m/z = 753.9010 (C56H35NO2, 753.2668) | 1-350 | m/z = 627.7430 (C46H29NO2, 627.2198) |
| 1-351 | m/z = 677.8030 (C50H31NO2, 677.2355) | 1-352 | m/z = 703.8410 (C52H33NO2, 703.2511) |
| 1-353 | m/z = 743.9060 (C55H37NO2, 743.2824) | 1-354 | m/z = 703.8410 (C52H33NO2, 703.2511) |
| 1-355 | m/z = 703.8410 (C52H33NO2, 703.2511) | 1-356 | m/z = 753.9010 (C56H35NO2, 753.2668) |
| 1-357 | m/z = 779.9390 (C58H37NO2, 779.2824) | 1-358 | m/z = 643.8040 (C46H29NOS, 643.1970) |
| 1-359 | m/z = 693.8640 (C50H31NOS, 693.2126) | 1-360 | m/z = 719.9020 (C52H33NOS, 719.2283) |
| 1-361 | m/z = 759.9670 (C55H37NOS, 759.2596) | 1-362 | m/z = 719.9020 (C52H33NOS, 719.2283) |
| 1-363 | m/z = 537.6620 (C40H27NO, 537.2093) | 1-364 | m/z = 587.7220 (C44H29NO, 587.2249) |
| 1-365 | m/z = 613.7600 (C46H31NO, 613.2406) | 1-366 | m/z = 653.8250 (C49H35NO, 653.2719) |
| 1-367 | m/z = 613.7600 (C46H31NO, 613.2406) | 1-368 | m/z = 663.8200 (C50H33NO, 663.2562) |
| 1-369 | m/z = 587.7220 (C44H29NO, 587.2249) | 1-370 | m/z = 703.8850 (C53H37NO, 703.2875) |
| 1-371 | m/z = 587.7220 (C44H29NO, 587.2249) | 1-372 | m/z = 637.7820 (C48H31NO, 637.2406) |
| 1-373 | m/z = 703.8850 (C53H37NO, 703.2875) | 1-374 | m/z = 577.7270 (C43H31NO, 577.2406) |
| 1-375 | m/z = 627.7870 (C47H33NO, 627.2562) | 1-376 | m/z = 653.8250 (C49H35NO, 653.2719) |
| 1-377 | m/z = 683.8690 (C49H33NOS, 683.2283) | 1-378 | m/z = 693.8900 (C52H39NO, 693.3032) |
| 1-379 | m/z = 653.8250 (C49H35NO, 653.2719) | 1-380 | m/z = 703.8850 (C53H37NO, 703.2875) |
| 1-3S1 | m/z = 701.8690 (C53H35NO, 701.2719) | 1-382 | m/z = 777.9670 (C59H39NO, 777.3032) |
| 1-383 | m/z = 751.9290 (C57H37NO, 751.2875) | 1-384 | m/z = 777.9670 (C59H39NO, 777.3032) |
| 1-385 | m/z = 699.8530 (C53H33NO, 699.2562) | 1-386 | m/z = 699.8530 (C53H33NO, 699.2562) |

TABLE 6-continued

| Compound | FD-Mass | Compound | FD-Mass |
|---|---|---|---|
| 1-387 | m/z = 775.9510 (C59H37NO, 775.2875) | 1-388 | m/z = 775.9510 (C59H37NO, 775.2875) |
| 1-389 | m/z = 551.6450 (C40H25NO2, 551.1885) | 1-390 | m/z = 627.7430 (C46H29NO2, 627.2198) |
| 1-391 | m/z = 677.8030 (C50H31NO2, 677.2355) | 1-392 | m/z = 703.8410 (C52H33NO2, 703.2511) |
| 1-393 | m/z = 627.7430 (C46H29NO2, 627.2198) | 1-394 | m/z = 703.8410 (C52H33NO2, 703.2511) |
| 1-395 | m/z = 677.8030 (C50H31NO2, 677.2355) | 1-396 | m/z = 793.9220 (C58H35NO3, 793.2617) |
| 1-397 | m/z = 820.0040 (C61H41NO2, 819.3137) | 1-398 | m/z = 703.8410 (C52H33NO2, 703.2511) |
| 1-399 | m/z = 779.9390 (C58H37NO2, 779.2824) | 1-400 | m/z = 537.6620 (C40H27NO, 537.2093) |
| 1-401 | m/z = 613.7600 (C46H31NO, 613.2406) | 1-402 | m/z = 663.8200 (C50H33NO, 663.2562) |
| 1-403 | m/z = 689.8580 (C52H35NO, 689.2719) | 1-404 | m/z = 729.9230 (C55H39NO, 729.3032) |
| 1-405 | m/z = 689.8580 (C52H35NO, 689.2719) | 1-406 | m/z = 689.8580 (C52H35NO, 689.2719) |
| 1-407 | m/z = 739.9180 (C56H37NO, 739.2875) | 1-408 | m/z = 765.9560 (C58H39NO, 765.3032) |
| 1-409 | m/z = 663.8200 (C50H33NO, 663.2562) | 1-410 | m/z = 713.8800 (C54H35NO, 713.2719) |
| 1-411 | m/z = 779.9830 (C59H41NO, 779.3188) | 1-412 | m/z = 653.8250 (C49H35NO, 653.2719) |
| 1-413 | m/z = 703.8850 (C53H37NO, 703.2875) | 1-414 | m/z = 729.9230 (C55H39NO, 729.3032) |
| 1-415 | m/z = 703.8850 (C53H37NO, 703.2875) | 1-416 | m/z = 779.9830 (C59H41NO, 779.3188) |
| 1-417 | m/z = 729.9230 (C55H39NO, 729.3032) | 1-418 | m/z = 769.9880 (C58H43NO, 769.3345) |
| 1-419 | m/z = 743.9060 (C55H37NO2, 743.2824) | 1-420 | m/z = 743.9060 (C55H37NO2, 743.2824) |
| 1-421 | m/z = 627.7430 (C46H29NO2, 627.2198) | 1-422 | m/z = 703.8410 (C52H33NO2, 703.2511) |
| 1-423 | m/z = 703.8410 (C52H33NO2, 703.2511) | 1-424 | m/z = 703.8410 (C52H33NO2, 703.2511) |
| 1-425 | m/z = 753.9010 (C56H35NO2, 753.2668) | 1-426 | m/z = 779.9390 (C58H37NO2, 779.2824) |
| 1-427 | m/z = 627.7430 (C46H29NO2, 627.2198) | 1-428 | m/z = 703.8410 (C52H33NO2, 703.2511) |
| 1-429 | m/z = 703.8410 (C52H33NO2, 703.2511) | 1-430 | m/z = 627.7430 (C46H29NO2, 627.2198) |
| 1-431 | m/z = 743.9060 (C55H37NO2, 743.2824) | 1-432 | m/z = 703.8410 (C52H33NO2, 703.2511) |
| 1-433 | m/z = 702.8570 (C52H34N2O, 702.2671) | 1-434 | m/z = 702.8570 (C52H34N2O, 702.2671) |
| 1-435 | m/z = 702.8570 (C52H34N2O, 702.2671) | 1-436 | m/z = 643.8040 (C46H29NOS, 643.1970) |
| 1-437 | m/z = 719.9020 (C52H33NOS, 719.2283) | 1-438 | m/z = 663.8200 (C50H33NO, 663.2562) |
| 1-439 | m/z = 677.8030 (C50H31NO2, 677.2355) | 1-440 | m/z = 677.8030 (C50H31NO2, 677.2355) |
| 1-441 | m/z = 677.8030 (C50H31NO2, 677.2355) | 1-442 | m/z = 693.8640 (C50H31NOS, 693.2126) |
| 1-443 | m/z = 677.8030 (C50H31NO2, 677.2355) | 1-444 | m/z = 677.8030 (C50H31NO2, 677.2355) |
| 1-445 | m/z = 727.8630 (C54H33NO2, 727.2511) | 1-446 | m/z = 693.8640 (C50H31NOS, 693.2126) |
| 1-447 | m/z = 743.9240 (C54H33NOS, 743.2283) | 1-448 | m/z = 703.8850 (C53H37NO, 703.2875) |
| 1-449 | m/z = 703.8850 (C53H37NO, 703.2875) | 1-450 | m/z = 753.9450 (C57H39NO, 753.3032) |
| 1-451 | m/z = 461.5640 (C34H23NO, 461.1780) | 1-452 | m/z = 537.6620 (C40H27NO, 537.2093) |
| 1-453 | m/z = 537.6620 (C40H27NO, 537.2093) | 1-454 | m/z = 587.7220 (C44H29NO, 587.2249) |
| 1-455 | m/z = 613.7600 (C46H31NO, 613.2406) | 1-456 | m/z = 653.8250 (C49H35NO, 653.2719) |
| 1-457 | m/z = 637.7820 (C48H31NO, 637.2406) | 1-458 | m/z = 613.7600 (C46H31NO, 613.2406) |
| 1-459 | m/z = 739.9180 (C56H37NO, 739.2875) | 1-460 | m/z = 613.7600 (C46H31NO, 613.2406) |
| 1-461 | m/z = 663.8200 (C50H33NO, 663.2562) | 1-462 | m/z = 689.8580 (C52H35NO, 689.2719) |
| 1-463 | m/z = 577.7270 (C43H31NO, 577.2406) | 1-464 | m/z = 653.8250 (C49H35NO, 653.2719) |
| 1-465 | m/z = 693.8900 (C52H39NO, 693.3032) | 1-466 | m/z = 653.8250 (C49H35NO, 653.2719) |
| 1-467 | m/z = 693.8900 (C52H39NO, 693.3032) | 1-468 | m/z = 810.0530 (C61H47NO, 809.3658) |
| 1-469 | m/z = 587.7220 (C44H29NO, 587.2249) | 1-470 | m/z = 587.7220 (C44H29NO, 587.2249) |
| 1-471 | m/z = 663.8200 (C50H33NO, 663.2562) | 1-472 | m/z = 637.7820 (C48H31NO, 637.2406) |
| 1-473 | m/z = 663.8200 (C50H33NO, 663.2562) | 1-474 | m/z = 703.8850 (C53H37NO, 703.2875) |
| 1-475 | m/z = 677.8030 (C50H31NO2, 677.2355) | 1-476 | m/z = 693.8640 (C50H31NOS, 693.2126) |
| 1-477 | m/z = 587.7220 (C44H29NO, 587.2249) | 1-478 | m/z = 663.8200 (C50H33NO, 663.2562) |
| 1-479 | m/z = 663.8200 (C50H33NO, 663.2562) | 1-480 | m/z = 753.9010 (C56H35NO2, 753.2668) |
| 1-481 | m/z = 587.7220 (C44H29NO, 587.2249) | 1-482 | m/z = 663.8200 (C50H33NO, 663.3562) |
| 1-483 | m/z = 551.6450 (C40H25NO2, 551.1885) | 1-484 | m/z = 627.7430 (C46H29NO2, 627.2198) |
| 1-485 | m/z = 703.8410 (C52H33NO2, 703.2511) | 1-486 | m/z = 743.9060 (C55H37NO2, 743.2824) |
| 1-487 | m/z = 703.8410 (C52H33NO2, 703.2511) | 1-488 | m/z = 743.9060 (C55H37NO2, 743.2824) |
| 1-489 | m/z = 551.6450 (C40H25NO2, 551.1885) | 1-490 | m/z = 627.7430 (C46H29NO2, 627.2198) |
| 1-491 | m/z = 703.8410 (C52H33NO2, 703.2511) | 1-492 | m/z = 601.7050 (C44H27NO2, 601.2042) |
| 1-493 | m/z = 627.7430 (C46H29NO2, 627.2198) | 1-494 | m/z = 703.8410 (C52H33NO2, 703.2511) |
| 1-495 | m/z = 753.9010 (C56H35NO2, 753.2668) | 1-496 | m/z = 743.9060 (C55H37NO2, 743.2824) |
| 1-497 | m/z = 551.6450 (C40H25NO2, 551.1885) | 1-498 | m/z = 601.7050 (C44H27NO2, 601.2042) |
| 1-499 | m/z = 627.7430 (C46H29NO2, 627.2198) | 1-500 | m/z = 703.8410 (C52H33NO2, 703.2511) |
| 1-501 | m/z = 627.7430 (C46H29NO2, 627.2198) | 1-502 | m/z = 627.7430 (C46H29NO2, 627.2198) |
| 1-503 | m/z = 703.8410 (C52H33NO2, 703.2511) | 1-504 | m/z = 779.9390 (C58H37NO2, 779.2824) |
| 1-505 | m/z = 551.6450 (C40H25NO2, 551.1885) | 1-506 | m/z = 627.7430 (C46H29NO2, 627.2198) |
| 1-507 | m/z = 703.8410 (C52H33NO2, 703.2511) | 1-508 | m/z = 703.8410 (C52H33NO2, 703.2511) |
| 1-509 | m/z = 743.9060 (C55H37NO2, 743.2824) | 1-510 | m/z = 717.8240 (C52H31NO3, 717.2304) |
| 1-511 | m/z = 779.9390 (C58H37NO2, 779.2824) | 1-512 | m/z = 643.8040 (C46H29NOS, 643.1970) |
| 1-513 | m/z = 719.9020 (C52H33NOS, 719.2283) | 1-514 | m/z = 719.9020 (C52H33NOS, 719.2283) |
| 1-515 | m/z = 759.9670 (C55H37NOS, 759.2596) | 1-516 | m/z = 643.8040 (C46H29NOS, 643.1970) |
| 1-517 | m/z = 693.8640 (C50H31NOS, 693.2126) | 1-518 | m/z = 719.9020 (C52H33NOS, 719.2283) |
| 1-519 | m/z = 759.9670 (C55H37NOS, 759.2596) | 1-520 | m/z = 719.9020 (C52H33NOS, 719.2283) |
| 1-521 | m/z = 643.8040 (C46H29NOS, 643.1970) | 1-522 | m/z = 719.9020 (C52H33NOS, 719.2283) |
| 1-523 | m/z = 719.9020 (C52H33NOS, 719.2283) | 1-524 | m/z = 693.8640 (C50H31NOS, 693.2126) |
| 1-525 | m/z = 719.9020 (C52H33NOS, 719.2283) | 1-526 | m/z = 702.8570 (C52H34N2O, 702.2671) |
| 1-527 | m/z = 778.9550 (C58H38N2O, 778.2984) | 1-528 | m/z = 702.8570 (C52H34N2O, 702.2671) |
| 1-529 | m/z = 752.9170 (C56H36N2O, 752.2828) | 1-530 | m/z = 702.8570 (C52H34N2O, 702.2671) |
| 1-531 | m/z = 537.6620 (C40H27NO, 537.2093) | 1-532 | m/z = 613.7600 (C46H31NO, 613.2406) |
| 1-533 | m/z = 613.7600 (C46H31NO, 613.2406) | 1-534 | m/z = 663.8200 (C50H33NO, 663.2562) |
| 1-535 | m/z = 689.8580 (C52H35NO, 689.2719) | 1-536 | m/z = 719.9020 (C52H33NOS, 719.2283) |
| 1-537 | m/z = 703.8410 (C52H33NO2, 703.2511) | 1-538 | m/z = 689.8580 (C52H35NO, 689.2719) |
| 1-539 | m/z = 689.8580 (C52H35NO, 689.2719) | 1-540 | m/z = 739.9180 (C56H37NO, 739.2875) |
| 1-541 | m/z = 806.0210 (C61H43NO, 805.3345) | 1-542 | m/z = 689.8580 (C52H35NO, 689.2719) |

TABLE 6-continued

| Compound | FD-Mass | Compound | FD-Mass |
|---|---|---|---|
| 1-543 | m/z = 765.9560 (C58H39NO, 765.3032) | 1-544 | m/z = 587.7220 (C44H29NO, 587.2249) |
| 1-545 | m/z = 637.7820 (C48H31NO, 637.2406) | 1-546 | m/z = 703.8850 (C53H37NO, 703.2875) |
| 1-547 | m/z = 713.8800 (C54H35NO, 713.2719) | 1-548 | m/z = 663.8200 (C50H33NO, 663.2562) |
| 1-549 | m/z = 663.8200 (C50H33NO, 663.2562) | 1-550 | m/z = 739.9180 (C56H37NO, 739.2875) |
| 1-551 | m/z = 739.9180 (C56H37NO, 739.2875) | 1-552 | m/z = 663.8200 (C50H33NO, 663.2562) |
| 1-553 | m/z = 769.9620 (C56H35NOS, 769.2439) | 1-554 | m/z = 663.8200 (C50H33NO, 663.2562) |
| 1-555 | m/z = 739.9180 (C56H37NO, 739.2875) | 1-556 | m/z = 739.9180 (C56H37NO, 739.2875) |
| 1-557 | m/z = 753.9010 (C56H35NO2, 753.2668) | 1-558 | m/z = 653.8250 (C49H35NO, 653.2719) |
| 1-559 | m/z = 729.9230 (C55H39NO, 729.3032) | 1-560 | m/z = 729.9230 (C55H39NO, 729.3032) |
| 1-561 | m/z = 806.0210 (C61H43NO, 805.3345) | 1-562 | m/z = 779.9830 (C59H41NO, 779.3188) |
| 1-563 | m/z = 729.9230 (C55H39NO, 729.3032) | 1-564 | m/z = 769.9880 (C58H43NO, 769.3345) |
| 1-565 | m/z = 777.9670 (C59H39NO, 777.3032) | 1-566 | m/z = 775.9510 (C59H37NO, 775.2875) |
| 1-567 | m/z = 775.9510 (C59H37NO, 775.2875) | 1-568 | m/z = 627.7430 (C46H29NO2, 627.2198) |
| 1-569 | m/z = 703.8410 (C52H33NO2, 703.2511) | 1-570 | m/z = 703.8410 (C52H33NO2, 703.2511) |
| 1-571 | m/z = 677.8030 (C50H31NO2, 677.2355) | 1-572 | m/z = 793.9220 (C58H35NO3, 793.2617) |
| 1-573 | m/z = 793.9220 (C58H35NO3, 793.2617) | 1-574 | m/z = 703.8410 (C52H33NO2, 703.2511) |
| 1-575 | m/z = 753.9010 (C56H35NO2, 753.2668) | 1-576 | m/z = 703.8410 (C52H33NO2, 703.2511) |
| 1-577 | m/z = 779.9390 (C58H37NO2, 779.2824) | 1-578 | m/z = 627.7430 (C46H29NO2, 627.2198) |
| 1-579 | m/z = 703.8410 (C52H33NO2, 703.2511) | 1-580 | m/z = 753.9010 (C56H35NO2, 753.2668) |
| 1-5S1 | m/z = 743.9060 (C55H37NO2, 743.2824) | 1-582 | m/z = 703.8410 (C52H33NO2, 703.2511) |
| 1-583 | m/z = 779.9390 (C58H37NO2, 779.2824) | 1-584 | m/z = 627.7430 (C46H29NO2, 627.2198) |
| 1-535 | m/z = 677.8030 (C50H31NO2, 677.2355) | 1-586 | m/z = 703.8410 (C52H33NO2, 703.2511) |
| 1-587 | m/z = 743.9060 (C55H37NO2, 743.2824) | 1-588 | m/z = 703.8410 (C52H33NO2, 703.2511) |
| 1-589 | m/z = 779.9390 (C58H37NO2, 779.2824) | 1-590 | m/z = 779.9390 (C58H37NO2, 779.2824) |
| 1-591 | m/z = 753.9010 (C56H35NO2, 753.2668) | 1-592 | m/z = 627.7430 (C46H29NO2, 627.2198) |
| 1-593 | m/z = 703.8410 (C52H33NO2, 703.2511) | 1-594 | m/z = 779.9390 (C58H37NO2, 779.2824) |
| 1-595 | m/z = 733.8850 (C52H31NO2S, 733.2075) | 1-596 | m/z = 703.8410 (C52H33NO2, 703.2511) |
| 1-597 | m/z = 779.9390 (C58H37NO2, 779.2824) | 1-598 | m/z = 779.9390 (C58H37NO2, 779.2824) |
| 1-599 | m/z = 643.8040 (C46H29NOS, 643.1970) | 1-600 | m/z = 719.9020 (C52H33NOS, 719.2283) |
| 1-601 | m/z = 719.9020 (C52H33NOS, 719.2283) | 1-602 | m/z = 759.9670 (C55H37NOS, 759.2596) |
| 1-603 | m/z = 719.9020 (C52H33NOS, 719.2283) | 1-604 | m/z = 796.0000 (C58H37NOS, 795.2596) |
| 1-605 | m/z = 643.8040 (C46H29NOS, 643.1970) | 1-606 | m/z = 693.8640 (C50H31NOS, 693.2126) |
| 1-607 | m/z = 719.9020 (C52H33NOS, 719.2283) | 1-608 | m/z = 719.9020 (C52H33NOS, 719.2283) |
| 1-609 | m/z = 796.0000 (C58H37NOS, 795.2596) | 1-610 | m/z = 643.8040 (C46H29NOS, 643.1970) |
| 1-611 | m/z = 719.9020 (C52H33NOS, 719.2283) | 1-612 | m/z = 759.9670 (C55H37NOS, 759.2596) |
| 1-613 | m/z = 719.9020 (C52H33NOS, 719.2283) | 1-614 | m/z = 769.9620 (C56H35NOS, 769.2439) |
| 1-615 | m/z = 769.9620 (C56H35NOS, 769.2439) | 1-616 | m/z = 643.8040 (C46H29NOS, 643.1970) |
| 1-617 | m/z = 719.9020 (C52H33NOS, 719.2283) | 1-618 | m/z = 796.0000 (C58H37NOS, 795.2596) |
| 1-619 | m/z = 719.9020 (C52H33NOS, 719.2283) | 1-620 | m/z = 702.8570 (C52H34N2O, 702.2671) |
| 1-621 | m/z = 702.8570 (C52H34N2O, 702.2671) | 1-622 | m/z = 778.9550 (C58H38N2O, 778.2984) |
| 1-623 | m/z = 704.8730 (C52H36N2O, 704.2828) | 1-624 | m/z = 461.5640 (C34H23NO, 461.1780) |
| 1-625 | m/z = 537.6620 (C40H27NO, 537.2093) | 1-626 | m/z = 613.7600 (C46H31NO, 613.2406) |
| 1-627 | m/z = 587.7220 (C44H29NO, 587.2249) | 1-628 | m/z = 627.7430 (C46H29NO2, 627.2198) |
| 1-629 | m/z = 653.8250 (C49H35NO, 653.2719) | 1-630 | m/z = 613.7600 (C46H31NO, 613.2406) |
| 1-631 | m/z = 689.8580 (C52H35NO, 689.2719) | 1-632 | m/z = 703.8410 (C52H33NO2, 703.2511) |
| 1-633 | m/z = 613.7600 (C46H31NO, 613.2406) | 1-634 | m/z = 587.7220 (C44H29NO, 587.2249) |
| 1-635 | m/z = 663.8200 (C50H33NO, 663.2562) | 1-636 | m/z = 587.7220 (C44H29NO, 587.2249) |
| 1-637 | m/z = 703.8850 (C53H37NO, 703.2875) | 1-638 | m/z = 677.8030 (C50H31NO2, 677.2355) |
| 1-639 | m/z = 663.8200 (C50H33NO, 663.2562) | 1-640 | m/z = 587.7220 (C44H29NO, 587.2249) |
| 1-641 | m/z = 663.8200 (C50H33NO, 663.2562) | 1-642 | m/z = 677.8030 (C50H31NO2, 677.2355) |
| 1-643 | m/z = 577.7270 (C43H31NO, 577.2406) | 1-644 | m/z = 653.8250 (C49H35NO, 653.2719) |
| 1-645 | m/z = 653.8250 (C49H35NO, 653.2719) | 1-646 | m/z = 653.8250 (C49H35NO, 653.2719) |
| 1-647 | m/z = 627.7870 (C47H33NO, 627.2562) | 1-648 | m/z = 743.9060 (C55H37NO2, 743.2824) |
| 1-649 | m/z = 693.8900 (C52H39NO, 693.3032) | 1-650 | m/z = 743.9500 (C56H41NO, 743.3188) |
| 1-651 | m/z = 701.8690 (C53H35NO, 701.2719) | 1-652 | m/z = 751.9290 (C57H37NO, 751.2875) |
| 1-653 | m/z = 699.8530 (C53H33NO, 699.2562) | 1-654 | m/z = 775.9510 (C59H37NO, 775.2875) |
| 1-655 | m/z = 699.8530 (C53H33NO, 699.2562) | 1-656 | m/z = 789.9340 (C59H35NO2, 789.2668) |
| 1-657 | m/z = 551.6450 (C40H25NO2, 551.1885) | 1-658 | m/z = 627.7430 (C46H29NO2, 627.2198) |
| 1-659 | m/z = 703.8410 (C52H33NO2, 703.2511) | 1-660 | m/z = 677.8030 (C50H31NO2, 677.2355) |
| 1-661 | m/z = 743.9060 (C55H37NO2, 743.2824) | 1-662 | m/z = 717.8240 (C52H31NO3, 717.2304) |
| 1-663 | m/z = 703.8410 (C52H33NO2, 703.2511) | 1-664 | m/z = 703.8410 (C52H33NO2, 703.2511) |
| 1-665 | m/z = 753.9010 (C56H35NO2, 753.2668) | 1-666 | m/z = 743.9060 (C55H37NO2, 743.2824) |
| 1-667 | m/z = 551.6450 (C40H25NO2, 551.1885) | 1-668 | m/z = 627.7430 (C46H29NO2, 627.2198) |
| 1-669 | m/z = 677.8030 (C50H31NO2, 677.2355) | 1-670 | m/z = 703.8410 (C52H33NO2, 703.2511) |
| 1-671 | m/z = 667.8080 (C49H33NO2, 667.2511) | 1-672 | m/z = 657.7870 (C46H27NO2S, 657.1762) |
| 1-673 | m/z = 627.7430 (C46H29NO2, 627.2198) | 1-674 | m/z = 703.8410 (C52H33NO2, 703.2511) |
| 1-675 | m/z = 703.8410 (C52H33NO2, 703.2511) | 1-676 | m/z = 743.9060 (C55H37NO2, 743.2824) |
| 1-677 | m/z = 551.6450 (C40H25NO2, 551.1885) | 1-678 | m/z = 627.7430 (C46H29NO2, 627.2198) |
| 1-679 | m/z = 703.8410 (C52H33NO2, 703.2511) | 1-680 | m/z = 717.8240 (C52H31NO3, 717.2304) |
| 1-681 | m/z = 627.7430 (C46H29NO2, 627.2198) | 1-682 | m/z = 703.8410 (C52H33NO2, 703.2511) |
| 1-683 | m/z = 677.8030 (C50H31NO2, 677.2355) | 1-684 | m/z = 703.8410 (C52H33NO2, 703.2511) |
| 1-685 | m/z = 551.6450 (C40H25NO2, 551.1885) | 1-686 | m/z = 627.7430 (C46H29NO2, 627.2198) |
| 1-687 | m/z = 703.8410 (C52H33NO2, 703.2511) | 1-688 | m/z = 717.8240 (C52H31NO3, 717.2304) |
| 1-689 | m/z = 627.7430 (C46H29NO2, 627.2198) | 1-690 | m/z = 677.8030 (C50H31NO2, 677.2355) |
| 1-691 | m/z = 703.8410 (C52H33NO2, 703.2511) | 1-692 | m/z = 703.8410 (C52H33NO2, 703.2511) |
| 1-693 | m/z = 567.7060 (C40H25NOS, 567.1657) | 1-694 | m/z = 617.7660 (C44H27NOS, 617.1813) |
| 1-695 | m/z = 643.8040 (C46H29NOS, 643.1970) | 1-696 | m/z = 733.8850 (C52H31NO2S, 733.2075) |
| 1-697 | m/z = 643.8040 (C46H29NOS, 643.1970) | 1-698 | m/z = 567.7060 (C40H25NOS, 567.1657) |

TABLE 6-continued

| Compound | FD-Mass | Compound | FD-Mass |
|---|---|---|---|
| 1-699 | m/z = 643.8040 (C46H29NOS, 643.1970) | 1-700 | m/z = 749.9460 (C52H31NOS2, 749.1847) |
| 1-701 | m/z = 643.8040 (C46H29NOS, 643.1970) | 1-702 | m/z = 643.8040 (C46H29NOS, 643.1970) |
| 1-703 | m/z = 617.7660 (C44H27NOS, 617.1813) | 1-704 | m/z = 567.7060 (C40H25NOS, 567.1657) |
| 1-705 | m/z = 643.8040 (C46H29NOS, 643.1970) | 1-706 | m/z = 719.9020 (C52H33NOS, 719.2283) |
| 1-707 | m/z = 626.7590 (C46H30N2O, 626.2358) | 1-708 | m/z = 676.8190 (C50H32N2O, 676.2515) |
| 1-709 | m/z = 742.9220 (C55H38N2O, 742.2984) | 1-710 | m/z = 732.9010 (C52H32N2OS, 732.2235) |
| 1-711 | m/z = 626.7590 (C46H30N2O, 626.2358) | 1-712 | m/z = 716.8400 (C52H32N2O2, 716.2464) |
| 1-713 | m/z = 778.9550 (C58H38N2O, 778.2984) | 1-714 | m/z = 626.7590 (C46H30N2O, 626.2358) |
| 1-715 | m/z = 537.6620 (C40H27NO, 537.2093) | 1-716 | m/z = 613.7600 (C46H31NO, 613.2406) |
| 1-717 | m/z = 653.8250 (C49H35NO, 653.2719) | 1-718 | m/z = 613.7600 (C46H31NO, 613.2406) |
| 1-719 | m/z = 613.7600 (C46H31NO, 613.2406) | 1-720 | m/z = 663.8200 (C50H33NO, 663.2562) |
| 1-721 | m/z = 689.8580 (C52H35NO, 689.2719) | 1-722 | m/z = 729.9230 (C55H39NO, 729.3032) |
| 1-723 | m/z = 689.8580 (C52H35NO, 689.2719) | 1-724 | m/z = 689.8580 (C52H35NO, 689.2719) |
| 1-725 | m/z = 689.8580 (C52H35NO, 689.2719) | 1-726 | m/z = 739.9180 (C56H37NO, 739.2875) |
| 1-727 | m/z = 806.0210 (C61H43NO, 805.3345) | 1-728 | m/z = 663.8200 (C50H33NO, 663.2562) |
| 1-729 | m/z = 663.8200 (C50H33NO, 663.2562) | 1-730 | m/z = 713.8800 (C54H35NO, 713.2719) |
| 1-731 | m/z = 753.9010 (C56H35NO2, 753.2668) | 1-732 | m/z = 779.9830 (C59H41NO, 779.3188) |
| 1-733 | m/z = 663.8200 (C50H33NO, 663.2562) | 1-734 | m/z = 739.9180 (C56H37NO, 739.2875) |
| 1-735 | m/z = 713.8800 (C54H35NO, 713.2719) | 1-736 | m/z = 739.9180 (C56H37NO, 739.2875) |
| 1-737 | m/z = 703.8850 (C53H37NO, 703.2875) | 1-738 | m/z = 753.9450 (C57H39NO, 753.3032) |
| 1-739 | m/z = 587.7220 (C44H29NO, 587.2249) | 1-740 | m/z = 663.8200 (C50H33NO, 663.2562) |
| 1-741 | m/z = 663.8200 (C50H33NO, 663.2562) | 1-742 | m/z = 703.8850 (C53H37NO, 703.2875) |
| 1-743 | m/z = 769.9620 (C56H35NOS, 769.2439) | 1-744 | m/z = 663.8200 (C50H33NO, 663.2562) |
| 1-745 | m/z = 653.8250 (C49H35NO, 653.2719) | 1-746 | m/z = 729.9230 (C55H39NO, 729.3032) |
| 1-747 | m/z = 703.8850 (C53H37NO, 703.2875) | 1-748 | m/z = 729.9230 (C55H39NO, 729.3032) |
| 1-749 | m/z = 769.9880 (C58H43NO, 769.3345) | 1-750 | m/z = 820.0480 (C62H45NO, 819.3501) |
| 1-751 | m/z = 777.9670 (C59H39NO, 777.3032) | 1-752 | m/z = 775.9510 (C59H37NO, 775.2875) |
| 1-753 | m/z = 775.9510 (C59H37NO, 775.2875) | 1-754 | m/z = 775.9510 (C59H37NO, 775.2875) |
| 1-755 | m/z = 627.7430 (C46H29NO2, 627.2198) | 1-756 | m/z = 703.8410 (C52H33NO2, 703.2511) |
| 1-757 | m/z = 753.9010 (C56H35NO2, 753.2668) | 1-758 | m/z = 733.8850 (C52H31NO2S, 733.2075) |
| 1-759 | m/z = 703.8410 (C52H33NO2, 703.2511) | 1-760 | m/z = 753.9010 (C56H35NO2, 753.2668) |
| 1-761 | m/z = 779.9390 (C58H37NO2, 779.2824) | 1-762 | m/z = 627.7430 (C46H29NO2, 627.2198) |
| 1-763 | m/z = 703.8410 (C52H33NO2, 703.2511) | 1-764 | m/z = 717.8240 (C52H31NO3, 717.2304) |
| 1-765 | m/z = 779.9390 (C58H37NO2, 779.2824) | 1-766 | m/z = 703.8410 (C52H33NO2, 703.2511) |
| 1-767 | m/z = 627.7430 (C46H29NO2, 627.2198) | 1-768 | m/z = 677.8030 (C50H31NO2, 677.2355) |
| 1-769 | m/z = 703.8410 (C52H33NO2, 703.2511) | 1-770 | m/z = 733.8850 (C52H31NO2S, 733.2075) |
| 1-771 | m/z = 703.8410 (C52H33NO2, 703.2511) | 1-772 | m/z = 627.7430 (C46H29NO2, 627.2198) |
| 1-773 | m/z = 703.8410 (C52H33NO2, 703.2511) | 1-774 | m/z = 703.8410 (C52H33NO2, 703.2511) |
| 1-775 | m/z = 743.9060 (C55H37NO2, 743.2824) | 1-776 | m/z = 703.8410 (C52H33NO2, 703.2511) |
| 1-777 | m/z = 753.9010 (C56H35NO2, 753.2663) | 1-778 | m/z = 779.9390 (C58H37NO2, 779.2824) |
| 1-779 | m/z = 643.8040 (C46H29NOS, 643.1970) | 1-780 | m/z = 719.9020 (C52H33NOS, 719.2283) |
| 1-731 | m/z = 769.9620 (C56H35NOS, 769.2439) | 1-782 | m/z = 719.9020 (C52H33NOS, 719.2283) |
| 1-7S3 | m/z = 643.8040 (C46H29NOS, 643.1970) | 1-784 | m/z = 719.9020 (C52H33NOS, 719.2283) |
| 1-735 | m/z = 693.8640 (C50H31NOS, 693.2126) | 1-786 | m/z = 643.8040 (C46H29NOS, 643.1970) |
| 1-787 | m/z = 759.9670 (C55H37NOS, 759.2596) | 1-788 | m/z = 719.9020 (C52H33NOS, 719.2283) |
| 1-739 | m/z = 719.9020 (C52H33NOS, 719.2283) | 1-790 | m/z = 702.8570 (C52H34N2O, 702.2671) |
| 1-791 | m/z = 752.9170 (C56H36N2O, 752.2828) | 1-792 | m/z = 702.8570 (C52H34N2O, 702.2671) |
| 1-793 | m/z = 778.9550 (C58H38N2O, 778.2984) | 1-794 | m/z = 702.8570 (C52H34N2O, 702.2671) |
| 1-795 | m/z = 677.8030 (C50H31NO2, 677.2355) | 1-796 | m/z = 677.8030 (C50H31NO2, 677.2355) |
| 1-797 | m/z = 677.8030 (C50H31NO2, 677.2355) | 1-798 | m/z = 703.8850 (C53H37NO, 703.2875) |
| 1-799 | m/z = 677.8030 (C50H31NO2, 677.2355) | 1-800 | m/z = 693.8640 (C50H31NOS, 693.2126) |
| 1-801 | m/z = 677.8030 (C50H31NO2, 677.2355) | 1-802 | m/z = 727.8630 (C54H33NO2, 727.2511) |
| 1-803 | m/z = 677.8030 (C50H31NO2, 677.2355) | 1-804 | m/z = 703.8850 (C53H37NO, 703.2875) |
| 1-805 | m/z = 618.7905 (C46H26D5NO, 618.2719) | 1-806 | m/z = 592.7525 (C44H24D5NO, 592.2563) |
| 1-807 | m/z = 668.8505 (C50H28D5NO, 668.2876) | 1-808 | m/z = 658.8555 (C49H30D5NO, 658.3032) |
| 1-809 | m/z = 564.8267 (C40D27NO, 564.3787) | 1-810 | m/z = 616.8990 (C44D29NO, 616.4069) |
| 1-811 | m/z = 697.0214 (C50D33NO, 696.4633) | 1-812 | m/z = 656.92 00 (C46D29NO2, 65 6.4019) |
| 1-813 | m/z = 618.7905 (C46H26D5NO, 618.2719) | 1-814 | m/z = 623.8210 (C46H21D10NO, 623.8210) |
| 1-815 | m/z = 642.8125 (C48H26D5NO, 642.2719) | 1-816 | m/z = 734.9535 (C55H34D5NO, 734.3345) |
| 1-817 | m/z = 667.9651 (C48D30NO, 667.4289) | 1-818 | m/z = 618.7905 (C46H26D5NO, 618.2719) |
| 1-819 | m/z = 648.8345 (C46H24D5NOS, 648.2284) | 1-820 | m/z = 618.7905 (C46H26D5NO, 618.2719) |
| 1-821 | m/z = 653.8650 (C46H19D10NOS, 653.2598) | 1-822 | m/z = 632.7735 (C46H24D5NO2, 632.2512) |
| 1-823 | m/z = 708.8715 (C52H28D5NO2, 708.2825) | 1-824 | m/z = 713.9020 (C52H23D10NO2, 713.3139) |
| 1-825 | m/z = 658.8555 (C49H30D5NO, 658.3032) | 1-826 | m/z = 734.9535 (C55H34D5NO, 734.3345) |
| 1-827 | m/z = 663.8860 (C49H25D10NO, 663.3346) | 1-828 | m/z = 648.8711 (C46H8D21NO2, 648.3516) |
| 1-829 | m/z = 564.8267 (C40D27NO, 564.3787) | 1-830 | m/z = 656.9200 (C46D29NO2, 656.4019) |
| 1-831 | m/z = 668.9712 (C48D31NO, 668.4351) | 1-832 | m/z = 737.0424 (C52D33NO2, 736.4583) |
| 1-833 | m/z = 542.6925 (C40H22D5NO, 542.2406) | 1-834 | m/z = 618.7905 (C46H26D5NO, 618.2719) |
| 1-835 | m/z = 658.8555 (C49H30D5NO, 658.3032) | 1-836 | m/z = 708.9155 (C53H32D5NO, 708.3189) |
| 1-837 | m/z = 658.8555 (C49H30D5NO, 658.3032) | 1-838 | m/z = 707.8875 (C52H29D5N2O, 707.2985) |
| 1-839 | m/z = 564.8267 (C40D27NO, 564.3787) | 1-840 | m/z = 616.8990 (C44D29NO, 616.4069) |
| 1-841 | m/z = 618.7905 (C46H26D5NO, 618.2719) | 1-842 | m/z = 668.8505 (C50H28D5NO, 668.2876) |
| 1-843 | m/z = 694.8885 (C52H30D5NO, 694.3032) | 1-844 | m/z = 658.8555 (C49H30D5NO, 658.3032) |
| 1-845 | m/z = 734.9535 (C55H34D5NO, 734.3345) | 1-846 | m/z = 632.7735 (C46H24D5NO2, 632.2512) |
| 1-847 | m/z = 636.9003 (C46H8D23NO, 636.3849) | 1-848 | m/z = 724.9325 (C52H28D5NOS, 724.2597) |
| 1-849 | m/z = 644.9492 (C46D31NO, 644.4351) | 1-850 | m/z = 616.8990 (C44D29NO, 616.4069) |
| 1-851 | m/z = 737.0645 (C52D34N2O, 736.48025) | 1-852 | m/z = 672.9810 (C46D29NOS, 672.3790) |
| 1-853 | m/z = 644.9492 (C46D31NO, 644.4351) | 1-854 | m/z = 689.0386 (C49D35NO, 688.4916) |

TABLE 6-continued

| Compound | FD-Mass | Compound | FD-Mass |
|---|---|---|---|
| 1-855 | m/z = 725.0716 (C52D35NO, 724.4916) | 1-856 | m/z = 769.1610 (C55D39NO, 768.5480) |
| 1-857 | m/z = 813.1768 (C59D37NO, 812.5198) | 1-858 | m/z = 817.2050 (C59D39NO, 816.5480) |
| 1-859 | m/z = 733.1280 (C52D39NO, 732.5480) | 1-860 | m/z = 769.1610 (C55D39NO, 768.5480) |
| 1-861 | m/z = 733.1280 (C52D39NO, 732.5480) | 1-862 | m/z = 689.0386 (C49D35NO, 688.4916) |
| 1-863 | m/z = 644.9492 (C46D31NO, 644.4351) | 1-864 | m/z = 781.1318 (C55D37NO2, 780.5147) |
| 1-865 | m/z = 737.0424 (C52D33NO2, 736.4583) | 1-866 | m/z = 769.1610 (C55D39NO, 768.5480) |
| 1-867 | m/z = 701.0094 (C49D33NO2, 700.4583) | 1-868 | m/z = 725.0716 (C52D35NO, 724.4916) |
| 1-869 | m/z = 644.9492 (C46D31NO, 644.4351) | 1-870 | m/z = 725.0716 (C52D35NO, 724.4916) |
| 1-871 | m/z = 672.9810 (C46D29NOS, 672.3790) | 1-872 | m/z = 656.9200 (C46D29NO2, 656.4019) |
| 1-873 | m/z = 644.9492 (C46D31NO, 644.4351) | 1-874 | m/z = 689.0386 (C49D35NO, 688.4916) |
| 1-875 | m/z = 689.0386 (C49D35NO, 688.4916) | 1-876 | m/z = 813.1768 (C59D37NO, 812.5198) |
| 1-877 | m/z = 781.1318 (C55D37NO2, 780.5147) | 1-878 | m/z = 701.0094 (C49D33NO2, 700.4583) |
| 1-879 | m/z = 656.9200 (C46D29NO2, 656.4019) | 1-880 | m/z = 737.0424 (C52D33NO2, 736.4583) |
| 1-881 | m/z = 813.1768 (C59D37NO, 812.5198) | 1-882 | m/z = 769.1610 (C55D39NO, 768.5480) |
| 1-883 | m/z = 725.0716 (C52D35NO, 724.4916) | 1-884 | m/z = 817.2050 (C59D39NO, 816.5480) |
| 1-885 | m/z = 817.2050 (C59D39NO, 816.5480) | 1-886 | m/z = 813.2504 (C58D43NO, 812.6044) |
| 1-887 | m/z = 781.1318 (C55D37NO2, 780.5147) | 1-888 | m/z = 813.2504 (C58D43NO, 812.6044) |
| 1-889 | m/z = 769.1610 (C55D39NO, 768.5480) | 1-890 | m/z = 725.0716 (C52D35NO, 724.4916) |
| 1-891 | m/z = 644.9492 (C46D31NO, 644.4351) | 1-892 | m/z = 813.1768 (C59D37NO, 812.5198) |
| 1-893 | m/z = 769.1610 (C55D39NO, 768.5480) | 1-894 | m/z = 805.1940 (C58D39NO, 804.5480) |
| 1-895 | m/z = 781.1318 (C55D37NO2, 780.5147) | 1-896 | m/z = 737.0424 (C52D33NO2, 736.4583) |
| 1-897 | m/z = 777.1438 (C56D37NO, 776.5198) | 1-898 | m/z = 616.8990 (C44D29NO, 616.4069) |
| 1-899 | m/z = 769.1610 (C55D39NO, 768.5480) | 1-900 | m/z = 725.0716 (C52D35NO, 724.4916) |
| 1-901 | m/z = 644.9492 (C46D31NO, 644.4351) | 1-902 | m/z = 769.1610 (C55D39NO, 768.5480) |
| 1-903 | m/z = 769.1610 (C55D39NO, 768.5480) | 1-904 | m/z = 769.1610 (C55D39NO, 768.5480) |
| 1-905 | m/z = 769.1610 (C55D39NO, 768.5480) | 1-906 | m/z = 861.2944 (C62D43NO, 860.6044) |
| 1-907 | m/z = 813.2504 (C58D43NO, 812.6044) | 1-908 | m/z = 769.1610 (C55D39NO, 768.5480) |
| 1-909 | m/z = 737.0424 (C52D33NO2, 736.4583) | 1-910 | m/z = 797.1928 (C55D37NOS, 796.4918) |
| 1-911 | m/z = 753.1034 (C52D33NOS, 752.4354) | 1-912 | m/z = 813.2504 (C58D43NO, 812.6044) |
| 1-913 | m/z = 709.1060 (C50D39NO, 708.5480) | 1-914 | m/z = 711.9413 (C47D30F3NO, 711.4163) |
| 1-915 | m/z = 725.0716 (C52D35NO, 724.4916) | 1-916 | m/z = 785.2002 (C56D41NO, 784.5762) |
| 1-917 | m/z = 793.1830 (C57D39NO, 792.5480) | 1-918 | m/z = 697.0214 (C50D33NO, 696.4633) |
| 1-919 | m/z = 697.0214 (C50D33NO, 696.4633) | 1-920 | m/z = 741.1108 (C53D37NO, 740.5198) |
| 1-921 | m/z = 821.2332 (C59D41NO, 820.5762) | 1-922 | m/z = 741.1108 (C53D37NO, 740.5198) |
| 1-923 | m/z = 697.0214 (C50D33NO, 696.4633) | 1-924 | m/z = 793.1830 (C57D39NO, 792.5480) |
| 1-925 | m/z = 805.1940 (C58D39NO, 804.5480) | 1-926 | m/z = 805.1940 (C58D39NO, 804.5480) |
| 1-927 | m/z = 725.0716 (C52D35NO, 724.4916) | 1-928 | m/z = 644.9492 (C46D31NO, 644.4351) |
| 1-929 | m/z = 769.1610 (C55D39NO, 768.5480) | 1-930 | m/z = 769.1610 (C55D39NO, 768.5480) |
| 1-931 | m/z = 725.0716 (C52D35NO, 724.4916) | 1-932 | m/z = 769.1610 (C55D39NO, 768.5480) |
| 1-933 | m/z = 821.2332 (C59D41NO, 820.5762) | 1-934 | m/z = 821.2332 (C59D41NO, 820.5762) |
| 1-935 | m/z = 701.0094 (C49D33NO2, 700.4583) | 1-936 | m/z = 608.9162 (C43D31NO, 608.4351) |
| 1-937 | m/z = 644.9492 (C46D31NO, 644.4351) | 1-938 | m/z = 689.0386 (C49D35NO, 688.4916) |
| 1-939 | m/z = 777.1438 (C56D37NO, 776.5198) | 1-940 | m/z = 777.1438 (C56D37NO, 776.5198) |
| 1-941 | m/z = 749.0936 (C54D35NO, 748.4916) | 1-942 | m/z = 689.0386 (C49D35NO, 688.4916) |
| 1-943 | m/z = 644.9492 (C46D31NO, 644.4351) | 1-944 | m/z = 713.0606 (C51D35NO, 712.4916) |
| 1-945 | m/z = 668.9712 (C48D31NO, 668.4351) | 1-946 | m/z = 713.0606 (C51D35NO, 712.4916) |
| 1-947 | m/z = 692.9932 (C50D31NO, 692.4351) | 1-948 | m/z = 721.0434 (C52D33NO, 720.4633) |
| 1-949 | m/z = 769.1610 (C55D39NO, 768.5480) | 1-950 | m/z = 725.0716 (C52D35NO, 724.4916) |
| 1-951 | m/z = 777.1438 (C56D37NO, 776.5198) | 1-952 | m/z = 777.1438 (C56D37NO, 776.5198) |
| 1-953 | m/z = 608.9162 (C43D31NO, 608.4351) | 1-954 | m/z = 608.9162 (C43D31NO, 608.4351) |
| 1-955 | m/z = 608.9162 (C43D31NO, 608.4351) | 1-956 | m/z = 608.9162 (C43D31NO, 608.4351) |
| 1-957 | m/z = 561.6840 (C42H27NO, 561.2093) | 1-958 | m/z = 637.7820 (C48H31NO, 637.2406) |
| 1-959 | m/z = 637.7820 (C48H31NO, 637.2406) | 1-960 | m/z = 677.8470 (C51H35NO, 677.2719) |
| 1-961 | m/z = 637.7820 (C48H31NO, 637.2406) | 1-962 | m/z = 637.7820 (C48H31NO, 637.2406) |
| 1-963 | m/z = 713.8800 (C54H35NO, 713.2719) | 1-964 | m/z = 713.8800 (C54H35NO, 713.2719) |
| 1-965 | m/z = 561.6840 (C42H27NO, 561.2093) | 1-966 | m/z = 637.7820 (C48H31NO, 637.2406) |
| 1-967 | m/z = 637.7820 (C48H31NO, 637.2406) | 1-968 | m/z = 667.8260 (C48H29NOS, 667.1970) |
| 1-969 | m/z = 637.7820 (C48H31NO, 637.2406) | 1-970 | m/z = 713.8800 (C54H35NO, 713.2719) |
| 1-971 | m/z = 713.8800 (C54H35NO, 713.2719) | 1-972 | m/z = 637.7820 (C48H31NO, 637.2406) |
| 1-973 | m/z = 713.8800 (C54H35NO, 713.2719) | 1-974 | m/z = 637.7820 (C48H31NO, 637.2406) |
| 1-975 | m/z = 713.8800 (C54H35NO, 713.2719) | 1-976 | m/z = 713.8800 (C54H35NO, 713.2719) |
| 1-977 | m/z = 713.8800 (C54H35NO, 713.2719) | 1-978 | m/z = 637.7820 (C48H31NO, 637.2406) |
| 1-979 | m/z = 713.8800 (C54H35NO, 713.2719) | 1-980 | m/z = 637.7820 (C48H31NO, 637.2406) |
| 1-981 | m/z = 713.8800 (C54H35NO, 713.2719) | 1-982 | m/z = 713.8800 (C54H35NO, 713.2719) |
| 1-983 | m/z = 713.8800 (C54H35NO, 713.2719) | 1-984 | m/z = 561.6840 (C42H27NO, 561.2093) |
| 1-985 | m/z = 637.7820 (C48H31NO, 637.2406) | 1-986 | m/z = 637.7820 (C48H31NO, 637.2406) |
| 1-987 | m/z = 687.8420 (C52H33NO, 687.2562) | 1-988 | m/z = 713.8800 (C54H35NO, 713.2719) |
| 1-989 | m/z = 713.8800 (C54H35NO, 713.2719) | 1-990 | m/z = 637.7820 (C48H31NO, 637.2406) |
| 1-991 | m/z = 713.8800 (C54H35NO, 713.2719) | 1-992 | m/z = 713.8800 (C54H35NO, 713.2719) |
| 1-993 | m/z = 789.9780 (C60H39NO, 789.3032) | 1-994 | m/z = 561.6840 (C42H27NO, 561.2093) |
| 1-995 | m/z = 637.7820 (C48H31NO, 637.2406) | 1-996 | m/z = 637.7820 (C48H31NO, 637.2406) |
| 1-997 | m/z = 637.7820 (C48H31NO, 637.2406) | 1-998 | m/z = 713.8800 (C54H35NO, 713.2719) |
| 1-999 | m/z = 637.7820 (C48H31NO, 637.2406) | 1-1000 | m/z = 713.8800 (C54H35NO, 713.2719) |
| 1-1001 | m/z = 713.8800 (C54H35NO, 713.2719) | 1-1002 | m/z = 561.6840 (C42H27NO, 561.2093) |
| 1-1003 | m/z = 637.7820 (C48H31NO, 637.2406) | 1-1004 | m/z = 637.7820 (C48H31NO, 637.2406) |
| 1-1005 | m/z = 713.8800 (C54H35NO, 713.2719) | 1-1007 | m/z = 637.7820 (C48H31NO, 637.2406) |
| 1-1007 | m/z = 713.8800 (C54H35NO, 713.2719) | 1-1008 | m/z = 713.8800 (C54H35NO, 713.2719) |
| 1-1009 | m/z = 637.7820 (C48H31NO, 637.2406) | 1-1010 | m/z = 713.8800 (C54H35NO, 713.2719) |

TABLE 6-continued

| Compound | FD-Mass | Compound | FD-Mass |
|---|---|---|---|
| 1-1011 | m/z = 713.8800 (C54H35NO, 713.2719) | 1-1012 | m/z = 713.8800 (C54H35NO, 713.2719) |
| 1-1013 | m/z = 561.6840 (C42H27NO, 561.2093) | 1-1014 | m/z = 637.7820 (C48H31NO, 637.2406) |
| 1-1015 | m/z = 637.7820 (C48H31NO, 637.2406) | 1-1016 | m/z = 713.8800 (C54H35NO, 713.2719) |
| 1-1017 | m/z = 637.7820 (C48H31NO, 637.2406) | 1-1018 | m/z = 713.8800 (C54H35NO, 713.2719) |
| 1-1019 | m/z = 713.8800 (C54H35NO, 713.2719) | 1-1020 | m/z = 637.7820 (C48H31NO, 637.2406) |
| 1-1021 | m/z = 637.7820 (C48H31NO, 637.2406) | 1-1022 | m/z = 637.7820 (C48H31NO, 637.2406) |
| 1-1023 | m/z = 637.7S20 (C48H31NO, 637.2406) | 1-1024 | m/z = 713.8800 (C54H35NO, 713.2719) |
| 1-1025 | m/z = 637.7820 (C48H31NO, 637.2406) | 1-1026 | m/z = 713.8800 (C54H35NO, 713.2719) |
| 1-1027 | m/z = 713.8800 (C54H35NO, 713.2719) | 1-1028 | m/z = 561.6840 (C42H27NO, 561.2093) |
| 1-1029 | m/z = 637.7820 (C48H31NO, 637.2406) | 1-1030 | m/z = 637.7820 (C48H31NO, 637.2406) |
| 1-1031 | m/z = 637.7820 (C48H31NO, 637.2406) | 1-1032 | m/z = 713.8800 (C54H35NO, 713.2719) |
| 1-1033 | m/z = 713.8800 (C54H35NO, 713.2719) | 1-1034 | m/z = 561.6840 (C42H27NO, 561.2093) |
| 1-1035 | m/z = 637.7820 (C48H31NO, 637.2406) | 1-1036 | m/z = 637.7820 (C48H31NO, 637.2406) |
| 1-1037 | m/z = 637.7820 (C48H31NO, 637.2406) | 1-1038 | m/z = 713.8800 (C54H35NO, 713.2719) |
| 1-1039 | m/z = 637.7820 (C48H31NO, 637.2406) | 1-1040 | m/z = 713.8800 (C54H35NO, 713.2719) |
| 1-1041 | m/z = 713.8800 (C54H35NO, 713.2719) | 1-1042 | m/z = 561.6840 (C42H27NO, 561.2093) |
| 1-1043 | m/z = 637.7820 (C48H31NO, 637.2406) | 1-1044 | m/z = 637.7820 (C48H31NO, 637.2406) |
| 1-1045 | m/z = 713.8800 (C54H35NO, 713.2719) | 1-1046 | m/z = 637.7820 (C48H31NO, 637.2406) |
| 1-1047 | m/z = 713.8800 (C54H35NO, 713.2719) | 1-1048 | m/z = 713.8800 (C54H35NO, 713.2719) |
| 1-1049 | m/z = 655.8918 (C48H13D18NO, 713.2719) | 1-1050 | m/z = 668.9712 (C48D31NO, 668.4351) |
| 1-1051 | m/z = 749.0936 (C54D35NO, 748.4916) | 1-1052 | m/z = 829.2160 (C60D39NO, 828.5480) |
| 1-1053 | m/z = 655.8918 (C48H13D18NO, 713.2719) | 1-1054 | m/z = 736.0142 (C54H13D22NO, 735.4100) |
| 1-1055 | m/z = 749.0936 (C54D35NO, 748.4916) | 1-1056 | m/z = 829.2160 (C60D39NO, 828.5480) |
| 2-33 | m/z = 651.7690 (C47H29N3O, 651.2311) | 2-34 | m/z = 650.7810 (C48H30N2O, 650.2358) |
| 2-90 | m/z = 601.7090 (C43H27N3O, 601.2154) | 2-91 | m/z = 651.7690 (C47H29N3O, 651.2311) |
| 2-172 | m/z = 625.7310 (C45H27N3O, 625.2154) | 2-183 | m/z = 651.7690 (C47H29N3O, 651.2311) |
| 2-250 | m/z = 601.7090 (C43H27N3O, 601.2154) | 3-5 | m/z = 575.6710 (C41H25N3O, 575.1998) |
| 3-67 | m/z = 525.6110 (C37H23N3O, 525.1841) | 3-74 | m/z = 575.6710 (C41H25N3O, 575.1998) |
| 2-313 | m/z = 651.7690 (C47H29N3O, 651.2311) | 2-314 | m/z = 651.7690 (C47H29N3O, 651.2311) |
| 2-315 | m/z = 575.6710 (C41H25N3O, 575.1998) | 2-316 | m/z = 625.7310 (C45H27N3O, 625.2154) |
| 2-317 | m/z = 651.7690 (C47H29N3O, 651.2311) | 2-318 | m/z = 651.7690 (C47H29N3O, 651.2311) |
| 2-319 | m/z = 651.7690 (C47H29N3O, 651.2311) | 2-320 | m/z = 701.8290 (C51H31N3O, 701.2467) |
| 2-321 | m/z = 727.8670 (C53H33N3O, 727.2624) | 2-322 | m/z = 727.8670 (C53H33N3O, 727.2624) |
| 2-323 | m/z = 701.8290 (C51H31N3O, 701.2467) | 2-324 | m/z = 727.8670 (C53H33N3O, 727.2624) |
| 2-325 | m/z = 741.8500 (C53H31N3O2, 741.2416) | 2-326 | m/z = 665.7520 (C47H27N3O2, 665.2103) |
| 2-327 | m/z = 715.8120 (C51H29N3O2, 715.2260) | 2-328 | m/z = 741.8500 (C53H31N3O2, 741.2416) |
| 2-329 | m/z = 741.8500 (C53H31N3O2, 741.2416) | 2-330 | m/z = 741.8500 (C53H31N3O2, 741.2416) |
| 2-331 | m/z = 665.7520 (C47H27N3O2, 665.2103) | 2-332 | m/z = 625.7310 (C45H27N3O, 625.2154) |
| 2-333 | m/z = 715.8120 (C51H29N3O2, 715.2260) | 2-334 | m/z = 675.7910 (C49H29N3O, 675.2311) |
| 2-335 | m/z = 751.8890 (C55H33N3O, 751.2624) | 2-336 | m/z = 725.8510 (C53H31N3O, 725.2467) |
| 2-337 | m/z = 741.8500 (C53H31N3O2, 741.2416) | 2-338 | m/z = 757.9110 (C53H31N3OS, 757.2188) |
| 2-339 | m/z = 701.8290 (C51H31N3O, 701.2467) | 2-340 | m/z = 741.8500 (C53H31N3O2, 741.2416) |
| 2-341 | m/z = 574.6830 (C42H26N2O, 574.2045) | 2-342 | m/z = 574.6830 (C42H26N2O, 574.2045) |
| 2-343 | m/z = 650.7810 (C48H30N2O, 650.2358) | 2-344 | m/z = 650.7810 (C48H30N2O, 650.2358) |
| 2-345 | m/z = 614.7040 (C44H26N2O2, 614.1994) | 2-346 | m/z = 690.8020 (C50H30N2O2, 690.2307) |
| 2-347 | m/z = 690.8020 (C50H30N2O2, 690.2307) | 2-348 | m/z = 651.7690 (C47H29N3O, 651.2311) |
| 2-349 | m/z = 625.7310 (C45H27N3O, 625.2154) | 2-350 | m/z = 675.7910 (C49H29N3O, 675.2311) |
| 2-351 | m/z = 701.8290 (C51H31N3O, 701.2467) | 2-352 | m/z = 727.8670 (C53H33N3O, 727.2624) |
| 2-353 | m/z = 741.8500 (C53H31N3O2, 741.2416) | 2-354 | m/z = 741.8500 (C53H31N3O2, 741.2416) |
| 2-355 | m/z = 665.7520 (C47H27N3O2, 665.2103) | 2-356 | m/z = 741.8500 (C53H31N3O2, 741.2416) |
| 2-357 | m/z = 625.7310 (C45H27N3O, 625.2154) | 2-358 | m/z = 675.7910 (C49H29N3O, 675.2311) |
| 2-359 | m/z = 651.7690 (C47H29N3O, 651.2311) | 2-360 | m/z = 701.8290 (C51H31N3O, 701.2467) |
| 2-361 | m/z = 524.6230 (C38H24N2O, 524.1889) | 2-362 | m/z = 574.6830 (C42H26N2O, 574.2045) |
| 2-363 | m/z = 614.7040 (C44H26N2O2, 614.1994) | 2-364 | m/z = 650.7810 (C48H30N2O, 650.2358) |
| 2-365 | m/z = 575.6710 (C41H25N3O, 575.1998) | 2-366 | m/z = 625.7310 (C45H27N3O, 625.2154) |
| 2-367 | m/z = 651.7690 (C47H29N3O, 651.2311) | 2-368 | m/z = 651.7690 (C47H29N3O, 651.2311) |
| 2-369 | m/z = 701.8290 (C51H31N3O, 701.2467) | 2-370 | m/z = 727.8670 (C53H33N3O, 727.2624) |
| 2-371 | m/z = 715.8120 (C51H29N3O2, 715.2260) | 2-372 | m/z = 665.7520 (C47H27N3O2, 665.2103) |
| 2-373 | m/z = 665.7520 (C47H27N3O2, 665.2103) | 2-374 | m/z = 701.8290 (C51H31N3O, 701.2467) |
| 2-375 | m/z = 575.6710 (C41H25N3O, 575.1998) | 2-376 | m/z = 625.7310 (C45H27N3O, 625.2154) |
| 2-377 | m/z = 665.7520 (C47H27N3O2, 665.2103) | 2-378 | m/z = 625.7310 (C45H27N3O, 625.2154) |
| 2-379 | m/z = 701.8290 (C51H31N3O, 701.2467) | 2-380 | m/z = 701.8290 (C51H31N3O, 701.2467) |
| 2-381 | m/z = 665.7520 (C47H27N3O2, 665.2103) | 2-382 | m/z = 665.7520 (C47H27N3O2, 665.2103) |
| 2-383 | m/z = 701.8290 (C51H31N3O, 701.2467) | 2-384 | m/z = 727.8670 (C53H33N3O, 727.2624) |
| 2-335 | m/z = 625.7310 (C45H27N3O, 625.2154) | 2-386 | m/z = 675.7910 (C49H29N3O, 675.2311) |
| 2-387 | m/z = 574.6830 (C42H26N2O, 574.2045) | 2-388 | m/z = 650.7810 (C48H30N2O, 650.2358) |
| 2-389 | m/z = 650.7810 (C48H30N2O, 650.2358) | 2-390 | m/z = 614.7040 (C44H26N2O2, 614.1994) |
| 2-391 | m/z = 575.6710 (C41H25N3O, 575.1998) | 2-392 | m/z = 625.7310 (C45H27N3O, 625.2154) |
| 2-393 | m/z = 625.7310 (C45H27N3O, 625.2154) | 2-394 | m/z = 701.8290 (C51H31N3O, 701.2467) |
| 2-395 | m/z = 727.8670 (C53H33N3O, 727.2624) | 2-396 | m/z = 665.7520 (C47H27N3O2, 665.2103) |
| 2-397 | m/z = 665.7520 (C47H27N3O2, 665.2103) | 2-398 | m/z = 701.8290 (C51H31N3O, 701.2467) |
| 2-399 | m/z = 574.6830 (C42H26N2O, 574.2045) | 2-400 | m/z = 624.7430 (C46H28N2O, 624.2202) |
| 2-401 | m/z = 650.7810 (C48H30N2O, 650.2358) | 2-402 | m/z = 614.7040 (C44H26N2O2, 614.1994) |
| 2-403 | m/z = 625.7310 (C45H27N3O, 625.2154) | 2-404 | m/z = 675.7910 (C49H29N3O, 675.2311) |
| 2-405 | m/z = 575.6710 (C41H25N3O, 575.1998) | 2-406 | m/z = 625.7310 (C45H27N3O, 625.2154) |
| 2-407 | m/z = 625.7310 (C45H27N3O, 625.2154) | 2-408 | m/z = 651.7690 (C47H29N3O, 651.2311) |
| 2-409 | m/z = 701.8290 (C51H31N3O, 701.2467) | 2-410 | m/z = 665.7520 (C47H27N3O2, 665.2103) |
| 2-411 | m/z = 665.7520 (C47H27N3O2, 665.2103) | 2-412 | m/z = 741.8500 (C53H31N3O2, 741.2416) |

TABLE 6-continued

| Compound | FD-Mass | Compound | FD-Mass |
|---|---|---|---|
| 2-413 | m/z = 651.7690 (C47H29N3O, 651.2311) | 2-414 | m/z = 701.8290 (C51H31N3O, 701.2467) |
| 2-415 | m/z = 625.7310 (C45H27N3O, 625.2154) | 2-416 | m/z = 675.7910 (C49H29N3O, 675.2311) |
| 2-417 | m/z = 574.6830 (C42H26N2O, 574.2045) | 2-418 | m/z = 650.7810 (C48H30N2O, 650.2358) |
| 2-419 | m/z = 650.7810 (C48H30N2O, 650.2358) | 2-420 | m/z = 614.7040 (C44H26N2O2, 614.1994) |
| 2-421 | m/z = 575.6710 (C41H25N3O, 575.1998) | 2-422 | m/z = 625.7310 (C45H27N3O, 625.2154) |
| 2-423 | m/z = 625.7310 (C45H27N3O, 625.2154) | 2-424 | m/z = 651.7690 (C47H29N3O, 651.2311) |
| 2-425 | m/z = 701.8290 (C51H31N3O, 701.2467) | 2-426 | m/z = 727.8670 (C53H33N3O, 727.2624) |
| 2-427 | m/z = 665.7520 (C47H27N3O2, 665.2103) | 2-428 | m/z = 741.8500 (C53H31N3O2, 741.2416) |
| 2-429 | m/z = 625.7310 (C45H27N3O, 625.2154) | 2-430 | m/z = 675.7910 (C49H29N3O, 675.2311) |
| 2-431 | m/z = 701.8290 (C51H31N3O, 701.2467) | 2-432 | m/z = 574.6830 (C42H26N2O, 574.2045) |
| 2-433 | m/z = 624.7430 (C46H28N2O, 624.2202) | 2-434 | m/z = 650.7810 (C48H30N2O, 650.2358) |
| 2-435 | m/z = 614.7040 (C44H26N2O2, 614.1994) | 2-436 | m/z = 575.6710 (C41H25N3O, 575.1998) |
| 2-437 | m/z = 625.7310 (C45H27N3O, 625.2154) | 2-438 | m/z = 651.7690 (C47H29N3O, 651.2311) |
| 2-439 | m/z = 701.8290 (C51H31N3O, 701.2467) | 2-440 | m/z = 665.7520 (C47H27N3O2, 665.2103) |
| 2-441 | m/z = 701.8290 (C51H31N3O, 701.2467) | 2-442 | m/z = 675.7910 (C49H29N3O, 675.2311) |
| 2-443 | m/z = 575.6710 (C41H25N3O, 575.1998) | 2-444 | m/z = 625.7310 (C45H27N3O, 625.2154) |
| 2-445 | m/z = 625.7310 (C45H27N3O, 625.2154) | 2-446 | m/z = 701.8290 (C51H31N3O, 701.2467) |
| 2-447 | m/z = 651.7690 (C47H29N3O, 651.2311) | 2-448 | m/z = 751.8890 (C55H33N3O, 751.2624) |
| 2-449 | m/z = 741.8500 (C53H31N3O2, 741.2416) | 2-450 | m/z = 675.7910 (C49H29N3O, 675.2311) |
| 2-451 | m/z = 651.7690 (C47H29N3O, 651.2311) | 2-452 | m/z = 701.8290 (C51H31N3O, 701.2467) |
| 2-453 | m/z = 701.8290 (C51H31N3O, 701.2467) | 2-454 | m/z = 665.7520 (C47H27N3O2, 665.2103) |
| 2-455 | m/z = 665.7520 (C47H27N3O2, 665.2103) | 2-456 | m/z = 741.8500 (C53H31N3O2, 741.2416) |
| 2-457 | m/z = 701.8290 (C51H31N3O, 701.2467) | 2-458 | m/z = 57 4.6830 (C42H26N2O, 574.2045) |
| 2-459 | m/z = 650.7810 (C48H30N2O, 650.2358) | 2-460 | m/z = 614.7040 (C44H26N2O2, 614.1994) |
| 2-461 | m/z = 625.7310 (C45H27N3O, 625.2154) | 2-462 | m/z = 701.8290 (C51H31N3O, 701.2467) |
| 2-463 | m/z = 681.8130 (C47H27N3OS, 681.1875) | 2-464 | m/z = 681.8130 (C47H27N3OS, 681.1875) |
| 2-465 | m/z = 675.7910 (C49H29N3O, 675.2311) | 2-466 | m/z = 625.7310 (C45H27N3O, 625.2154) |
| 2-467 | m/z = 651.7690 (C47H29N3O, 651.2311) | 2-468 | m/z = 701.8290 (C51H31N3O, 701.2467) |
| 2-469 | m/z = 741.8500 (C53H31N3O2, 741.2416) | 2-470 | m/z = 625.7310 (C45H27N3O, 625.2154) |
| 2-471 | m/z = 675.7910 (C49H29N3O, 675.2311) | 2-472 | m/z = 701.8290 (C51H31N3O, 701.2467) |
| 2-473 | m/z = 651.7690 (C47H29N3O, 651.2311) | 2-474 | m/z = 701.8290 (C51H31N3O, 701.2467) |
| 2-475 | m/z = 727.8670 (C53H33N3O, 727.2624) | 2-476 | m/z = 665.7520 (C47H27N3O2, 665.2103) |
| 2-477 | m/z = 675.7910 (C49H29N3O, 675.2311) | 2-478 | m/z = 574.6830 (C42H26N2O, 574.2045) |
| 2-479 | m/z = 650.7810 (C48H30N2O, 650.2358) | 2-480 | m/z = 651.7690 (C47H29N3O, 651.2311) |
| 2-481 | m/z = 701.8290 (C51H31N3O, 701.2467) | 2-482 | m/z = 727.8670 (C53H33N3O, 727.2624) |
| 2-483 | m/z = 665.7520 (C47H27N3O2, 665.2103) | 2-484 | m/z = 665.7520 (C47H27N3O2, 665.2103) |
| 2-485 | m/z = 701.8290 (C51H31N3O, 701.2467) | 2-486 | m/z = 727.8670 (C53H33N3O, 727.2624) |
| 2-487 | m/z = 701.8290 (C51H31N3O, 701.2467) | 2-488 | m/z = 741.8500 (C53H31N3O2, 741.2416) |
| 2-489 | m/z = 675.7910 (C49H29N3O, 675.2311) | 2-490 | m/z = 625.7310 (C45H27N3O, 625.2154) |
| 2-491 | m/z = 701.8290 (C51H31N3O, 701.2467) | 2-492 | m/z = 701.8290 (C51H31N3O, 701.2467) |
| 2-493 | m/z = 665.7520 (C47H27N3O2, 665.2103) | 2-494 | m/z = 681.8130 (C47H27N3OS, 681.1875) |
| 2-495 | m/z = 675.7910 (C49H29N3O, 675.2311) | 2-496 | m/z = 701.8290 (C51H31N3O, 701.2467) |
| 2-497 | m/z = 614.7040 (C44H26N2O2, 614.1994) | 2-498 | m/z = 614.7040 (C44H26N2O2, 614.1994) |
| 2-499 | m/z = 665.7520 (C47H27N3O2, 665.2103) | 2-500 | m/z = 741.8500 (C53H31N3O2, 741.2416) |
| 2-501 | m/z = 651.7690 (C47H29N3O, 651.2311) | 2-502 | m/z = 651.7690 (C47H29N3O, 651.2311) |
| 2-503 | m/z = 741.8500 (C53H31N3O2, 741.2416) | 2-504 | m/z = 701.8290 (C51H31N3O, 701.2467) |
| 2-505 | m/z = 727.8670 (C53H33N3O, 727.2624) | 2-506 | m/z = 701.8290 (C51H31N3O, 701.2467) |
| 2-507 | m/z = 675.7910 (C49H29N3O, 675.2311) | 2-508 | m/z = 625.7310 (C45H27N3O, 625.2154) |
| 2-509 | m/z = 701.8290 (C51H31N3O, 701.2467) | 2-510 | m/z = 701.8290 (C51H31N3O, 701.2467) |
| 2-511 | m/z = 727.8670 (C53H33N3O, 727.2624) | 2-512 | m/z = 675.7910 (C49H29N3O, 675.2311) |
| 2-513 | m/z = 741.8500 (C53H31N3O2, 741.2416) | 2-514 | m/z = 741.8500 (C53H31N3O2, 741.2416) |
| 2-515 | m/z = 651.7690 (C47H29N3O, 651.2311) | 2-516 | m/z = 701.8290 (C51H31N3O, 701.2467) |
| 2-517 | m/z = 675.7910 (C49H29N3O, 675.2311) | 2-518 | m/z = 701.8290 (C51H31N3O, 701.2467) |
| 2-519 | m/z = 727.8670 (C53H33N3O, 727.2624) | 2-520 | m/z = 675.7910 (C49H29N3O, 675.2311) |
| 2-521 | m/z = 665.7520 (C47H27N3O2, 665.2103) | 2-522 | m/z = 665.7520 (C47H27N3O2, 665.2103) |
| 2-523 | m/z = 701.8290 (C51H31N3O, 701.2467) | 2-524 | m/z = 650.7810 (C48H30N2O, 650.2358) |
| 2-525 | m/z = 614.7040 (C44H26N2O2, 614.1994) | 2-526 | m/z = 651.7690 (C47H29N3O, 651.2311) |
| 2-527 | m/z = 701.8290 (C51H31N3O, 701.2467) | 2-528 | m/z = 741.8500 (C53H31N3O2, 741.2416) |
| 2-529 | m/z = 675.7910 (C49H29N3O, 675.2311) | 2-530 | m/z = 625.7310 (C45H27N3O, 625.2154) |
| 2-531 | m/z = 701.8290 (C51H31N3O, 701.2467) | 2-532 | m/z = 701.8290 (C51H31N3O, 701.2467) |
| 2-533 | m/z = 675.7910 (C49H29N3O, 675.2311) | 2-534 | m/z = 665.7520 (C47H27N3O2, 665.2103) |
| 2-535 | m/z = 741.8500 (C53H31N3O2, 741.2416) | 2-536 | m/z = 665.7520 (C47H27N3O2, 665.2103) |
| 2-537 | m/z = 701.8290 (C51H31N3O, 701.2467) | 2-538 | m/z = 614.7040 (C44H26N2O2, 614.1994) |
| 2-539 | m/z = 614.7040 (C44H26N2O2, 614.1994) | 2-540 | m/z = 574.6830 (C42H26N2O, 574.2045) |
| 2-541 | m/z = 625.7310 (C45H27N3O, 625.2154) | 2-542 | m/z = 651.7690 (C47H29N3O, 651.2311) |
| 2-543 | m/z = 701.8290 (C51H31N3O, 701.2467) | 2-544 | m/z = 665.7520 (C4 7H27N3O2, 665.2103) |
| 2-545 | m/z = 741.8500 (C53H31M3O2, 741.2416) | 2-546 | m/z = 665.7520 (C47H27N3O2, 665.2103) |
| 2-547 | m/z = 691.7900 (C49H29N3O2, 691.2260) | 2-548 | m/z = 677.8070 (C49H31N3O, 677.2467) |
| 2-549 | m/z = 675.7910 (C49H29N3O, 675.2311) | 2-550 | m/z = 651.7690 (C47H29N3O, 651.2311) |
| 2-551 | m/z = 701.8290 (C51H31N3O, 701.2467) | 2-552 | m/z = 727.8670 (C53H33N3O, 727.2624) |
| 2-553 | m/z = 741.8500 (C53H31N3O2, 741.2416) | 2-554 | m/z = 675.7910 (C49H29N3O, 675.2311) |
| 2-555 | m/z = 701.8290 (C51H31N3O, 701.2467) | 2-556 | m/z = 650.7810 (C48H30N2O, 650.2358) |
| 2-557 | m/z = 614.7040 (C44H26N2O2, 614.1994) | 2-558 | m/z = 651.7690 (C47H29N3O, 651.2311) |
| 2-559 | m/z = 701.8290 (C51H31N3O, 701.2467) | 2-560 | m/z = 741.8500 (C53H31N3O2, 741.2416) |
| 2-561 | m/z = 662.8361 (C47H18D11N3O, 662.3001) | 2-562 | m/z = 670.8849 (C47H10D19N3O, 670.3503) |
| 2-563 | m/z = 680.9460 (C47D29N3O, 680.4131) | 2-564 | m/z = 773.0392 (C53D31N3O2, 772.4362) |
| 2-565 | m/z = 638.8103 (C45H14D13N3O, 638.2970) | 2-566 | m/z = 652.8957 (C45D27N3O, 652.3849) |
| 2-567 | m/z = 733.0182 (C51D31N3O, 732.4413) | 2-568 | m/z = 670.8849 (C47H10D19N3O, 670.3503) |

TABLE 6-continued

| Compound | FD-Mass | Compound | FD-Mass |
|---|---|---|---|
| 2-569 | m/z = 680.9460 (C47D29N3O, 680.4131) | 2-570 | m/z = 714.9083 (C51H18D13N3O, 714.3283) |
| 2-571 | m/z = 733.0182 (C51D31N3O, 732.4413) | 2-572 | m/z = 652.8957 (C45D27N3O, 652.3849) |
| 3-85 | m/z = 651.7690 (C47H29N3O, 651.2311) | 3-86 | m/z = 677.8070 (C49H31N3O, 677.2467) |
| 3-87 | m/z = 701.8290 (C51H31N3O, 701.2467) | 3-88 | m/z = 727.8670 (C53H33N3O, 727.2624) |
| 3-89 | m/z = 665.7520 (C47H27N3O2, 665.2103) | 3-90 | m/z = 741.8500 (C53H31N3O2, 741.2416) |
| 3-91 | m/z = 675.7910 (C49H29N3O, 675.7910) | 3-92 | m/z = 701.8290 (C51H31N3O, 701.2467) |
| 3-93 | m/z = 625.7310 (C45H27N3O, 625.2154) | 3-94 | m/z = 701.8290 (C51H31N3O, 701.2467) |
| 3-95 | m/z = 727.8670 (C53H33N3O, 727.2624) | 3-96 | m/z = 665.7520 (C47H27N3O2, 665.2103) |
| 3-97 | m/z = 665.7520 (C47H27N3O2, 665.2103) | 3-98 | m/z = 741.8500 (C53H31N3O2, 741.2416) |
| 3-99 | m/z = 727.8670 (C53H33N3O, 727.2624) | 3-100 | m/z = 675.7910 (C49H29N3O, 675.7910) |
| 3-101 | m/z = 701.8290 (C51H31N3O, 701.2467) | 3-102 | m/z = 614.7040 (C44H26N2O2, 614.1994) |
| 3-103 | m/z = 690.8020 (C50H30N2O2, 690.2307) | 3-104 | m/z = 574.6830 (C42H26N2O, 574.2045) |
| 3-105 | m/z = 650.7810 (C48H30N2O, 650.2358) | 3-106 | m/z = 575.6710 (C41H25N3O, 575.1998) |
| 3-107 | m/z = 601.7090 (C43H27N3O, 601.2154) | 3-108 | m/z = 625.7310 (C45H27N3O, 625.2154) |
| 3-109 | m/z = 701.8290 (C51H31N3O, 701.2467) | 3-110 | m/z = 727.8670 (C53H33N3O, 727.2624) |
| 3-111 | m/z = 665.7520 (C47H27N3O2, 665.2103) | 3-112 | m/z = 741.8500 (C53H31N3O2, 741.2416) |
| 3-113 | m/z = 675.7910 (C49H29N3O, 675.7910) | 3-114 | m/z = 701.8290 (C51H31N3O, 701.2467) |
| 3-115 | m/z = 614.7040 (C44H26N2O2, 614.1994) | 3-116 | m/z = 650.7810 (C48H30N2O, 650.2358) |
| 3-117 | m/z = 651.7690 (C47H29N3O, 651.2311) | 3-118 | m/z = 701.8290 (C51H31N3O, 701.2467) |
| 3-119 | m/z = 727.8670 (C53H33N3O, 727.2624) | 3-120 | m/z = 665.7520 (C47H27N3O2, 665.2103) |
| 3-121 | m/z = 665.7520 (C47H27N3O2, 665.2103) | 3-122 | m/z = 701.8290 (C51H31N3O, 701.2467) |
| 3-123 | m/z = 574.6830 (C42H26N2O, 574.2045) | 3-124 | m/z = 650.7810 (C48H30N2O, 650.2358) |
| 3-125 | m/z = 575.6710 (C41H25N3O, 575.1998) | 3-126 | m/z = 575.6710 (C41H25N3O, 575.1998) |
| 3-127 | m/z = 575.6710 (C41H25N3O, 575.1998) | 3-128 | m/z = 525.6110 (C37H23N3O, 525.1841) |
| 3-129 | m/z = 525.6110 (C37H23N3O, 525.1841) | 3-130 | m/z = 525.6110 (C37H23N3O, 525.1841) |
| 3-131 | m/z = 575.6710 (C41H25N3O, 575.1998) | 3-132 | m/z = 575.6710 (C41H25N3O, 575.1998) |
| 3-133 | m/z = 549.6330 (C39H23N3O, 549.1841) | 3-134 | m/z = 599.6930 (C43H25N3O, 599.1998) |
| 3-135 | m/z = 625.7310 (C45H27N3O, 625.2154) | 3-136 | m/z = 549.6330 (C39H23N3O, 549.1841) |
| 3-137 | m/z = 575.6710 (C41H25N3O, 575.1998) | 3-138 | m/z = 625.7310 (C45H27N3O, 625.2154) |
| 3-139 | m/z = 575.6710 (C41H25N3O, 575.1998) | 3-140 | m/z = 625.7310 (C45H27N3O, 625.2154) |
| 3-141 | m/z = 708.8717 (C51H24D7N3O, 708.2906) | 3-142 | m/z = 733.0182 (C51D31N3O, 732.4413) |
| 3-143 | m/z = 761.0684 (C53D33N3O, 760.4695) | 3-144 | m/z = 582.7137 (C41H18D7N3O, 582.2437) |
| 3-145 | m/z = 588.7503 (C41H12D13N3O, 588.2814) | 3-146 | m/z = 761.0684 (C53D33N3O, 760.4695) |
| 3-147 | m/z = 593.7808 (C41H7D18N3O, 593.3127) | 3-148 | m/z = 600.8235 (C41D25N3O, 600.3567) |

TABLE 7

| | |
|---|---|
| 1-1 | δ = 8.01~7.91(m, 5H), 7.78~7.69(m, 6H), 7.61~7.40(m, 10H), 7.35~7.33(m, 5H), 7.24~7.22(t, 1H) |
| 1-4 | δ = 8.03~7.90(m, 5H), 7.80~7.69(m, 6H), 7.55~7.40(m, 8H), 7.35~7.34(m, 6H) |
| 1-10 | δ = 8.03~7.90(m, 5H), 7.80~7.69(m, 6H), 7.58~7.41(m, 10H), 7.34~7.30(m, 8H), 1.47(s, 6H) |
| 1-22 | δ = 8.04~7.90(m, 6H), 7.81~7.68(m, 7H), 7.57~7.34(m, 18H), 1.48(s, 6H) |
| 1-24 | δ = 8.03~7.90(m, 5H), 7.80~7.69(m, 6H), 7.55~7.28(m, 18H) |
| 1-49 | δ = 8.54~8.52(d, 1H), 8.17(s, 1H), 8.01~7.99(m, 2H), 7.76~7.72(d, 1H), 7.69~7.40(m, 12H), 7.33~7.22(m, 13H), 7.09~7.05(t, 1H) |
| 1-52 | δ = 8.55~8.53(d, 1H), 8.17(s, 1H), 8.01~7.99(m, 2H), 7.76~7.72(d, 1H), 7.69~7.60(m, 2H), 7.58~7.41(m, 14H), 7.33~7.29(t, 3H), 7.25~7.22(m, 10H), 7.09~7.05(t, 1H) |
| 1-55 | δ = 8.54~8.52(d, 1H), 8.01~7.89(m, 4H), 7.69~7.43(m, 10H), 7.33~7.22(m, 13H), 7.11~7.10(t, 1H), 1.48(s, 6H) |
| 1-56 | δ = 8.54~8.52(d, 1H), 8.00~7.89(m, 4H), 7.72~7.41(m, 13H), 7.35~7.22(m, 14H), 7.08~7.06(t, 1H), 1.48(s, 6H) |
| 1-60 | δ = 8.56~8.54(d, 1H), 8.01~7.79(m, 6H), 7.71~7.43(m, 16H), 7.33~7.22(m, 15H), 7.04~7.01(t, 1H) |
| 1-66 | δ = 8.56~8.54(d, 1H), 8.01~7.79(m, 6H), 7.71~7.43(m, 10H), 7.33~7.22(m, 14H), 7.10~7.08(t, 1H), 7.04~7.01(t, 1H) |
| 1-175 | δ = 8.08~8.01(m, 5H), 7.85~7.70(m, 6H), 7.60~7.45(m, 8H), 7.35~7.28(m, 7H), 7.15~7.13(5, 1H) |
| 1-274 | δ = 8.58~8.56(d, 1H), 8.05~7.95(m, 6H), 7.70~7.43(m, 15H), 7.36~7.28(m, 8H), 7.13~7.10(t, 1H) |
| 1-275 | δ = 8.58~8.56(d, 1H), 8.04~7.96(m, 6H), 7.69~7.41(m, 17H), 7.36~7.28(m, 8H), 7.12~7.10(5, 1H) |
| 1-280 | δ = 8.59~8.58(d, 1H), 8.05~7.95(m, 6H), 7.68~7.45(m, 13H), 7.37~7.29(m, 8H), 7.11~7.10(5, 1H), 1.47(s, 6H) |
| 1-290 | δ = 8.57~8.56(d, 1H), 8.04~7.96(m, 6H), 7.69~7.41(m, 17H), 7.36~7.25(m, 9H), |
| 1-300 | δ = 8.56~8.54(d, 1H), 8.00~7.90(m, 6H), 7.65~7.40(m, 17H), 7.35~7.25(m, 8H), 7.08~7.06(5, 1H) |
| 1-401 | δ = 8.70~8.68(d, 1H), 8.00~7.90(m, 5H), 7.78~7.60(m, 8H), 7.55~7.40(m, 10H), 7.25~7.18(m, 7H) |
| 1-402 | δ = 8.70~8.68(d, 1H), 8.01~7.90(m, 5H), 7.80~7.60(m, 9H), 7.55~7.35(m, 11H), 7.30~7.25(m, 6H), 7.11~7.09(5, 1H) |
| 1-409 | δ = 8.70~8.68(d, 1H), 8.01~7.90(m, 5H), 7.75~7.61(m, 9H), 7.55~7.35(m, 11H), 7.30~7.19(m, 7H) |

TABLE 7-continued

| | |
|---|---|
| 1-412 | δ = 8.70~8.68(d, 1H), 8.10~7.97(m, 5H), 7.80~7.60(m, 8H), 7.55~7.40(m, 9H), 7.30~7.18(m, 6H), 1.47(s, 6H) |
| 1-460 | δ = 7.97~7.91(m, 5H), 7.70~7.63(m, 6H), 7.61~7.40(m, 15H), 7.35~7.34(m, 5H) |
| 1-532 | δ = 8.55~8.53(d, 1H), 8.02~7.98(m, 4H), 7.95~7.93(d, 1H), 7.67~7.43(m, 15H), 7.36~7.34(m, 5H), 7.30~7.28(m, 4H), 7.13~7.10(5, 1H) |
| 1-538 | δ = 8.56~8.54(d, 1H), 8.05~7.99(m, 4H), 7.96~7.94(d, 1H), 7.69~7.63(m, 6H), 7.60~7.40(m, 17H), 7.36~7.34(m, 6H) |
| 1-545 | δ = 8.56~8.54(d, 1H), 8.05~7.93(m, 5H), 7.69~7.63(m, 5H), 7.60~7.40(m, 15H), 7.36~7.29(m, 5H) |
| 1-549 | δ = 8.55~8.53(d, 1H), 8.00~7.97(m, 5H), 7.89~7.87(d, 1H), 7.67~7.48(m, 20H), 7.31~7.29(m, 5H), 7.04~7.03(5, 1H) |
| 1-554 | δ = 8.54~8.52(d, 1H), 8.17~8.16(d, 1H), 8.00~7.97(m, 5H), 7.93~7.91(d, 1H), 7.66~7.44(m, 19H), 7.31~7.29(m, 5H), 7.04~7.03(t, 1H) |
| 1-558 | δ = 8.53~8.51(d, 1H), 8.01~7.98(m, 4H), 7.94~7.92(d, 1H), 7.68~7.46(m, 12H), 7.42~7.41(d, 1H), 7.35~7.28(m, 8H), 7.19~7.17(d, 1H), 7.11~7.10(t, 1H), 1.46(s, 6H) |
| 1-559 | δ = 8.54~8.52(d, 1H), 8.04~7.99(m, 4H), 7.95~7.93(d, 1H), 7.69~7.34(m, 26H), 7.23~7.22(t, 1H), 1.48(s, 6H) |
| 1-572 | δ = 8.57~8.54(d, 1H), 8.05~7.94(m, 5H), 7.69~7.63(m, 6H), 7.60~7.40(m, 17H), 7.36~7.34(m, 6H) |
| 1-577 | δ = 8.55~8.53(d, 1H), 8.03~7.94(m, 5H), 7.70~7.63 (m, 7H), 7.60~7.40(m, 18H), 7.36~7.29(m, 6H) |
| 1-805 | δ = 8.54~8.52(d, 1H), 8.17(s, 1H), 8.01~7.99(m, 2H) , 7.76~7.72(d, 1H), 7.69~7.40(m, 9H), 7.33~7.22(m, 11H), 7.09~7.05(t, 1H) |
| 1-841 | δ = 8.55~8.53(d, 1H), 8.02~7.98(m, 4H), 7.95~7.93(d, 1H), 7.67~7.43(m, 11H), 7.36~7.34(m, 5H), 7.30~7.28(m, 3H), 7.13~7.10(t, 1H) |
| 1-845 | δ = 8.54~8.52(d, 1H), 8.04~7.99(m, 4H), 7.95~7.93(d, 1H), 7.69~7.34(m, 21H), 7.23~7.22(t, 1H), 1.48(s, 6H) |
| 2-33 | δ = 9.36(s, 1H), 8.90~8.88(d, 4H), 8.62~8.60(d, 1H), 8.17~8.08(m, 4H), 8.00~7.92(m, 4H), 7.77~7.75(d, 2H), 7.70~7.67(t, 3H), 7.64~7.50(m, 9H), 7.40~7.37(t, 1H) |
| 2-34 | δ = 8.82~8.79(m, 3H), 8.42~8.39(d, 2H), 8.16~8.06(m, 5H), 7.98~7.84(m, 5H), 7.76~7.74(d, 2H), 7.67~7.49(m, 12H), 7.38~7.25(t, 1H) |
| 2-90 | δ = 9.27(s, 1H), 8.91~8.89(d, 4H), 8.79(s, 1H), 8.15(s, 1H), 8.10(s, 1H), 8.00~7.85(m, 8H), 7.68~7.60(m, 7H), 7.56~7.54(m, 3H), 7.41~7.37(t, 1H) |
| 2-91 | δ = 9.28(s, 1H), 8.91~8.89(d, 4H), 8.80(s, 1H), 8.16(s, 1H), 8.11(s, 1H), 8.02~7.85(m, 10H), 7.69~7.60(m, 7H), 7.56~7.54(m, 3H), 7.41~7.37(t, 1H) |
| 2-172 | δ = 9.28(s, 1H), 8.76~8.72(m, 3H), 8.65~8.63(m, 2H), 8.48~8.46(d, 1H), 8.04~7.97(m, 3H), 7.86~7.81(t, 2H), 7.73~7.68(m, 4H), 7.59~7.36(m, 9H), 7.30~7.28(d, 1H), 7.17~7.15(d, 1H) |
| 2-183 | δ = 8.75~8.739(d, 4H), 8.67(s, 1H), 8.64~8.63(d, 1H), 8.51~8.49(d, 1H), 8.15~8.13(d, 1H), 8.03~7.90(m, 5H), 7.75~7.68(m, 3H), 7.62~7.44(m, 13H) |
| 2-250 | δ = 8.86~8.82(m, 4H), 8.74~8.72(d, 1H), 8.48~8.46(d, 1H), 8.03~7.89(m, 3H), 7.75~7.55(m, 5H), 7.62~7.44(m, 13H) |
| 3-5 | δ = 9.40(s, 1H), 8.90~8.87(m, 3H), 8.80(s, 1H), 8.66~8.64(d, 1H), 8.29(s, 1H), 8.18 (s, 1H), 8.08~7.93(m, 8H), 7.71~7.53(m, 9H) |
| 3-67 | δ = 9.04(s, 1H), 8.87~8.83(m, 5H), 8.18~8.13 (m, 3H), 7.99~7.95(m, 3H), 7.92~7.86(m, 2H), 7.81~7.79(d, 1H), 7.63~7.53(m, 8H) |
| 3-74 | δ = 9.38(s, 1H), 9.08(s, 1H), 8.91~8.86(m, 4H), 8.18~8.13(m, 4H), 8.06~8.04(d, 1H), 8.00~7.86(m, 6H), 7.81~7.79(d, 1H), 7.67~7.51(m, 7H) |
| 2-337 | δ = 9.43~9.40(m, 2H), 8.93~8.90(5, 2H), 8.73~8.71(d, 1H), 8.60~8.51(m, 2H), 8.20~7.96(m, 8H), 7.85~7.78(m, 5H), 7.73~7.52(m, 9H), 7.45~7.42(t, 1H), 7.25~7.22(t, 1H) |
| 2-339 | δ = 9.43(s, 1H), 9.25~8.23(d, 1H), 9.15(s, 1H), 8.88~8.85(m, 3H), 8.60~8.53(m, 3H), 8.21~7.96(m, 2H), 8.20~7.96(m, 6H), 7.85~7.52(m, 12H), 7.45~7.42(t, 1H), 7.25~7.22(t, 1H) |
| 2-348 | δ = 9.31(s, 1H), 8.78~8.76(d, 4H), 8.48~8.46(d, 1H), 8.35(s, 1H), 8.15~7.97(m, 7H), 7.89~7.78(m, 3H), 7.70~7.40(m, 10H), 7.35~7.30(m, 2H) |
| 2-351 | δ = 9.35(s, 2H), 9.31(s, 1H), 9.18(s, 1H), 9.00~8.92(m, 3H), 8.68~8.66(d, 1H), 8.55~8.53(d, 1H), 8.14~7.75(m, 9H), 7.60~7.40(m, 13H) |
| 2-369 | δ = 9.44(s, 2H), 9.35(s, 1H), 9.20(s, 1H), 9.00~8.95(m, 4H), 8.70~8.68(d, 1H), 8.18~7.75(m, 9H), 7.65~7.45(m, 13H) |
| 2-466 | δ = 9.43(s, 2H), 9.22(s, 1H), 9.06~9.04(d, 1H), 8.93~8.91(d, 2H), 8.79~8.77(d, 1H), 8.63~8.61(d, 1H), 8.18~7.79(m, 9H), 7.65~7.52(m, 10H) |
| 2-468 | δ = 9.43(s, 2H), 9.21(s, 1H), 9.05~8.92(m, 3H), 8.73~8.71(d, 1H), 8.63~8.61(d, 1H), 8.18~7.79(m, 10H), 7.65~7.48(m, 13H) |
| 2-472 | δ = 9.23~8.20(d, 1H), 9.10(s, 1H), 8.84~8.78(m, 3H), 8.60~8.53(m, 3H), 8.16~8.09(m, 2H), 7.92(s, 1H), 7.80~7.78(m, 4H), 7.72~7.51(m, 16H) |
| 2-490 | δ = 9.42(s, 2H), 9.18~9.13(m, 2H), 8.92~8.90(d, 2H), 8.79~8.77(d, 1H), 8.63~8.61(d, 1H), 8.15~7.73(m, 9H), 7.65~7.50 (m, 10H) |
| 2-491 | δ = 9.42(s, 2H), 9.18~9.16(d, 1H), 8.95~8.89 (m, 3H), 8.72~8.70(d, 1H), 8.60~8.58(d, 1H), 8.14~7.70(m, 10H), 7.65~7.48(m, 13H) |
| 2-501 | δ = 8.76~8.74(d, 4H), 8.67~8.63 (m, 2H), 8.51~8.49(d, 1H), 8.16~8.13(d, 1H), 8.04~7.90(m, 5H), 7.76~7.70(m, 3H), 7.62~7.44(m, 13H) |
| 2-504 | δ = 9.38(s, 2H), 9.18(s, 1H), 9.00~8.90(m, 3H), 8.70~8.68(d, 1H), 8.60~8.58(d, 1H), 8.14~7.91(m, 6H), 7.75~7.70(m, 4H), 7.62~7.44(m, 13H) |
| 2-506 | δ = 9.38(s, 1H), 9.32~9.30(d, 1H), 8.88~8.85(m, 3H), 8.68~8.66(d, 1H), 8.59~8.57(d, 1H), 8.14~8.06(m, 2H), 7.98~7.85(m, 5H), 7.74~7.56(m, 8H), 7.51~7.42(m, 3H), 7.31~7.21(m, 4H), 7.15~7.05(m, 2H) |

TABLE 7-continued

| | |
|---|---|
| 2-530 | δ = 9.35(s, 2H), 9.15(s, 1H), 8.99~8.97(d, 1H), 8.85~8.77(m, 2H), 8.45~8.43(d, 1H), 8.10~7.75(m, 10H), 7.55~7.38(m, 10H) |
| 2-532 | δ = 9.36(s, 2H), 9.15(s, 1H), 8.99~8.95(m, 3H), 8.85~8.83(d, 1H), 8.45~8.43(d, 1H), 8.11~7.76(m, 10H), 7.56~7.37(m, 13H) |
| 2-542 | δ = 9.10(s, 1H), 8.78~8.75(m, 3H), 8.35~8.33(d, 1H), 8.05~7.77(m, 10H), 7.54~7.35(m, 13H), 7.23~7.20(t, 1H) |
| 2-561 | δ = 9.15(s, 1H), 8.96~8.88(m, 5H), 8.55~8.53(d, 1H), 7.95~7.83(m, 4H), 7.75~7.55(m, 6H), 7.25~7.23(t, 1H) |
| 2-562 | δ = 8.96~8.88(m, 4H), 7.85~7.83(d, 2H), 7.75~7.62(m, 4H) |
| 3-87 | δ = 9.40(s, 2H), 9.20(s, 1H), 8.90~8.87(m, 4H), 8.85~8.80(m, 2H), 8.66~8.64(d, 1H), 8.29(s, 1H), 8.18(s, 1H), 8.08~7.93(m, 9H), 7.71~7.53(m, 10H) |
| 3-110 | δ = 9.38(s, 1H), 9.25(s, 1H), 9.08(s, 1H), 8.91~8.86(m, 5H), 8.65~8.63(d, 1H), 8.18~7.99(m, 7H), 7.98~7.79(m, 8H), 7.67~7.51 (m, 9H) |
| 3-125 | δ = 9.43(s, 2H), 8.94~8.90(t, 2H), 8.73~8.71(d, 1H), 8.52~8.50(d, 1H), 8.16~7.96(m, 6H), 7.85~7.78(m, 4H), 7.73~7.52(m, 7H), 7.45~7.42(t, 1H), 7.25~7.22(t, 1H) |
| 3-130 | δ = 9.21(s, 1H), 8.95~8.93(d, 1H), 8.89~8.85(d, 2H), 8.81~8.79(d, 2H), 8.23~8.15(m, 3H), 7.85~7.78(m, 4H), 7.73~7.45(m, 9H), 7.25~7.22(t, 1H) |
| 3-137 | δ = 9.45(s, 2H), 9.38~9.36(d, 1H), 8.95~8.93(d, 2H), 8.75~8.74(d, 1H), 8.17~8.01(m, 4H), 7.99~7.97(d, 2H), 7.84~7.58(m, 10H), 7.46~7.34(m, 3H), 6.99~6.95(t, 1H), 6.81~6.79(d, 1H) |

1) Manufacture of Organic Light Emitting Device (Red Host)

A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO surface treatment and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. The light emitting layer was deposited to 400 Å by depositing a single compound or two types thereof described in the following Table 8 in one source of supply as a red host, and, using (piq)2(Ir)(acac) as a red phosphorescent dopant, doping the Ir compound by 3 wt % to the host. After that, Bphen was deposited to 30 Å as a hole blocking layer, and $Alq_3$ was deposited to 250 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-8}$ torr to $10^{-6}$ torr for each material to be used in the OLED manufacture.

For each of the organic electroluminescent devices manufactured as above, electroluminescent (EL) properties were measured using M7000 manufactured by McScience Inc., and with the measurement results, T90 was measured when standard luminance was 6,000 cd/m$^2$ through a lifetime measurement system (M6000) manufactured by McScience Inc.

TABLE 8

| | Light Emitting Layer | Ratio (P:N) | Turn-on (V) | Driving Voltage (V) | Efficiency (cd/A) | Color Coordinate (x, y) | Lifetime ($T_{90}$) |
|---|---|---|---|---|---|---|---|
| Comparative Example 1 | A | | 4.55 | 8.20 | 7.50 | (0.684, 0.316) | 3 |
| Comparative Example 2 | B | | 4.53 | 8.19 | 7.52 | (0.684, 0.316) | 3 |
| Comparative Example 3 | C | | 4.49 | 8.20 | 8.10 | (0.684. 0.316) | 2 |
| Comparative Example 4 | D | | 4.41 | 8.11 | 8.99 | (0.685. 0.315) | 3 |
| Comparative Example 5 | E | | 4.00 | 7.58 | 11.68 | (0.685, 0.315) | 10 |
| Comparative Example 6 | F | | 3.90 | 7.55 | 11.00 | (0.685, 0.315) | 10 |
| Comparative Example 7 | G | | 4.40 | 8.00 | 9.89 | (0.684, 0.316) | 3 |
| Comparative Example 8 | H | | 4.39 | 8.01 | 9.85 | (0.684. 0.316) | 5 |
| Comparative Example 9 | E:2-33 | 1:1 | 3.00 | 4.55 | 40.00 | (0.685, 0.315) | 300 |
| Comparative Example 10 | H:3:5 | 1:1 | 3.30 | 4.80 | 41.00 | (0.685, 0.315) | 350 |

TABLE 8-continued

| | Light Emitting Layer | Ratio (P:N) | Turn-on (V) | Driving Voltage (V) | Efficiency (cd/A) | Color Coordinate (x, y) | Lifetime ($T_{90}$) |
|---|---|---|---|---|---|---|---|
| Comparative Example 11 | 2-33 | | 4.20 | 6.78 | 57.00 | (0.684, 0.316) | 10 |
| Comparative Example 12 | 2-40 | | 4.00 | 6.55 | 62.15 | (0.684, 0.316) | 30 |
| Comparative Example 13 | 2-172 | | 4.30 | 6.85 | 62.50 | (0.684, 0.316) | 20 |
| Comparative Example 14 | 2-468 | | 4.25 | 6.70 | 65.95 | (0.684, 0.316) | 15 |
| Comparative Example 15 | 2-562 | | 4.05 | 6.60 | 61.05 | (0.685, 0.315) | 45 |
| Comparative Example 16 | 3-5 | | 4.30 | 6.80 | 65.10 | (0.685, 0.315) | 10 |
| Comparative Example 17 | 3-125 | | 4.40 | 6.91 | 50.50 | (0.685, 0.315 | 10 |
| Example 1 | 1-1 | | 3.60 | 7.20 | 16.60 | (0.685, 0.315) | 10 |
| Example 2 | 1-4 | | 3.65 | 7.24 | 16.61 | (0.685, 0.315) | 11 |
| Example 3 | 1-10 | | 3.55 | 7.13 | 15.50 | (0.685, 0.315) | 10 |
| Example 4 | 1-22 | | 3.62 | 7.23 | 15.30 | (0.685, 0.315) | 11 |
| Example 5 | 1-24 | | 3.73 | 7.50 | 14.50 | (0.685, 0.315) | 10 |
| Example 6 | 1-49 | | 3.45 | 7.00 | 18.10 | (0.685, 0.315) | 11 |
| Example 7 | 1-55 | | 3.40 | 6.97 | 17.05 | (0.685, 0.315) | 11 |
| Example 8 | 1-56 | | 3.40 | 6.98 | 17.15 | (0.684. 0.316) | 10 |
| Example 9 | 1-60 | | 3.50 | 7.20 | 16.70 | (0.684. 0.316) | 13 |
| Example 10 | 1-66 | | 3.65 | 7.30 | 16.55 | (0.684. 0.316) | 10 |
| Example 11 | 1-175 | | 3.50 | 7.11 | 17.00 | (0.685, 0.315) | 10 |
| Example 12 | 1-274 | | 3.35 | 6.85 | 19.10 | (0.685, 0.315) | 11 |
| Example 13 | 1-275 | | 3.38 | 6.91 | 18.90 | (0.685, 0.315) | 11 |
| Example 14 | 1-280 | | 3.30 | 6.75 | 17.90 | (0.685, 0.315) | 10 |
| Example 15 | 1-290 | | 3.45 | 7.13 | 18.30 | (0.684. 0.316) | 11 |
| Example 16 | 1-300 | | 3.60 | 7.30 | 18.45 | (0.684. 0.316) | 12 |
| Example 17 | 1-401 | | 3.48 | 7.20 | 17.50 | (0.685, 0.315) | 9 |
| Example 18 | 1-402 | | 3.55 | 7.21 | 17.20 | (0.685, 0.315) | 8 |
| Example 19 | 1-409 | | 3.60 | 7.29 | 16.95 | (0.685, 0.315) | 9 |
| Example 20 | 1-412 | | 3.40 | 6.99 | 16.15 | (0.684. 0.316) | 9 |
| Example 21 | 1-460 | | 3.80 | 7.42 | 18.55 | (0.684. 0.316) | 10 |
| Example 22 | 1-532 | | 3.59 | 7.15 | 22.30 | (0.684. 0.316) | 9 |
| Example 23 | 1-538 | | 3.59 | 7.14 | 22.25 | (0.684. 0.316) | 9 |
| Example 24 | 1-545 | | 3.78 | 7.40 | 20.35 | (0.685, 0.315) | 10 |
| Example 25 | 1-549 | | 3.77 | 7.35 | 19.85 | (0.685, 0.315) | 9 |
| Example 26 | 1-554 | | 3.61 | 7.15 | 21.50 | (0.685, 0.315) | 9 |
| Example 27 | 1-558 | | 3.40 | 6.99 | 18.80 | (0.685, 0.315) | 9 |
| Example 28 | 1-559 | | 3.41 | 7.02 | 18.78 | (0.685, 0.315) | 10 |
| Example 29 | 1-572 | | 3.85 | 7.50 | 19.11 | (0.684. 0.316) | 10 |
| Example 30 | 1-577 | | 3.89 | 7.53 | 18.30 | (0.684. 0.316) | 10 |
| Example 31 | 1-532:2:33 | 3:1 | 2.55 | 4.35 | 60.70 | (0.684. 0.316) | 650 |
| Example 32 | 1-532:2:33 | 1:1 | 2.40 | 4.15 | 71.05 | (0.684. 0.316) | 850 |
| Example 33 | 1-532:2:33 | 1:3 | 2.45 | 4.25 | 63.11 | (0.684. 0.316) | 700 |
| Example 34 | 1-538:2:34 | 1:1 | 2.99 | 4.55 | 45.50 | (0.684. 0.316) | 400 |
| Example 35 | 1-538:2-90 | 1:1 | 2.55 | 4.30 | 60.85 | (0.684. 0.316) | 650 |
| Example 36 | 1-538:2-91 | 1:1 | 2.58 | 4.25 | 68.33 | (0.684. 0.316) | 750 |
| Example 37 | 1-1:2-172 | 1:1 | 2.75 | 4.40 | 48.11 | (0.684. 0.316) | 650 |
| Example 38 | 1-558:3-5 | 1:1 | 2.45 | 4.20 | 65.00 | (0.684. 0.316) | 750 |
| Example 39 | 1-24:3-67 | 1:1 | 2.80 | 4.45 | 63.11 | (0.684. 0.316) | 655 |
| Example 40 | 1-559:3-74 | 1:1 | 2.43 | 4.16 | 67.00 | (0.684. 0.316) | 730 |
| Example 41 | 1-849:2:33 | 1:1 | 2.40 | 4.15 | 71.11 | (0.684. 0.316) | 1000 |
| Example 42 | 1-841:2:33 | 1:1 | 2.40 | 4.15 | 71.00 | (0.684. 0.316) | 900 |
| Example 43 | 1:532:2-40 | 1:1 | 2.35 | 4.10 | 71.99 | (0.684, 0.316) | 1015 |
| Example 44 | 1-532:2-561 | 1:1 | 2.36 | 4.15 | 71.56 | (0.684, 0.316) | 1010 |
| Example 45 | 1-532:2-562 | 1:1 | 2.38 | 4.18 | 71.00 | (0.684, 0.316) | 1200 |
| Example 46 | 1-532:2-563 | 1:1 | 2.40 | 4.24 | 70.65 | (0.684, 0.316) | 1195 |
| Example 47 | 1-532:2-339 | 1:1 | 2.51 | 4.55 | 58.75 | (0.685, 0.315) | 650 |
| Example 49 | 1-532:2-468 | 1:1 | 2.41 | 4.25 | 70.99 | (0.684, 0.316) | 950 |
| Example 50 | 1-532:2-490 | 1:1 | 2.60 | 4.88 | 35.50 | (0.685, 0.315) | 200 |
| Example 51 | 1-532:2-504 | 1:1 | 2.45 | 4.40 | 70.15 | (0.685, 0.315) | 855 |
| Example 52 | 1-532:2-530 | 1:1 | 2.40 | 4.35 | 74.95 | (0.685, 0.315 | 900 |
| Example 53 | 1-532:3-87 | 1:1 | 2.40 | 4.51 | 68.19 | (0.684, 0.316) | 815 |
| Example 54 | 1-532:3-110 | 1:1 | 2.45 | 4.60 | 67.50 | (0.685, 0.315) | 830 |
| Example 55 | 1-532:3-125 | 1:1 | 2.55 | 4.85 | 60.15 | (0.685, 0.315 | 650 |
| Example 56 | 1-532:3-130 | 1:1 | 2.70 | 4.99 | 50.15 | (0.684, 0.316) | 500 |

TABLE 8-continued
| Light Emitting Layer | Ratio (P:N) | Turn-on (V) | Driving Voltage (V) | Efficiency (cd/A) | Color Coordinate (x, y) | Lifetime ($T_{90}$) |
|---|---|---|---|---|---|---|
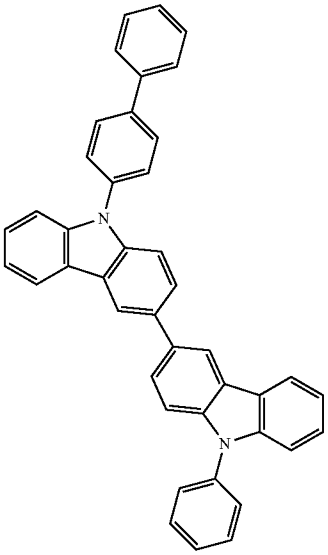 [SMILES: c1ccc(-c2ccc(-n3c4ccccc4c4cc(-c5ccc6c(c5)c5ccccc5n6-c5ccccc5)ccc43)cc2)cc1]
A
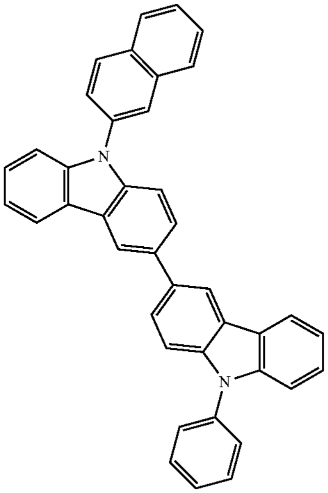 [SMILES: c1ccc(-n2c3ccccc3c3cc(-c4ccc5c(c4)c4ccccc4n5-c4ccc5ccccc5c4)ccc32)cc1]
B
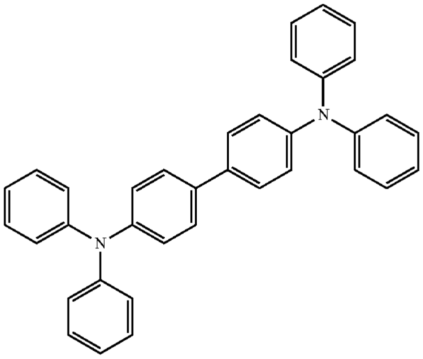 [SMILES: c1ccc(N(c2ccccc2)c2ccc(-c3ccc(N(c4ccccc4)c4ccccc4)cc3)cc2)cc1]
C TABLE 8-continued
| Light Emitting Layer | Ratio (P:N) | Turn-on (V) | Driving Voltage (V) | Efficiency (cd/A) | Color Coordinate (x, y) | Lifetime ($T_{90}$) |
|---|---|---|---|---|---|---|
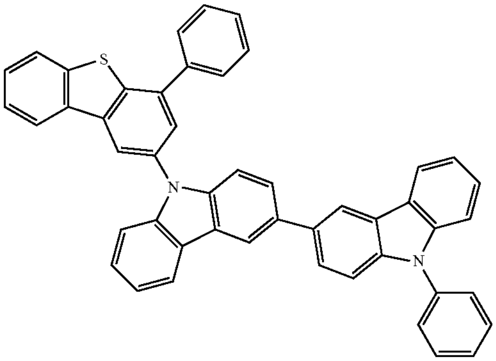 [SMILES: c1ccc(-c2cc(-n3c4ccccc4c4cc(-c5ccc6c(c5)c5ccccc5n6-c5ccccc5)ccc43)cc3c2sc2ccccc23)cc1]
D
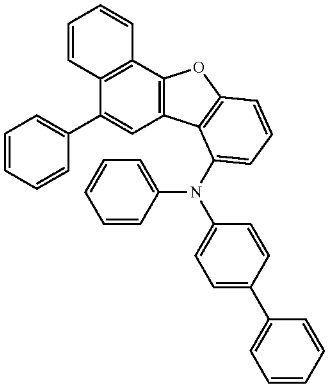 [SMILES: c1ccc(-c2ccc(N(c3ccccc3)c3cccc4oc5c6ccccc6c(-c6ccccc6)cc5c34)cc2)cc1]
E
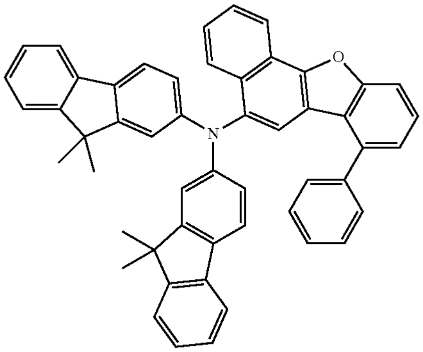 [SMILES: CC1(C)c2ccccc2-c2ccc(N(c3ccc4c(c3)C(C)(C)c3ccccc3-4)c3cc4c(oc5cccc(-c6ccccc6)c54)c4ccccc34)cc21]
F
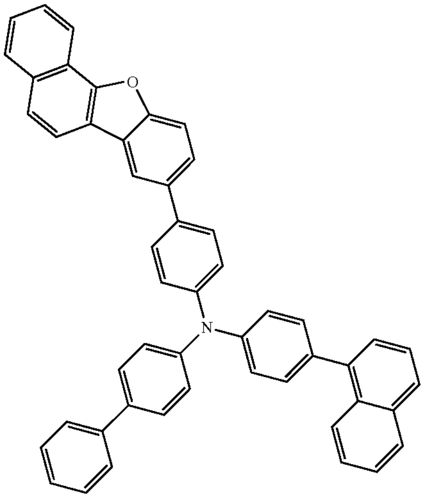 [SMILES: c1ccc(-c2ccc(N(c3ccc(-c4ccc5oc6c7ccccc7ccc6c5c4)cc3)c3ccc(-c4cccc5ccccc45)cc3)cc2)cc1]
G TABLE 8-continued

| | Light Emitting Layer | Ratio (P:N) | Turn-on (V) | Driving Voltage (V) | Efficiency (cd/A) | Color Coordinate (x, y) | Lifetime ($T_{90}$) |
|---|---|---|---|---|---|---|---|
| 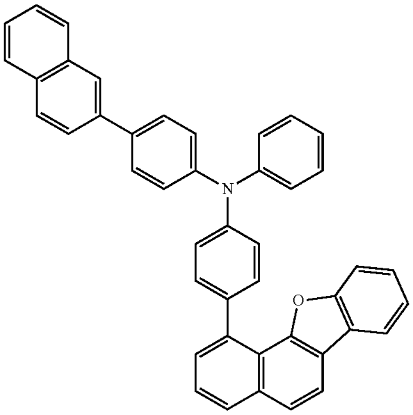 [SMILES: c1ccc(N(c2ccc(-c3ccc4ccccc4c3)cc2)c2ccc(-c3cccc4ccc5c6ccccc6oc5c34)cc2)cc1] | | | | | | | H |

The heterocyclic compound of Chemical Formula 1 of the present disclosure has proper molecular weight and band gap while having high thermal stability. A proper band gap of a light emitting layer has favorable hole transfer ability and prevents electron loss, and thereby helps with effective formation of a recombination zone. Accordingly, as seen from the device evaluation, it was identified that the compounds of the present disclosure had improved performance compared to the comparative examples.

In addition, the combination of Chemical Formula 1 and Chemical Formula A or the combination of Chemical Formula 1 and Chemical Formula B in the light emitting layer enhances driving, efficiency and lifetime. This is due to the fact that, when using a donor (p-host, Chemical Formula 1) having a favorable hole transfer ability and an acceptor (n-host, Chemical Formula A, Chemical Formula B) having a favorable electron transfer ability as a host of the light emitting layer, a driving voltage at which electrons and holes are injected is lowered, and efficiency and lifetime are enhanced through effective formation of a recombination zone.

2) Manufacture of Organic Light Emitting Device (Red Host)

A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine), a hole transfer layer NPB (N,N'-di(1-naphthyl)-N,N'-diphenyl-(1,1'-biphenyl)-4,4'-diamine) and an electron blocking layer TAPC (cyclohexylidenebis[N,N-bis(4-methylphenyl)benzenamine] or an exciton blocking layer TCTA (tris(4-carbazoyl-9-ylphenyl)amine), which are common layers, were formed.

A light emitting layer was thermal vacuum deposited thereon as follows. The light emitting layer was deposited to 400 Å by depositing a single compound or two types thereof described in the following Table 9 in one source of supply as a red host, and, using (piq)2(Ir)(acac) as a red phosphorescent dopant, doping the Ir compound by 3 wt % to the host. After that, Bphen was deposited to 30 Å as a hole blocking layer, and TPBI was deposited to 250 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-8}$ torr to $10^{-6}$ torr for each material to be used in the OLED manufacture.

For each of the organic electroluminescent devices manufactured as above, electroluminescent (EL) properties were measured using M7000 manufactured by McScience Inc., and with the measurement results, $T_{90}$ was measured when standard luminance was 6,000 cd/$m^2$ through a lifetime measurement system (M6000) manufactured by McScience Inc.

TABLE 9

| | Light Emitting Layer | Ratio (P:N) | Turn-on (V) | Driving Voltage (V) | Efficiency (cd/A) | Color Coordinate (x, y) | Lifetime ($T_{90}$) |
|---|---|---|---|---|---|---|---|
| Comparative Example 1 | A | — | 3.99 | 7.69 | 8.11 | (0.684, 0.316) | 3 |

TABLE 9-continued

| | Light Emitting Layer | Ratio (P:N) | Turn-on (V) | Driving Voltage (V) | Efficiency (cd/A) | Color Coordinate (x, y) | Lifetime ($T_{90}$) |
|---|---|---|---|---|---|---|---|
| Comparative Example 2 | E | — | 3.56 | 7.27 | 13.55 | (0.685, 0.315) | 9 |
| Comparative Example 3 | H | — | 3.78 | 7.50 | 10.00 | (0.684. 0.316) | 5 |
| Comparative Example 4 | A:2-183 | 1:1 | 3.51 | 5.10 | 30.78 | (0.685, 0.315) | 250 |
| Comparative Example 5 | H:2-183 | 1:1 | 3.21 | 4.81 | 40.79 | (0.685, 0.315) | 350 |
| Example 1 | 1-1 | — | 3.20 | 6.85 | 18.10 | (0.685, 0.315) | 10 |
| Example 2 | 1-10 | — | 2.95 | 6.63 | 16.50 | (0.685, 0.315) | 10 |
| Example 3 | 1-52 | — | 3.10 | 6.73 | 19.55 | (0.685, 0.315) | 11 |
| Example 4 | 1-66 | — | 3.30 | 6.95 | 18.61 | (0.684. 0.316) | 10 |
| Example 5 | 1-300 | — | 3.15 | 6.78 | 21.50 | (0.684. 0.316) | 12 |
| Example 6 | 1-409 | — | 3.23 | 6.85 | 20.15 | (0.685, 0.315) | 10 |
| Example 7 | 1-554 | — | 3.31 | 6.90 | 25.65 | (0.685, 0.315) | 9 |
| Example 8 | 1-558 | — | 3.38 | 6.99 | 23.80 | (0.685, 0.315) | 9 |
| Example 9 | 1-572 | — | 3.48 | 7.11 | 24.55 | (0.684. 0.316) | 10 |
| Example 10 | 1-577 | — | 3.50 | 7.15 | 24.20 | (0.685, 0.315) | 10 |
| Example 11 | 1-558:2-183 | 1:1 | 2.44 | 3.93 | 70.33 | (0.685, 0.315) | 875 |
| Example 12 | 1-558:3-5 | 1:1 | 2.32 | 3.95 | 70.35 | (0.684. 0.316) | 800 |
| Example 13 | 1-66:2-250 | 1:1 | 2.45 | 4.11 | 55.35 | (0.685, 0.315) | 685 |

The heterocyclic compound of Chemical Formula 1 of the present disclosure has proper molecular weight and band gap while having high thermal stability. A proper band gap of a light emitting layer has favorable hole transfer ability and prevents electron loss, and thereby helps with effective formation of a recombination zone. Accordingly, as seen from the device evaluation, it was identified that the compounds of the present disclosure had improved performance compared to the comparative examples. In addition, the combination of Chemical Formula 1 and Chemical Formula A or the combination of Chemical Formula 1 and Chemical Formula B in the light emitting layer enhances driving, efficiency and lifetime. This is due to the fact that, when using a donor (p-host, Chemical Formula 1) having a favorable hole transfer ability and an acceptor (n-host, Chemical Formula A, Chemical Formula B) having a favorable electron transfer ability as a host of the light emitting layer, electrons and holes are efficiently injected, and efficiency is enhanced by having balanced charges and holes and thereby forming a proper recombination zone.

3) Manufacture of Organic Light Emitting Device (Red Host)

A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

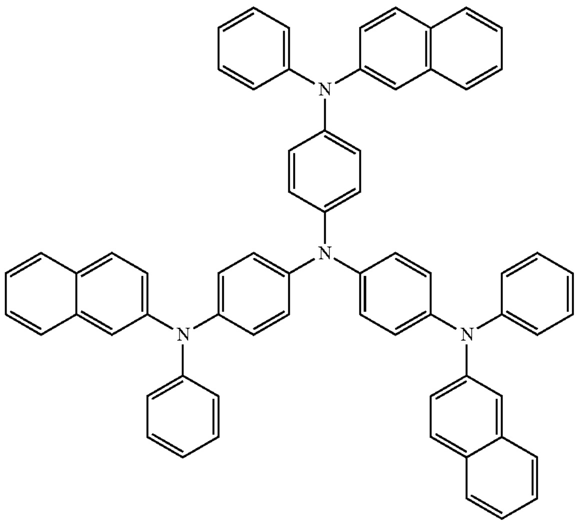

2-TNATA

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

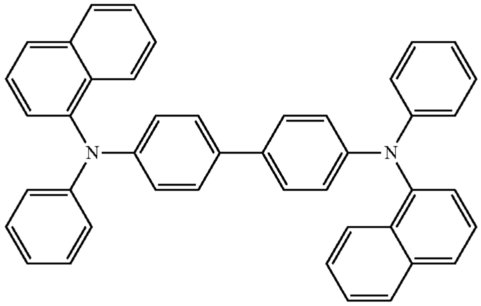

NPB

After that, a compound described in the following Table 10 was deposited to 100 Å to form a hole transfer auxiliary layer.

A light emitting layer was thermal vacuum deposited thereon as follows. The light emitting layer was deposited to 400 Å by depositing a single compound or two types thereof described in the following Table 10 in one source of supply as a red host, and, using (piq)2(Ir)(acac) as a red phosphorescent dopant, doping the Ir compound by 3 wt % to the host. After that, Bphen was deposited to 30 Å as a hole blocking layer, and TPBI was deposited to 250 Å thereon as an electron transfer layer.

Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-8}$ torr to $10^{-6}$ torr for each material to be used in the OLED manufacture.

For each of the organic electroluminescent devices manufactured as above, electroluminescent (EL) properties were measured using M7000 manufactured by McScience Inc., and with the measurement results, $T_{90}$ was measured when standard luminance was 6,000 cd/$m^2$ through a lifetime measurement system (M6000) manufactured by McScience Inc.

TABLE 10

| | Hole Transfer Auxiliary Layer | Light Emitting Layer Compound | Ratio | Driving Voltage (V) | Efficiency (cd/A) | Life-time ($T_{90}$) |
|---|---|---|---|---|---|---|
| Comparative Example 1 | C | 1-15 | — | 7.27 | 18.10 | 256 |
| Comparative Example 2 | C | 2-11 | | 7.50 | 16.50 | 260 |
| Comparative Example 3 | 1-15 | A | — | 6.85 | 13.55 | 290 |
| Comparative Example 4 | 1-39 | B | — | 6.63 | 10.00 | 275 |
| Comparative Example 5 | NPB | A:2-183 | 1:1 | 5.10 | 30.78 | 300 |
| Comparative Example 6 | NPB | H:2-183 | 1:1 | 4.81 | 40.79 | 304 |
| Example 1 | 1-15 | 1-17:2-170 | 1:1 | 4.43 | 101.1 | 354 |
| Example 2 | 1-35 | 1-450:2-42 | 1:1 | 4.31 | 111.1 | 310 |
| Example 3 | 1-853 | 1-558:2-183 | 1:1 | 3.93 | 70.33 | 1030 |
| Example 4 | 1-854 | 1-558:3-5 | 1:1 | 3.95 | 70.35 | 1200 |
| Example 5 | 1-873 | 1-131:2-7 | 1:2 | 3.53 | 103.1 | 920 |
| Example 6 | 1-874 | 1-31:2-7 | 1:1 | 3.47 | 110.3 | 960 |

C

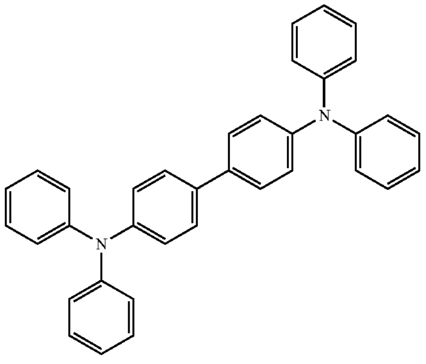 [SMILES: c1ccc(N(c2ccccc2)c2ccc(-c3ccc(N(c4ccccc4)c4ccccc4)cc3)cc2)cc1]

As seen from Table 10, the organic light emitting devices of Examples 1 to 9 of Table 10 using the compound according to the present application when forming the hole transfer auxiliary layer effectively prevents electrons from coming over from the opposite side of the hole transfer layer while stabilizing the HOMO (Highest Occupied Molecular Orbital) energy by having a structure in which naphthobenzofuran is substituted with two specific substituents including an amine group, and thereby delocalizing the HOMO energy level. As a result, superior efficiency was obtained, and lifetime was significantly improved when manufacturing the light emitting device in the case of forming the hole transfer auxiliary layer having hydrogen replaced by deuterium compared to the unsubstituted materials, and it was identified that light emission efficiency and lifetime were superior compared to the organic light emitting devices of Comparative Examples 1 to 6 of Table 10 not using the compound according to the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

The invention claimed is:

1. A heterocyclic compound represented by the following Chemical Formula 1:

[Chemical Formula 1]

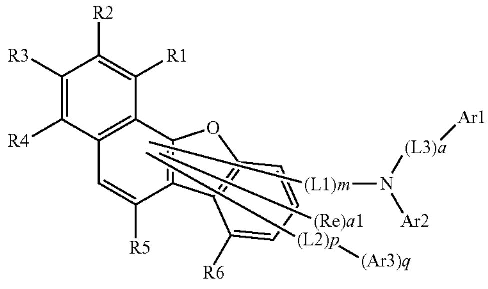

wherein, in Chemical Formula 1,

R1 to R6 and Re are the same as or different from each other, and each independently selected from the group consisting of hydrogen; and deuterium;

L1 to L3 are the same as or different from each other, and each independently a direct bond; or a substituted or unsubstituted C6 to C60 arylene group;

Ar1 and Ar2 are the same as or different from each other, and each independently selected from the group consisting of a substituted or unsubstituted C6 to C60 aryl group; and a substituted or unsubstituted C2 to C60 heteroaryl group;

Ar3 is a phenyl group unsubstituted or substituted with a t-butyl group or $CF_3$; a biphenyl group unsubstituted or substituted with a phenyl group; a terphenyl group; a naphthyl group; a dimethylfluorenyl group; a diphenylfluorenyl group; a spirobifluorenyl group; a dibenzofuran group; or a dibenzothiophene group;

"substituted or unsubstituted" means being substituted with one or more substituents selected from the group consisting of deuterium; a halogen group; a cyano group; C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; and —P(=O)RR'; or being unsubstituted, or being substituted with a substituent linking two or more substituents selected from among the substituents described above or being unsubstituted, and R, R' and R" are the same as or different from each other, and each independently a substituted or unsubstituted C1 to C60 alkyl group; a substituted or unsubstituted C6 to C60 aryl group; or a substituted or unsubstituted C2 to C60 heteroaryl group;

q is an integer of 1 to 4;

a1 is an integer of 0 to 2;

p, a and m are an integer of 0 to 4; and when q, p, a and m are an integer of 2 to 4 or a1 is an integer of 2, substituents in the parentheses are the same as or different from each other.

2. The heterocyclic compound of claim 1, wherein Chemical Formula 1 is represented by the following Chemical Formula 2 or 3:

[Chemical Formula 2]

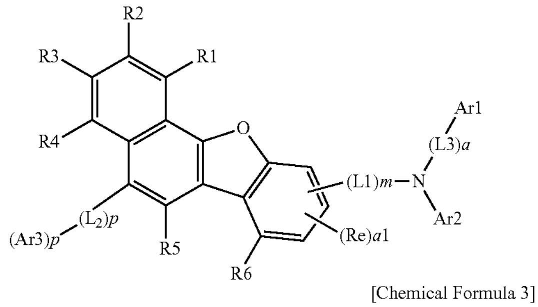

[Chemical Formula 3]

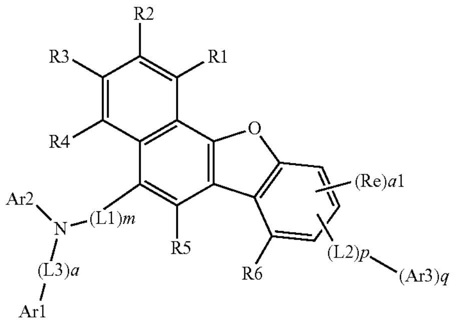

in Chemical Formulae 2 and 3,

R1 to R6, Re, L1 to L3, Ar1 to Ar3, a1, p, q, m and a have the same definitions as in Chemical Formula 1.

3. The heterocyclic compound of claim 2, wherein Chemical Formula 2 is represented by any one of the following Chemical Formulae 2-1 to 2-3:

[Chemical Formula 2-1]

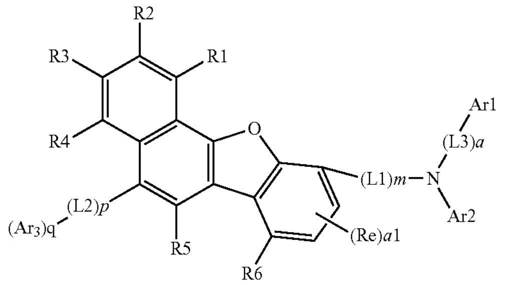

[Chemical Formula 2-2]

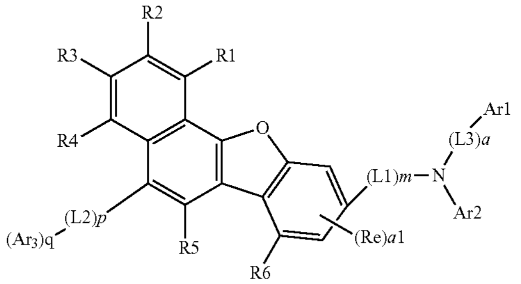

[Chemical Formula 2-3]

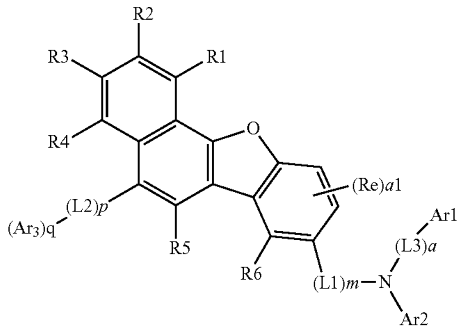

in Chemical Formulae 2-1 to 2-3,

R1 to R6, Re, L1 to L3, Ar1 to Ar3, a1, p, q, m and a have the same definitions as in Chemical Formula 2.

4. The heterocyclic compound of claim 2, wherein Chemical Formula 3 is represented by any one of the following Chemical Formulae 3-1 to 3-3:

[Chemical Formula 3-1]

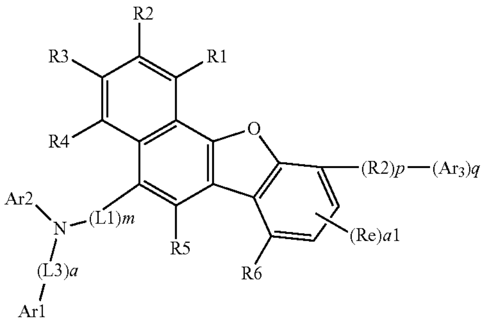

-continued

[Chemical Formula 3-2]

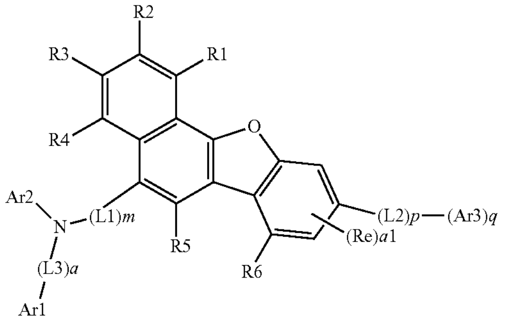

[Chemical Formula 3-3]

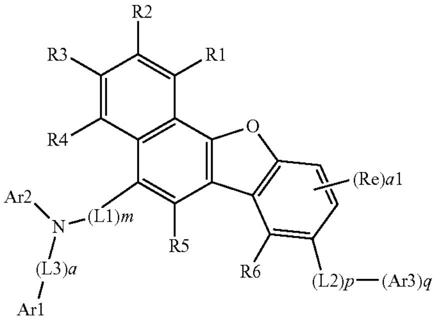

in Chemical Formulae 3-1 to 3-3,

R1 to R6, Re, L1 to L3, Ar1 to Ar3, a1, p, q, m and a have the same definitions as in Chemical Formula 3.

5. The heterocyclic compound of claim 1, wherein

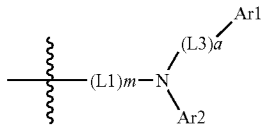

is represented by any one of the following Chemical Formulae 1-1 to 1-4:

[Chemical Formula 1-1]

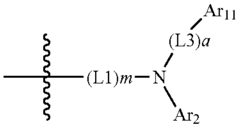

[Chemical Formula 1-2]

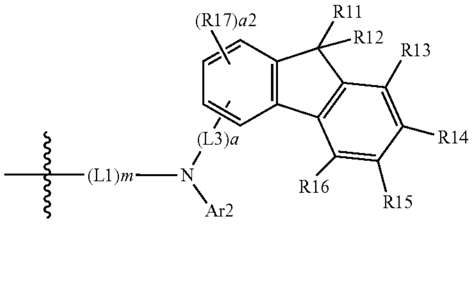

-continued

[Chemical Formula 1-3]

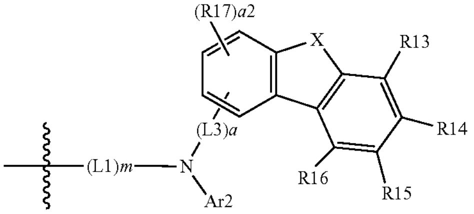

[Chemical Formula 1-4]

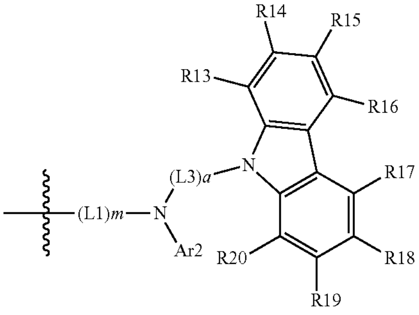

in Chemical Formulae 1-1 to 1-4,

L1, m, L3, a and Ar2 have the same definitions as in Chemical Formula 1;

Ar11 is a substituted or unsubstituted C6 to C20 aryl group,

X is O; S; or NRa;

R11 and R12 are the same as or different from each other, and each independently a substituted or unsubstituted C1 to C60 alkyl group; a substituted or unsubstituted C6 to C60 aryl group; or a substituted or unsubstituted C2 to C60 heteroaryl group, or two groups adjacent to each other bond to each other to form a substituted or unsubstituted C6 to C60 aromatic hydrocarbon ring;

R13 to R20 and Ra are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(=O)RR'; and —SiRR'R", or two or more groups adjacent to each other bond to each other to form a substituted or unsubstituted C6 to C60 aliphatic or aromatic hydrocarbon ring or a substituted or unsubstituted C2 to C60 aliphatic or aromatic heteroring;

a2 is an integer of 0 to 3, and when a2 is 2 or 3, substituents in the parentheses are the same as or different from each other;

"substituted or unsubstituted" means being substituted with one or more substituents selected from the group consisting of deuterium; a halogen group; a cyano group; C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; and —P(═O)RR'; or being unsubstituted, or being substituted with a substituent linking two or more substituents selected from among the substituents described above or being unsubstituted, and R, R' and R" have the same definitions as in Chemical Formula 1.

6. The heterocyclic compound of claim 1, wherein Chemical Formula 1 is represented by any one of the following compounds:

1-1

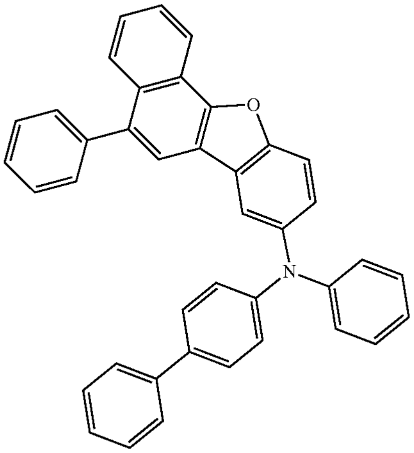

1-2

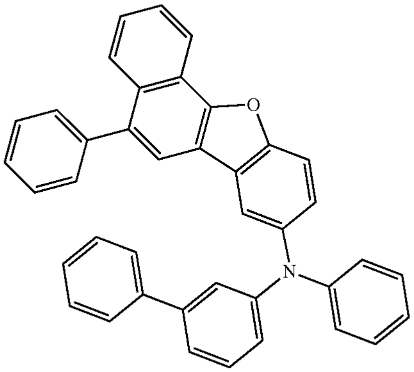

1-3

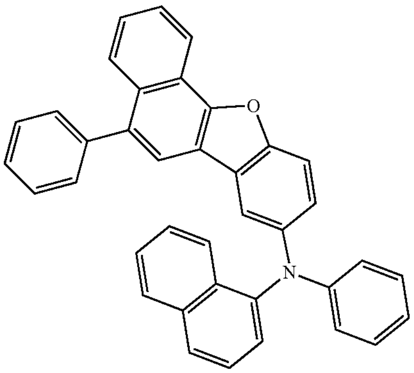

-continued 1-4

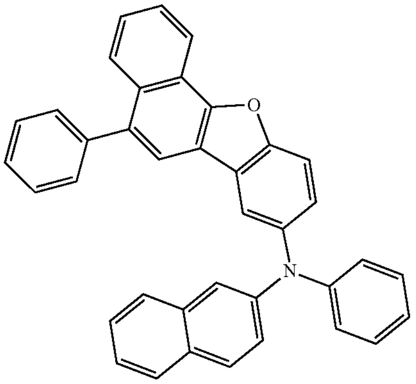

1-5

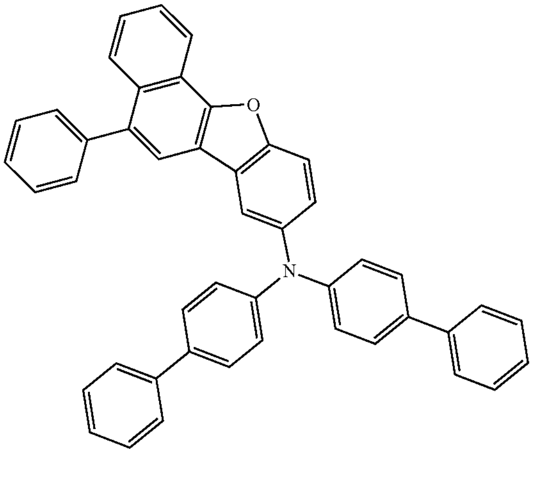

1-6

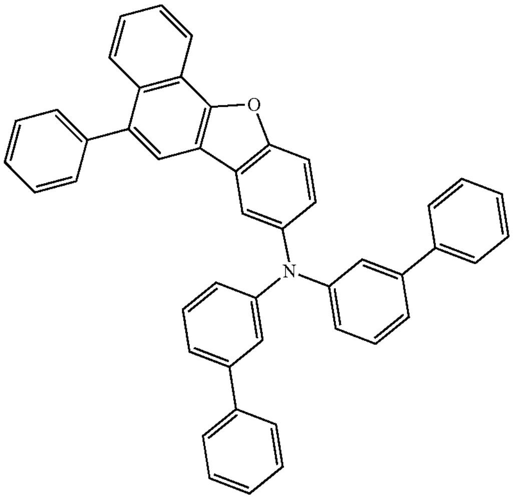

-continued
1-7
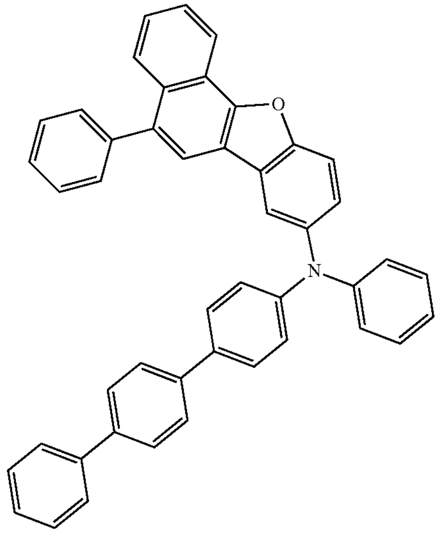
1-8
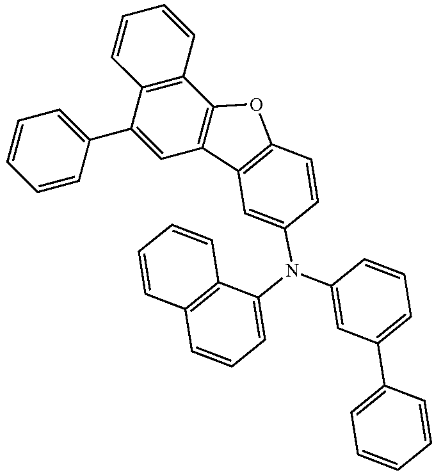
1-9
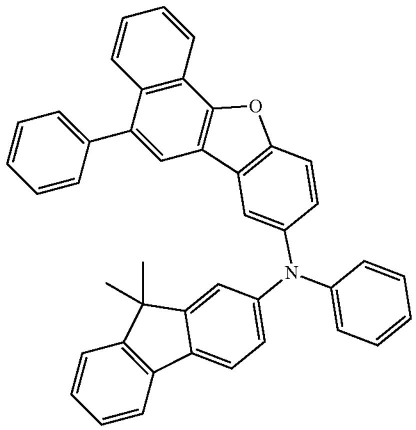
-continued
1-10
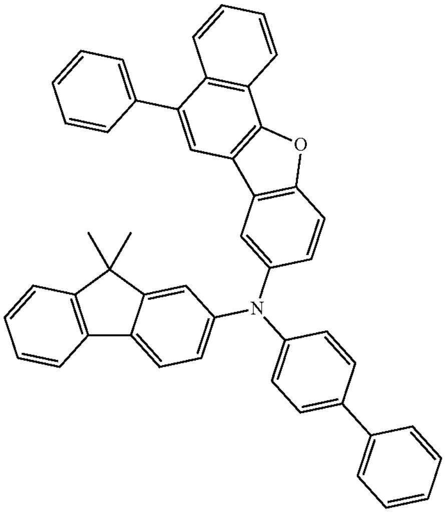
1-11
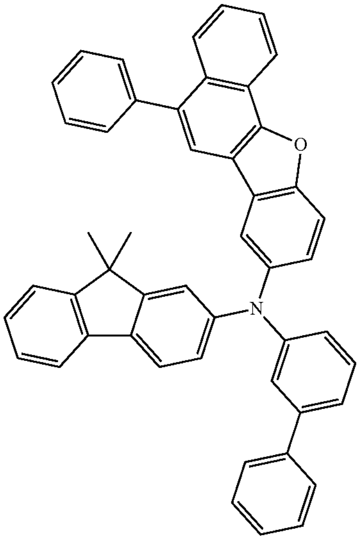
1-12
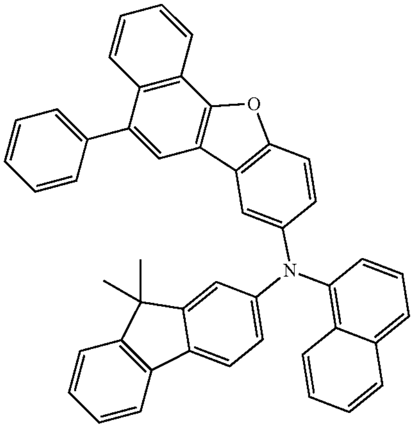

-continued
1-13
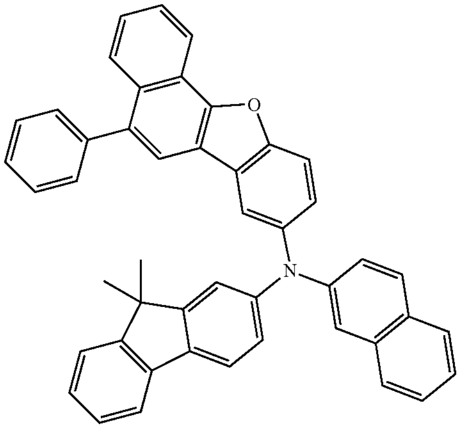
1-14
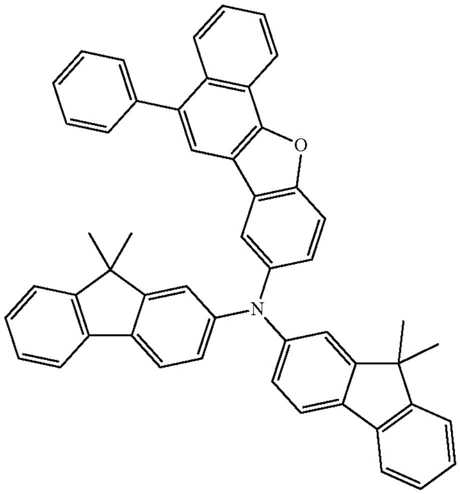
1-15
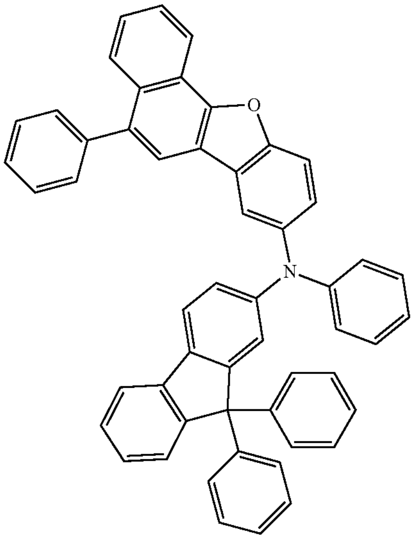
-continued
1-16
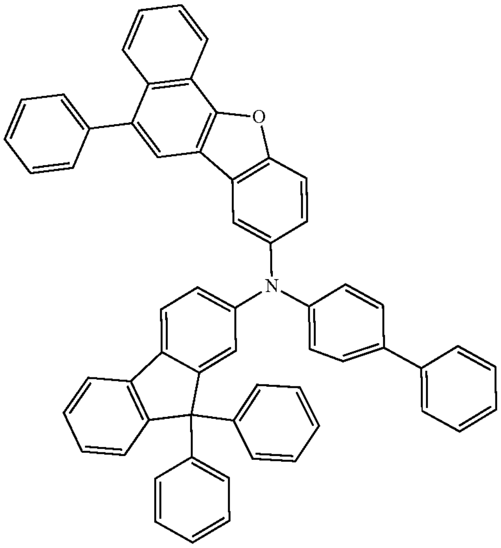
1-17
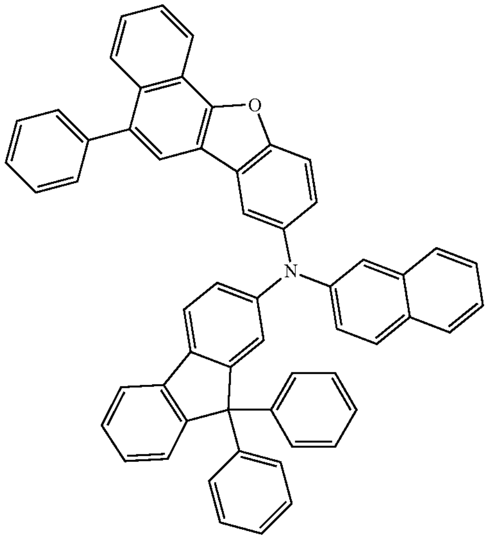
1-18
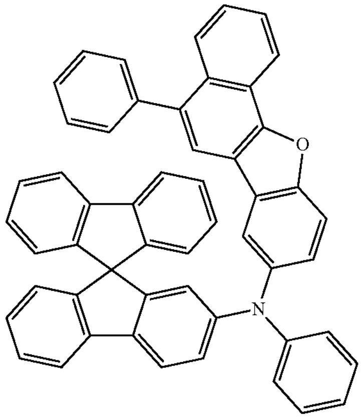

-continued
1-19
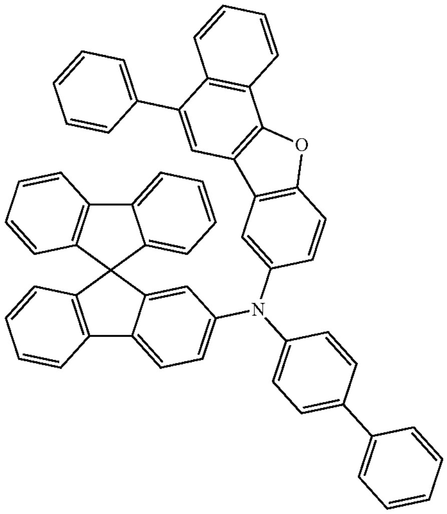
1-20
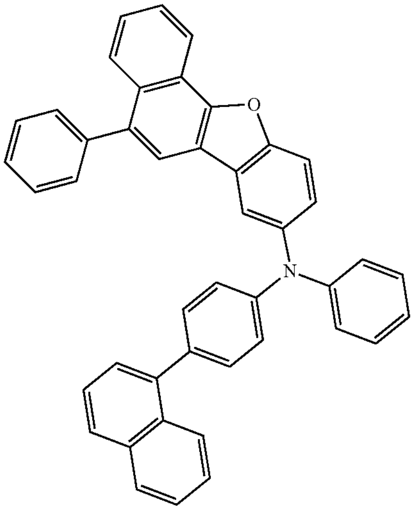
1-21
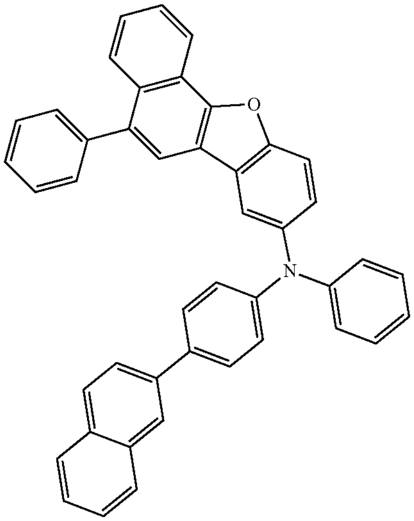
-continued
1-22
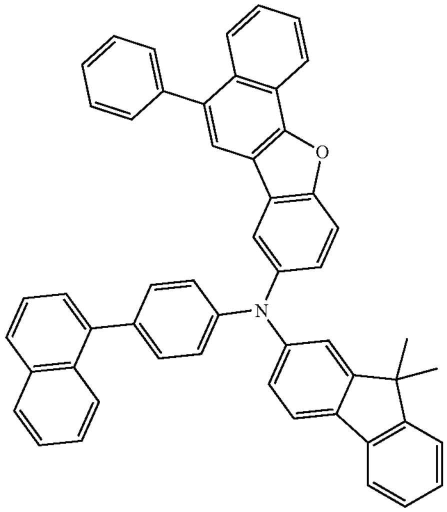
1-23
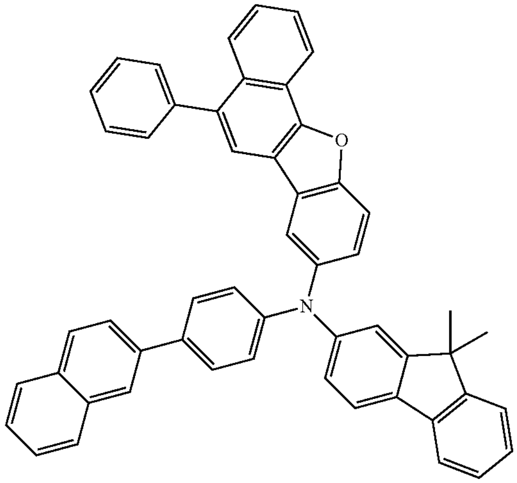
1-24
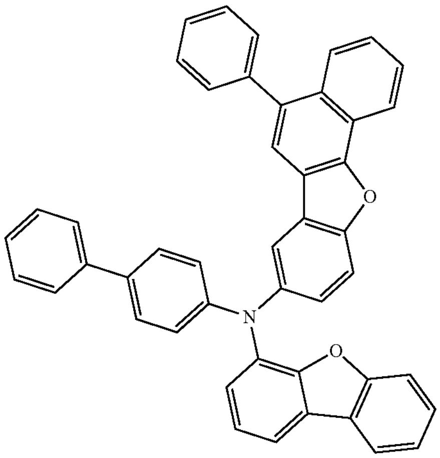

-continued
1-25
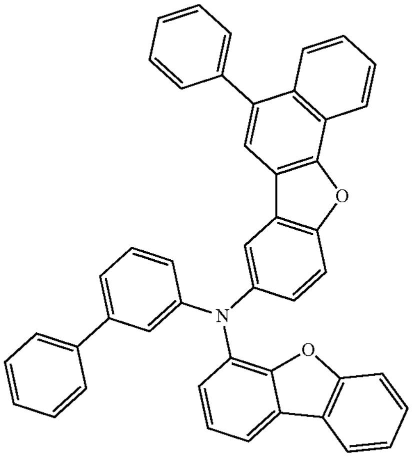
1-26
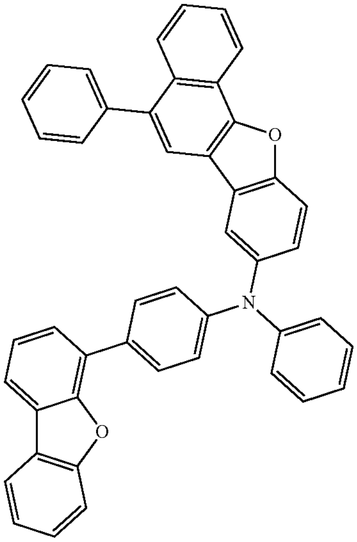
1-27
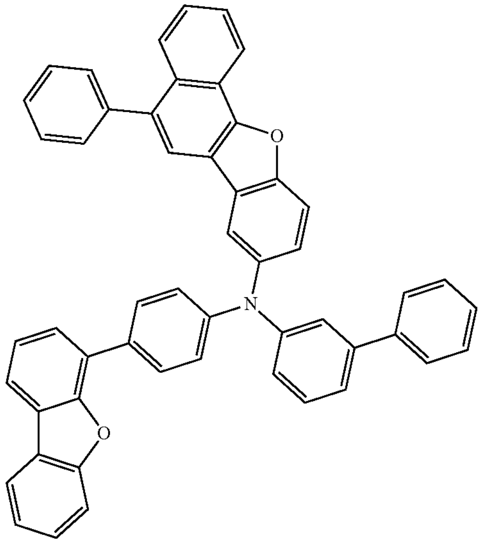
-continued
1-28
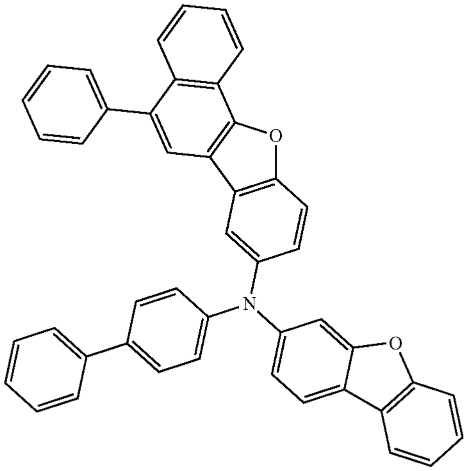
1-29
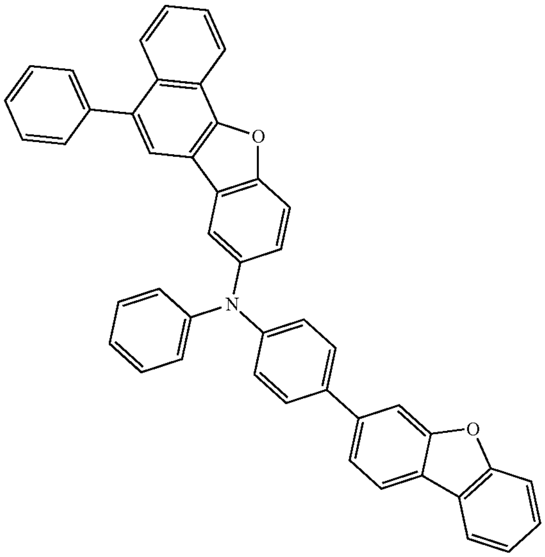

-continued
1-30
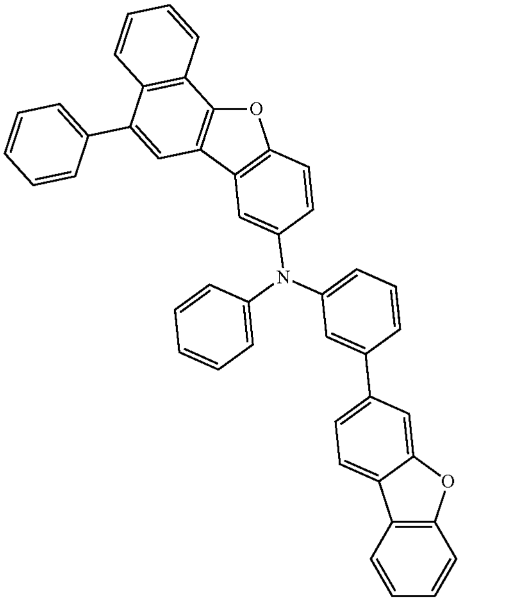
1-31
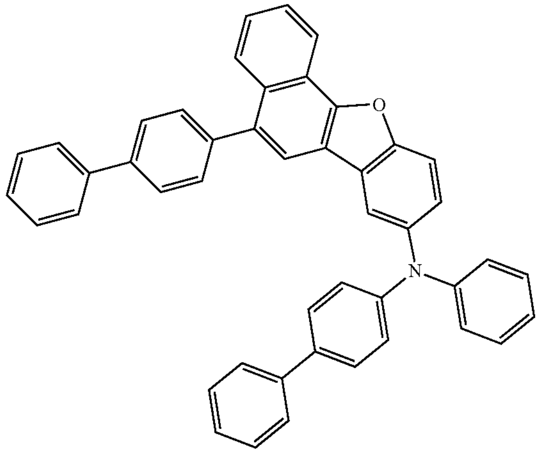
1-32
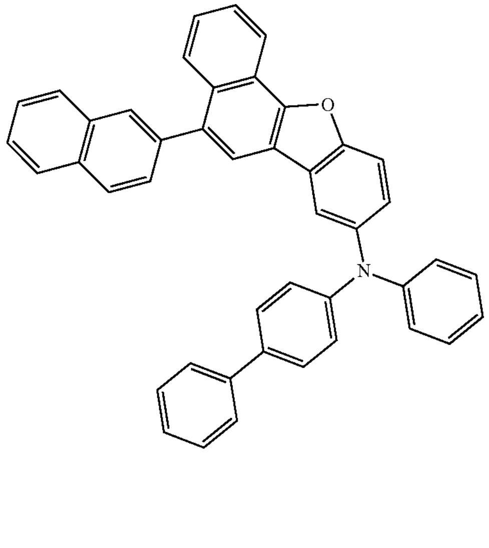
-continued
1-33
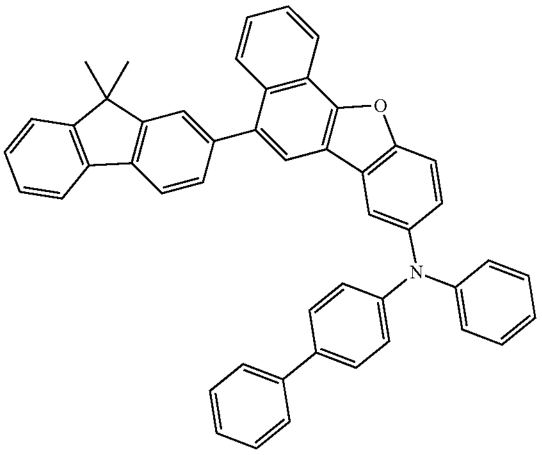
1-34
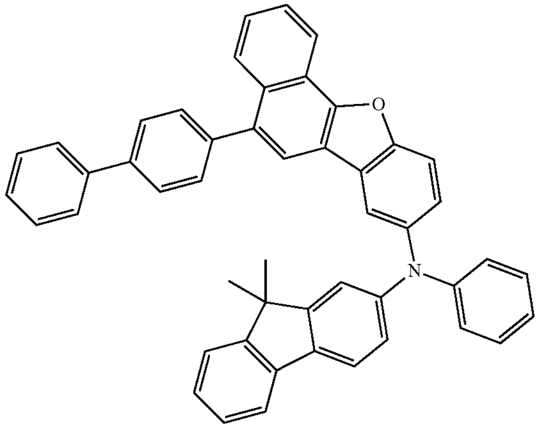
1-35
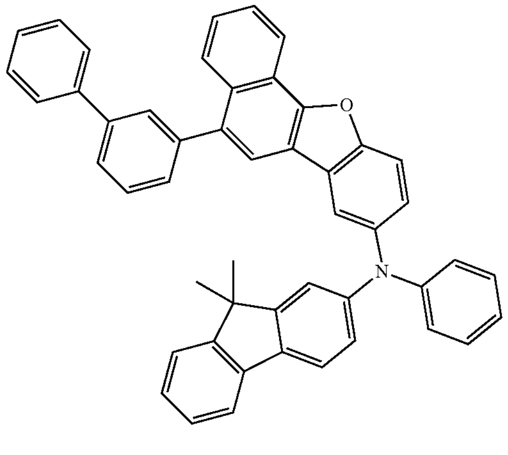

-continued
1-36
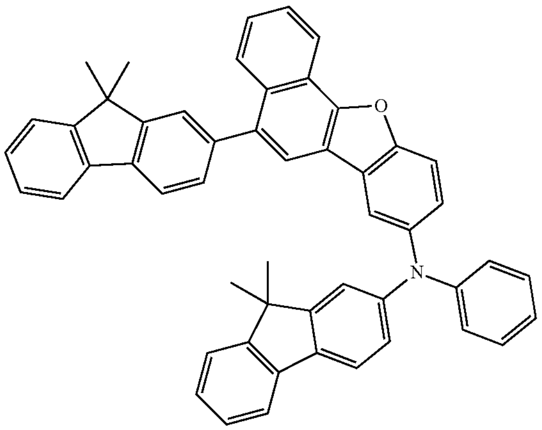
1-37
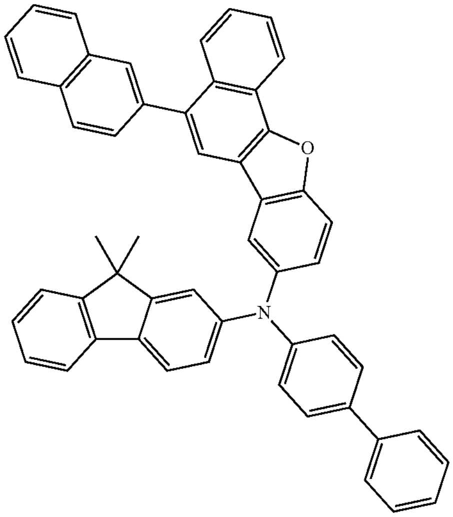
1-38
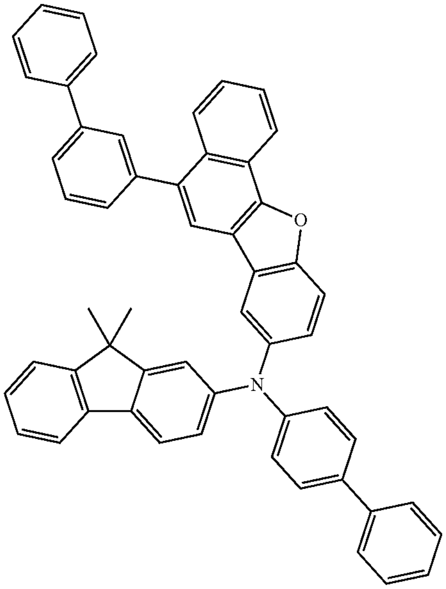
-continued
1-39
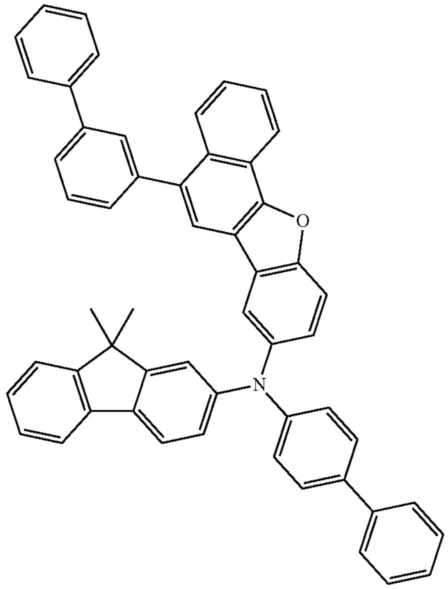
1-40
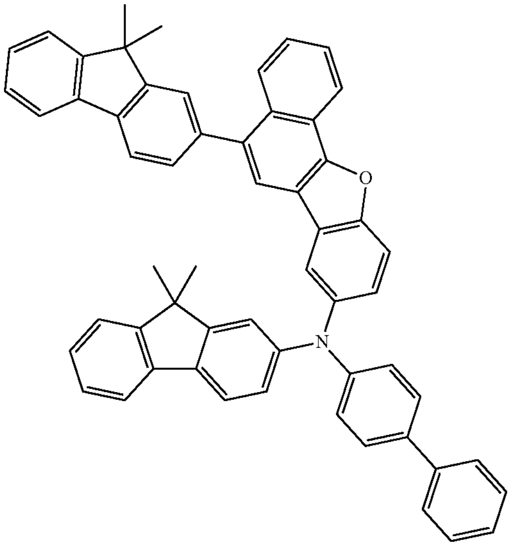

-continued
1-41
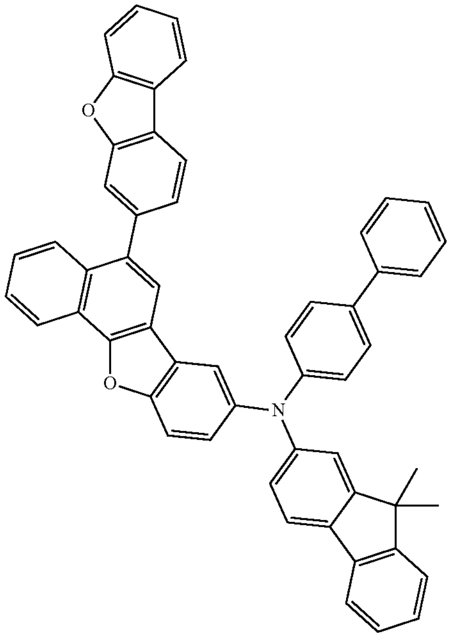
1-42
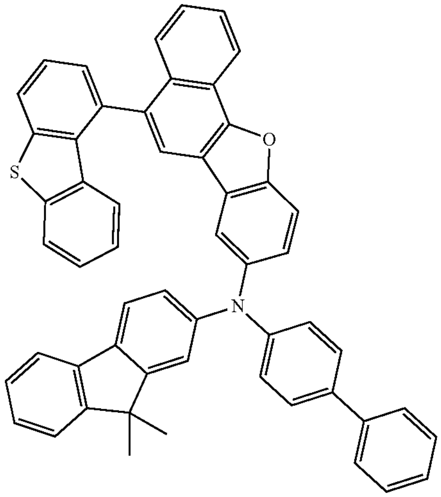
-continued
1-43
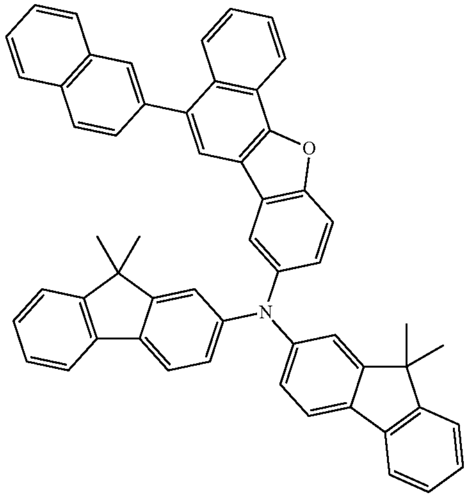
1-44
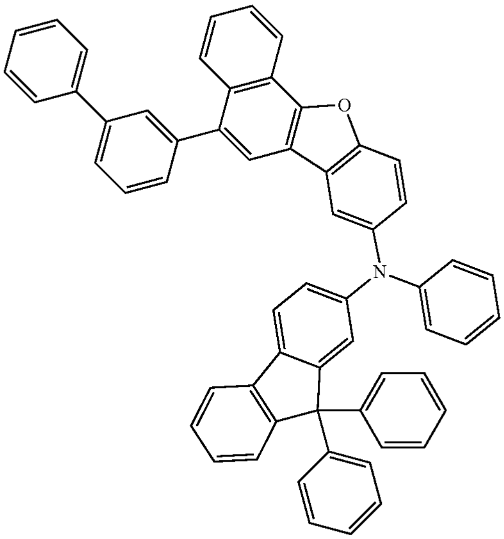
1-45
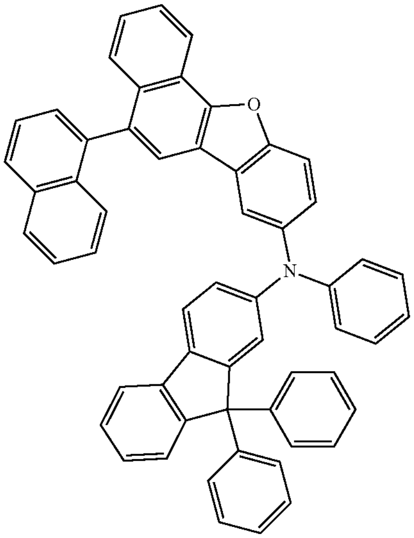

-continued
1-46
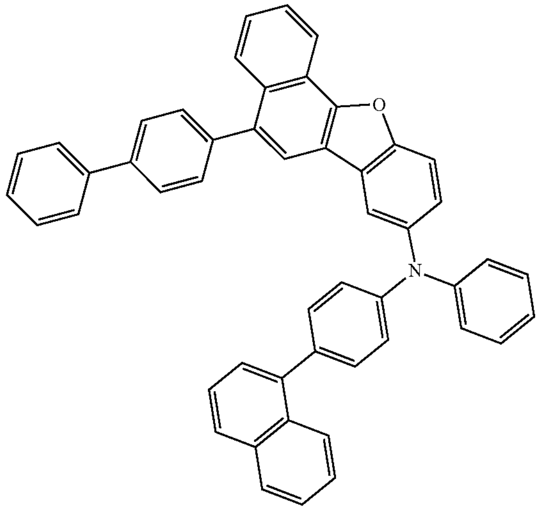
1-47
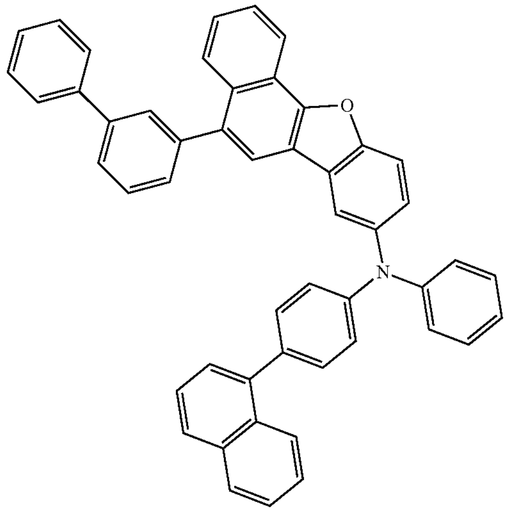
1-48
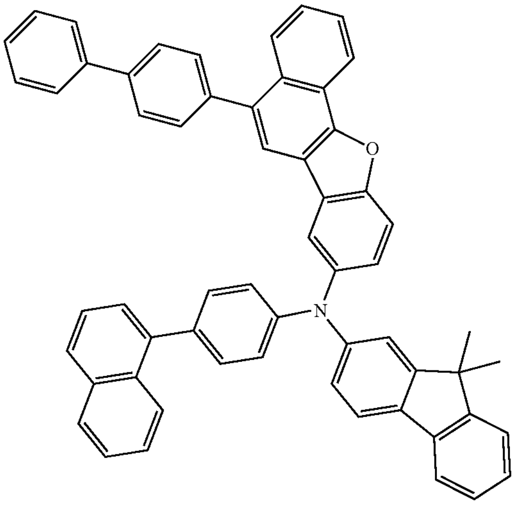
-continued
1-49
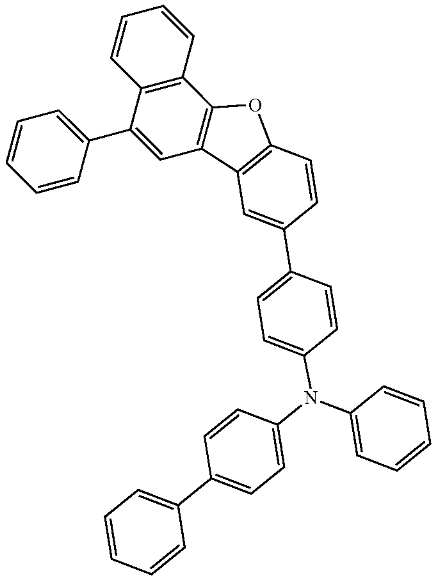
1-50
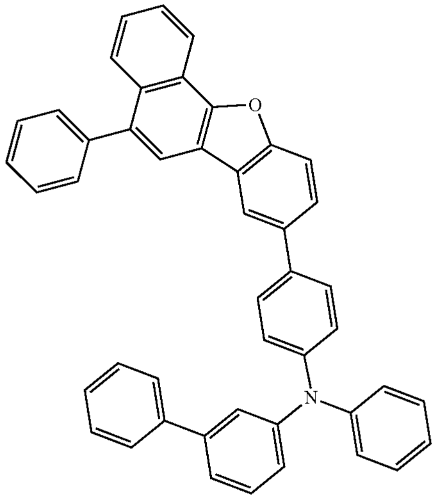
1-51
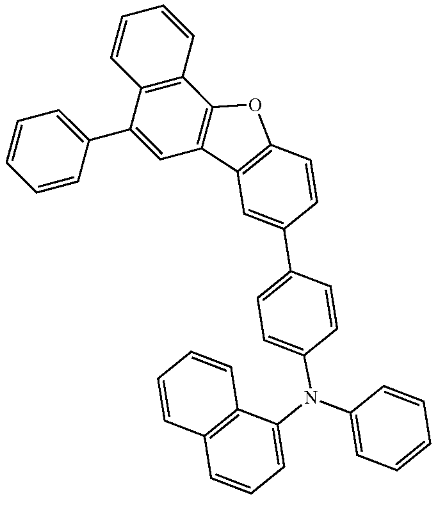

-continued
1-52
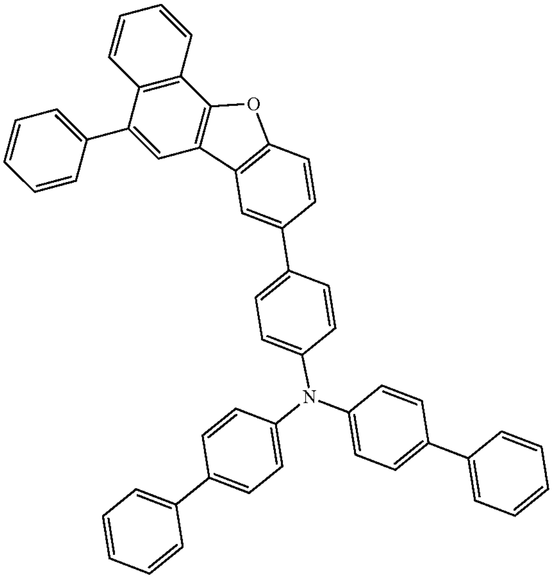
1-53
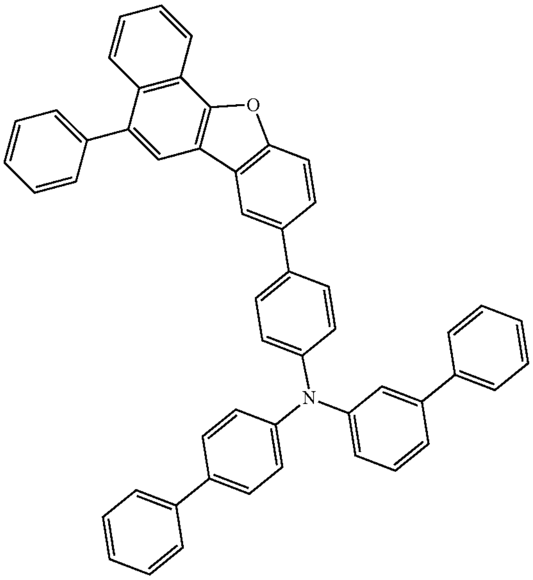
-continued
1-54
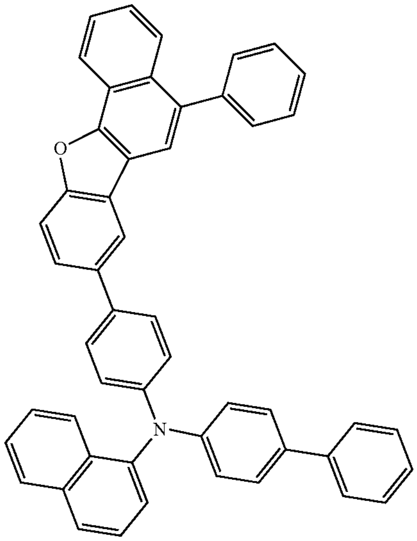
1-55
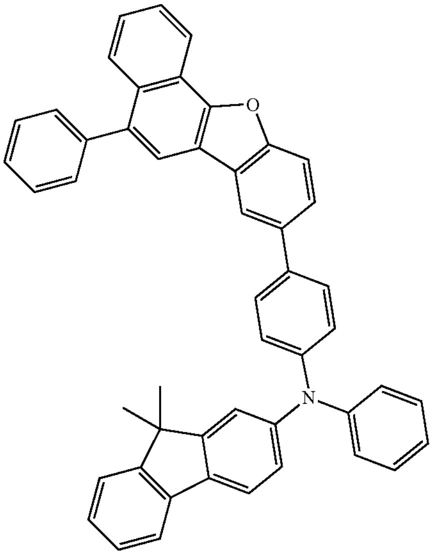

1-56
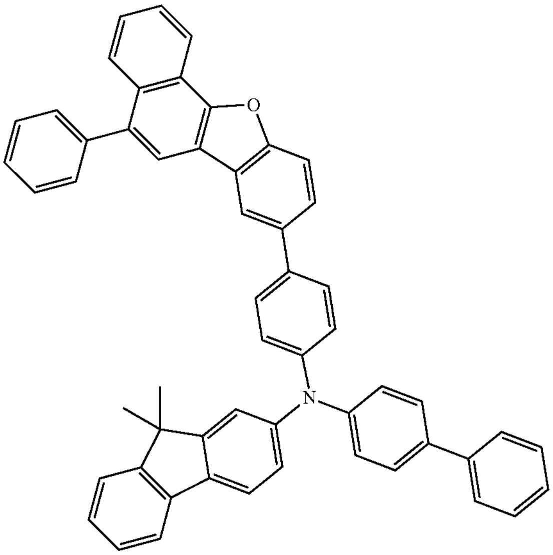
1-57
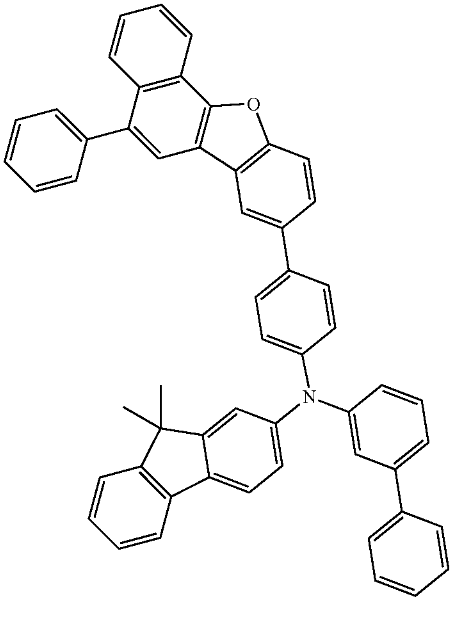
1-58
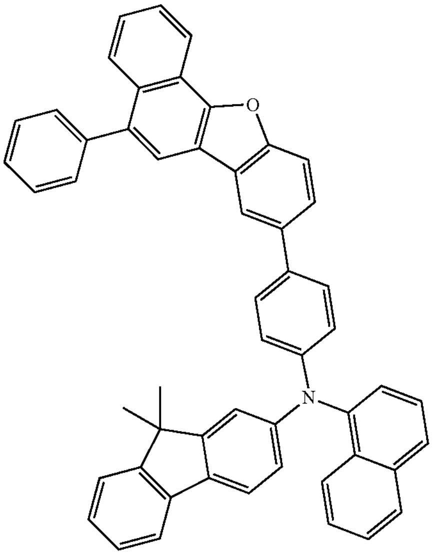
1-59
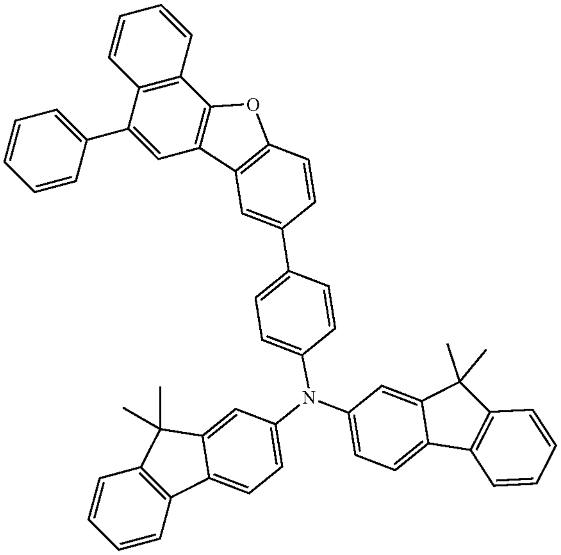

-continued
1-60
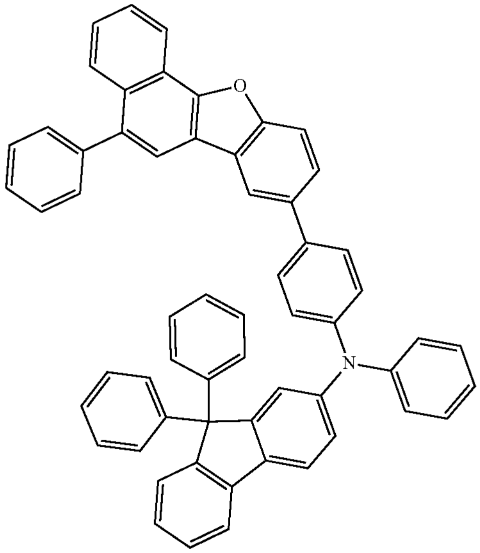
1-61
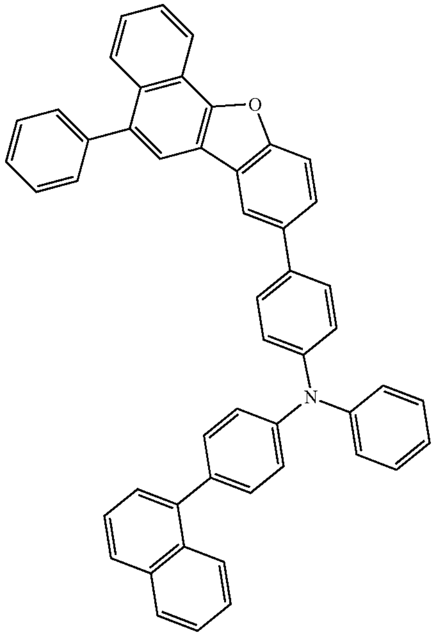
-continued
1-62
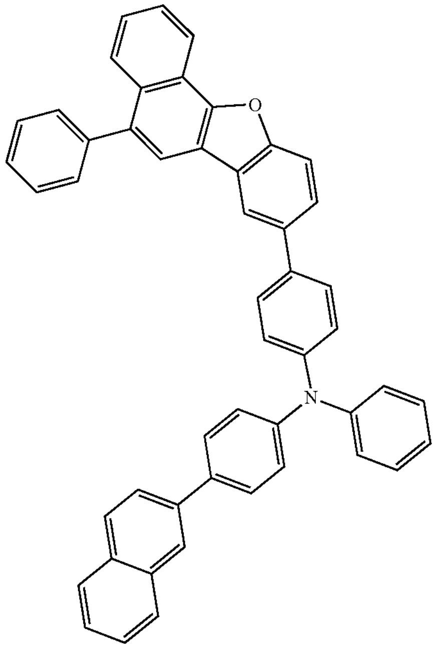
1-63
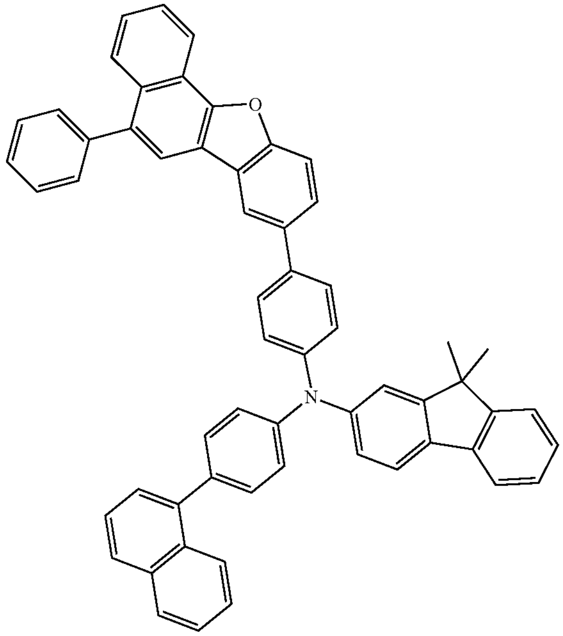

-continued
1-64
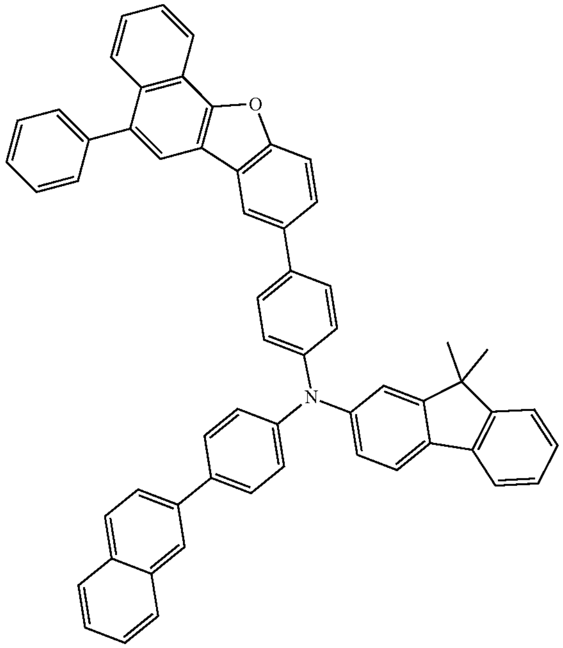
1-65
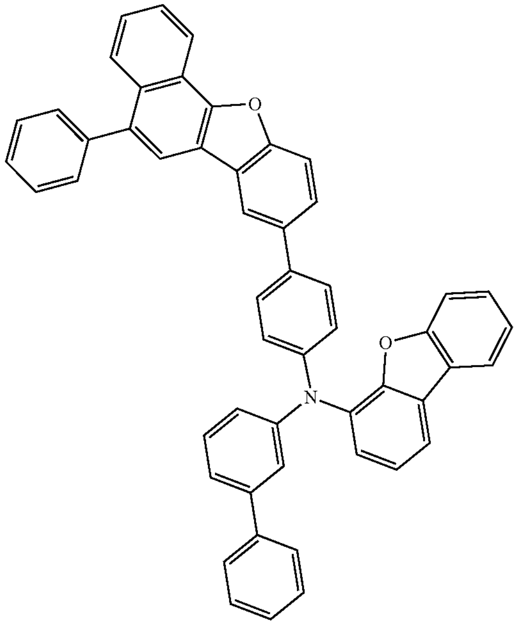
-continued
1-66
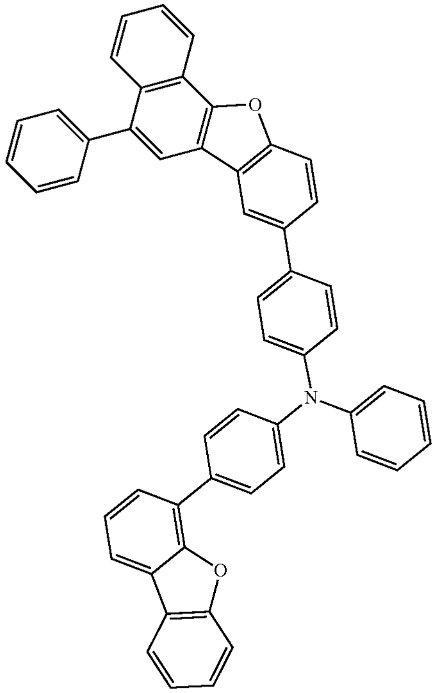
1-67
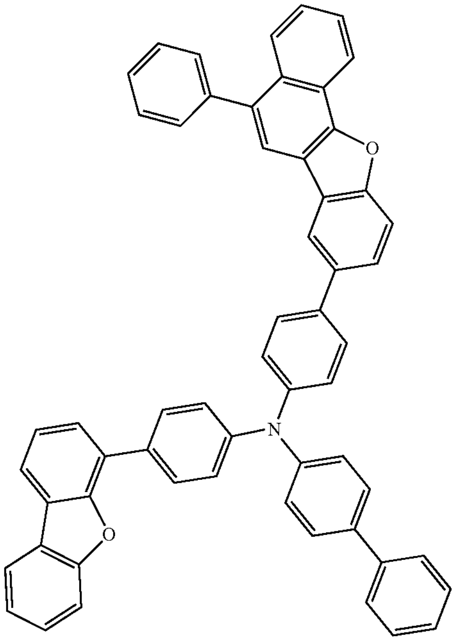

-continued
1-68
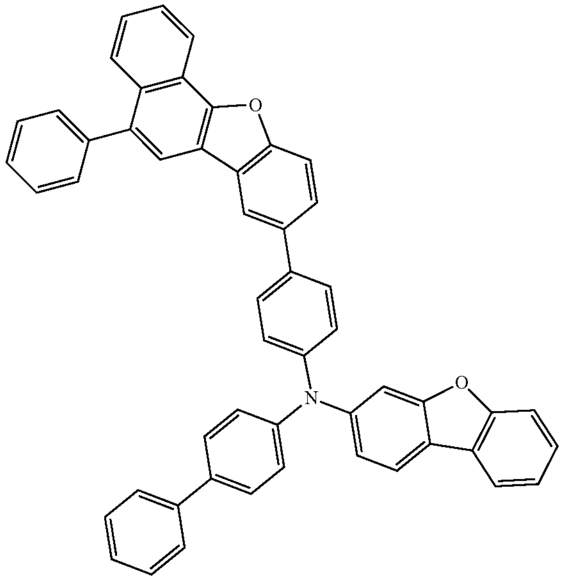
1-69
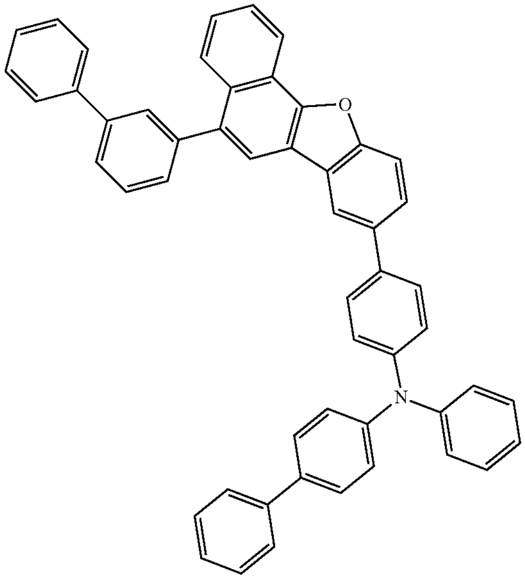
-continued
1-70
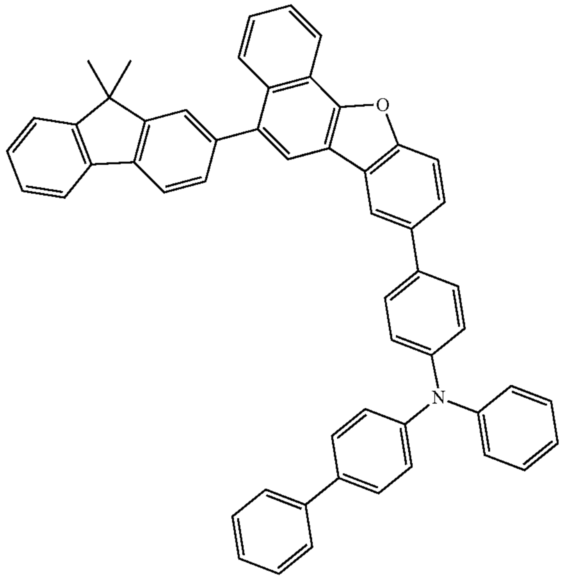
1-71
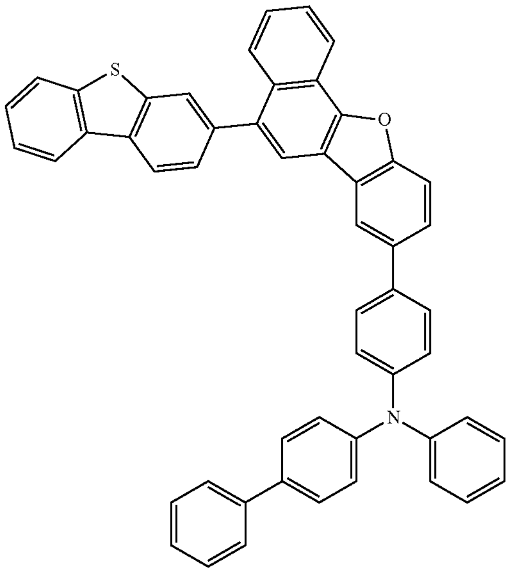

-continued
1-72
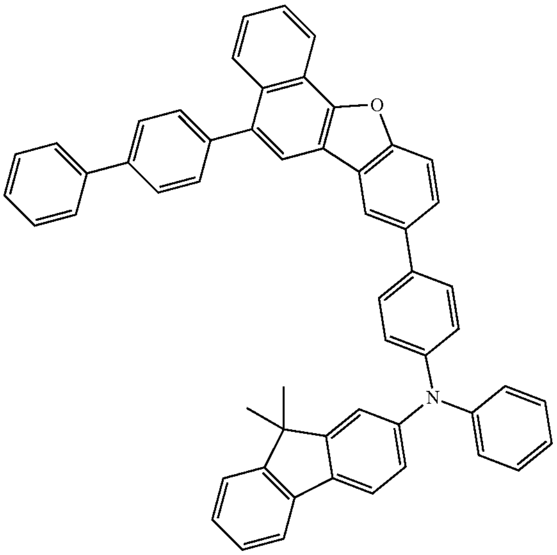
1-74
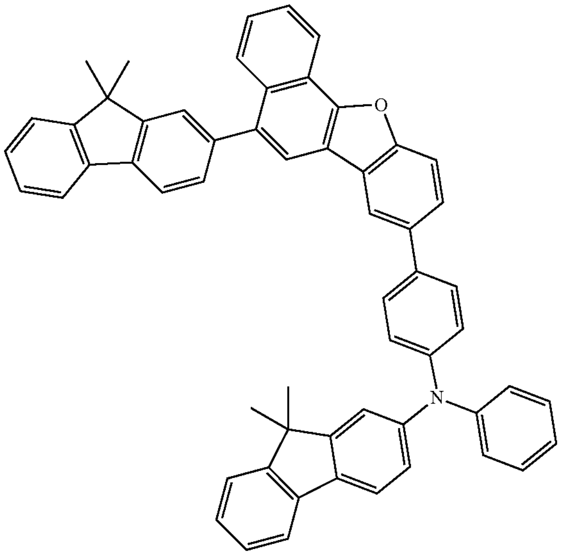
1-73
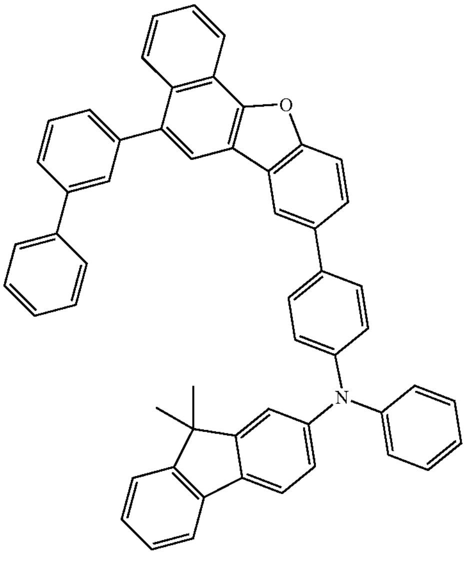
1-75
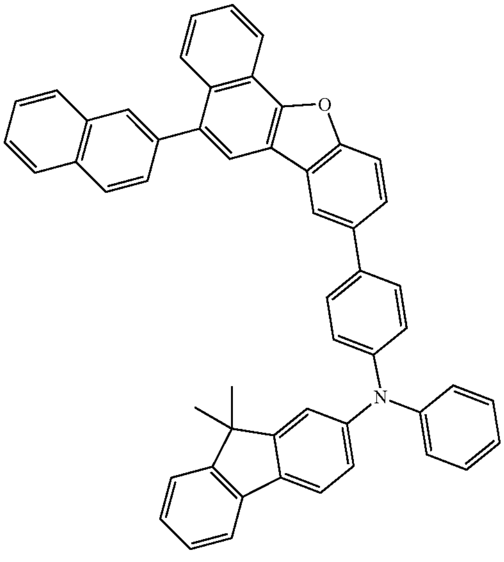

1-76
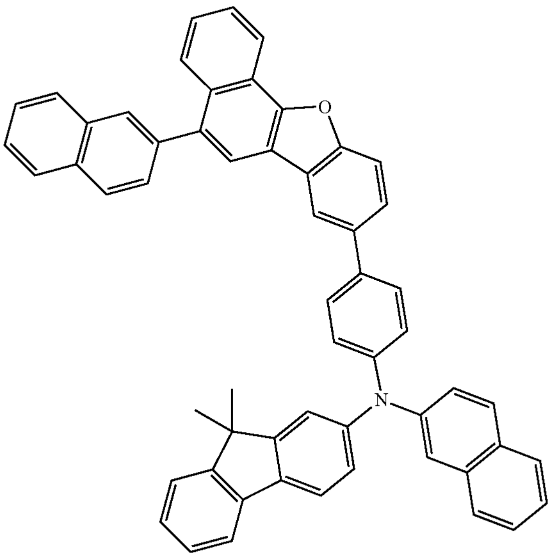
1-77
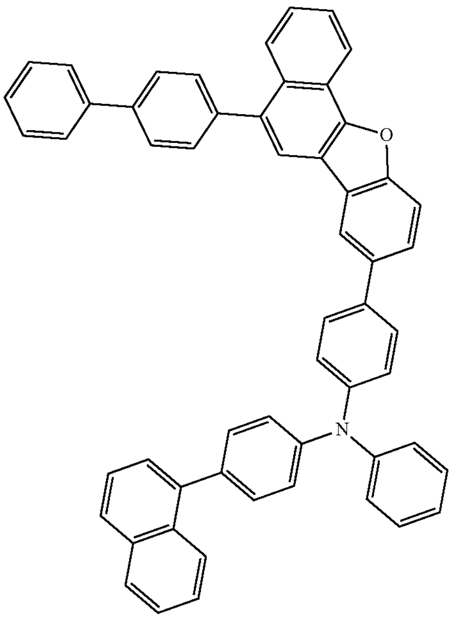
1-78
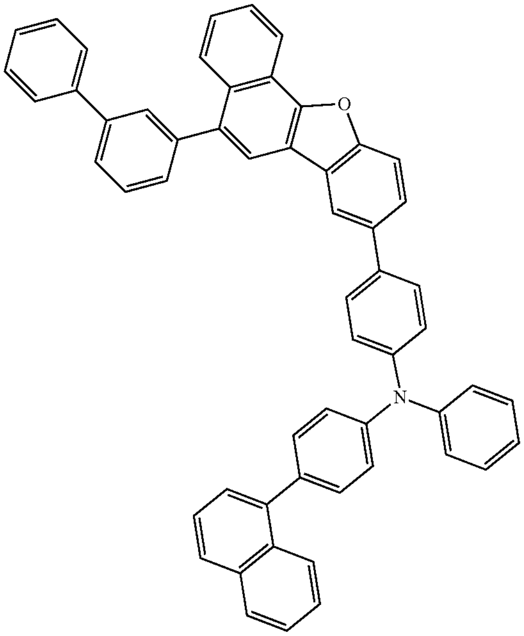
1-79
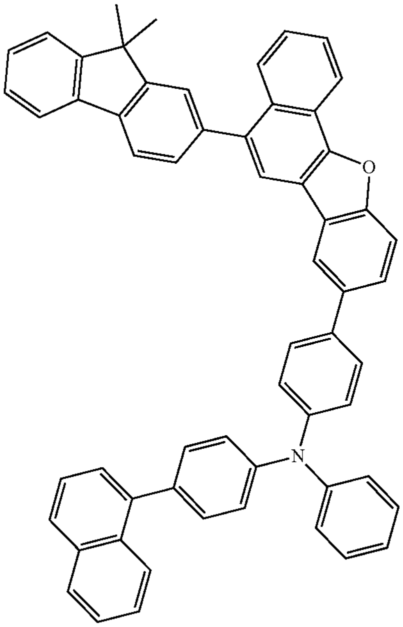

1-80
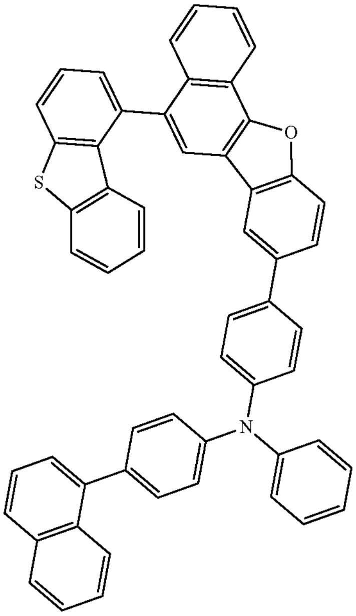
1-81
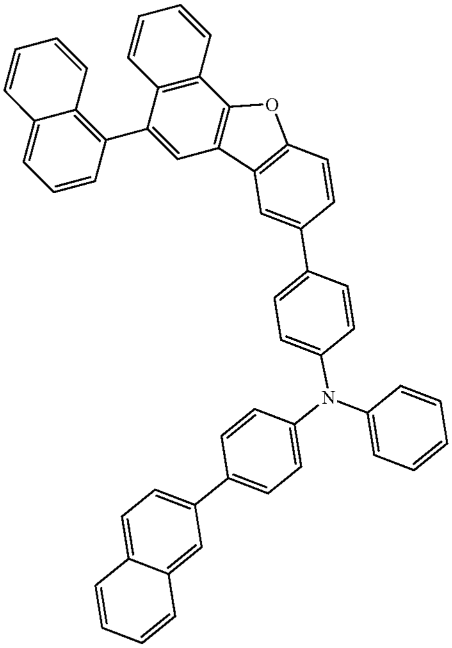
1-82
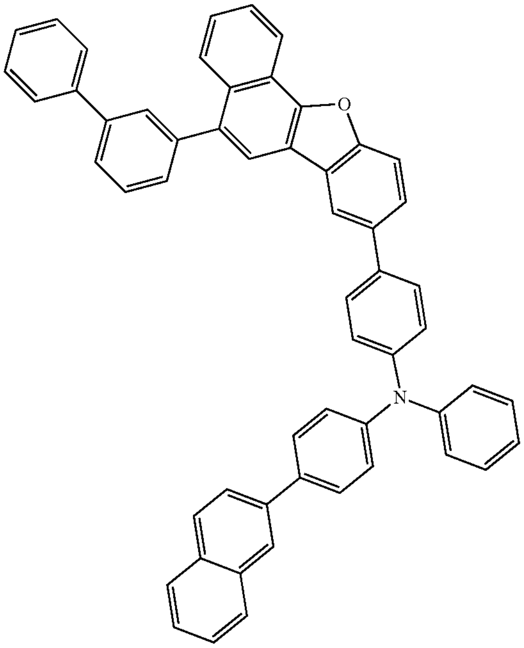
1-83
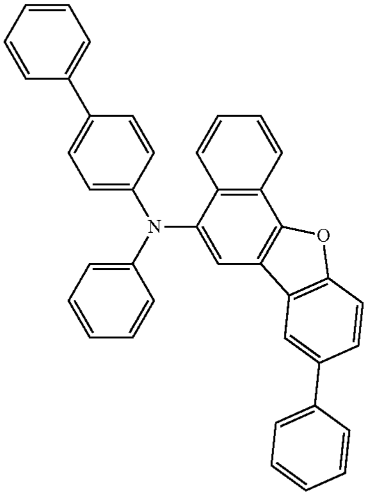
1-84
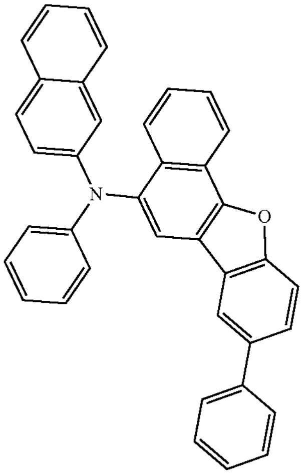

-continued
1-85
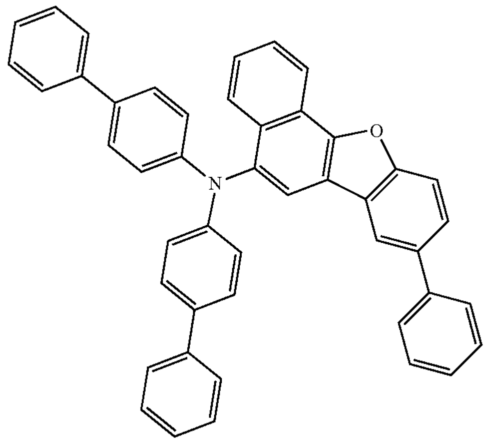
1-86
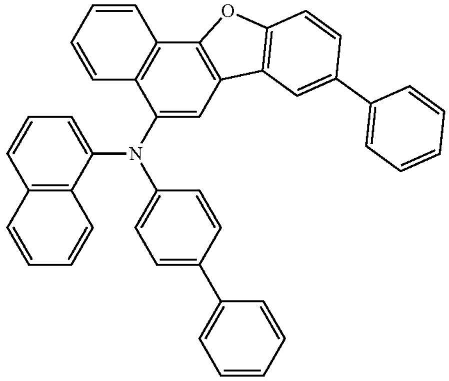
1-87
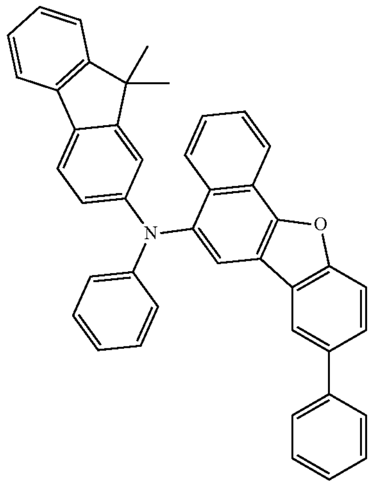
-continued
1-88
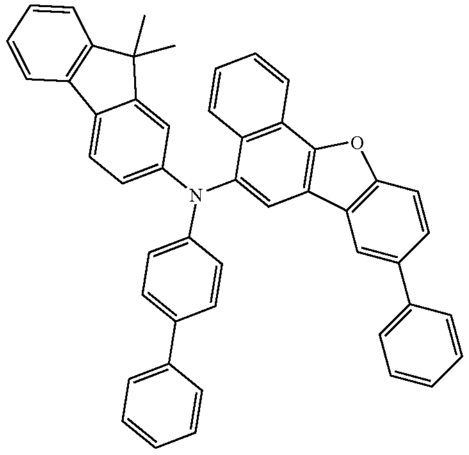
1-89
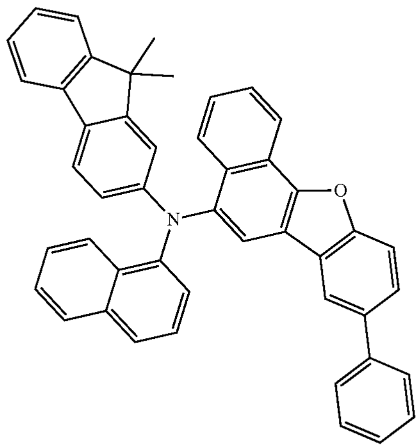
1-90
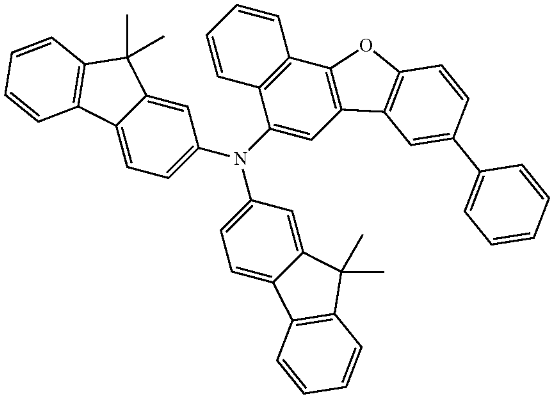

-continued
1-91
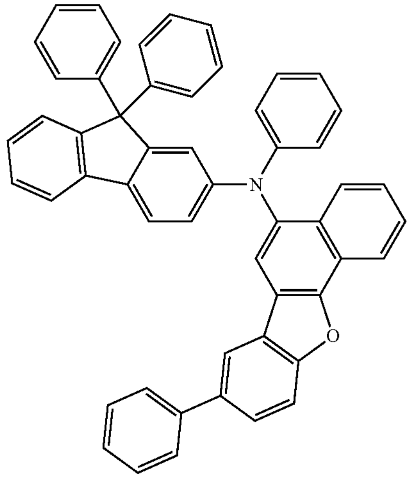
1-92
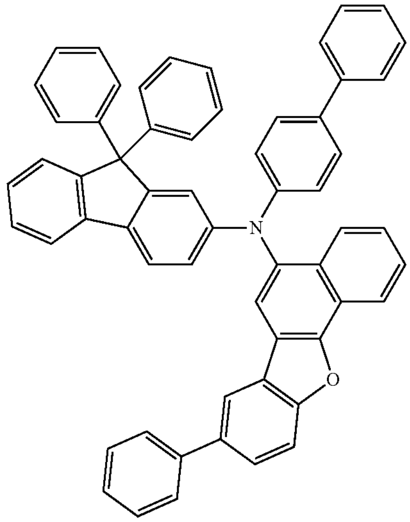
1-93
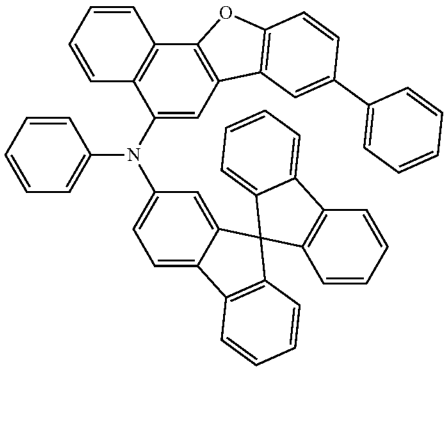
-continued
1-94
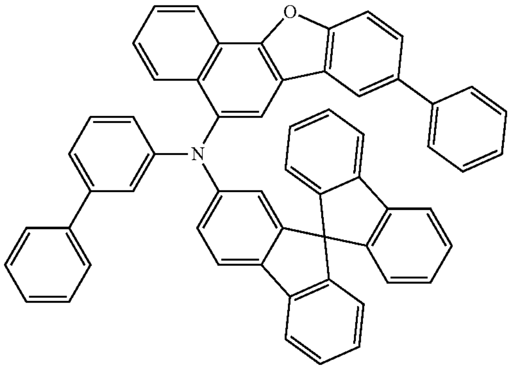
1-95
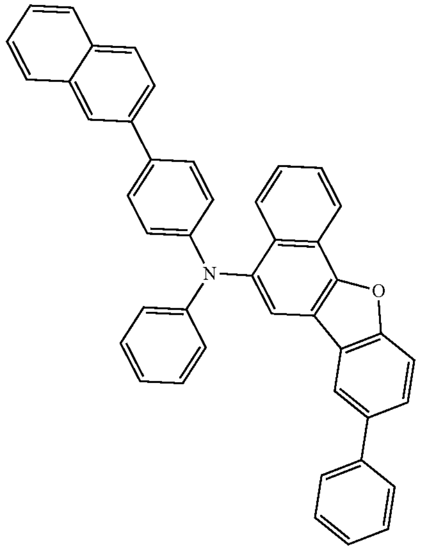
1-96
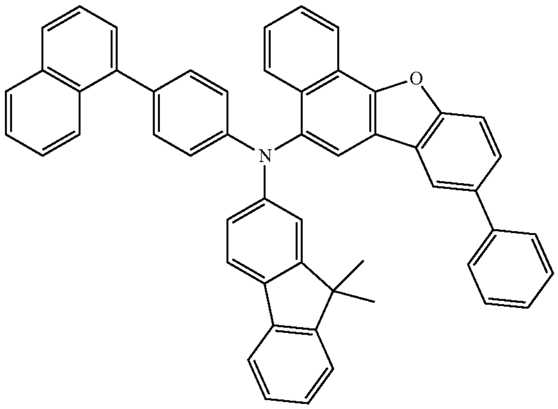

-continued
1-97
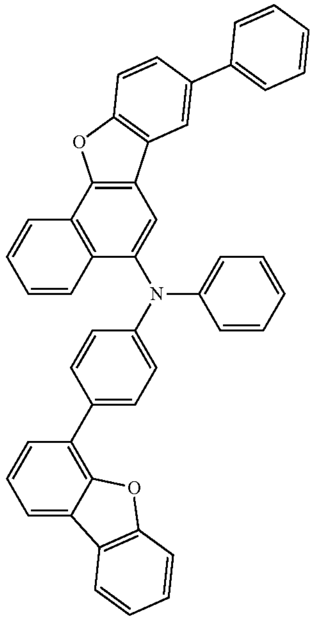
1-98
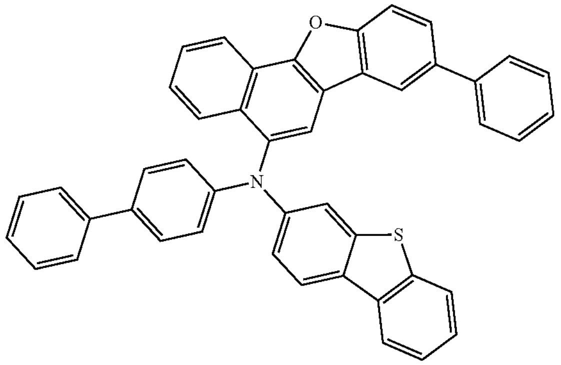
1-99
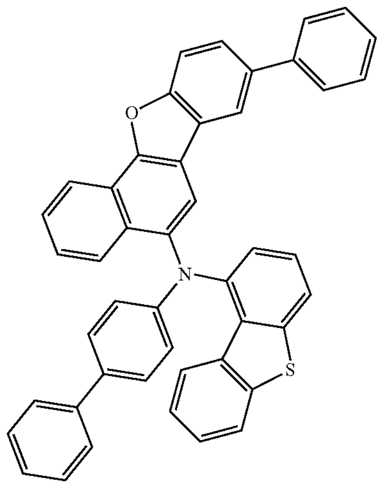
-continued
1-100
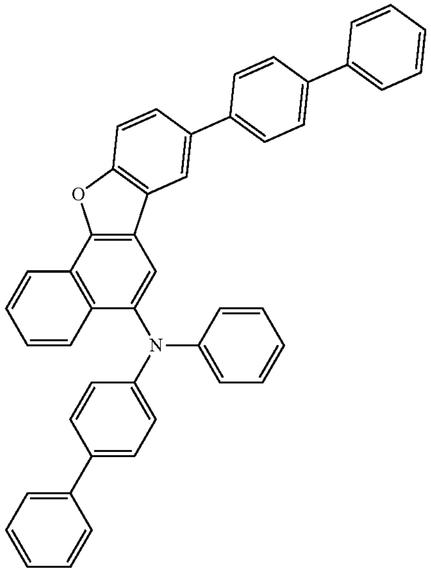
1-101
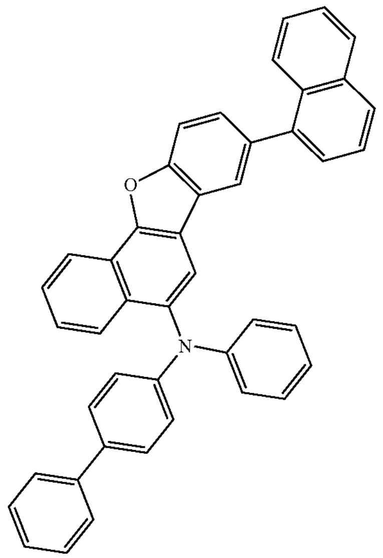

-continued
1-102
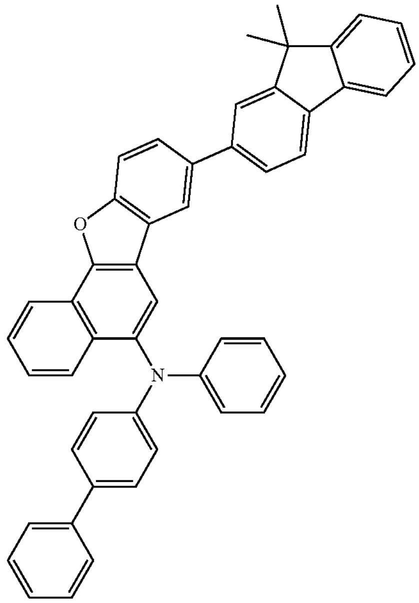
1-103
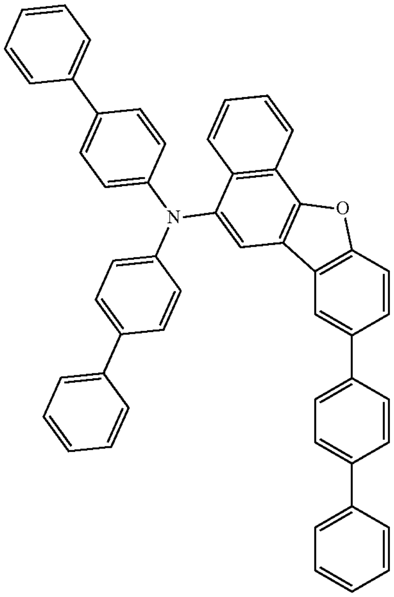
-continued
1-104
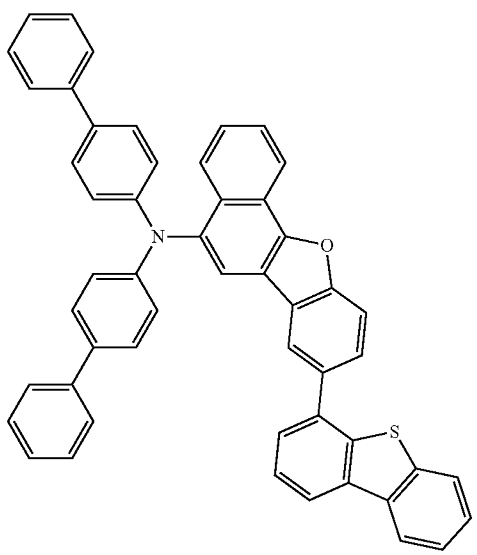
1-105
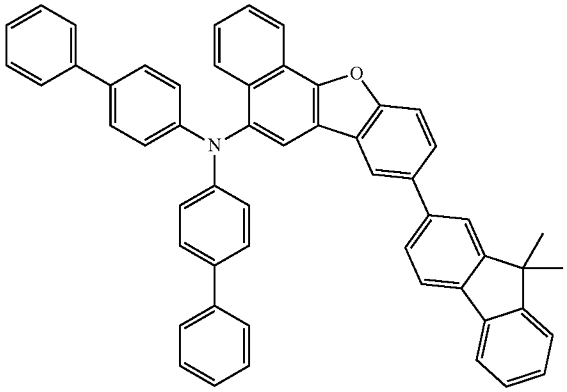
1-106
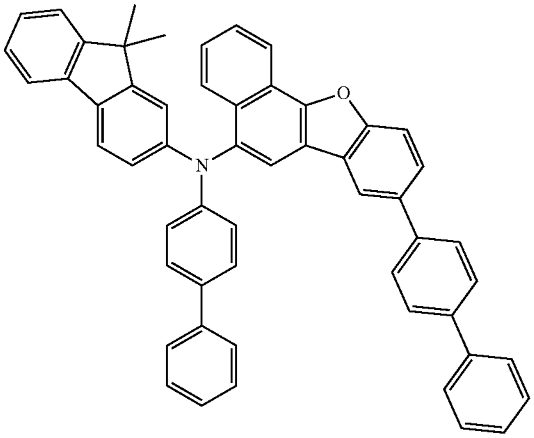

-continued
1-107
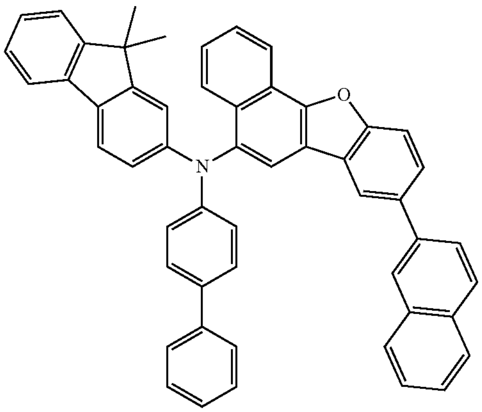
1-108
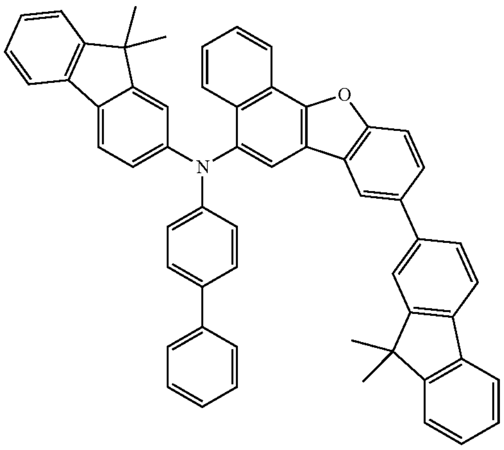
1-109
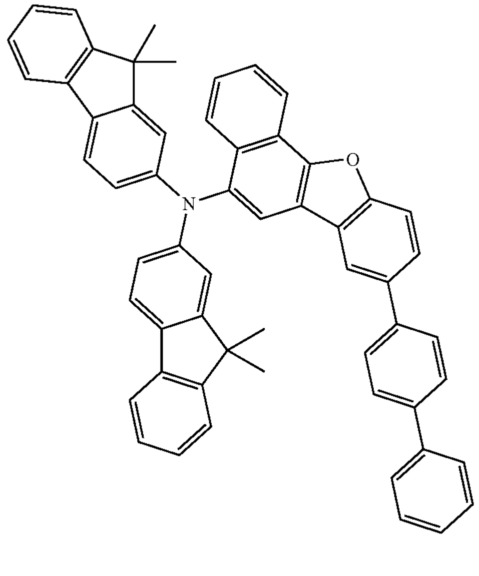
-continued
1-110
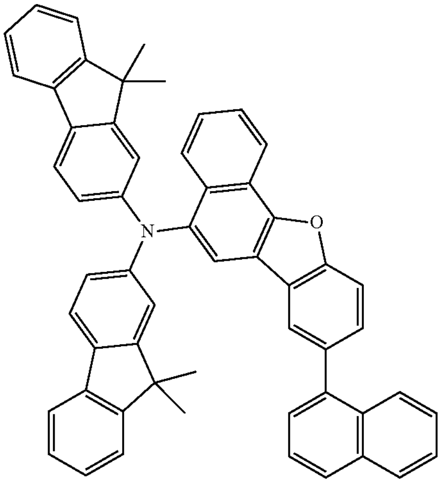
1-111
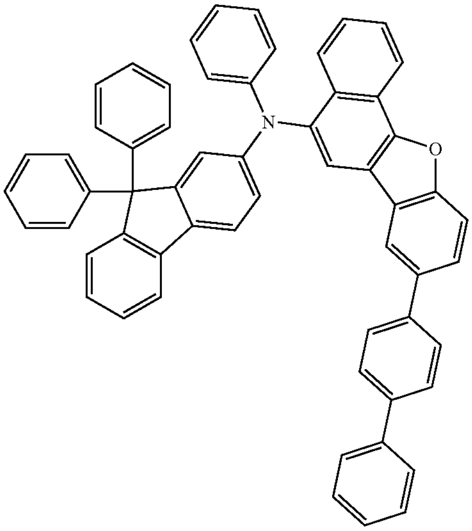
1-112
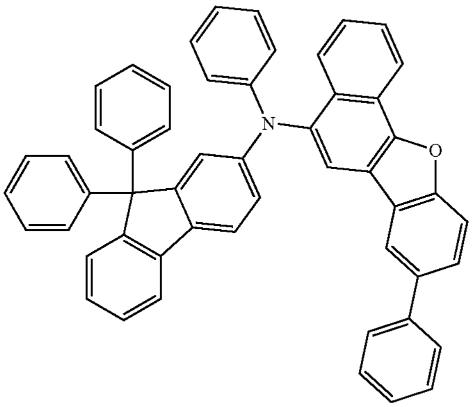

-continued
1-113
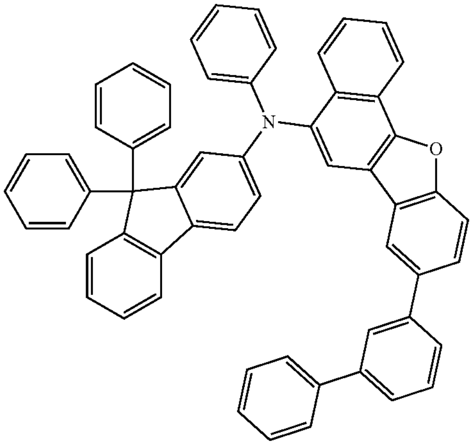
1-114
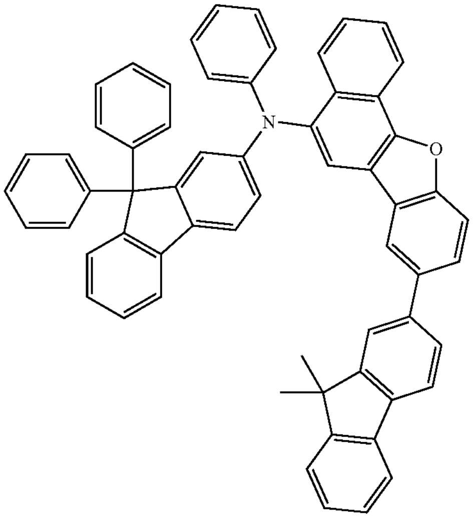
1-115
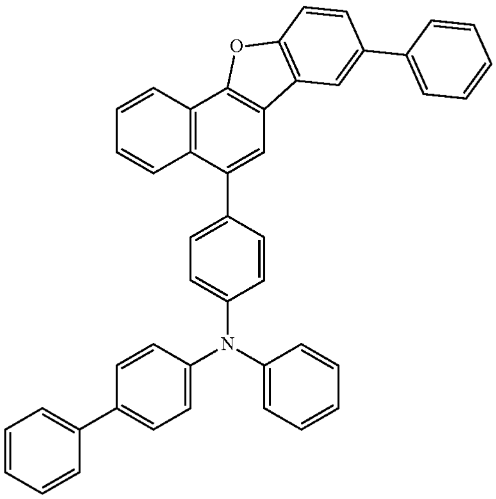
-continued
1-116
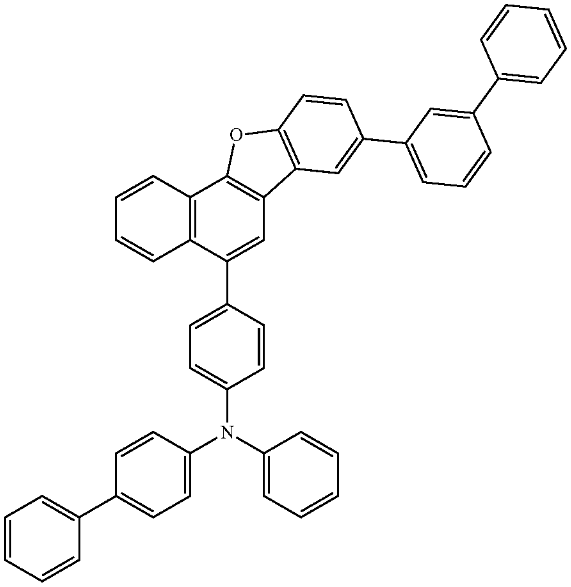
1-117
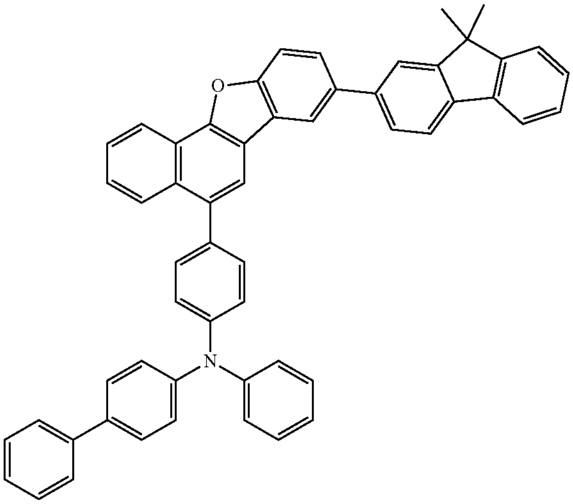

-continued
1-118
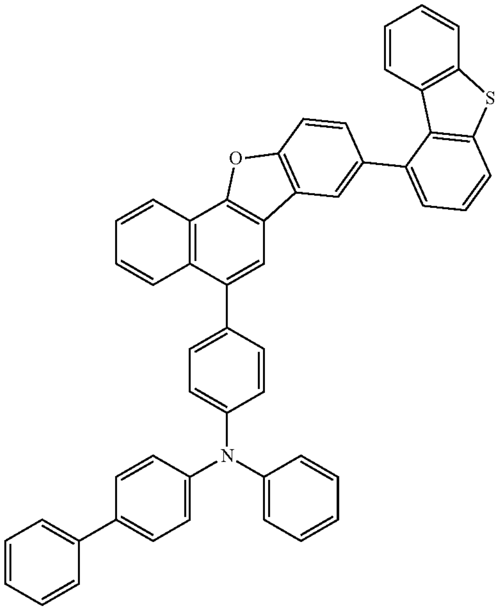
1-119
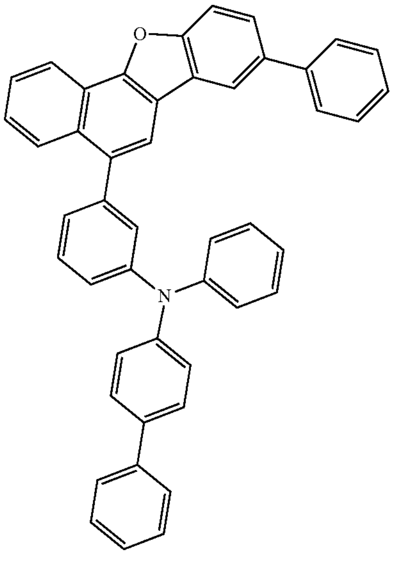
-continued
1-120
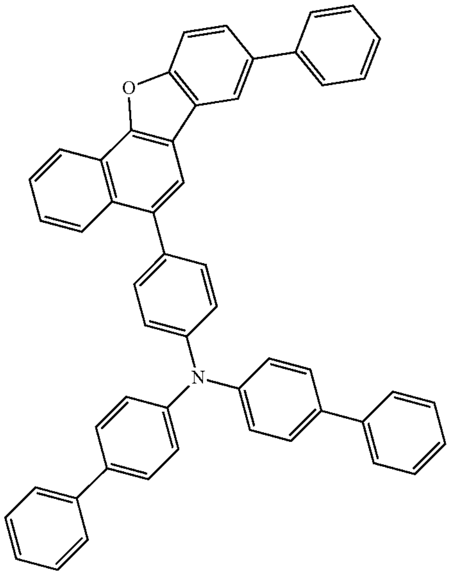
1-121
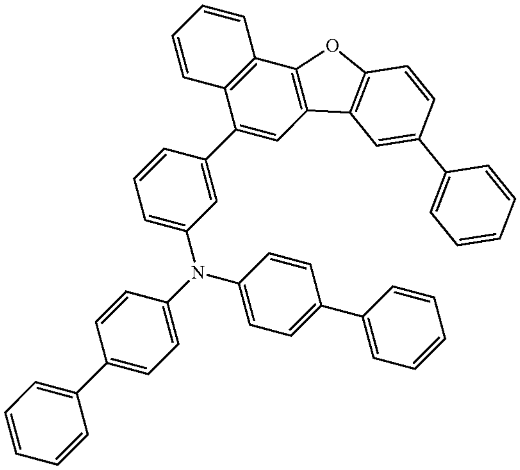

-continued
1-122
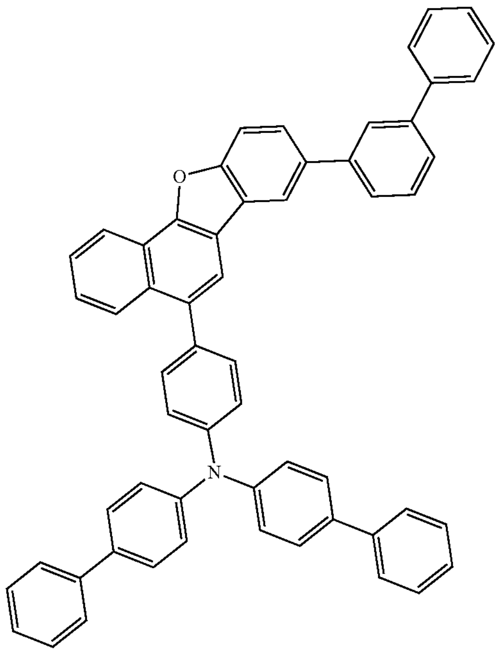
1-123
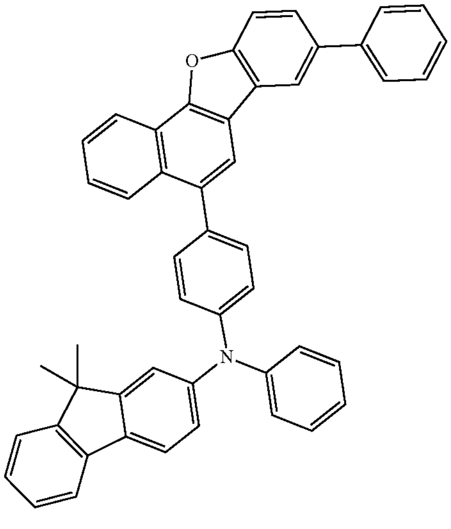
-continued
1-124
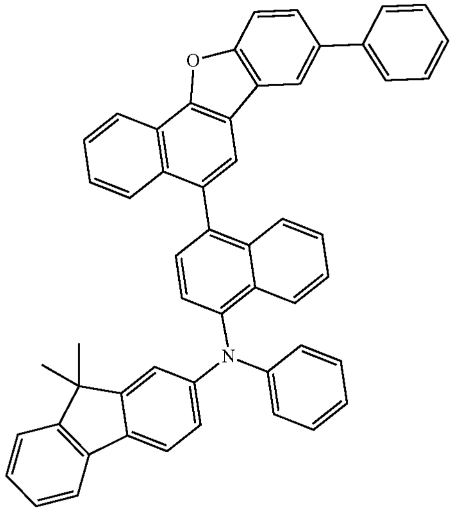
1-125
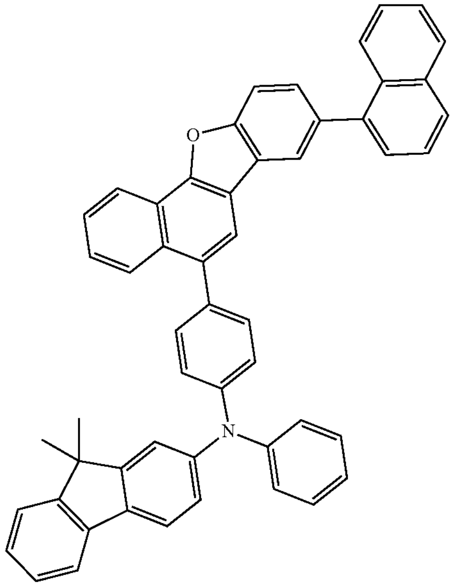

-continued
1-126
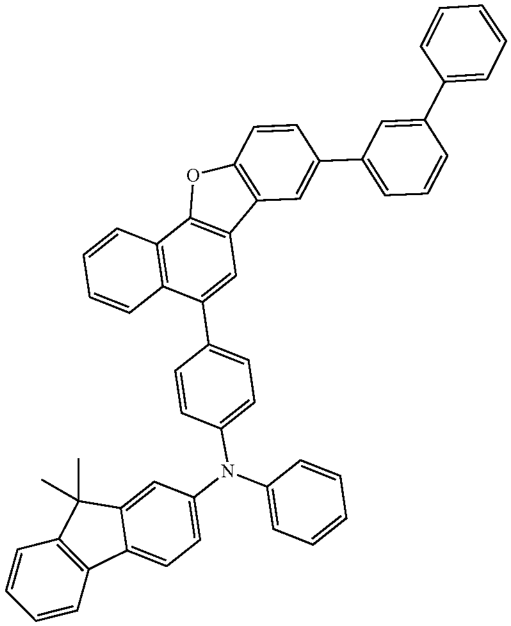
1-127
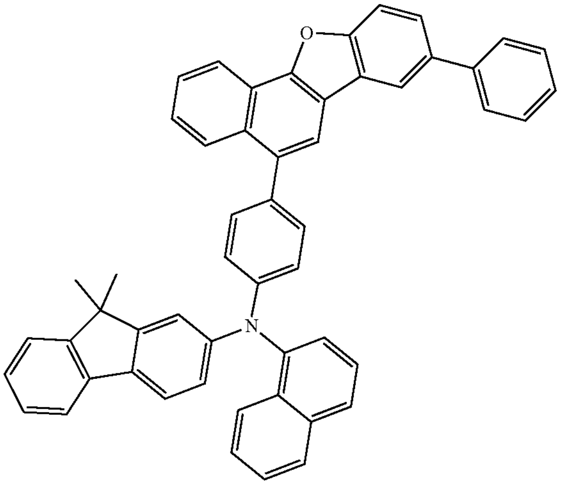
1-128
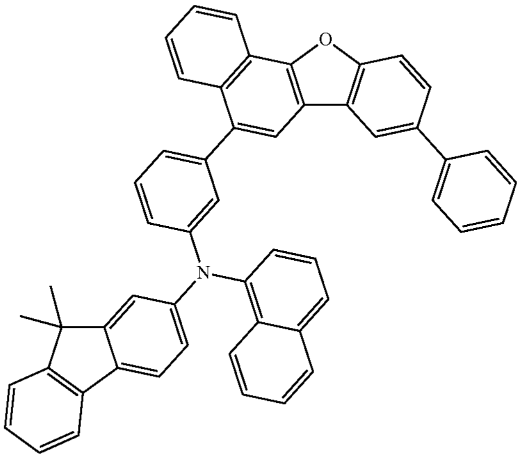
-continued
1-129
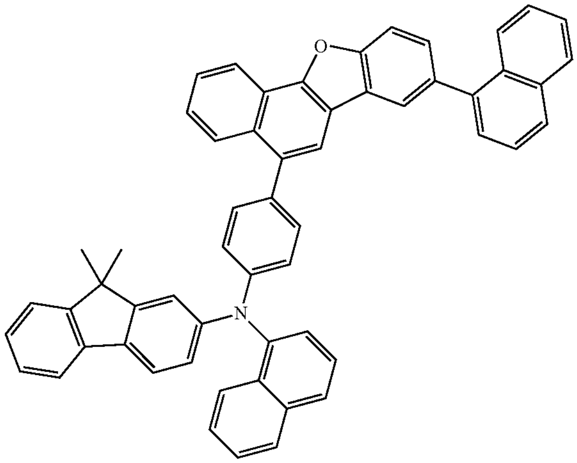
1-130
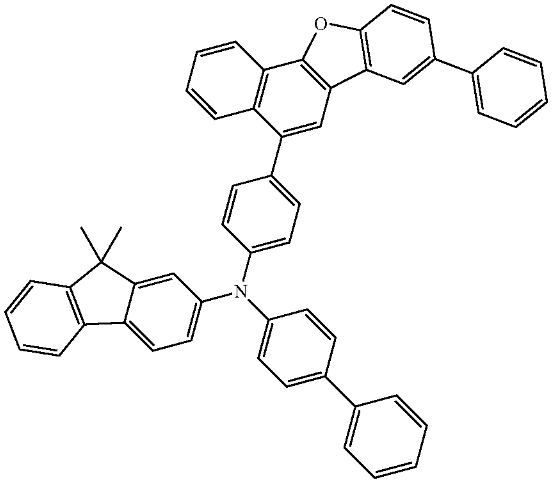
1-131
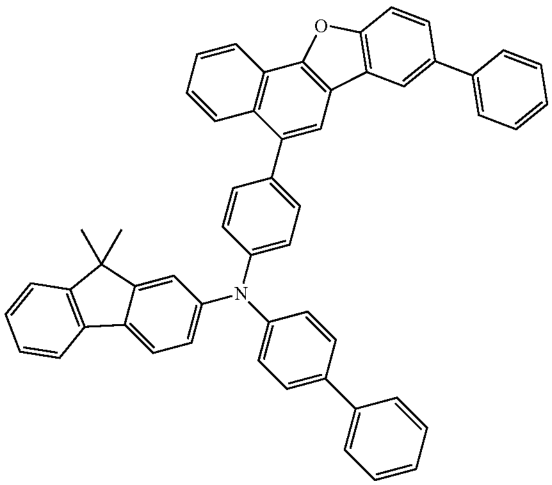

-continued
1-132
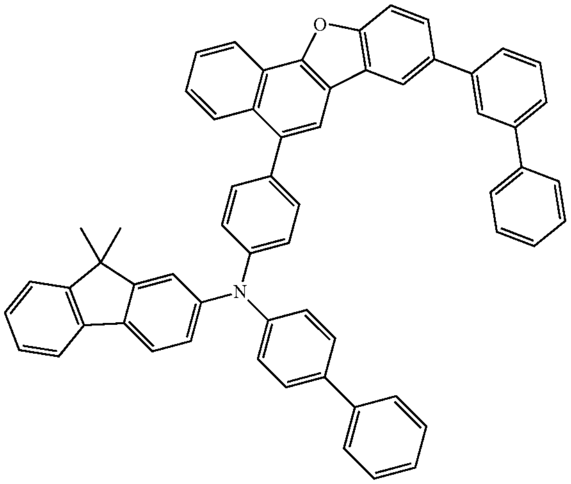
1-133
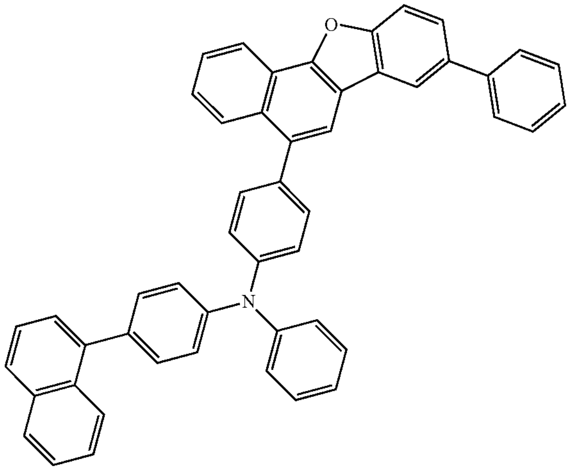
1-134
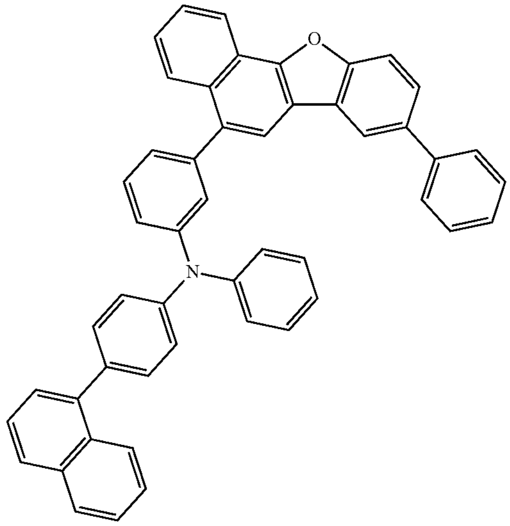
-continued
1-135
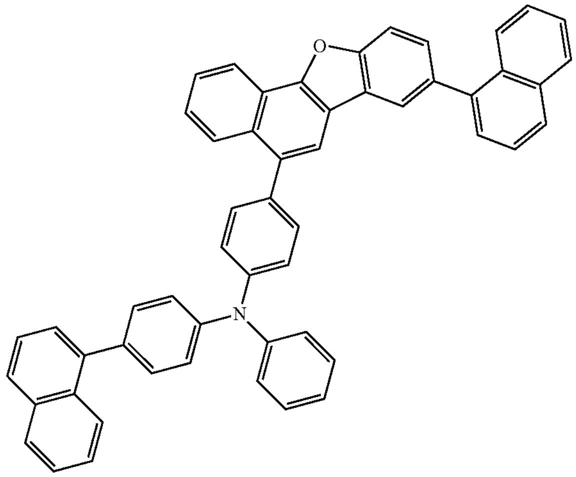
1-136
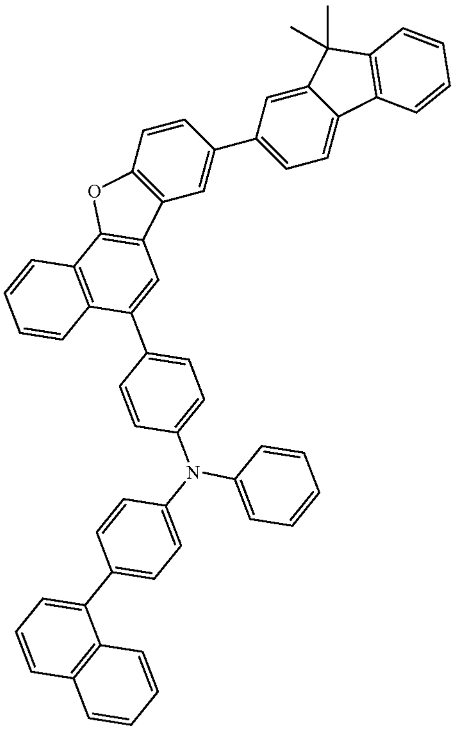

1-137
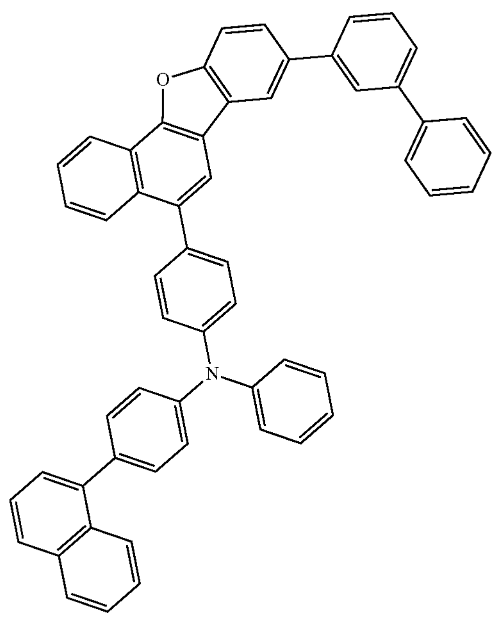
1-138
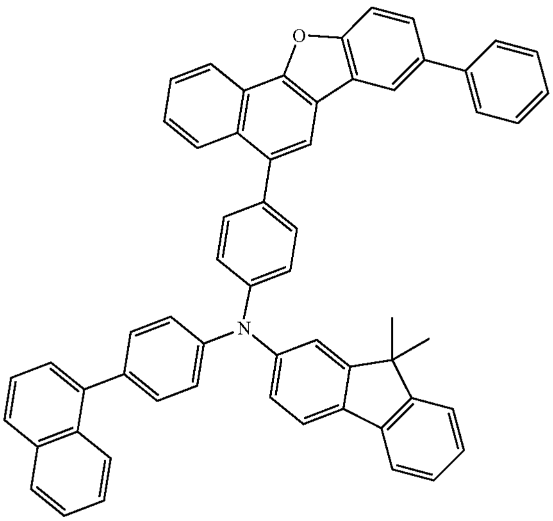
1-139
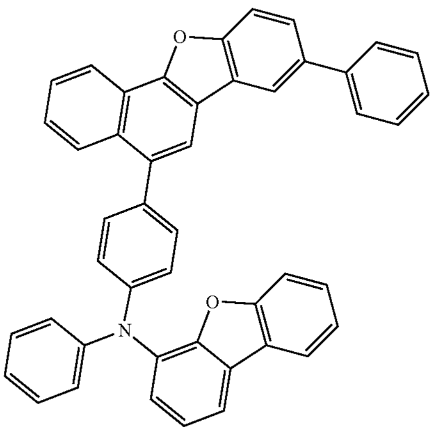
1-140
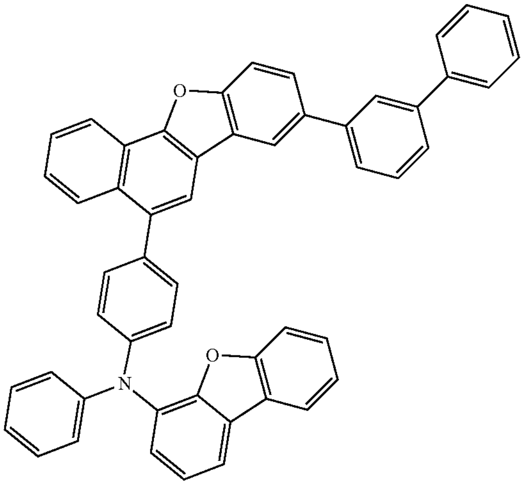
1-141
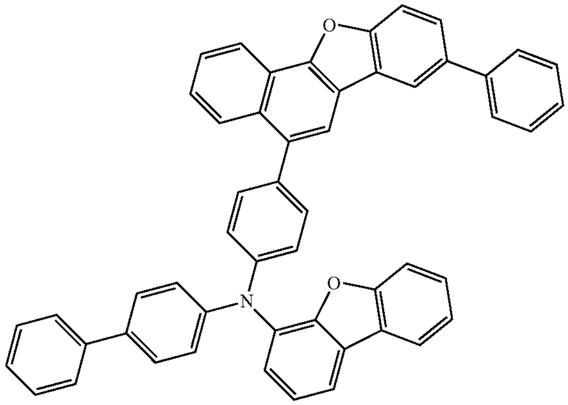
1-142
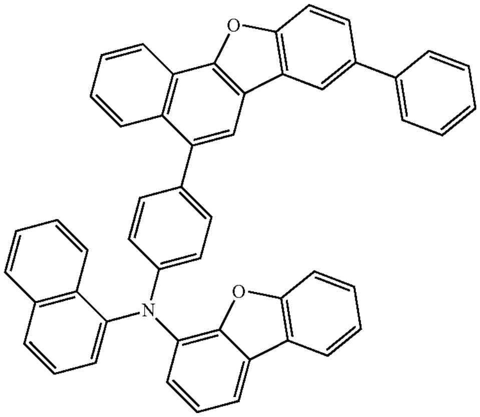

-continued
1-143
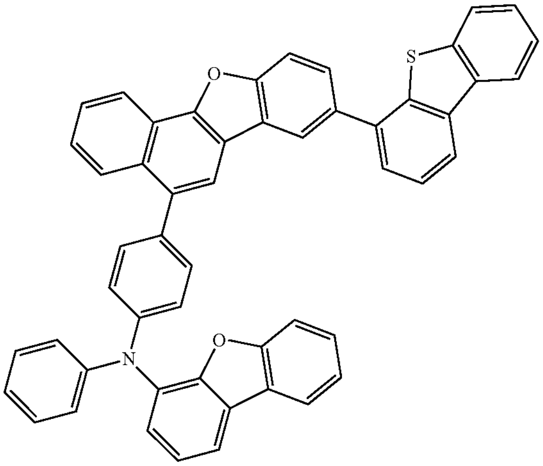
1-144
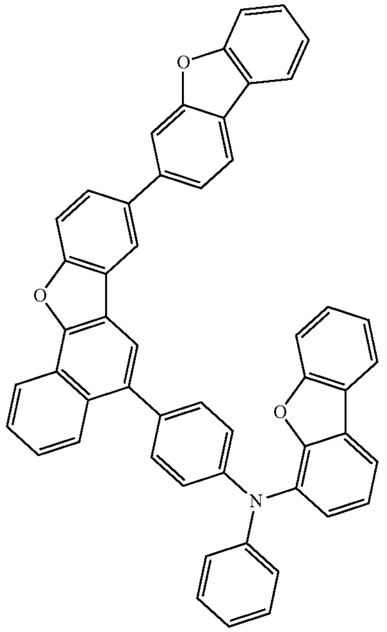
-continued
1-145
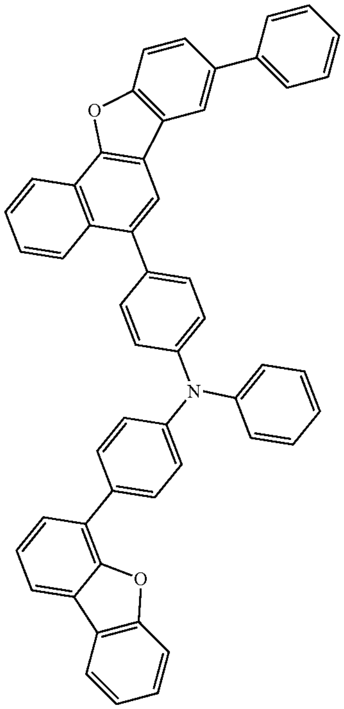
1-146
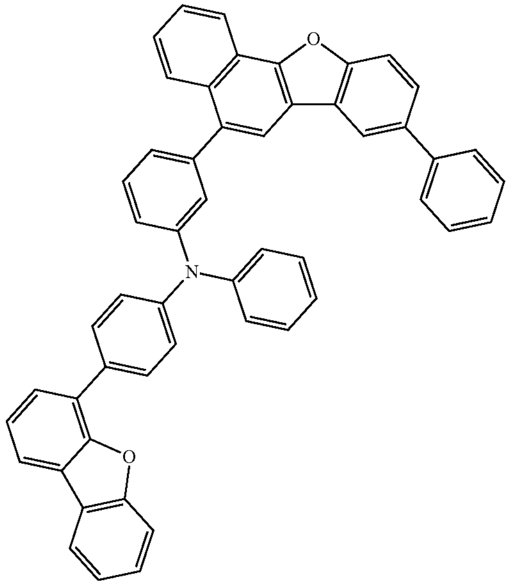

-continued
1-147
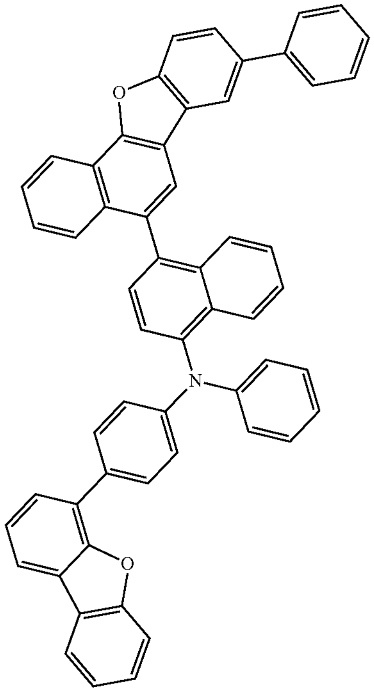
1-148
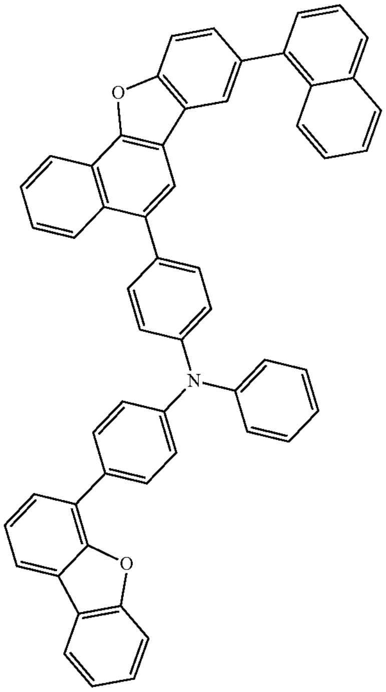
-continued
1-149
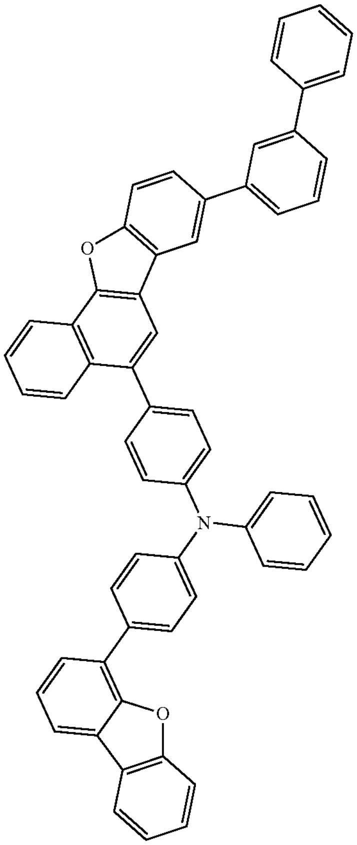
1-150
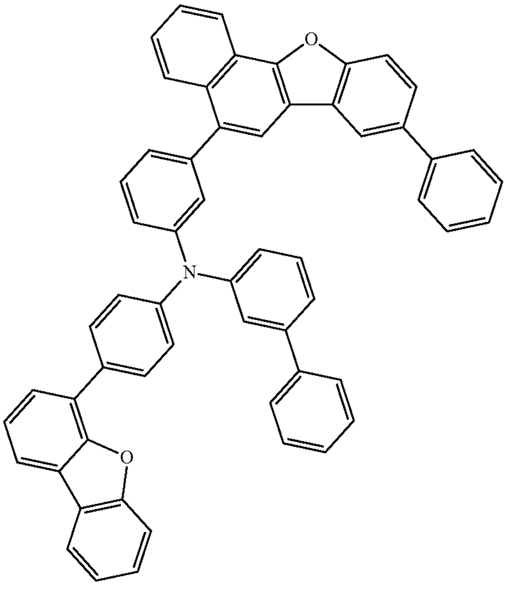

-continued
1-151
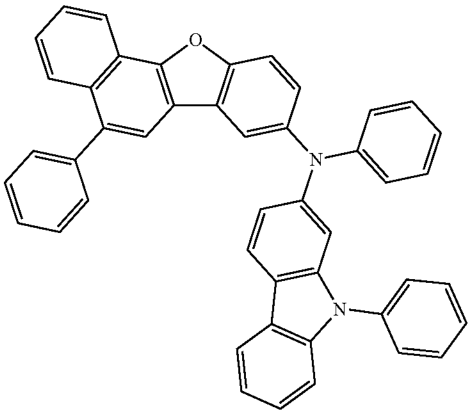
1-152
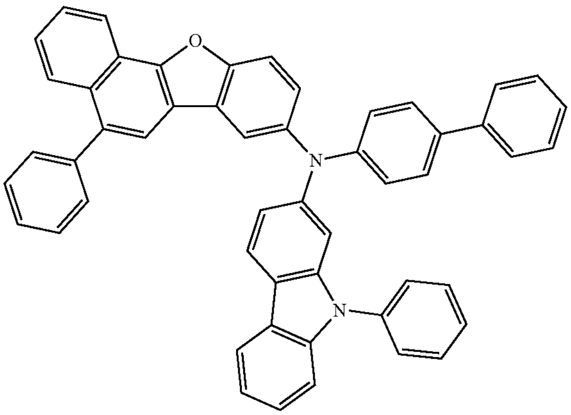
1-153
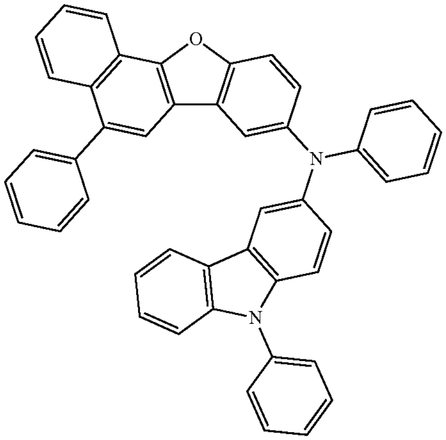
-continued
1-154
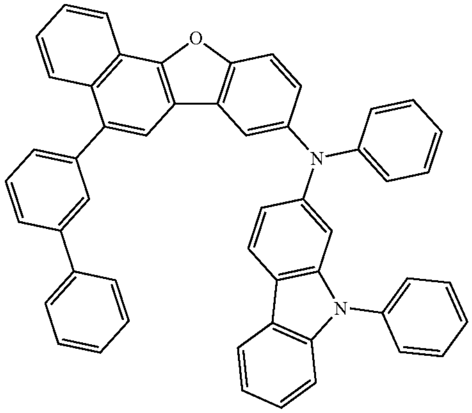
1-155
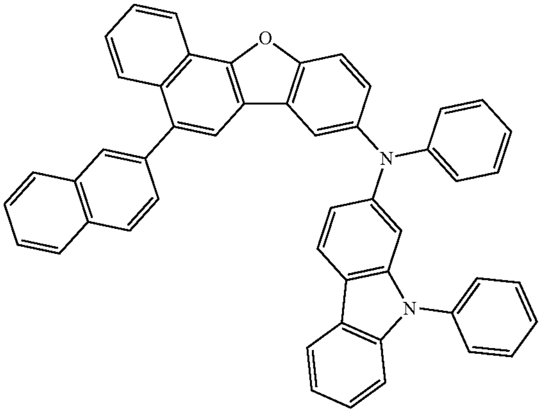
1-156
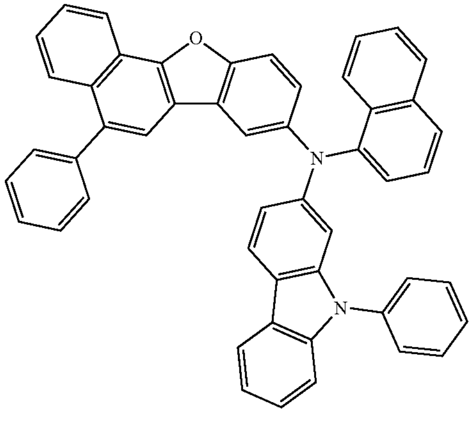

-continued
1-157
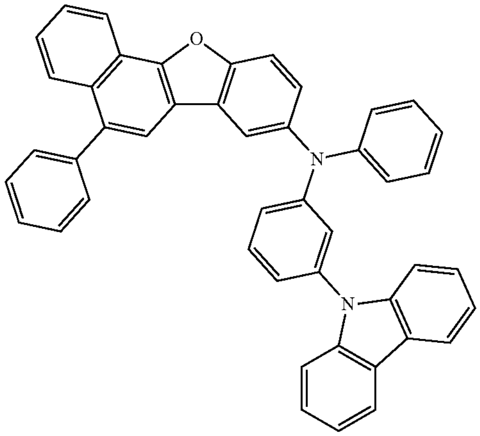
1-158
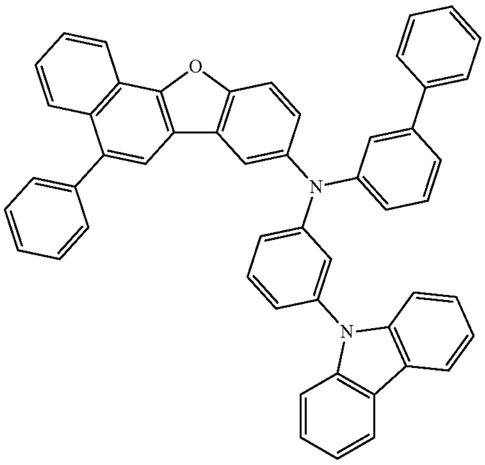
1-159
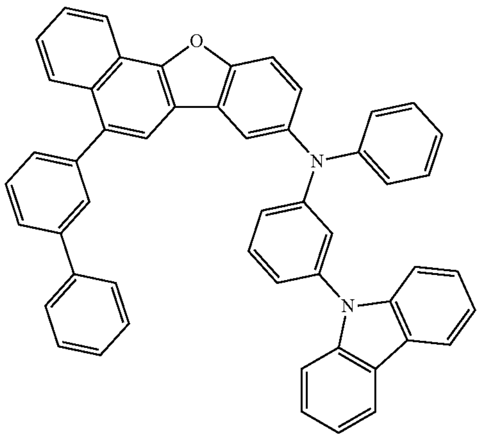
-continued
1-160
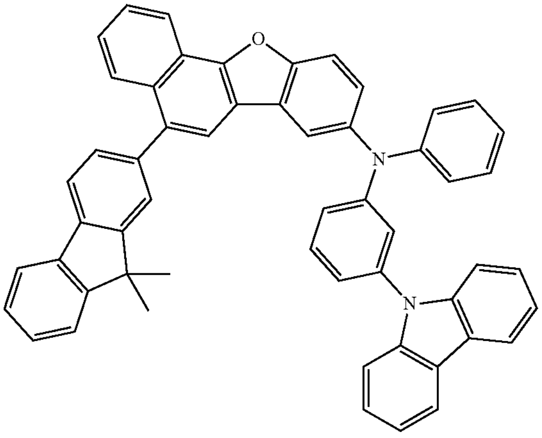
1-161
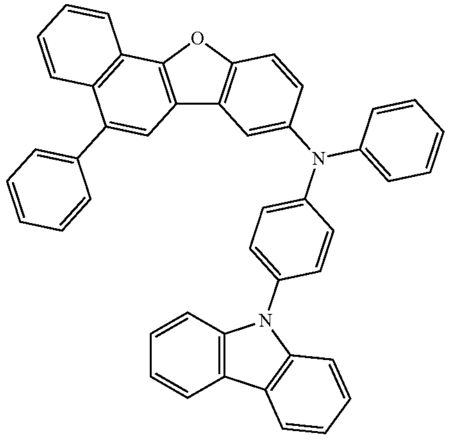
1-162
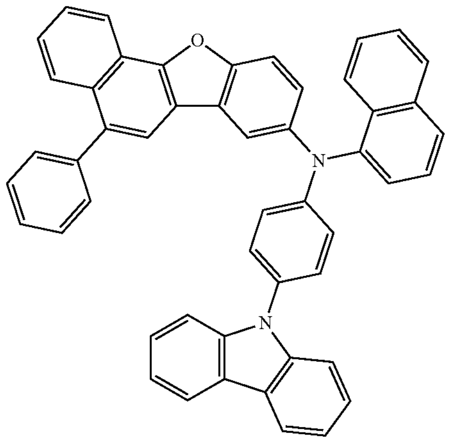

-continued
1-163
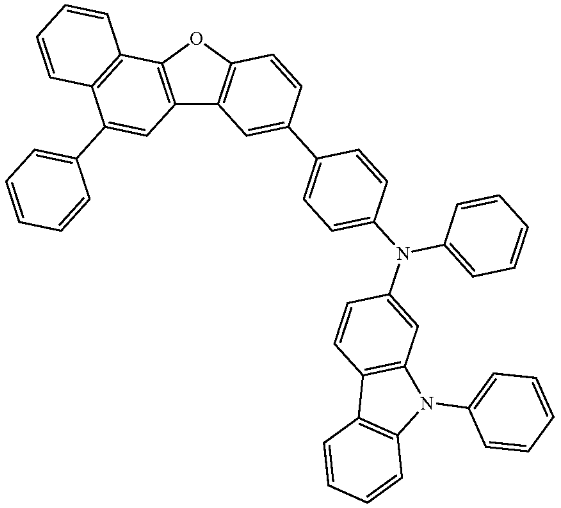
1-164
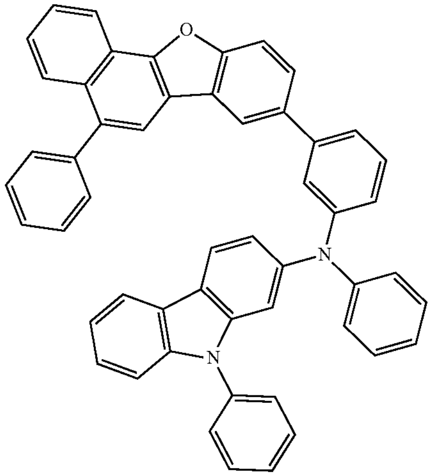
1-165
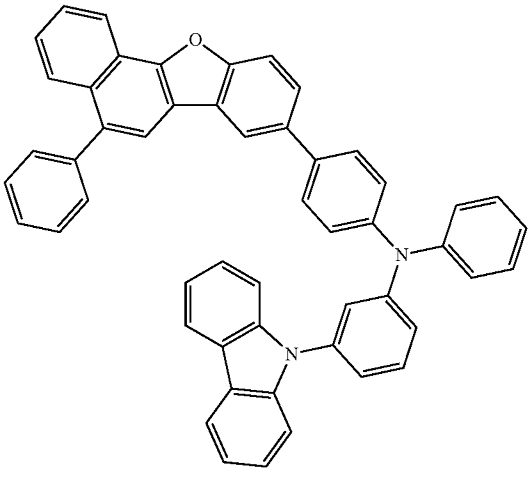
-continued
1-166
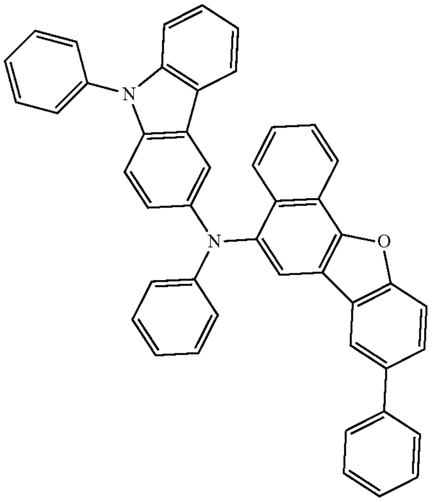
1-167
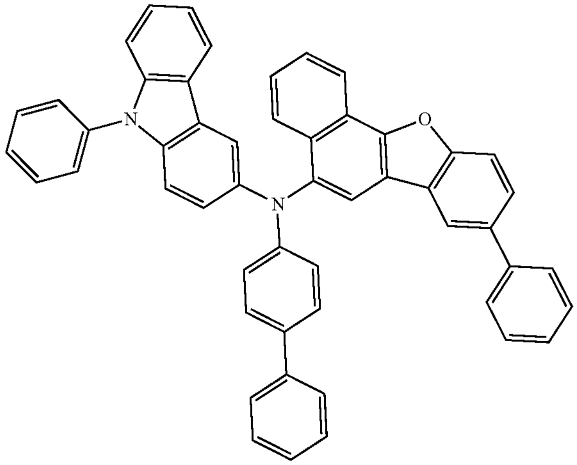
1-168
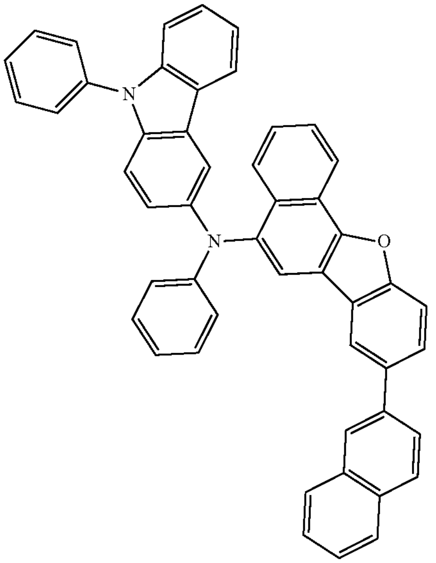

-continued
1-169
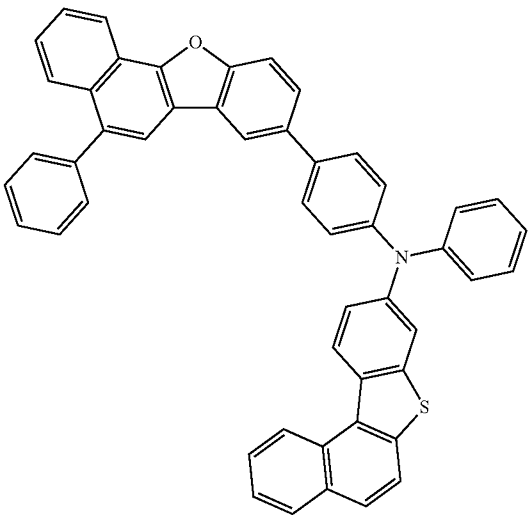
1-170
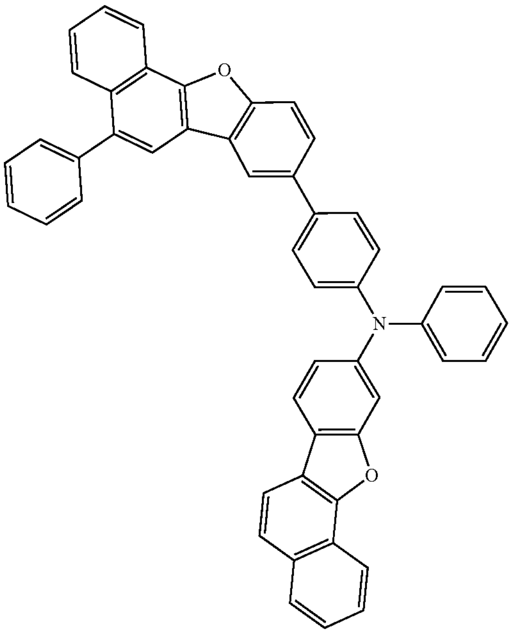
-continued
1-171
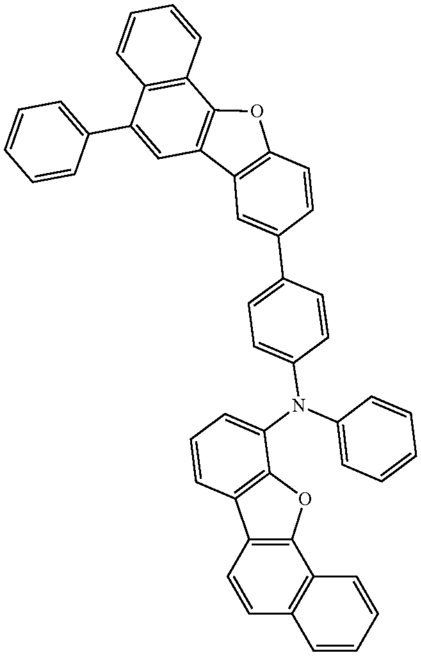
1-172
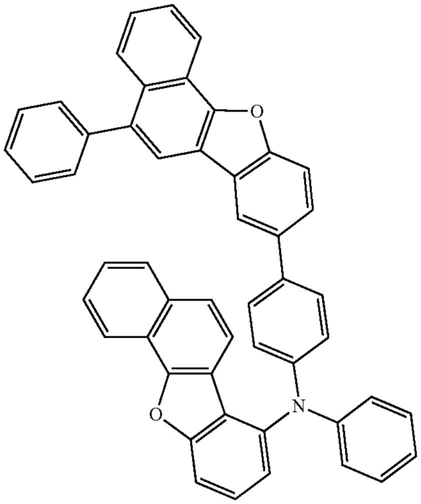
1-173
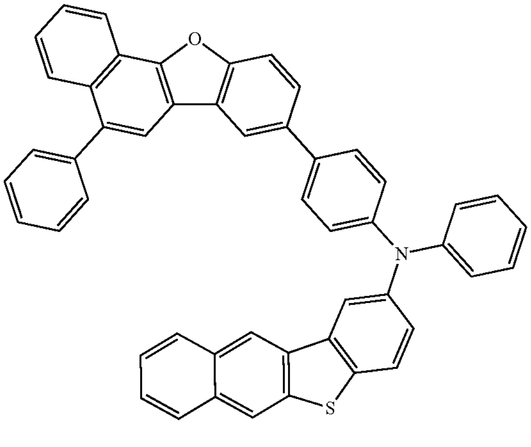

-continued
1-174
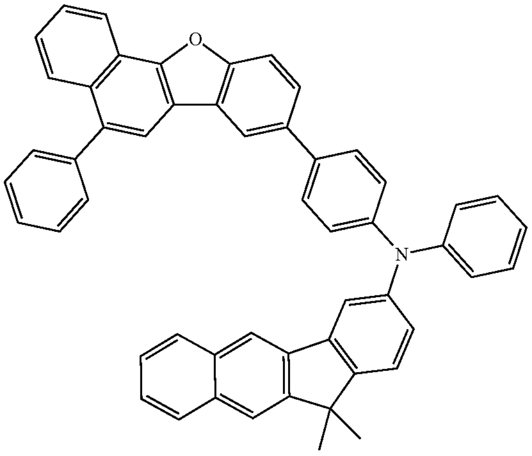
1-175
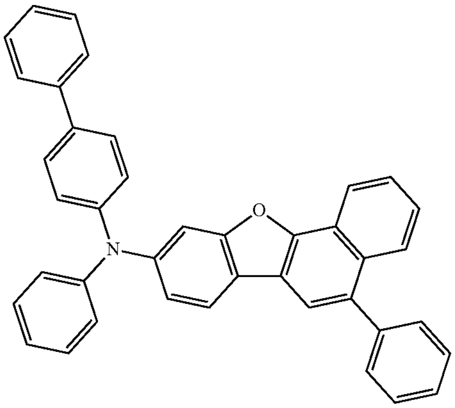
1-176
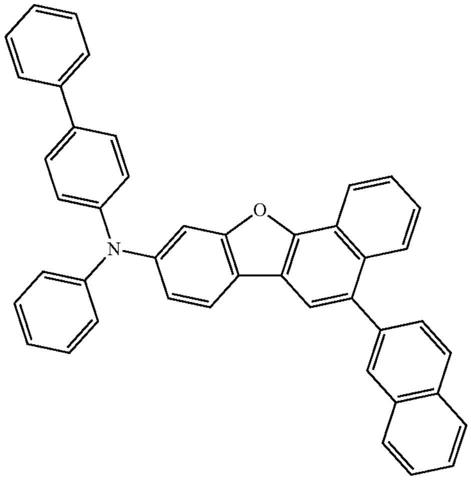
-continued
1-177
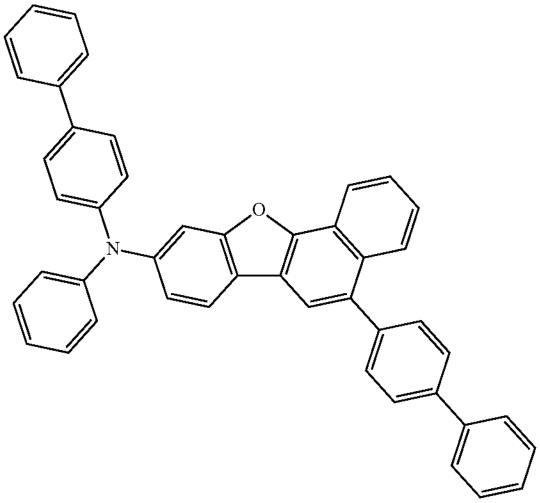
1-178
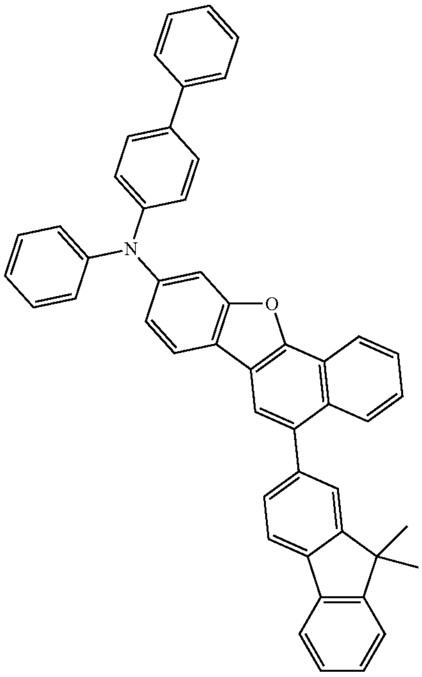

-continued
1-179
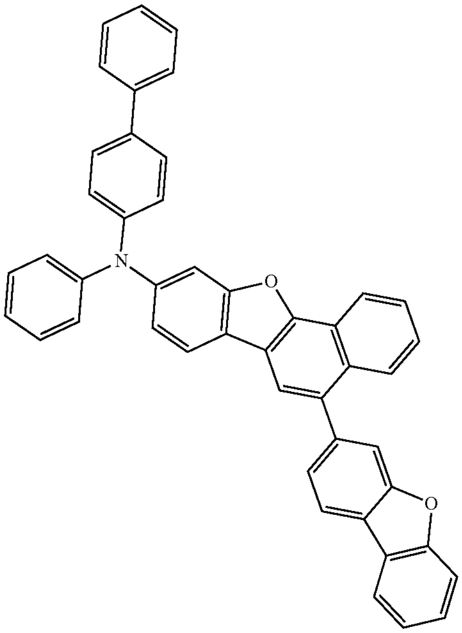
1-180
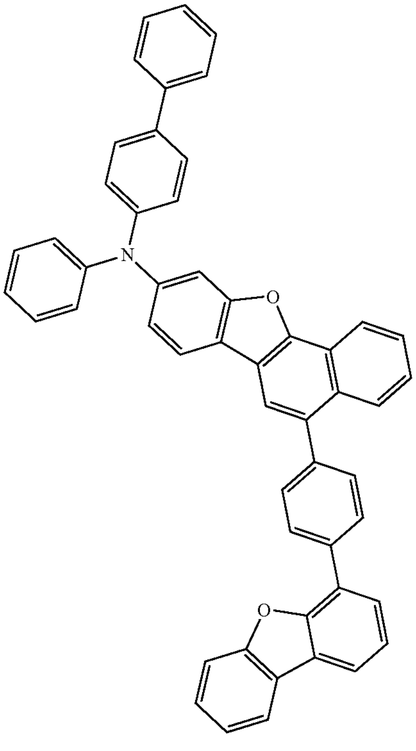
1-181
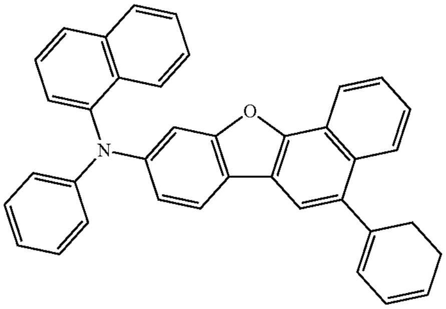
1-182
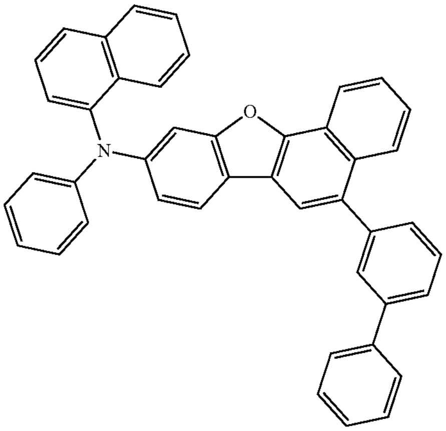
1-183
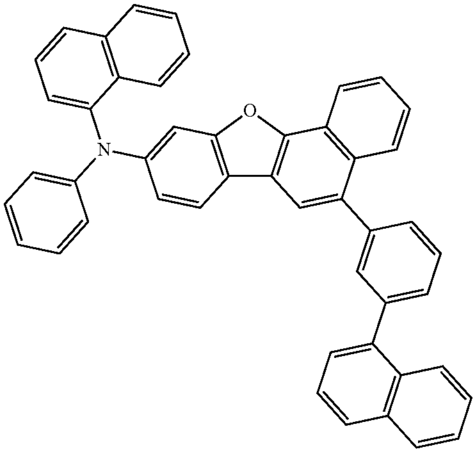
1-184
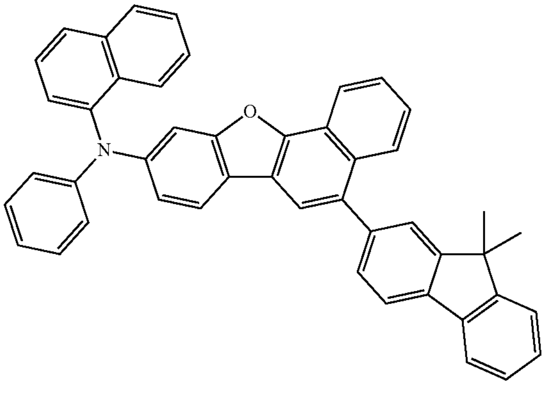

1-185
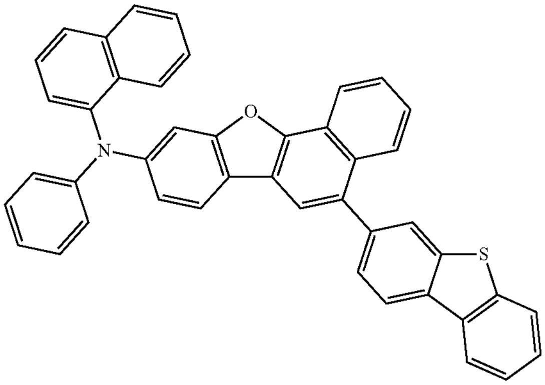
1-186
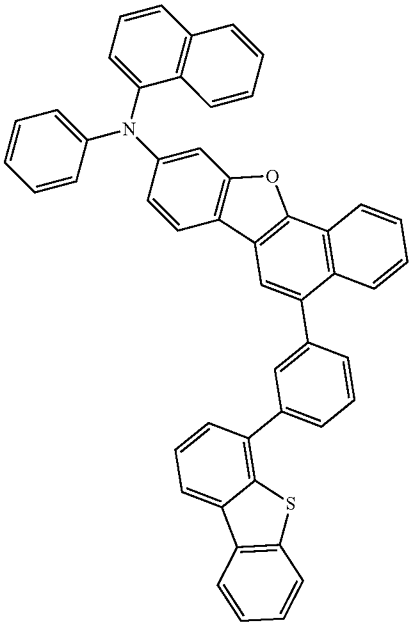
1-187
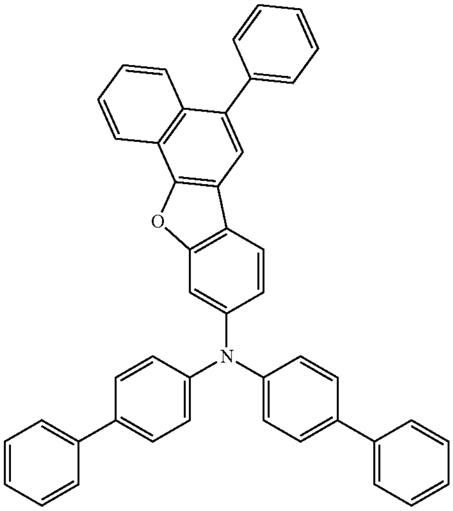
1-188
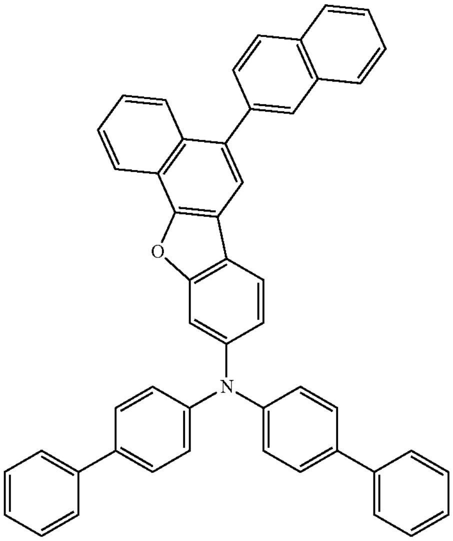
1-189
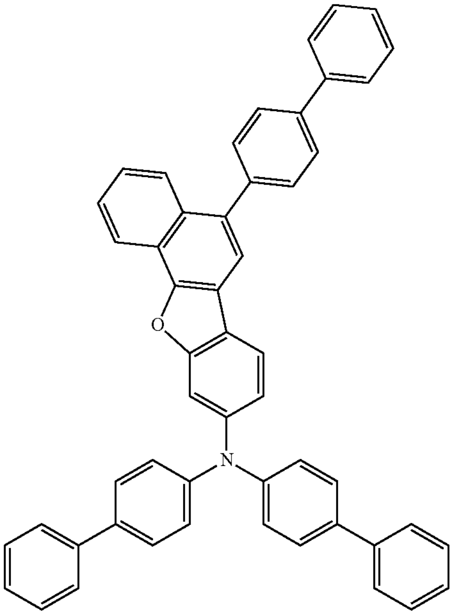

-continued
1-190
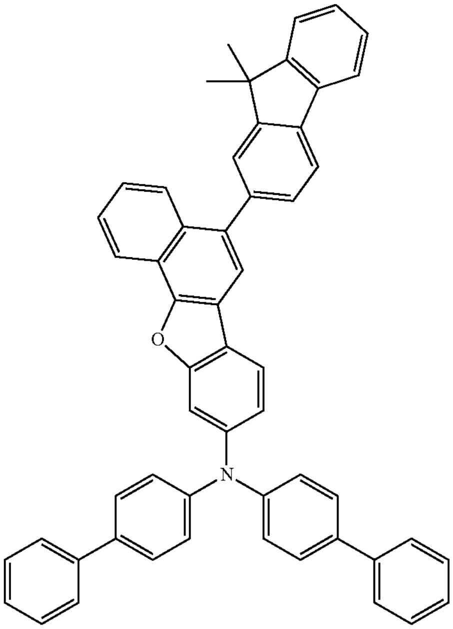
1-191
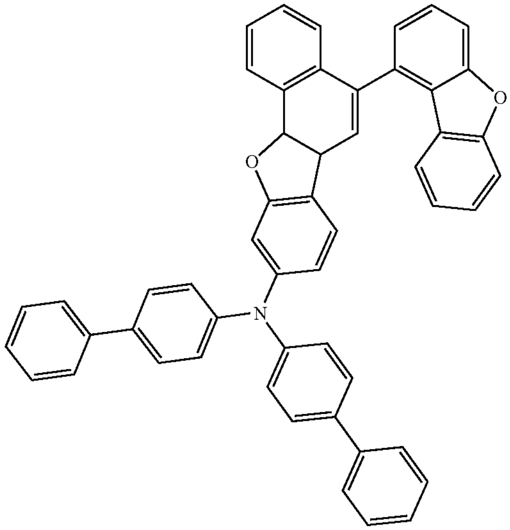
-continued
1-192
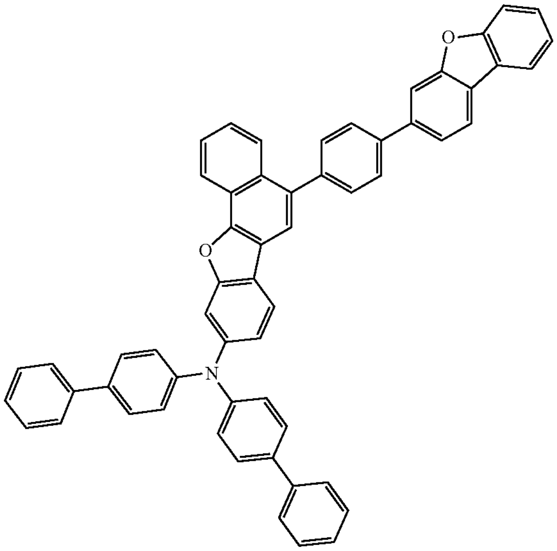
1-193
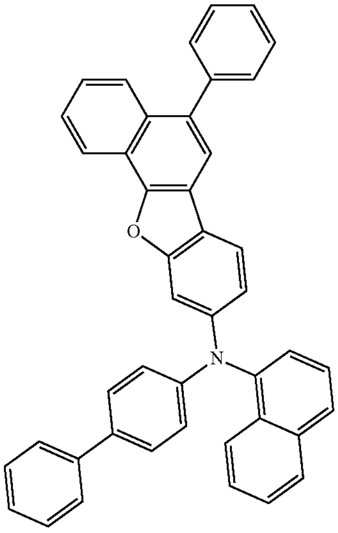
1-194
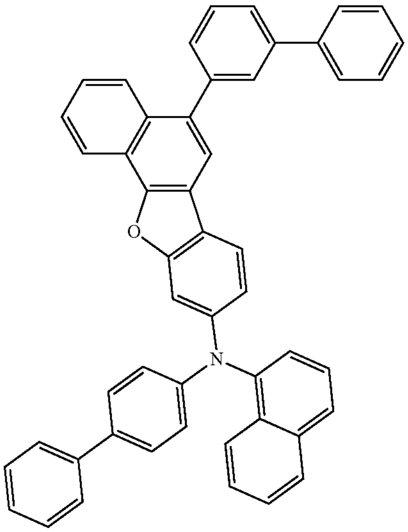

-continued
1-195
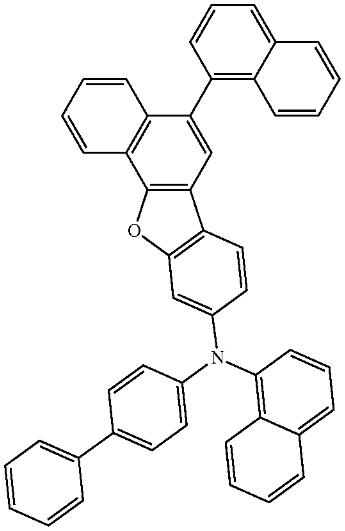
1-196
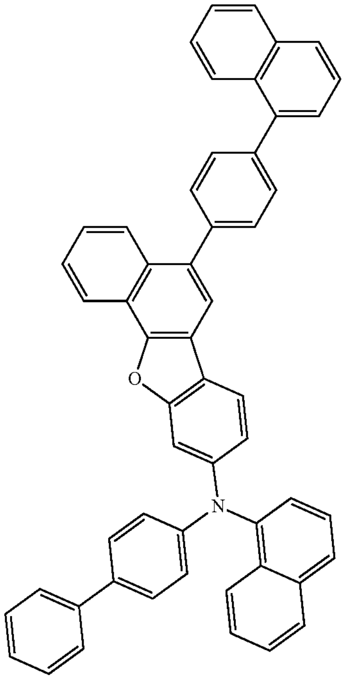
-continued
1-197
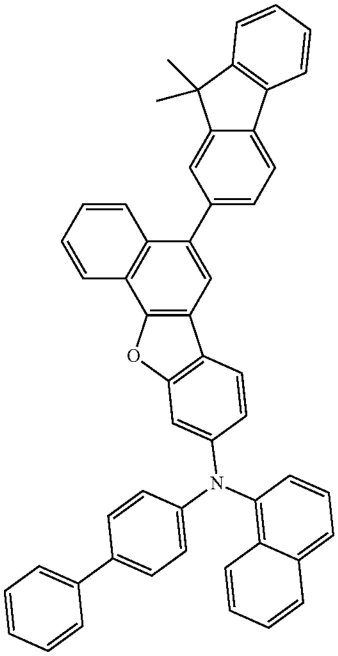
1-198
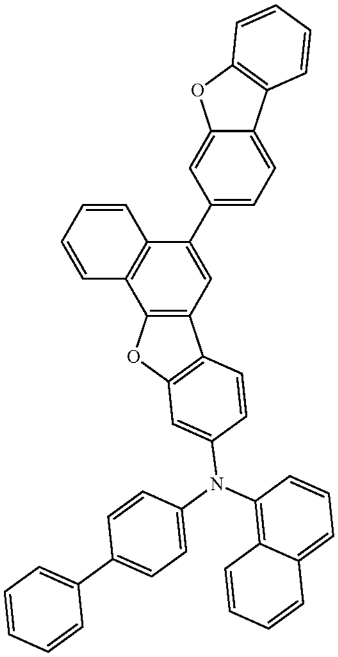

-continued
1-199
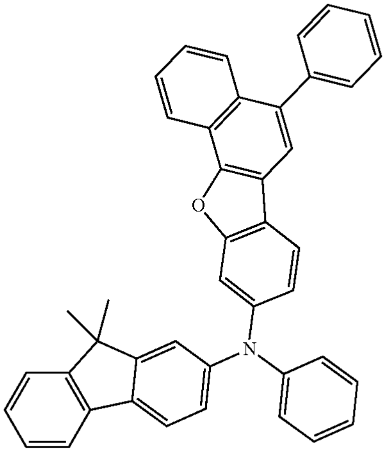
1-200
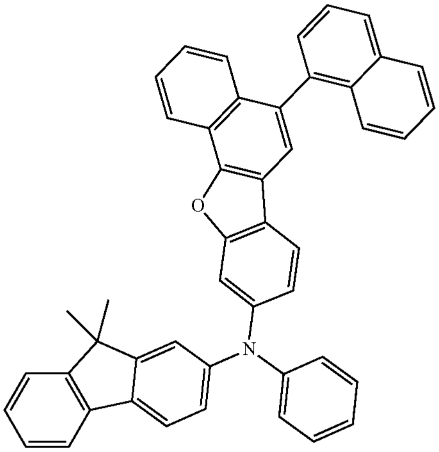
1-201
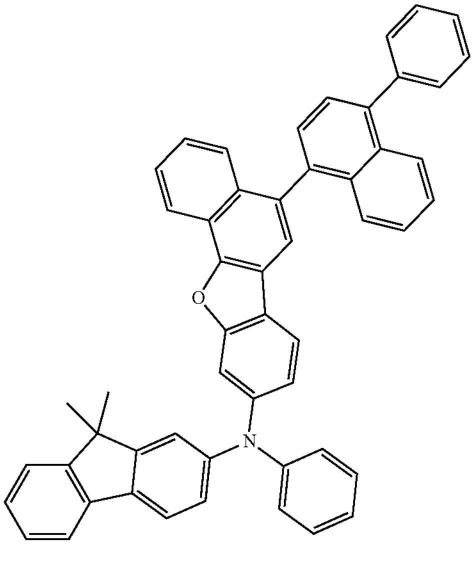
-continued
1-202
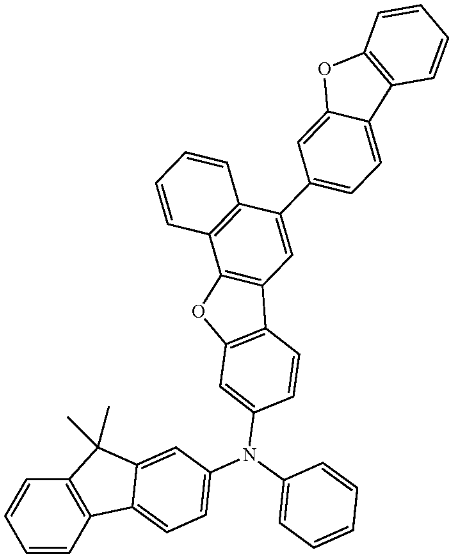
1-203
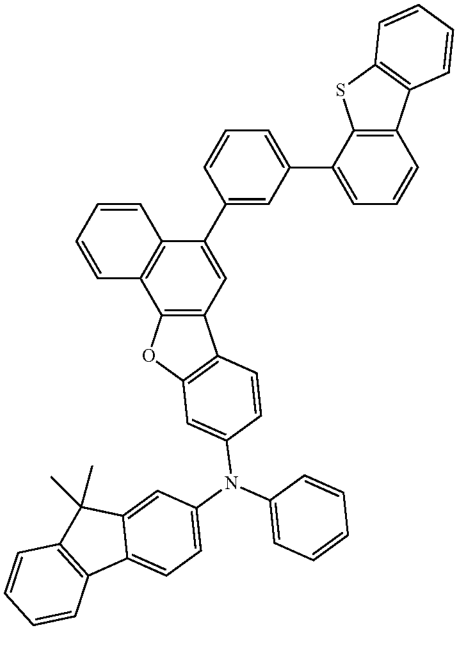

-continued
1-205
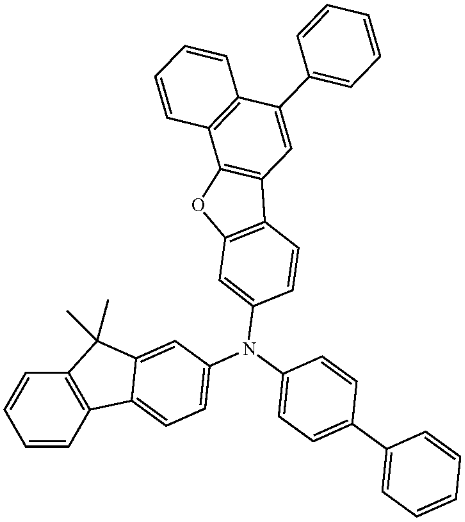
1-206
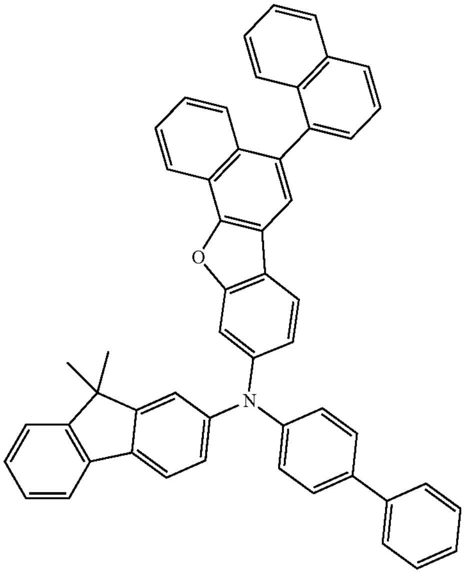
-continued
1-207
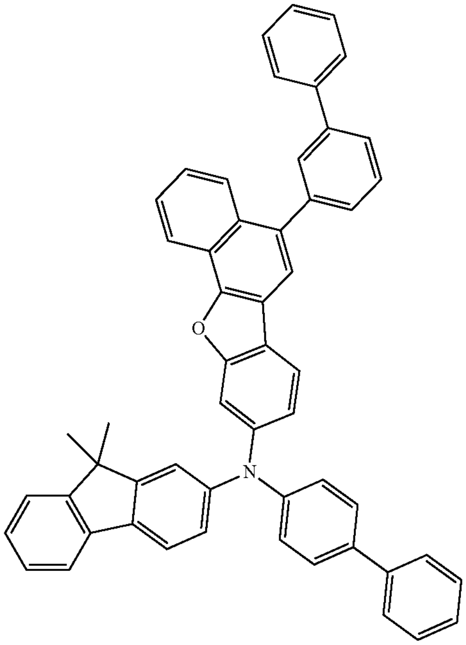
1-208
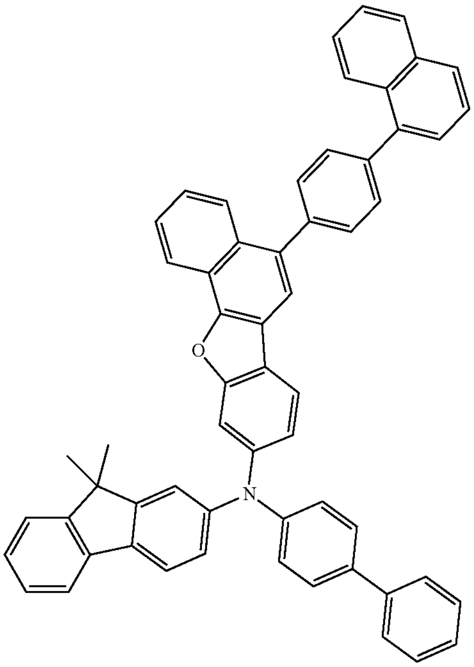

-continued
1-209
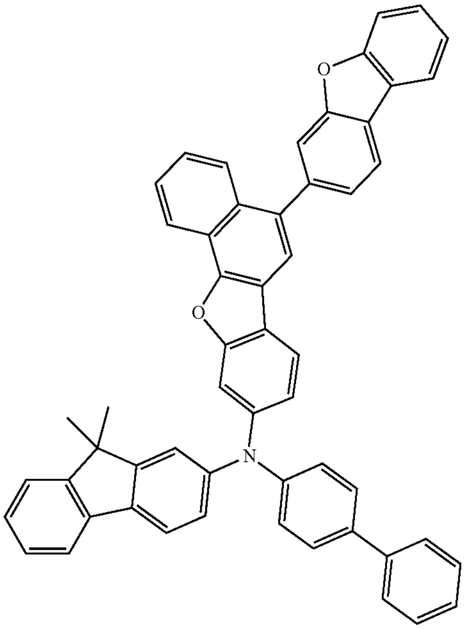
1-210
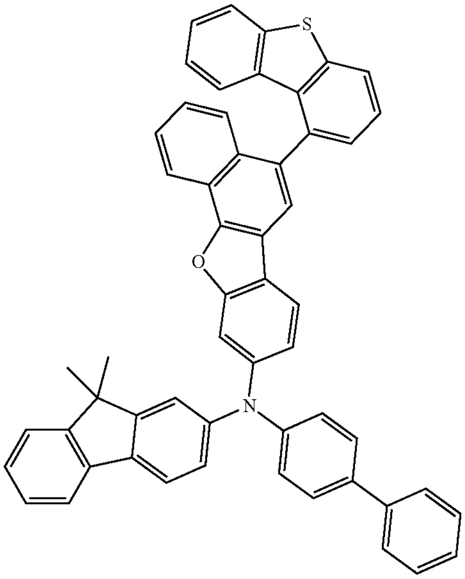
-continued
1-211
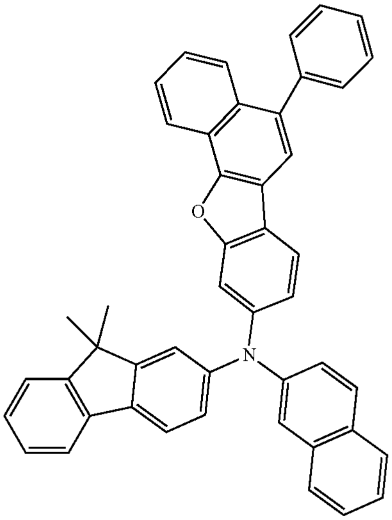
1-212
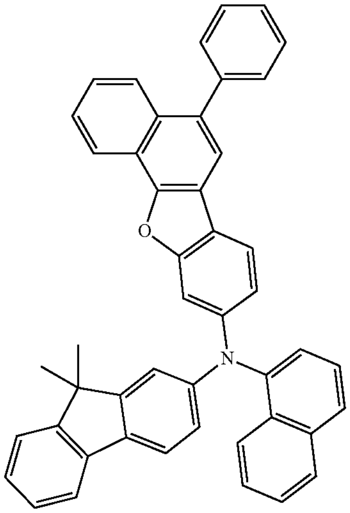
1-213
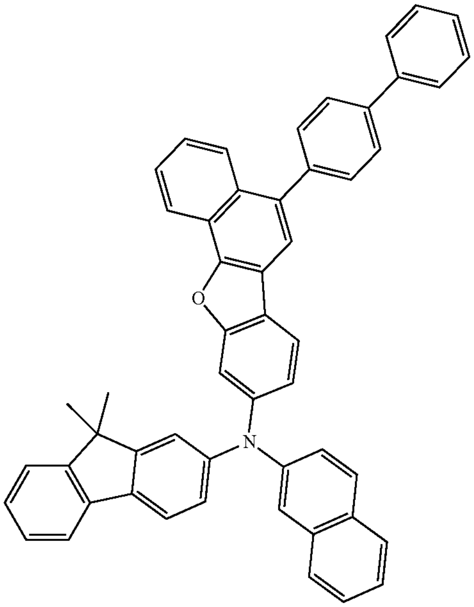

-continued
1-214
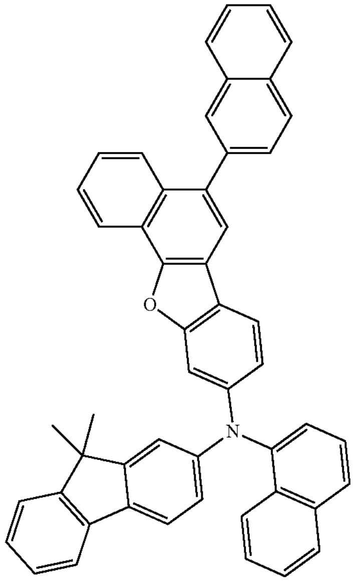
1-215
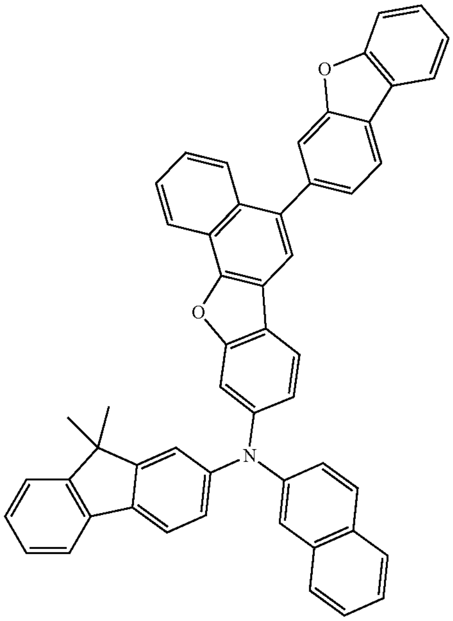
-continued
1-216
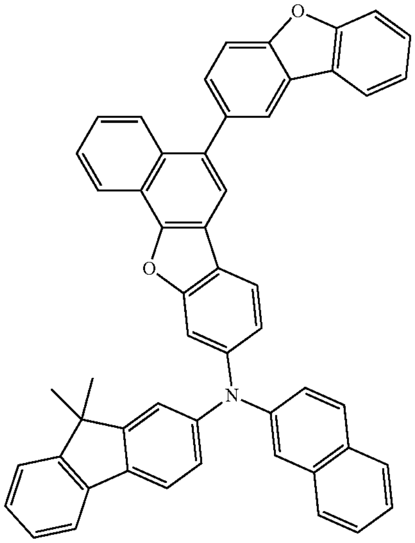
1-217
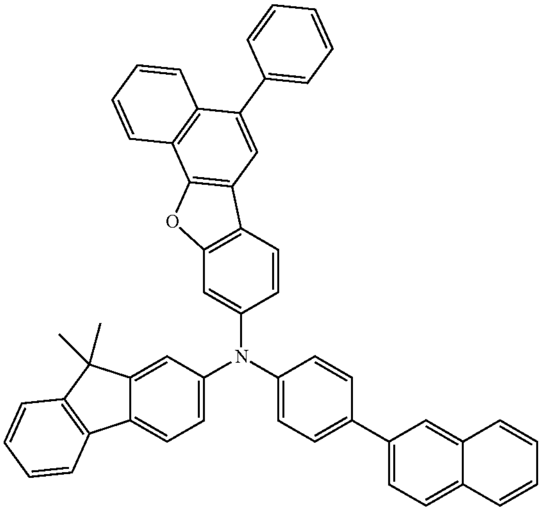
1-218
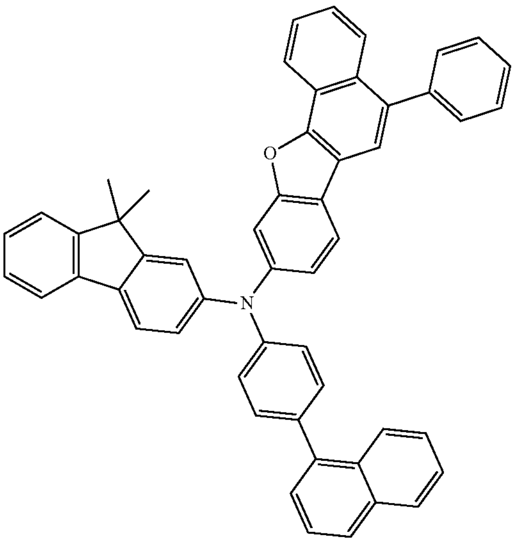

-continued
1-219
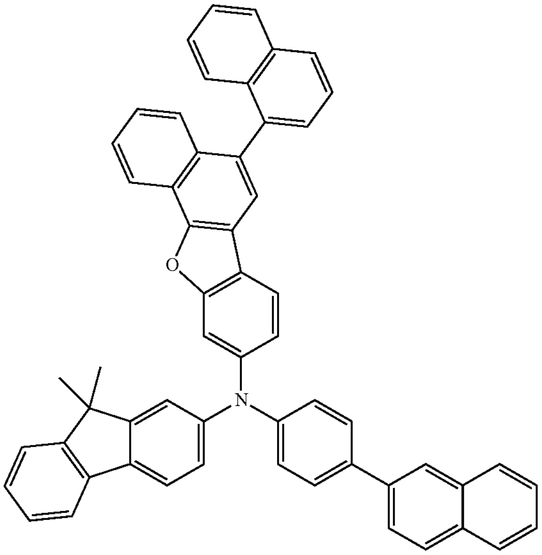
1-220
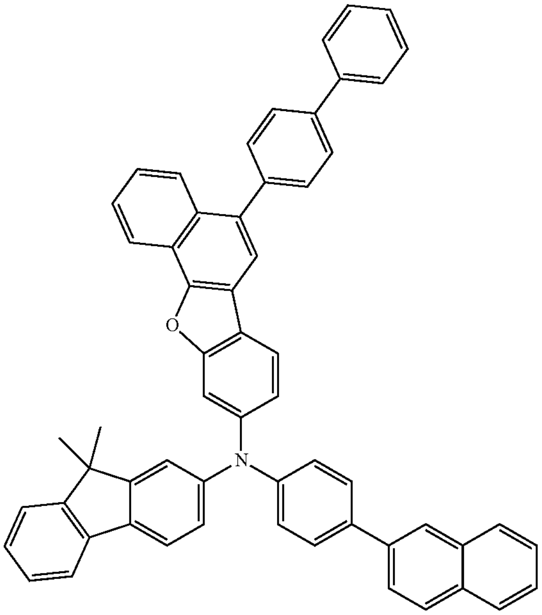
-continued
1-221
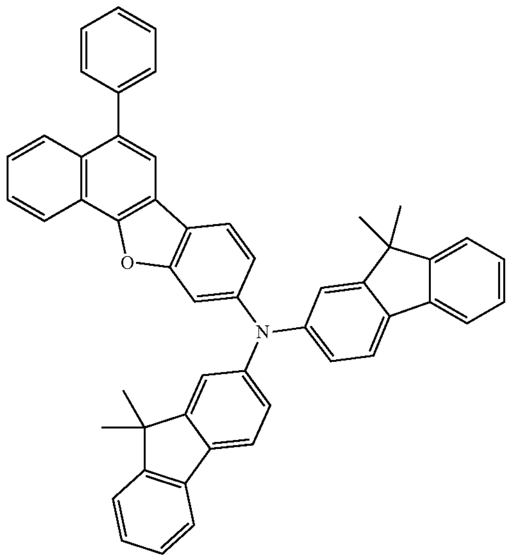
1-222
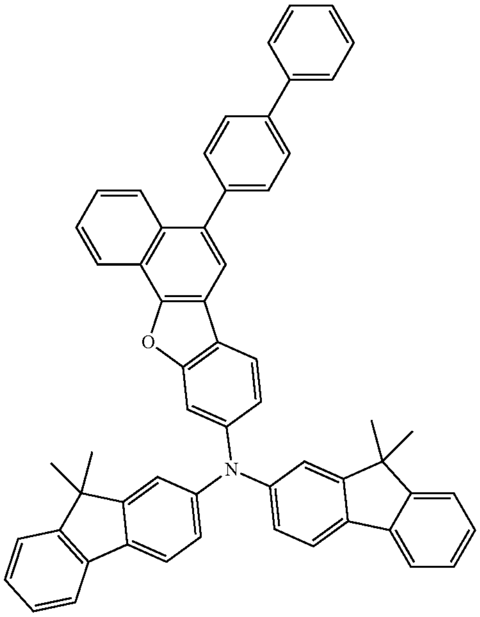
1-223
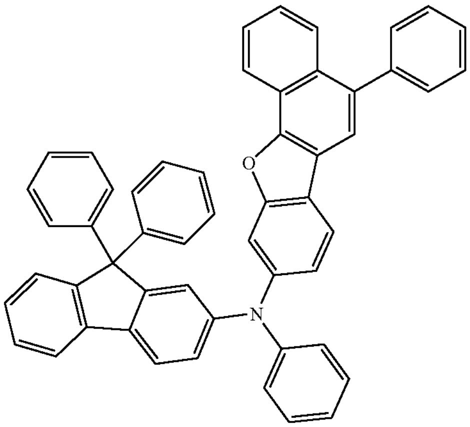

-continued
1-224
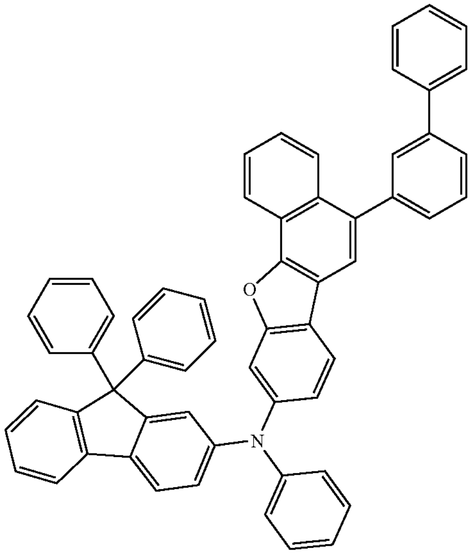
1-225
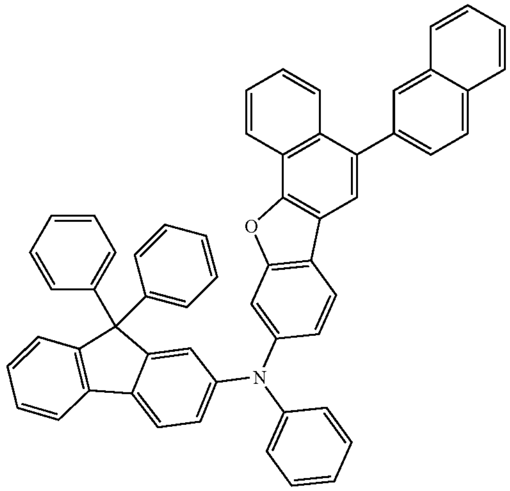
1-226
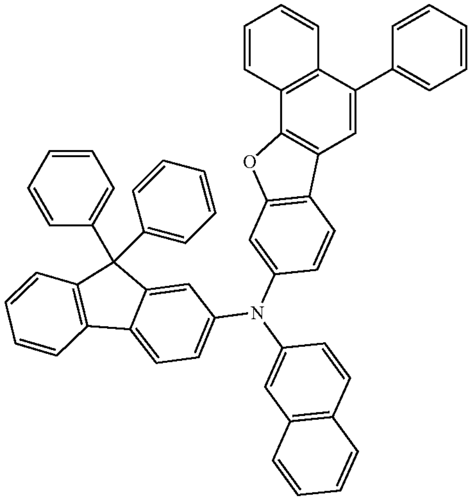
-continued
1-227
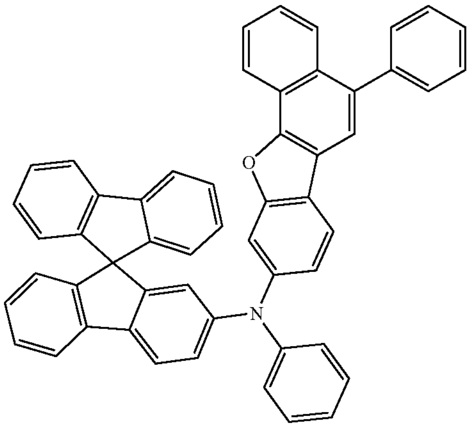
1-228
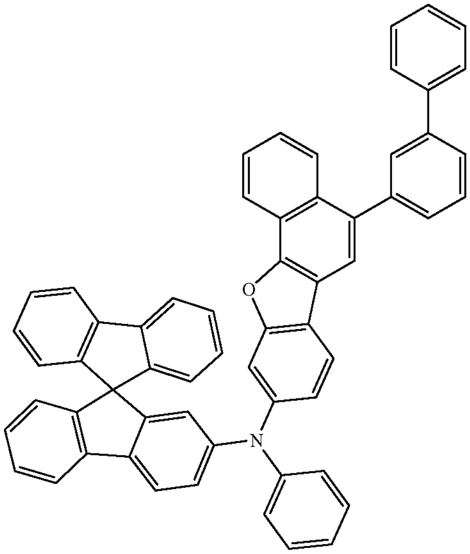
1-229
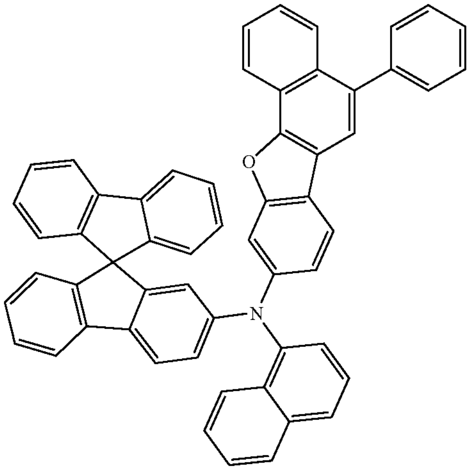

1-230
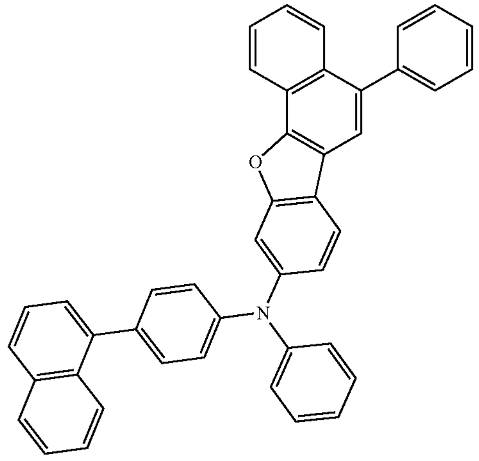
1-231
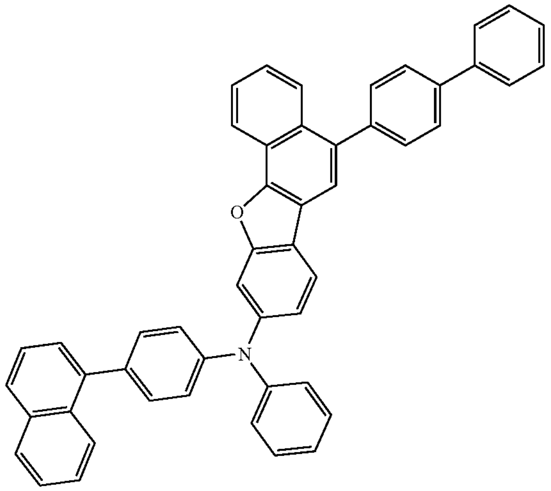
1-232
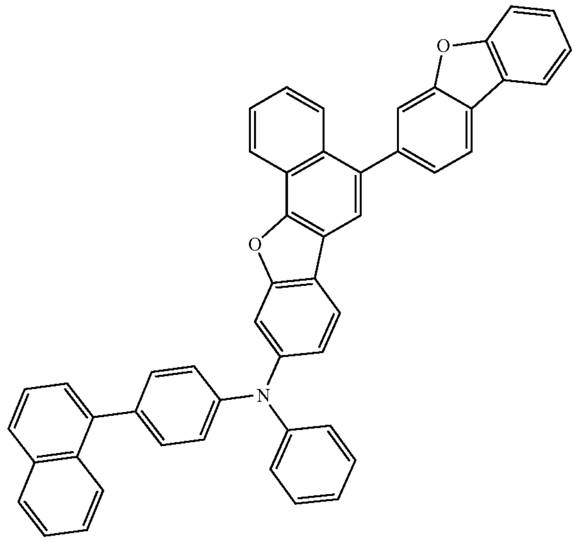
1-233
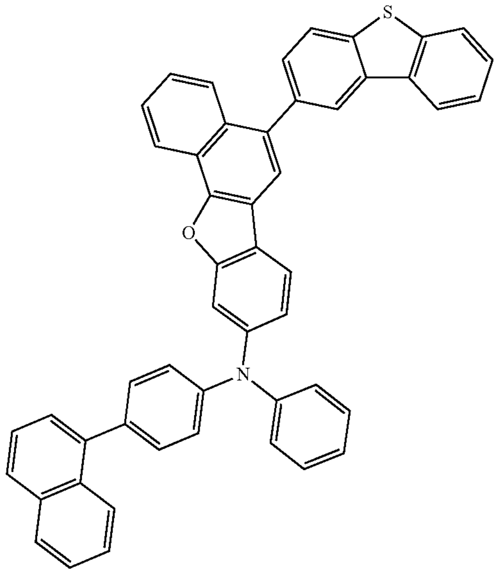
1-234
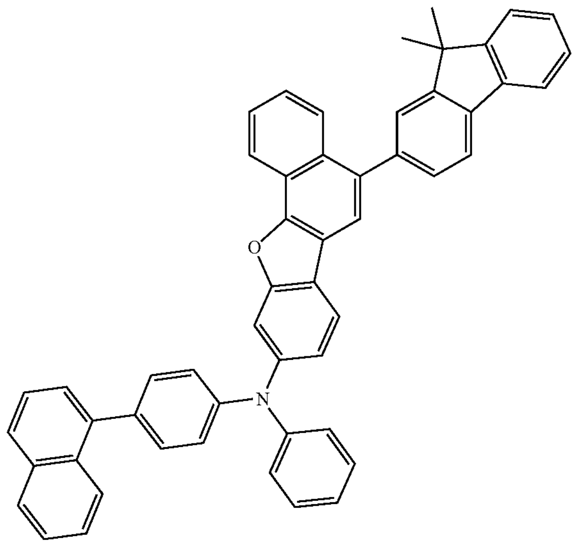

-continued
1-235
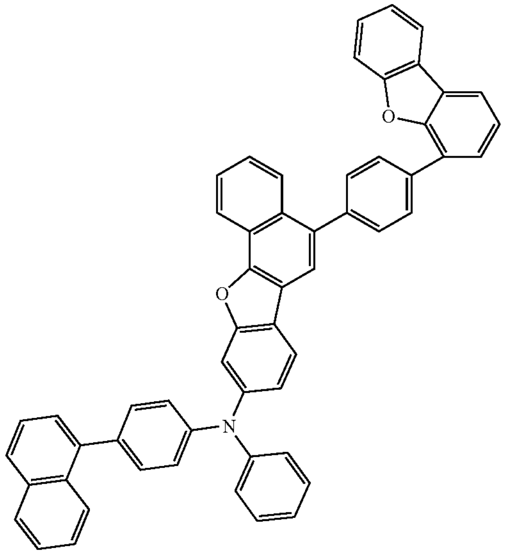
1-236
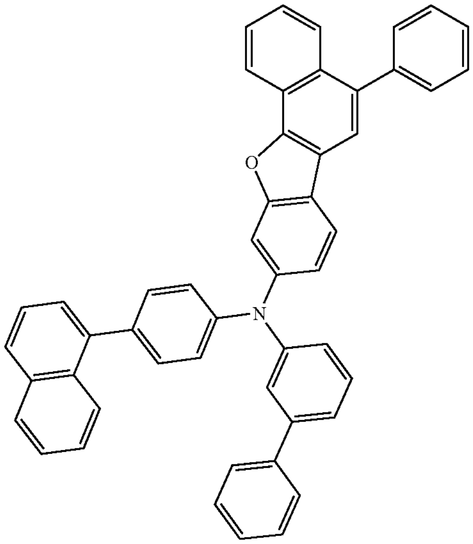
1-237
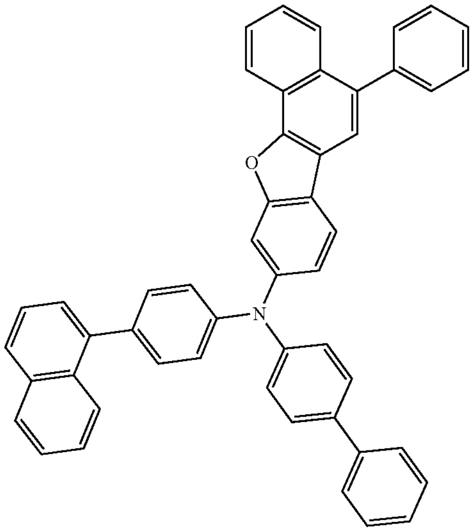
-continued
1-238
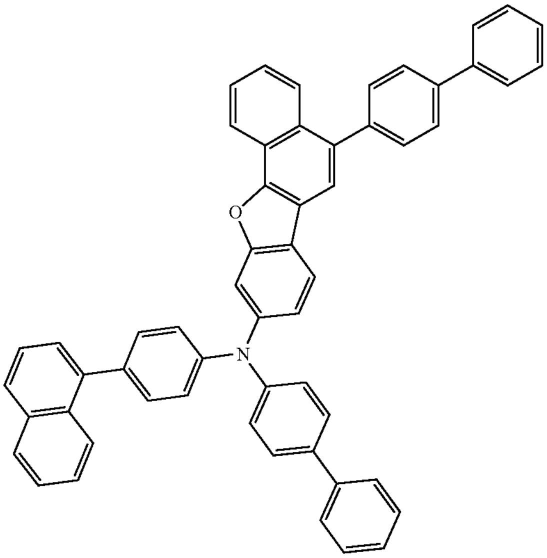
1-239
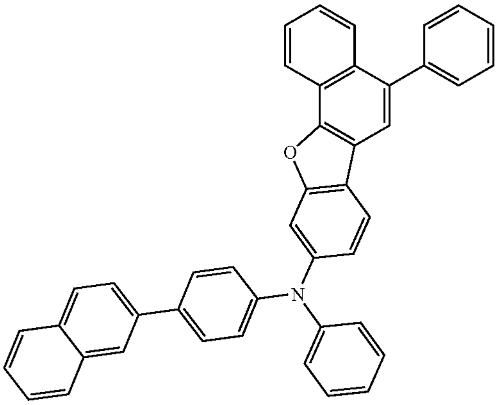
1-240
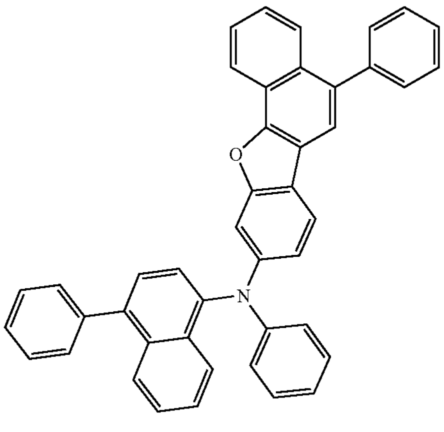

-continued
1-241
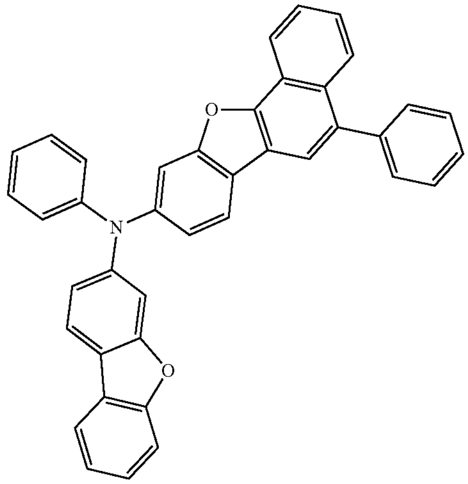
1-242
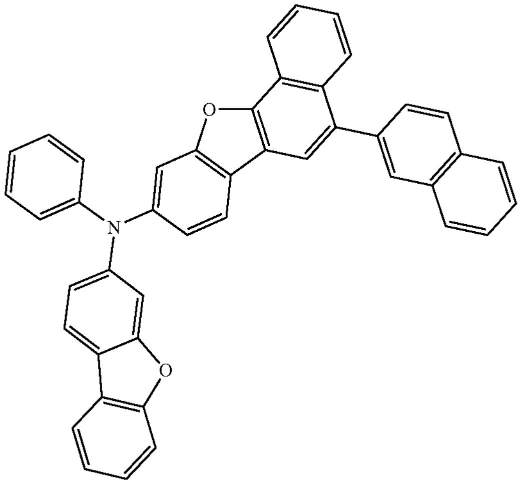
1-243
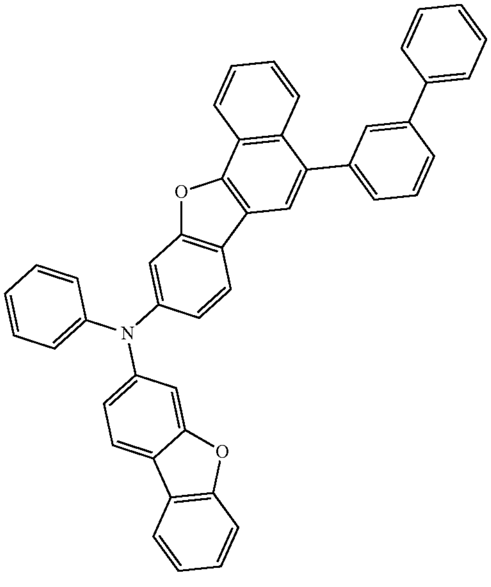
-continued
1-244
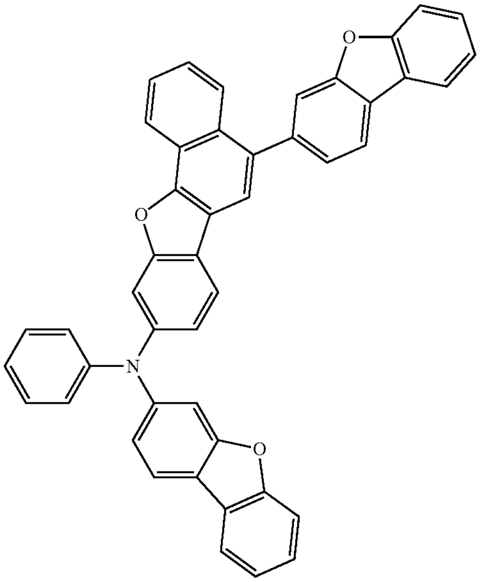
1-245
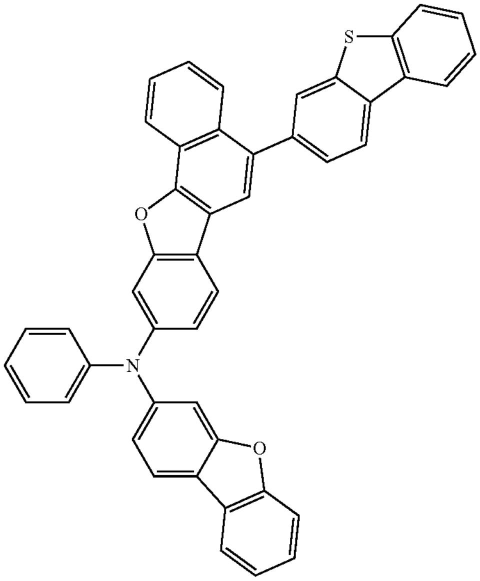

-continued
1-246
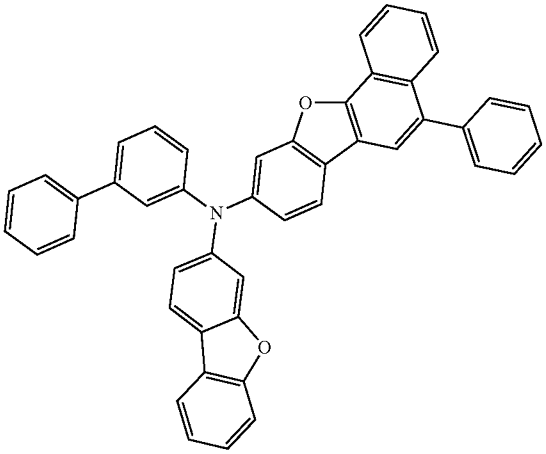
1-247
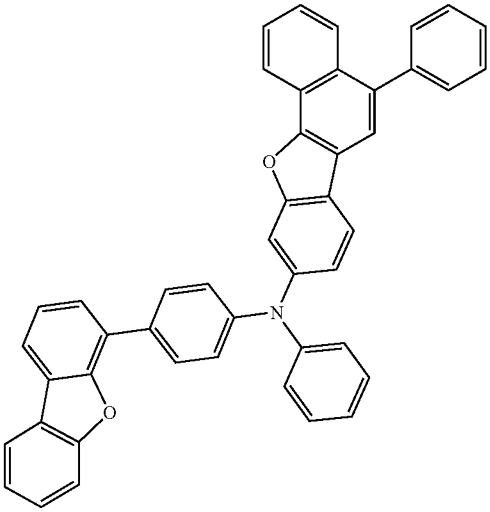
1-248
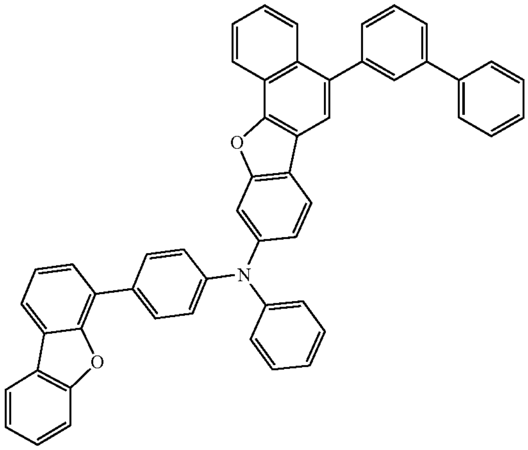
-continued
1-249
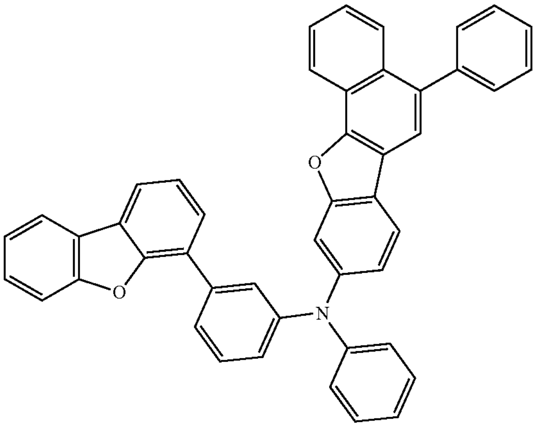
1-250
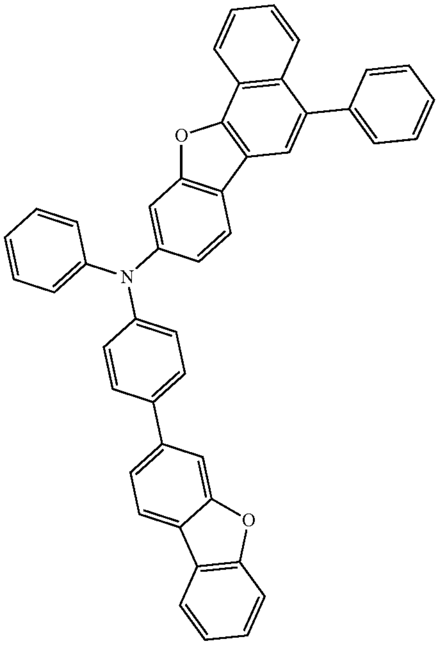

-continued
1-251
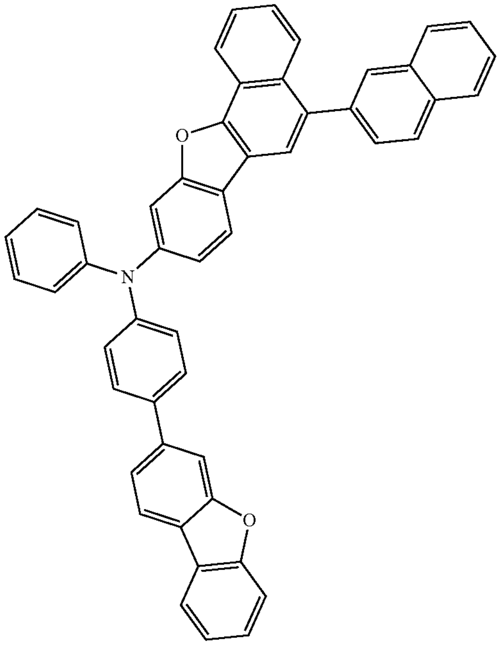
1-252
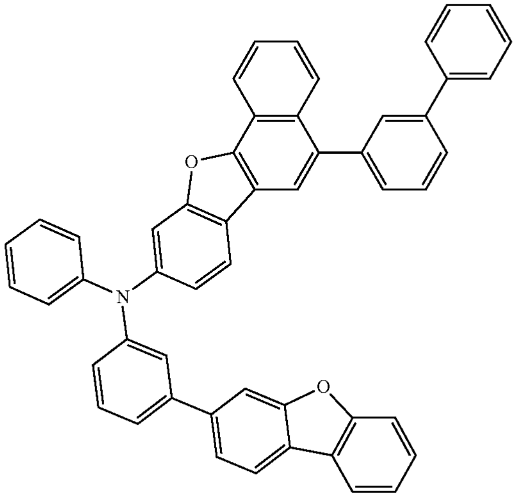
-continued
1-253
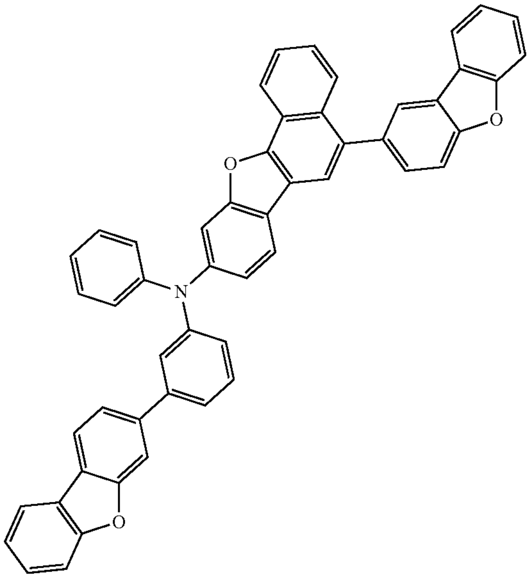
1-254
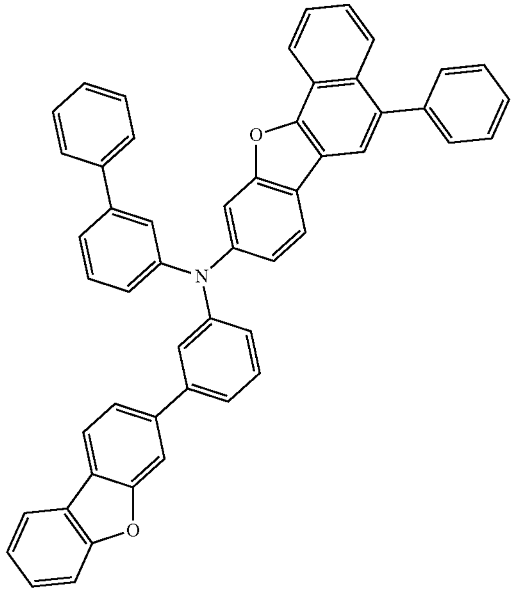

-continued
1-255
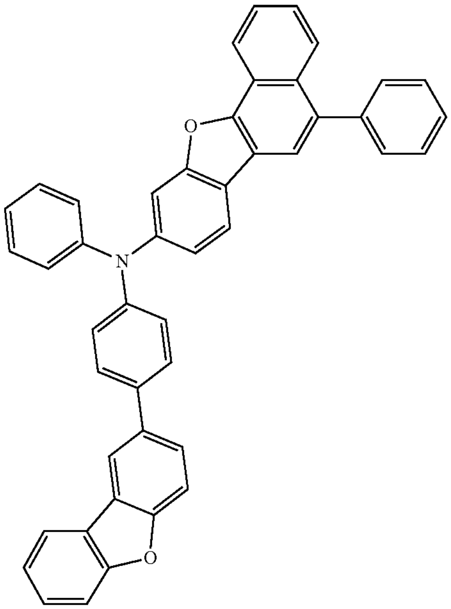
-continued
1-257
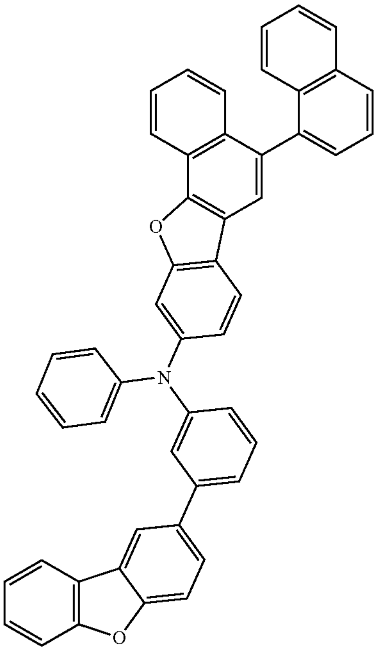
1-256
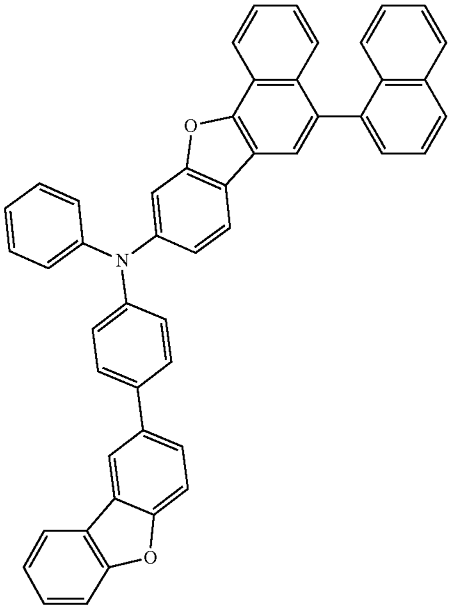
1-258
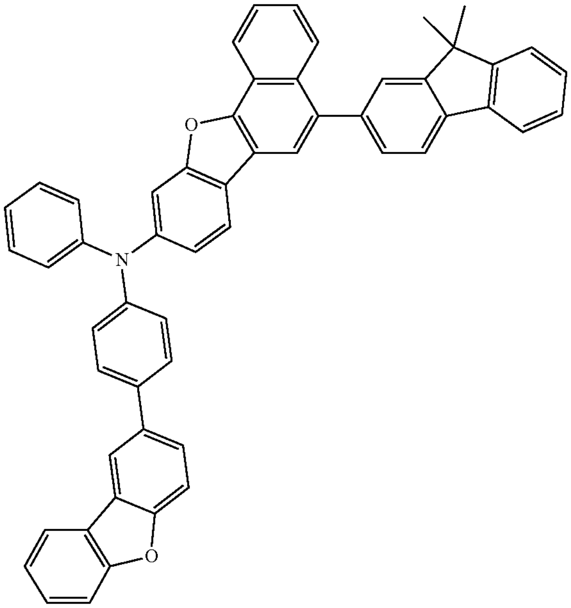

1-259
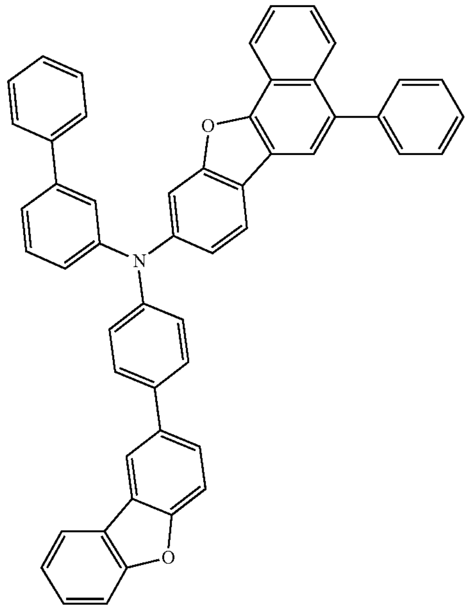
1-260
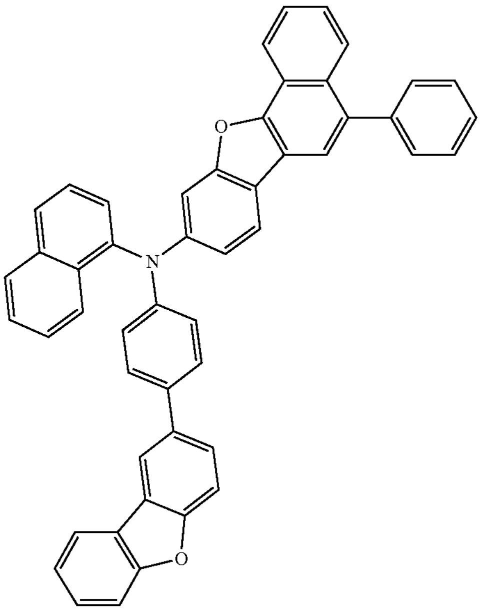
1-261
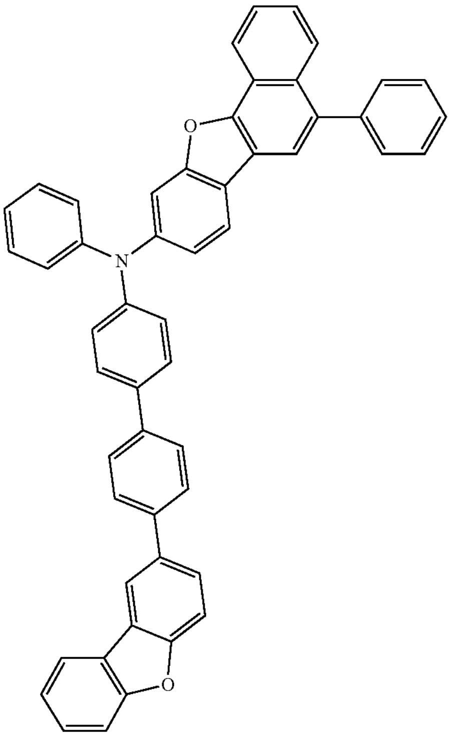
1-262
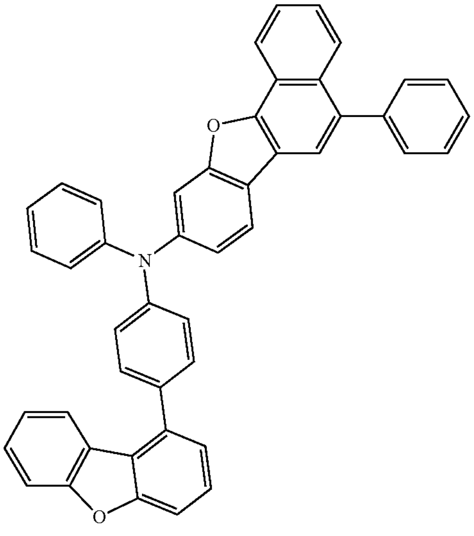

-continued
1-263
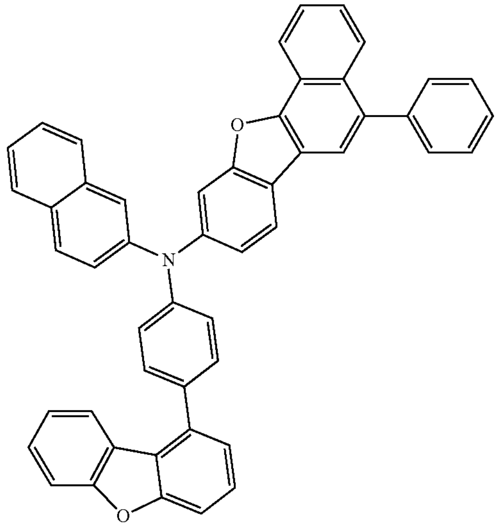
1-264
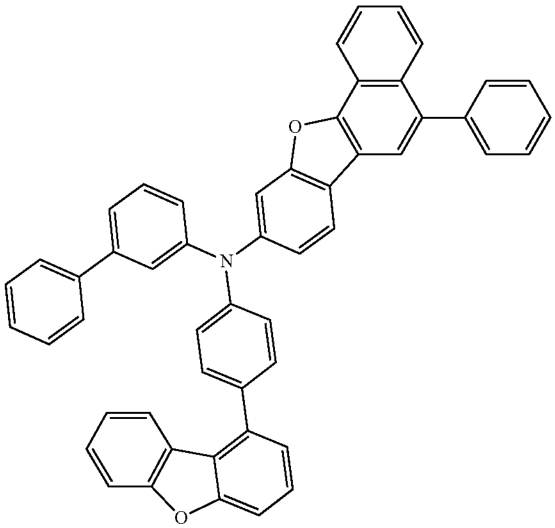
1-265
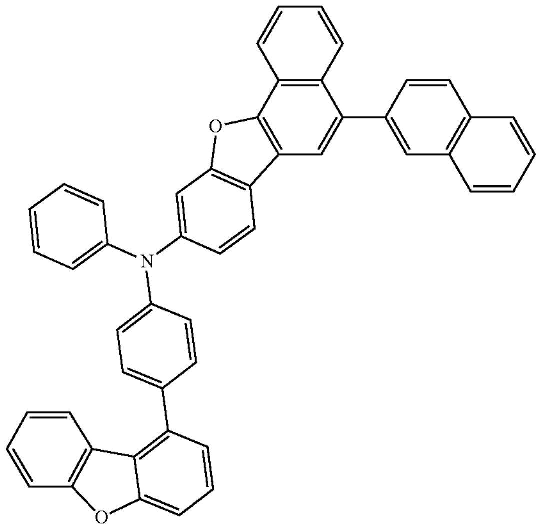
-continued
1-266
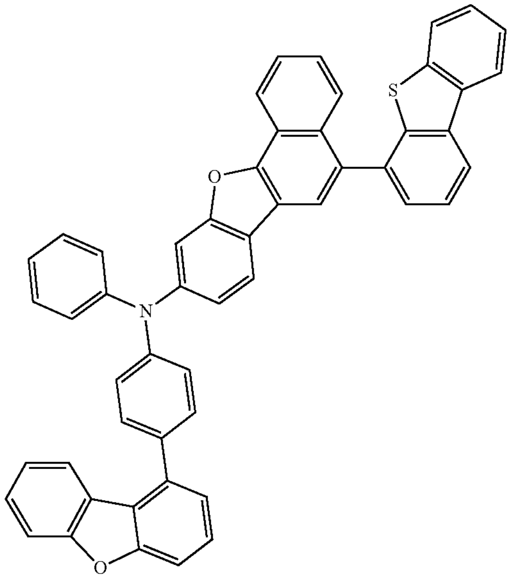
1-267
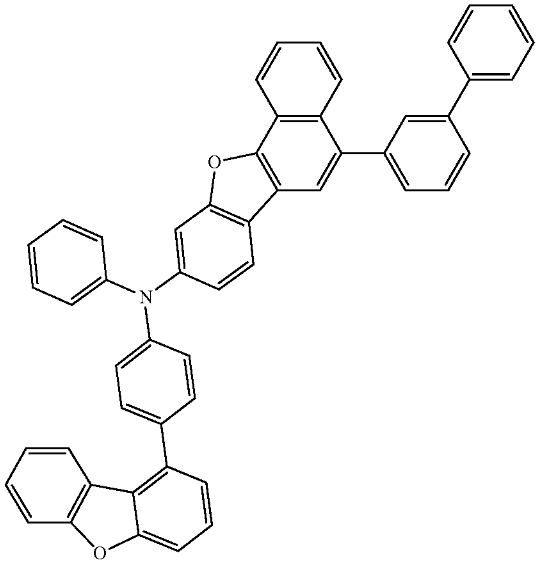
1-268
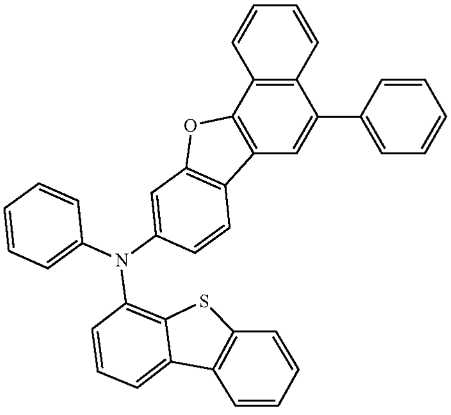

-continued
1-269
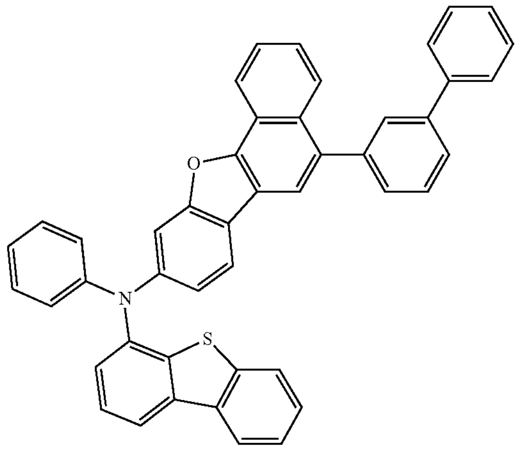
1-270
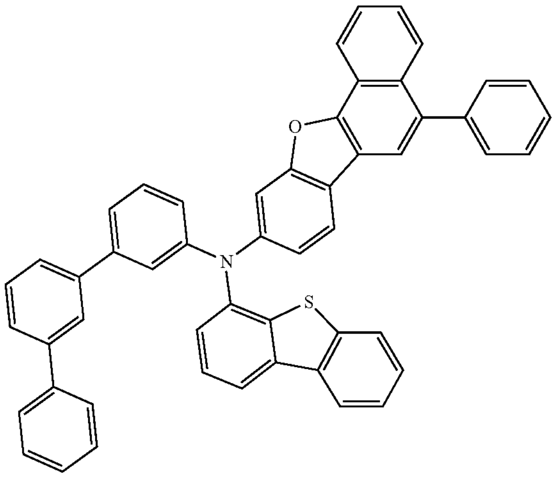
1-271
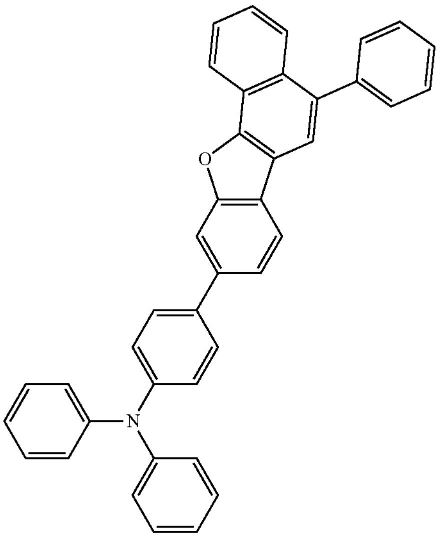
-continued
1-272
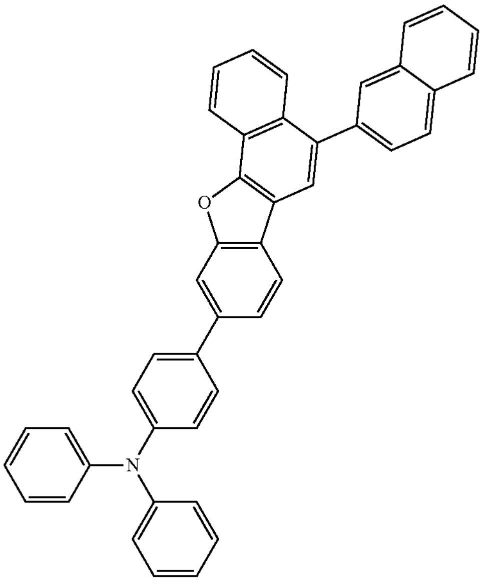
1-273
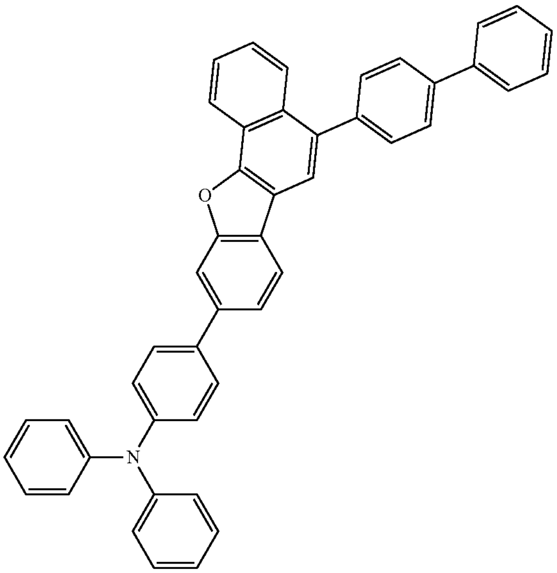

-continued
1-274
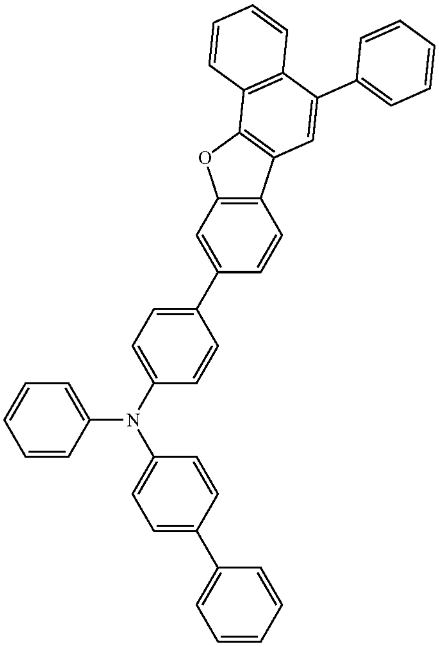
1-275
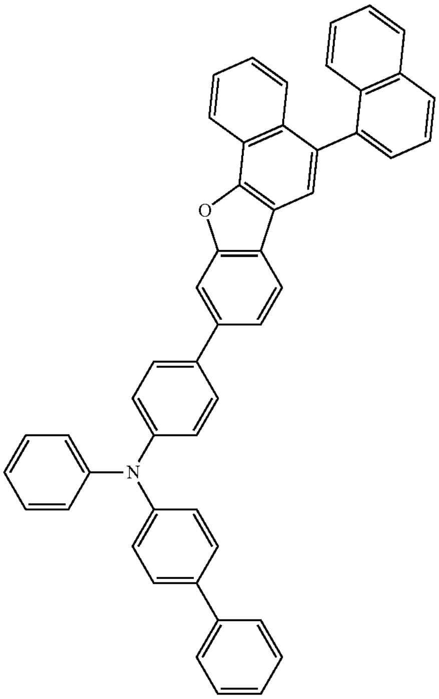
-continued
1-276
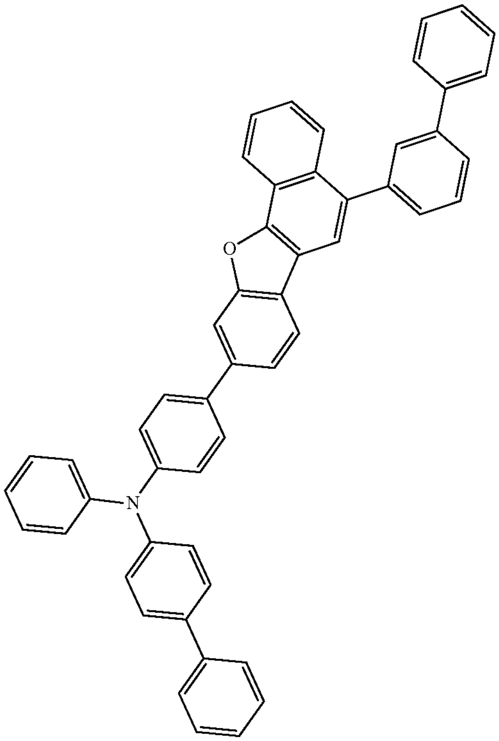
1-277
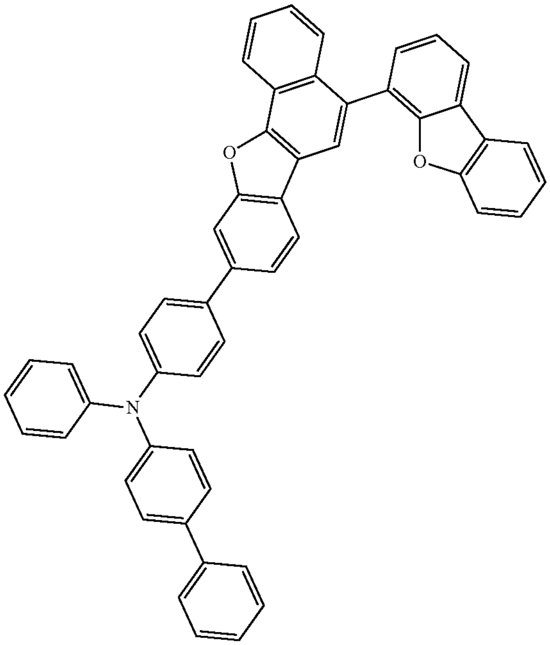

-continued
1-278
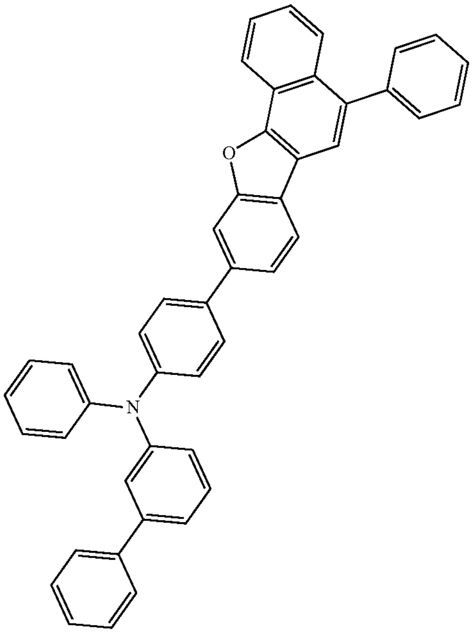
1-279
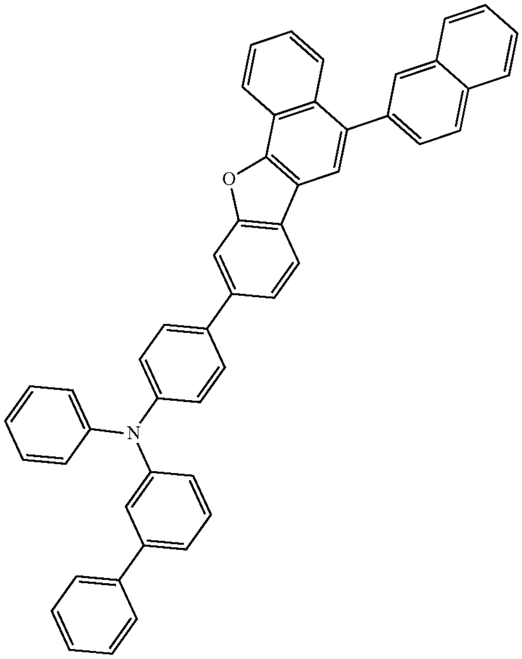
-continued
1-280
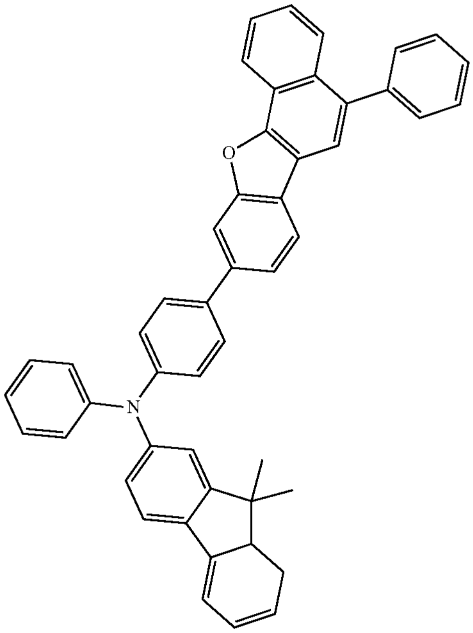
1-281
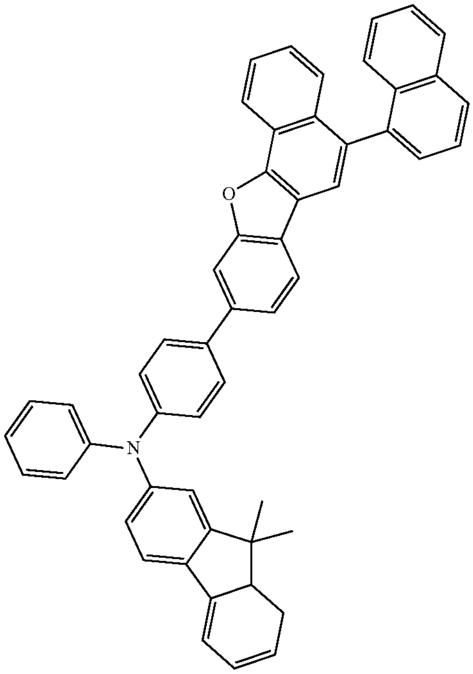

-continued
1-282
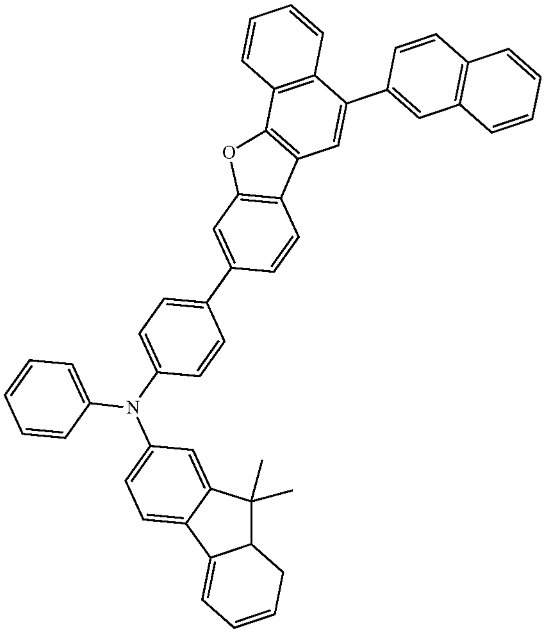
1-283
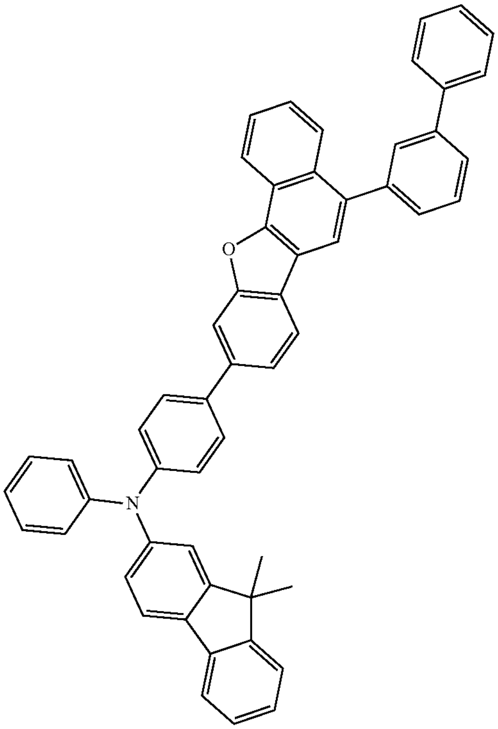
-continued
1-284
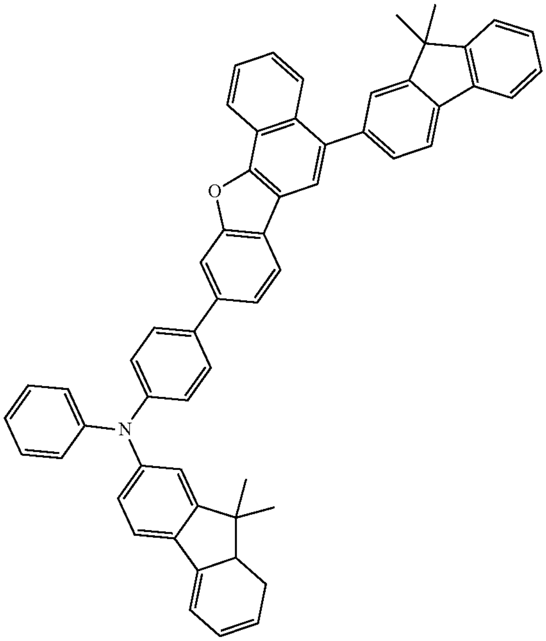
1-285
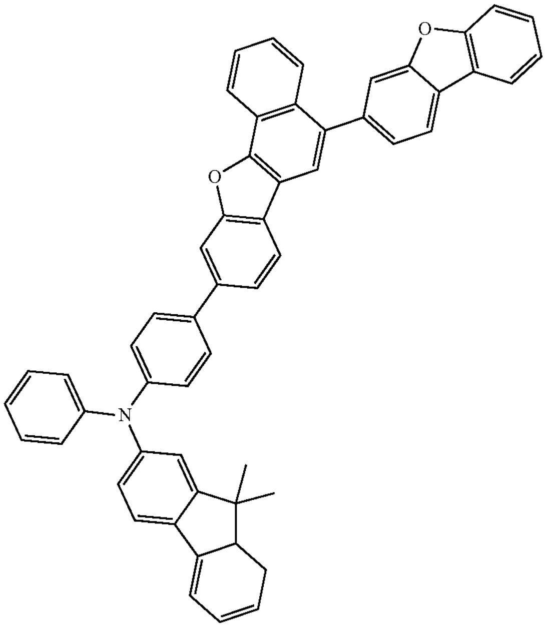

-continued
286
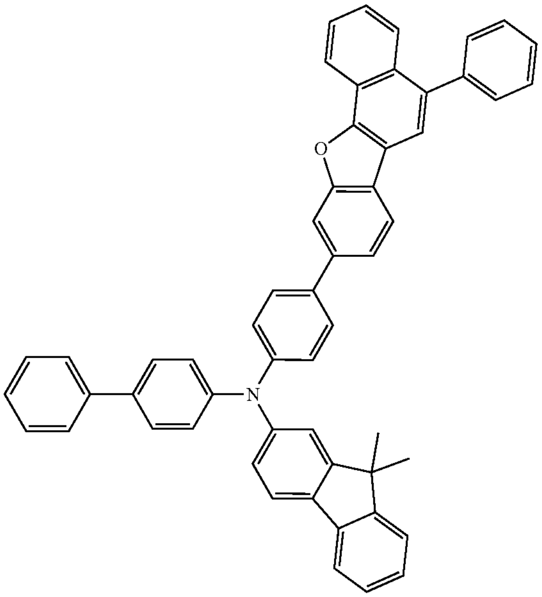
287
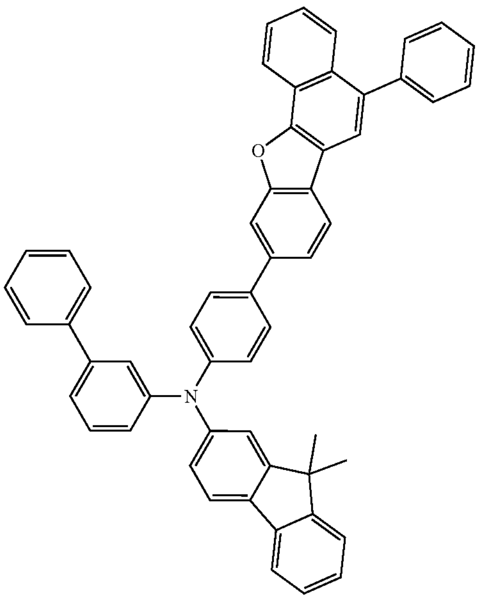
-continued
1-288
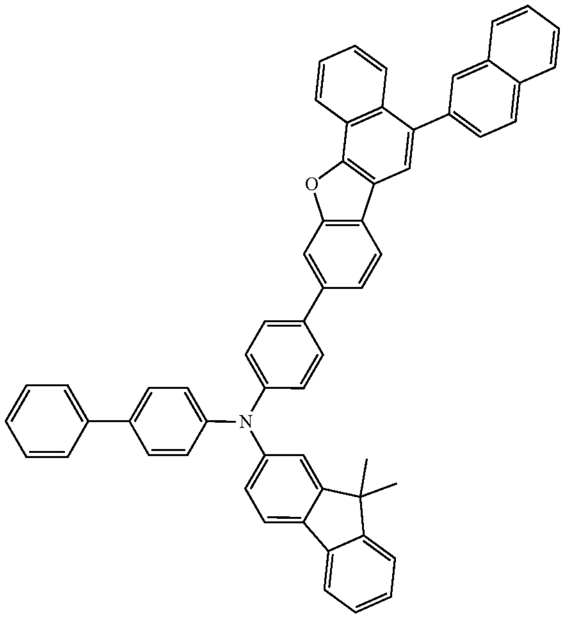
1-289
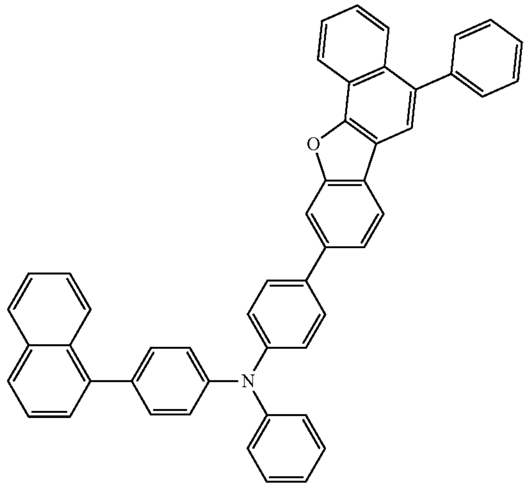
1-290
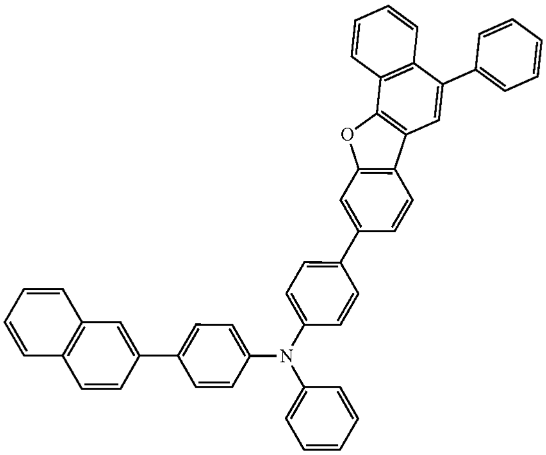

1-291
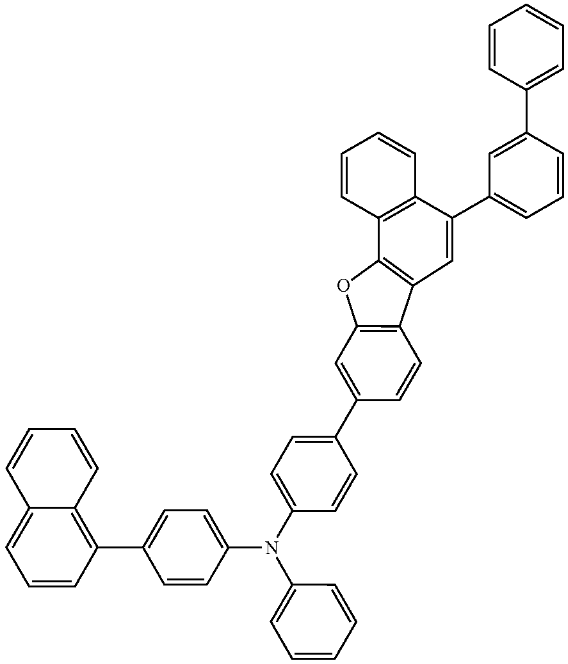
1-292
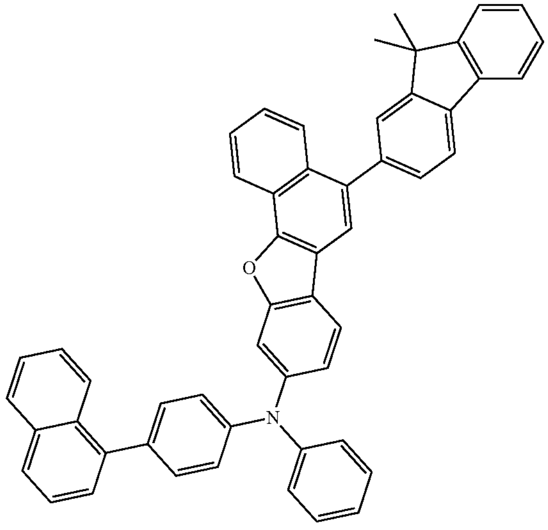
1-293
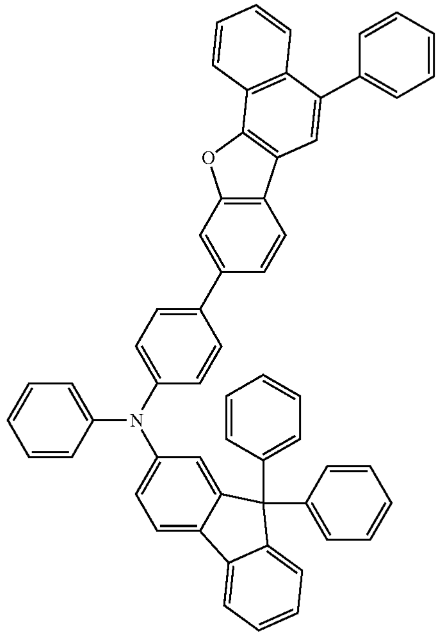
1-294
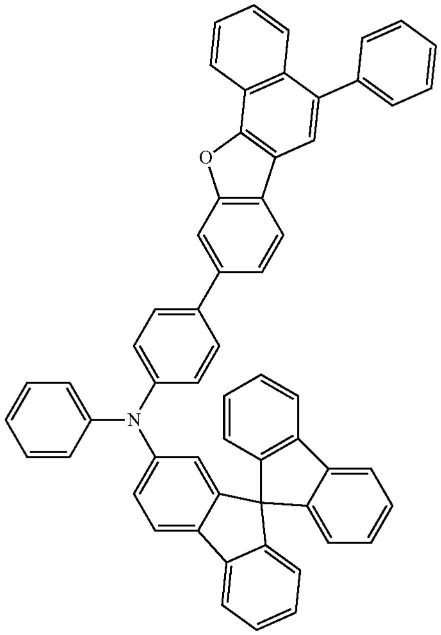

1-295
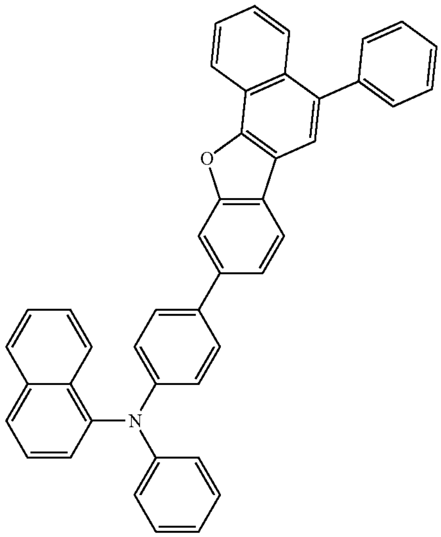
1-296
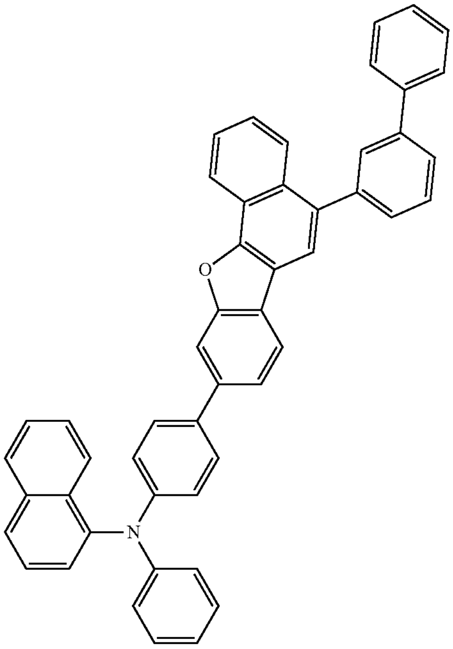
1-297
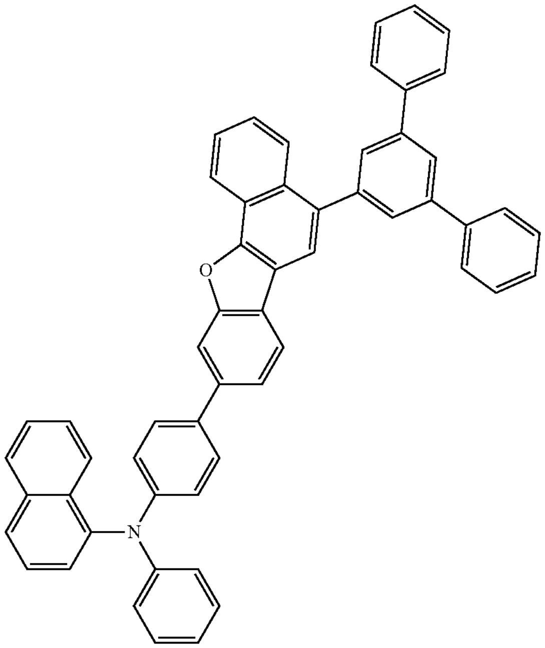
1-298
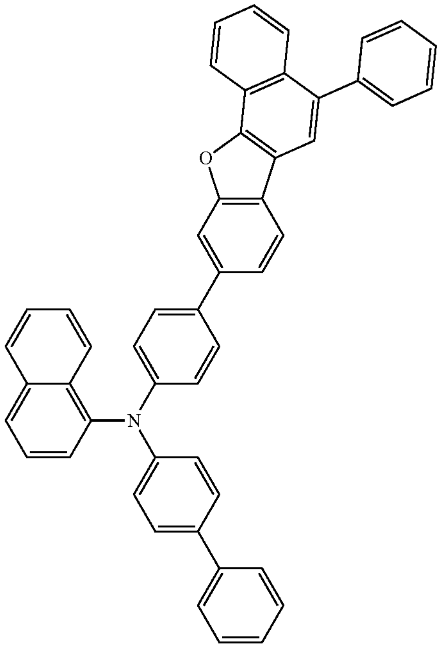

-continued
1-299
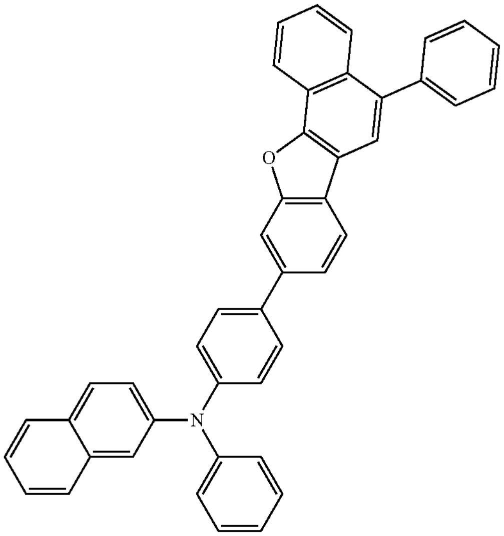
1-300
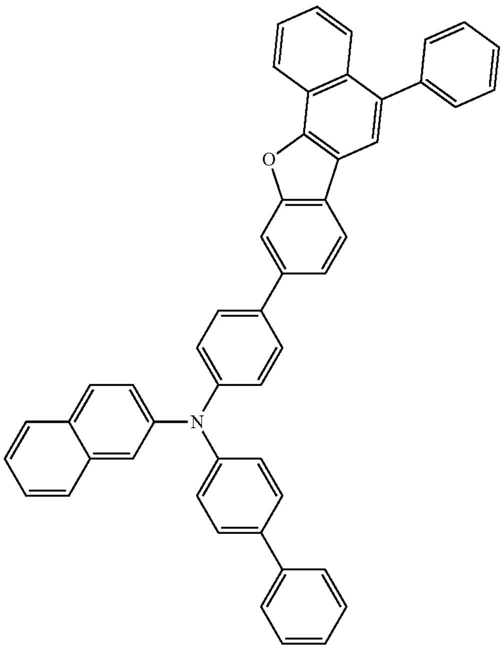
-continued
1-301
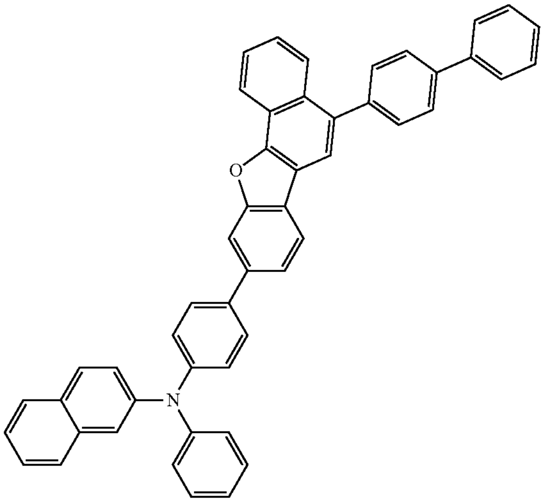
1-302
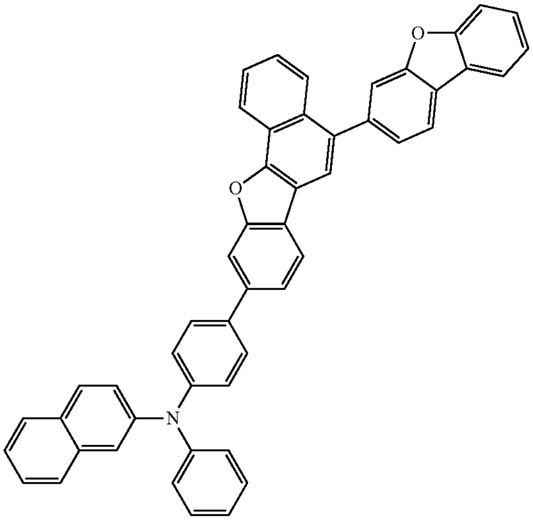

-continued
1-303
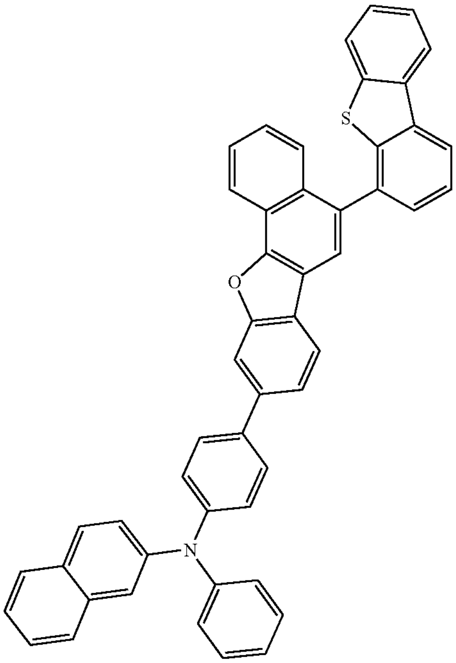
1-304
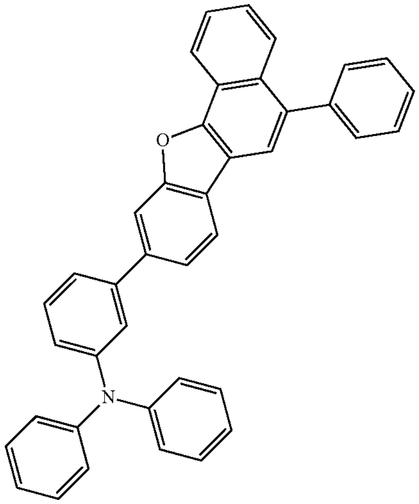
-continued
1-305
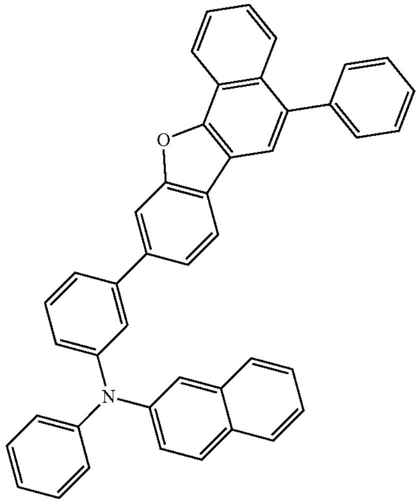
1-306
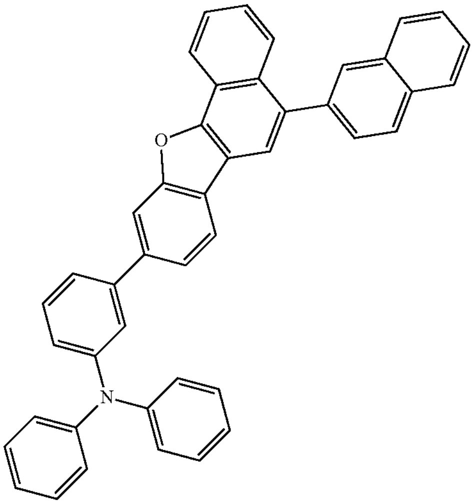
1-307
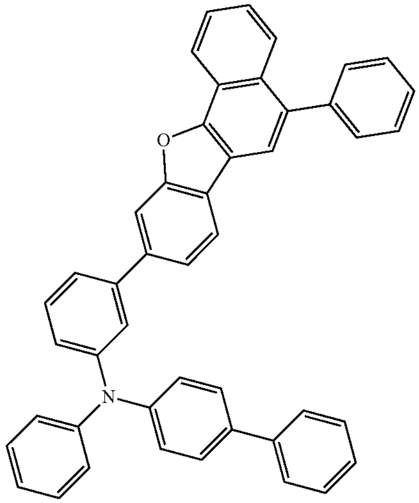

-continued
1-308
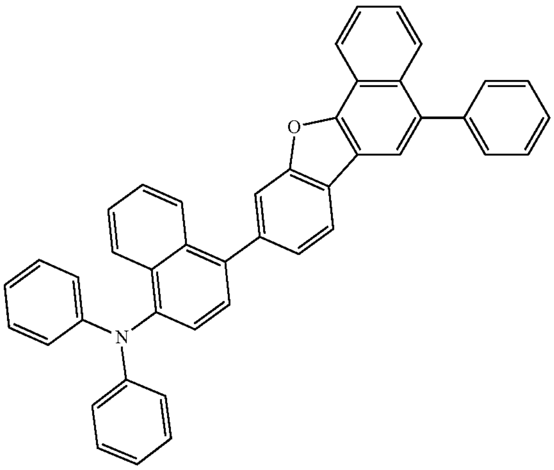
1-309
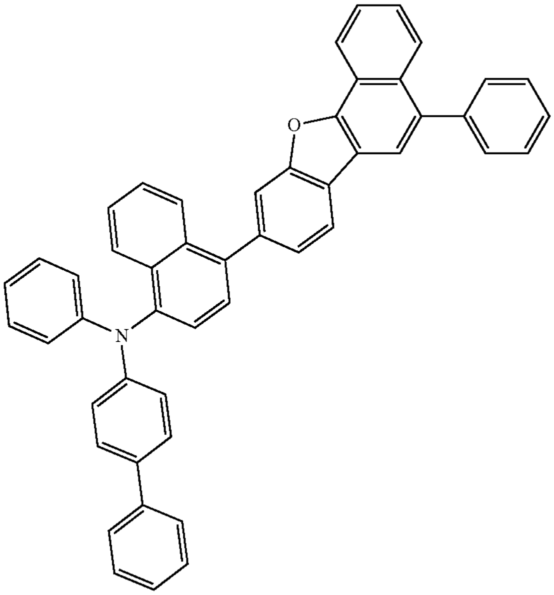
1-310
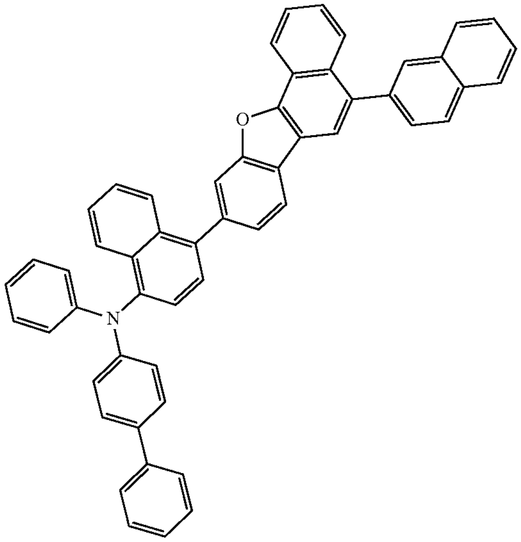
-continued
1-311
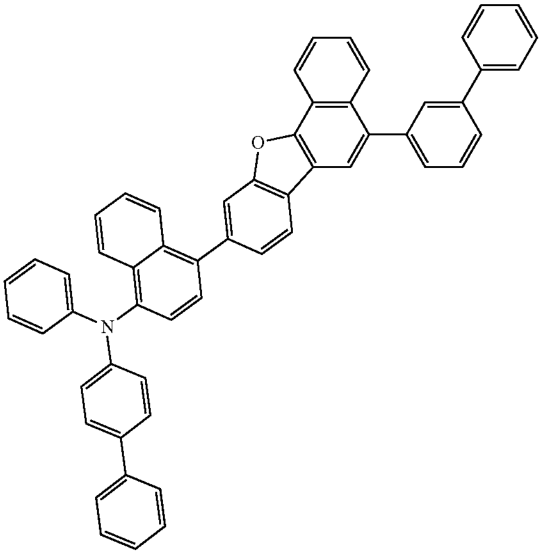
1-312
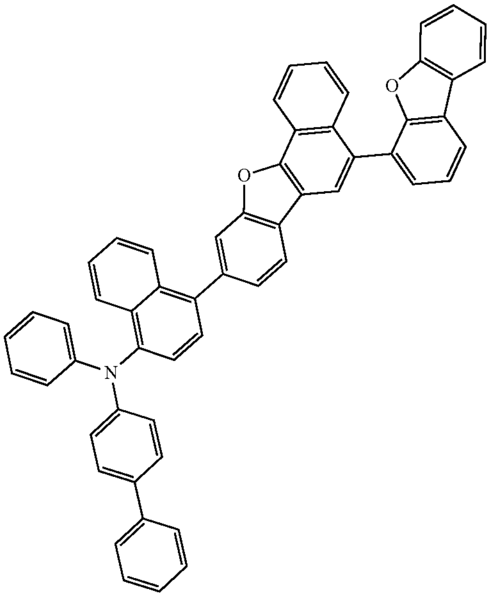

-continued
1-313
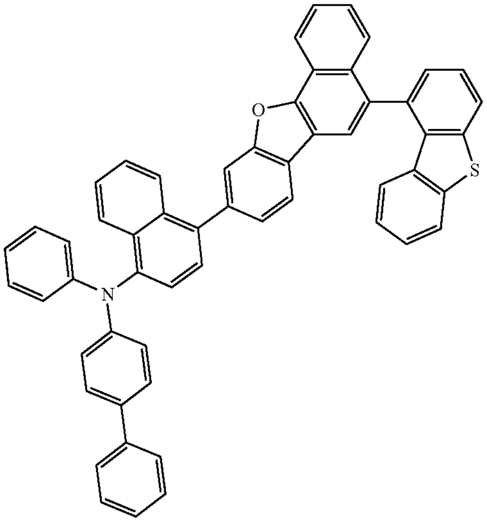
1-314
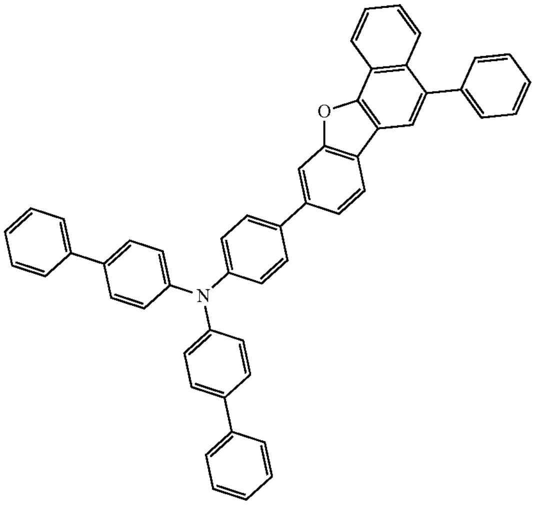
1-315
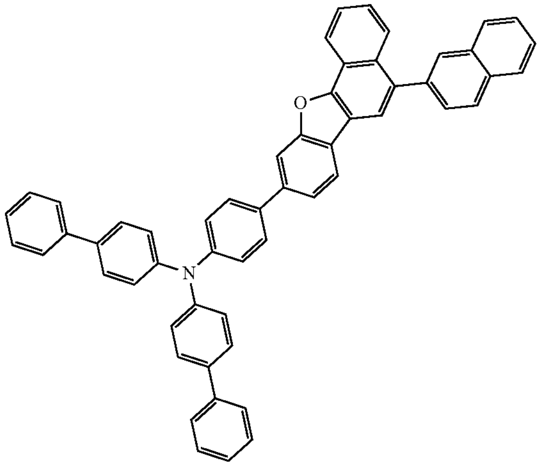
-continued
1-316
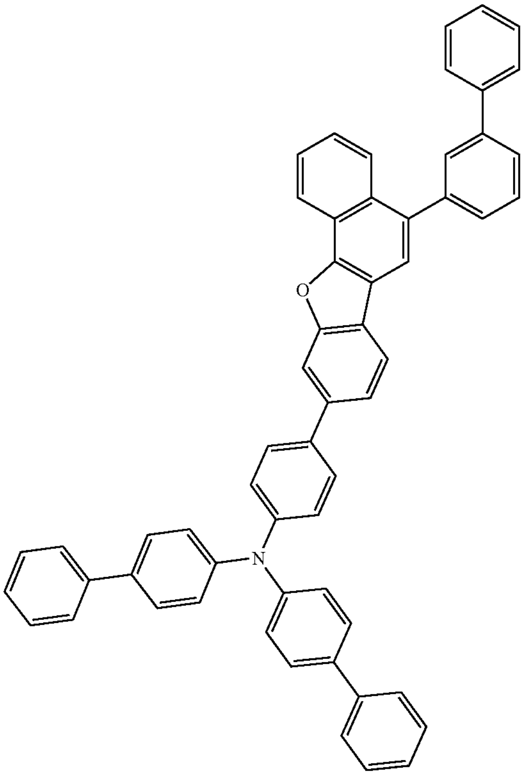
1-317
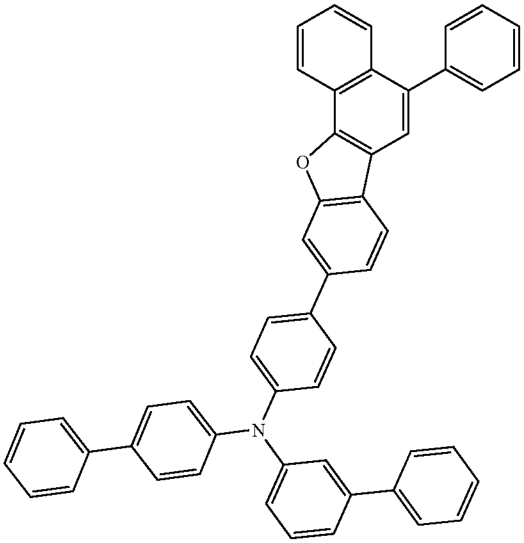

1-318
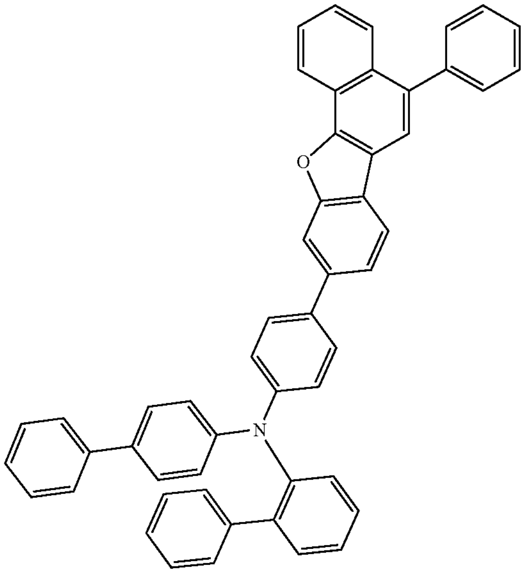
1-319
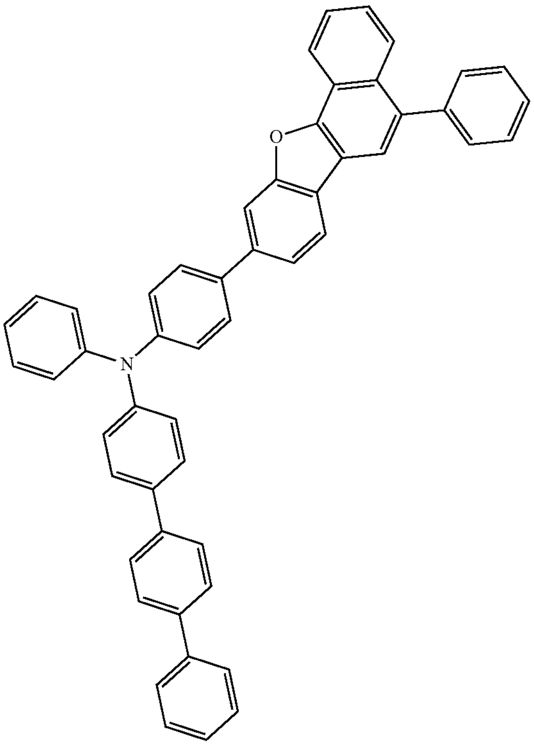
-continued
1-320
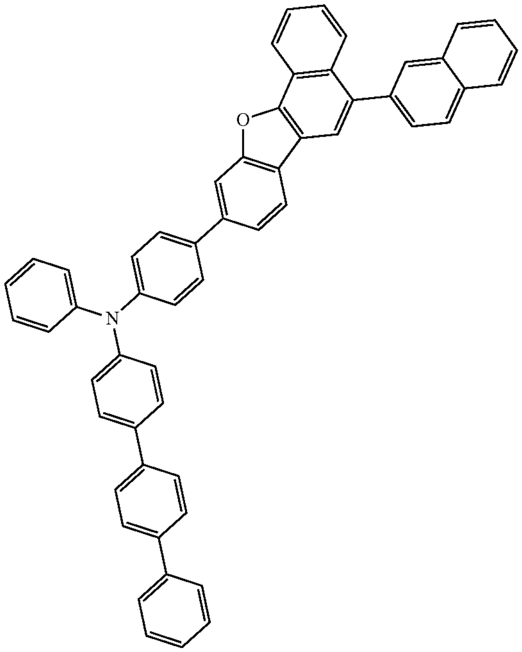
1-321
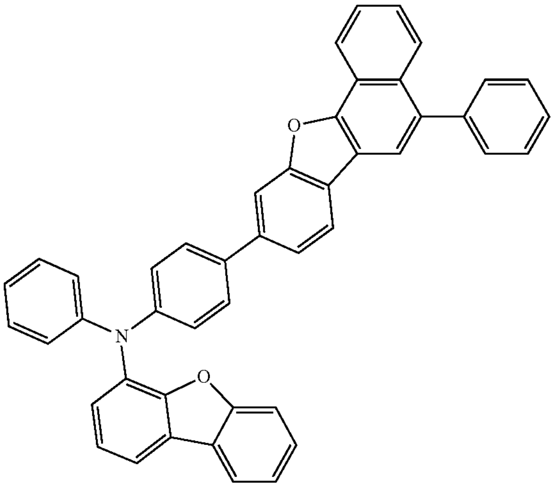

1-322
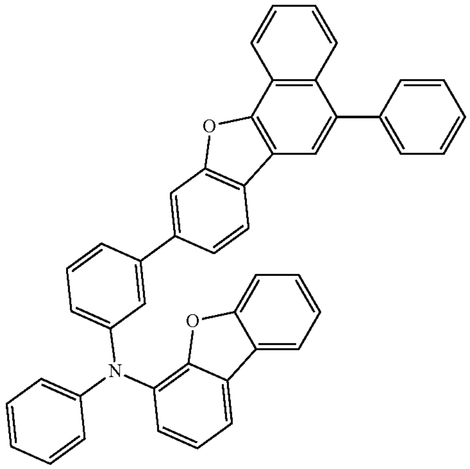
1-323
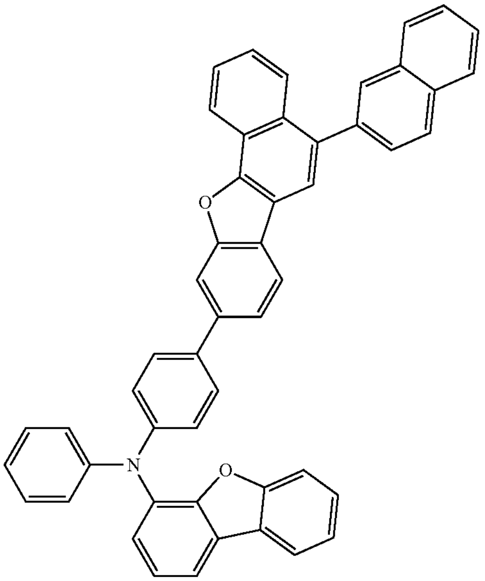
1-324
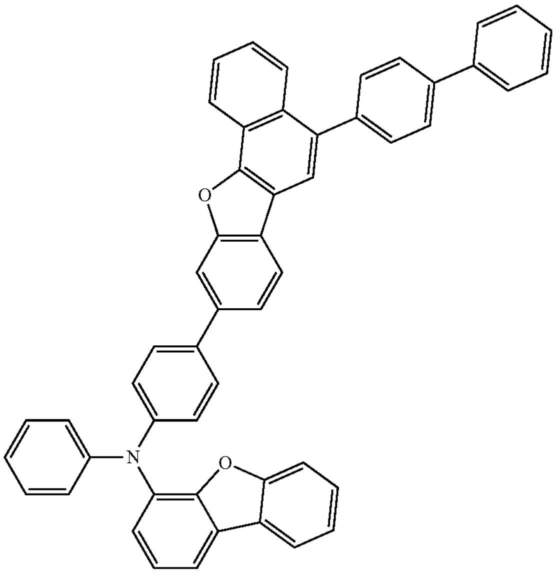
1-325
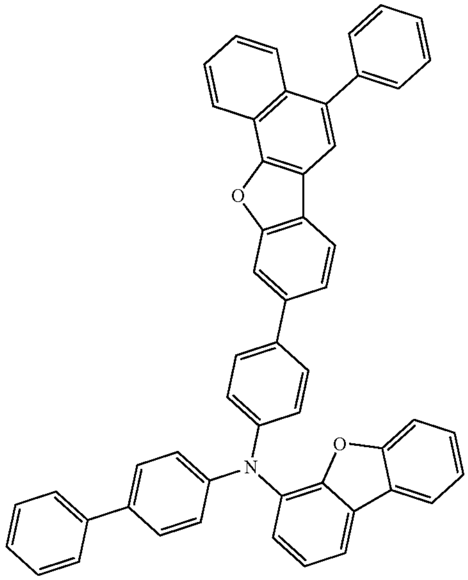
1-326
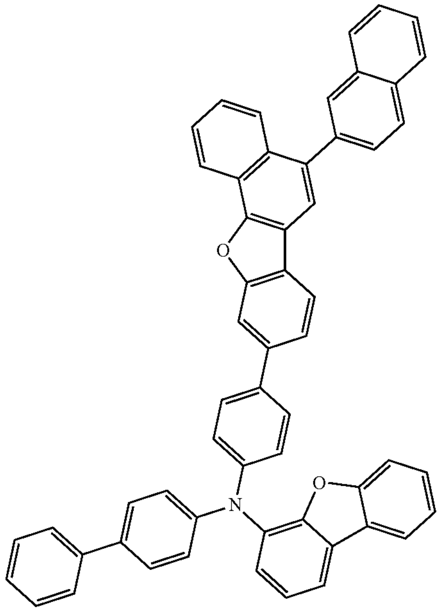

1-327
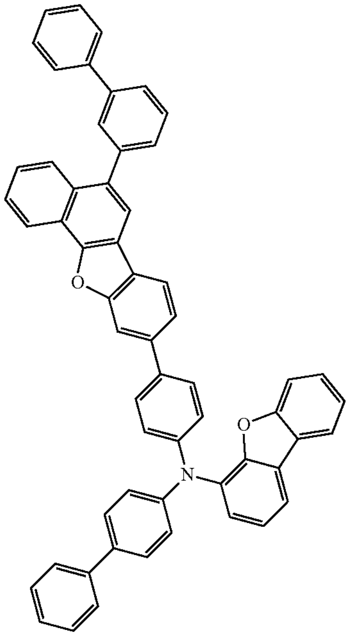
1-328
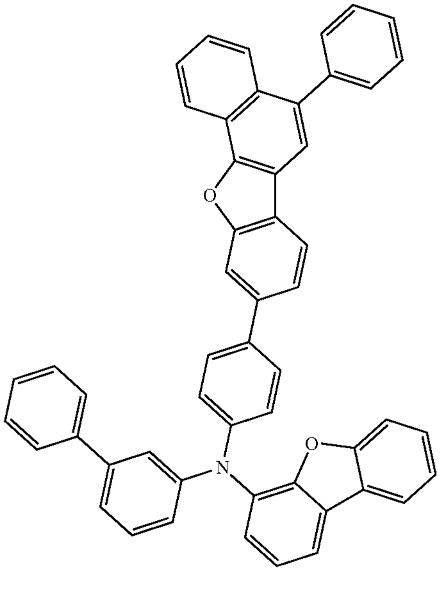
1-329
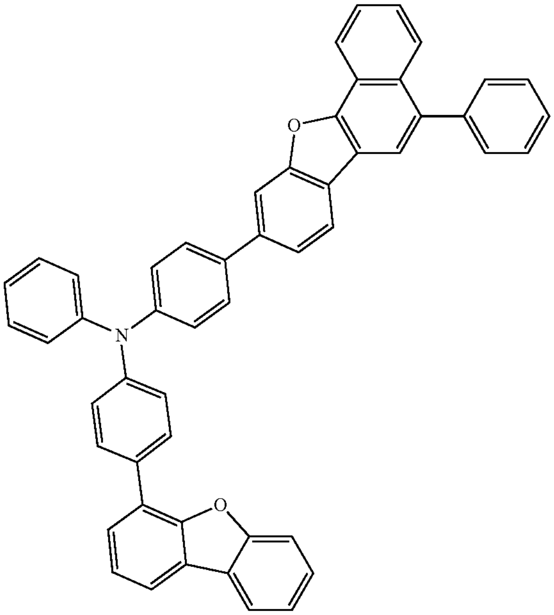
1-330
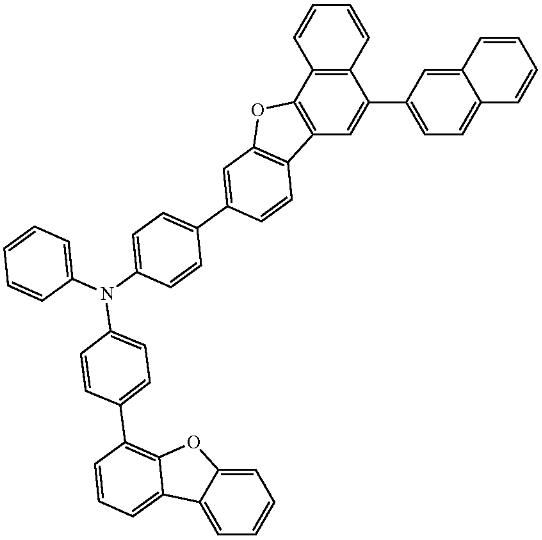

1-331
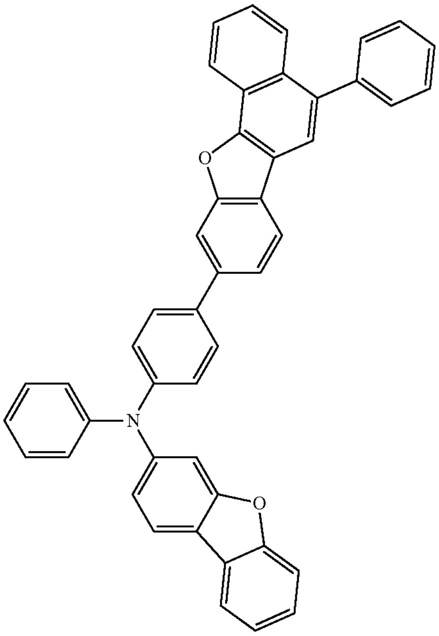
1-332
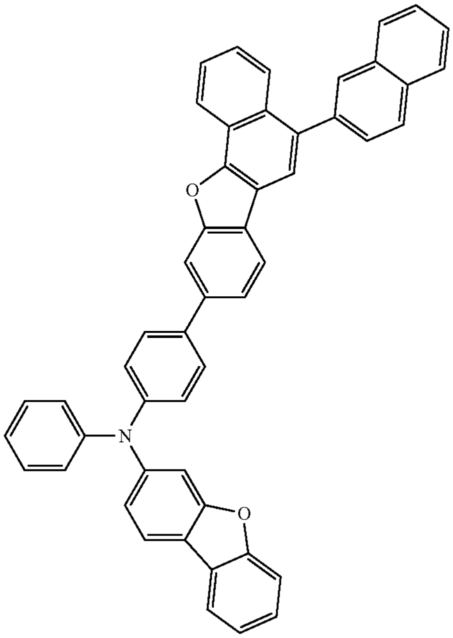
1-333
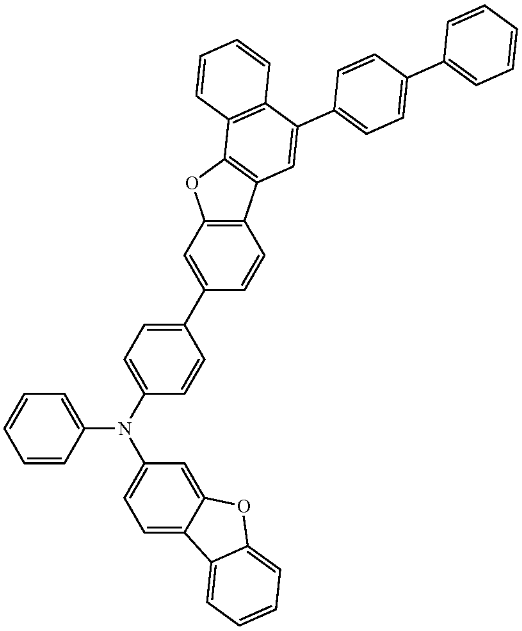
1-334
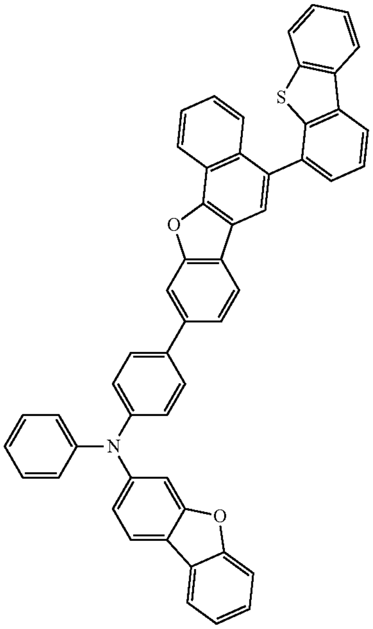

1-335
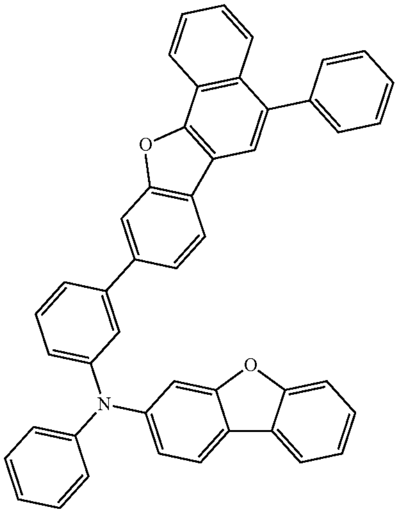
1-336
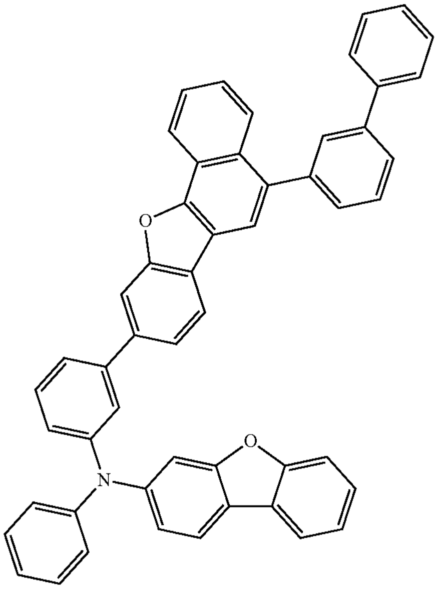
1-337
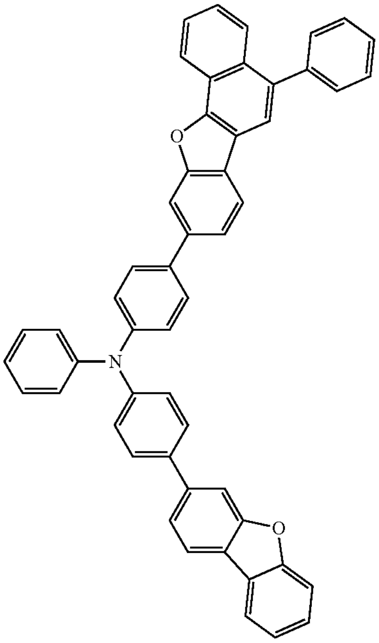
1-338
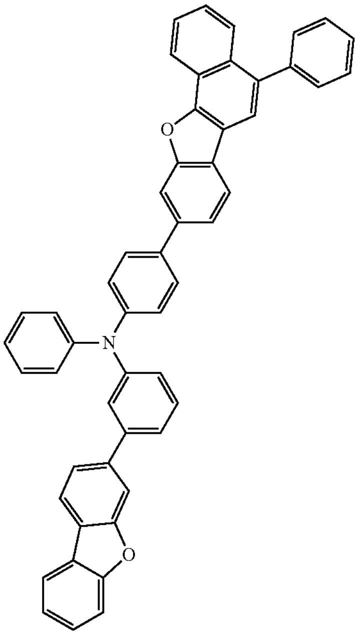

-continued
1-339
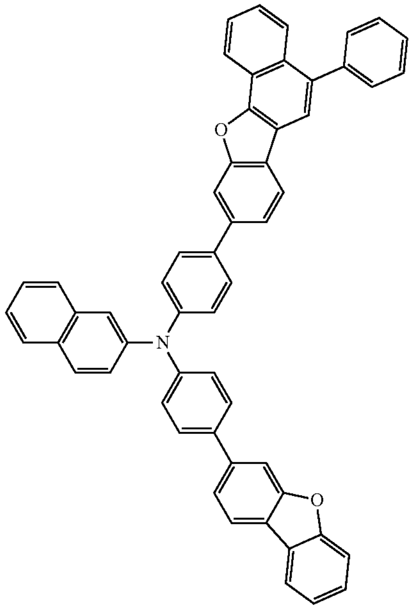
1-340
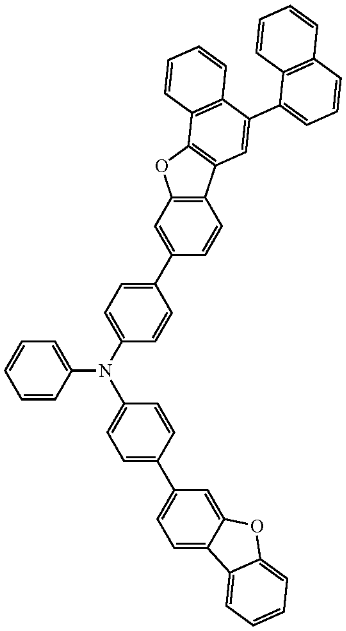
-continued
1-341
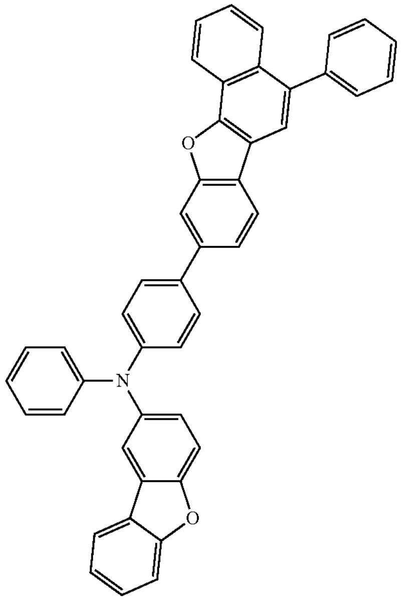
1-342
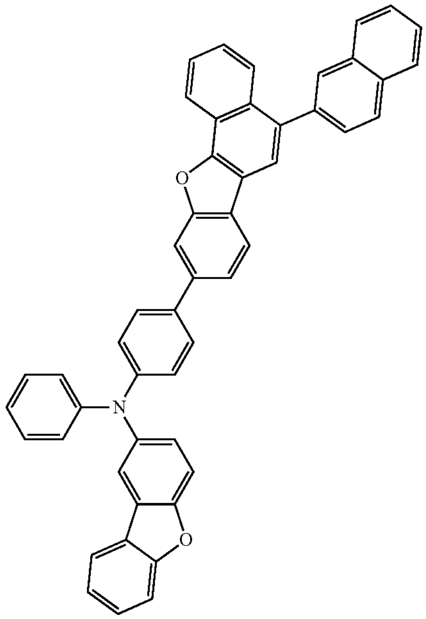

-continued
1-343
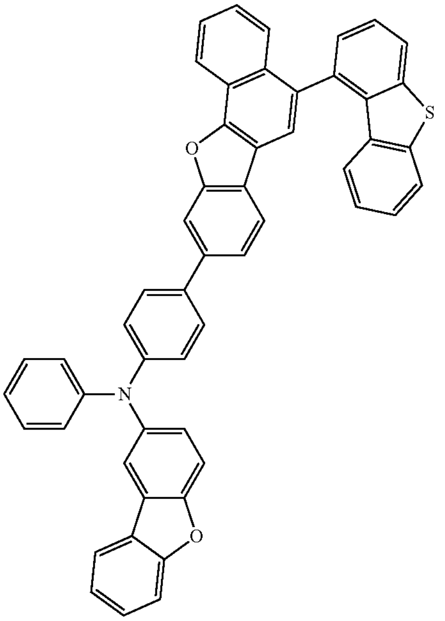
1-344
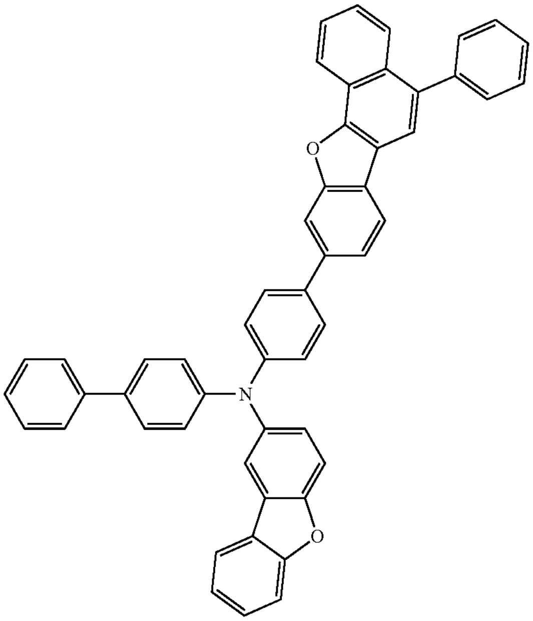
-continued
1-345
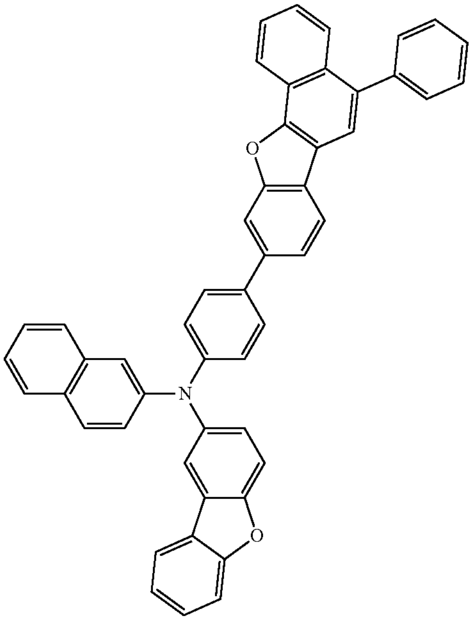
1-346
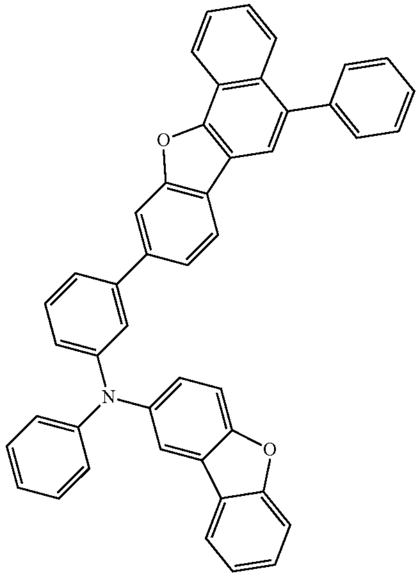

-continued
1-347
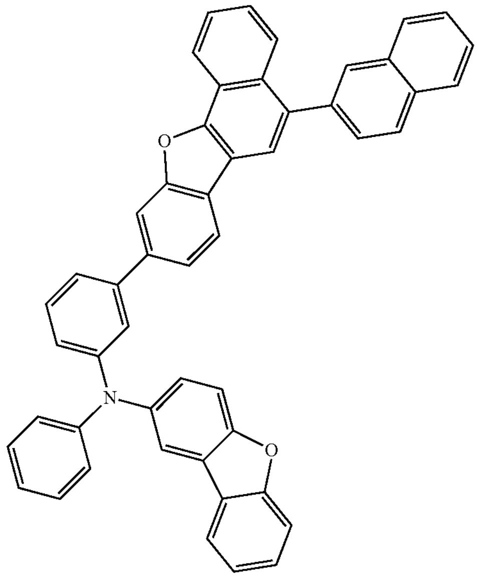
1-348
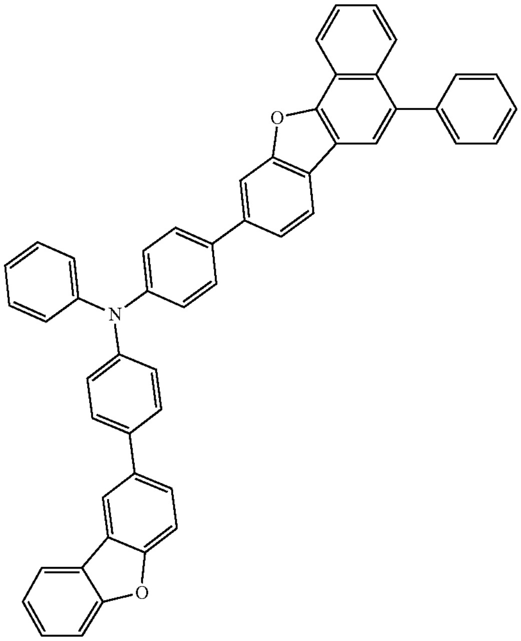
-continued
1-349
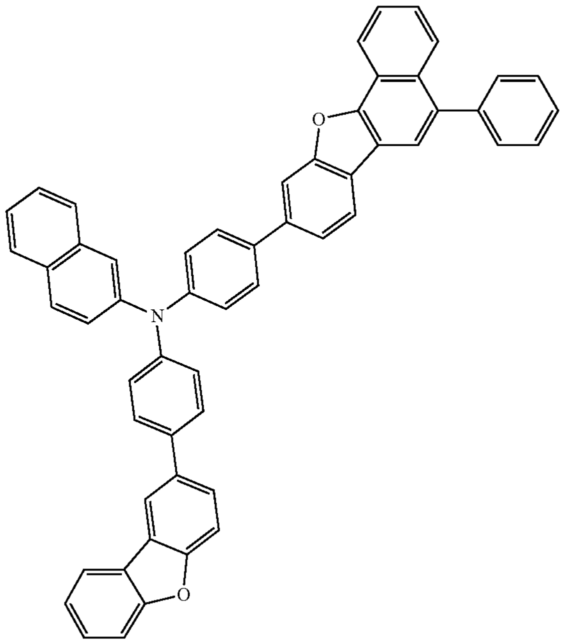
1-350
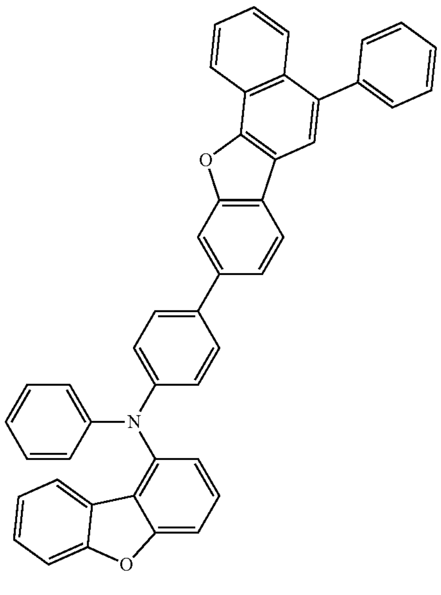

-continued
1-351
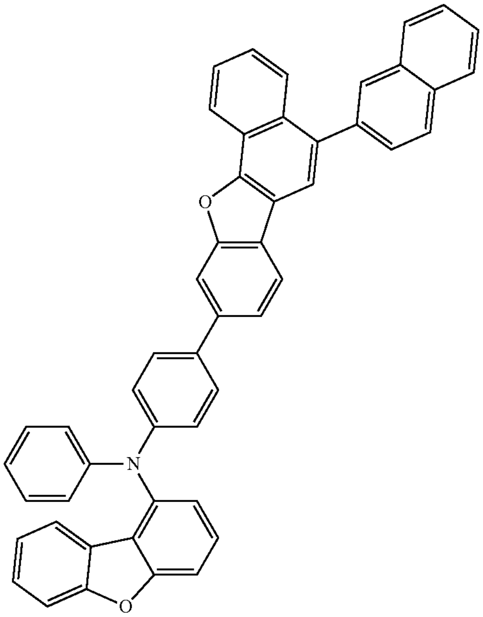
1-352
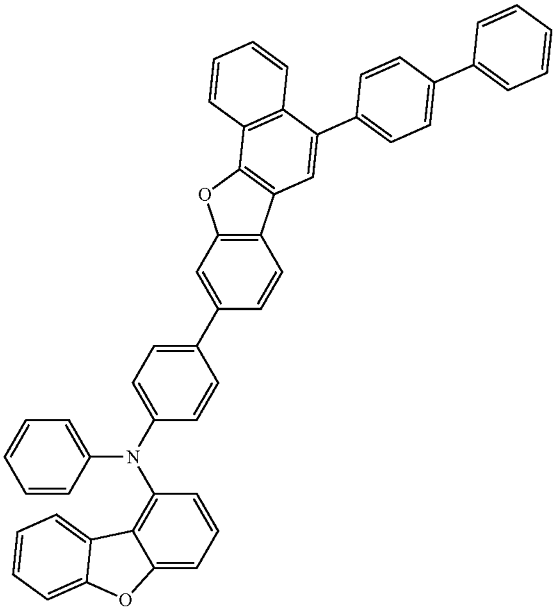
-continued
1-353
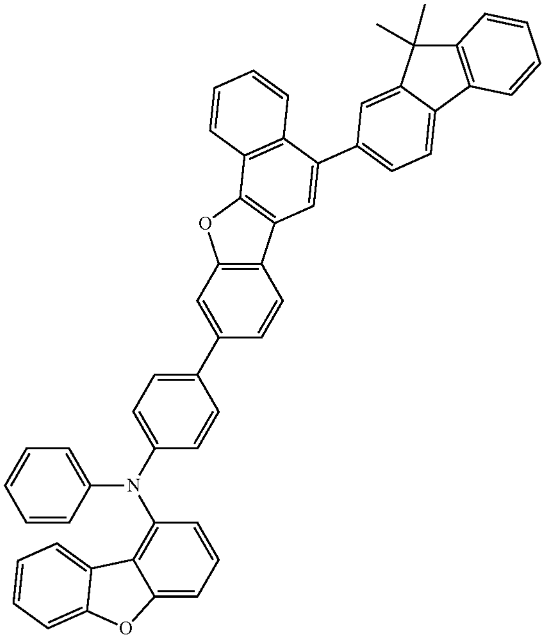
1-354
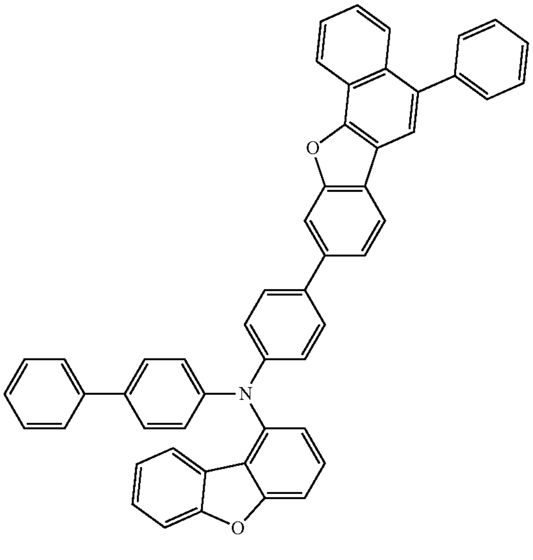

1-355
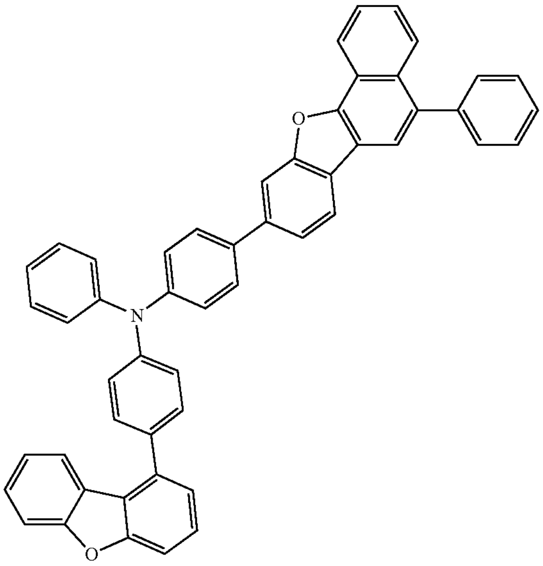
1-356
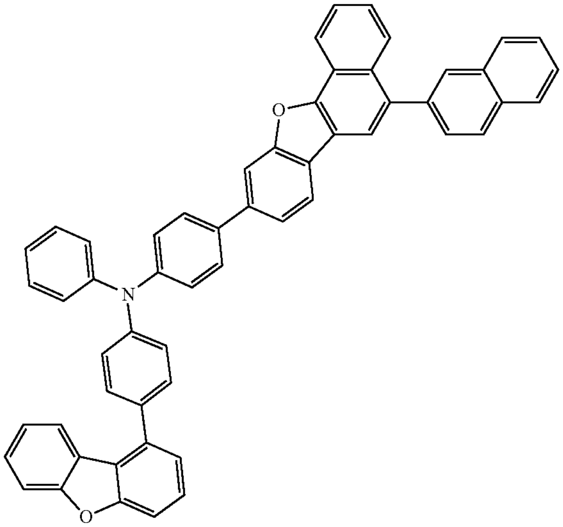
1-357
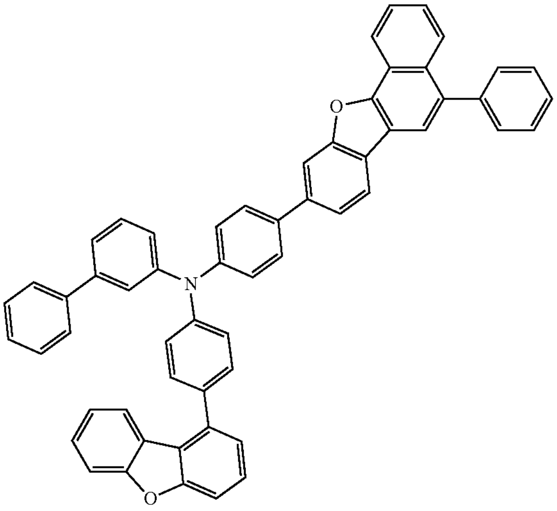
1-358
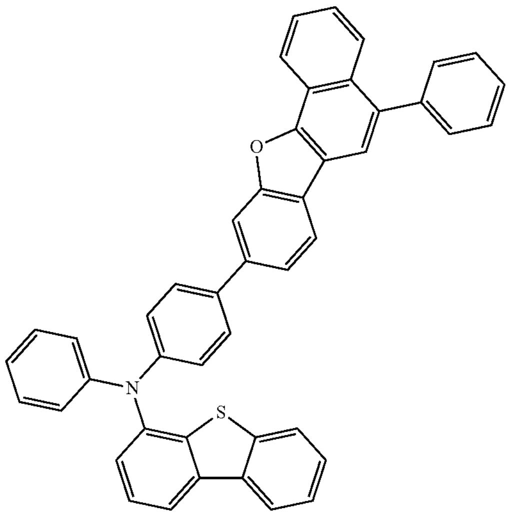
1-359
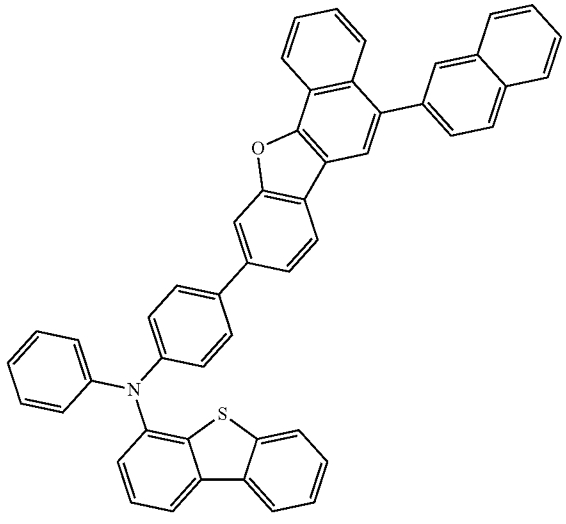

-continued
1-360
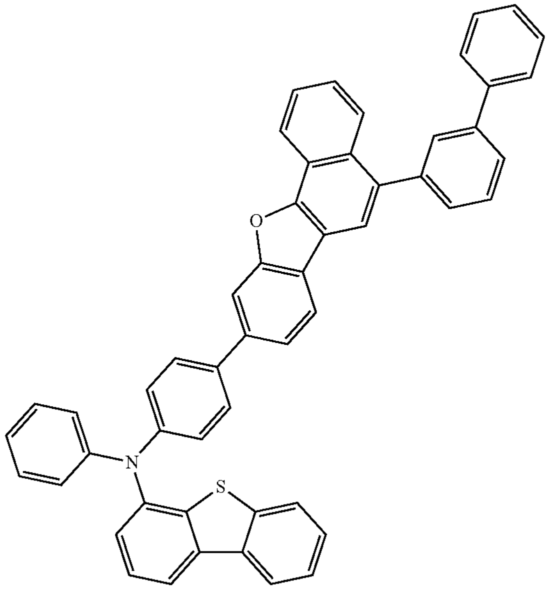
1-361
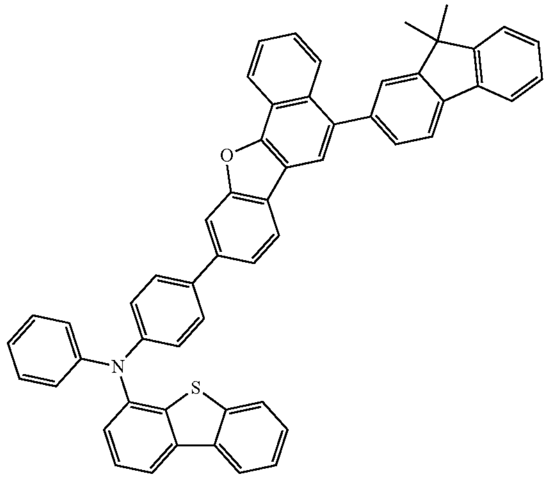
-continued
1-362
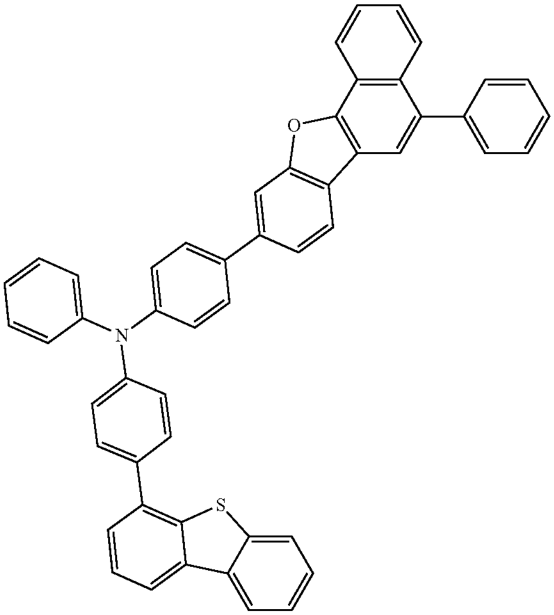
1-363
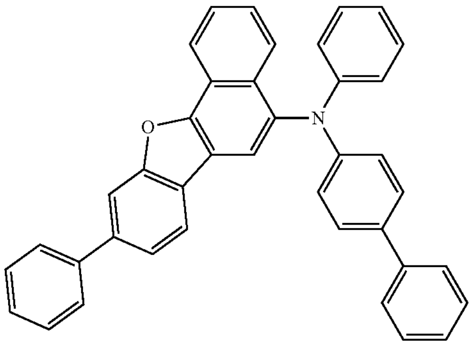
1-364
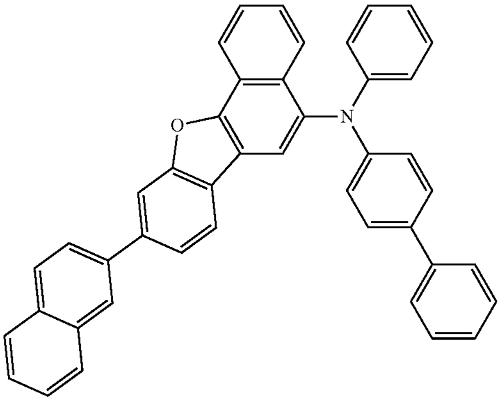

1-365
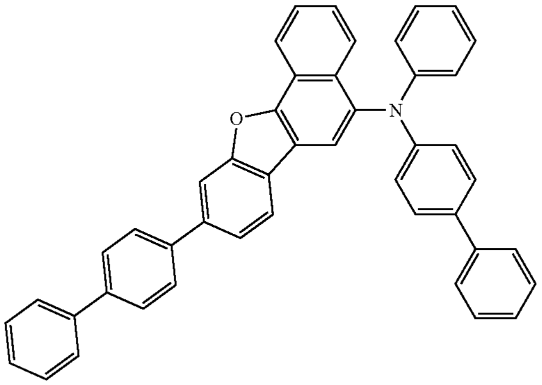
1-366
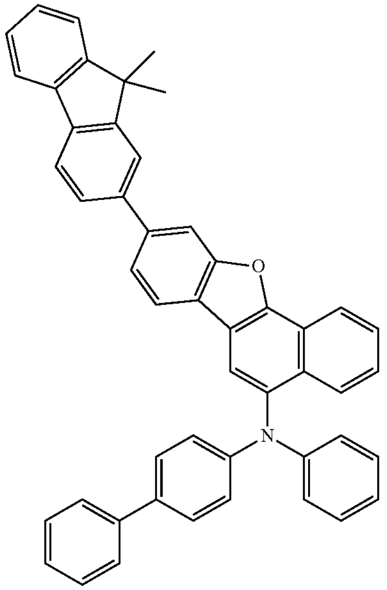
1-367
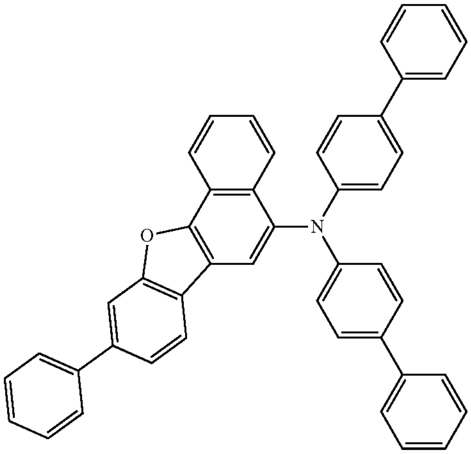
1-368
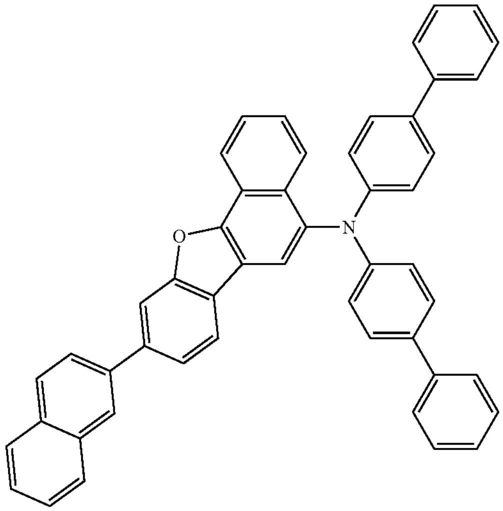
1-369
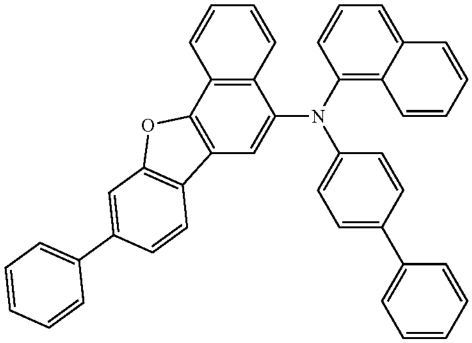
1-370
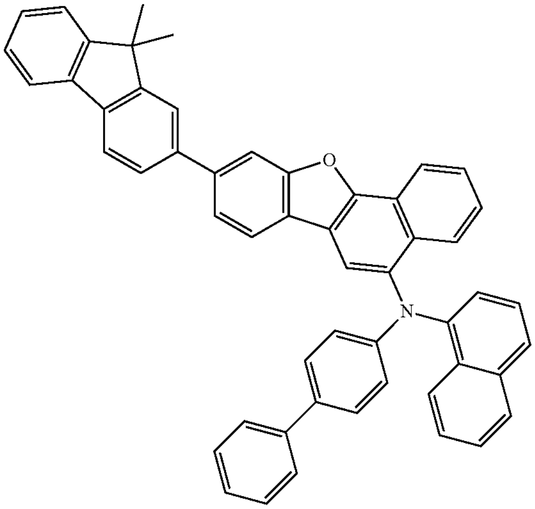

-continued
1-371
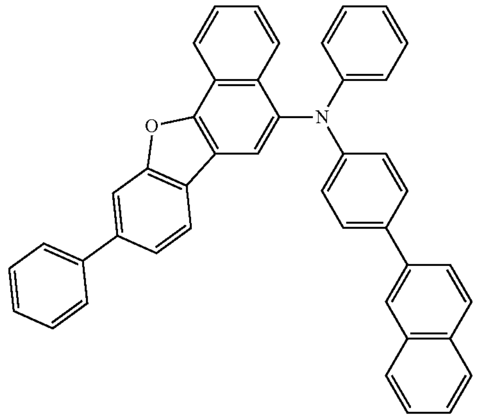
1-372
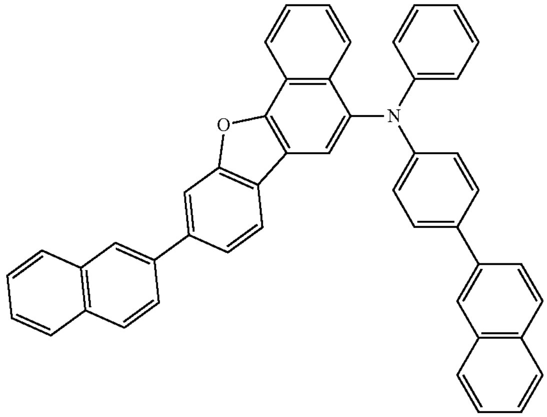
1-373
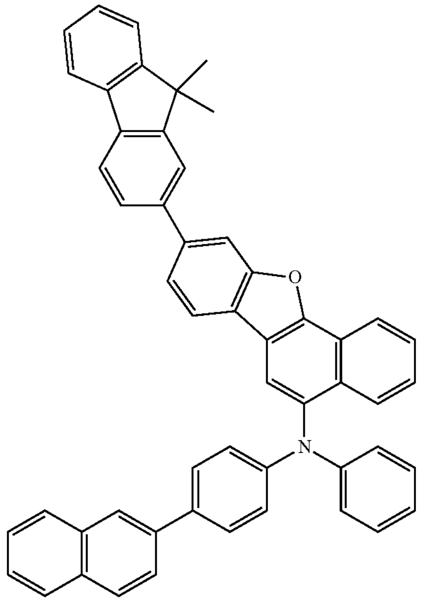
-continued
1-374
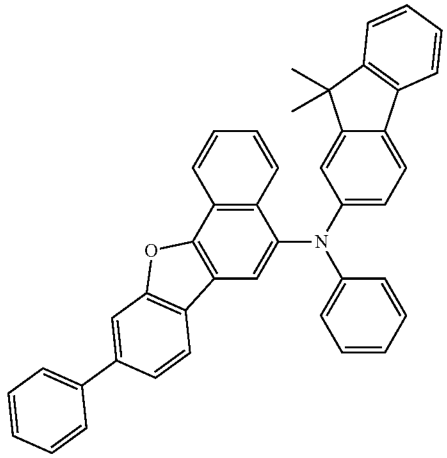
1-375
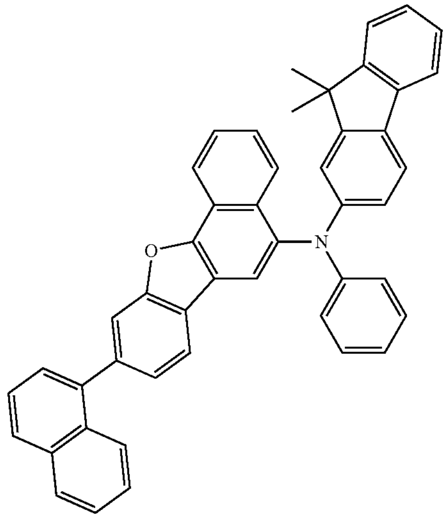
1-376
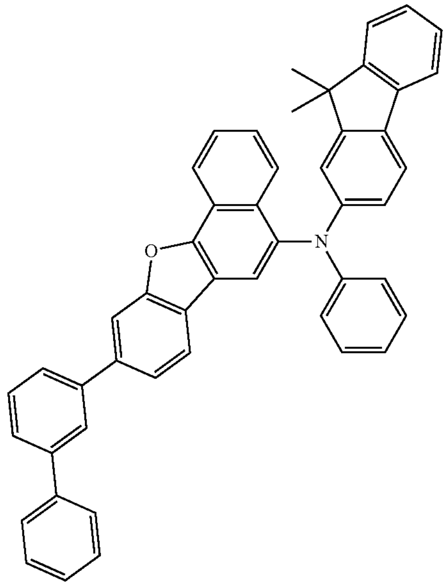

1-377
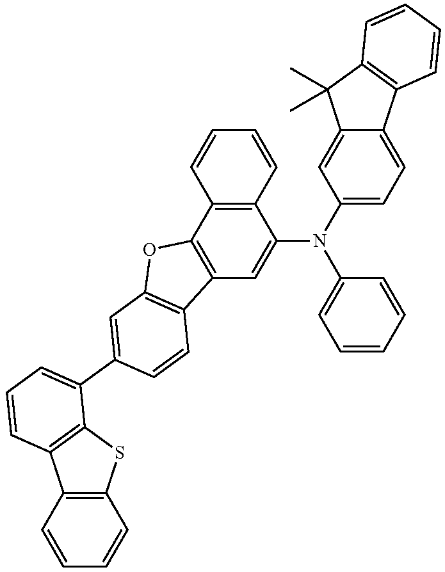
1-378
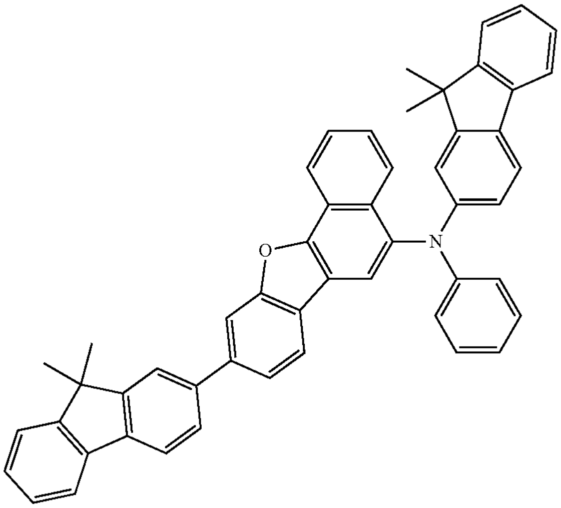
1-379
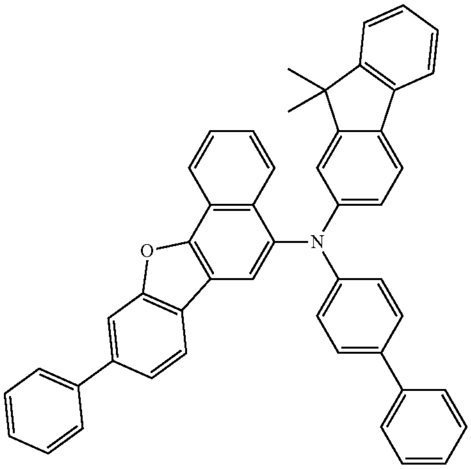
1-380
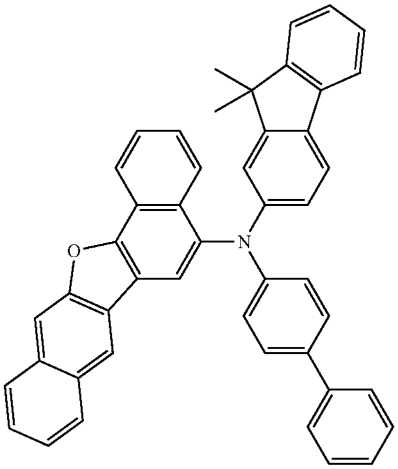
1-381
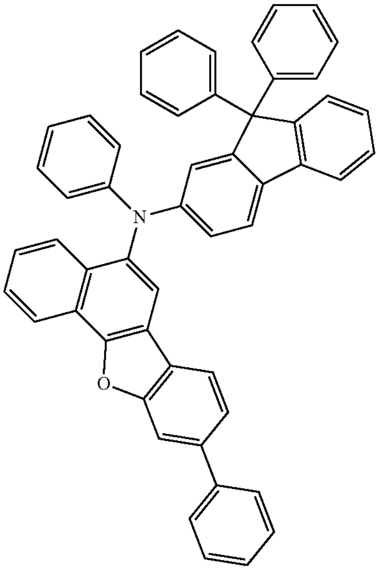
1-382
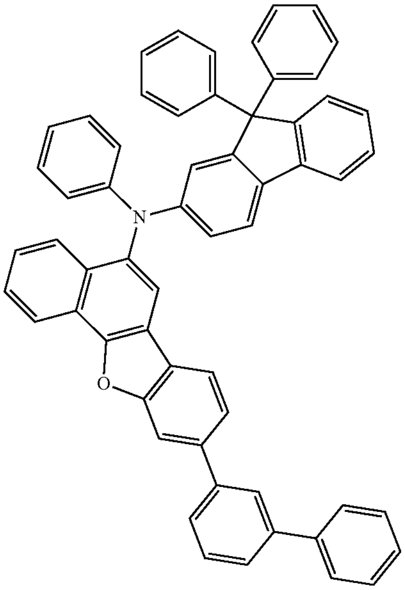

-continued
1-383
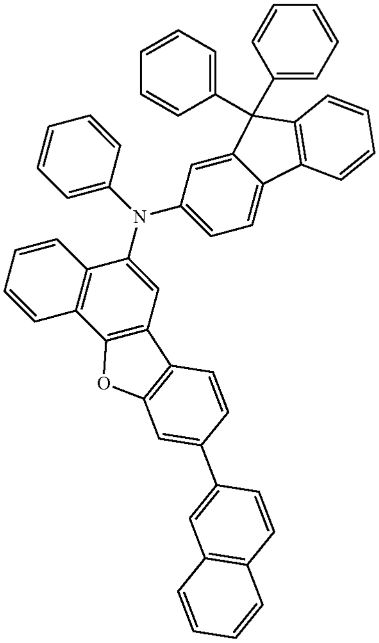
1-384
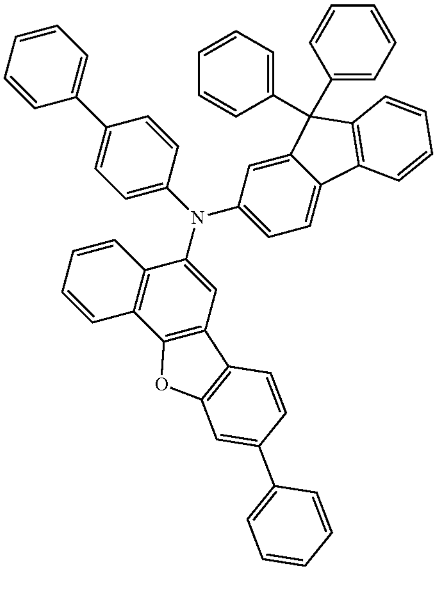
-continued
1-385
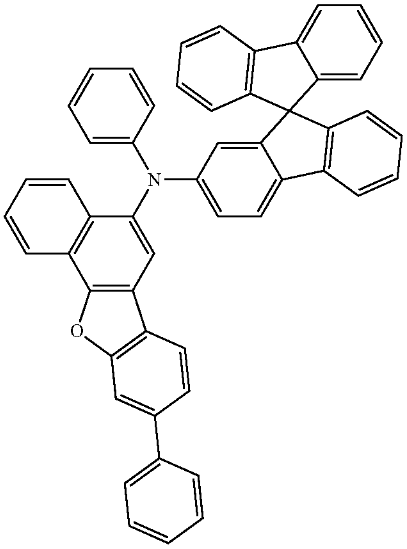
1-386
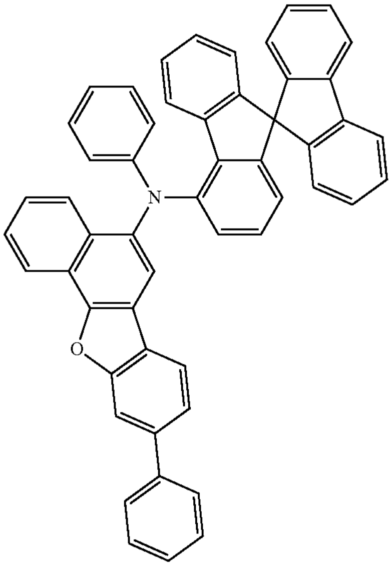

1-387
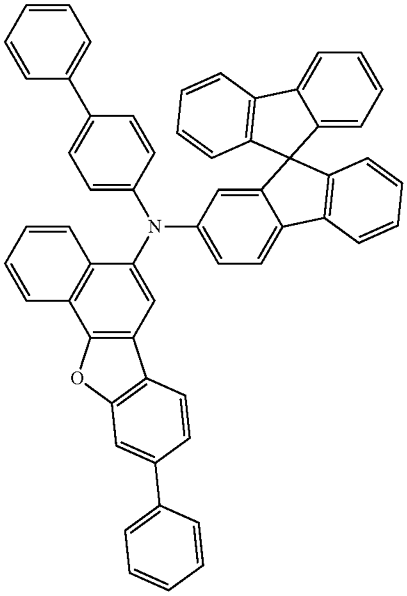
1-388
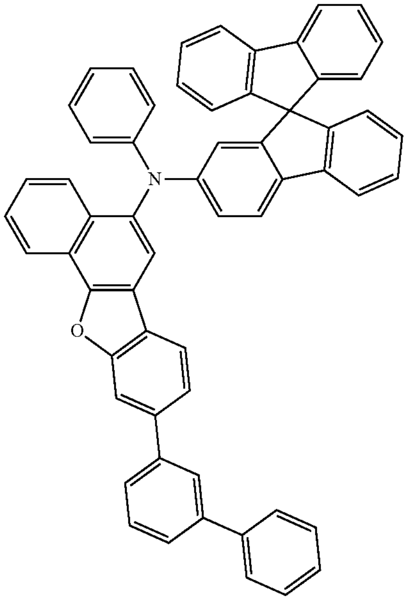
1-389
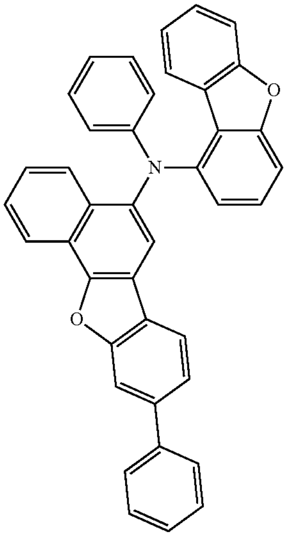
1-390
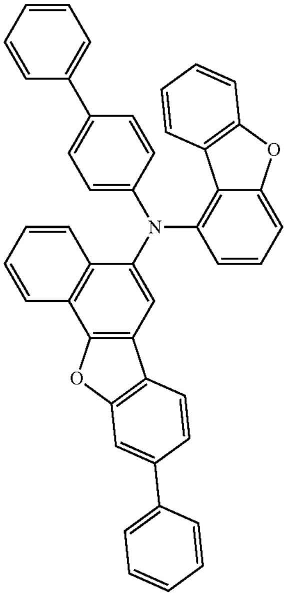

-continued
1-391
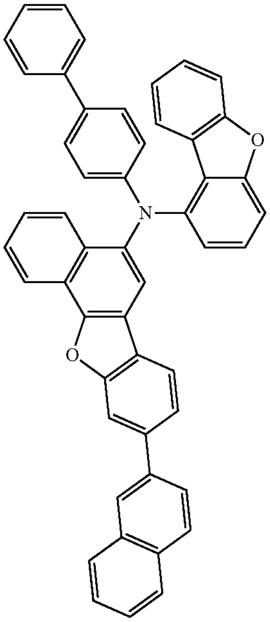
1-392
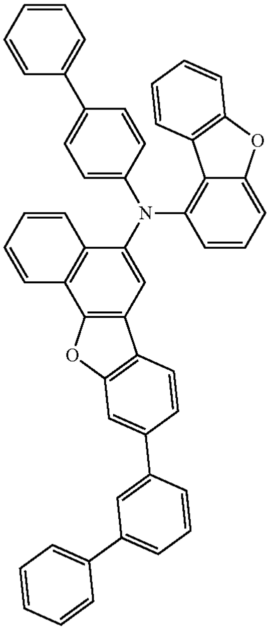
-continued
1-393
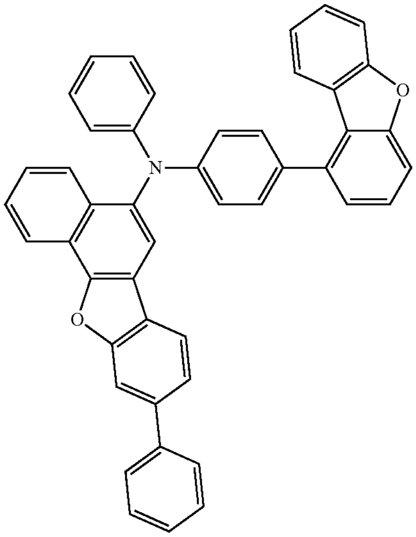
1-394
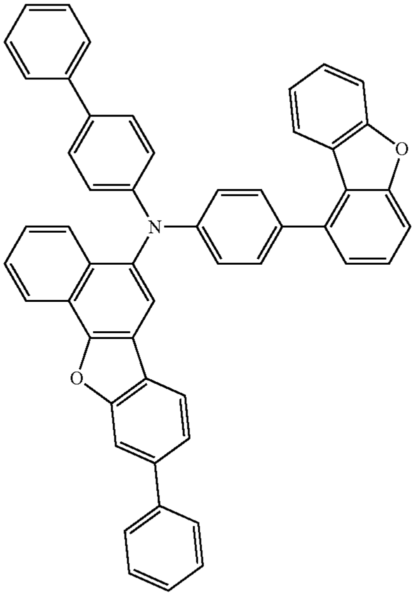

-continued
1-395
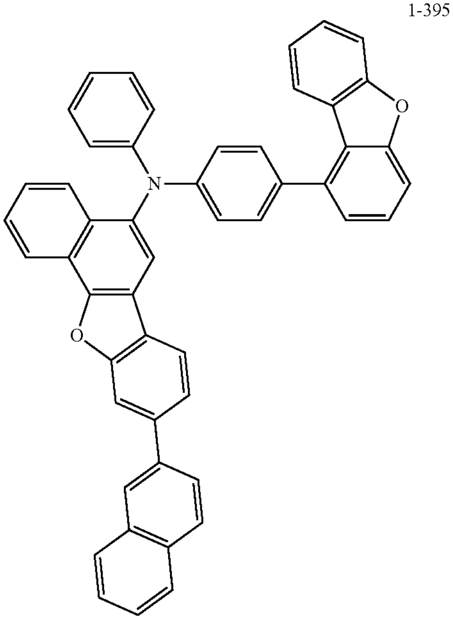
1-396
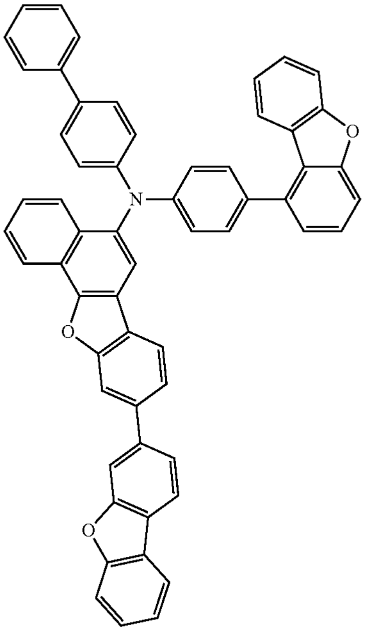
-continued
1-397
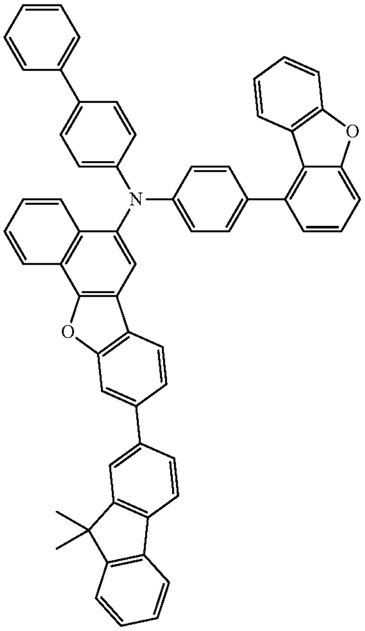
1-398
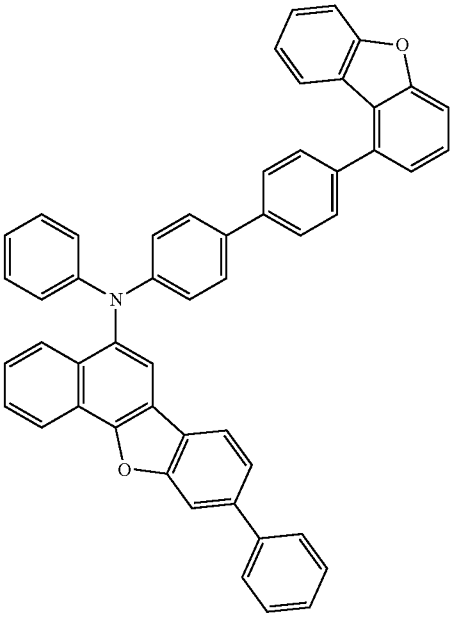

1-399
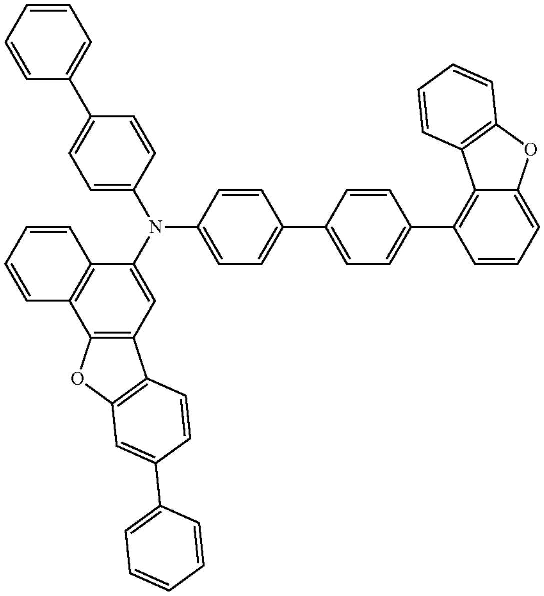
1-400
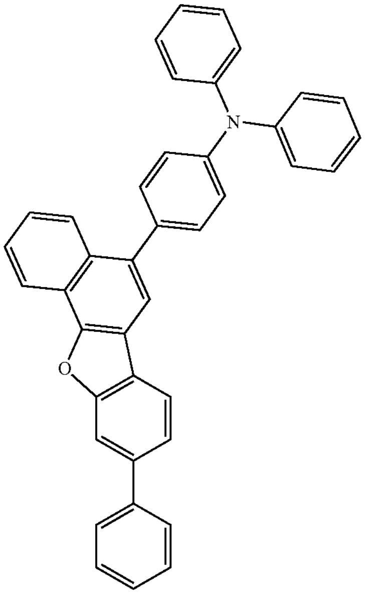
1-401
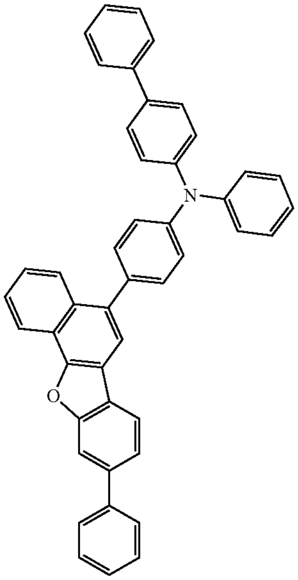
1-402
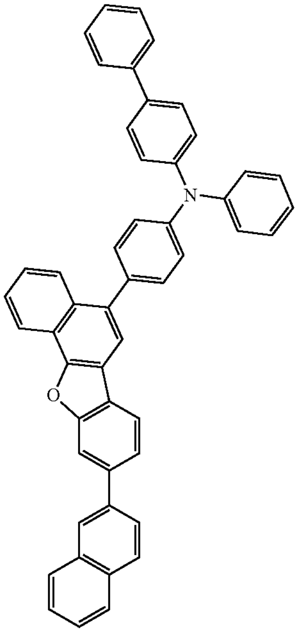

-continued
1-403
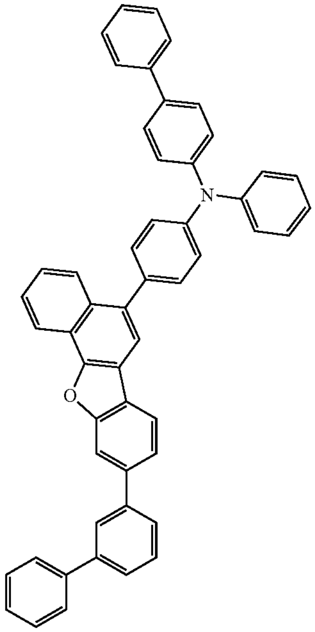
1-404
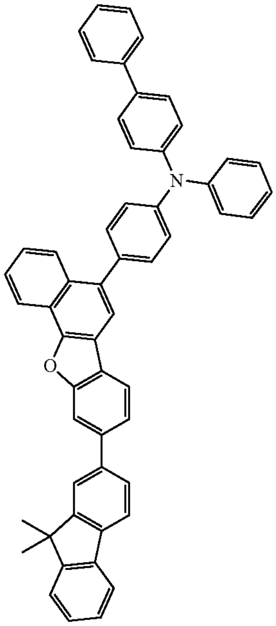
-continued
1-405
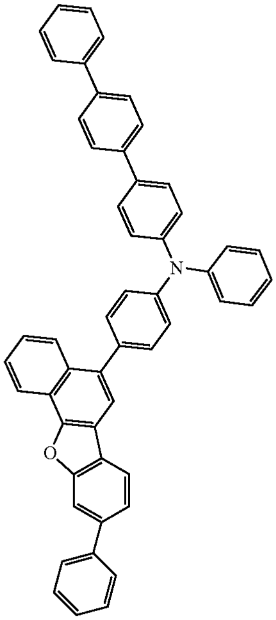
1-406
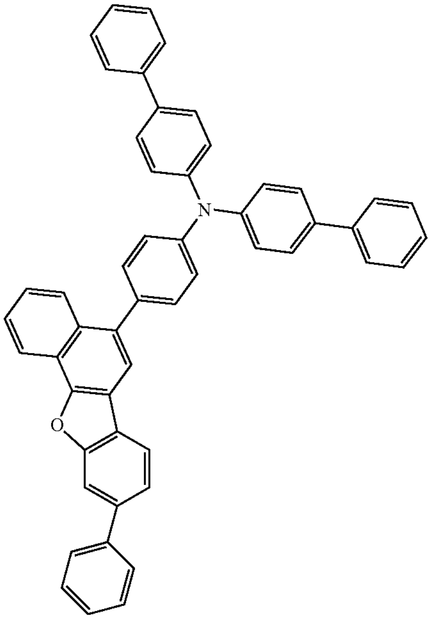

-continued
1-407
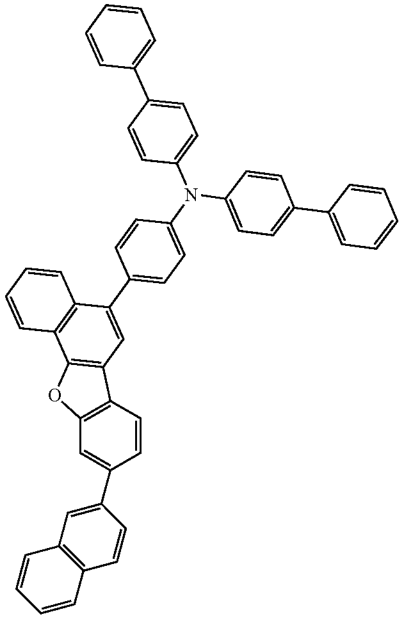
1-408
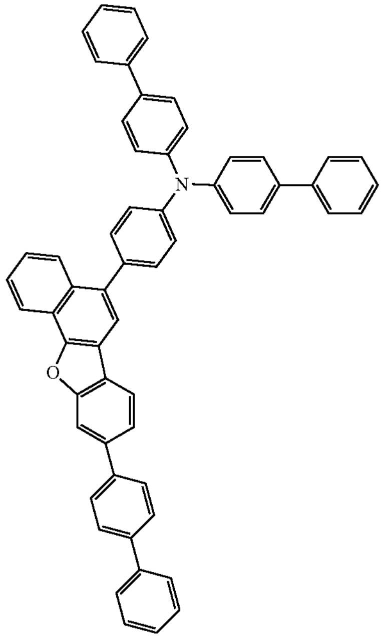
-continued
1-409
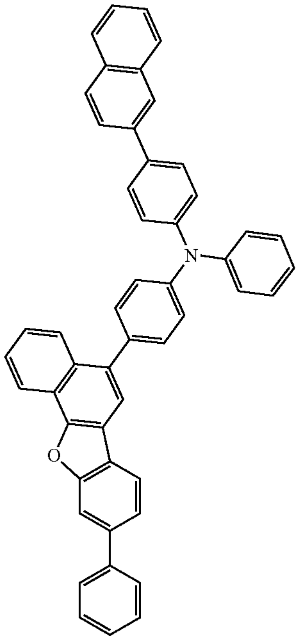
1-410
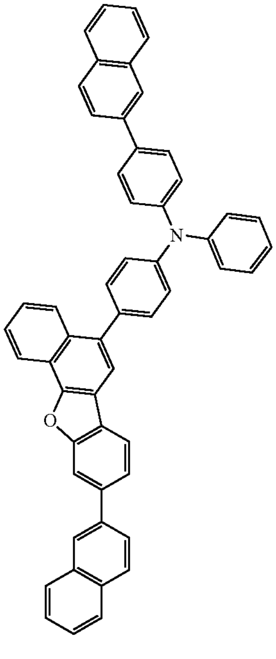

1-411
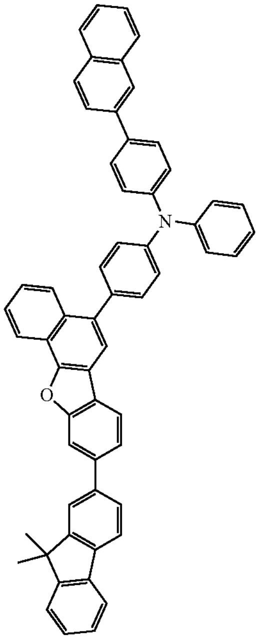
1-412
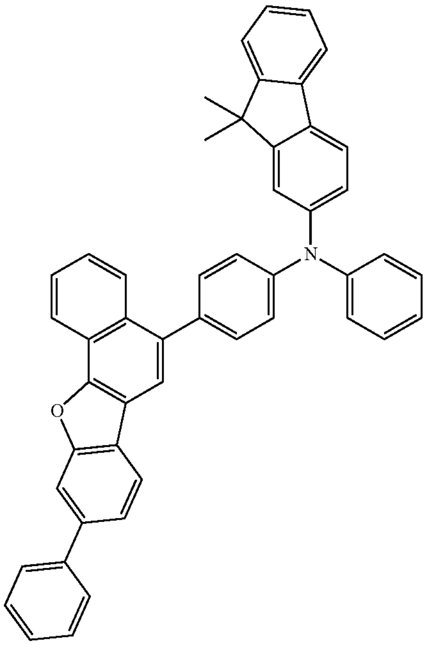
1-413
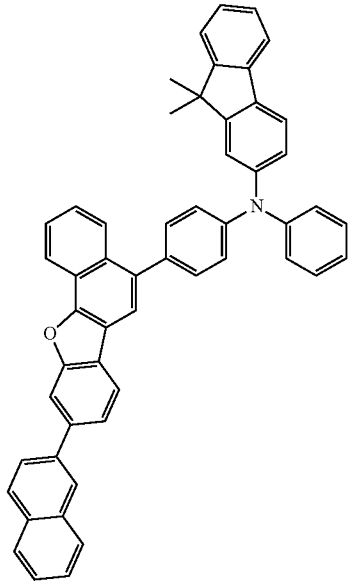
1-414
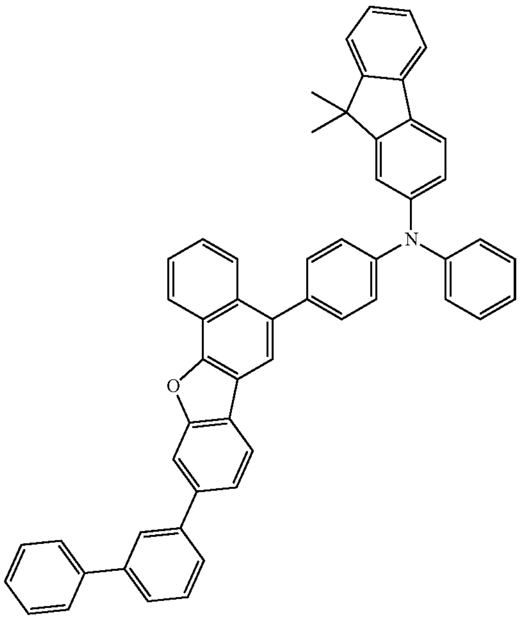

-continued
1-415
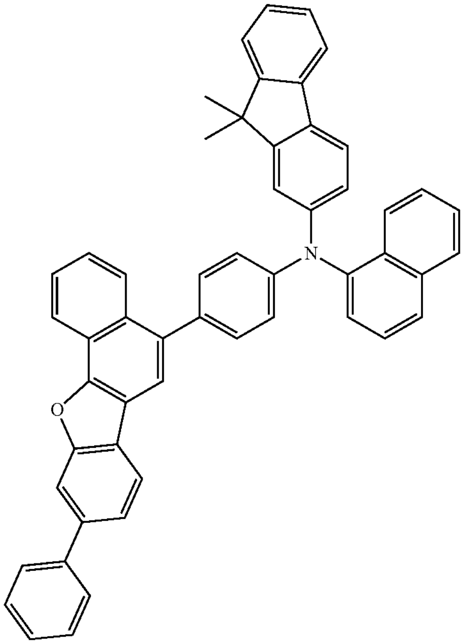
1-416
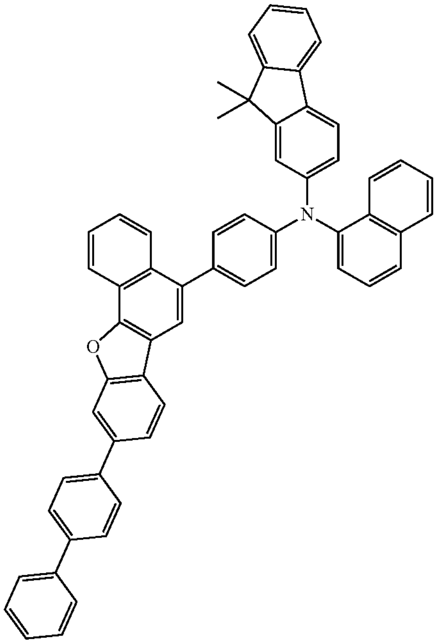
-continued
1-417
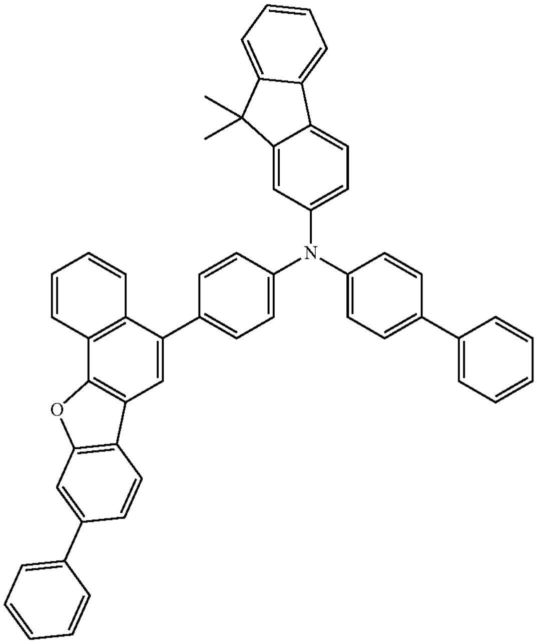
1-418
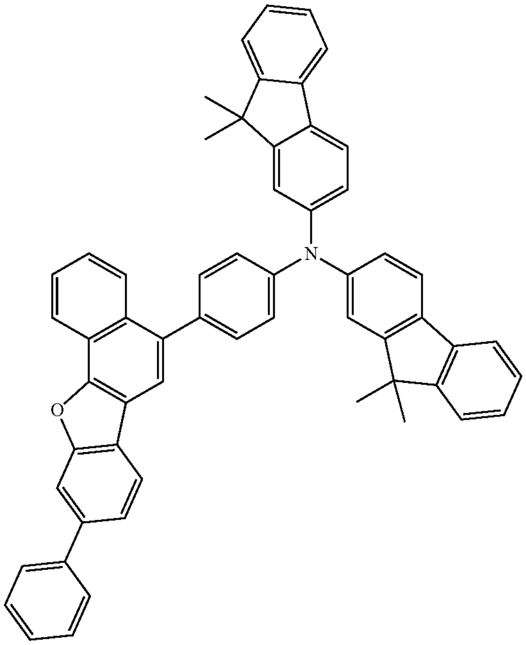

-continued
1-419
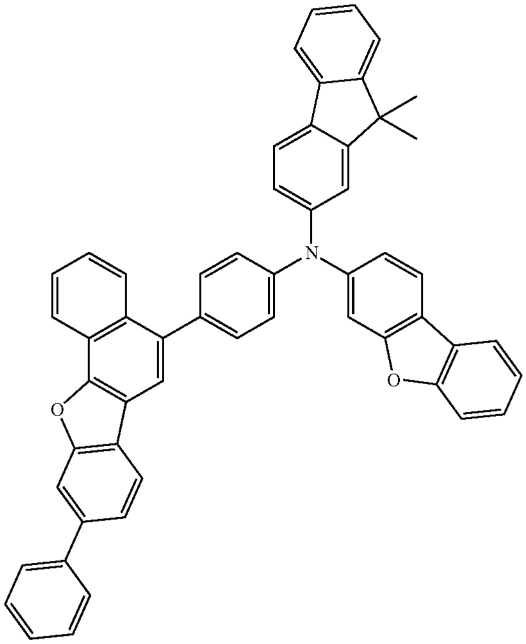
1-420
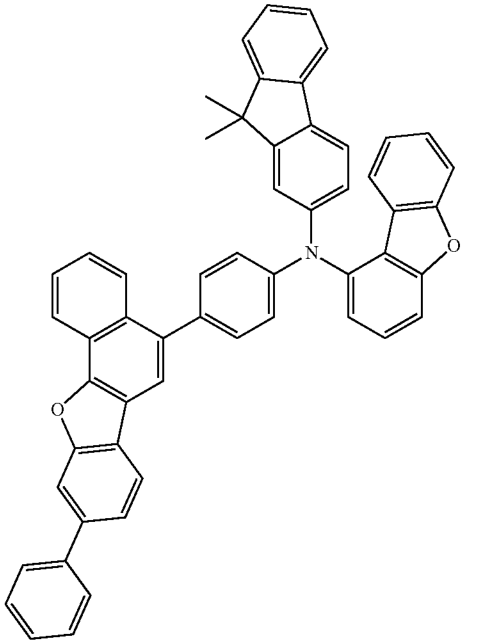
-continued
1-421
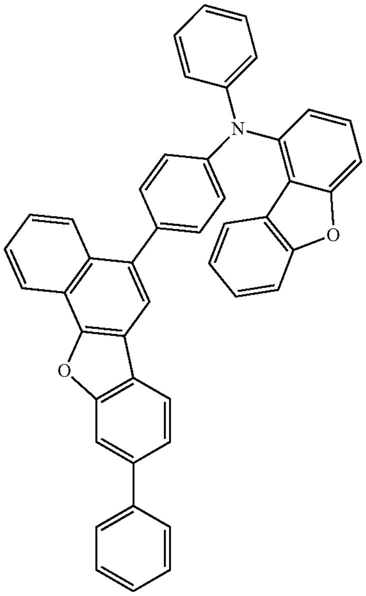
1-422
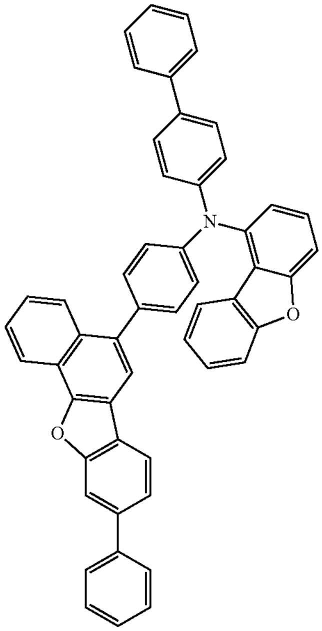

-continued
1-423
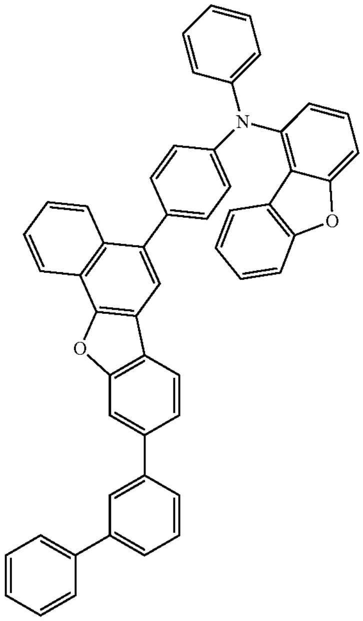
1-424
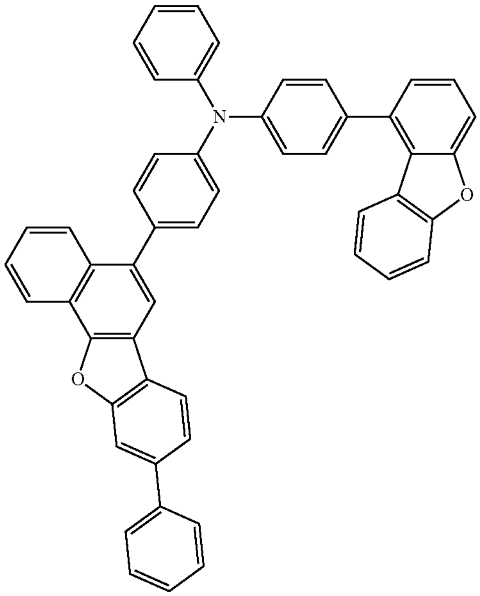
-continued
1-425
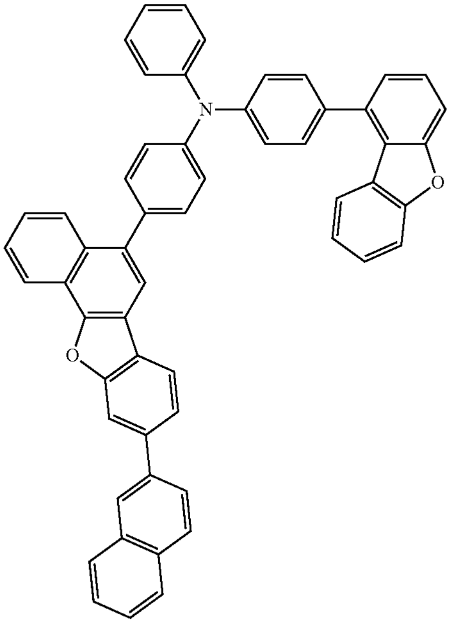
1-426
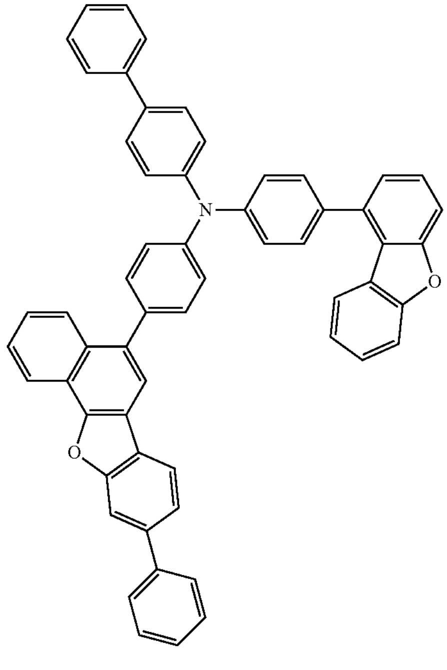

-continued
1-427
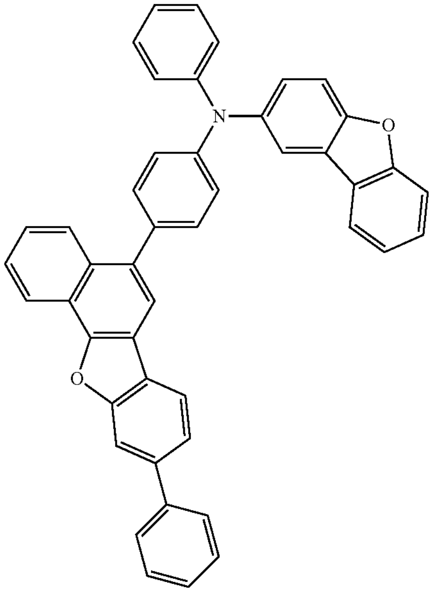
-continued
1-429
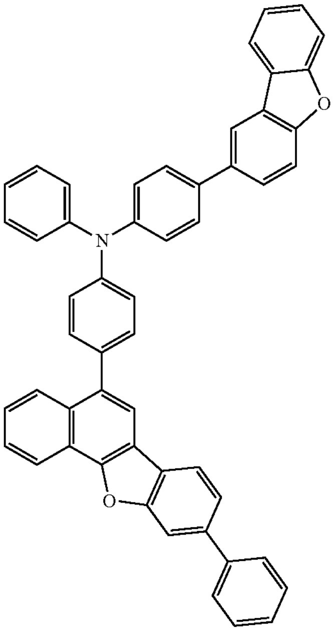
1-428
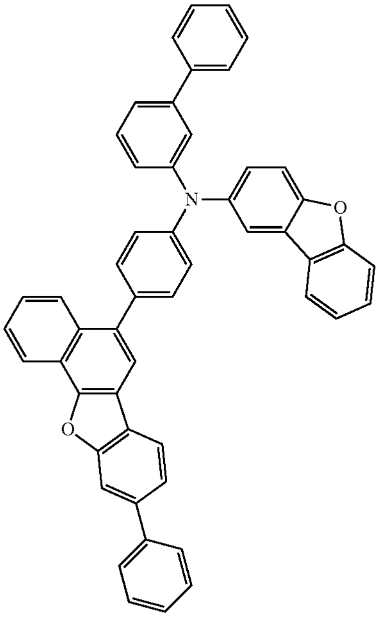
1-430
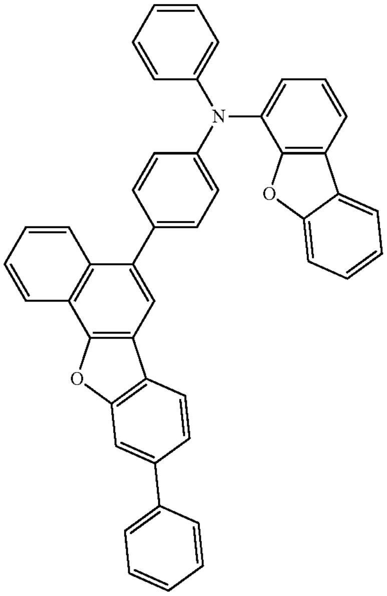

-continued
1-431
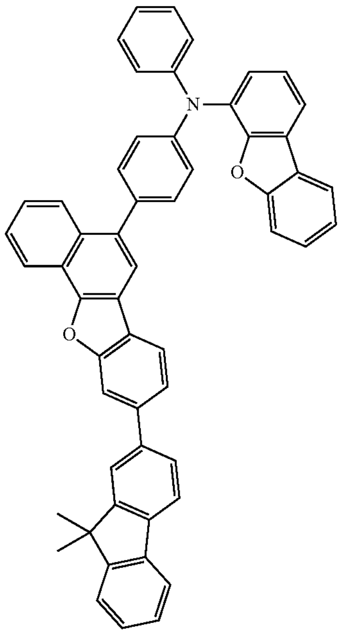
1-432
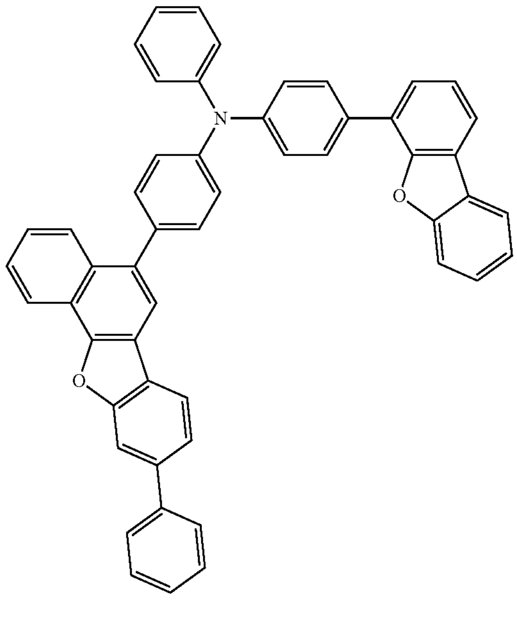
-continued
1-433
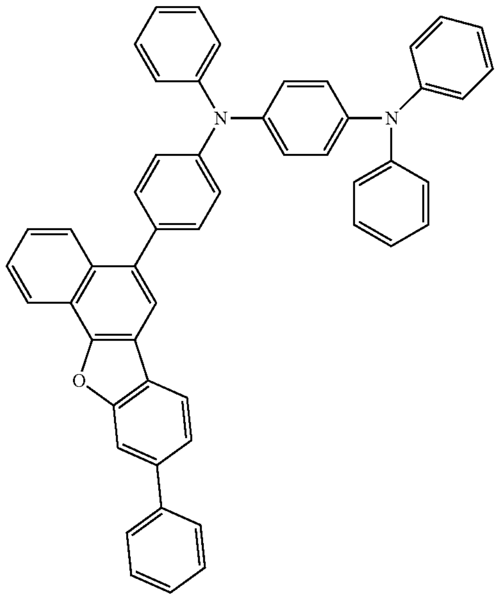
1-434
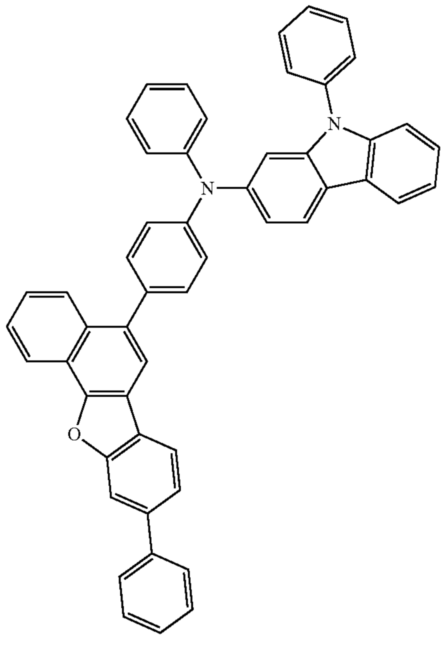

1-435
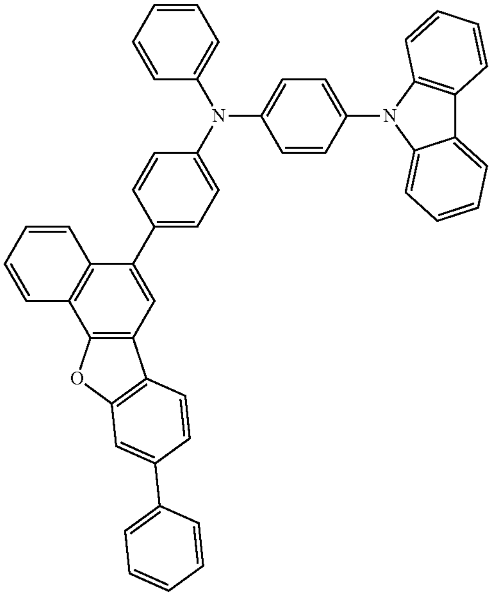
1-436
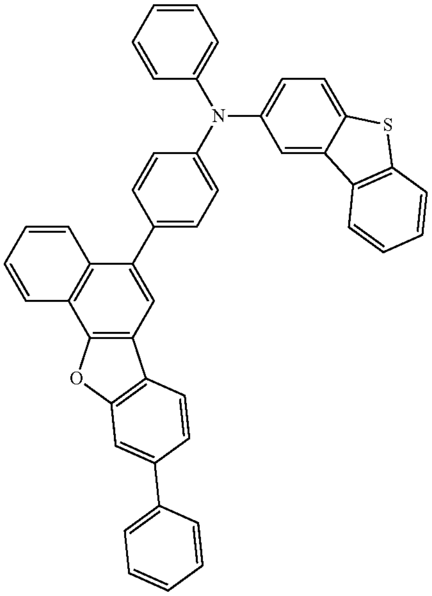
1-437
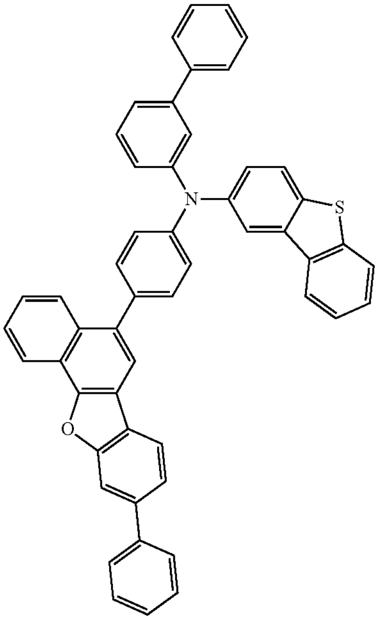
1-438
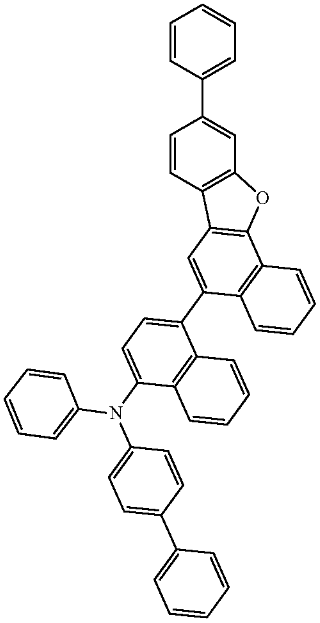

-continued
1-439
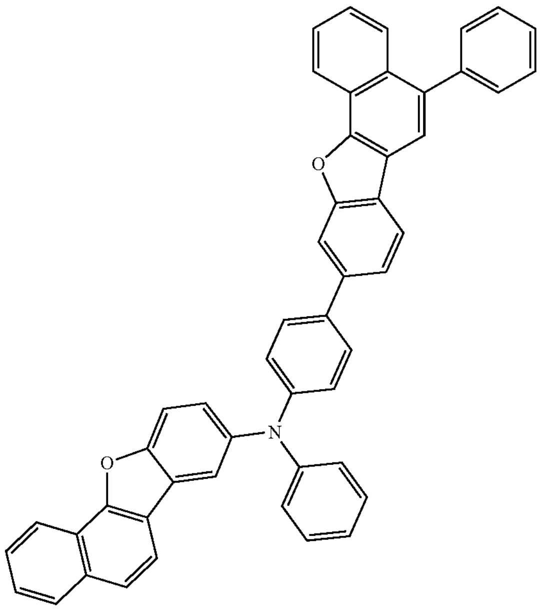
1-440
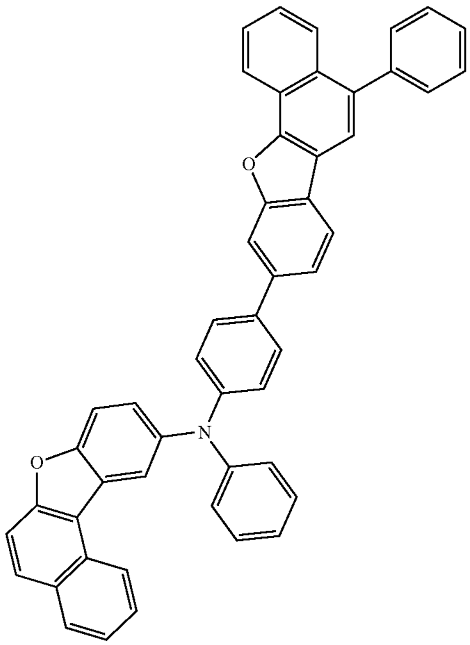
-continued
1-441
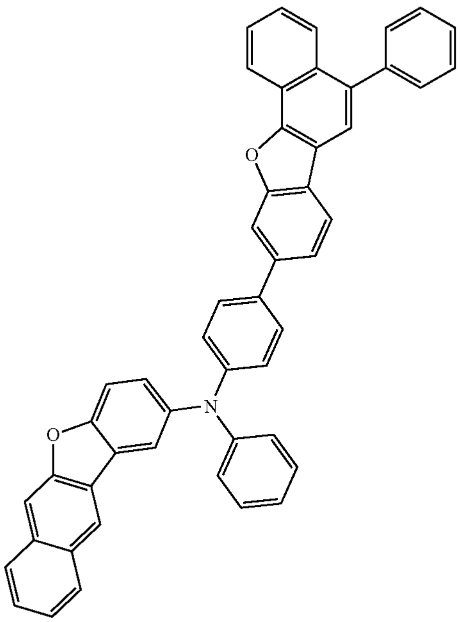
1-442
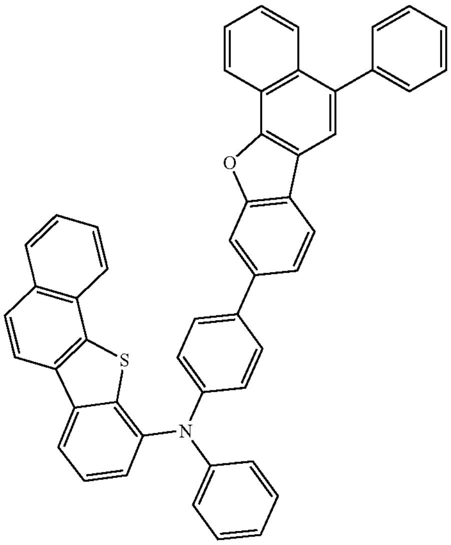

-continued
1-443
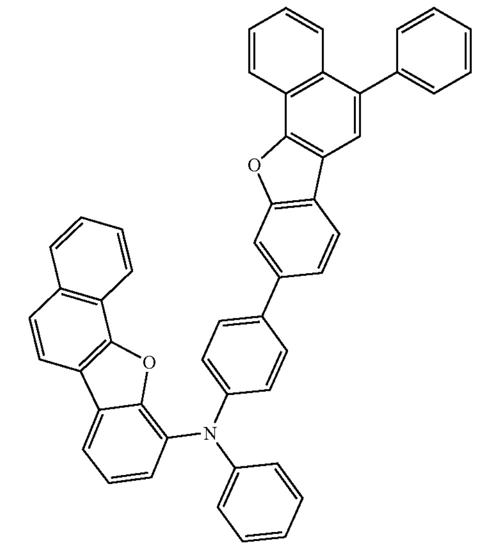
1-444
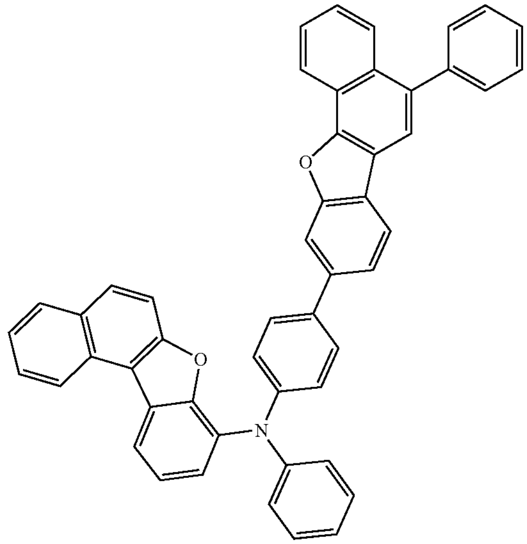
-continued
1-445
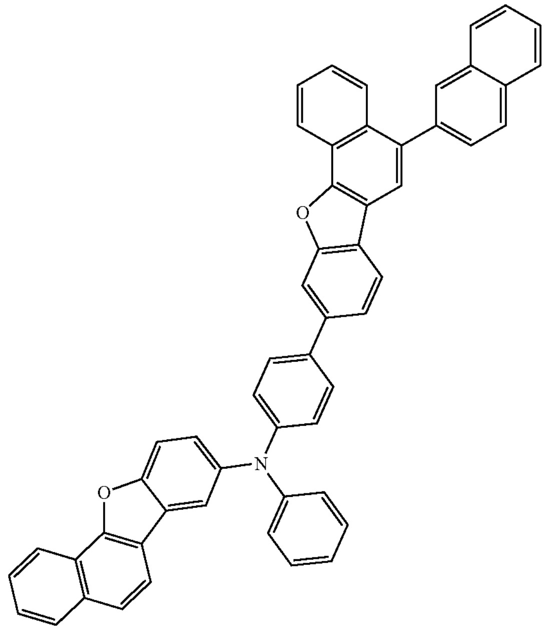
1-446
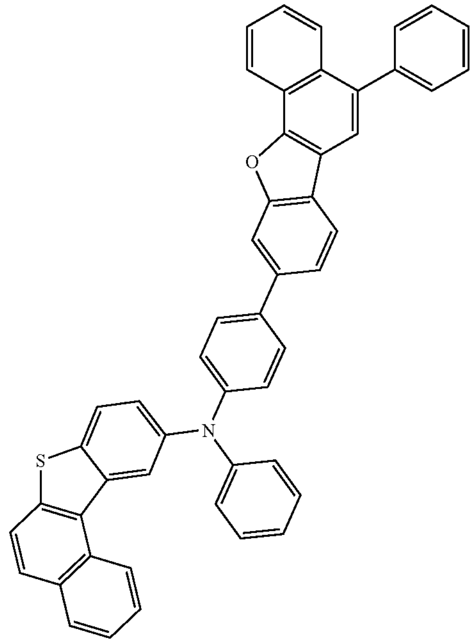

-continued
1-447
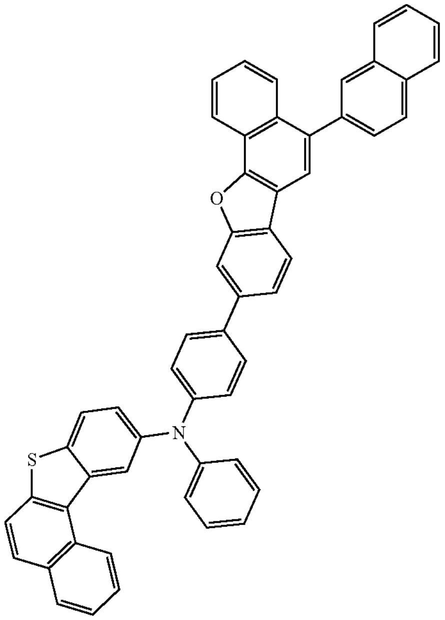
1-448
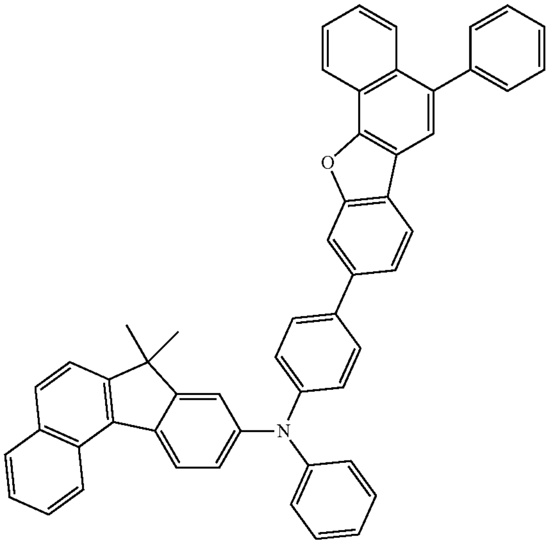
-continued
1-449
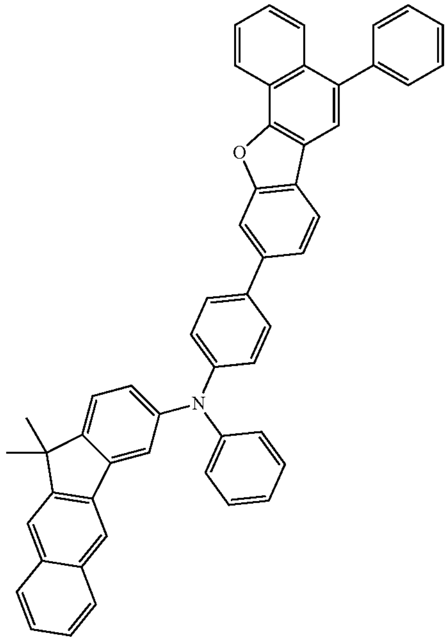
1-450
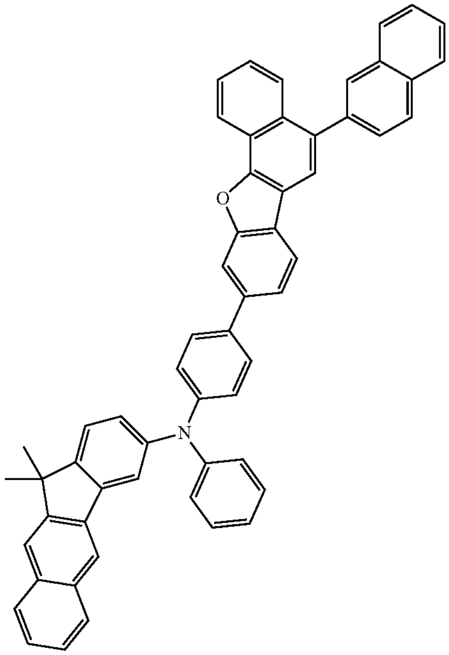
1-451
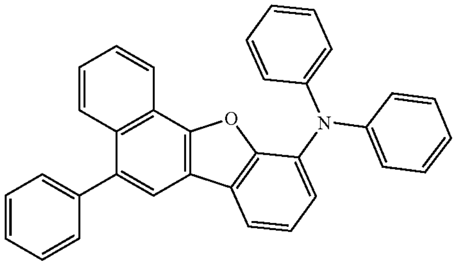

-continued
1-452
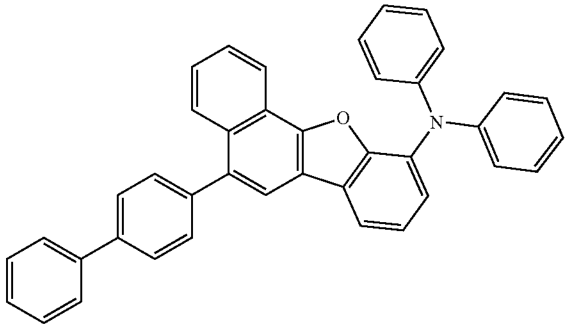
1-453
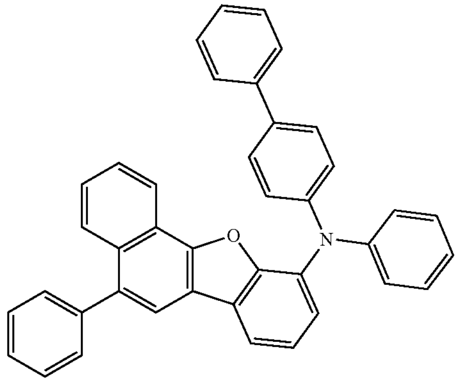
1-454
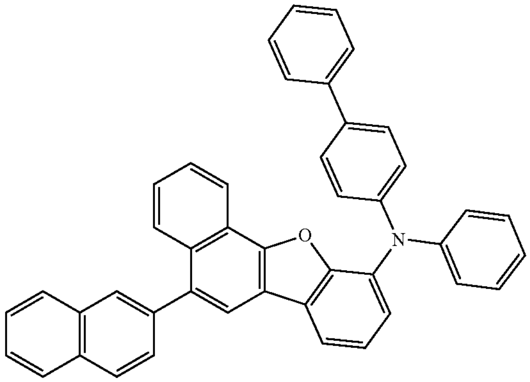
1-455
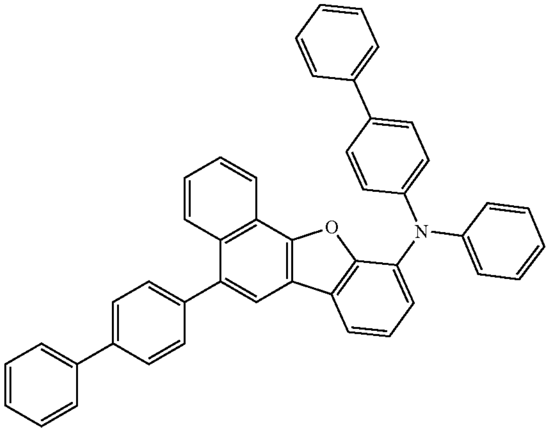
-continued
1-456
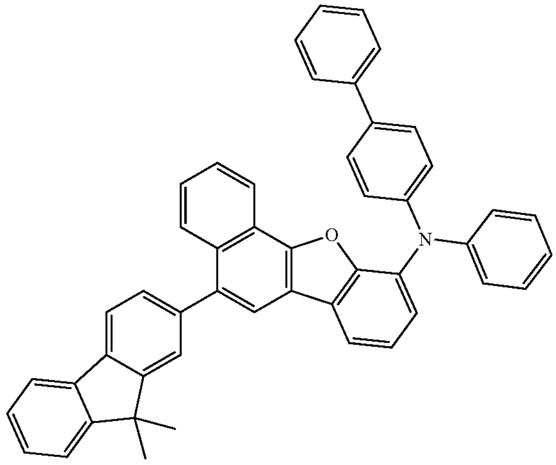
1-457
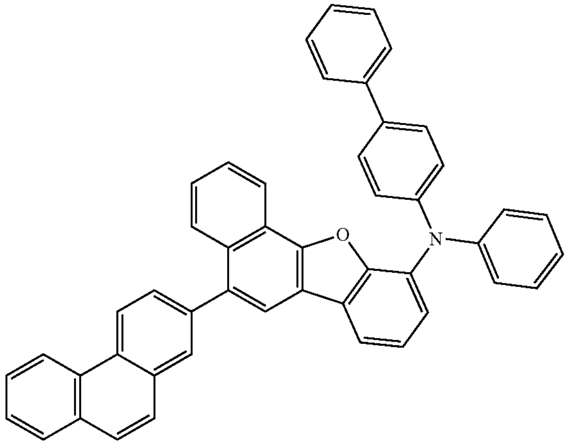
1-458
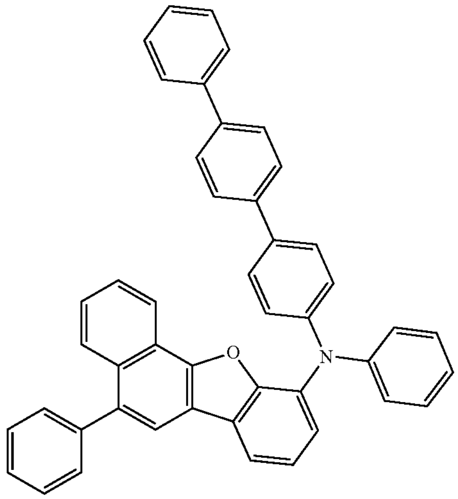

-continued
1-459
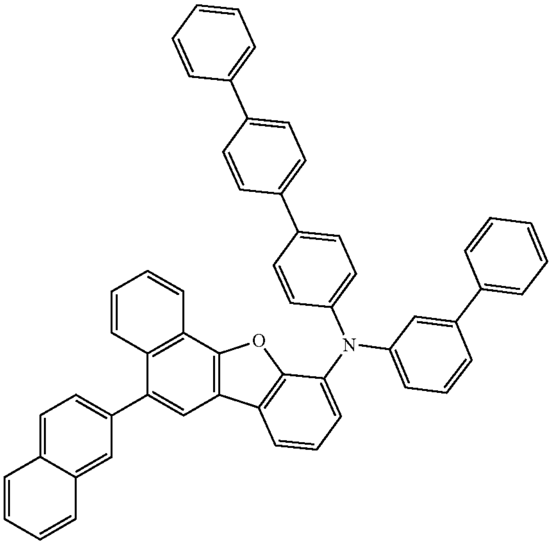
1-460
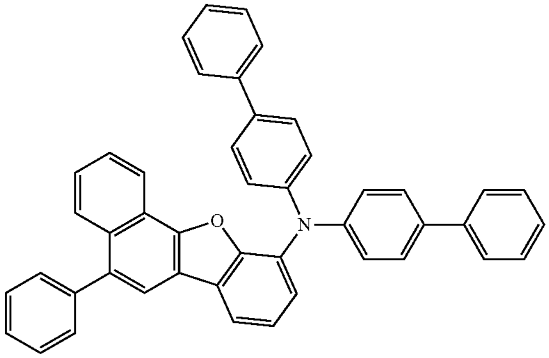
1-461
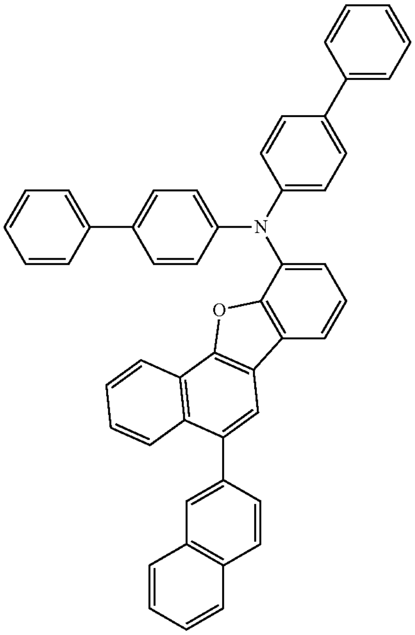
-continued
1-462
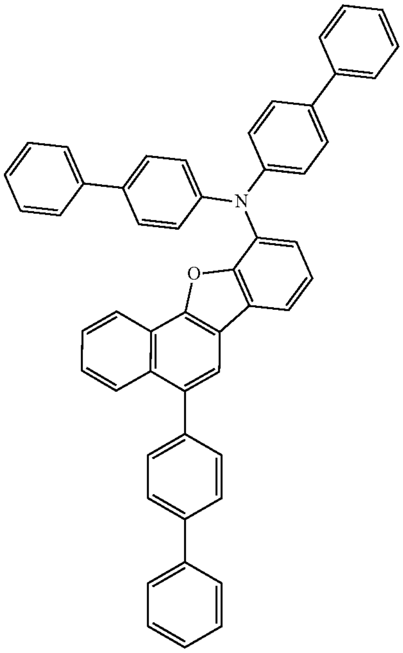
1-463
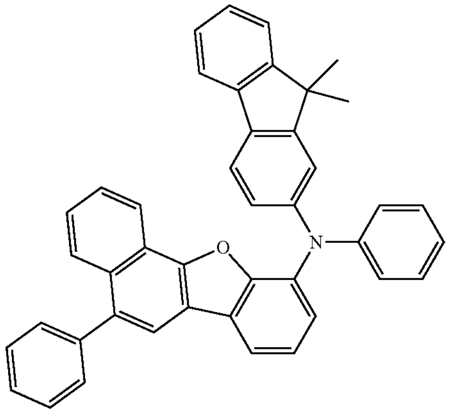
1-464
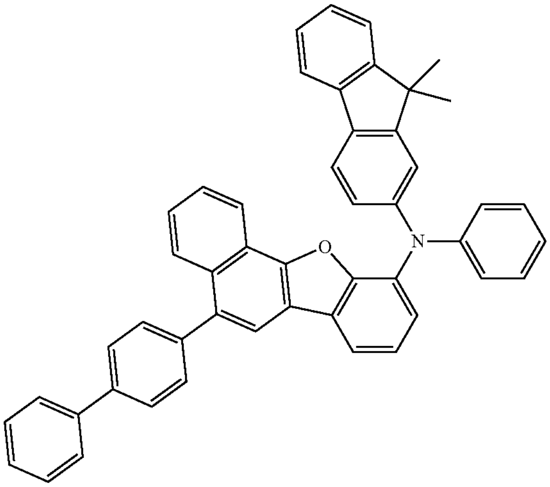

-continued
1-465
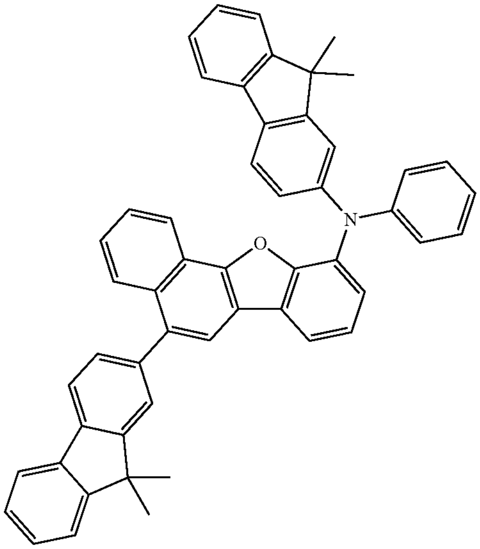
1-466
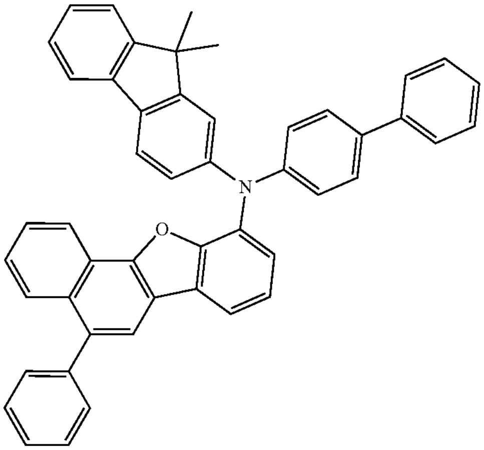
1-467
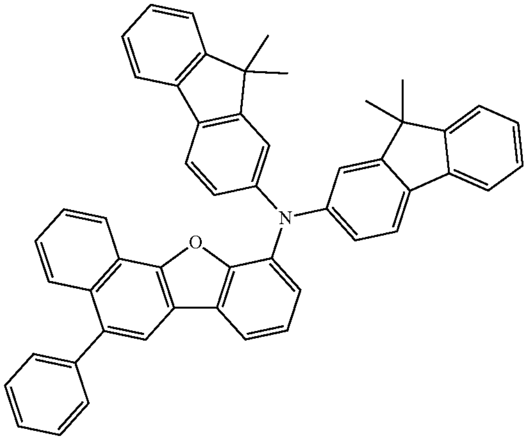
-continued
1-468
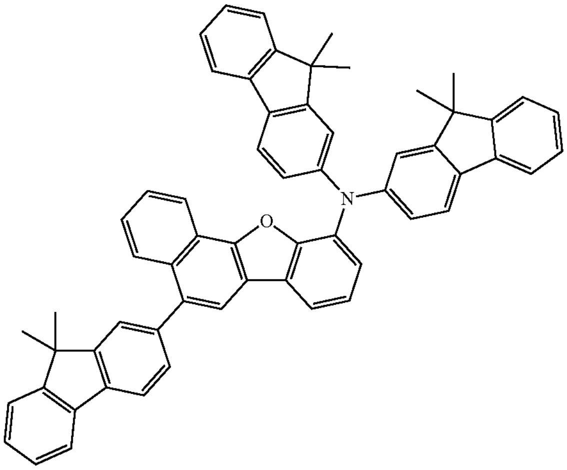
1-469
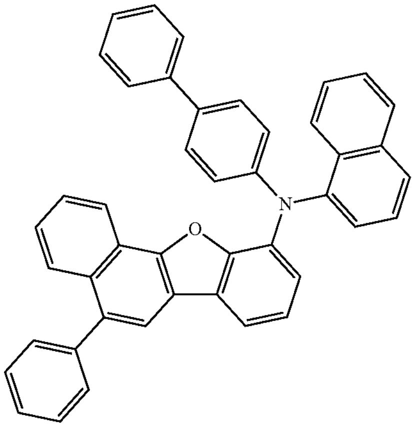
1-470
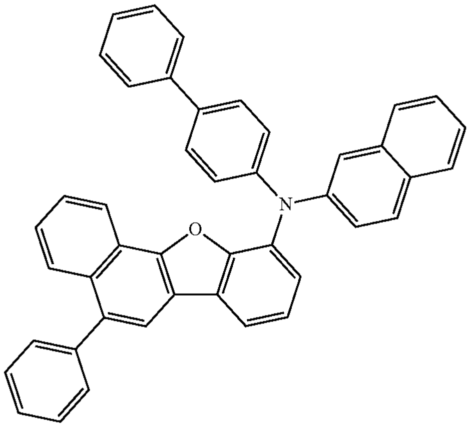

-continued
1-471
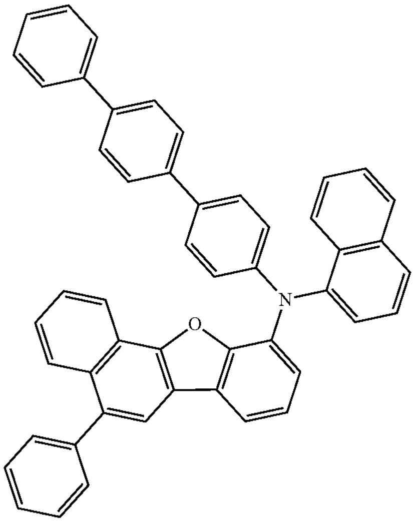
1-472
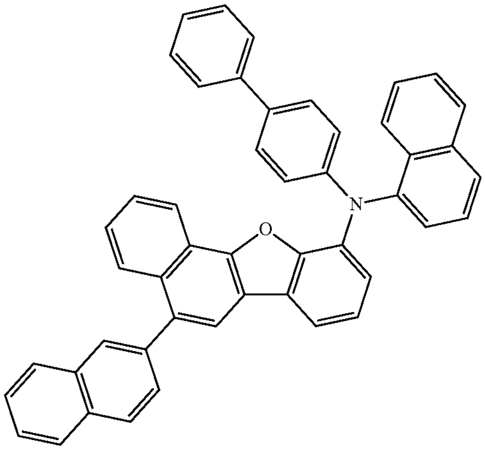
1-473
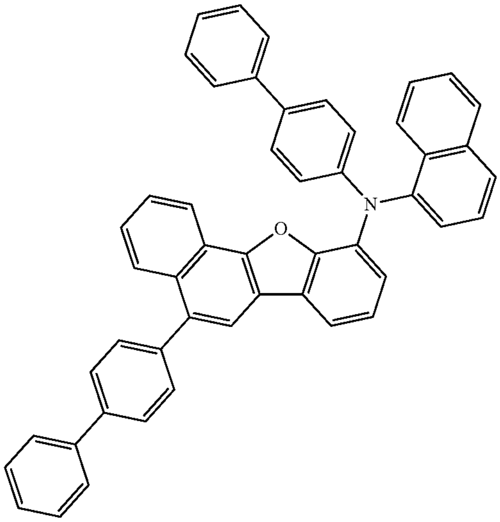
-continued
1-474
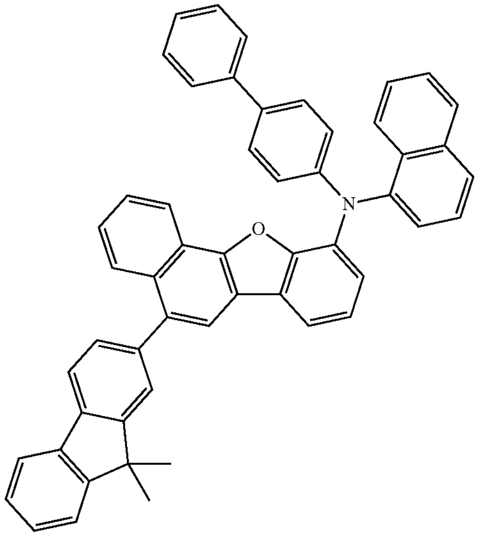
1-475
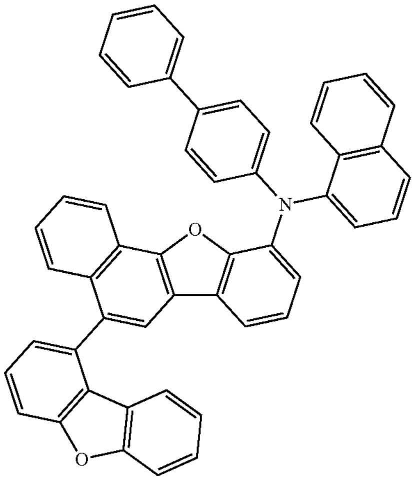
1-476
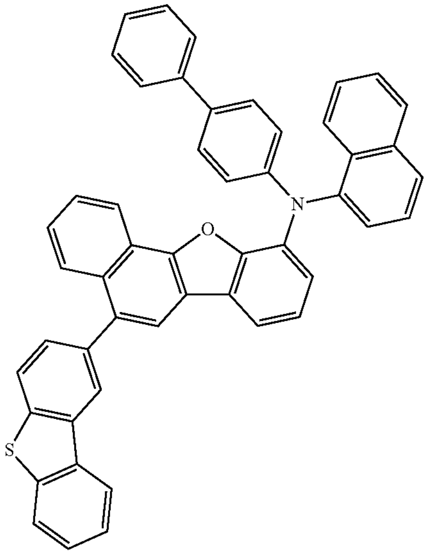

-continued
1-477
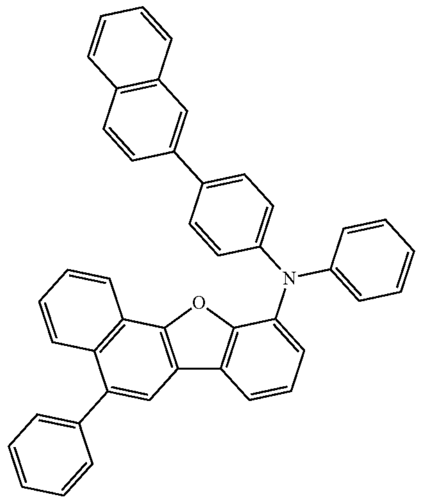
1-478
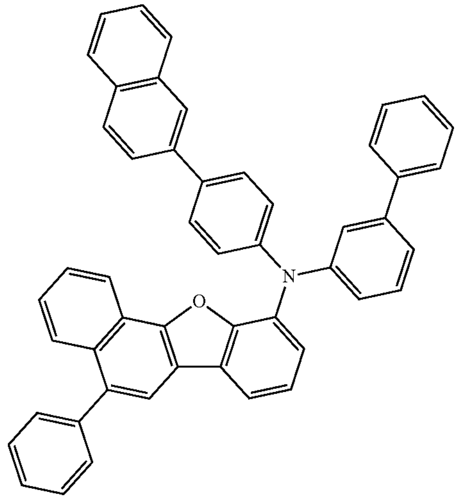
1-479
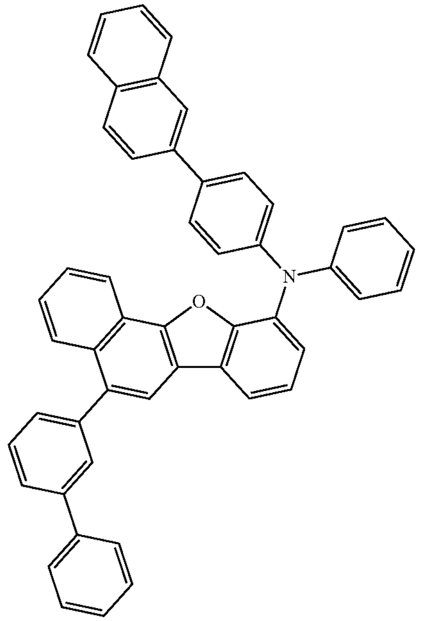
-continued
1-480
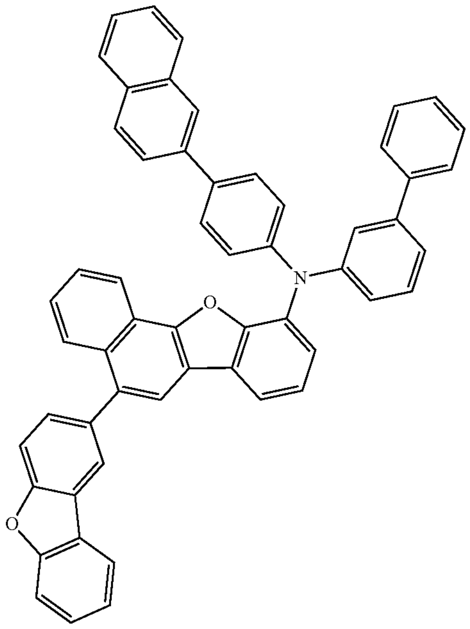
1-481
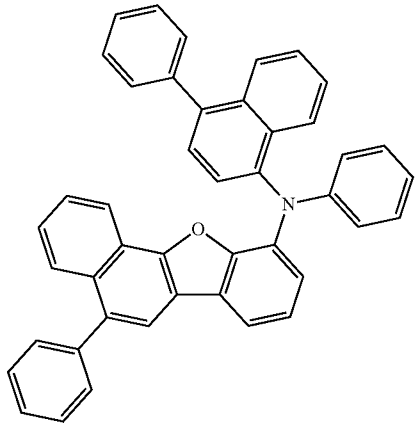
1-482
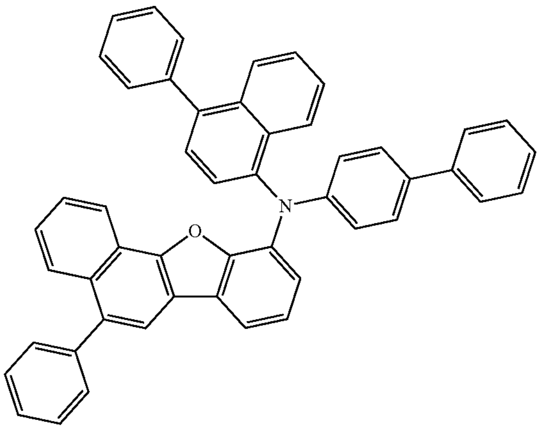

-continued
1-483
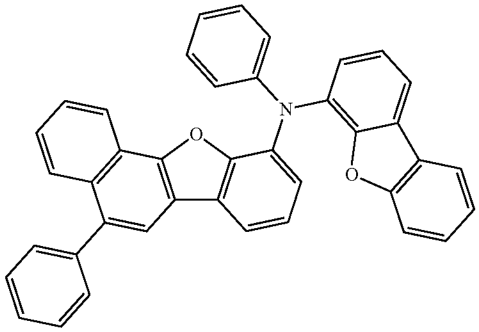
1-484
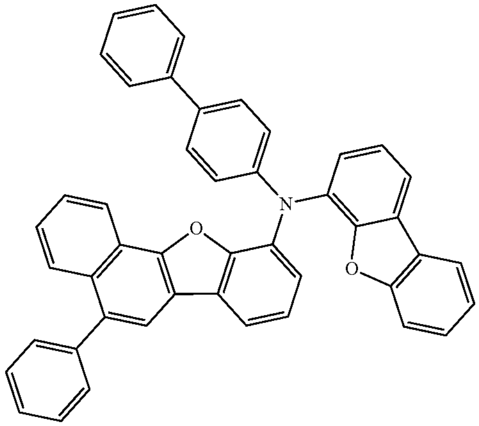
1-485
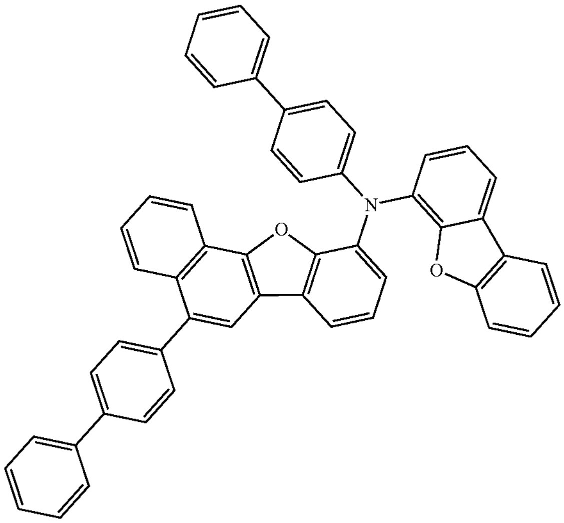
-continued
1-486
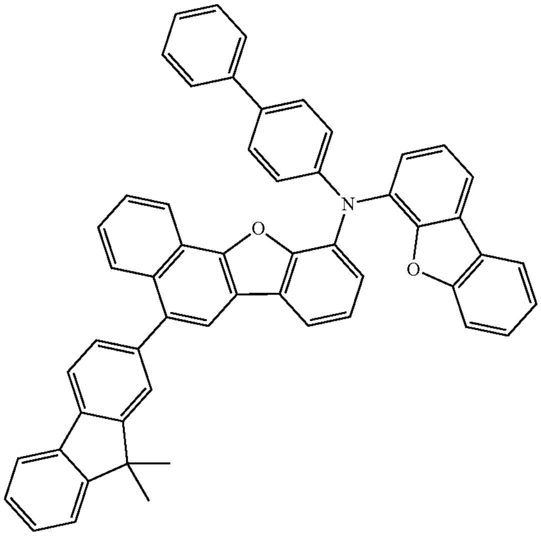
1-487
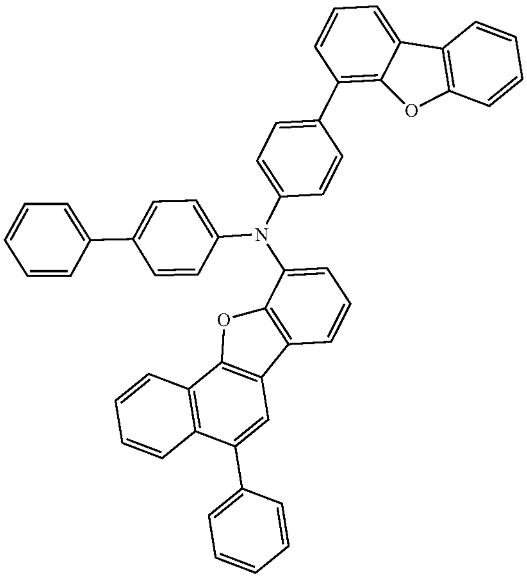

-continued
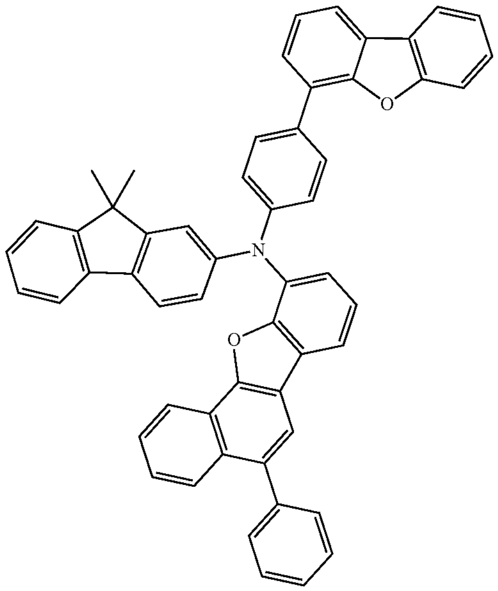
1-489
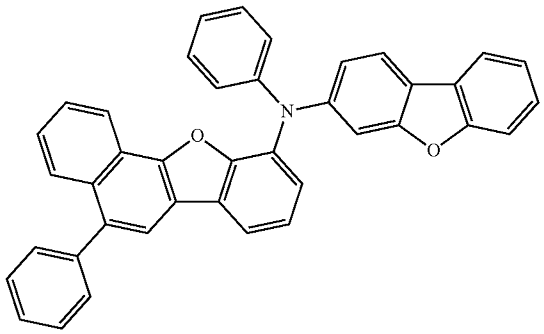
1-490
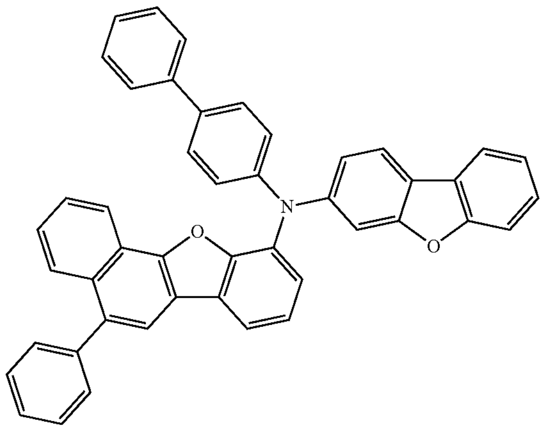
-continued
1-491
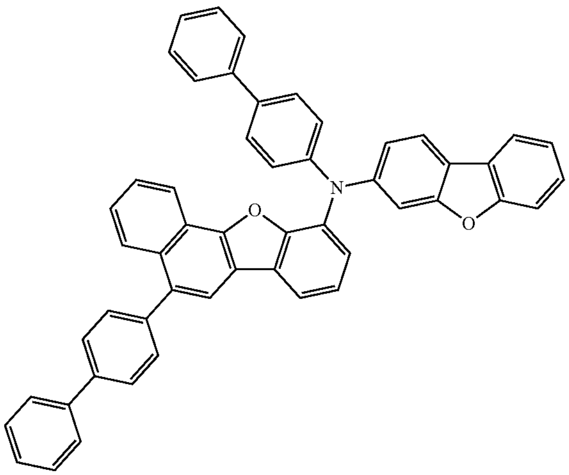
1-492
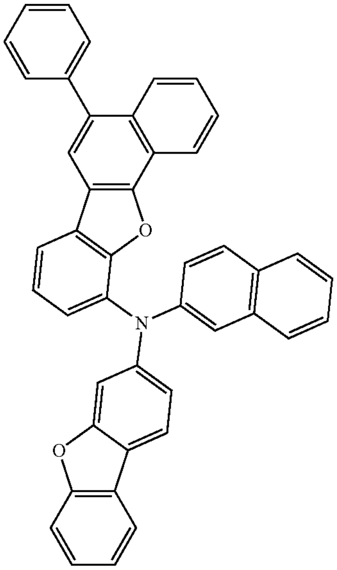

-continued
1-493
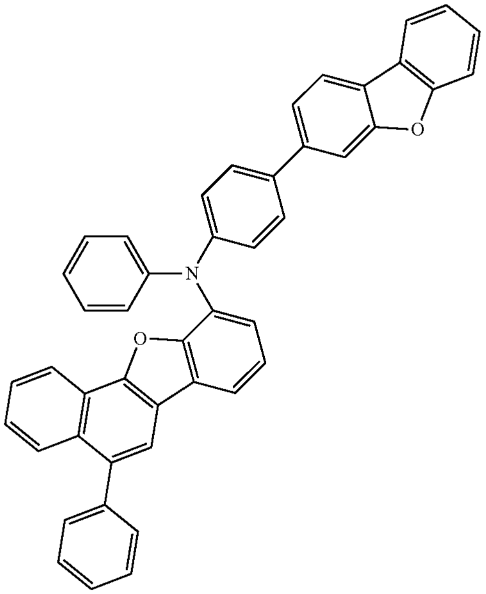
1-494
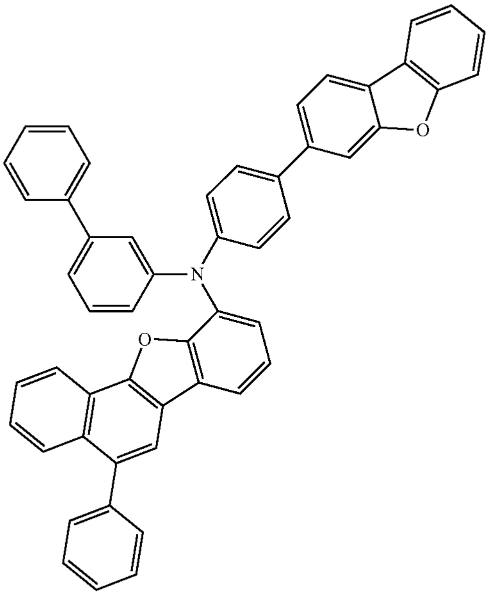
-continued
1-495
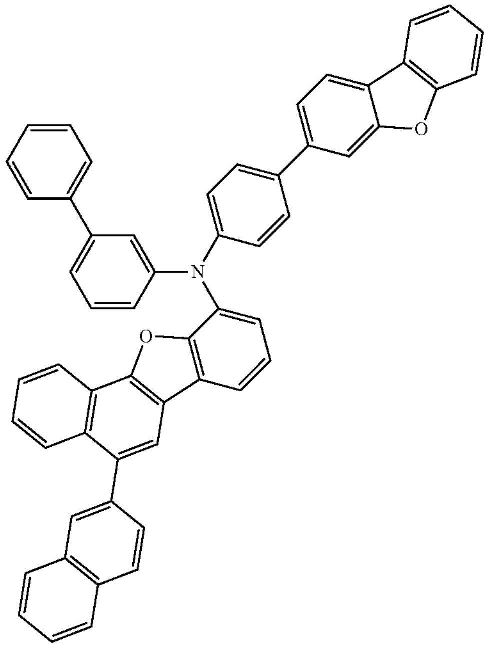
1-496
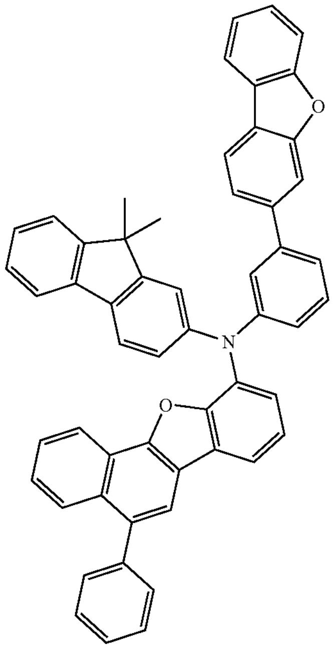

-continued
1-497
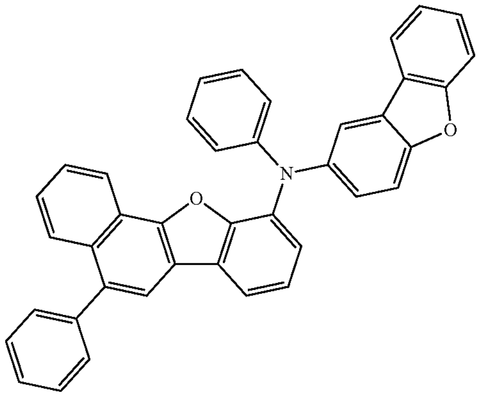
1-498
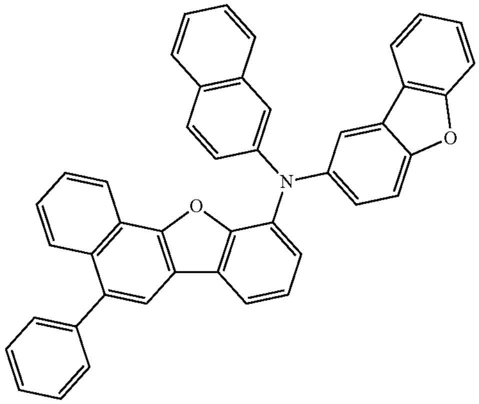
1-499
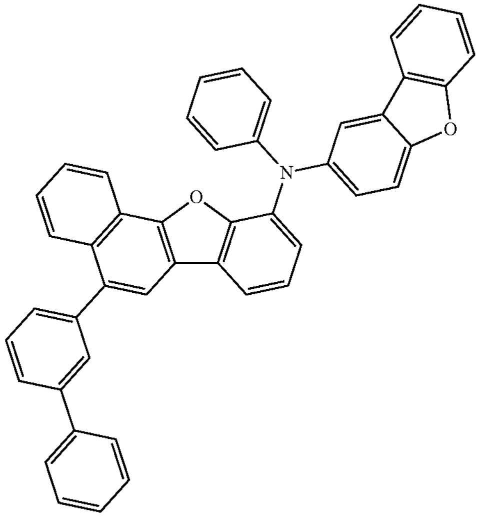
-continued
1-500
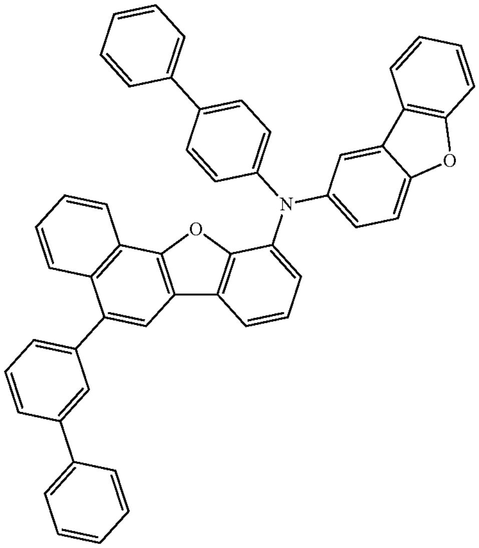
1-501
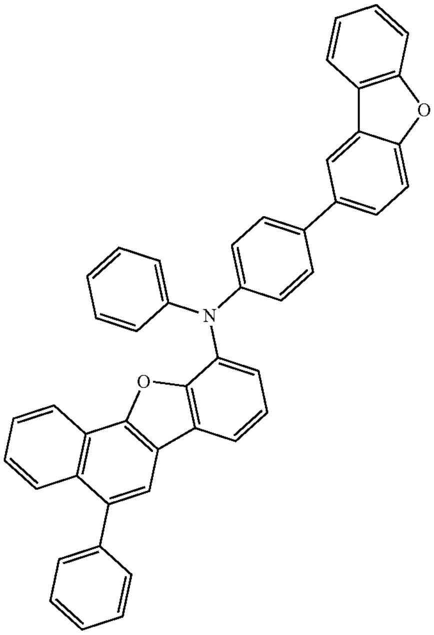

1-502
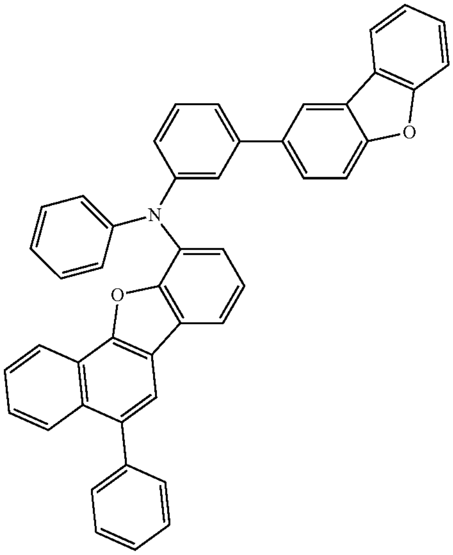
1-503
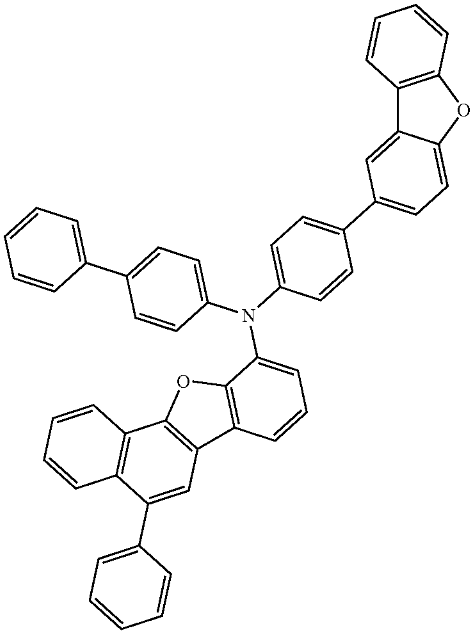
1-504
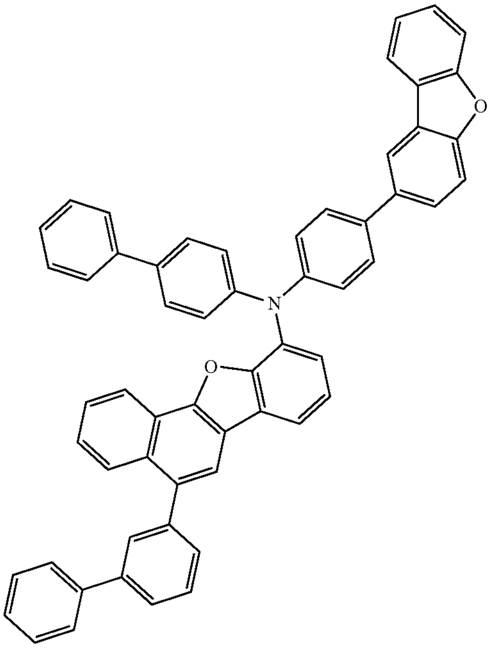
1-505
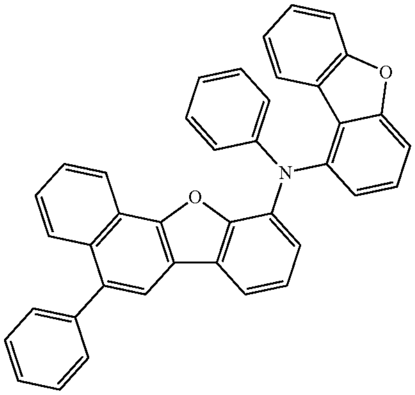
1-506
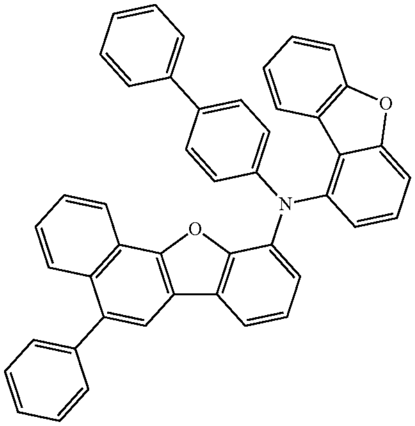

-continued
1-507
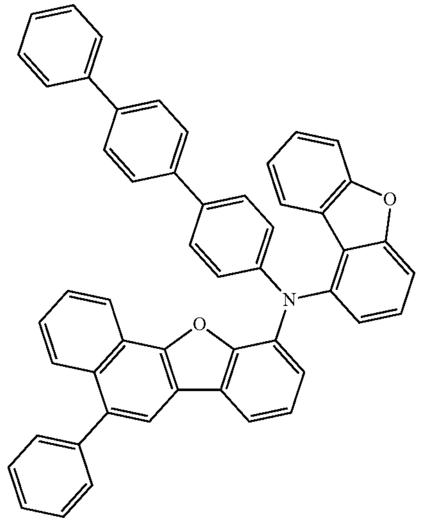
1-508
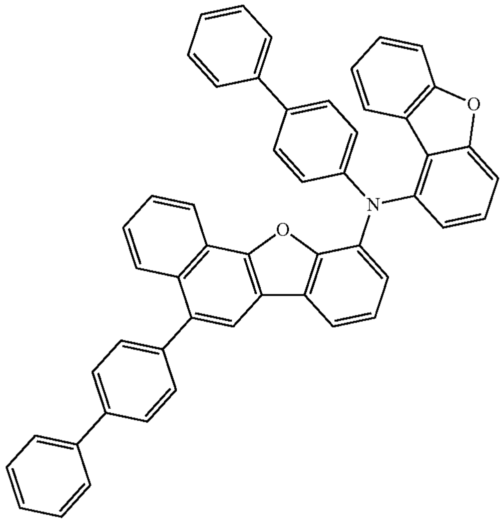
1-509
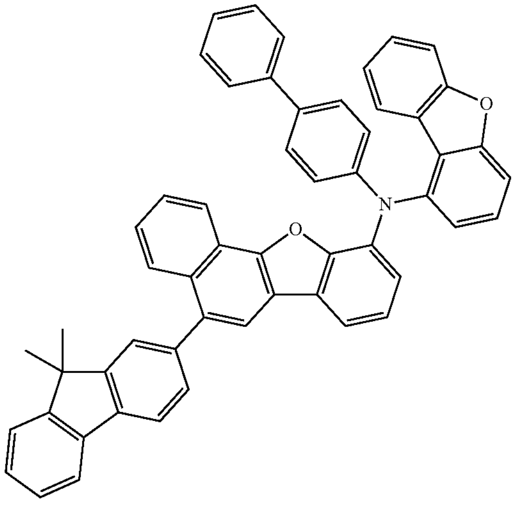
-continued
1-510
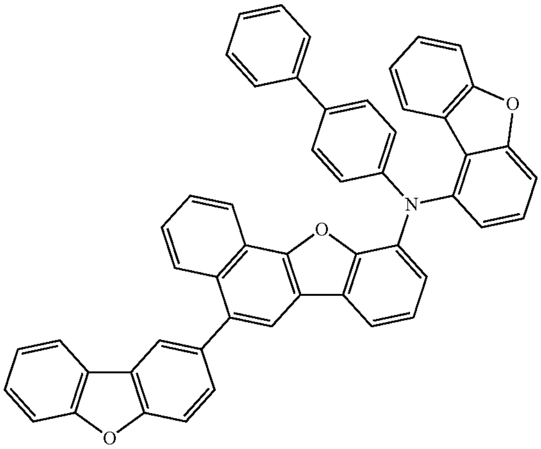
1-511
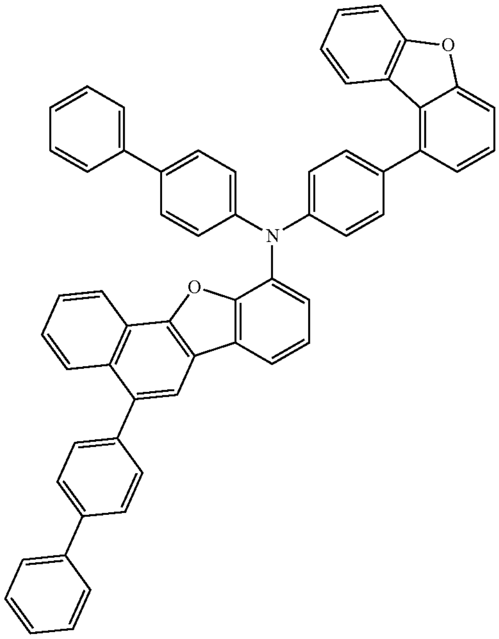
1-512
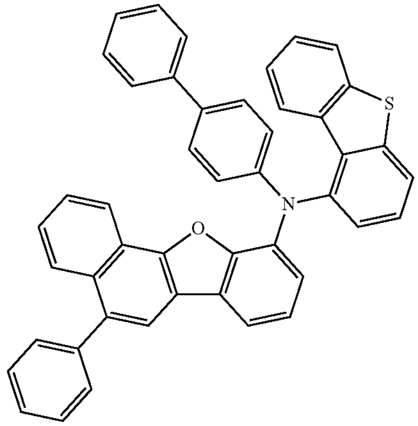

-continued
1-513
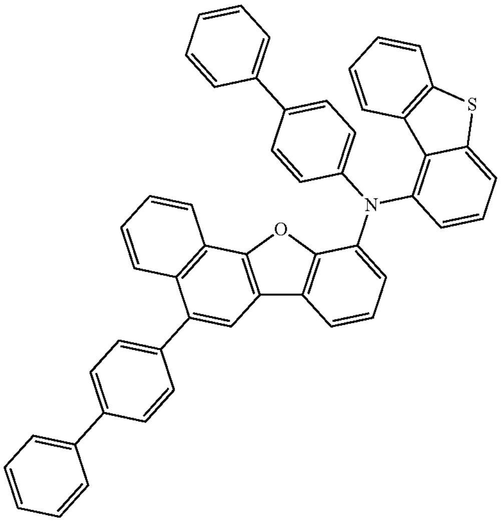
1-514
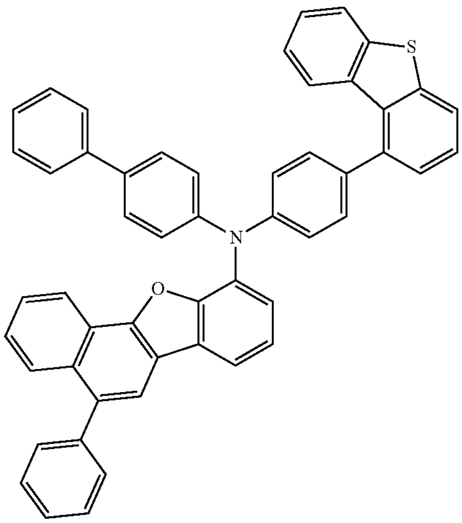
1-515
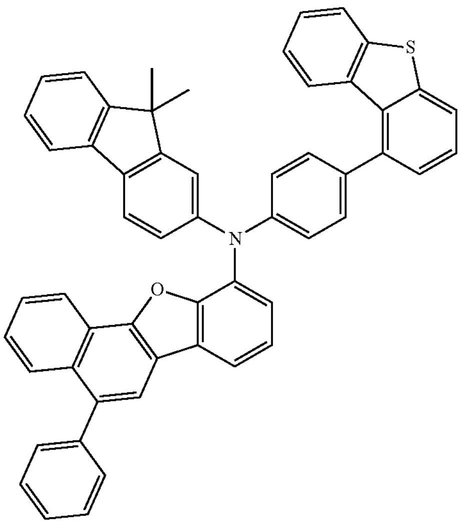
-continued
1-516
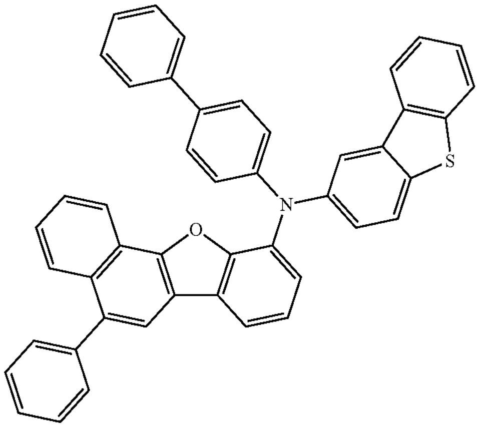
1-517
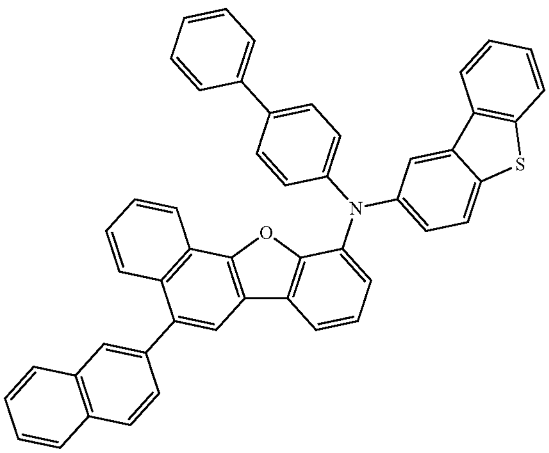
1-518
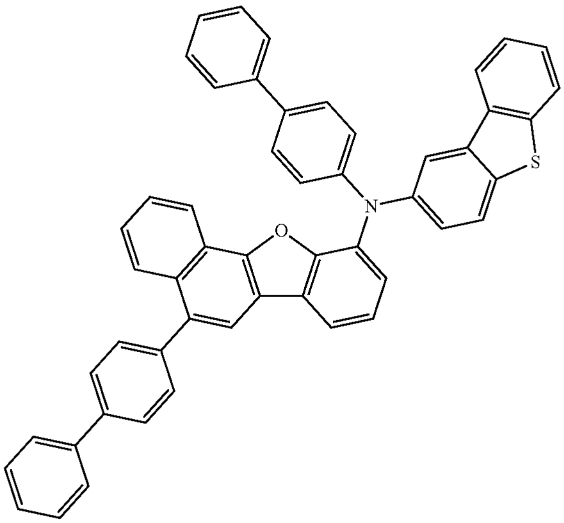

-continued
1-519
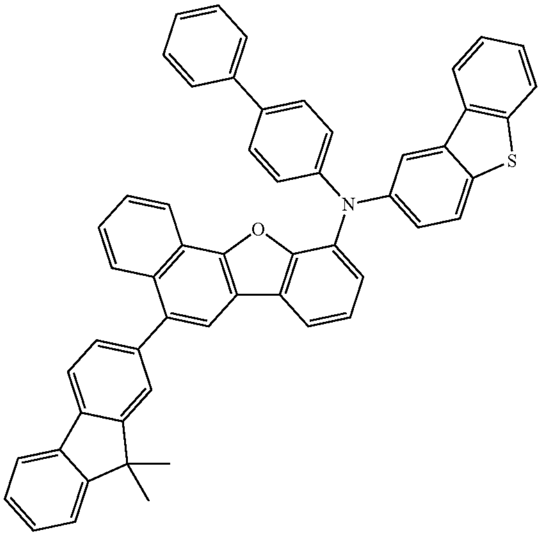
1-520
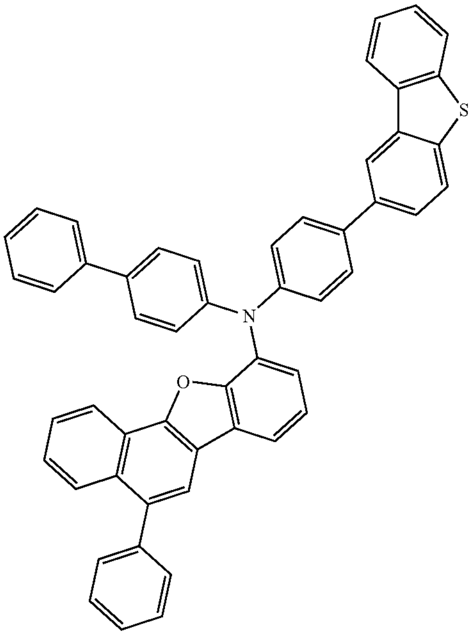
1-521
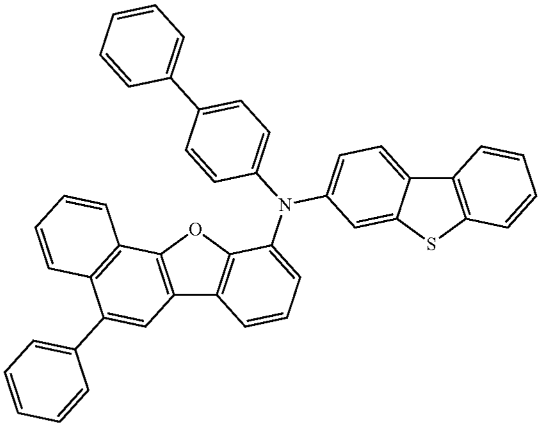
-continued
1-522
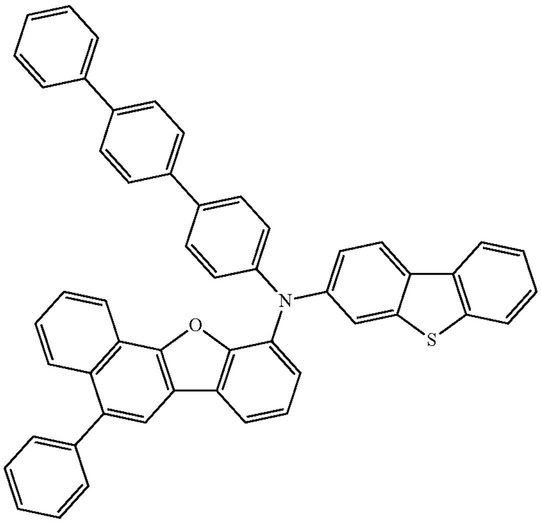
1-523
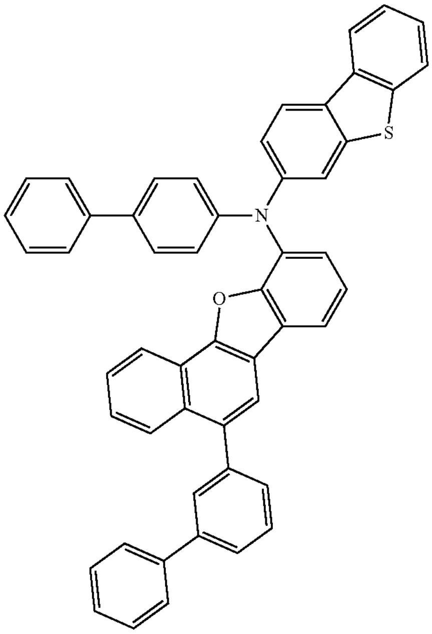
1-524
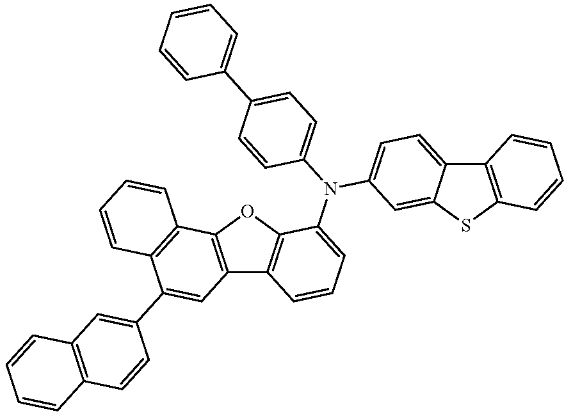

-continued
1-525
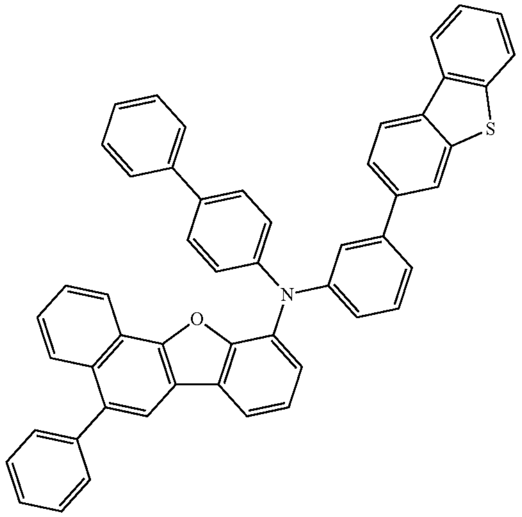
1-526
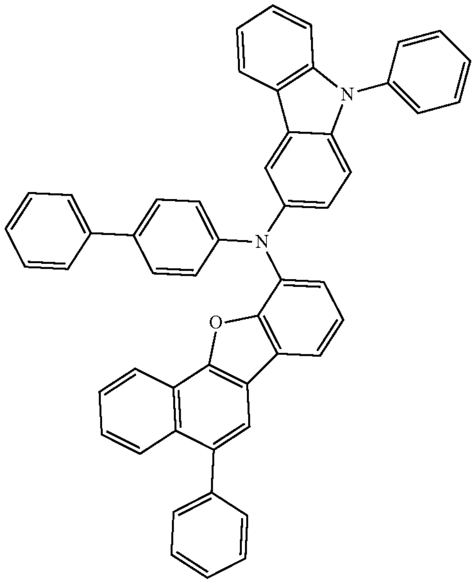
-continued
1-527
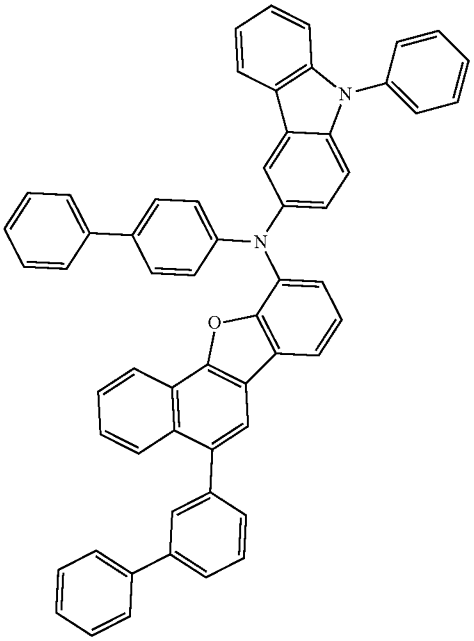
1-528
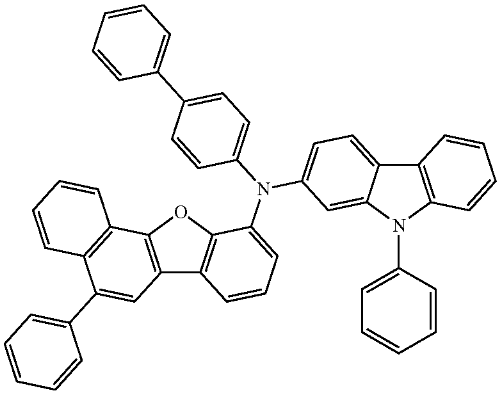

-continued
1-529
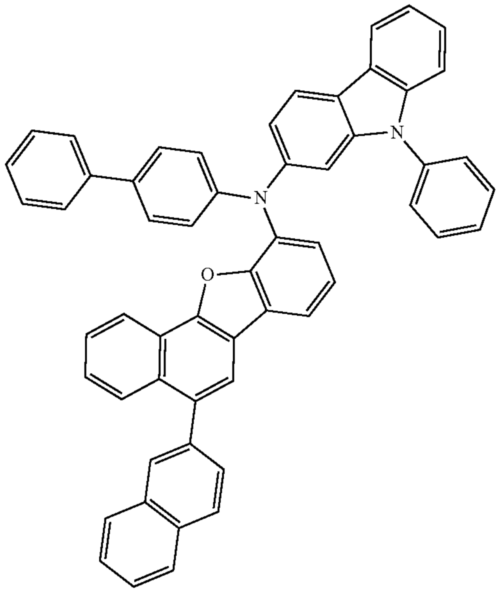
1-530
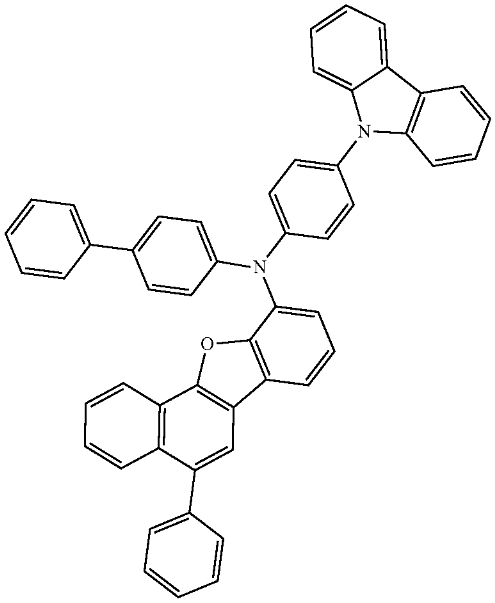
-continued
1-531
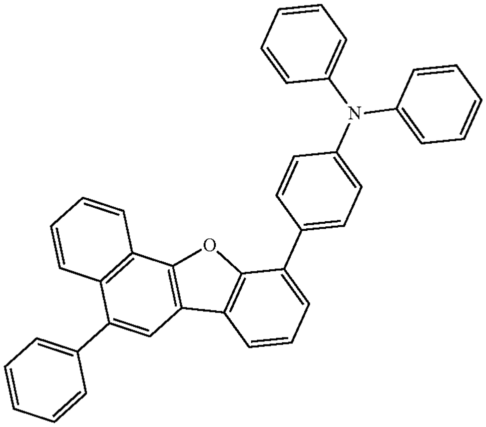
1-532
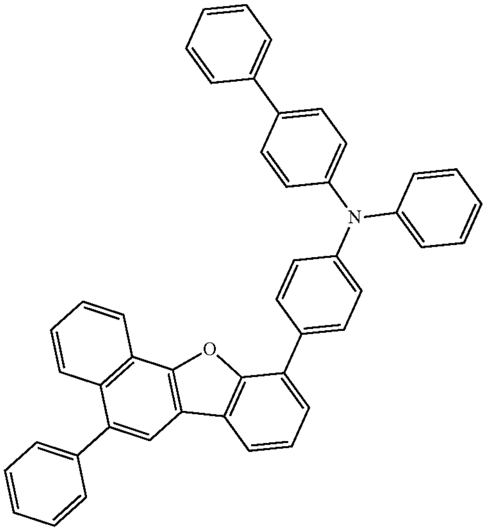
1-533
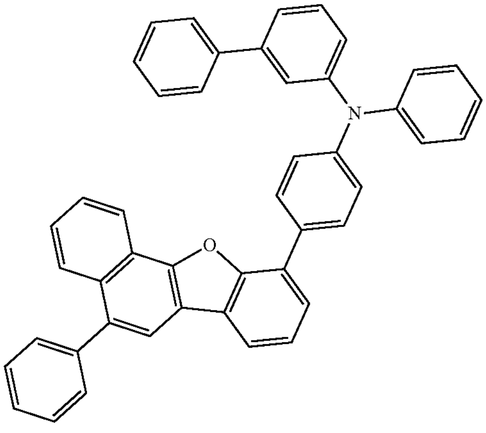

-continued
1-534
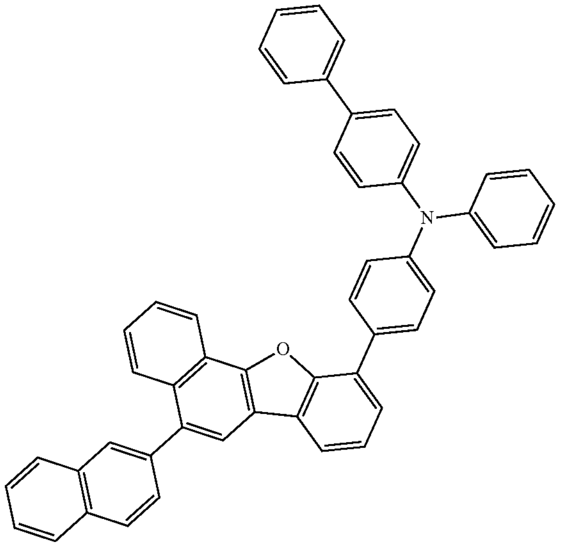
1-535
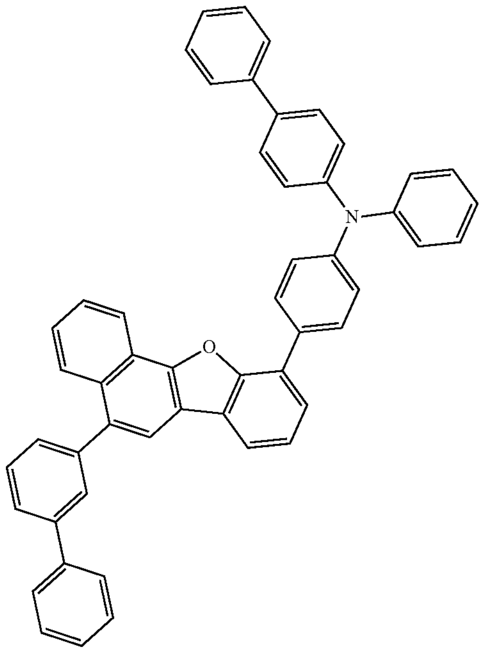
-continued
1-536
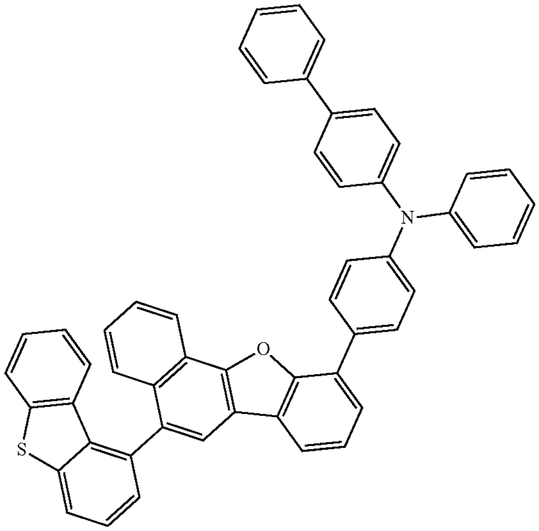
1-537
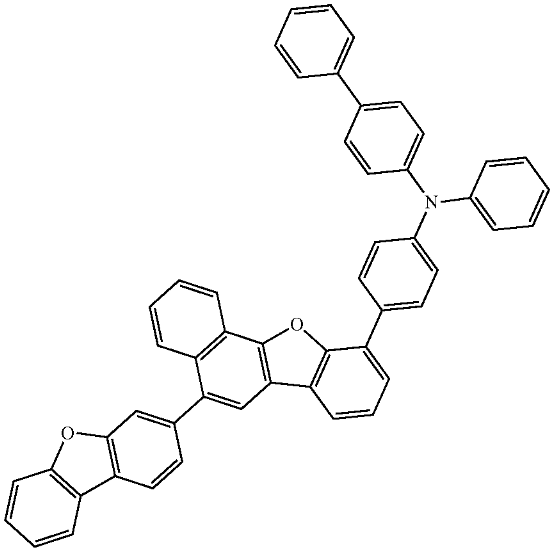

-continued
1-538
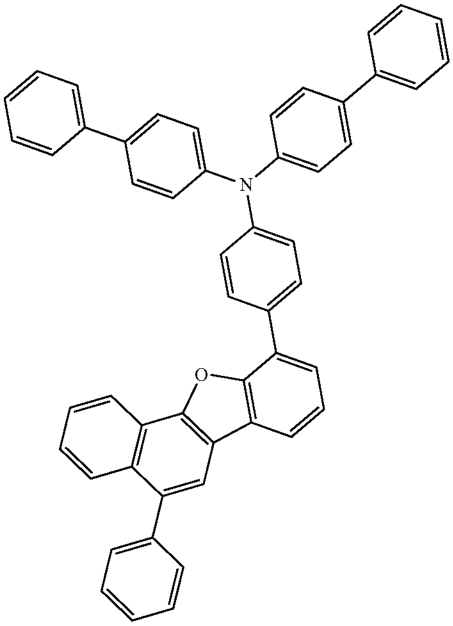
1-539
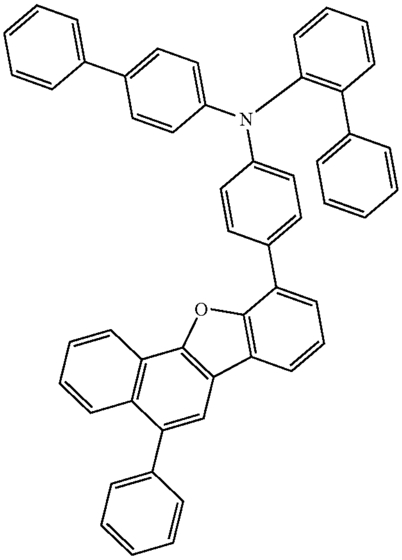
-continued
1-540
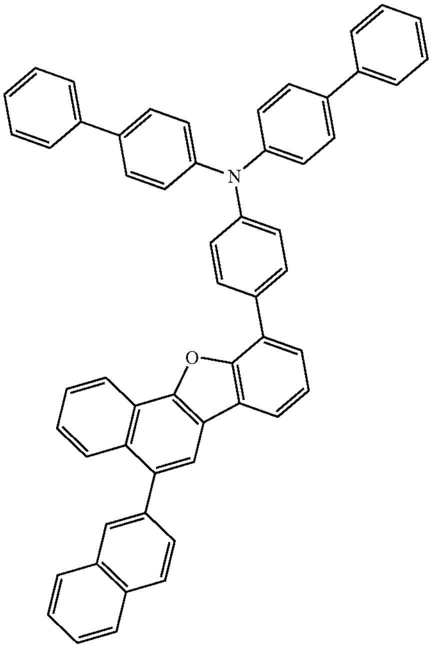
1-541
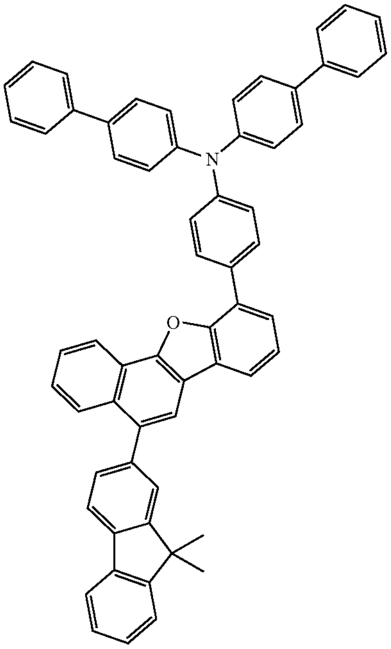

-continued
1-542
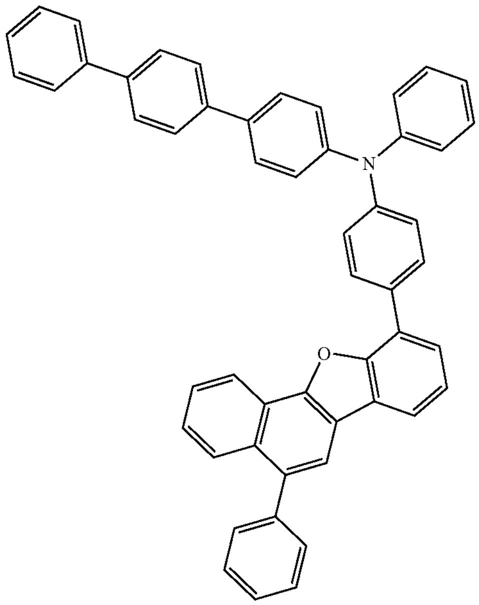
1-543
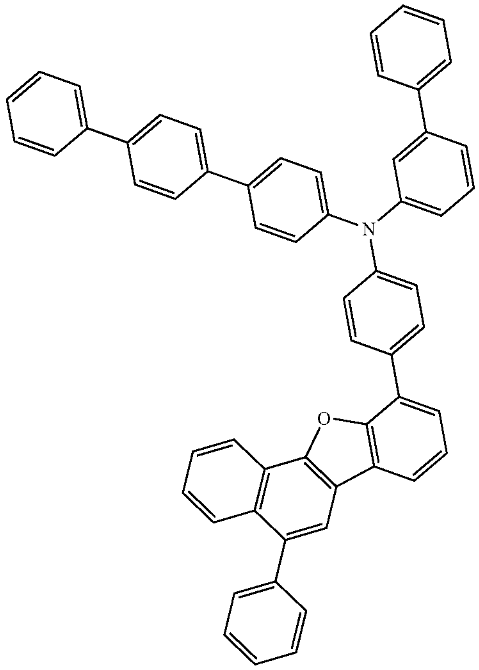
-continued
1-544
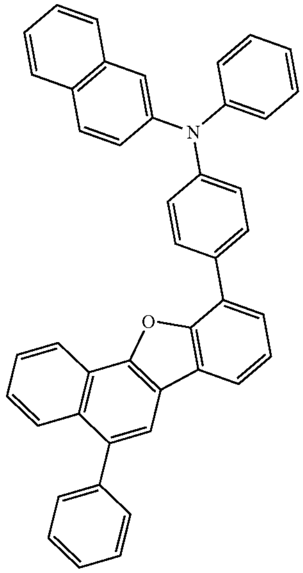
1-545
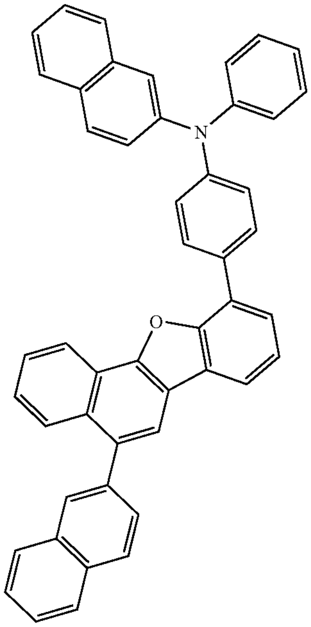

1-546
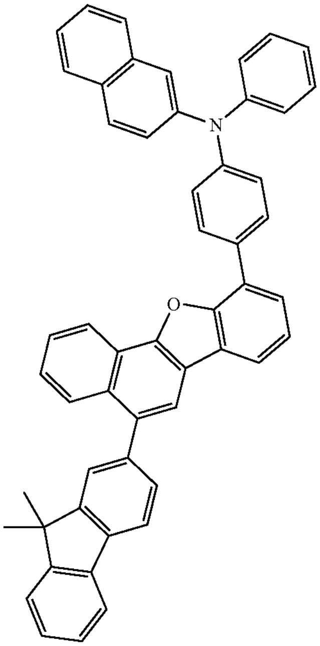
1-547
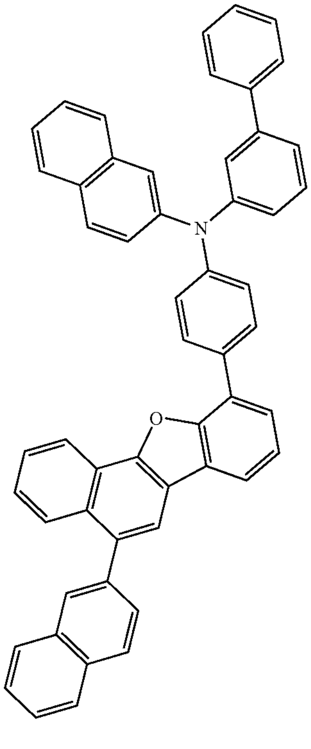
1-548
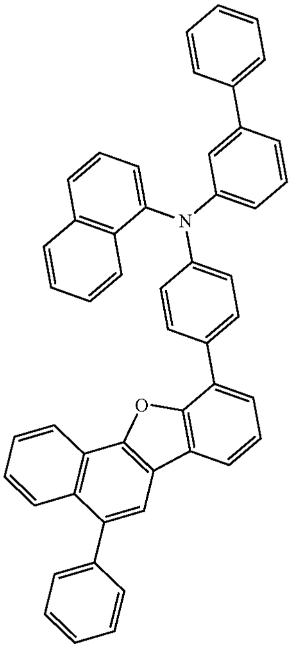
1-549
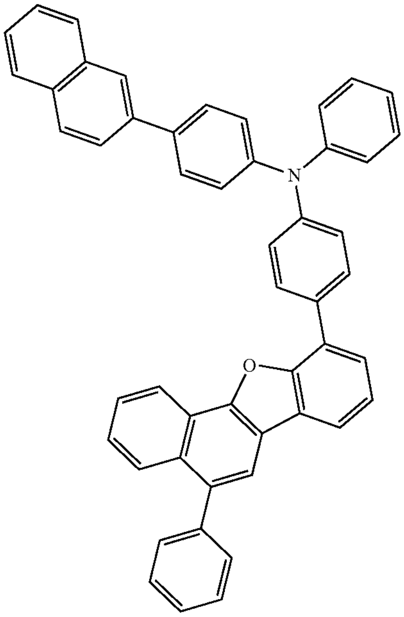

-continued
1-550
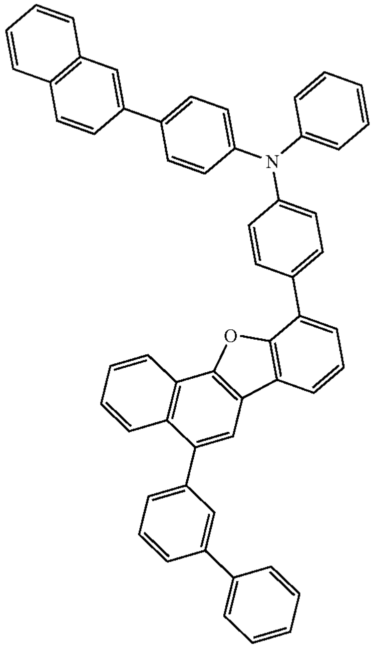
1-551
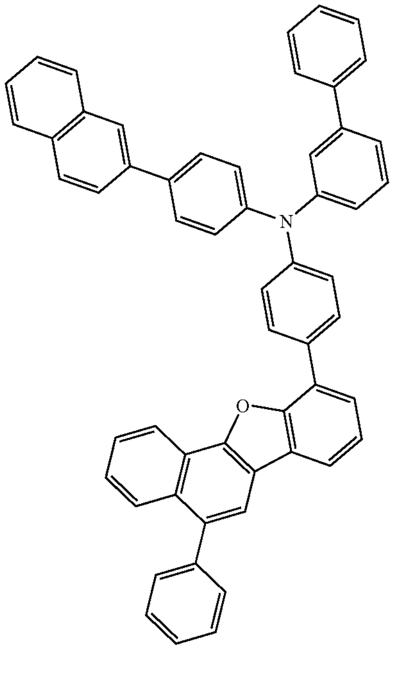
-continued
1-552
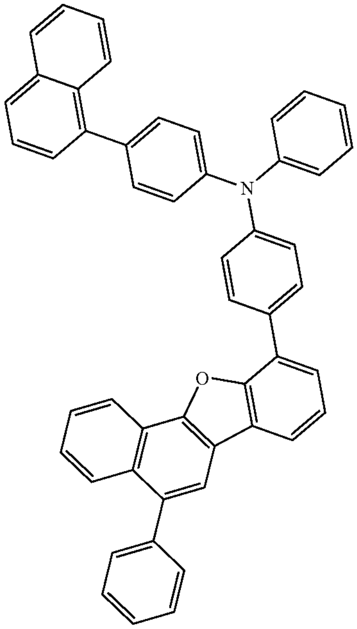
1-553
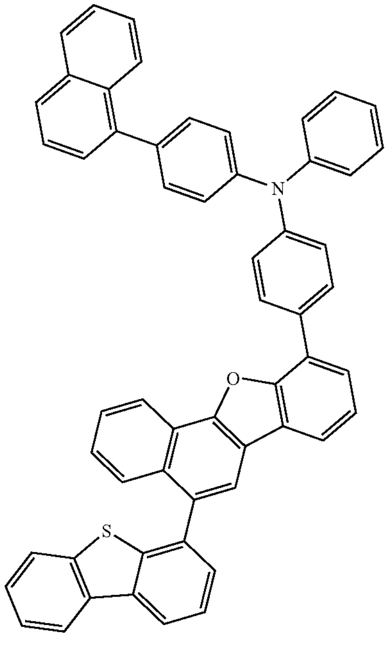

-continued
1-554
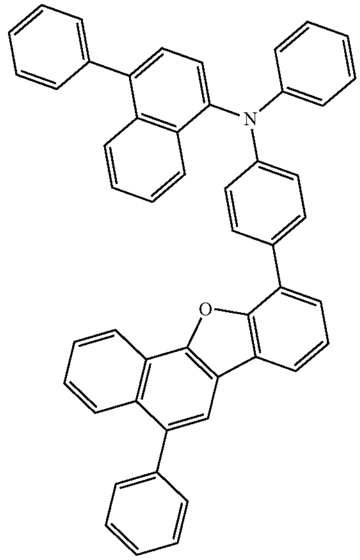
1-555
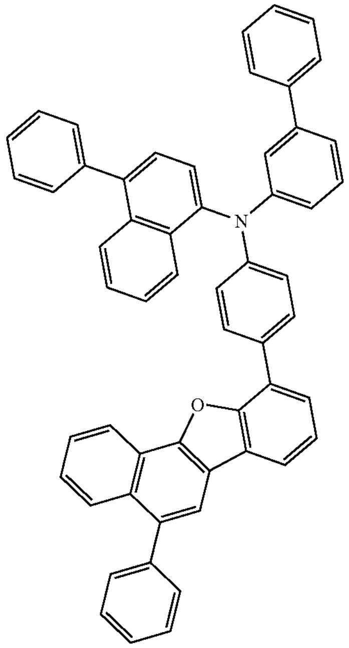
-continued
1-556
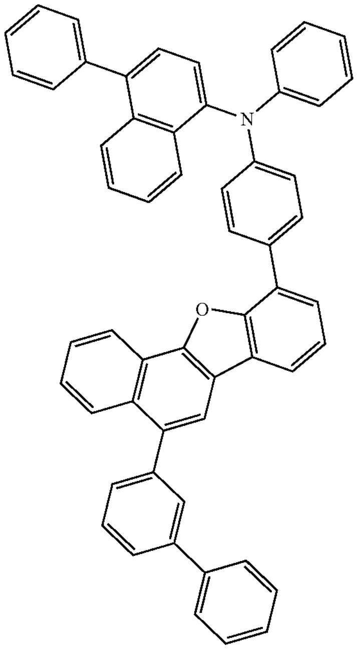
1-557
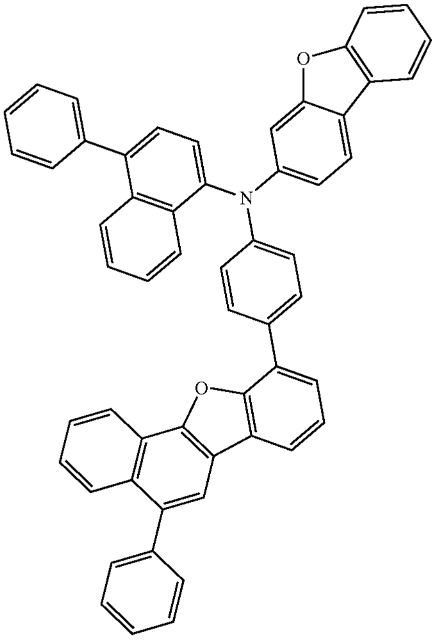

1-558
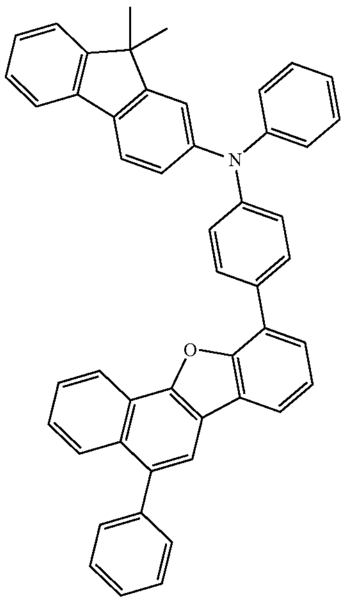
1-559
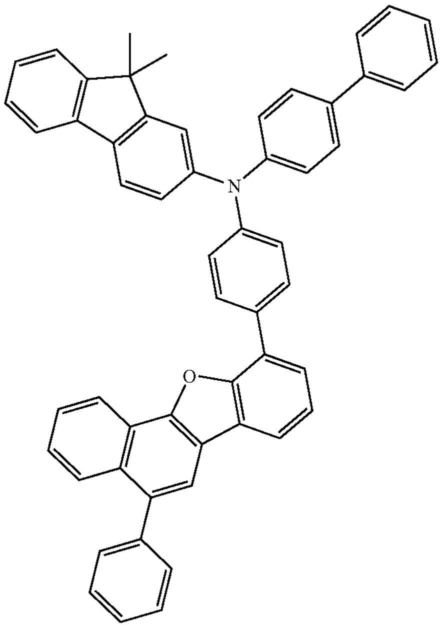
1-560
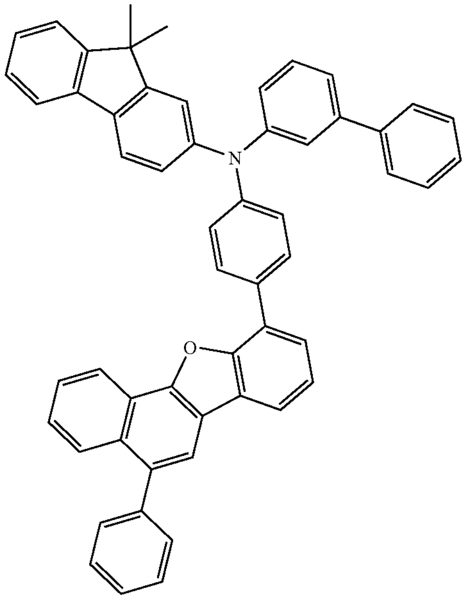
1-561
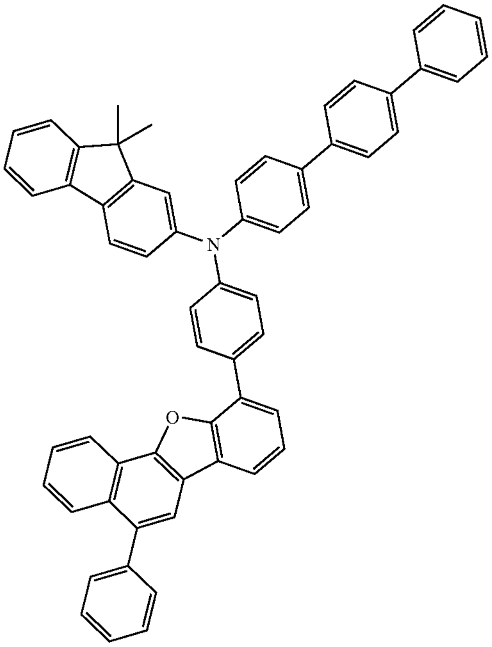

-continued
1-562
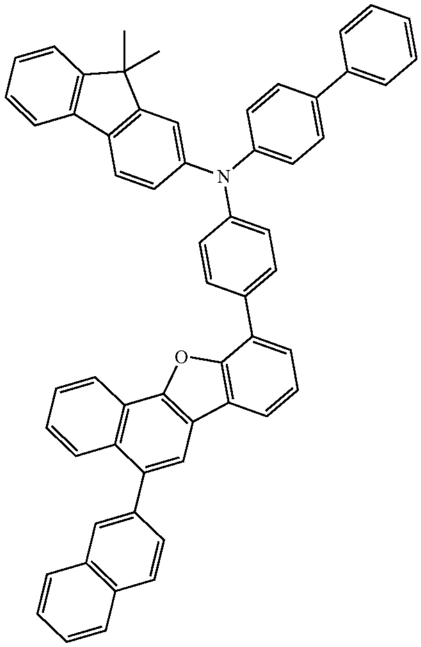
1-563
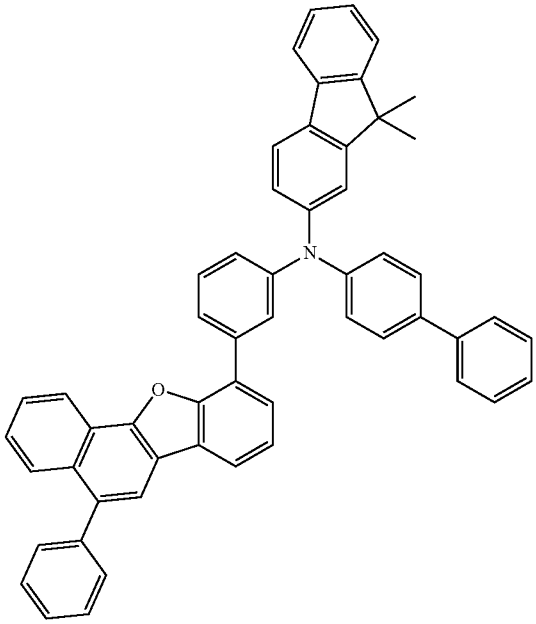
-continued
1-564
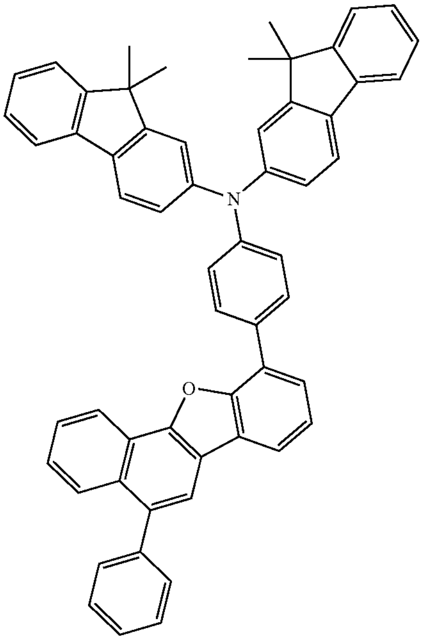
1-565
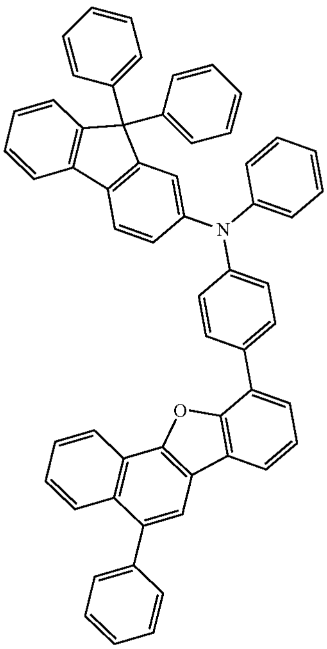

-continued
1-566
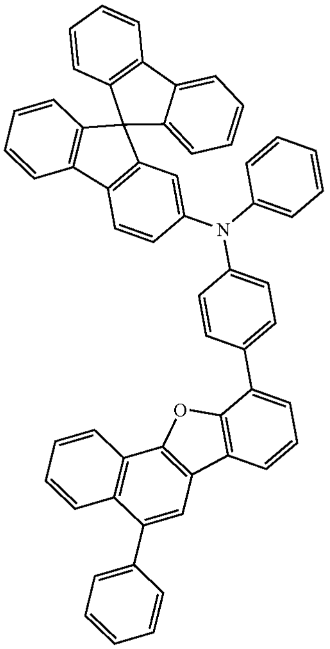
1-567
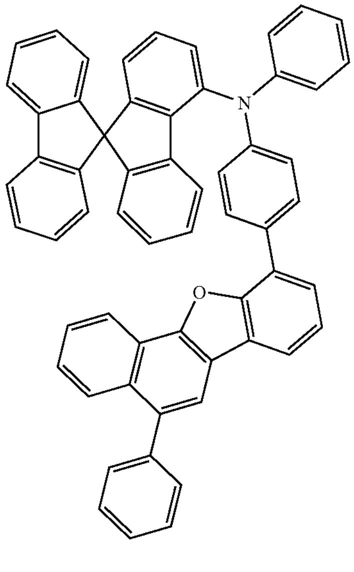
-continued
1-568
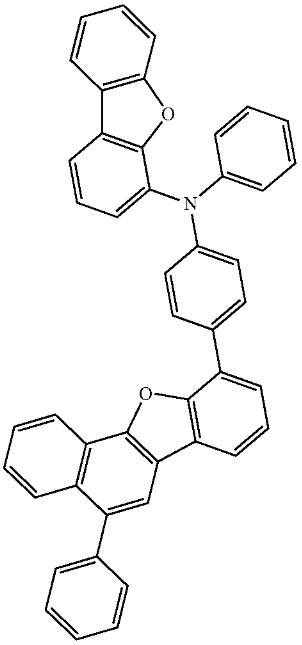
1-569
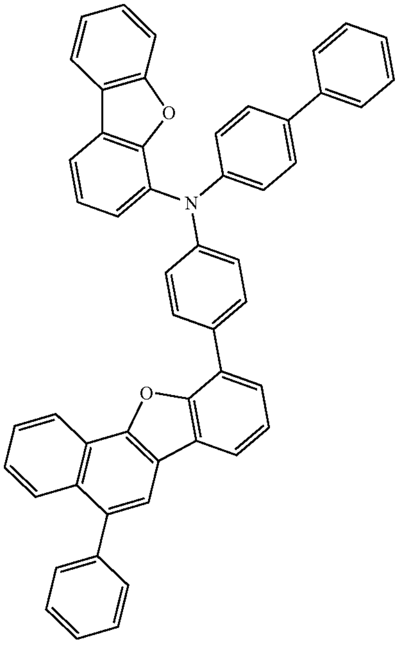

-continued
1-570
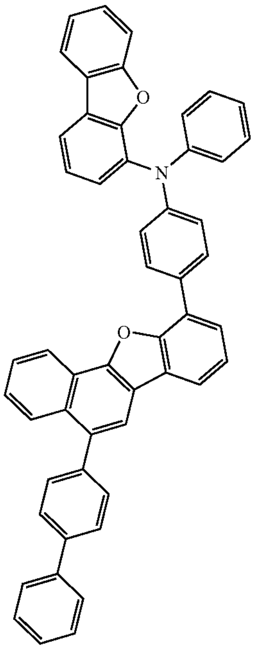
1-571
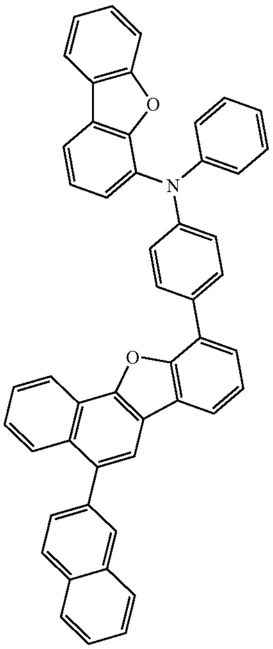
-continued
1-572
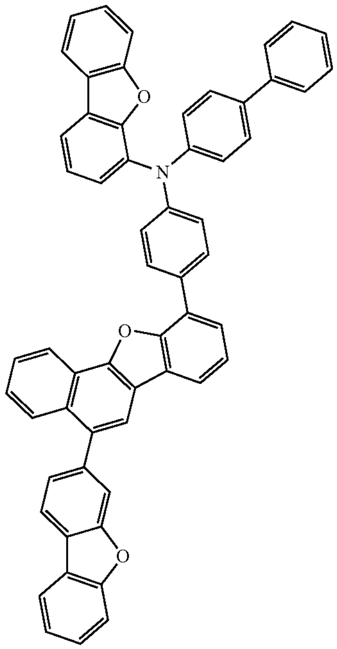
1-573
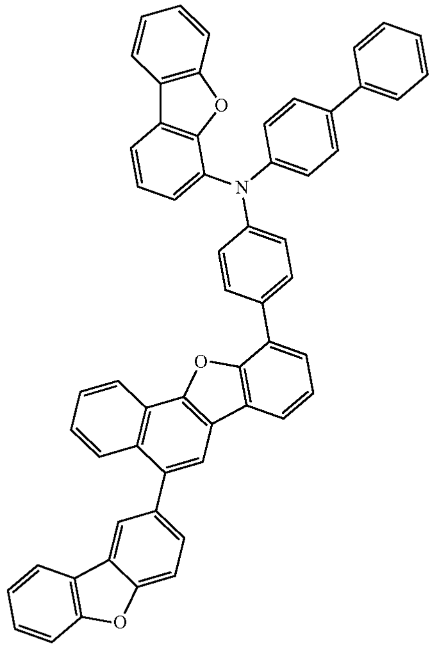

-continued
1-574
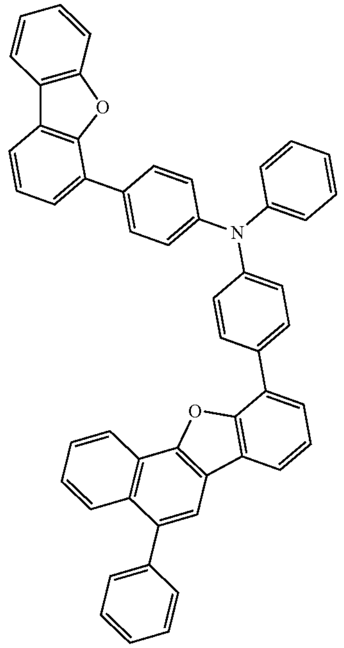
1-575
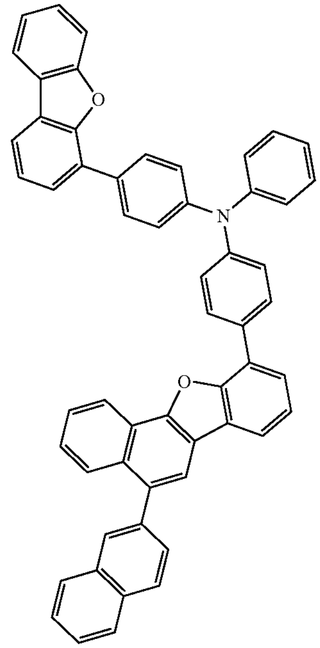
-continued
1-576
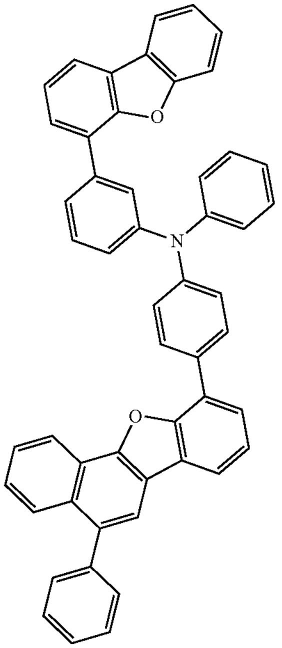
1-577
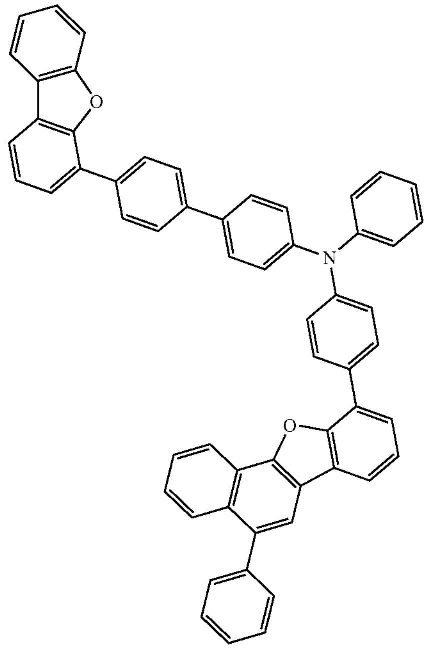

-continued
1-578
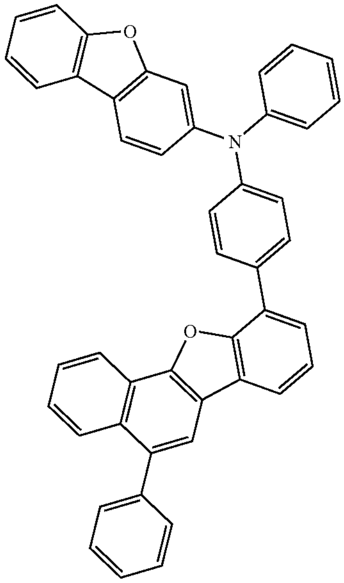
1-579
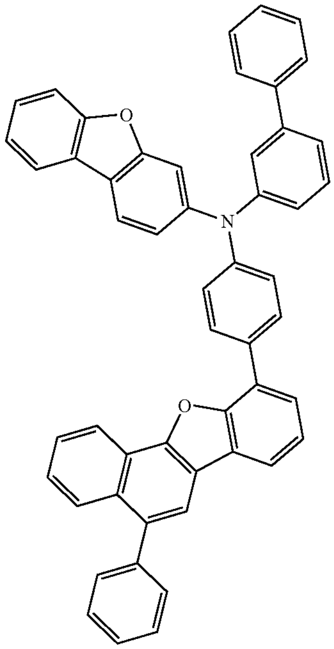
-continued
1-580
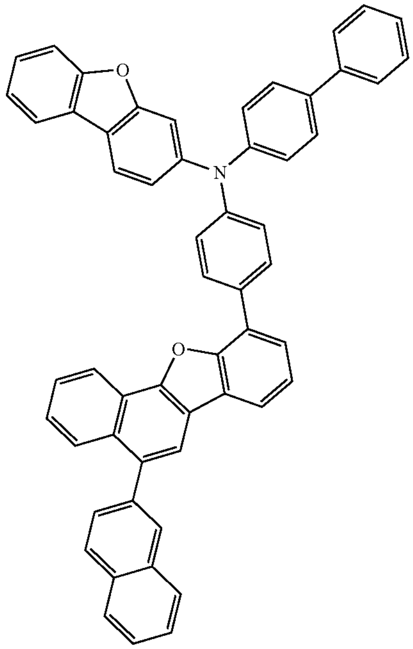
1-581
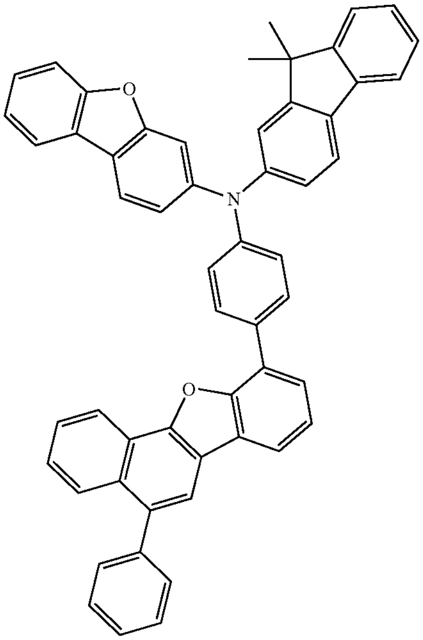

-continued
1-582
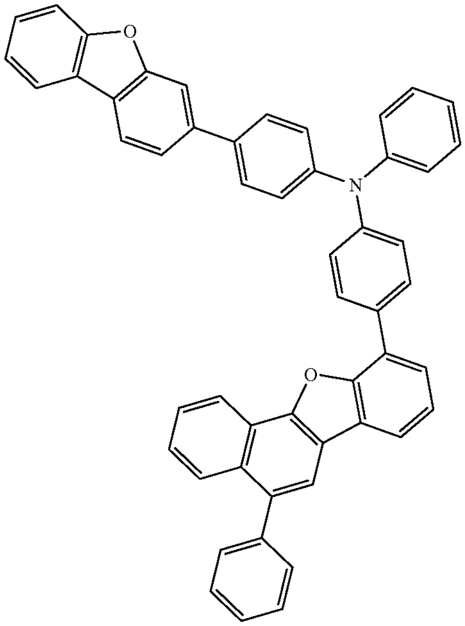
1-583
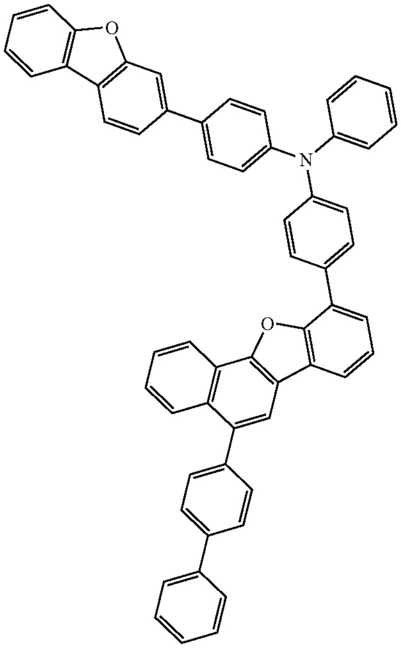
-continued
1-584
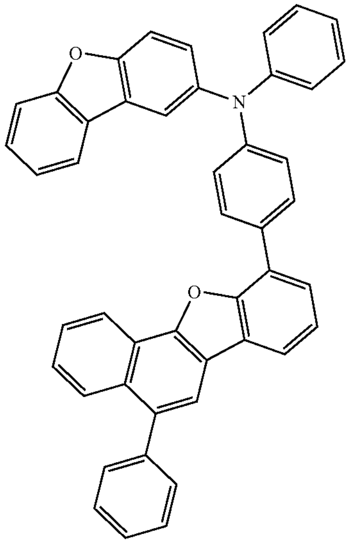
1-585
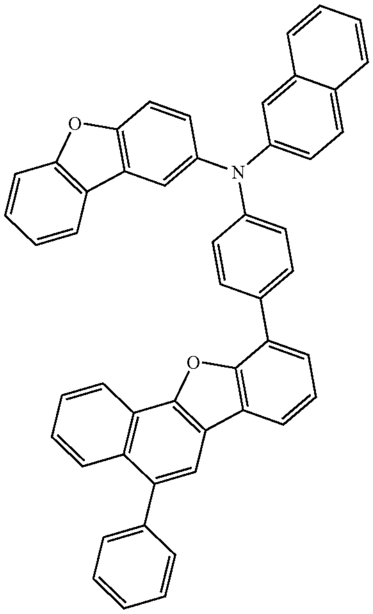

-continued
1-586
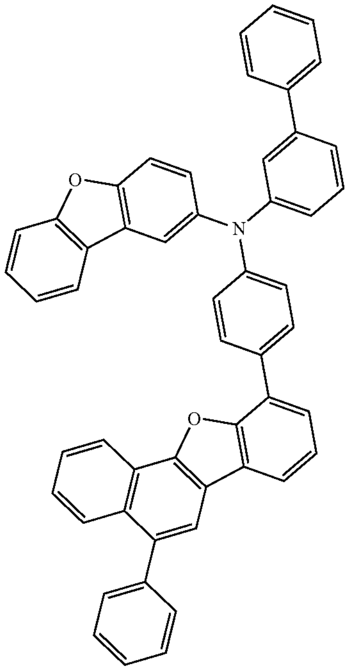
1-587
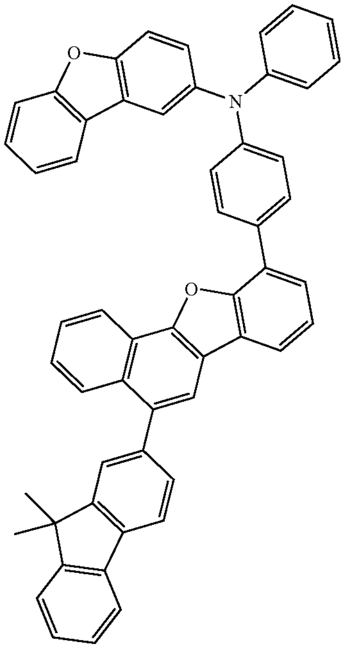
-continued
1-588
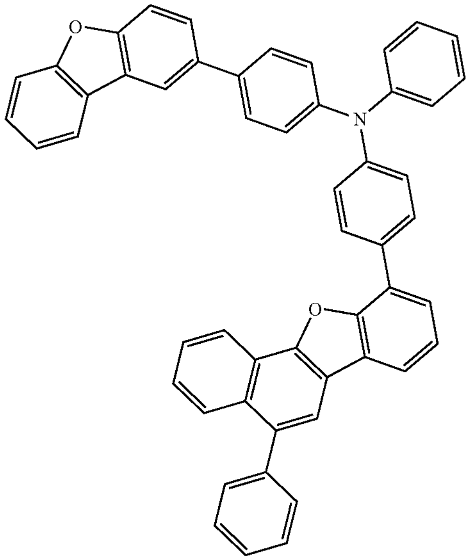
1-589
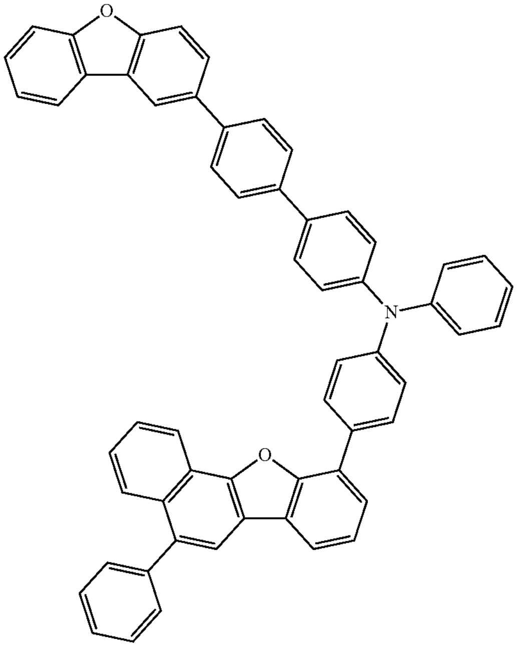

-continued
1-590
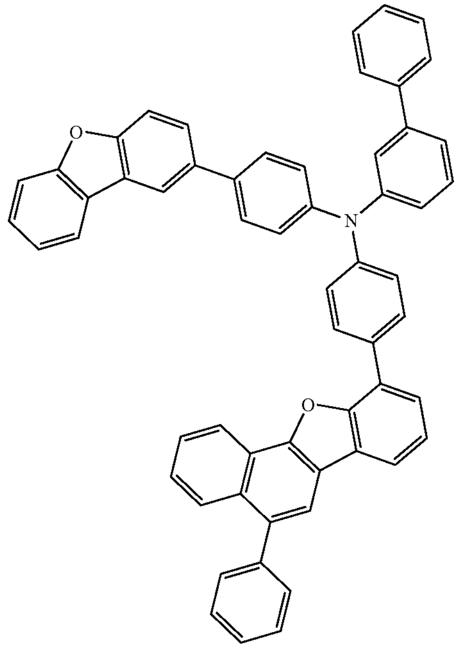
1-591
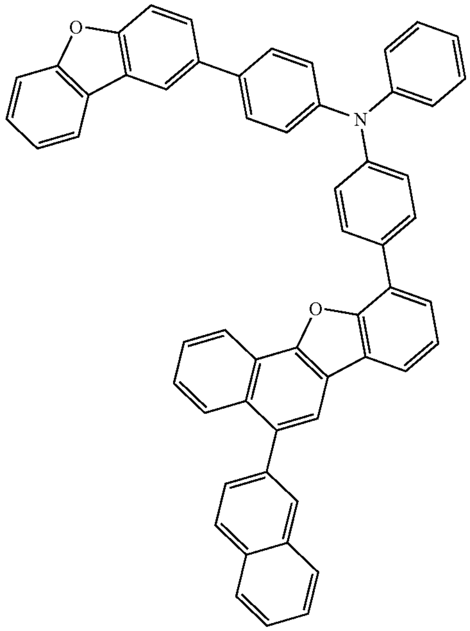
-continued
1-592
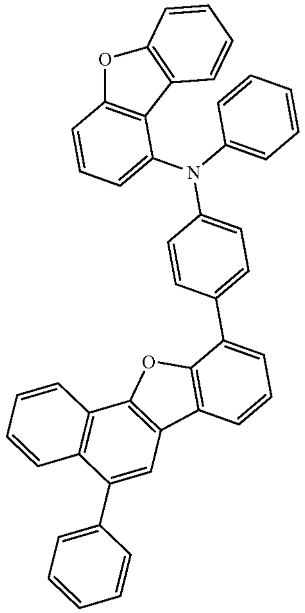
1-593
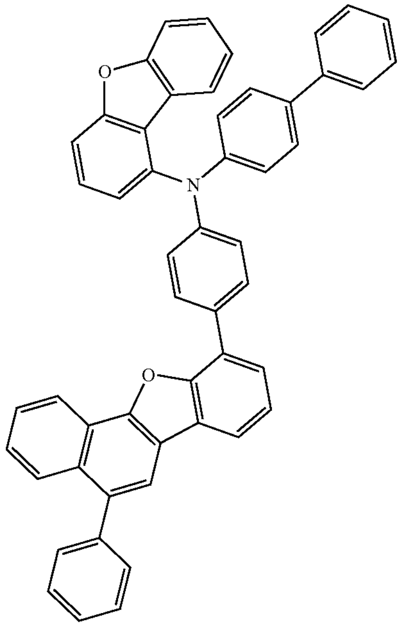

-continued
1-594
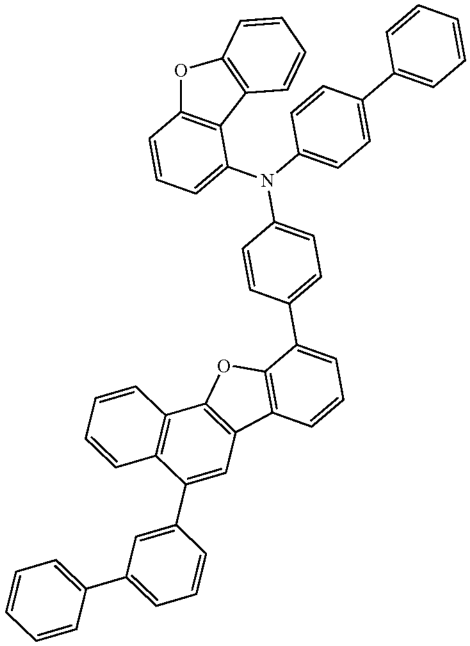
1-595
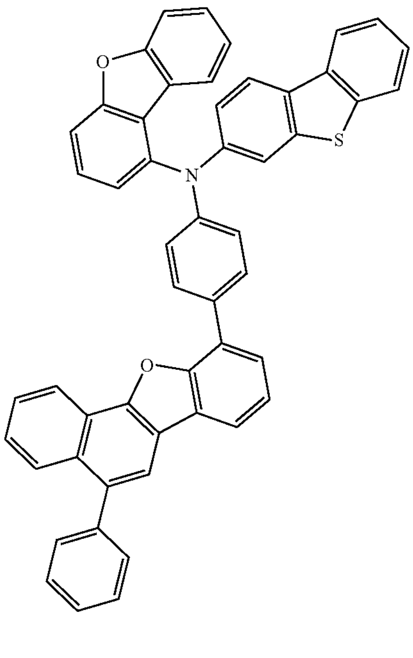
1-596
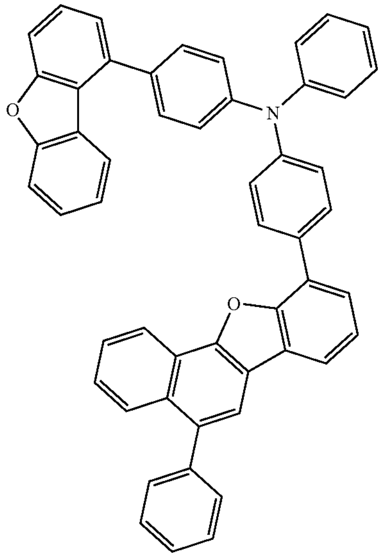
1-597
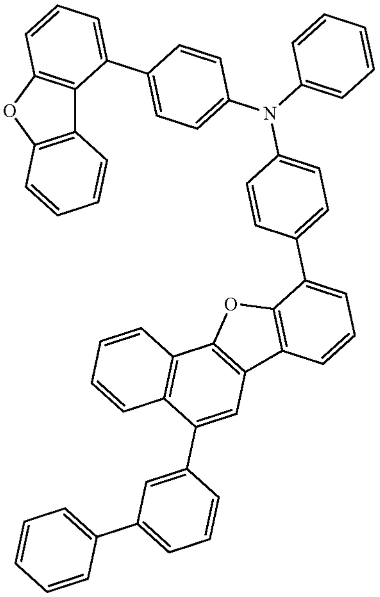

-continued
1-598
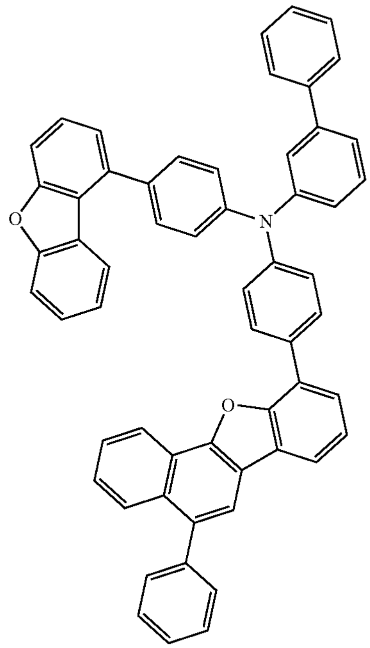
1-599
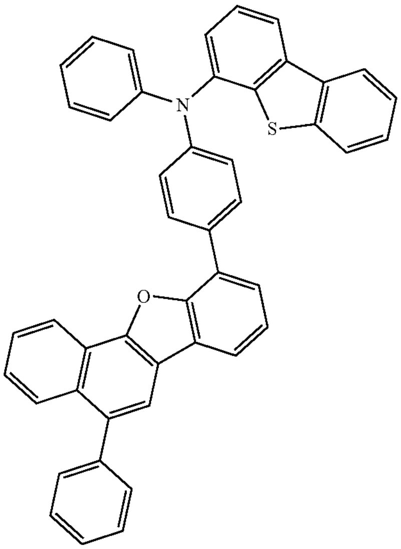
-continued
1-600
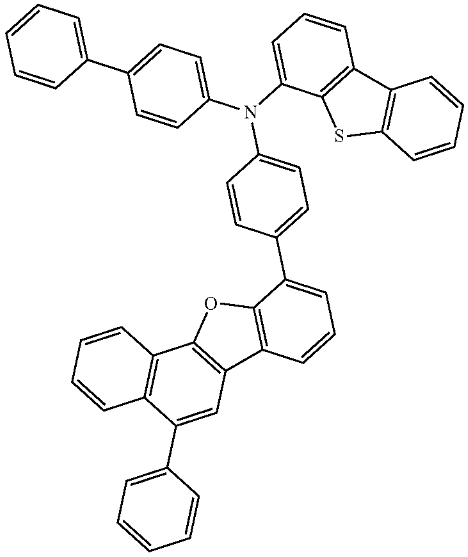
1-601
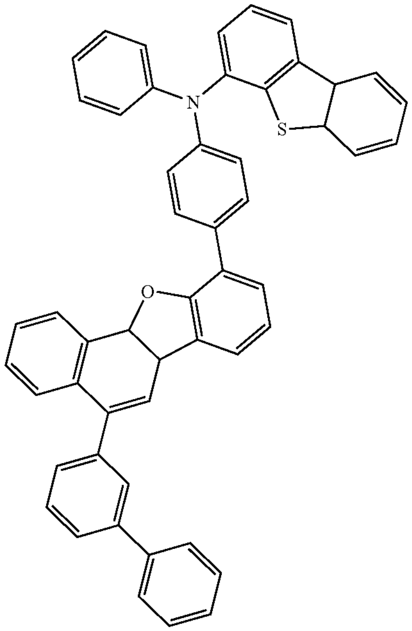

-continued
1-602
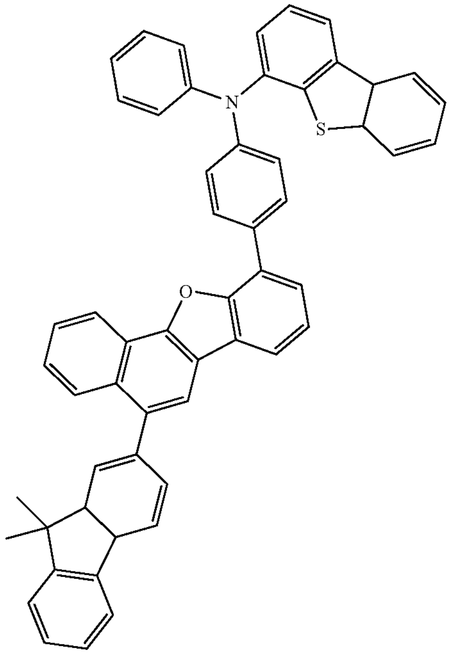
1-603
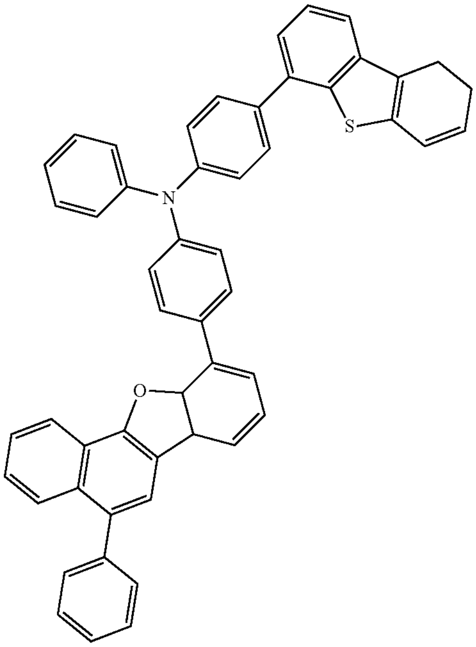
-continued
1-604
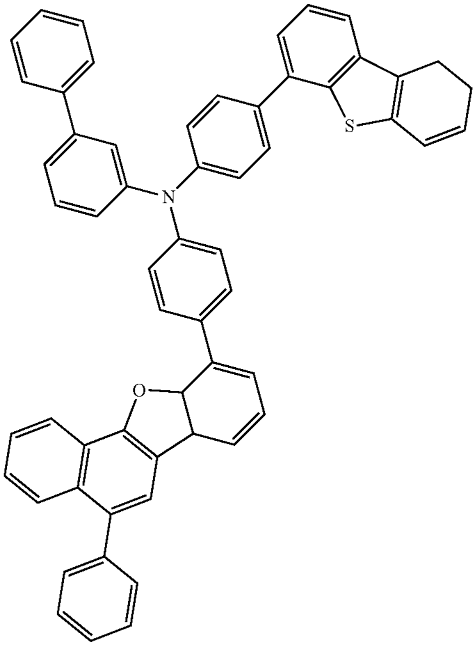
1-605
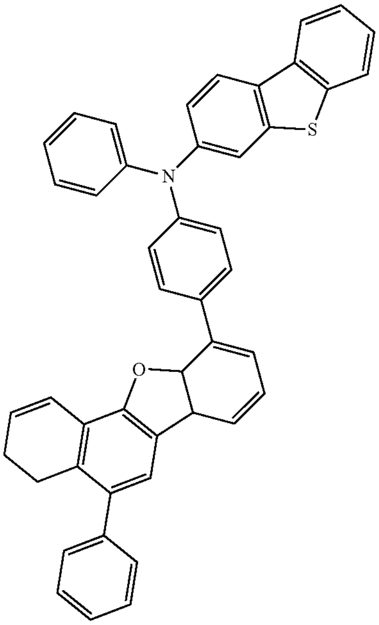

-continued
1-606
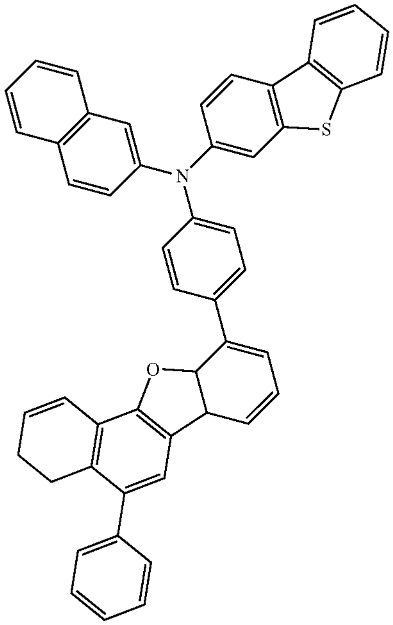
1-607
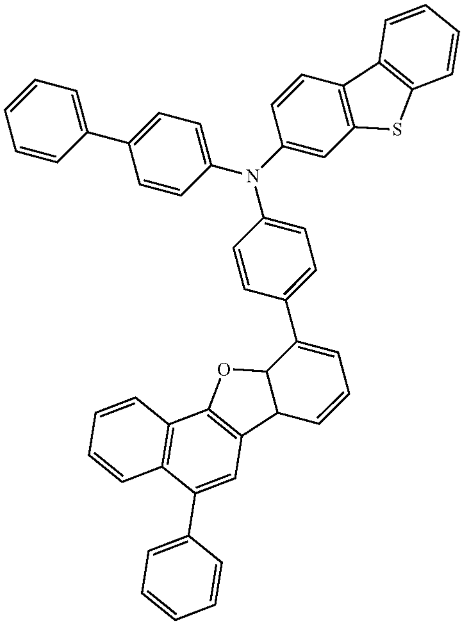
-continued
1-608
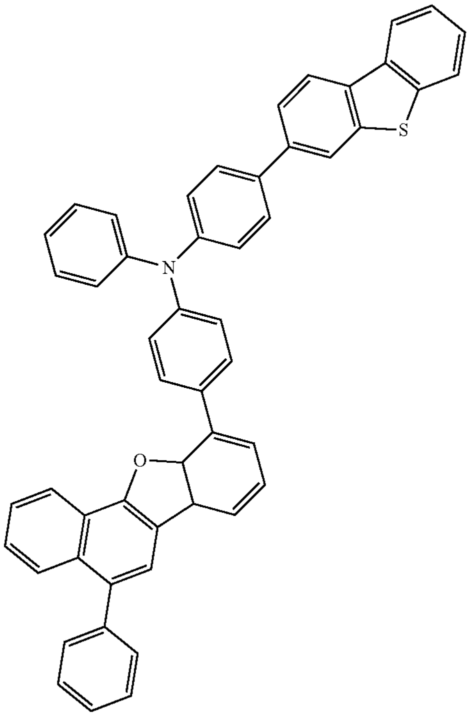
1-609
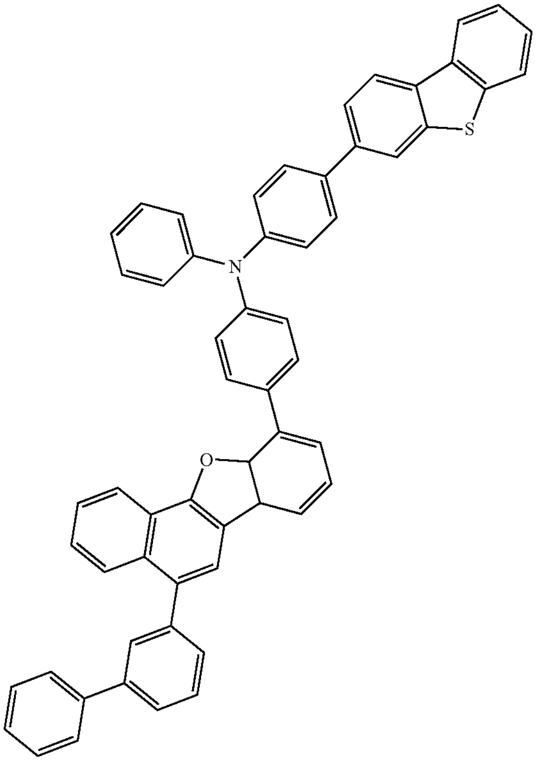

-continued
1-610
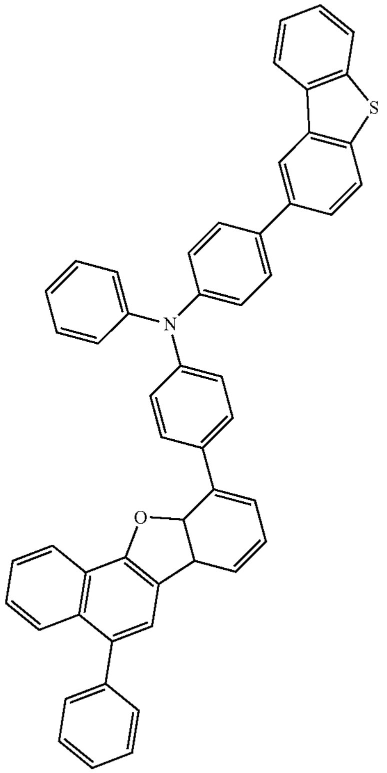
1-611
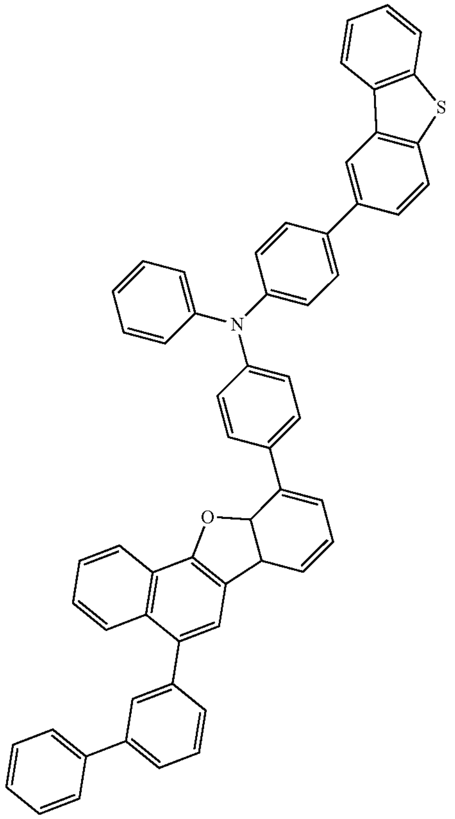
-continued
1-612
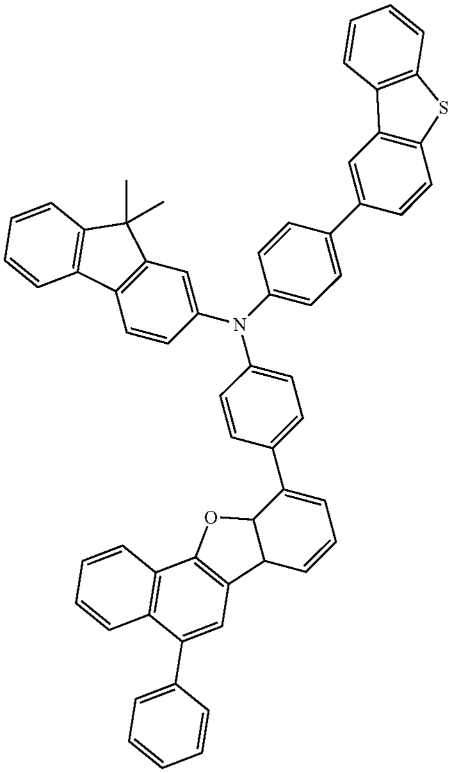
1-613
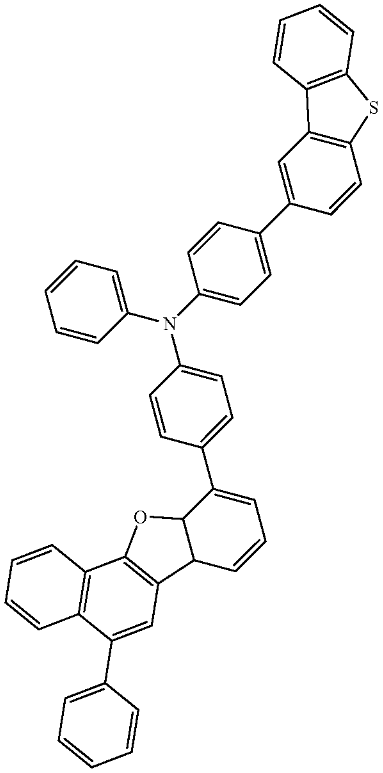

-continued
1-614
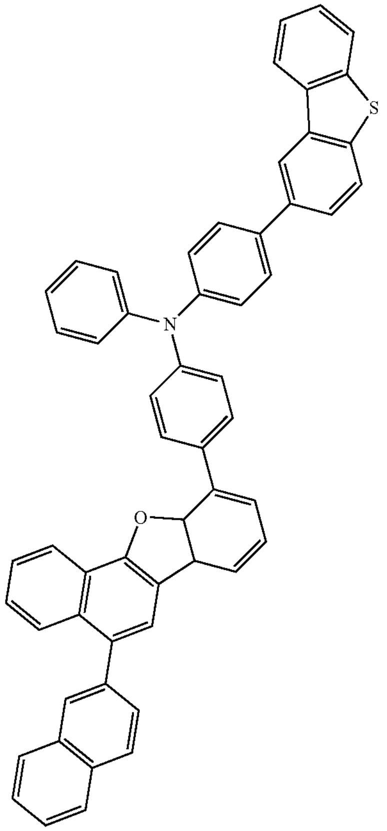
1-615
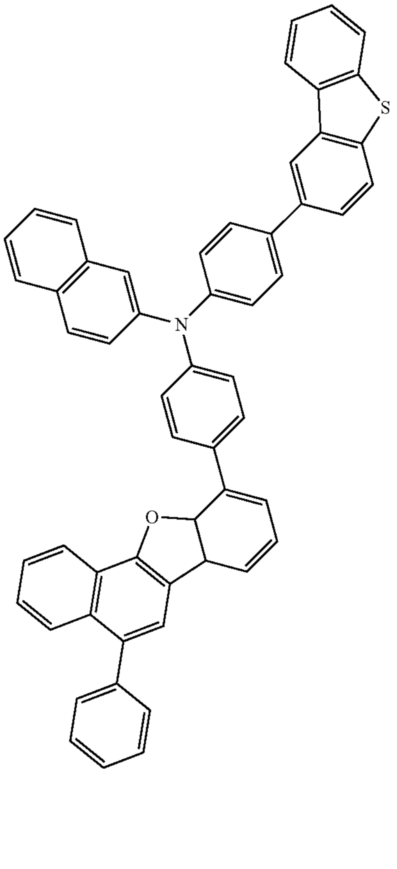
-continued
1-616
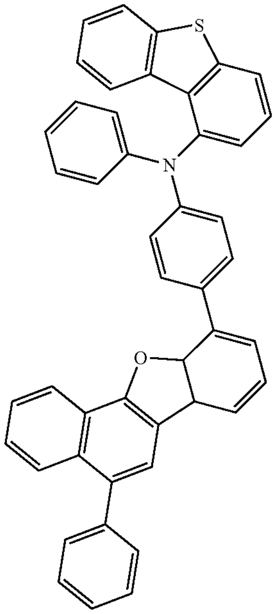
1-617
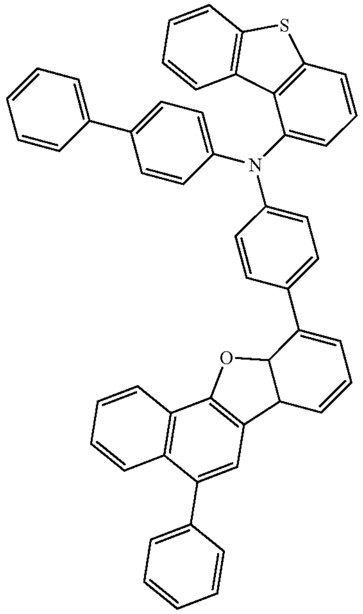

-continued
1-618
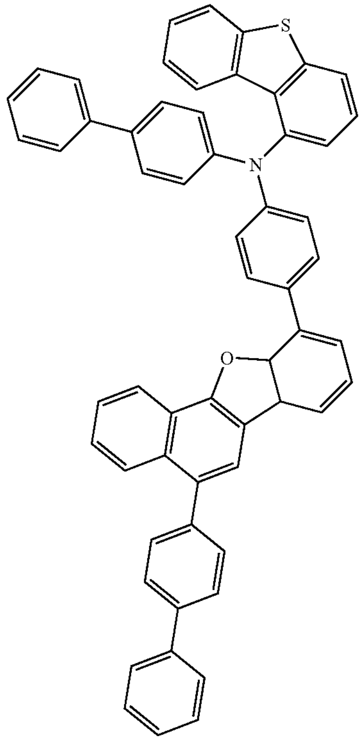
1-619
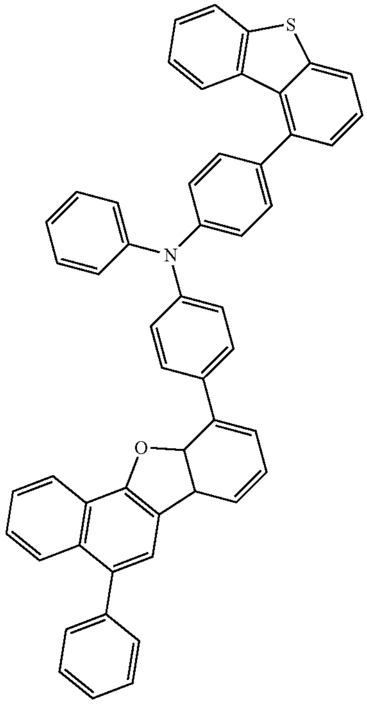
-continued
1-620
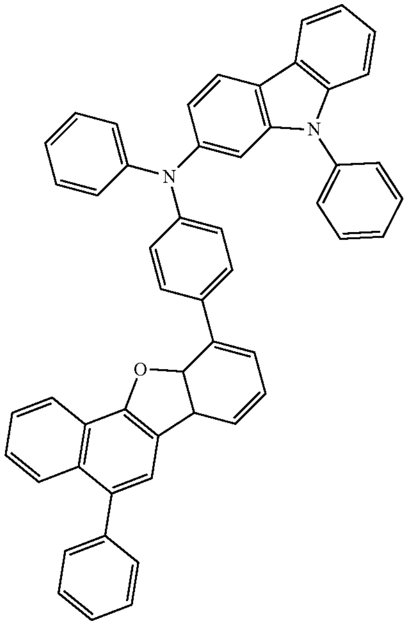
1-621
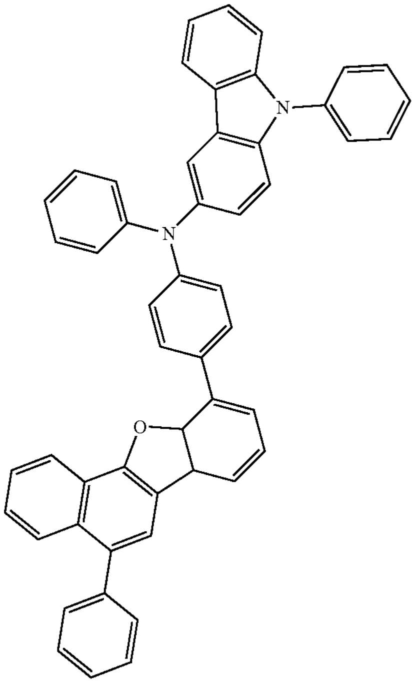

1-622
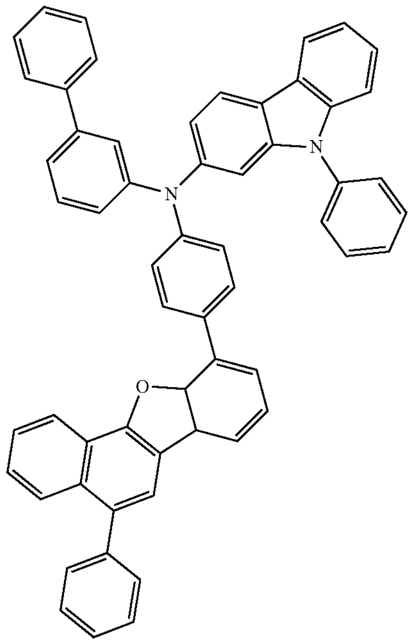
1-623
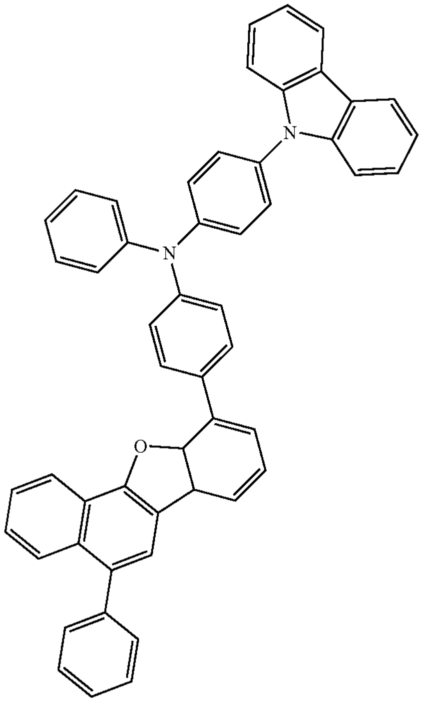
1-624
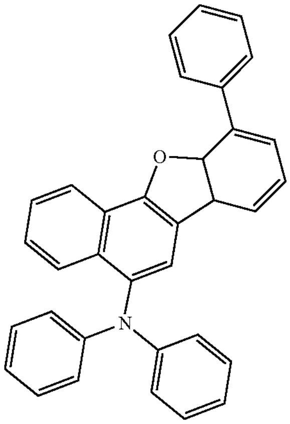
1-625
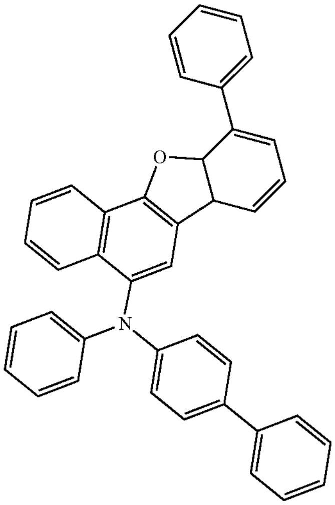
1-626
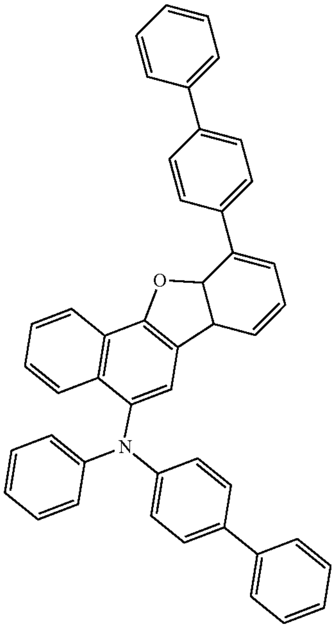

-continued
1-627
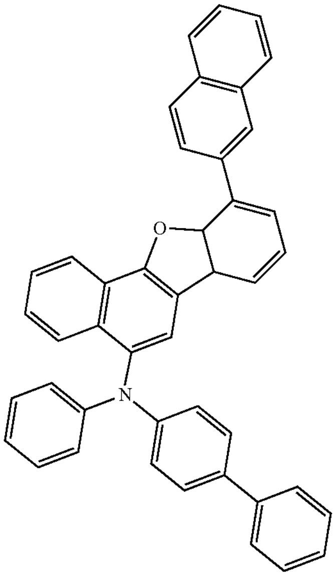
1-628
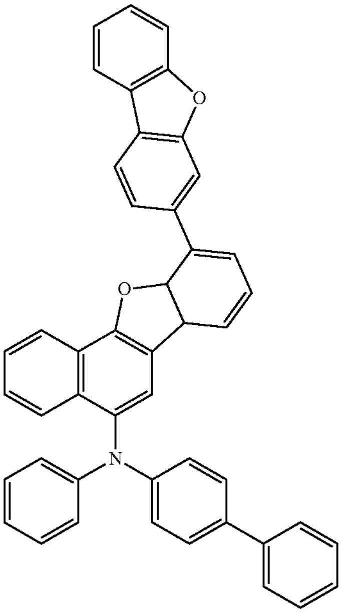
-continued
1-629
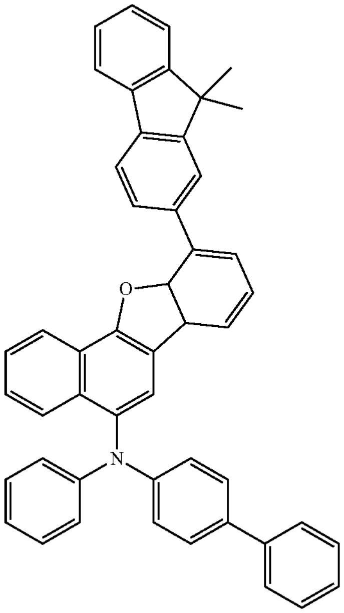
1-630
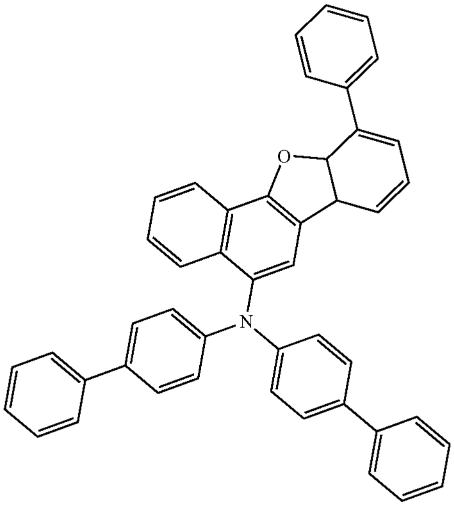

-continued
1-631
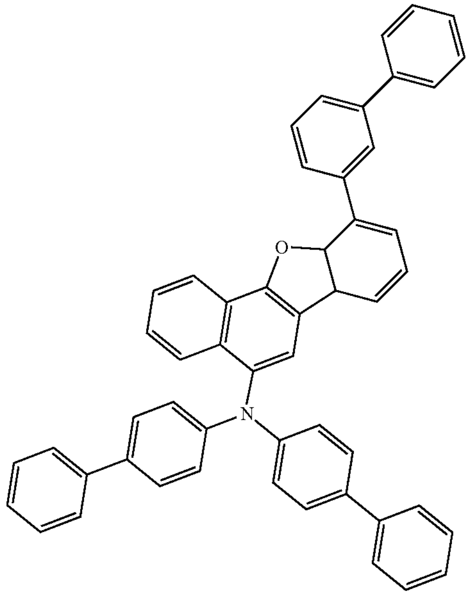
1-632
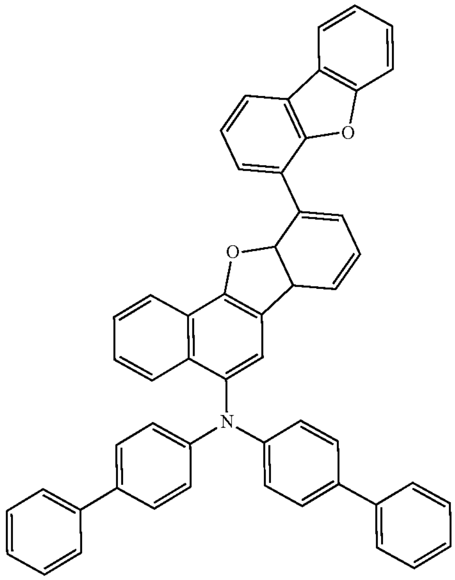
-continued
1-633
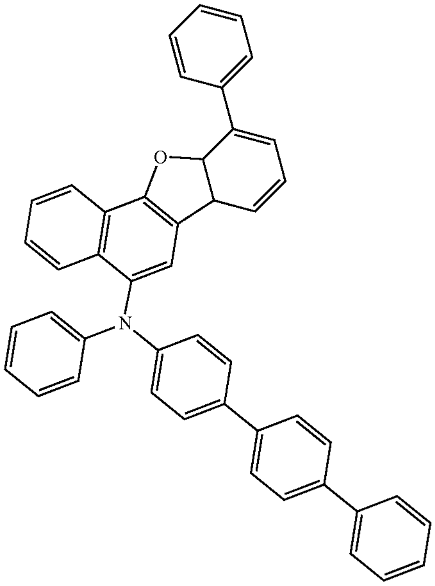
1-634
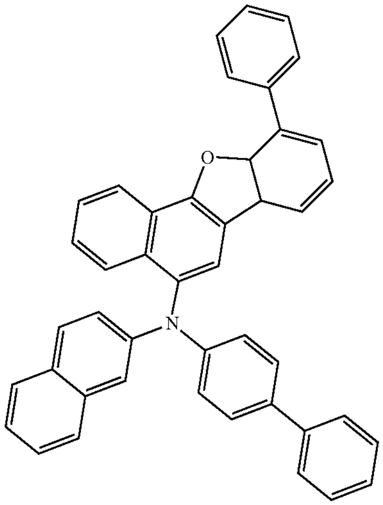

-continued
1-635
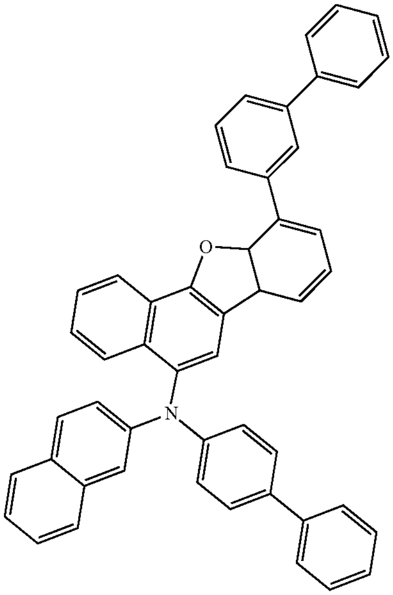
1-636
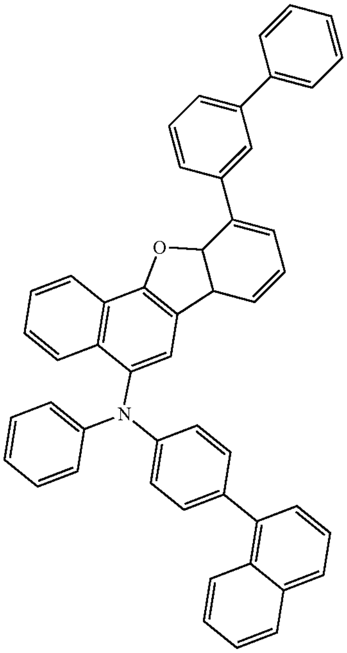
-continued
1-637
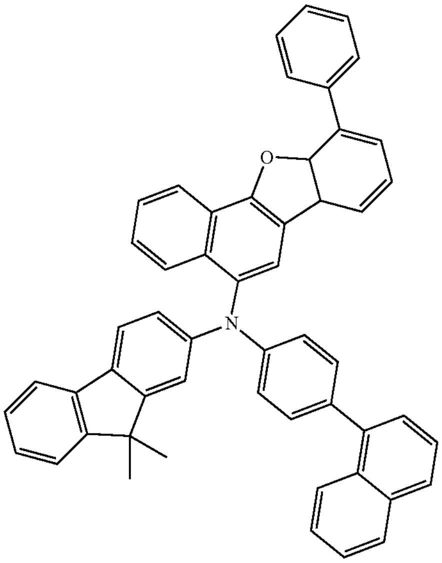
1-638
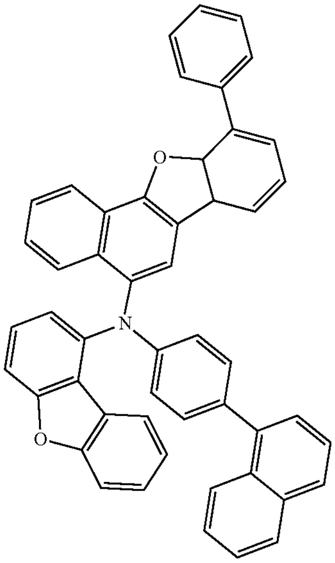

-continued
1-639
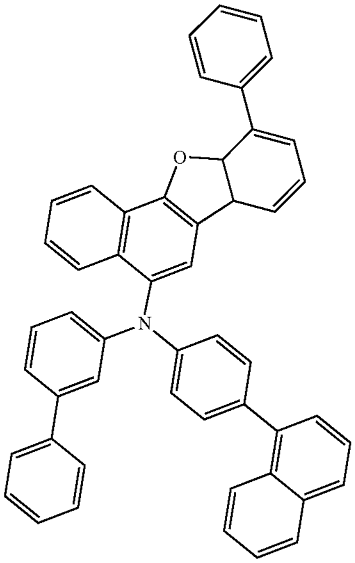
1-640
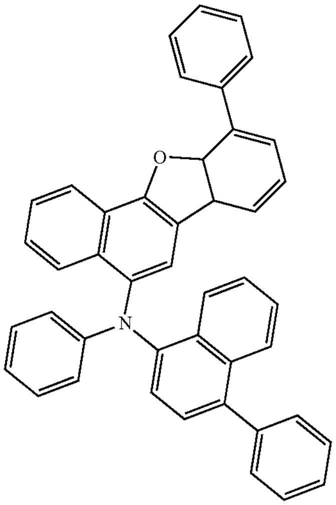
1-641
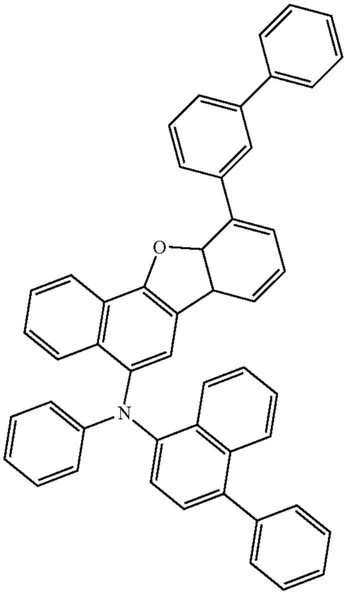
-continued
1-642
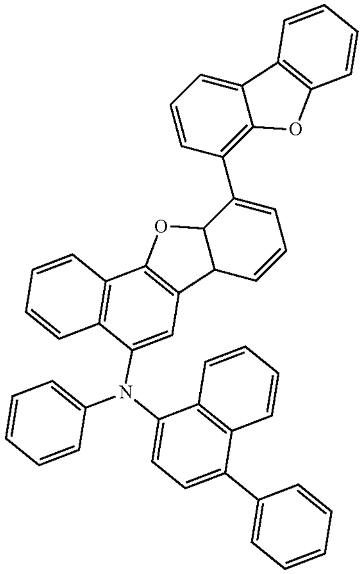
1-643
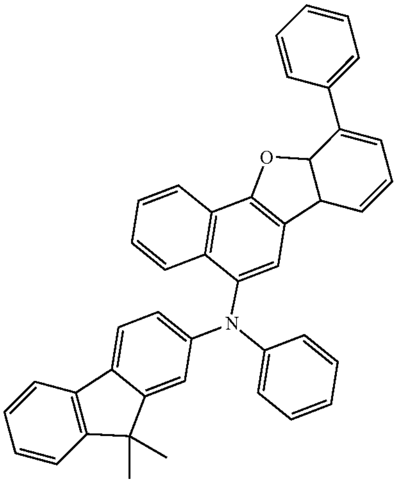
1-644
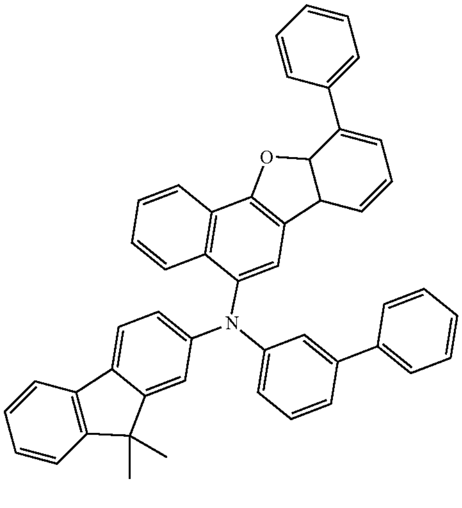

-continued
1-645
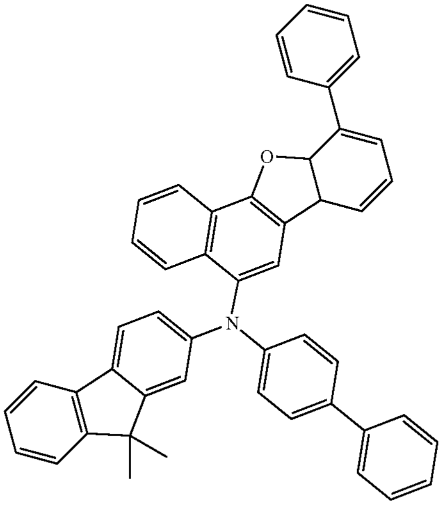
1-646
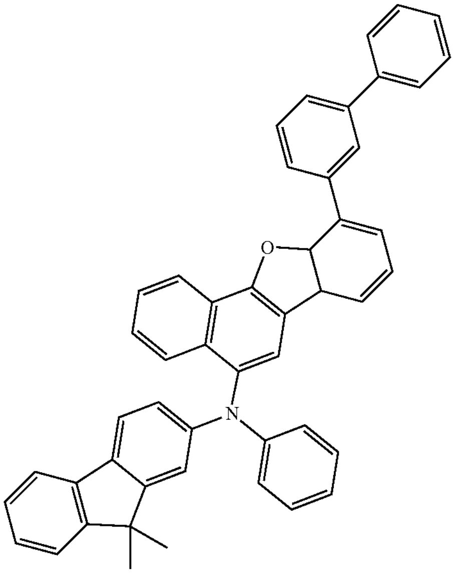
1-647
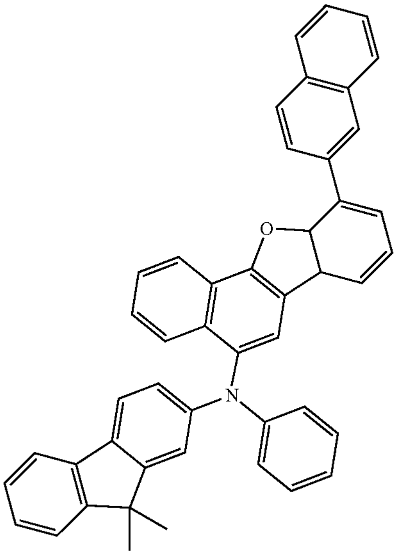
-continued
1-648
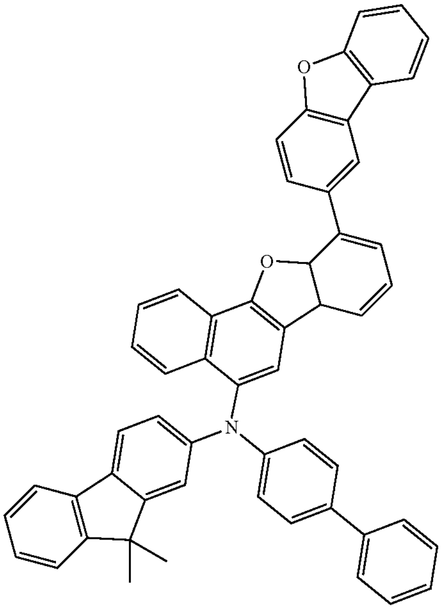
1-649
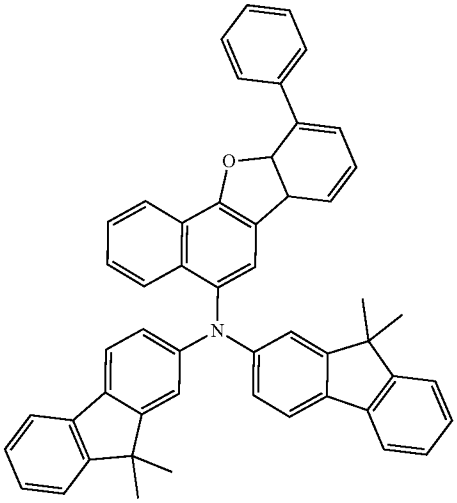

-continued
1-650
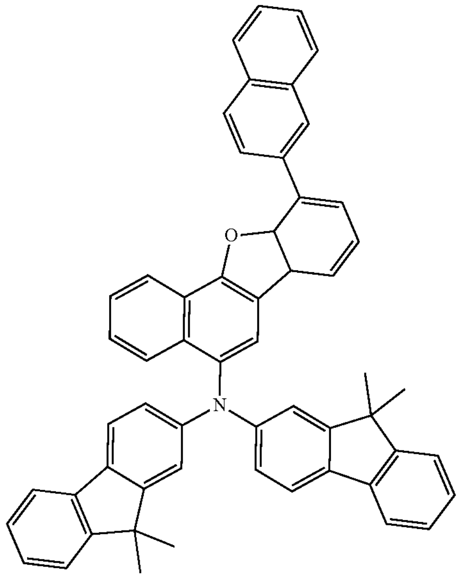
1-651
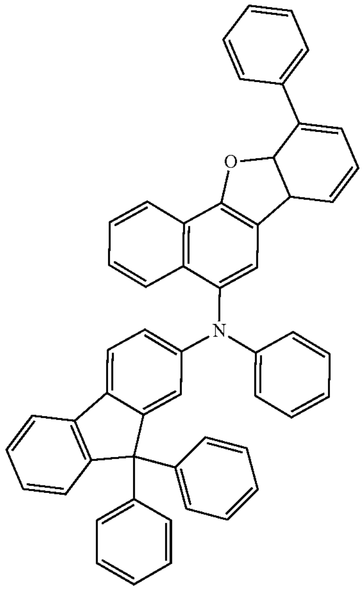
-continued
1-652
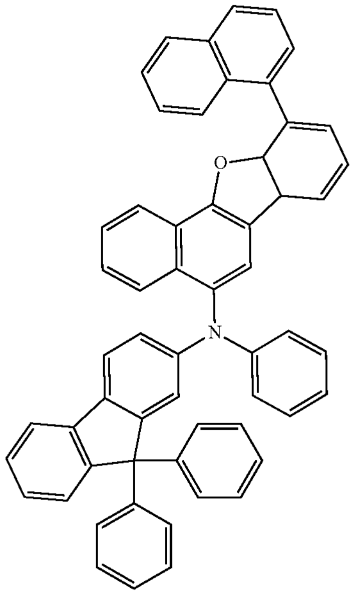
1-653
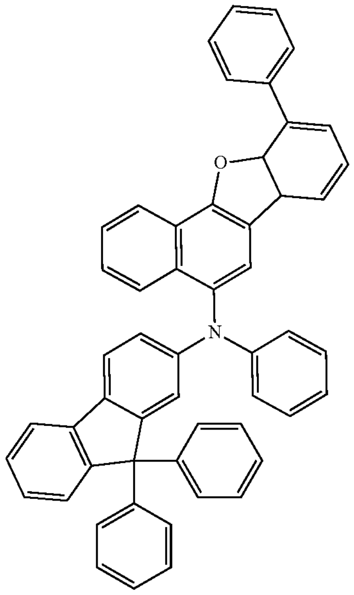

-continued
1-654
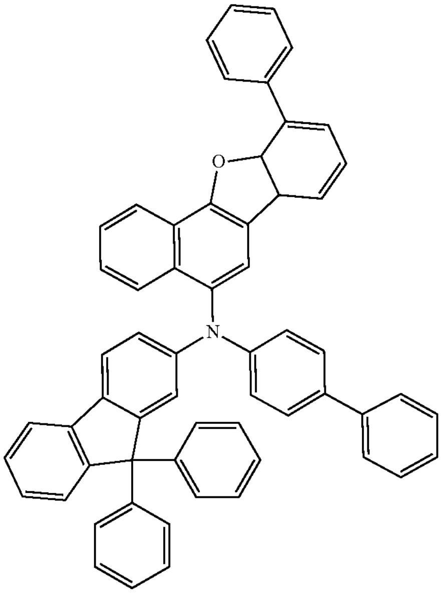
1-655
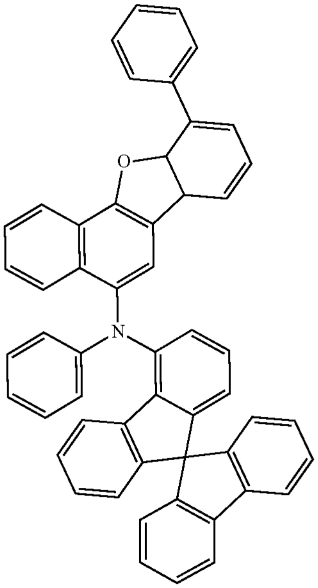
-continued
1-656
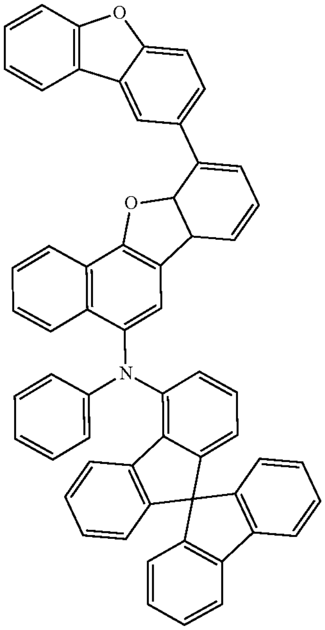
1-657
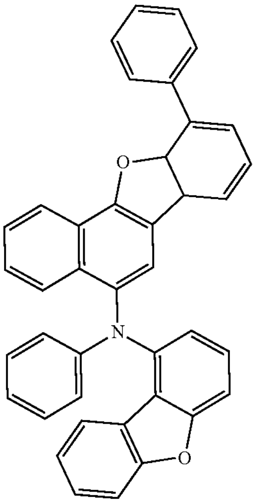
1-658
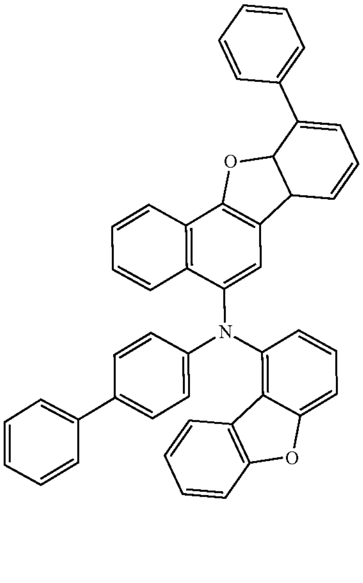

-continued
1-659
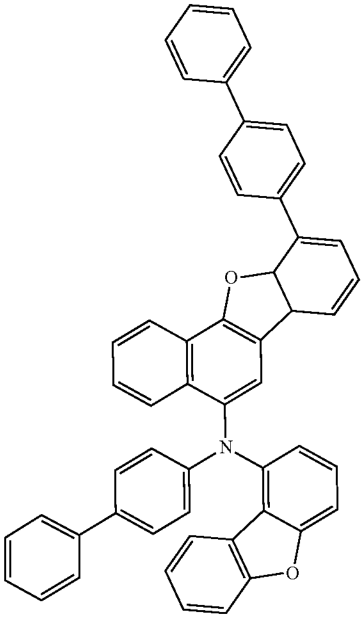
1-660
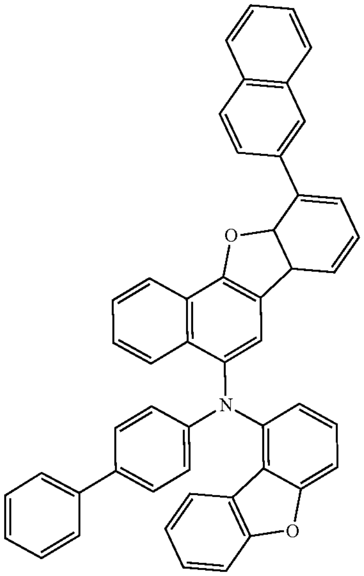
-continued
1-661
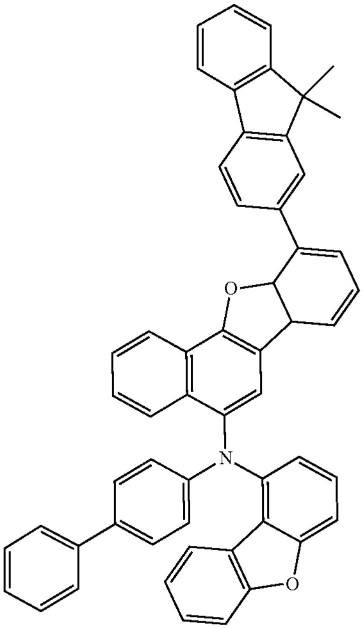
1-662
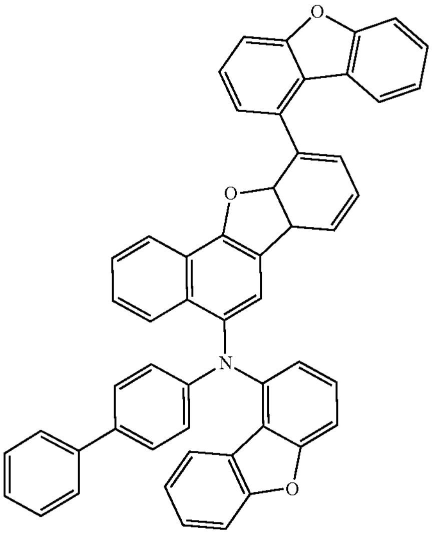

-continued
1-663
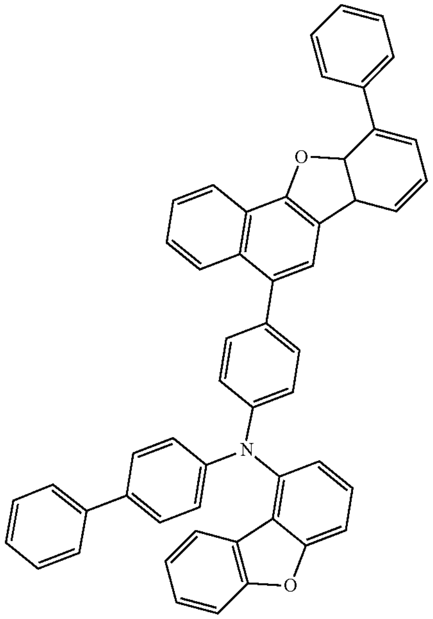
1-664
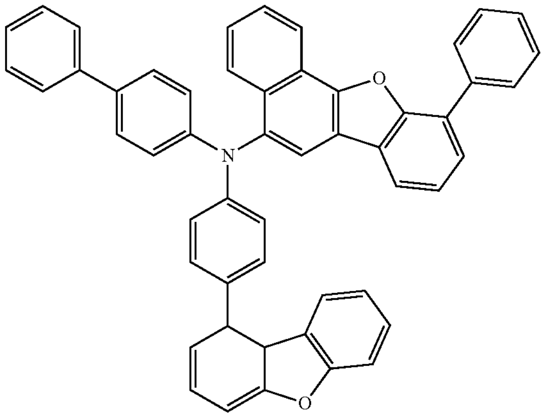
-continued
1-665
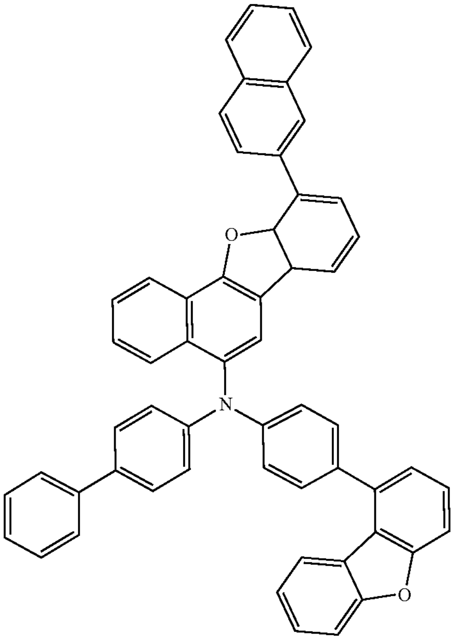
1-666
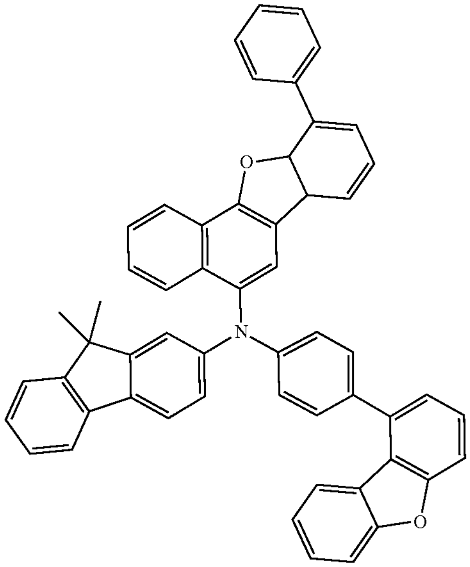

-continued
1-667
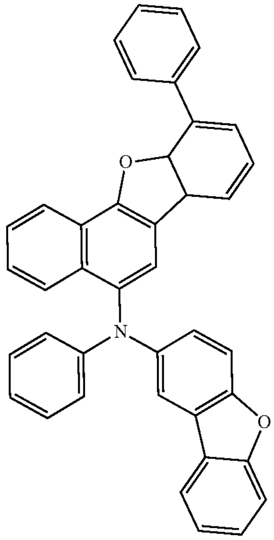
1-668
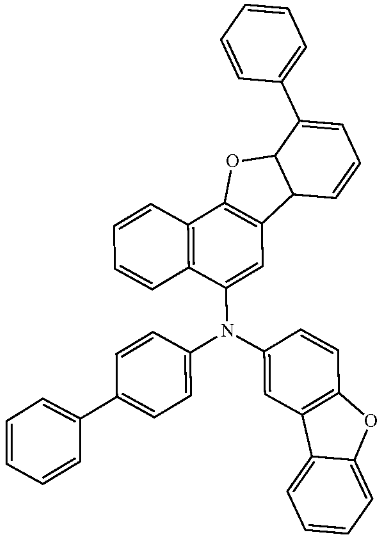
-continued
1-669
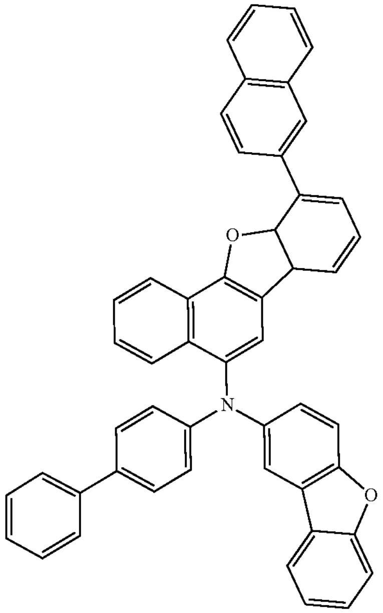
1-670
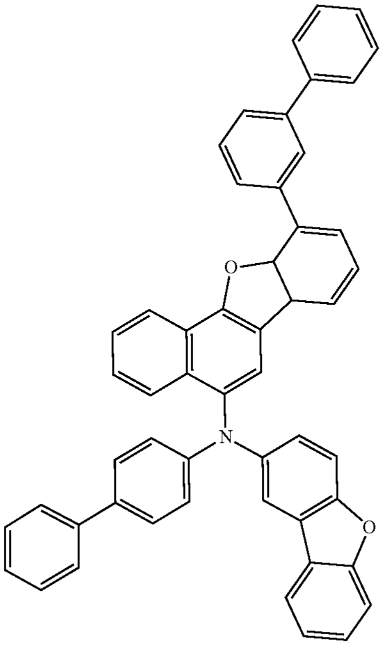

1-671
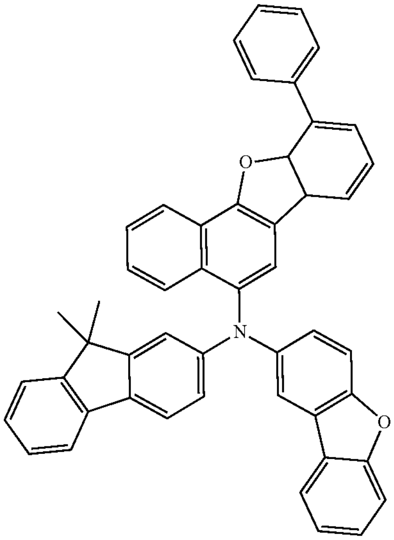
1-672
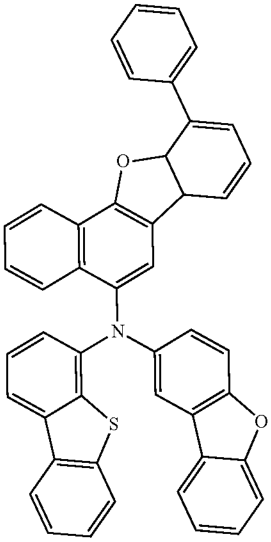
1-673
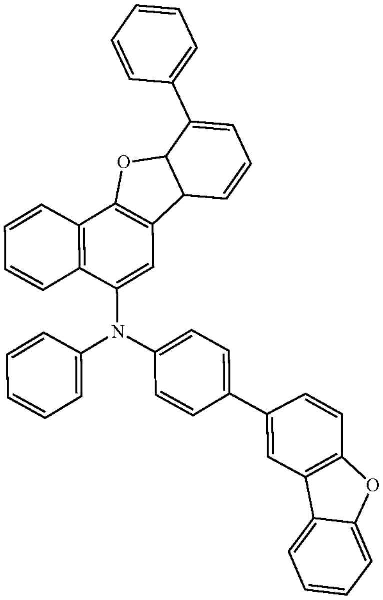
1-674
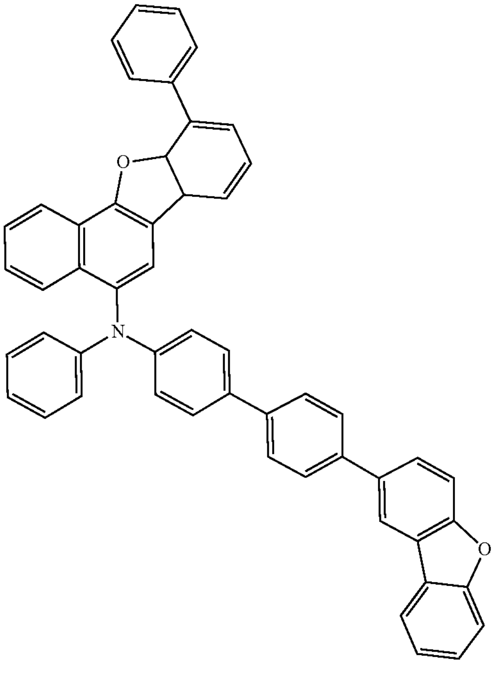

-continued
1-675
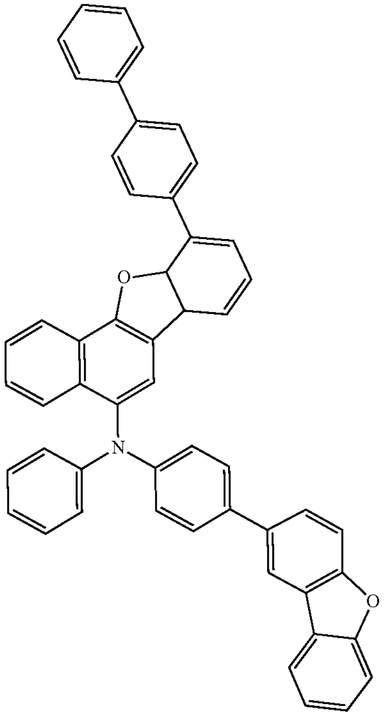
1-676
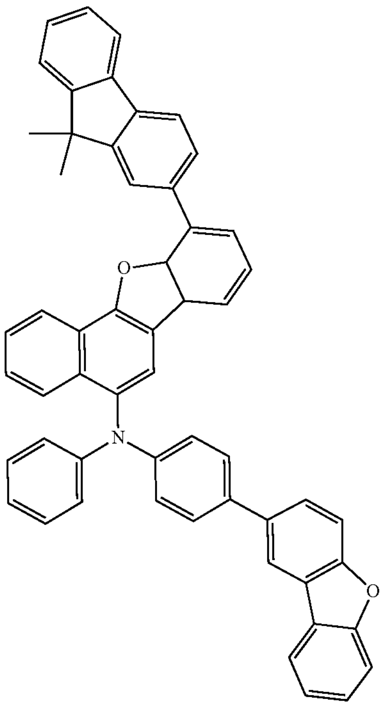
-continued
1-677
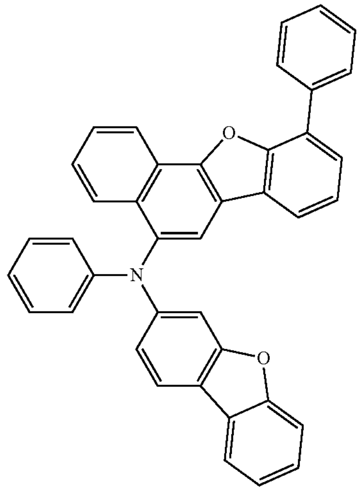
1-678
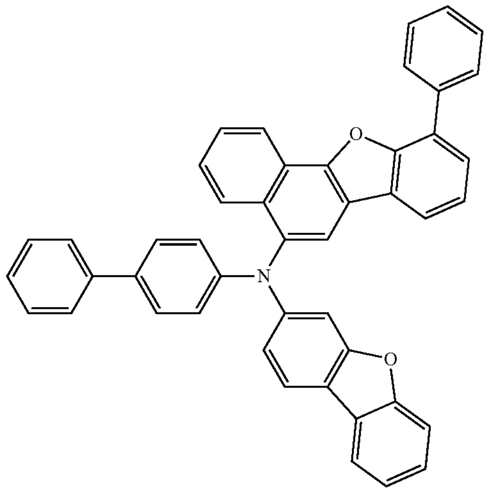
1-679
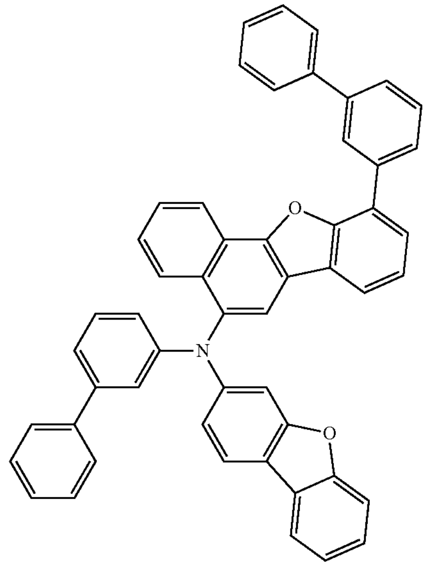

-continued
1-680
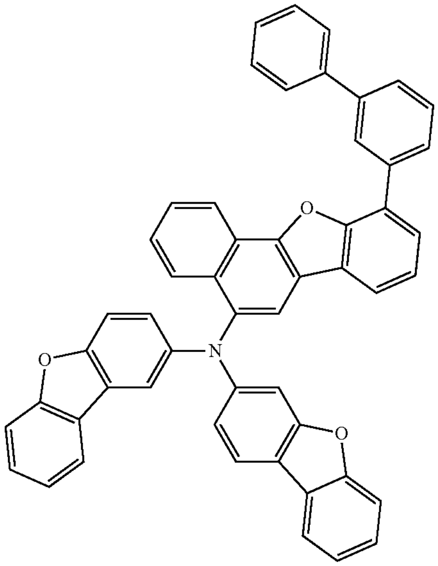
1-681
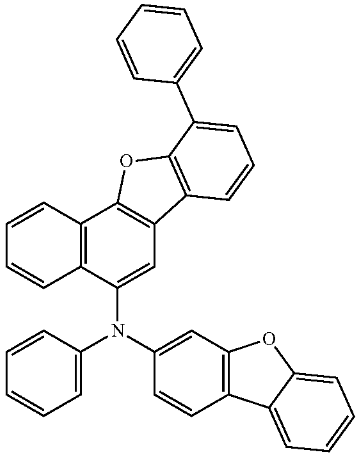
-continued
1-682
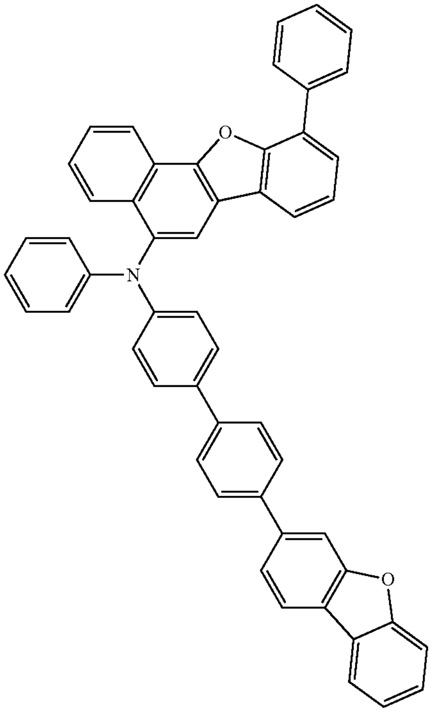
1-683
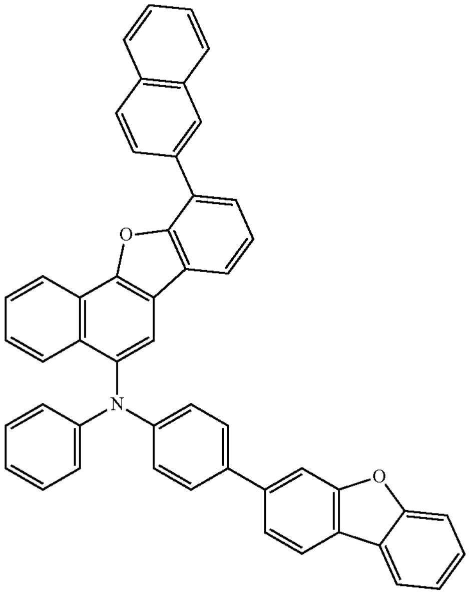

-continued
1-684
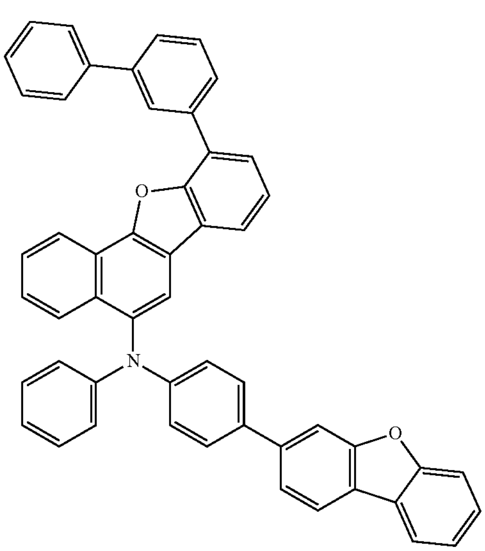
1-685
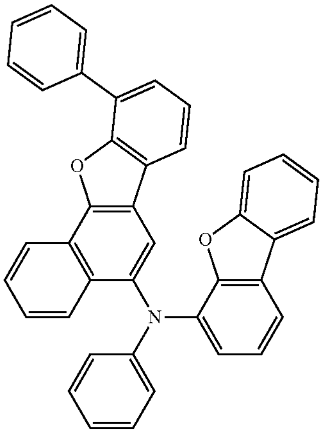
1-686
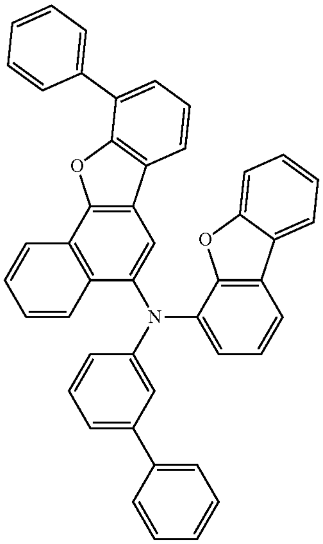
-continued
1-687
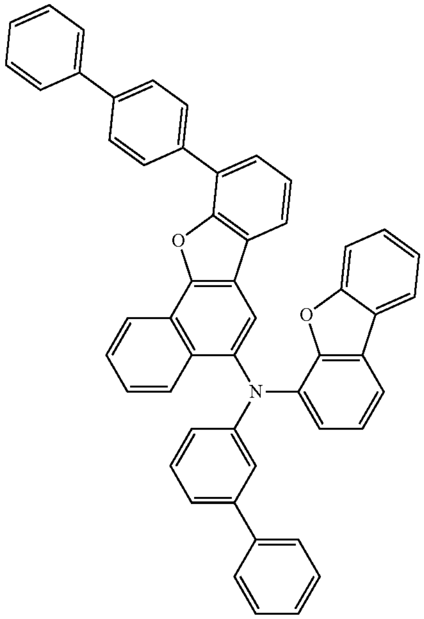
1-688
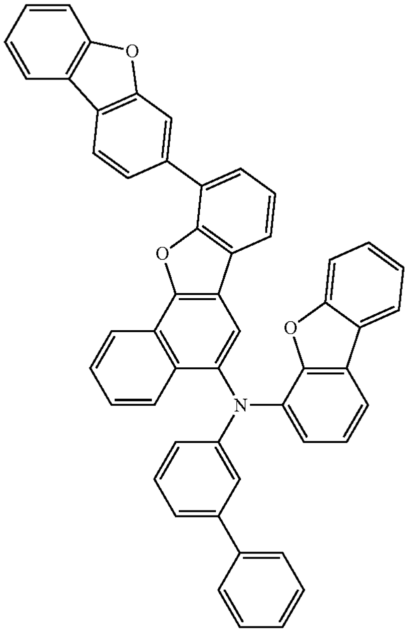

-continued
1-689
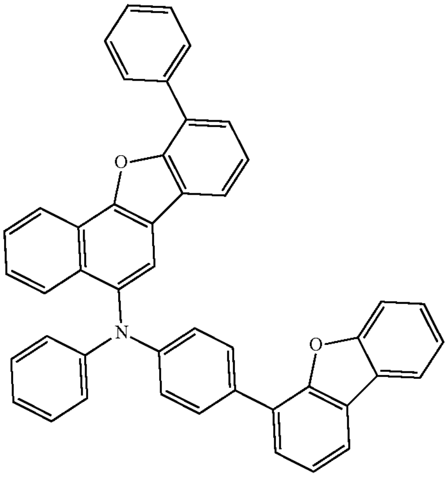
1-690
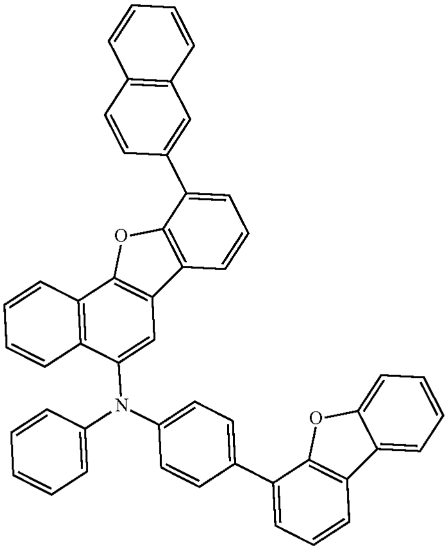
1-691
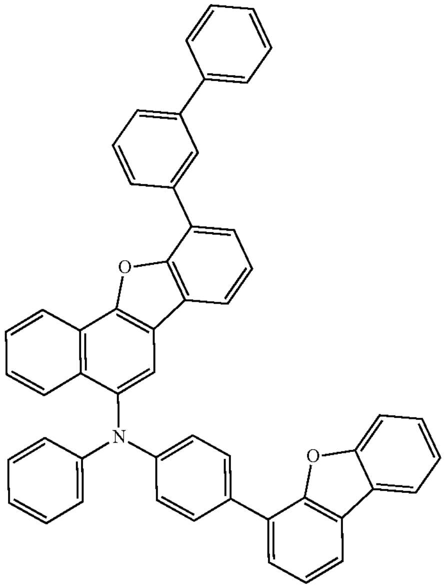
-continued
1-692
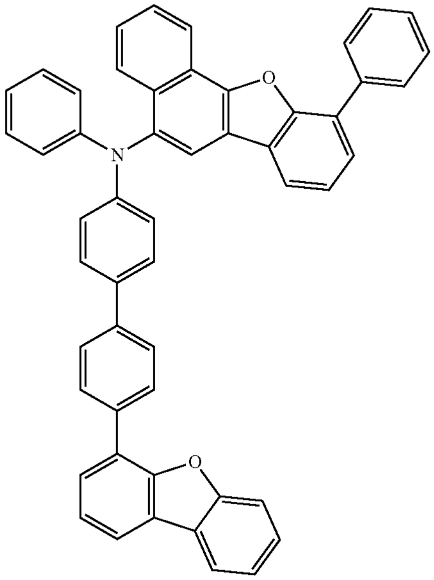
1-693
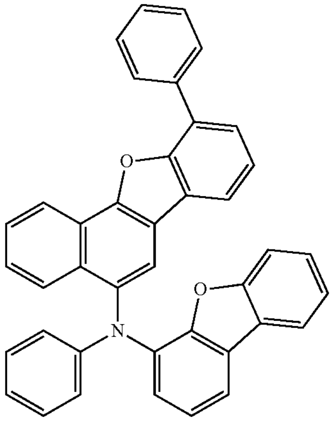
1-694
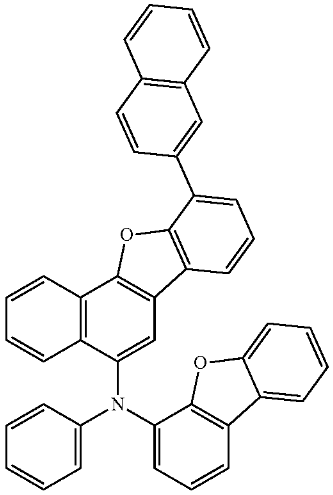

-continued
1-695
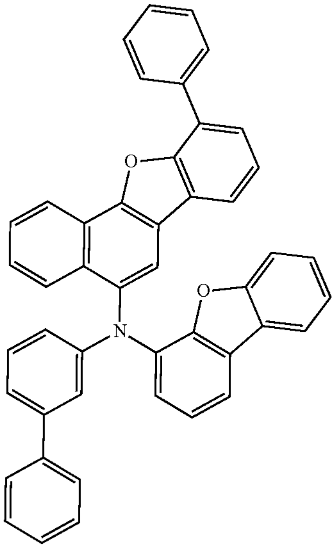
1-696
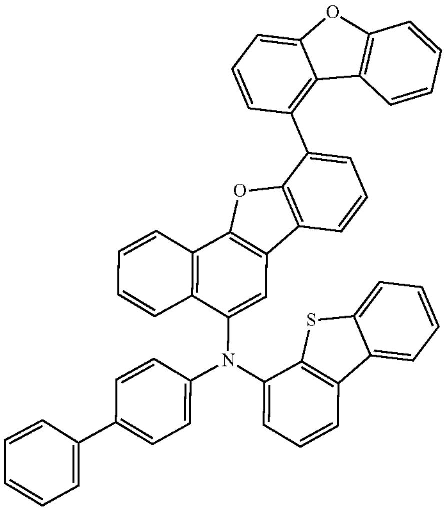
1-697
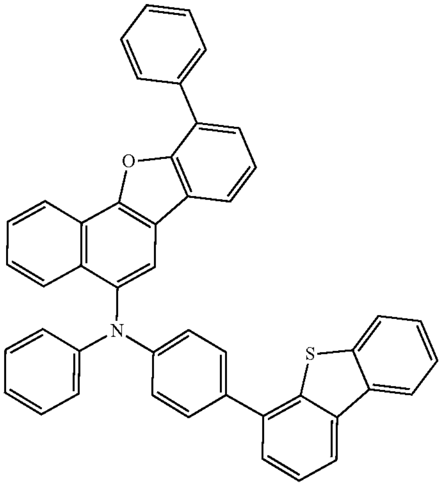
1-698
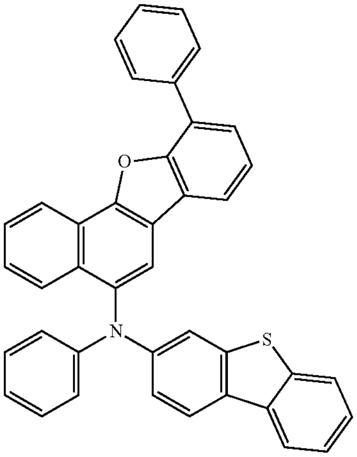
1-699
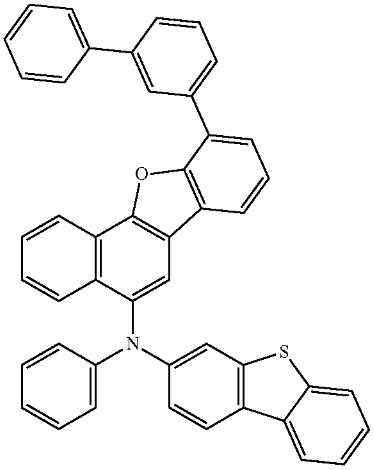
1-700
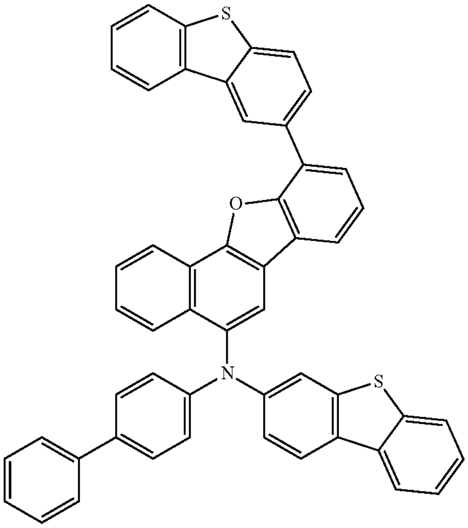

-continued
1-701
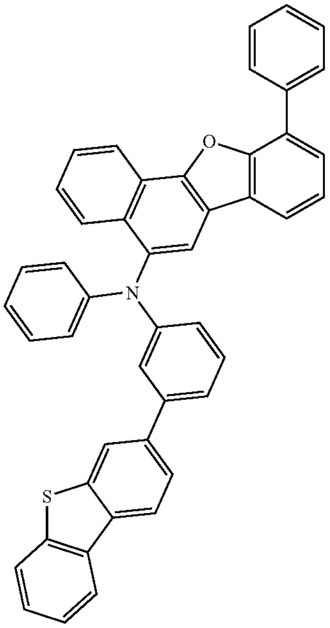
1-702
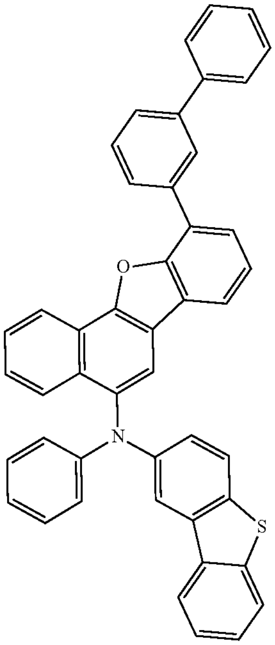
-continued
1-703
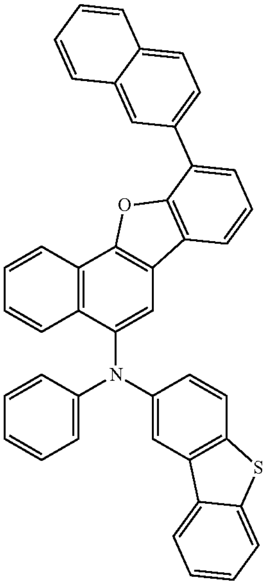
1-704
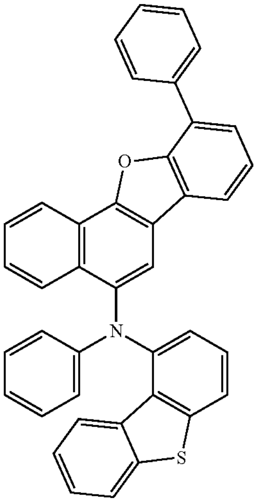
1-705
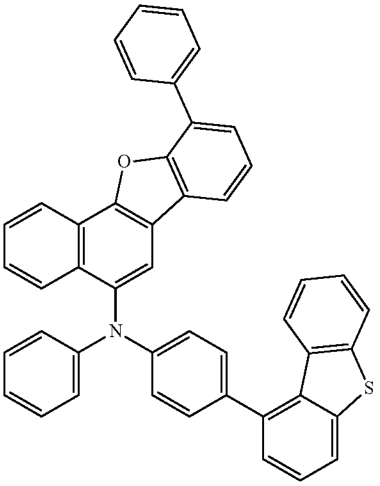

-continued
1-706
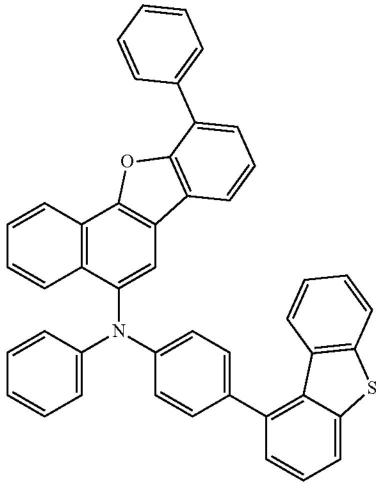
1-707
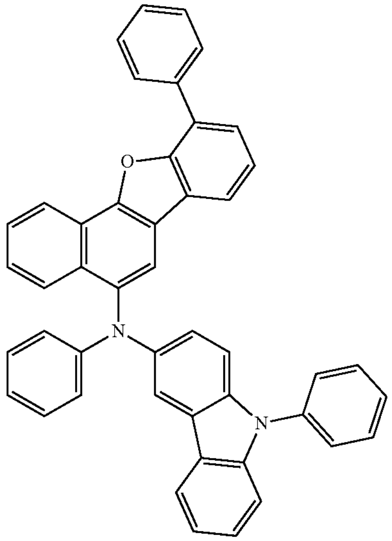
1-708
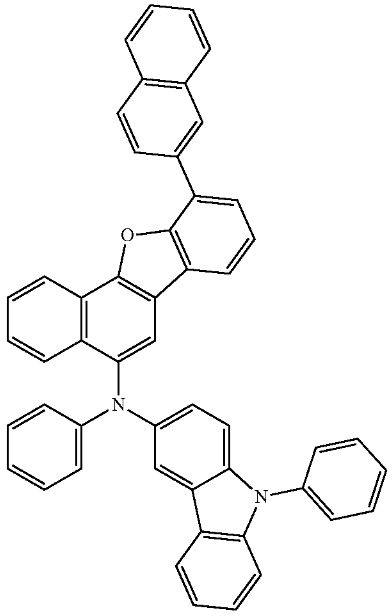
-continued
1-709
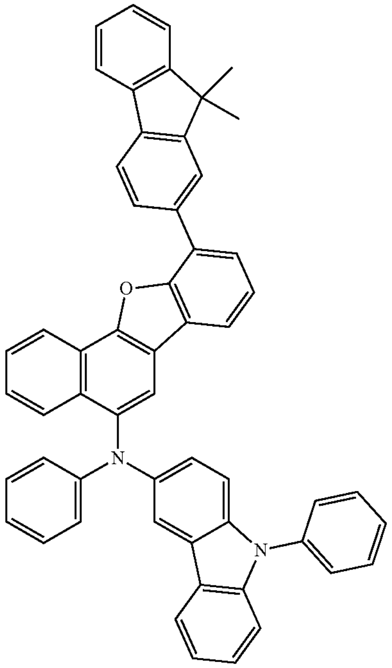
1-710
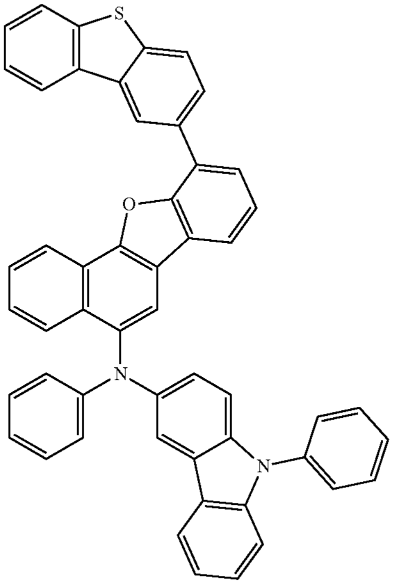

-continued
1-711
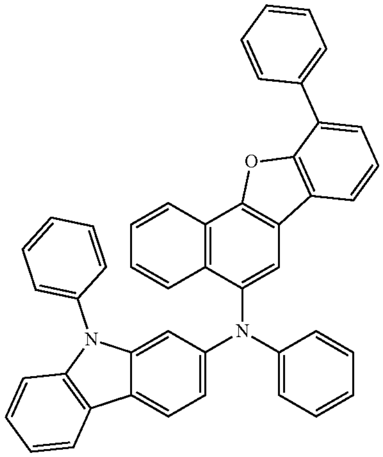
1-712
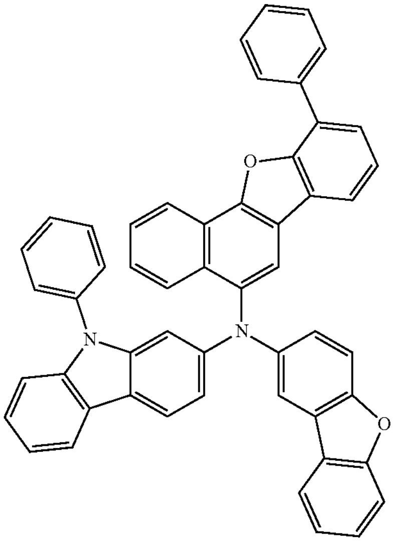
1-713
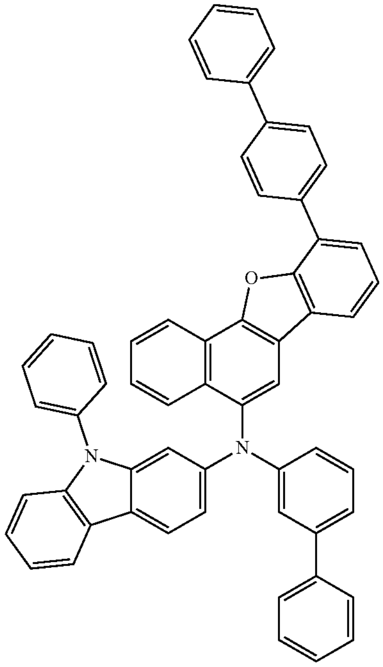
-continued
1-714
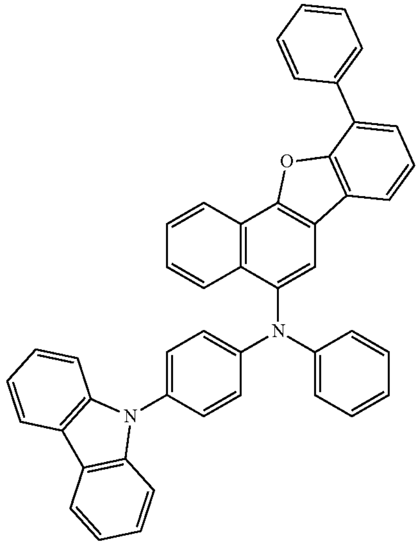
1-715
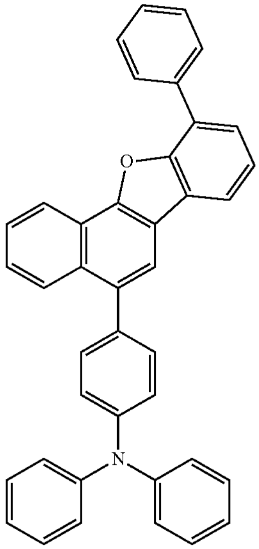

-continued
1-716
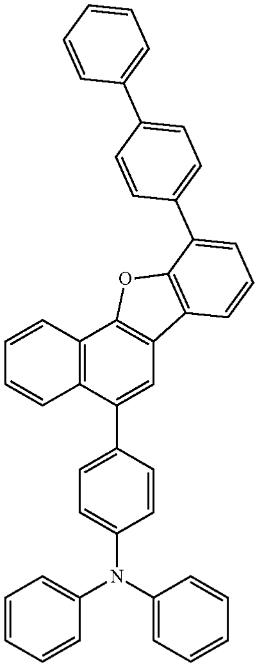
1-717
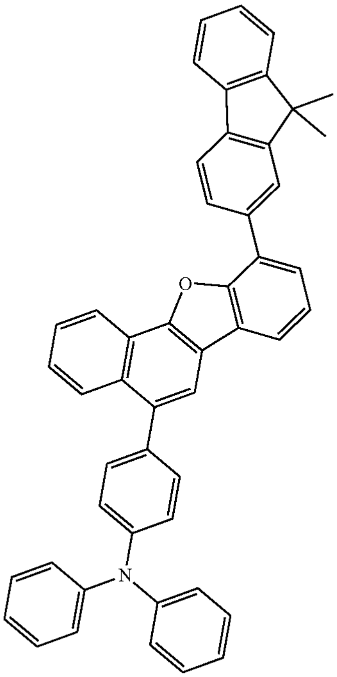
-continued
1-718
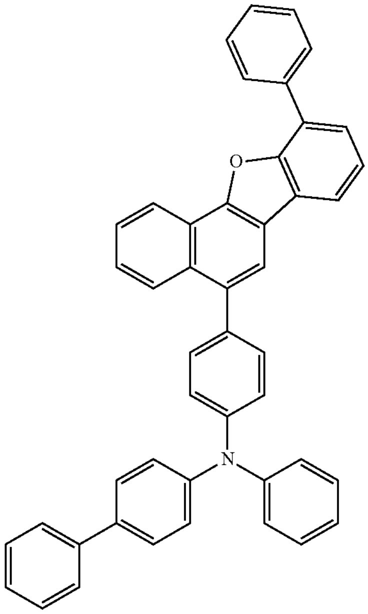
1-719
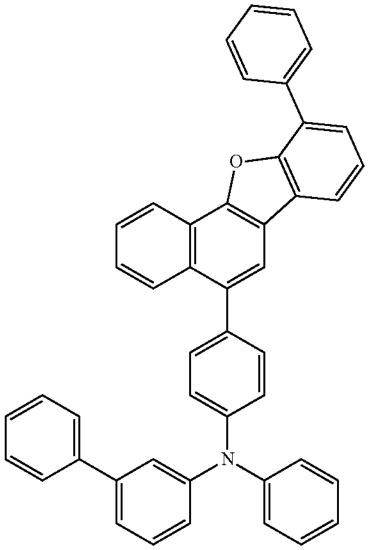

1-720
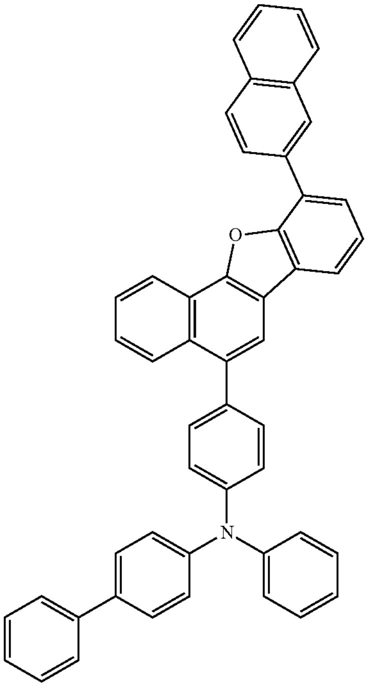
1-721
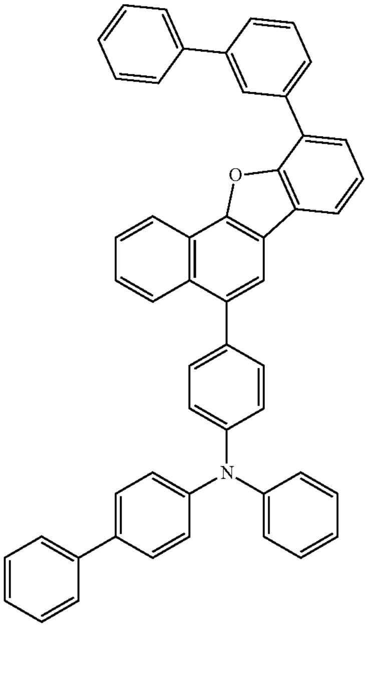
1-722
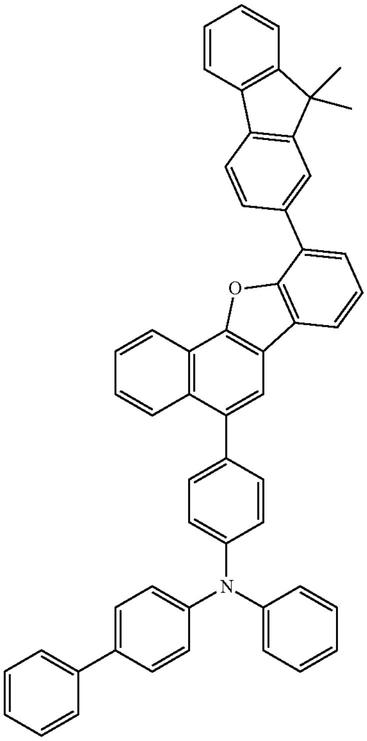
1-723
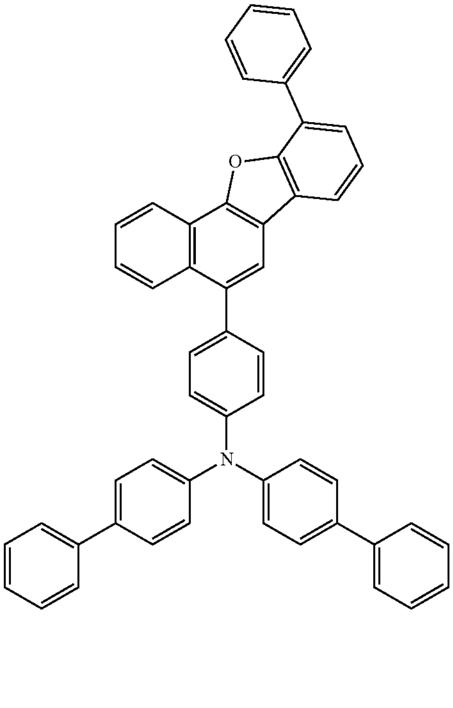

-continued
1-724
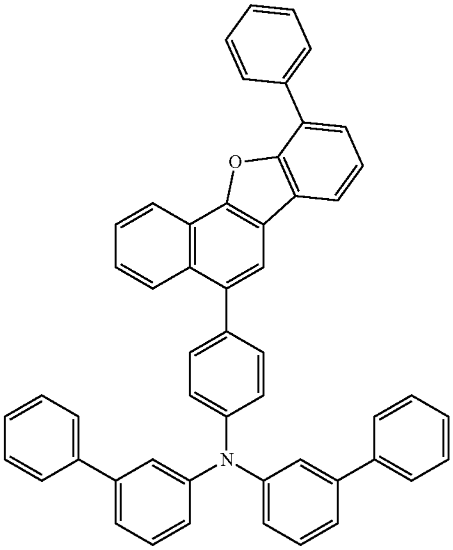
1-725
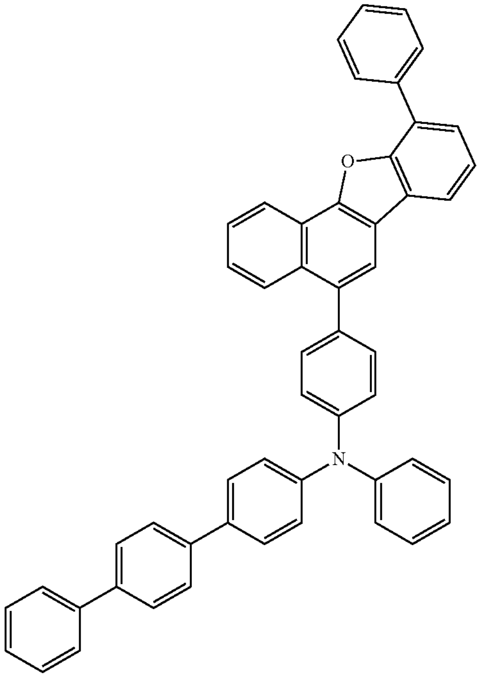
-continued
1-726
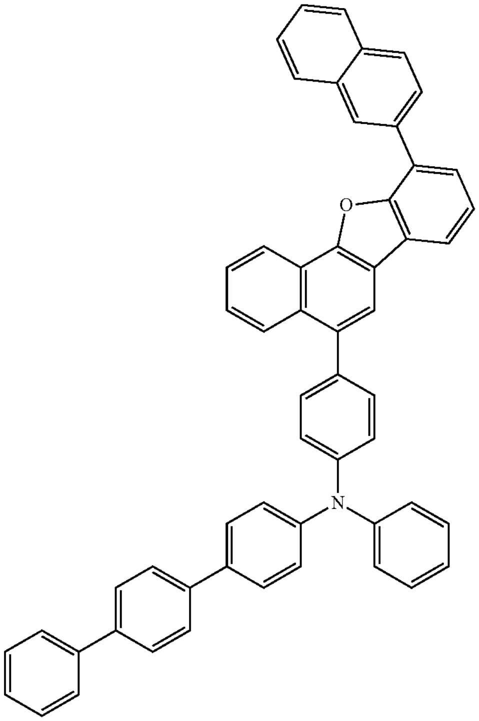
1-727
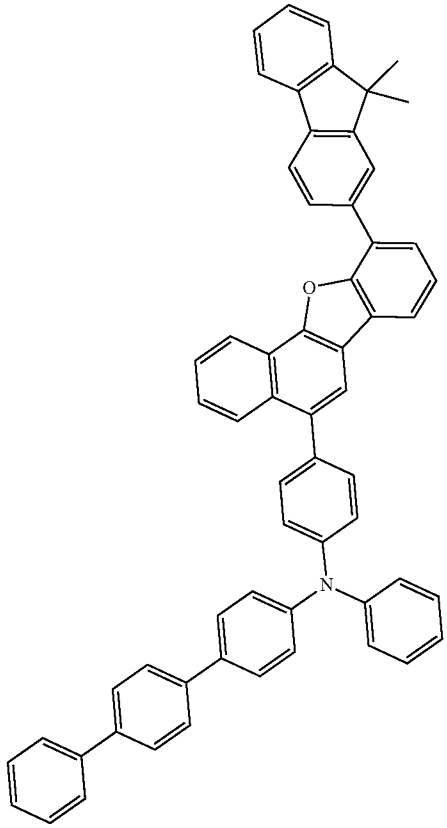

-continued
1-728
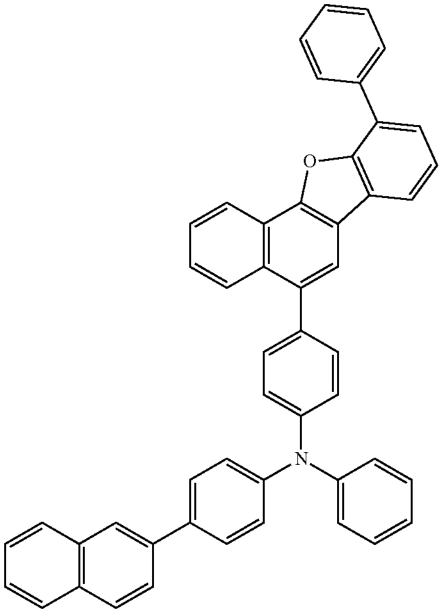
1-729
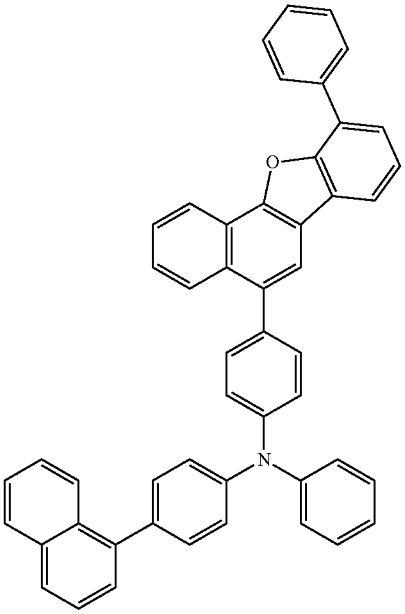
-continued
1-730
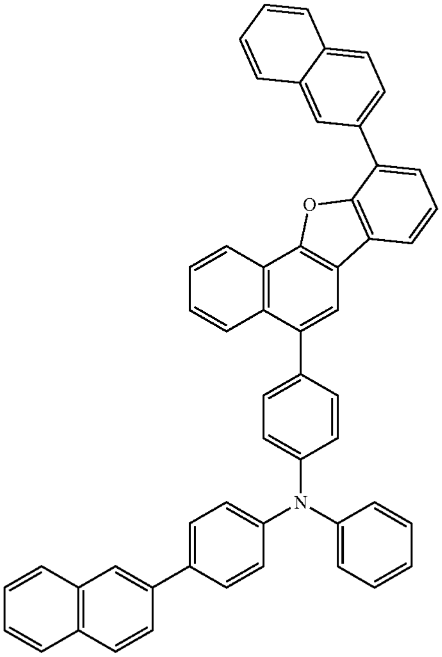
1-731
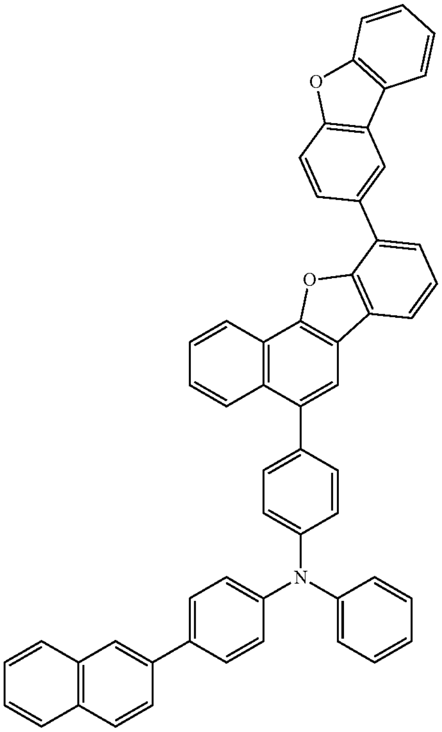

-continued
1-732
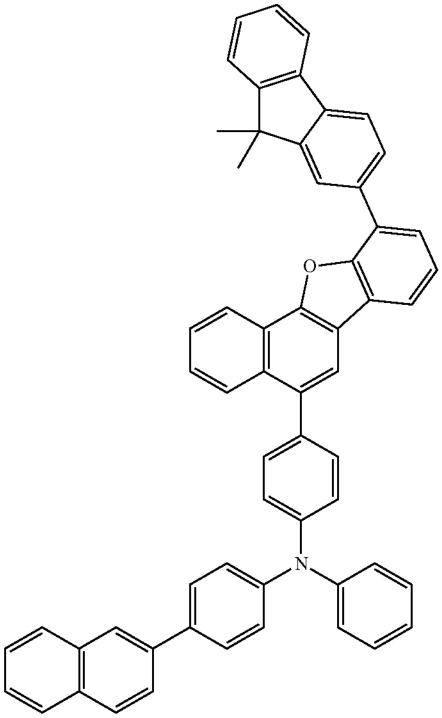
1-733
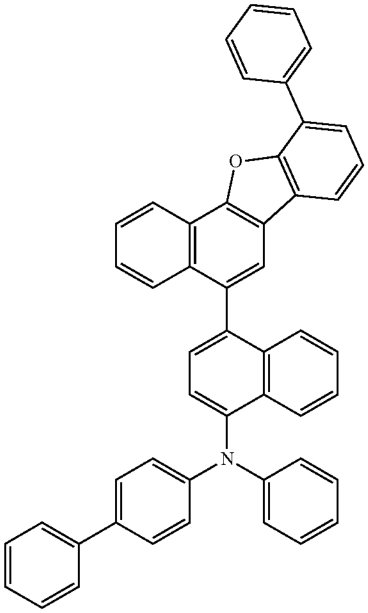
-continued
1-734
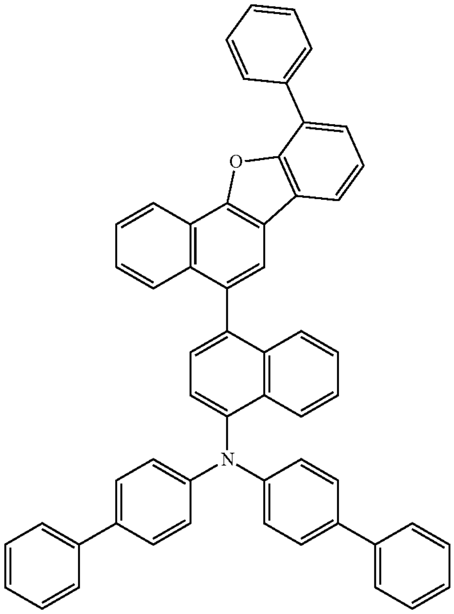
1-735
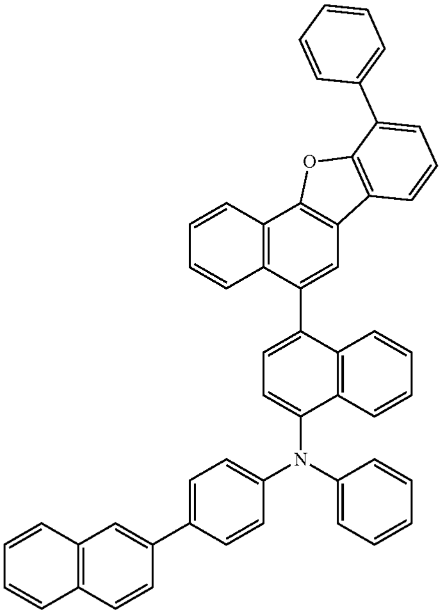

-continued
1-736
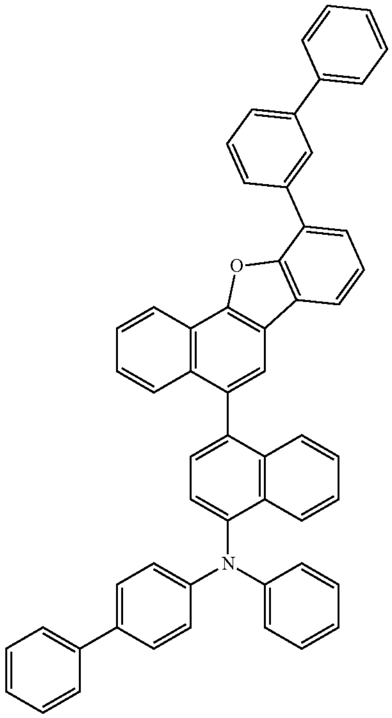
1-737
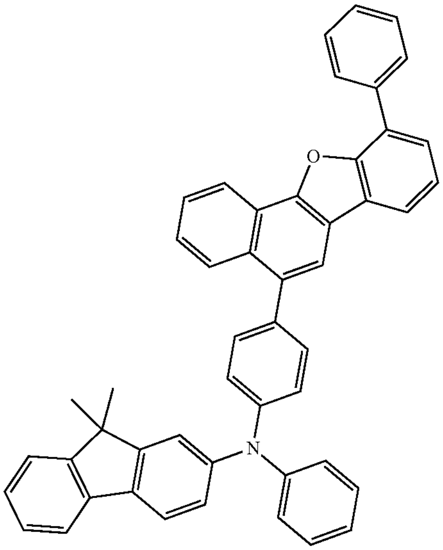
-continued
1-738
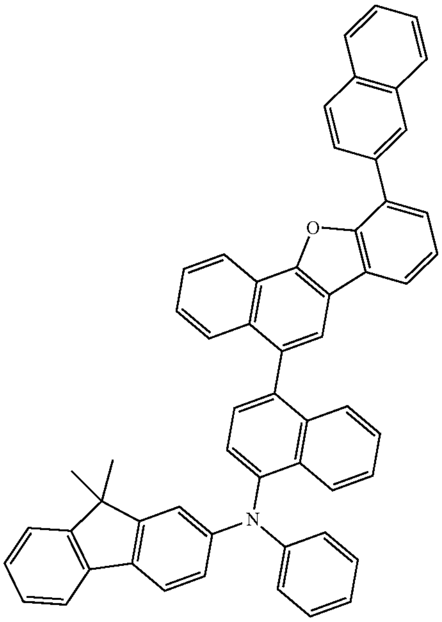
1-739
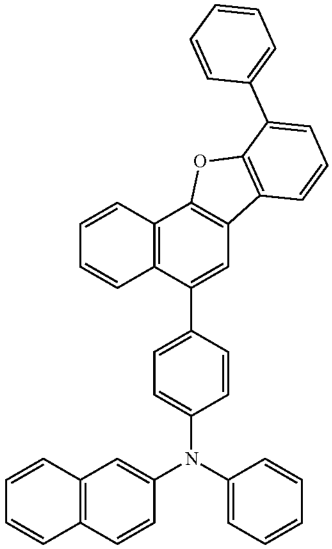

-continued
1-740
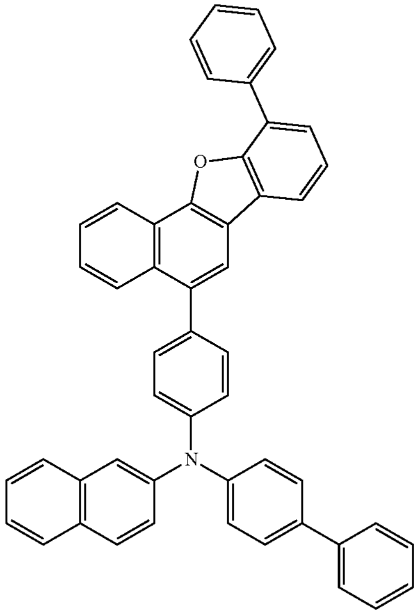
1-741
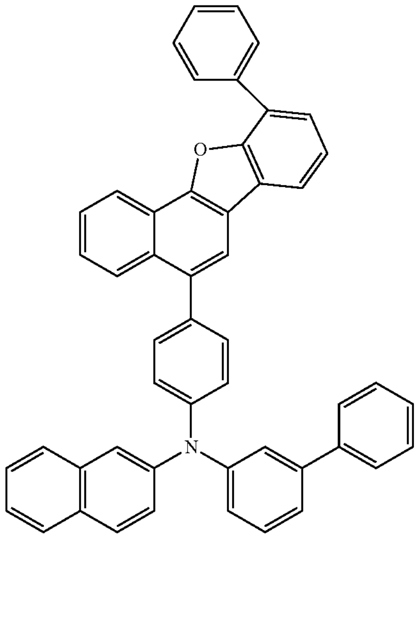
-continued
1-742
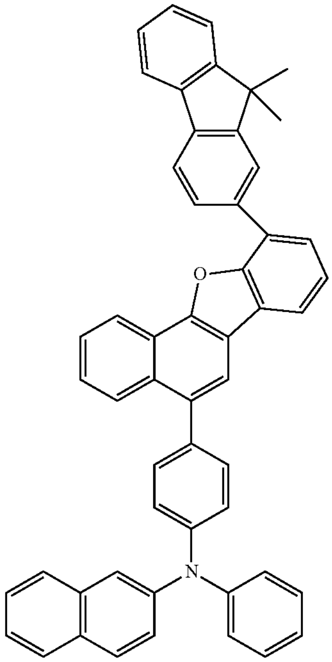
1-743
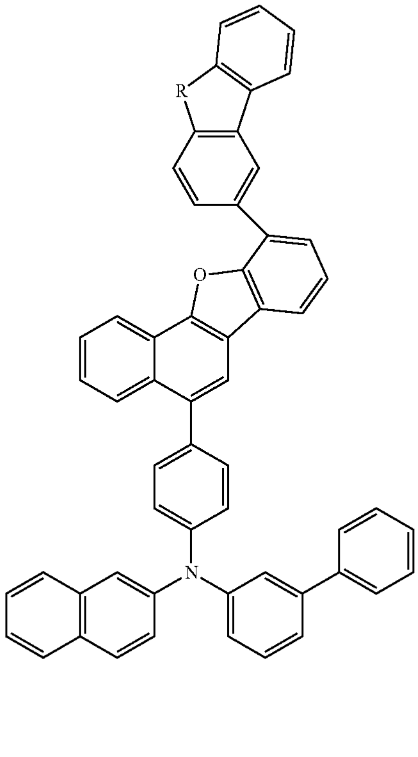

-continued
1-744
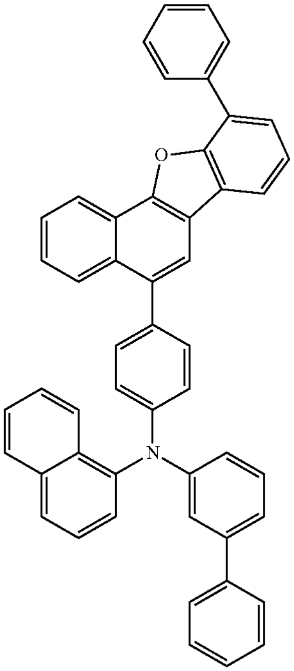
1-745
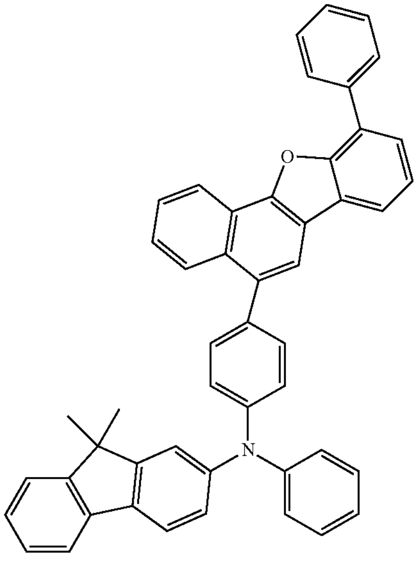
-continued
1-746
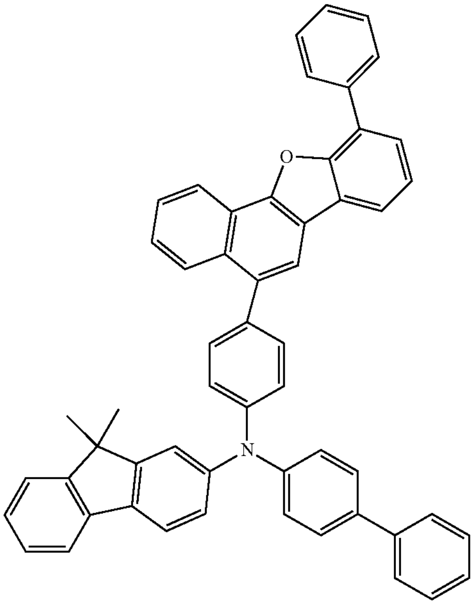
1-747
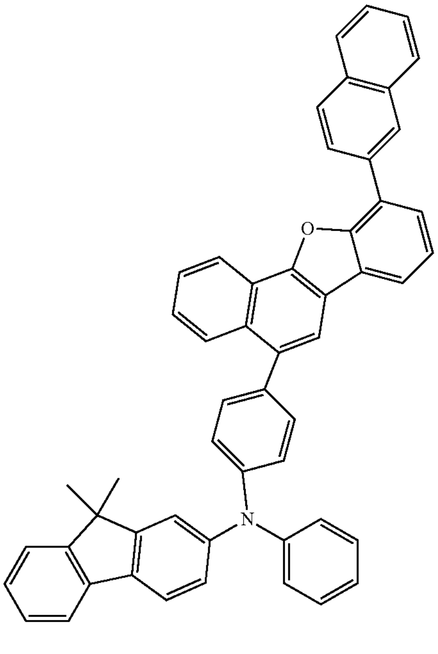

-continued
1-748
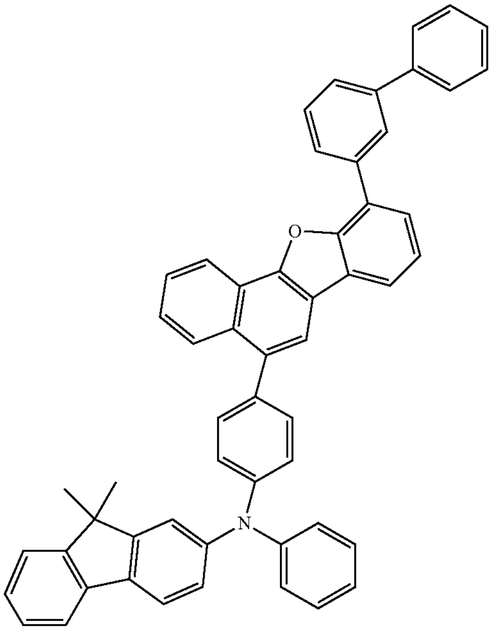
1-749
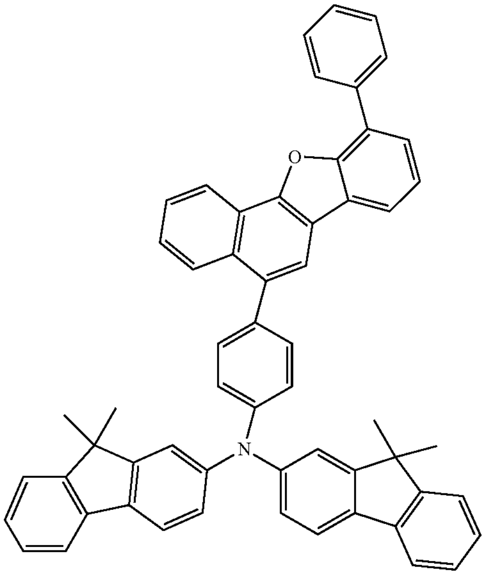
-continued
1-750
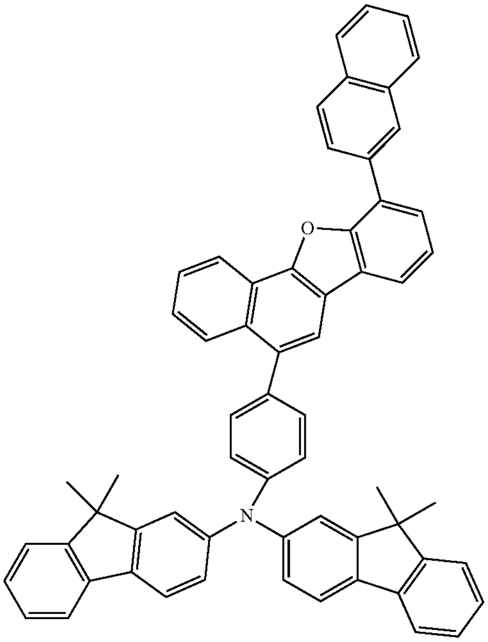
1-751
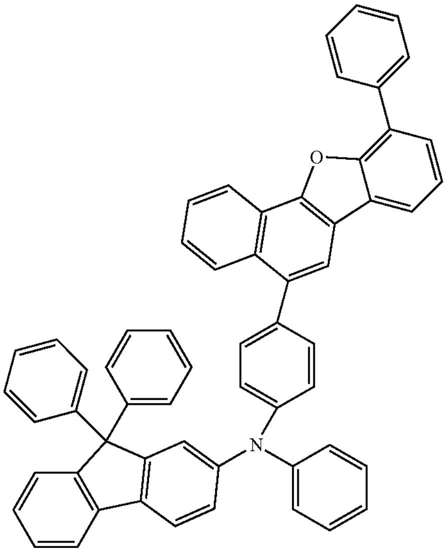

-continued
1-752
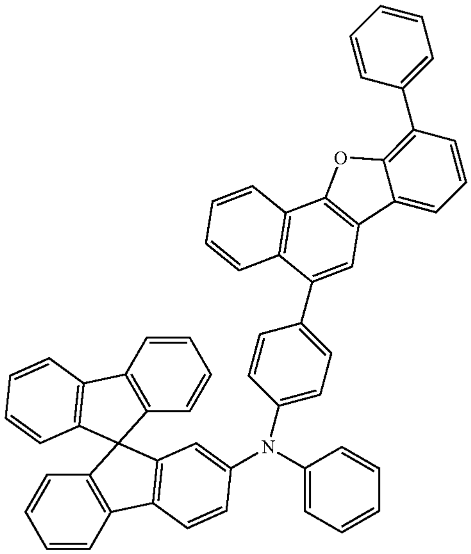
1-753
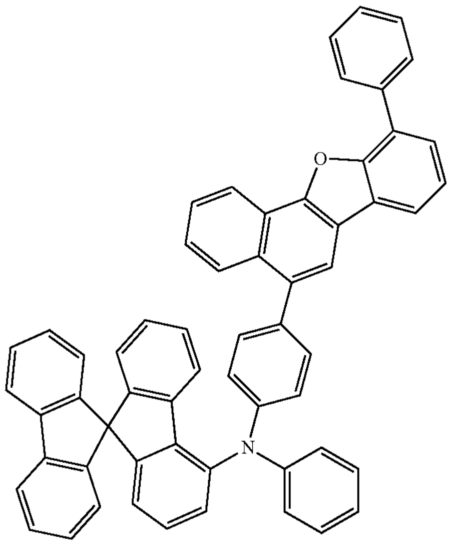
-continued
1-754
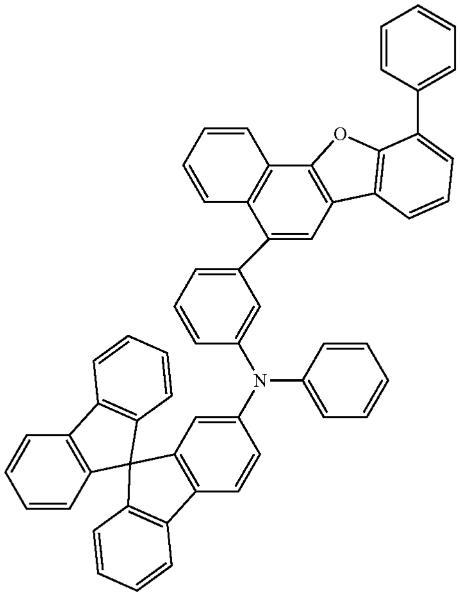
1-755
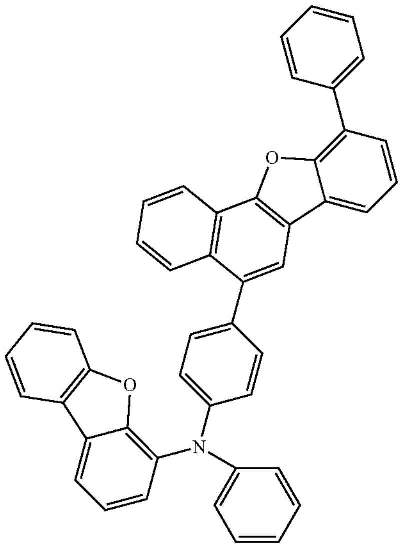

-continued
1-756
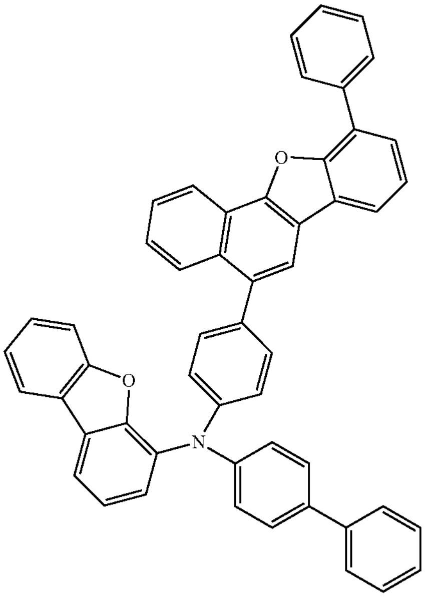
1-757
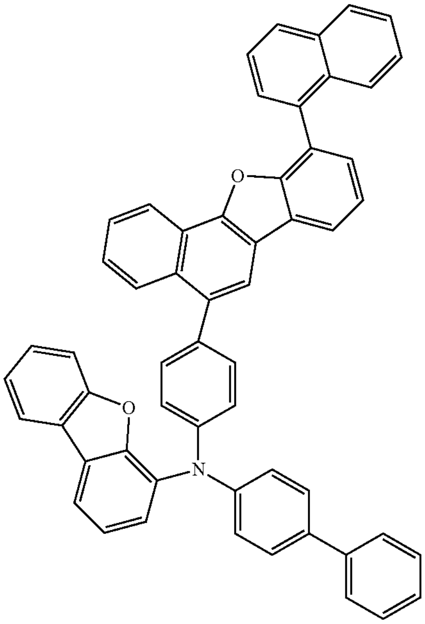
-continued
1-758
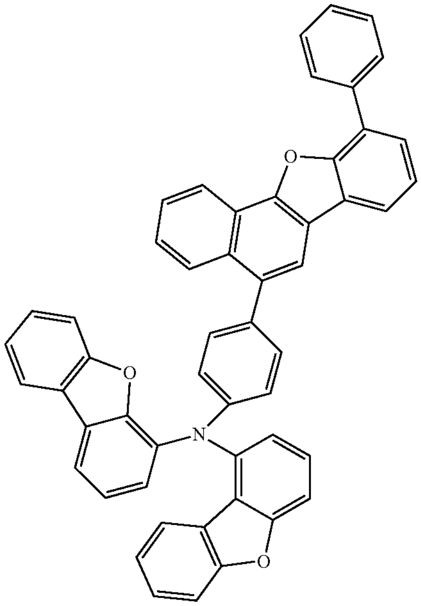
1-759
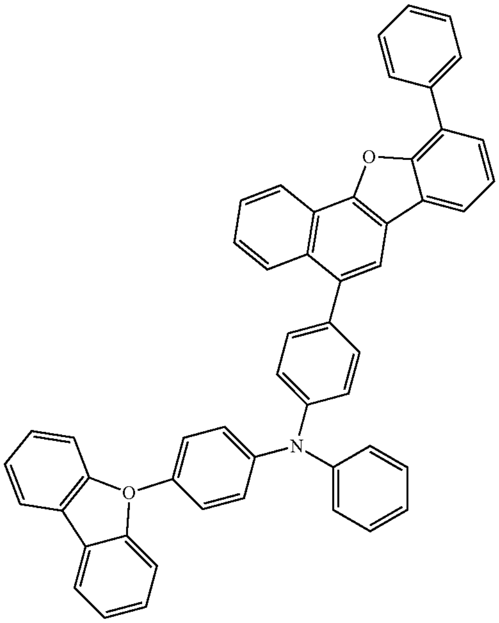

-continued
1-760
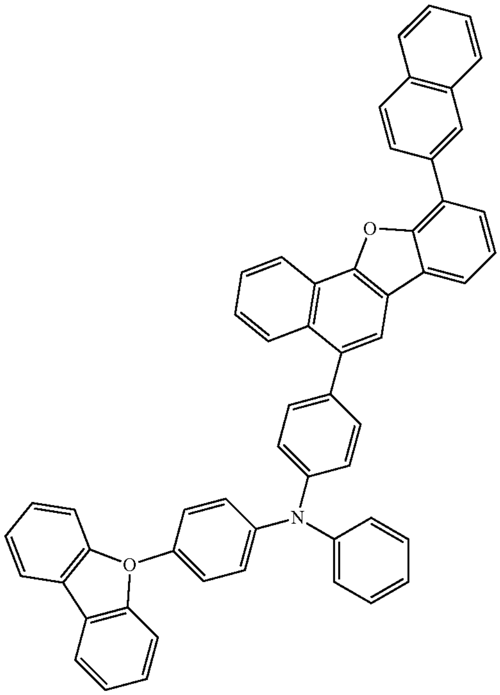
1-761
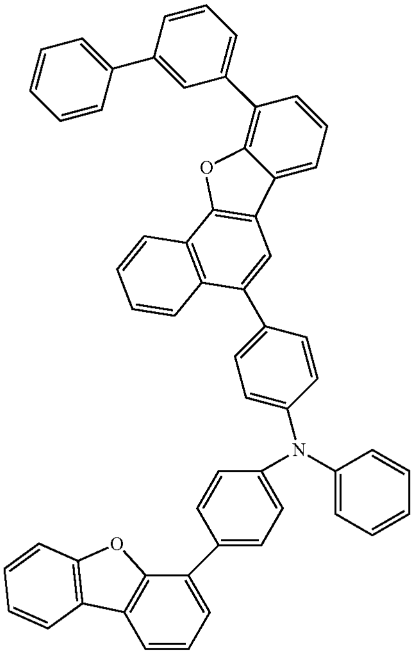
-continued
1-762
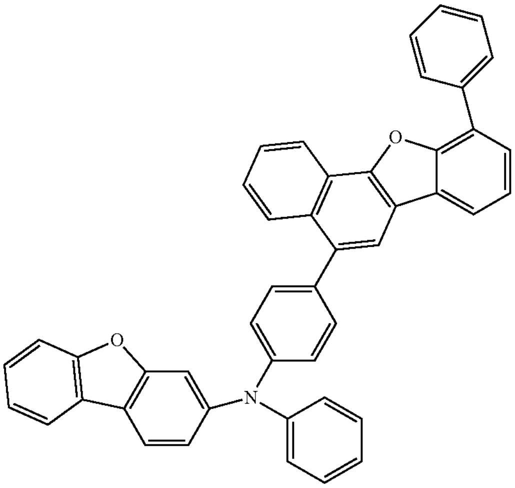
1-763
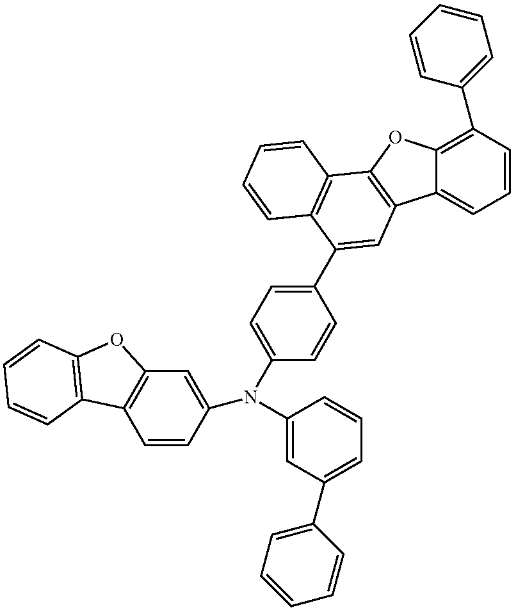

-continued
1-764
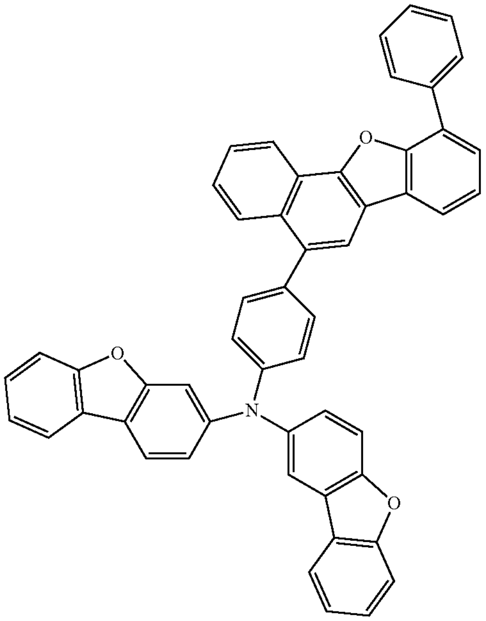
1-765
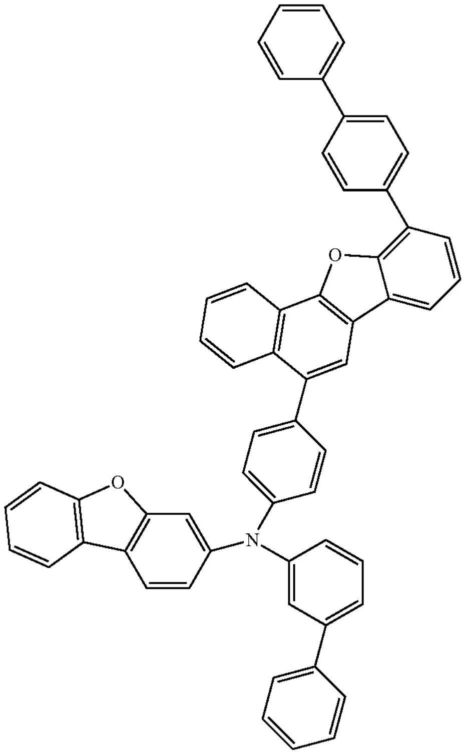
-continued
1-766
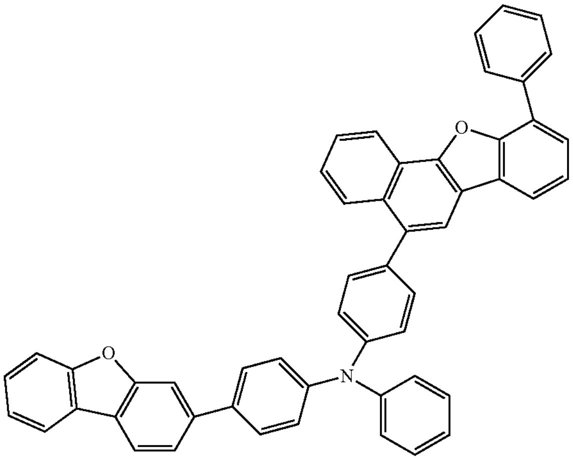
1-767
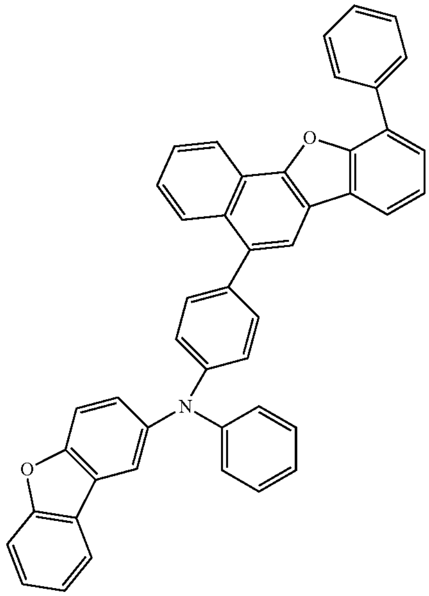
1-768
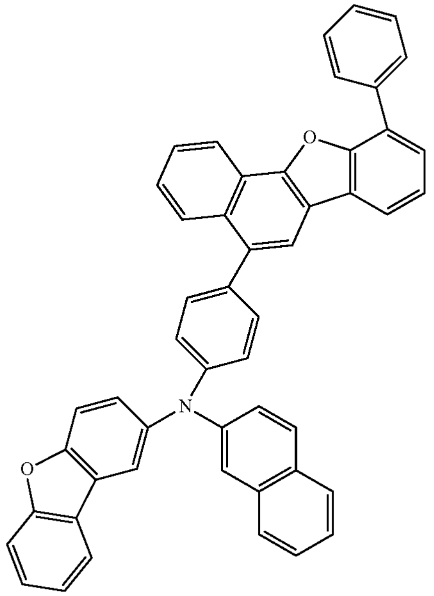

-continued
1-769
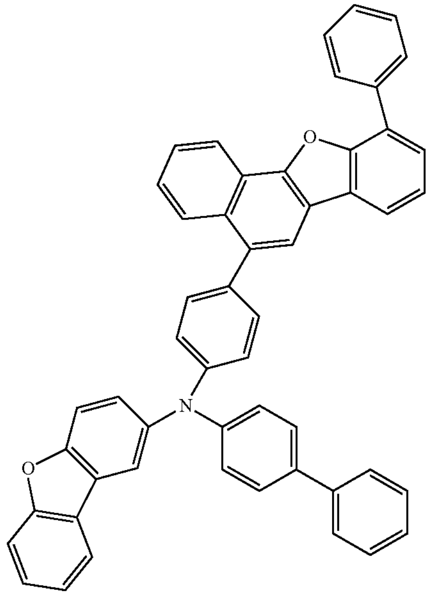
1-770
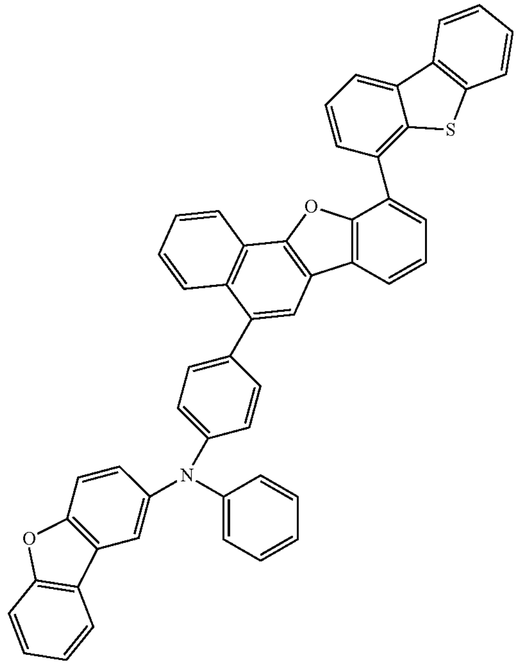
-continued
1-771
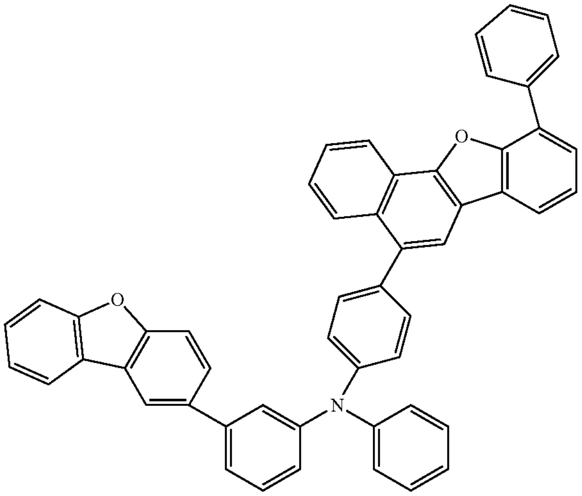
1-772
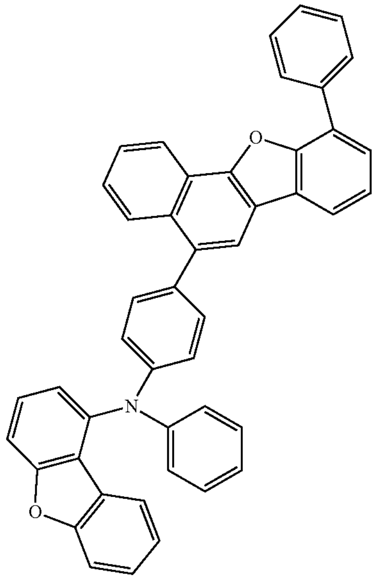

-continued
1-773
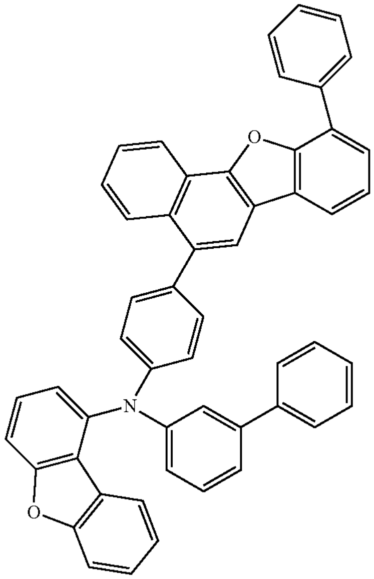
1-774
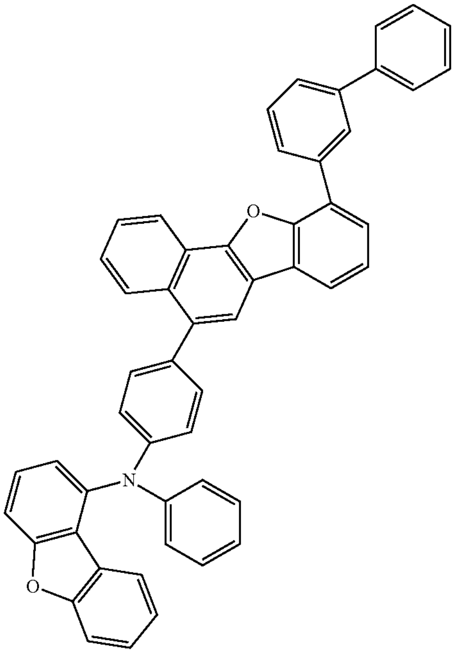
-continued
1-775
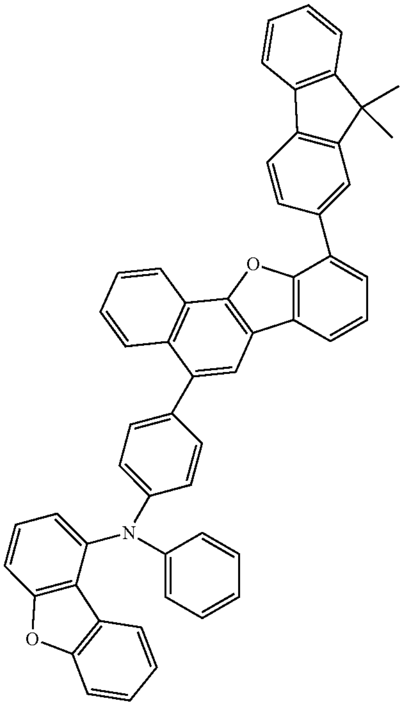
1-776
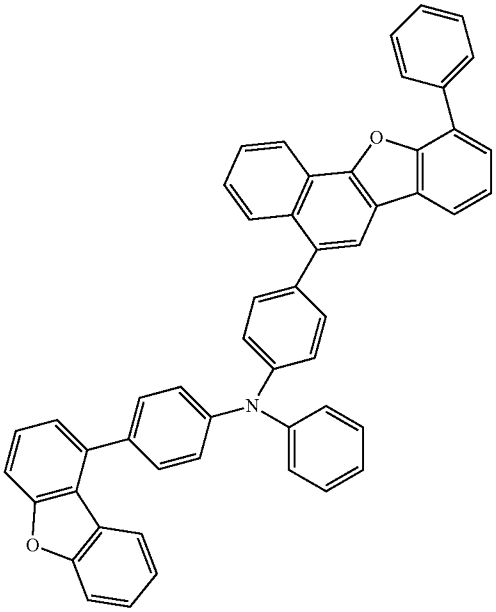

-continued
1-777
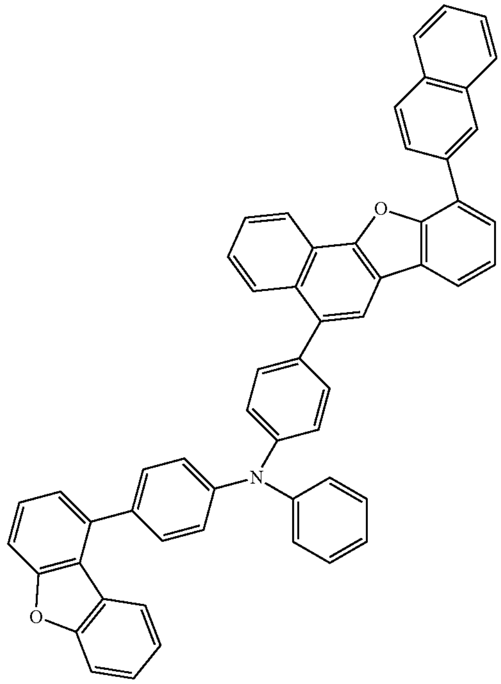
1-778
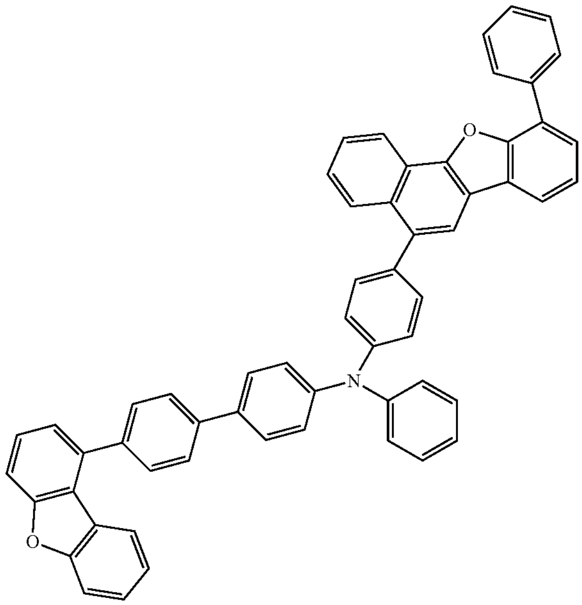
-continued
1-779
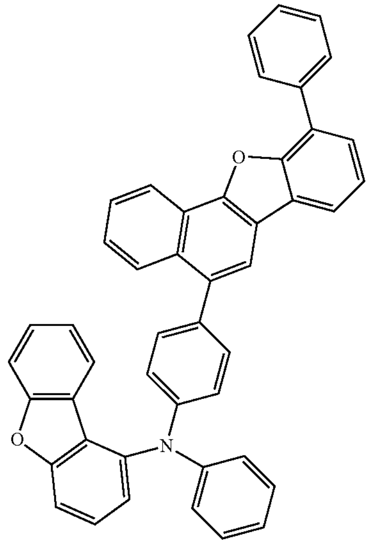
1-780
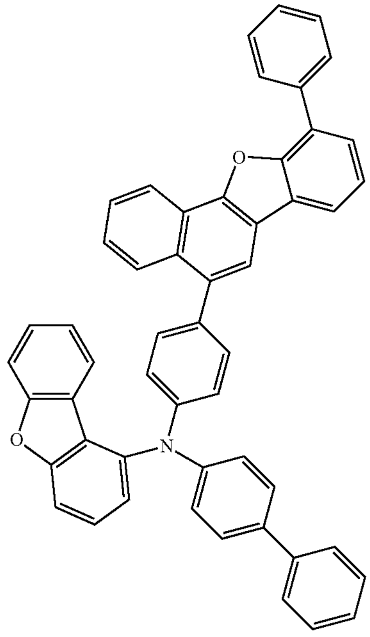

-continued
1-781
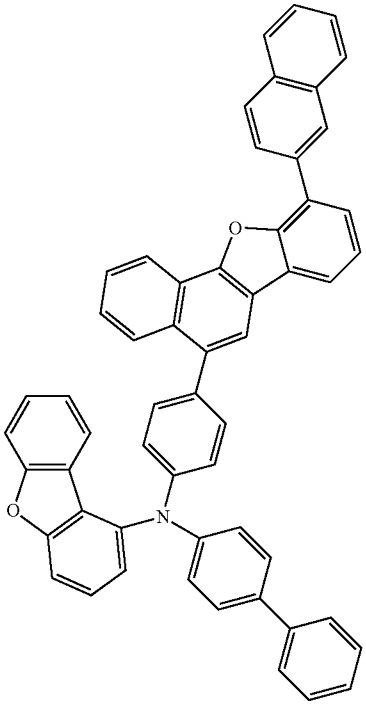
1-782
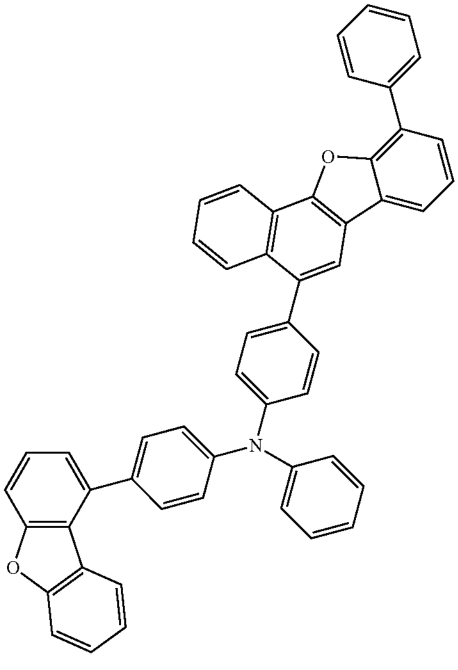
-continued
1-783
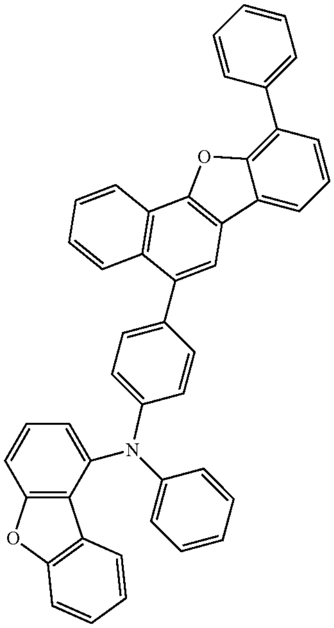
1-784
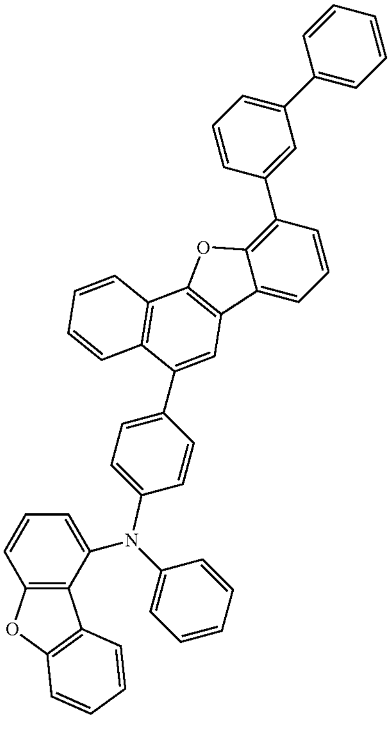

-continued
1-785
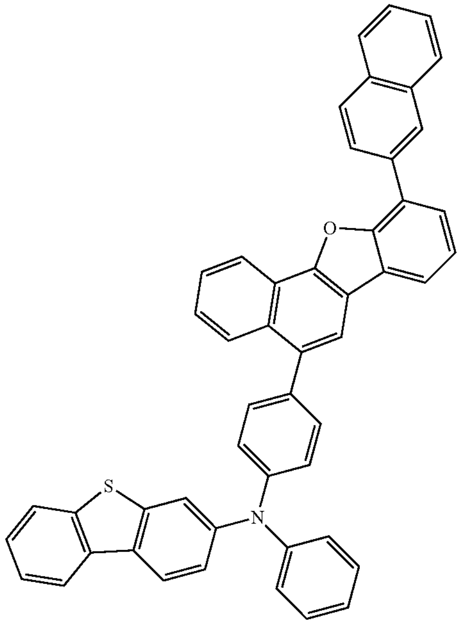
1-786
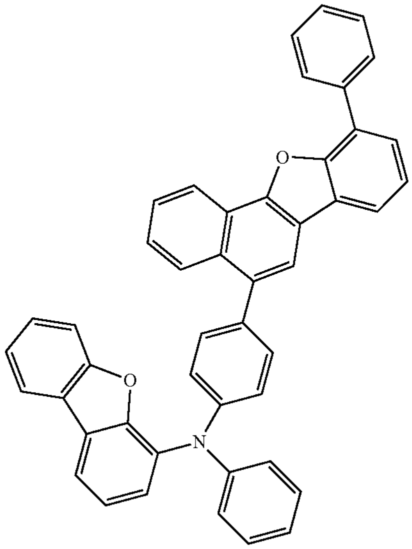
-continued
1-787
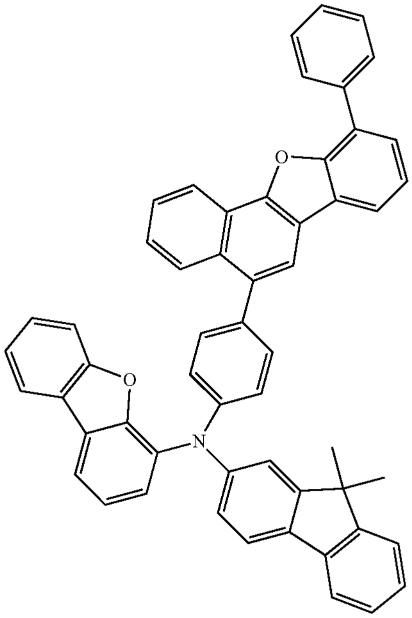
1-788
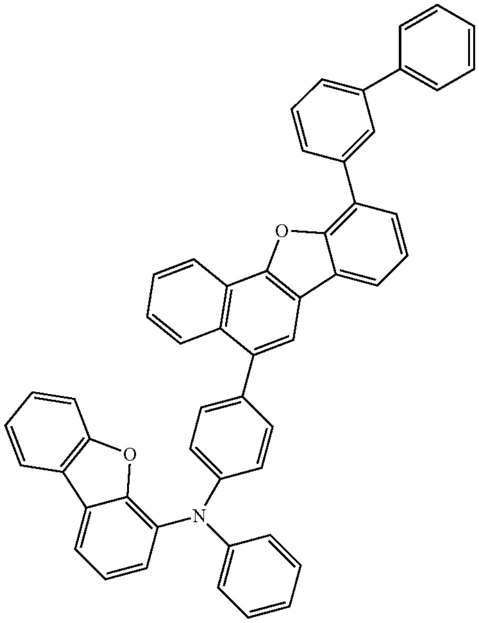

-continued
1-789
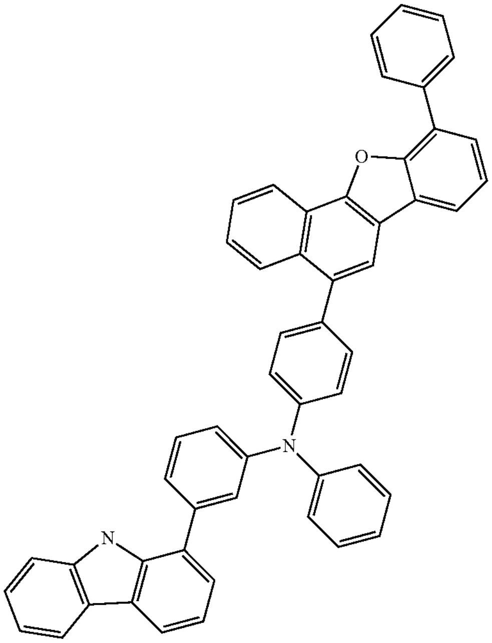
1-790
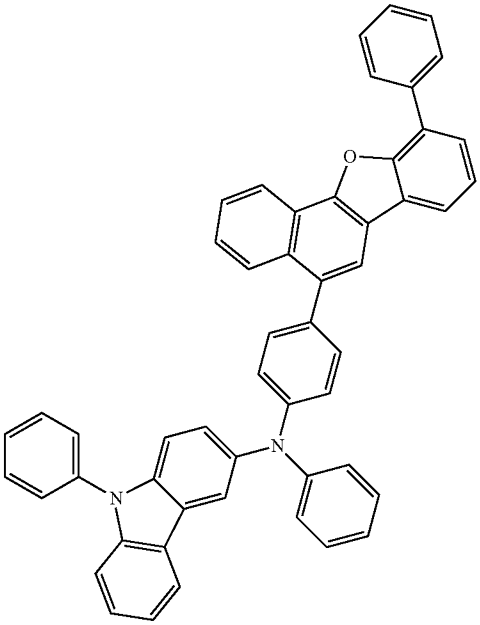
-continued
1-791
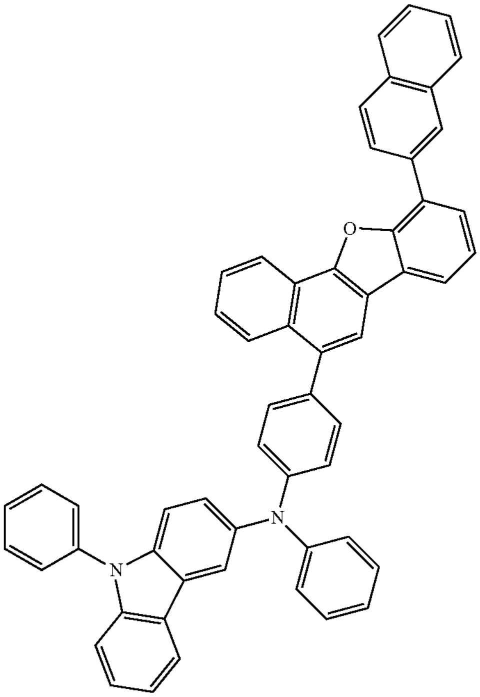
1-792
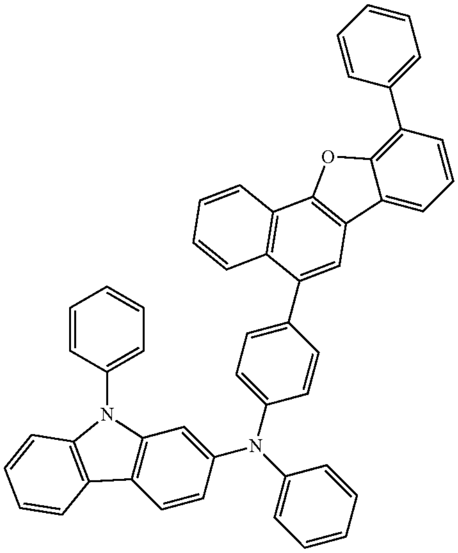

-continued
1-793
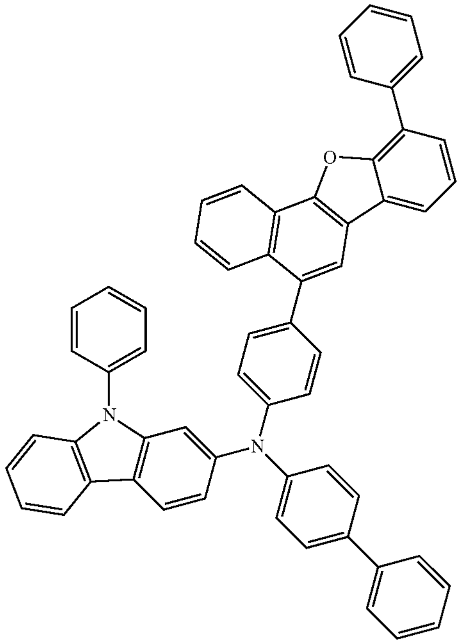
1-794
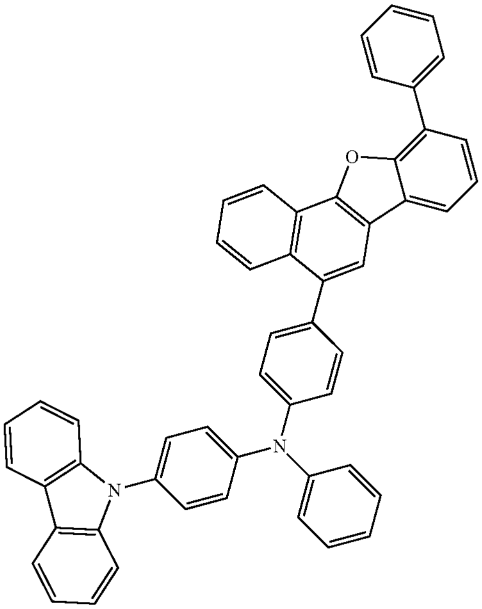
-continued
1-795
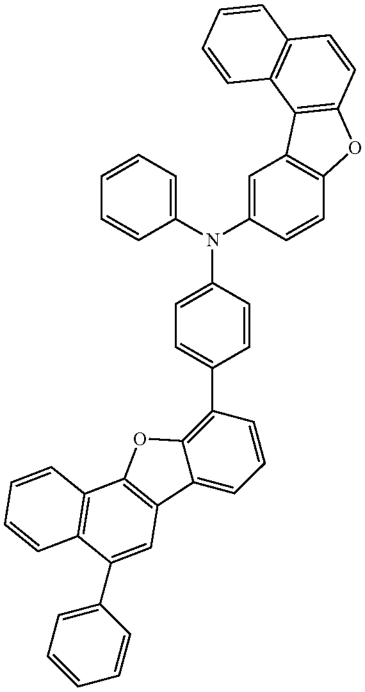
1-796
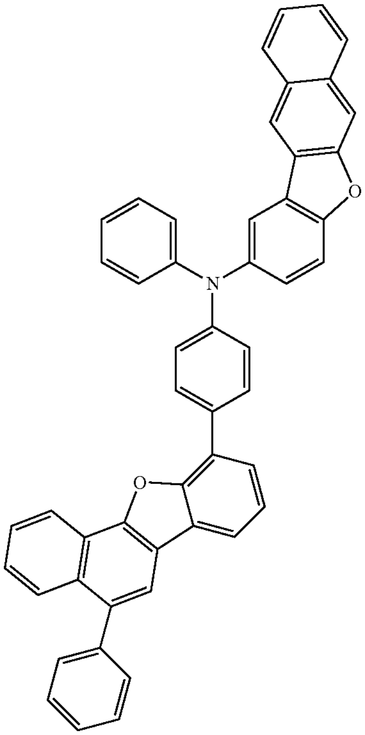

-continued
1-797
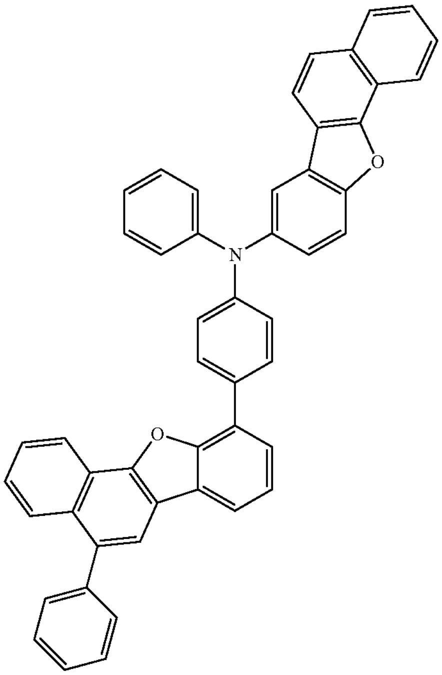
1-798
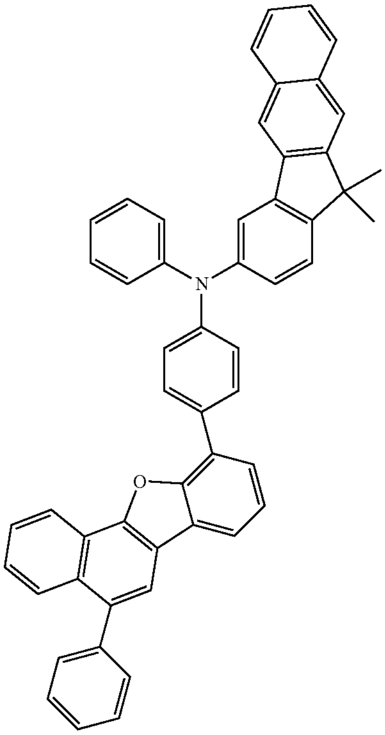
-continued
1-799
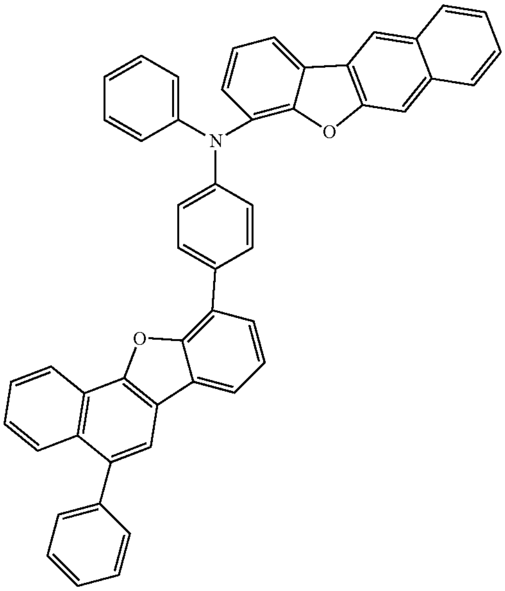
1-800
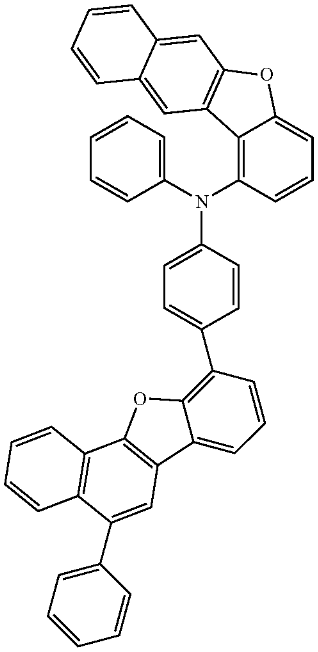

-continued
1-801
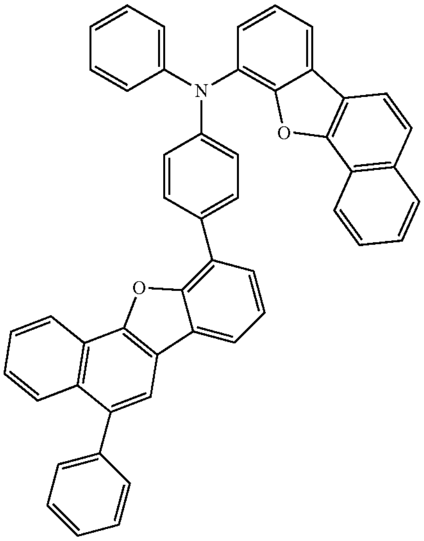
1-802
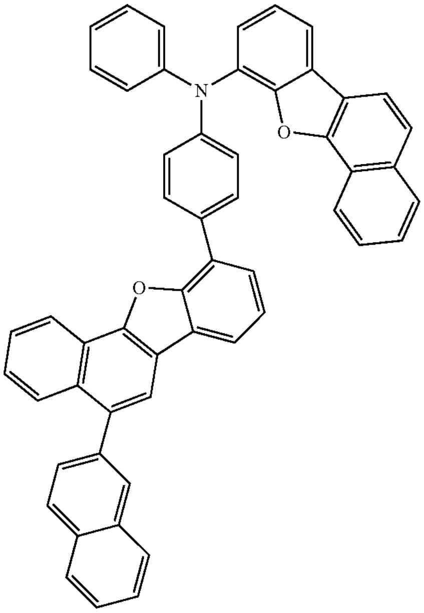
1-803
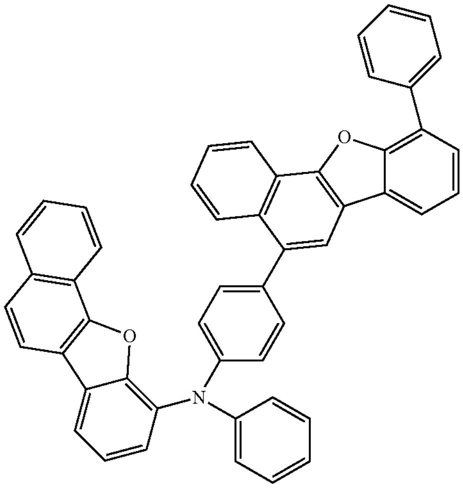
-continued
1-804
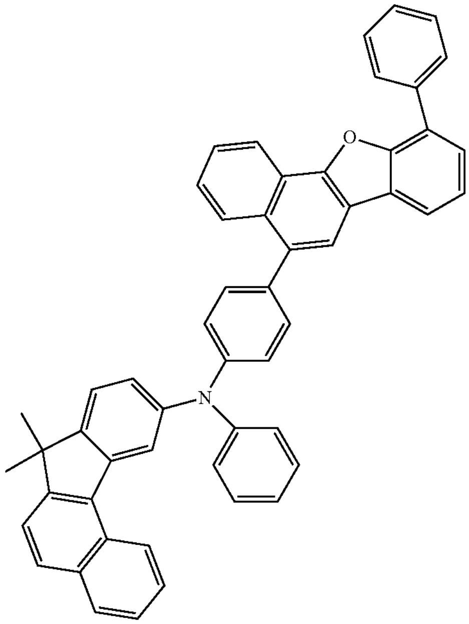
1-805
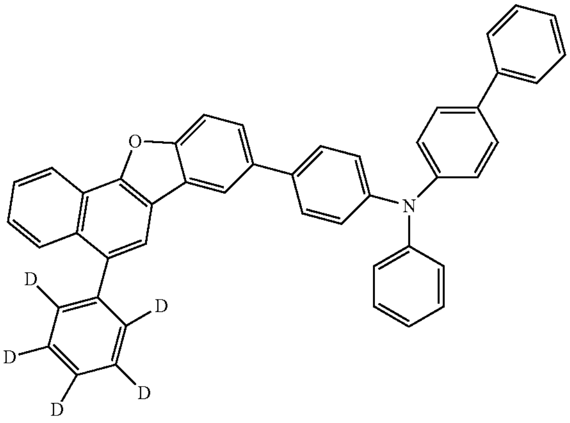
1-806
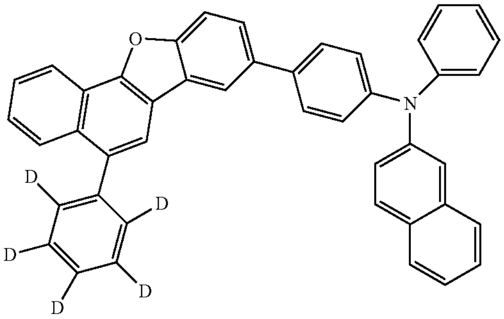

-continued
1-807
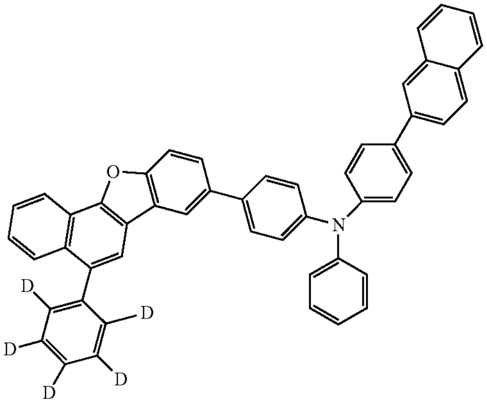
1-808
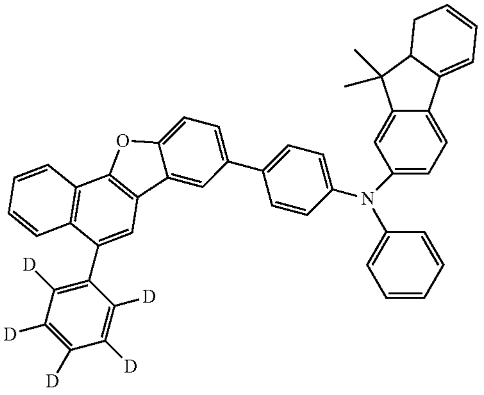
1-809
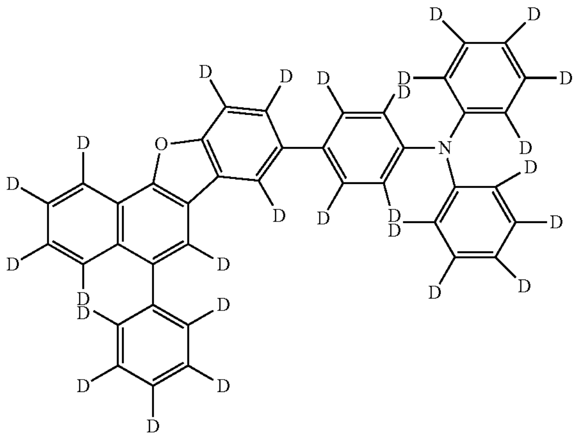
-continued
1-810
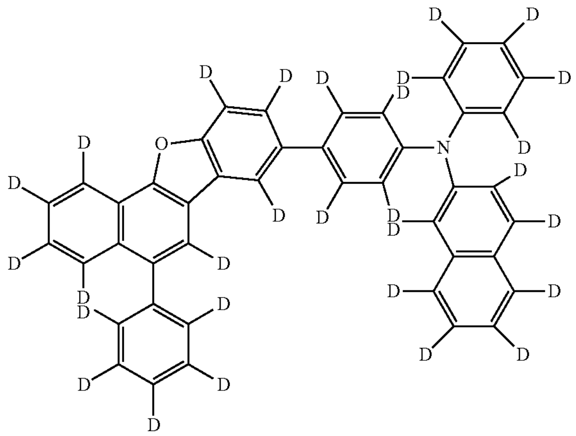
1-811
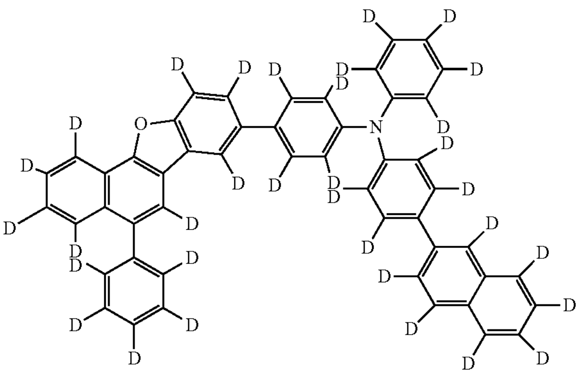
1-812
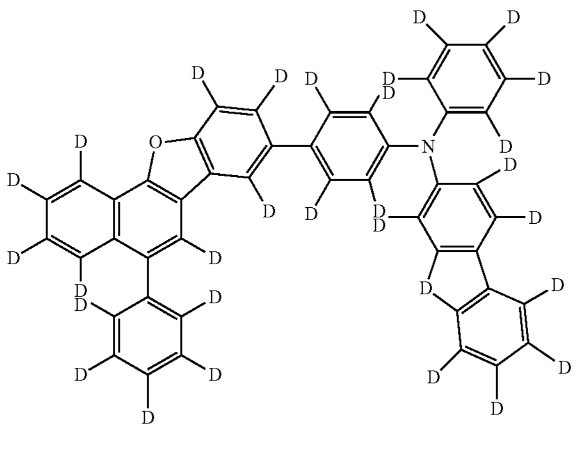

-continued
1-813
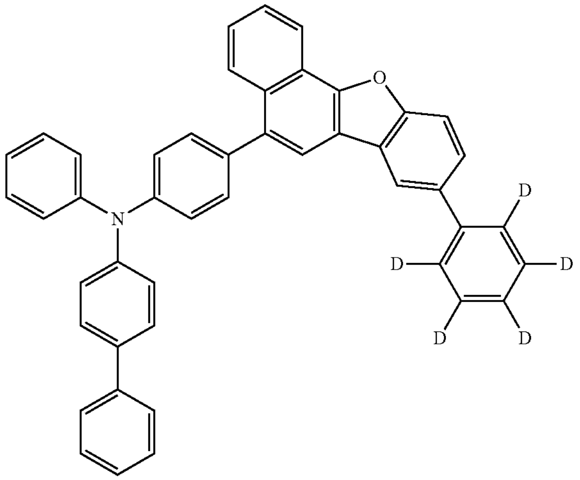
1-814
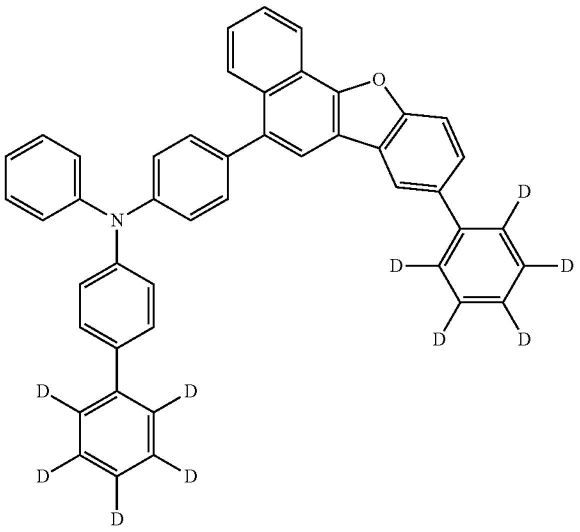
1-815
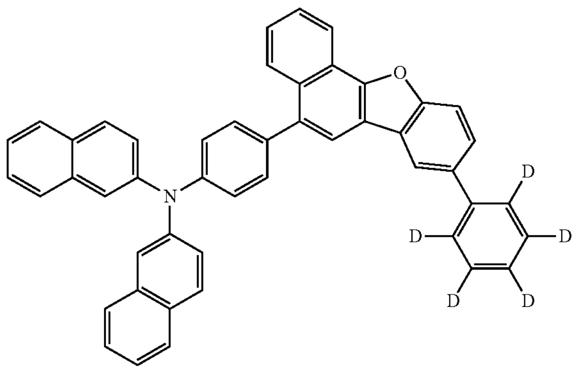
-continued
1-816
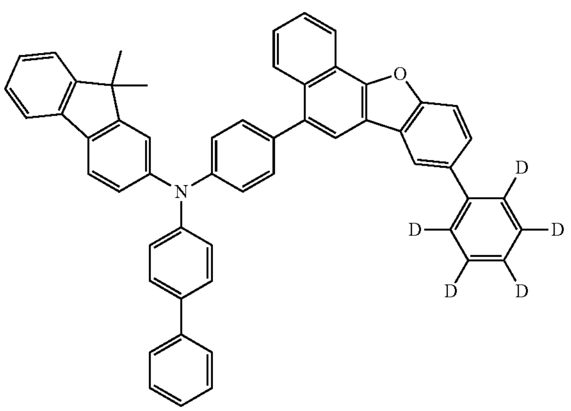
1-817
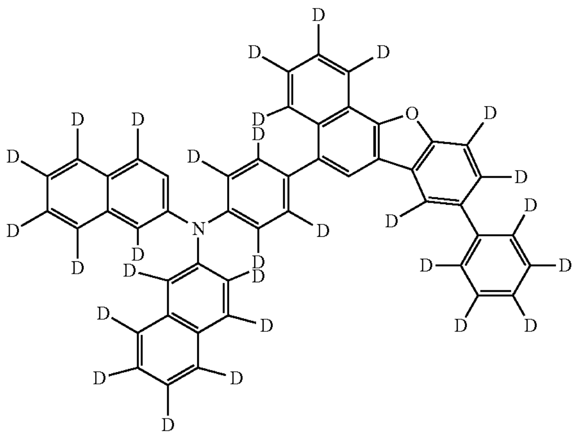
1-818
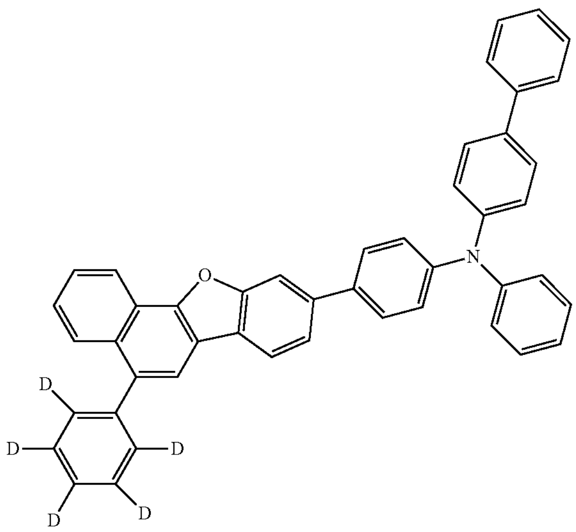

-continued
1-819
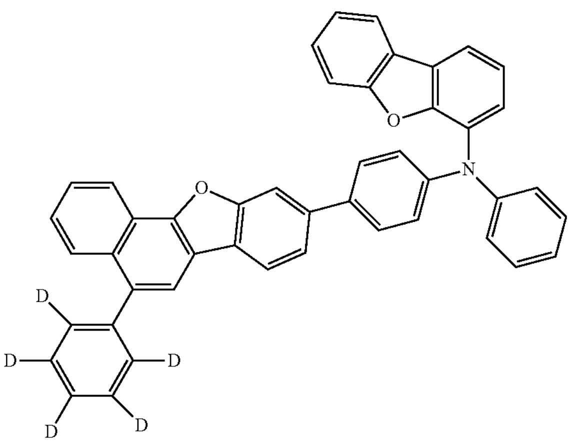
1-820
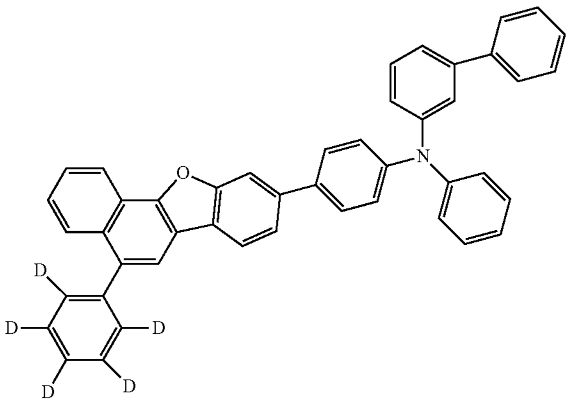
1-821
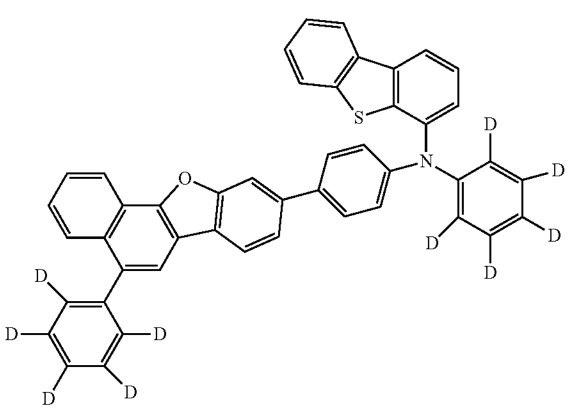
-continued
1-822
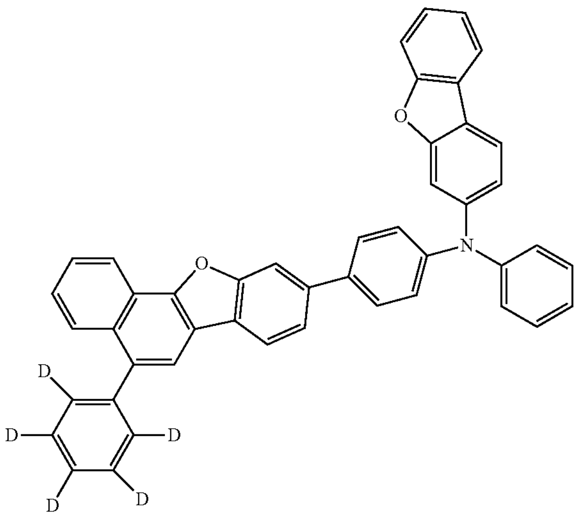
1-823
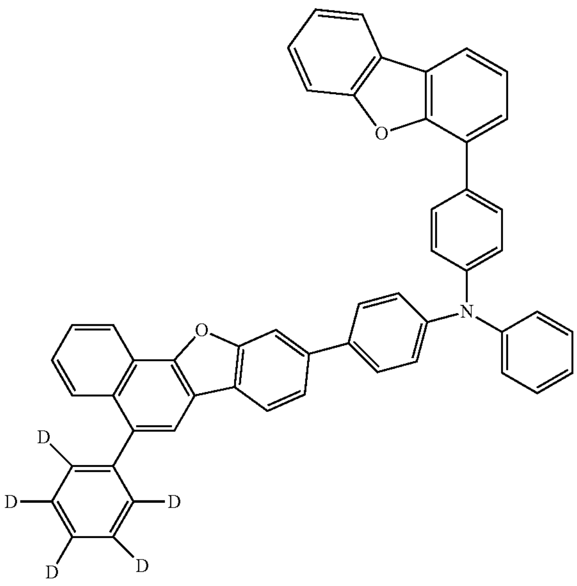
1-824
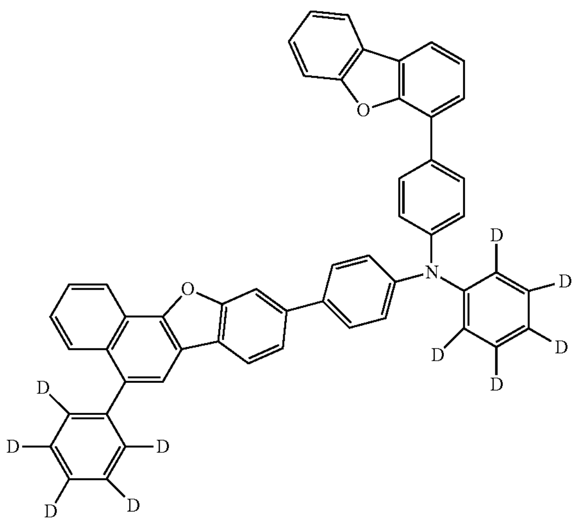

-continued
1-825
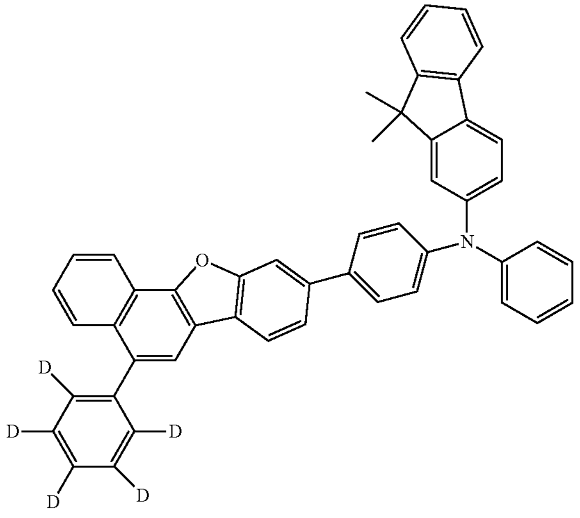
1-826
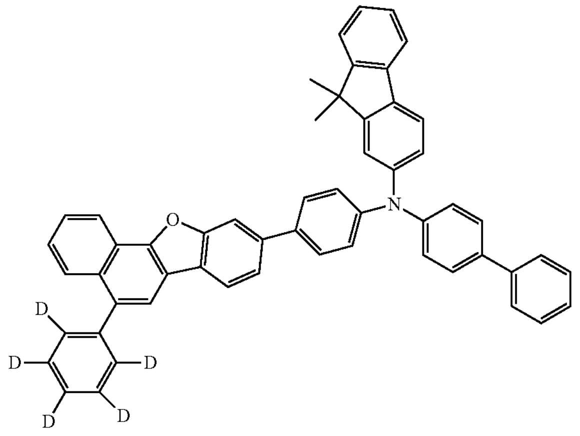
1-827
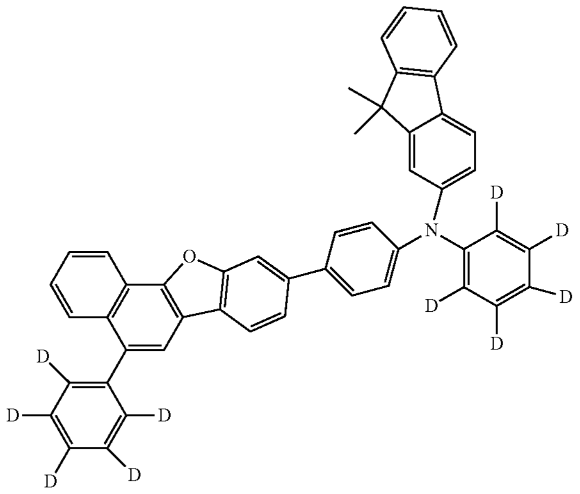
-continued
1-828
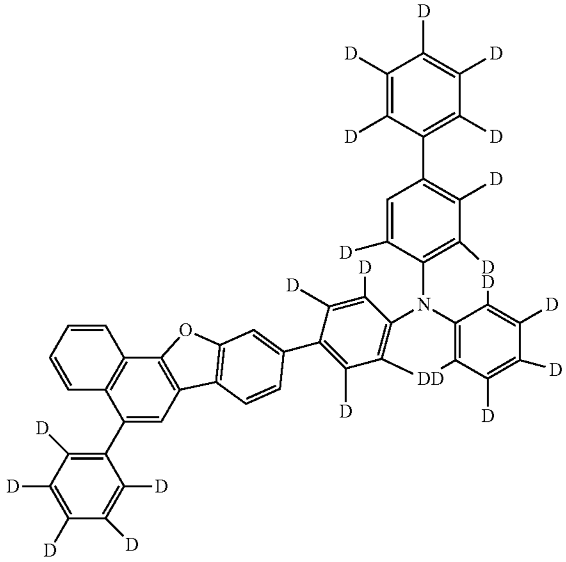
1-829
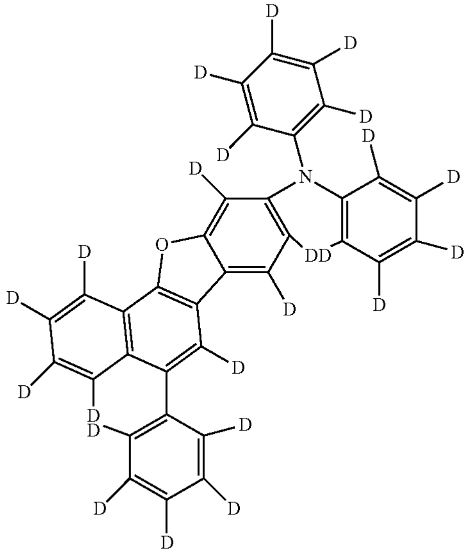

-continued
1-830
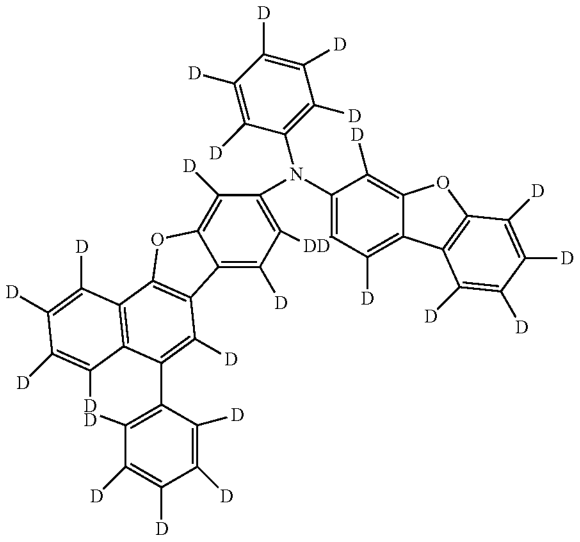
1-831
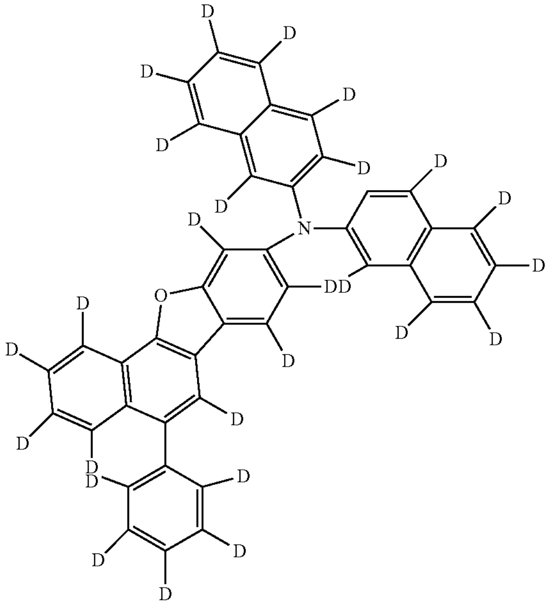
-continued
1-832
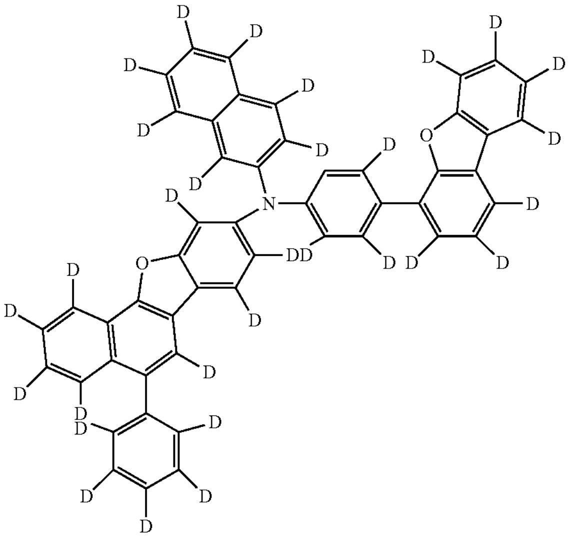
1-833
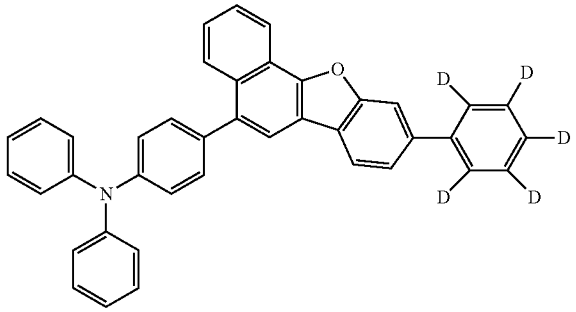
1-834
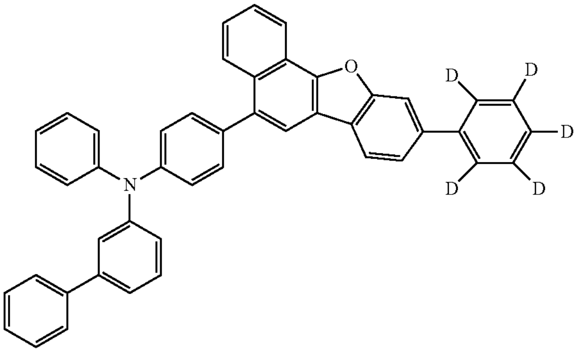

-continued
1-835
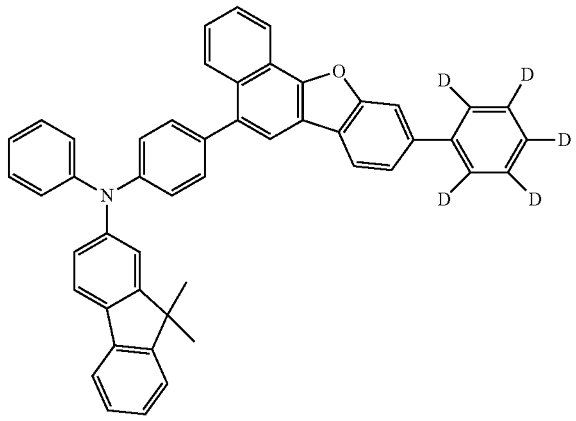
1-836
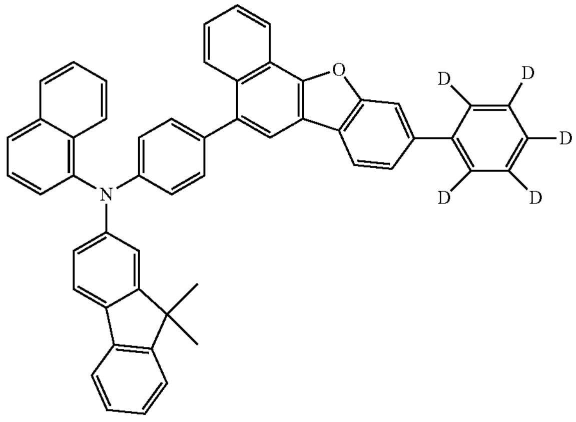
1-837
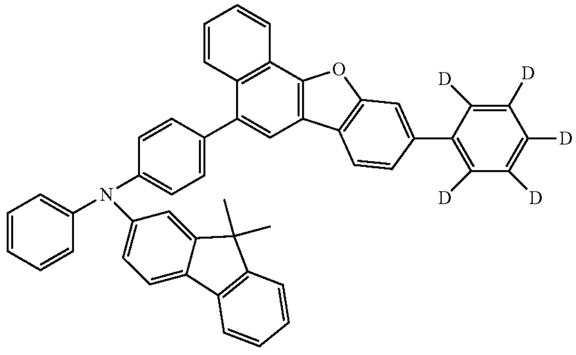
-continued
1-838
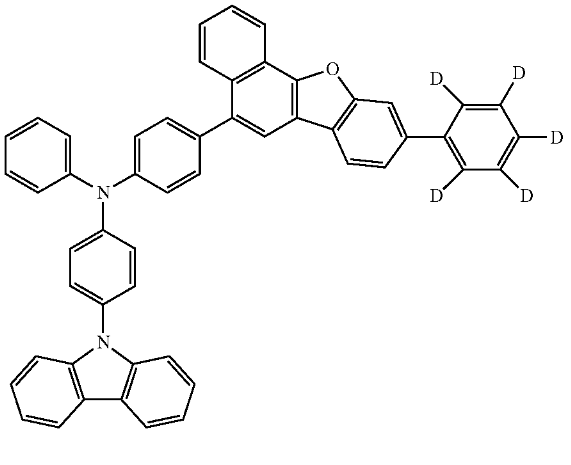
1-839
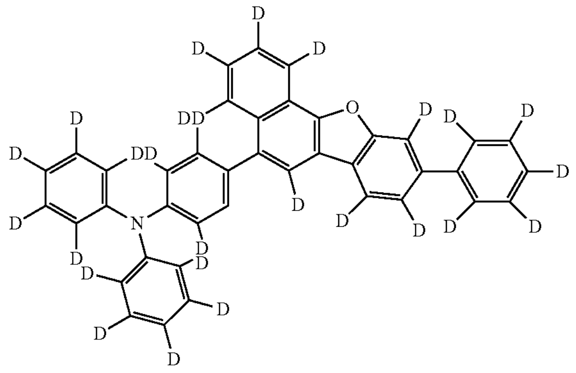
1-840
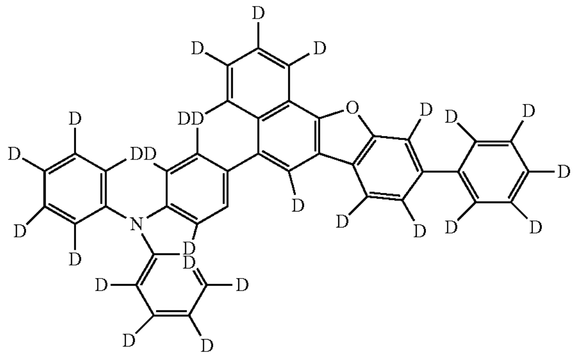

-continued
1-841
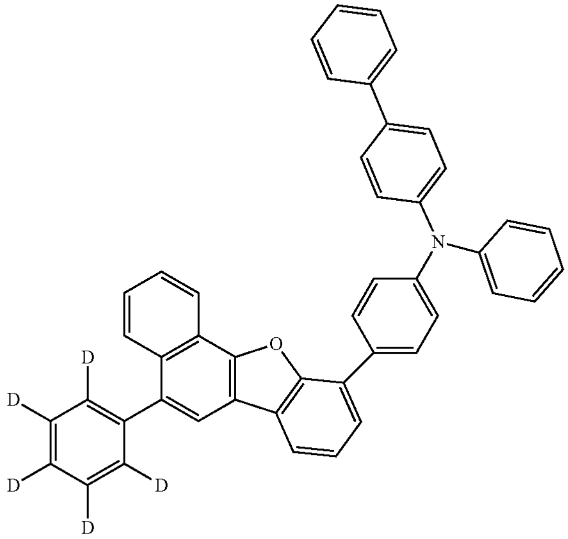
1-842
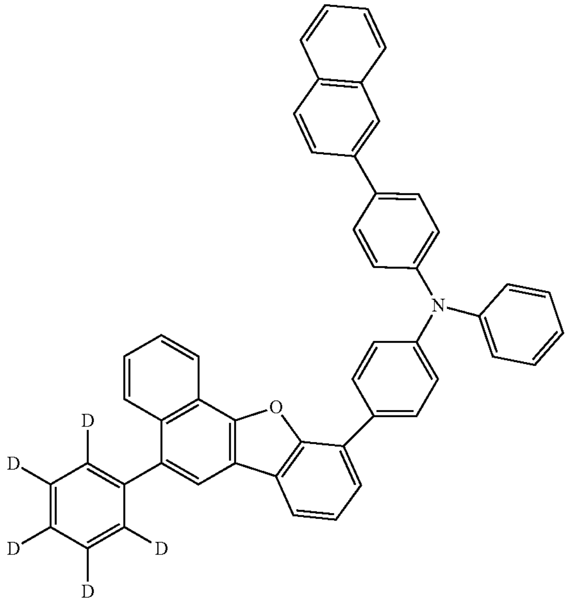
1-843
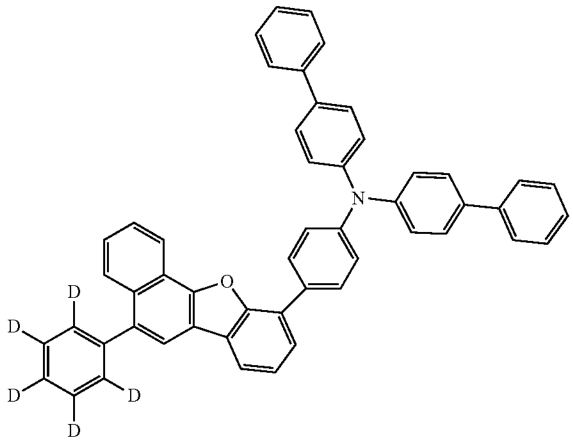
1-844
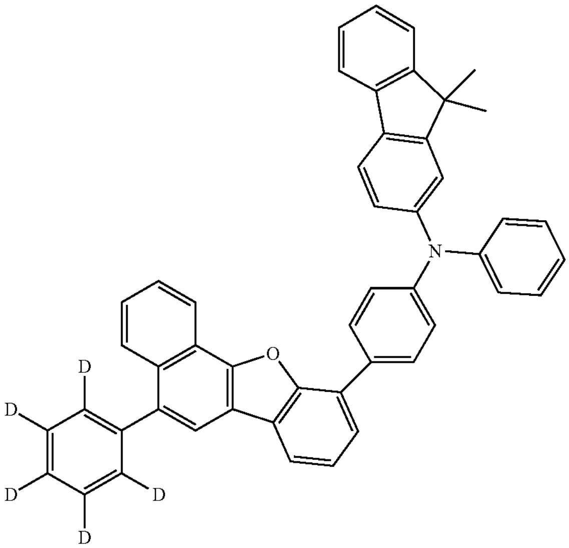
1-845
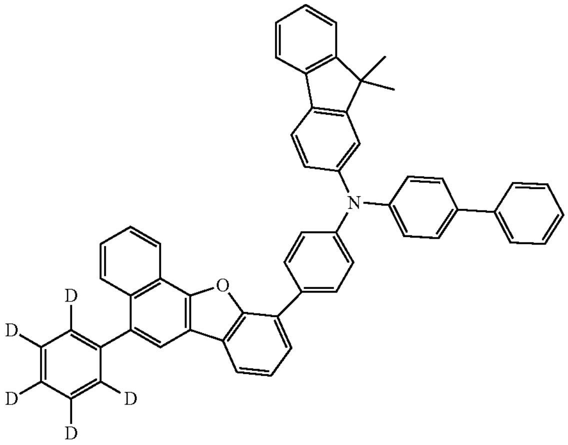
1-846
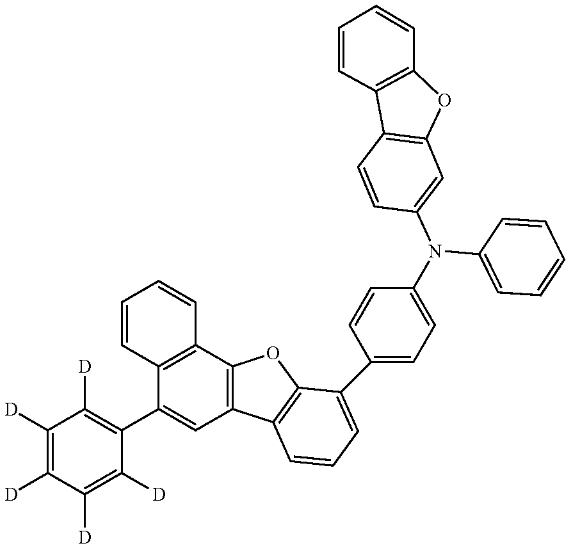

-continued
1-847
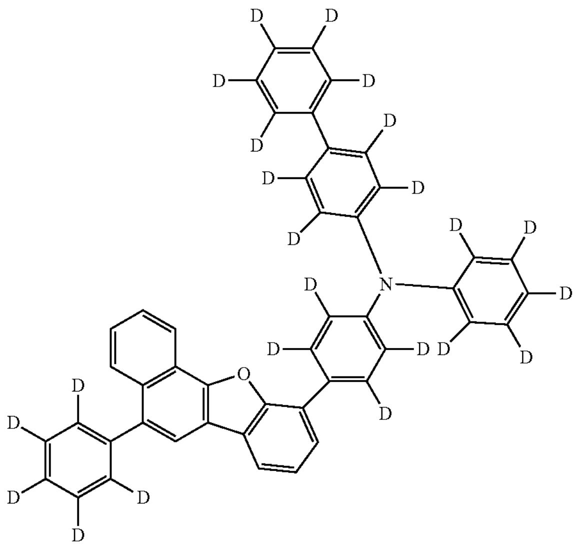
1-848
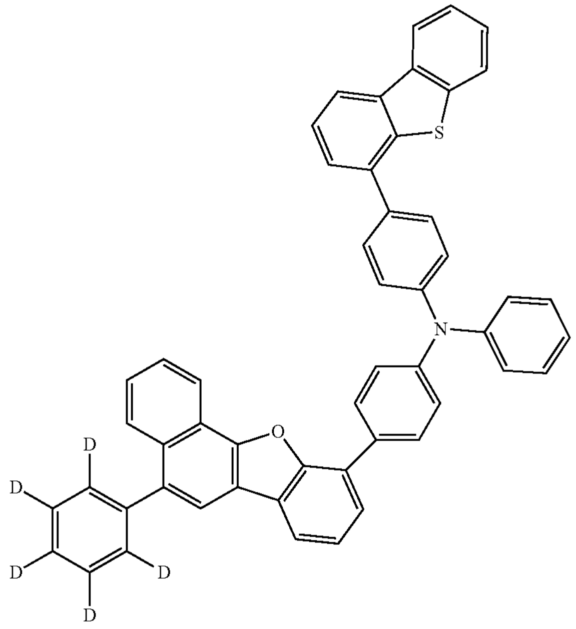
-continued
1-849
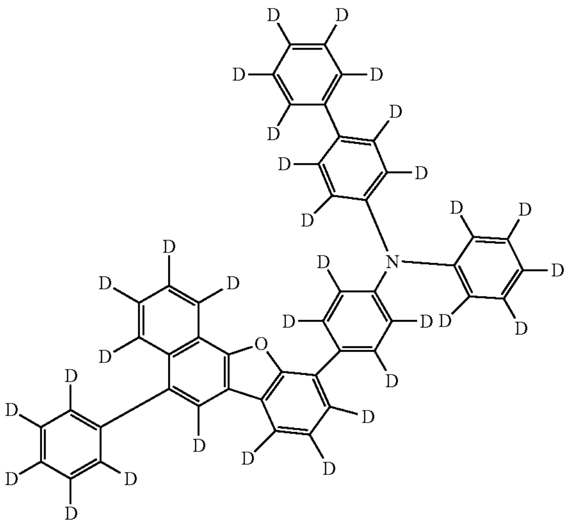
1-850
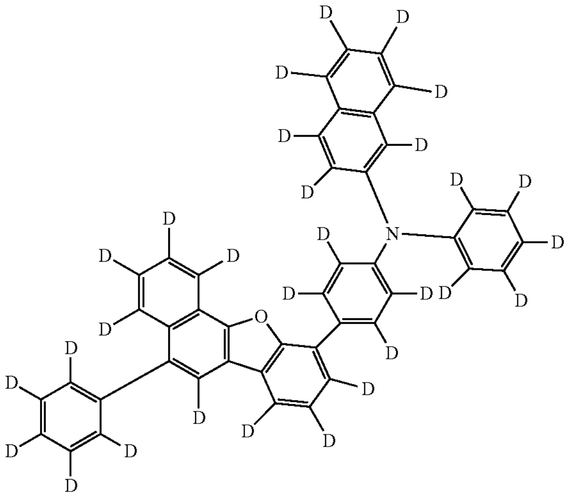
1-851
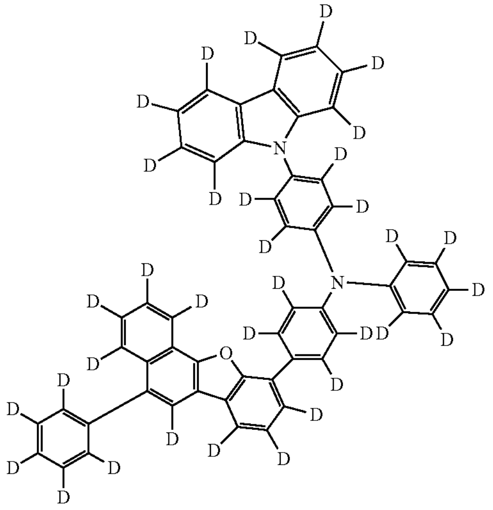

-continued
1-852
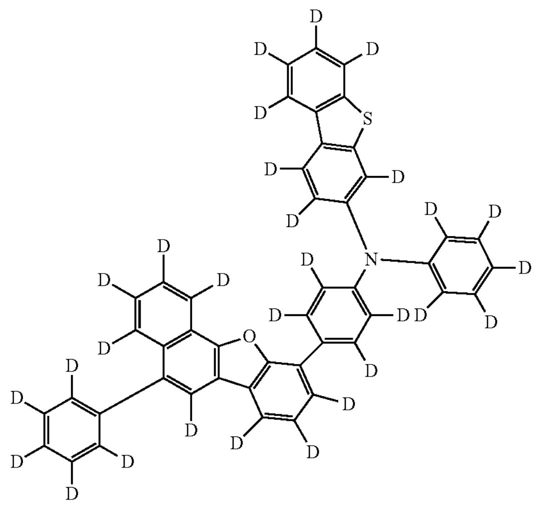
1-853
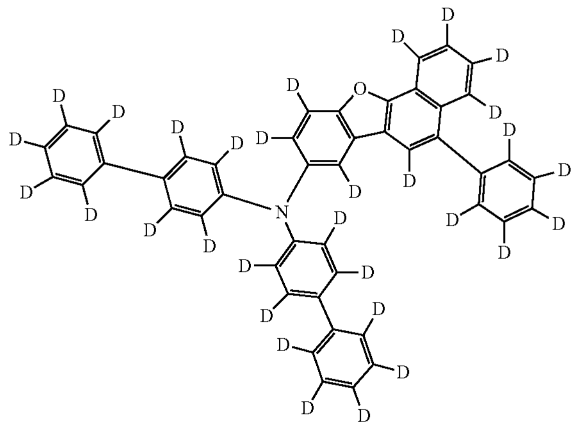
1-854
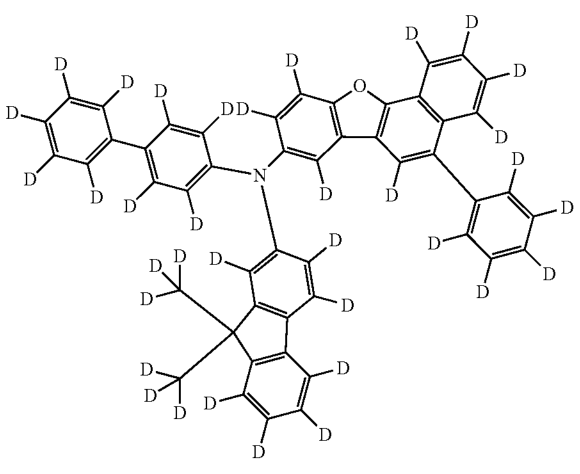
-continued
1-855
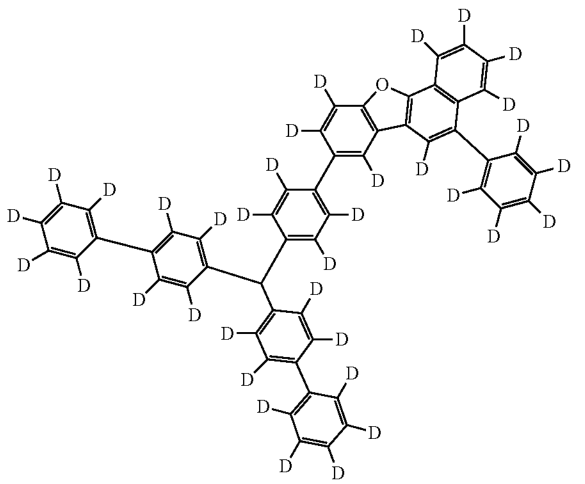
1-856
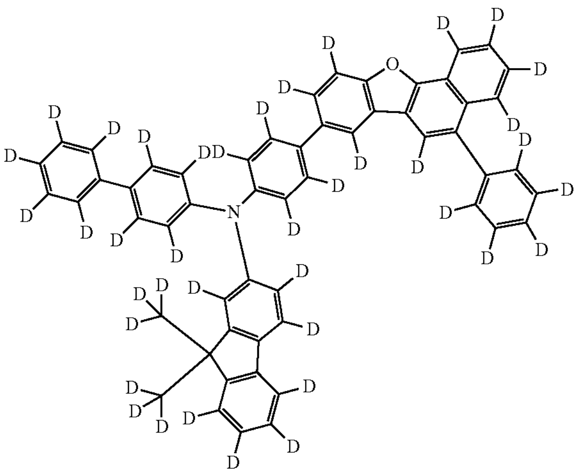
1-857
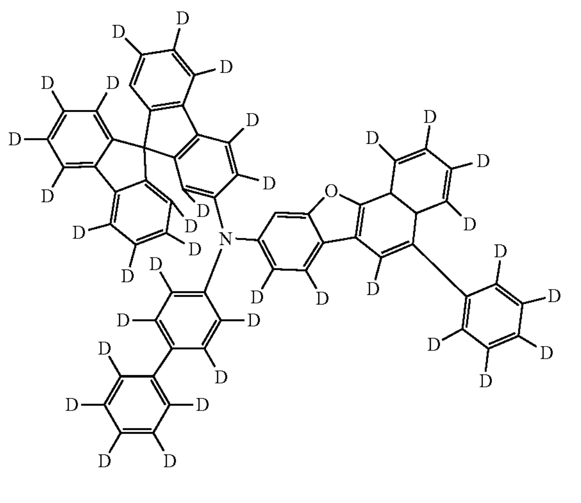

-continued
1-858
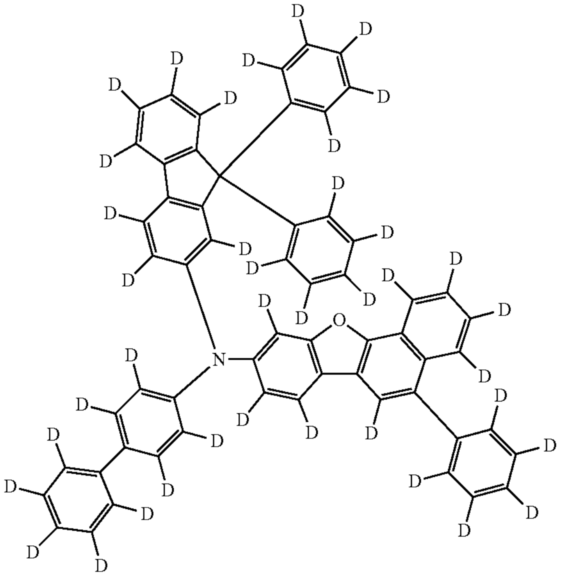
1-859
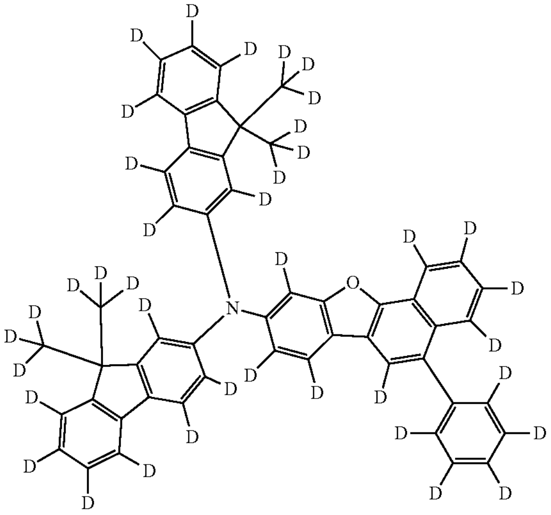
-continued
1-860
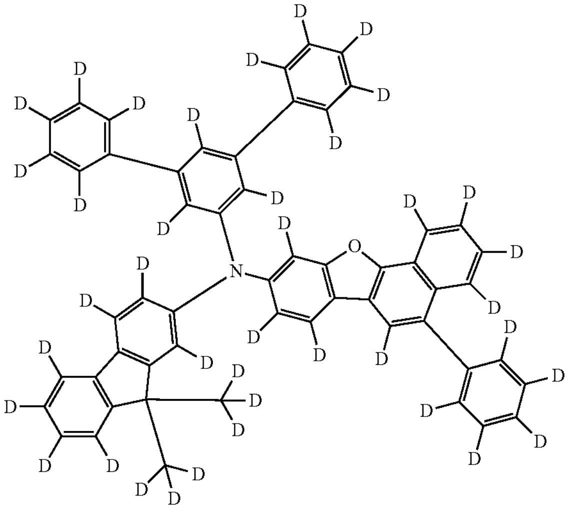
1-861
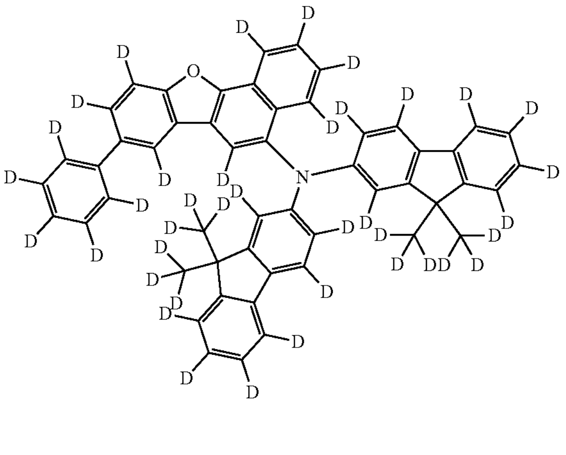
1-862
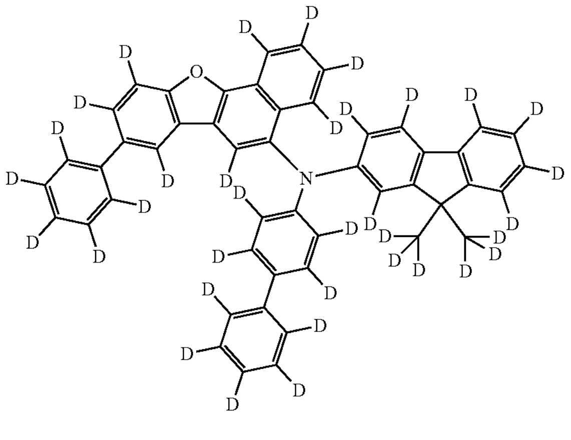

-continued
1-863
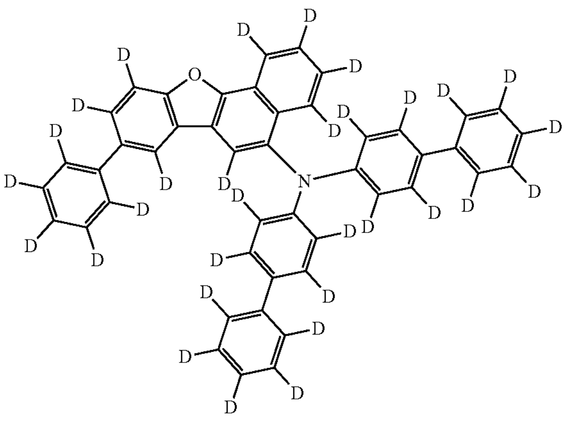
1-864
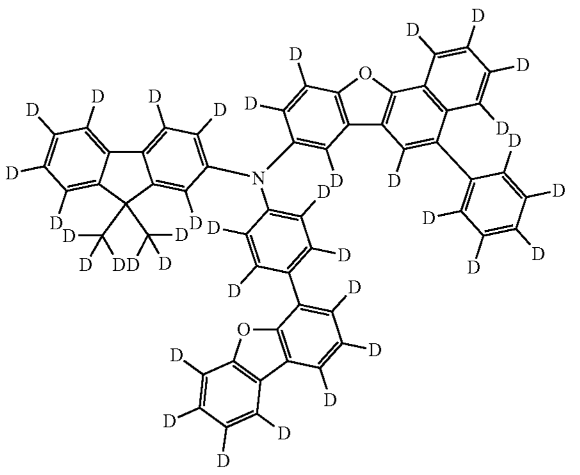
1-865
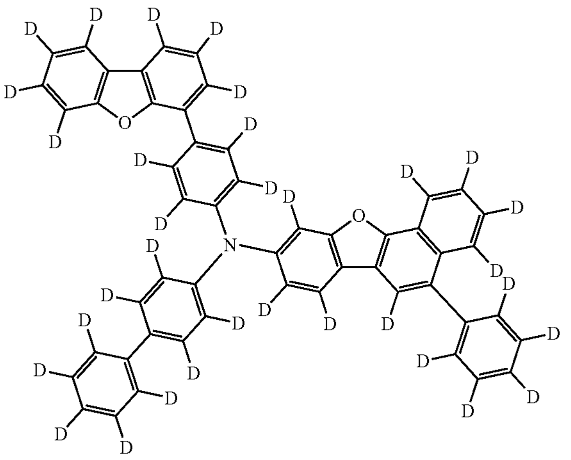
1-866
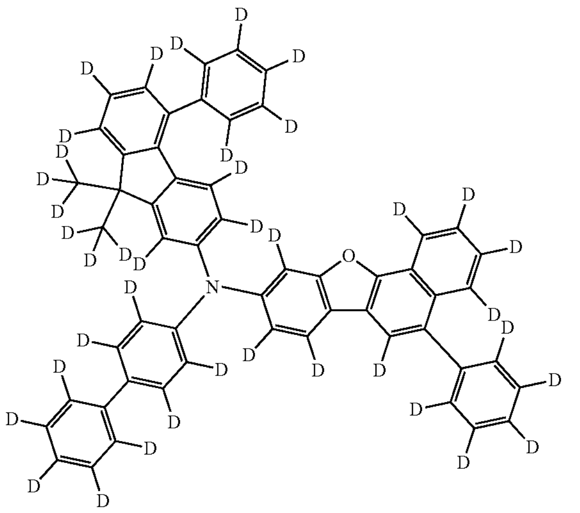
1-867
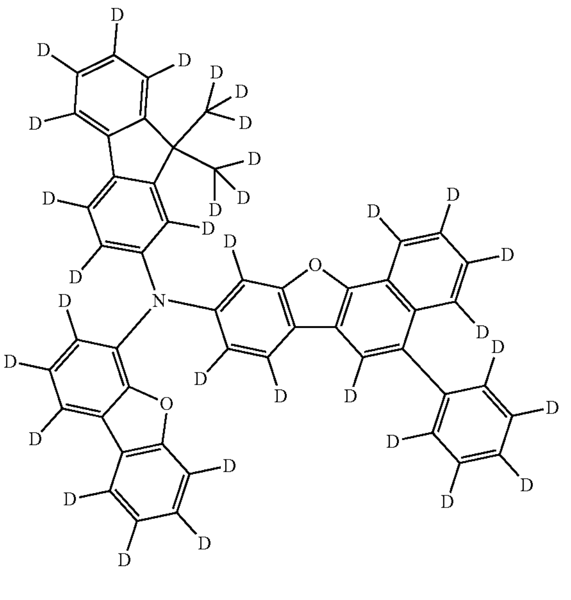
1-868
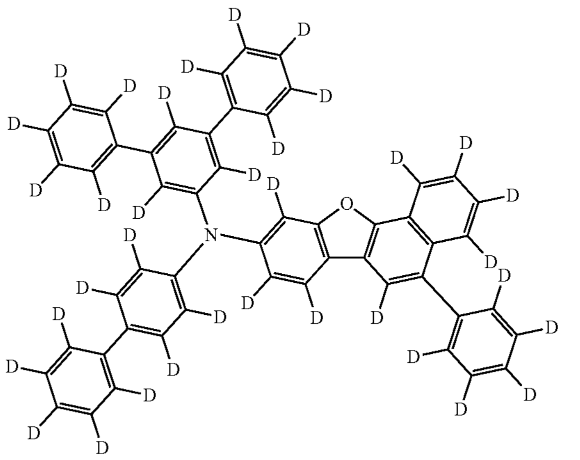

-continued
1-869
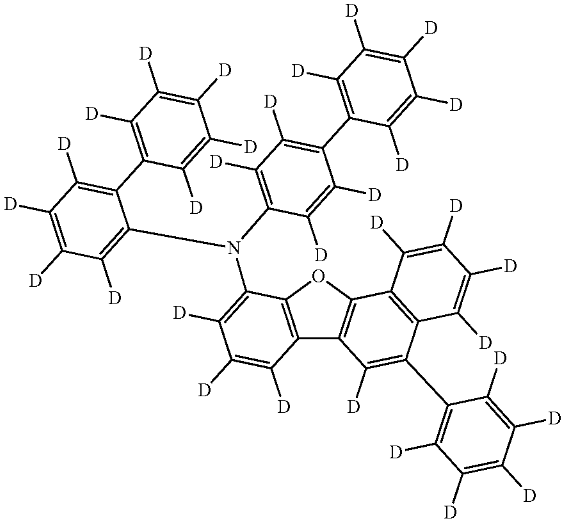
1-870
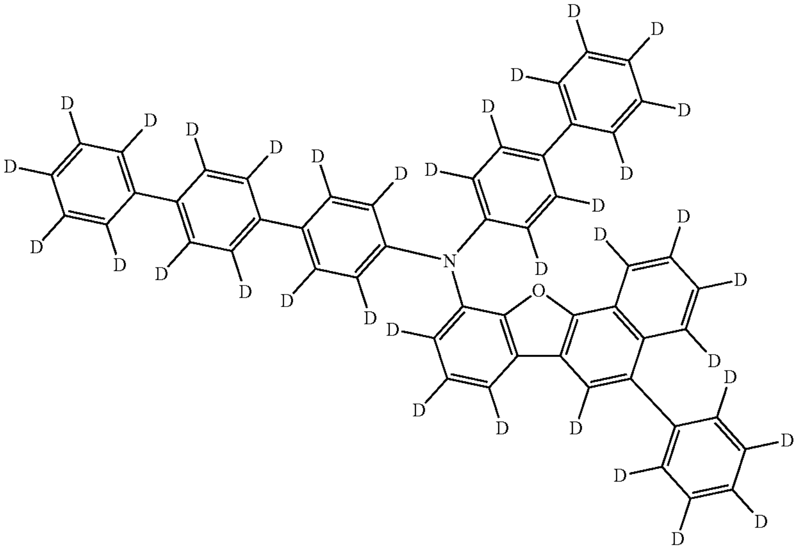
1-871
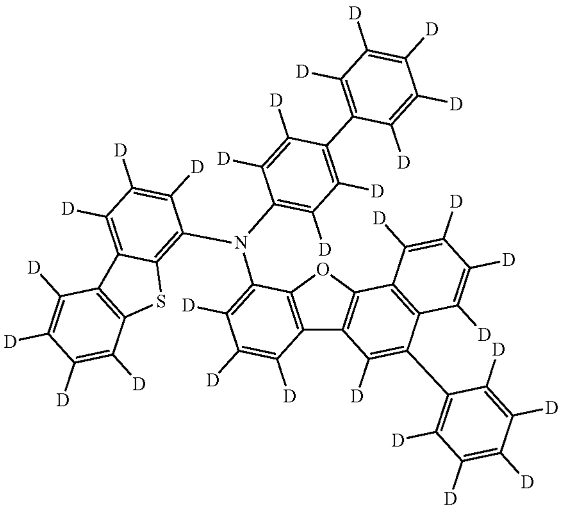
1-872
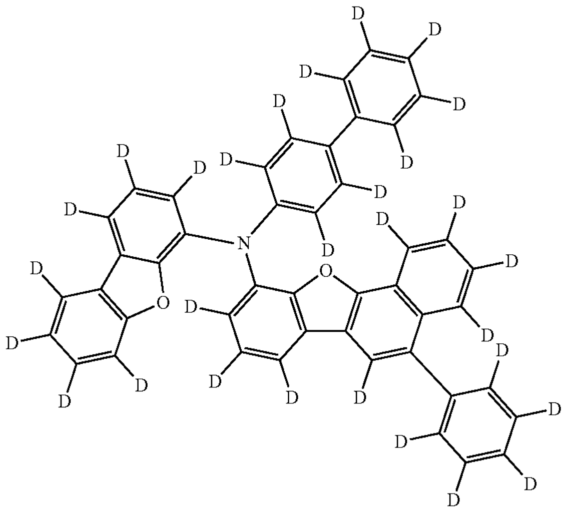

-continued
1-873
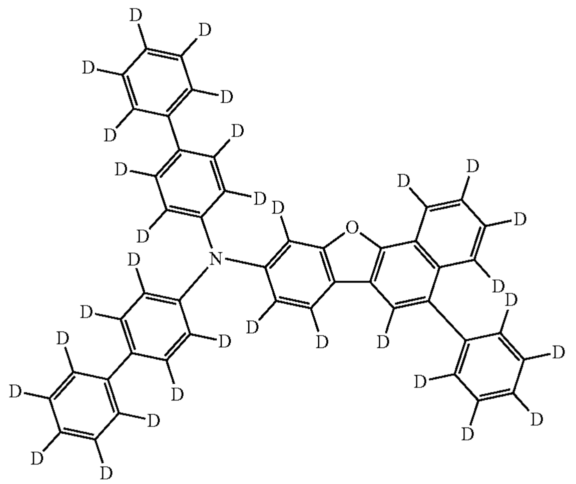
1-874
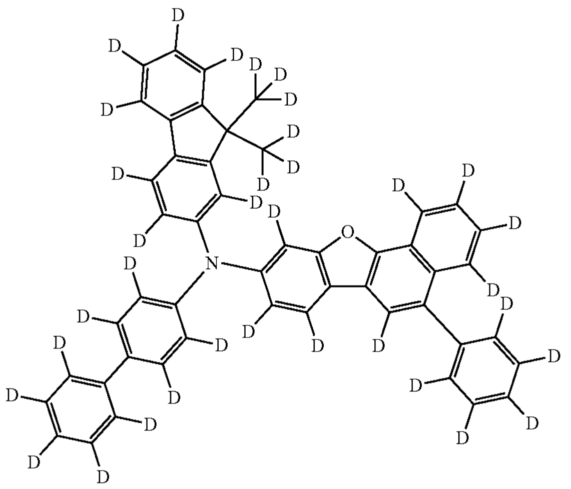
1-875
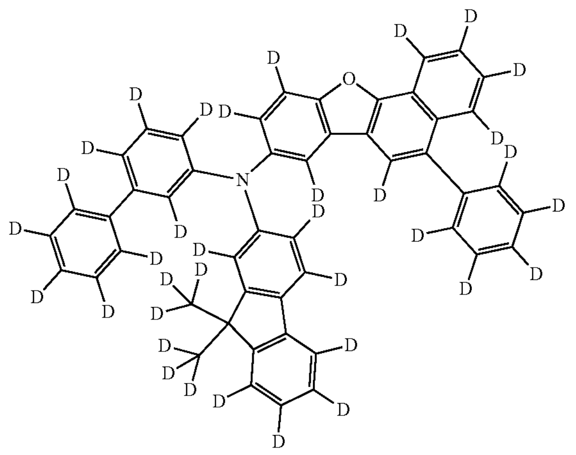
1-876
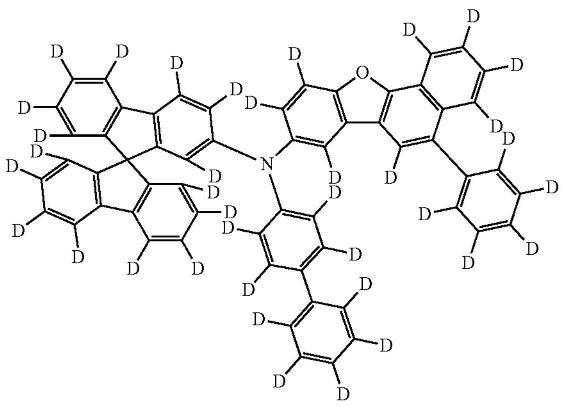
1-877
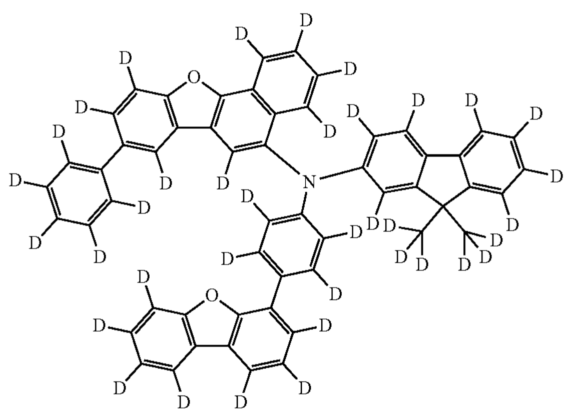
1-878
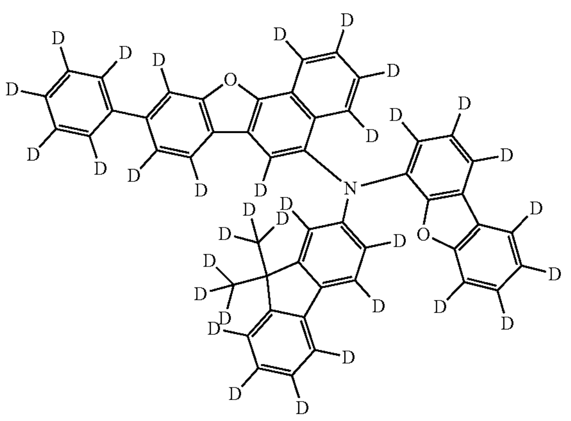

-continued
1-879
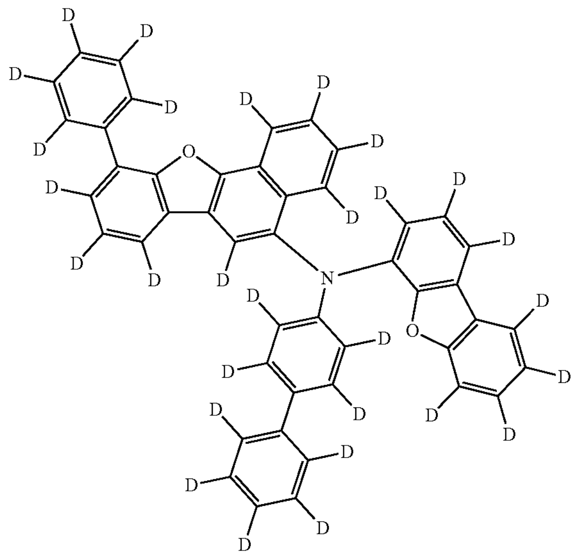
1-880
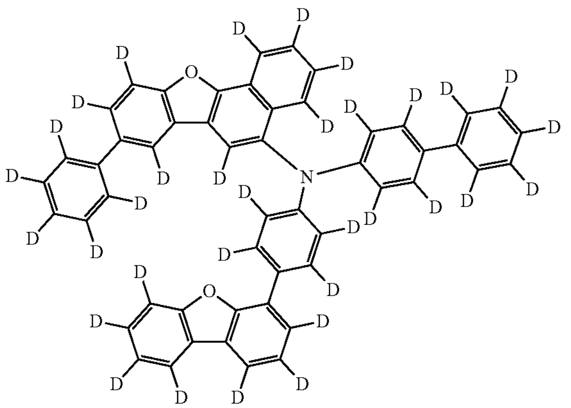
1-881
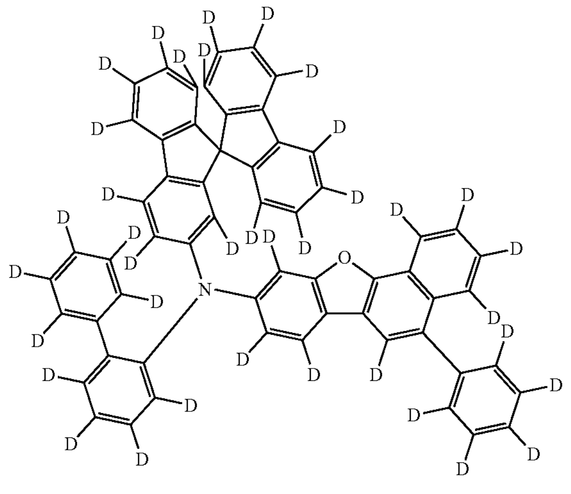
1-882
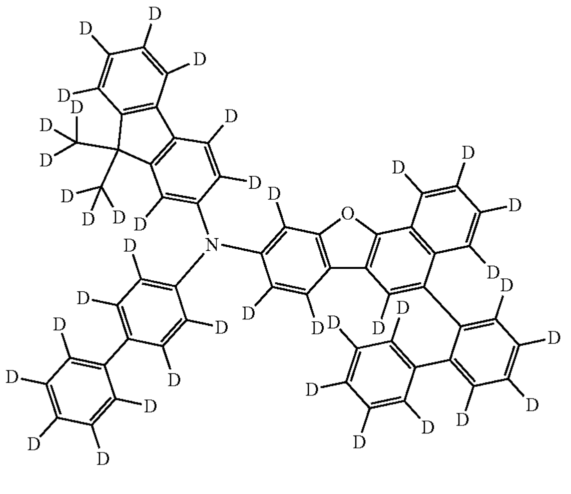

1-883
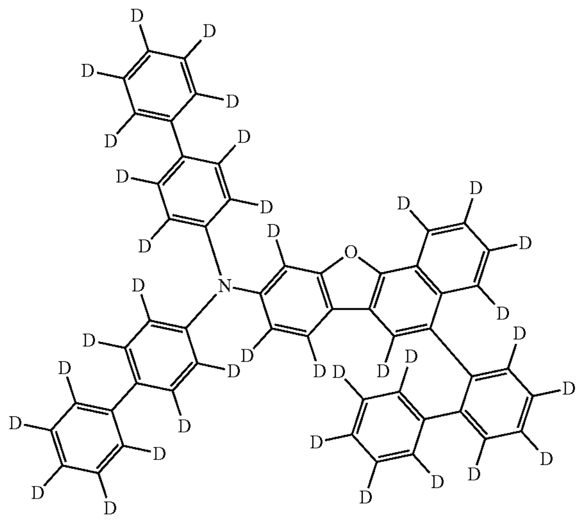
1-884
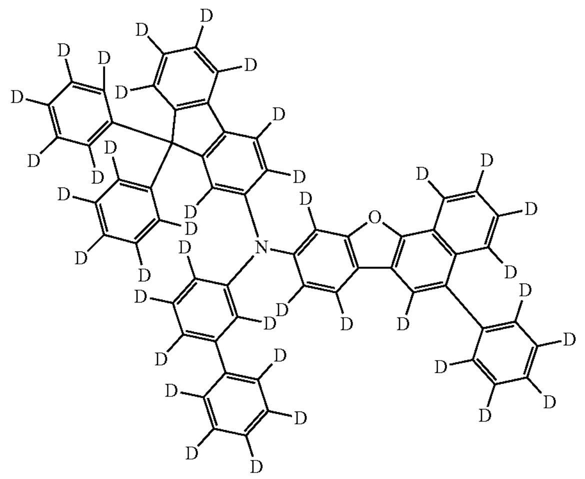
1-885
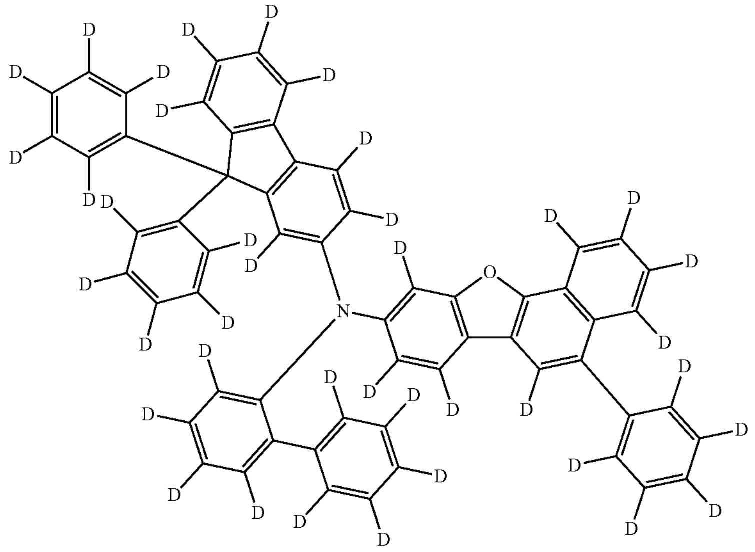

-continued
1-886
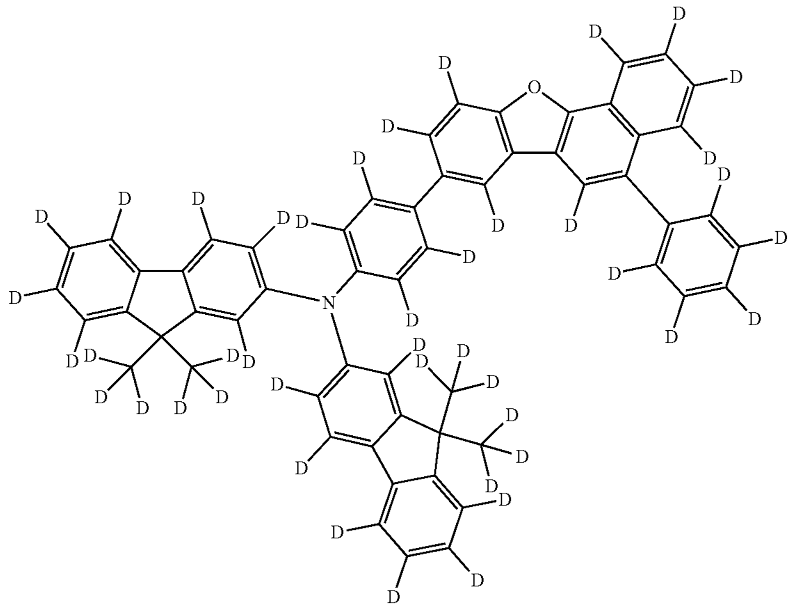
1-887
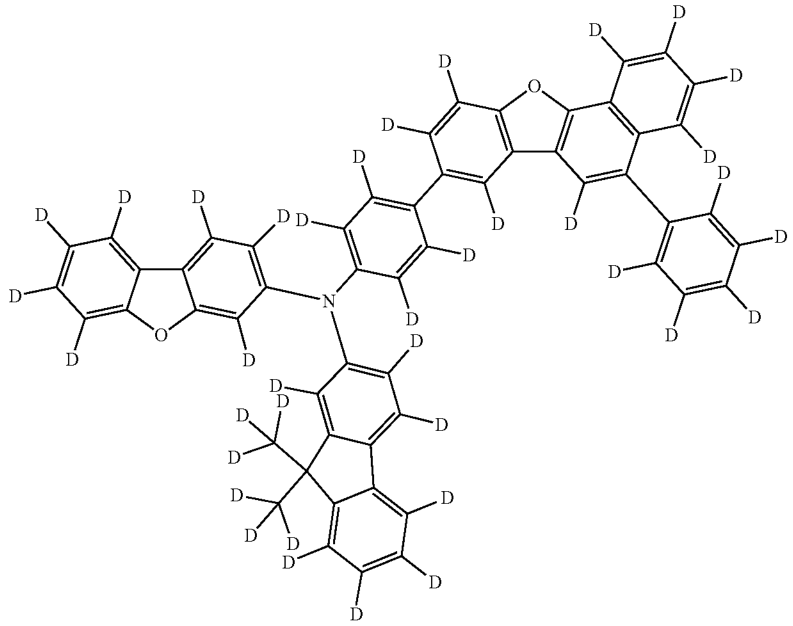

-continued
1-888
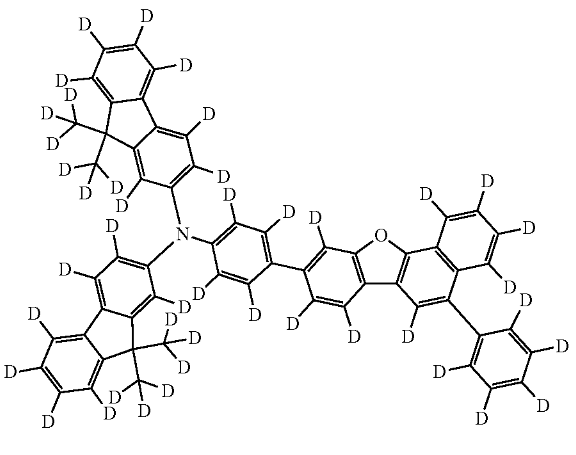
1-889
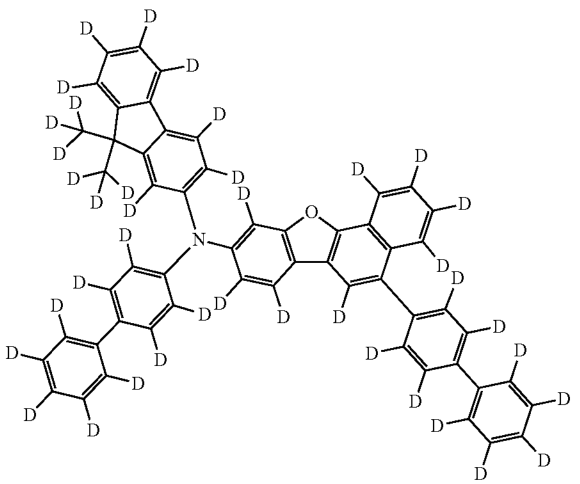
1-890
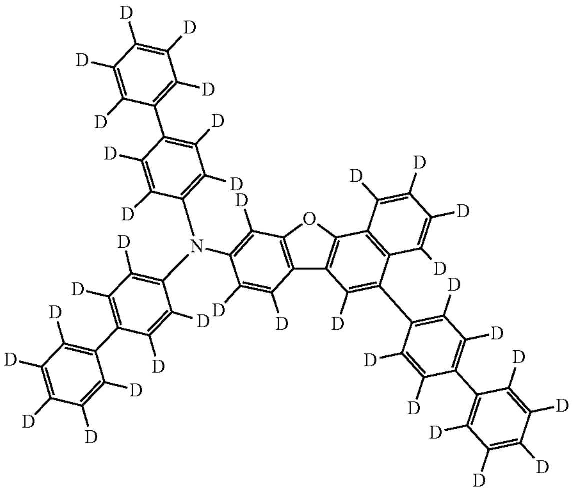
1-891
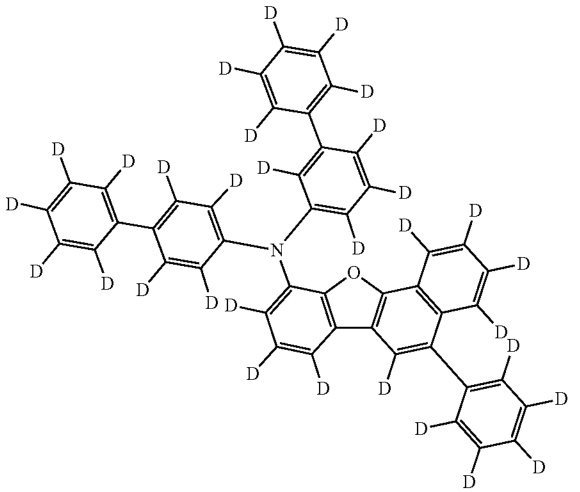
1-892
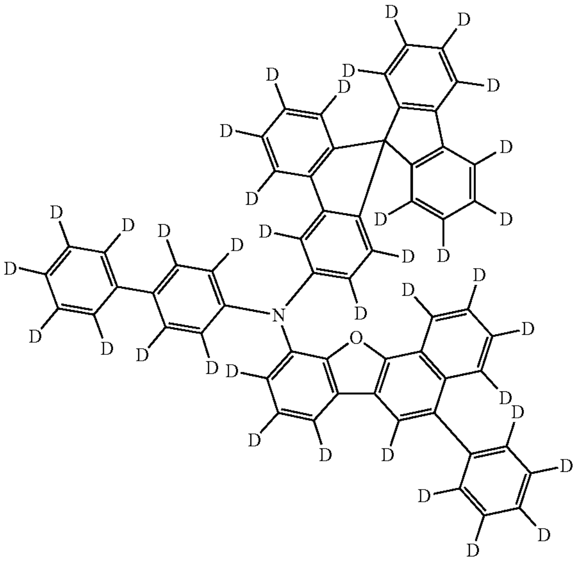
1-893
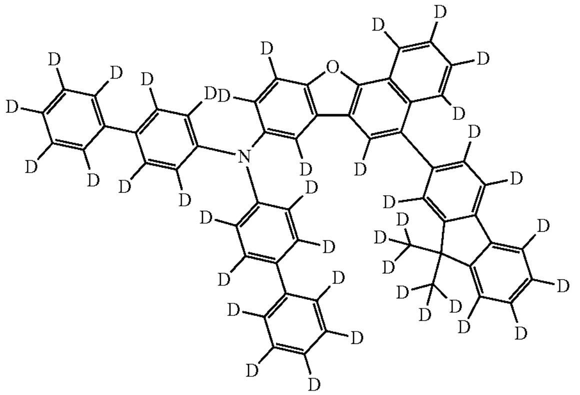

-continued
1-894
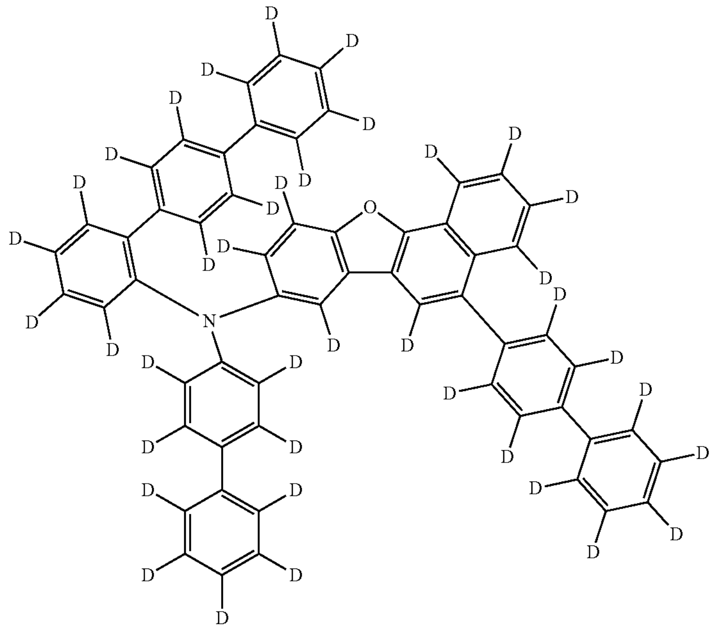
1-895
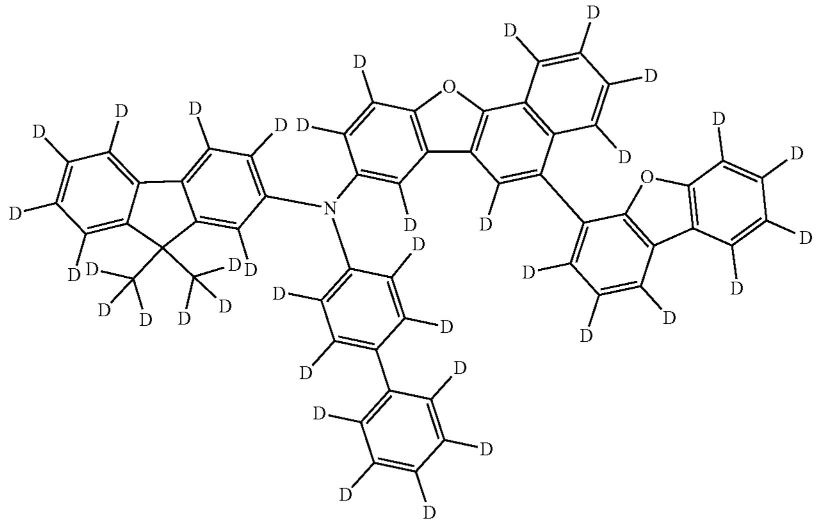
1-896
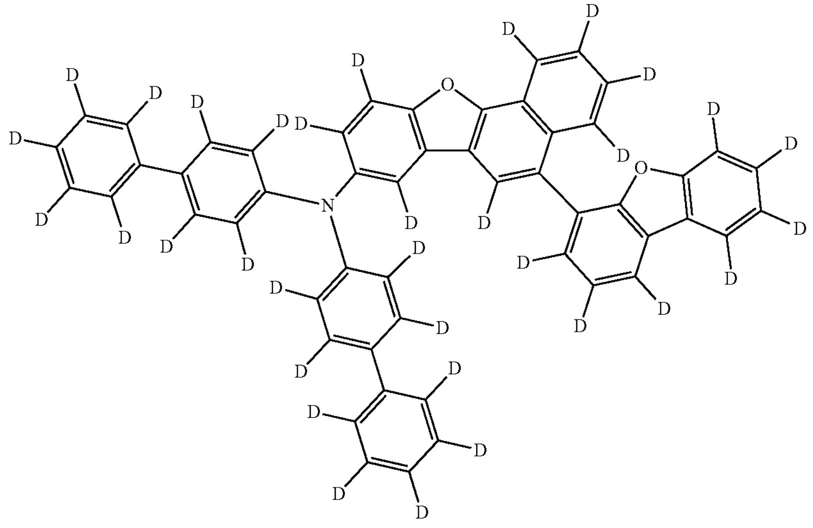

-continued
1-897
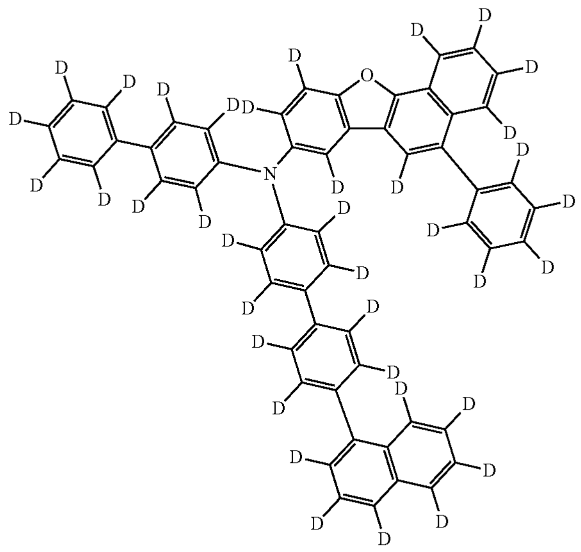
1-898
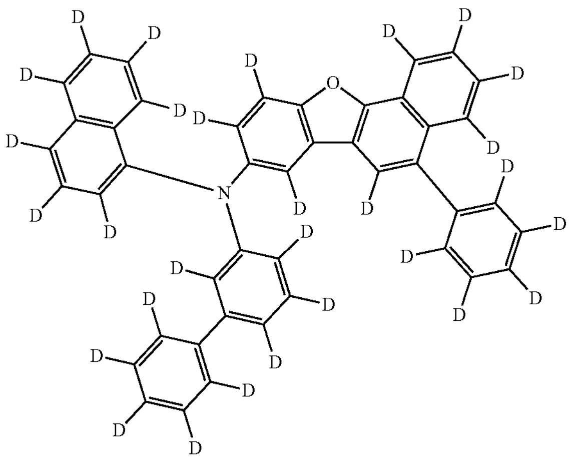
1-899
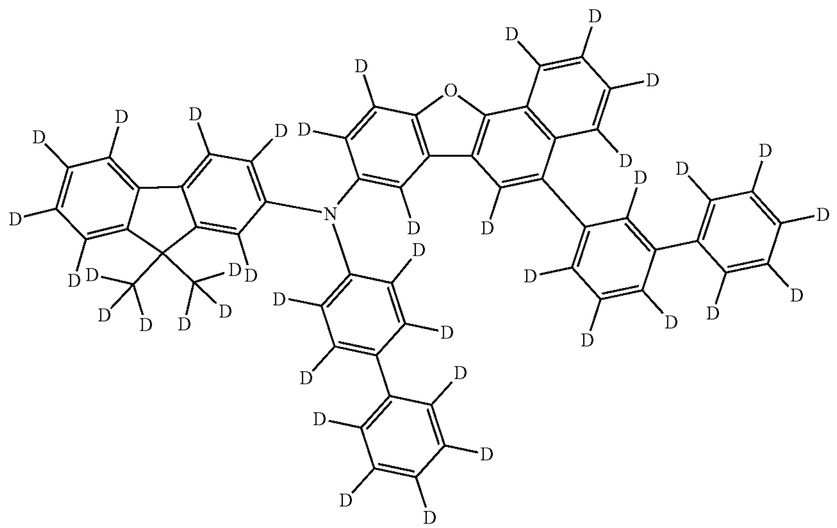
1-900
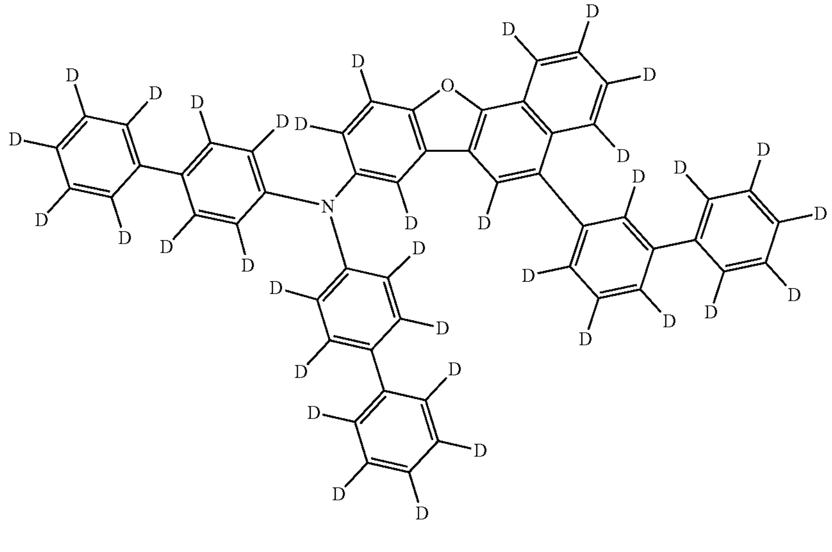

-continued
1-901
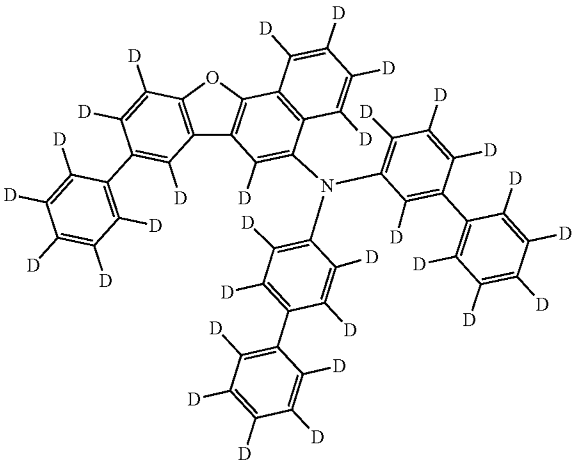
1-902
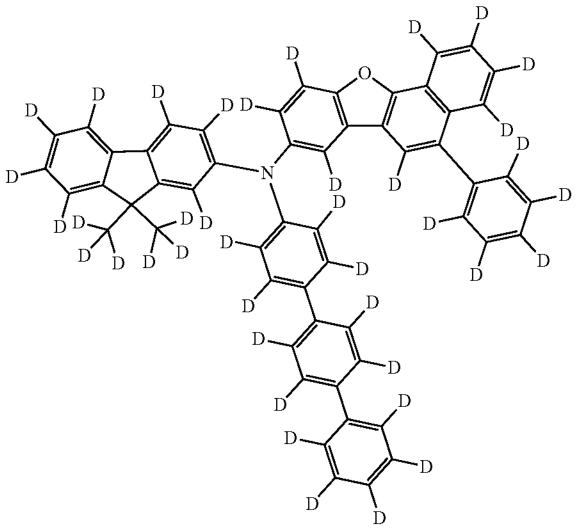
1-903
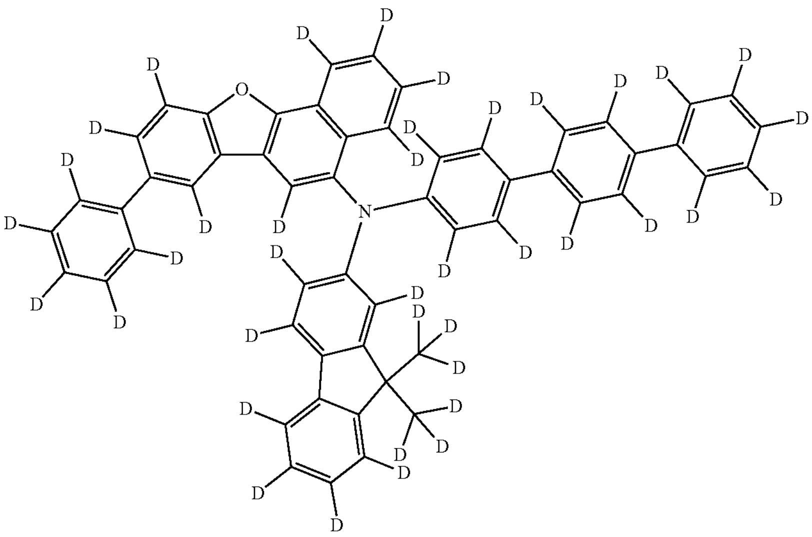
1-904
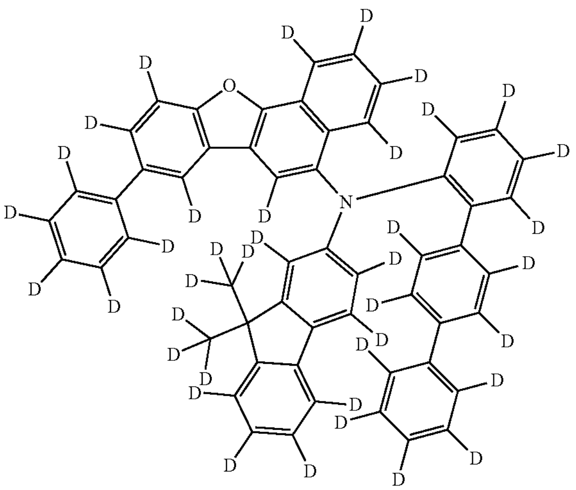
1-905
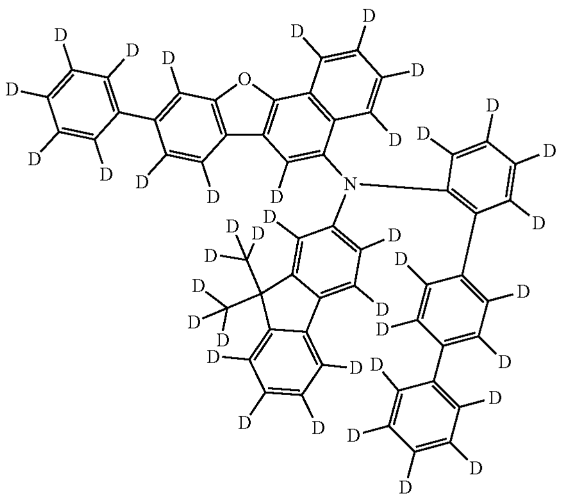

-continued
1-906
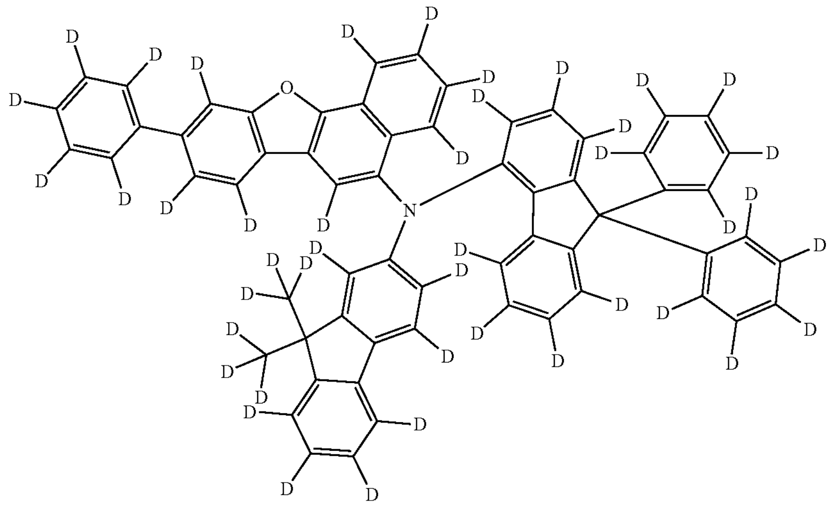
1-907
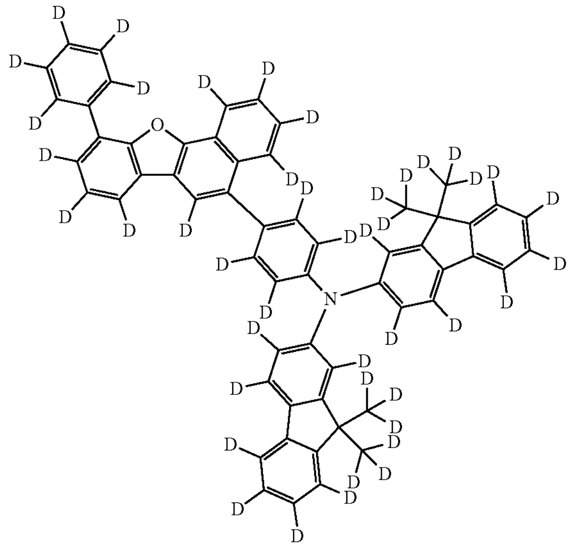
1-908
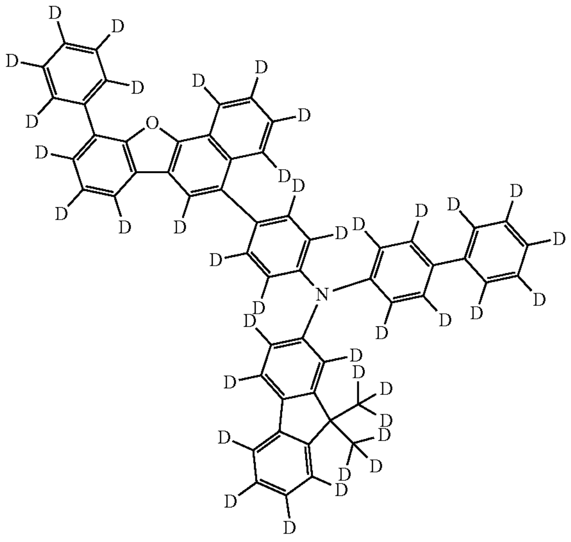

-continued
1-909
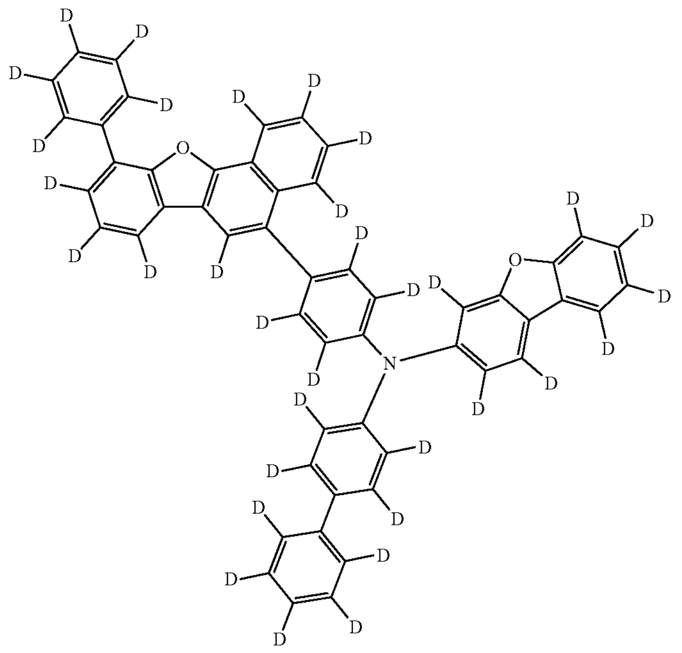
1-910
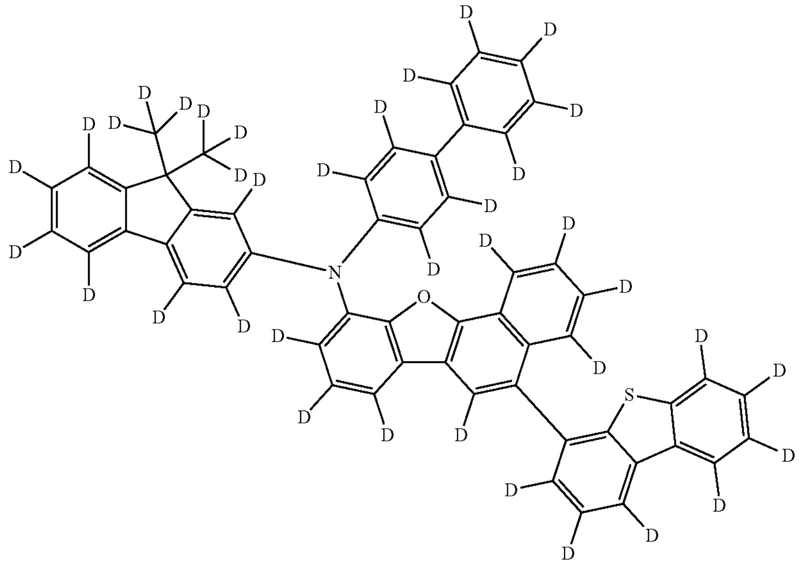

-continued
1-911
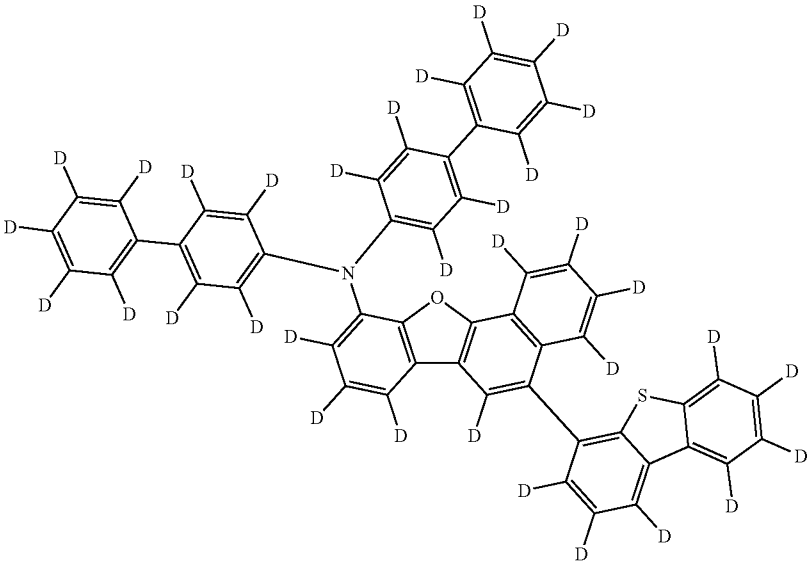
1-912
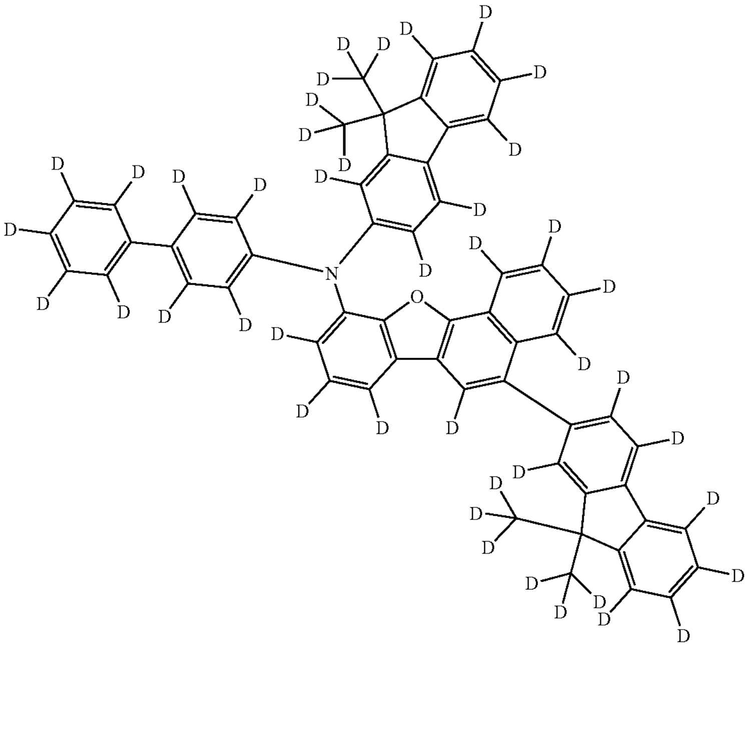

-continued
1-913
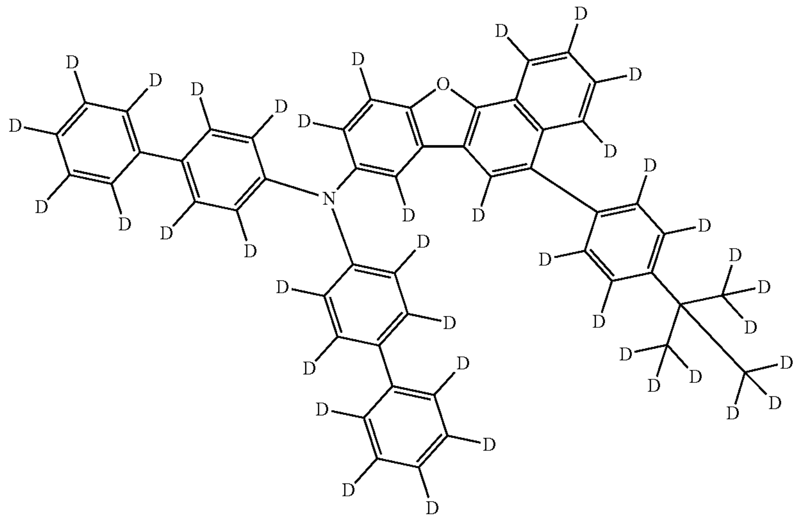
1-914
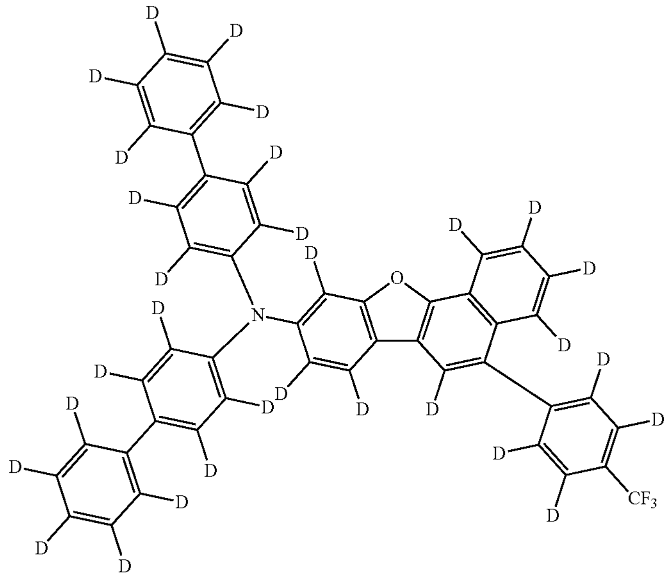

-continued
1-915
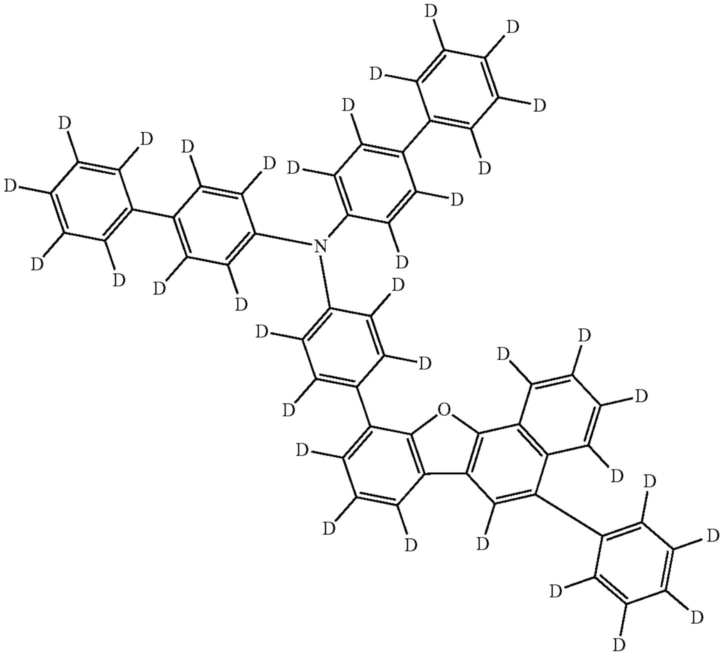
1-916
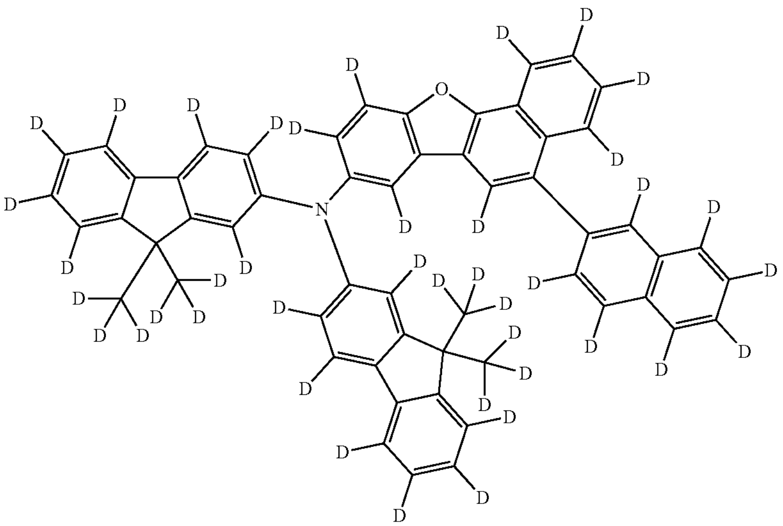

-continued
1-917
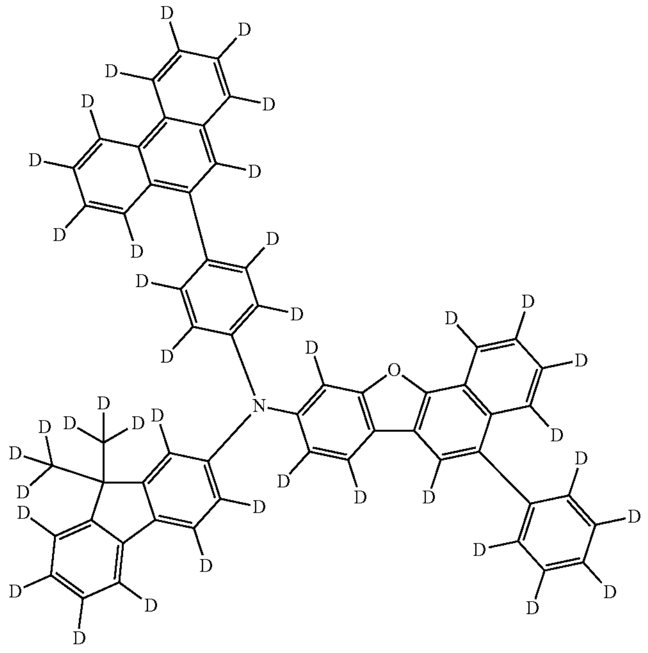
1-918
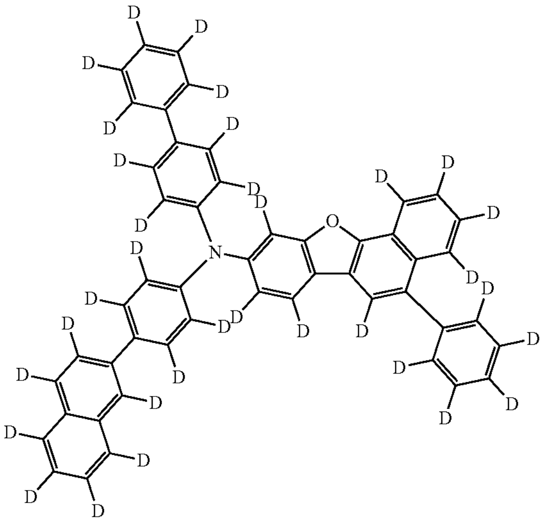
1-919
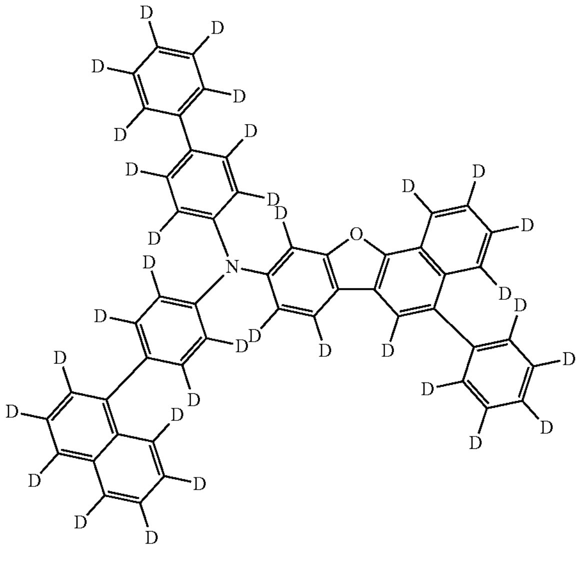

-continued
1-920
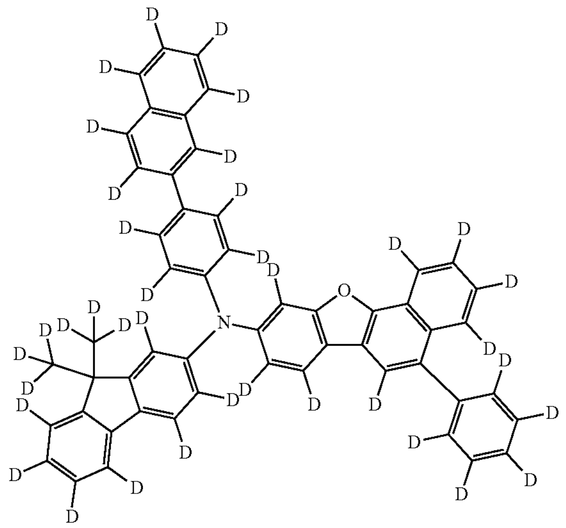
1-921
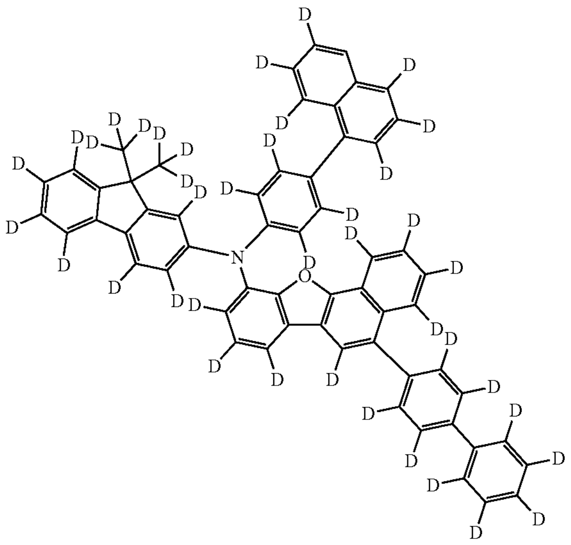
1-922
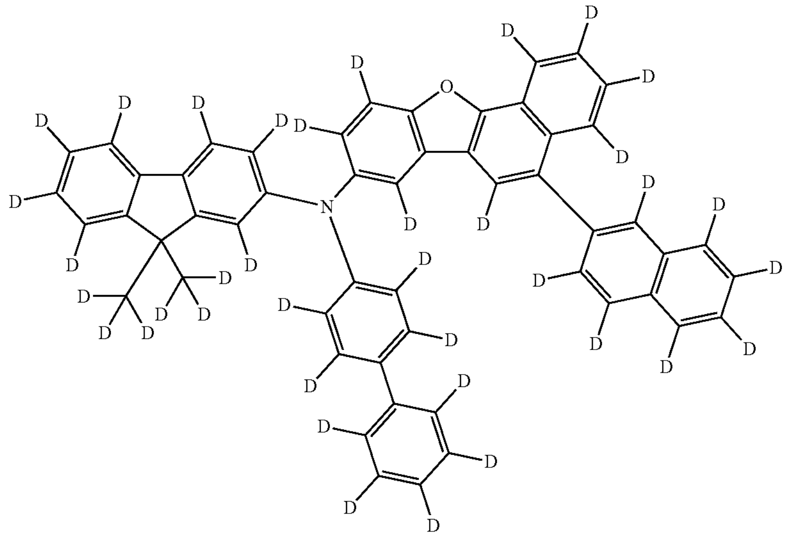
1-923
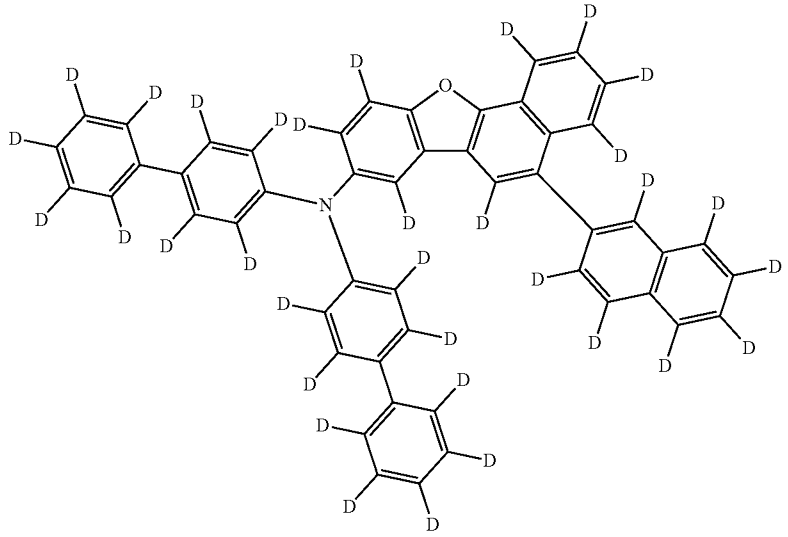

-continued
1-924
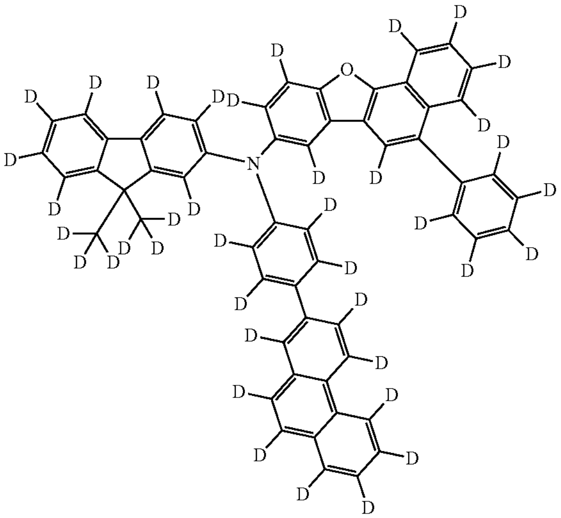
1-925
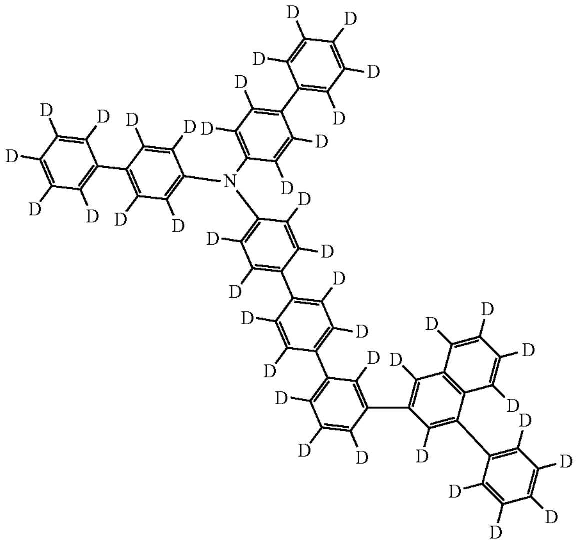
1-926
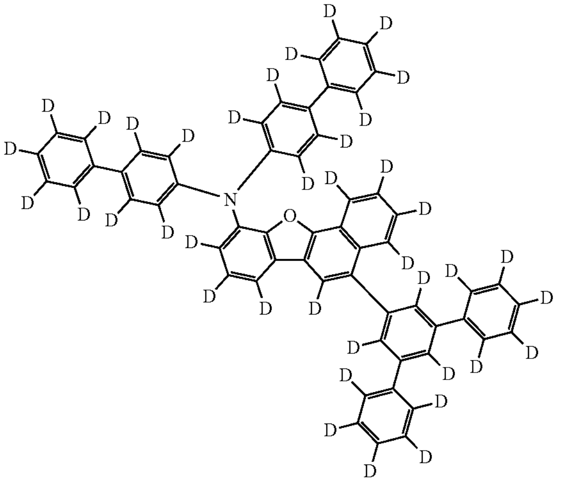
1-927
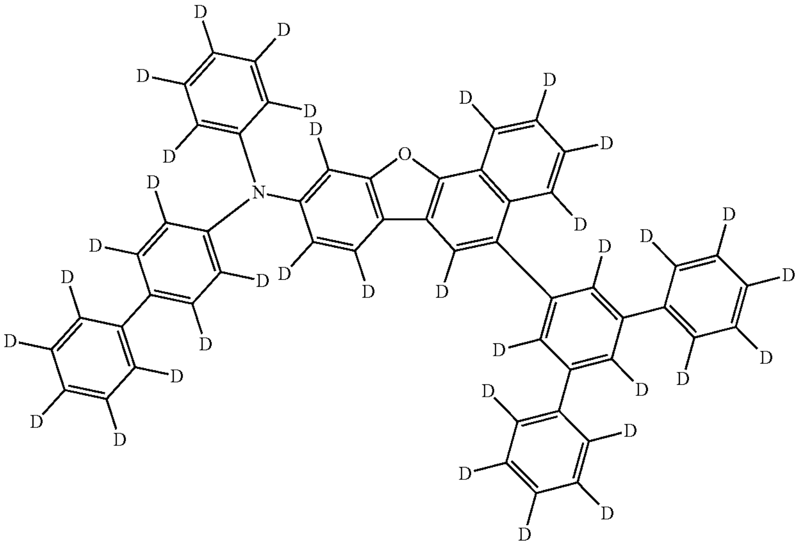

-continued
1-928
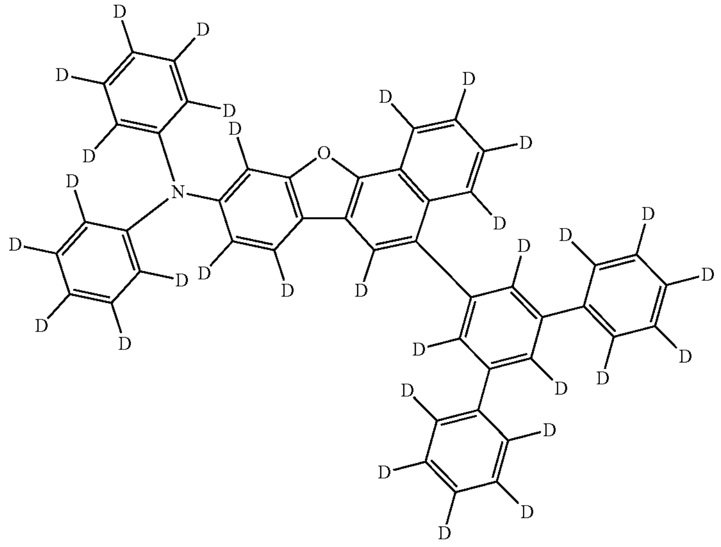
1-929
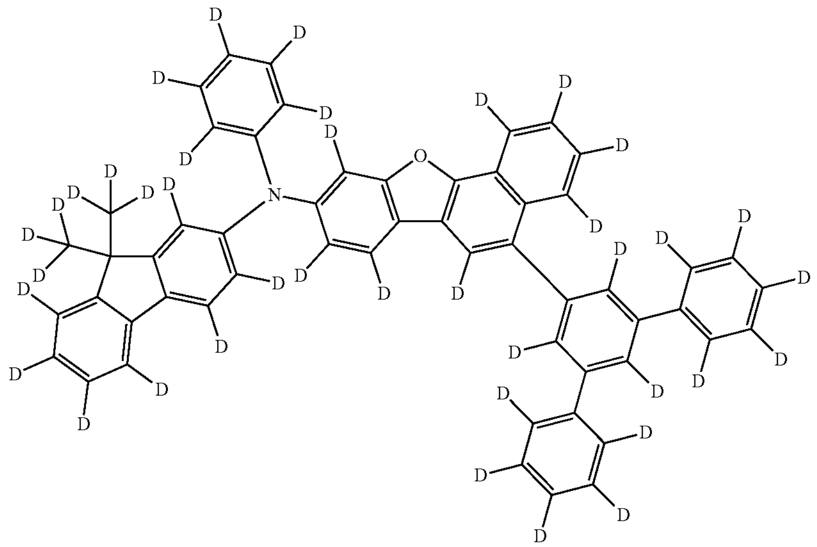
1-930
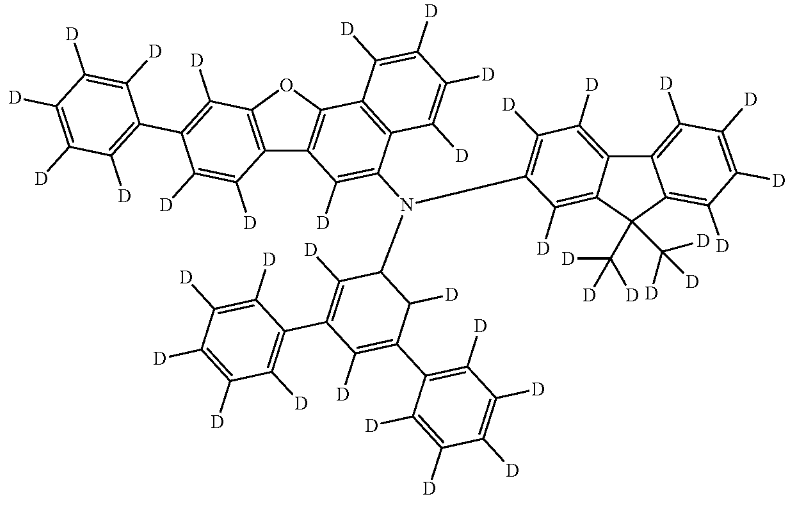

1-931
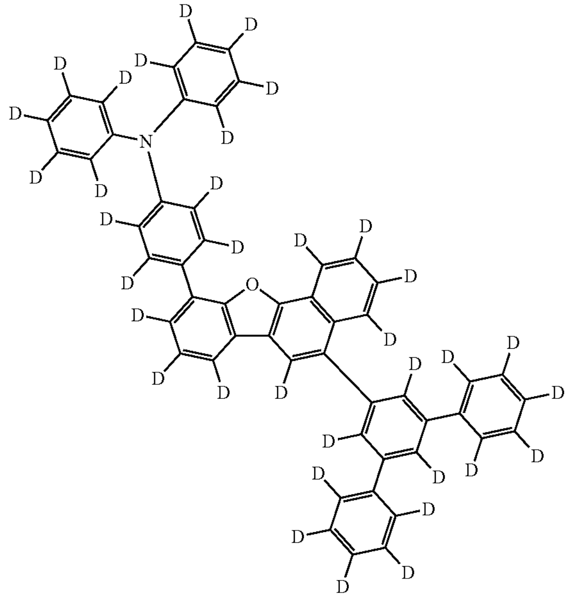
1-932
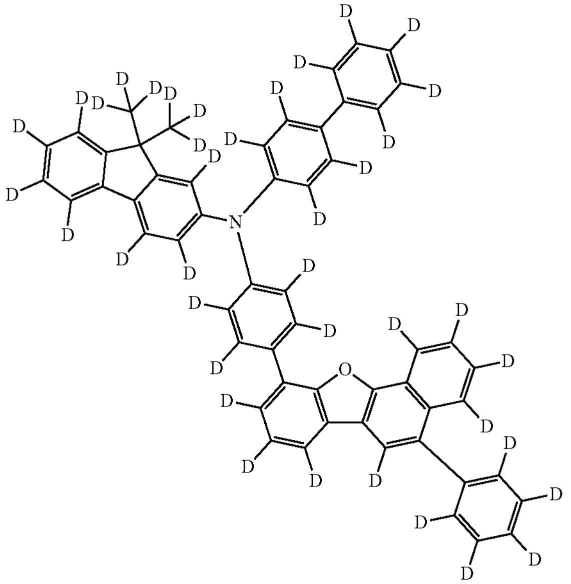
1-933
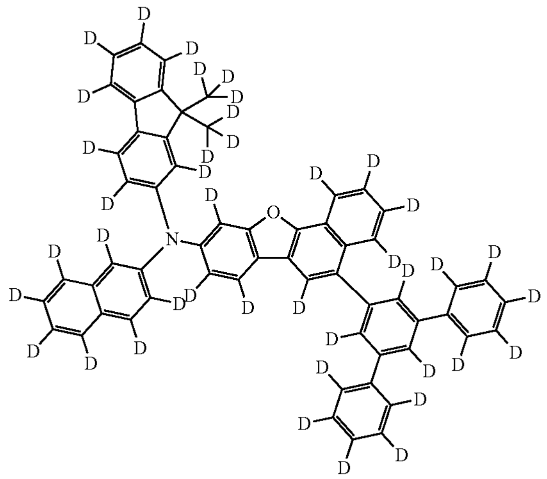
1-934
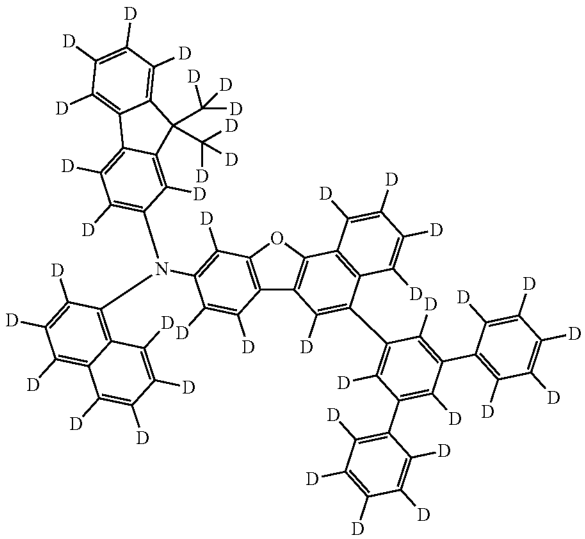

-continued
1-935
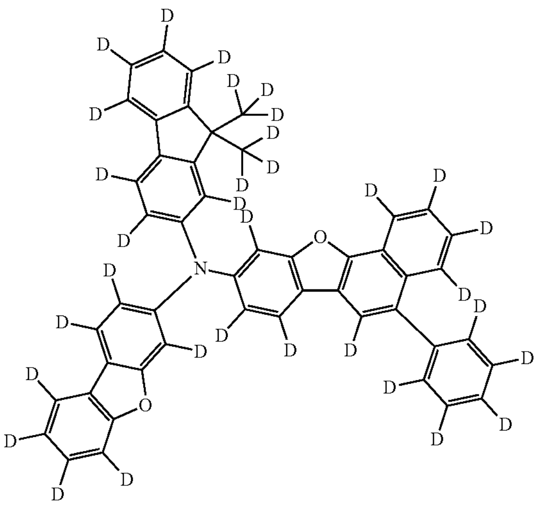
1-936
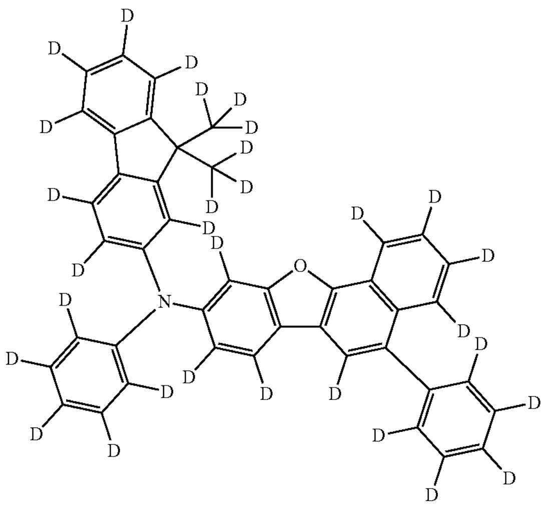
1-937
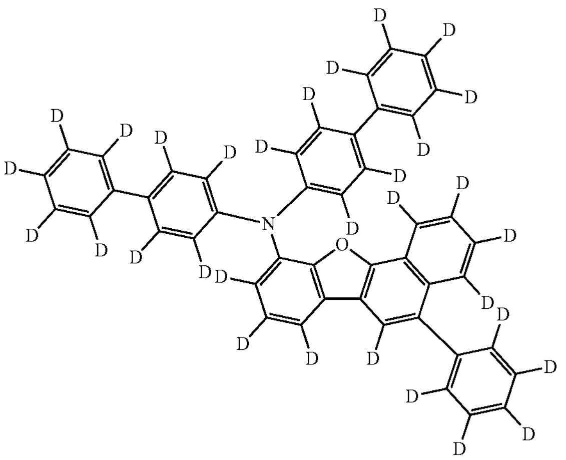
1-938
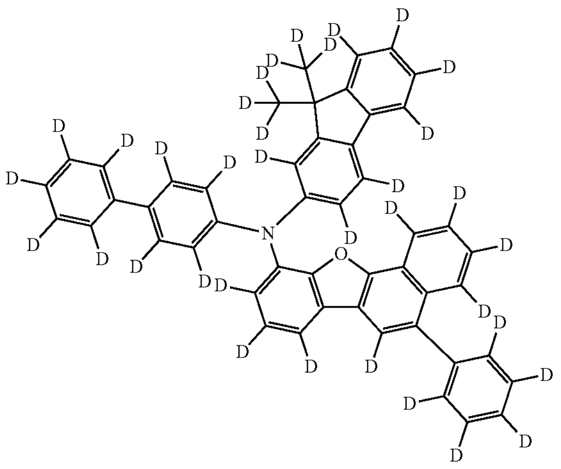
1-939
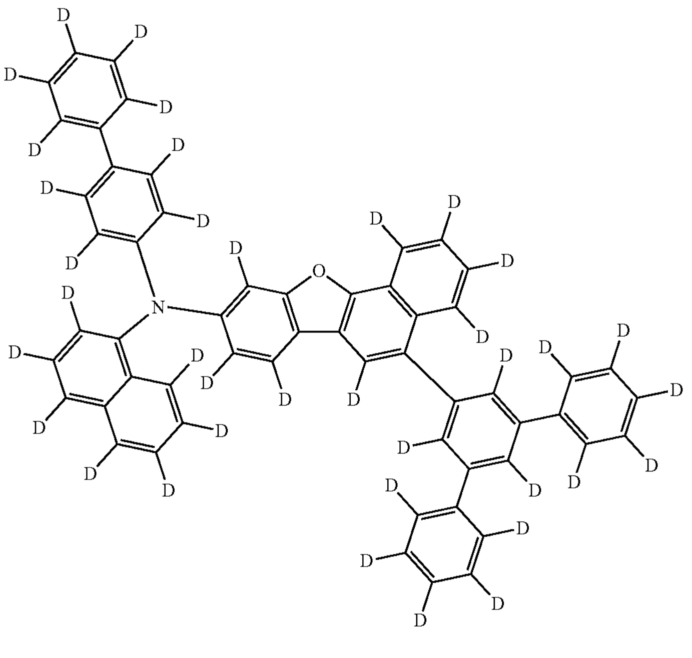

-continued
1-940
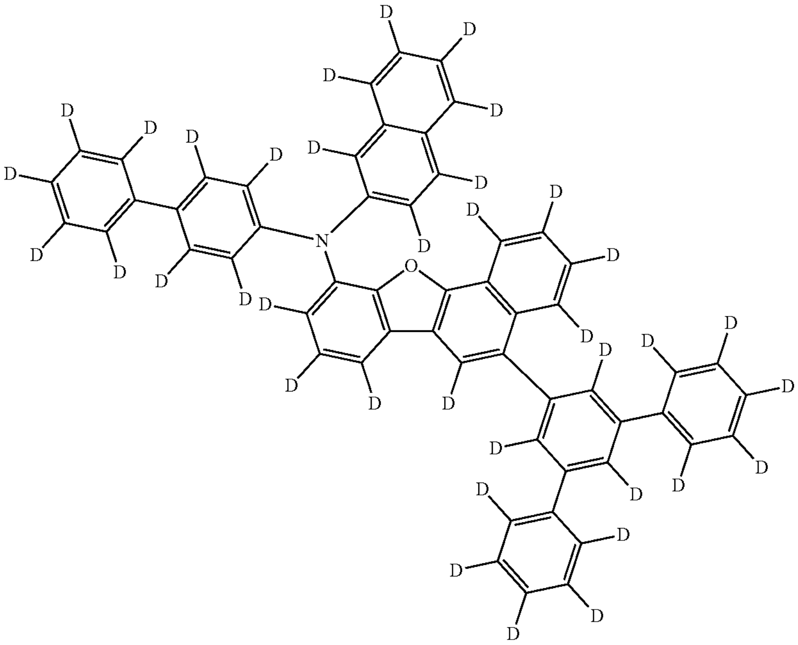
1-941
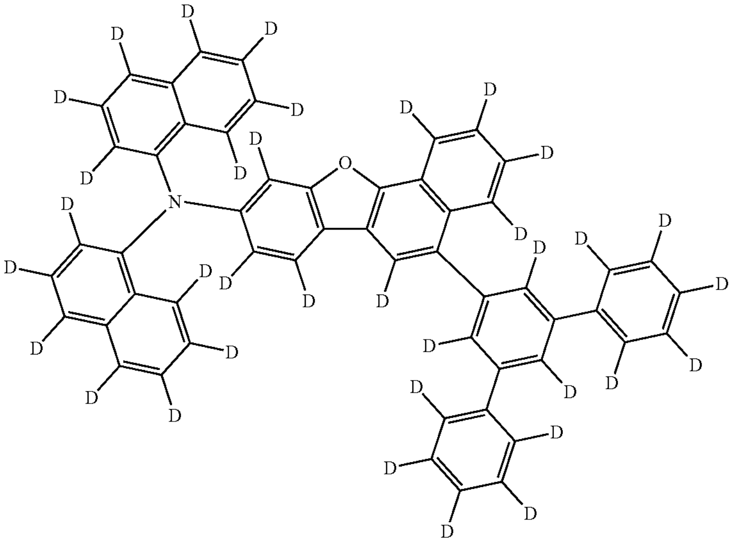

-continued
1-942
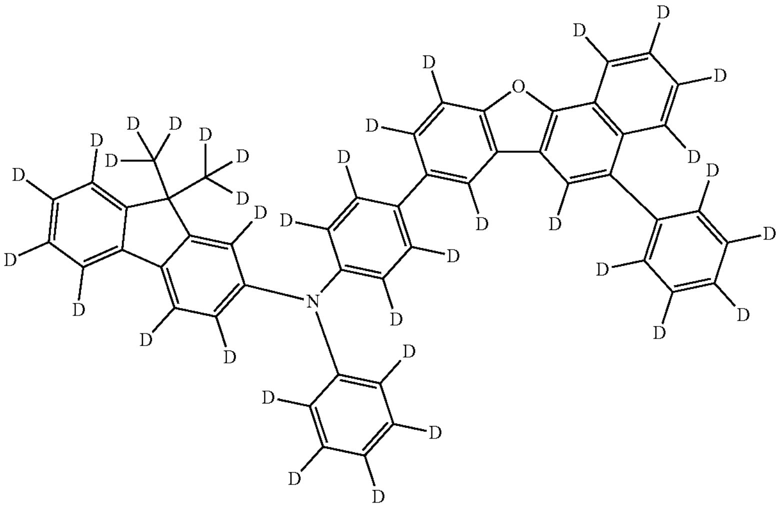
1-943
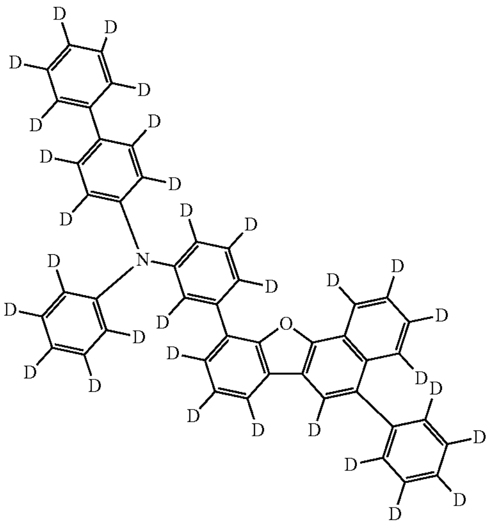
1-944
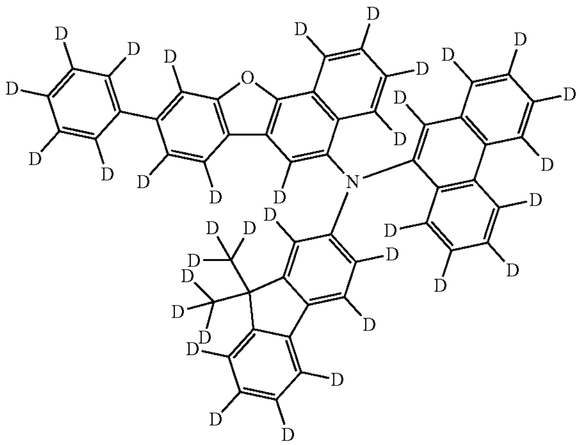
1-945
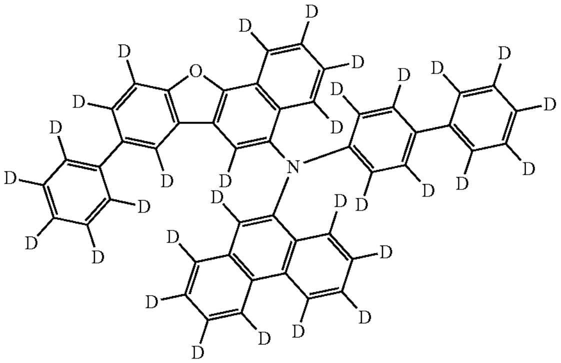
1-946
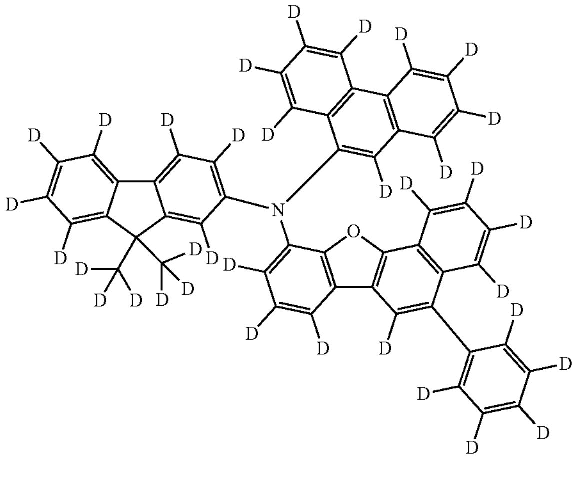

-continued
1-947
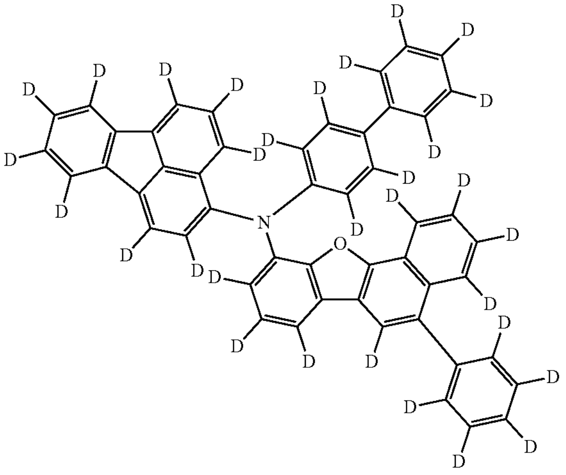
1-948
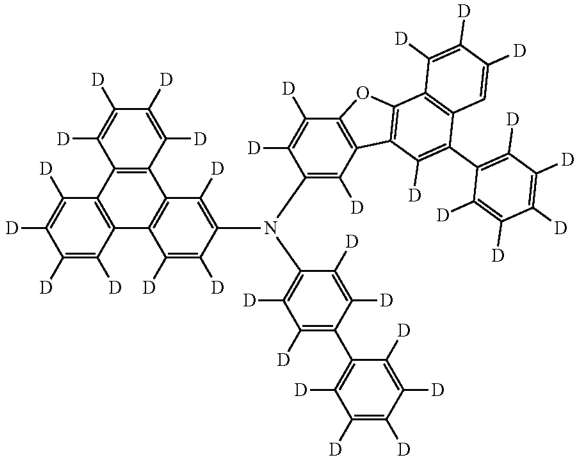
1-949
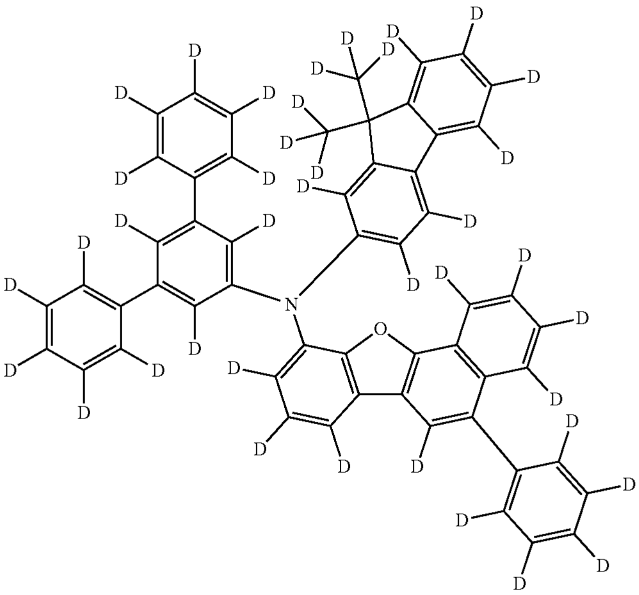

-continued
1-950
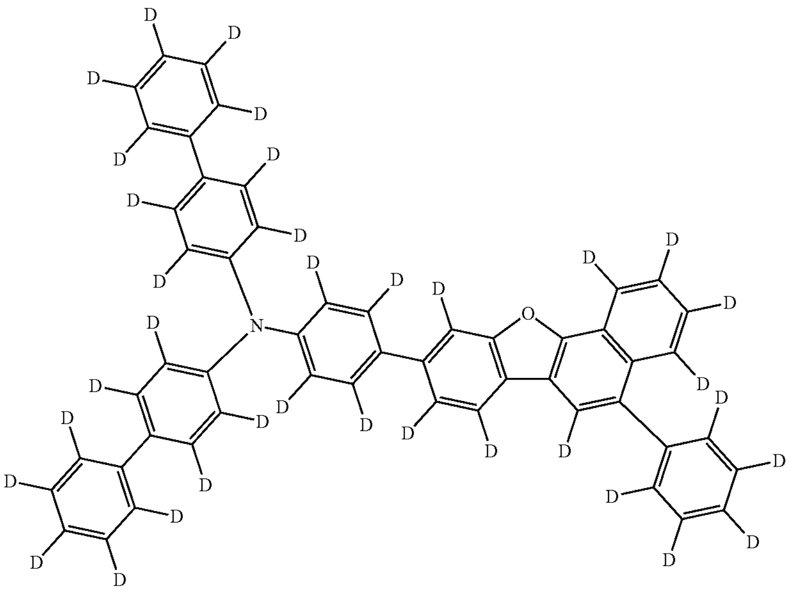
1-951
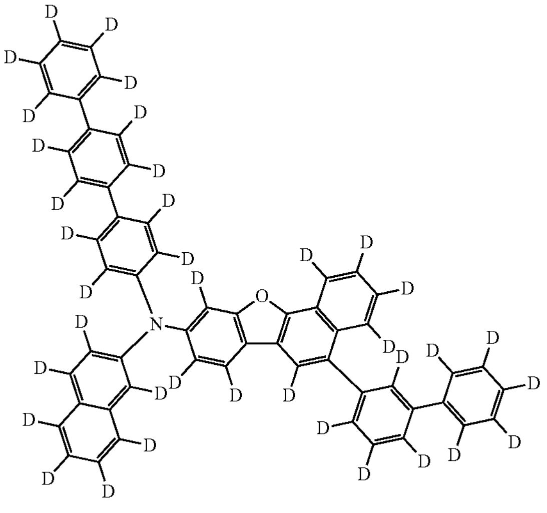
1-952
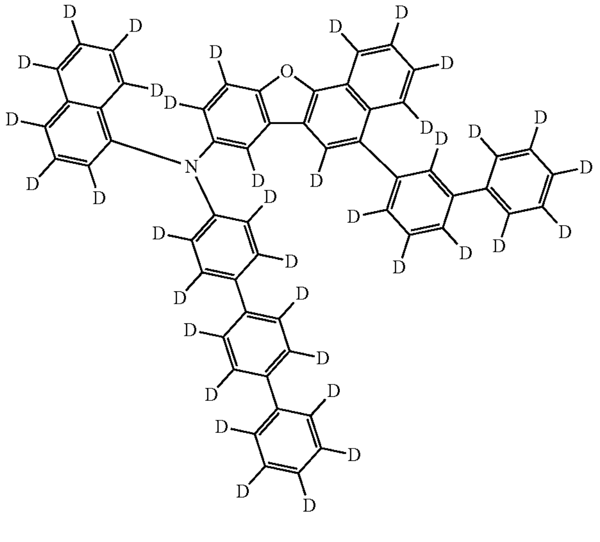

-continued
1-953
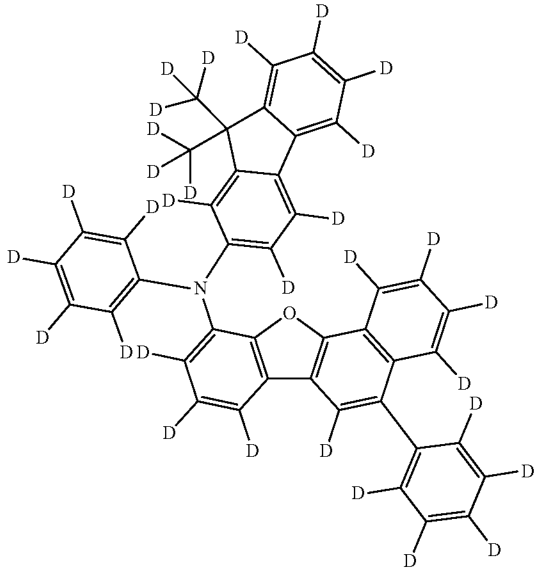
1-954
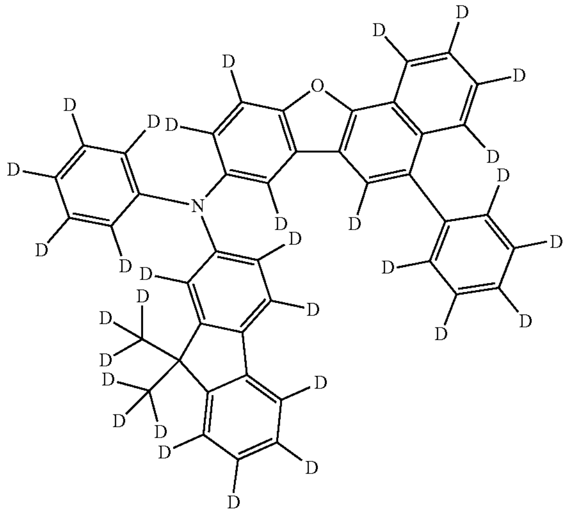
1-955
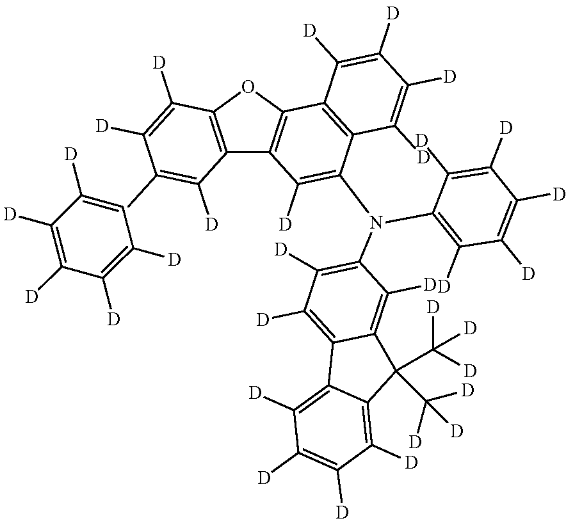
1-956
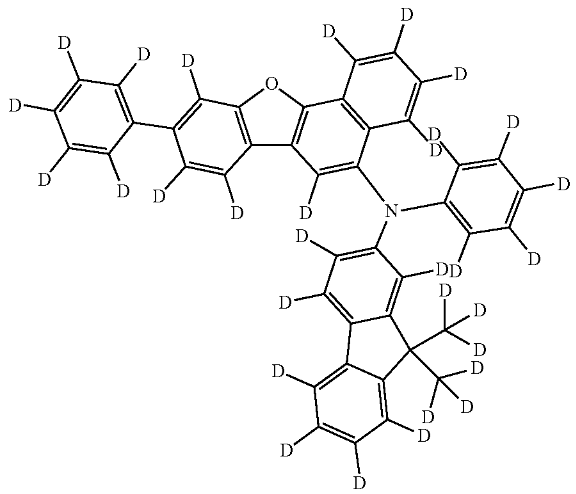
1-957
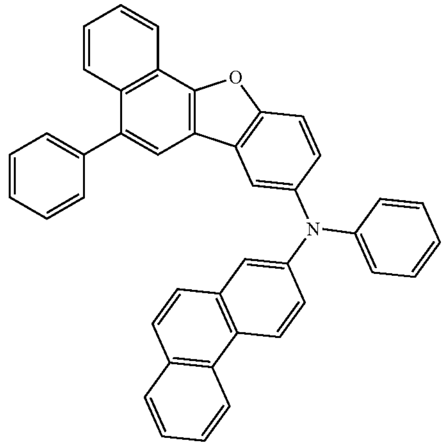
1-958
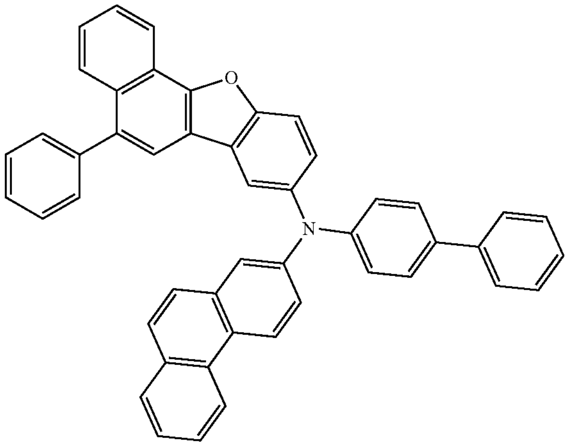

-continued
1-959
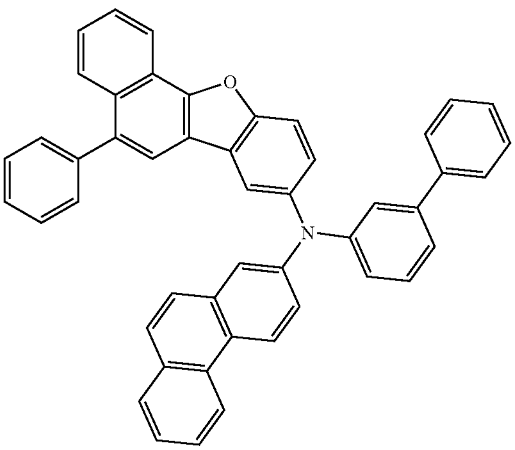
1-960
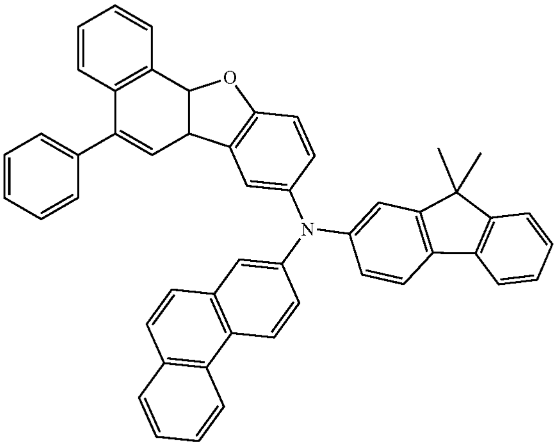
1-961
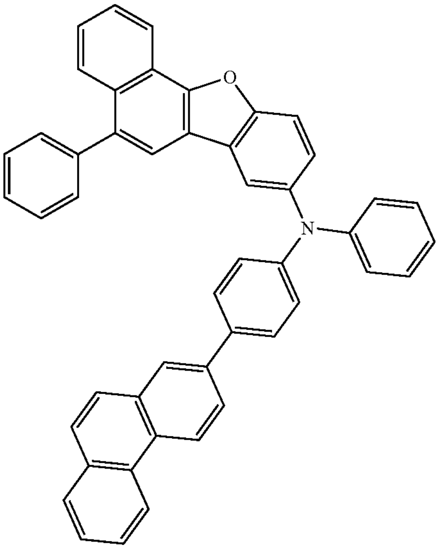
-continued
1-962
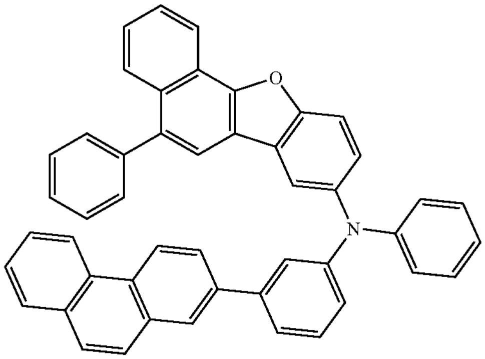
1-963
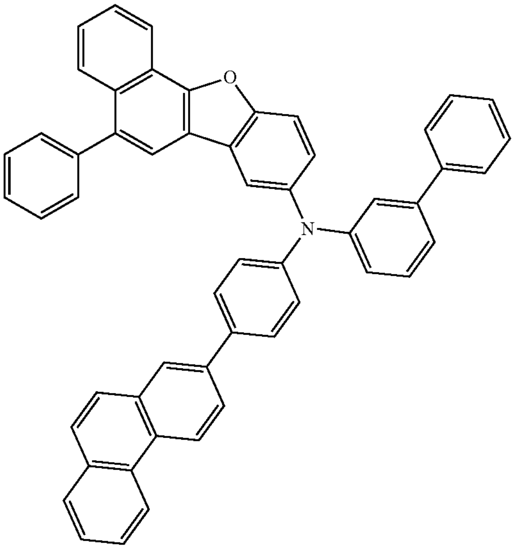
1-964
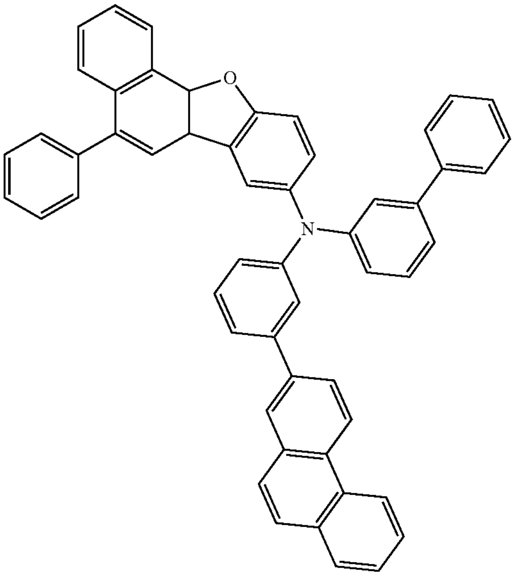

-continued
1-965
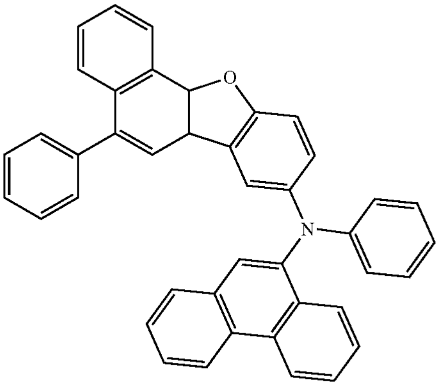
1-966
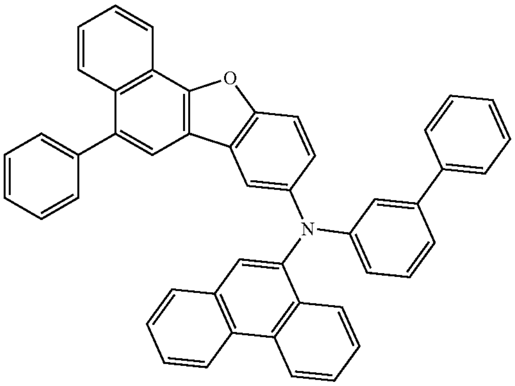
1-967
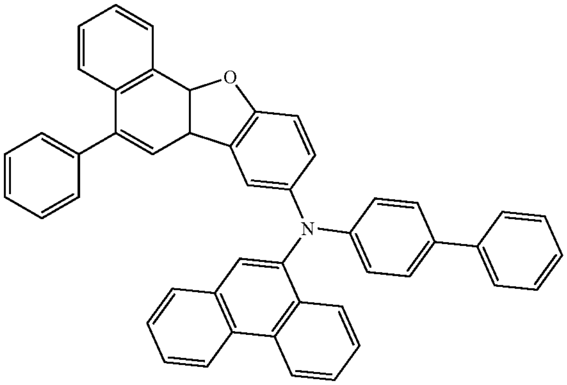
1-968
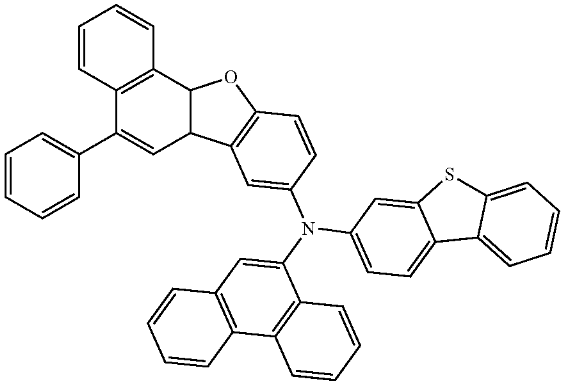
-continued
1-969
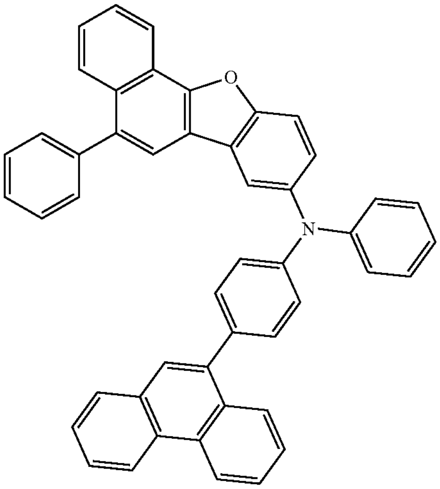
1-970
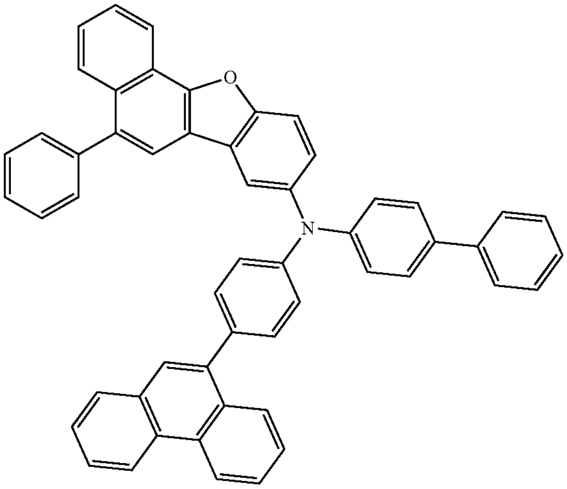
1-971
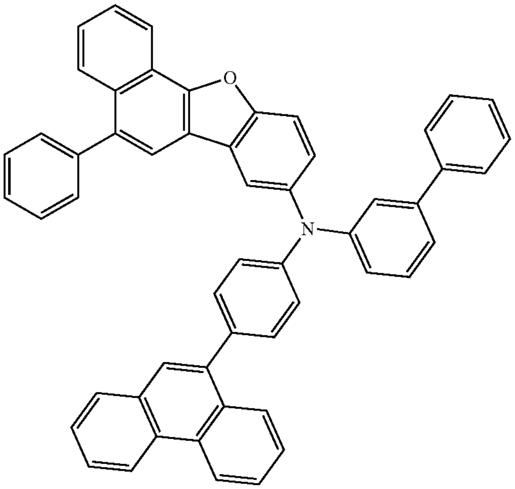

-continued
1-972
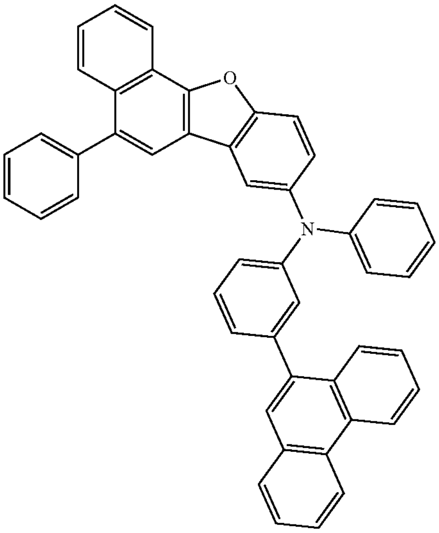
1-973
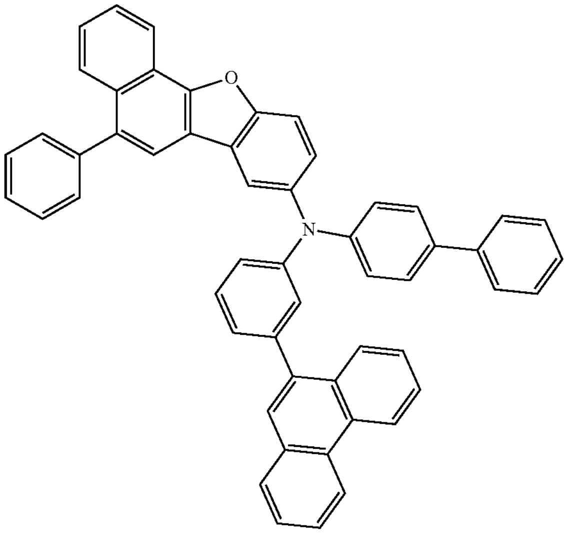
1-974
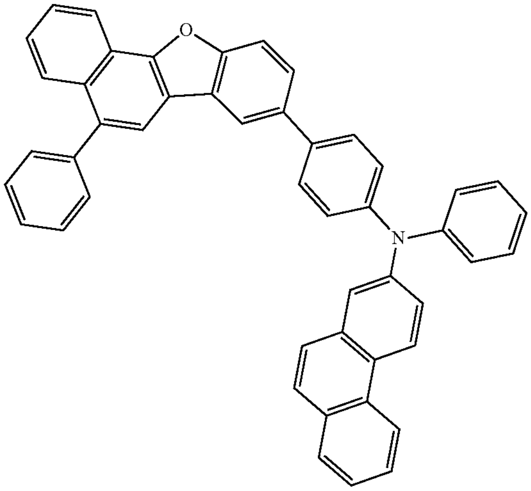
-continued
1-975
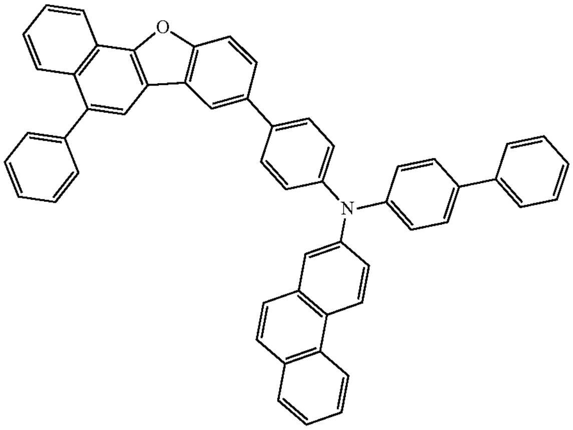
1-976
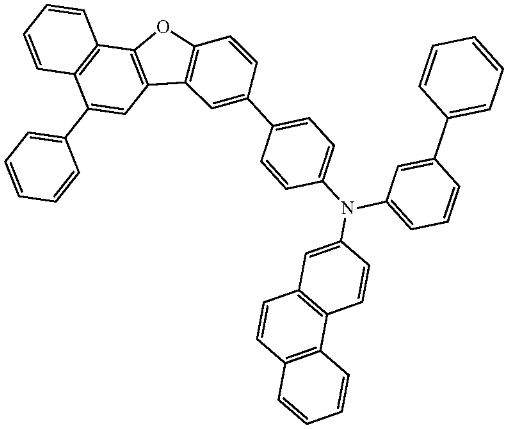
1-977
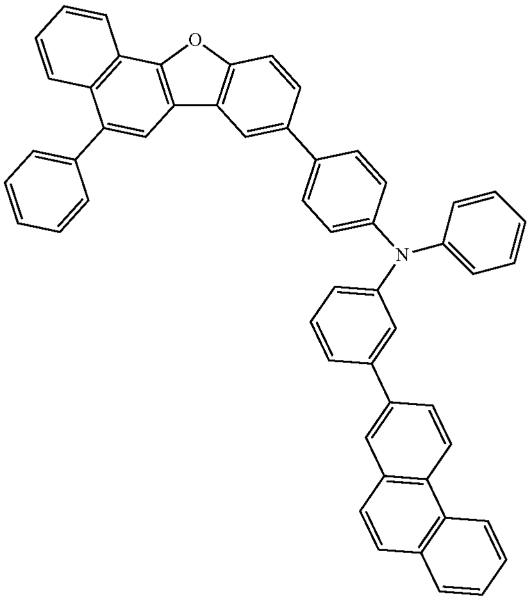

-continued
1-978
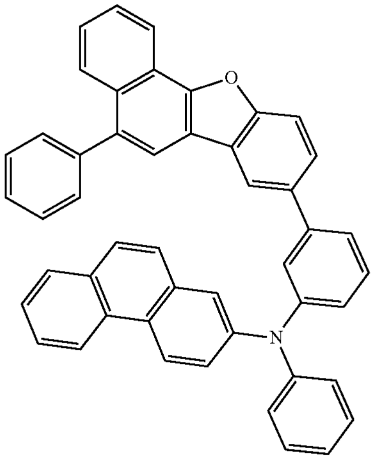
1-979
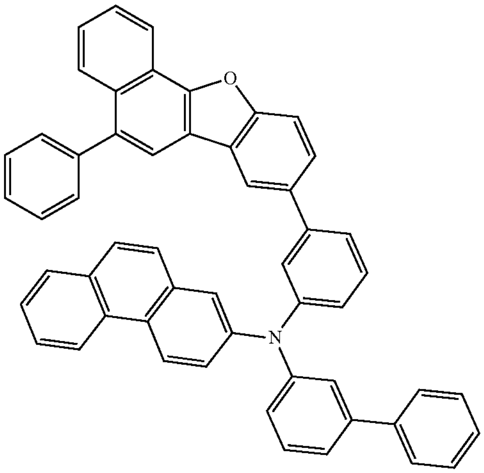
1-980
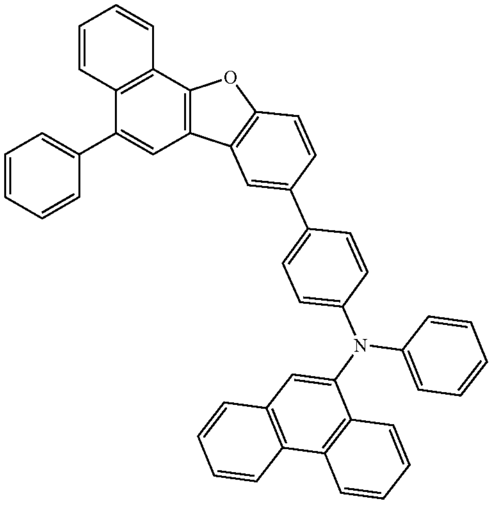
-continued
1-981
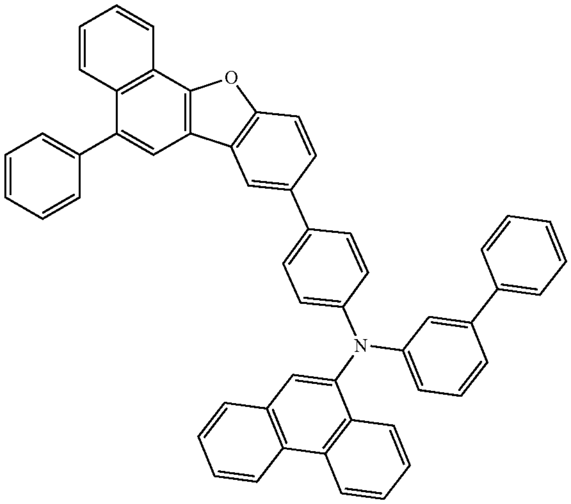
1-982
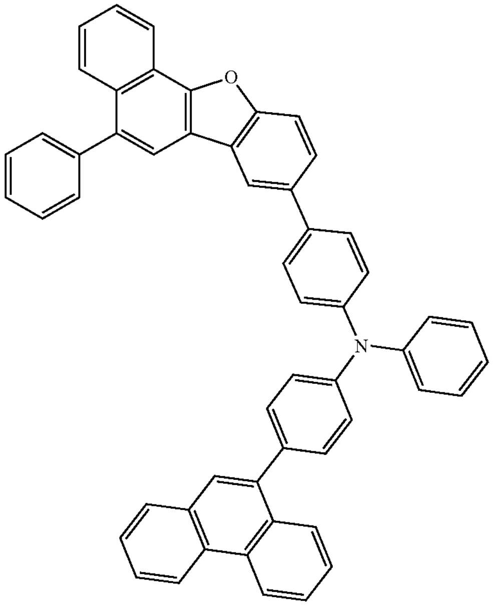
1-983
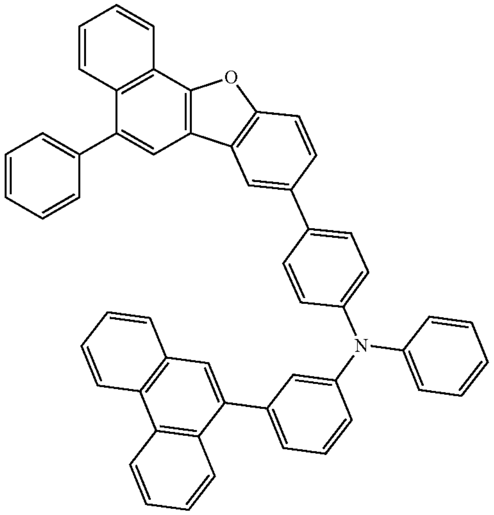

-continued
1-984
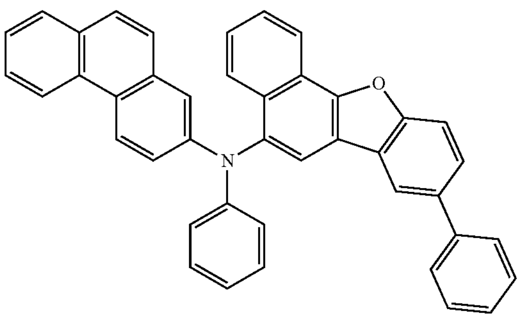
1-985
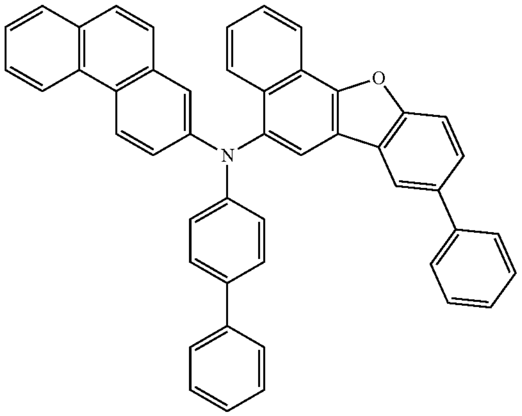
1-986
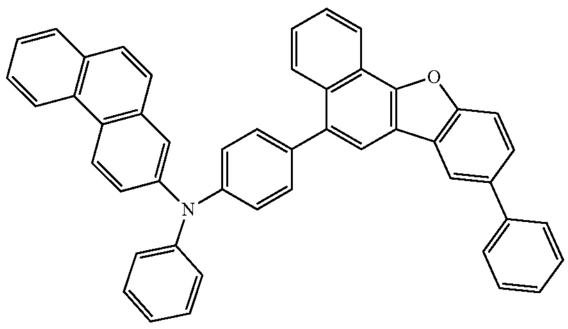
1-987
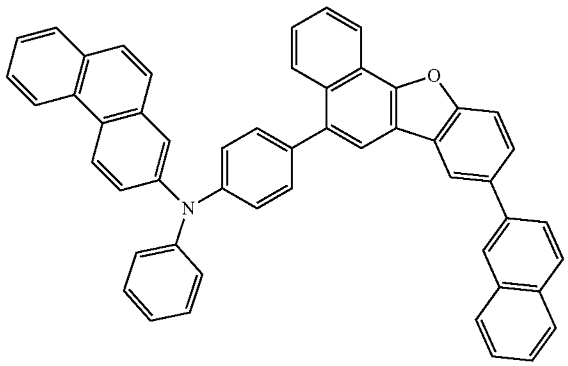
-continued
1-988
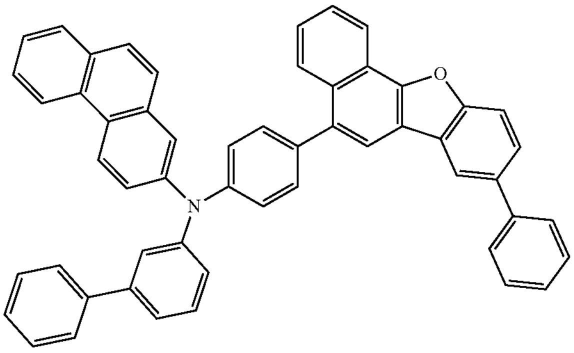
1-989
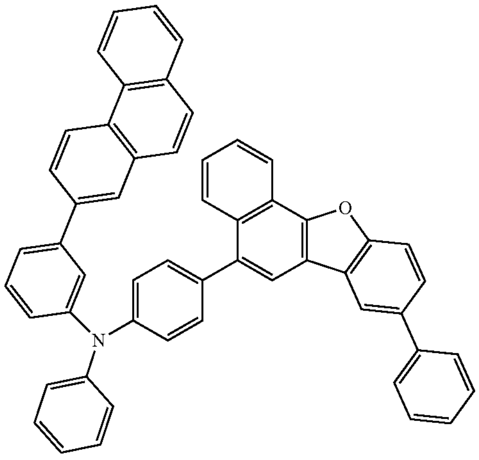
1-990
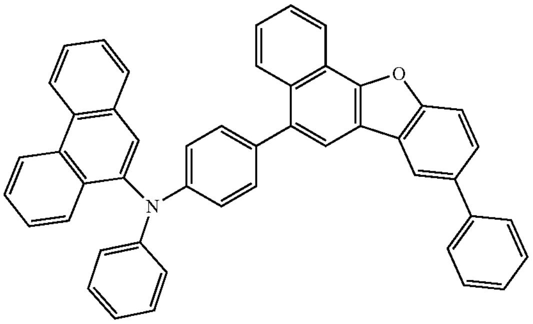
1-991
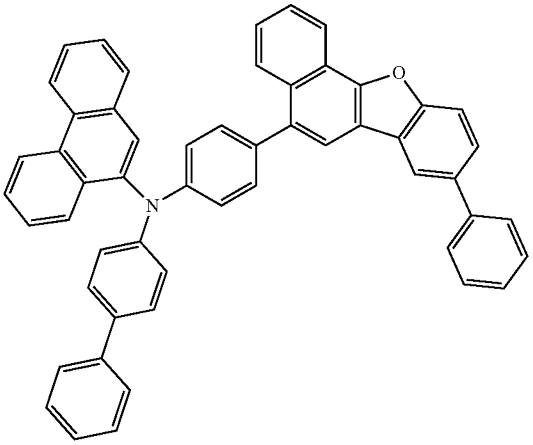

-continued
1-992
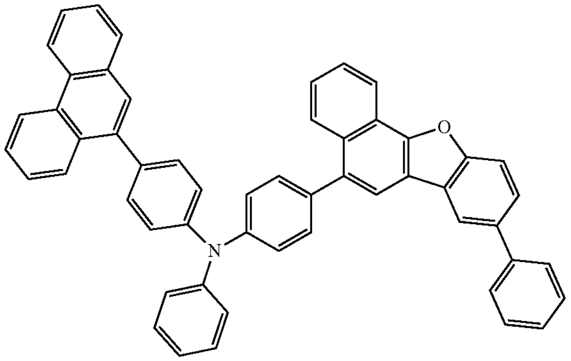
1-993
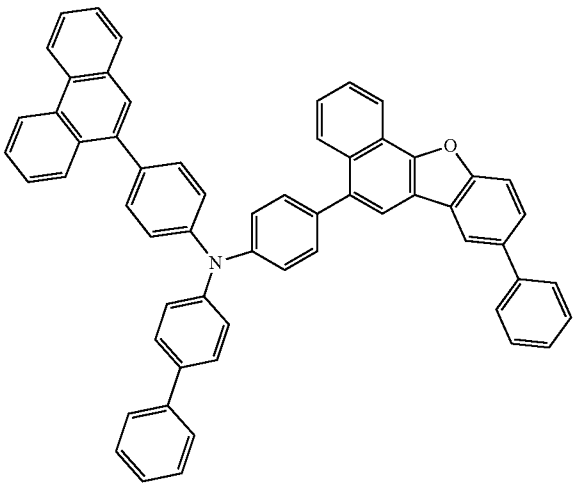
1-994
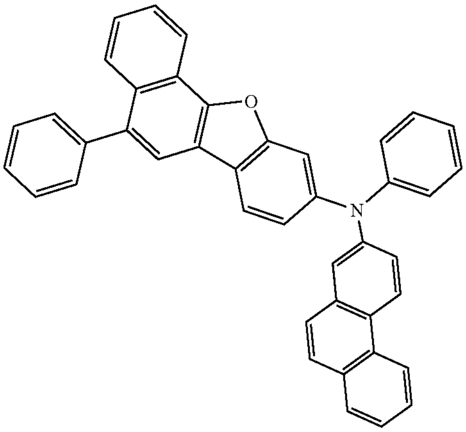
-continued
1-995
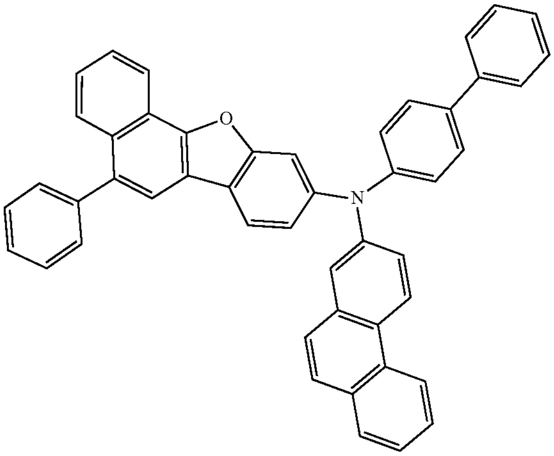
1-996
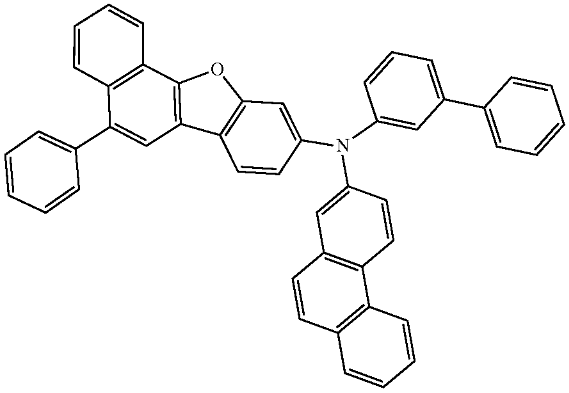
1-997
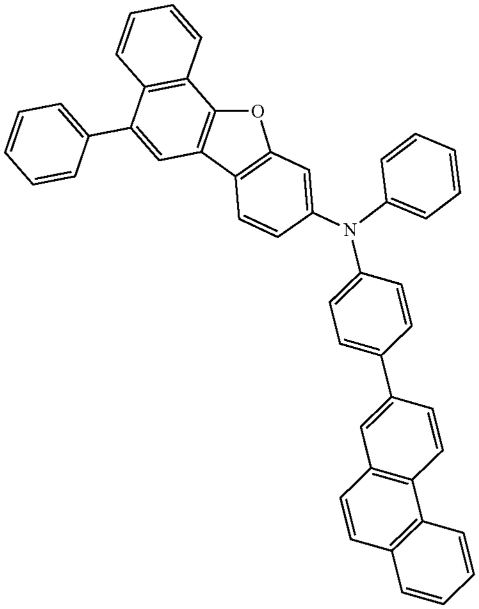

-continued
1-998
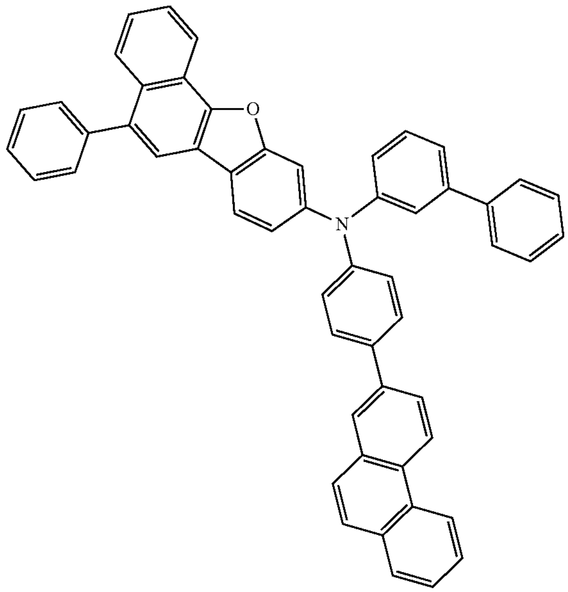
1-999
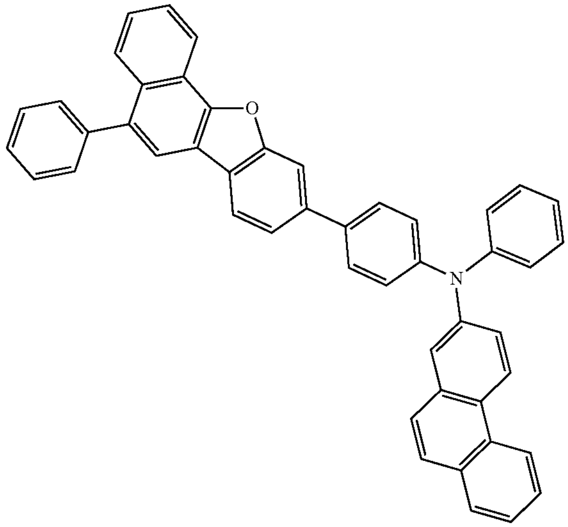
-continued
1-1000
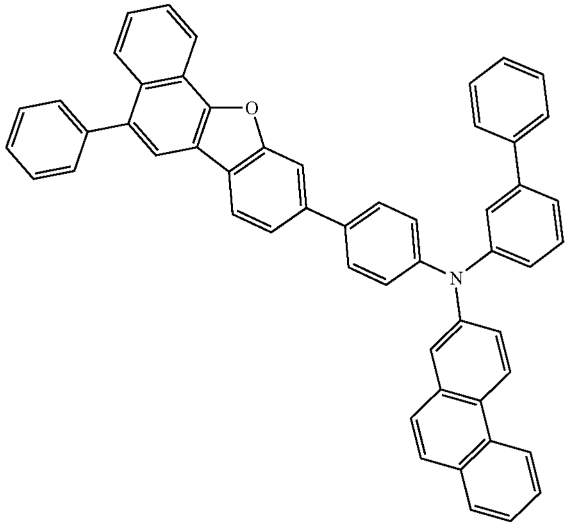
1-1001
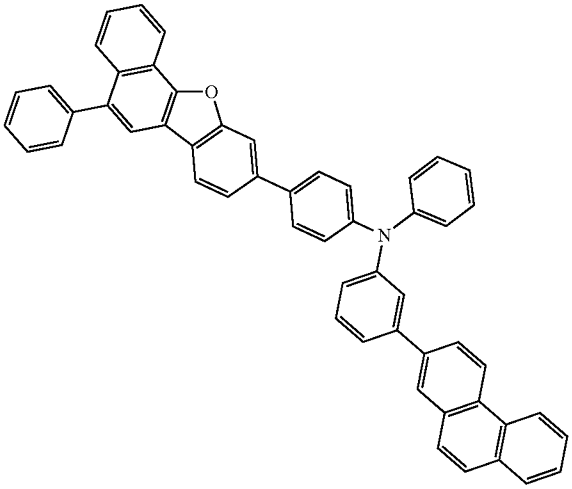
1-1002
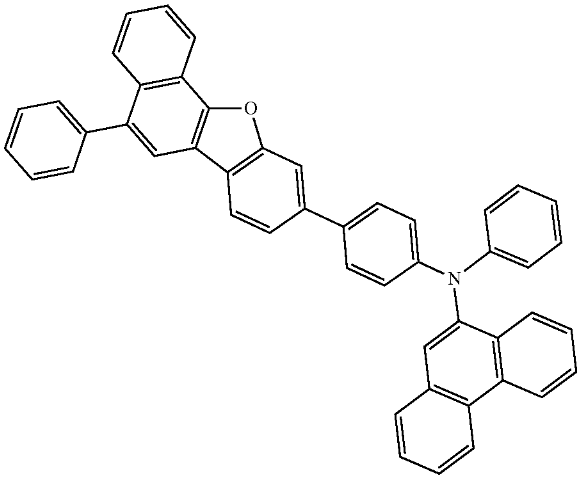

1-1003
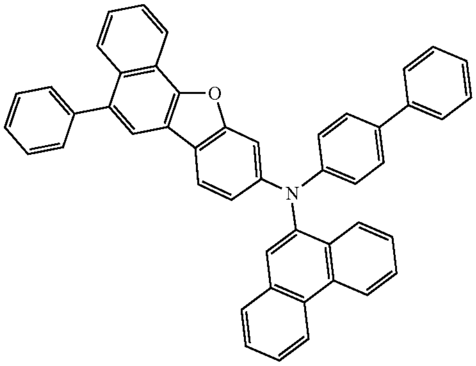
1-1004
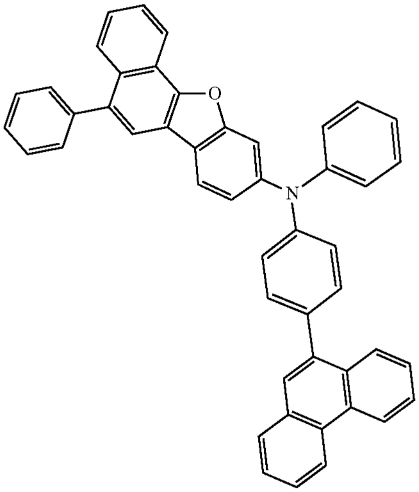
1-1005
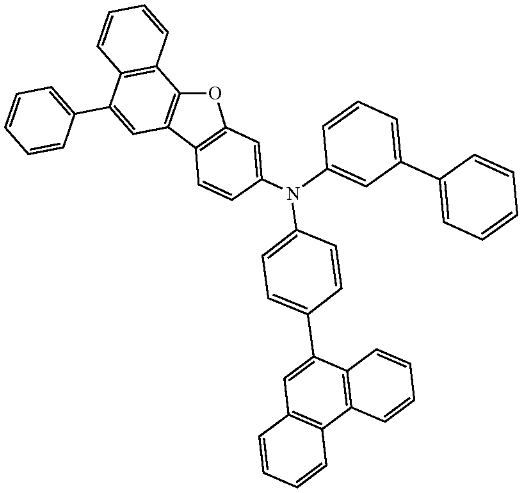
1-1006
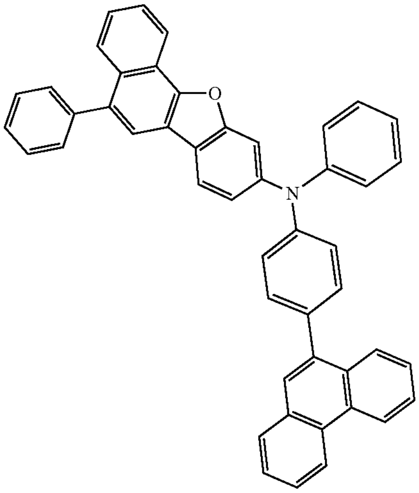
1-1007
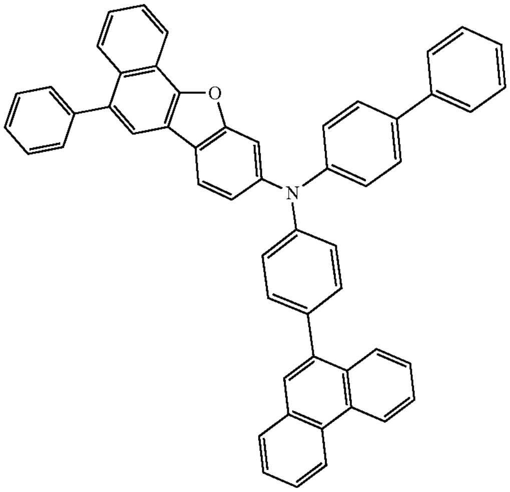
1-1008
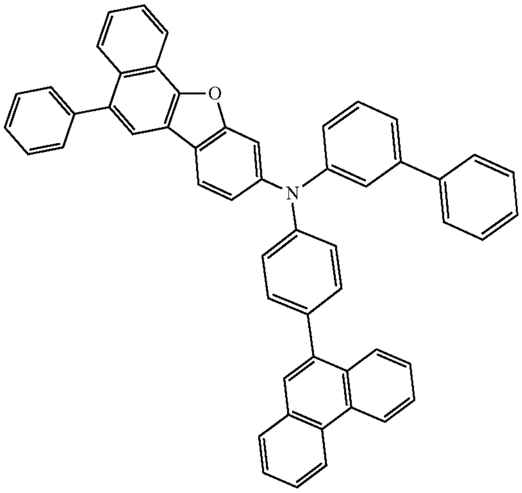

-continued
1-1009
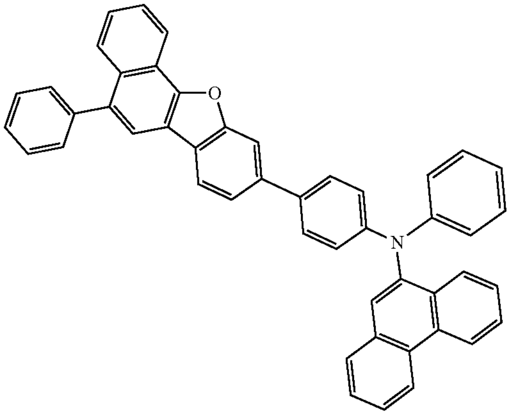
1-1010
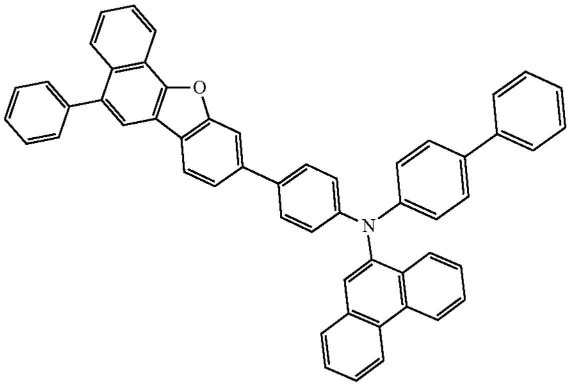
1-1011
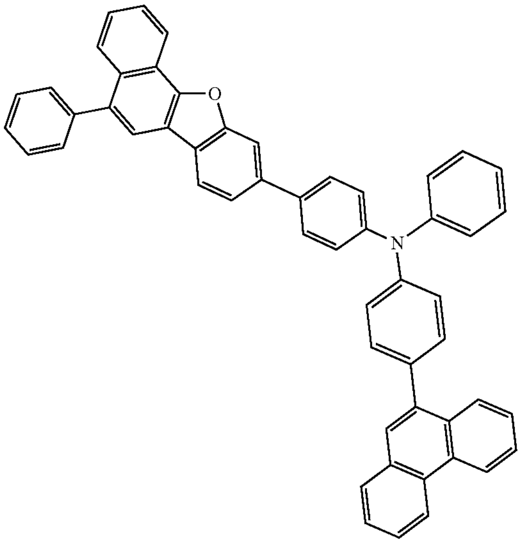
-continued
1-1012
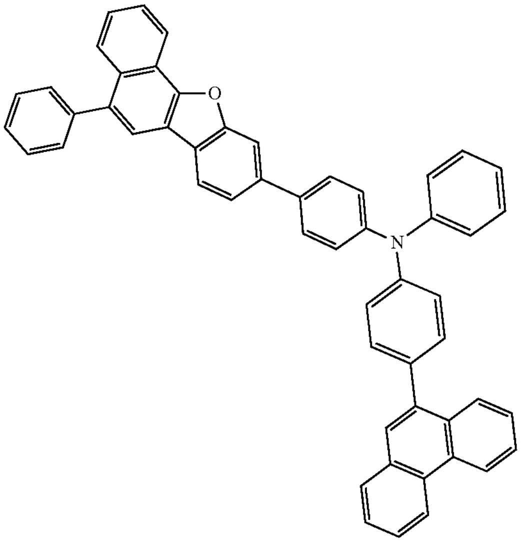
1-1013
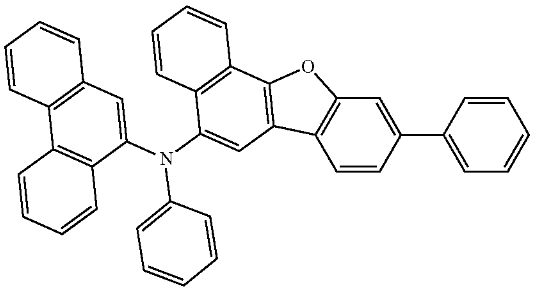
1-1014
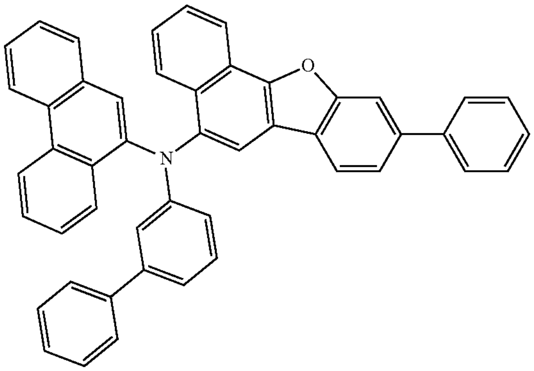
1-1015
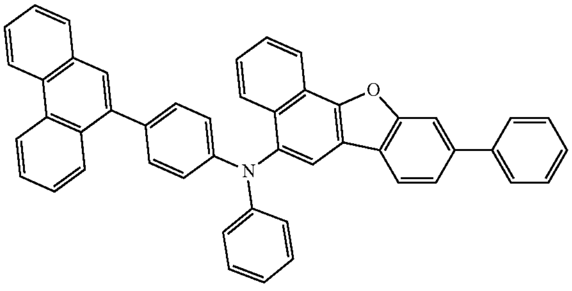

-continued
1-1016
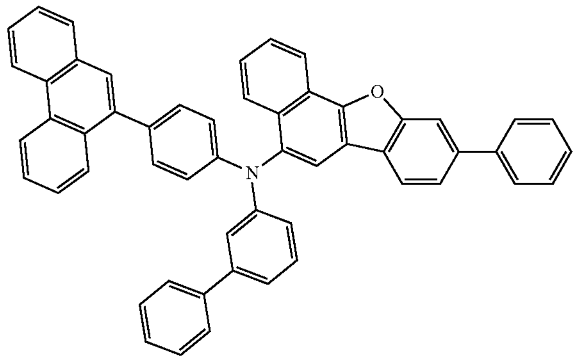
1-1017
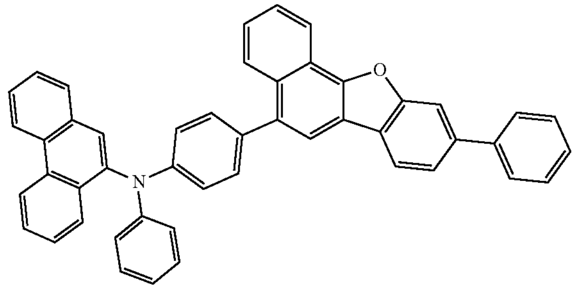
1-1018
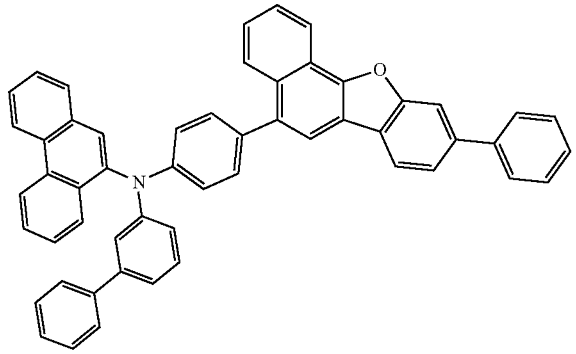
1-1019
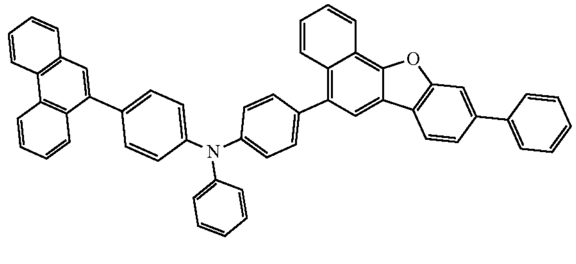
-continued
1-1020
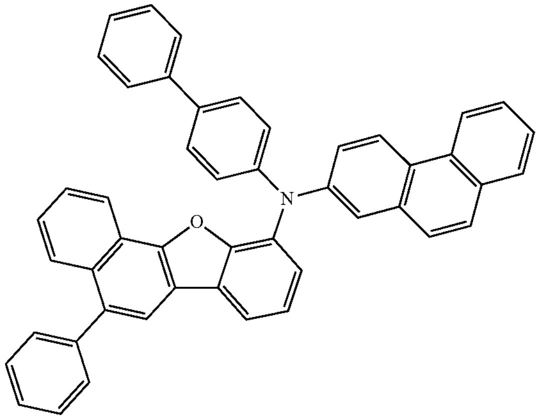
1-1021
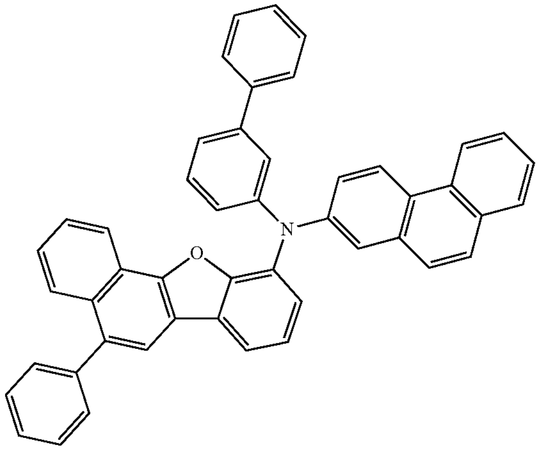
1-1022
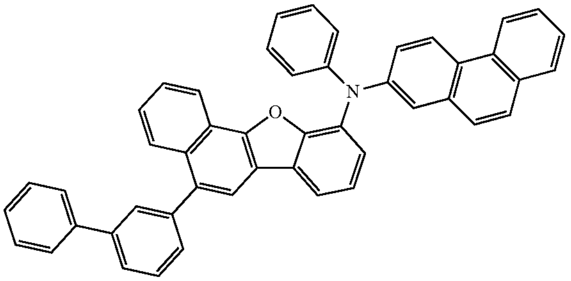
1-1023
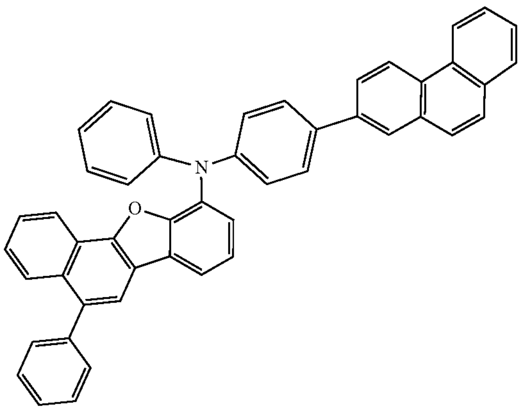

-continued
1-1024
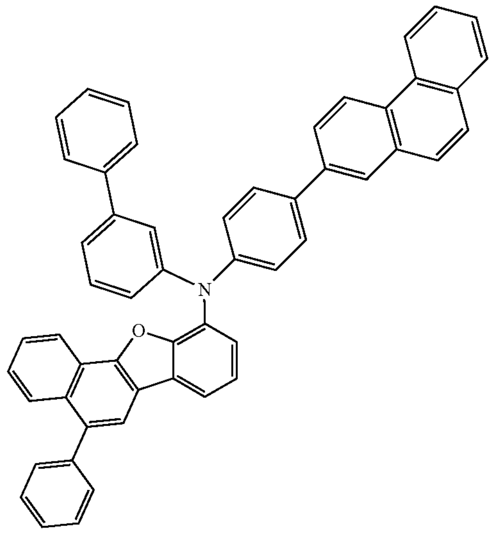
1-1025
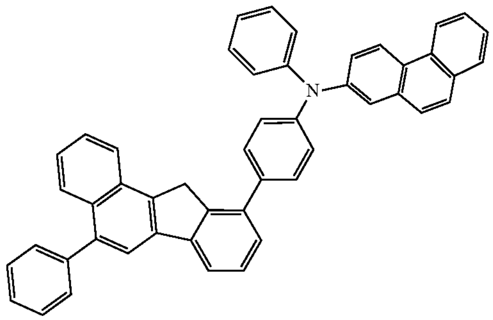
1-1026
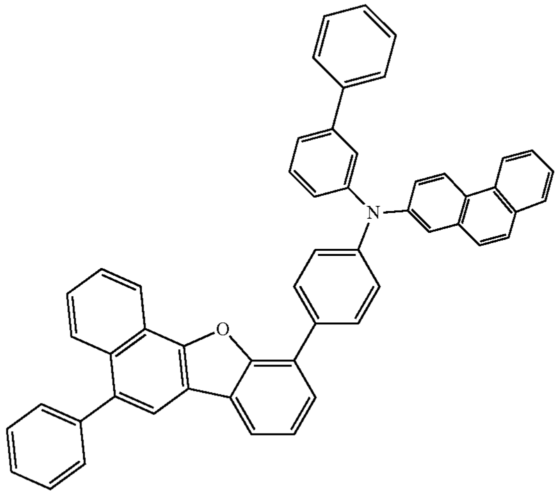
-continued
1-1027
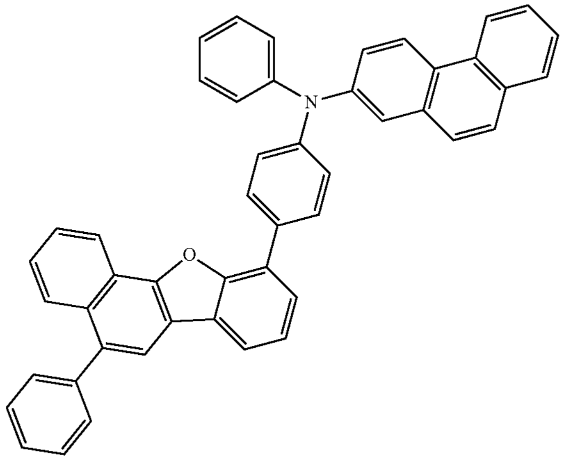
1-1028
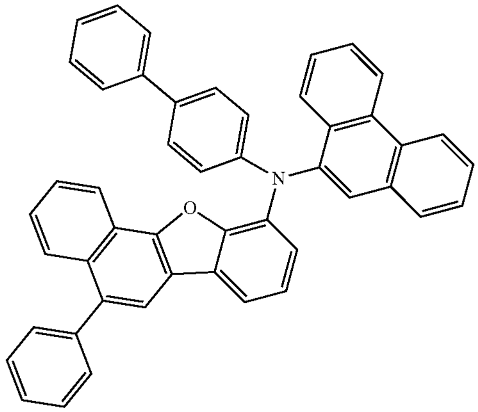
1-1029
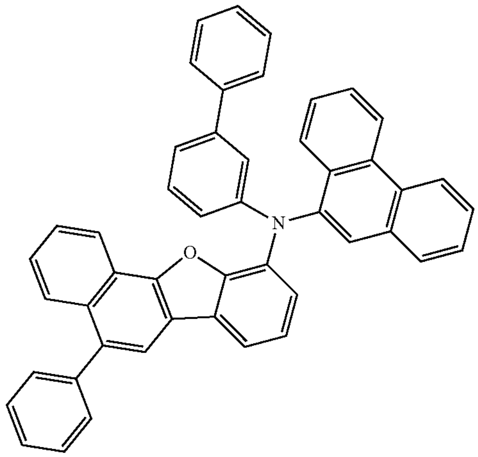

-continued
1-1030
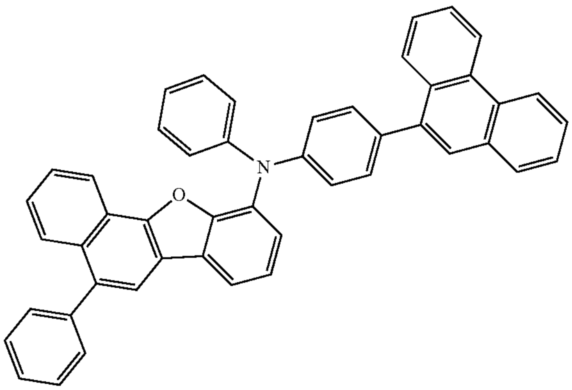
1-1031
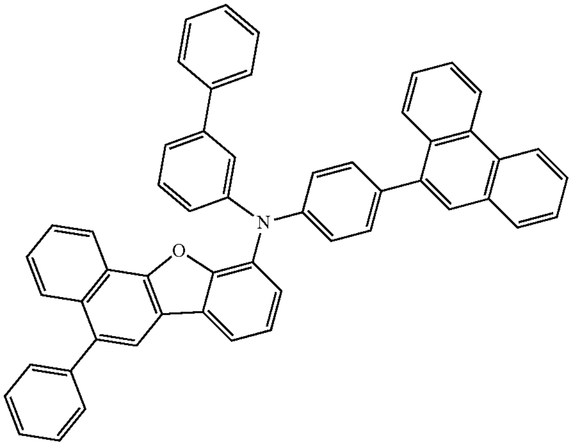
1-1032
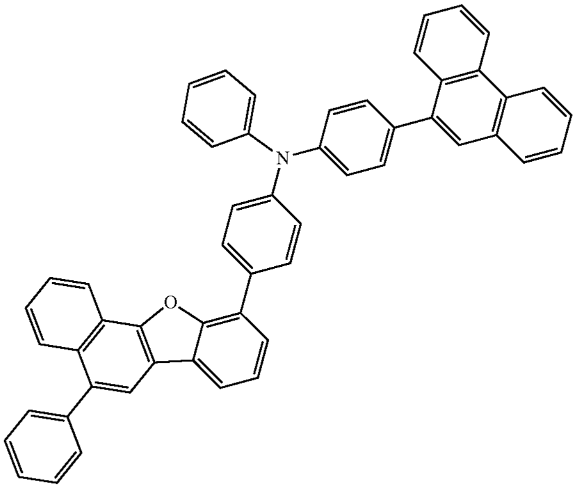
-continued
1-1034
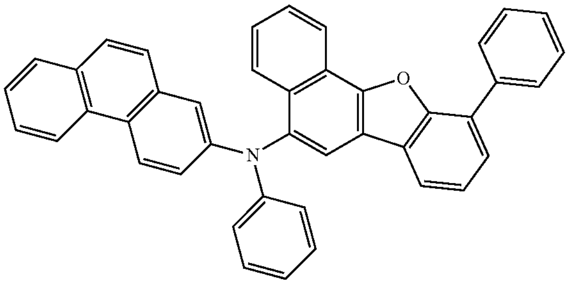
1-1035
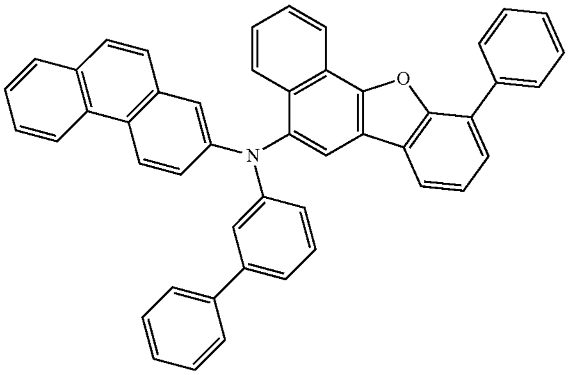
1-1036
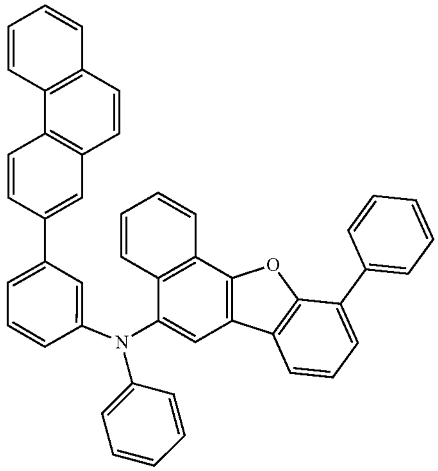

-continued
1-1037
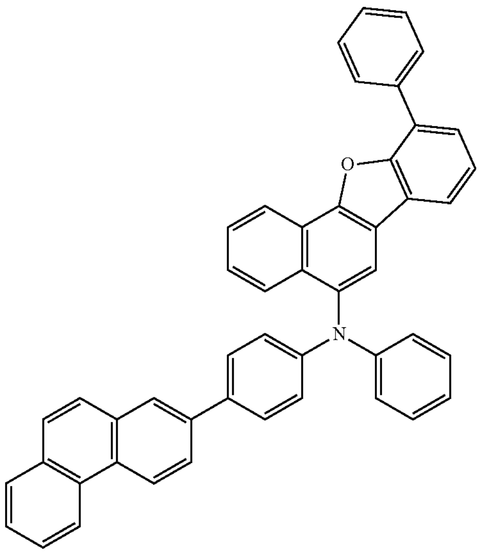
1-1038
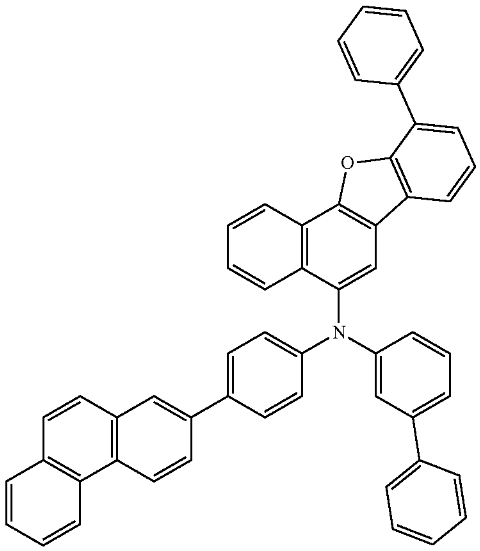
1-1039
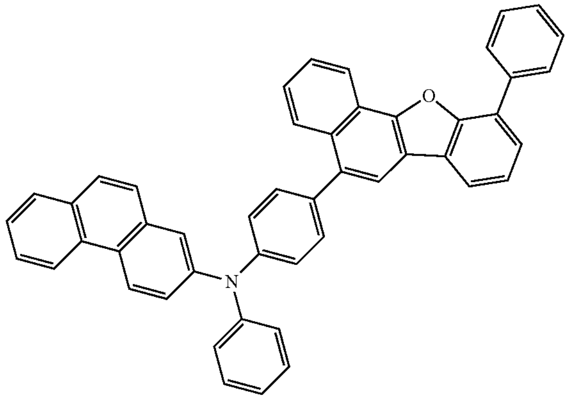
-continued
1-1040
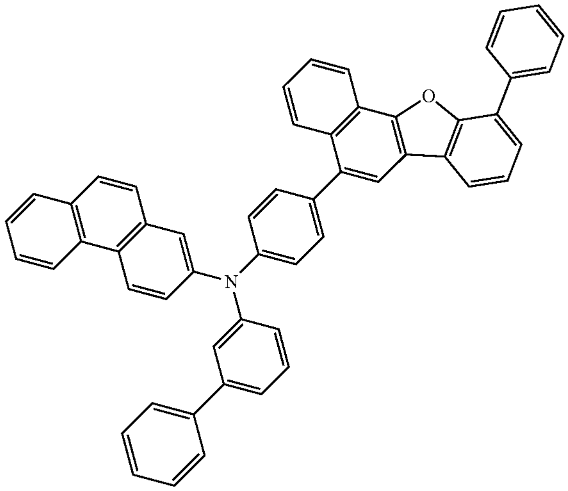
1-1041
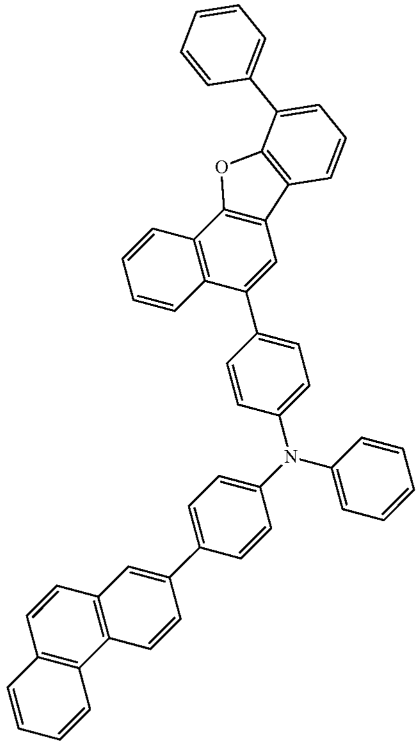
1-1042
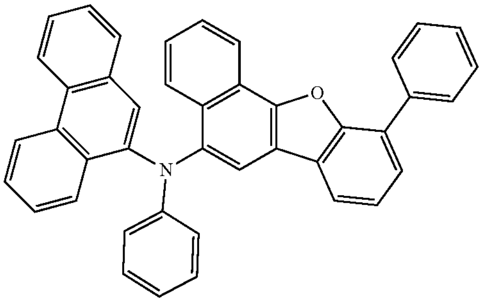

1-1043
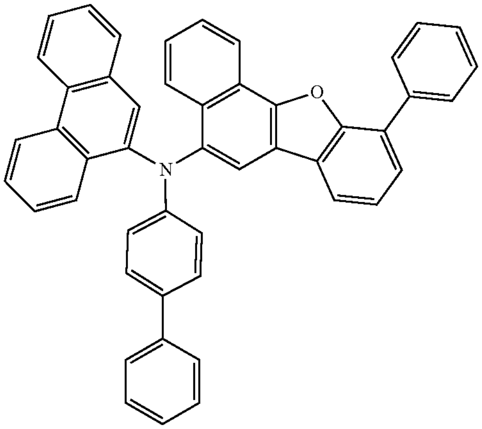
1-1044
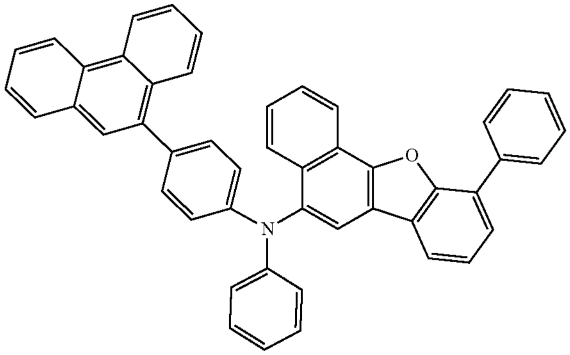
1-1045
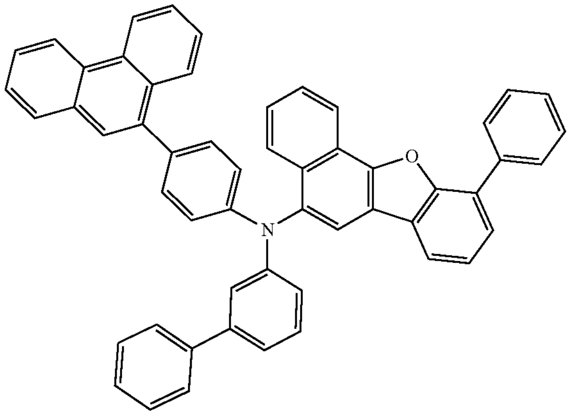
1-1046
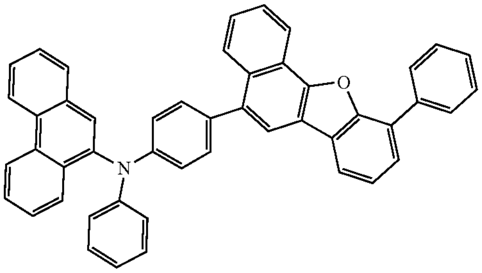
1-1047
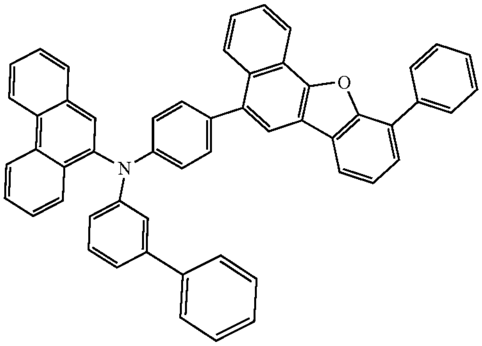
1-1048
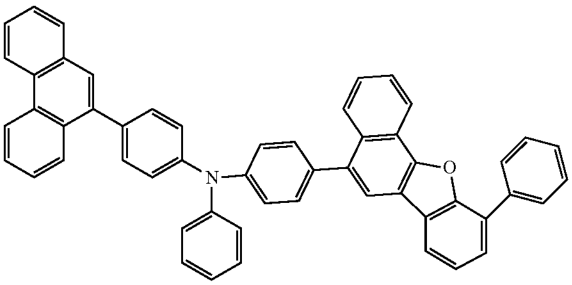
1-1049
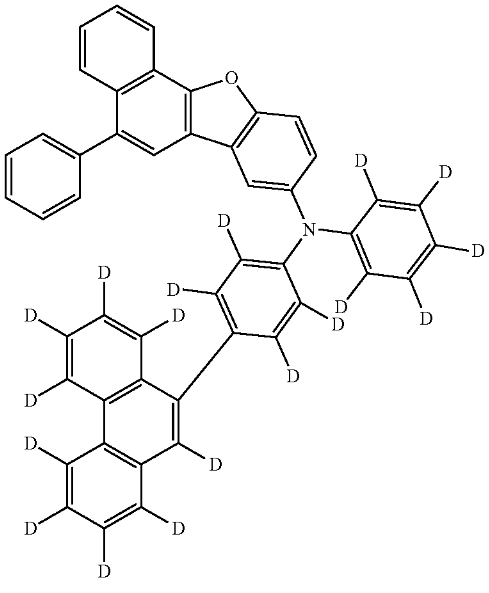

-continued
1-1050
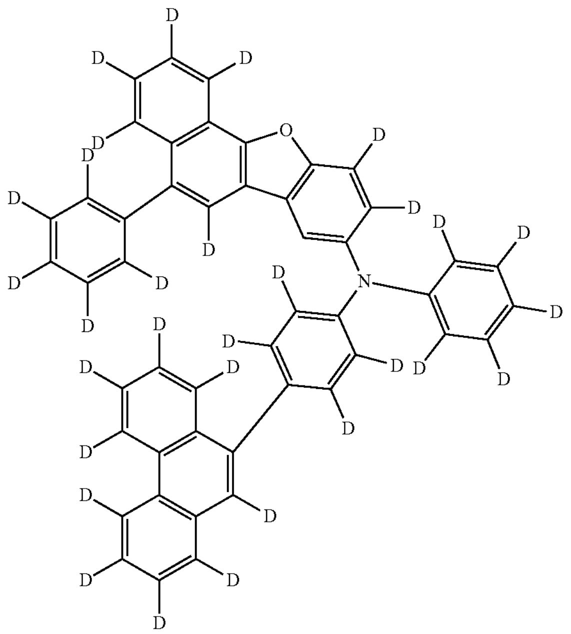
1-1051
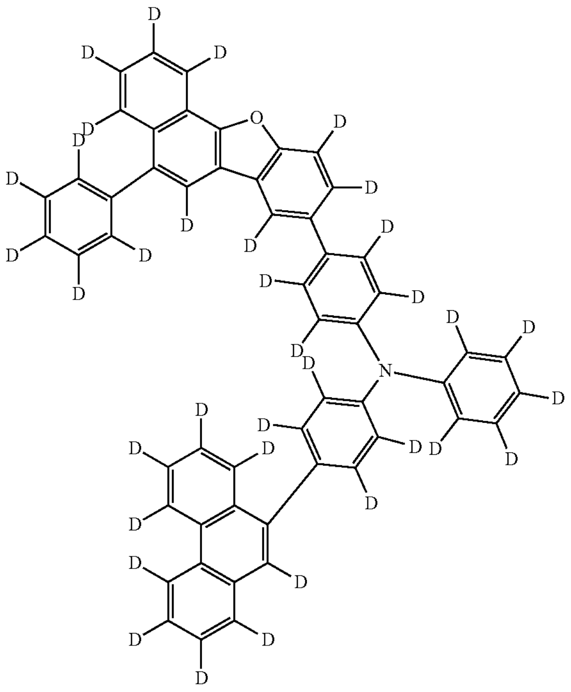
-continued
1-1052
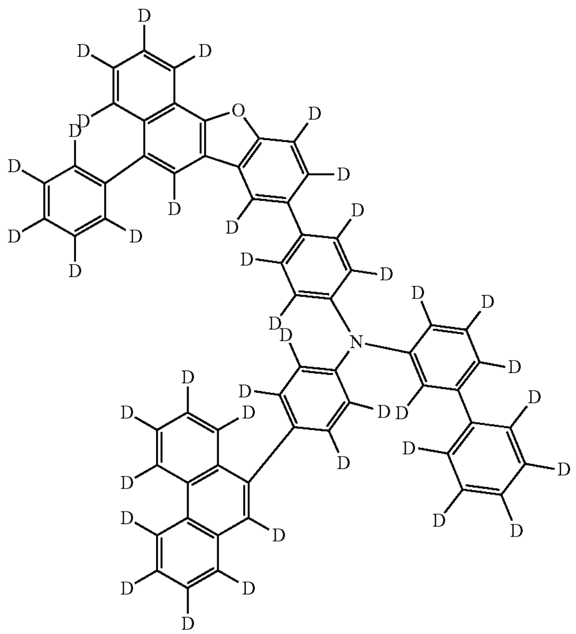
1-1053
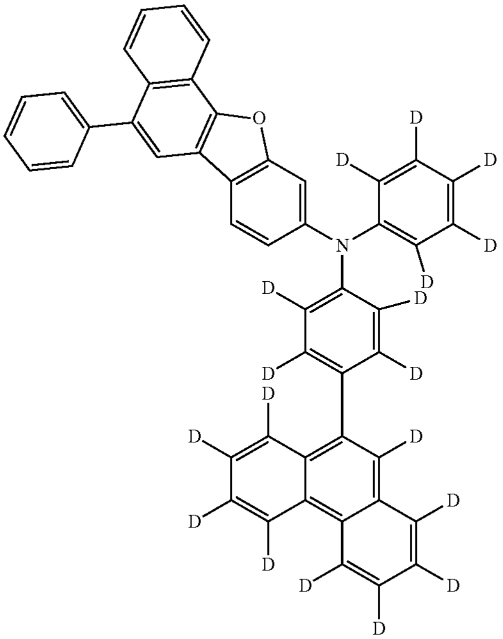

-continued 1-1054

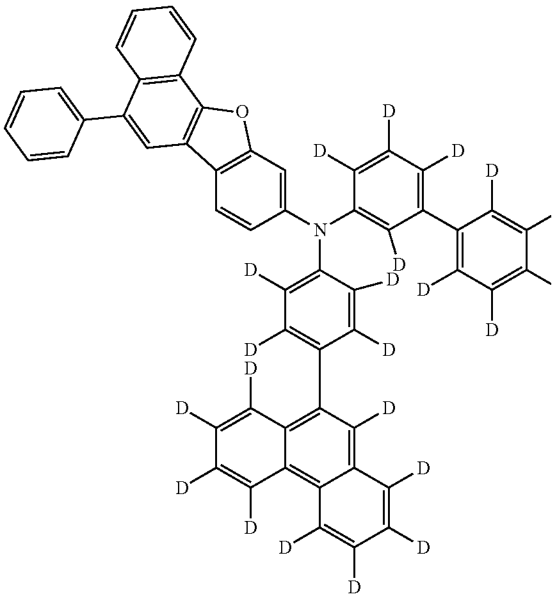

1-1055

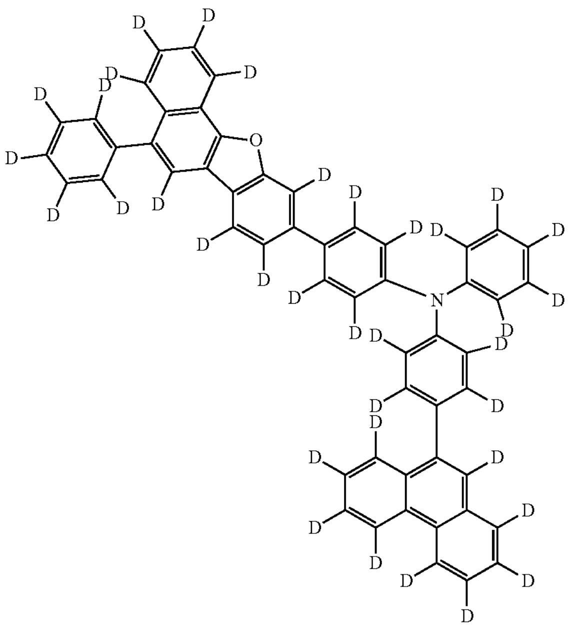

-continued 1-1056

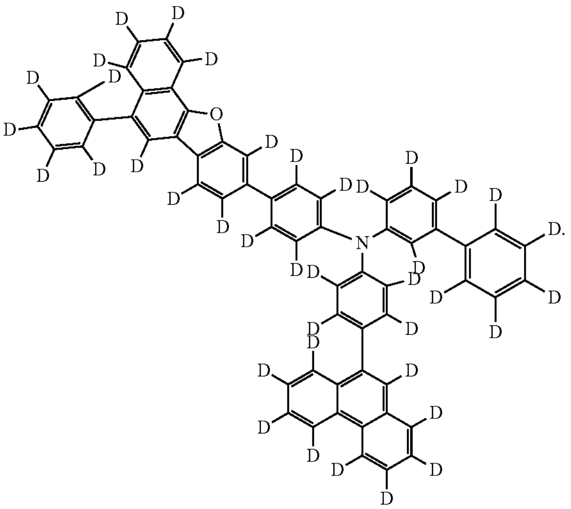

7. An organic light emitting device comprising:

a first electrode;

a second electrode provided opposite to the first electrode; and one or more organic material layers provided between the first electrode and the second electrode, wherein one or more layers of the organic material layers include the heterocyclic compound of claim 1.

8. The organic light emitting device of claim 7, wherein the organic material layer including the heterocyclic compound further includes a heterocyclic compound represented by the following Chemical Formula A; or a heterocyclic compound represented by the following Chemical Formula B:

[Chemical Formula A]

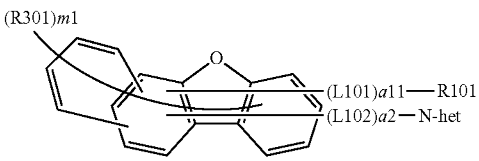

[Chemical Formula B]

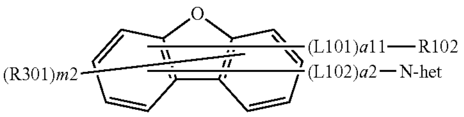

in Chemical Formulae A and B,

L101 and L102 are the same as or different from each other, and each independently a direct bond; a substituted or unsubstituted C6 to C60 arylene group; or a substituted or unsubstituted C2 to C60 heteroarylene group;

N-het is a monocyclic or polycyclic heterocyclic group substituted or unsubstituted and including one or more Ns;

R101 is a substituted or unsubstituted C1 to C60 alkyl group; a substituted or unsubstituted C6 to C60 aryl group; a substituted or unsubstituted C2 to C60 heteroaryl group; or —NR103R104;

R102 is hydrogen; deuterium; a substituted or unsubstituted C1 to C60 alkyl group; a substituted or unsubstituted C6 to C60 aryl group; a substituted or unsubstituted C2 to C60 heteroaryl group; or —NR103R104;

R301 is selected from the group consisting of hydrogen; deuterium; halogen; a cyano group; a substituted or unsubstituted C1 to C60 alkyl group; a substituted or unsubstituted C6 to C60 aryl group; and a substituted or unsubstituted C2 to C60 heteroaryl group;

R103 and R104 are the same as or different from each other, and each independently a substituted or unsubstituted C1 to C60 alkyl group; a substituted or unsubstituted C6 to C60 aryl group; or a substituted or unsubstituted C2 to C60 heteroaryl group;

m1 is an integer of 0 to 8;

m2 is an integer of 0 to 6; and a11 and a2 are an integer of 0 to 4, and when m1 is 2 to 8, m2 is 2 to 6, or a11 and a2 are 2 to 4, substituents in the parentheses are the same as or different from each other.

9. The organic light emitting device of claim 8, wherein the heterocyclic compound represented by Chemical Formula A is any one selected from among the following compounds:

2-1

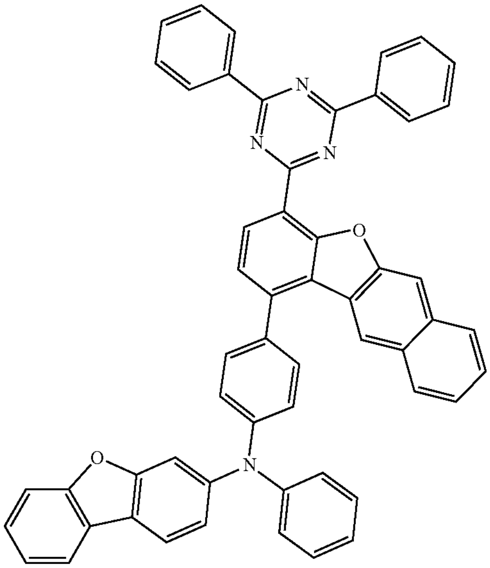

2-2

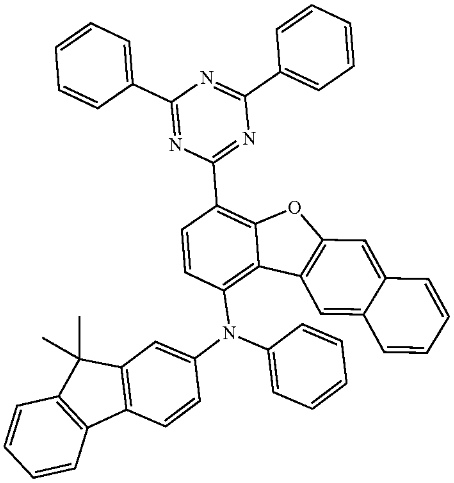

-continued 2-3

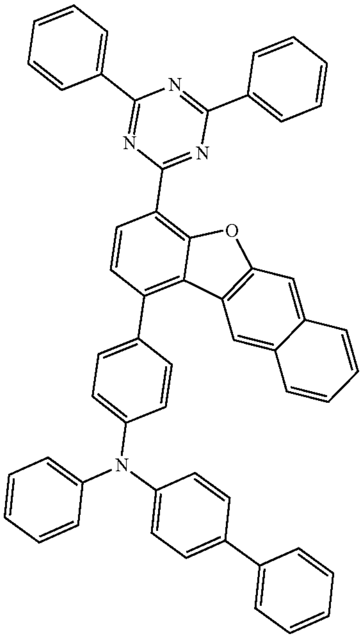

2-4

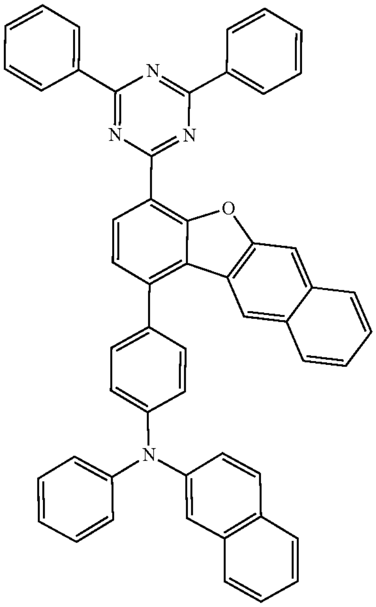

-continued
2-5
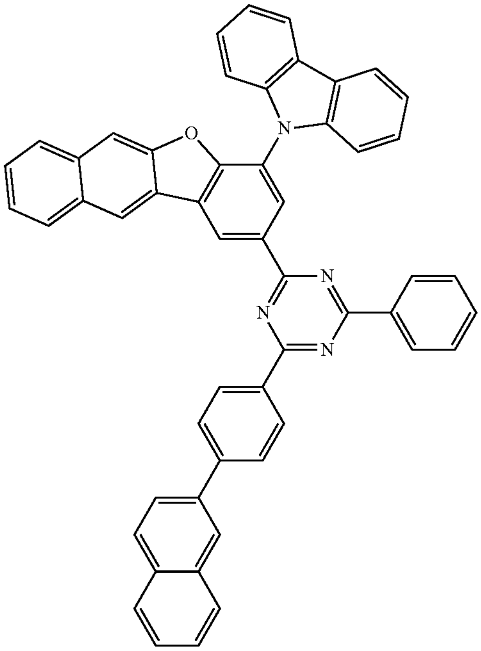
2-6
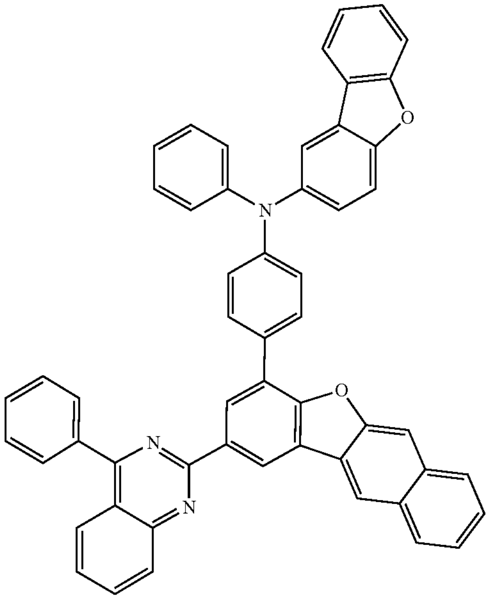
-continued
2-7
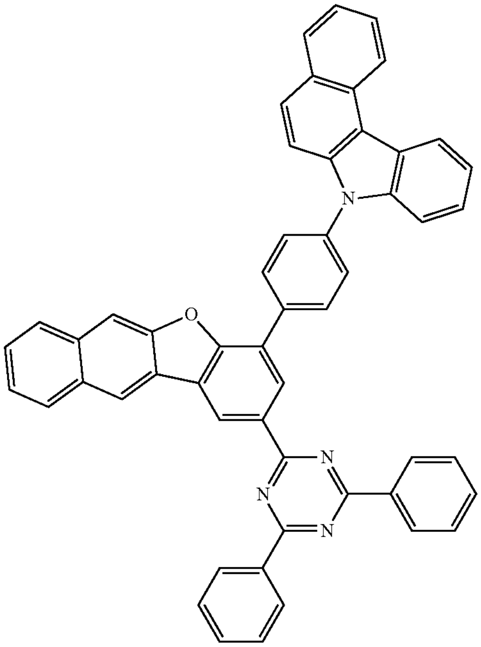
2-8
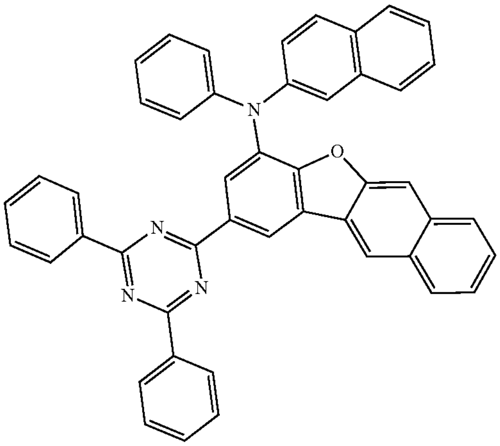
2-9
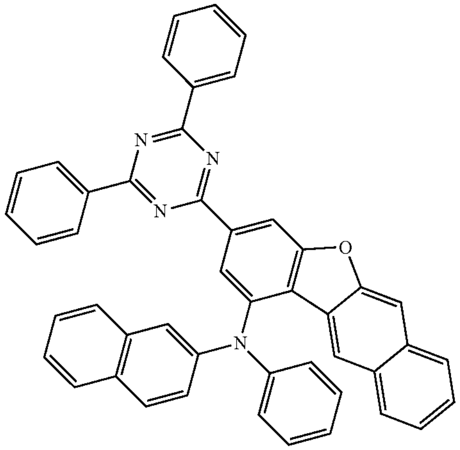

2-10
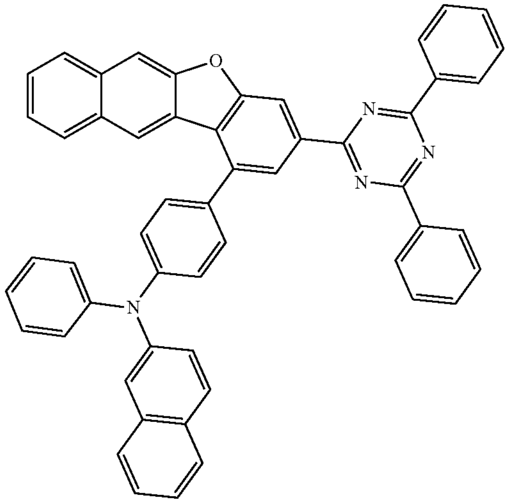
2-11
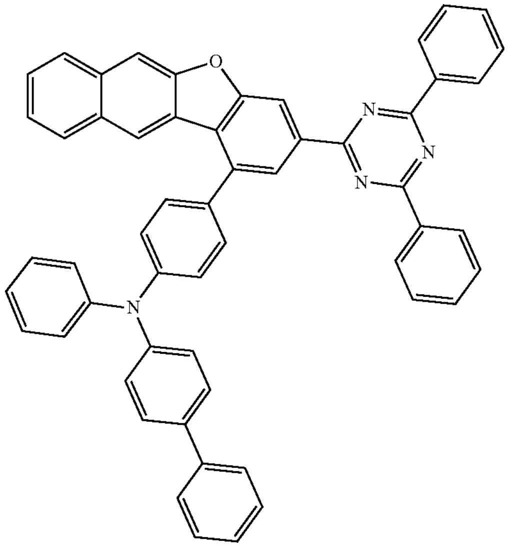
2-12
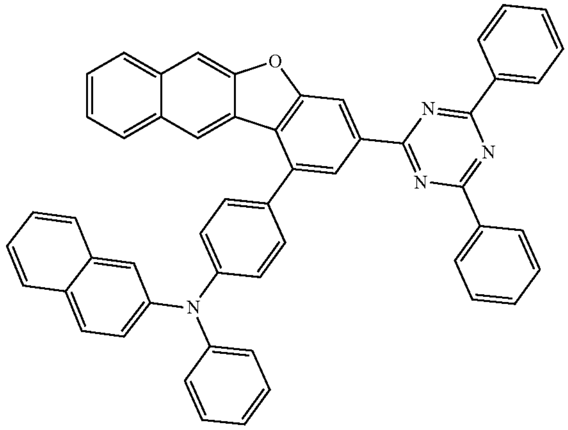
-continued
2-13
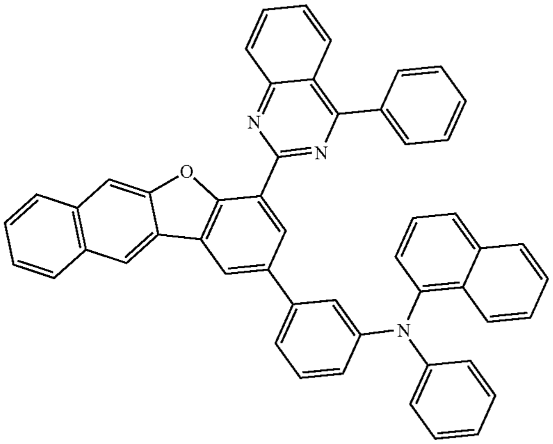
2-14
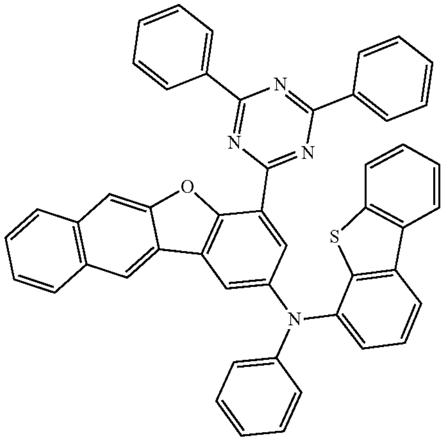
2-15
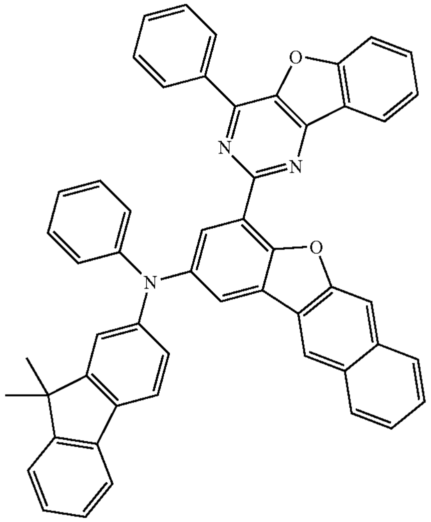

-continued
2-16
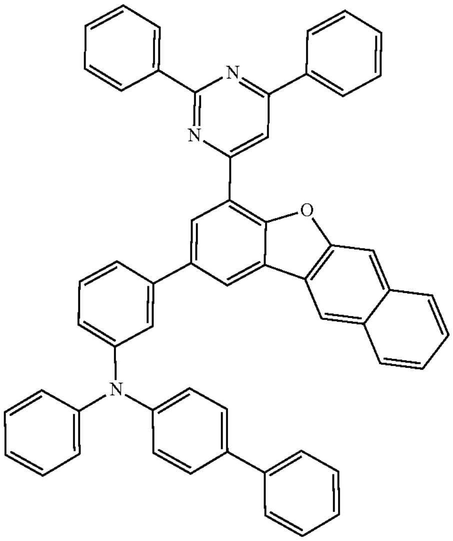
2-17
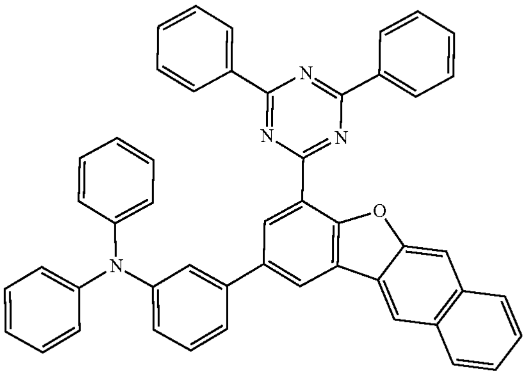
2-18
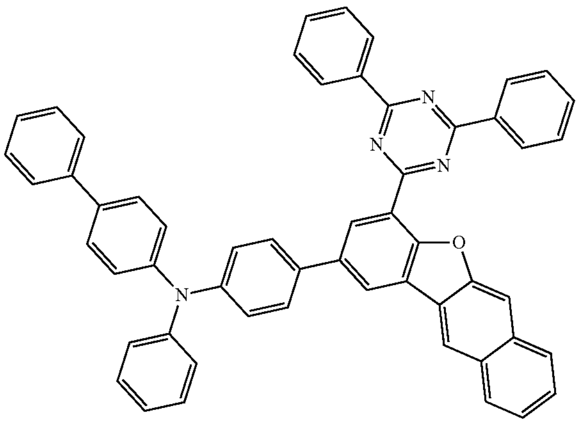
-continued
2-19
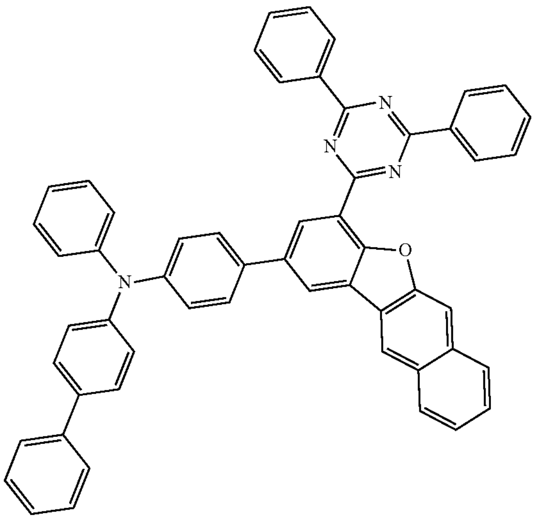
2-20
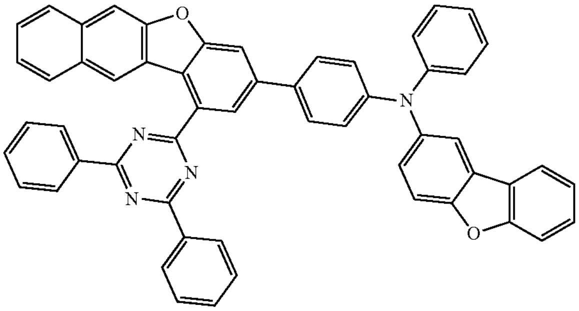
2-21
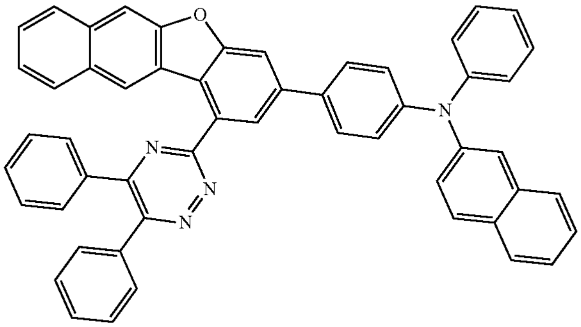
2-22
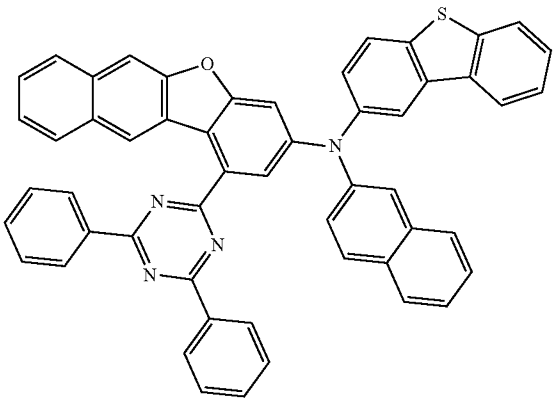

-continued
2-23
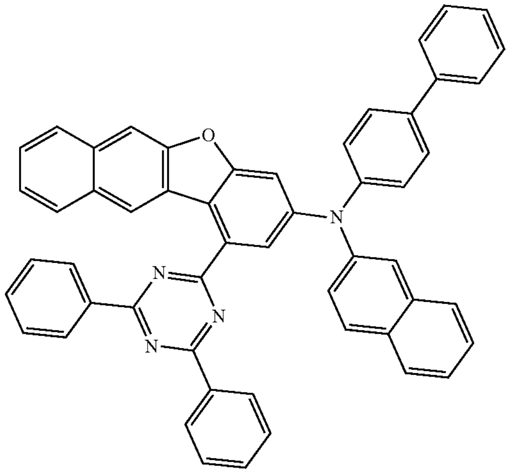
2-24
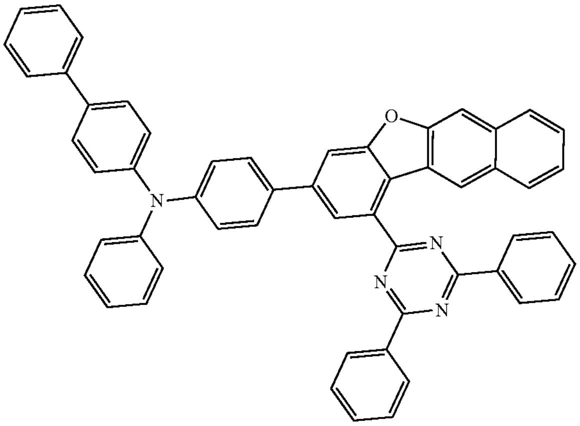
2-25
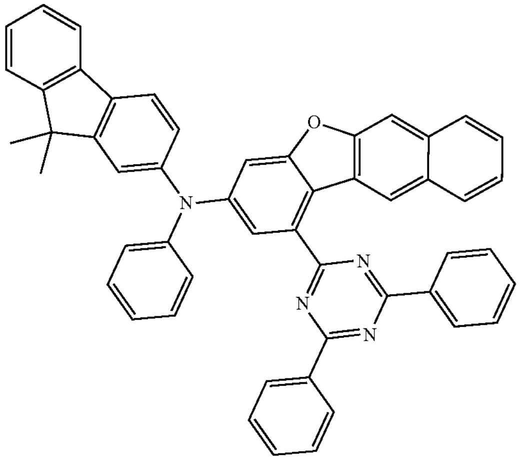
-continued
2-26
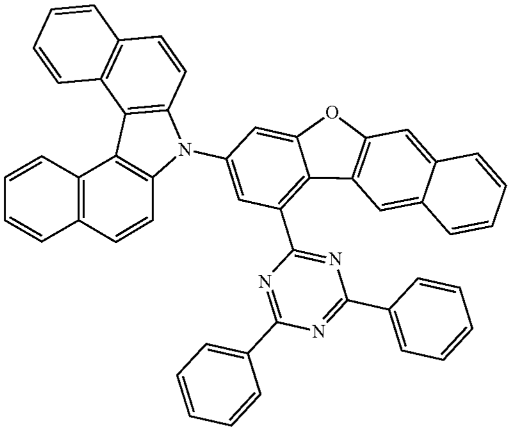
2-27
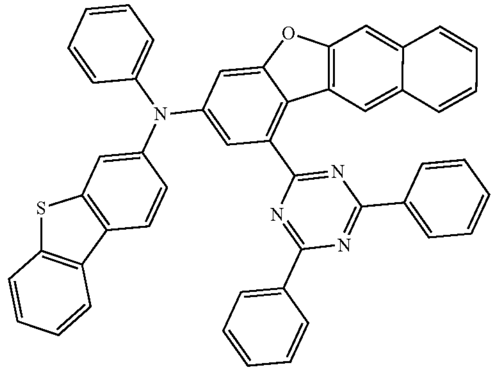
2-28
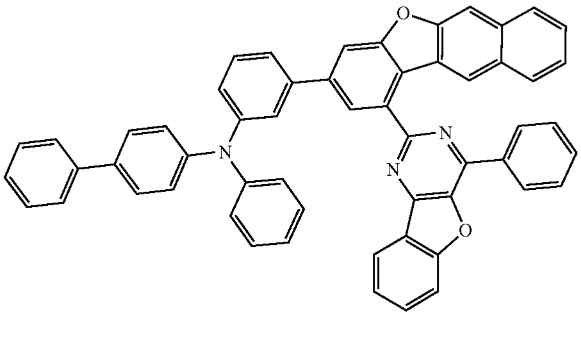

-continued
2-29
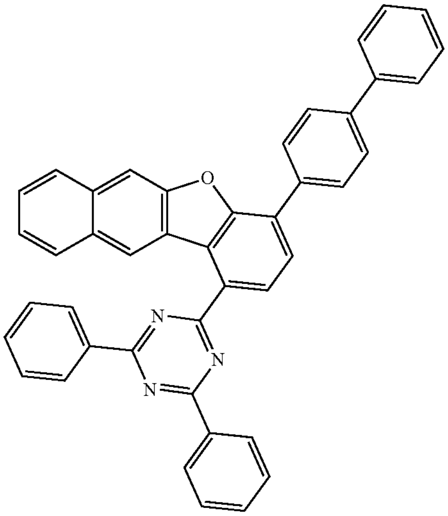
2-30
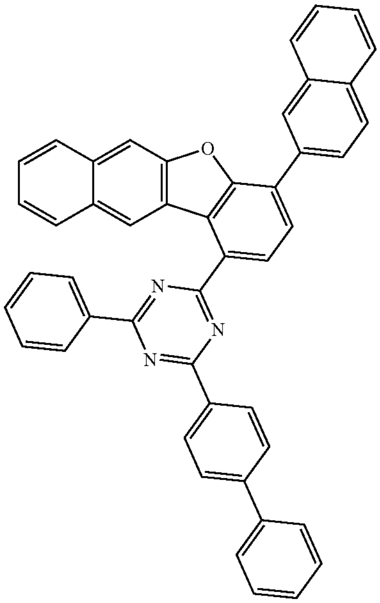
-continued
2-31
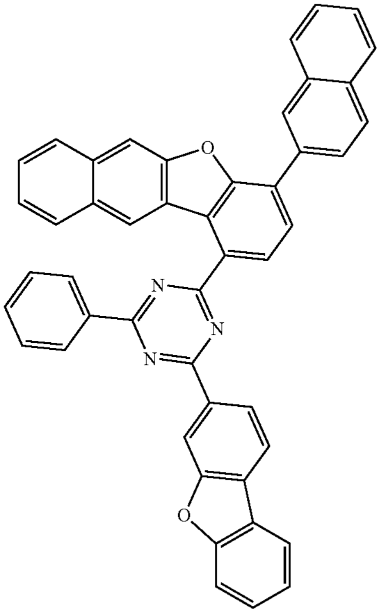
2-32
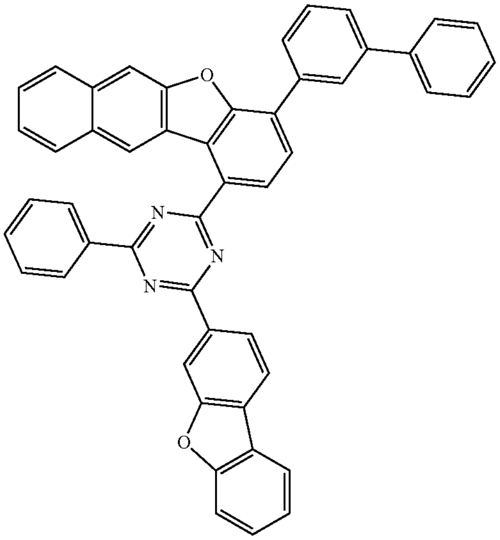
2-33
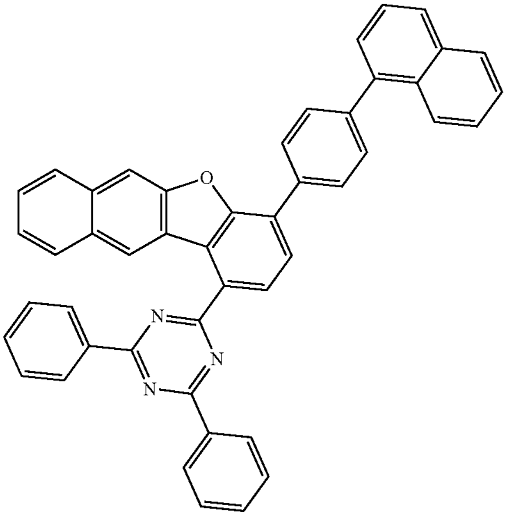

-continued
2-34
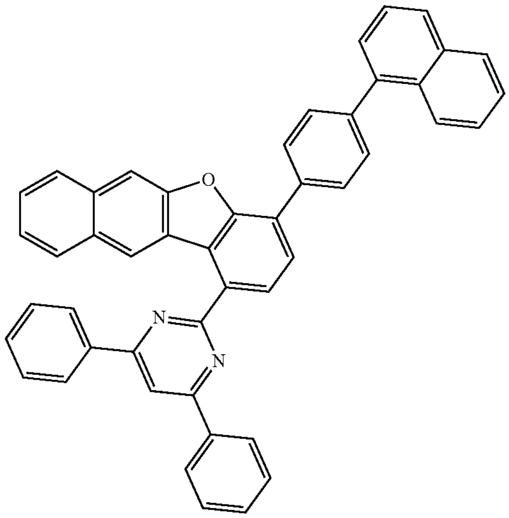
2-35
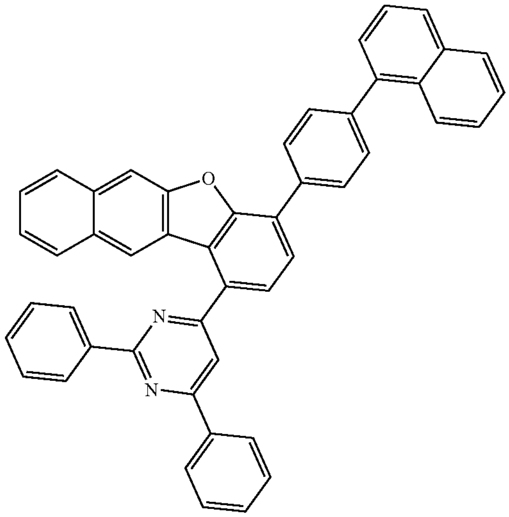
2-36
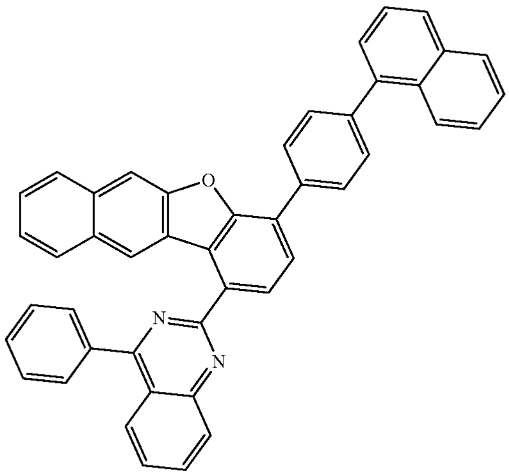
-continued
2-37
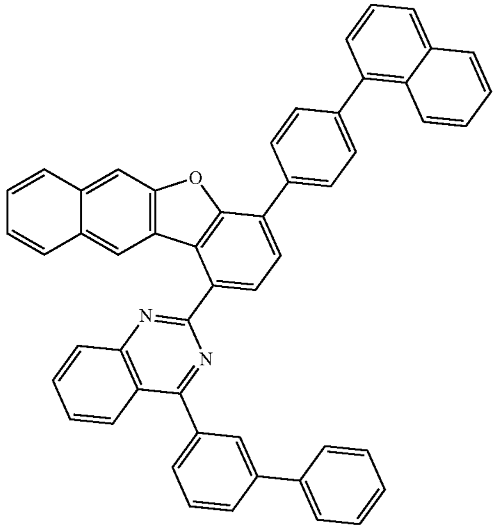
2-38
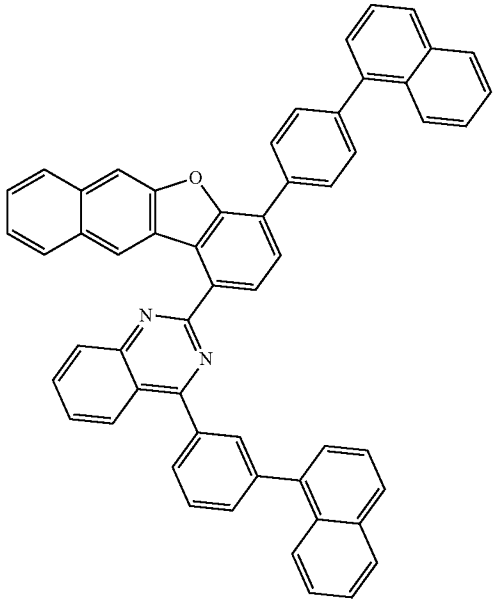
2-39
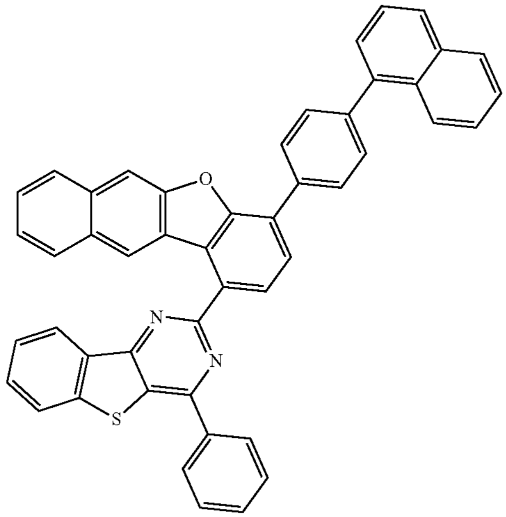

-continued
2-40
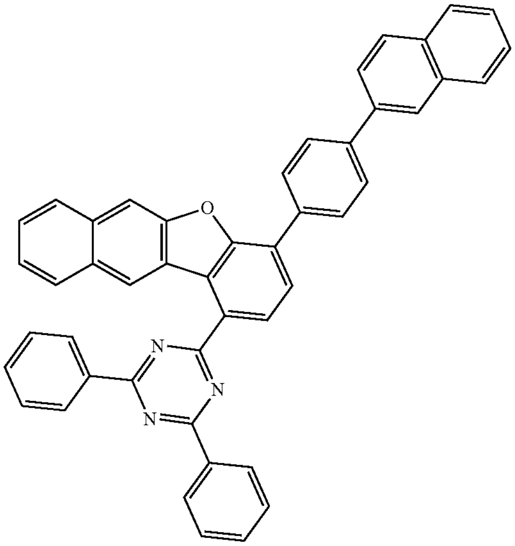
2-41
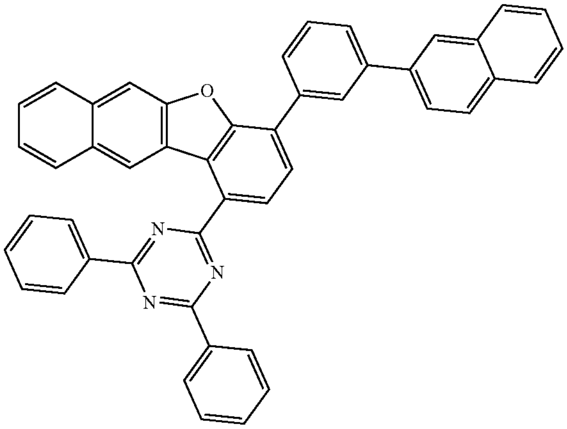
2-42
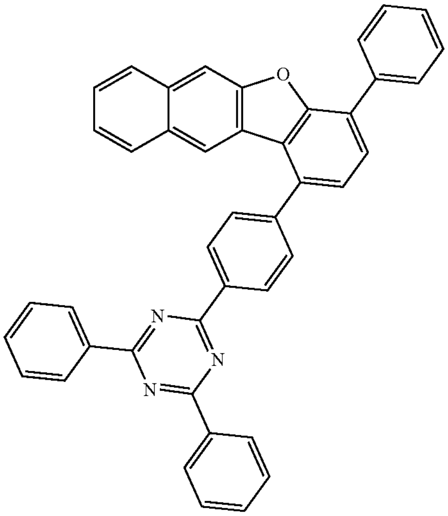
-continued
2-43
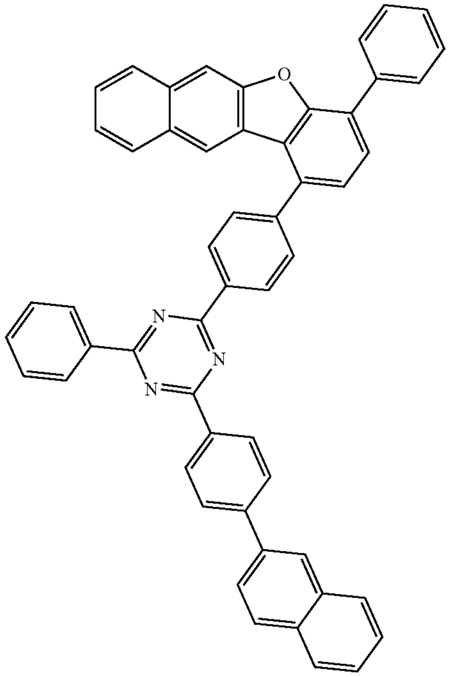
2-44
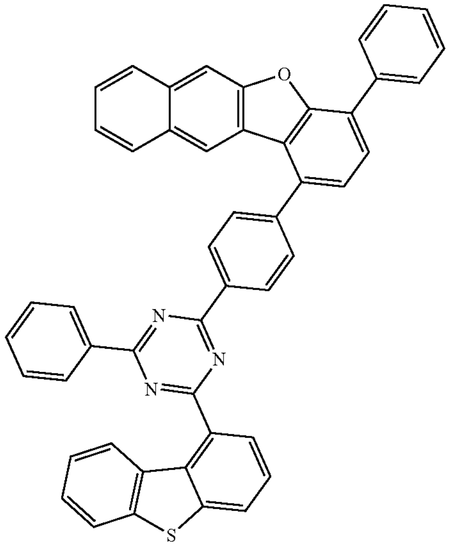

-continued
2-45
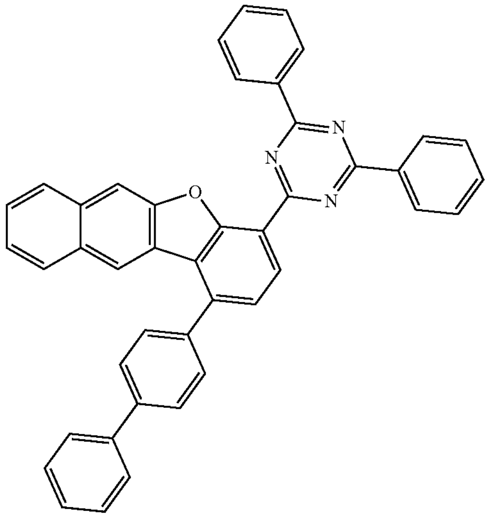
2-46
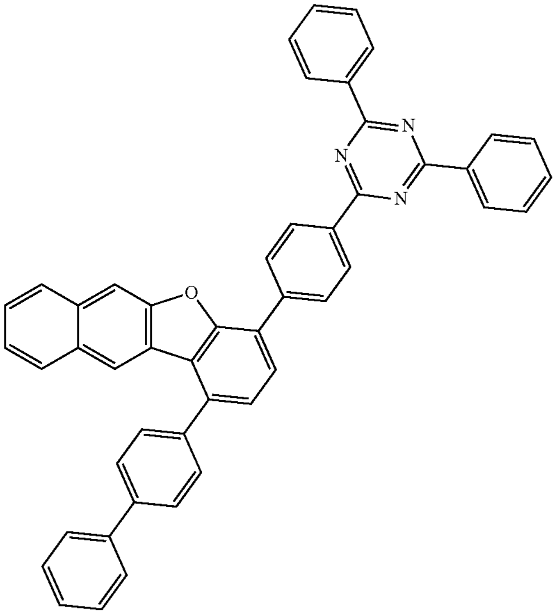
-continued
2-47
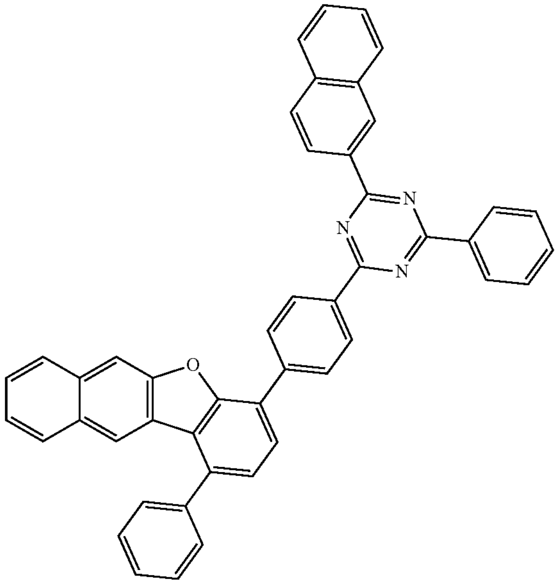
2-48
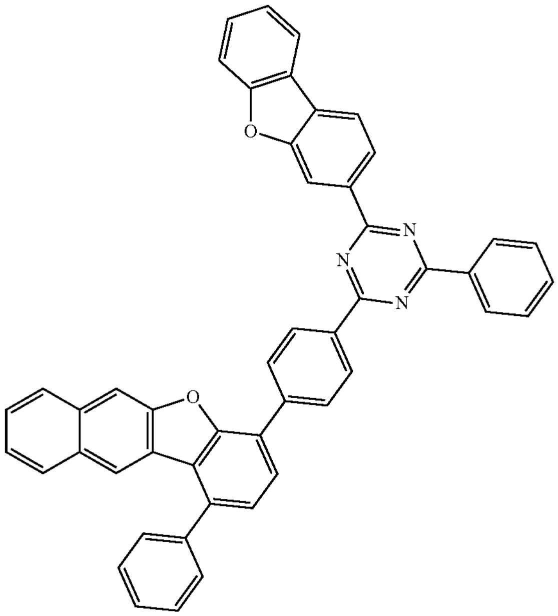

-continued
2-49
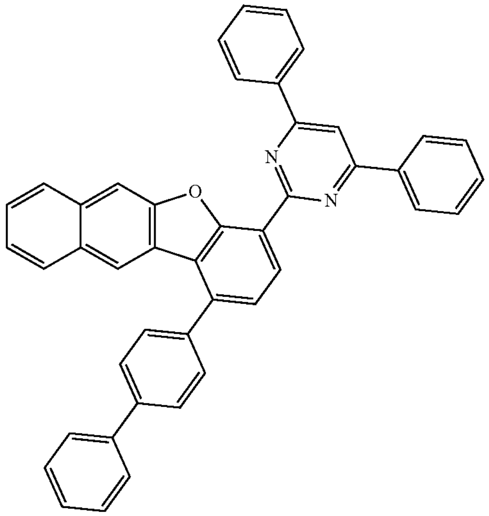
2-50
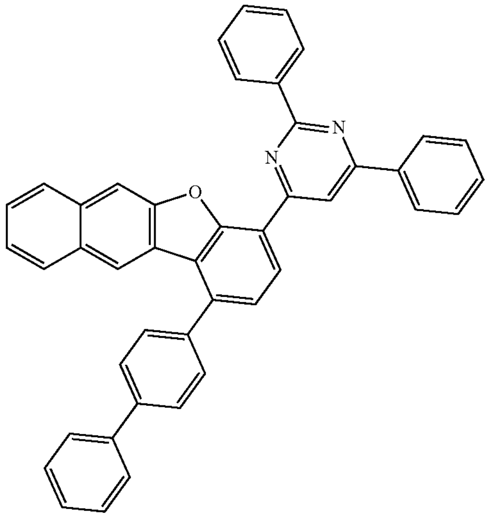
-continued
2-51
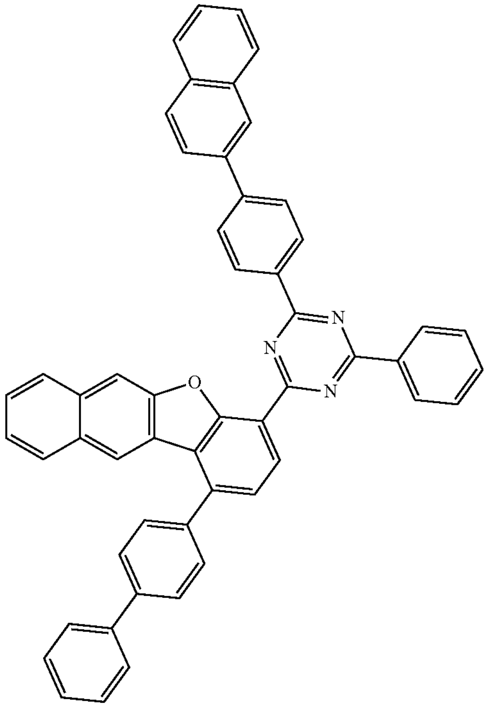
2-52
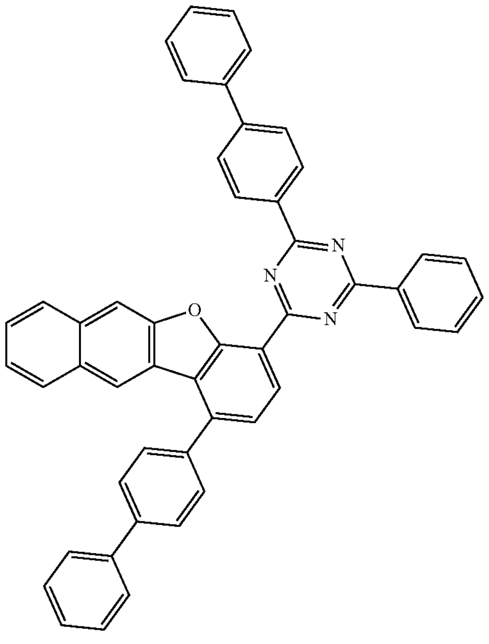

2-53
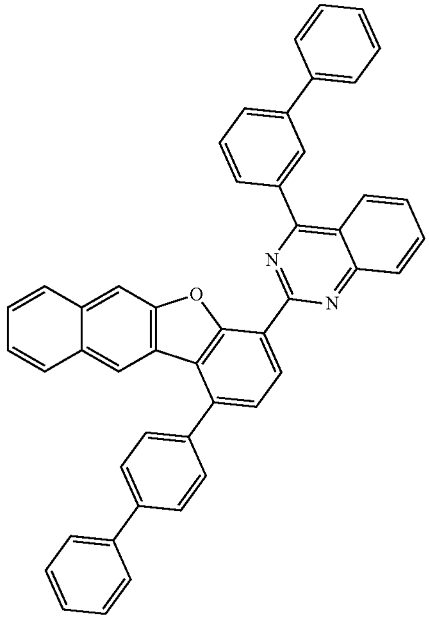
2-54
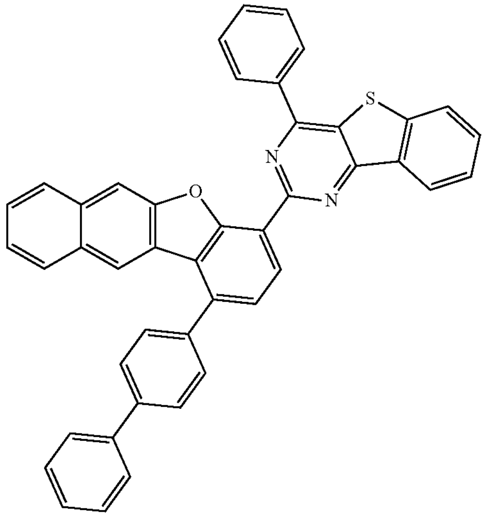
2-55
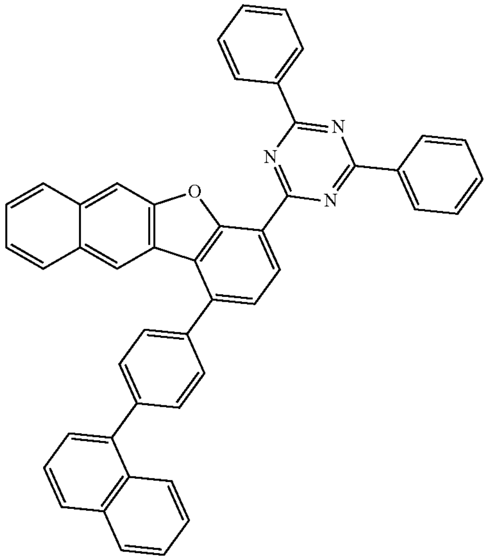
2-56
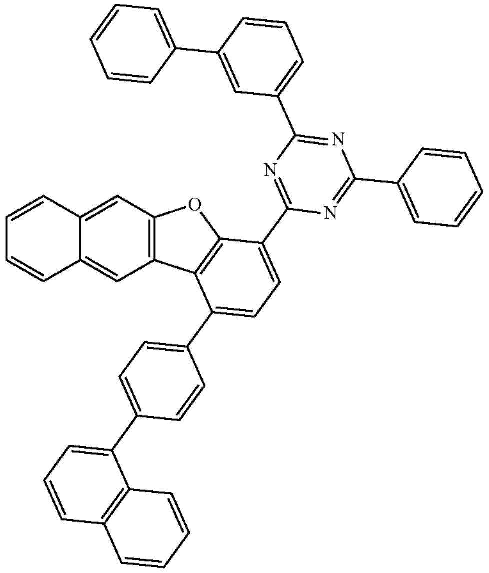

-continued
2-57
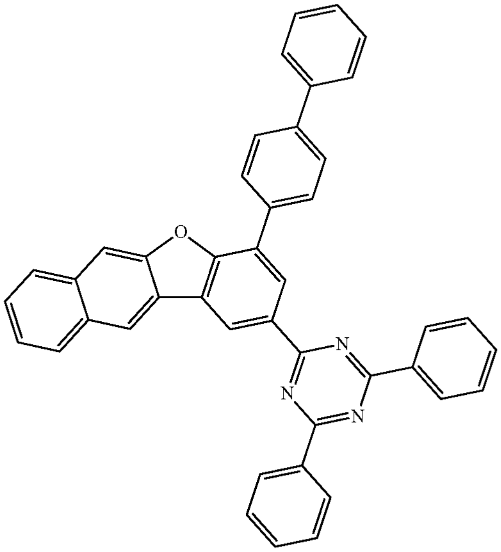
2-58
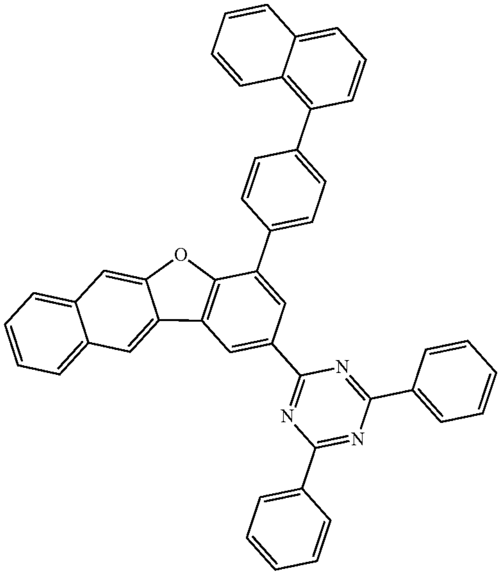
-continued
2-59
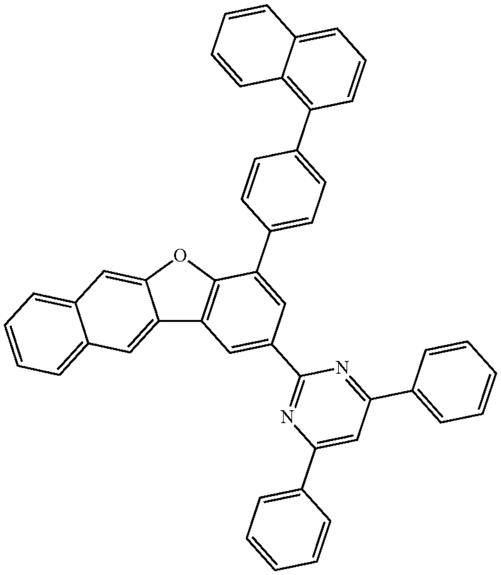
2-60
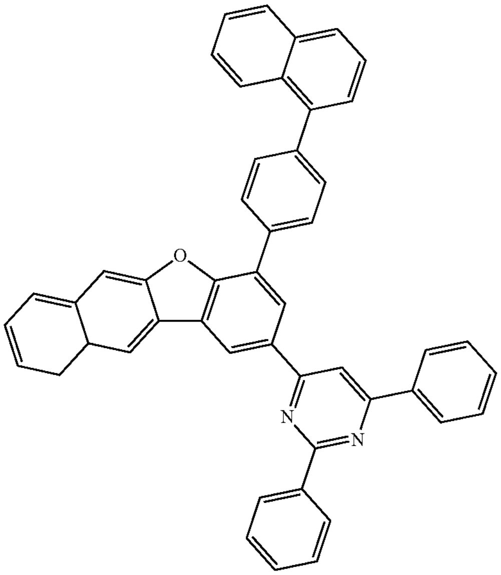

-continued
2-61
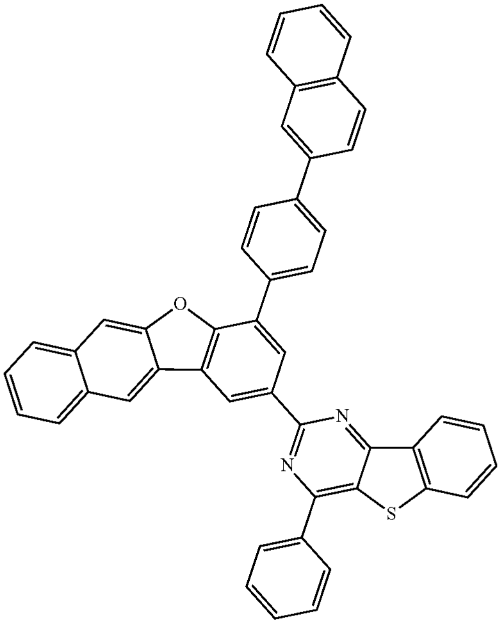
2-62
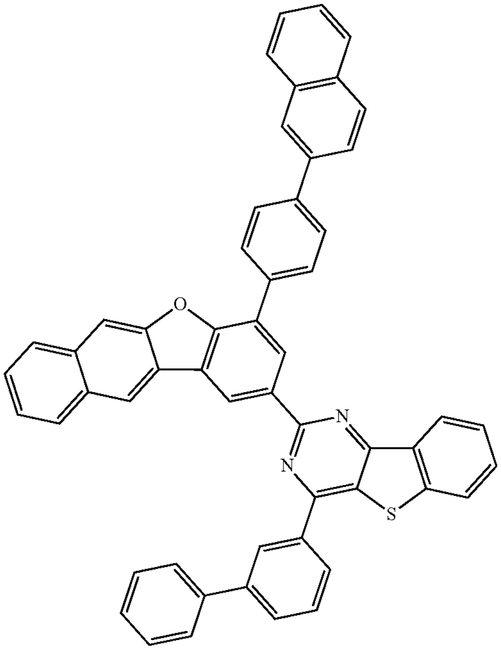
-continued
2-63
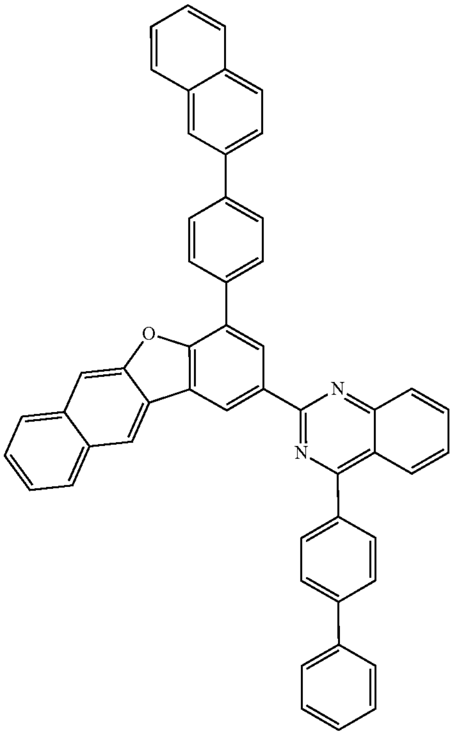
2-64
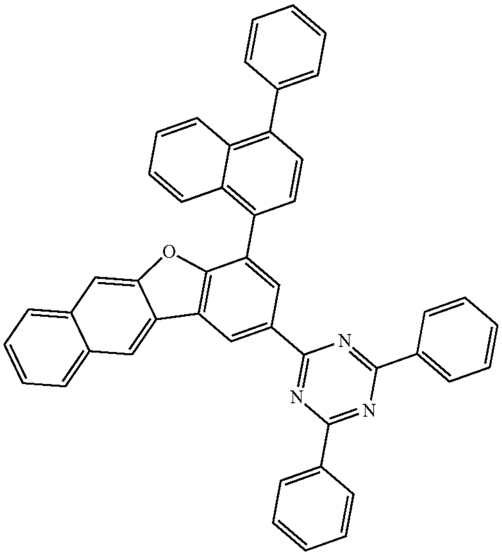

2-65
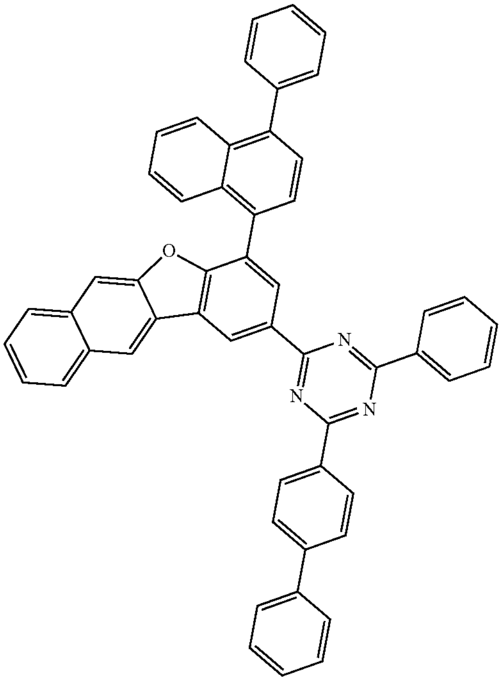
2-66
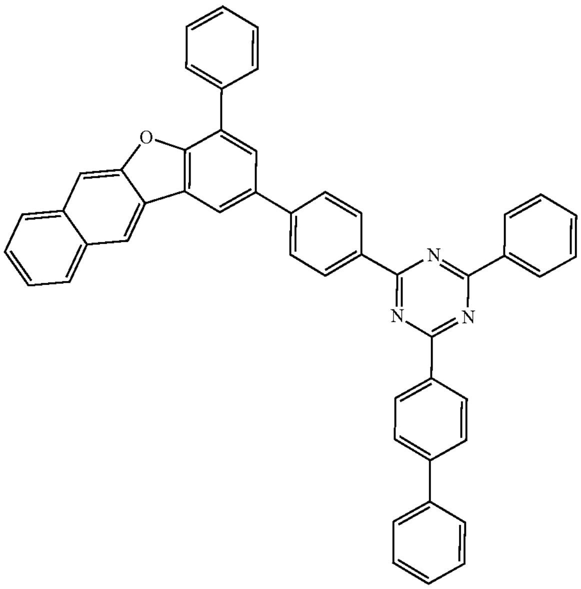
2-67
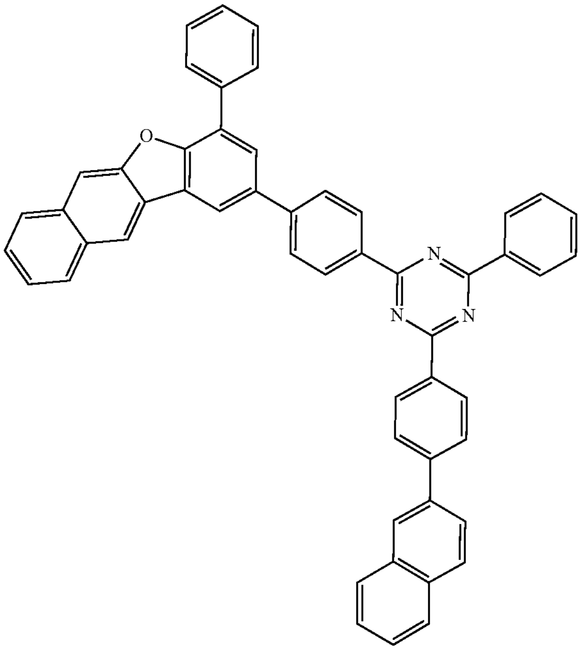
2-68
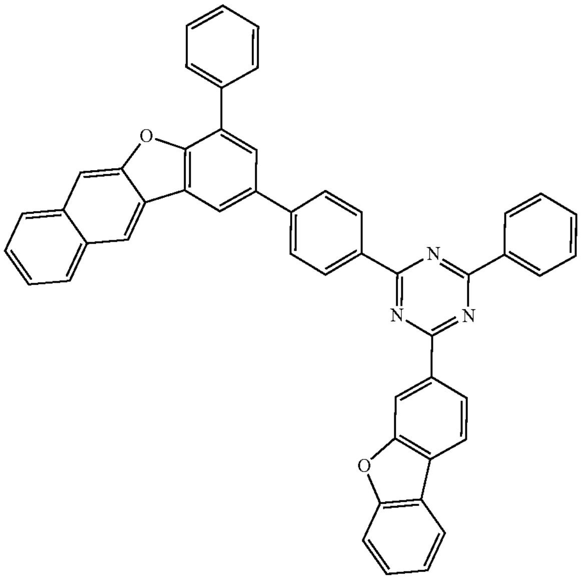

2-69
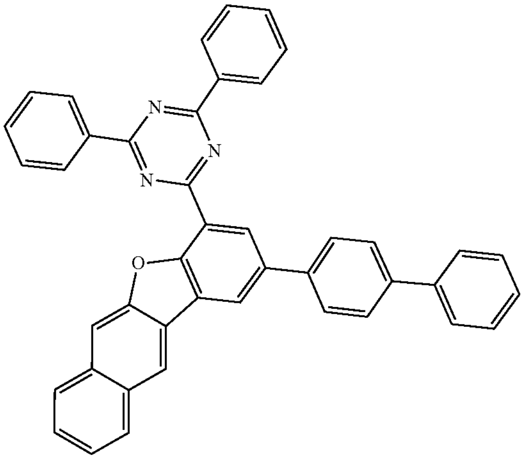
2-70
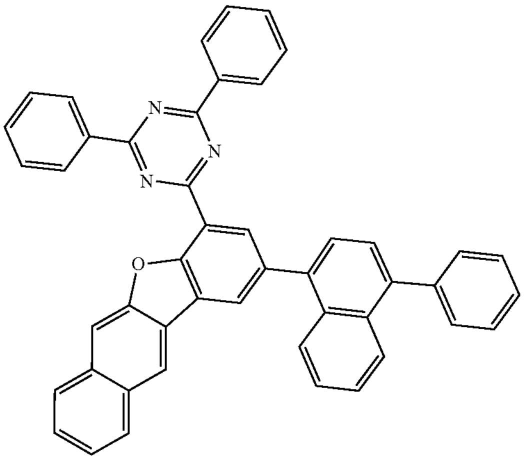
2-71
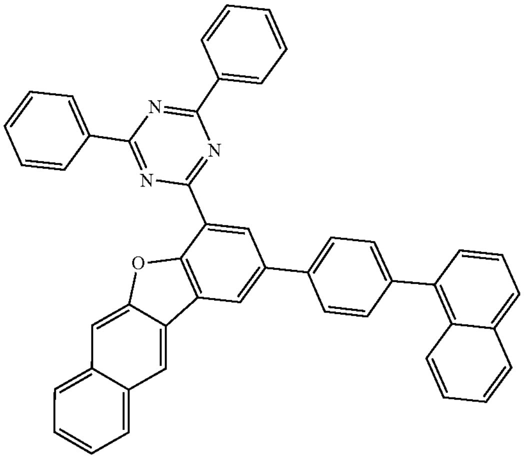
2-71
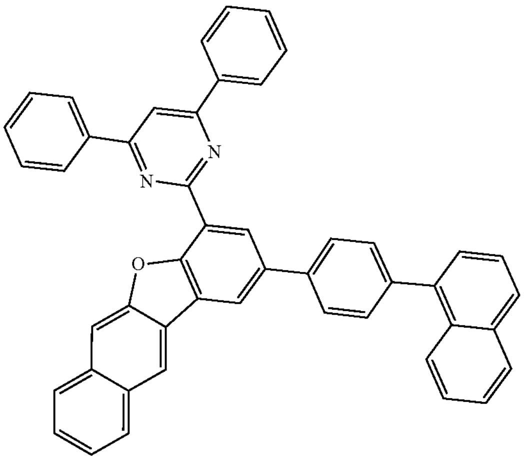
2-72
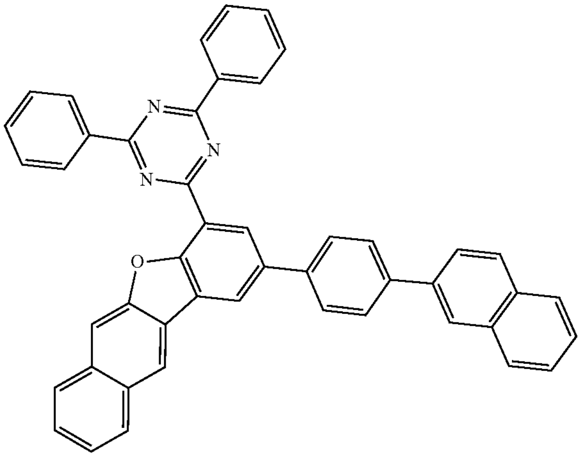
2-73
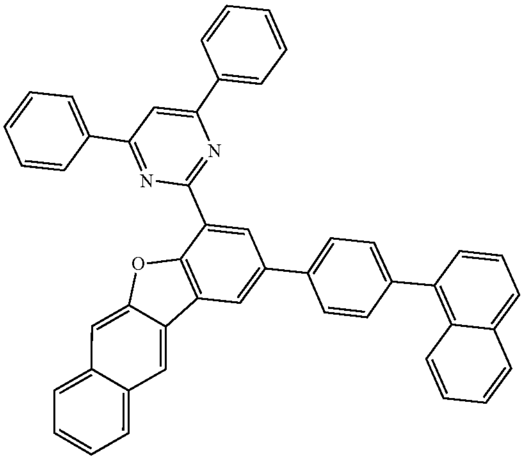

-continued
2-74
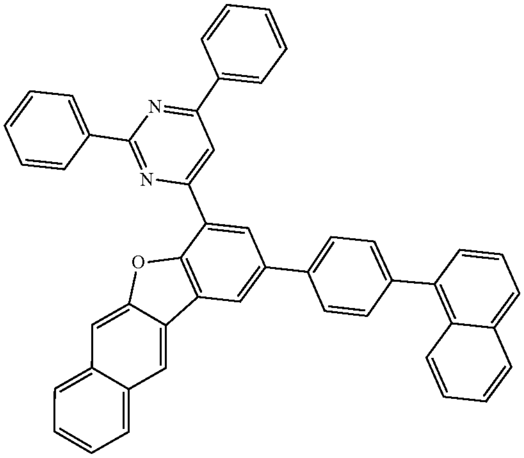
2-75
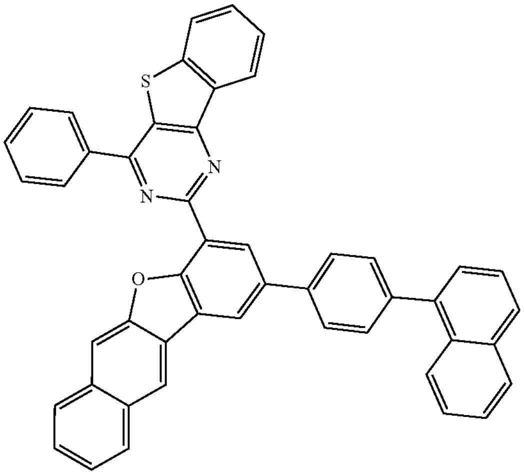
2-76
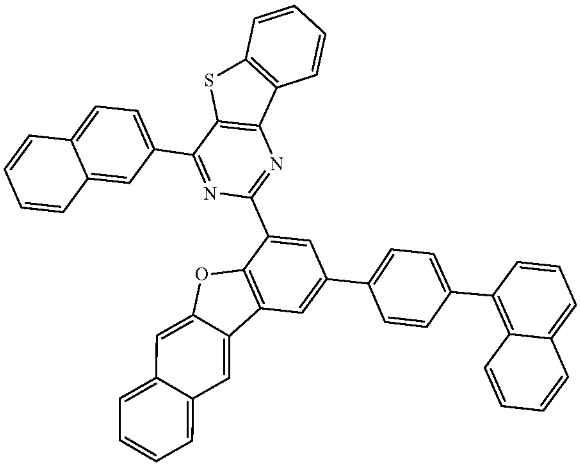
-continued
2-77
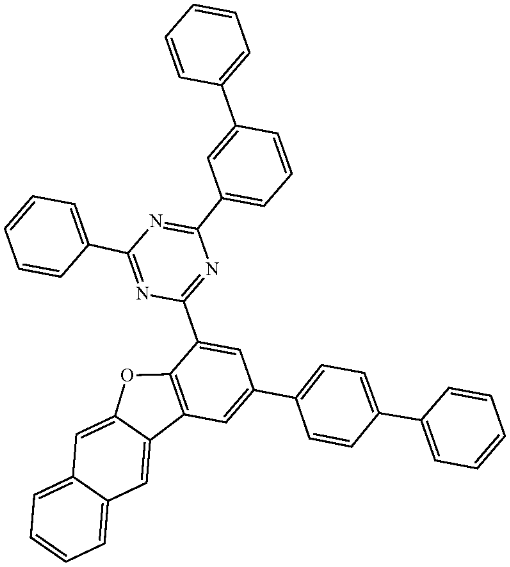
2-78
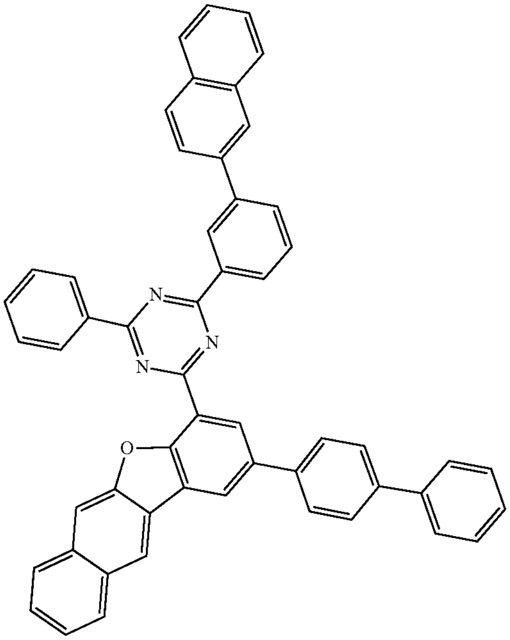

-continued
2-79
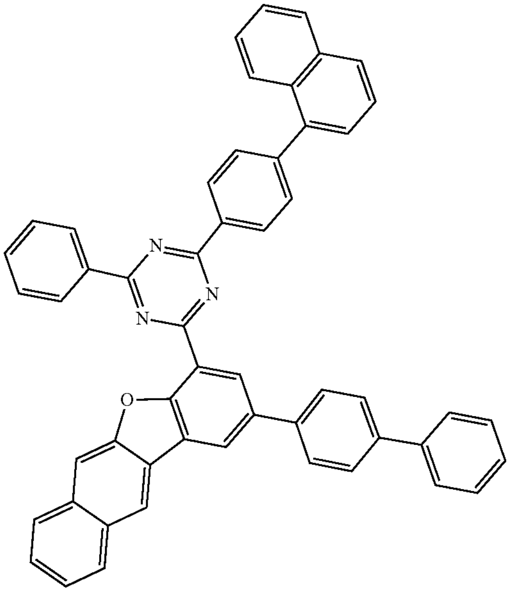
2-80
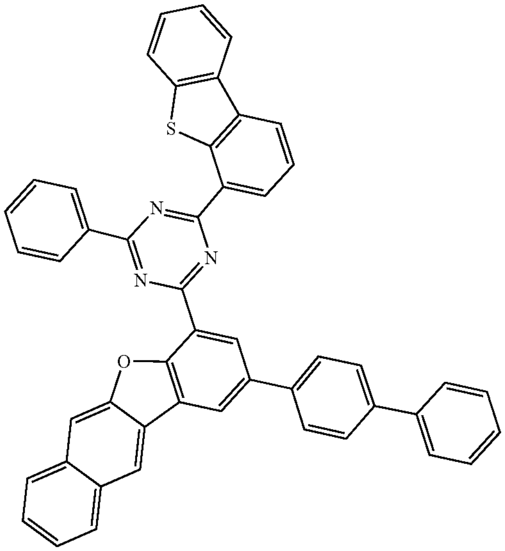
-continued
2-81
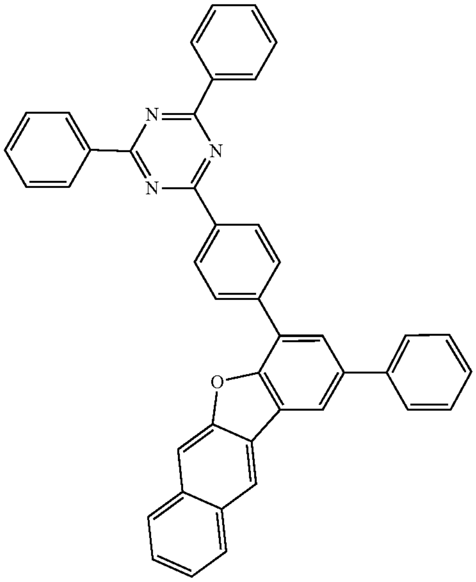
2-82
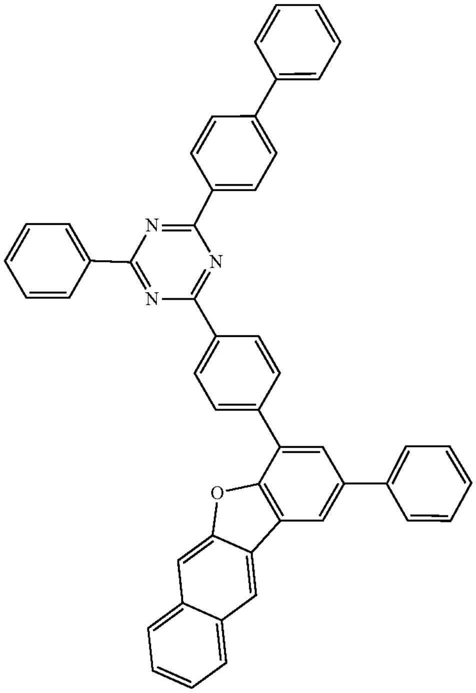

-continued
2-83
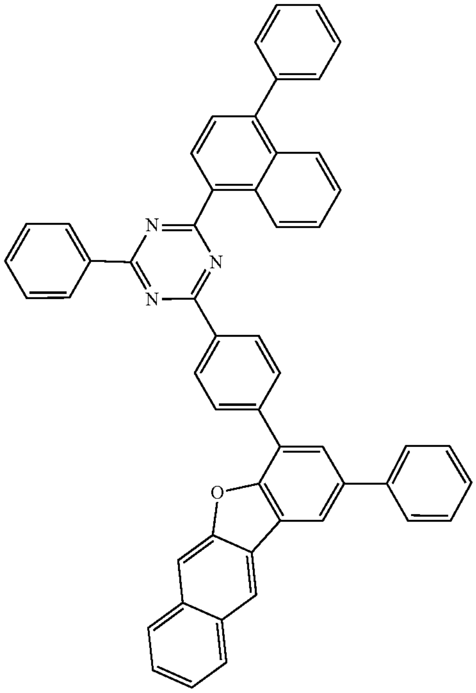
2-84
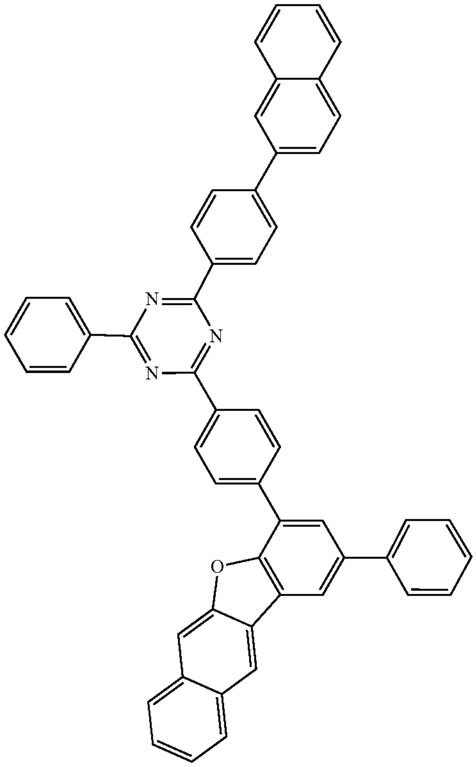
-continued
2-85
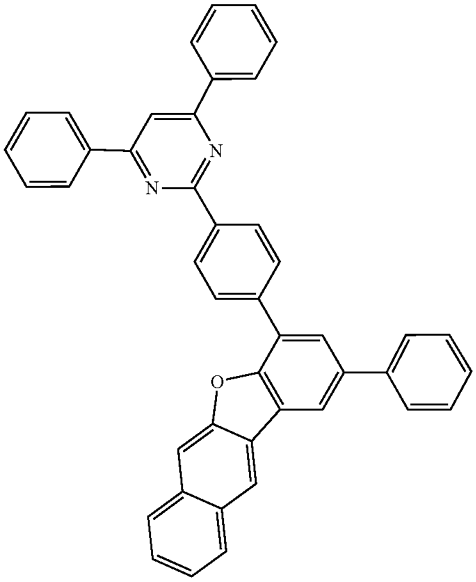
2-86
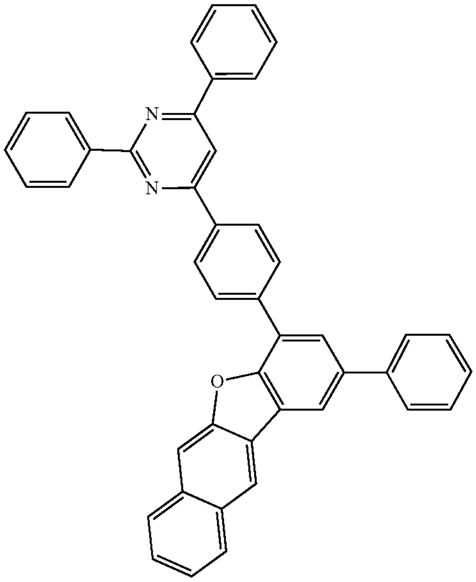

-continued
2-87
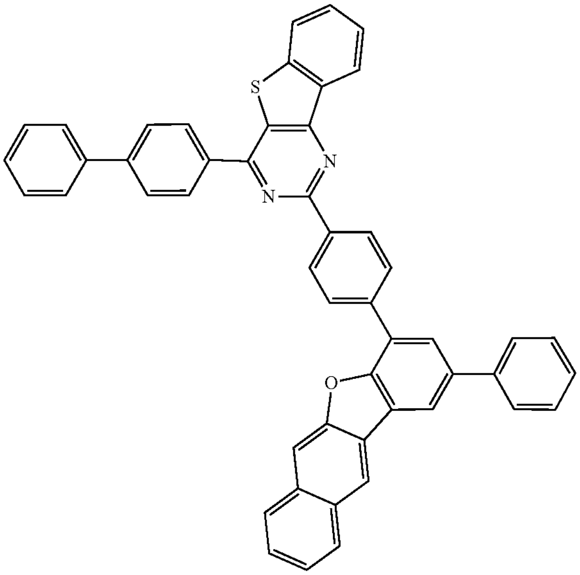
2-88
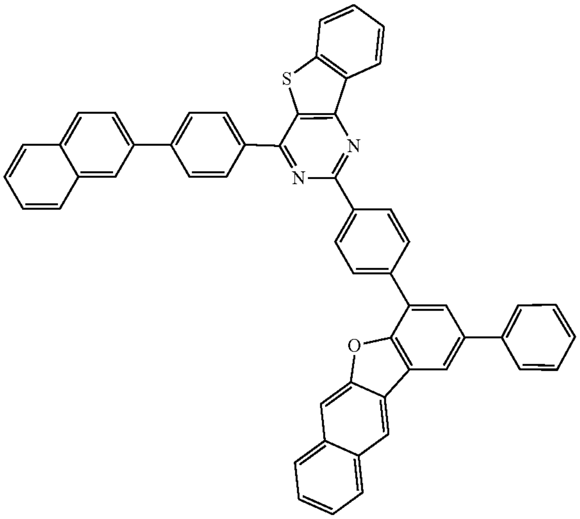
2-89
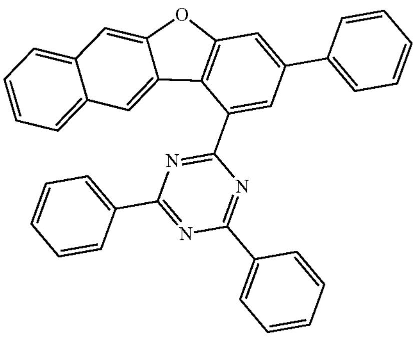
-continued
2-90
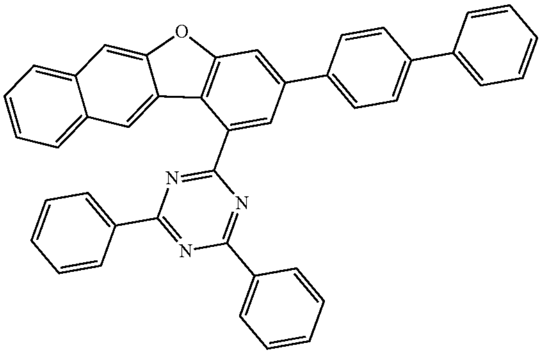
2-91
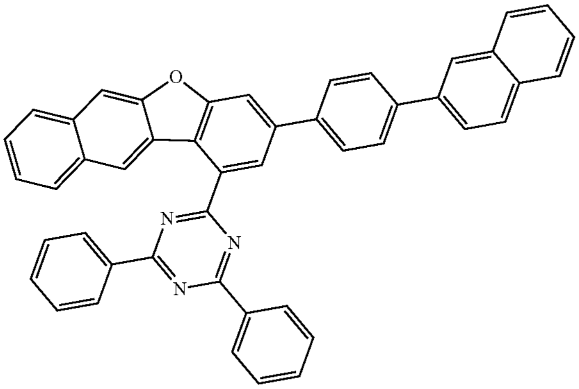
2-92
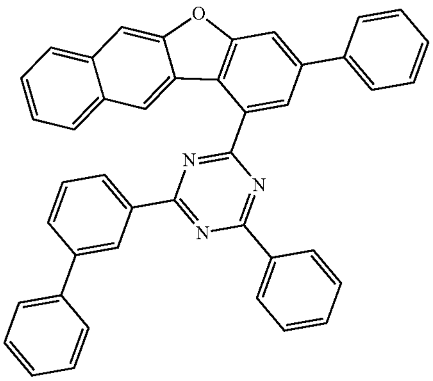
2-93
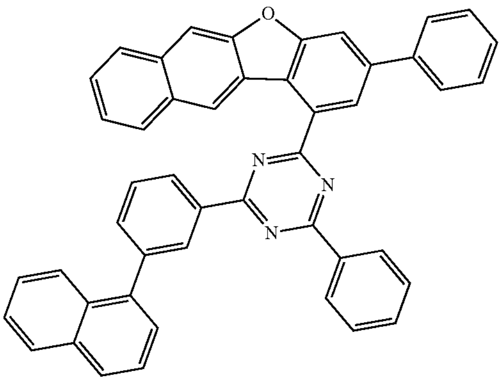

-continued
2-94
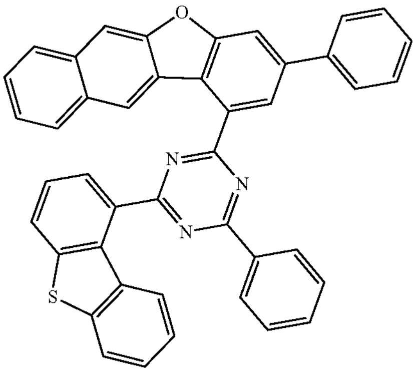
2-95
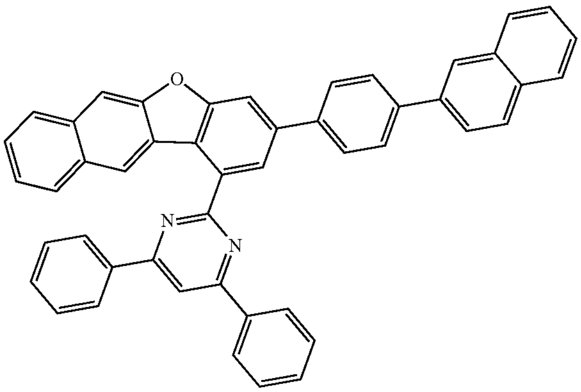
2-96
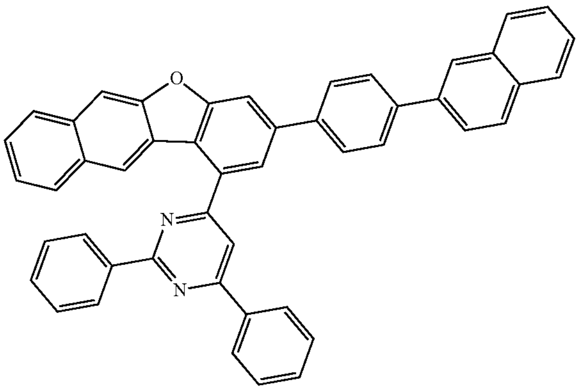
-continued
2-97
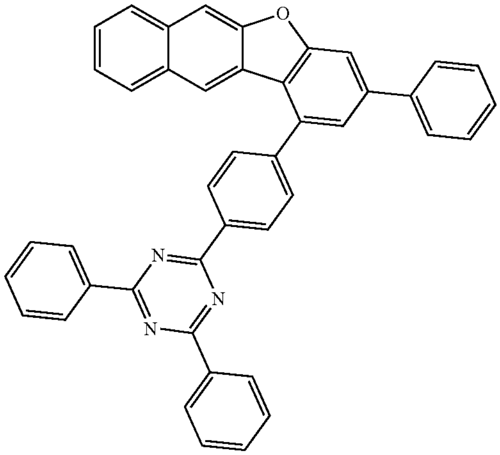
2-98
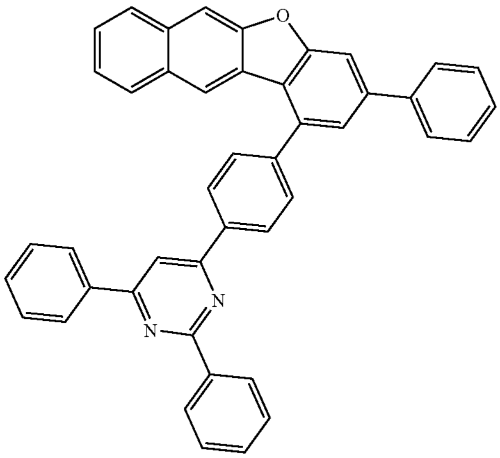
2-99
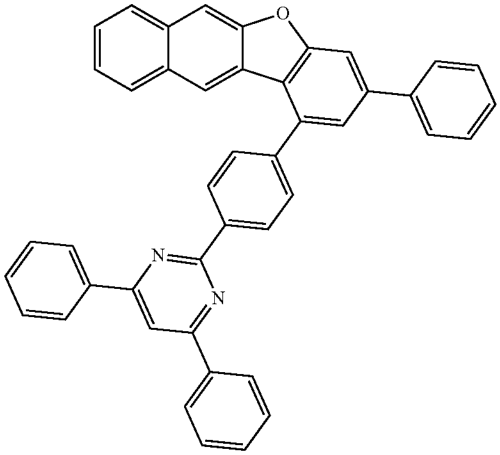

-continued
2-100
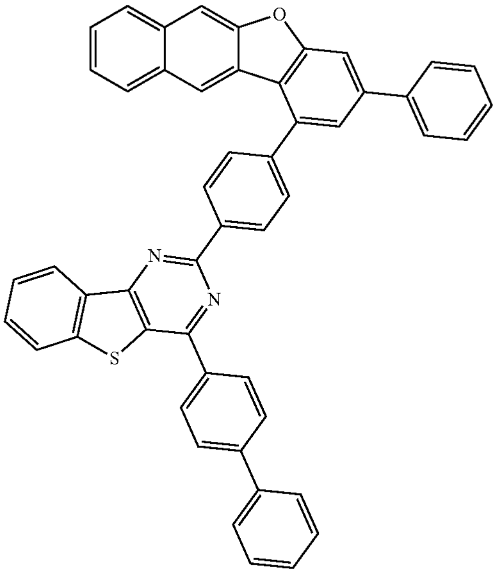
2-101
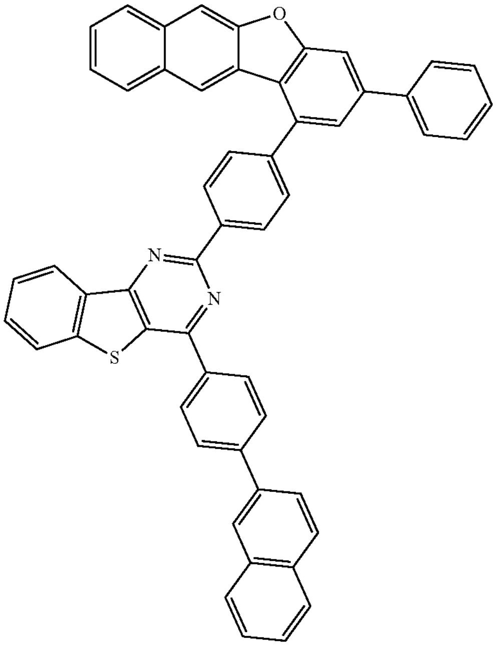
-continued
2-102
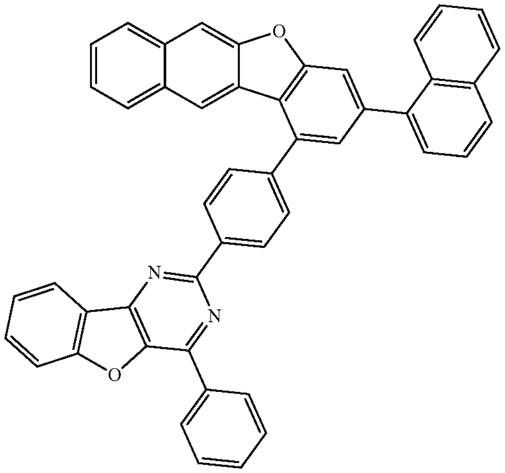
2-103
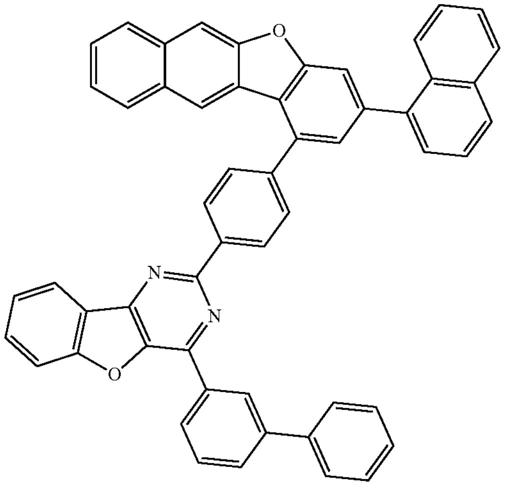
2-104
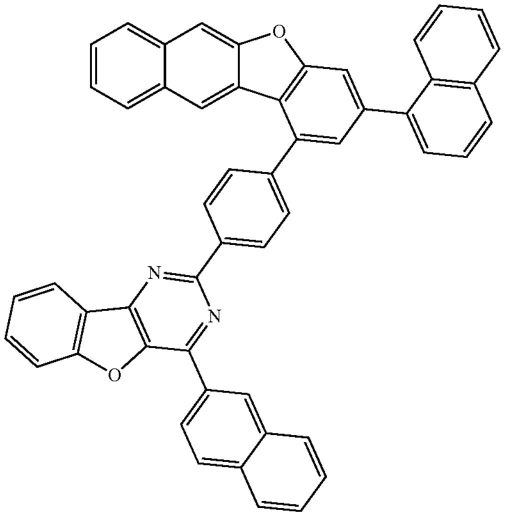

-continued
2-105
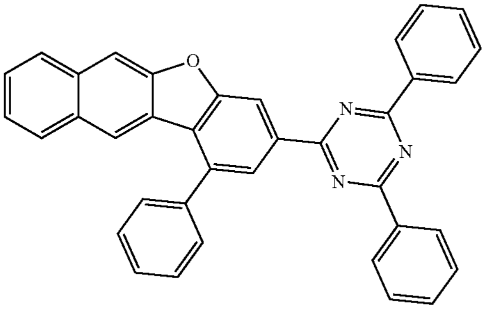
2-106
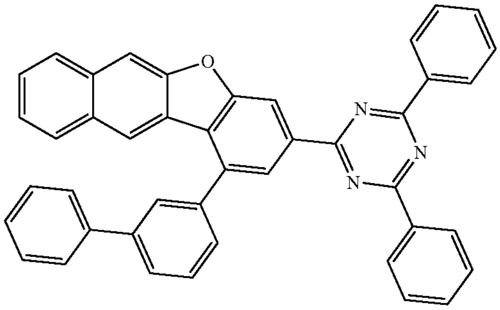
2-107
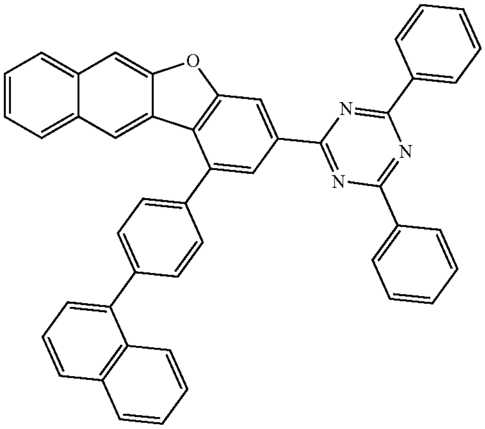
2-108
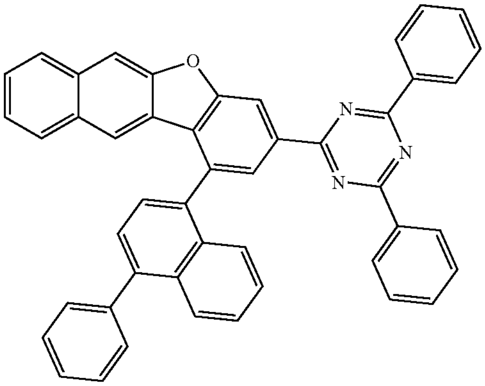
-continued
2-109
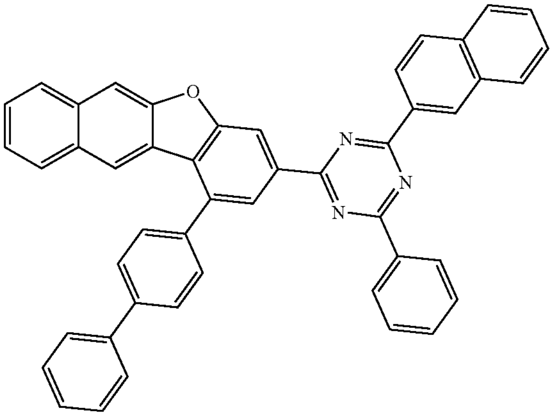
2-110
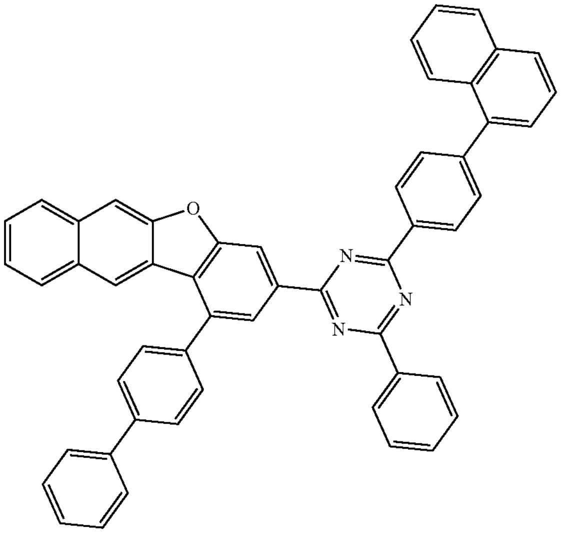
2-111
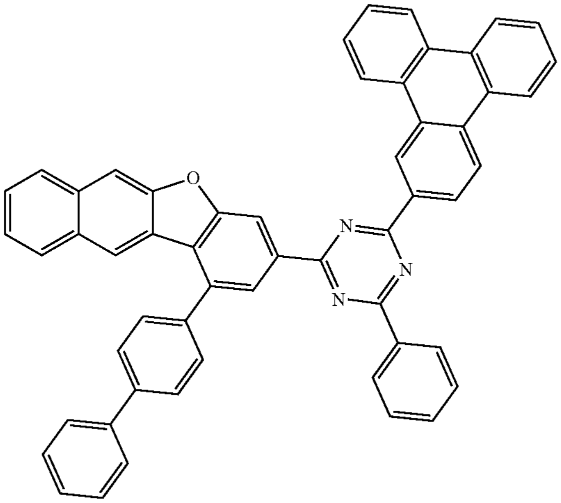

-continued
2-112
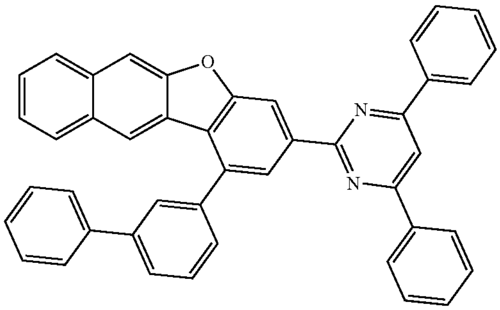
2-113
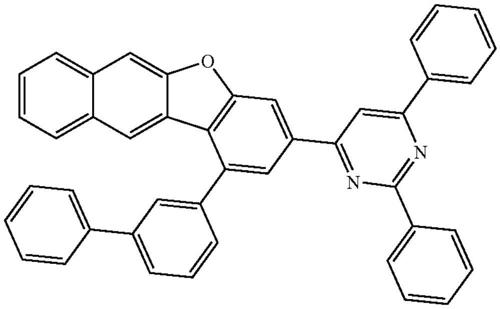
2-114
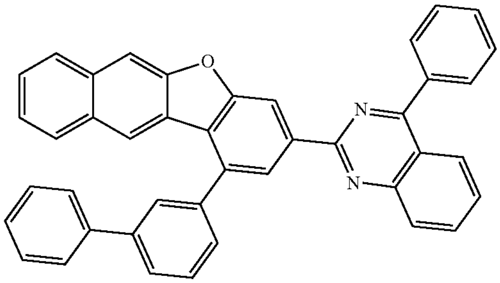
2-115
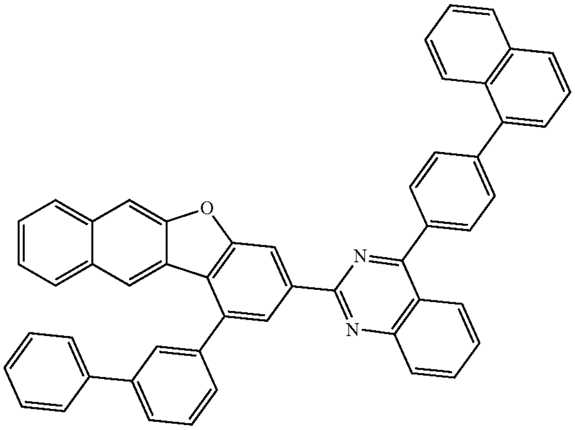
-continued
2-116
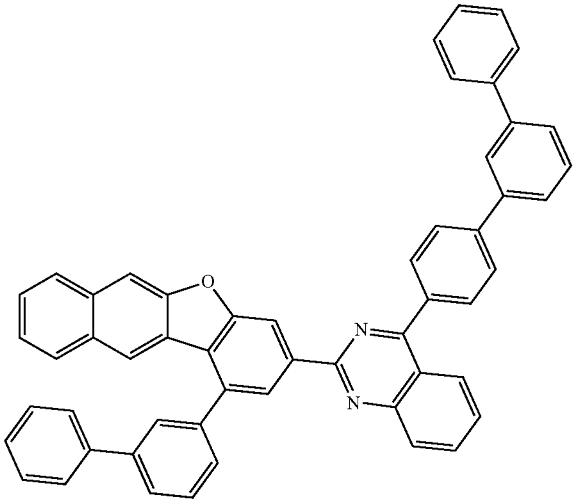
2-117
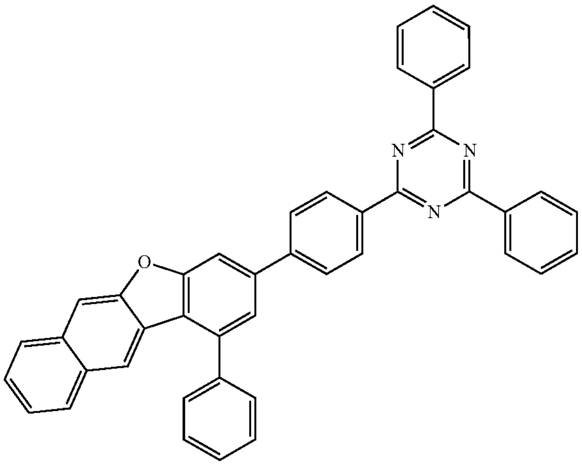

-continued
2-118
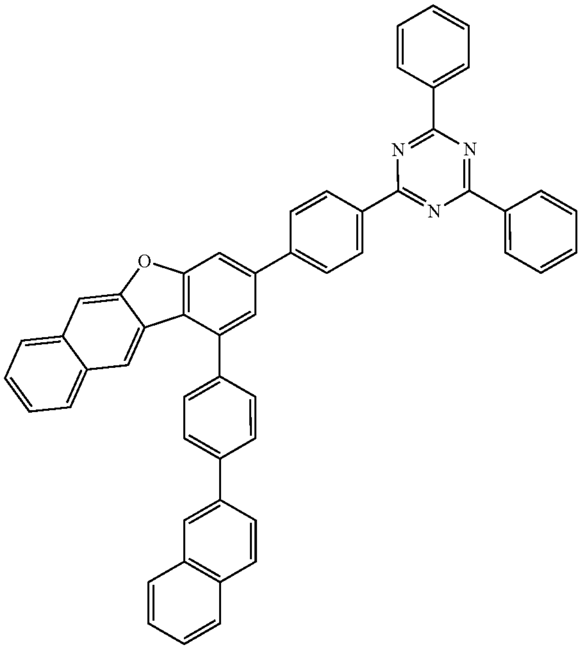
2-119
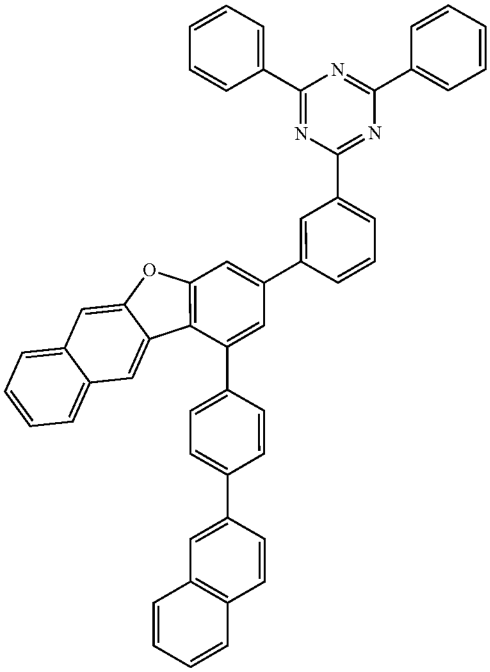
-continued
2-120
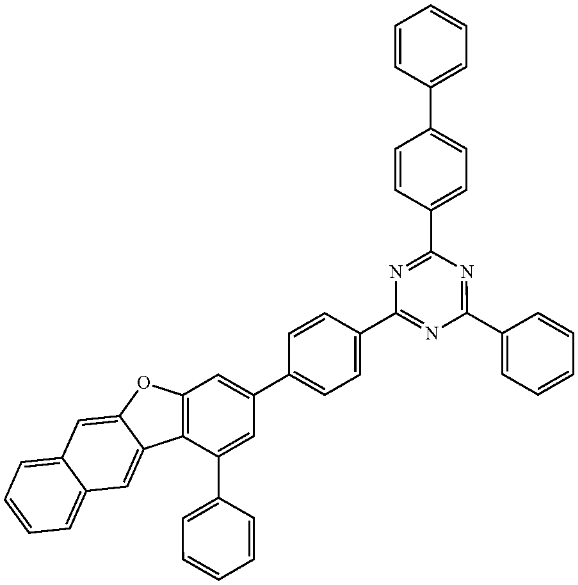
2-121
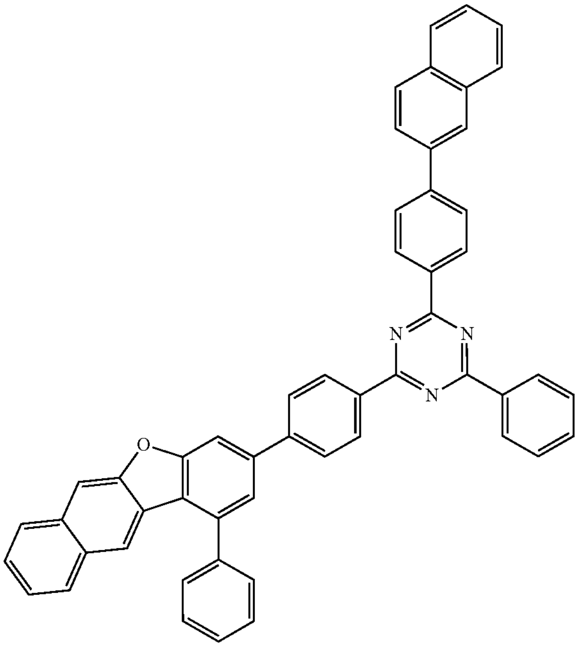

-continued
2-122
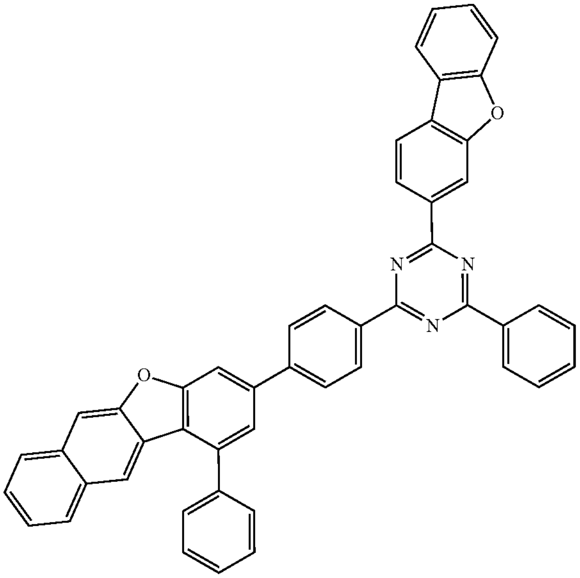
2-123
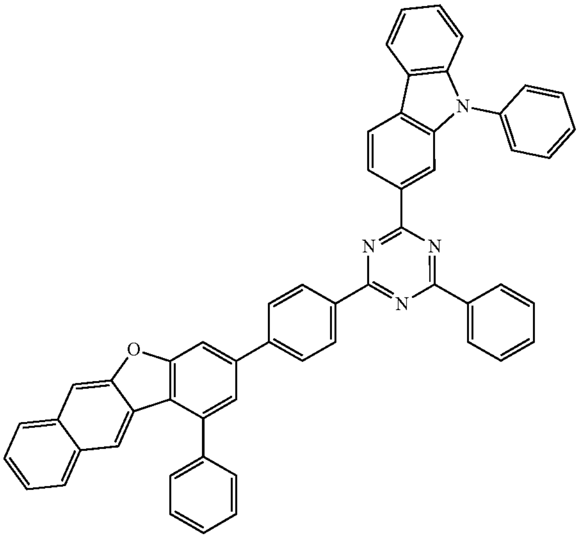
2-124
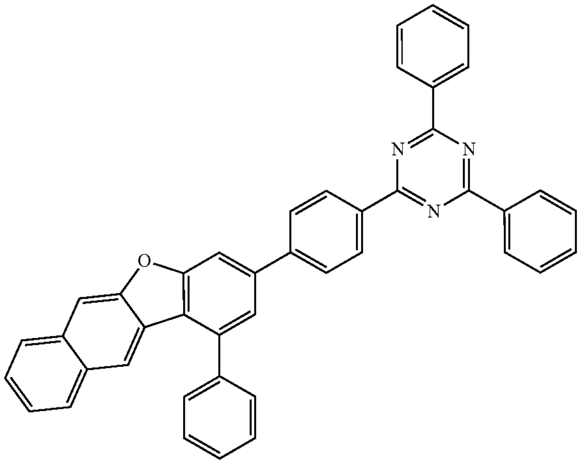
-continued
2-125
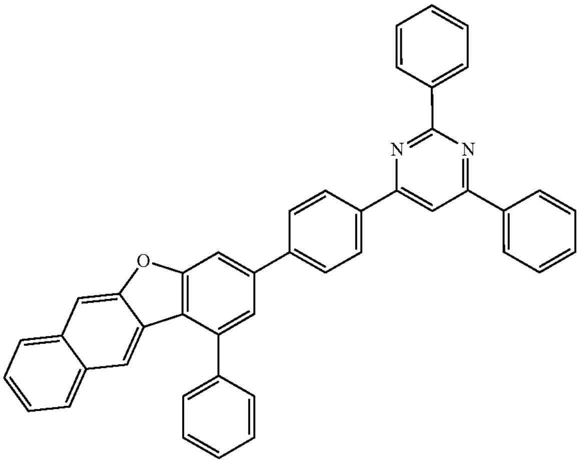
2-126
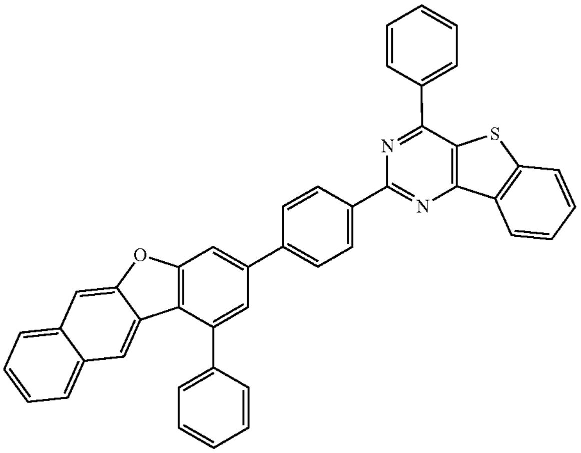
2-127
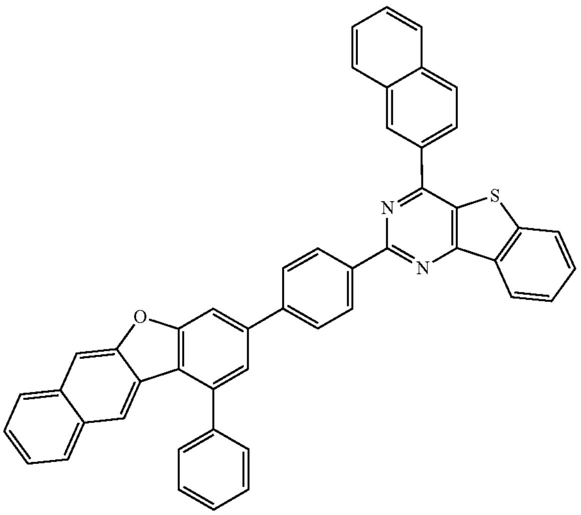

-continued
2-128
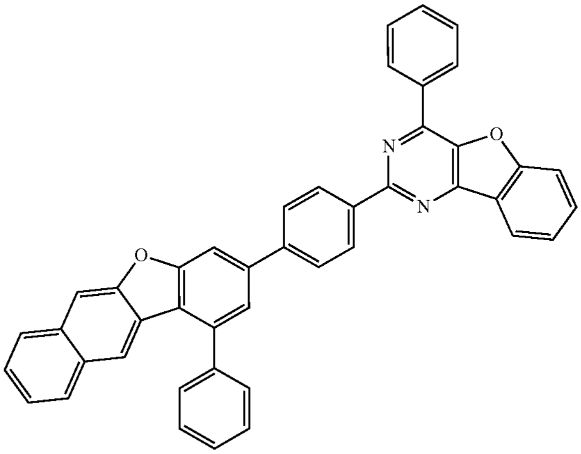
2-129
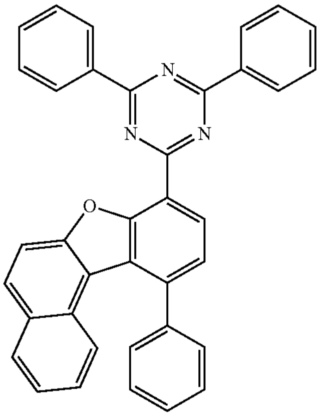
2-130
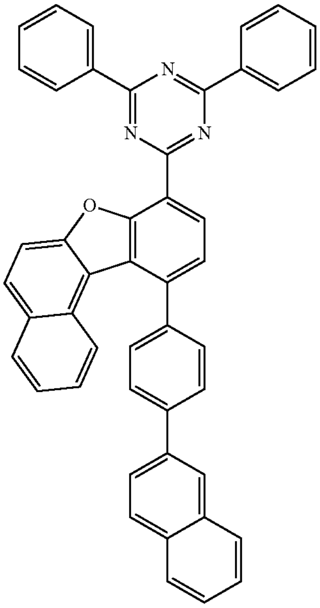
-continued
2-131
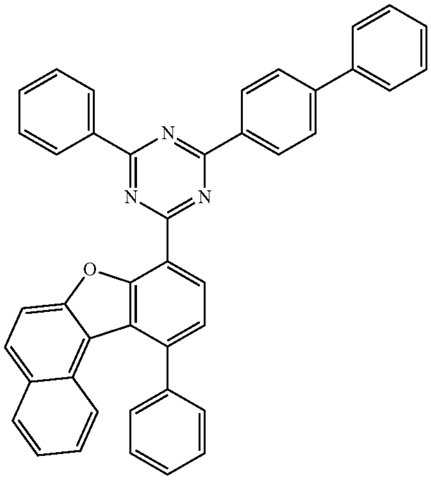
2-132
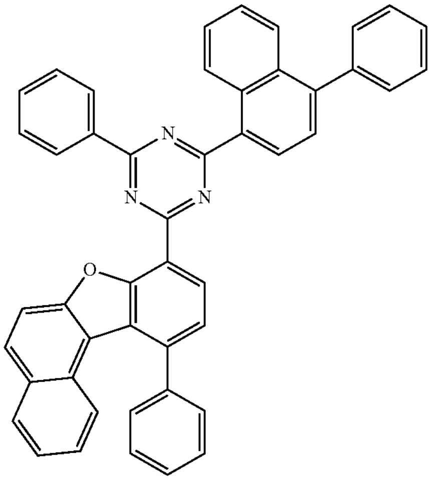
2-133
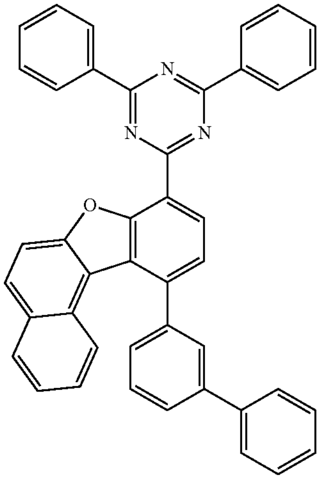

-continued
2-134
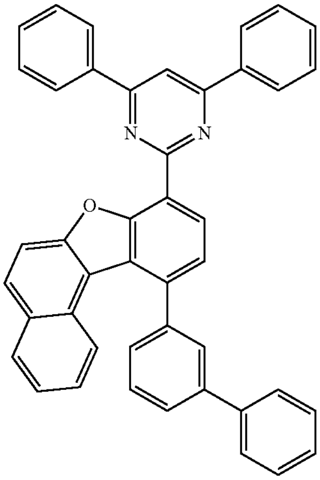
2-135
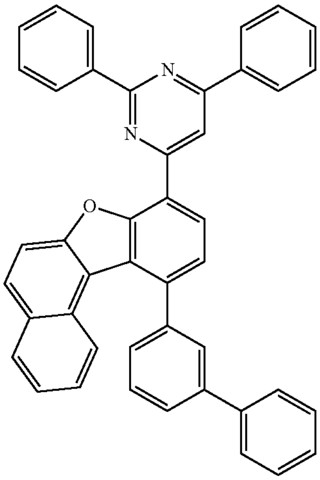
2-136
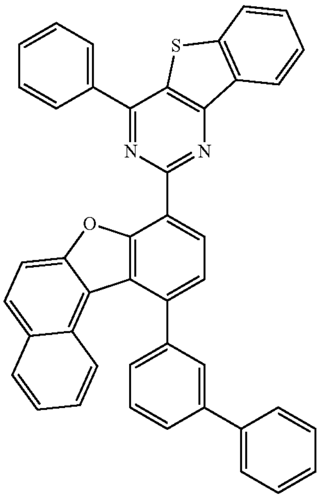
-continued
2-137
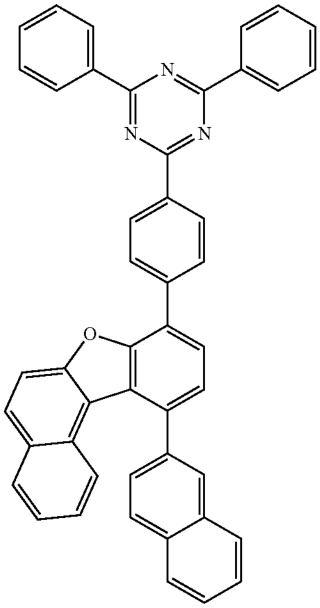
2-138
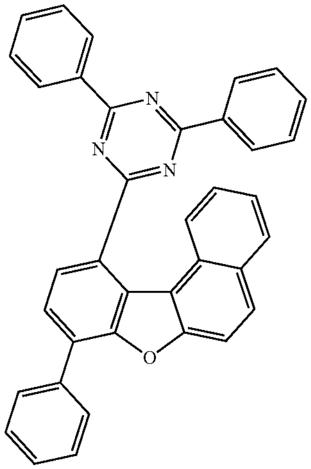

-continued
2-139
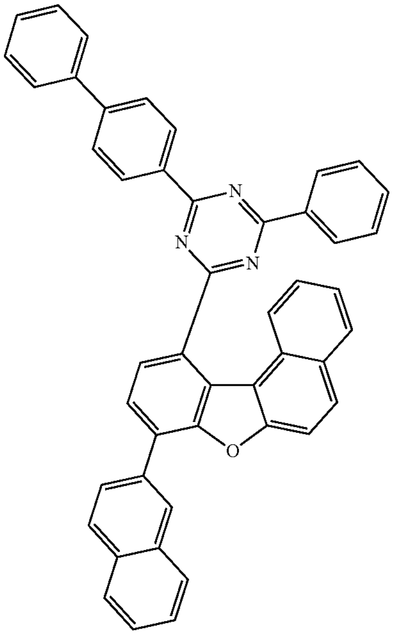
2-140
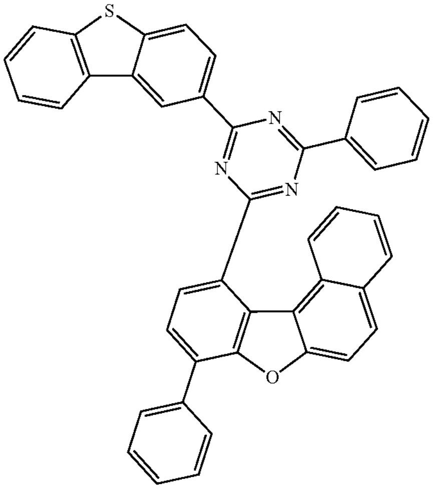
-continued
2-141
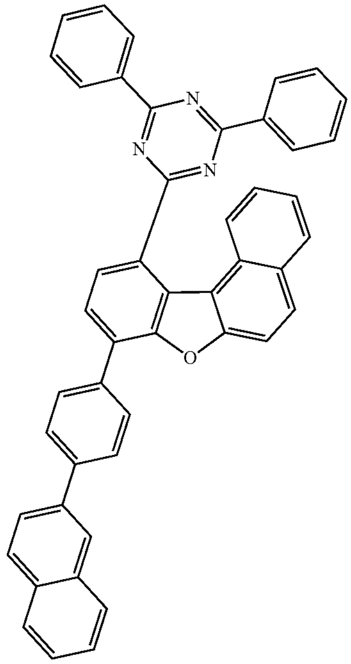
2-142
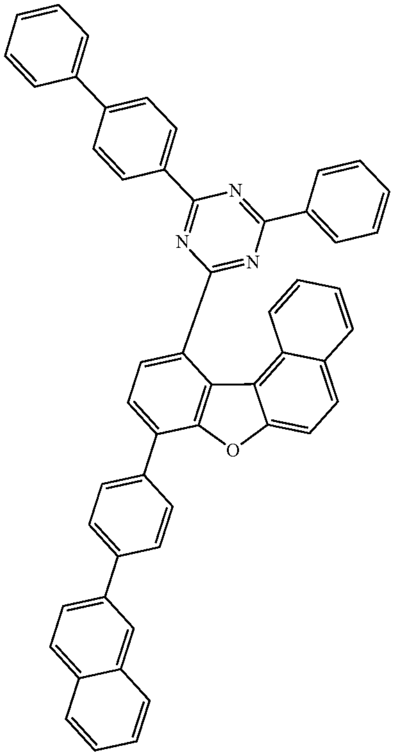

-continued
2-143
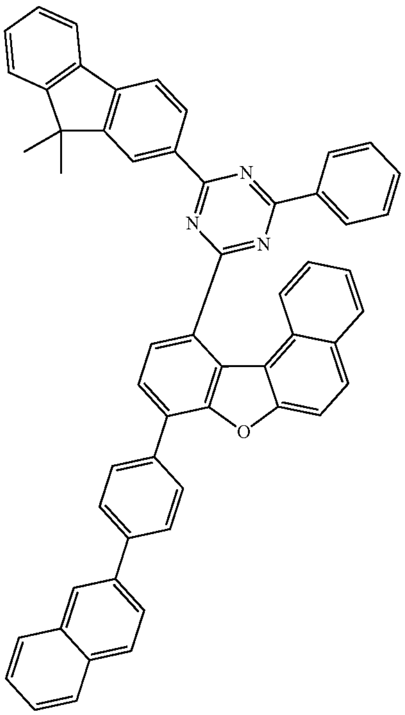
2-144
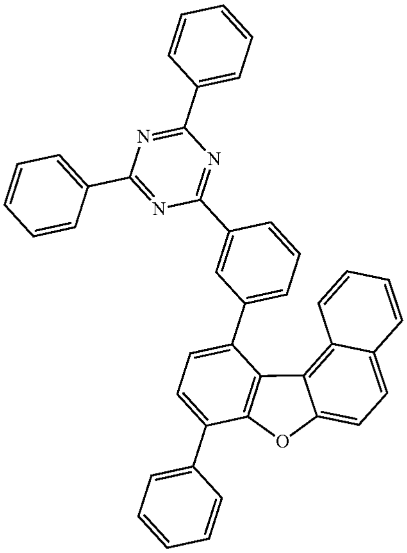
-continued
2-145
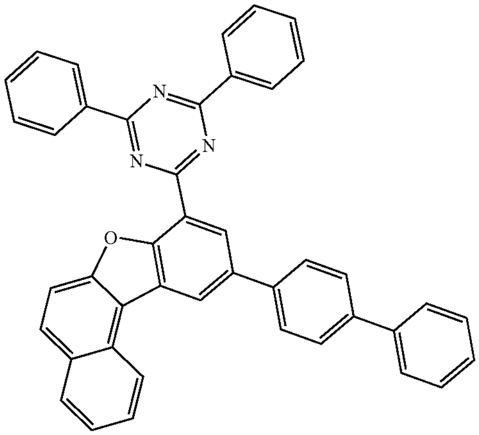
2-146
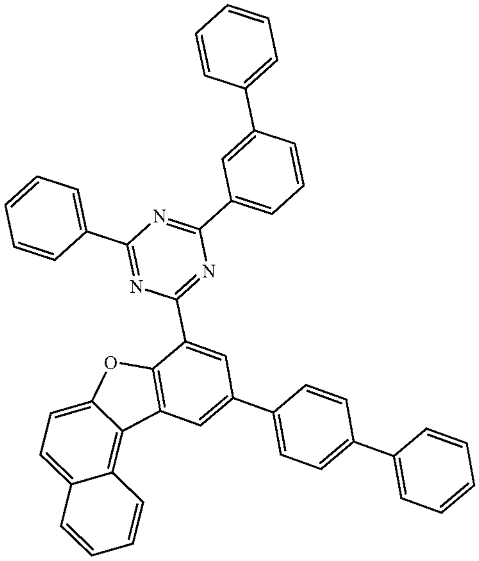
2-147
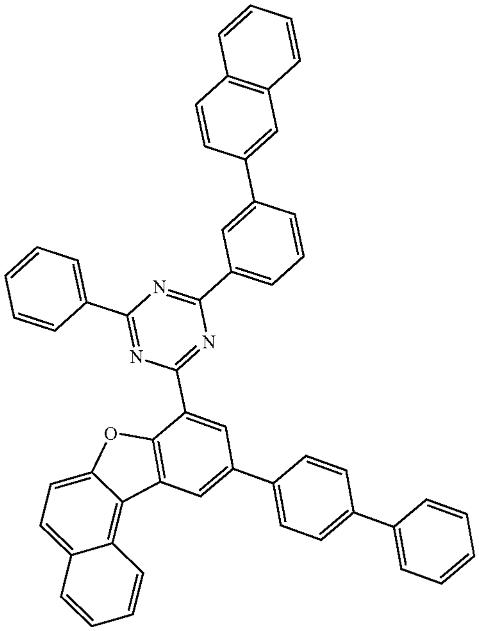

-continued
2-148
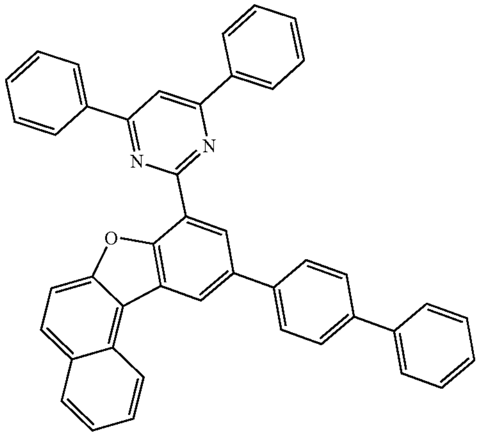
2-149
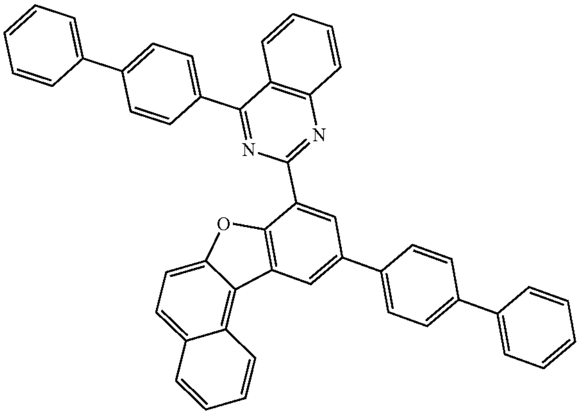
2-150
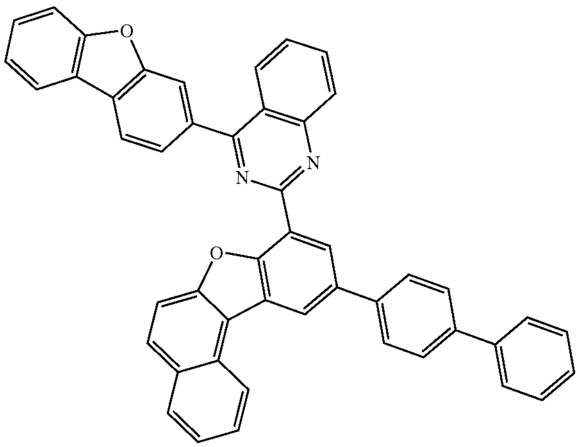
-continued
2-151
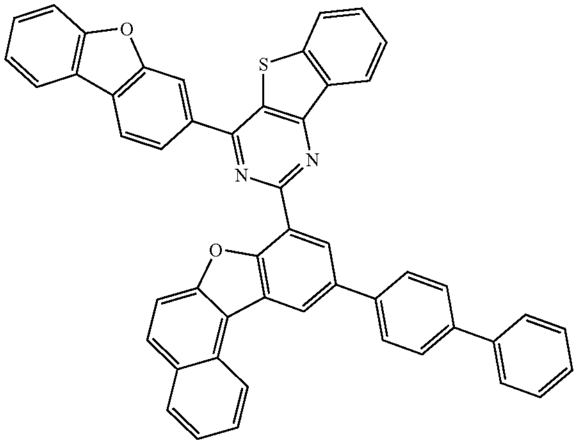
2-152
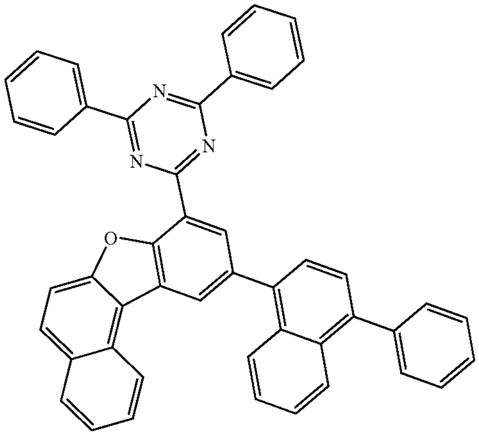
2-153
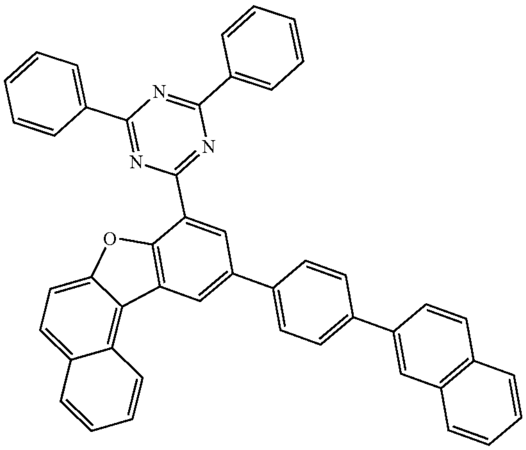

-continued
2-154
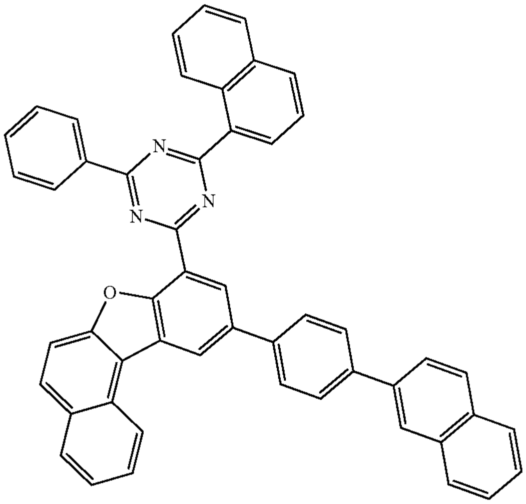
2-155
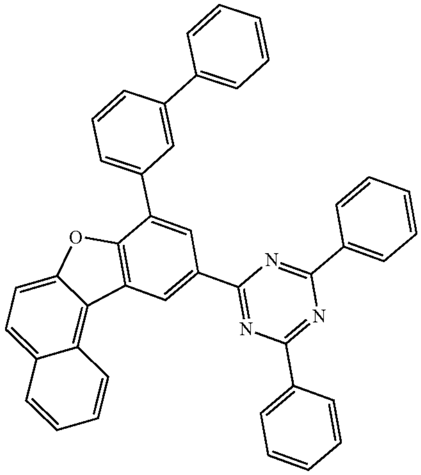
2-156
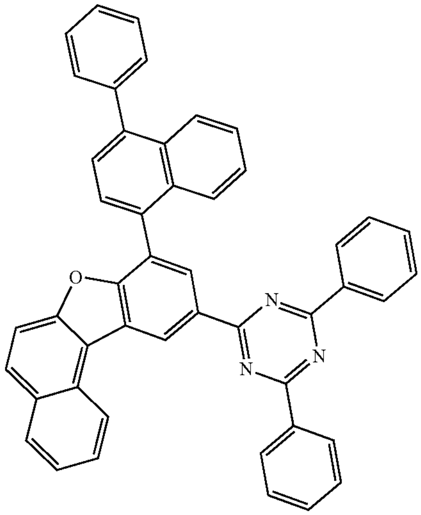
-continued
2-157
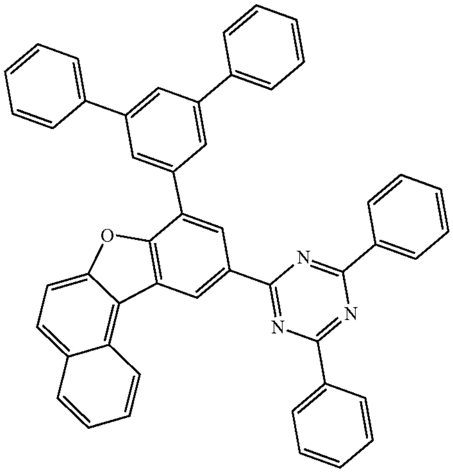
2-158
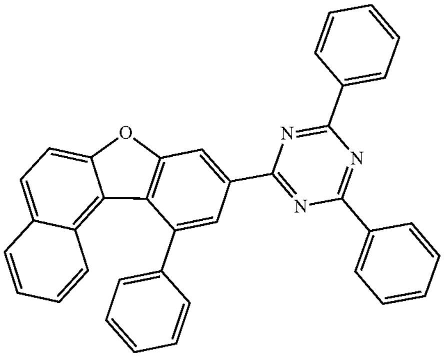
2-159
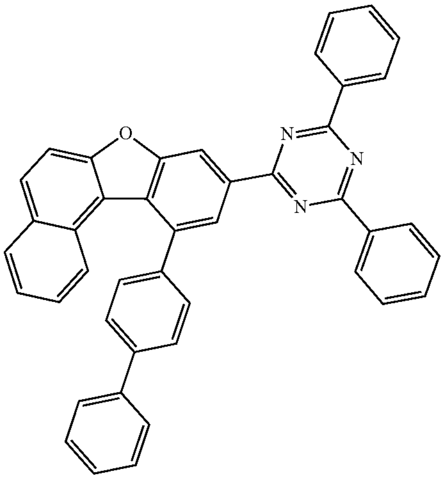

-continued
2-160
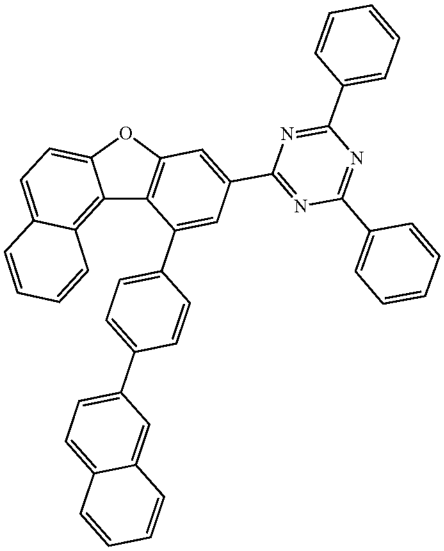
2-161
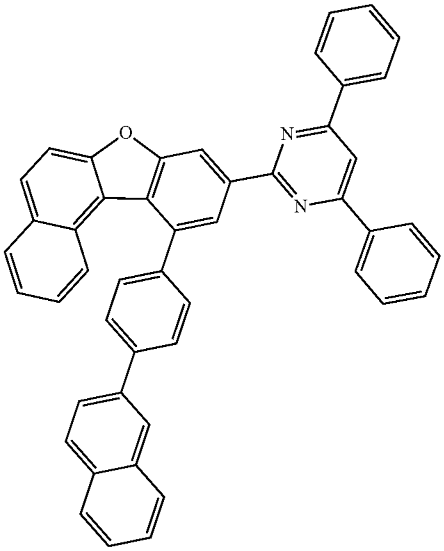
2-162
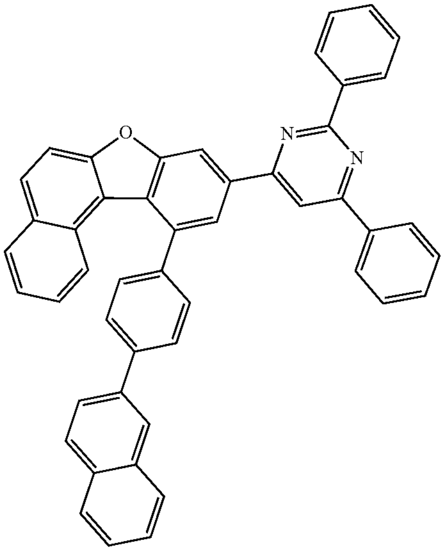
-continued
2-163
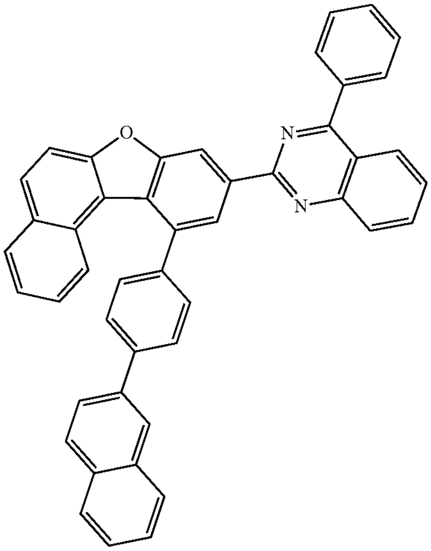
2-164
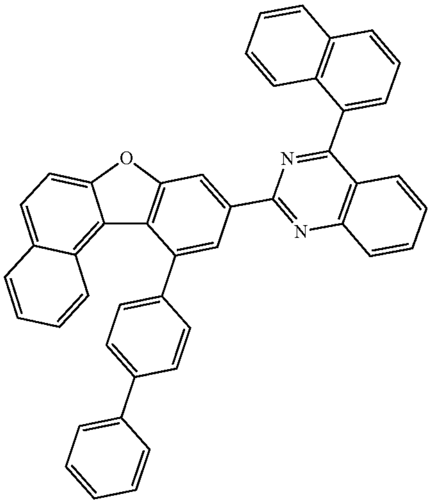
2-165
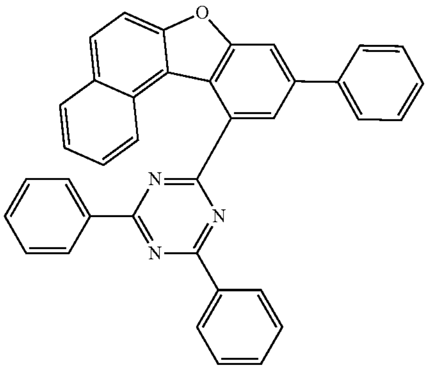

-continued
2-166
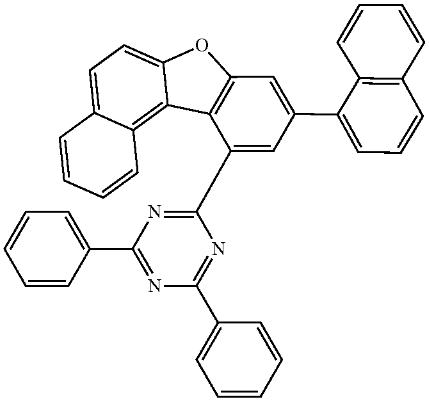
2-167
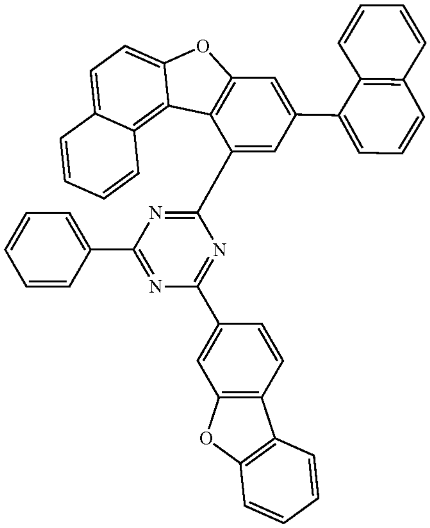
2-168
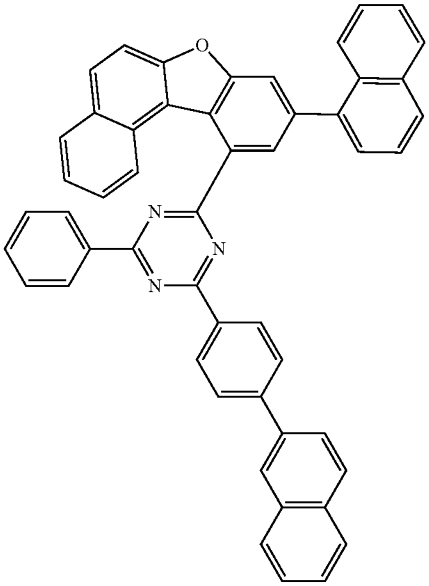
-continued
2-169
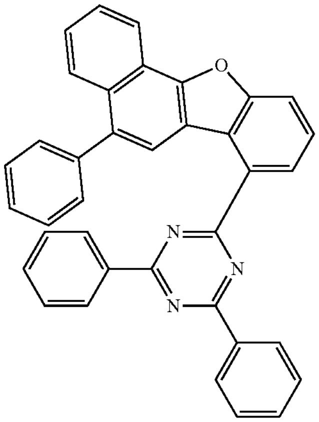
2-170
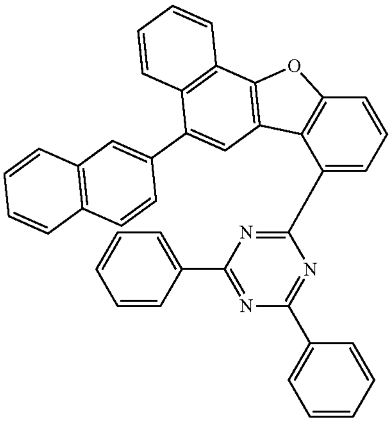
2-171
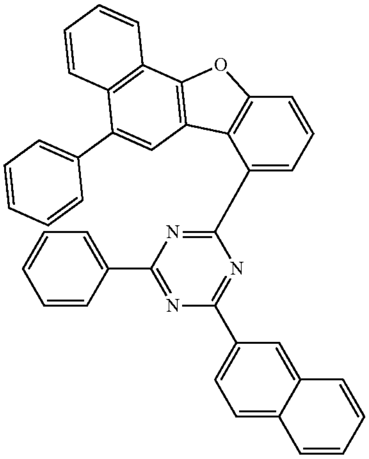

-continued
2-172
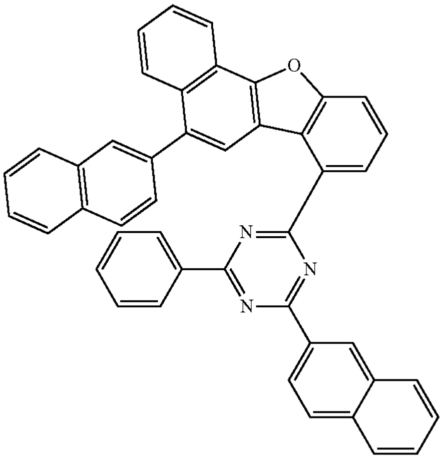
2-173
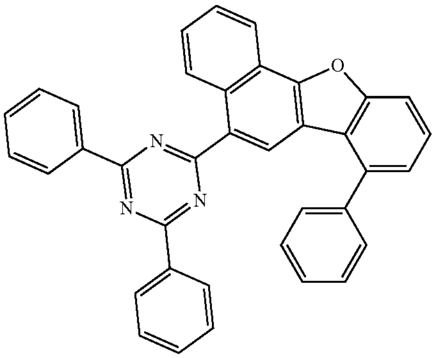
2-174
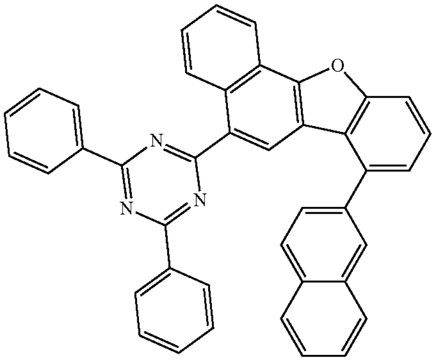
2-175
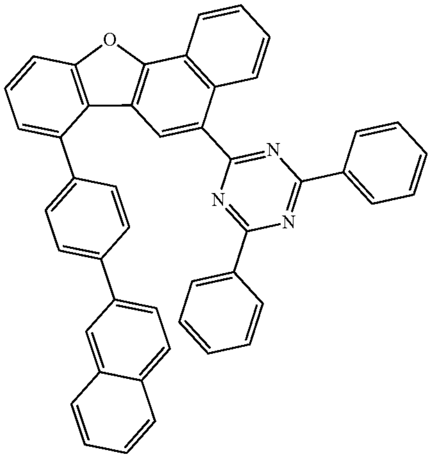
-continued
2-176
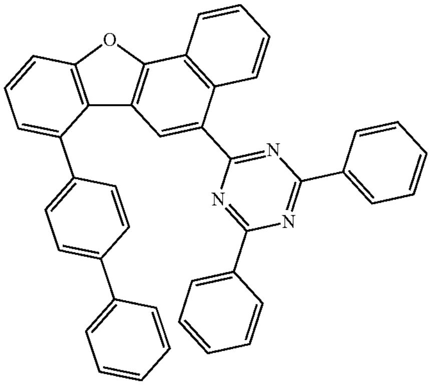
2-177
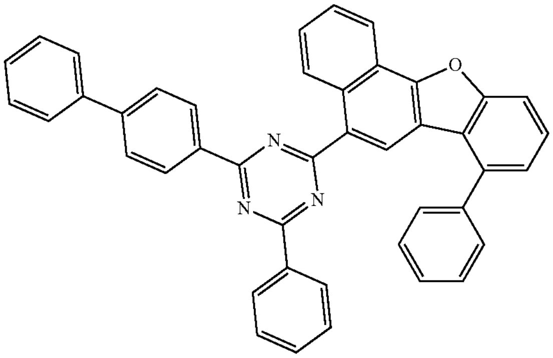
2-178
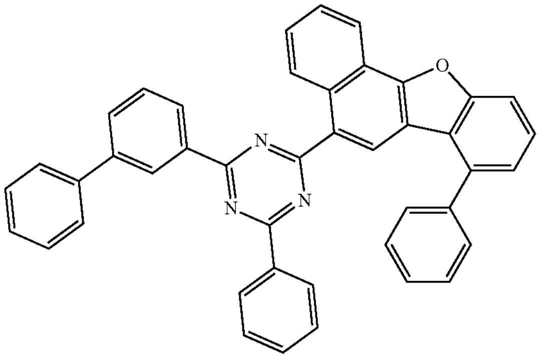
2-179
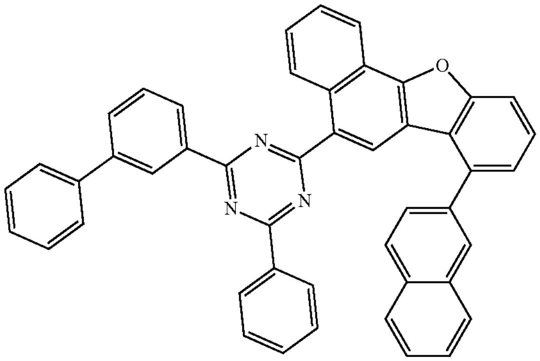

-continued
2-180
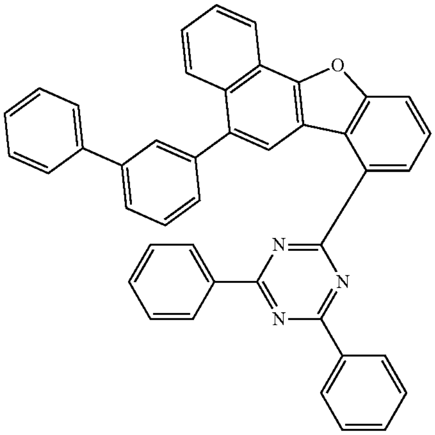
2-181
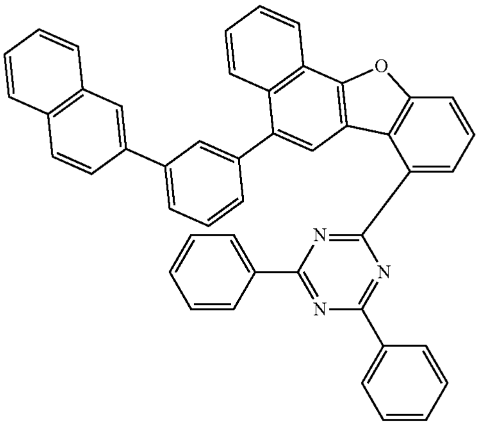
2-182
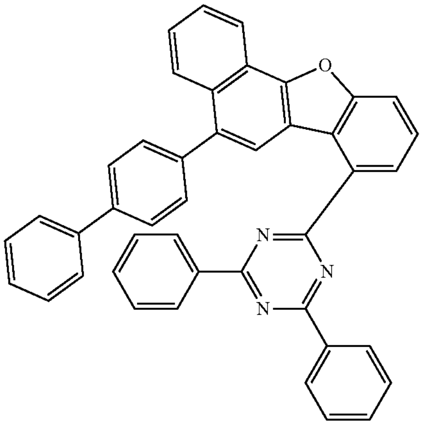
-continued
2-183
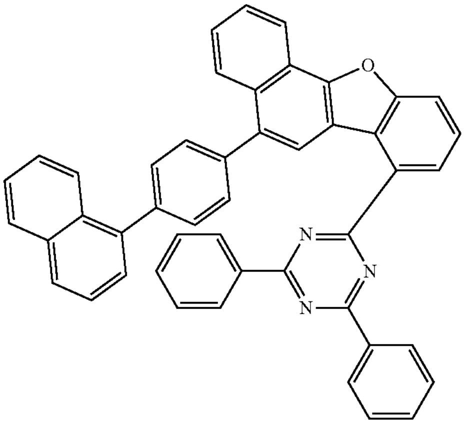
2-184
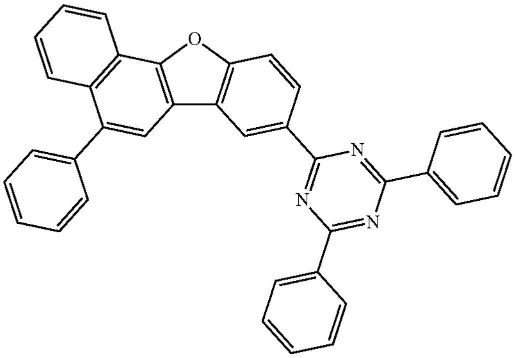
2-185
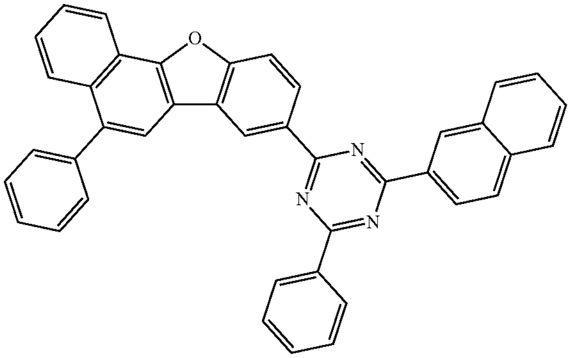
2-186
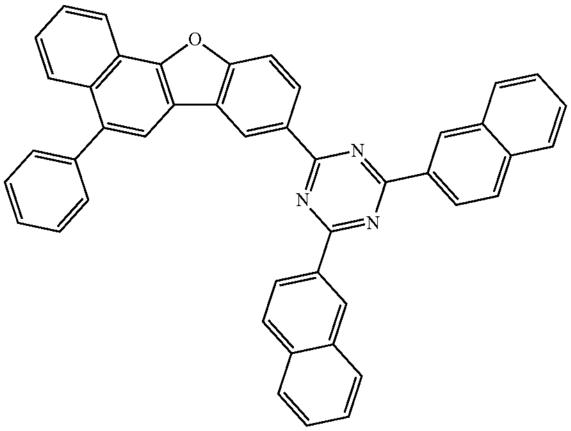

-continued
2-187
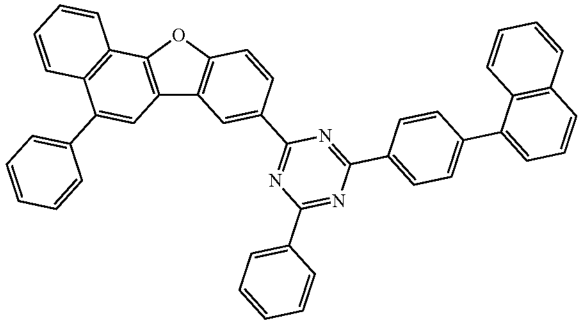
2-188
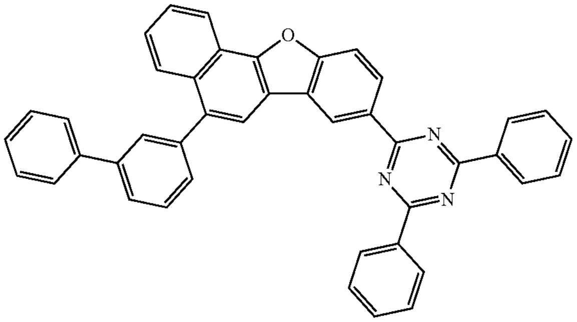
2-189
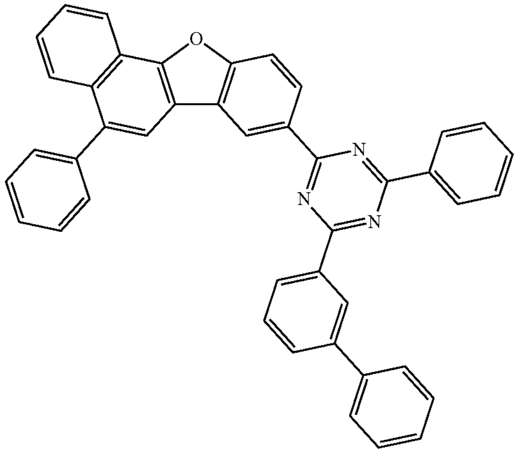
2-190
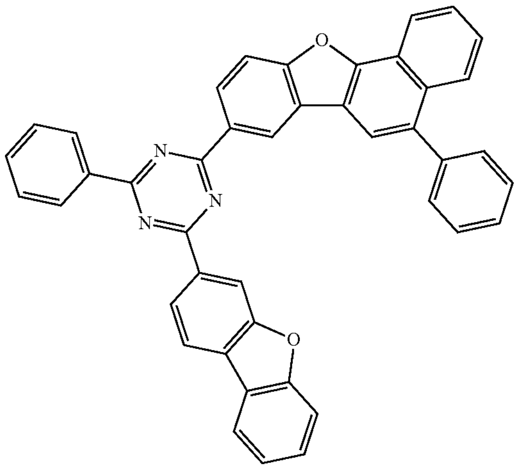
-continued
2-191
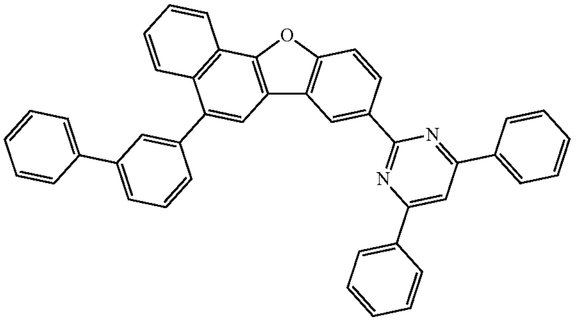
2-192
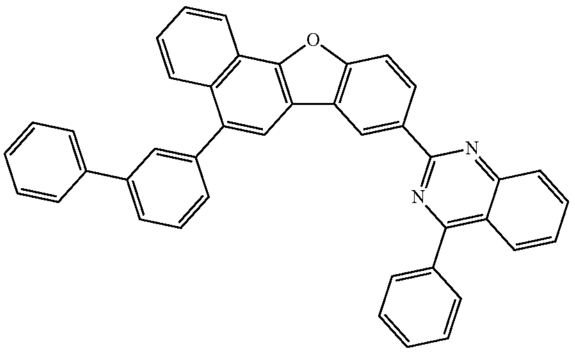
2-193
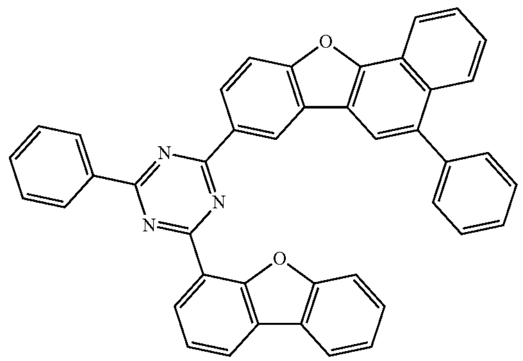
2-194
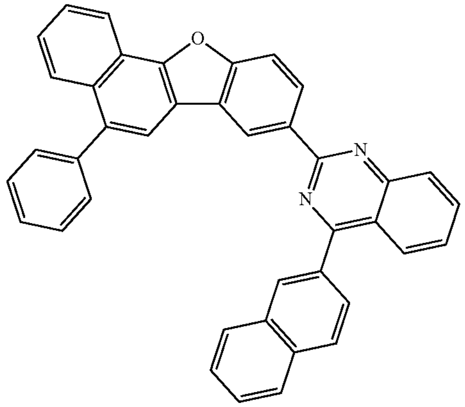

-continued
2-195
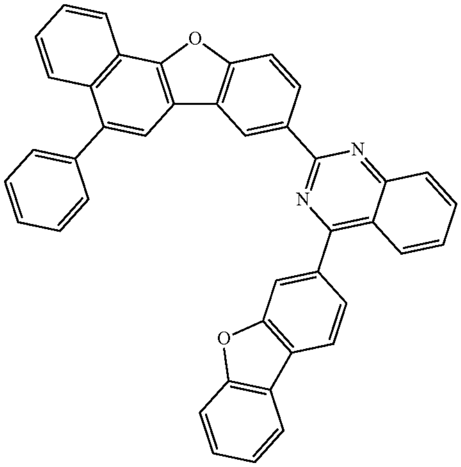
2-196
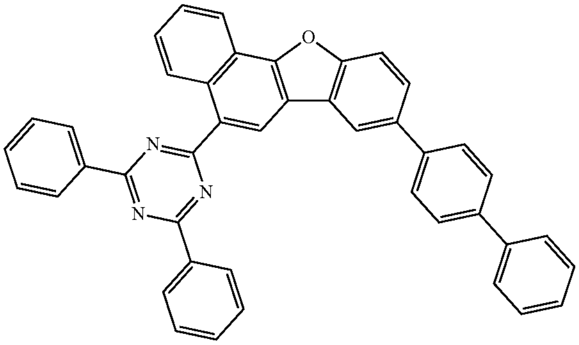
2-197
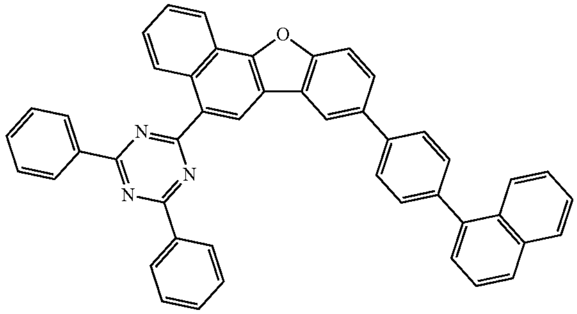
2-198
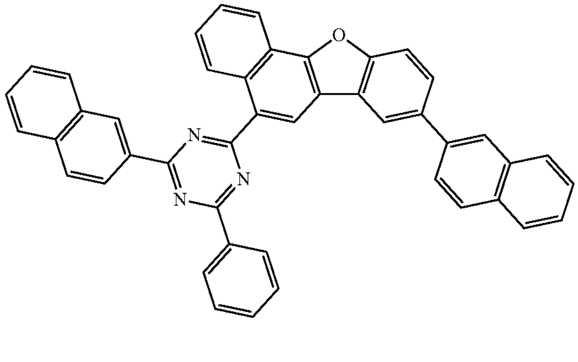
-continued
2-199
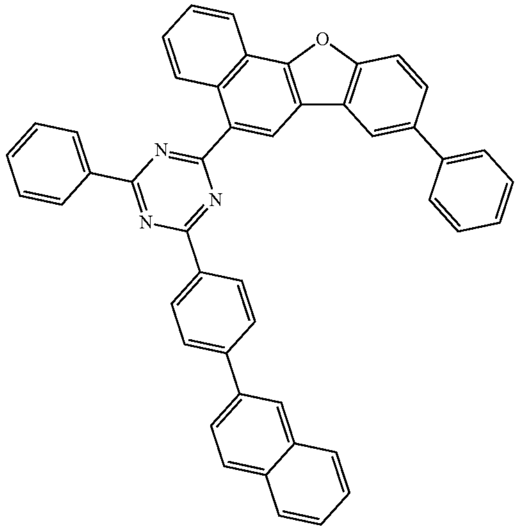
2-200
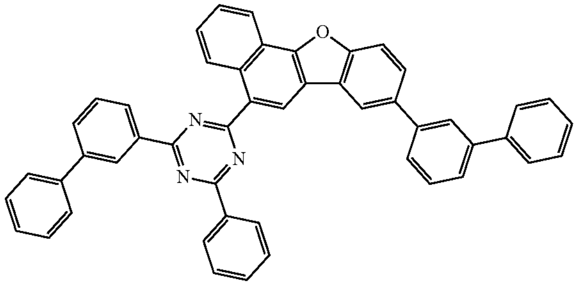
2-201
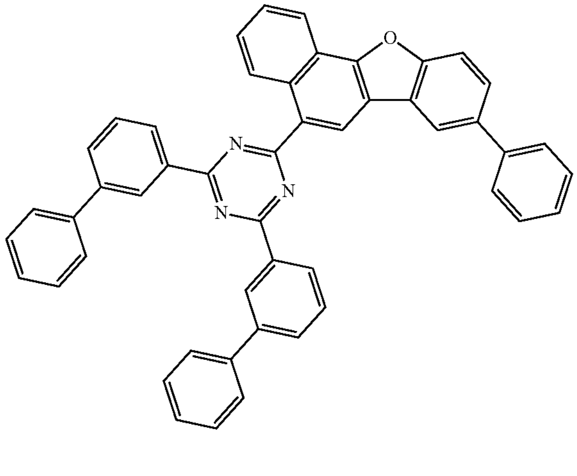

-continued
2-202
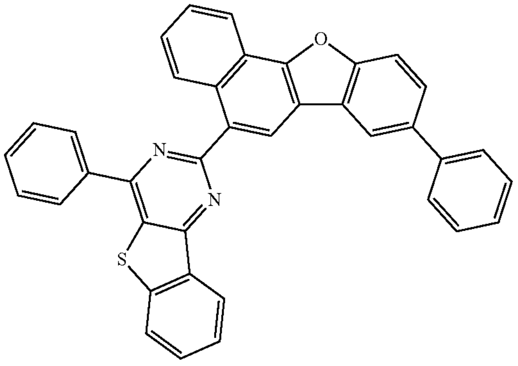
2-203
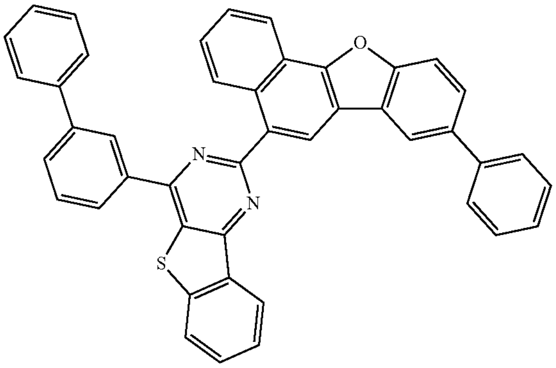
2-204
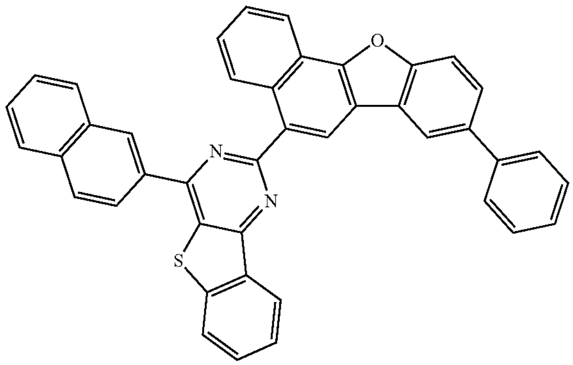
2-205
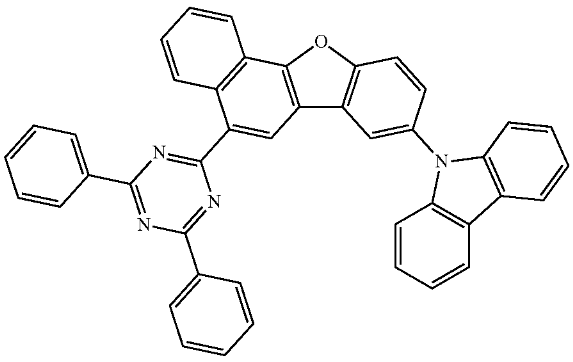
-continued
2-206
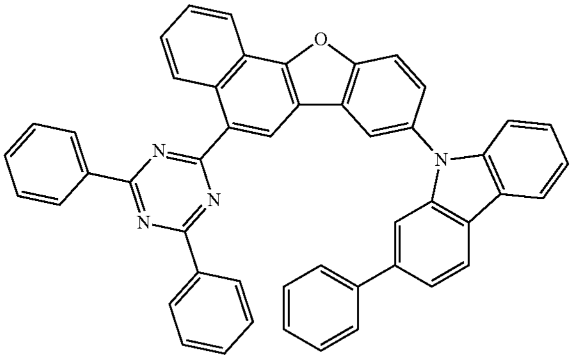
2-207
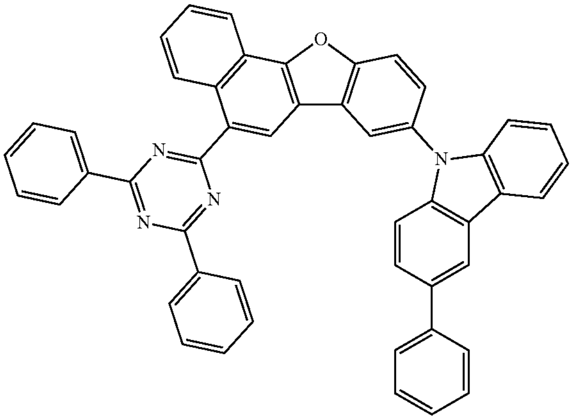
2-208
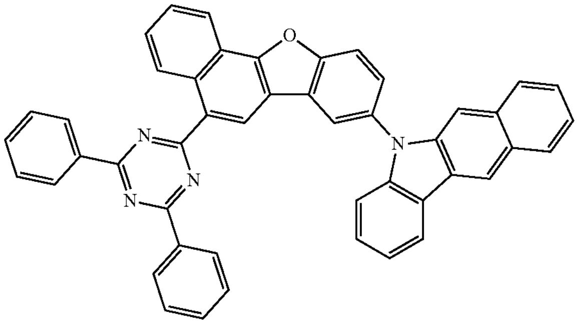
2-209
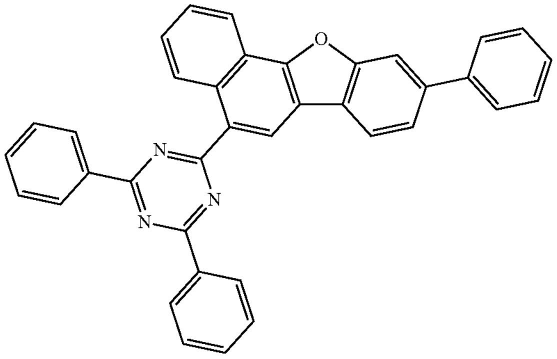

-continued
2-210
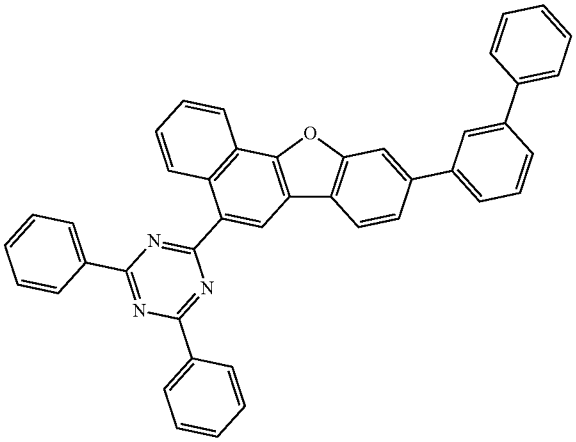
2-211
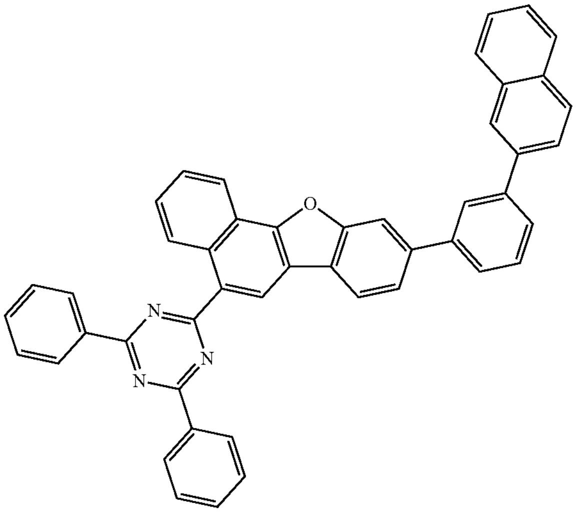
2-212
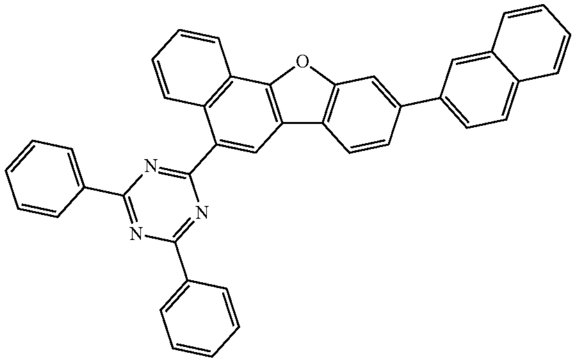
-continued
2-213
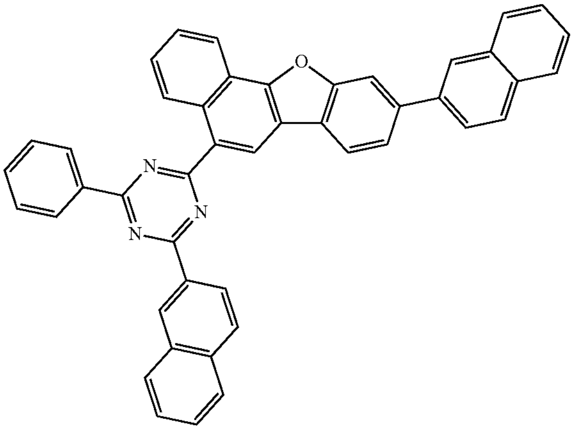
2-214
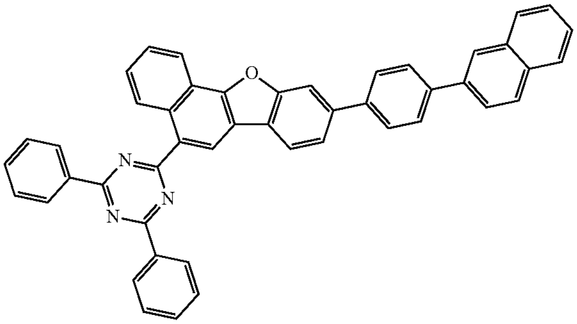
2-215
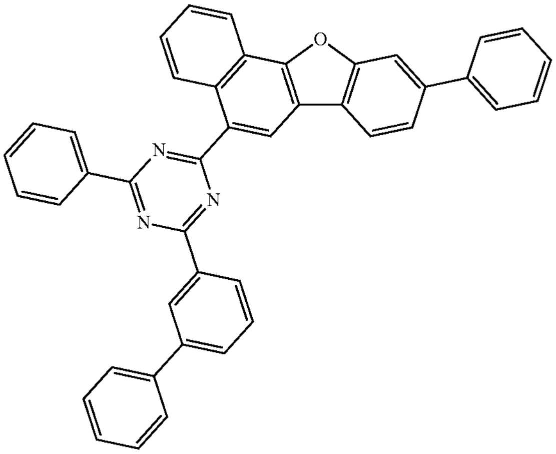
2-216
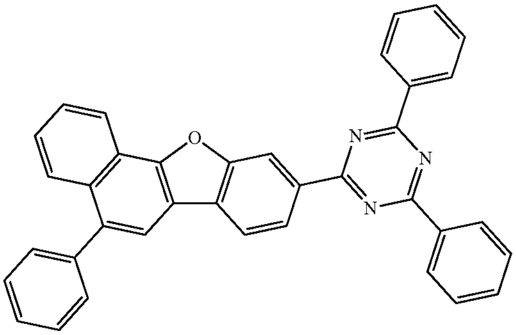

-continued
2-217
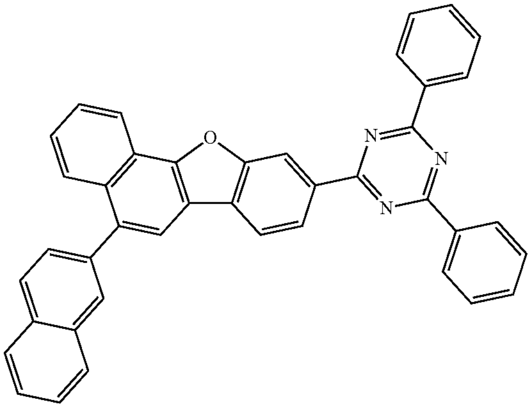
2-218
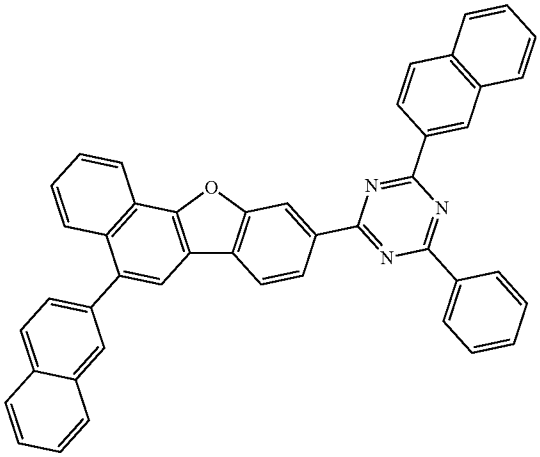
2-219
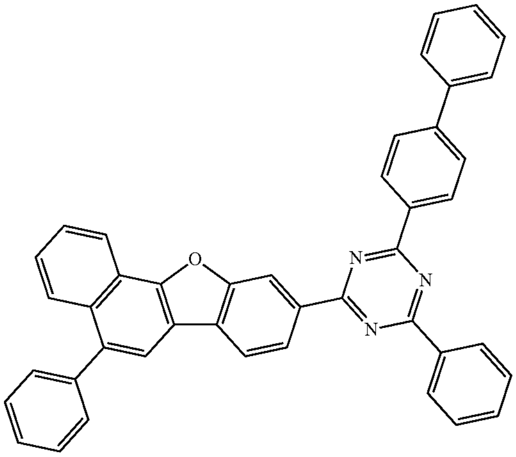
-continued
2-220
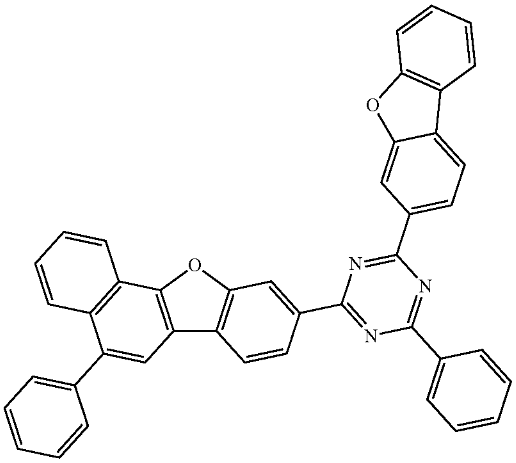
2-221
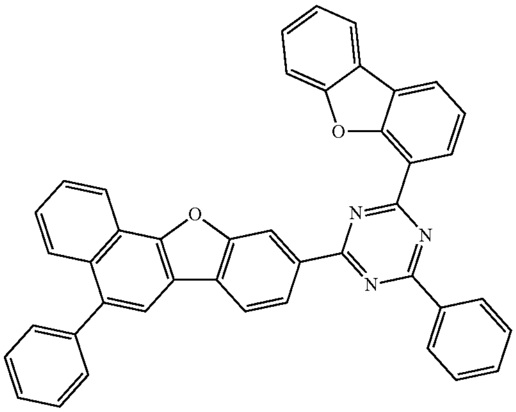
2-222
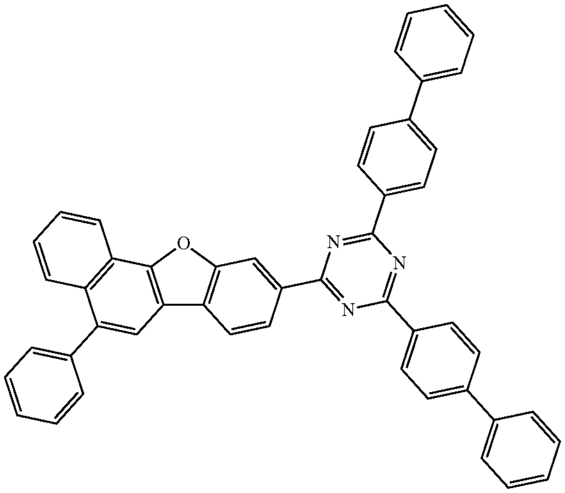

-continued
2-223
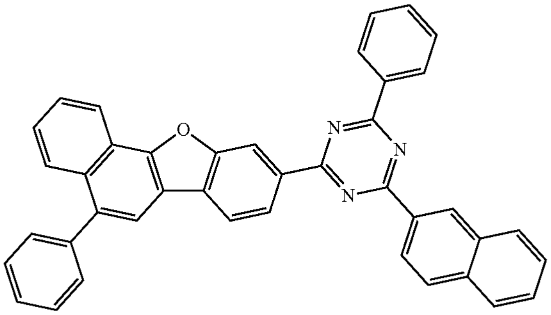
2-224
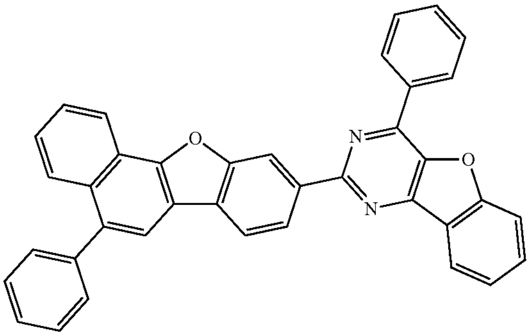
2-225
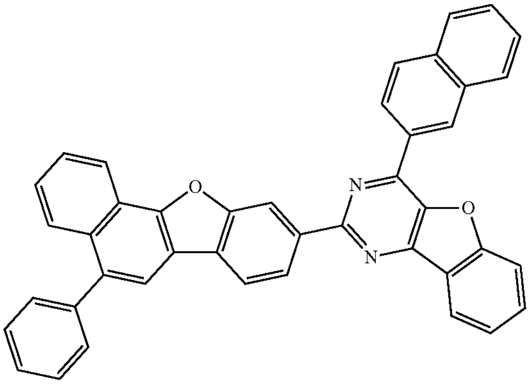
2-226
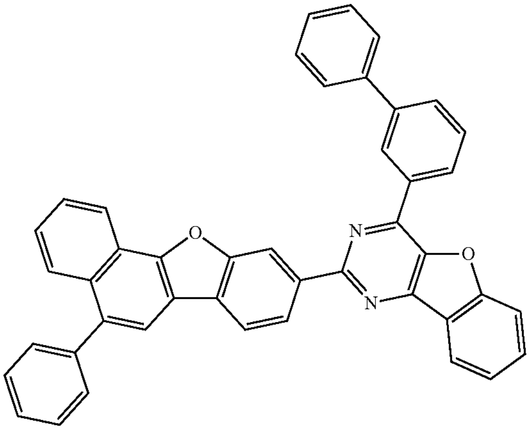
-continued
2-227
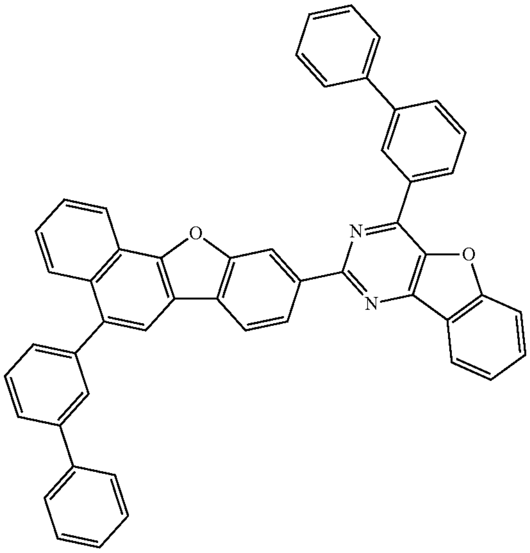
2-228
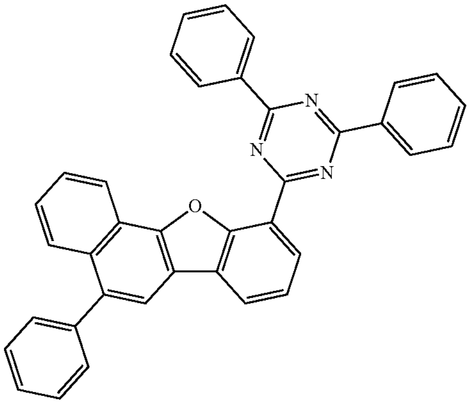
2-229
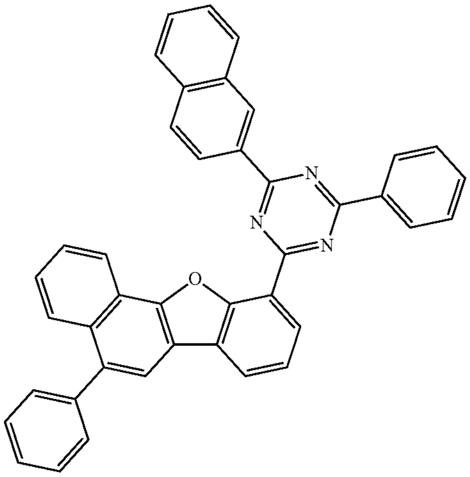

-continued
2-230
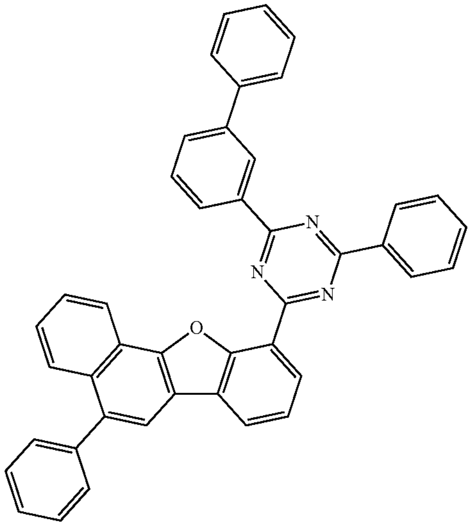
2-231
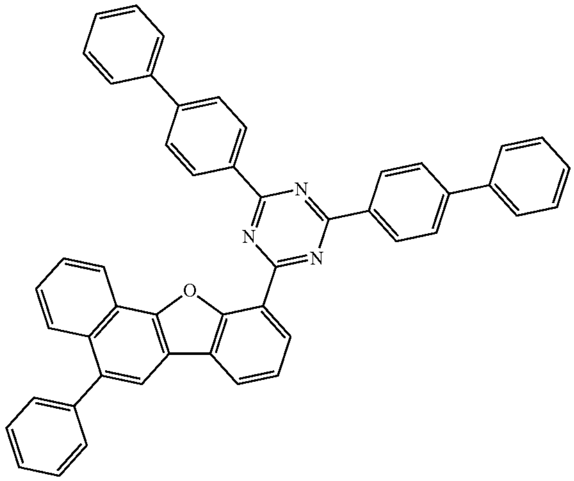
2-232
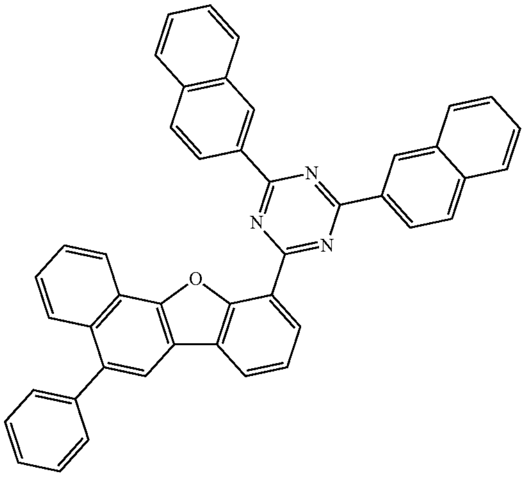
-continued
2-233
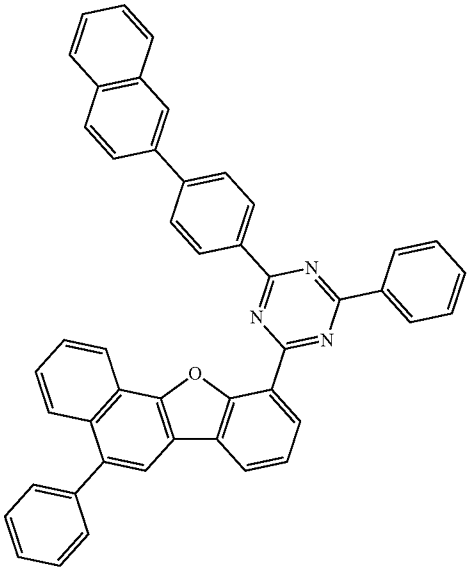
2-234
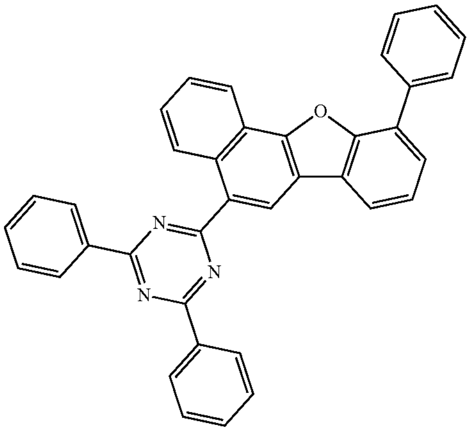
2-235
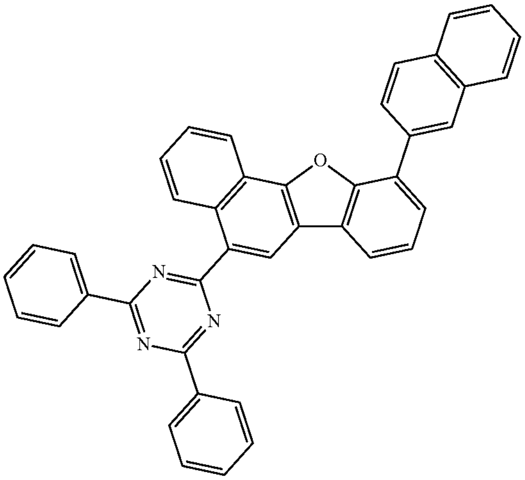

-continued
2-236
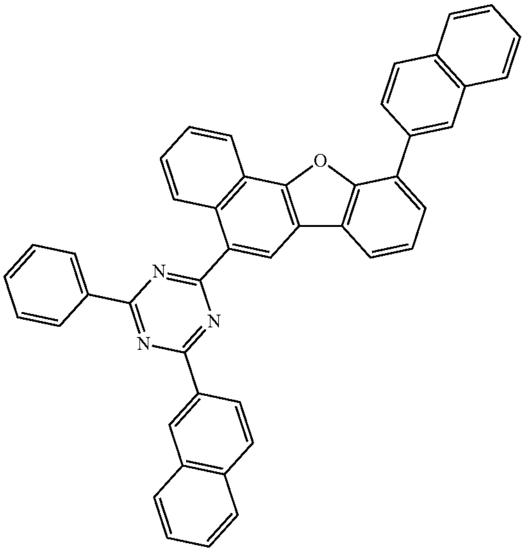
2-237
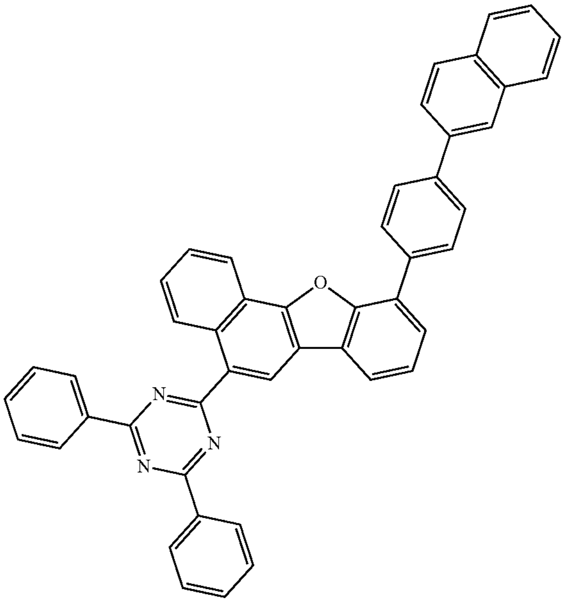
-continued
2-238
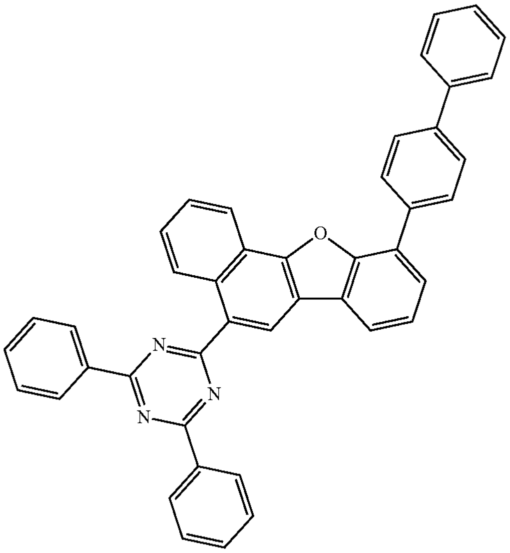
2-239
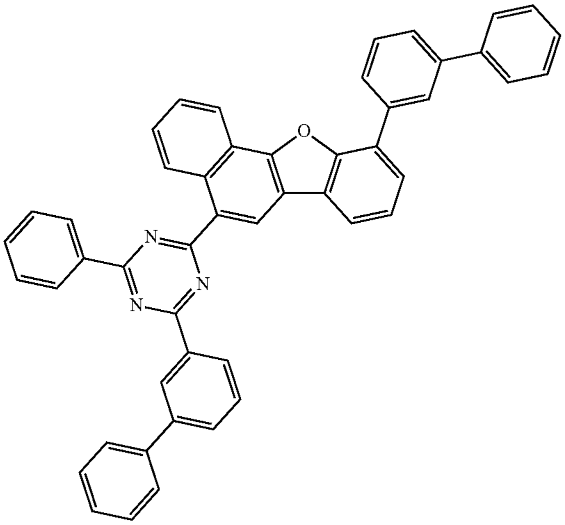
2-240
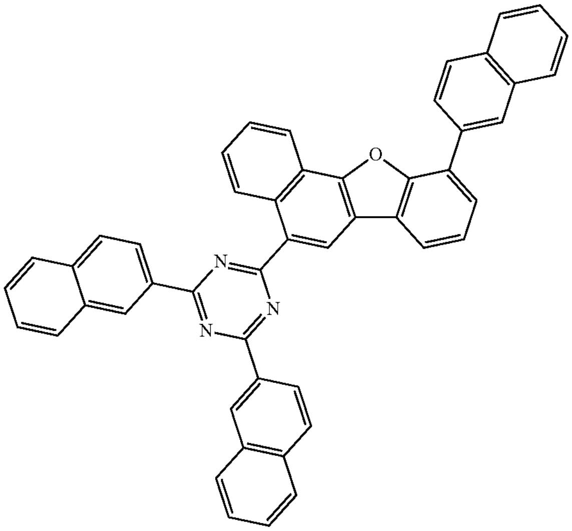

-continued
2-241
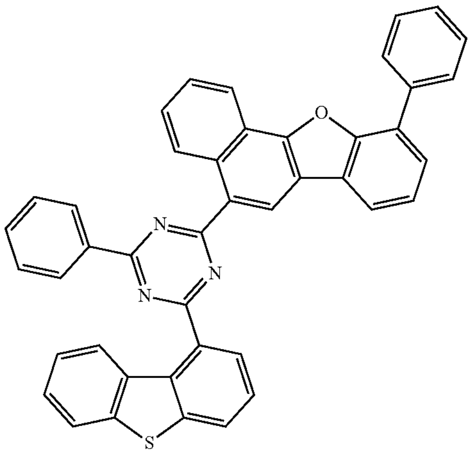
2-242
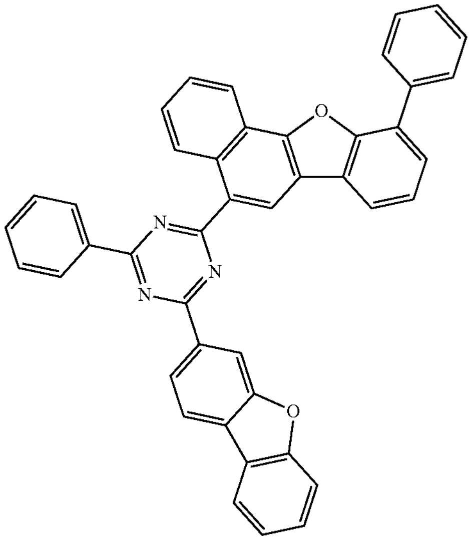
2-243
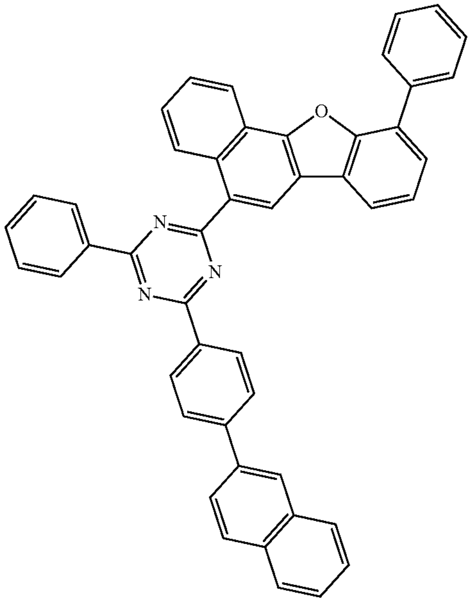
-continued
2-244
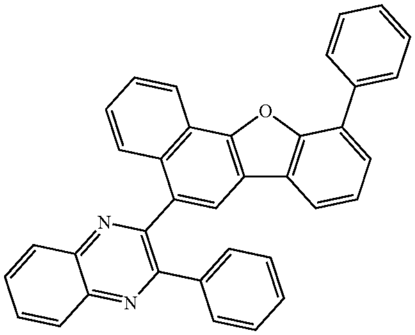
2-245
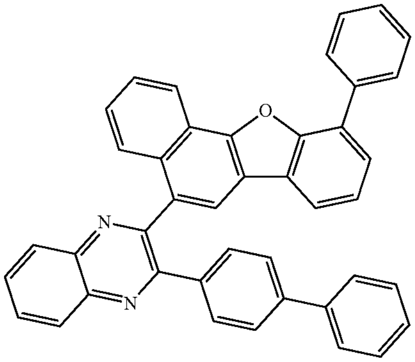
2-246
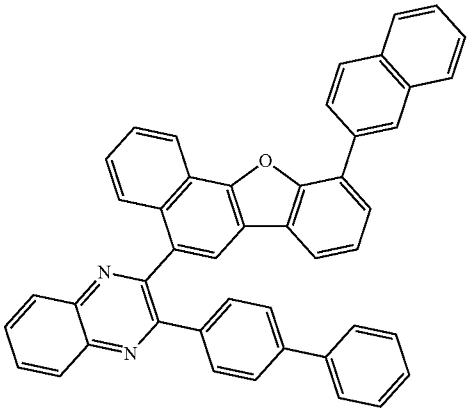
2-247
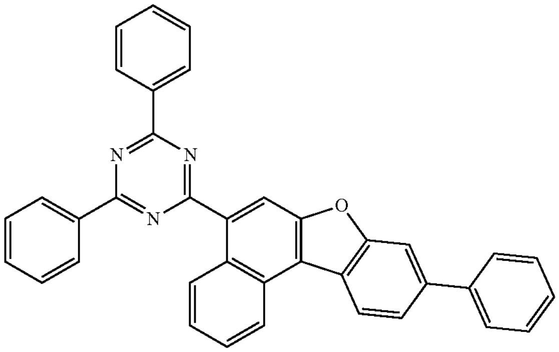

-continued
2-248
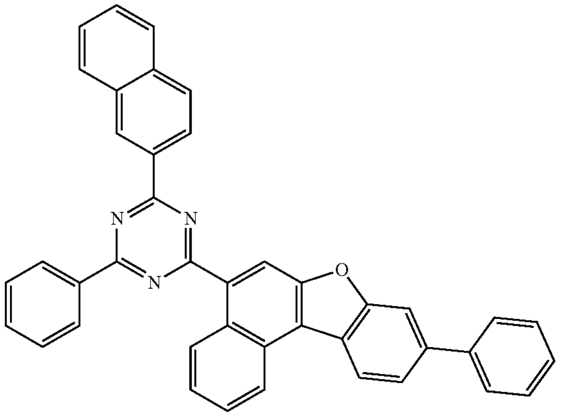
2-249
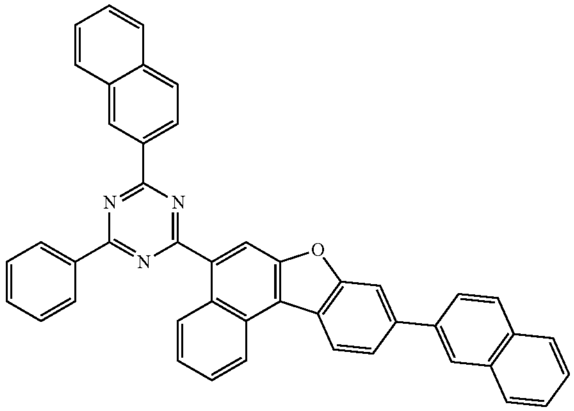
2-250
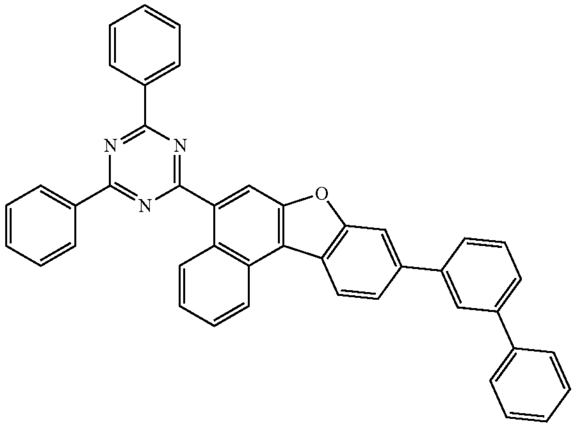
2-251
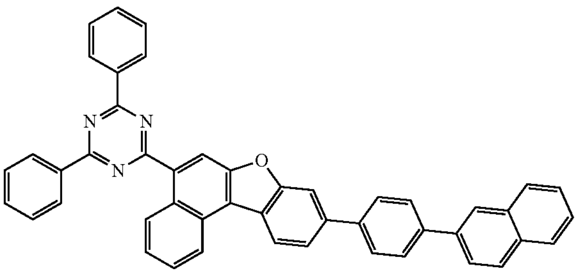
-continued
2-252
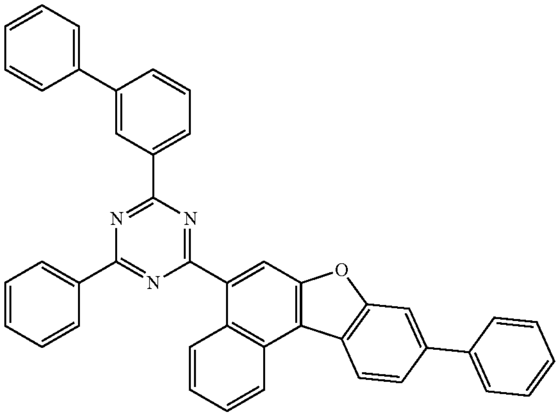
2-253
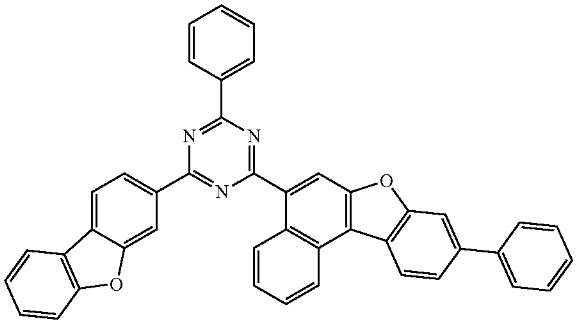
2-254
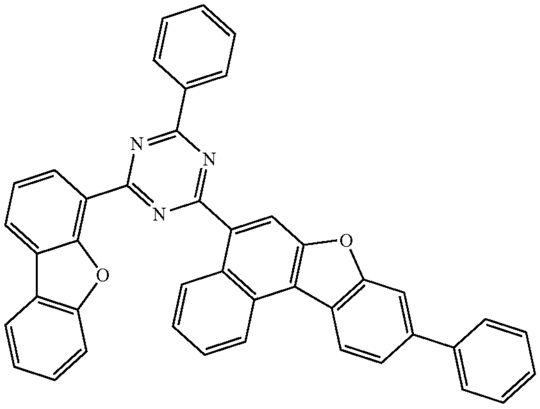

-continued
2-255
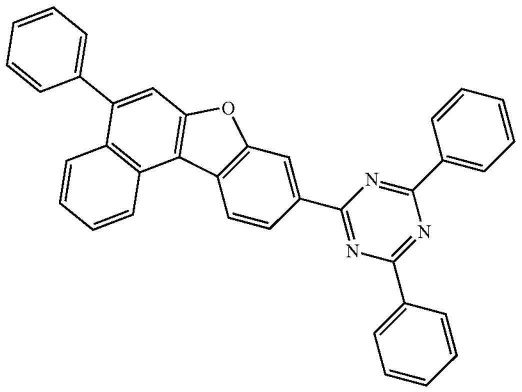
2-256
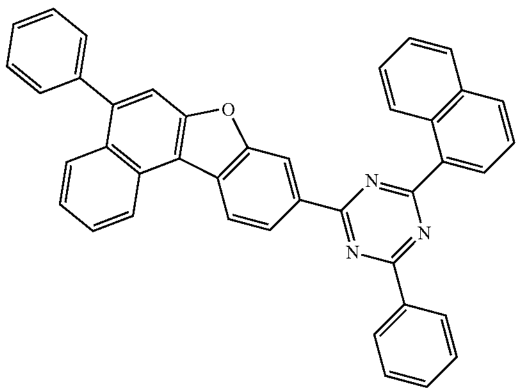
2-257
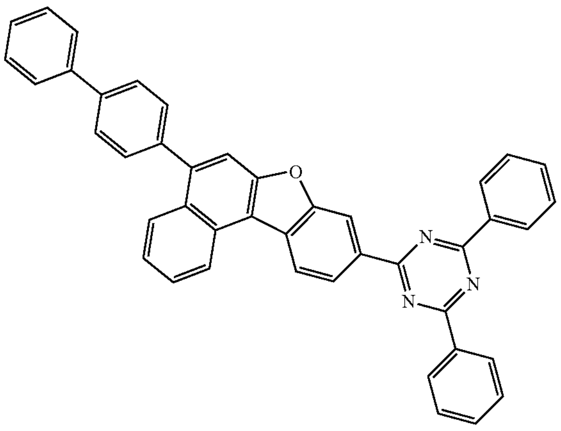
2-258
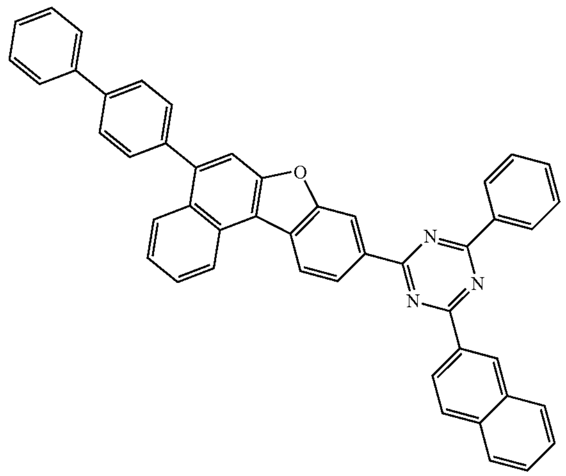
2-259
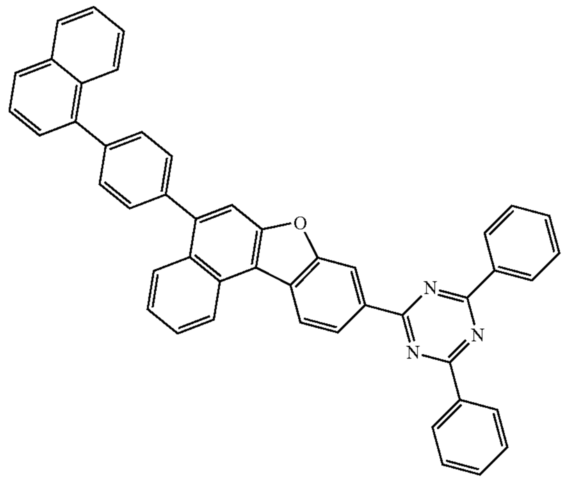
2-260
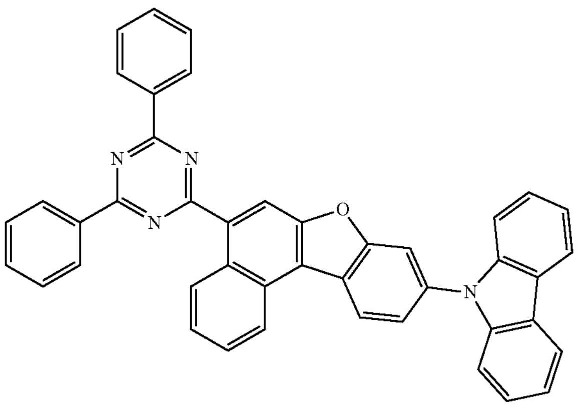

-continued
2-261
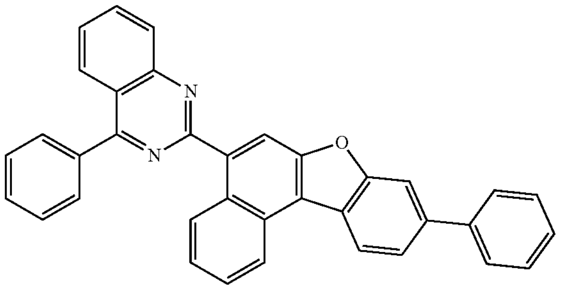
2-262
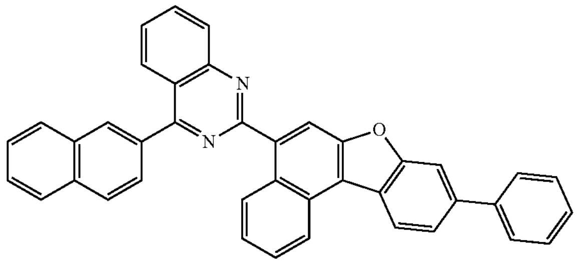
2-263
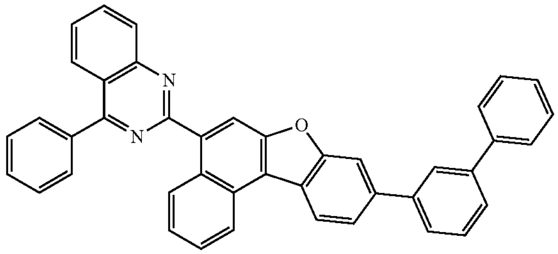
2-264
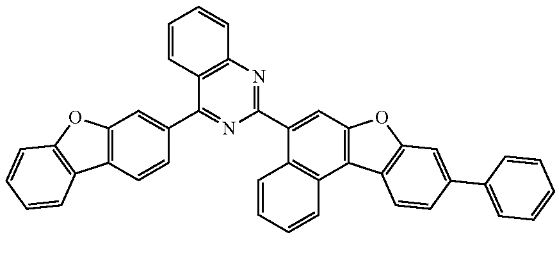
2-265
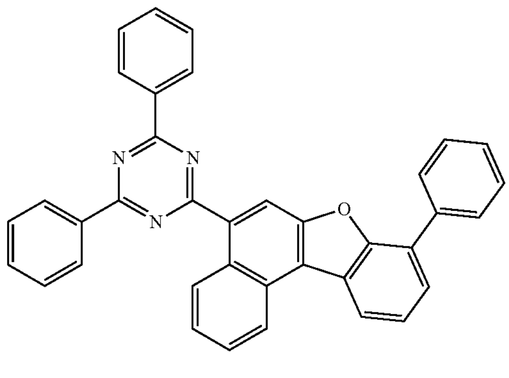
-continued
2-266
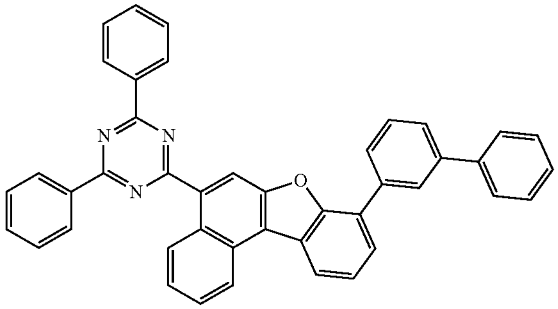
2-267
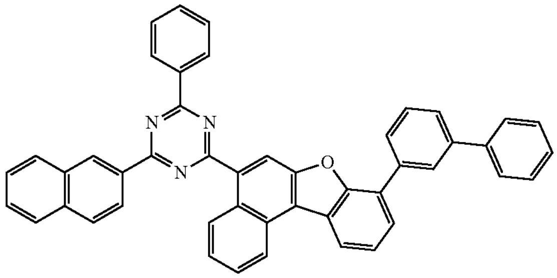
2-268
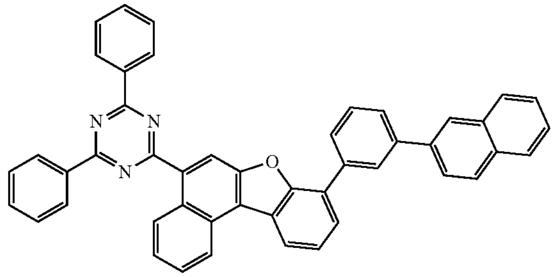
2-269
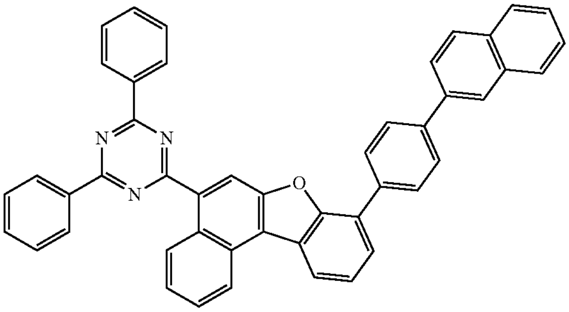
2-270
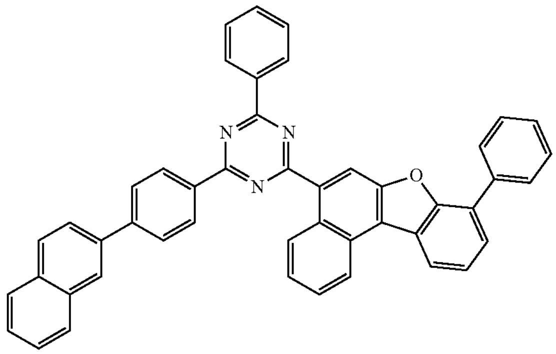

-continued
2-271
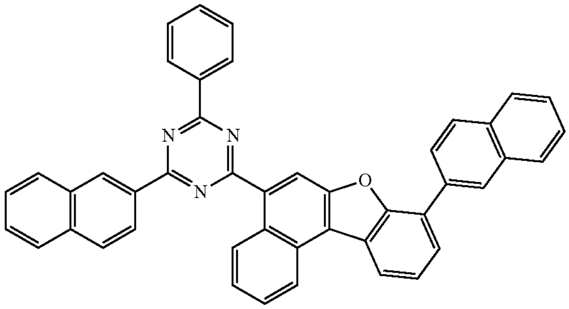
2-272
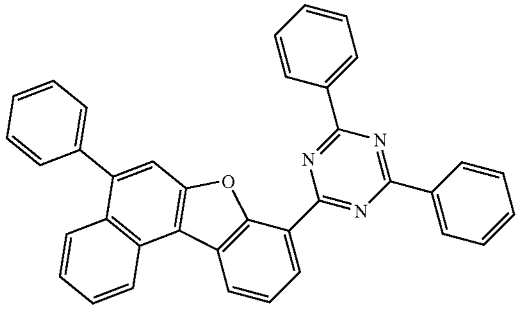
2-273
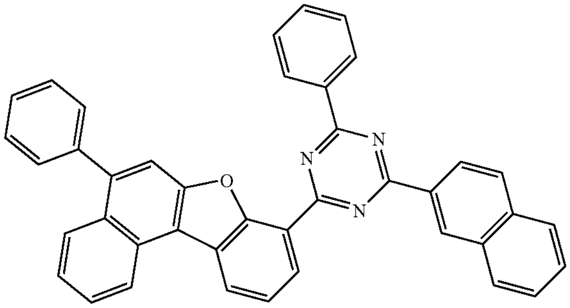
2-274
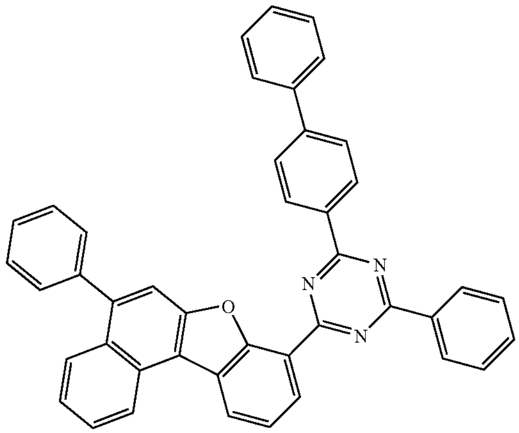
-continued
2-275
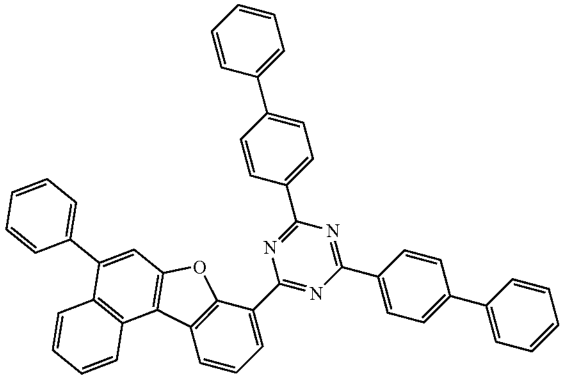
2-276
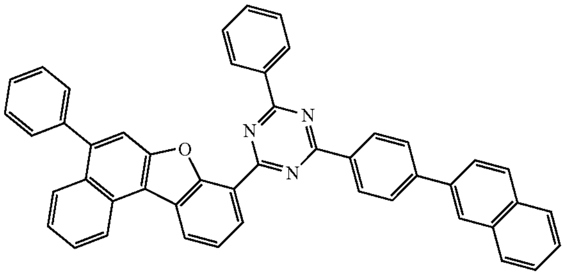
2-277
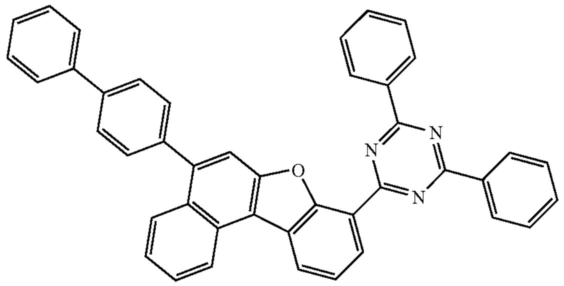
2-278
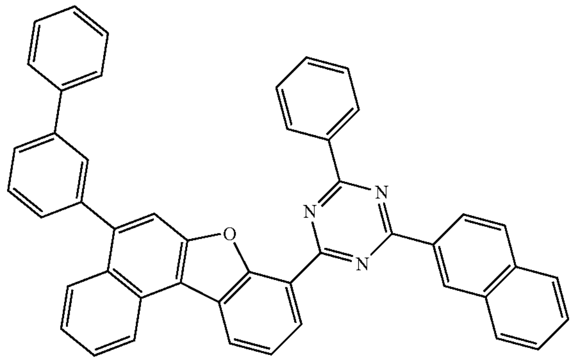

-continued
2-279
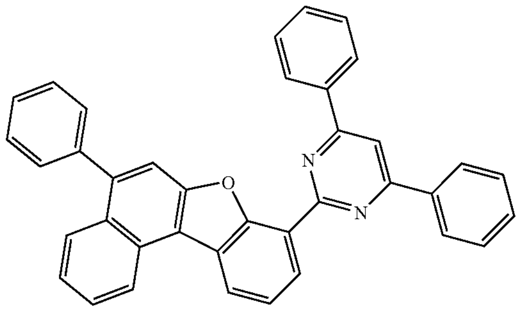
2-280
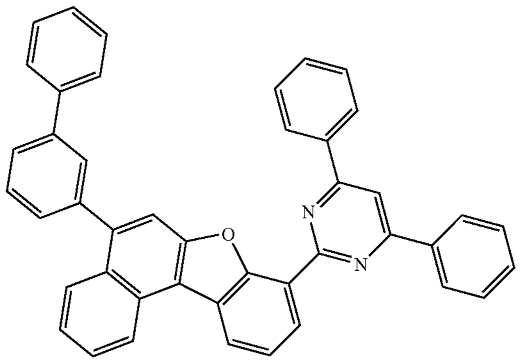
2-281
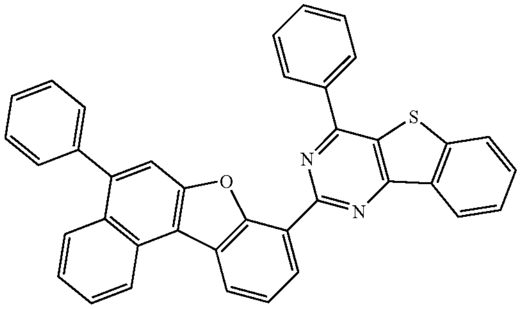
2-282
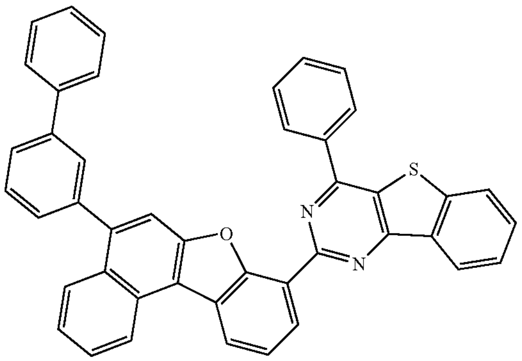
-continued
2-283
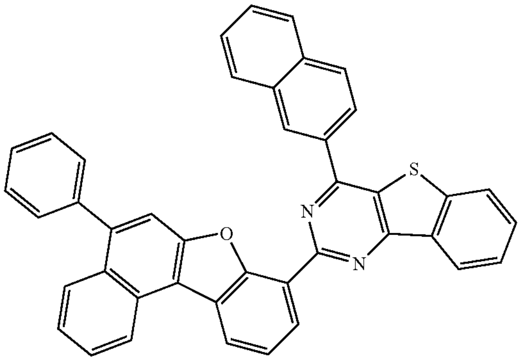
2-284
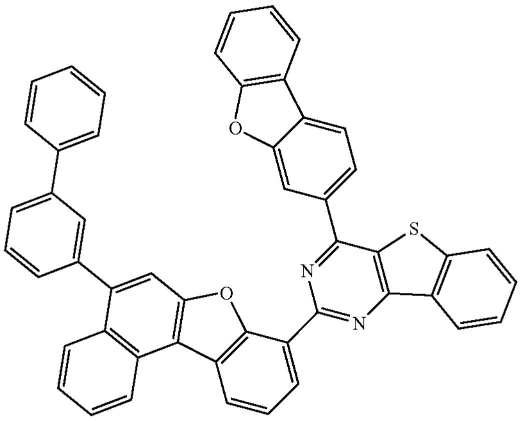
2-285
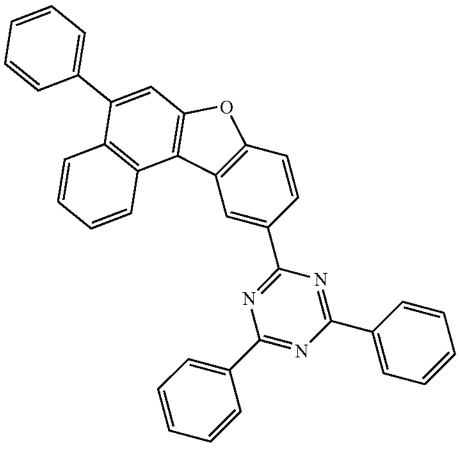

-continued
2-286
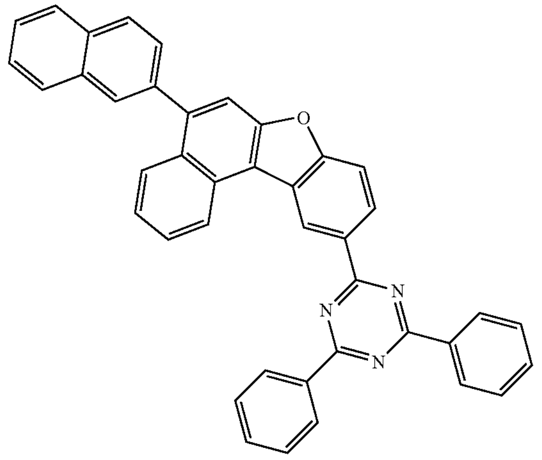
2-287
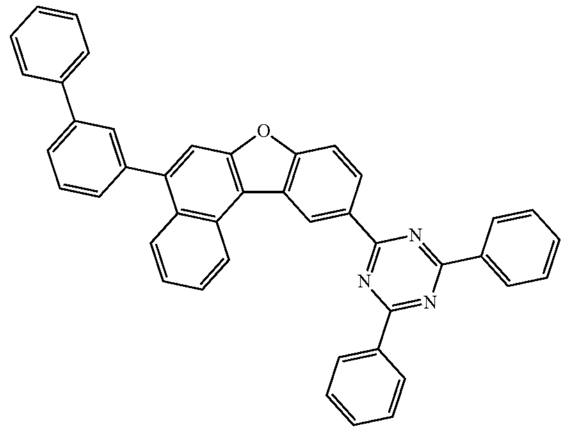
2-288
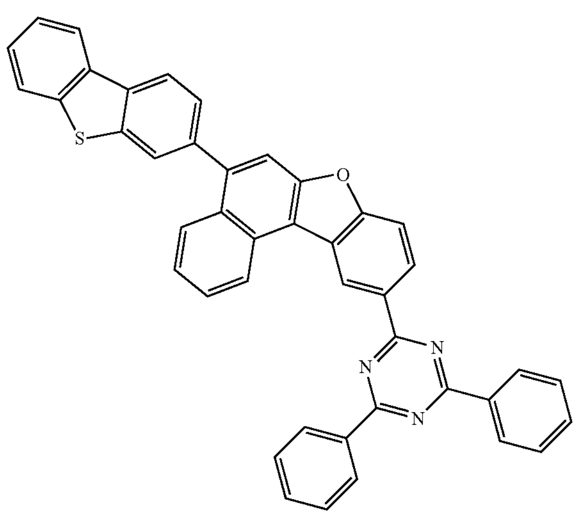
-continued
2-289
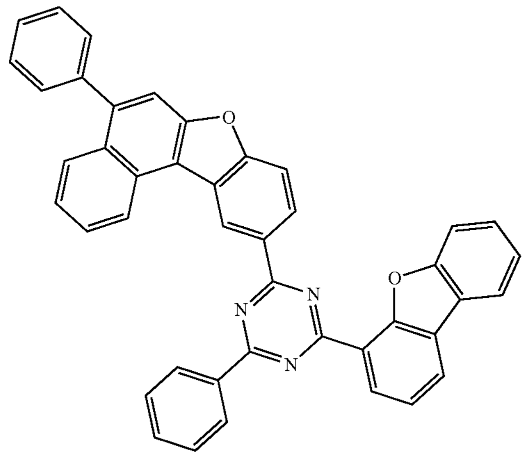
2-290
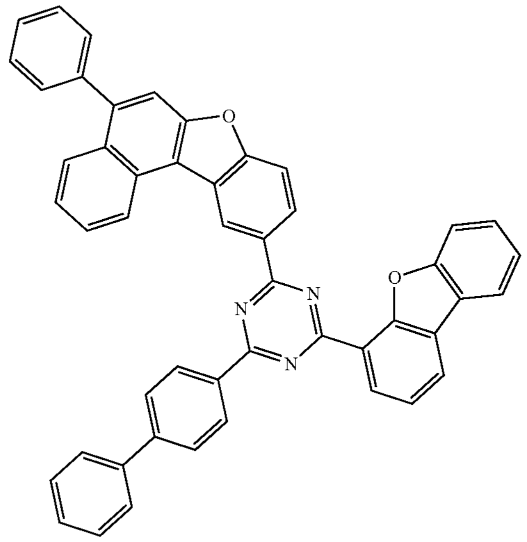
2-291
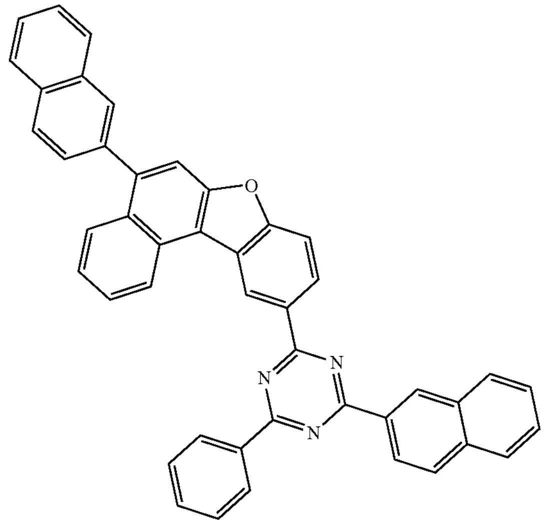

-continued
2-292
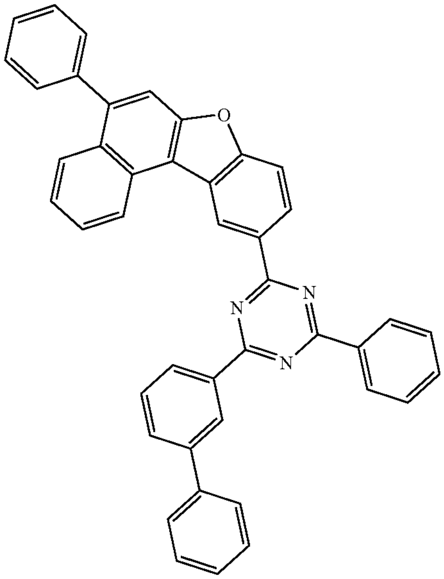
2-293
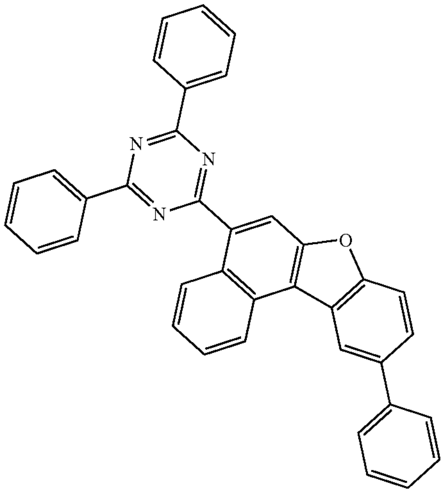
2-294
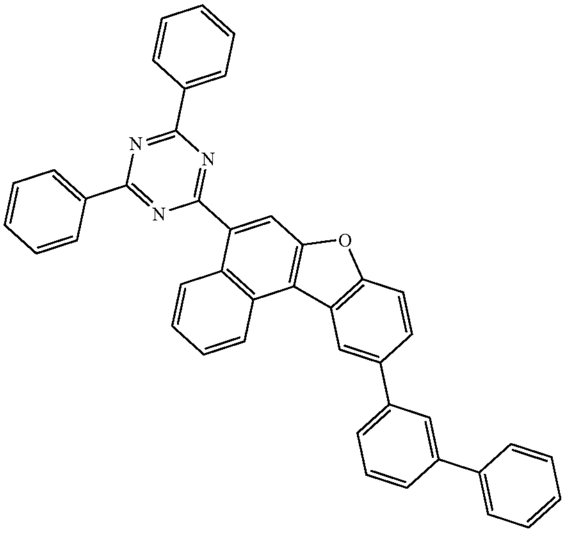
2-295
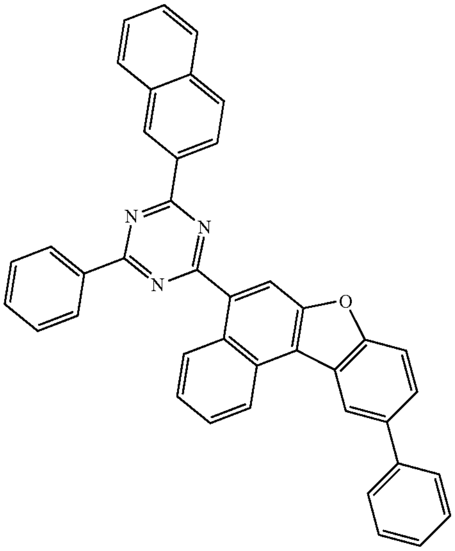
2-296
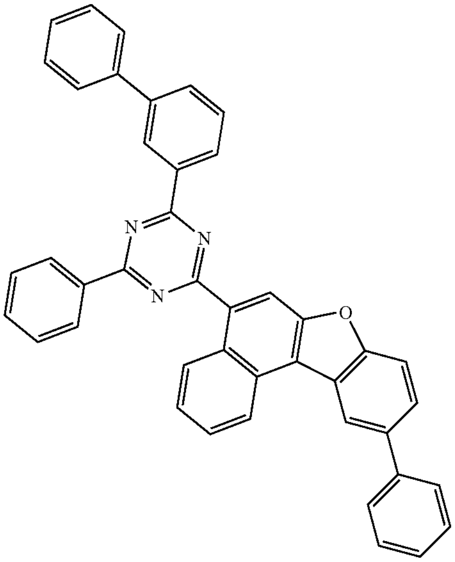

-continued
2-297
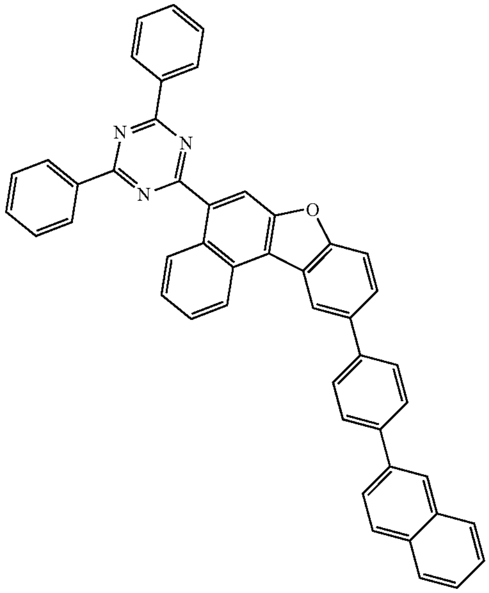
2-298
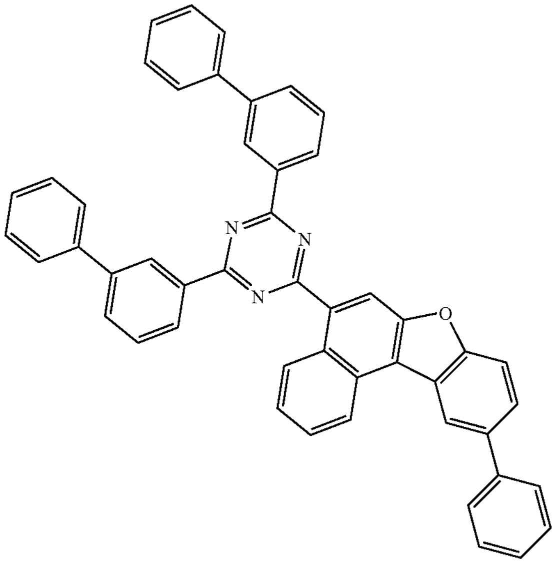
2-299
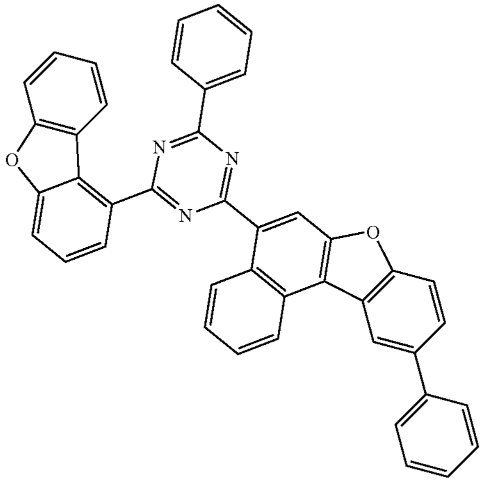
-continued
2-300
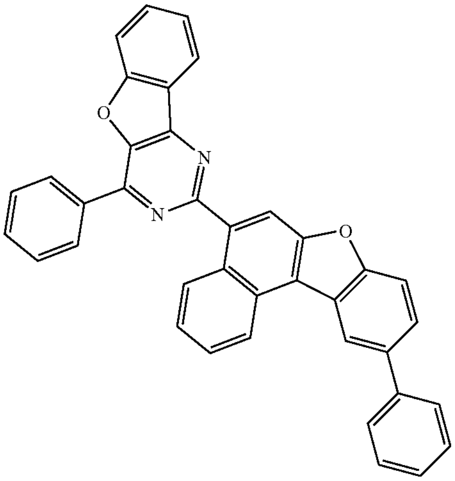
2-301
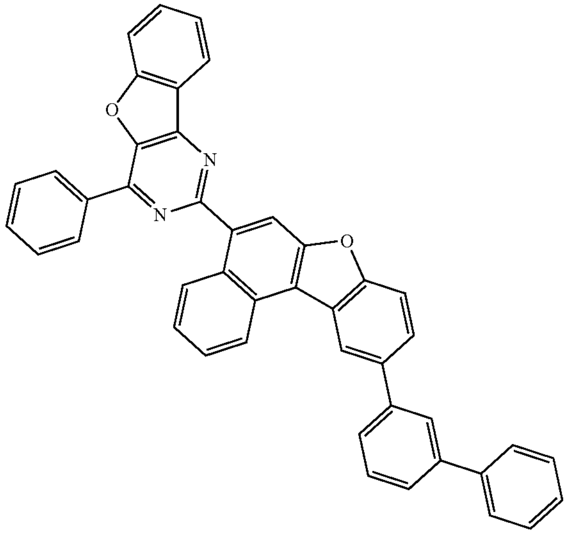
2-302
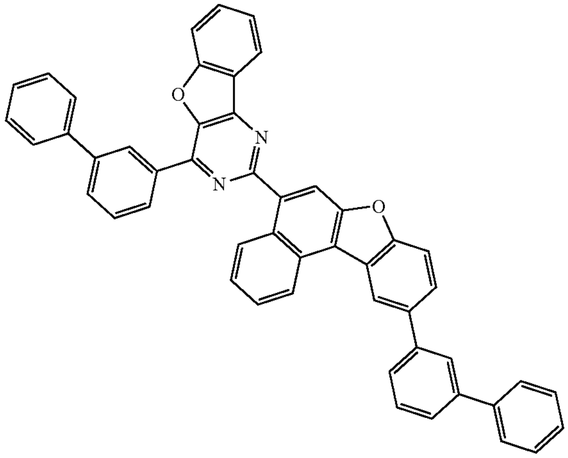

-continued
2-303
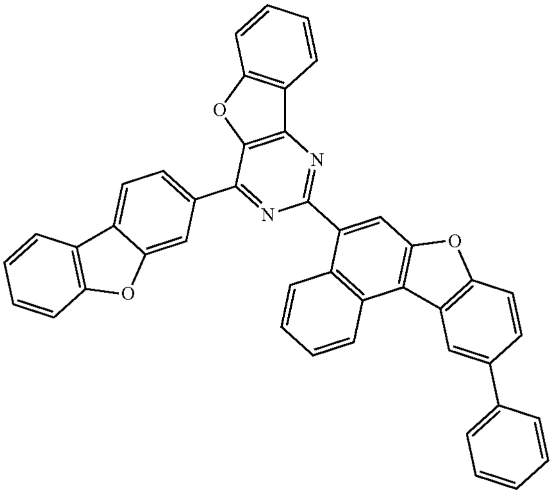
2-304
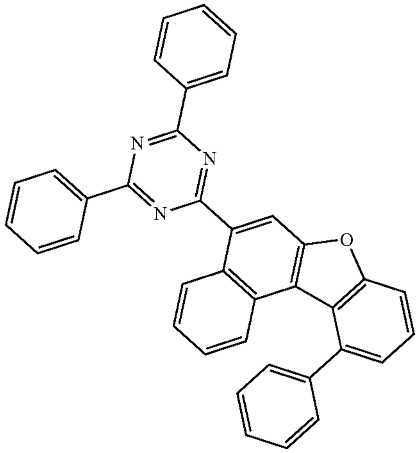
2-305
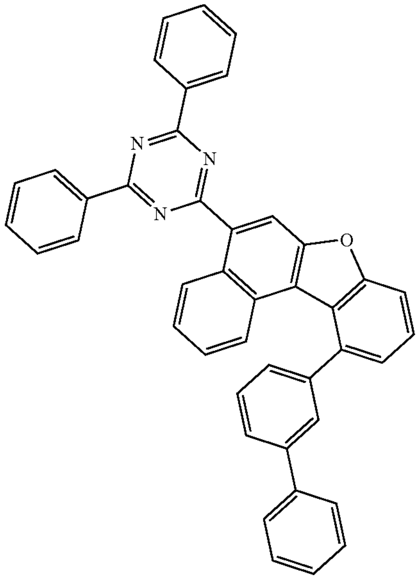
-continued
2-306
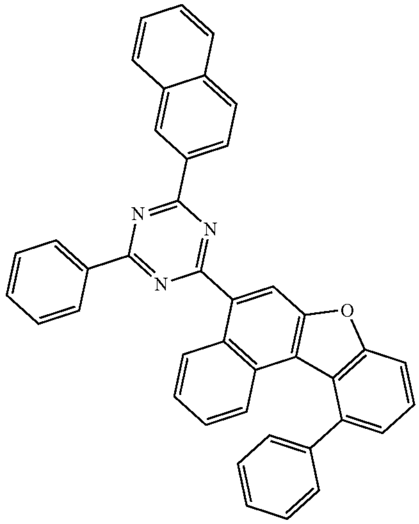
2-307
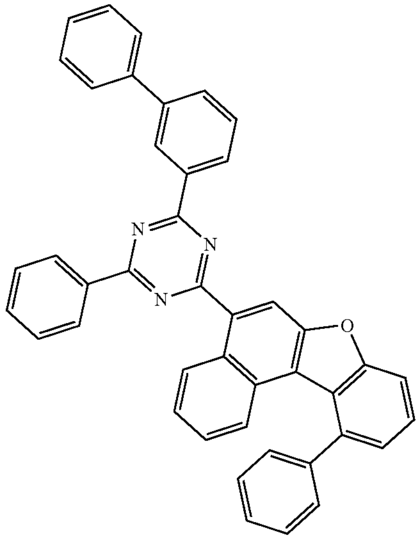
2-308
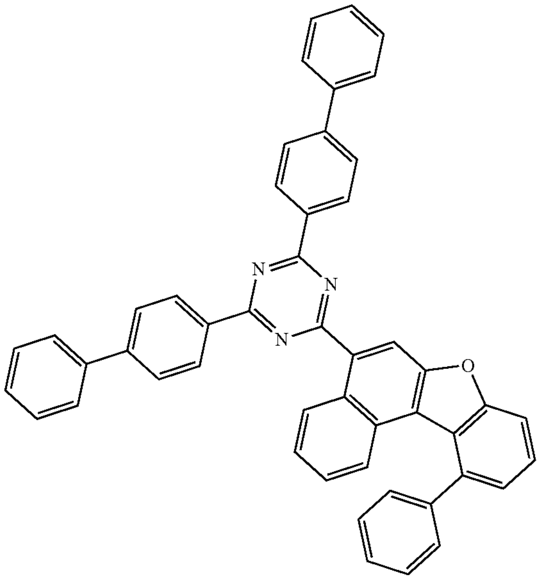

-continued
2-309
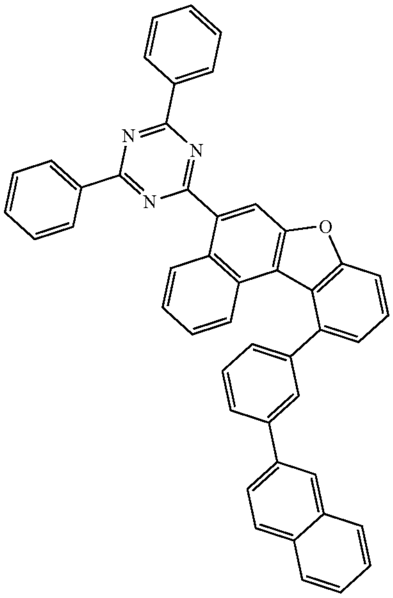
2-310
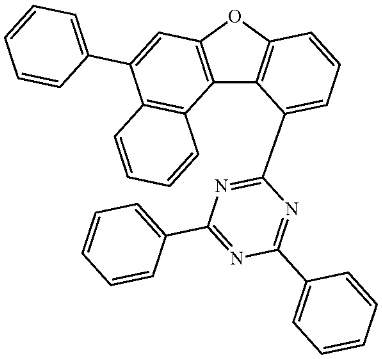
2-311
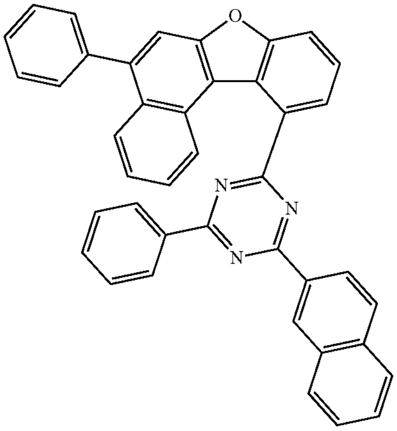
-continued
2-312
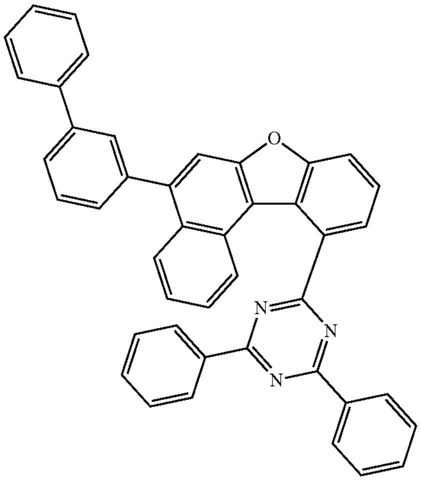
2-313
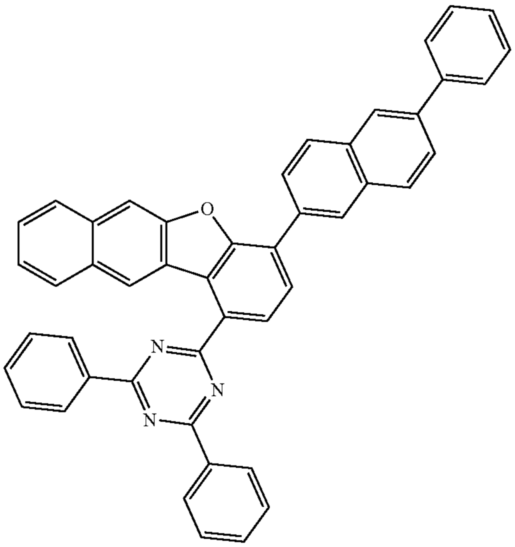
2-314
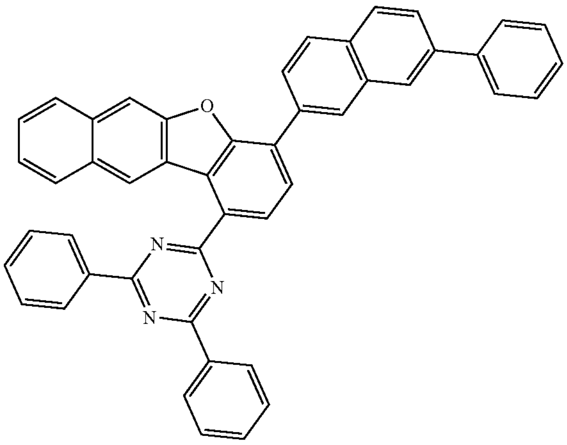

-continued
2-315
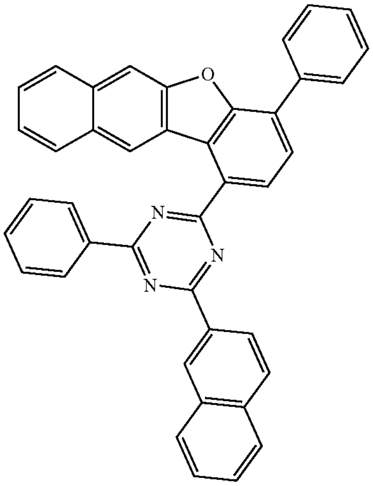
2-316
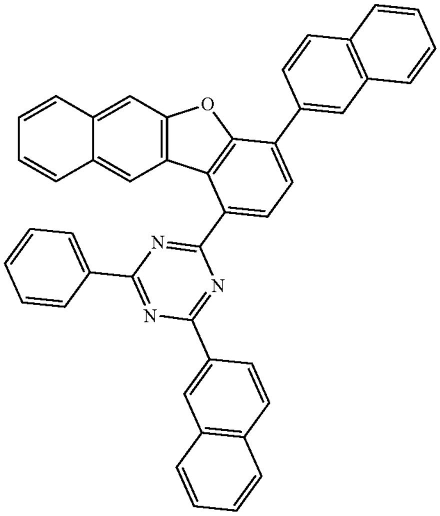
2-317
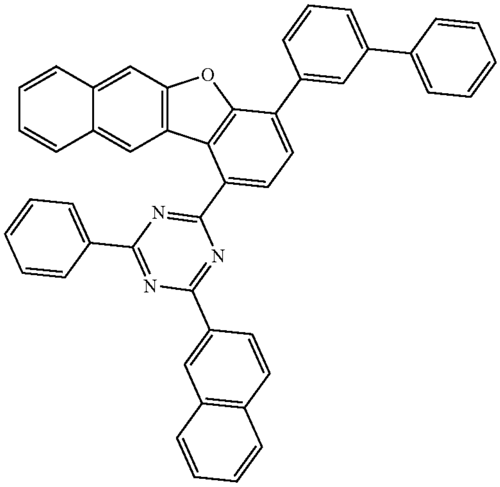
-continued
2-318
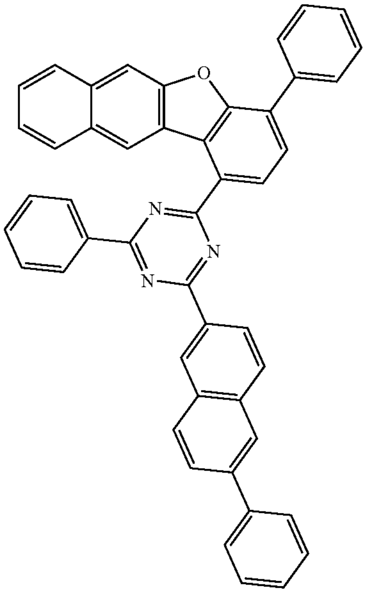
2-319
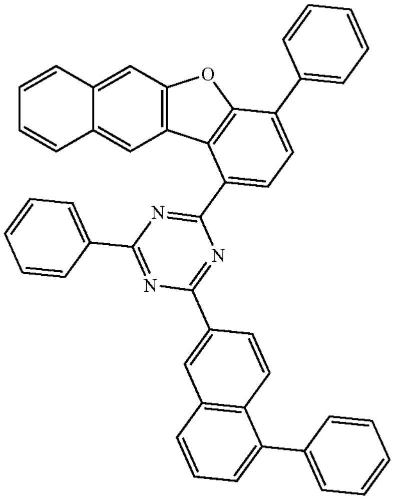

-continued
2-320
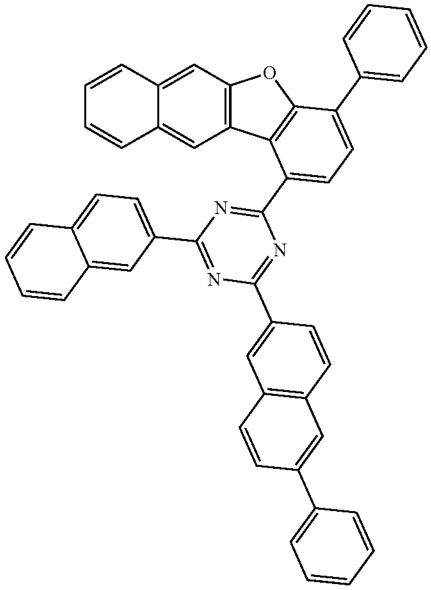
2-321
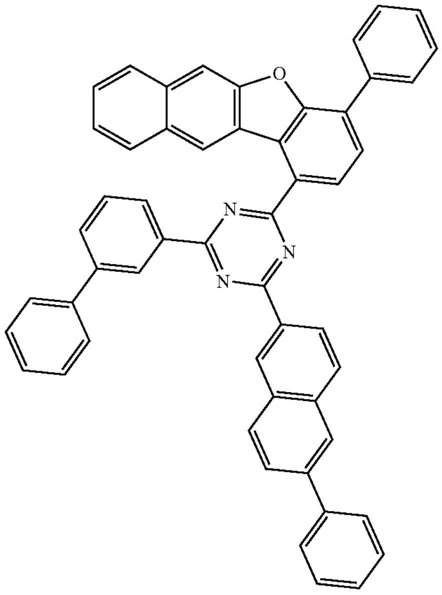
-continued
2-322
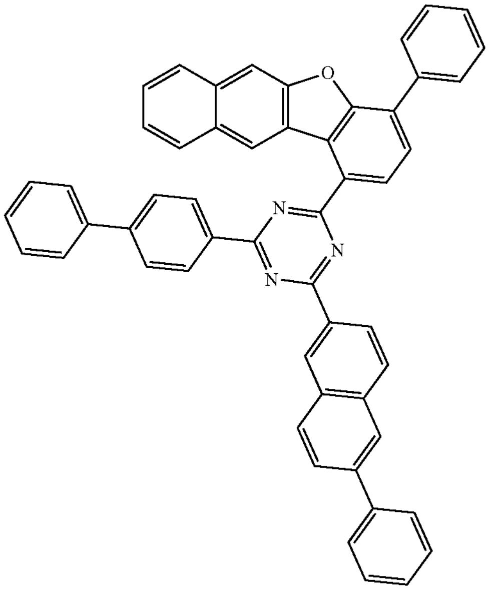
2-323
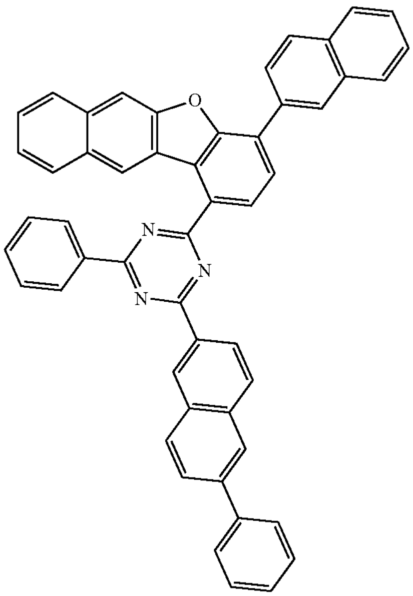

-continued
3-324
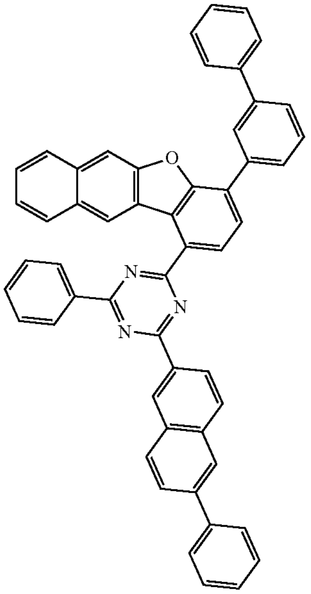
2-325
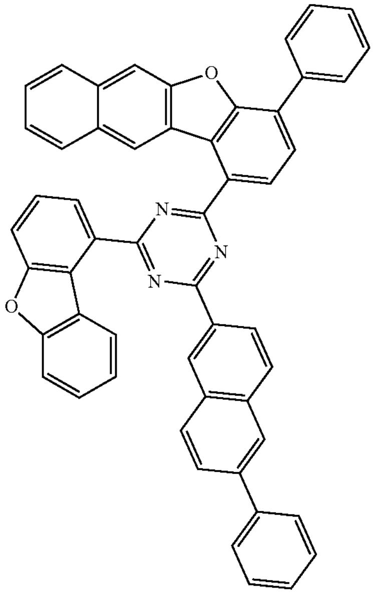
-continued
2-326
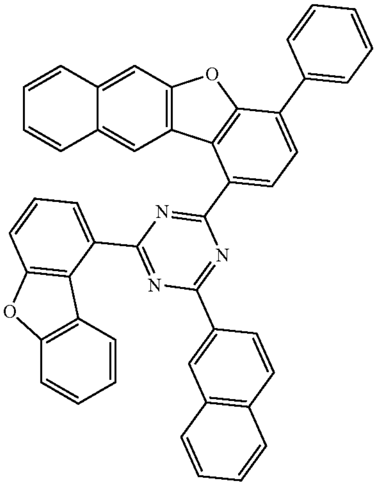
2-327
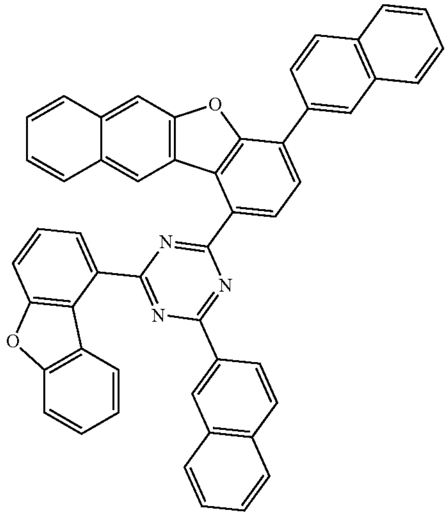
2-328
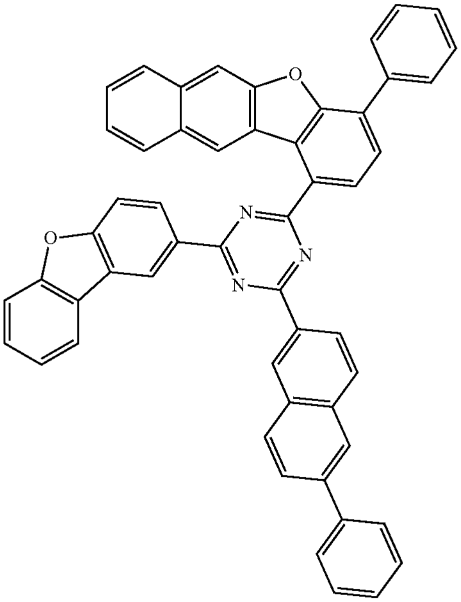

-continued
2-329
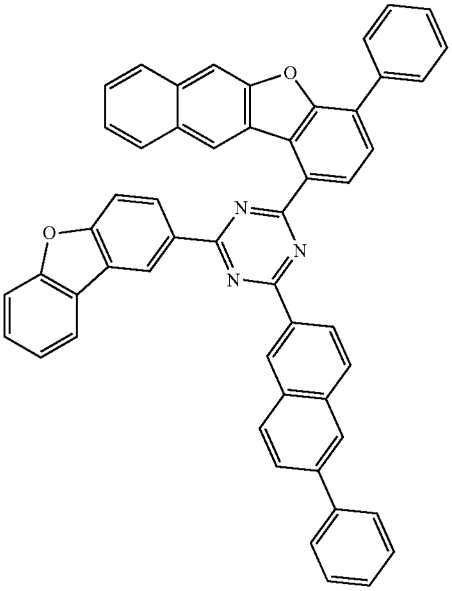
2-330
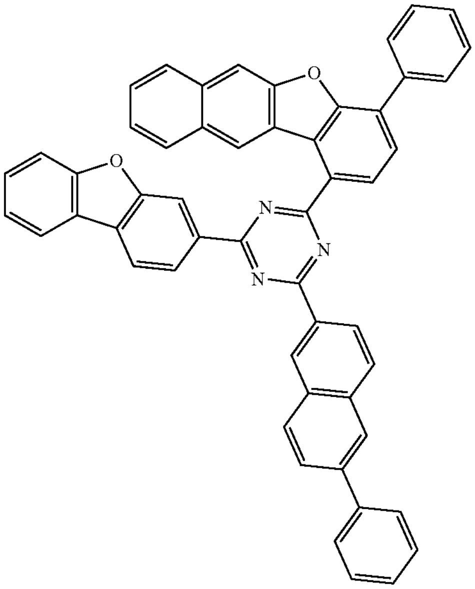
2-331
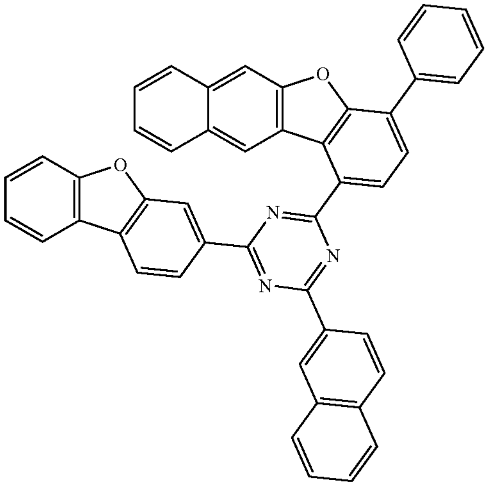
-continued
2-332
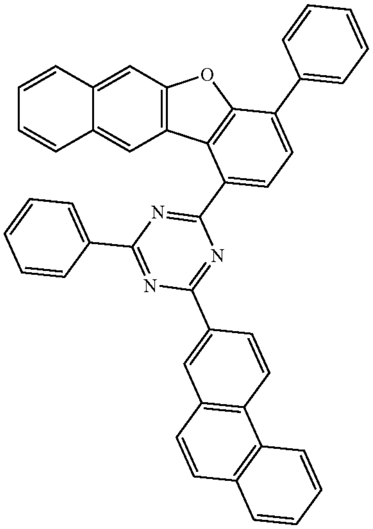
2-333
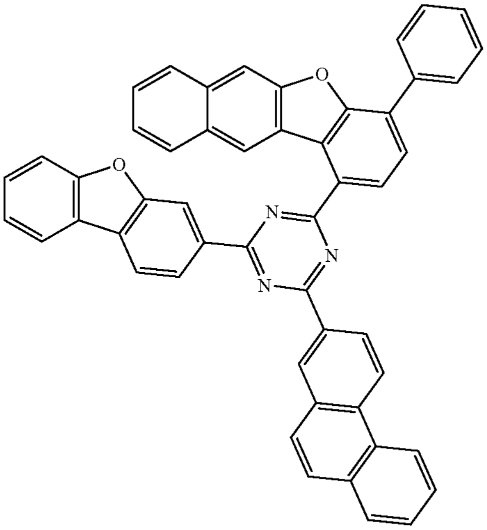
2-334
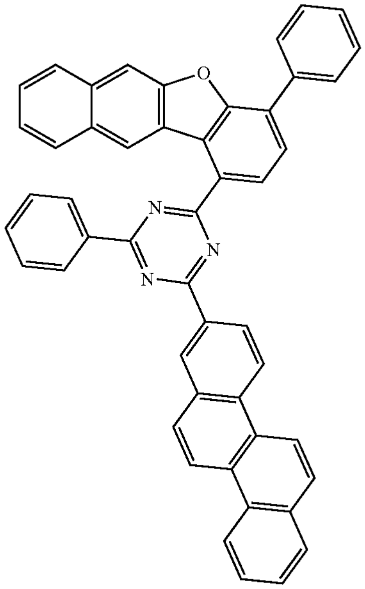

-continued
2-335
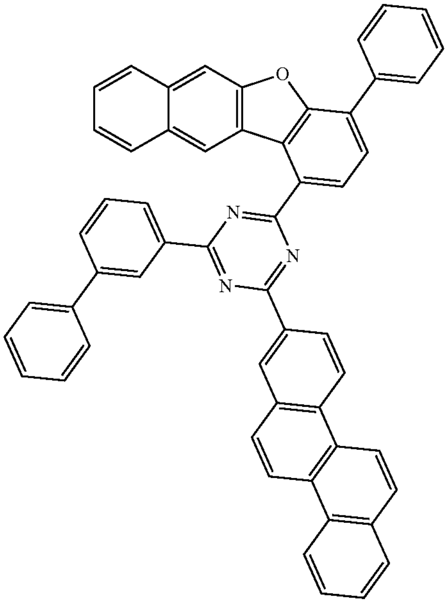
2-336
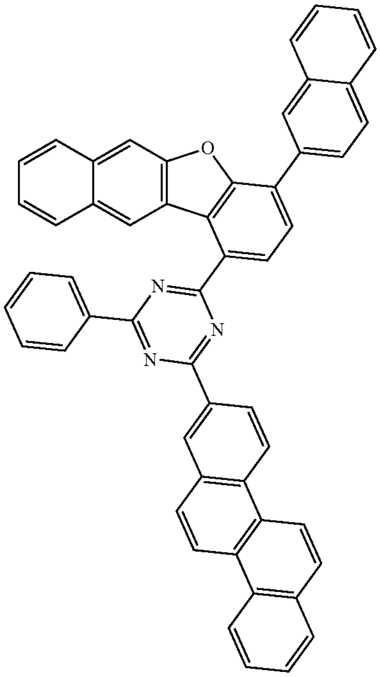
2-337
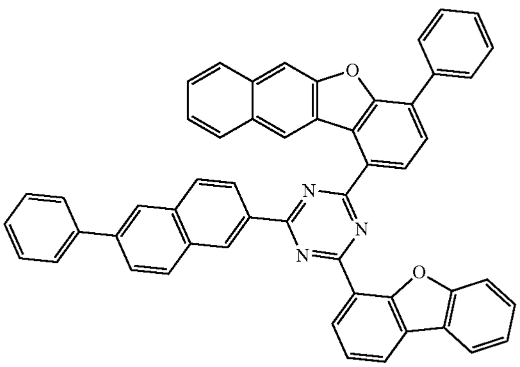
2-338
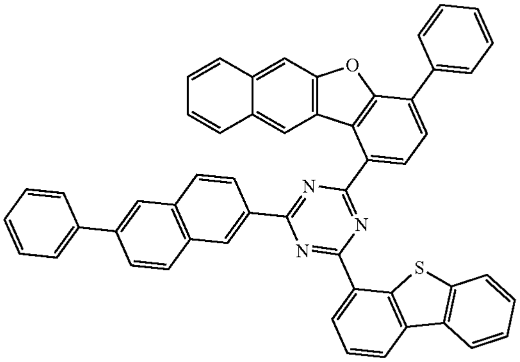
2-339
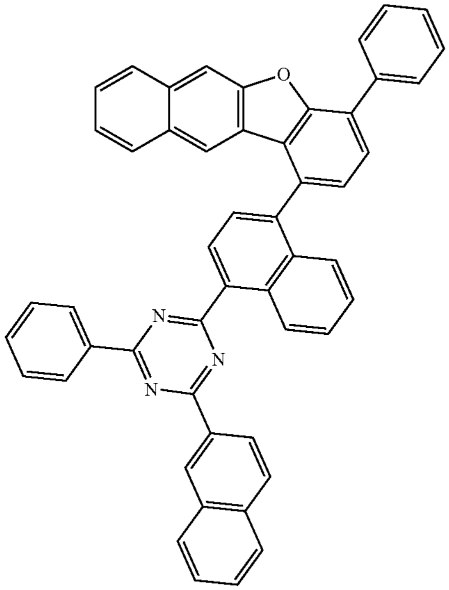
2-340
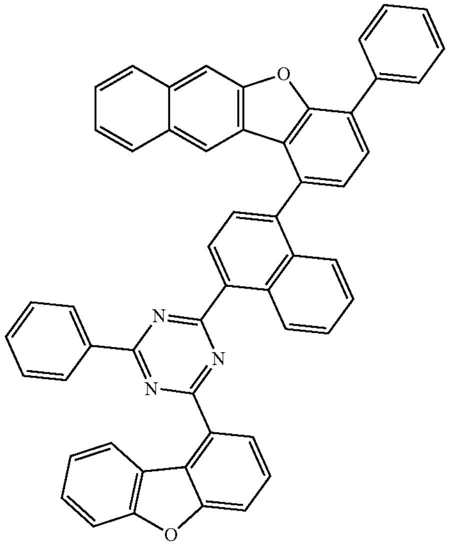

-continued
2-341
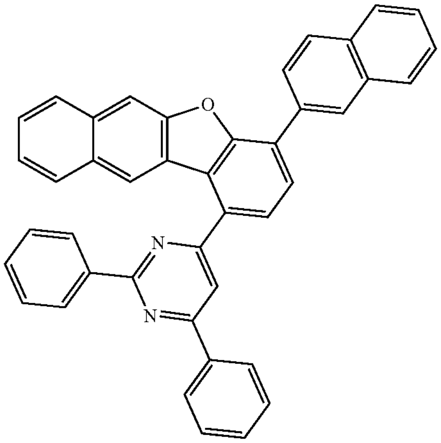
2-342
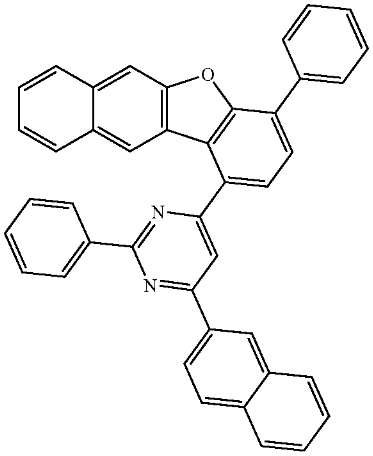
2-343
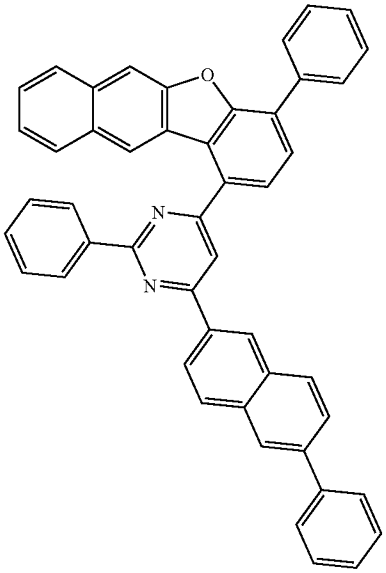
-continued
2-344
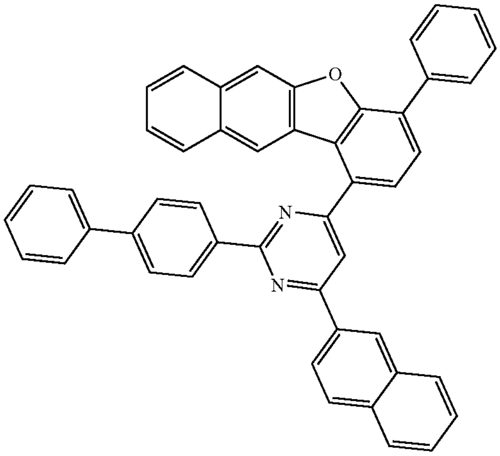
2-345
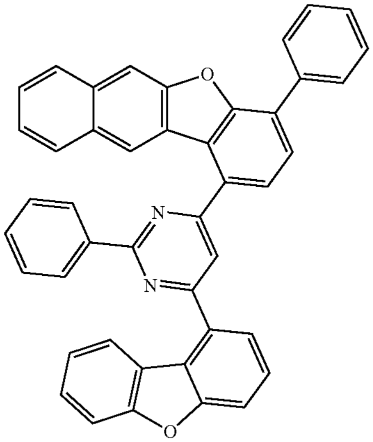
2-346
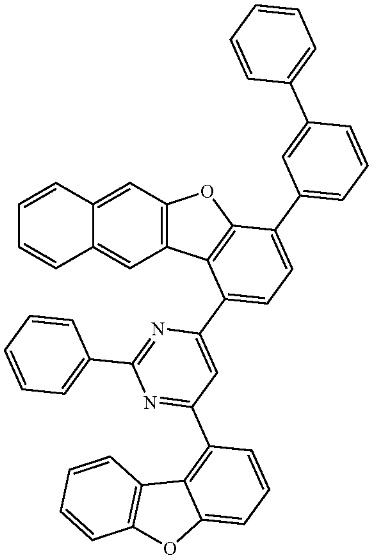

2-347
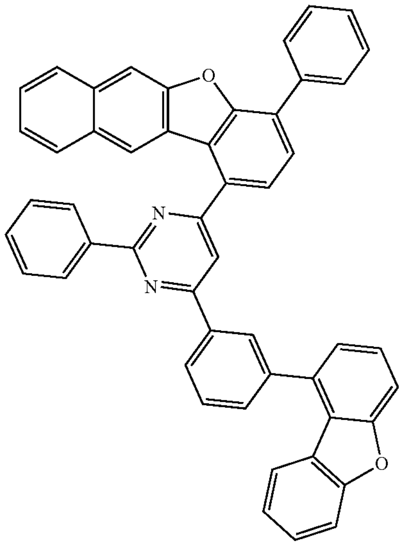
2-348
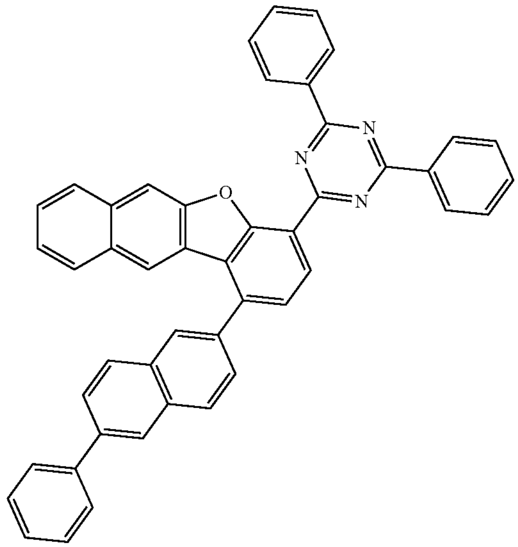
2-349
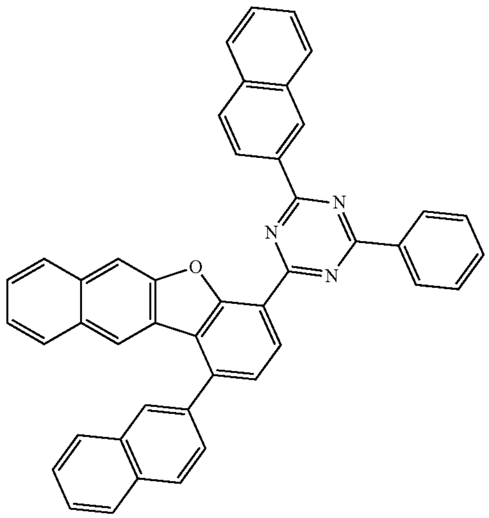
2-350
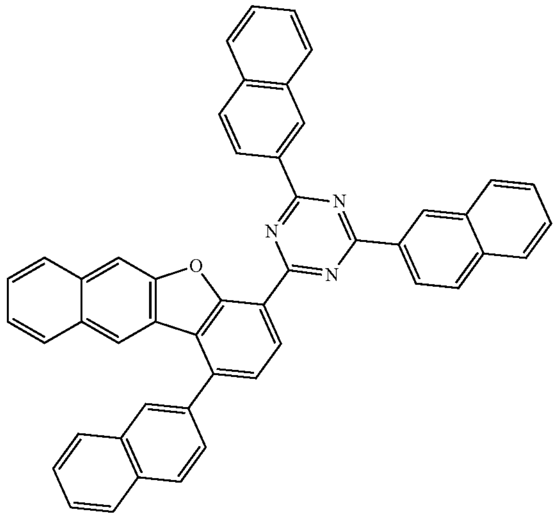
2-351
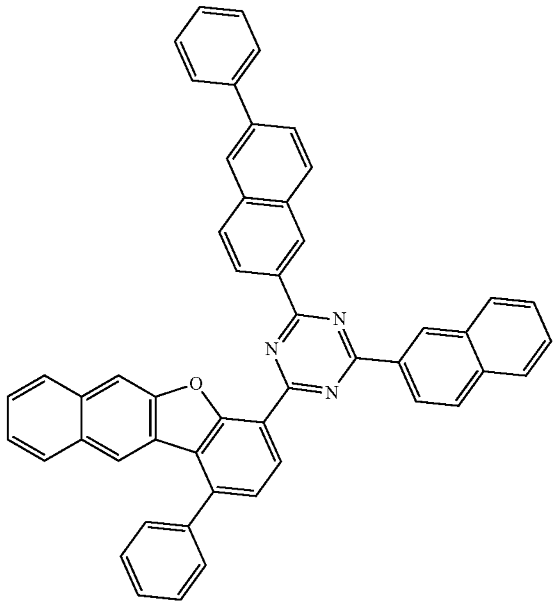

-continued
2-352
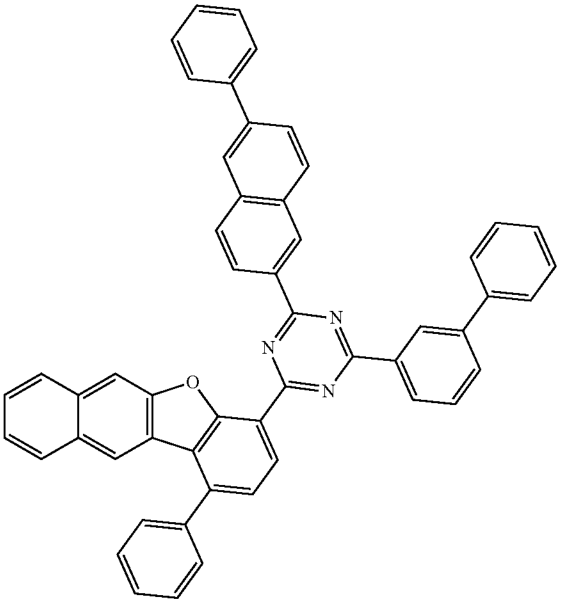
2-353
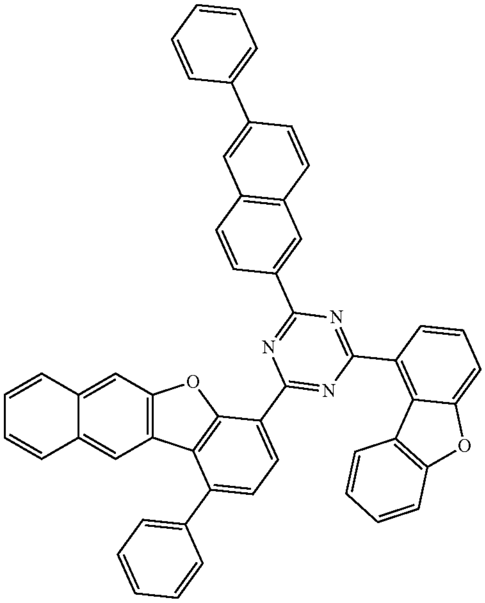
-continued
2-354
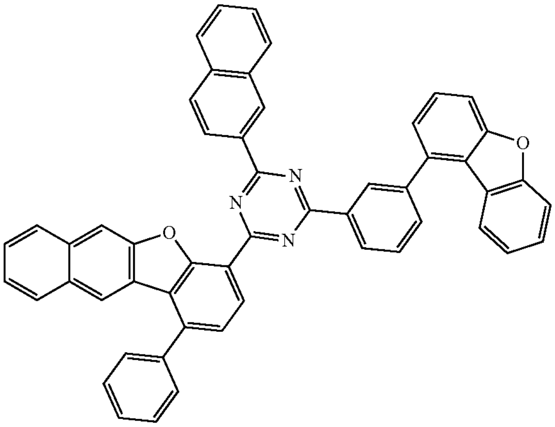
2-355
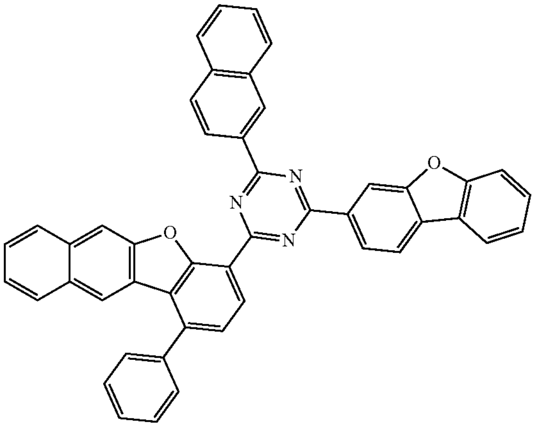
2-356
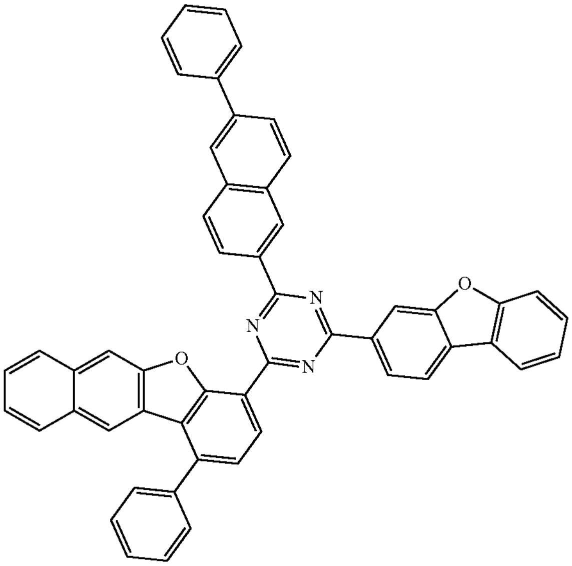

-continued
2-357
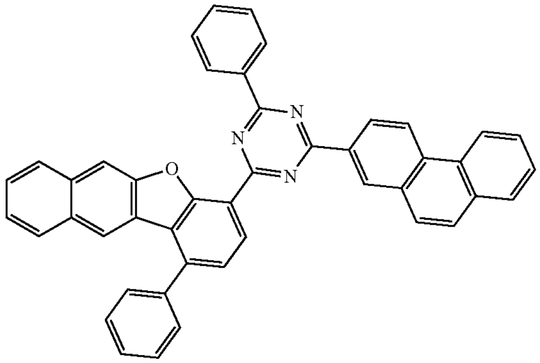
2-358
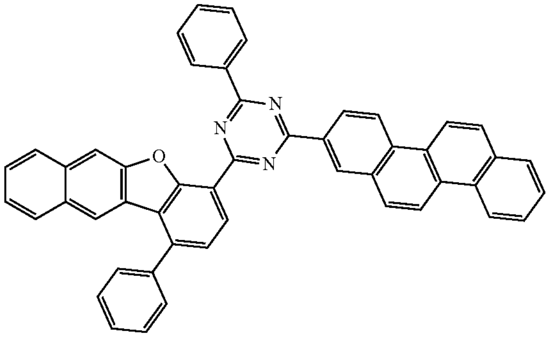
2-359
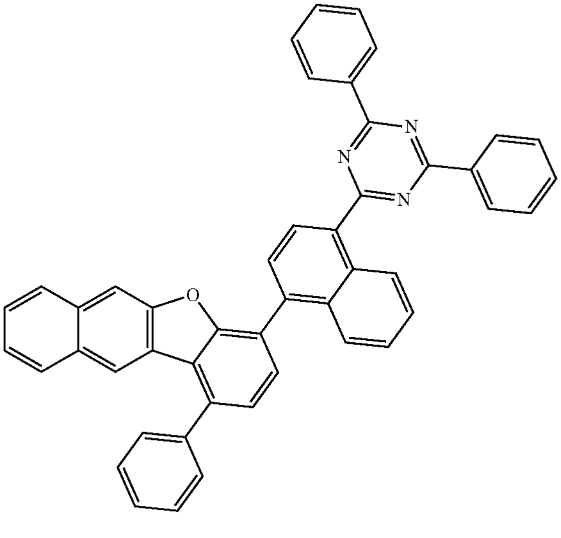
-continued
2-360
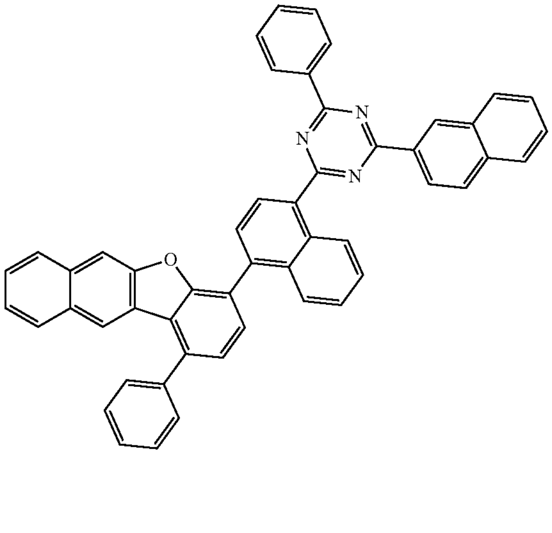
2-361
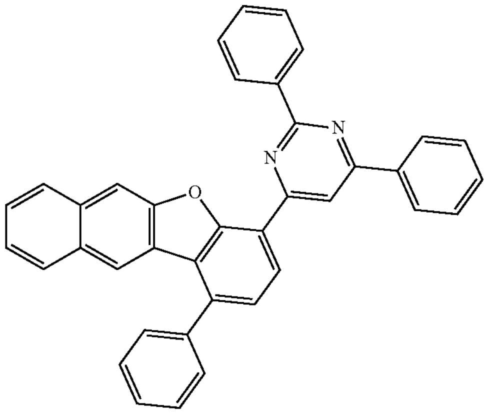
2-362
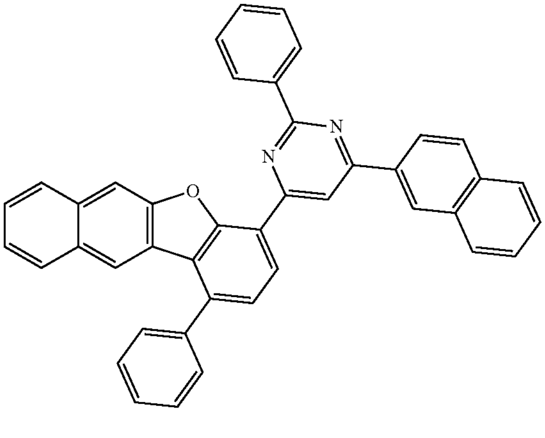

-continued
2-363
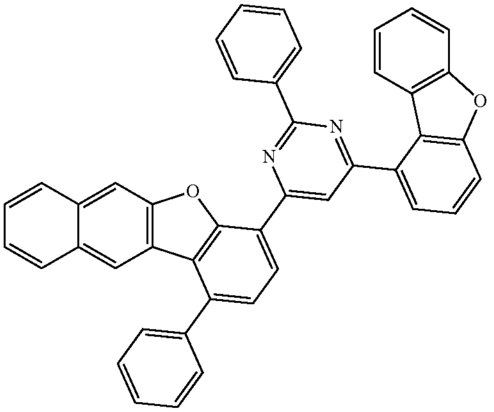
2-364
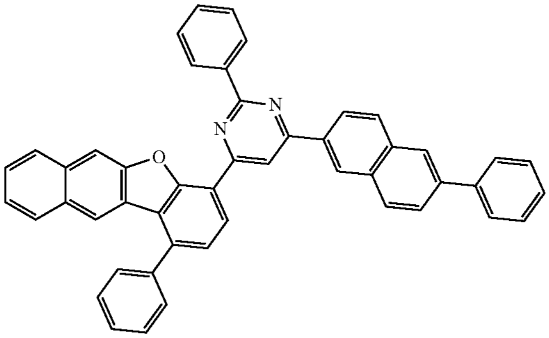
2-365
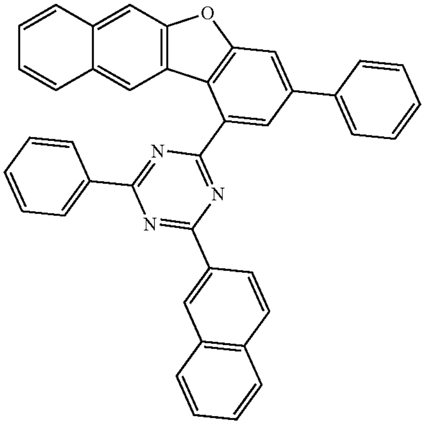
2-366
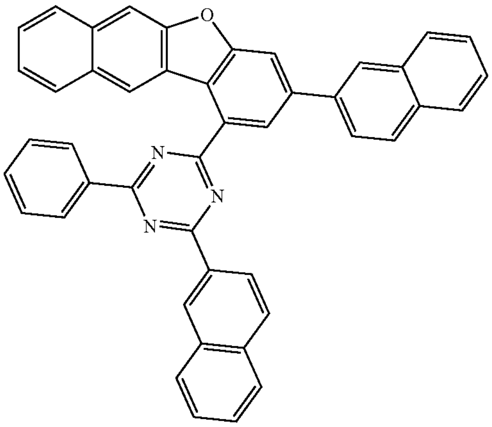
-continued
2-367
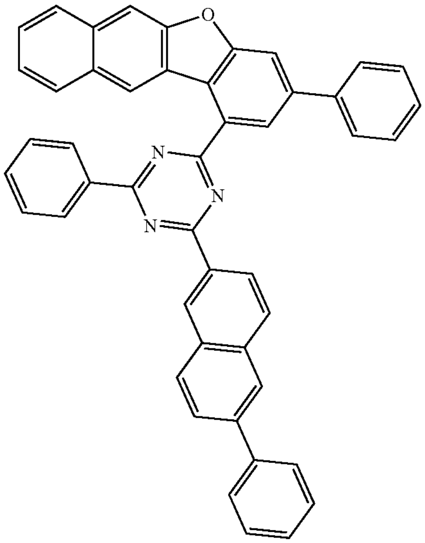
2-368
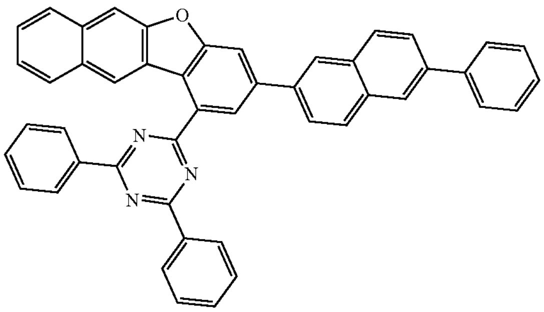
2-369
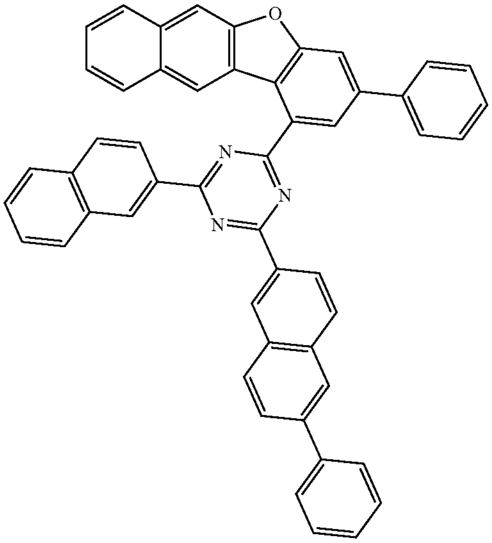

-continued
2-370
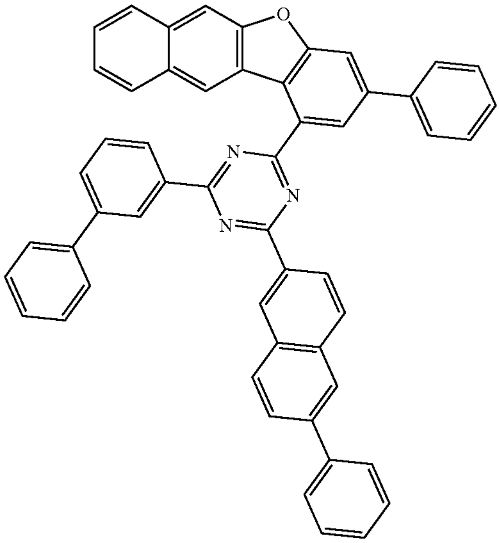
2-371
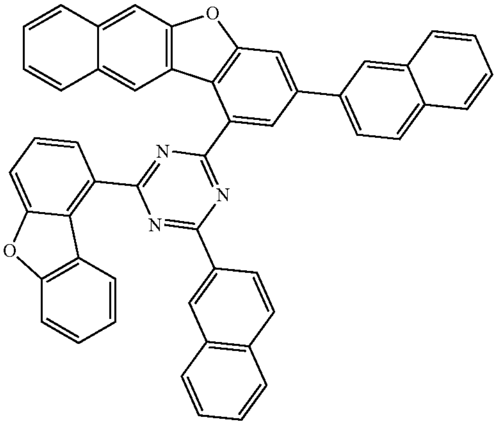
2-372
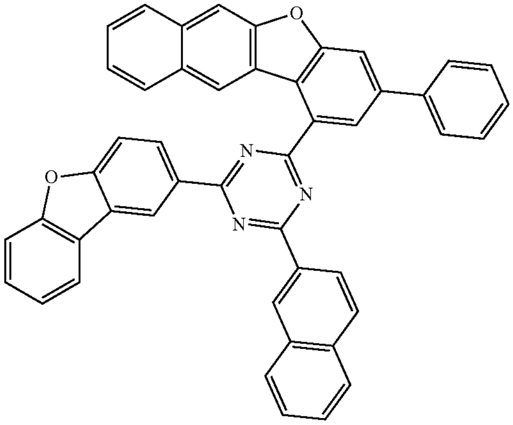
-continued
2-373
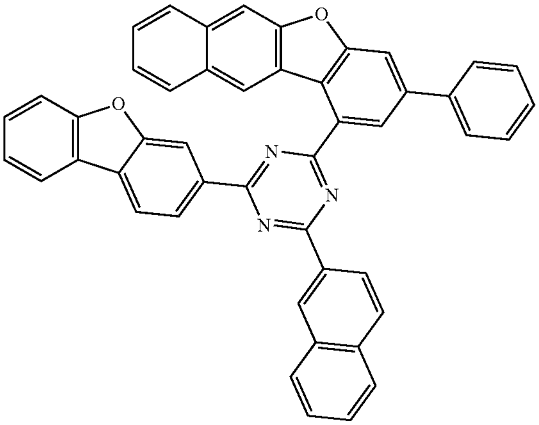
2-374
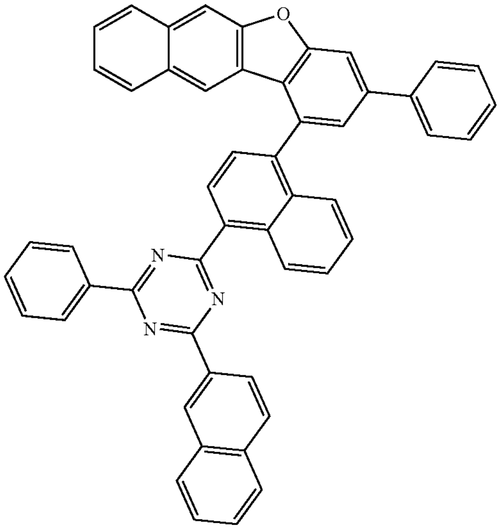
2-375
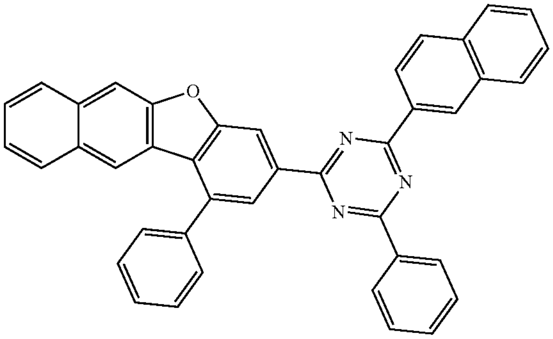

2-376
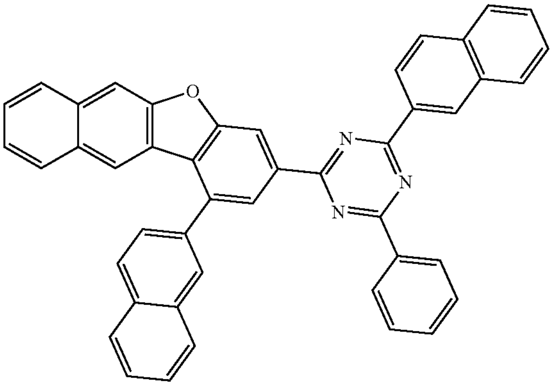
2-377
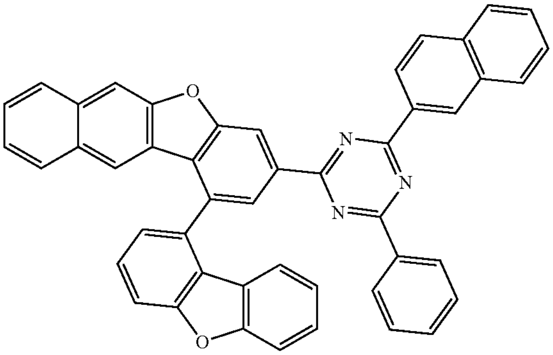
2-378
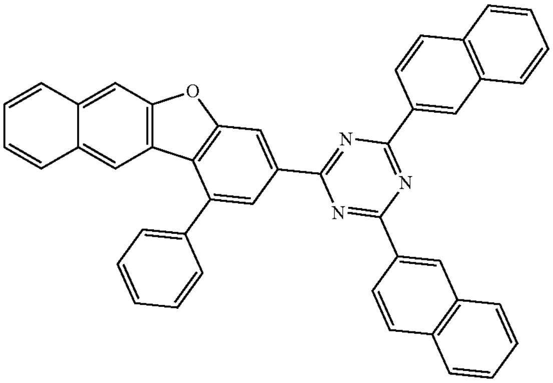
2-379
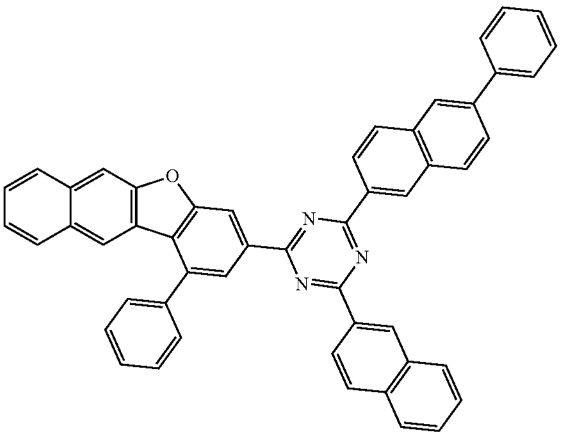
2-380
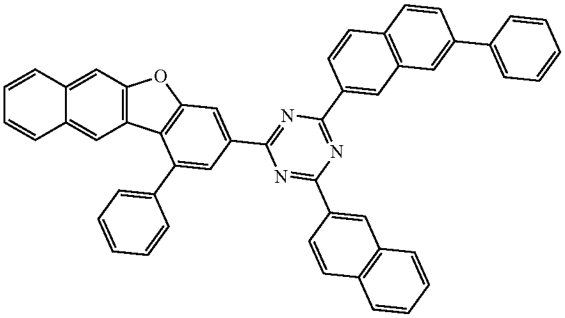
2-381
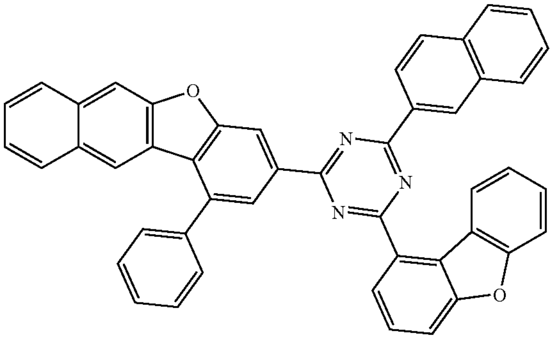
2-382
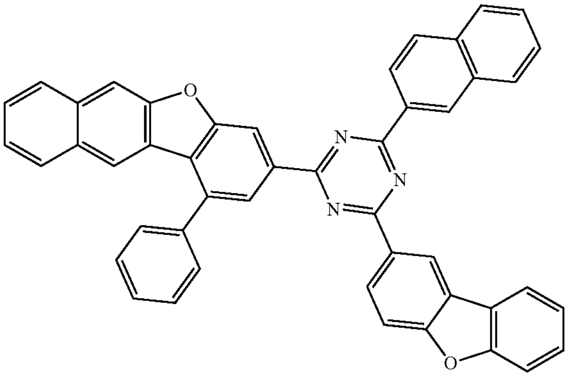
2-383
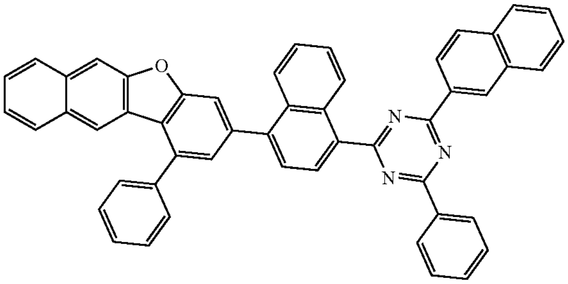

-continued
2-384
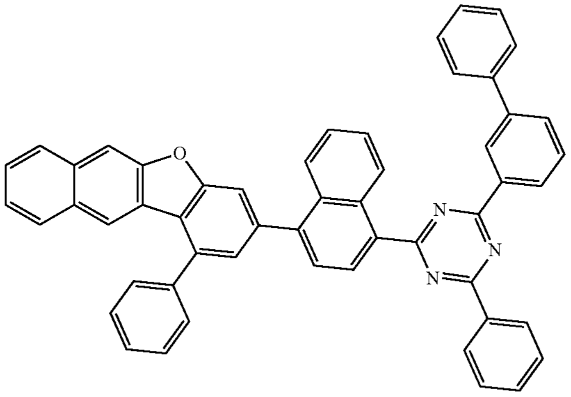
2-385
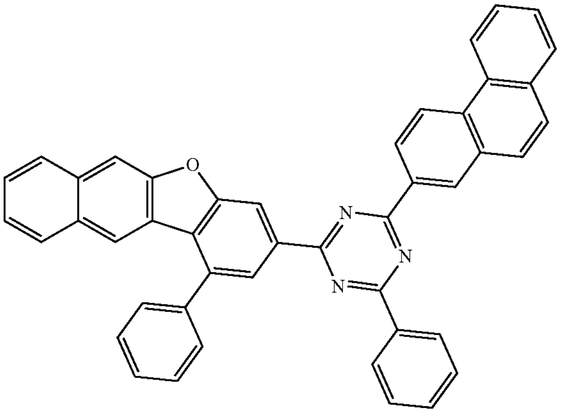
2-386
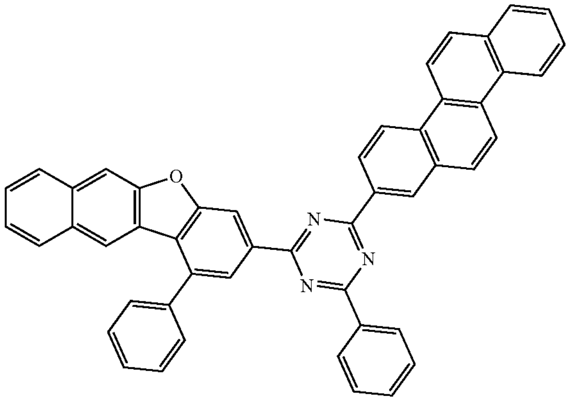
2-387
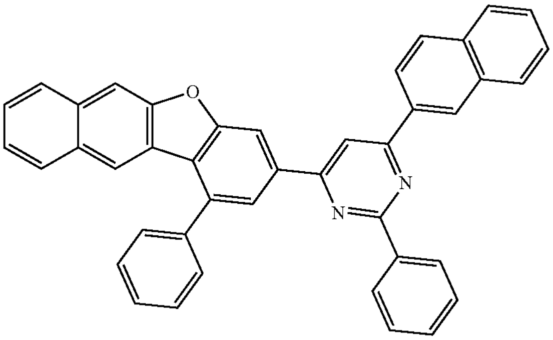
-continued
2-388
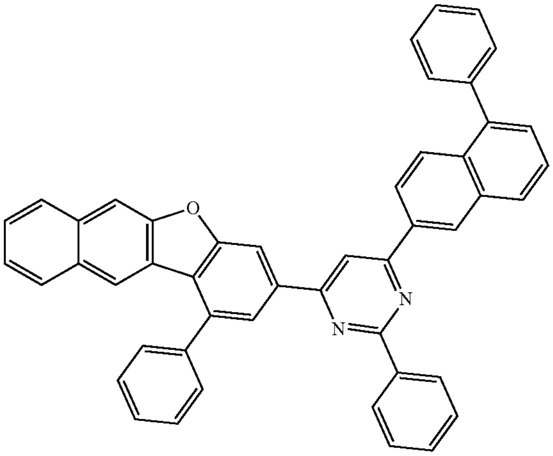
2-389
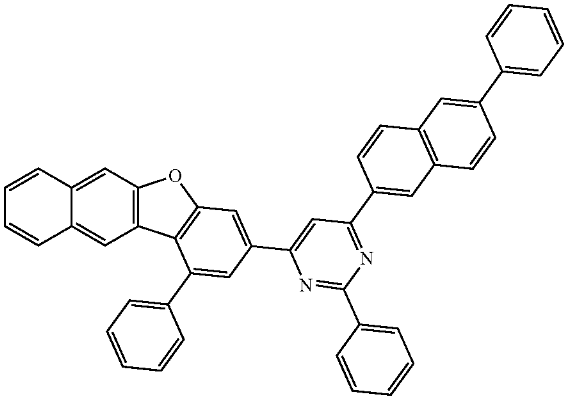
2-390
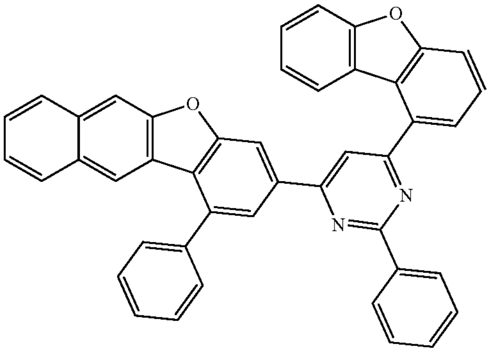

-continued
2-391
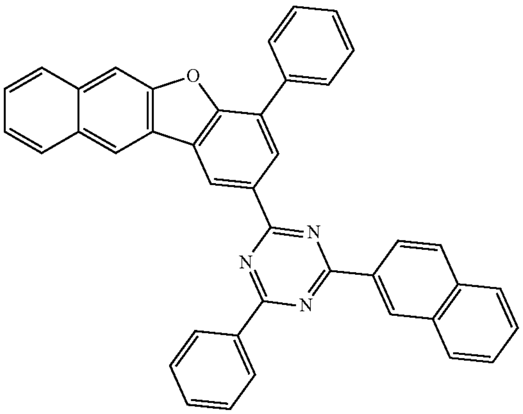
2-392
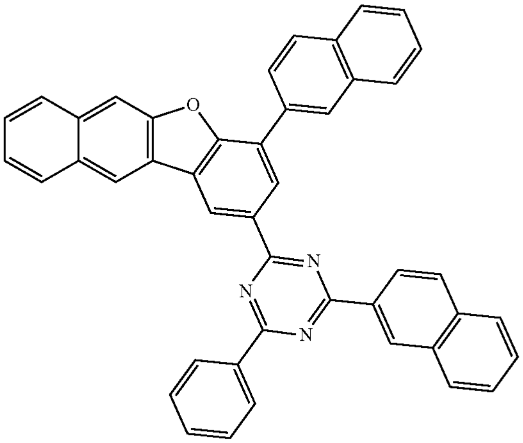
2-393
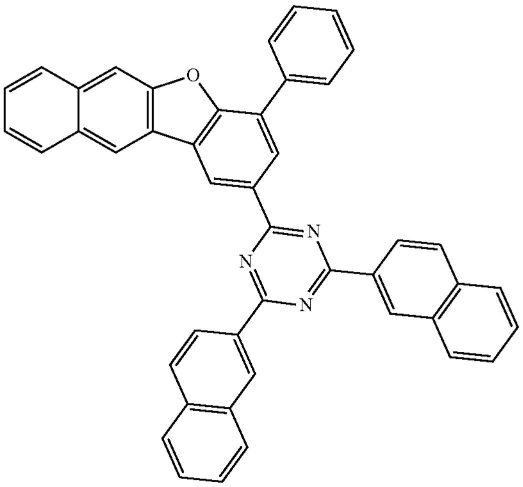
-continued
2-394
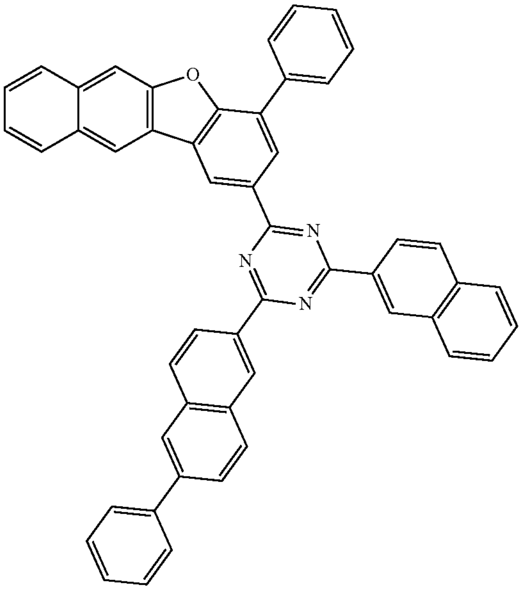
2-395
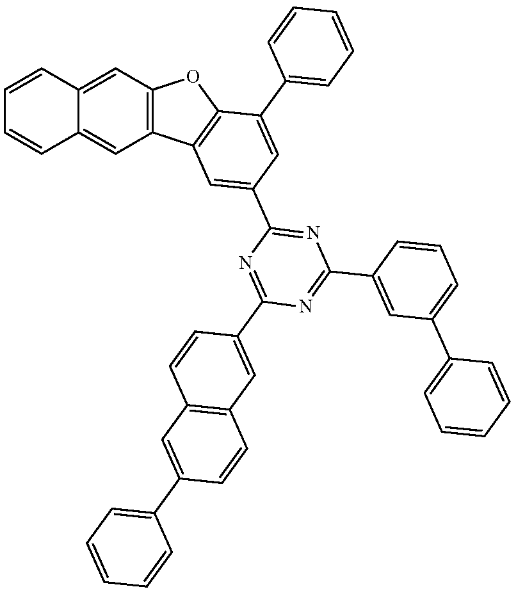

-continued
2-396
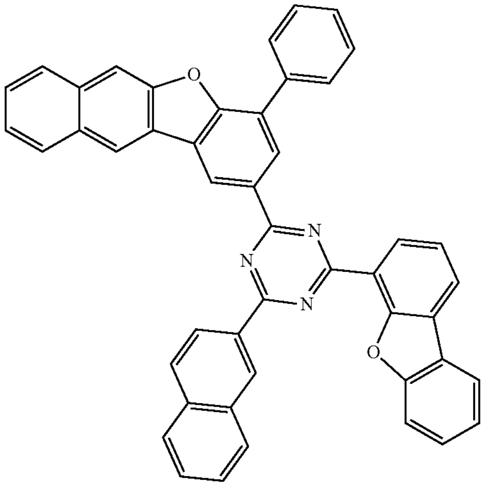
2-397
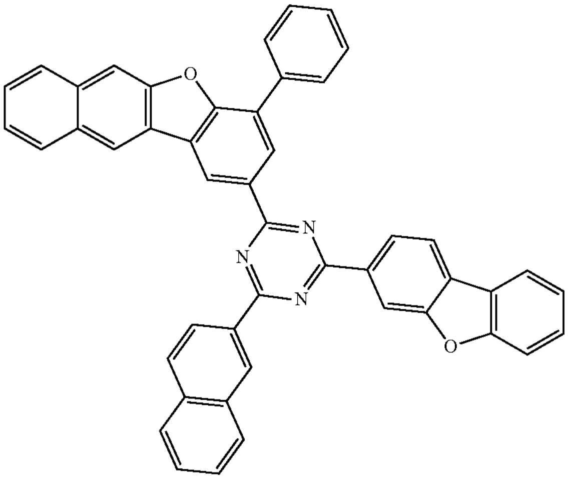
2-398
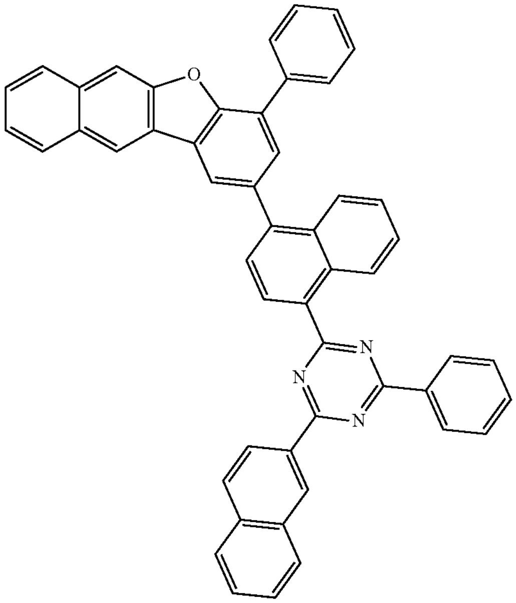
-continued
2-399
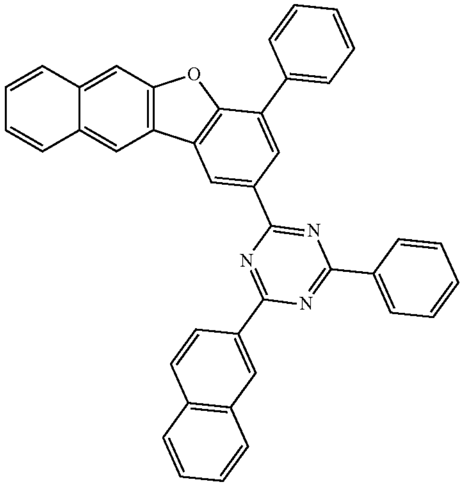
2-400
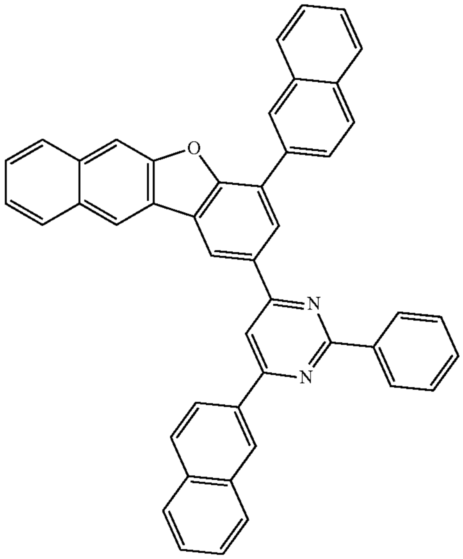
2-401
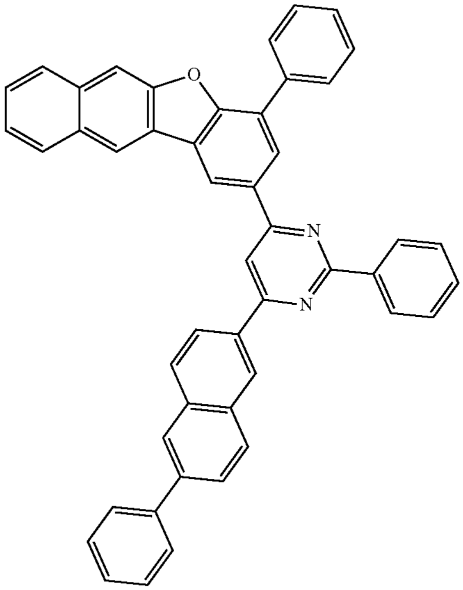

-continued
2-402
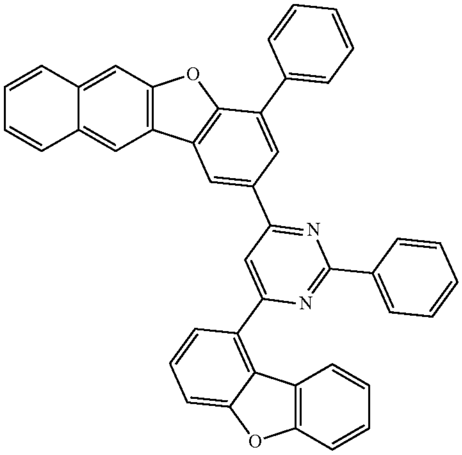
2-403
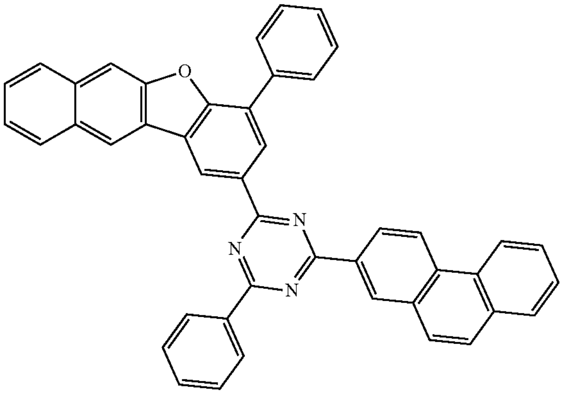
2-404
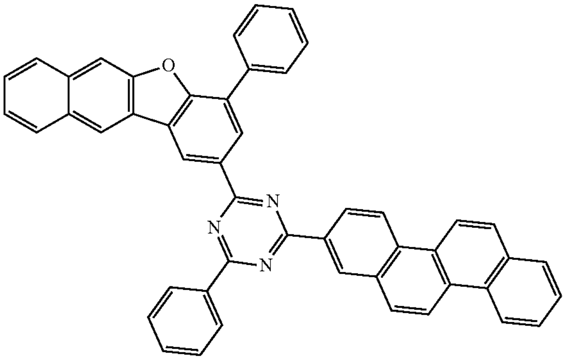
-continued
2-405
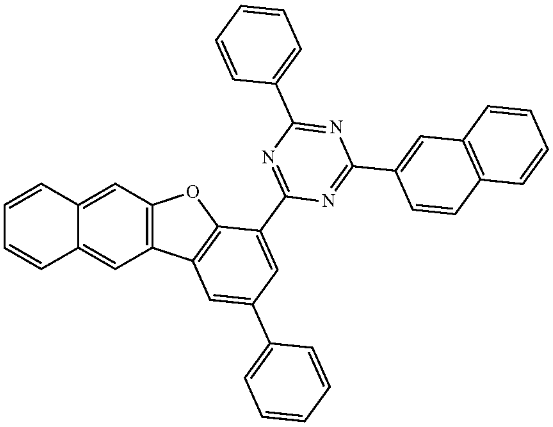
2-406
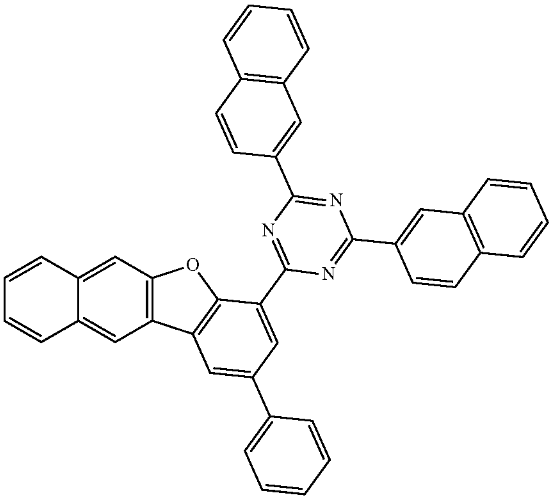
2-407
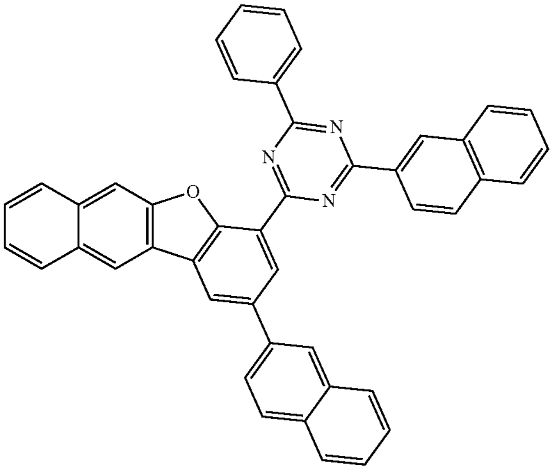

-continued
2-408
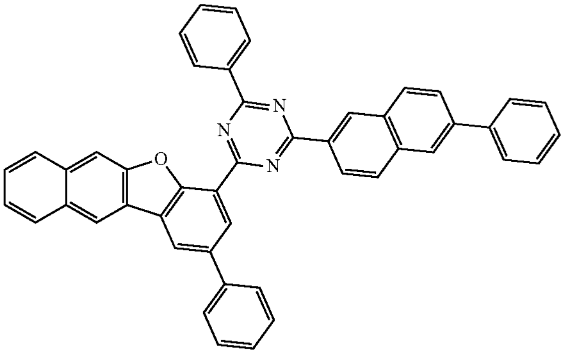
2-409
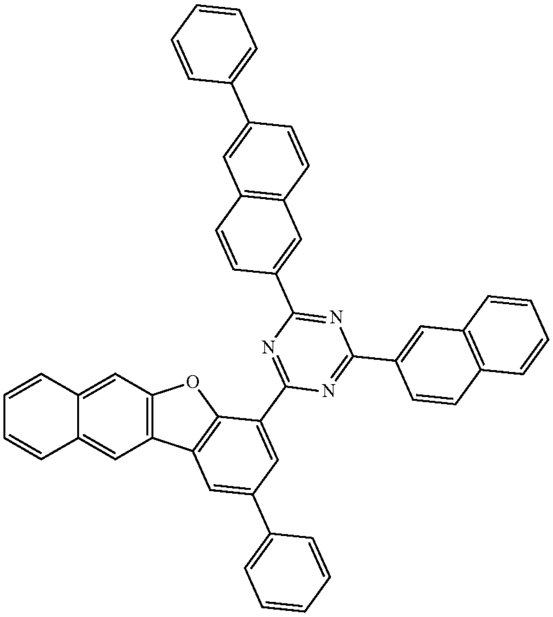
2-410
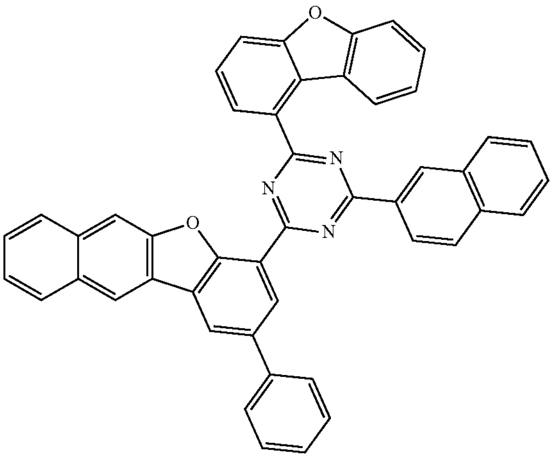
-continued
2-411
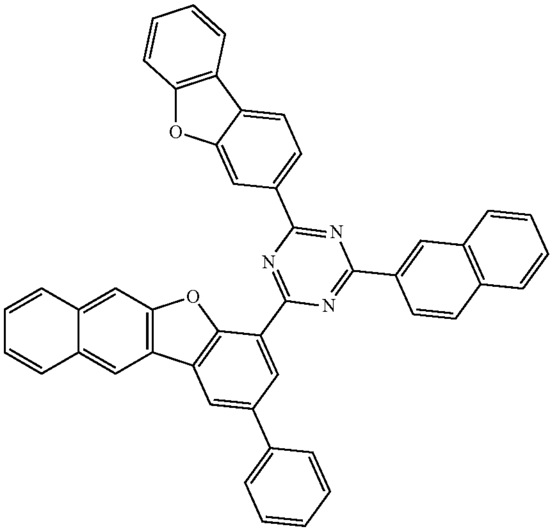
2-412
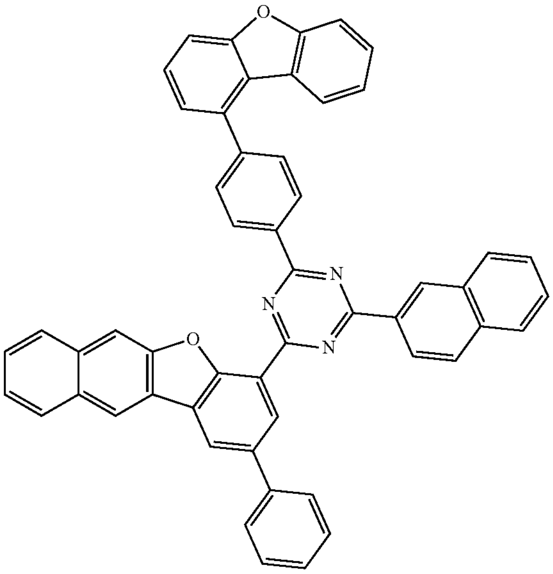

-continued
2-413
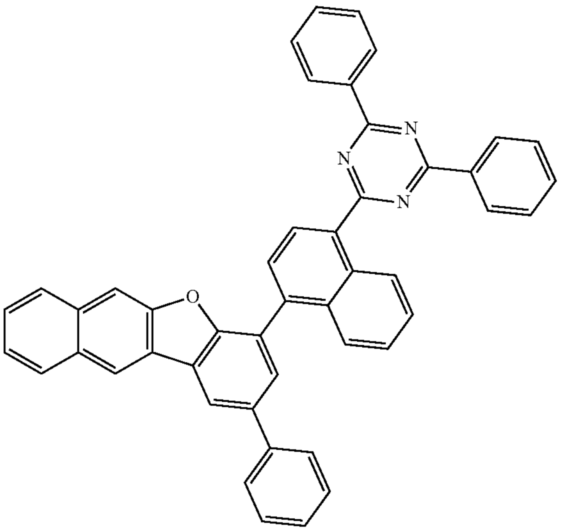
2-414
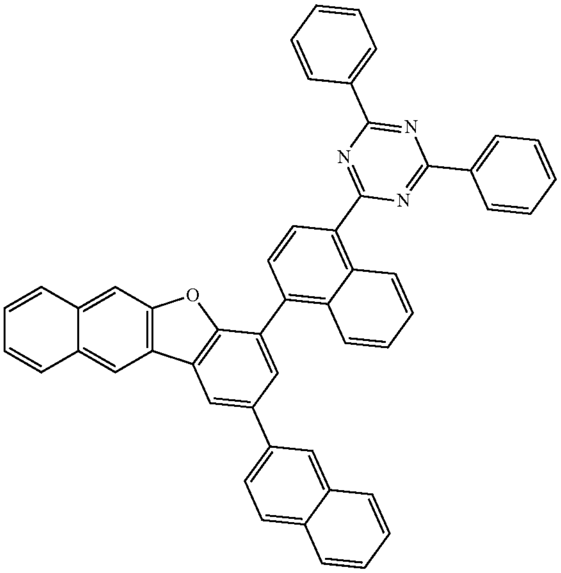
2-415
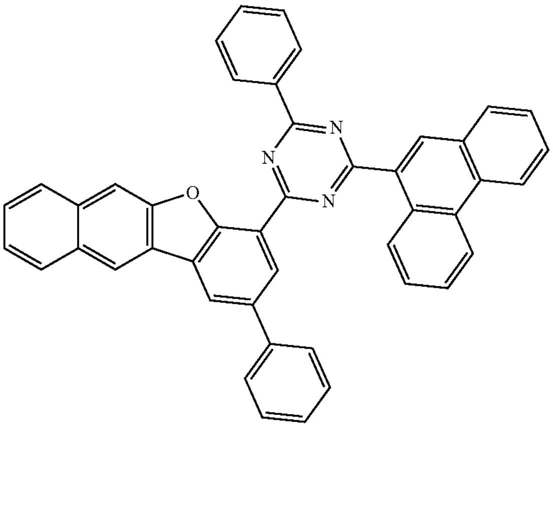
-continued
2-416
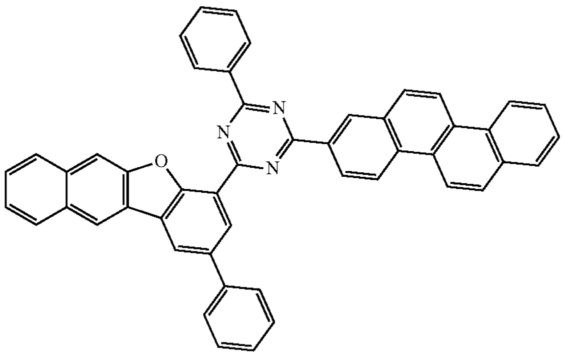
2-417
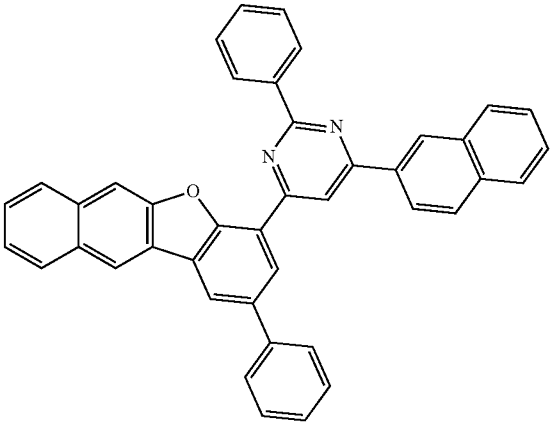
2-418
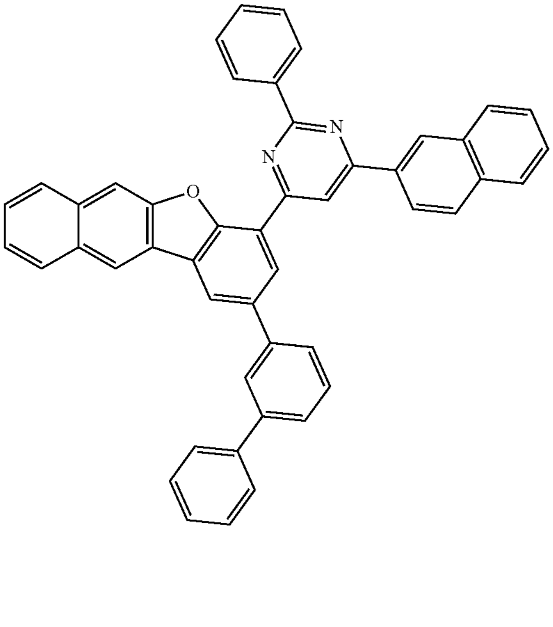

-continued
2-419
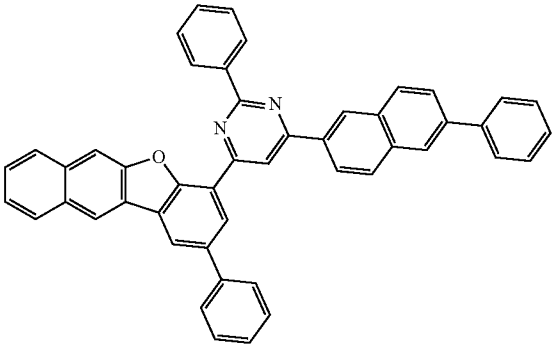
2-420
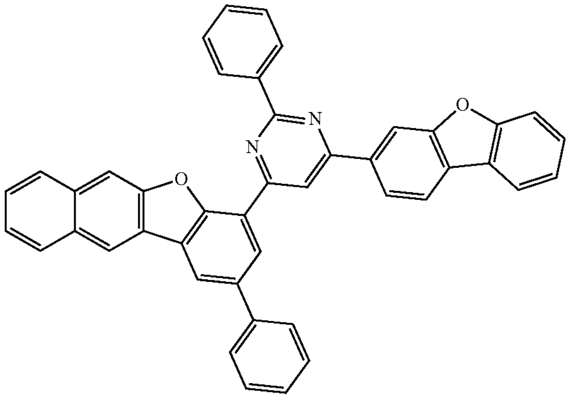
2-421
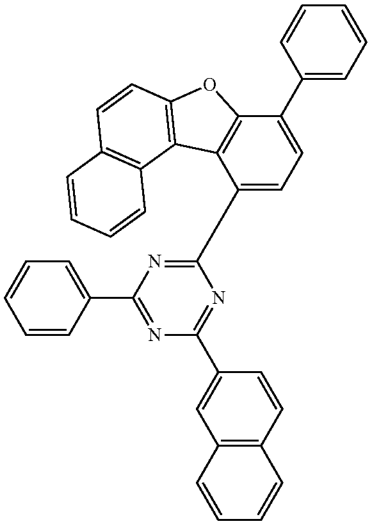
-continued
2-422
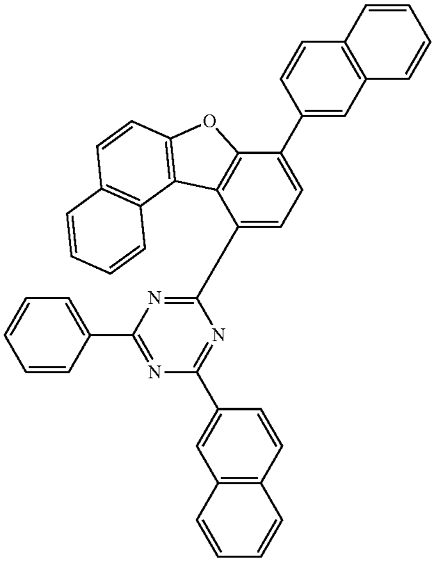
2-423
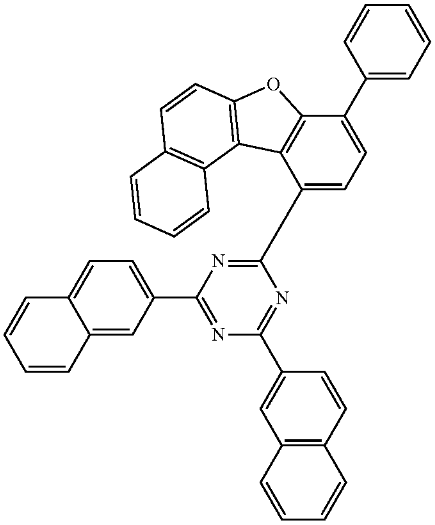

-continued
2-424
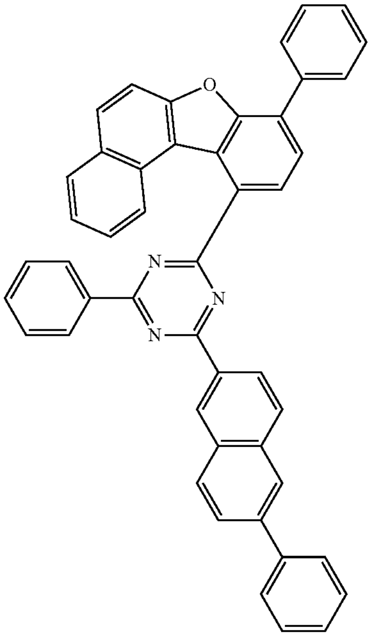
2-425
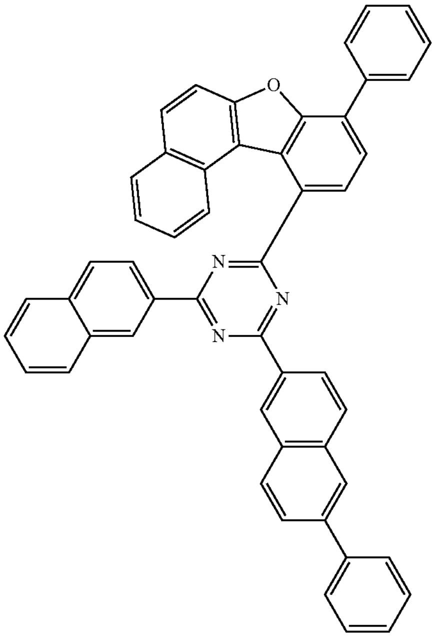
-continued
2-426
2-426
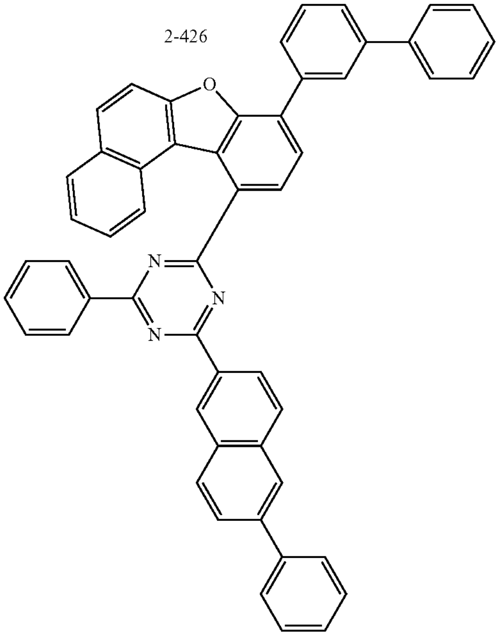
2-427
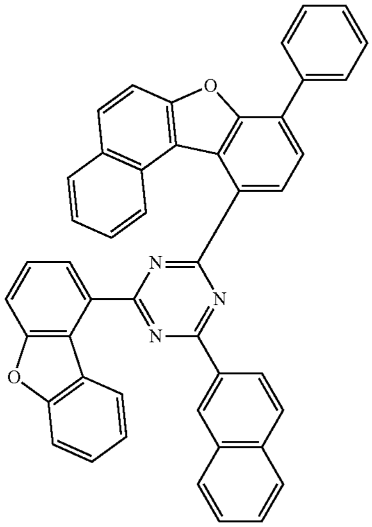

-continued
2-428
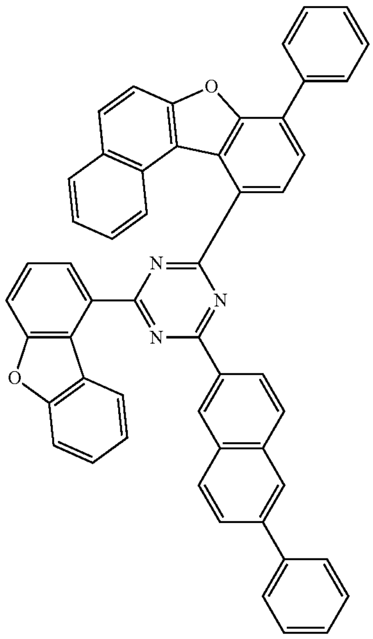
2-429
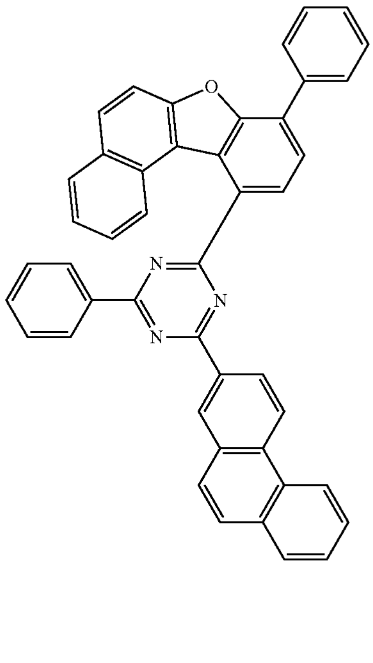
-continued
2-430
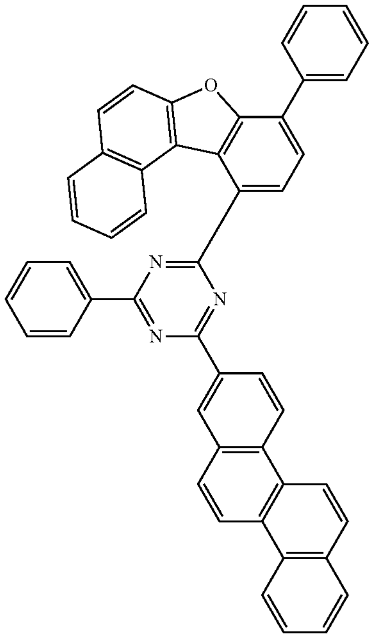
2-431
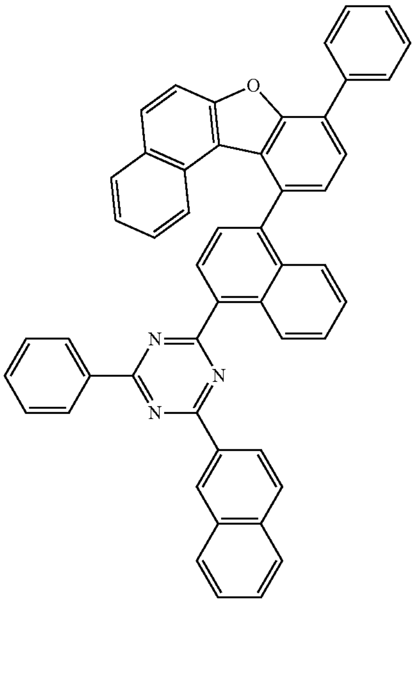

-continued
2-432
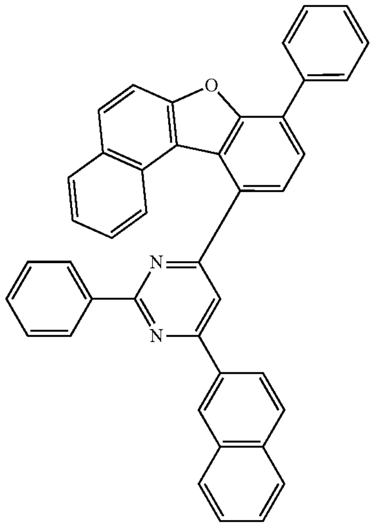
2-433
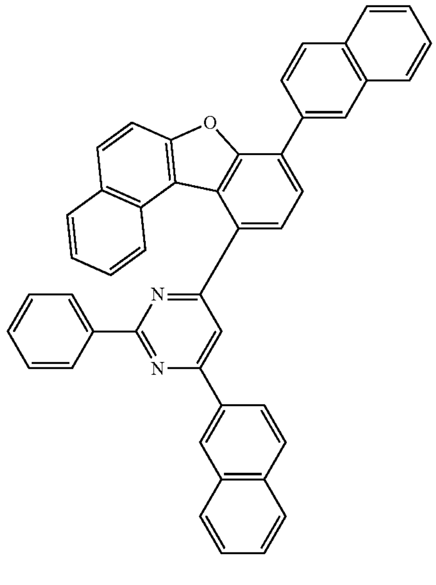
-continued
2-434
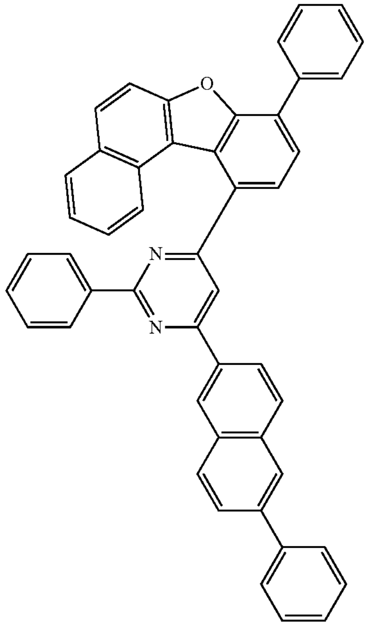
2-435
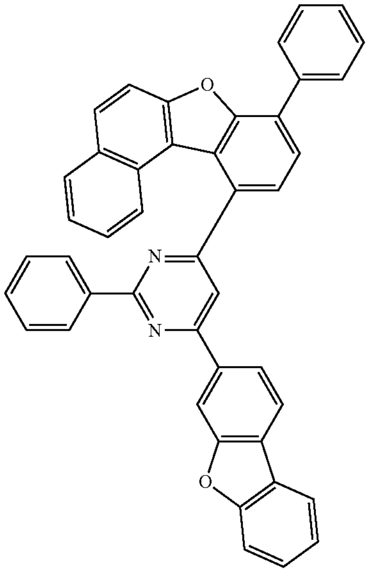
2-436
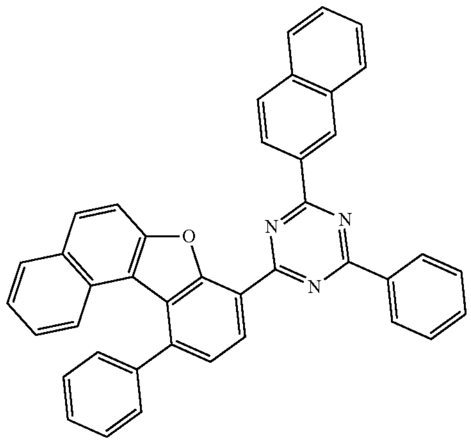

-continued
2-437
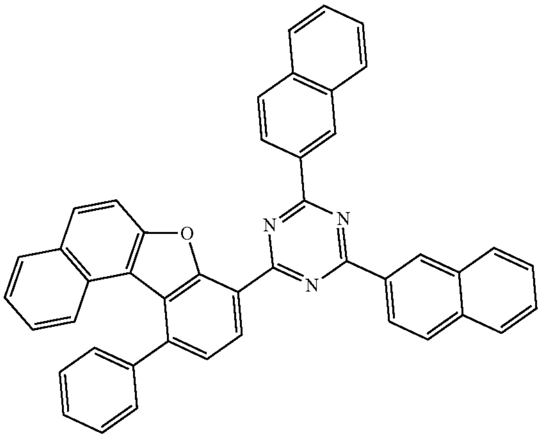
2-438
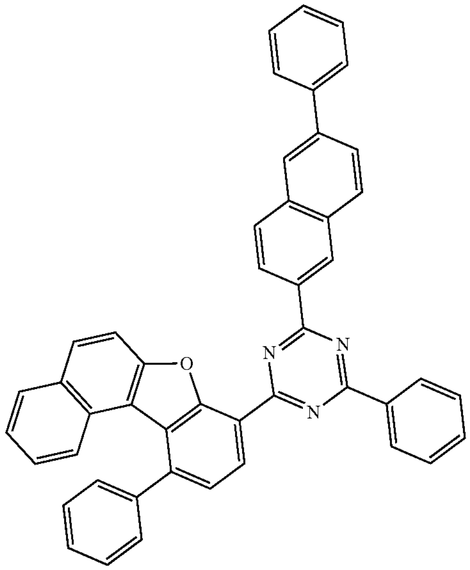
2-439
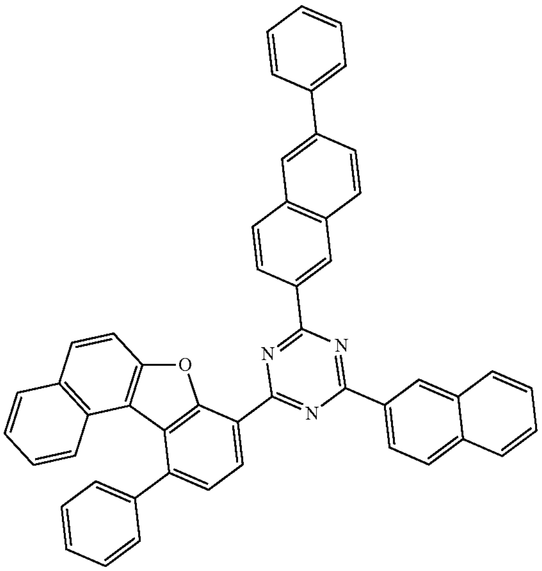
-continued
2-440
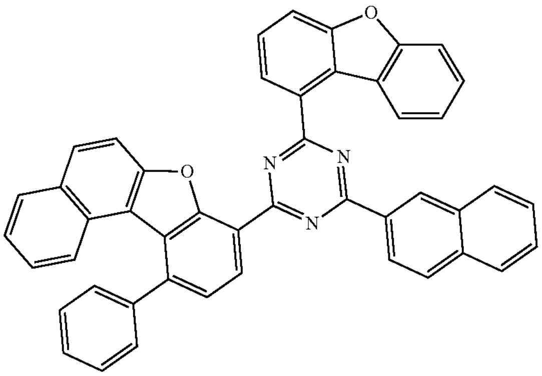
2-441
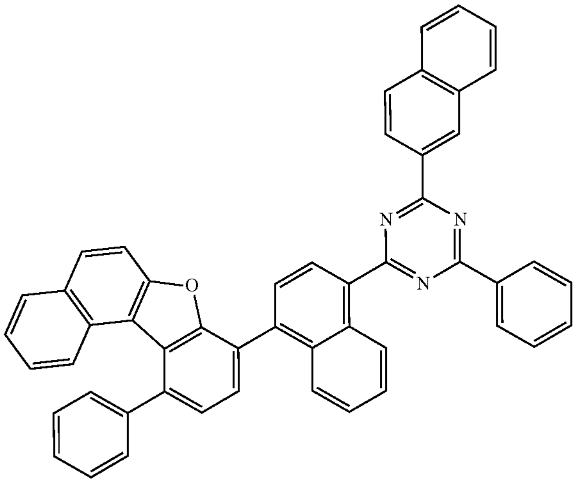
2-442
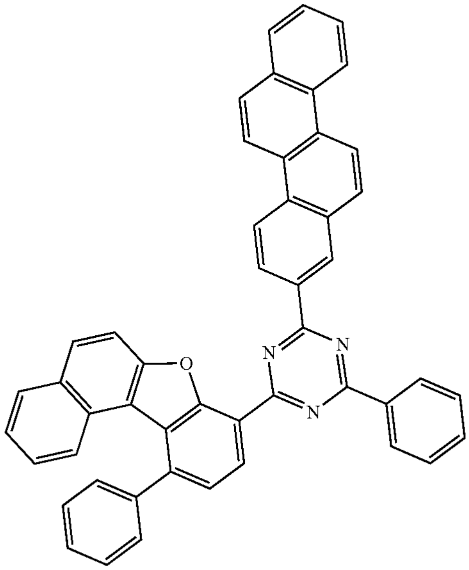

-continued
2-443
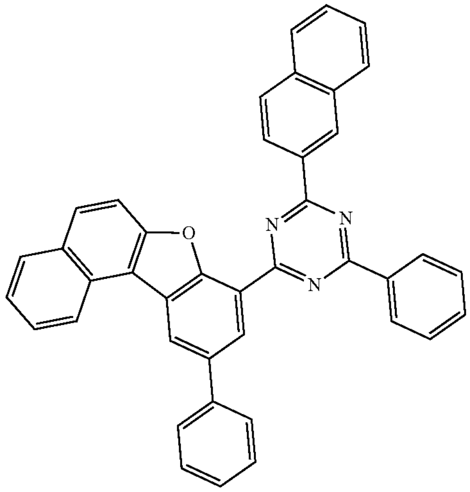
2-444
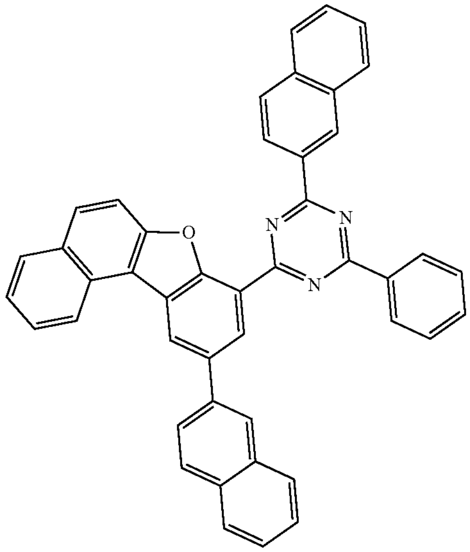
2-445
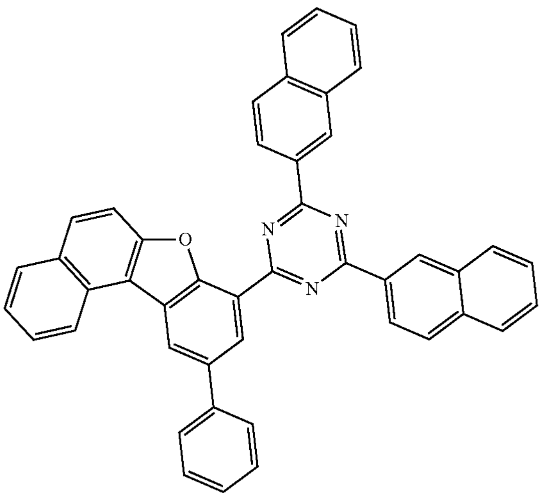
-continued
2-446
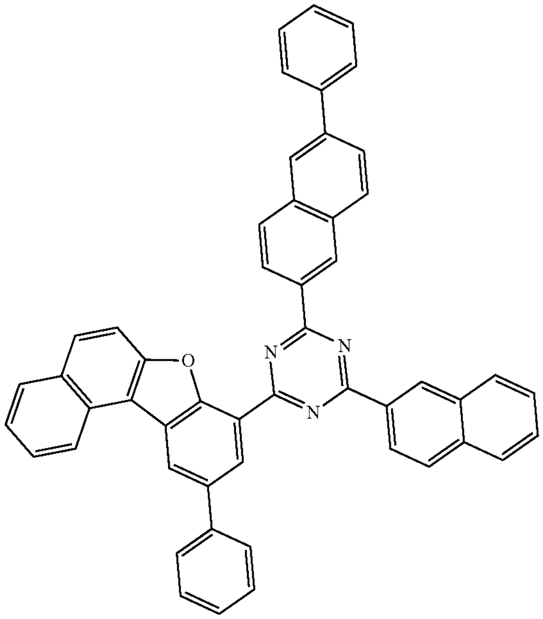
2-447
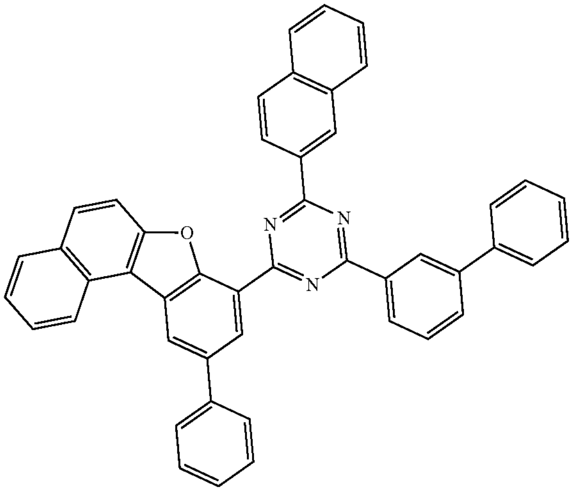

-continued
2-448
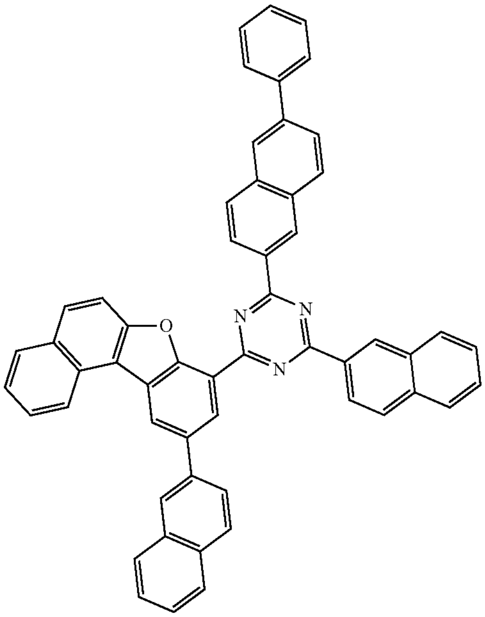
2-449
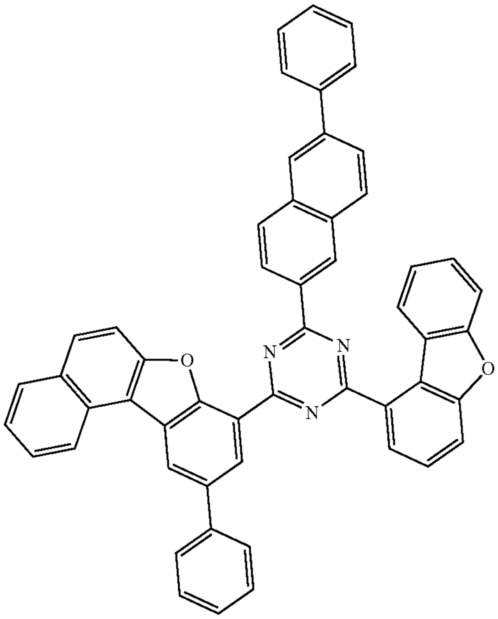
-continued
2-450
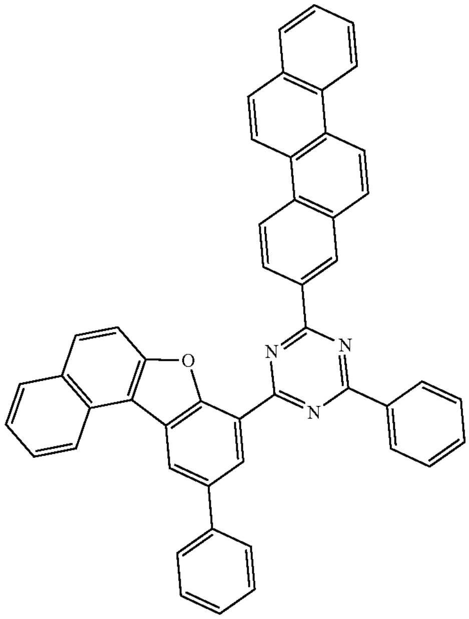
2-451
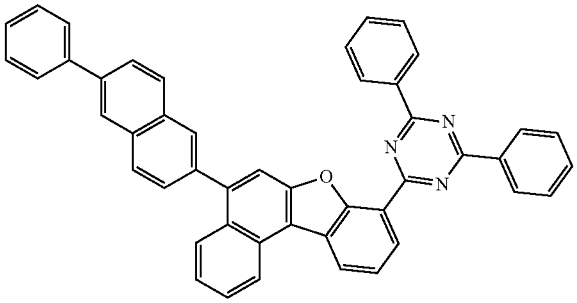
2-452
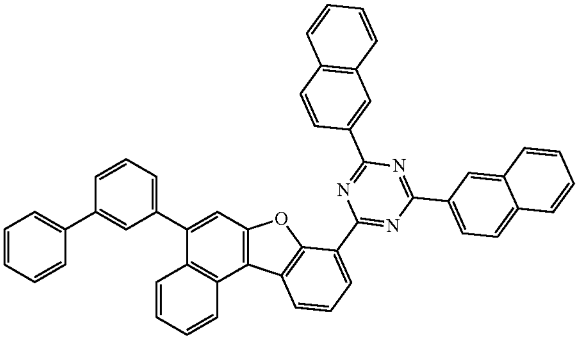

-continued
2-453
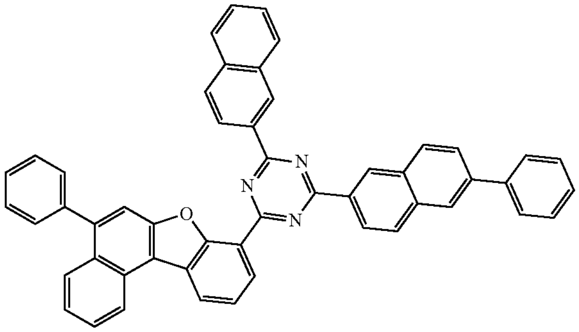
2-454
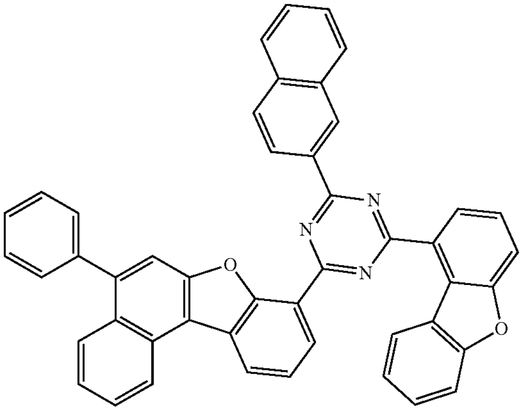
2-455
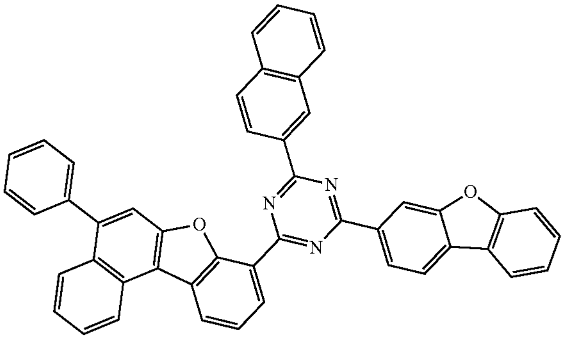
2-456
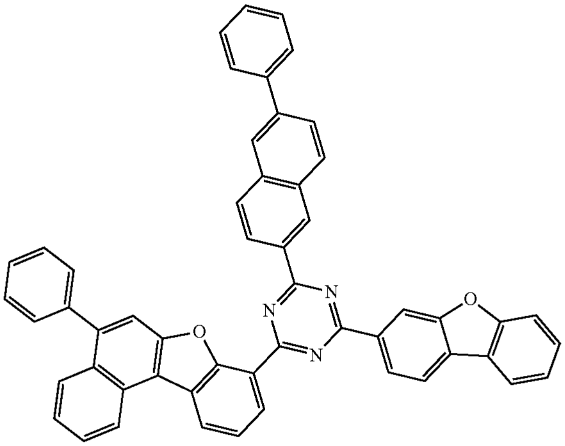
-continued
2-457
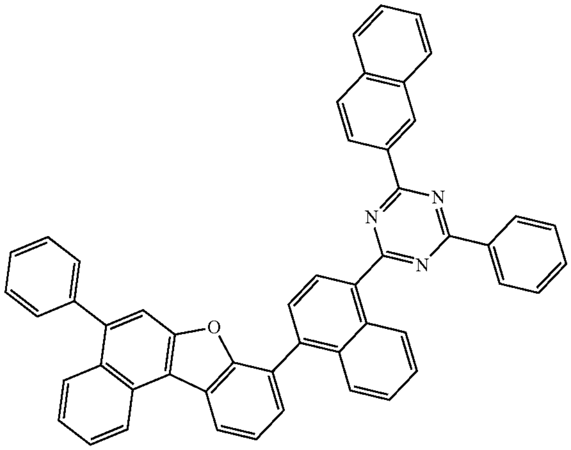
2-458
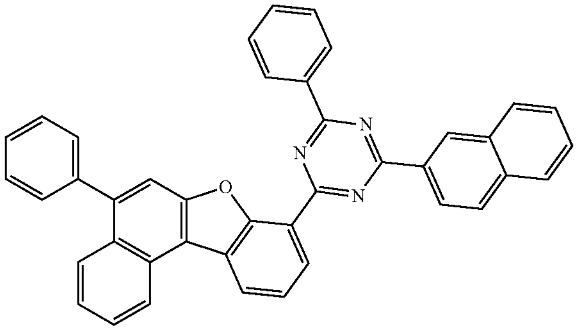
2-459
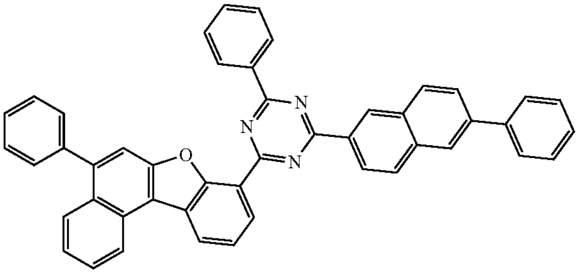
2-460
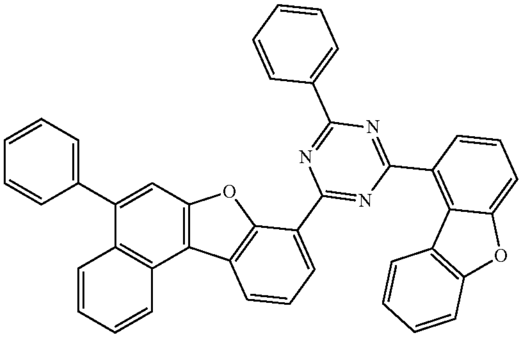

-continued
2-461
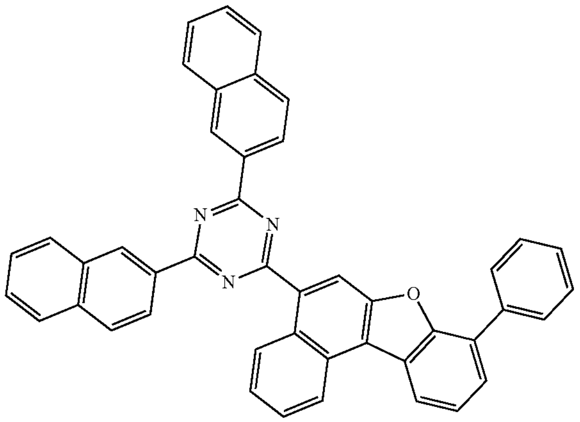
2-462
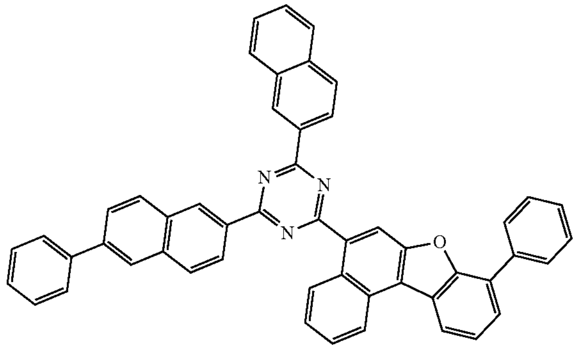
2-463
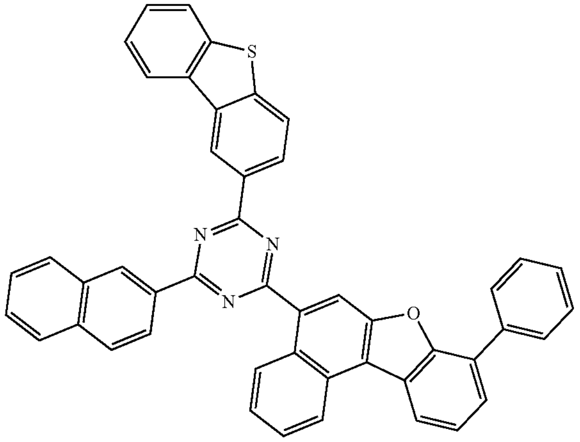
-continued
2-464
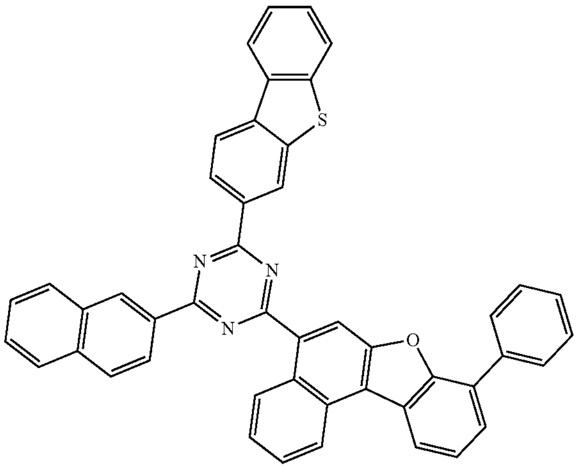
2-465
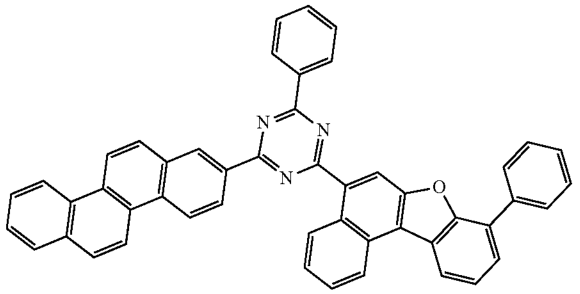
2-466
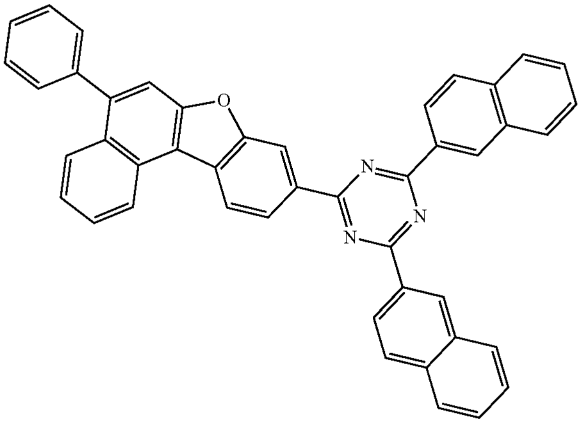

-continued
2-467
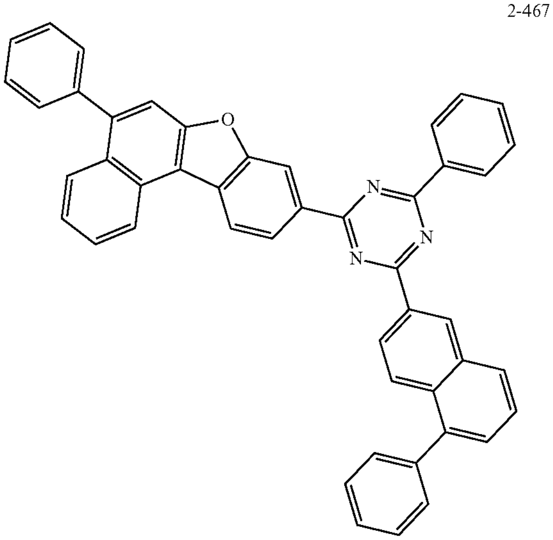
2-469
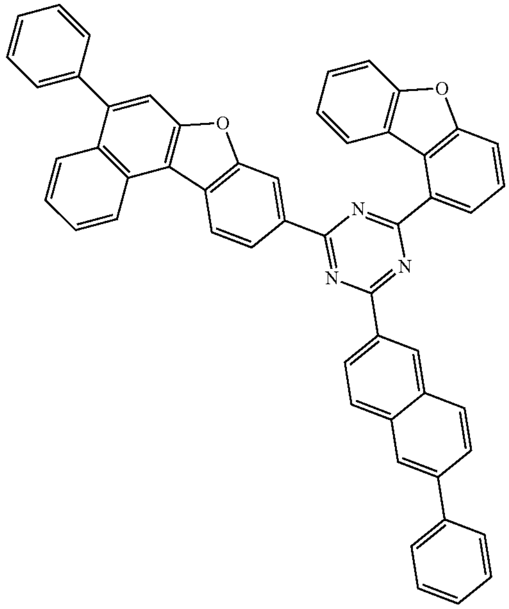
2-468
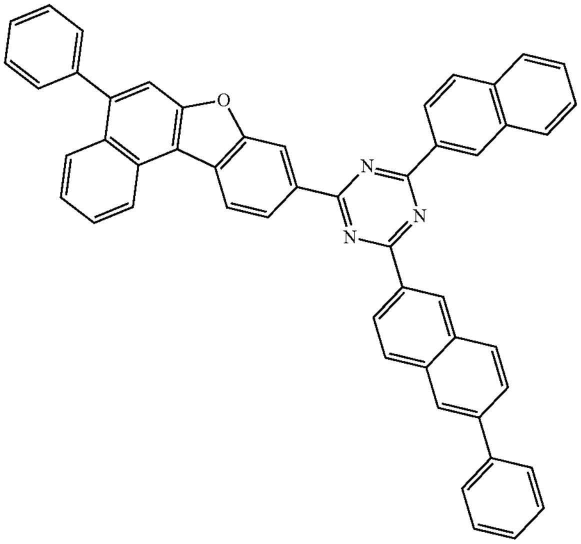
2-470
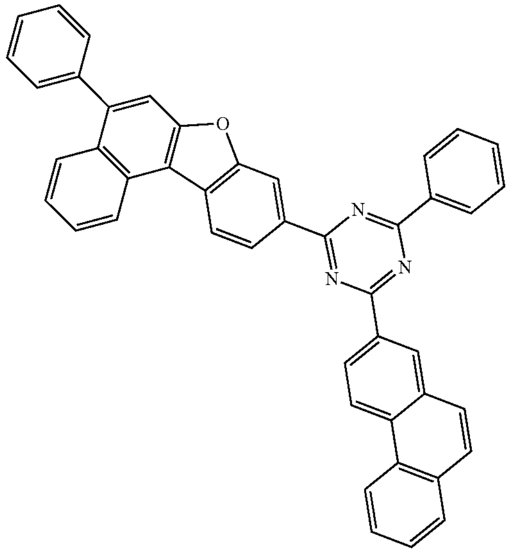

-continued
2-471
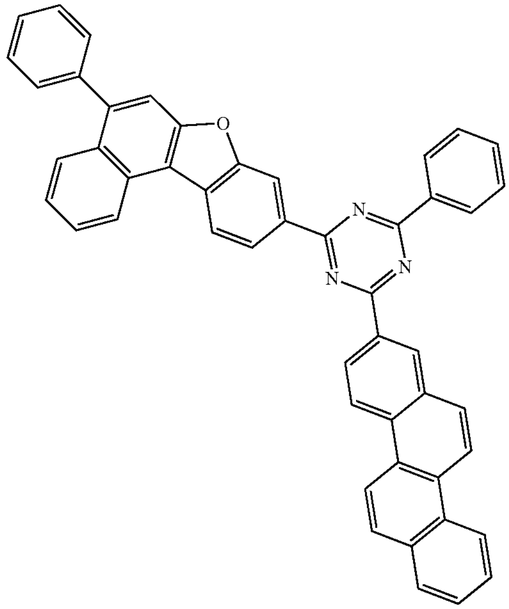
2-472
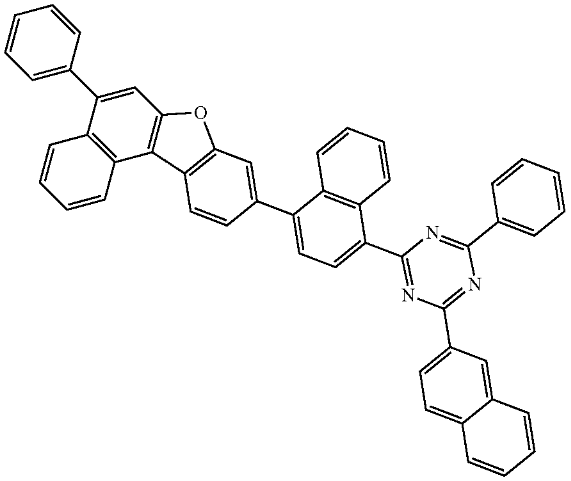
2-473
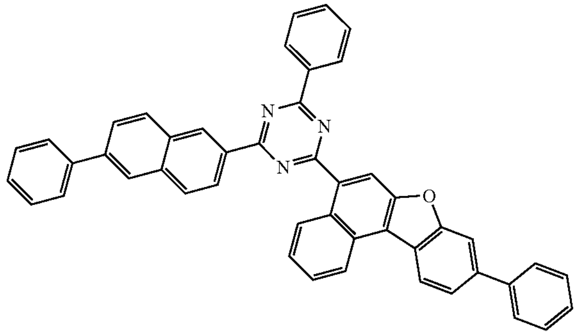
-continued
2-474
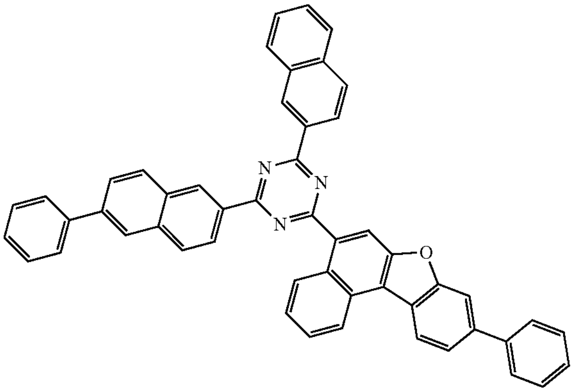
2-475
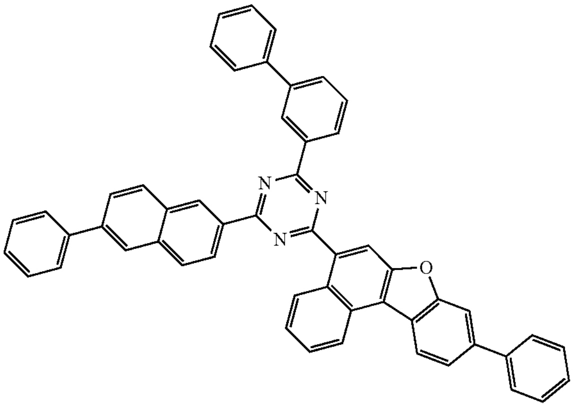
2-476
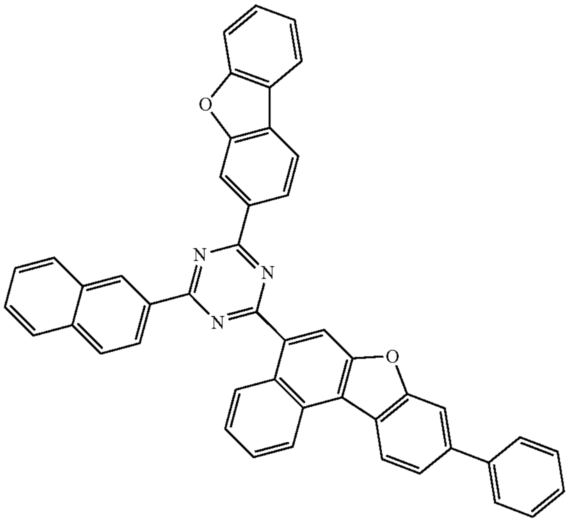

-continued
2-477
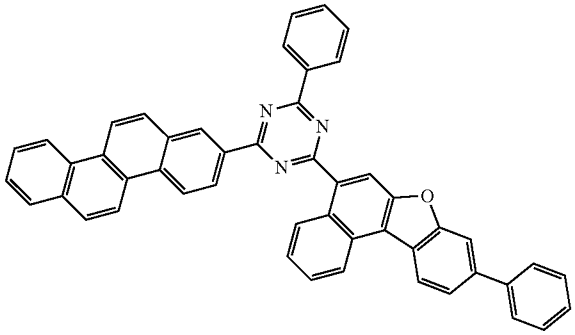
2-478
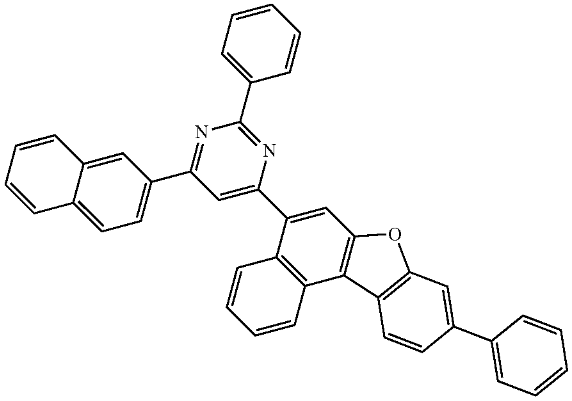
2-479
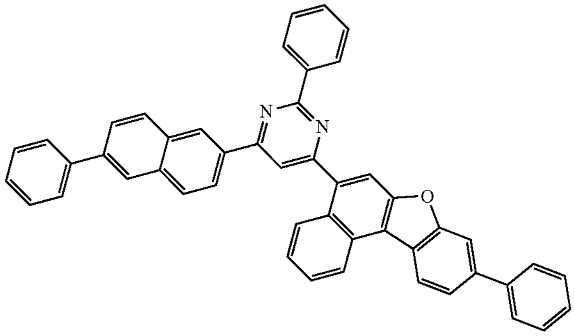
-continued
2-480
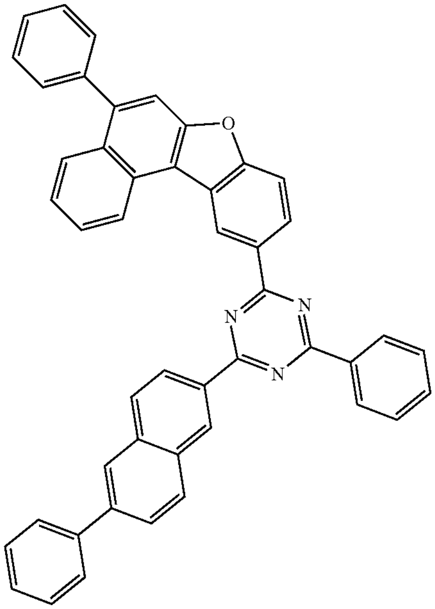
2-481
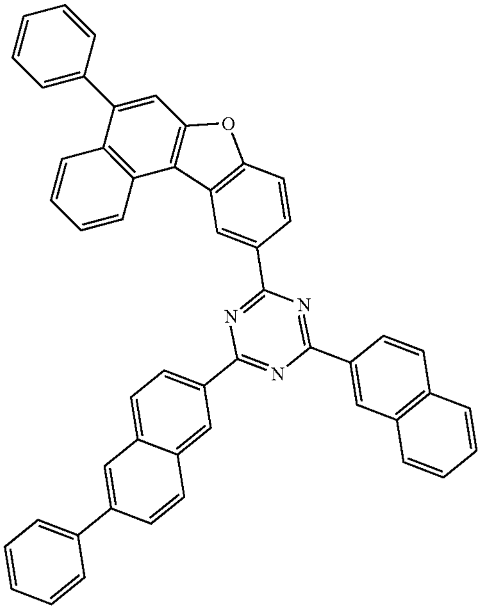

-continued
2-482
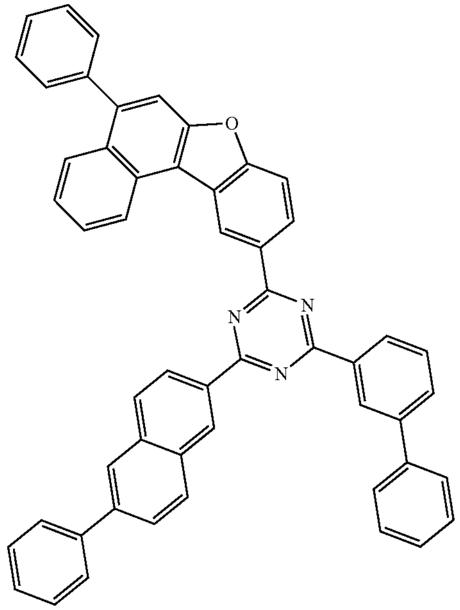
2-483
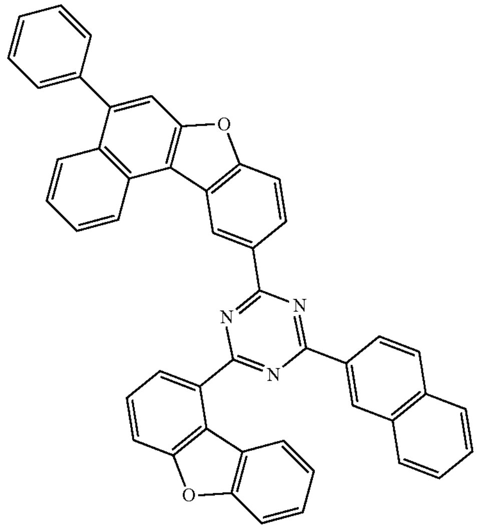
-continued
2-484
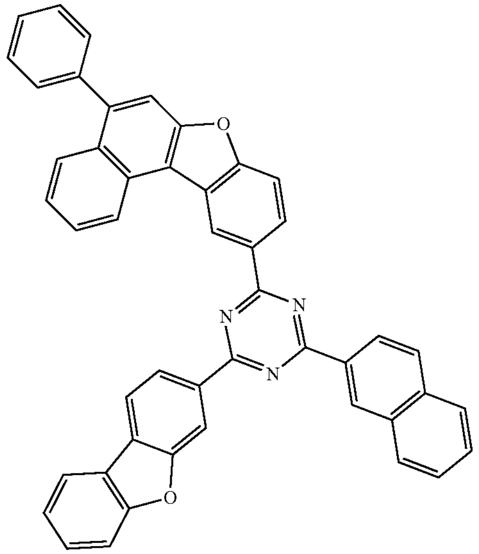
2-485
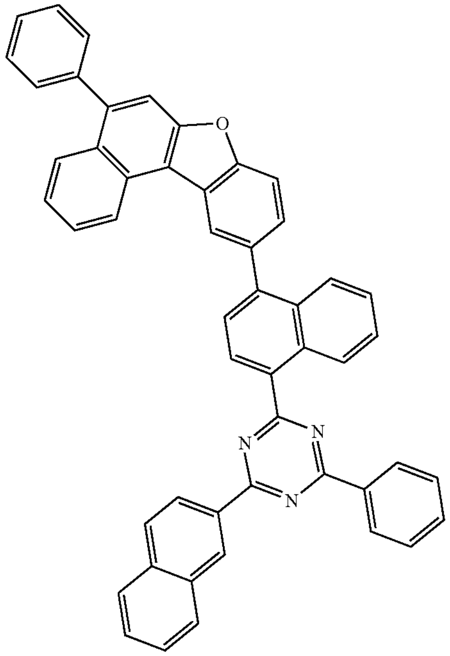

-continued
2-486
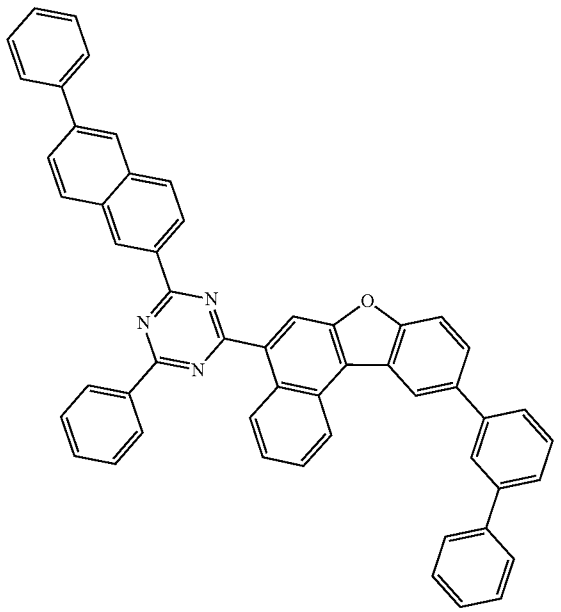
2-487
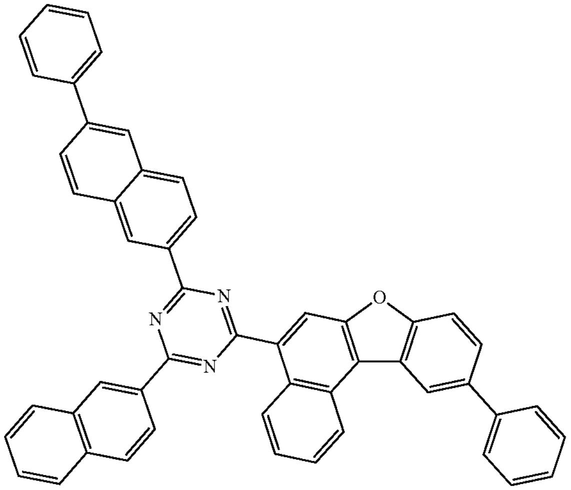
2-488
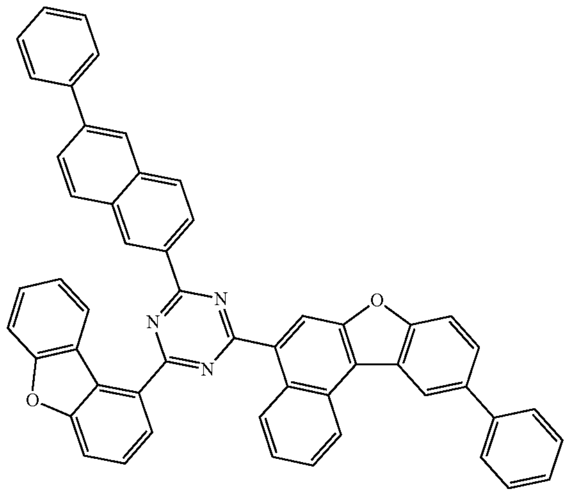
-continued
2-489
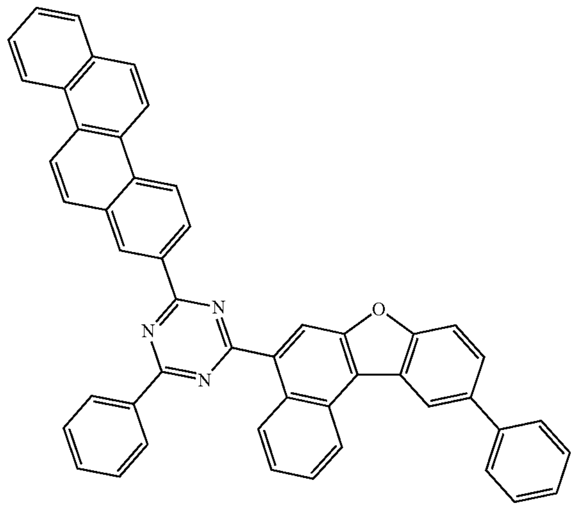
2-490
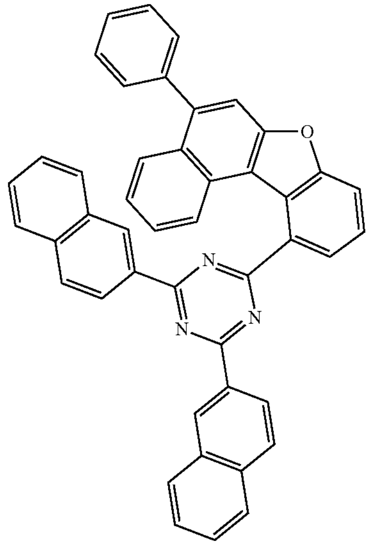

-continued
2-491
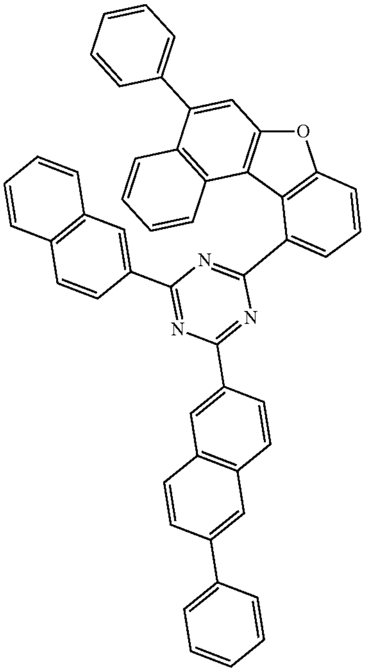
2-492
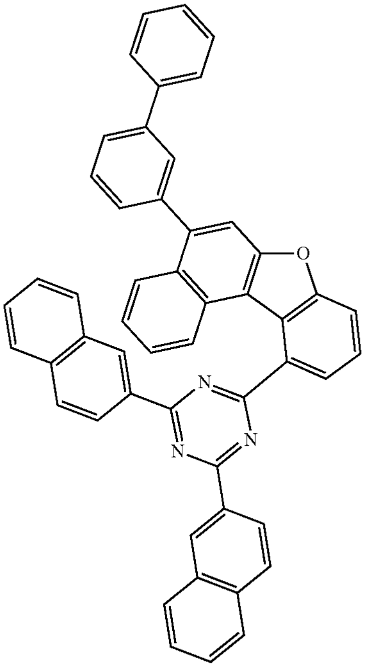
-continued
2-493
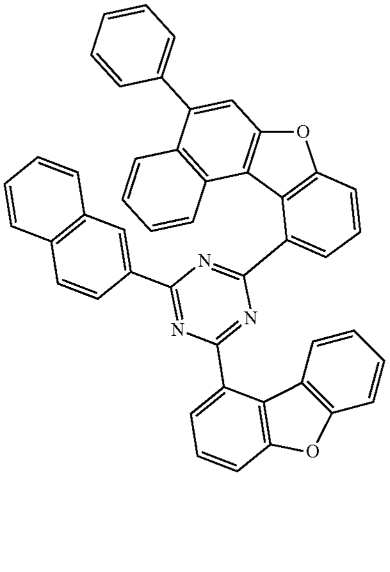
2-494
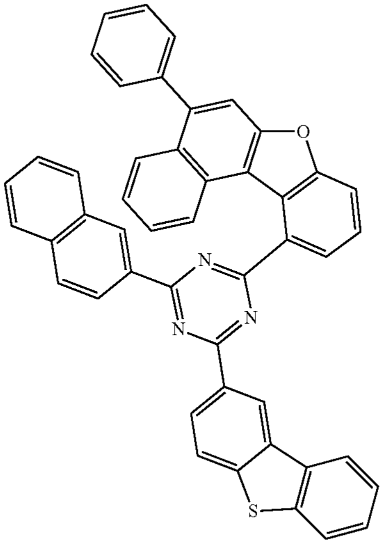

-continued
2-495
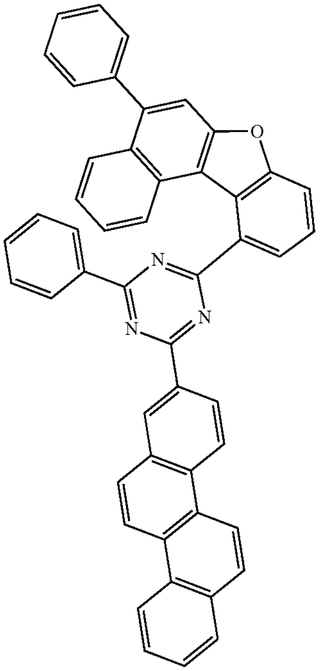
2-496
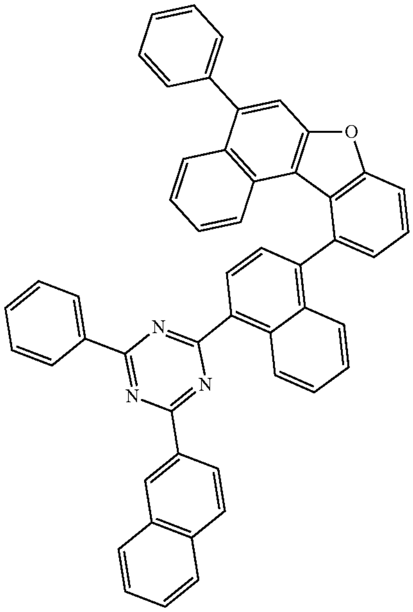
2-497
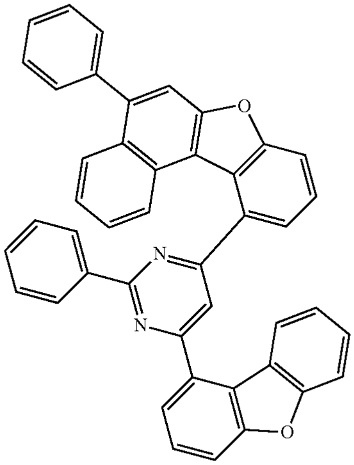
2-498
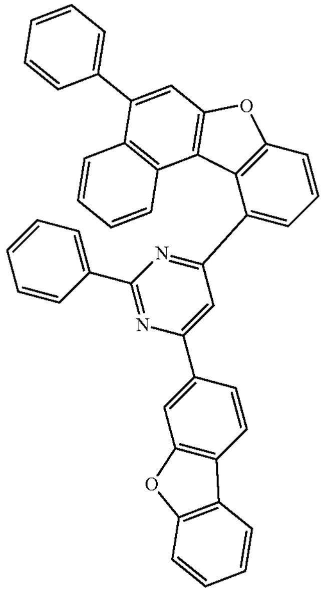
2-499
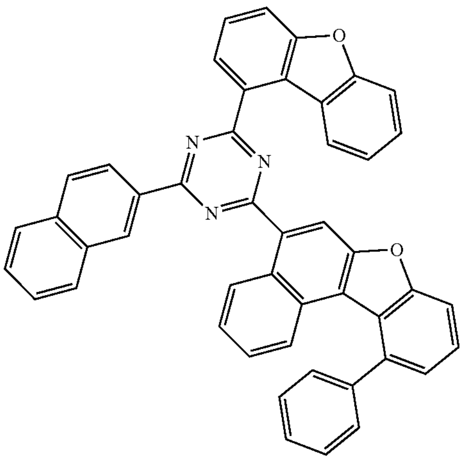

-continued
2-500
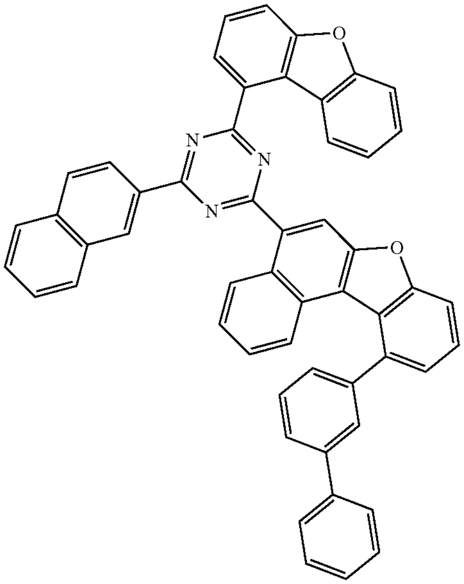
2-501
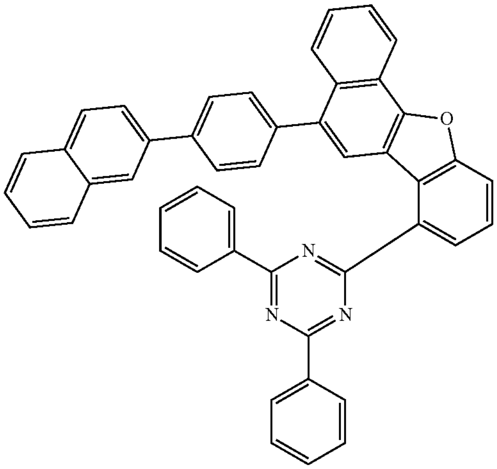
2-502
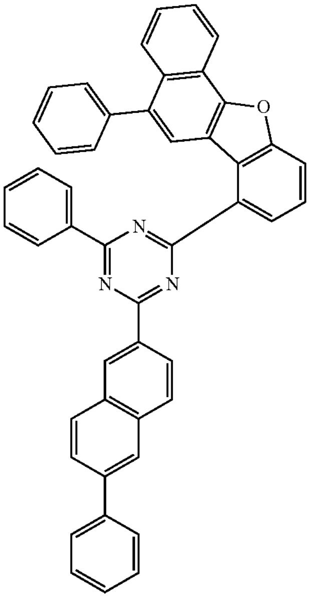
-continued
2-503
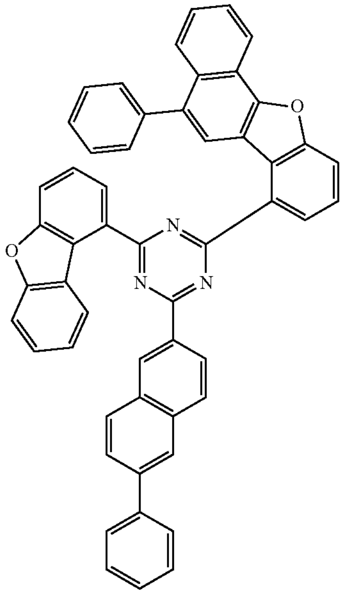
2-504
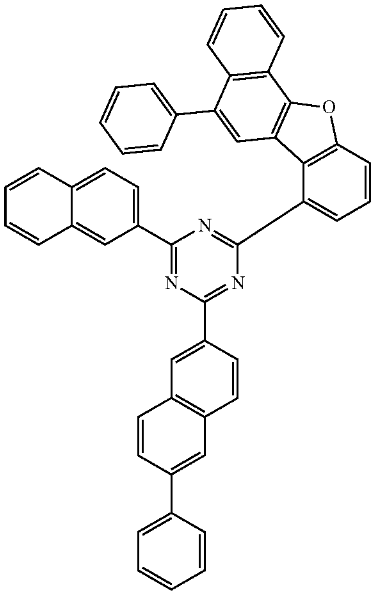

-continued
2-505
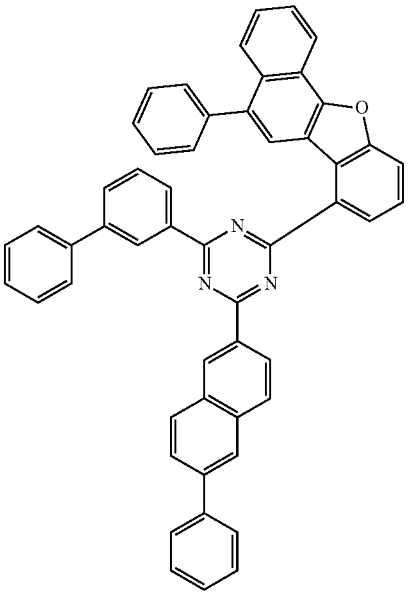
2-506
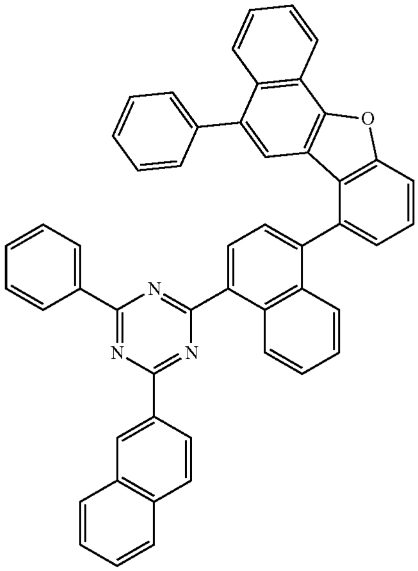
-continued
2-507
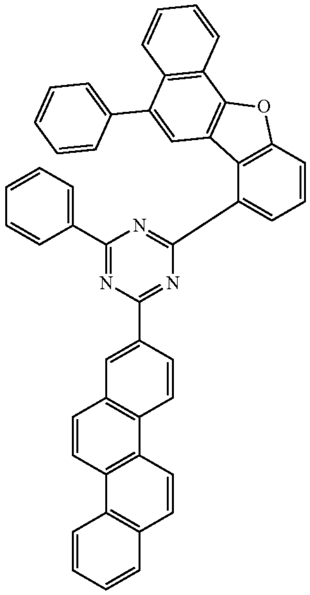
2-508
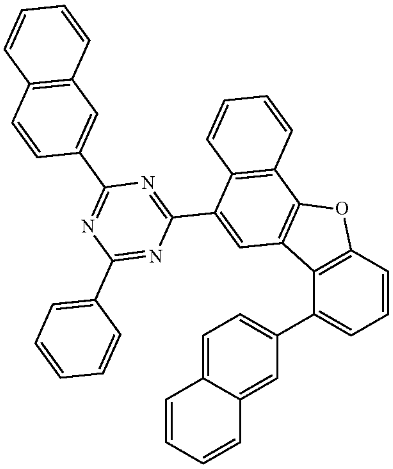
2-509
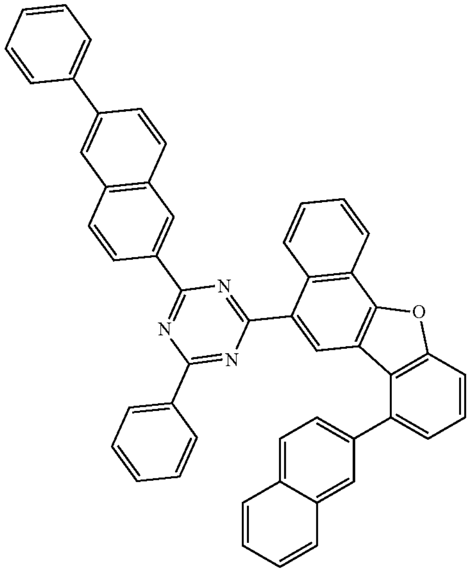

-continued
2-510
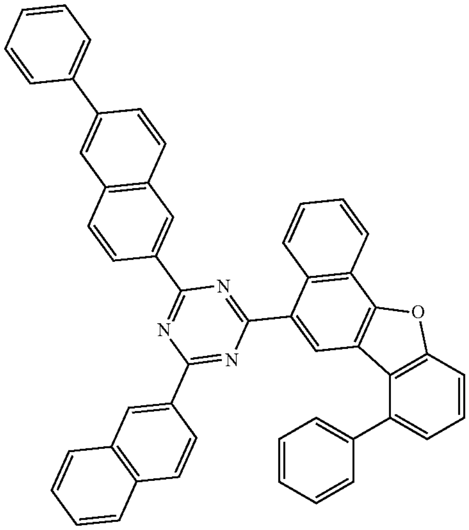
2-511
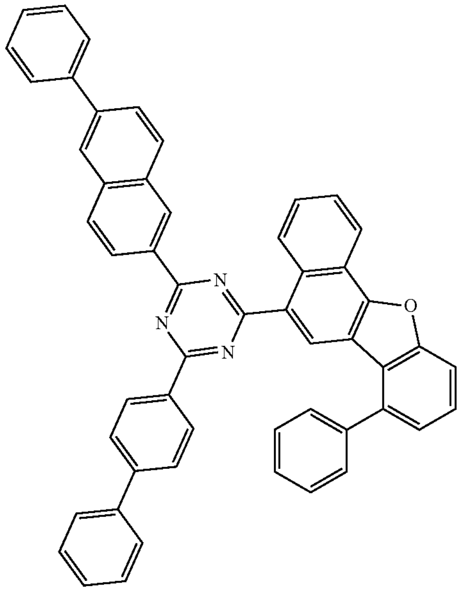
2-512
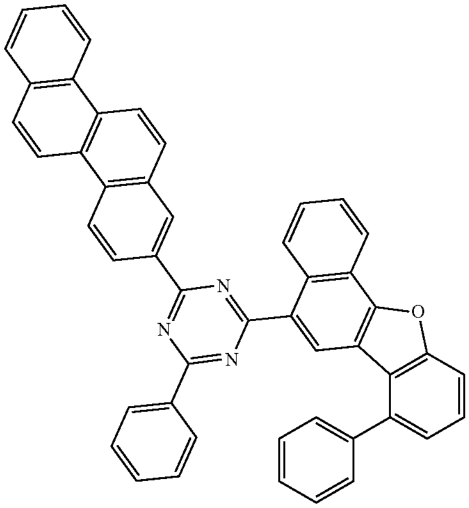
-continued
2-513
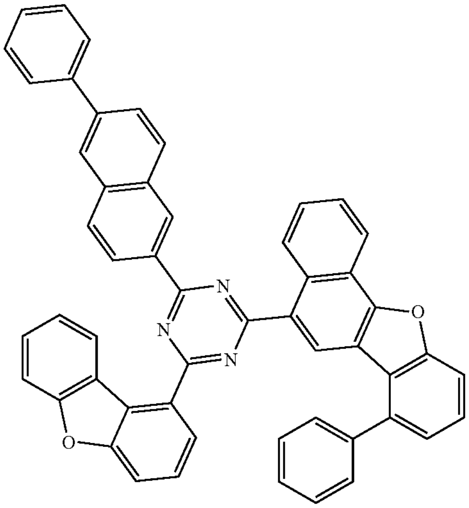
2-514
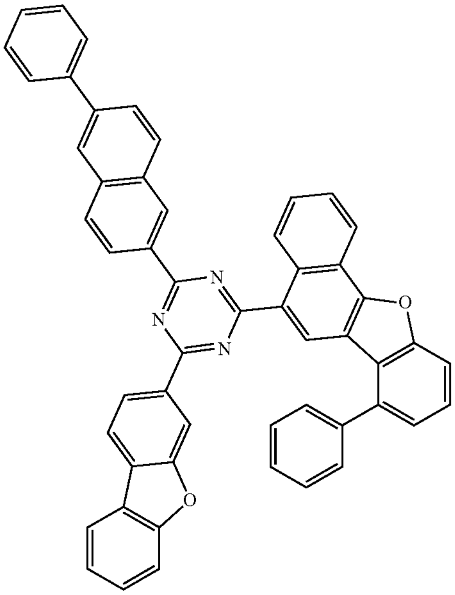
2-515
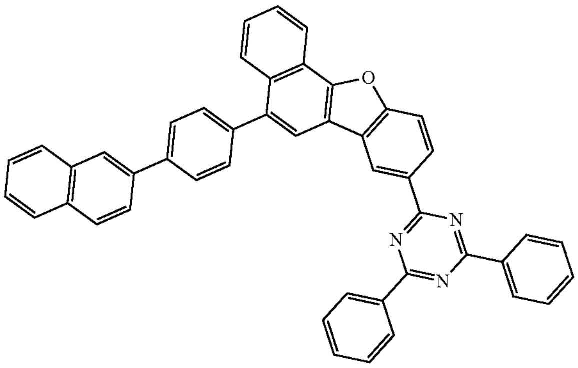

2-516
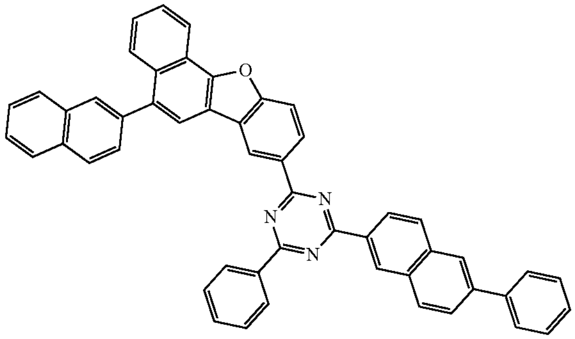
2-517
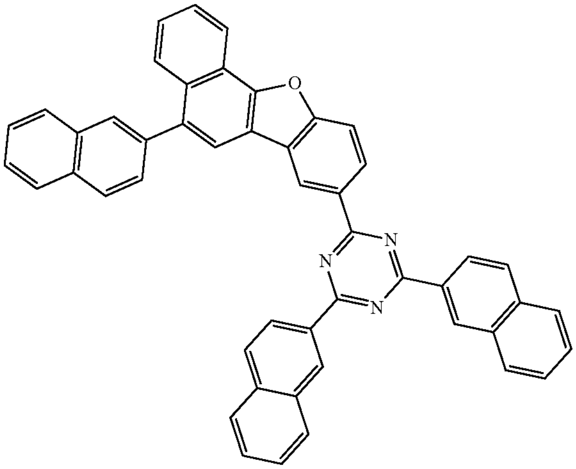
2-518
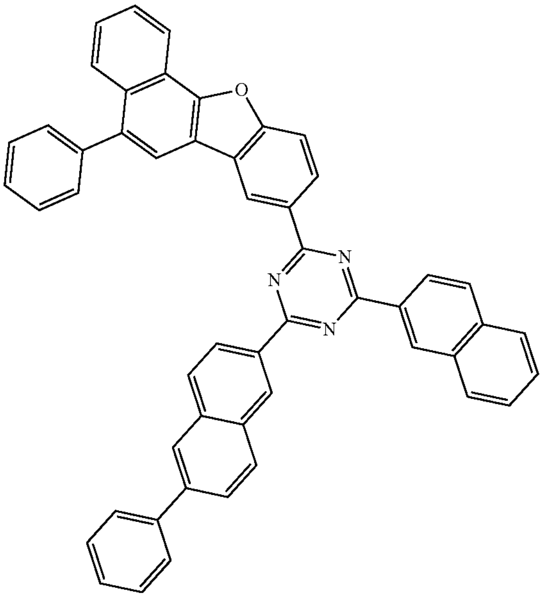
2-519
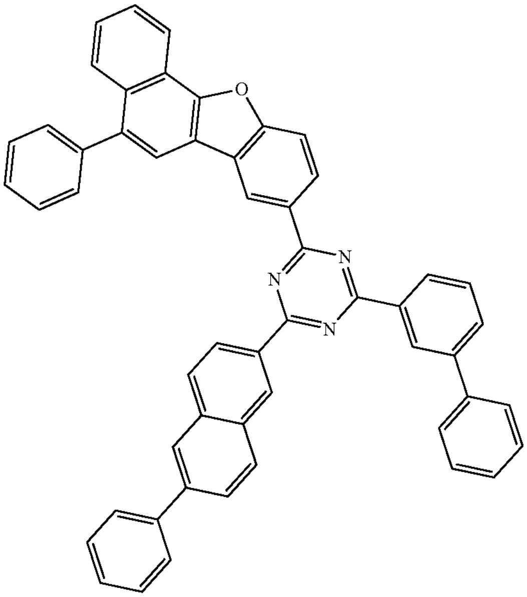
2-520
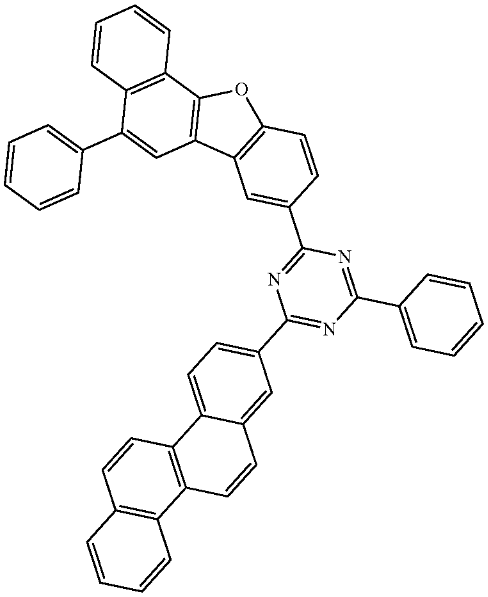

-continued
2-521
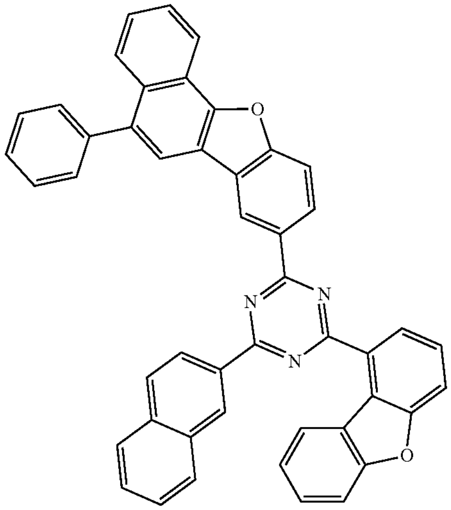
2-523
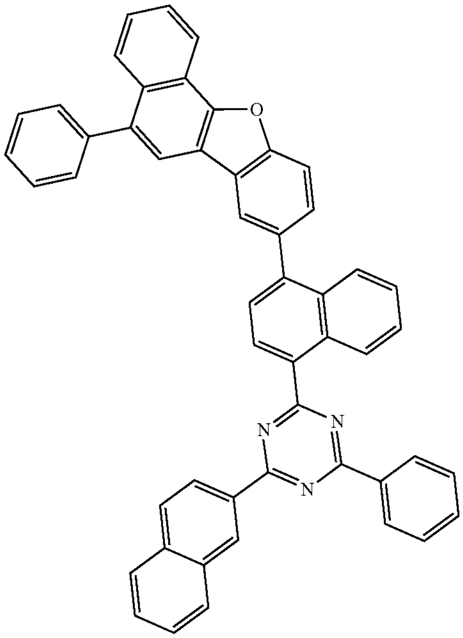
2-522
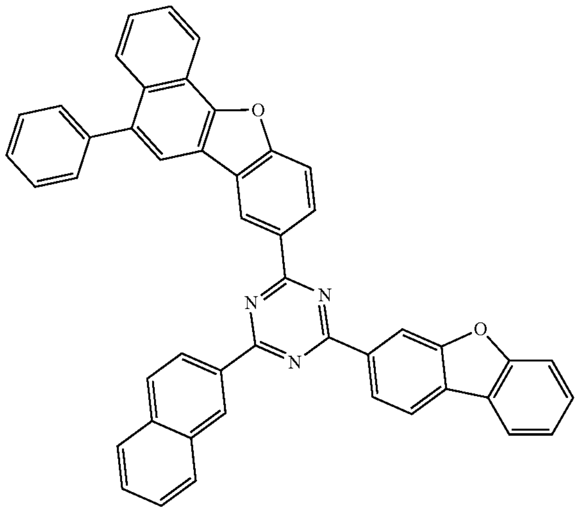
2-524
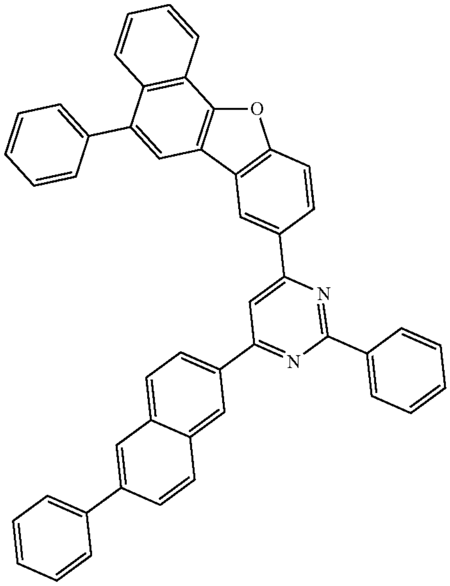

-continued
2-525
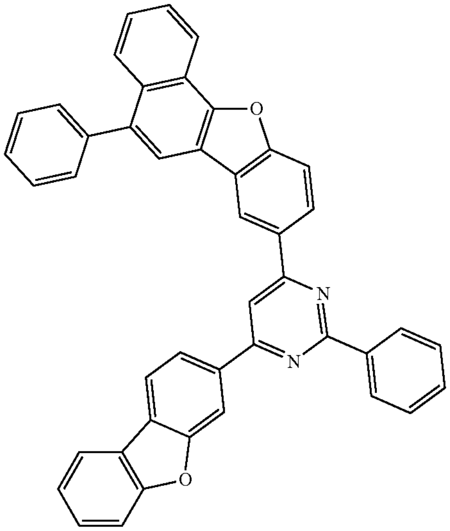
2-527
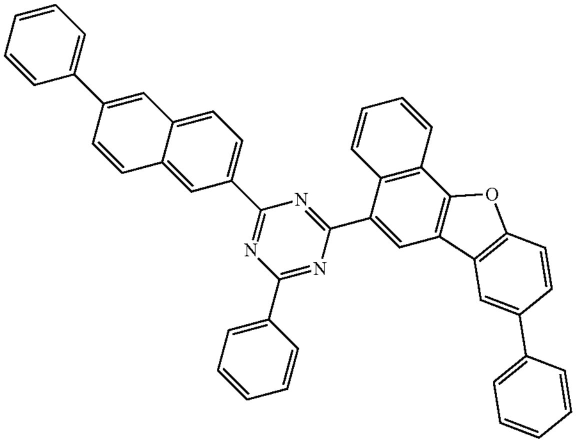
2-528
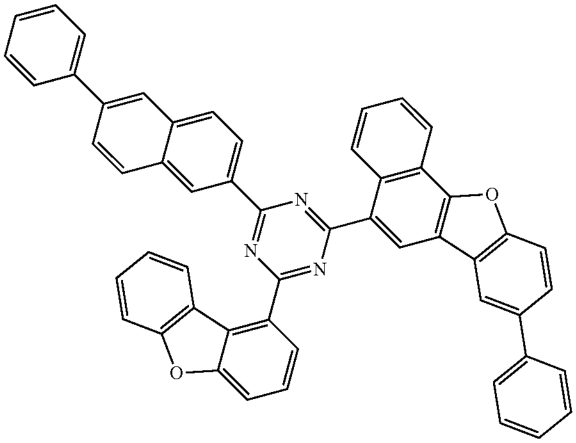
-continued
2-529
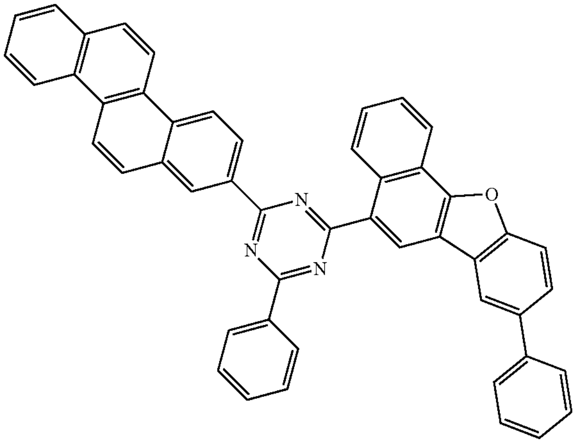
2-530
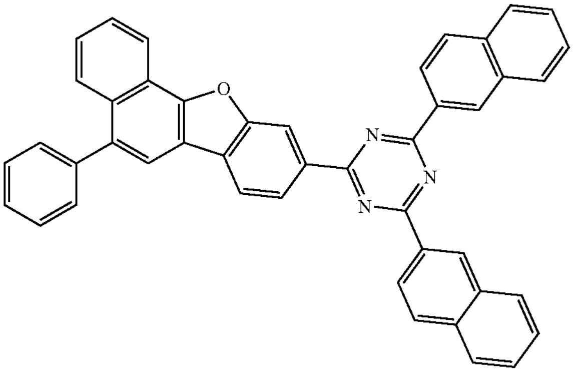
2-531
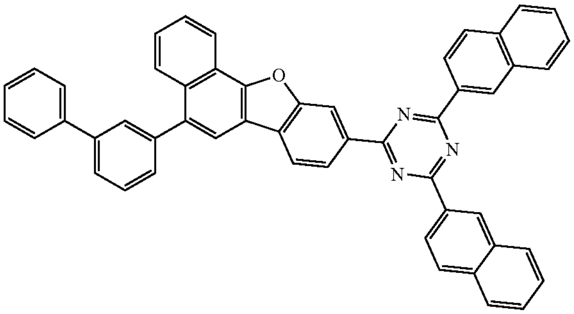

-continued
2-532
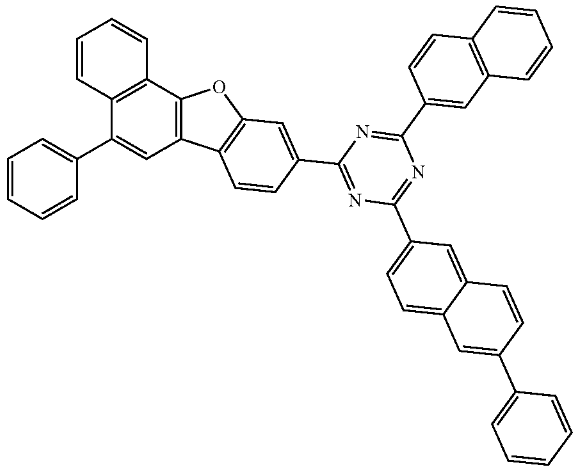
2-533
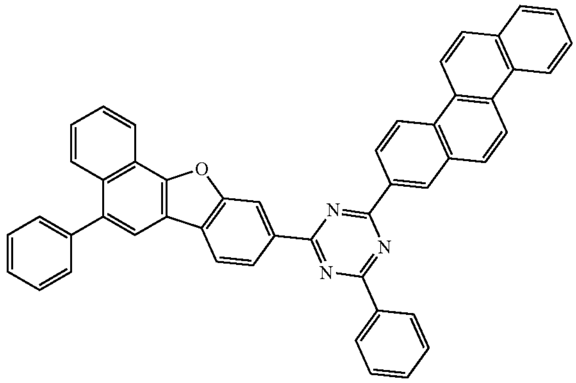
2-534
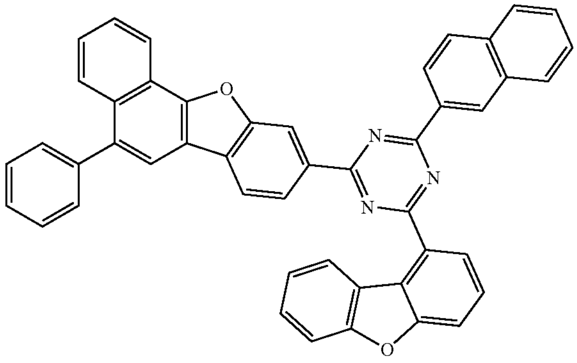
-continued
2-535
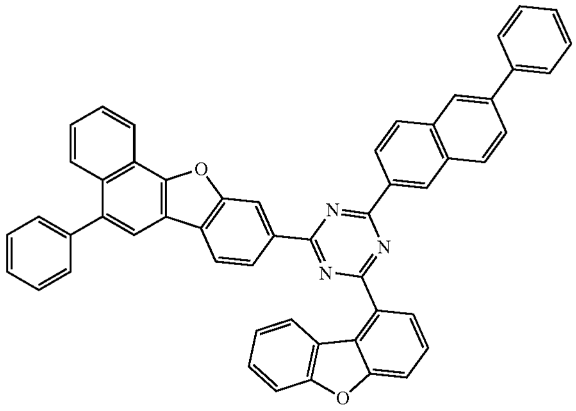
2-536
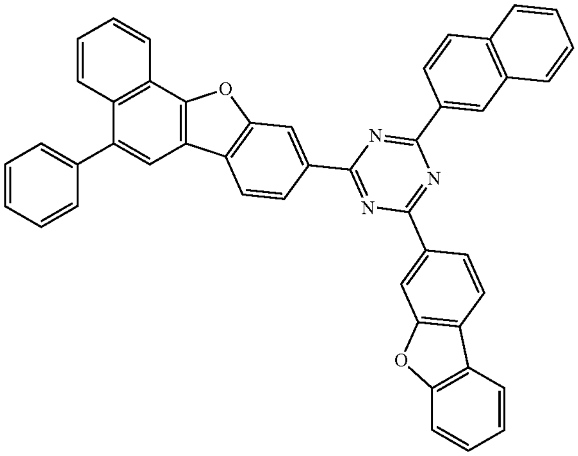
2-537
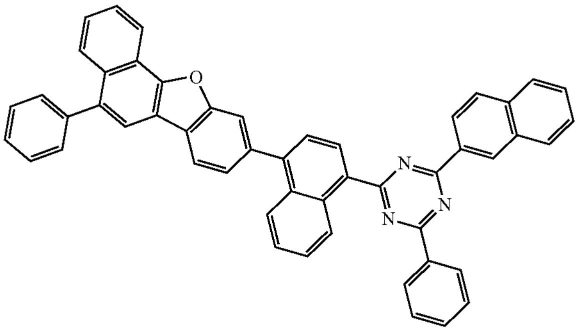
2-538
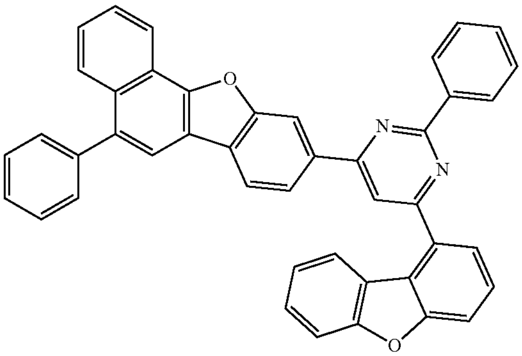

-continued
2-539
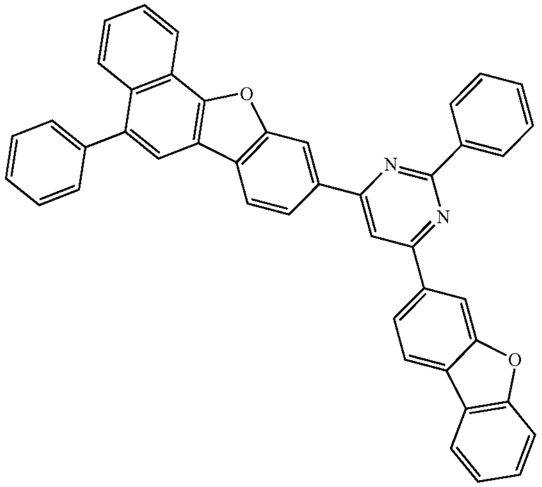
2-540
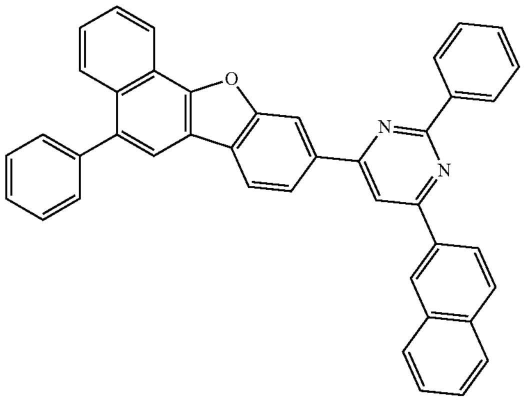
2-541
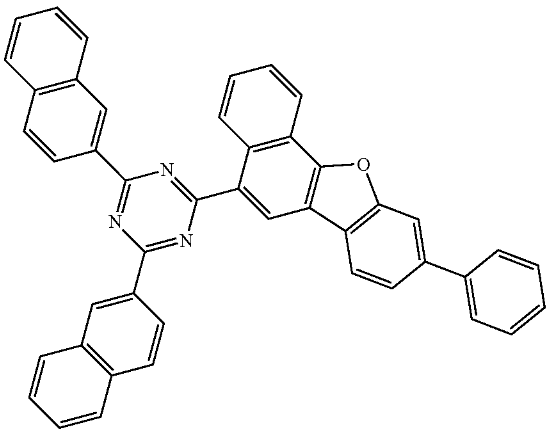
-continued
2-542
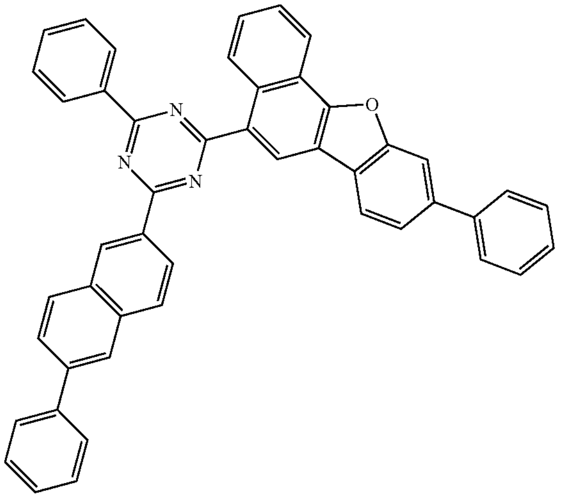
2-543
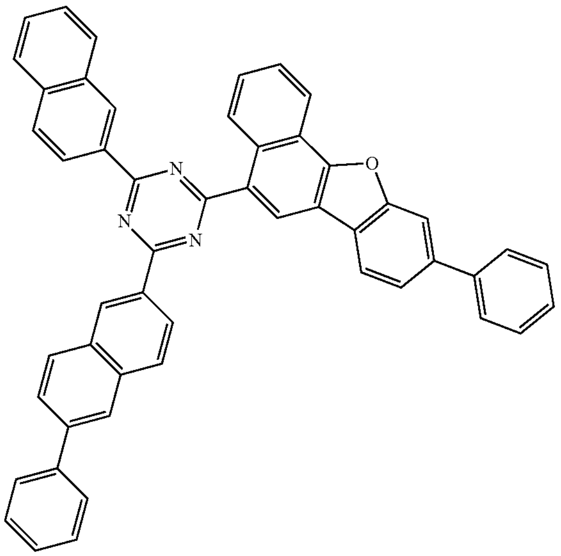
2-544
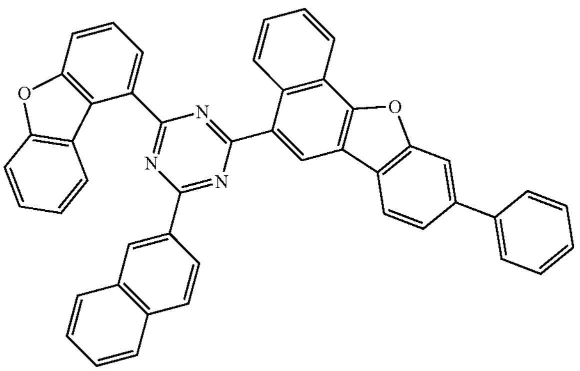

-continued
2-545
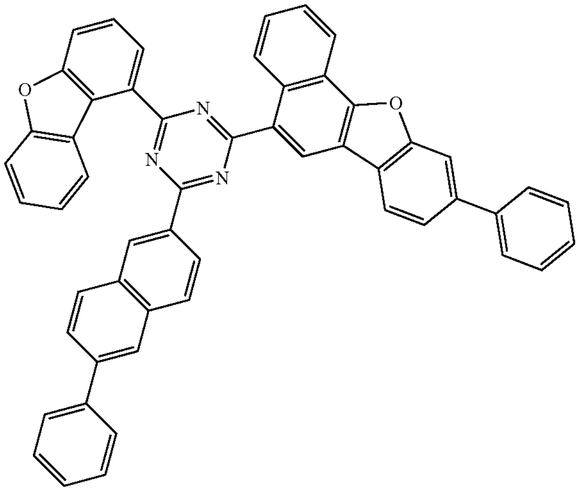
2-546
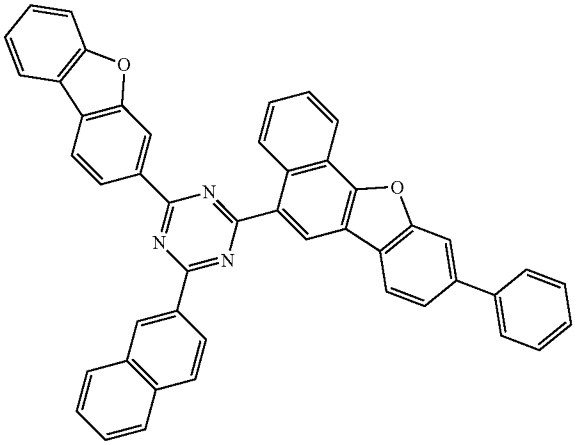
2-547
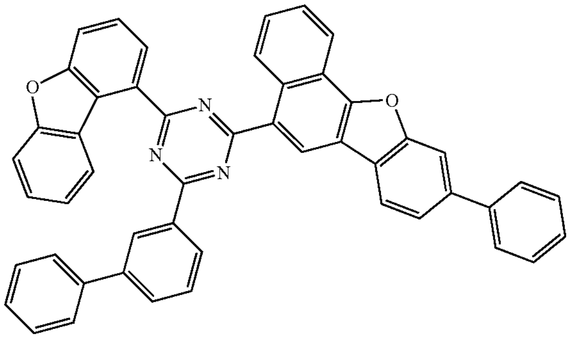
-continued
2-548
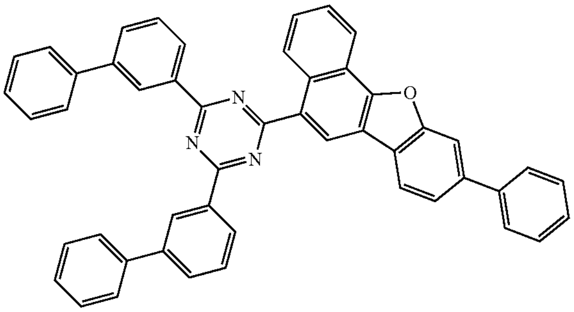
2-549
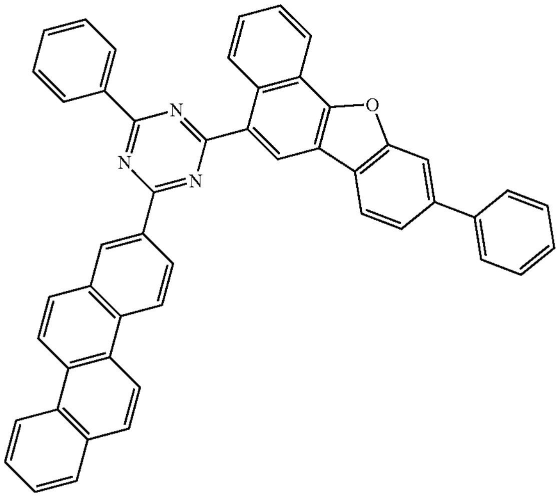
2-550
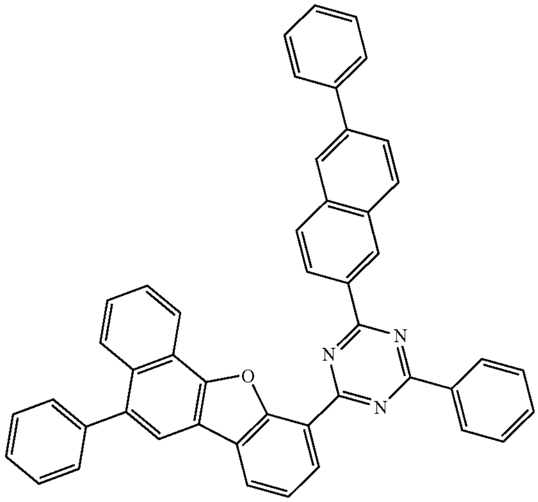

-continued
2-551
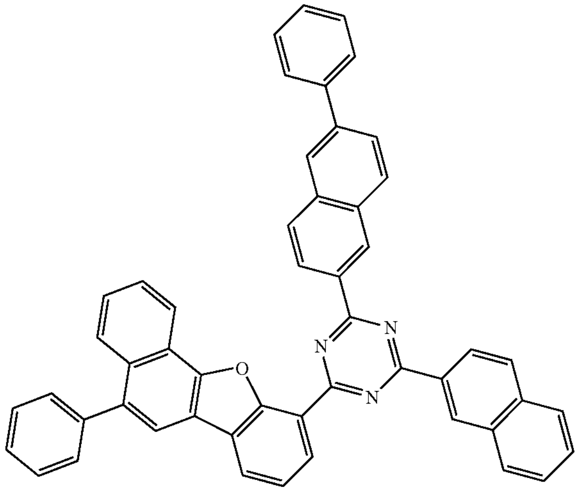
2-552
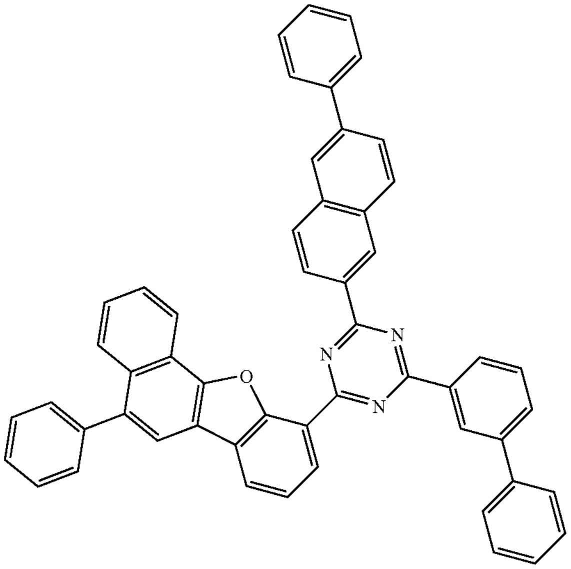
2-553
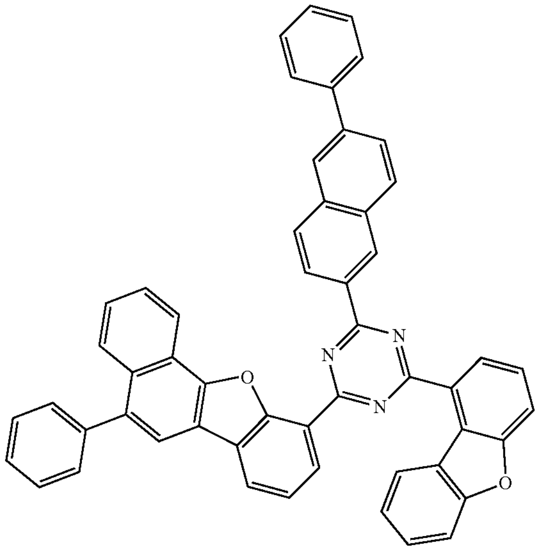
2-554
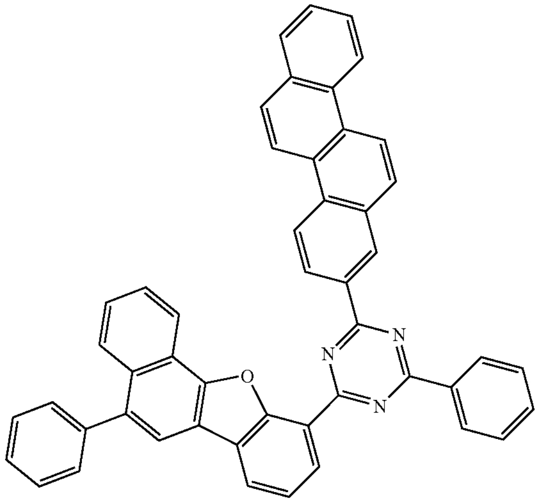
2-555
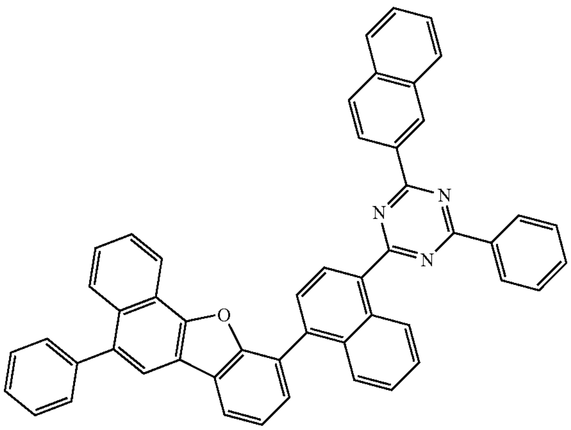

-continued
2-556
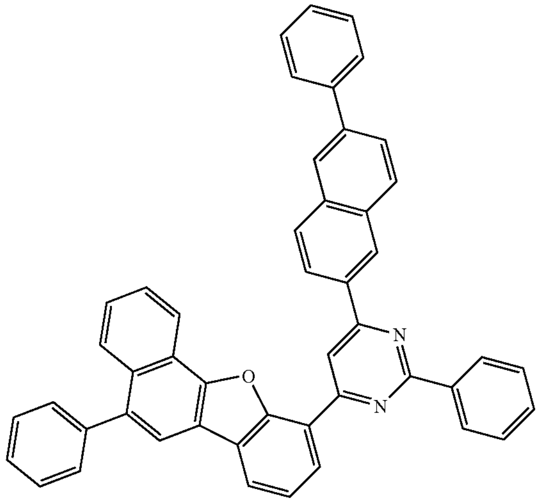
2-557
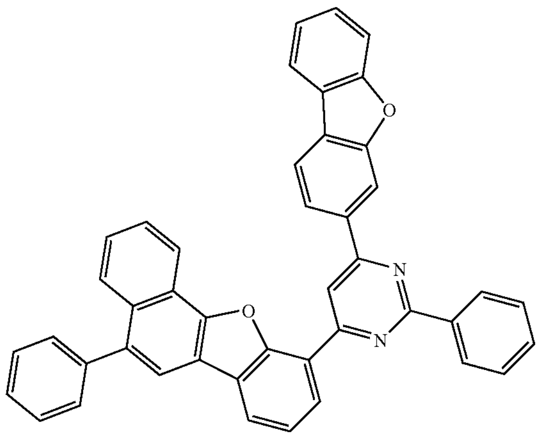
2-558
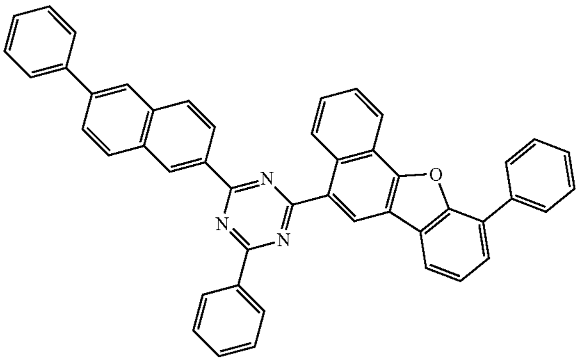
-continued
2-559
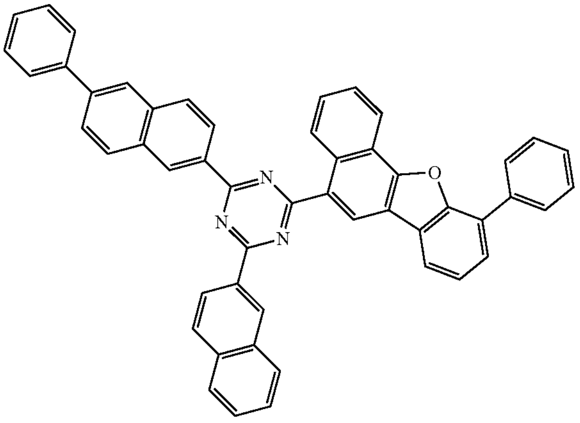
2-560
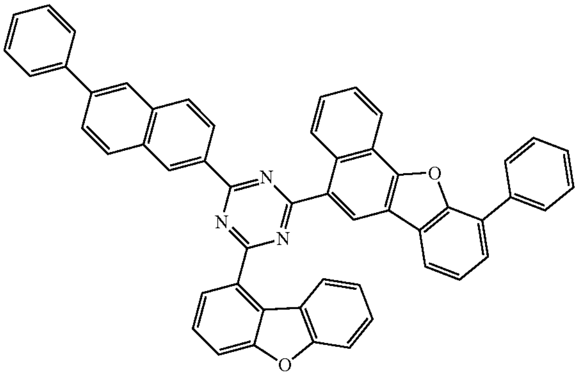
2-561
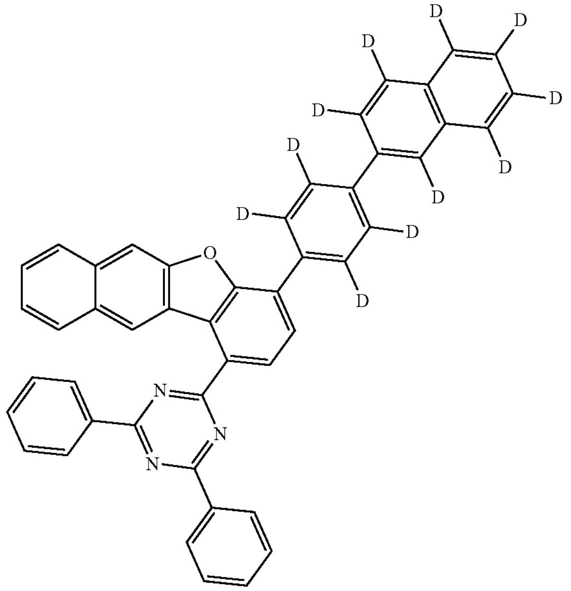

-continued
2-562
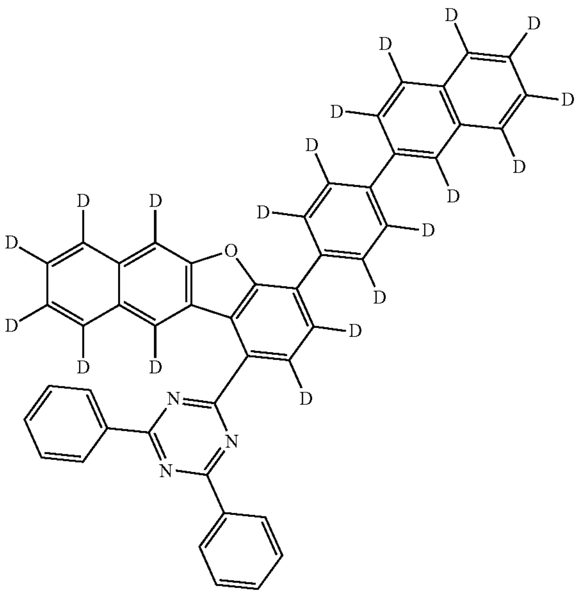
2-563
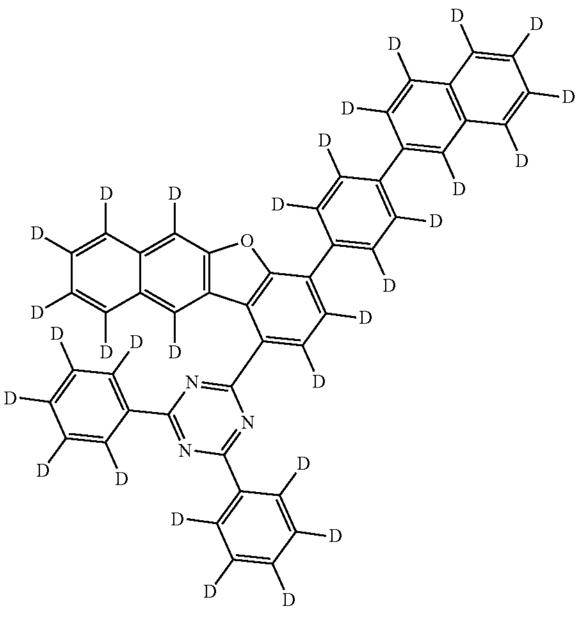
-continued
2-564
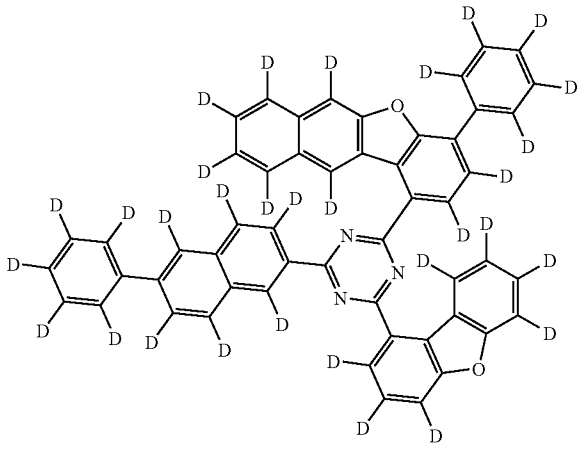
2-565
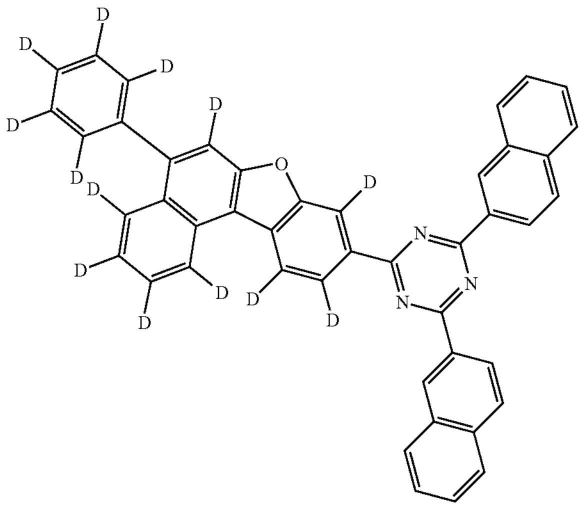
2-566
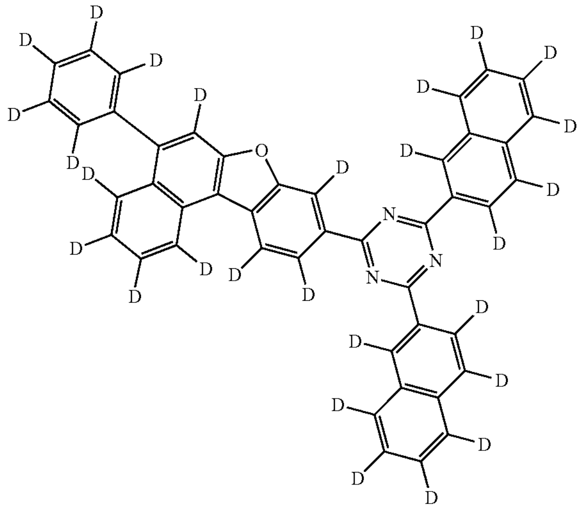

-continued
2-567
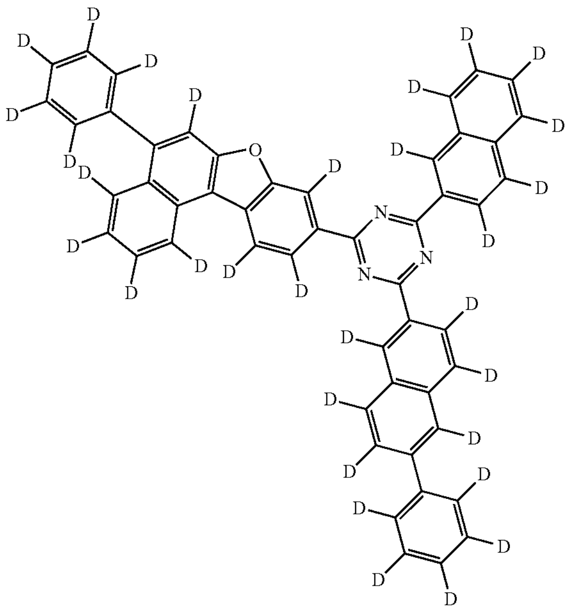
2-568
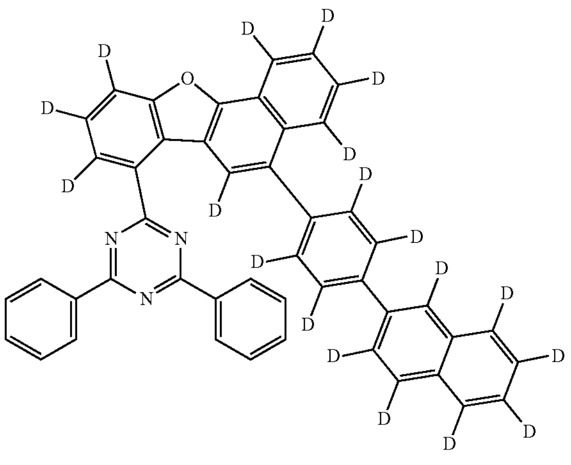
-continued
2-569
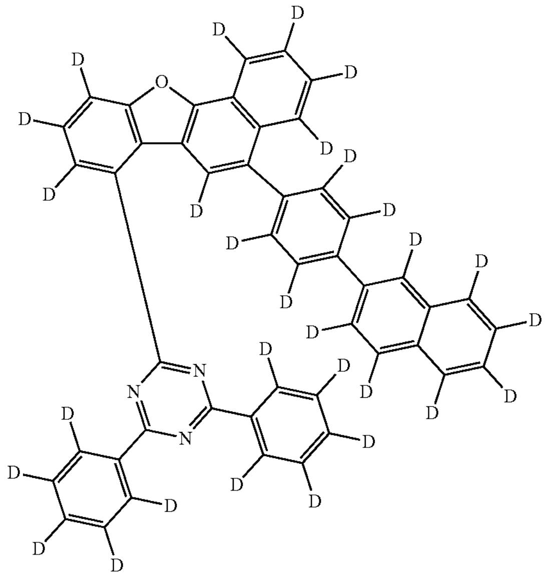
2-570
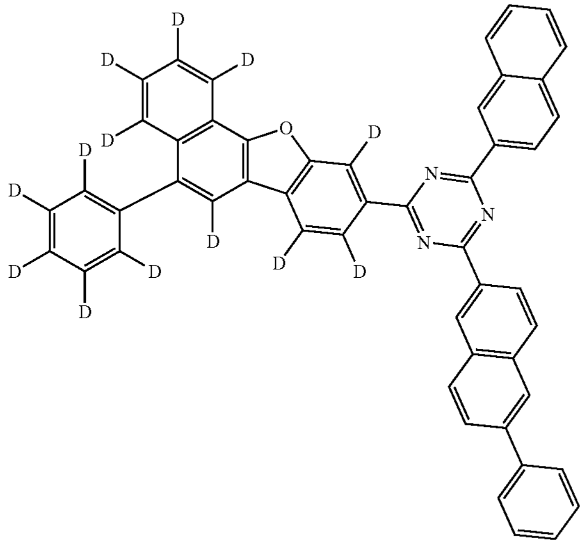

-continued
2-571
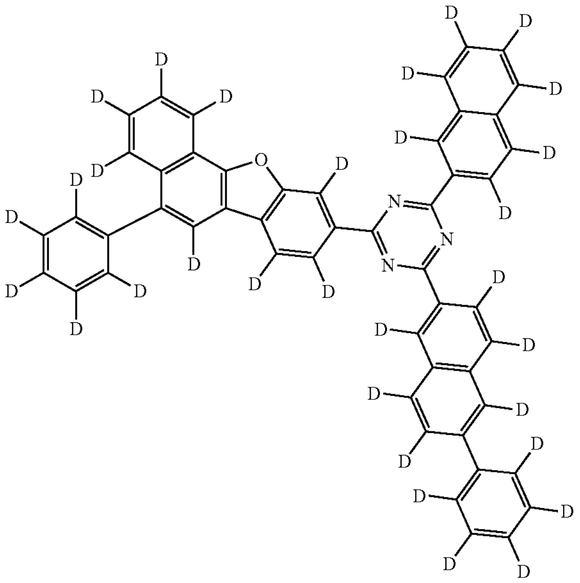
2-572
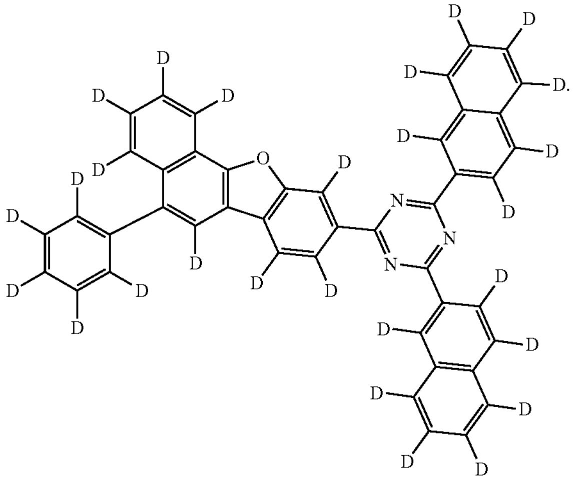
10. The organic light emitting device of claim 8, wherein the heterocyclic compound of Chemical Formula B is represented by any one of the following compounds:
3-1
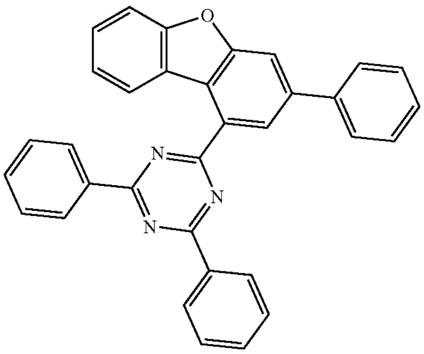
-continued
3-2
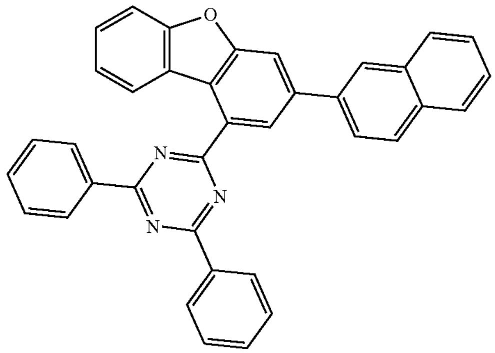
3-3
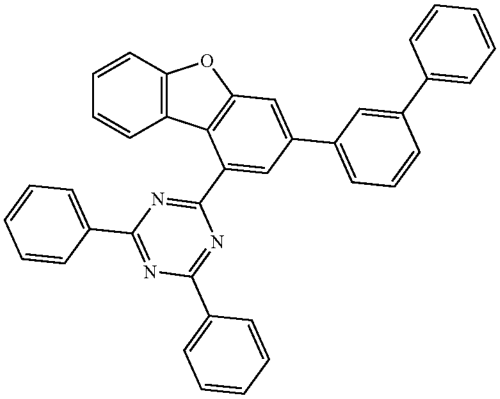
3-4
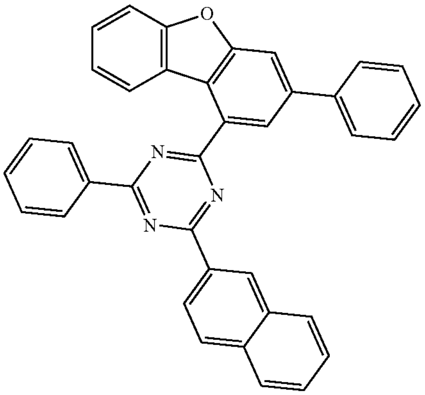
3-5
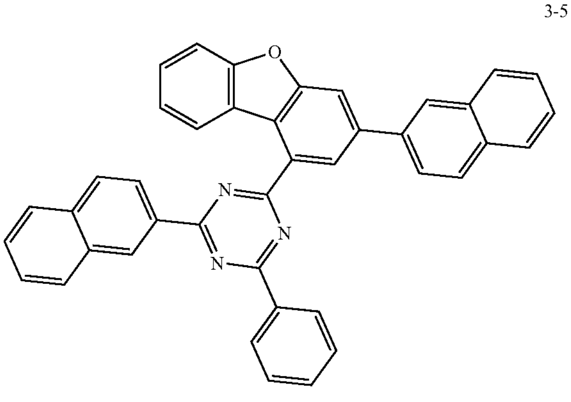

-continued
3-6
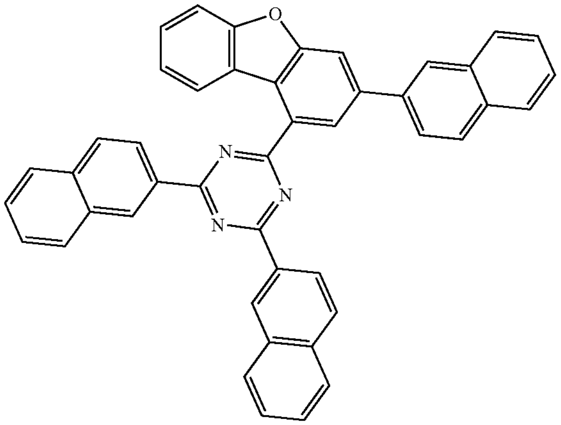
3-7
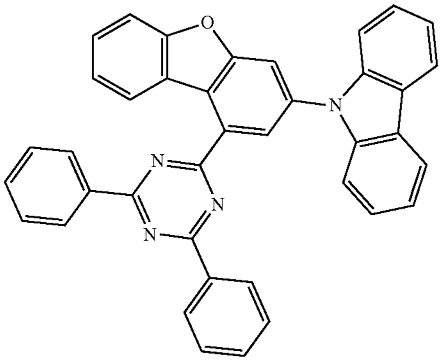
3-8
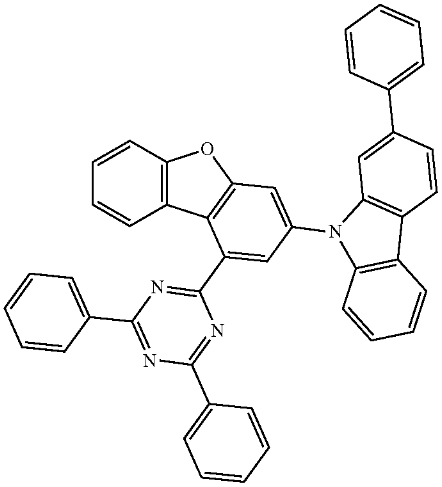
-continued
3-9
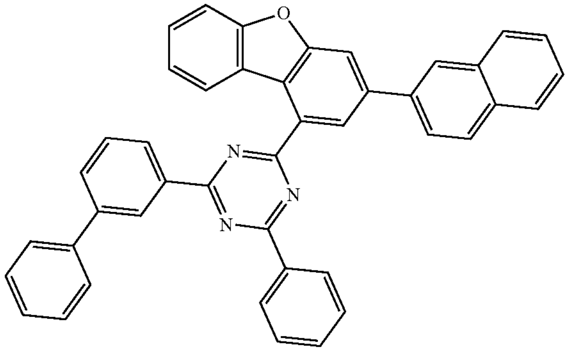
3-10
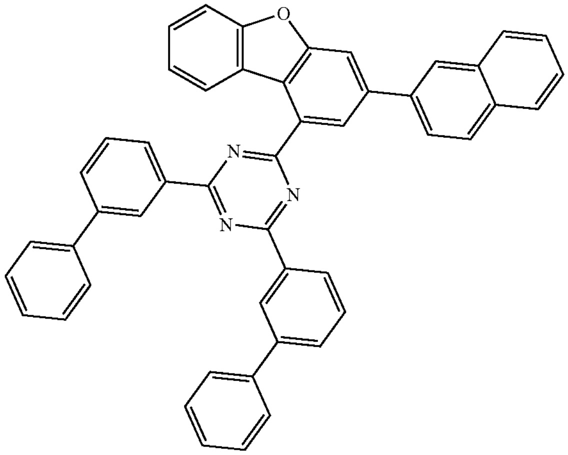
3-11
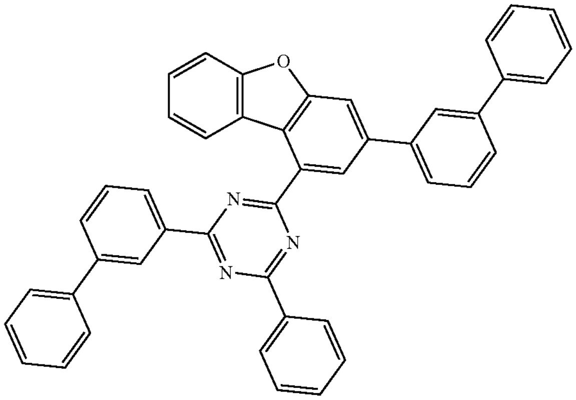
3-12
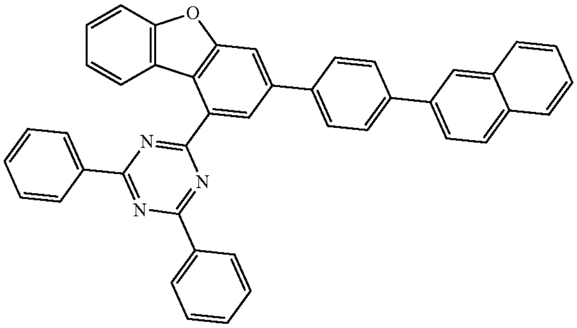

-continued
3-13
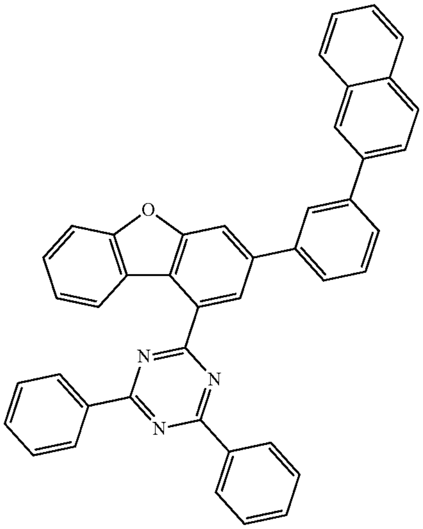
3-14
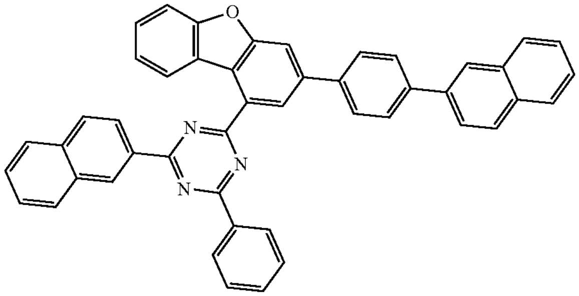
3-15
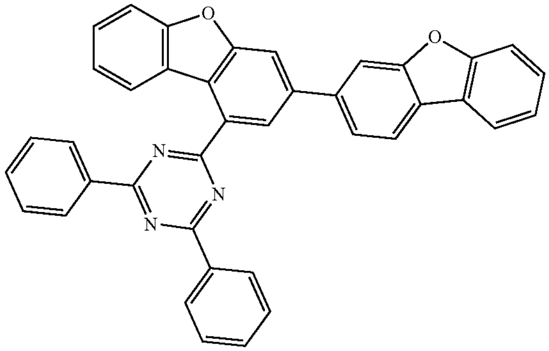
3-16
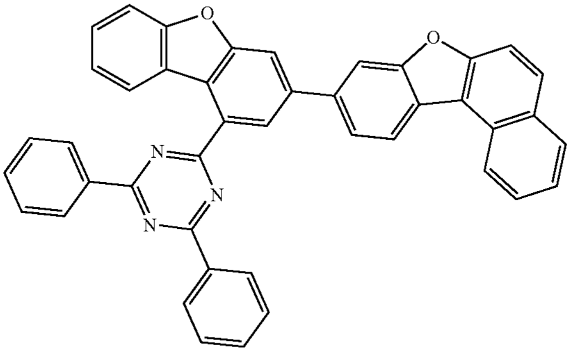
-continued
3-17
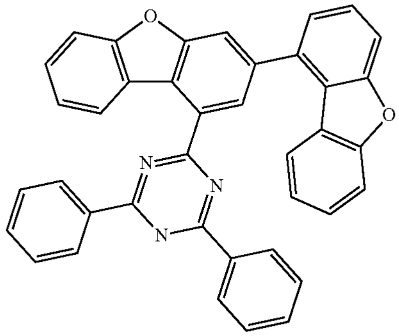
3-18
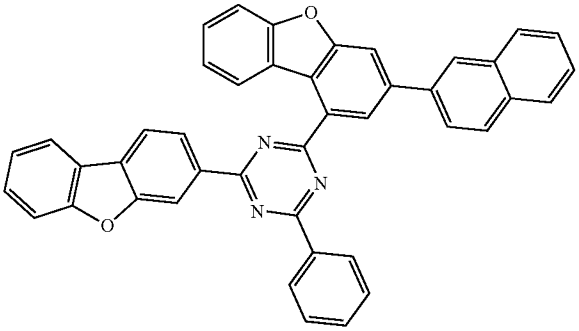
3-19
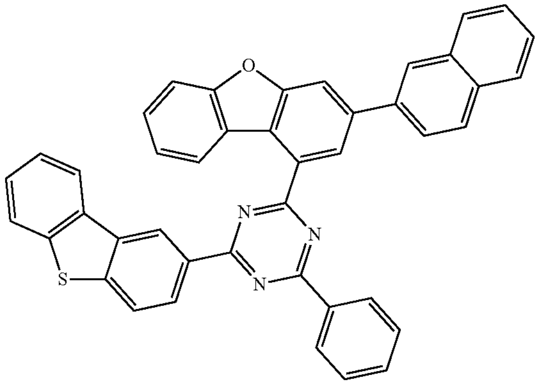
3-20
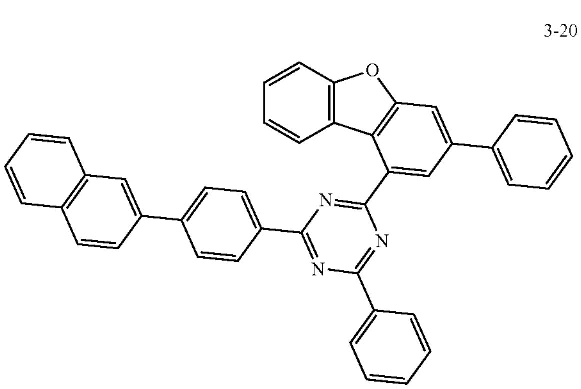

-continued
3-21
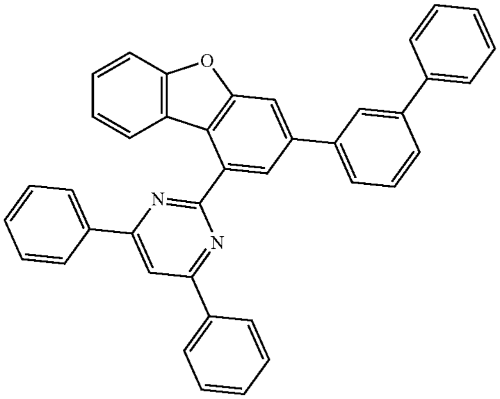
3-22
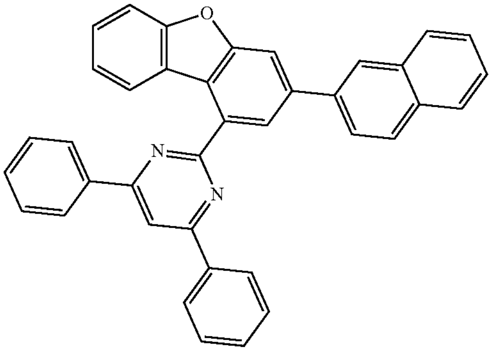
3-23
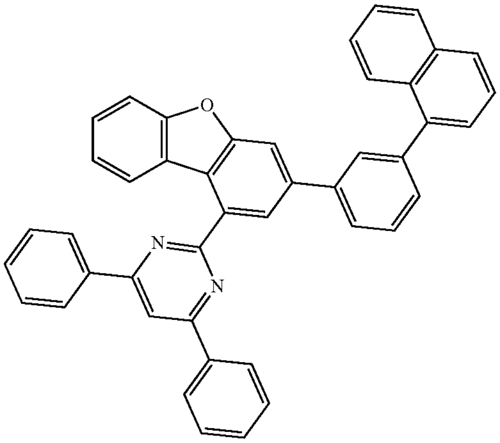
3-24
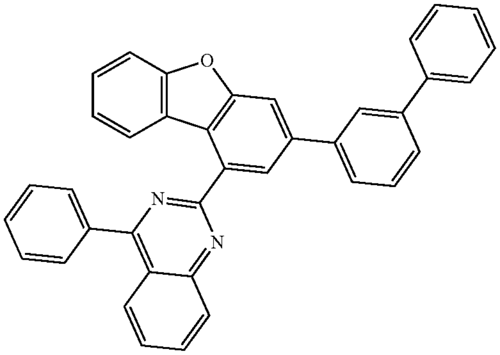
-continued
3-25
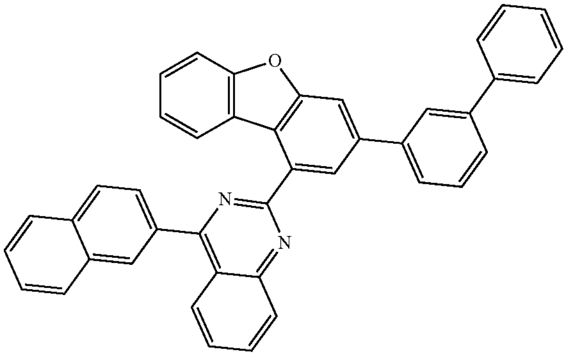
3-26
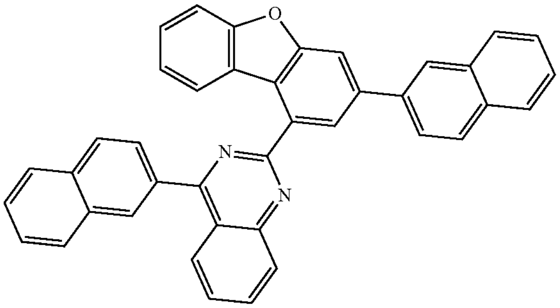
3-27
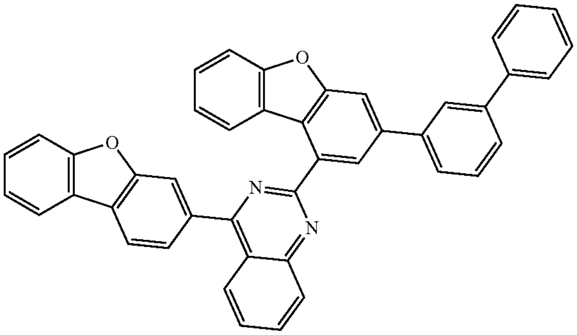
3-28
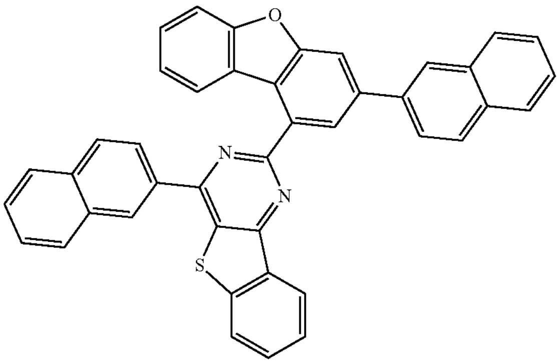

-continued
3-29
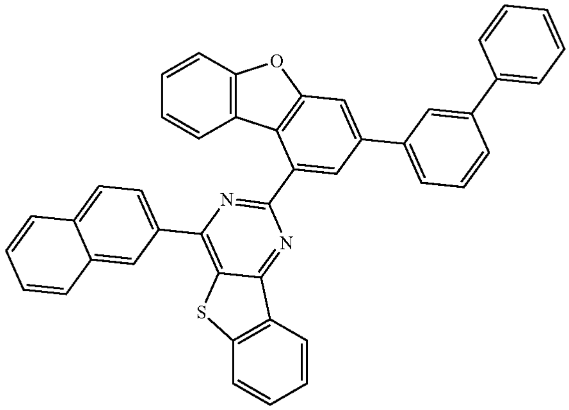
3-30
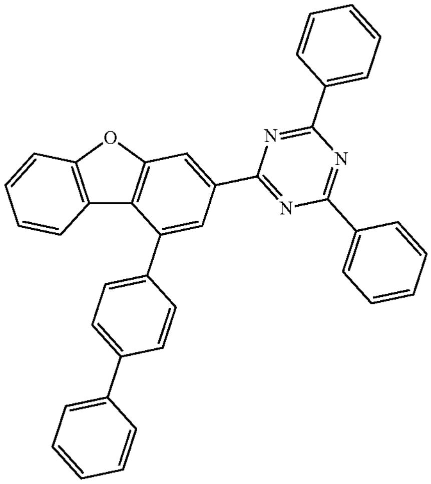
3-31
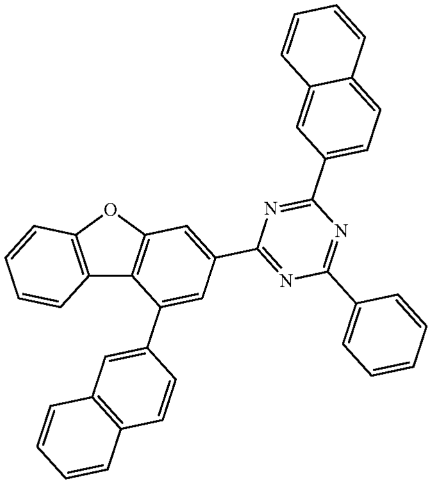
-continued
3-32
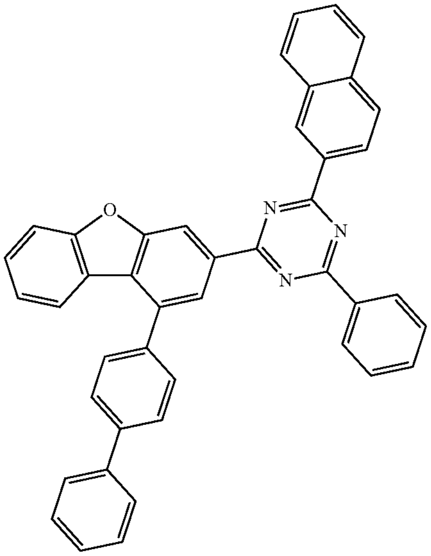
3-33
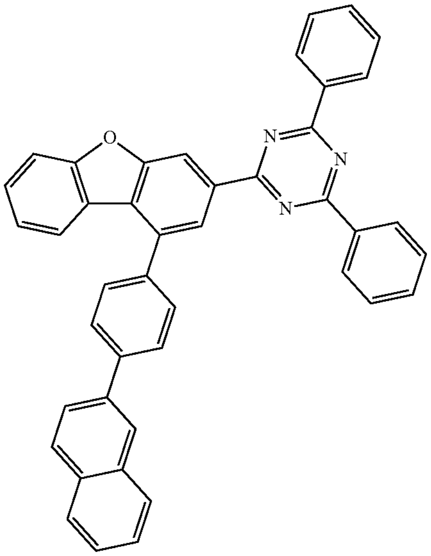
3-34
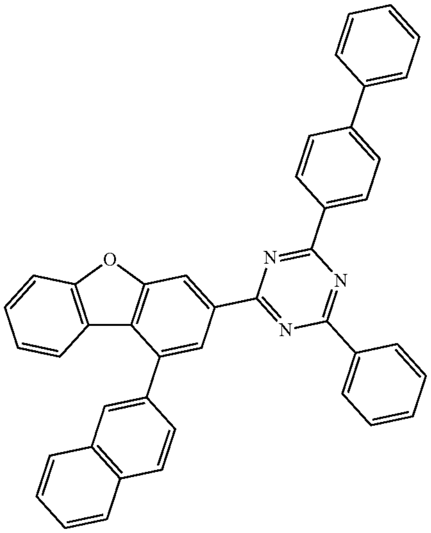

-continued
3-35
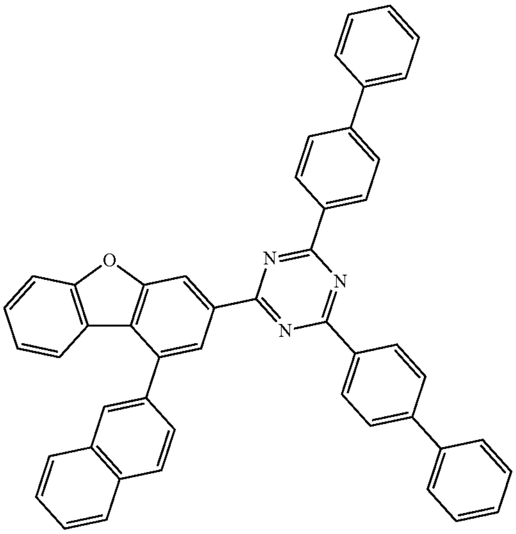
3-36
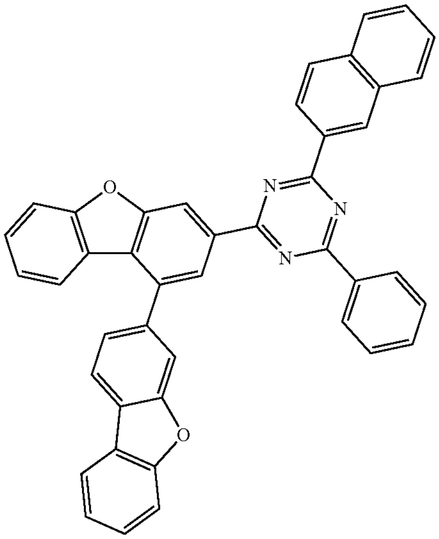
3-37
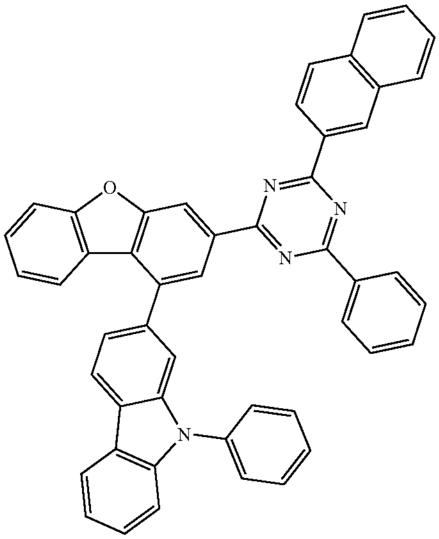
-continued
3-38
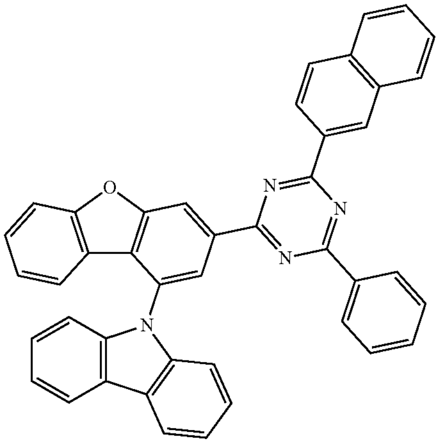
3-39
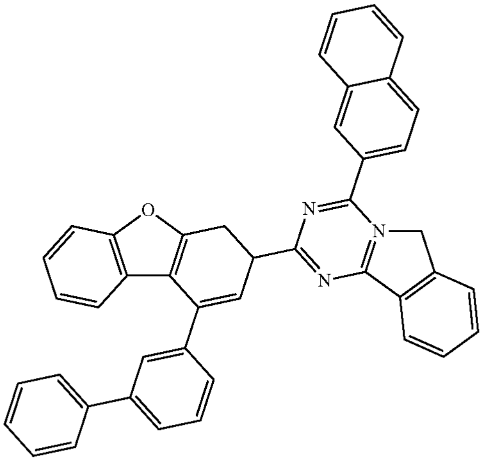
3-40
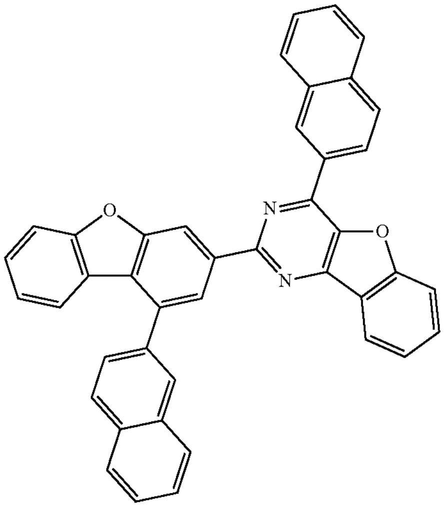

-continued
3-41
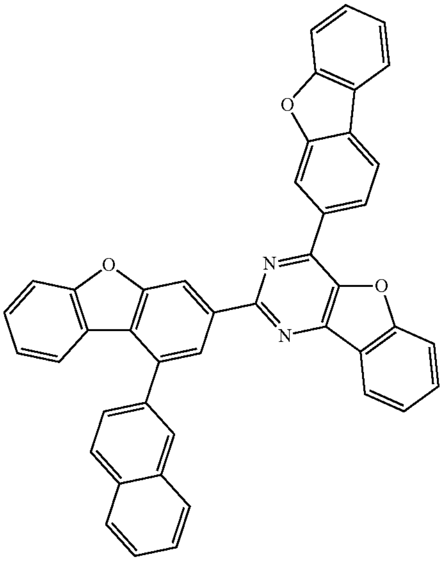
3-42
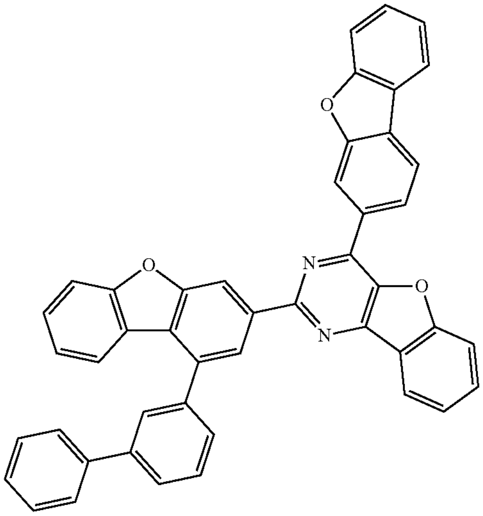
3-43
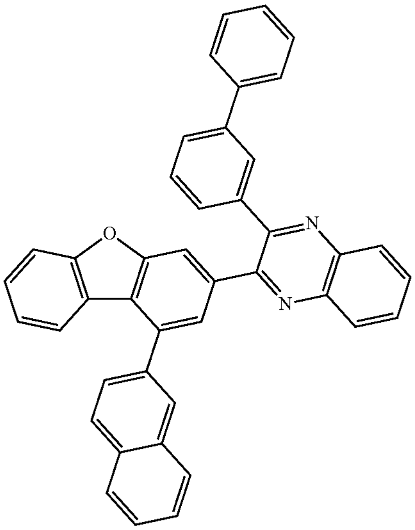
-continued
3-44
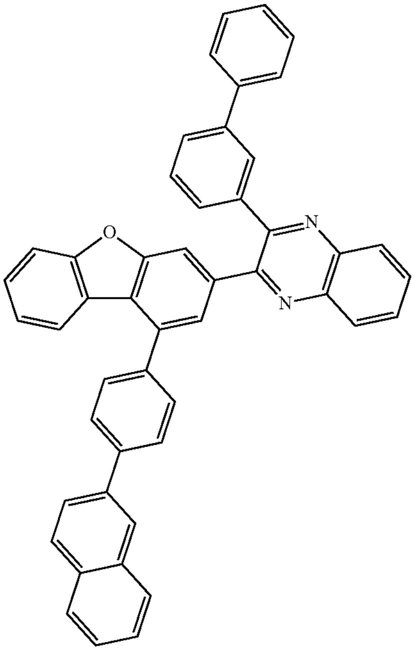
3-45
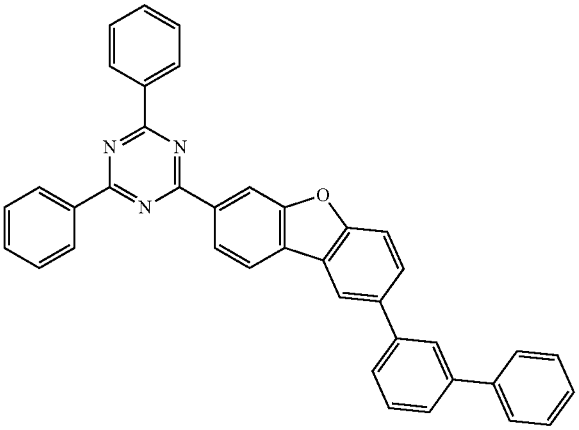
3-46
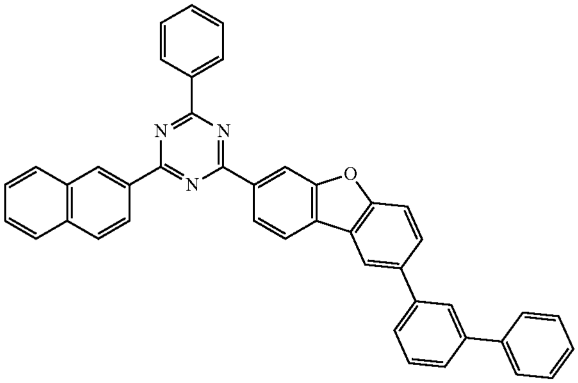

-continued
3-47
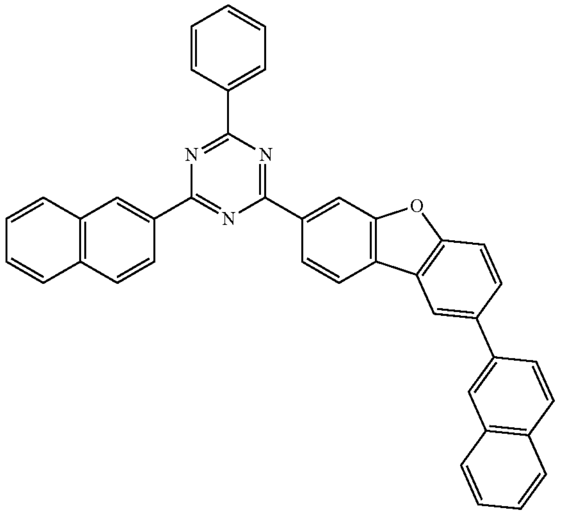
3-48
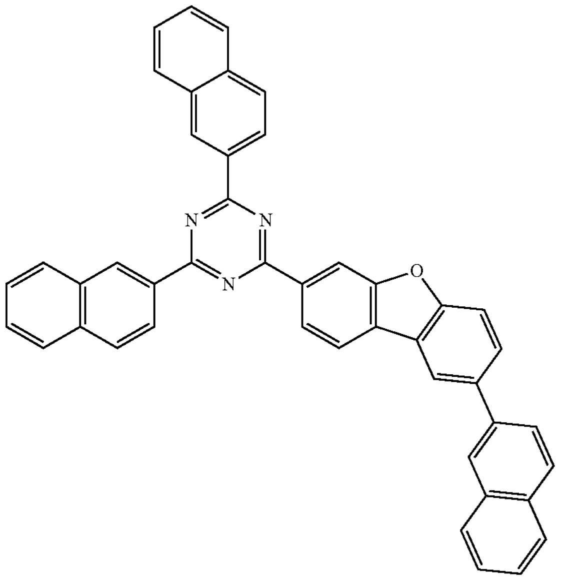
-continued
3-49
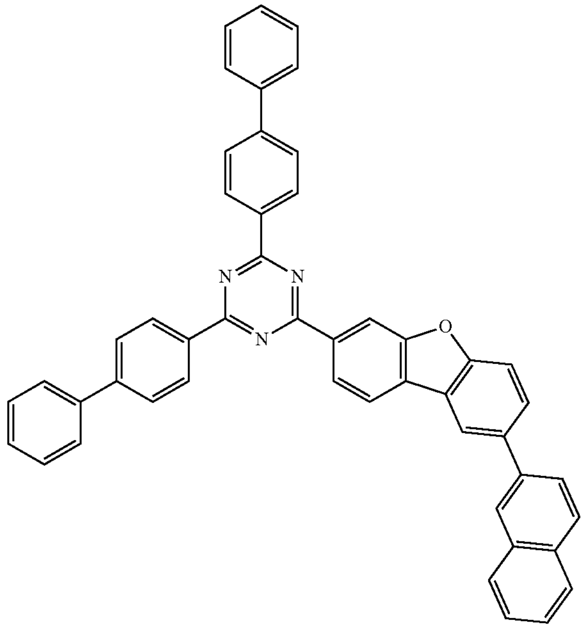
3-50
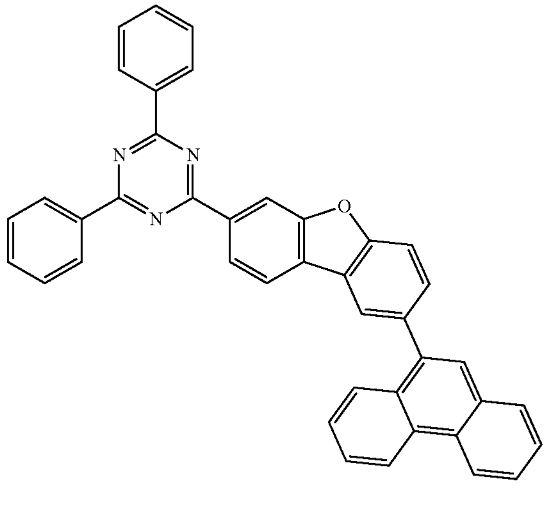

-continued
3-51
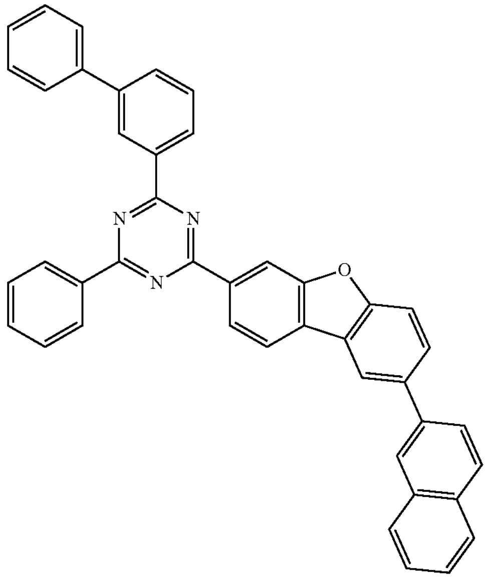
3-52
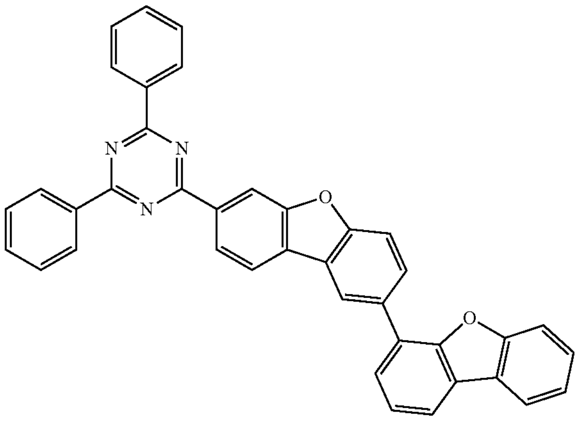
3-53
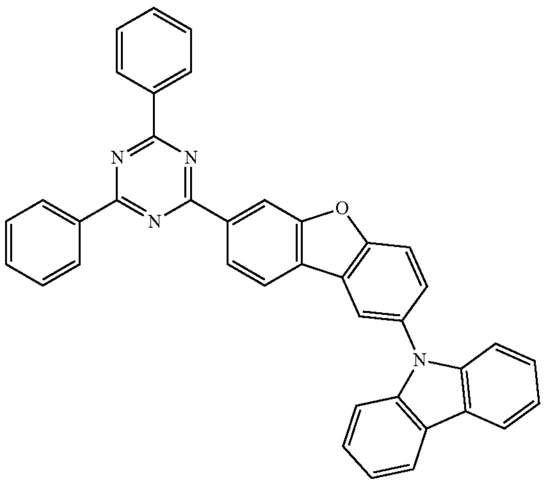
-continued
3-54
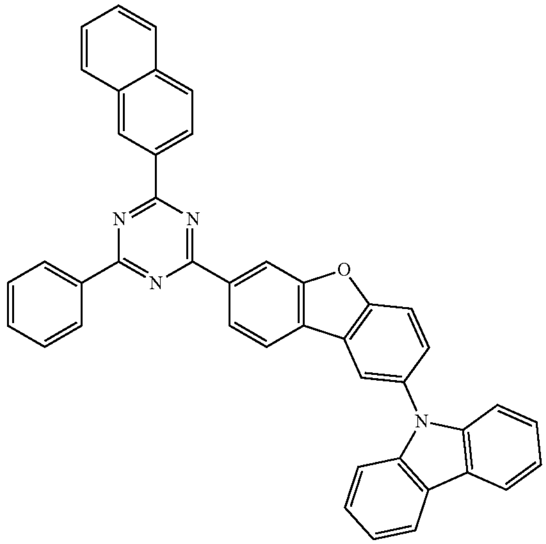
3-55
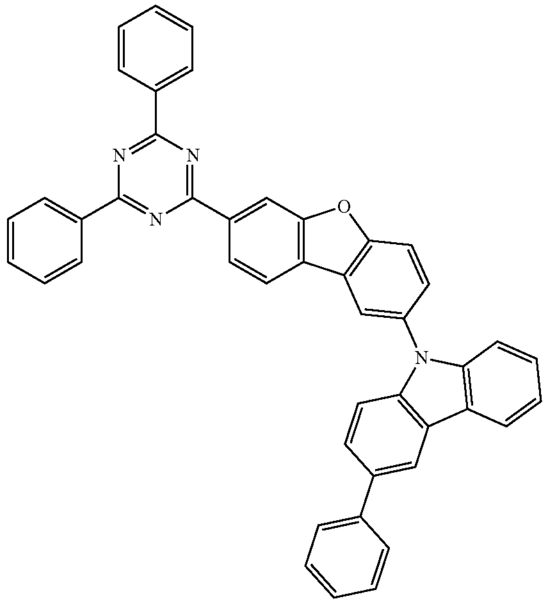
3-56
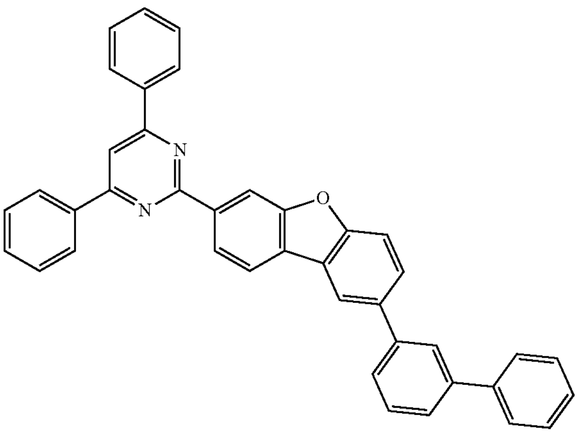

-continued
3-57
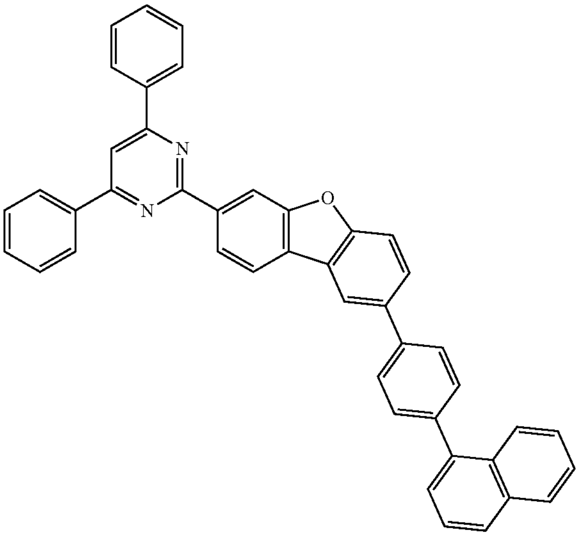
3-58
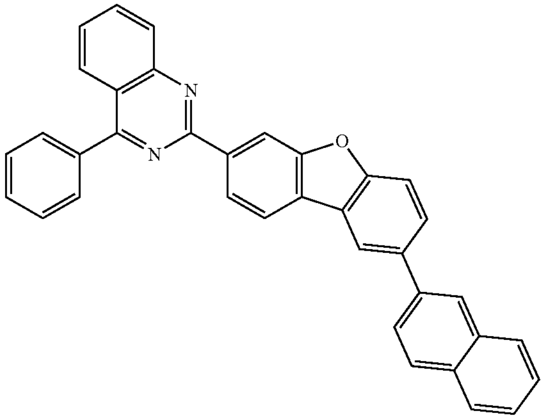
3-59
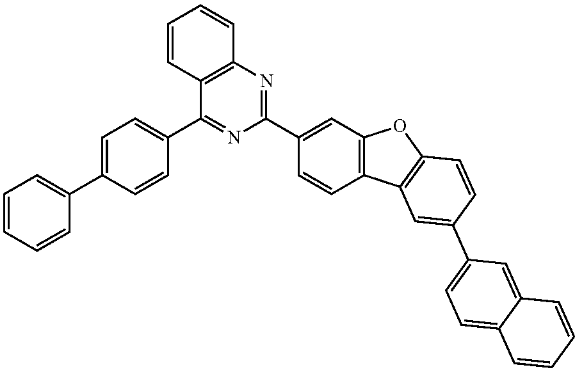
-continued
3-60
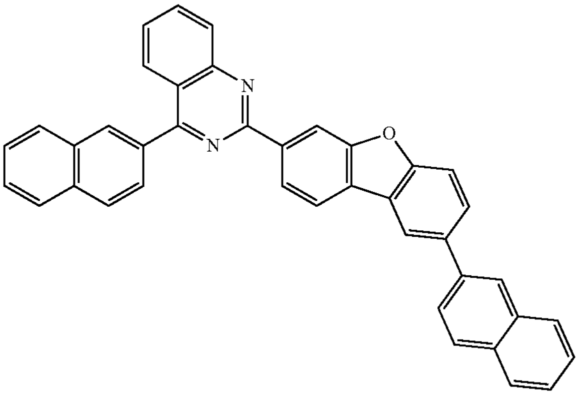
3-61
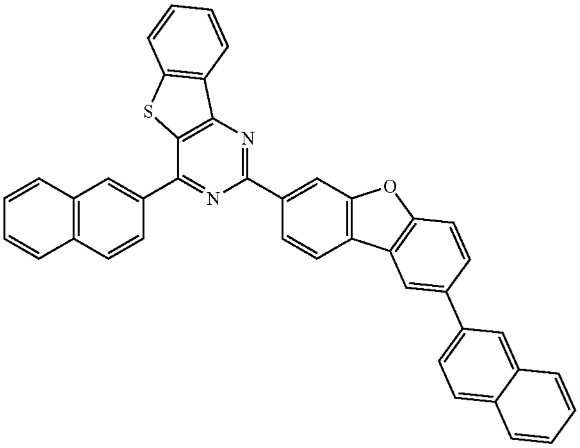
3-62
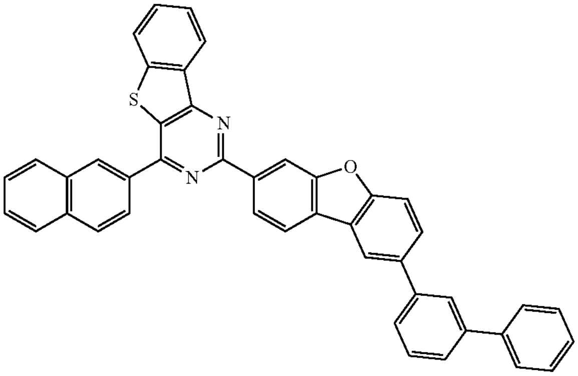

-continued
3-63
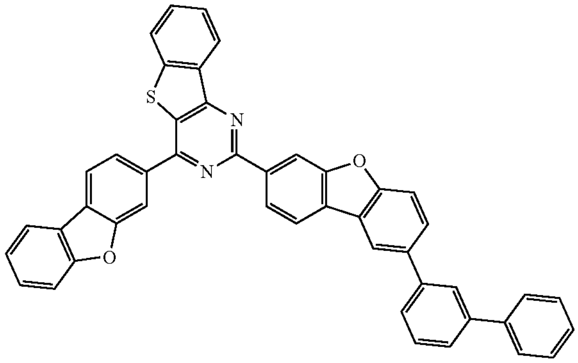
3-64
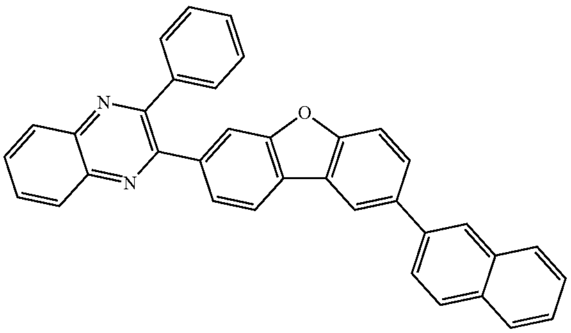
3-65
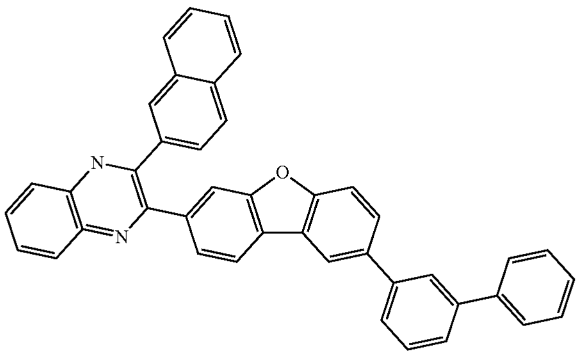
3-66
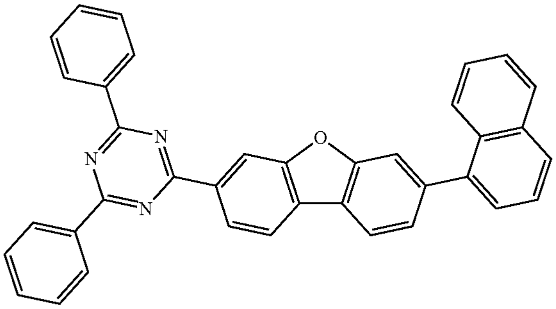
-continued
3-67
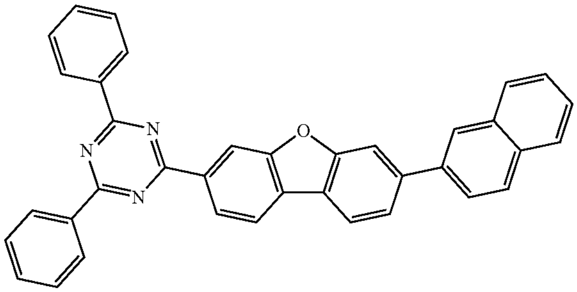
3-68
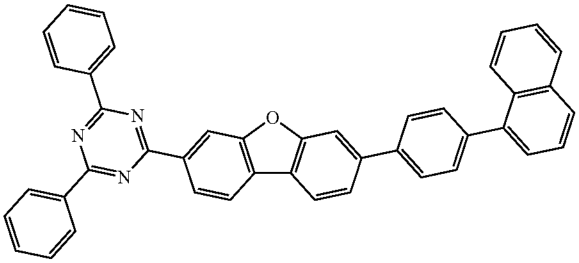
3-69
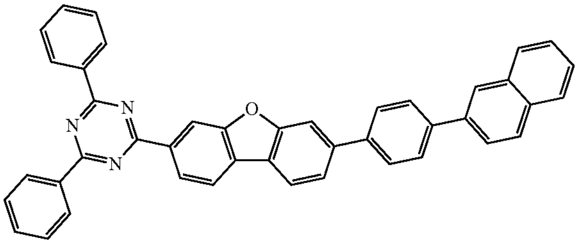
3-70
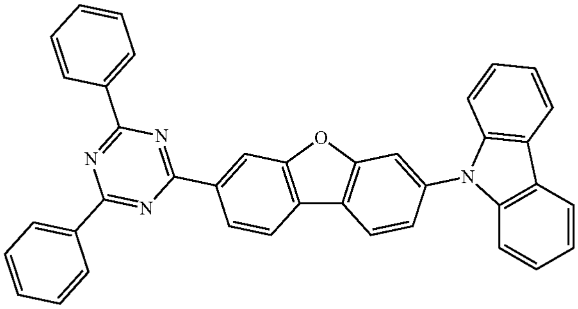
3-71
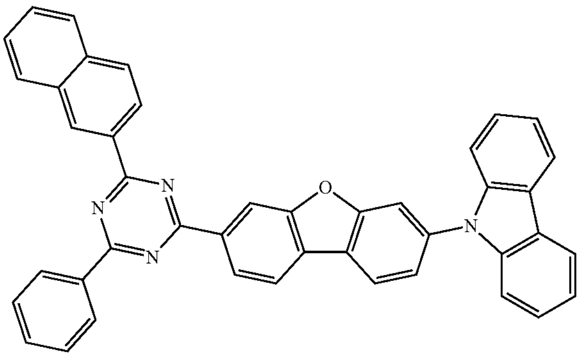

-continued
3-72
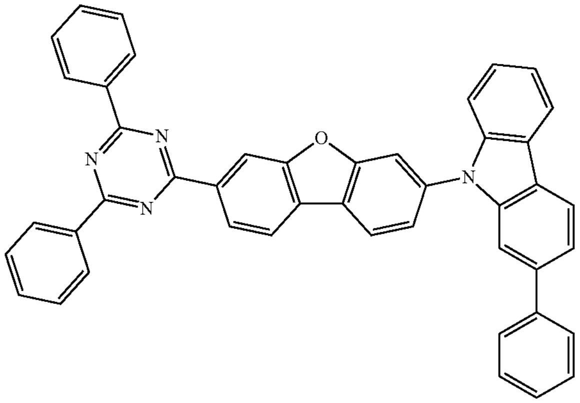
3-73
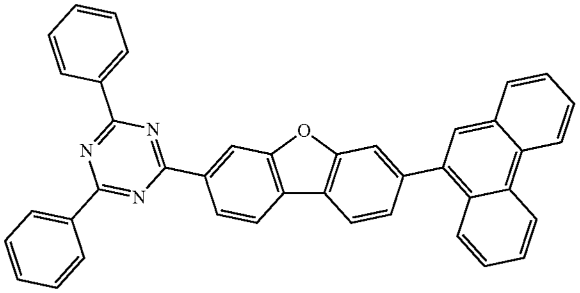
3-74
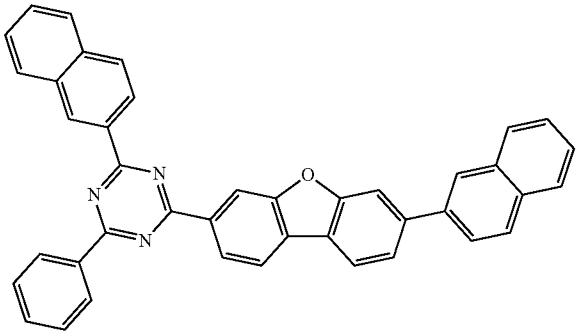
3-75
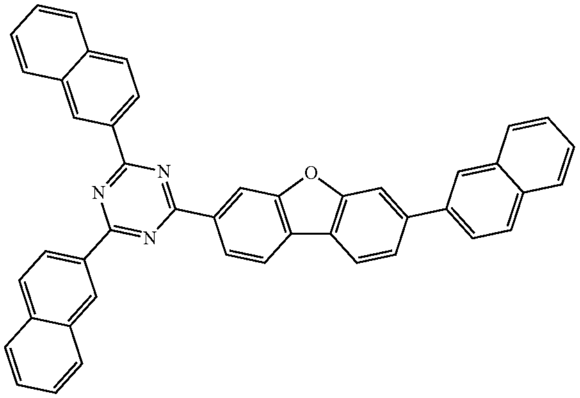
-continued
3-76
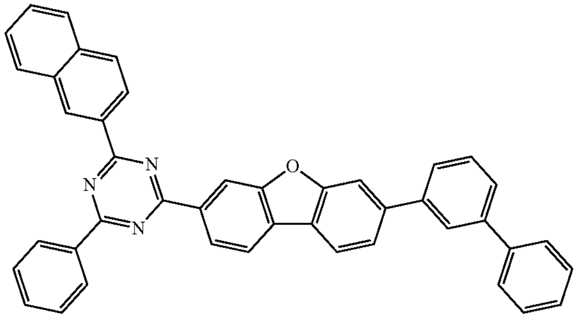
3-77
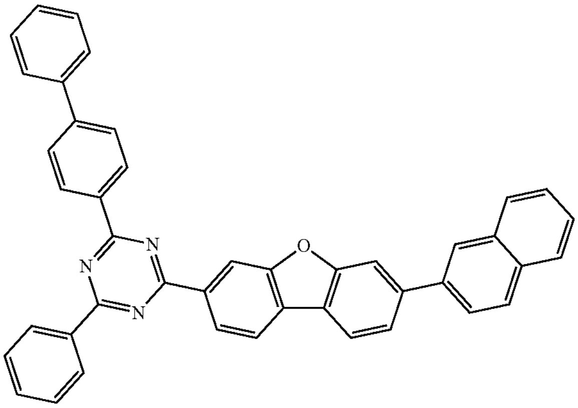
3-78
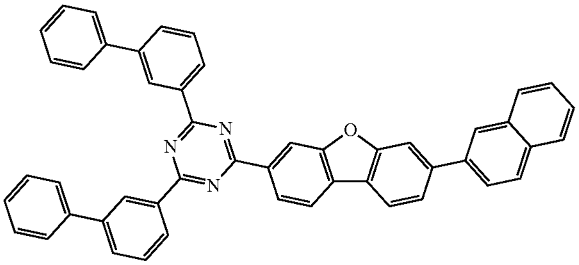
3-79
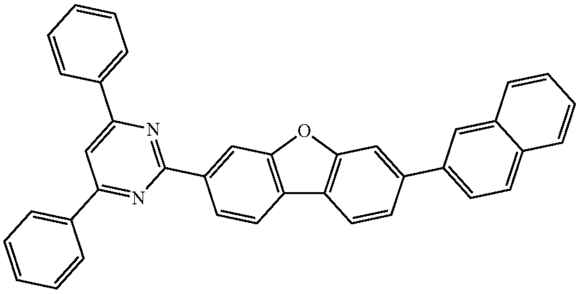

-continued
3-80
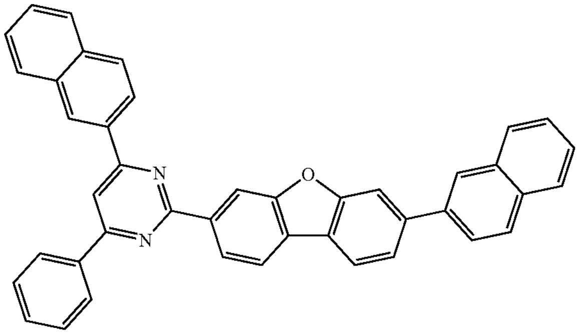
3-81
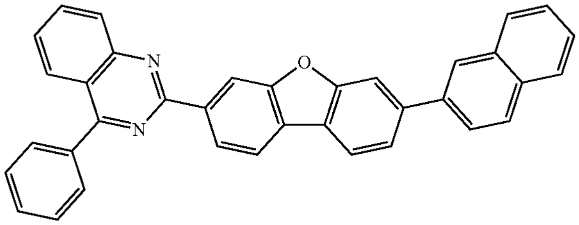
3-82
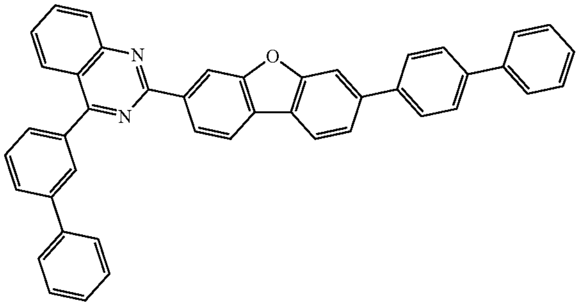
3-83
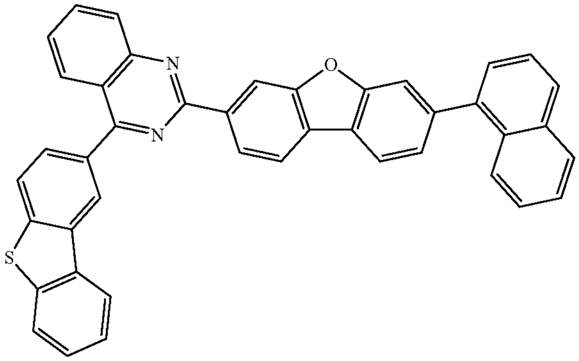
-continued
3-84
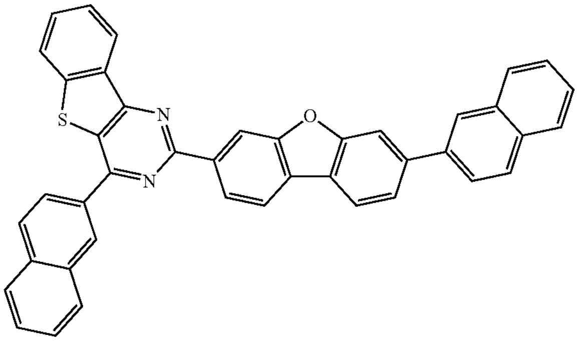
3-85
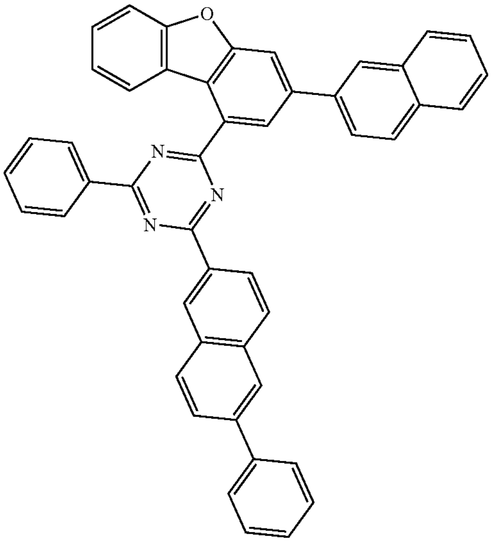
3-86
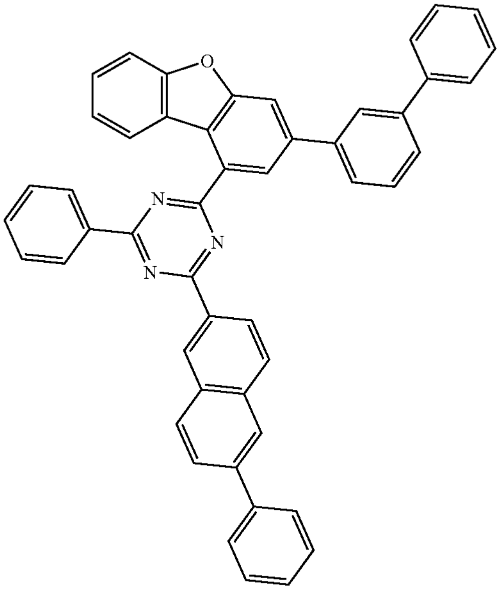

-continued
3-87
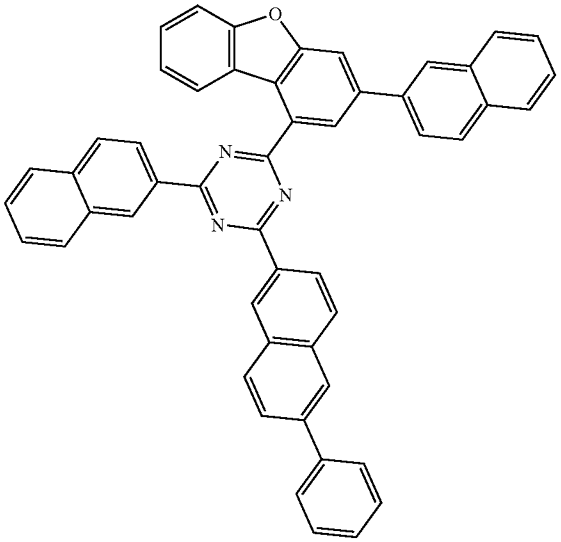
3-88
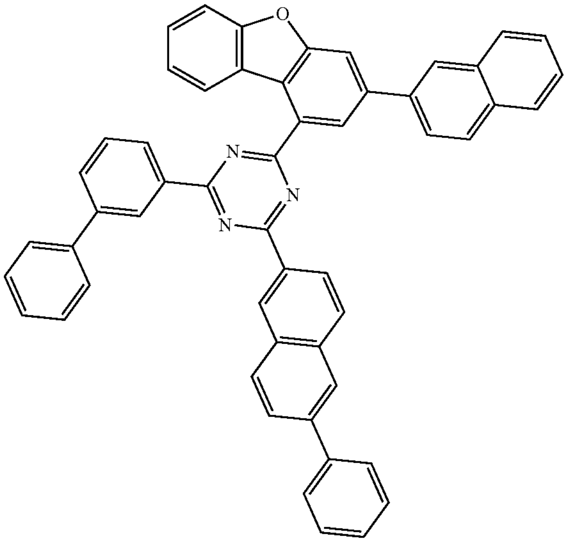
3-89
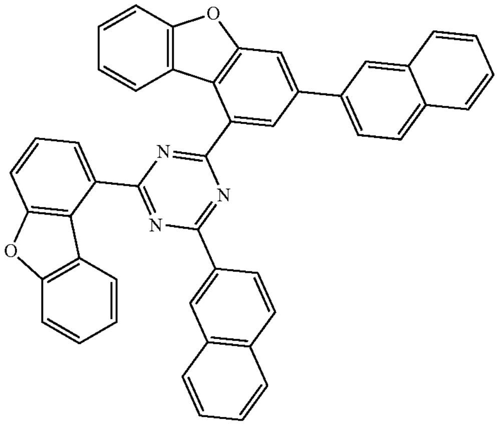
-continued
3-90
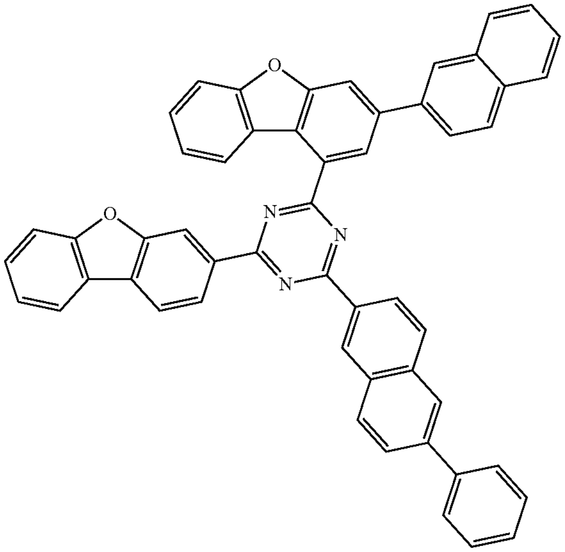
3-91
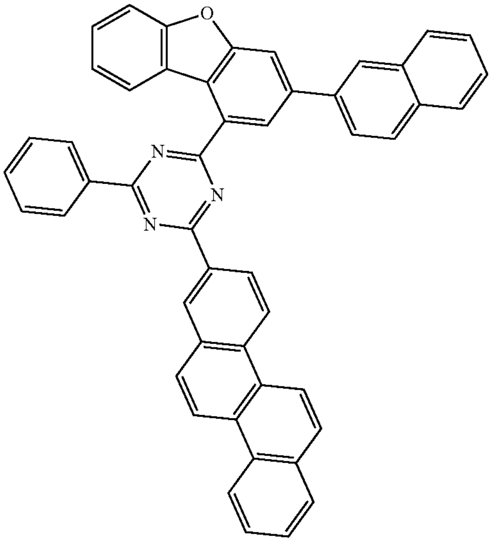
3-92
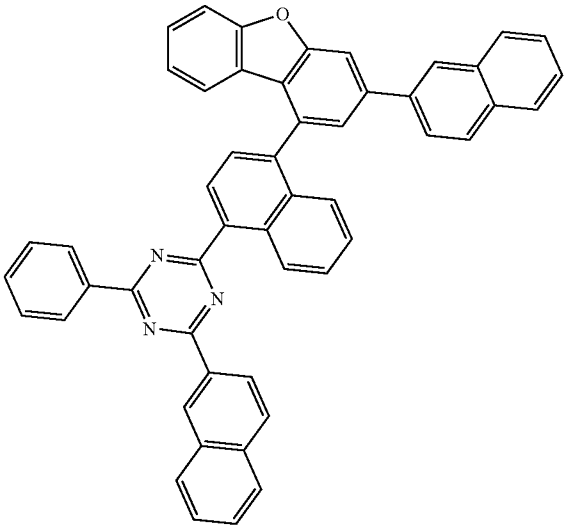

-continued
3-93
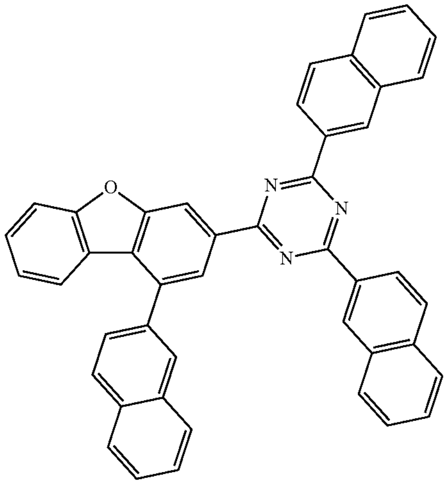
3-94
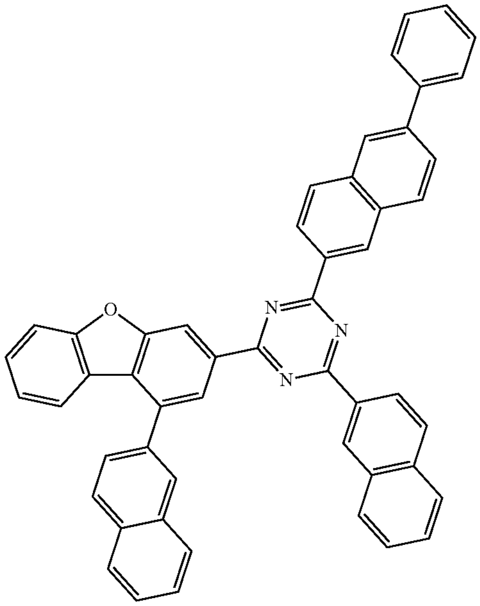
-continued
3-95
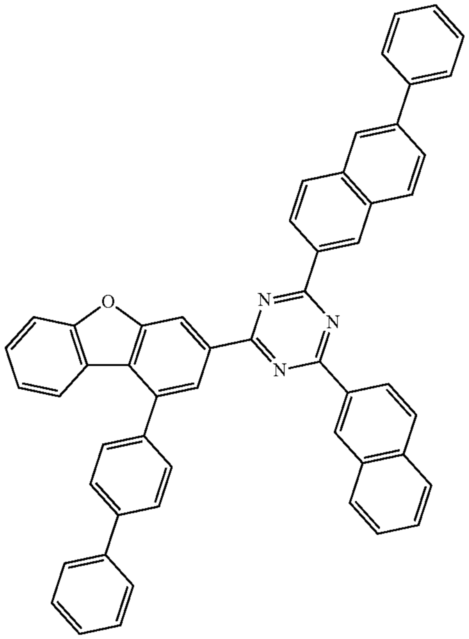
3-96
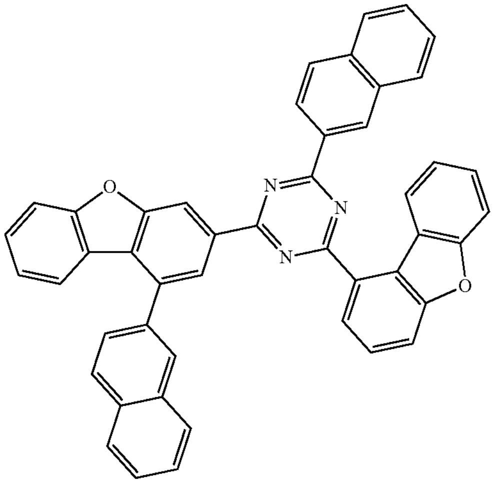
3-97
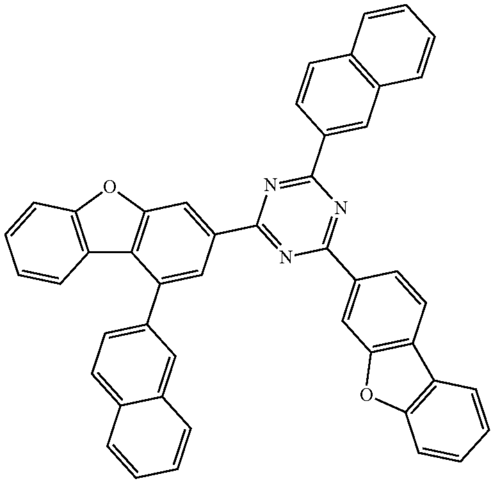

-continued
3-98
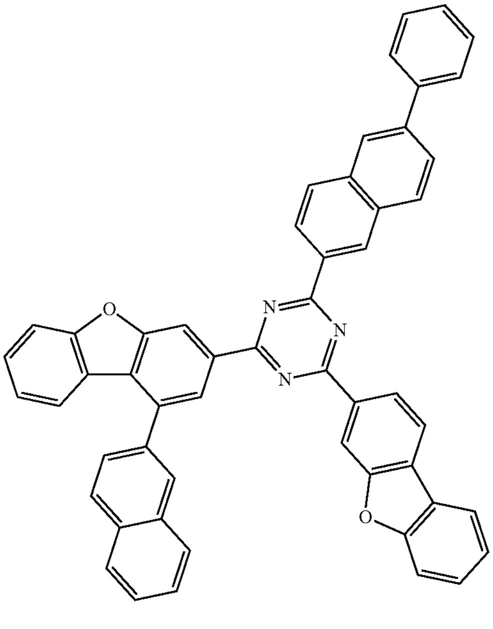
3-99
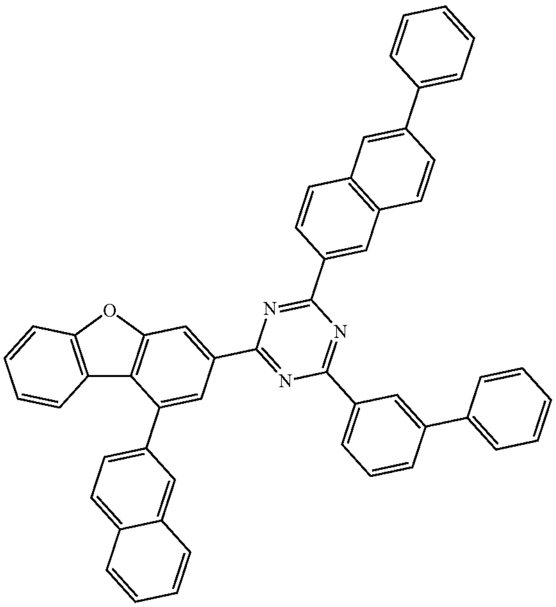
-continued
3-100
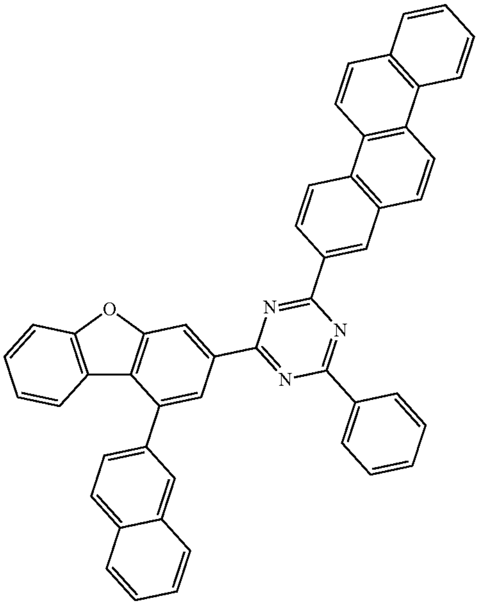
3-101
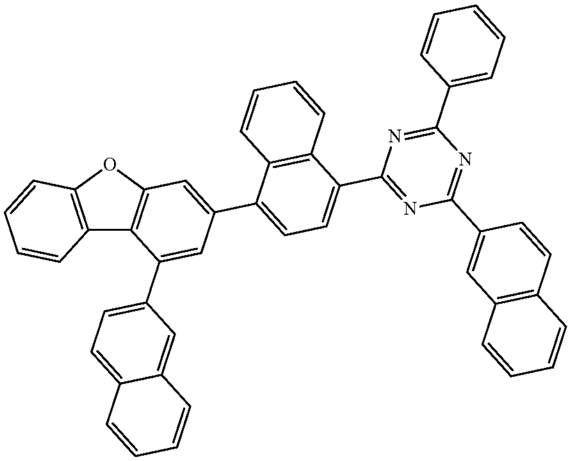
3-102
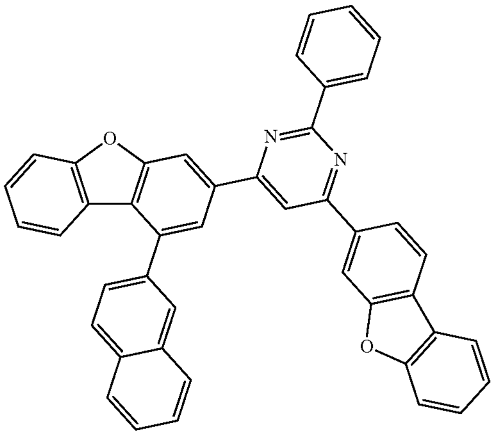

-continued
3-103
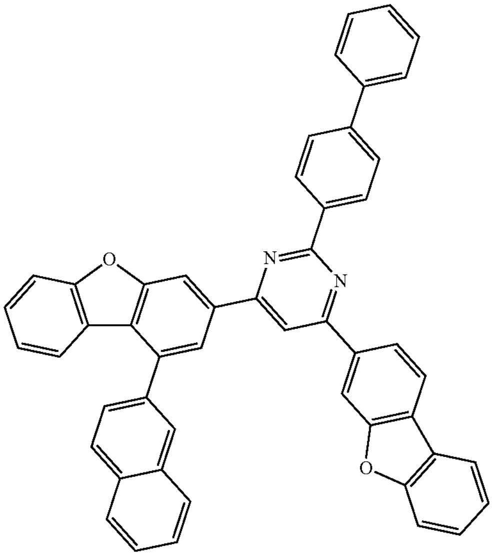
3-104
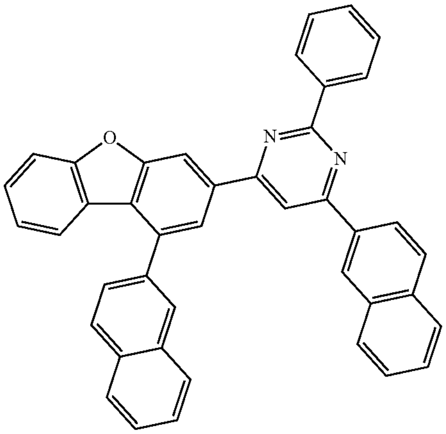
3-105
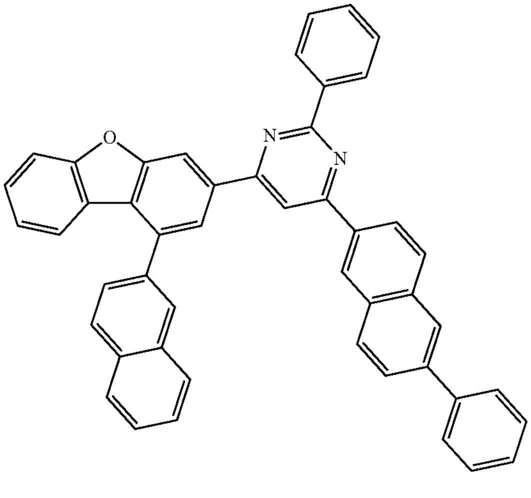
-continued
3-106
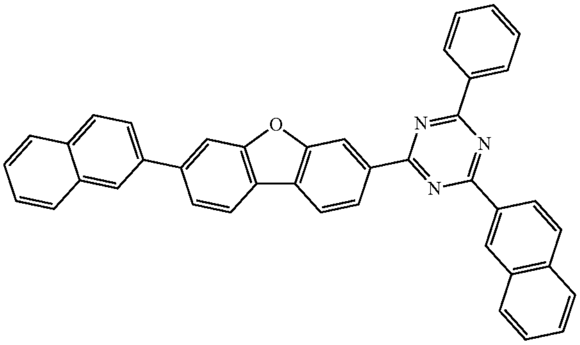
3-107
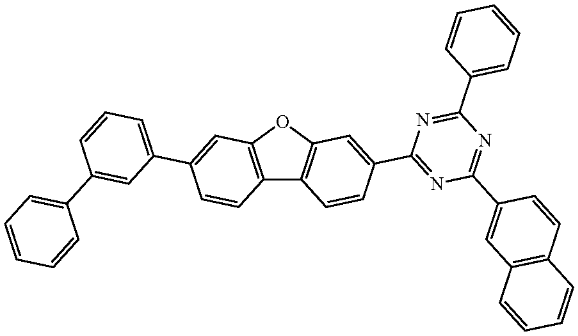
3-108
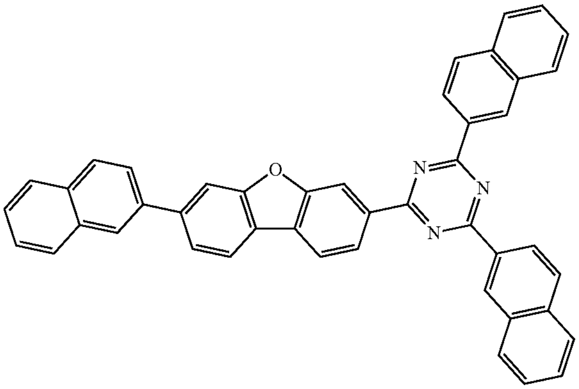
3-109
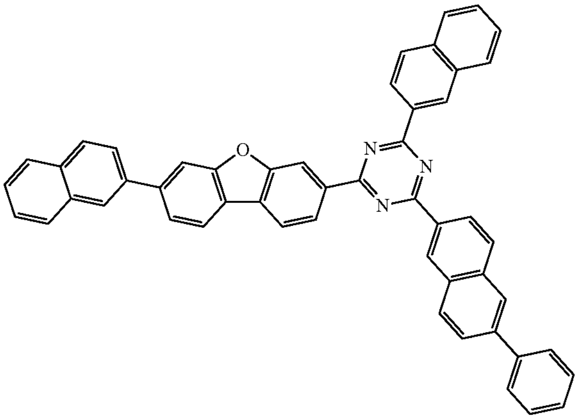

-continued
3-110
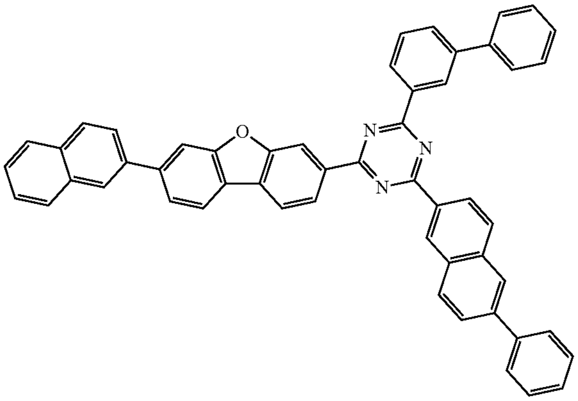
3-111
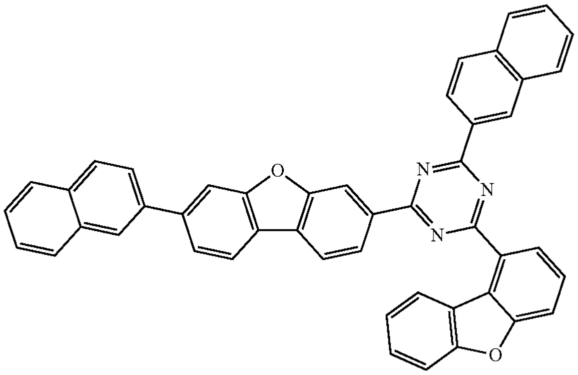
3-112
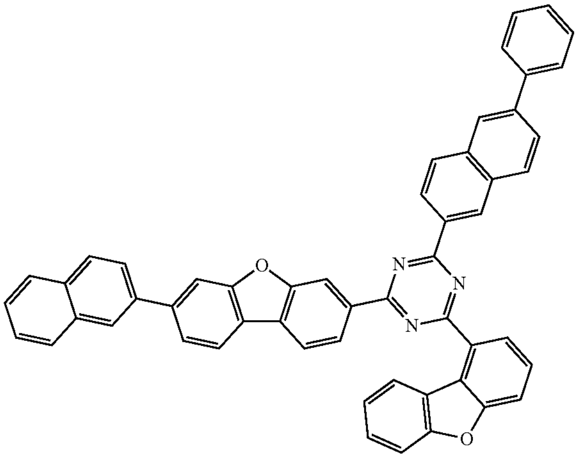
-continued
3-113
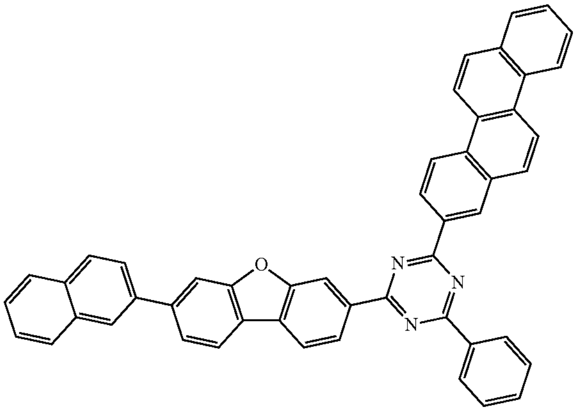
3-114
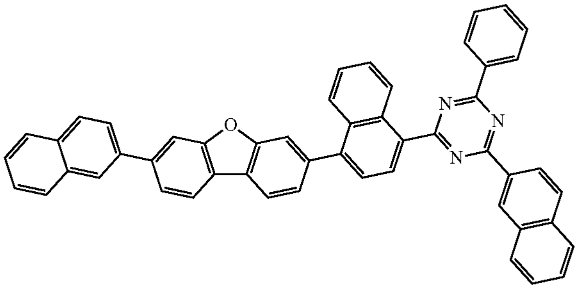
3-115
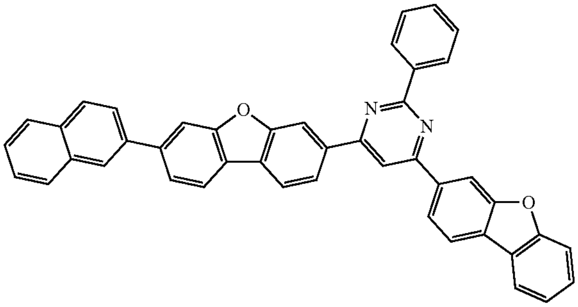
3-116
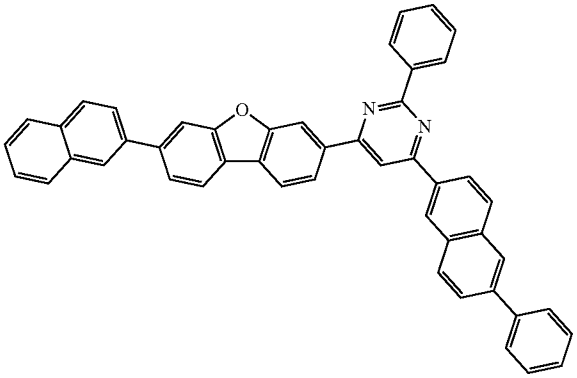

-continued
3-117
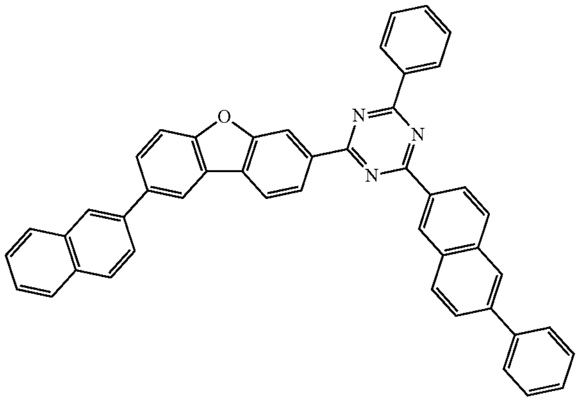
3-118
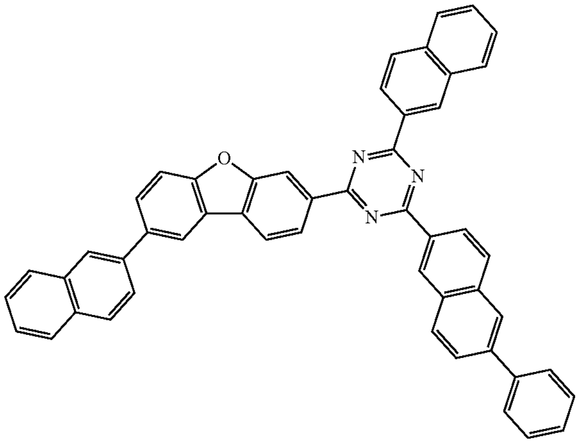
3-119
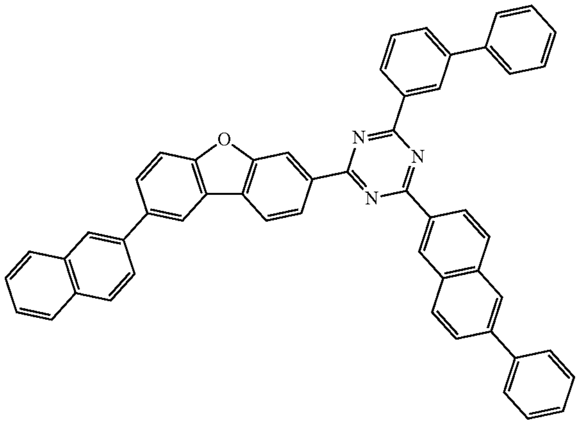
-continued
3-120
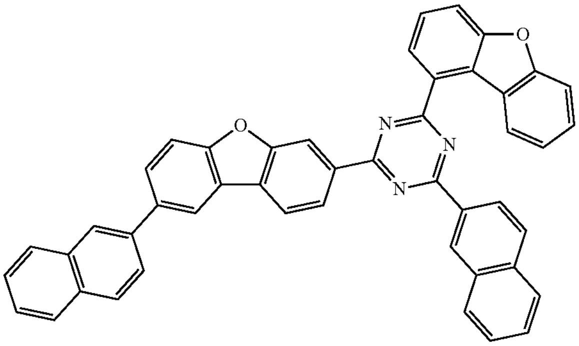
3-121
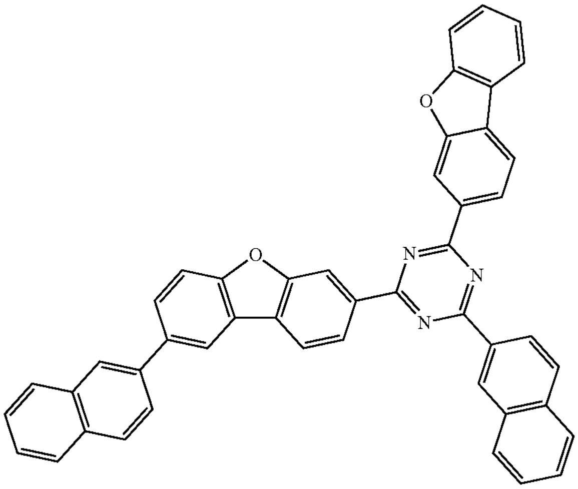
3-122
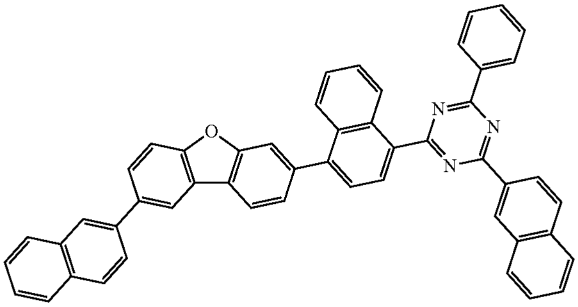
3-123
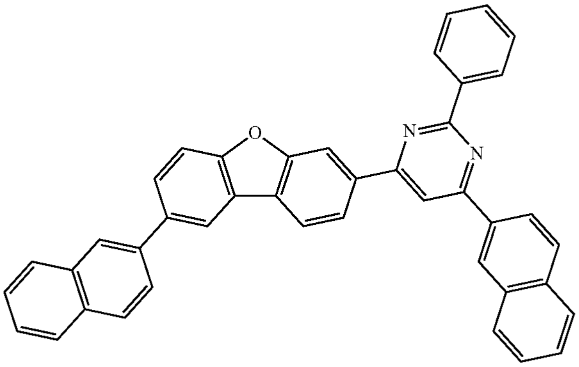

-continued
3-124
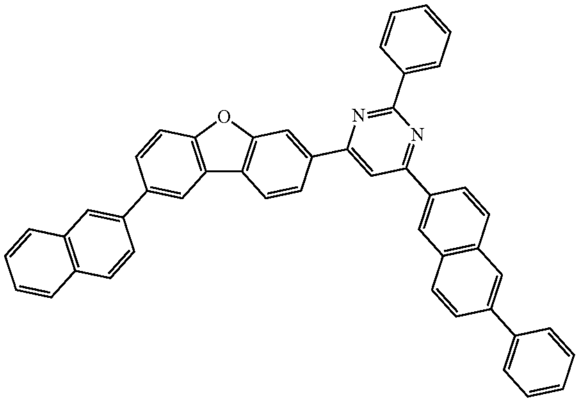
3-125
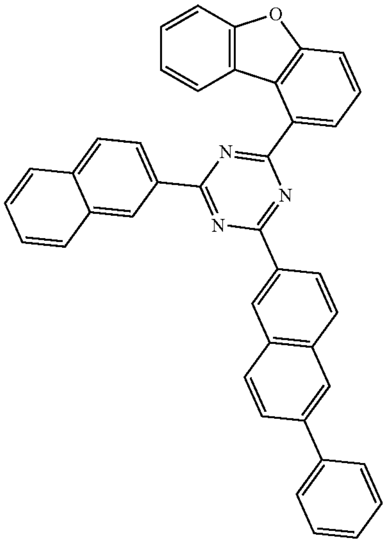
3-126
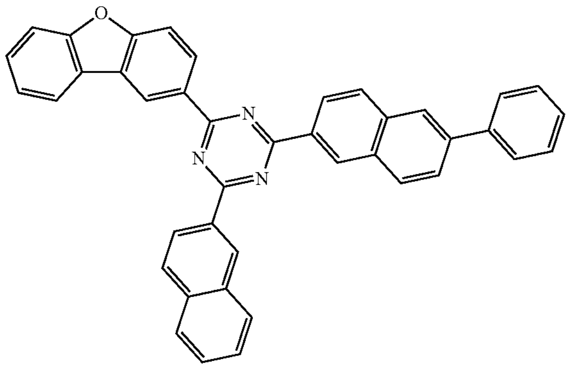
-continued
3-127
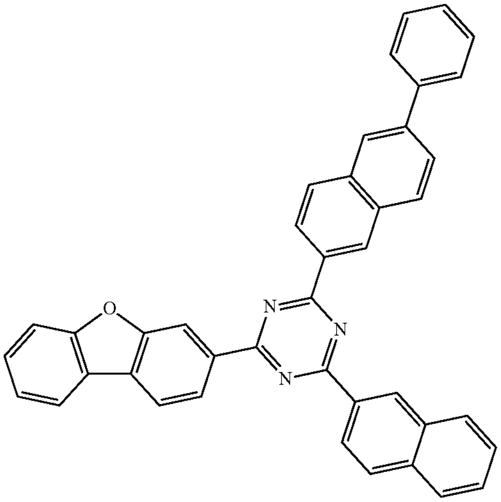
3-128
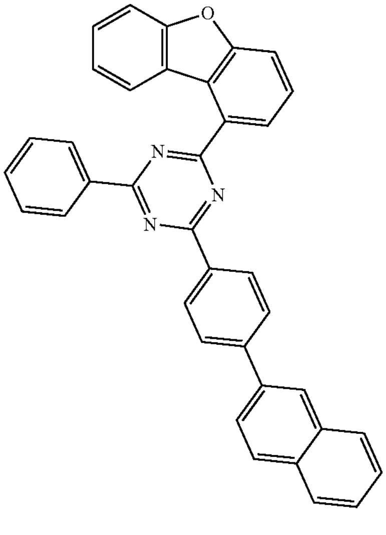
3-129
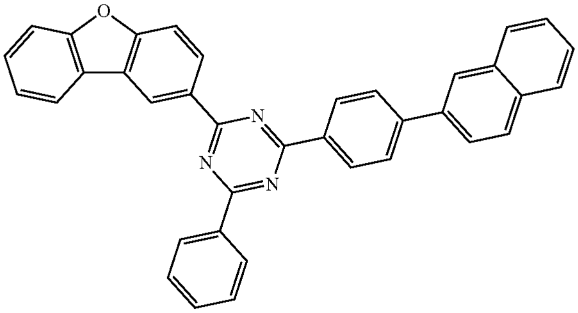

-continued
3-130
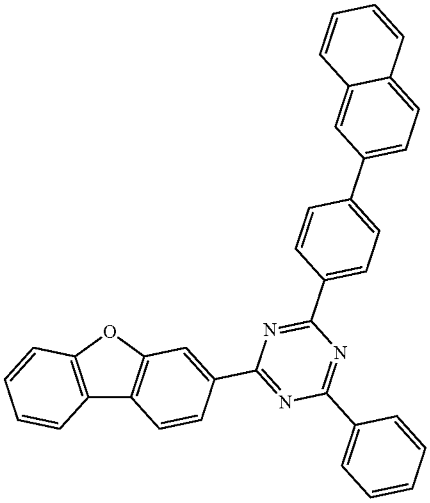
3-131
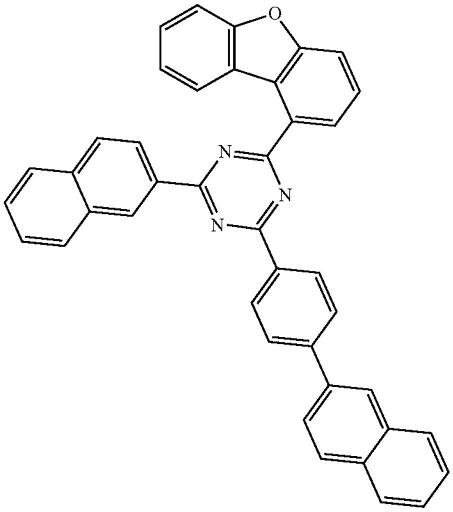
3-132
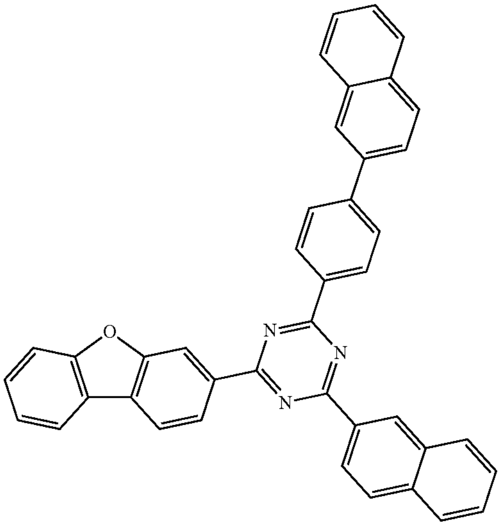
-continued
3-133
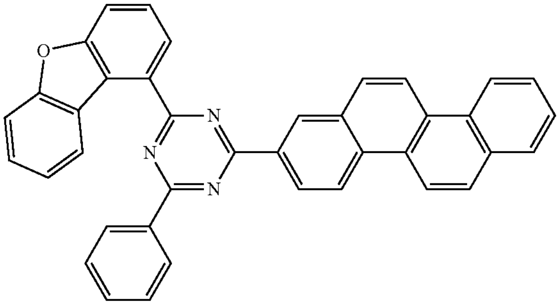
3-134
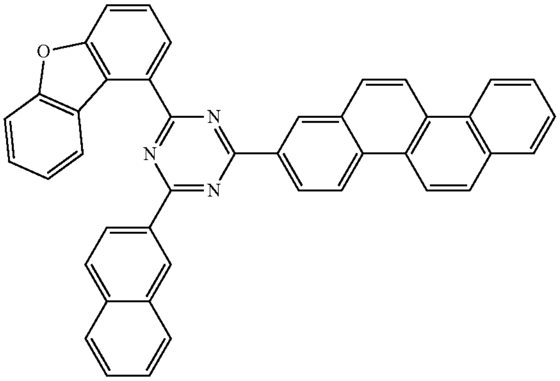
3-135
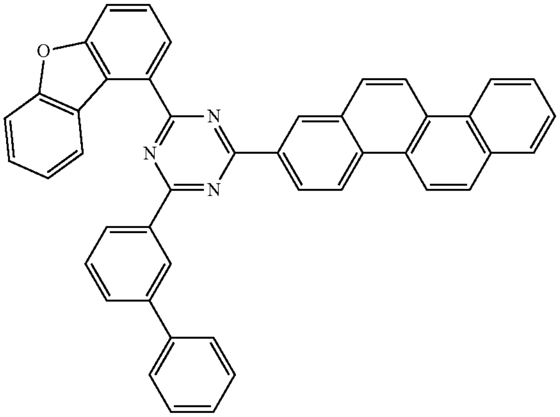
3-136
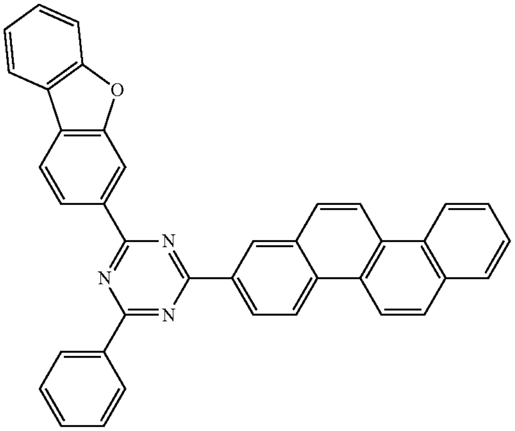

-continued
3-137
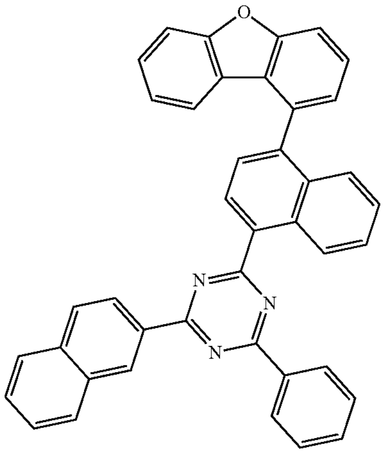
3-138
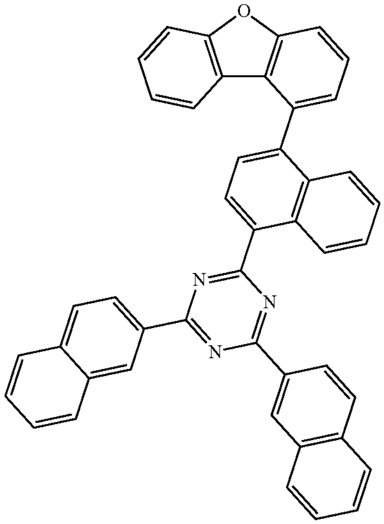
3-139
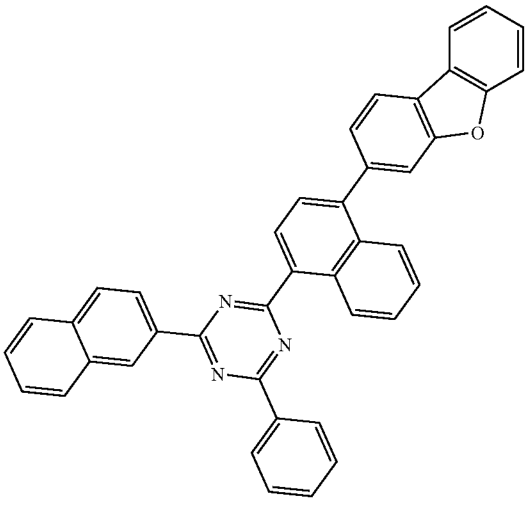
-continued
3-140
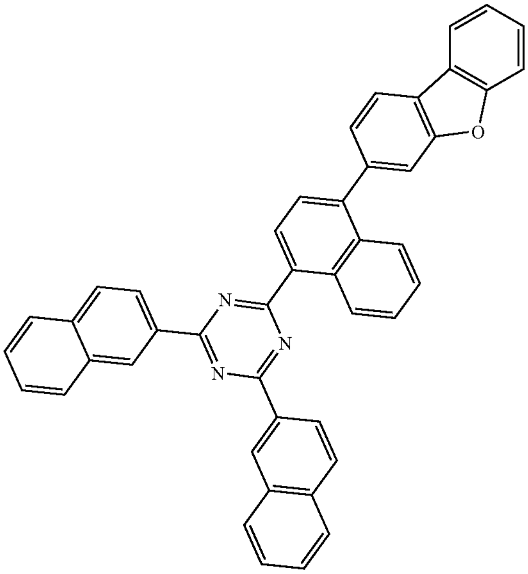
3-141
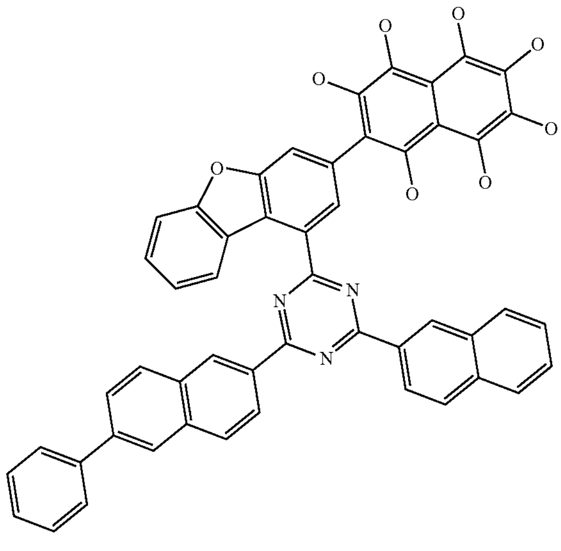

-continued
3-142
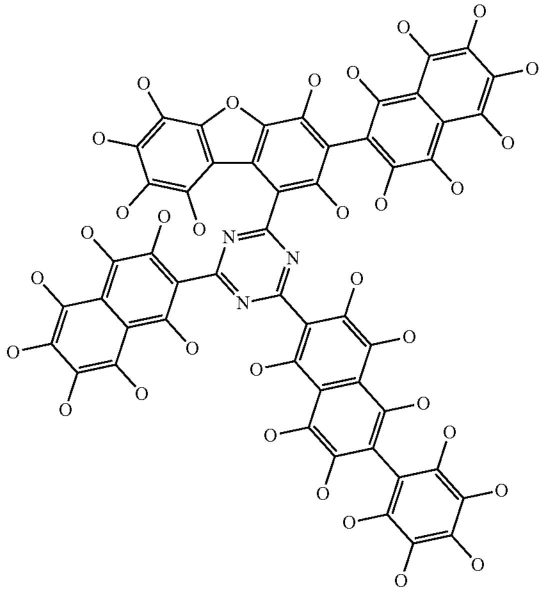
3-143
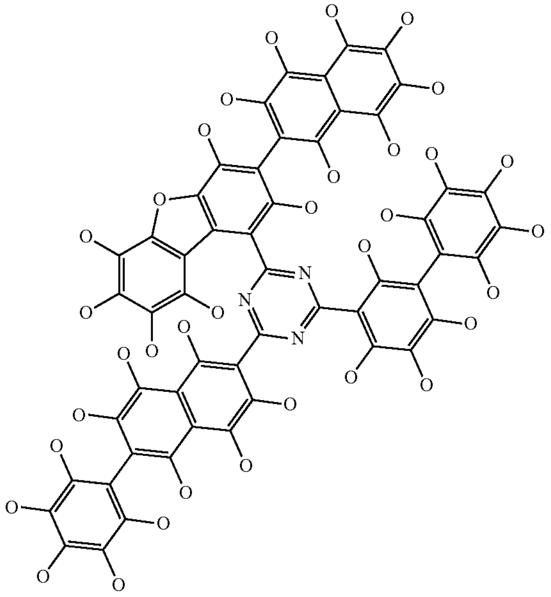
3-144
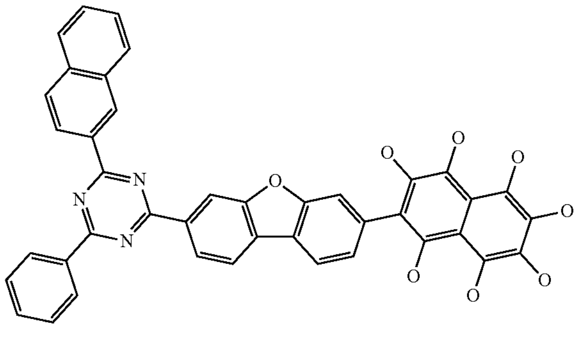
-continued
3-145
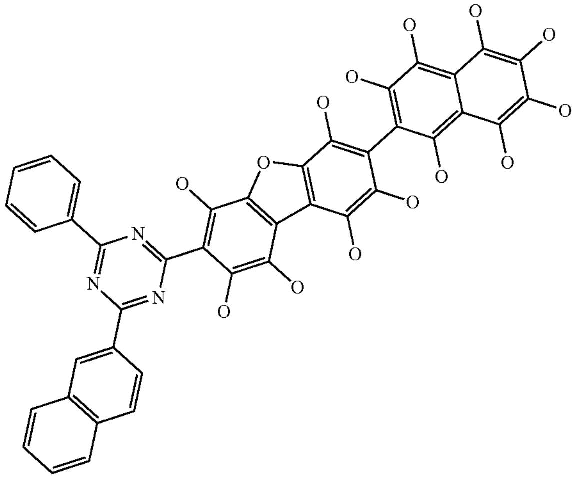
3-146
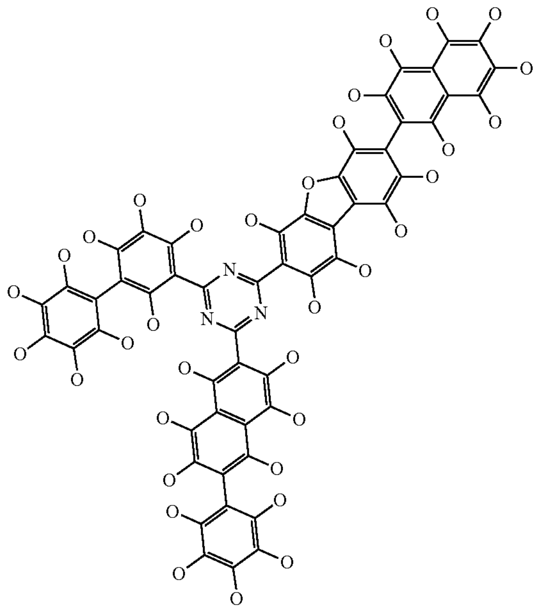

-continued 3-147

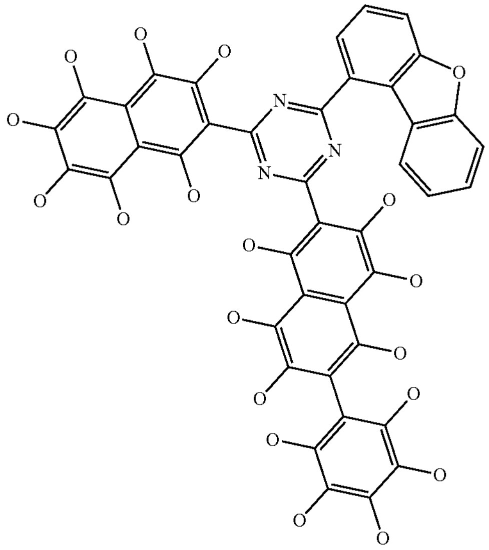

3-148

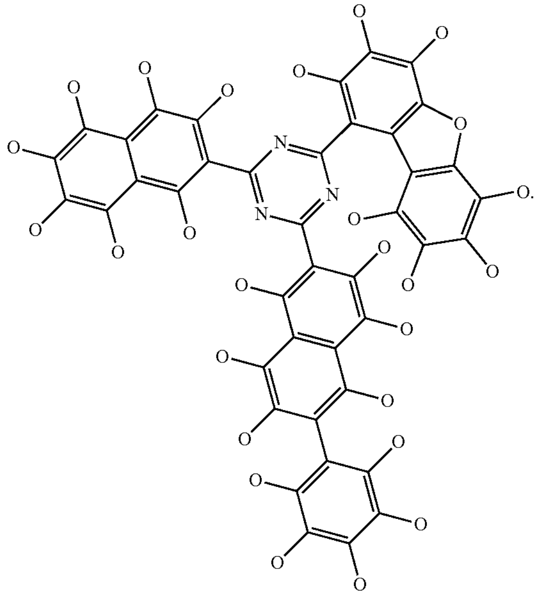

11. The organic light emitting device of claim 7, wherein the organic material layer includes a light emitting layer, and the light emitting layer includes the heterocyclic compound of Chemical Formula 1.

12. The organic light emitting device of claim 7, wherein the organic material layer includes a light emitting layer, the light emitting layer includes a host material, and the host material includes the heterocyclic compound of Chemical Formula 1.

13. The organic light emitting device of claim 7, further comprising one, two or more layers selected from the group consisting of a light emitting layer, a hole injection layer, a hole transfer layer, an electron injection layer, an electron transfer layer, an electron blocking layer and a hole blocking layer.

14. A composition for an organic material layer of an organic light emitting device, the composition comprising:

the heterocyclic compound of claim 1; and a heterocyclic compound represented by the following Chemical Formula A or the following Chemical Formula B:

[Chemical Formula A]

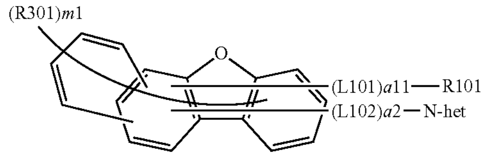

[Chemical Formula B]

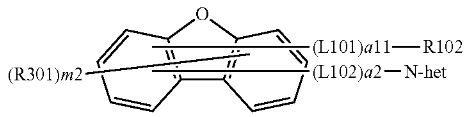

wherein, in Chemical Formulae A and B,

L101 and L102 are the same as or different from each other, and each independently a direct bond; a substituted or unsubstituted C6 to C60 arylene group; or a substituted or unsubstituted C2 to C60 heteroarylene group;

N-het is a monocyclic or polycyclic heterocyclic group substituted or unsubstituted and including one or more Ns;

R101 is a substituted or unsubstituted C1 to C60 alkyl group; a substituted or unsubstituted C6 to C60 aryl group; a substituted or unsubstituted C2 to C60 heteroaryl group; or —NR103R104;

R102 is hydrogen; deuterium; a substituted or unsubstituted C1 to C60 alkyl group; a substituted or unsubstituted C6 to C60 aryl group; a substituted or unsubstituted C2 to C60 heteroaryl group; or —NR103R104;

R301 is selected from the group consisting of hydrogen; deuterium; halogen; a cyano group; a substituted or unsubstituted C1 to C60 alkyl group; a substituted or unsubstituted C6 to C60 aryl group; and a substituted or unsubstituted C2 to C60 heteroaryl group;

R103 and R104 are the same as or different from each other, and each independently a substituted or unsubstituted C1 to C60 alkyl group; a substituted or unsubstituted C6 to C60 aryl group; or a substituted or unsubstituted C2 to C60 heteroaryl group;

m1 is an integer of 0 to 8;

m2 is an integer of 0 to 6; and a11 and a2 are an integer of 0 to 4, and when m1, m2, a11 and a2 are 2 or greater, substituents in the parentheses are the same as or different from each other.

15. The composition for an organic material layer of an organic light emitting device of claim 14, wherein, in the composition, the heterocyclic compound: the heterocyclic compound represented by Chemical Formula A or Chemical Formula B have a weight ratio of 1:10 to 10:1.

16. A method for manufacturing an organic light emitting device, the method comprising:

preparing a substrate;

forming a first electrode on the substrate;

forming one or more organic material layers on the first electrode; and forming a second electrode on the organic material layers, wherein the forming of organic material layers includes forming one or more organic material layers using the composition for an organic material layer of claim 14.

17. The method for manufacturing an organic light emitting device of claim 16, wherein the forming of organic material layers is forming using a thermal vacuum deposition method after pre-mixing the heterocyclic compound of Chemical Formula 1; and the heterocyclic compound of Chemical Formula A or the heterocyclic compound of Chemical Formula B.

* * * * *